US012692253B2

(12) United States Patent
Looper et al.

(10) Patent No.: US 12,692,253 B2
(45) Date of Patent: Jul. 28, 2026

(54) ANTIMICROBIAL COMPOUNDS AND METHODS

(71) Applicants: Curza Global, LLC, Salt Lake City, UT (US); The University of Utah Research Foundation, Salt Lake City, UT (US)

(72) Inventors: Ryan E. Looper, Salt Lake City, UT (US); Paul Sebahar, Sandy, UT (US); Hariprasada R. Kanna Reddy, Salt Lake City, UT (US); Travis J. Haussener, Salt Lake City, UT (US); Charles A. Testa, North Salt Lake, UT (US); BenIsaac C. Tresco, Salt Lake City, UT (US); Seth Grant, West Jordan, UT (US); Carmela Napolitano, Verona (IT); Fabio Maria Sabbatini, Verona (IT)

(73) Assignees: Curza Global, LLC, Salt Lake City, UT (US); The University of Utah Research Foundation, Salt Lake City, UT (US)

( * ) Notice: Subject to any disclaimer, the term of this patent is extended or adjusted under 35 U.S.C. 154(b) by 1092 days.

(21) Appl. No.: 17/423,422

(22) PCT Filed: Jan. 15, 2020

(86) PCT No.: PCT/US2020/013717

§ 371 (c)(1),
(2) Date: Jul. 15, 2021

(87) PCT Pub. No.: WO2020/150372

PCT Pub. Date: Jul. 23, 2020

(65) Prior Publication Data

US 2023/0072397 A1 Mar. 9, 2023

Related U.S. Application Data

(60) Provisional application No. 62/793,122, filed on Jan. 16, 2019, provisional application No. 62/793,131, filed on Jan. 16, 2019, provisional application No. 62/793,160, filed on Jan. 16, 2019.

(51) Int. Cl.

| | |
|---|---|
| ***C07D 403/10*** | (2006.01) |
| ***A61P 31/04*** | (2006.01) |
| ***C07D 239/47*** | (2006.01) |
| ***C07D 401/04*** | (2006.01) |
| ***C07D 401/10*** | (2006.01) |
| ***C07D 401/14*** | (2006.01) |
| ***C07D 403/04*** | (2006.01) |
| ***C07D 403/14*** | (2006.01) |
| ***C07D 405/14*** | (2006.01) |
| ***C07D 413/14*** | (2006.01) |
| ***C07D 451/04*** | (2006.01) |
| ***C07D 471/04*** | (2006.01) |
| ***C07D 471/08*** | (2006.01) |
| ***C07D 471/10*** | (2006.01) |
| ***C07D 487/04*** | (2006.01) |
| ***C07D 487/10*** | (2006.01) |

(52) U.S. Cl.

CPC ............ *C07D 403/10* (2013.01); *A61P 31/04* (2018.01); *C07D 239/47* (2013.01); *C07D 401/10* (2013.01); *C07D 401/14* (2013.01); *C07D 403/14* (2013.01); *C07D 405/14* (2013.01); *C07D 413/14* (2013.01); *C07D 451/04* (2013.01); *C07D 471/04* (2013.01); *C07D 471/08* (2013.01); *C07D 471/10* (2013.01); *C07D 487/04* (2013.01); *C07D 487/10* (2013.01)

(58) Field of Classification Search

CPC .. C07D 403/10; C07D 403/14; C07D 403/04; C07D 239/47; C07D 401/10; C07D 401/14; C07D 401/04; C07D 405/14; C07D 413/14; C07D 451/04; C07D 471/04; C07D 471/08; C07D 471/10; C07D 487/04; C07D 487/10; A61P 31/04; Y02A 50/30

See application file for complete search history.

(56) References Cited

U.S. PATENT DOCUMENTS

| | | | |
|---|---|---|---|
| 2013/0090326 | A1 | 4/2013 | Duffy et al. |
| 2018/0065966 | A1 | 3/2018 | Bhattacharjee et al. |

FOREIGN PATENT DOCUMENTS

| | | | |
|---|---|---|---|
| JP | 2021541568 | | 5/2023 |
| WO | 2011047319 | A2 | 4/2011 |
| WO | 2011047323 | A3 | 8/2011 |
| WO | 2012173689 | A2 | 12/2012 |
| WO | 2015035421 | A1 | 3/2015 |
| WO | 2015035426 | A1 | 3/2015 |
| WO | 2016145417 | A1 | 9/2016 |
| WO | 2017193016 | A1 | 11/2017 |

(Continued)

OTHER PUBLICATIONS

International Search Report for PCT/US2020/013717 mailed Apr. 21, 2020.

(Continued)

*Primary Examiner* — Sun Jae Yoo

(74) *Attorney, Agent, or Firm* — Honigman LLP; Heidi Berven; Tyler Whittemore

(57) ABSTRACT

The invention is directed to compounds that are active as antibacterial agents. The invention compounds are active against gram-positive and gram-negative bacteria and can be used to treat infections caused by gram-positive and gram-negative bacteria. Also disclosed are processes and intermediates for making the compounds.

13 Claims, No Drawings

(56) References Cited

FOREIGN PATENT DOCUMENTS

| | | | |
|---|---|---|---|
| WO | 2017193017 | A1 | 11/2017 |
| WO | 2017193023 | A1 | 11/2017 |
| WO | 2018236692 | A1 | 12/2018 |
| WO | 2019013789 | A1 | 1/2019 |
| WO | 2019164880 | A1 | 8/2019 |
| WO | 2020150372 | A1 | 7/2020 |
| WO | 2020150385 | A1 | 7/2020 |

OTHER PUBLICATIONS

Yamada, et al. "Synthesis of Novel Iso-4'-thionucleosides Using the Mitsunobu Reaction", The Journal of Organic Chemistry, 1998, pp. 6891-6899.
International Search Report for PCTUS2020/013733 dated Apr. 21, 2020.
International Search Report for PCT/US2020/060185 dated Mar. 21, 2021.
International Search Report for PCT/US2022/082474 dated Apr. 26, 2023.

ANTIMICROBIAL COMPOUNDS AND METHODS

CROSS-REFERENCE TO RELATED APPLICATIONS

This application is a United States National Phase filing of PCT/US2020/013717, filed Jan. 15, 2020, which claims the benefit of priority to U.S. Provisional Application No. 62/793,160, filed Jan. 16, 2019, U.S. Provisional Application No. 62/793,131, filed Jan. 16, 2019, and U.S. Provisional Application No. 62/793,122, filed Jan. 16, 2019. The entire contents of which are incorporated herein by reference.

This invention was made with government support under grant AI127724 awarded by the National Institutes of Health. The government has certain rights in this invention.

FIELD OF THE INVENTION

The present disclosure relates to compounds that are active as antibacterial agents. The present disclosure also relates to methods of treating bacterial infections with the present compounds.

BACKGROUND OF THE INVENTION

Antibacterial resistance is a worldwide problem. Both gram-positive and gram-negative bacteria are increasingly becoming resistant to antibiotics.

Gram-positive bacteria such as methicillin resistant *Staphylococcus aureus* (MRSA) are resistant to most antibiotics that are related to penicillin. MRSA strains are commonly involved in infections acquired in health care facilities and can cause infections in greater communities.

Gram-negative bacteria are believed to be more resistant to antibiotics than Gram-positive bacteria, because of the impermeability of their cell walls. According to the National Institutes of Health (NIH), Gram-negative bacteria can cause many types of infections and are spread to humans in a variety of ways. Several species, including *Escherichia coli*, are common causes of foodborne disease. *Vibrio cholerae*, the bacteria responsible for cholera, is a waterborne pathogen. Gram-negative bacteria can also cause respiratory infections, such as certain types of pneumonia, and sexually transmitted diseases, including gonorrhea. *Yersinia pestis*, the Gram-negative bacterium responsible for plague, is transmitted to people through the bite of an infected insect or handling an infected animal. See www.niaid.nih.gov/research/gram-negative-bacteria (last visited Jan. 7, 2020).

Certain types of Gram-negative bacteria have become increasingly resistant to available antibiotic drugs. Some strains are now resistant to many, most, or all available treatments resulting in increased illness and death from bacterial infections and contributing to escalating healthcare costs. Examples of Gram-negative bacteria that have demonstrated drug resistance include: *E. coli*, which causes the majority of urinary tract infections; *Acinetobacter baumanii*, which causes disease mainly in healthcare settings; *Pseudomonas aeruginosa*, which causes bloodstream infections and pneumonia in hospitalized patients and is a common cause of pneumonia in patients with cystic fibrosis; *Klebsiella pneumoniae*, which causes many types of healthcare-associated infections, including pneumonia, urinary tract infections, and bloodstream infections; and *Neisseria gonorrhoeae*, which causes the sexually transmitted disease gonorrhea and is the second most commonly reported infectious disease in the United States.

As a result, new drugs to combat Gram-positive and Gram-negative bacterial infections are needed.

SUMMARY OF THE INVENTION

These and other needs are met by the present invention which provides in one aspect a compound of formula I:

I

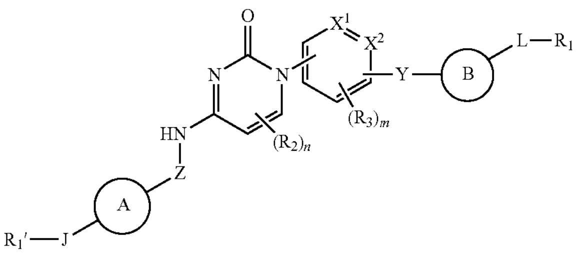

or a pharmaceutically acceptable salt thereof, wherein:

Z is (C═O), (C═S), (C═$NR_z$) S═O, or $SO_2$, wherein $R_z$ is H, CN, or $C_1$-$C_6$ alkyl;

ring A is a monocyclic heterocycloalkylene or bicyclic heterocycloalkylene, wherein the monocyclic heterocycloalkylene and bicyclic heterocycloalkylene are optionally substituted with up to three substituents independently selected from the group consisting of $C_1$-$C_6$ alkyl, $C_1$-$C_6$ alkoxy, halo, CN, $C_1$-$C_6$ haloalkyl, phenyl, OH, $NH_2NH(C_1$-$C_6$ alkyl), $N(C_1$-$C_6$ alkyl$)_2$, COO($C_1$-$C_6$ alkyl), $CONH_2$, and oxo;

J is absent or is $C_1$-$C_6$ alkylene, heterocycloalkylene, $C_1$-$C_6$ alkylene-heterocycloalkylene or $C_1$-$C_6$ alkylene-cycloalkylene, any of which may be optionally substituted with up to three substituents independently selected from halo, $C_1$-$C_6$ alkyl, $C_1$-$C_6$ alkoxy, $C_1$-$C_6$ haloalkyl, $NH_2CN$, or OH; wherein at each occurrence of $C_1$-$C_6$ alkylene, one or two methylene units of the $C_1$-$C_6$ alkylene may independently and optionally be replaced with O, S, $SO_2C$═O, or

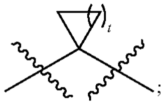

wherein t is 1, 2, 3, 4, 5 or 6;

$X^1$ and $X^2$ are each independently C—H or N;

Y is a linear $C_1$-$C_8$ alkylene, $C_2$-$C_8$ alkenylene, or $C_2$-$C_8$ alkynylene, any of which are optionally substituted with OH, $NH_2CN$, halo, $C_1$-$C_6$ alkyl, $C_1$-$C_6$ haloalkyl, COO($C_1$-$C_6$ alkyl), COOH, $CONH_2$ or $C_1$-$C_6$ alkoxy, and wherein up to two carbon atoms of the $C_1$-$C_8$ alkylene, $C_3$-$C_8$ alkenylene, or $C_3$-$C_8$ alkynylene are optionally and independently replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-cycloalkyl), NH(C═O), N—($C_{1-6}$ alkyl) (C═O), or (C═O);

ring B is a bicyclic heterocycloalkylene or bicyclic cycloalkylene, wherein the bicyclic heterocycloalkylene and bicyclic cycloalkylene are optionally substituted with up to three substituents independently selected from the group consisting of $C_1$-$C_6$ alkyl, $C_1$-$C_6$ alkoxy, halo, CN, $C_1$-$C_6$ haloalkyl, OH, COO($C_1$-$C_6$ alkyl), $CONH_2$, and $C_1$-$C_6$ hydroxyalkyl;

L is absent, or is a linear or branched $C_1$-$C_6$ alkylene, wherein up to two methylene units of the $C_1$-$C_6$ alkylene may be independently replaced with O, NH, (C═O), NH(C═O), N—($C_{1-6}$ alkyl)(C═O), (C═NH), NH(C═N), or N—($C_{1-6}$ alkyl), and wherein the $C_1$-$C_6$ alkylene is optionally substituted with up to three substituents independently selected from the group consisting of $C_1$-$C_6$ alkoxy, halo, CN, $C_1$-$C_6$ haloalkyl, OH, $NH_2$COO($C_1$-$C_6$ alkyl), $CONH_2$$C_1$-$C_6$ aminoalkyl and $C_1$-$C_6$ hydroxyalkyl;

$R_1$ is H or $NR_{x'}R_{y'}$, wherein $R_{x'}$ and $R_{y'}$ are each independently H, $C_1$-$C_6$ alkyl, $C_1$-$C_6$ alkyl-$SO_3$CO($C_1$-$C_6$ alkyl), or an amino protecting group;

$R_{1'}$ is H or $NR_xR_y$, wherein $R_x$ and $R_y$ are each independently H, $C_1$-$C_6$ alkyl, $C_1$-$C_6$ alkyl-$SO_3$CO($C_1$-$C_6$ alkyl), or an amino protecting group;

$R_2$ and $R_3$ are each independently $C_1$-$C_6$ alkyl, halo, CN, OH, $NH_2$NH($C_1$-$C_6$ alkyl), O($C_1$-$C_6$ haloalkyl), N($C_1$-$C_6$ alkyl)$_2$, COO($C_1$-$C_6$ alkyl), $CONH_2$$C_1$-$C_6$ haloalkyl, or $C_1$-$C_6$ alkoxy; and m and n are each independently 0, 1, 2 or 3.

In another aspect, the invention provides methods of using compounds of formula I or a pharmaceutically acceptable salt thereof for the treatment of bacterial infections.

In another aspect, the invention provides pharmaceutical compositions comprising a compound of formula I or a pharmaceutically acceptable salt thereof and a pharmaceutically acceptable carrier.

In a further aspect, the invention provides processes for making compounds of formula I or a pharmaceutically acceptable salt thereof, as well as compound intermediates used in the processes, as depicted in the synthetic schemes.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety, including U.S. Pat. Publ. No. 2013/0090326. In case of conflict, the present specification, including these definitions, will control.

The terms "a," "an," and "the" as used herein not only include aspects with one member, but also include aspects with more than one member.

The term "about" as used herein means "approximately" and is used to modify a numerical value indicates a defined range around that value. If "X" were the value, "about X" would generally indicate a value from 0.95X to 1.05X. Any reference to "about X" specifically indicates at least the values X, 0.95X, 0.96X, 0.97X, 0.98X, 0.99X, 1.01X, 1.02X, 1.03X, 1.04X, and 1.05X. Thus, "about X" is intended to teach and provide written description support for a claim limitation of, e.g., "0.98X." When the quantity "X" only includes whole-integer values (e.g., "X carbons"), "about X" indicates from (X−1) to (X+1). In this case, "about X" as used herein specifically indicates at least the values X, X−1, and X+1.

When "about" is applied to the beginning of a numerical range, it applies to both ends of the range. Thus, "from about 5 to 20%" is equivalent to "from about 5% to about 20%." When "about" is applied to the first value of a set of values, it applies to all values in that set. Thus, "about 7, 9 or 11%" is equivalent to "about 7%, about 9%, or about 11%."

As used herein, a wavy line drawn on a structure can be used to show the attachment point of the structure, such as

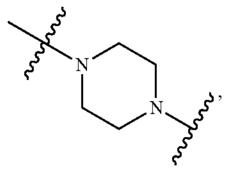 [SMILES: *N1CCN(*)CC1]

wherein "〰" indicates points of attachment.

The term "acyl" as used herein includes an alkanoyl, aroyl, heterocycloyl, or heteroaroyl group as defined herein. Examples of acyl groups include, but are not limited to, acetyl, benzoyl, and nicotinoyl.

The term "alkanoyl" as used herein includes an alkyl-C(O)— group wherein the alkyl group is as defined herein. Examples of alkanoyl groups include, but are not limited to, acetyl and propanoyl.

The term "agent" as used herein includes a compound or mixture of compounds that, when added to a composition, tend to produce a particular effect on the composition's properties. For example, a composition comprising a thickening agent is likely to be more viscous than an otherwise identical comparative composition that lacks the thickening agent.

The term "alkyl" as used herein includes an aliphatic hydrocarbon chain that may be straight chain or branched. The chain may contain an indicated number of carbon atoms: For example, $C_1$-$C_{10}$ indicates that the group may have from 1 to 10 (inclusive) carbon atoms in it. If not otherwise indicated, an alkyl group contains from 1 to about 20 carbon atoms. In some aspects, alkyl groups have 1 to about 10 carbon atoms. In some aspects, alkyl groups ("lower alkyl") have 1 to 8, 1 to 6 or 1 to 3 carbon atoms in the chain. Examples may include, but are not limited to, methyl, ethyl, propyl, isopropyl (iPr), 1-butyl, 2-butyl, isobutyl (iBu), tert-butyl, pentyl, 2-methylbutyl, 1,1-dimethylpropyl, hexyl, heptyl, octyl, nonyl, decyl, docecyl, cyclopentyl, or cyclohexyl.

An alkyl group can be unsubstituted or optionally substituted. When optionally substituted, one or more hydrogen atoms of the alkyl group (e.g., from 1 to 4 from 1 to 2 or 1) may be replaced with a moiety independently selected from the group consisting of fluoro, hydroxy, alkoxy, amino, alkylamino, acylamino, thio, and alkylthio. In some aspects, the alkyl group is unsubstituted or not optionally substituted.

"Alkylene" as used herein includes an alkyl group that is substituted at two points. An example is methylene (—$CH_2$—), propylene (—$CH_2CH_2CH_2$—), and the like.

The term "alkenyl" as used herein includes a straight or branched chain hydrocarbon containing at least one carbon-carbon double bond. The chain may contain an indicated number of carbon atoms. For example, "$C_1$-$C_{12}$ alkenyl" indicates that the group may have from 1 to 12 (inclusive) carbon atoms and at least one carbon-carbon double bond.

When the indicated number of carbon atoms is 1, then the $C_i$ alkenyl is double bonded to a carbon (i.e., a carbon equivalent to an oxo group). In certain aspects, the chain includes 1 to 12 about 2 to 15 about 2 to 12 about 2 to 8 or about 2 to 6 carbon atoms. An alkenyl group can be preferably one stereoisomer (i.e., cis- or, alternatively, trans-). Examples of an alkenyl group may include, but are not limited to, ethenyl (i.e., vinyl), allyl, propenyl, butenyl, crotyl, pentenyl, hexenyl, heptenyl, octenyl, nonenyl, decenyl, dodecenyl, cyclopentenyl, cyclohexenyl, 2-isopentenyl, allenyl, butadienyl, pentadienyl, pentadienyl), and hexadienyl.

An alkenyl group can be unsubstituted or optionally substituted. When optionally substituted, one or more hydrogen atoms of the alkenyl group (e.g., from 1 to 4 from 1 to 2, or 1) may be replaced with a moiety independently selected from the group consisting of fluoro, hydroxy, alkoxy, amino, alkylamino, acylamino, thio, and alkylthio, with the proviso that no hydrogen atom substituent on the carbon-carbon double bond is replaced by a hydroxy, amino, or thio group. In some aspects, the alkenyl group is unsubstituted or not optionally substituted.

"Alkenylene" as used herein includes an alkenyl group that is substituted at two points. An example is but-2-enylene ($—CH_2CH═CHCH_2—$) and the like.

The term "alkynyl" as used herein includes a straight, branched, or cyclic hydrocarbon containing at least one carbon-carbon triple bond. Examples may include, but are not limited to, ethynyl, propargyl, propynyl, butynyl, pentynyl, hexynyl, heptynyl, octynyl, nonynyl, decynyl, or decynyl.

An alkynyl group can be unsubstituted or optionally substituted. When optionally substituted, one or more hydrogen atoms of the alkynyl group (e.g., from 1 to 4 from 1 to 2, or 1) may be replaced with a moiety independently selected from the group consisting of fluoro, hydroxy, alkoxy, amino, alkylamino, acylamino, thio, and alkylthio, with the proviso that no sp-hybridized hydrogen atom substituent is replaced by a hydroxy, amino, or thio group. In some aspects, the alkynyl group is unsubstituted or not optionally substituted.

"Alkynylene" as used herein includes an alkynyl group that is substituted at two points. An example is 2-butynylene ($—CH_2CCCH_2—$) and the like.

The term "alkoxy" as used herein includes a straight or branched chain saturated or unsaturated hydrocarbon containing at least one oxygen atom in an ether group (e.g., EtO—). The chain may contain an indicated number of carbon atoms. For example, "$C_1$-$C_{12}$ alkoxy" indicates that the group may have from 1 to 12 (inclusive) carbon atoms and at least one oxygen atom. Examples of a $C_1$-$C_{12}$ alkoxy group include, but are not limited to, methoxy, ethoxy, isopropoxy, butoxy, n-pentoxy, isopentoxy, neopentoxy, and hexoxy.

An alkoxy group can be unsubstituted or optionally substituted. When optionally substituted, one or more hydrogen atoms of the alkoxy group (e.g., from 1 to 4 from 1 to 2, or 1) may be replaced with a moiety independently selected from the group consisting of fluoro, hydroxy, alkoxy, amino, alkylamino, acylamino, thio, and alkylthio, with the proviso that no hydrogen atom alpha to the ether oxygen is replaced by a hydroxy, amino, or thio group. In some aspects, the alkoxy group is unsubstituted or not optionally substituted.

The term "aryl" as used herein includes cyclic aromatic carbon ring systems containing from 6 to 18 carbons. Examples of an aryl group include, but are not limited to, phenyl, naphthyl, anthracenyl, tetracenyl, biphenyl and phenanthrenyl.

The term "cycloalkyl" as used herein includes non-aromatic saturated monocyclic or multicyclic ring system that may contain an indicated number of carbon atoms. For example, $C_3$-$C_{12}$ indicates that the group may have from 3 to 12 (inclusive) carbon atoms in it. If not otherwise indicated, a cycloalkyl group includes about 3 to about 20 carbon atoms. In some aspects, cyclo alkyl groups have 3 to about 12 carbon atoms in the group. In some aspects, cycloalkyl groups have 3 to about 7 carbon atoms in the group. Examples may include, but are not limited to, cyclopropyl, cyclobutyl, cyclopentyl, cyclohexyl, 4,4-dimethylcyclohexyl, and cycloheptyl. The term "cycloalkyl" also includes multicyclic rings such as a bicyclic cycloalkyl, or a tricyclic cycloalkyl which may be in a fused, bridged, or spiro orientation.

The term "cycloalkylene" as used herein includes a cycloalkyl group that is substituted at two points.

The terms "disorder" and "disease" are used herein interchangeably for a condition in a subject. A disorder is a disturbance or derangement that affects the normal function of the body of a subject. A disease is a pathological condition of an organ, a body part, or a system resulting from various causes, such as infection, genetic defect, or environmental stress that is characterized by an identifiable group of symptoms. A disorder or disease can refer to a biofilm-related disorder or disorder caused by a planktonic bacterial phenotype that is characterized by a disease-related growth of bacteria.

The term "effective amount" or "effective dose" as used herein includes an amount sufficient to achieve the desired result and accordingly will depend on the ingredient and its desired result. Nonetheless, once the desired effect is identified, determining the effective amount is within the skill of a person skilled in the art.

As used herein, "fluoroalkyl" includes an alkyl group wherein the alkyl group includes one or more fluoro-substituents. Examples include, but are not limited to, trifluoromethyl.

As used herein, "geminal" substitution includes two or more substituents that are directly attached to the same atom. An example is 3,3-dimethyl substitution on a cyclohexyl or spirocyclohexyl ring.

As used herein, "halo" or "halogen" includes fluoro, chloro, bromo, and iodo.

As used herein, "heterocycloalkyl" includes a non-aromatic saturated ring of about 3 to about 12 ring atoms (e.g., 5 to about 10 ring atoms, 3 to about 8 ring atoms, or 3 to about 6 ring atoms), in which one or more of the atoms in the ring system is an element or elements other than carbon, e.g., nitrogen, oxygen or sulfur. A heterocycloalkyl group optionally comprises at least one $sp^2$-hybridized atom (e.g., a ring incorporating a carbonyl, endocyclic olefin, or exocyclic olefin). In some embodiments, a nitrogen or sulfur atom of the heterocycloalkyl is optionally oxidized to the corresponding N-oxide, S-oxide or S,S-dioxide. The monocyclic heterocycle means a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycloalkyl include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyridazin-3 (2H)-onyl, pyridin-2 (1H)-onyl, pyrrolinyl, pyrrolidinyl, tetrahydrofuranyl, tetrahydropyranyl, tetrahydropyridinyl, tetrahydropyrimidinyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The term "heterocycloalkylene" as used herein includes a heterocycloalkyl group that is substituted at two points.

The term "heterocycloalkyl" also includes multicyclic rings such as a bicyclic heterocycle, or a tricyclic heterocycle which may be in a fused, bridged, or spiro orientation. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3 or 4 carbon atoms, or an alkenylene bridge of two, three, or four carbon atoms. Representative examples of bicyclic heterocycles include, but are not limited to, 3-azabicyclo[3.1.0]hexane, 3-azabicyclo[4.1.0]heptane, 3-azabicyclo[3.2.0]heptane, (3aR,6aS)-hexahydro-1H-2$\lambda_2$-cyclopenta[c]pyrrole, (3aR,7aS)-octahydro-2$\lambda_2$-isoindole.

Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3 or 4 carbon atoms, or an alkenylene bridge of two, three, or four carbon atoms.

A heterocycloalkyl group can be unsubstituted or optionally substituted. When optionally substituted, one or more hydrogen atoms of the group (e.g., from 1 to 4 from 1 to 2 or 1) may be replaced with a moiety independently selected from the group consisting of fluoro, hydroxy, alkoxy, amino, alkylamino, acylamino, thio, and alkylthio. In some aspects, a substituted heterocycyl group can incorporate an exo- or endocyclic alkene (e.g., cyclohex-2-en-1-yl). In some aspects, the heterocycloalkyl group is unsubstituted or not optionally substituted.

The monocyclic, bicyclic, and tricyclic heterocycles are connected to the parent molecular moiety through any carbon atom or any nitrogen atom contained within the rings, and can be unsubstituted or substituted.

As used herein, the term "hydrophilic moiety" or "hydrophilic group" includes a moiety or a functional group that has a strong affinity to water. Examples may include, but are not limited to, a charged moiety, such as a cationic moiety or an anionic moiety, or a polar uncharged moiety, such as an alkoxy group or an amine group.

As used herein, the term "hydroxyalkyl" includes an alkyl group where at least one hydrogen substituent has been replaced with an alcohol (—OH) group. In certain aspects, the hydroxyalkyl group has one alcohol group. In certain aspects, the hydroxyalkyl group has one or two alcohol groups, each on a different carbon atom. In certain aspects, the hydroxyalkyl group has 1, 2, 3, 4, 5 or 6 alcohol groups. Examples may include, but are not limited to, hydroxymethyl, 2-hydroxyethyl, and 1-hydroxyethyl.

When any two substituent groups or any two instances of the same substituent group are "independently selected" from a list of alternatives, the groups may be the same or different. For example, if $R^a$ and $R^b$ are independently selected from the group consisting of alkyl, fluoro, amino, and hydroxyalkyl, then a molecule with two $R^a$ groups and two $R^b$ groups could have all groups be an alkyl group (e.g., four different alkyl groups). Alternatively, the first $R^a$ could be alkyl, the second $R^a$ could be fluoro, the first $R^b$ could be hydroxyalkyl, and the second $R^b$ could be amino (or any other substituents taken from the group). Alternatively, both $R^a$ and the first $R^b$ could be fluoro, while the second $R^b$ could be alkyl (i.e., some pairs of substituent groups may be the same, while other pairs may be different).

"Amino protecting group" is a protecting group that is suitable for preventing undesired reactions at an amino nitrogen. Representative amino-protecting groups include, but are not limited to, formyl; acyl groups, for example alkanoyl groups, such as acetyl and trifluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; and the like.

"Hydroxyl protecting group" is a protecting group that is suitable for preventing undesired reactions at a hydroxyl oxygen. Representative hydroxy-protecting groups include, but are not limited to, acyl groups, for example alkanoyl groups, such as acetyl; arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBDMS); and the like.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

"Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, orotic acid, methanesulfonic acid, ethanesulfonic acid, p-toluenesulfonic acid, salicylic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

As used herein, "or" should in general be construed non-exclusively. For example, an embodiment of "a composition comprising A or B" would typically present an aspect with a composition comprising both A and B. "Or" should, however, be construed to exclude those aspects presented that cannot be combined without contradiction (e.g., a composition pH that is between 9 and 10 or between 7 and 8).

As used herein, "spiro bicyclic cycloalkyl" includes a cycloalkyl in which geminal substituents on a carbon atom are replaced to join in forming a 1,1-substituted ring. For example, but without limitation, for a —$C(R^1)(R^2)$— group that was part of a longer carbon chain, if $R^1$ and $R^2$ joined to form a cyclopropyl ring incorporating the carbon to which $R^1$ and $R^2$ were bonded, this would be a spiro bicyclic cycloalkyl group (i.e., spirocyclopropyl).

The term "spiro bicyclic cycloalkylene" as used herein includes a spiro bicyclic cycloalkyl group that is substituted at two points.

As used herein, "spiro bicyclic heterocycloalkyl" includes a heterocycloalkyl in which geminal substituents on a carbon atom are replaced to join in forming a 1,1-substituted ring. For example, but without limitation, for a —$C(R^1)(R^2)$— group that was part of a longer carbon chain, if $R^1$ and $R^2$ joined to form a pyrrolidine ring incorporating the carbon to which $R^1$ and $R^2$ were bonded, this would be a spiro bicyclic heterocycloalkyl group.

The term "spiro bicyclic heterocycloalkylene" as used herein includes a spiro bicyclic heterocycloalkyl group that is substituted at two points.

Some compounds disclosed herein are characterized by the presence of amino functional groups. One of ordinary skill would therefore understand that compounds can be isolated as salts wherein the amino functional group nitrogen is quarternized.

As used herein, the term "treat," "treating," or "treatment" includes administering or applying a composition (e.g., a composition described herein) in an amount, manner (e.g., schedule of administration), and mode (e.g., route of administration) that is effective to improve a disorder or a symptom thereof, or to retard, or to slow the progression of a disorder or a symptom thereof. Such improvements can include, but are not limited to, alleviation or amelioration of one or more symptoms or conditions, diminishment of the extent of a disease, stabilizing (i.e., not worsening) the state of disease, delaying or slowing of disease progression, amelioration or palliation of the disease state, diminishment of the reoccurrence of disease, and remission, whether partial or total and whether detectable or undetectable.

EMBODIMENTS

Compounds

In a first aspect, the disclosure provides a compound of Formula I:

I

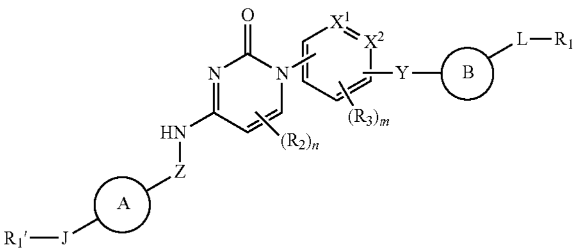

or a pharmaceutically acceptable salt thereof, wherein:

- Z is (C═O), (C═S), (C═$NR_z$), S═O, or $SO_2$ wherein $R_z$ is H, CN, or $C_1$-$C_6$ alkyl;
- ring A is a monocyclic heterocycloalkylene or bicyclic heterocycloalkylene, wherein the monocyclic heterocycloalkylene and bicyclic heterocycloalkylene are optionally substituted with up to three substituents independently selected from the group consisting of $C_1$-$C_6$ alkyl, $C_1$-$C_6$ alkoxy, halo, CN, $C_1$-$C_6$ haloalkyl, phenyl, OH, $NH_2NH(C_1$-$C_6$ alkyl), $N(C_1$-$C_6$ alkyl$)_2$, $COO(C_1$-$C_6$ alkyl), $CONH_2$, and oxo;
- J is absent or is $C_1$-$C_6$ alkylene, heterocycloalkylene, $C_1$-$C_6$ alkylene-heterocycloalkylene or $C_1$-$C_6$ alkylene-cycloalkylene, any of which may be optionally substituted with up to three substituents independently selected from halo, $C_1$-$C_6$ alkyl, $C_1$-$C_6$ alkoxy, $C_1$-$C_6$ haloalkyl, $NH_2CN$, or OH; wherein at each occurrence of $C_1$-$C_6$ alkylene, one or two methylene units of the $C_1$-$C_6$ alkylene may independently and optionally be replaced with O, S, $SO_2C$═O, or

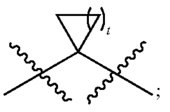

wherein t is 1, 2, 3, 4, 5 or 6;

$X^1$ and $X^2$ are each independently C—H or N;

Y is a linear $C_1$-$C_8$ alkylene, $C_2$-$C_8$ alkenylene, or $C_2$-$C_8$ alkynylene, any of which are optionally substituted with OH, $NH_2CN$, halo, $C_1$-$C_6$ alkyl, $C_1$-$C_6$ haloalkyl, COO($C_1$-$C_6$ alkyl), COOH, $CONH_2$ or $C_1$-$C_6$ alkoxy, and wherein up to two carbon atoms of the $C_1$-$C_8$ alkylene, $C_3$-$C_8$ alkenylene, or $C_3$-$C_8$ alkynylene are optionally and independently replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-cycloalkyl), NH(C═O), N—($C_{1-6}$ alkyl) (C═O), or (C═O);

ring B is a bicyclic heterocycloalkylene or bicyclic cycloalkylene, wherein the bicyclic heterocycloalkylene and bicyclic cycloalkylene are optionally substituted with up to three substituents independently selected from the group consisting of $C_1$-$C_6$ alkyl, $C_1$-$C_6$ alkoxy, halo, CN, $C_1$-$C_6$ haloalkyl, OH, COO ($C_1$-$C_6$ alkyl), $CONH_2$, and $C_1$-$C_6$ hydroxyalkyl;

L is absent, or is a linear or branched $C_1$-$C_6$ alkylene, wherein up to two methylene units of the $C_1$-$C_6$ alkylene may be independently replaced with O, NH, (C═O), NH(C═O), N—($C_{1-6}$ alkyl)(C═O), (C═NH), NH(C═N), or N—($C_{1-6}$ alkyl), and wherein the $C_1$-$C_6$ alkylene is optionally substituted with up to three substituents independently selected from the group consisting of $C_1$-$C_6$ alkoxy, halo, CN, $C_1$-$C_6$ haloalkyl, OH, $NH_2COO$($C_1$-$C_6$ alkyl), $CONH_2C_1$-$C_6$ aminoalkyl and $C_1$-$C_6$ hydroxyalkyl;

$R_1$ is H or $NR_{x'}R_{y'}$, wherein $R_{x'}$ and $R_{y'}$ are each independently H, $C_1$-$C_6$ alkyl, $C_1$-$C_6$ alkyl-$SO_3$, CO($C_1$-$C_6$ alkyl), or an amino protecting group;

$R_{1'}$ is H or $NR_xR_y$, wherein $R_x$ and $R_y$ are each independently H, $C_1$-$C_6$ alkyl, $C_1$-$C_6$ alkyl-$SO_3$CO($C_1$-$C_6$ alkyl), or an amino protecting group;

$R_2$ and $R_3$ are each independently $C_1$-$C_6$ alkyl, halo, CN, OH, $NH_2NH$($C_1$-$C_6$ alkyl), O($C_1$-$C_6$ haloalkyl), N($C_1$-$C_6$ alkyl)$_2$, COO($C_1$-$C_6$ alkyl), $CONH_2C_1$-$C_6$ haloalkyl, or $C_1$-$C_6$ alkoxy; and m and n are each independently 0, 1, 2 or 3.

In one embodiment of a compound of formula I or a pharmaceutically acceptable salt thereof, Z is (C═S), (C═$NR_z$), S═O, or $SO_2$ wherein $R_z$ is H, CN, or $C_1$-$C_6$ alkyl.

In another embodiment of a compound of formula I or a pharmaceutically acceptable salt thereof, Z is C═NH, C═N ($C_1$-$C_6$ alkyl), or C═N—CN.

In another embodiment of a compound of formula I or a pharmaceutically acceptable salt thereof, Z is —(C═O)—.

In another embodiment of a compound of formula I or a pharmaceutically acceptable salt thereof, ring A is a 4 to 8 membered monocyclic heterocycloalkylene or a 6 to 12 membered bicyclic heterocycloalkylene, wherein the monocyclic heterocycloalkylene and bicyclic heterocycloalkylene are optionally substituted with up to three substituents independently selected from the group consisting of $C_1$-$C_6$ alkyl, $C_1$-$C_6$ alkoxy, halo, CN, $C_1$-$C_6$ haloalkyl, phenyl, OH, $NH_2$, and oxo.

In another embodiment, ring A is a 4 to 7 membered monocyclic heterocycloalkylene optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, and oxo. In another embodiment, ring A is a 4 to 7 membered monocyclic heterocycloalkylene optionally substituted with $C_1$-$C_6$ alkyl, $C_1$-$C_6$ alkoxy, halo, CN, $C_1$-$C_6$ haloalkyl, phenyl, OH, $NH_2$ or oxo, wherein the monocyclic heterocycloalkylene contains up to two heteroatoms selected from nitrogen or oxygen. In another embodiment, ring A is a 4 to 7 membered monocyclic heterocycloalkylene optionally substituted with $C_1$-$C_6$ alkyl, phenyl, or oxo, wherein the monocyclic heterocycloalkylene contains up to two heteroatoms selected from nitrogen or oxygen. In another embodiment, ring A contains two nitrogen atoms. In another embodiment, ring A is a 6 membered monocyclic heterocycloalkylene optionally substituted with $C_1$-$C_6$ alkyl, phenyl, or oxo, wherein the monocyclic heterocycloalkylene contains two nitrogen atoms.

In another embodiment, ring A is a 6 to 12 membered bicyclic heterocycloalkylene optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, and oxo. In another embodiment, ring A is a 6 to 11 membered bicyclic heterocycloalkylene optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, and oxo, wherein the bicyclic heterocycloalkylene contains up to two heteroatoms selected from nitrogen or oxygen. In another embodiment, ring A is a 6 to 11 membered bicyclic heterocycloalkylene, wherein the bicyclic heterocycloalkylene contains up to two heteroatoms selected from nitrogen or oxygen. In another embodiment, ring A is a 6 to 11 membered bicyclic heterocycloalkylene containing up to two nitrogen atoms. In another embodiment, ring A is a 6 to 11 membered fused or spiro bicyclic heterocycloalkylene containing up to two nitrogen atoms.

In another embodiment of a compound of formula I or a pharmaceutically acceptable salt thereof, ring A is selected from the moieties provided in Table 1:

TABLE 1

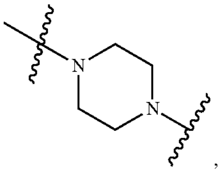 [SMILES: *N1CCN(*)CC1]

,

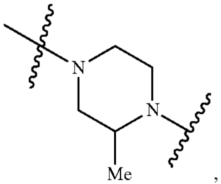 [SMILES: *N1CCN(*)C(C)C1]

,

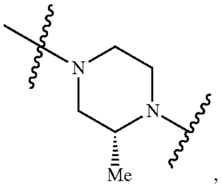 [SMILES: *N1CCN(*)[C@H](C)C1]

,

TABLE 1-continued
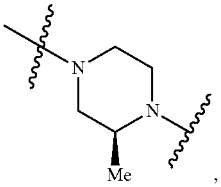 [SMILES: *N1CCN(*)[C@@H](C)C1],
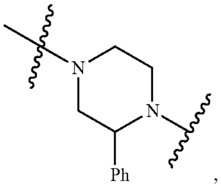 [SMILES: *N1CCN(*)C(c2ccccc2)C1],
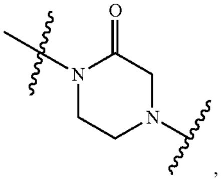 [SMILES: *N1CCN(*)C(=O)C1],
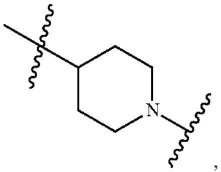 [SMILES: *C1CCN(*)CC1],
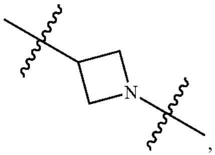 [SMILES: *C1CN(*)C1],
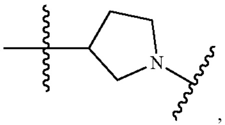 [SMILES: *C1CCN(*)C1],
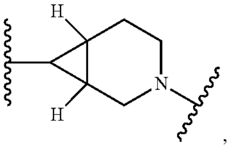 [SMILES: *C1C2CCN(*)CC12],
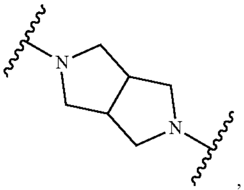 [SMILES: *N1CC2CN(*)CC2C1],
TABLE 1-continued
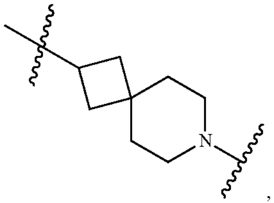 [SMILES: *C1CC2(CCN(*)CC2)C1],
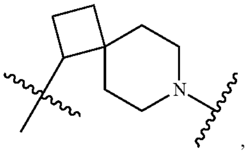 [SMILES: *C1CCC12CCN(*)CC2],
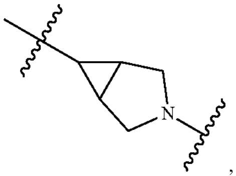 [SMILES: *C1C2CN(*)CC12],
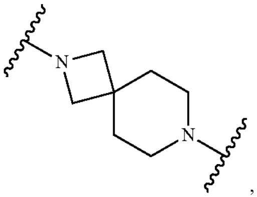 [SMILES: *N1CCC2(CC1)CN(*)C2],
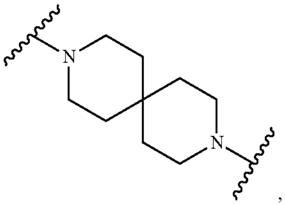 [SMILES: *N1CCC2(CC1)CCN(*)CC2],
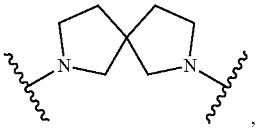 [SMILES: *N1CCC2(CCN(*)C2)C1],
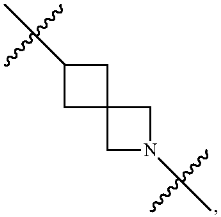 [SMILES: *C1CC2(C1)CN(*)C2],
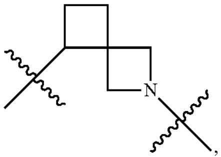 [SMILES: *C1CCC12CN(*)C2], TABLE 1-continued

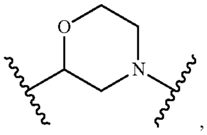 [SMILES: *C1CN(*)CCO1]
,

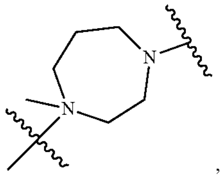
,

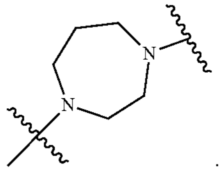 [SMILES: *N1CCCN(*)CC1]
.

In another embodiment of a compound of formula I or a pharmaceutically acceptable salt thereof, J is absent.

In another embodiment of a compound of formula I or a pharmaceutically acceptable salt thereof, J is $C_1$-$C_6$ alkylene, heterocycloalkylene, $C_1$-$C_6$ alkylene-heterocycloalkylene or $C_1$-$C_6$ alkylene-cycloalkylene, any of which may be optionally substituted with up to substituents independently selected from halo, $C_1$-$C_6$ alkyl, $C_1$-$C_6$ alkoxy, $C_1$-$C_6$ haloalkyl, $NH_2CN$, or OH, wherein at each occurrence of $C_1$-$C_6$ alkylene, one or two methylene units of the $C_1$-$C_6$ alkylene may independently and optionally be replaced with C═O or

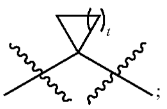
;

wherein t is 1, 2 or 3.

In another embodiment, J is $C_1$-$C_6$ alkylene, $C_1$-$C_6$ alkylene-heterocycloalkylene or $C_1$-$C_6$ alkylene-cycloalkylene, wherein one methylene unit of the $C_1$-$C_6$ alkylene may be replaced with —(C═O)—. In another embodiment, J is $C_1$-$C_6$ alkylene, wherein one methylene unit of the $C_1$-$C_6$ alkylene may be replaced with —(C═O)—. In another embodiment, J is (C═O)-heterocycloalkylene. In another embodiment, J is (C═O)—($C_3$-$C_6$ cycloalkylene).

In another embodiment, J is $C_1$-$C_6$ alkylene optionally substituted with halo, $C_1$-$C_6$ alkoxy, $C_1$-$C_6$ haloalkyl, $NH_2$ or OH, wherein one methylene unit of the $C_1$-$C_6$ alkylene may be replaced with —(C═O)—. In another embodiment, J is $C_1$-$C_6$ alkylene, wherein one methylene unit of the $C_1$-$C_6$ alkylene may be replaced with —(C═O)—, and another methylene unit of the $C_1$-$C_6$ alkylene may be replaced by

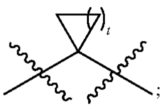
;

wherein t is 1, 2, 3 or 4. In another embodiment, t is 1 or 2.

In another embodiment, J is a $C_1$-$C_6$ alkylene optionally substituted with F, $CF_3$, $NH_2OMe$ or OH, wherein one methylene unit of the optionally substituted $C_1$-$C_6$ alkylene may be replaced with —(C═O)—.

In another embodiment of a compound of formula I or a pharmaceutically acceptable salt thereof, J is $C_1$-$C_6$ alkylene. In another embodiment, J is 5-6 membered heterocycloalkylene.

In another embodiment of a compound of formula I or a pharmaceutically acceptable salt thereof, J is selected from the moieties provided in Table 2:

TABLE 2

—$CH_2$—,
—$CH_2CH_2$—,

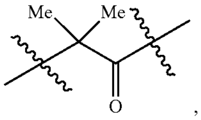 [SMILES: *C(=O)C(*)(C)C]
,

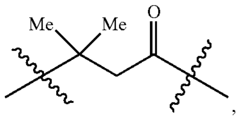 [SMILES: *C(=O)CC(*)(C)C]
,

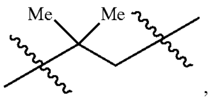 [SMILES: *CC(*)(C)C]
,

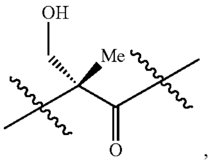 [SMILES: *C(=O)[C@@](*)(C)CO]
,

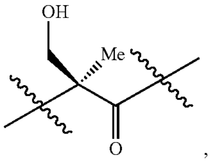 [SMILES: *C(=O)[C@](*)(C)CO]
,

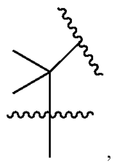 [SMILES: *C(*)(C)C]
,

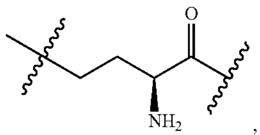 [SMILES: *CC[C@H](N)C(*)=O]
,

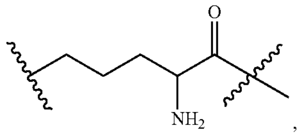 [SMILES: *CCCC(N)C(*)=O]
,

TABLE 2-continued
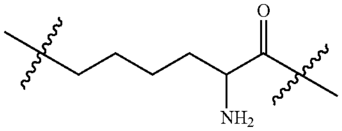,
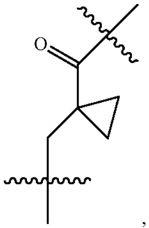 [SMILES: *CC1(C(*)=O)CC1],
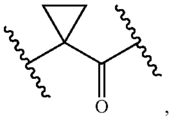 [SMILES: *C(=O)C1(*)CC1],
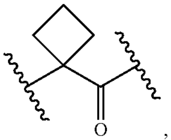 [SMILES: *C(=O)C1(*)CCC1],
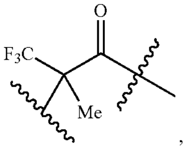,
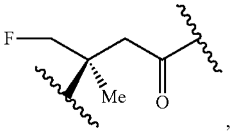 [SMILES: *C(=O)C[C@](*)(C)CF],
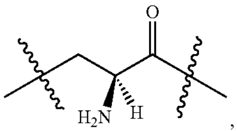 [SMILES: *C[C@H](N)C(*)=O],
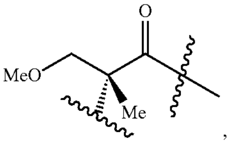 [SMILES: *C(=O)[C@@](*)(C)COC],
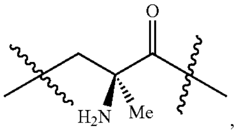 [SMILES: *C[C@](C)(N)C(*)=O],
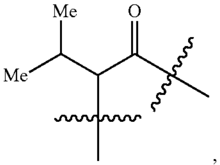 [SMILES: *C(=O)C(*)C(C)C],
TABLE 2-continued
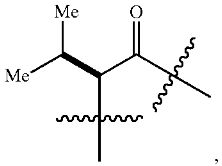,
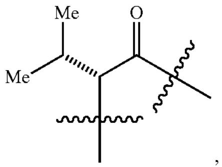,
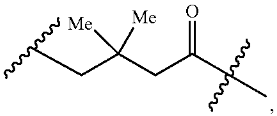 [SMILES: *CC(C)(C)CC(*)=O],
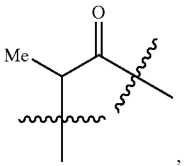 [SMILES: *C(=O)C(*)C],
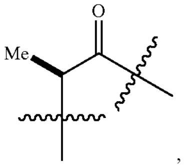 [SMILES: *C(=O)[C@@H](*)C],
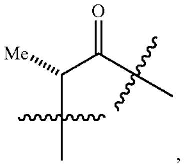 [SMILES: *C(=O)[C@H](*)C],
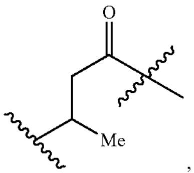 [SMILES: *C(=O)CC(*)C],
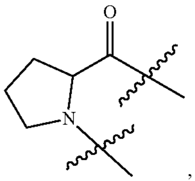 [SMILES: *C(=O)C1CCCN1*],
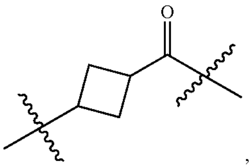 [SMILES: *C(=O)C1CC(*)C1], TABLE 2-continued

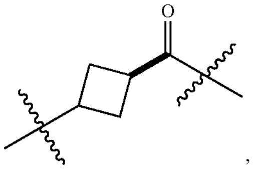

,

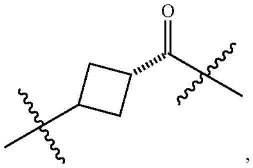

,

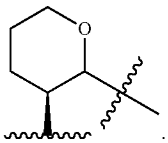 [SMILES: *C1OCCC[C@@H]1*]

.

In another embodiment of a compound of formula I or a pharmaceutically acceptable salt thereof, $R_{1'}$ is H, $NH_2NH$ ($C_1$-$C_6$ alkyl), N($C_1$-$C_6$ alkyl)$_2$, NHCO($C_1$-$C_6$ alkyl), NH($C_1$-$C_6$ alkyl-$SO_3^-$), or an amino protecting group. In another embodiment, $R_{1'}$ is H, $NH_2$, or NH($C_1$-$C_6$ alkyl). In another embodiment, $R_{1'}$ is H or $NH_2$. In another embodiment, $R_{1'}$ is H. In another embodiment, $R_{1'}$ is $NH_2$.

In another embodiment of a compound of formula I or a pharmaceutically acceptable salt thereof, Z is —(C═O)—ring A is a 4 to 7 membered monocyclic heterocycloalkylene optionally substituted with $C_1$-$C_6$ alkyl, $C_1$-$C_6$ alkoxy, halo, CN, $C_1$-$C_6$ haloalkyl, phenyl, OH, $NH_2$ or oxo, wherein the monocyclic heterocycloalkylene contains up to two heteroatoms selected from nitrogen or oxygen; J is $C_1$-$C_6$ alkylene, heterocycloalkylene, $C_1$-$C_6$ alkylene-heterocycloalkylene or $C_1$-$C_6$ alkylene-cycloalkylene, any of which may be optionally substituted with up to two substituents independently selected from halo, $C_1$-$C_6$ alkyl, $C_1$-$C_6$ alkoxy, C haloalkyl, $NH_2CN$, or OH, wherein at each occurrence of $C_1$-$C_6$ alkylene, one or two methylene units of the $C_1$-$C_6$ alkylene may independently and optionally be replaced with C═O or

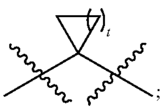

;

wherein t is 1, 2 or 3, and $R_{1'}$ is H, $NH_2$ or NH($C_1$-$C_6$ alkyl). In another embodiment, Z is —(C═O)—ring A is any one of the moieties provided in Table 1J is any one of the moieties provided in Table 2, and $R_{1'}$ is H, $NH_2$ or NH($C_1$-$C_6$ alkyl).

In another embodiment of a compound of formula I or a pharmaceutically acceptable salt thereof,

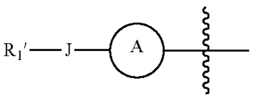

is selected from the moieties provided in Table 3:

TABLE 3

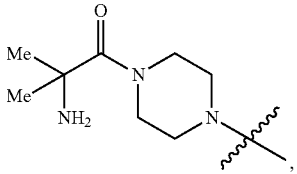

,

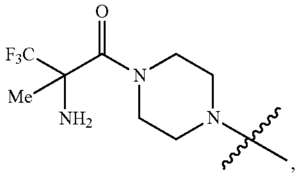 [SMILES: *N1CCN(C(=O)C(C)(C)N)CC1]

,

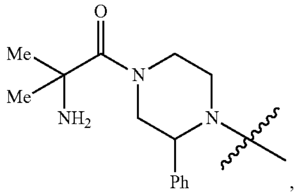 [SMILES: *N1CCN(C(=O)C(C)(C)N)CC1c1ccccc1]

,

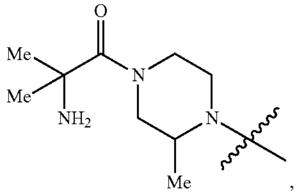 [SMILES: *N1CCN(C(=O)C(C)(C)N)CC1C]

,

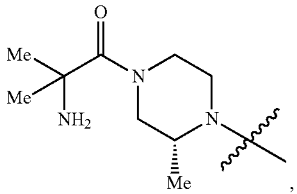 [SMILES: *N1CCN(C(=O)C(C)(C)N)C[C@H]1C]

,

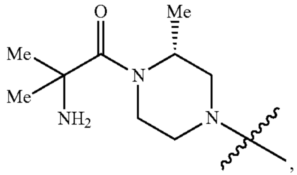 [SMILES: *N1CCN(C(=O)C(C)(C)N)[C@H](C)C1]

,

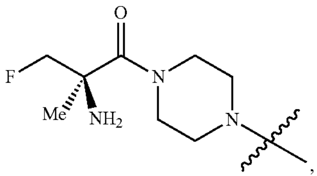 [SMILES: *N1CCN(C(=O)[C@@](C)(N)CF)CC1]

,

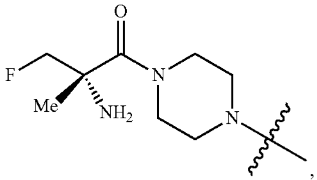 [SMILES: *N1CCN(C(=O)[C@](C)(N)CF)CC1]

,

TABLE 3-continued
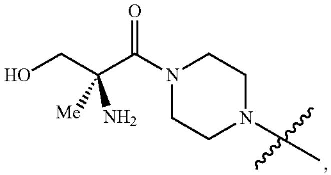 [SMILES: *N1CCN(C(=O)[C@@](C)(N)CO)CC1],
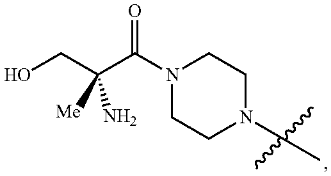 [SMILES: *N1CCN(C(=O)[C@](C)(N)CO)CC1],
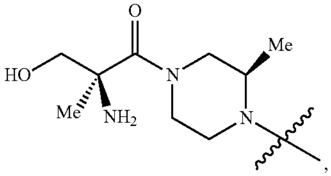 [SMILES: *N1CCN(C(=O)[C@@](C)(N)CO)C[C@H]1C],
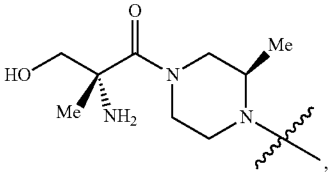 [SMILES: *N1CCN(C(=O)[C@](C)(N)CO)C[C@H]1C],
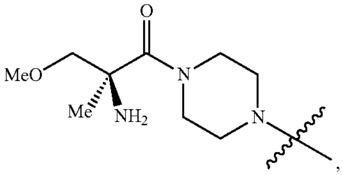 [SMILES: *N1CCN(C(=O)[C@@](C)(N)COC)CC1],
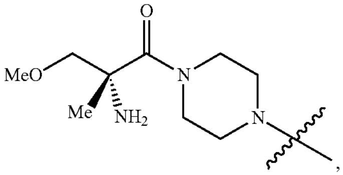 [SMILES: *N1CCN(C(=O)[C@](C)(N)COC)CC1],
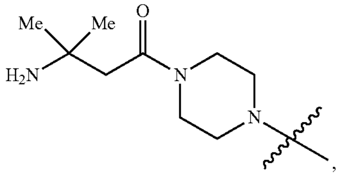 [SMILES: *N1CCN(C(=O)CC(C)(C)N)CC1],
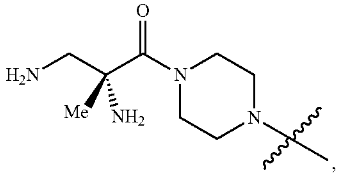 [SMILES: *N1CCN(C(=O)[C@](C)(N)CN)CC1],
TABLE 3-continued
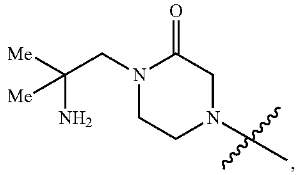 [SMILES: *N1CCN(CC(C)(C)N)C(=O)C1],
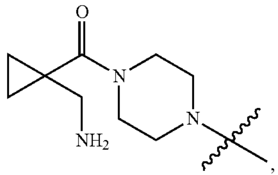 [SMILES: *N1CCN(C(=O)C2(CN)CC2)CC1],
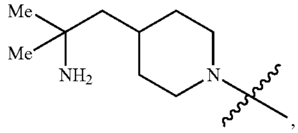 [SMILES: *N1CCC(CC(C)(C)N)CC1],
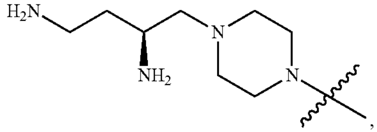 [SMILES: *N1CCN(C[C@@H](N)CCN)CC1],
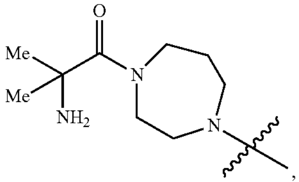 [SMILES: *N1CCCN(C(=O)C(C)(C)N)CC1],
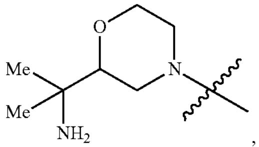 [SMILES: *N1CCOC(C(C)(C)N)C1],
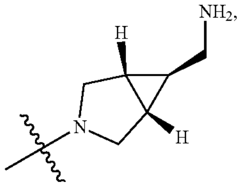 [SMILES: *N1C[C@@H]2[C@@H](CN)[C@@H]2C1]
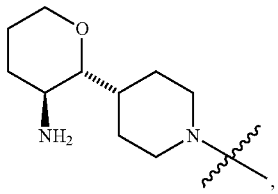,
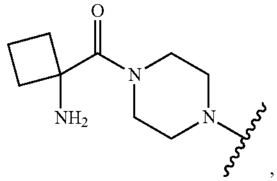 [SMILES: *N1CCN(C(=O)C2(N)CCC2)CC1], TABLE 3-continued
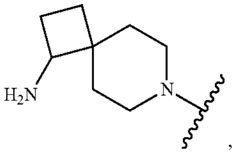 [SMILES: *N1CCC2(CCC2N)CC1]
,
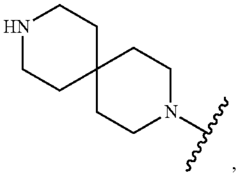 [SMILES: *N1CCC2(CCNCC2)CC1]
,
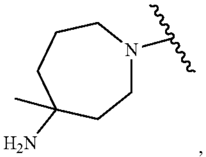 [SMILES: *N1CCCC(C)(N)CC1]
,
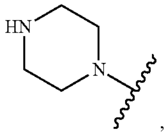
,
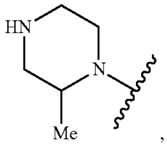
,
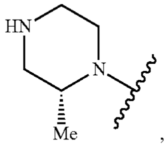
,
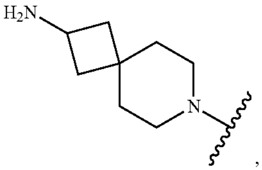 [SMILES: *N1CCC2(CC1)CC(N)C2]
,
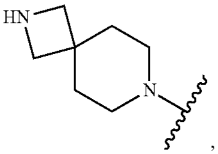 [SMILES: *N1CCC2(CC1)CNC2]
,
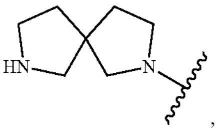 [SMILES: *N1CCC2(CCNC2)C1]
,
TABLE 3-continued
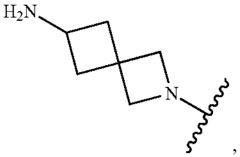
,
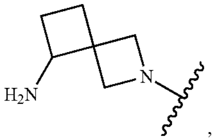 [SMILES: *N1CC2(CCC2N)C1]
,
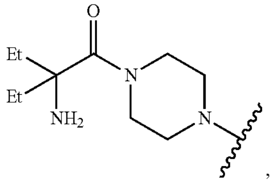 [SMILES: *N1CCN(C(=O)C(N)(CC)CC)CC1]
,
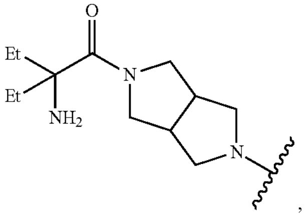 [SMILES: *N1CC2CN(C(=O)C(N)(CC)CC)CC2C1]
,
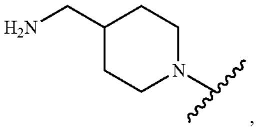
,
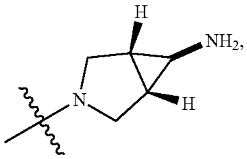 [SMILES: *N1C[C@@H]2[C@@H](N)[C@@H]2C1]
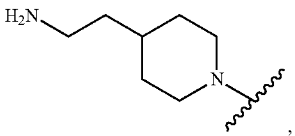 [SMILES: *N1CCC(CCN)CC1]
,
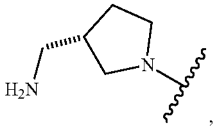 [SMILES: *N1CC[C@@H](CN)C1]
,
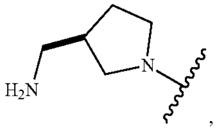 [SMILES: *N1CC[C@H](CN)C1]
, TABLE 3-continued
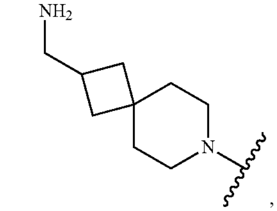 [SMILES: *N1CCC2(CC1)CC(CN)C2],
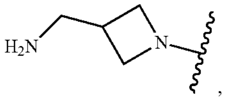 [SMILES: *N1CC(CN)C1],
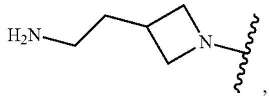 [SMILES: *N1CC(CCN)C1],
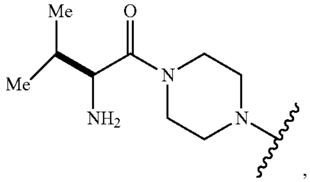 [SMILES: *N1CCN(C(=O)[C@@H](N)C(C)C)CC1],
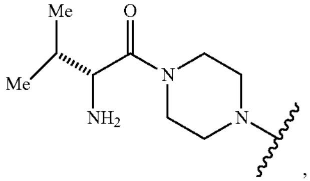 [SMILES: *N1CCN(C(=O)[C@H](N)C(C)C)CC1],
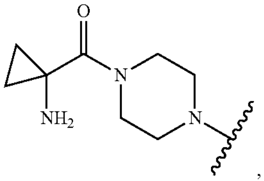 [SMILES: *N1CCN(C(=O)C2(N)CC2)CC1],
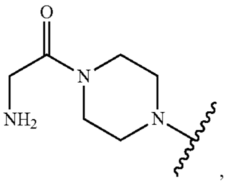 [SMILES: *N1CCN(C(=O)CN)CC1],
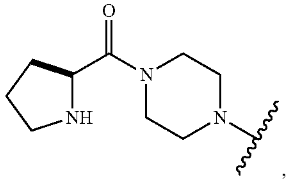 [SMILES: *N1CCN(C(=O)[C@@H]2CCCN2)CC1],
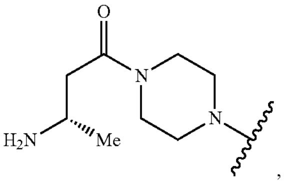 [SMILES: *N1CCN(C(=O)C[C@H](C)N)CC1],
TABLE 3-continued
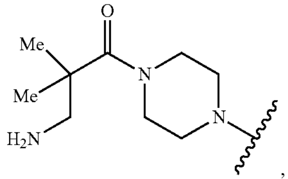 [SMILES: *N1CCN(C(=O)C(C)(C)CN)CC1],
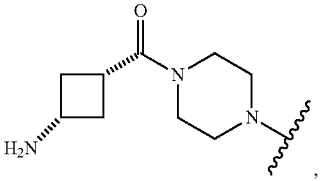 [SMILES: *N1CCN(C(=O)[C@H]2C[C@@H](N)C2)CC1],
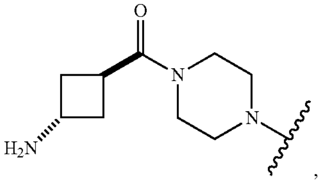 [SMILES: *N1CCN(C(=O)[C@H]2C[C@H](N)C2)CC1],
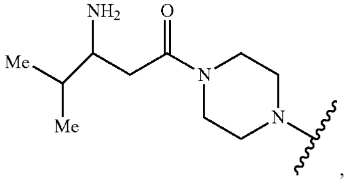 [SMILES: *N1CCN(C(=O)CC(N)C(C)C)CC1],
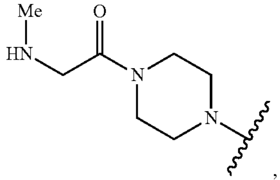 [SMILES: *N1CCN(C(=O)CNC)CC1],
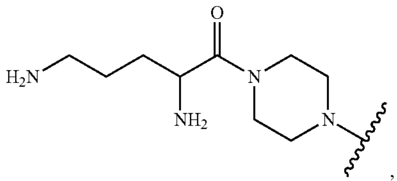 [SMILES: *N1CCN(C(=O)C(N)CCCN)CC1],
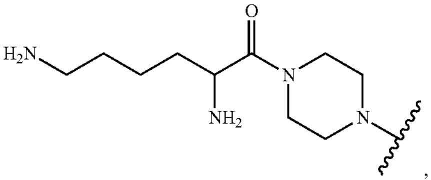 [SMILES: *N1CCN(C(=O)C(N)CCCCN)CC1], TABLE 3-continued

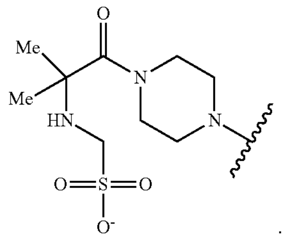 [SMILES: *N1CCN(C(=O)C(C)(C)NCS(=O)(=O)[O-])CC1]

.

In another embodiment of a compound of formula I or a pharmaceutically acceptable salt thereof,

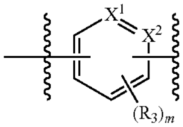 is 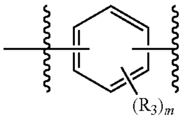 or 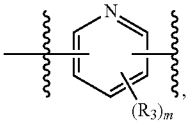, wherein each $R_3$ is independently selected from $C_1$-$C_6$ alkyl, halo, CN, OH, $NH_2NH(C_1$-$C_6$ alkyl), $O(C_1$-$C_6$ haloalkyl), $N(C_1$-$C_6$ alkyl$)_2$, $COO(C_1$-$C_6$ alkyl), $CONH_2C_1$-$C_6$ haloalkyl, or $C_1$-$C_6$ alkoxy, wherein m is 0, 1, 2 or 3.

In another embodiment,

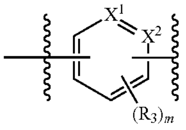 is 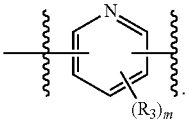.

In another embodiment,

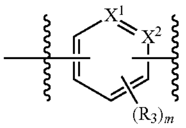 is 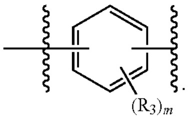.

In another embodiment,

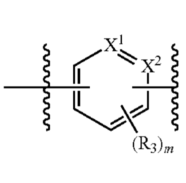 is 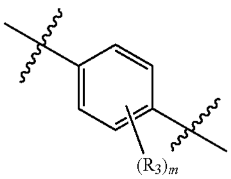 or

-continued

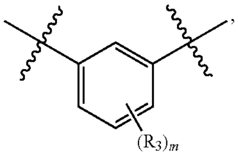, wherein each $R_3$ is independently $C_1$-$C_6$ alkyl, halo, CN, OH, $NH_2NH(C_1$-$C_6$ alkyl), $O(C_1$-$C_6$ haloalkyl), $N(C_1$-$C_6$ alkyl$)_2$, $COO(C_1$-$C_6$ alkyl), $CONH_2C_1$-$C_6$ haloalkyl, or $C_1$-$C_6$ alkoxy, wherein m is 0, 1, or 2. In another embodiment, each $R_3$ is independently $C_1$-$C_6$ alkyl, halo, $C_1$-$C_6$ alkoxy, or $C_1$-$C_6$ haloalkyl.

In another embodiment,

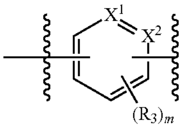 is 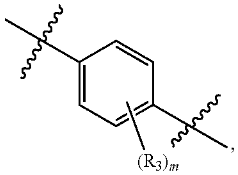, wherein each $R_3$ is independently $C_1$-$C_6$ alkyl, halo, $C_1$-$C_6$ alkoxy, or $C_1$-$C_6$ haloalkyl, wherein m is 0, 1 or 2.

In another embodiment,

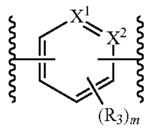 is 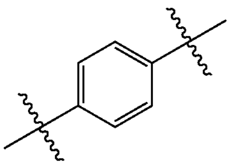,

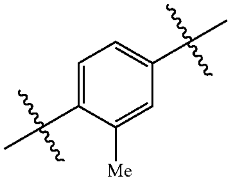, 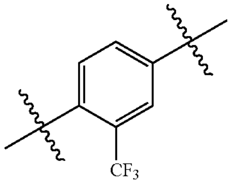,

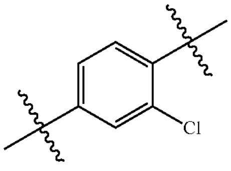, 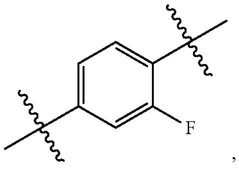,

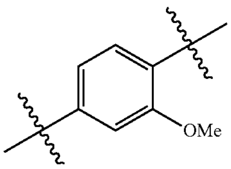, 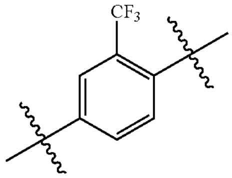,

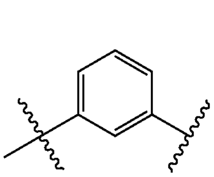, 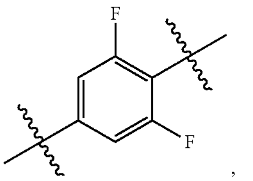, or

-continued

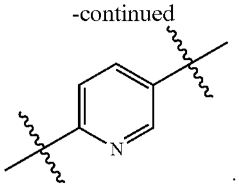

.

In one embodiment of a compound of formula I or a pharmaceutically acceptable salt thereof, Y is a linear $C_1$-$C_8$ alkylene optionally substituted with OH, $NH_2CN$, halo, $C_1$-$C_6$ alkyl, $C_1$-$C_6$ haloalkyl, COO($C_1$-$C_6$ alkyl), COOH, $CONH_2$ or $C_1$-$C_6$ alkoxy, wherein up to two methylene units of the $C_1$-$C_8$ alkylene are optionally and independently replaced by 0, NH, N—($C_1$-$C_6$ alkyl), N—($C_1$-$C_6$ hydroxyalkyl), N—($C_1$-$C_6$ haloalkyl), N—($C_1$-6 alkylene-$C_3$-8 cycloalkyl), NH(C═O), N—($C_{1-6}$ alkyl)(C═O), or (C═O). In another embodiment, Y is a linear $C_1$-$C_6$ alkylene optionally substituted with OH, $NH_2CN$, halo, $C_1$-$C_6$ alkyl, $C_1$-$C_6$ haloalkyl, COO($C_1$-$C_6$ alkyl), COOH, $CONH_2$ or $C_1$-$C_6$ alkoxy, wherein up to two methylene units of the $C_1$-$C_6$ alkylene are optionally and independently replaced by O, NH, N—($C_1$-$C_6$ alkyl), N—($C_1$-$C_6$ hydroxyalkyl), N—($C_1$-$C_6$ haloalkyl), N—($C_1$-6 alkylene-$C_{3-8}$ cycloalkyl), or (C═O). In another embodiment, Y is a linear $C_1$-$C_4$ alkylene optionally substituted with $NH_2C_1$-$C_6$ alkyl, COO($C_1$-$C_6$ alkyl), or COOH, wherein up to two methylene units of the $C_1$-$C_4$ alkylene are optionally and independently replaced by O, NH, N—($C_1$-$C_6$ alkyl), N—($C_1$-$C_6$ hydroxyalkyl), N—($C_1$-$C_6$ haloalkyl), N—($C_1$-6 alkylene-$C_{3-8}$ cycloalkyl), or (C═O).

In another embodiment, Y is $CR_iR_{ii}$ wherein $R_i$ and $R_{ii}$ are each independently H, OH, $NH_2CN$, halo, $C_1$-$C_6$ alkyl, $C_1$-$C_6$ haloalkyl, COO($C_1$-$C_6$ alkyl), COOH, $CONH_2$ or $C_1$-$C_6$ alkoxy. In another embodiment, $R_i$ and $R_{ii}$ are each independently H, $C_1$-$C_6$ alkyl, COO($C_1$-$C_6$ alkyl), or COOH. In another embodiment, CRR is $CH_2CH$($C_1$-$C_6$ alkyl), C($C_1$-$C_6$ alkyl)$_2$, CHCOO($C_1$-$C_6$ alkyl) and CHCOOH. In another embodiment, CRR is $CH_2$, CH($CH_3$), CH(COOEt), or CH(COOH). In another embodiment, CRR is $CH_2$.

In another embodiment, Y is —C($R_iR_j$)—C($R_{i'}R_{j'}$)— wherein $R_i$, $R_j$, $R_{i'}$, $R_{j'}$ are each independently H or $C_1$-$C_6$ alkyl, wherein C($R_iR_j$) and C($R_{i'}R_{j'}$) are each independently and optionally replaced with NH, N—($C_1$-6 alkyl), or (C═O).

In another embodiment, Y is —C($R_iR_j$)—C($R_{i'}R_{j'}$)— which is

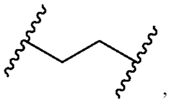 , 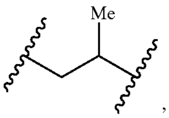 , 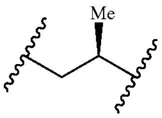 ,

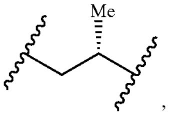 , 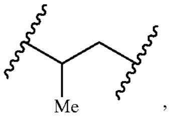 , 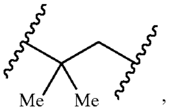 ,

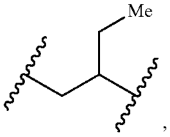 , 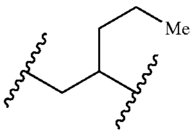 , 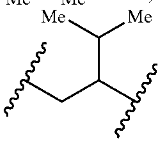 ,

-continued

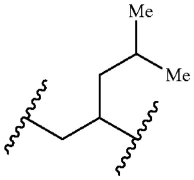 , 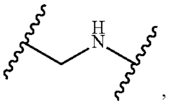 , 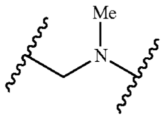 ,

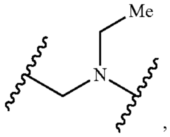 , or 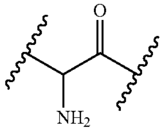 .

In another embodiment, Y is a linear $C_3$-$C_8$ alkylene, $C_3$-$C_8$ alkenylene, or $C_3$-$C_8$ alkynylene, any of which are optionally substituted with OH, $NH_2$, halo, $C_1$-$C_6$ alkyl, or $C_1$-$C_6$ alkoxy, wherein up to two carbon atoms of the $C_3$-$C_8$ alkylene, $C_3$-$C_8$ alkenylene, or $C_3$-$C_8$ alkynylene are optionally and independently replaced by O, NH, N—($C_1$-$C_6$ alkyl), N—($C_1$-$C_6$ hydroxyalkyl), N—($C_1$-$C_6$ haloalkyl), N—($C_1$-6 alkylene-cycloalkyl), NH(C═O), N—($C_{1-6}$ alkyl) (C═O), or (C═O). In another embodiment, Y is $C_3$-$C_8$ alkylene optionally substituted with OH, $NH_2$, halo, $C_1$-$C_6$ alkyl, or $C_1$-$C_6$ alkoxy, wherein up to two one methylene units of the $C_3$-$C_8$ alkylene are optionally and independently replaced by O, NH, N—($C_1$-$C_6$ alkyl), N—($C_1$-$C_6$ hydroxyalkyl), N—($C_1$-$C_6$ haloalkyl), N—($C_1$-6 alkylene-$C_{3-8}$ cycloalkyl), or (C═O).

In another embodiment, Y is the $C_3$-$C_8$ alkylene, which is

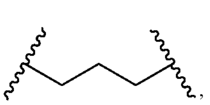 , 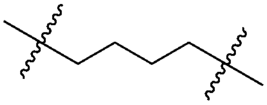 ,

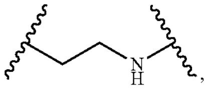 , 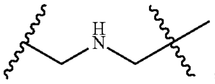 ,

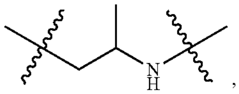 , 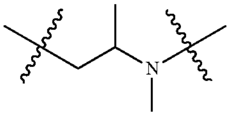 ,

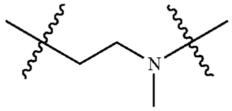 , 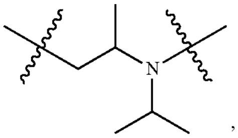 ,

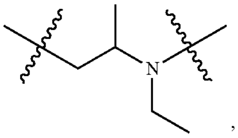 , 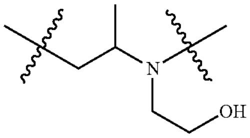 ,

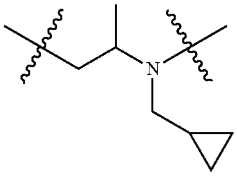 , 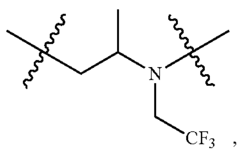 ,

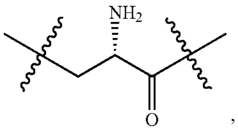 , 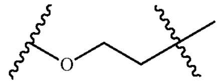 ,

-continued
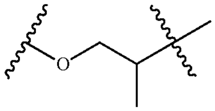,
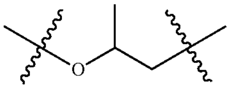, or
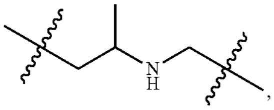,
In another embodiment, Y is selected from any moieties provided in Table 4:
TABLE 4
$CH_2$,
$CH(CH_3)$,
CH(COOEt) CH(COOH),
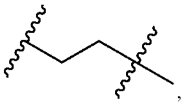 [SMILES: *CC*],
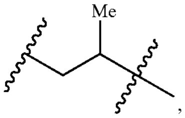 [SMILES: *CC(*)C],
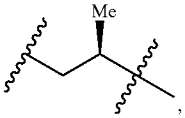 [SMILES: *C[C@H](*)C],
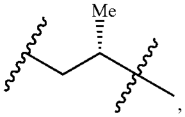,
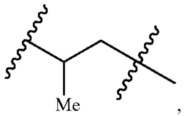 [SMILES: *CC(*)C],
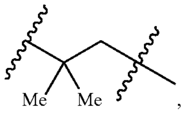 [SMILES: *CC(*)(C)C],
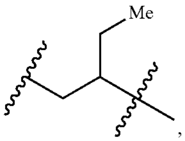 [SMILES: *CC(*)CC],
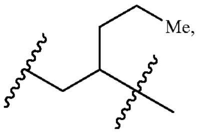 [SMILES: *CC(*)CCC]
TABLE 4-continued
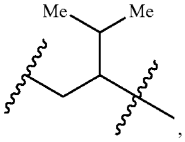 [SMILES: *CC(*)C(C)C],
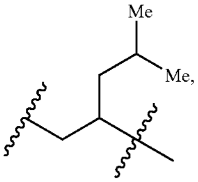 [SMILES: *CC(*)CC(C)C]
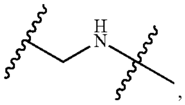 [SMILES: *CN*],
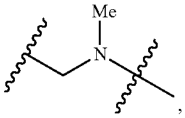 [SMILES: *CN(*)C],
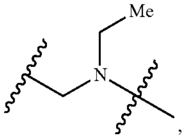 [SMILES: *CN(*)CC],
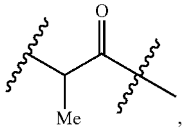 [SMILES: *C(=O)C(*)C],
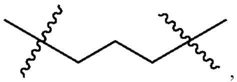,
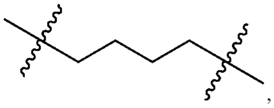 [SMILES: *CCCC*],
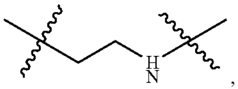 [SMILES: *CCN*],
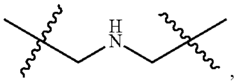 [SMILES: *CNC*],
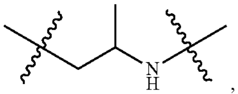,
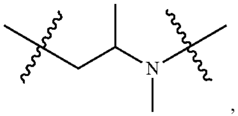 [SMILES: *CC(C)N(*)C], TABLE 4-continued

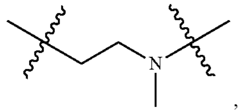 [SMILES: *CCN(*)C],

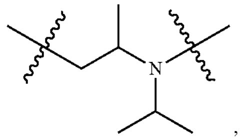 [SMILES: *CC(C)N(*)C(C)C],

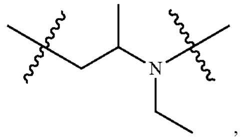 [SMILES: *CC(C)N(*)CC],

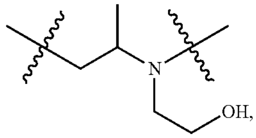 [SMILES: *CC(C)N(*)CCO],

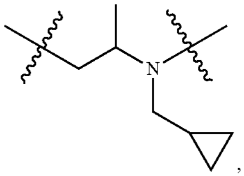 [SMILES: *CC(C)N(*)CC1CC1],

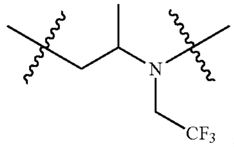,

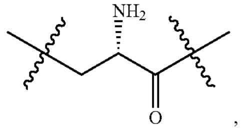 [SMILES: *C[C@H](N)C(*)=O],

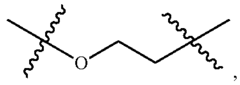 [SMILES: *CCO*],

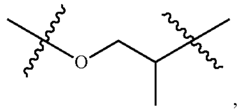 [SMILES: *OCC(*)C],

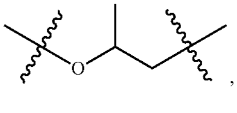, or

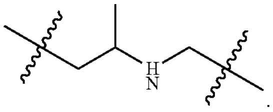 [SMILES: *CNC(C)C*].

In another embodiment of a compound of formula I or a pharmaceutically acceptable salt thereof, ring B is a bicyclic heterocycloalkylene optionally substituted with up to three substituents selected from the group consisting of $C_1$-$C_6$ alkyl, $C_1$-$C_6$ alkoxy, halo, $C_1$-$C_6$ haloalkyl, OH, and $C_1$-$C_6$ hydroxyalkyl.

In another embodiment, ring B is a 5 to 12 membered fused, spiro, or bridged bicyclic heterocycloalkylene containing up to 3 nitrogen atoms, wherein the fused, spiro, or bridged bicyclic heterocycloalkylene is optionally substituted with up to three substituents independently selected from the group consisting of $C_1$-$C_6$ alkyl, $C_1$-$C_6$ alkoxy, halo, $C_1$-$C_6$ haloalkyl, OH, and $C_1$-$C_6$ hydroxyalkyl.

In another embodiment, ring B is a 6 to 12 membered fused bicyclic heterocycloalkylene containing up to two nitrogen atoms, wherein the fused bicyclic heterocycloalkylene is optionally substituted with $C_1$-$C_6$ alkyl or $C_1$-$C_6$ hydroxyalkyl. In another embodiment, ring B is a 6 to 11 membered fused bicyclic heterocycloalkylene containing up to two nitrogen atoms, wherein the fused bicyclic heterocycloalkylene is optionally substituted with $C_1$-$C_6$ alkyl or $C_1$-$C_6$ hydroxyalkyl. In another embodiment, ring B is a 6 membered fused bicyclic heterocycloalkylene containing one nitrogen atom, wherein the 6 membered fused bicyclic heterocycloalkylene is optionally substituted with $C_1$-$C_6$ alkyl or $C_1$-$C_6$ hydroxyalkyl. In another embodiment, ring B is a 6 membered fused bicyclic heterocycloalkylene containing one nitrogen atom.

In another embodiment, ring B is a 6 to 12 membered spiro bicyclic heterocycloalkylene containing up to two nitrogen atoms. In another embodiment, ring B is a 6 to 11 membered spiro bicyclic heterocycloalkylene containing up to two nitrogen atoms.

In another embodiment, ring B is a 5 to 10 membered bridged bicyclic heterocycloalkylene containing up to two nitrogen atoms. In another embodiment, ring B is a 6 to 9 membered bridged bicyclic heterocycloalkylene containing up to two nitrogen atoms. In another embodiment, ring B is a 6 to 9 membered bridged bicyclic heterocycloalkylene containing one nitrogen atom. In another embodiment, ring B is a 8 membered bridged bicyclic heterocycloalkylene containing one nitrogen atom.

In another embodiment, ring B is a ring 5 to 12 membered bicyclic cycloalkylene optionally substituted with up to three substituents selected from the group consisting of $C_1$-$C_6$ alkyl, $C_1$-$C_6$ alkoxy, halo, $C_1$-$C_6$ haloalkyl, OH, and $C_1$-$C_6$ hydroxyalkyl.

In another embodiment, ring B is a 5 to 12 membered fused, spiro, or bridged bicyclic cycloalkylene optionally substituted with up to two substituents selected from the group consisting of $C_1$-$C_6$ alkyl, $C_1$-$C_6$ alkoxy, halo, $C_1$-$C_6$ haloalkyl, OH, and $C_1$-$C_6$ hydroxyalkyl.

In another embodiment, ring B is a 5 to 11 membered fused bicyclic cycloalkylene.

In another embodiment, ring B is a 6 to 11 membered spiro bicyclic cycloalkylene. In another embodiment, ring B is a 6 to 9 membered spiro bicyclic cycloalkylene. In another embodiment, ring B is a 7 or 8 membered spiro bicyclic cycloalkylene.

In another embodiment, ring B is a 5 to 10 membered bridged bicyclic cycloalkylene.

In another embodiment, ring B is selected from any of the moieties provided in Table 5:
TABLE 5
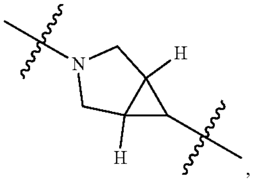 [SMILES: *C1C2CN(*)CC12]
,
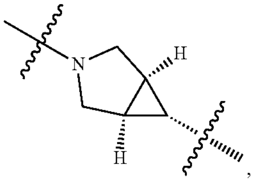
,
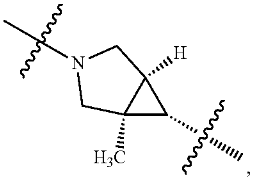
,
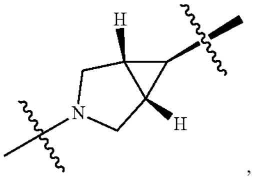
,
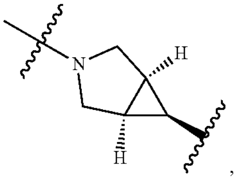 [SMILES: *[C@H]1[C@H]2CN(*)C[C@@H]12]
,
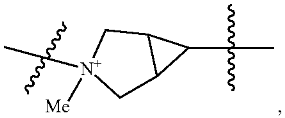 [SMILES: *C1C2C[N+](*)(C)CC12]
,
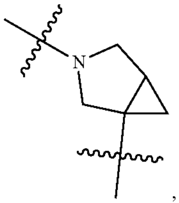 [SMILES: *N1CC2CC2(*)C1]
,
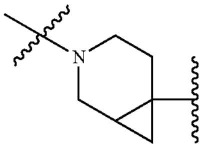
,
TABLE 5-continued
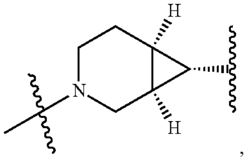 [SMILES: *[C@@H]1[C@H]2CN(*)CC[C@@H]12]
,
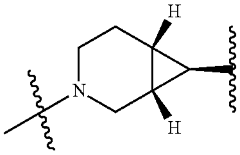
,
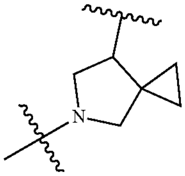
,
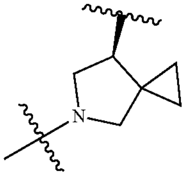
,
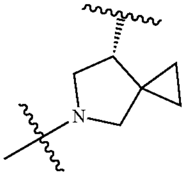
,
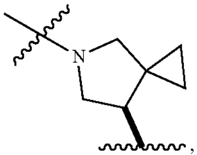 [SMILES: *[C@H]1CN(*)CC12CC2]
,
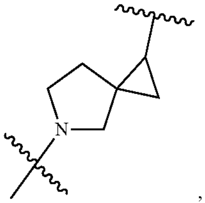 [SMILES: *C1CC12CCN(*)C2]
,
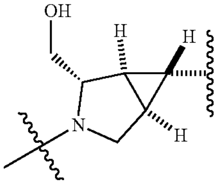
, TABLE 5-continued
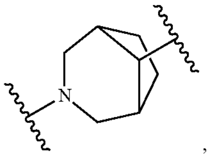 [SMILES: *C1C2CCC1CN(*)C2]
,
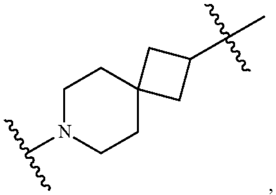 [SMILES: *C1CC2(CCN(*)CC2)C1]
,
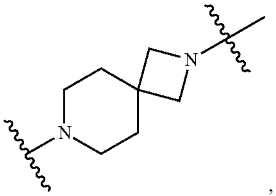 [SMILES: *N1CCC2(CC1)CN(*)C2]
,
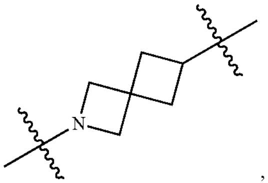 [SMILES: *C1CC2(C1)CN(*)C2]
,
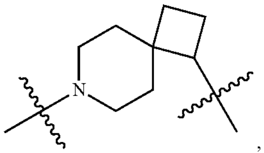 [SMILES: *C1CCC12CCN(*)CC2]
,
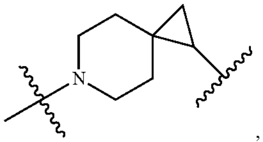 [SMILES: *C1CC12CCN(*)CC2]
,
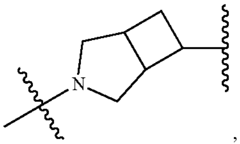 [SMILES: *C1CC2CN(*)CC12]
,
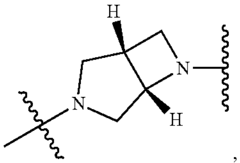 [SMILES: *N1C[C@@H]2CN(*)[C@@H]2C1]
,
TABLE 5-continued
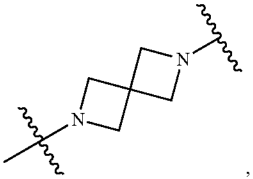 [SMILES: *N1CC2(C1)CN(*)C2]
,
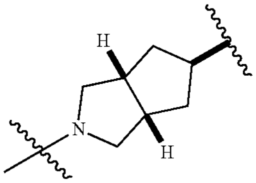
,
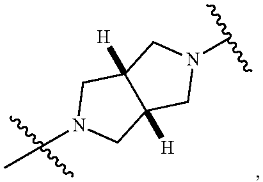 [SMILES: *N1C[C@H]2CN(*)C[C@H]2C1]
,
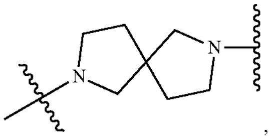 [SMILES: *N1CCC2(CCN(*)C2)C1]
,
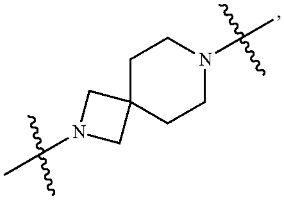
,
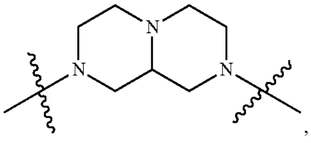 [SMILES: *N1CCN2CCN(*)CC2C1]
,
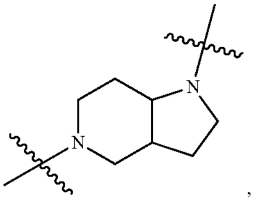 [SMILES: *N1CCC2C(CCN2*)C1]
,
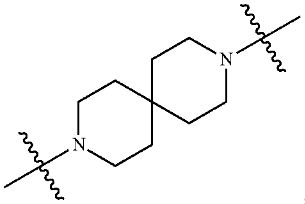
, TABLE 5-continued

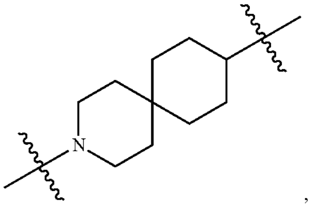 [SMILES: *C1CCC2(CC1)CCN(*)CC2],

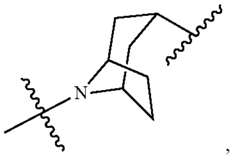 [SMILES: *C1CC2CCC(C1)N2*],

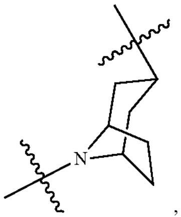 [SMILES: *C1CC2CCC(C1)N2*],

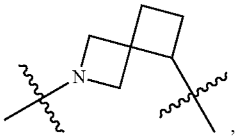 [SMILES: *C1CCC12CN(*)C2],

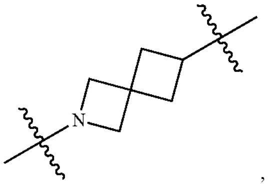 [SMILES: *C1CC2(C1)CN(*)C2],

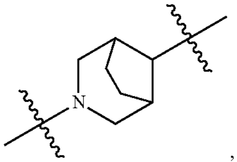 [SMILES: *C1C2CCC1CN(*)C2],

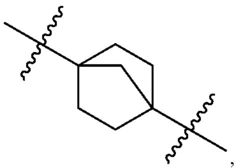 [SMILES: *C12CCC(*)(CC1)C2],

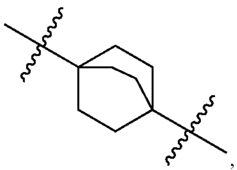 [SMILES: *C12CCC(*)(CC1)CC2],

TABLE 5-continued

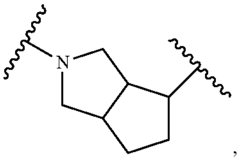 [SMILES: *C1CCC2CN(*)CC12],

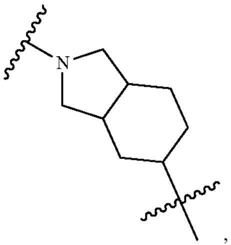 [SMILES: *C1CCC2CN(*)CC2C1],

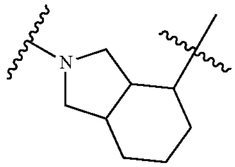,

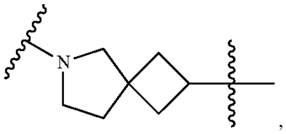, or

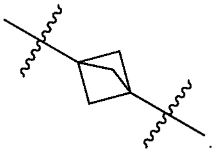 [SMILES: *C12CC(*)(C1)C2].

In another embodiment of a compound of formula I or a pharmaceutically acceptable salt thereof, L is absent.

In another embodiment of a compound of formula I or a pharmaceutically acceptable salt thereof, L is a linear or branched $C_1$-$C_6$ alkylene optionally substituted with $C_1$-$C_6$ alkoxy, halo, CN, OH, $NH_2COO(C_1$-$C_6$ alkyl), or $CONH_2$ wherein one methylene unit of the $C_1$-$C_6$ alkylene may be replaced with O, NH, (C═O), or N—($C_{1-6}$ alkyl). In another embodiment, L is a linear or branched $C_1$-$C_6$ alkylene optionally substituted with OH or $NH_2$, wherein one methylene unit of the $C_1$-$C_6$ alkylene may be replaced with (C═O). In another embodiment, L is a linear or branched $C_1$-$C_4$ alkylene optionally substituted with OH or $NH_2$, wherein one methylene unit of the $C_1$-$C_4$ alkylene may be replaced with (C═O). In another embodiment, L is $C_1$-$C_4$ alkylene or (C═O)

In another embodiment, L is absent or is $CH_2$.

In another embodiment of a compound of formula I or a pharmaceutically acceptable salt thereof, $R_1$ is H or $NR_{x'}R_{y'}$, wherein $R_{x'}$ and $R_{y'}$ are each independently H, $C_1$-$C_6$ alkyl, $C_1$-$C_6$ alkyl-$SO_3CO(C_1$-$C_6$ alkyl), or an amino protecting group. In another embodiment, $R_1$ is H, $NH_2NH(C_1$-$C_6$ alkyl), $NHCO(C_1$-$C_6$ alkyl), or $NH(C_1$-$C_6$ alkyl-$SO_3$). In another embodiment, $R_1$ is H, $NH_2$ or $NH(C_1$-$C_6$ alkyl). In another embodiment, $R_1$ is H, $NH_2$ or $NHCH_3$. In another embodiment, $R_1$ is H or $NH_2$.

In another embodiment of a compound of formula I or a pharmaceutically acceptable salt thereof, Y is any one of the moieties provided in Table 4; ring B is any one of the moieties provided in Table 5L is a linear or branched $C_1$-$C_4$ alkylene optionally substituted with OH or $NH_2$ wherein one methylene unit of the C alkylene may be replaced with (C═O); and $R_1$ is H, $NH_2$ or NH($C_1$-$C_6$ alkyl). In another embodiment, Y is any one of the moieties provided in Table 4; ring B is selected from any of the moieties provided in Table 5L is absent or is $CH_2$, and $R_1$ is H or $NH_2$.

In another embodiment of a compound of formula I or a pharmaceutically acceptable salt thereof,

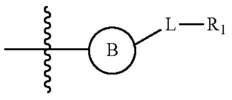

is selected from any moieties provided in Table 6:

TABLE 6

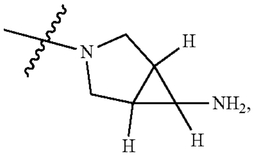 [SMILES: *N1CC2C(N)C2C1]

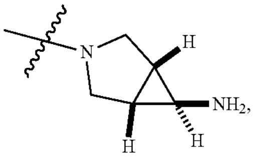 [SMILES: *N1C[C@@H]2[C@@H](N)[C@@H]2C1]

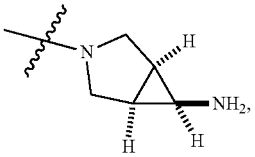 [SMILES: *N1C[C@@H]2[C@H](N)[C@@H]2C1]

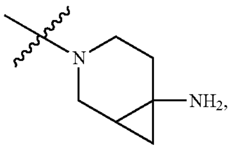 [SMILES: *N1CCC2(N)CC2C1]

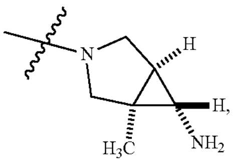

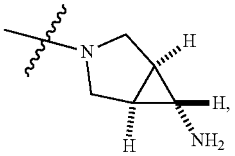

TABLE 6-continued

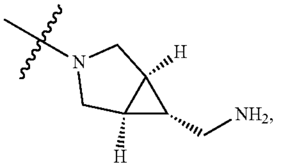 [SMILES: *N1C[C@@H]2[C@@H](CN)[C@@H]2C1]

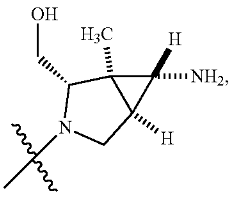 [SMILES: *N1C[C@@H]2[C@@H](N)[C@]2(C)[C@H]1CO]

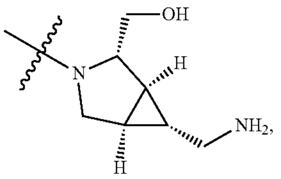 [SMILES: *N1C[C@@H]2[C@@H](CN)[C@@H]2[C@H]1CO]

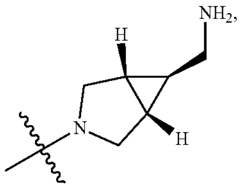 [SMILES: *N1C[C@@H]2[C@@H](CN)[C@@H]2C1]

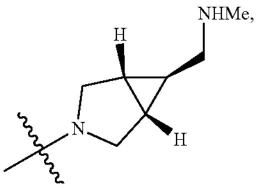 [SMILES: *N1C[C@@H]2[C@@H](CNC)[C@@H]2C1]

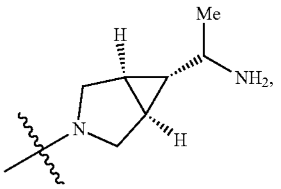 [SMILES: *N1C[C@@H]2[C@H](C1)[C@H]2C(C)N]

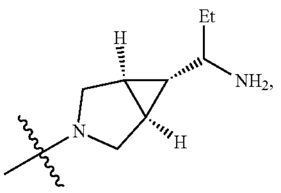 [SMILES: *N1C[C@@H]2[C@H](C1)[C@H]2C(N)CC]

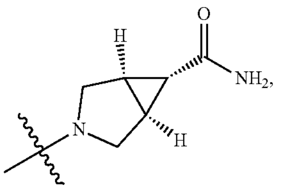 [SMILES: *N1C[C@@H]2[C@H](C1)[C@H]2C(N)=O]

TABLE 6-continued
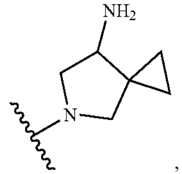 [SMILES: *N1CC(N)C2(CC2)C1]
,
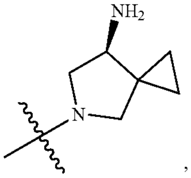 [SMILES: *N1C[C@@H](N)C2(CC2)C1]
,
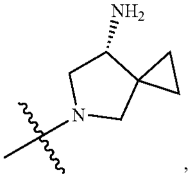 [SMILES: *N1C[C@H](N)C2(CC2)C1]
,
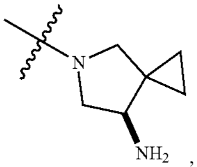 [SMILES: *N1C[C@H](N)C2(CC2)C1]
,
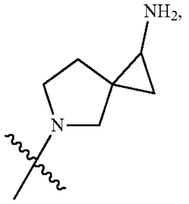 [SMILES: *N1CCC2(CC2N)C1]
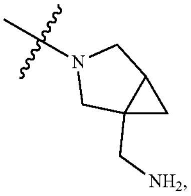 [SMILES: *N1CC2CC2(CN)C1]
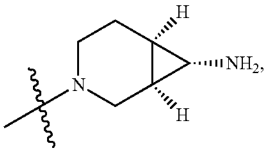 [SMILES: *N1CC[C@H]2[C@H](N)[C@H]2C1]
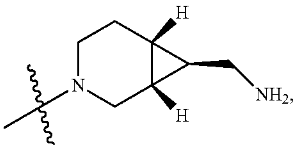 [SMILES: *N1CC[C@@H]2[C@@H](CN)[C@@H]2C1]
TABLE 6-continued
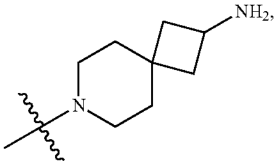 [SMILES: *N1CCC2(CC1)CC(N)C2]
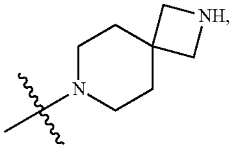 [SMILES: *N1CCC2(CC1)CNC2]
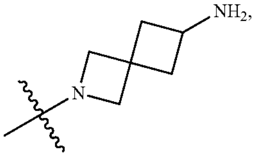 [SMILES: *N1CC2(CC(N)C2)C1]
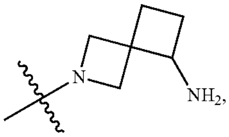 [SMILES: *N1CC2(CCC2N)C1]
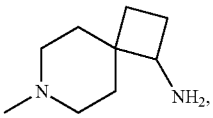
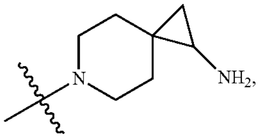 [SMILES: *N1CCC2(CC1)CC2N]
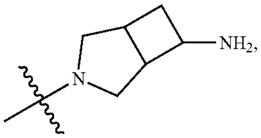 [SMILES: *N1CC2CC(N)C2C1]
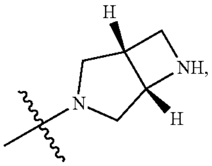 [SMILES: *N1C[C@@H]2CN[C@@H]2C1]
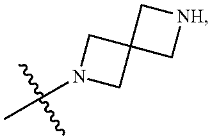 [SMILES: *N1CC2(CNC2)C1]
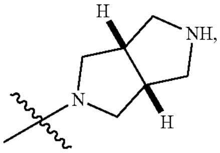 [SMILES: *N1C[C@H]2CNC[C@H]2C1]

TABLE 6-continued
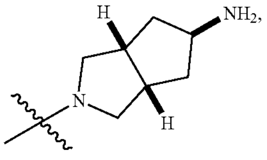 [SMILES: *N1C[C@H]2C[C@H](N)C[C@H]2C1]
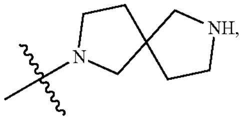 [SMILES: *N1CCC2(CCNC2)C1]
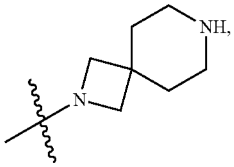 [SMILES: *N1CC2(CCNCC2)C1]
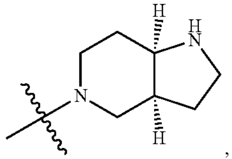 [SMILES: *N1CC[C@H]2NCC[C@H]2C1]
,
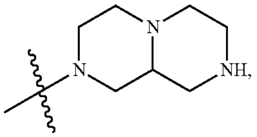 [SMILES: *N1CCN2CCNCC2C1]
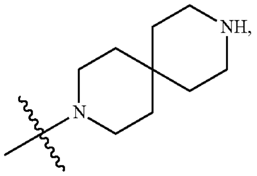 [SMILES: *N1CCC2(CCNCC2)CC1]
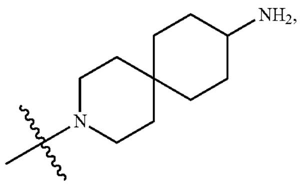 [SMILES: *N1CCC2(CCC(N)CC2)CC1]
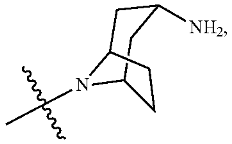 [SMILES: *N1C2CCC1CC(N)C2]
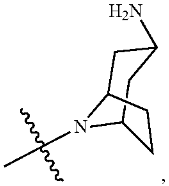 [SMILES: *N1C2CCC1CC(N)C2]
,
TABLE 6-continued
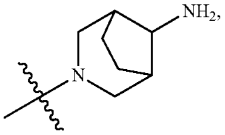 [SMILES: *N1CC2CCC(C1)C2N]
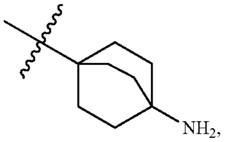 [SMILES: *C12CCC(N)(CC1)CC2]
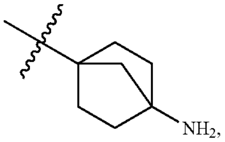 [SMILES: *C12CCC(N)(CC1)C2]
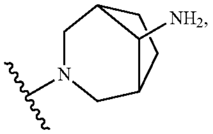 [SMILES: *N1CC2CCC(C1)C2N]
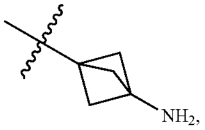
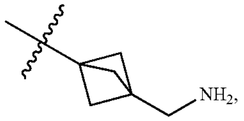 [SMILES: *C12CC(CN)(C1)C2]
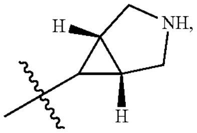 [SMILES: *C1[C@H]2CNC[C@@H]12]
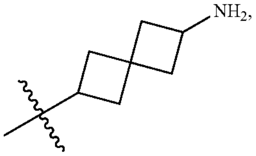 [SMILES: *C1CC2(C1)CC(N)C2]
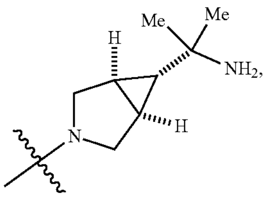 [SMILES: *N1C[C@@H]2[C@H](C1)[C@H]2C(C)(C)N]
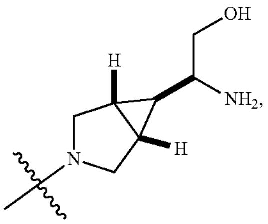 [SMILES: *N1C[C@@H]2[C@H](C1)[C@H]2C(N)CO]

TABLE 6-continued

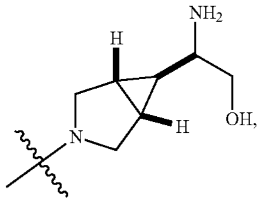 [SMILES: *N1C[C@@H]2[C@H](C1)[C@H]2C(N)CO]

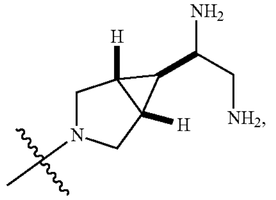 [SMILES: *N1C[C@@H]2[C@H](C1)[C@H]2C(N)CN]

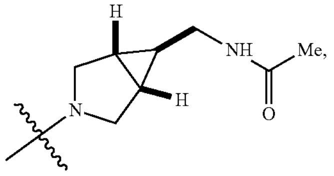 [SMILES: *N1C[C@@H]2[C@@H](CNC(C)=O)[C@@H]2C1]

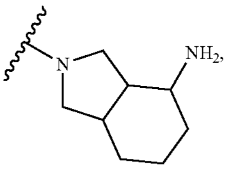 [SMILES: *N1CC2CCCC(N)C2C1]

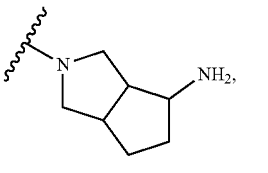 [SMILES: *N1CC2CCC(N)C2C1]

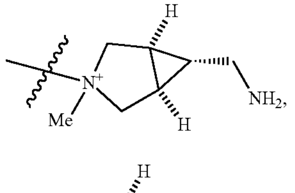

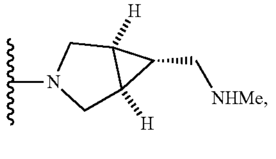 [SMILES: *N1C[C@@H]2[C@@H](CNC)[C@@H]2C1]

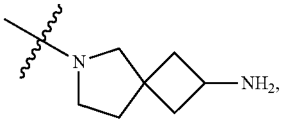 [SMILES: *N1CCC2(CC(N)C2)C1]

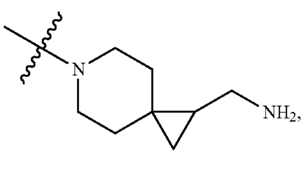 [SMILES: *N1CCC2(CC1)CC2CN]

TABLE 6-continued

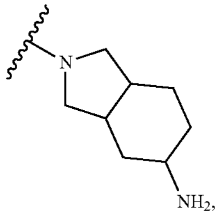

or

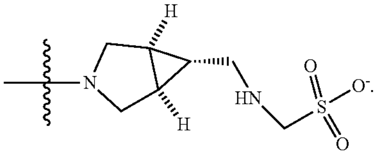

In another embodiment of a compound of formula I or a pharmaceutically acceptable salt thereof, each $R_2$ and $R_3$ is independently selected from the group consisting of $C_1$-$C_6$ alkyl, halo, $C_1$-$C_6$ haloalkyl, $O(C_1$-$C_6$ haloalkyl), and $C_1$-$C_6$ alkoxy, and m and n are each independently 0, 1 or 2. In another embodiment, $R_2$ and $R_3$ are each independently selected from the group consisting of $C_1$-$C_6$ alkyl, halo, $C_1$-$C_6$ haloalkyl. In another embodiment, each $R_3$ is independently $C_1$-$C_6$ alkyl, halo, or $C_1$-$C_6$ haloalkyl, and m is 0, 1 or 2.

In another embodiment, $R_2$ and $R_3$ are each independently selected from the group consisting of $C_1$-$C_6$ alkyl, halo, $C_1$-$C_6$ haloalkyl, and m and n are each independently 0 or 1.

In another embodiment of a compound of formula I or a pharmaceutically acceptable salt thereof, n is 0, m is 0, 1 or 2, and each $R_3$ is independently selected from the group consisting $CH_3C_1F$, $OCH_3$, and $CF_3$.

In another embodiment, m and n are each independently 0, 1 or 2. In another embodiment, n is 0 and m is 1 or 2. In another embodiment, m and n are 0.

In another embodiment, the compound of formula I is a compound of formula I-1:

I-1

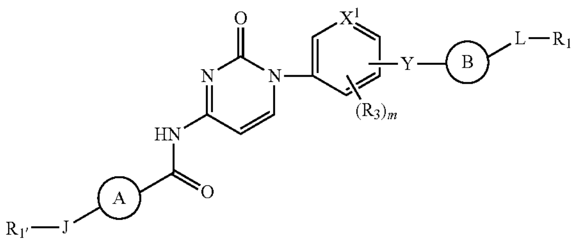

or a pharmaceutically acceptable salt thereof, wherein ring A, ring B, J, L, Y, $R_1$, $R_{1'}$, $R_3$, $X^1$, and m are the same as defined herein.

In another embodiment, the compound of formula I or I-1 is a compound of formula I-2:

I-2

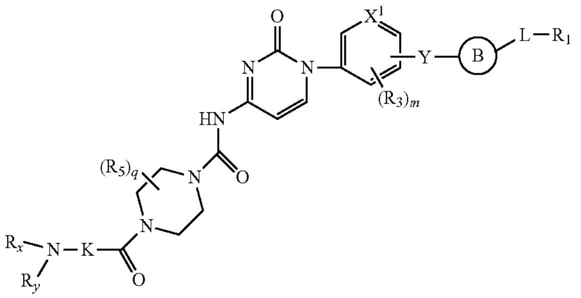

or a pharmaceutically acceptable salt thereof, wherein ring B, L, Y, $R_1R_3$, $R_x$, $R_yX^1$, and m are the same as defined herein; K is $C_1$-$C_5$ alkylene, 4 to 7 membered heterocycloalkylene, or 4 to 6 membered cycloalkylene, any of which may be optionally substituted with halo, $C_1$-$C_6$ alkyl, $C_1$-$C_6$ alkoxy, $C_1$-$C_6$ haloalkyl, $NH_2CN$, or OH, wherein one methylene unit of the $C_1$-$C_5$ alkylene is optionally replaced with

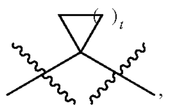

wherein t is 1, 2, 3 or 4, each $R_5$ is independently $C_1$-$C_6$ alkyl, $C_1$-$C_6$ alkoxy, halo, CN, $C_1$-$C_6$ haloalkyl, phenyl, OH, $NH_2$ or oxo; and q is 0, 1, 2 or 3.

In another embodiment of a compound of formula I-2 or a pharmaceutically acceptable salt thereof, K is $C_1$-$C_5$ alkylene optionally substituted with $C_1$-$C_6$ haloalkyl, $NH_2$, or OH, wherein one methylene unit of the $C_1$-$C_8$ alkylene is optionally replaced with

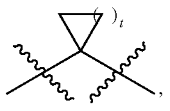

wherein t is 1 or 2, each $R_5$ is independently $C_1$-$C_6$ alkyl, phenyl, or oxo; and q is 0, 1 or 2.

In another embodiment, the compound of formula I, I-1 or I-2 is a compound of formula I-3:

I-3

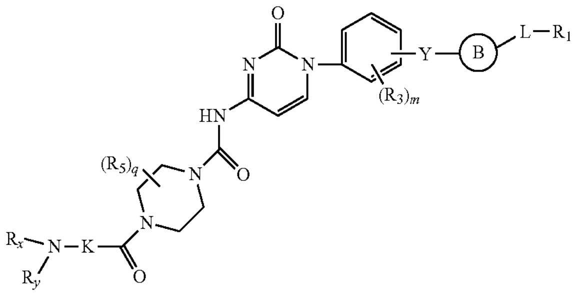

or a pharmaceutically acceptable salt thereof, wherein ring B, L, Y, K, $R_1$, $R_3$, $R_5$, $R_x$, $R_y$, q, and m are the same as defined herein.

In another embodiment of a compound of formula I-3 or a pharmaceutically acceptable salt thereof, K is $C_1$-$C_5$ alkylene optionally substituted with halo, $C_1$-$C_6$ alkoxy, $C_1$-$C_6$ haloalkyl, $NH_2$ or OH; each $R_5$ is independently $C_1$-$C_6$ alkyl, $C_1$-$C_6$ alkoxy, halo, CN, $C_1$-$C_6$ haloalkyl, phenyl, or oxo; q is 0 or 1, each $R_3$ is independently $C_1$-$C_6$ alkyl, halo, $C_1$-$C_6$ haloalkyl, and $C_1$-$C_6$ alkoxy; and m is 0, 1 or 2. In another embodiment, K is $C_1$-$C_4$ alkylene optionally substituted with $C_1$-$C_6$ haloalkyl, $NH_2$ or OH; each $R_5$ is independently $C_1$-$C_6$ alkyl, phenyl, or oxo; q is 0 or 1, each $R_3$ is independently $C_1$-$C_6$ alkyl, halo, $C_1$-$C_6$ haloalkyl, and $C_1$-$C_6$ alkoxy; and m is 0, 1 or 2.

In another embodiment, the compound of formula I, I-1, 1-2 or 1-3 is a compound of formula I-4:

I-4

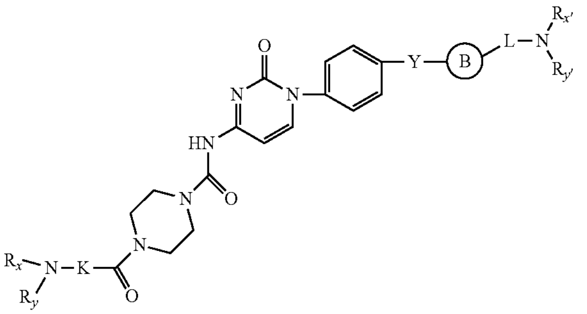

or a pharmaceutically acceptable salt thereof, wherein ring B, L, Y, K, $R_x$, $R_y$, $R_{x'}$ and $R_{y'}$ are the same as defined herein.

In another embodiment, the compound of formula I, I-1, 1-2, 1-3 or 1-4 is a compound of formula I-5:

I-5

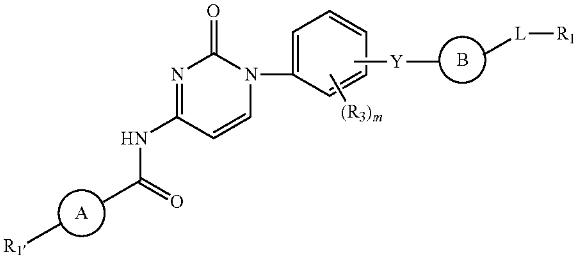

or a pharmaceutically acceptable salt thereof, wherein ring A, ring B, L, Y, $R_1$, $R_3$, and m are the same as defined herein; and $R_{1'}$ is H or $NH_2$.

In another aspect, the disclosure provides a compound of Formula IIA:

IIA

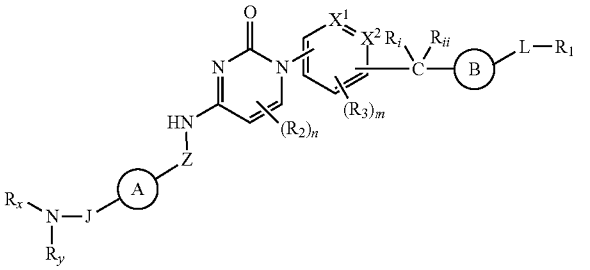

or a pharmaceutically acceptable salt thereof, wherein:

Z is —(C═O)—;

ring A is a monocyclic heterocycloalkylene or bicyclic heterocycloalkylene, wherein the monocyclic heterocycloalkylene and bicyclic heterocycloalkylene are optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2NH(C_1$-$C_6$ alkyl), $N(C_1$-$C_6$ alkyl$)_2$, —COO($C_1$-$C_6$ alkyl), —$COONH_2$, and oxo;

J is $C_1$-$C_6$ alkylene, heterocycloalkylene, $C_1$-$C_6$ alkylene-heterocycloalkylene or $C_1$-$C_6$ alkylene-cycloalkylene, any of which may be optionally substituted with halo, $C_1$-$C_6$ alkoxy, $C_1$-$C_6$ haloalkyl, $NH_2CN$, or OH, and wherein one or two carbons of the optionally substituted $C_1$-$C_6$ alkylene may optionally be replaced with O, S, $SO_2C$═O, or

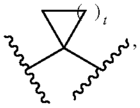, wherein t is 1, 2, 3, 4, 5 or 6;

$R_x$ and $R_y$ are each independently H or $C_1$-$C_6$ alkyl;

$X^1$ and $X^2$ are each independently C—H or N;

$R_i$ and $R_{ii}$ are each independently H, OH, $NH_2CN$, halo, $C_1$-$C_6$ alkyl, $C_1$-$C_6$ haloalkyl, COO($C_1$-$C_6$ alkyl), COOH, $CONH_2$ or $C_1$-$C_6$ alkoxy;

ring B is a bicyclic heterocycloalkylene or bicyclic cycloalkylene, wherein the bicyclic heterocycloalkylene and bicyclic cycloalkylene are optionally substituted with up to three substituents selected from the group consisting of $C_1$-$C_6$ alkyl, $C_1$-$C_6$ alkoxy, halo, CN, $C_1$-$C_6$ haloalkyl, OH, —COO($C_1$-$C_6$ alkyl), —$COONH_2$, and $C_1$-$C_6$ hydroxyalkyl;

L is absent, or is a linear or branched $C_1$-$C_6$ alkylene, wherein up to two carbon atoms of the $C_1$-$C_6$ alkylene may be replaced with O, NH, (C═O), NH(C═O), N—($C_{1-6}$ alkyl)(C═O), (C═NH), NH(C═N), or N—($C_{1-6}$ alkyl);

$R_1$ is H or $NR_{x'}R_{y'}$, wherein $R_{x'}$ and $R_{y'}$ are each independently H or $C_1$-$C_6$ alkyl;

$R_2$ and $R_3$ are each independently selected from the group consisting of $C_1$-$C_6$ alkyl, halo, CN, OH, $NH_2NH(C_1$-$C_6$ alkyl), $N(C_1$-$C_6$ alkyl$)_2$, —COO($C_1$-$C_6$ alkyl), —$COONH_2C_1$-$C_6$ haloalkyl, and $C_1$-$C_6$ alkoxy; and m and n are each independently 0, 1, 2 or 3.

In another embodiment of a compound of formula IIA or a pharmaceutically acceptable salt thereof, Z is —(C═O)—.

In another embodiment of a compound of formula I or IIA or a pharmaceutically acceptable salt thereof, ring A is a monocyclic heterocycloalkylene optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, and oxo.

In another embodiment, ring A is a bicyclic heterocycloalkylene optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, and oxo.

In another embodiment, ring A is

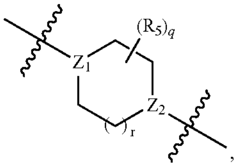, 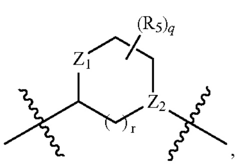, or

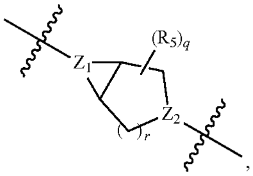, wherein $Z_1$ and $Z_2$ are each independently selected from the group consisting of CH, $CH_2N$, NH and O; each $R_5$ is independently selected from the group consisting of $C_1$-$C_6$ alkyl, $C_1$-$C_6$ alkoxy, halo, CN, $C_1$-$C_6$ haloalkyl, phenyl, OH, $NH_2$, and oxo, and q and r are each independently 0, 1, 2 or 3.

In another embodiment, ring A is selected from the group consisting of

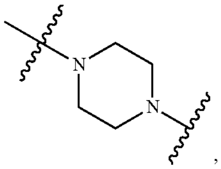, 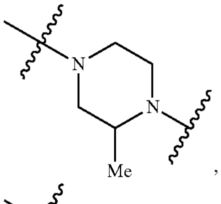,

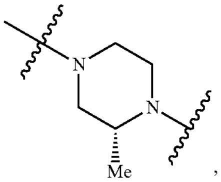, 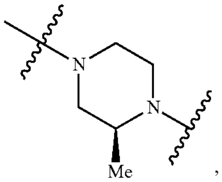,

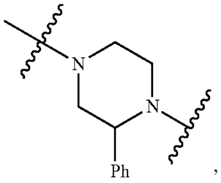, 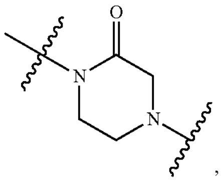,

-continued

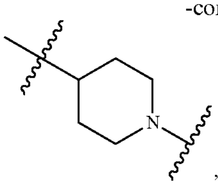 , 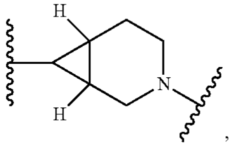 ,

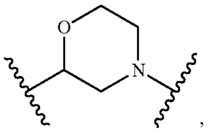 , and 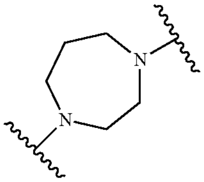 .

In another embodiment of a compound of formula I or IIA or a pharmaceutically acceptable salt thereof, J is $C_1$-$C_6$ alkylene.

In another embodiment, one of the $C_1$-$C_6$ alkylene carbons of J is —(C═O)—.

In another embodiment, J is optionally substituted with up to three substituents selected from the group consisting of halo, $C_1$-$C_6$ alkoxy, $C_1$-$C_6$ haloalkyl, —$NH_2$, and —OH, wherein up to two carbon atoms of the optionally substituted $C_1$-$C_6$ alkylene may be replaced by

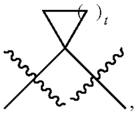 , wherein t is 1, 2, 3 or 4.

In another embodiment, J is a $C_1$-$C_6$ alkylene optionally substituted with F, $CF_3$—$NH_2$OMe or —OH, wherein one methylene unit of the optionally substituted $C_1$-$C_6$ alkylene may be replaced by

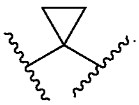 [SMILES: *C1(*)CC1] .

In another embodiment, J is selected from the group consisting of —$CH_2$—,

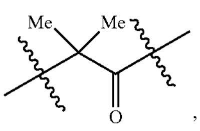 , 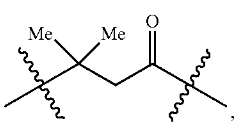 ,

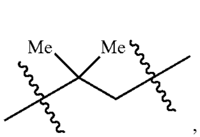 , 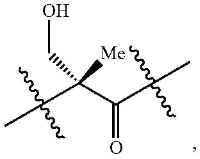 ,

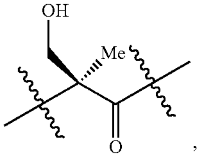 , 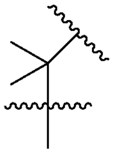 ,

-continued

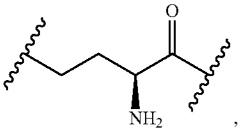 , 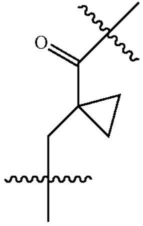 ,

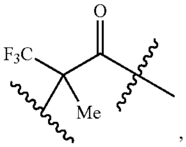 , 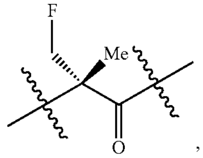 ,

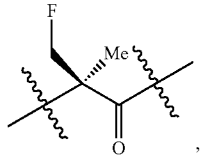 , 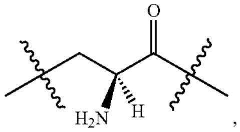 ,

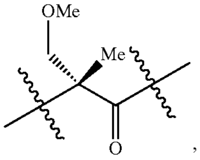 , 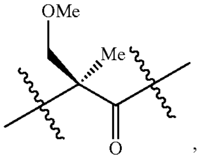 ,

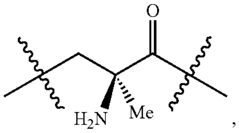 , and 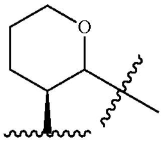 .

In another embodiment of a compound of formula I or IIA or a pharmaceutically acceptable salt thereof, $R_x$ and $R_y$ are each independently H or $C_1$-$C_6$ alkyl.

In another embodiment, $R_x$ and $R_y$ are each independently H.

In another embodiment of a compound of formula IIA or a pharmaceutically acceptable salt thereof, R—$R_y$N-J is selected from the group consisting of:

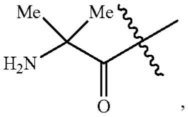 , 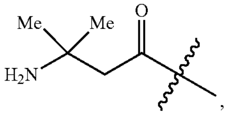 ,

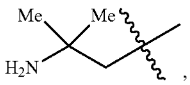 , 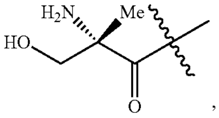 ,

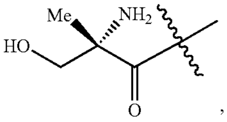 , 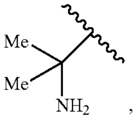 ,

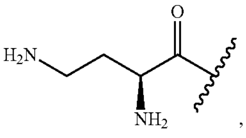 , 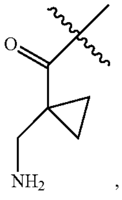 ,

-continued
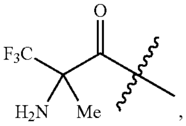
,
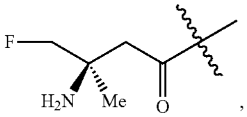
,
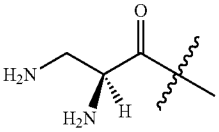
,
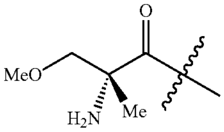
,
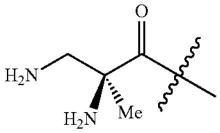
, and
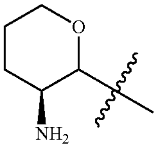
.
In another embodiment of a compound of formula I or IIA or a pharmaceutically acceptable salt thereof,
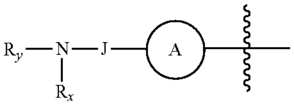
is selected from the group consisting of
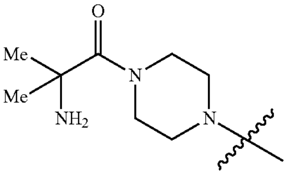
,
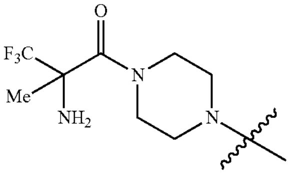
,
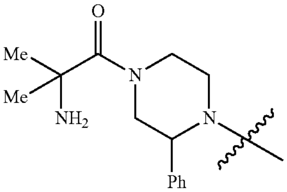
,
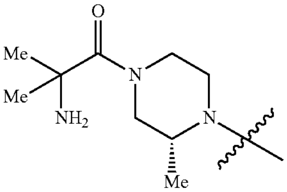
,
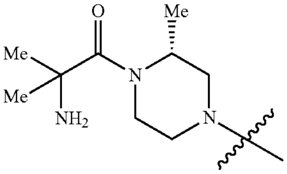
,
-continued
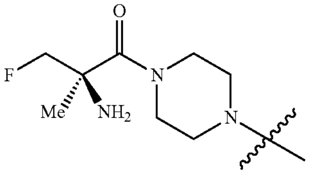
,
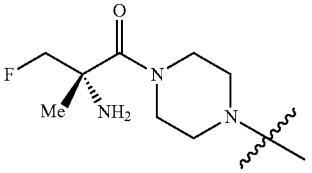
,
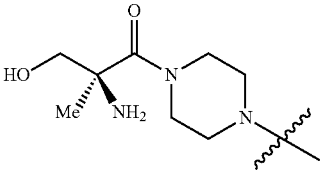
,
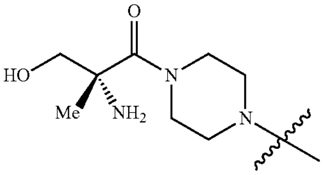
,
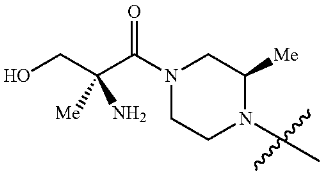
,
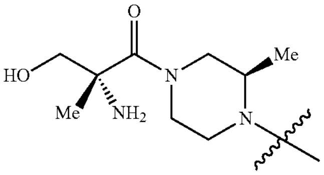
,
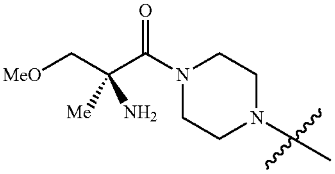
,
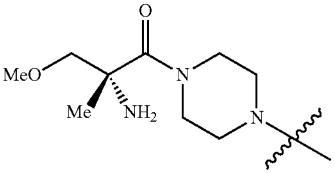
,
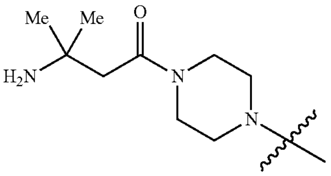
, -continued

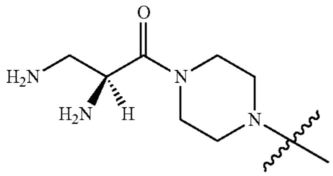

,

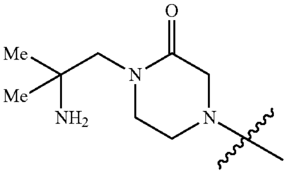

,

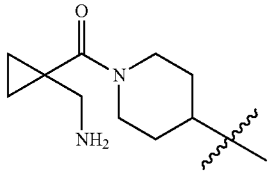

,

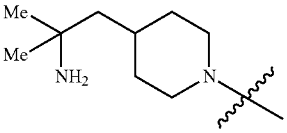

,

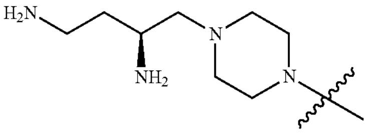

,

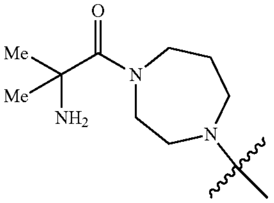

,

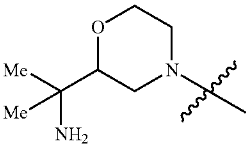

,

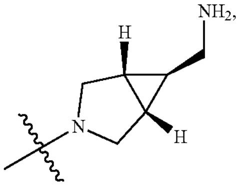

and

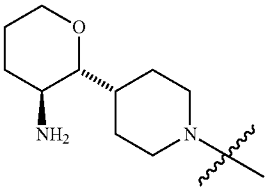

.

In another embodiment of a compound of formula I or IIA or a pharmaceutically acceptable salt thereof,

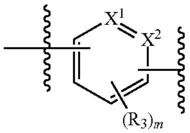

is

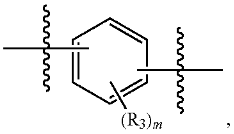

,

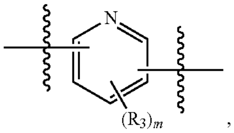

, or

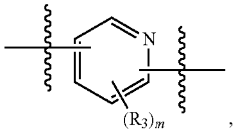

, wherein each $R_3$ is independently selected from the group consisting of $C_1$-$C_6$ alkyl, halo, $C_1$-$C_6$ haloalkyl, wherein m is 0, 1 or 2.

In another embodiment,

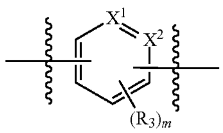

is

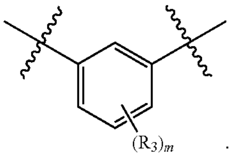

.

In another embodiment,

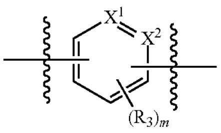

is

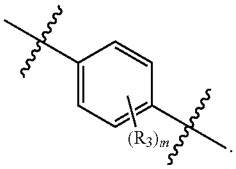

.

In another embodiment of a compound of formula IIA or a pharmaceutically acceptable salt thereof, each $R_3$ is independently selected from the group consisting of Me, halo, and $CF_3$ wherein m is 0, 1 or 2.

In another embodiment of a compound of formula I or IIA or a pharmaceutically acceptable salt thereof,

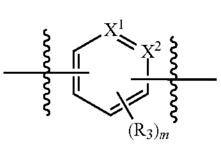

is

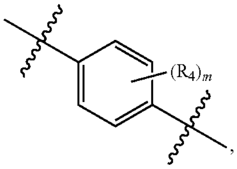

, wherein each $R_4$ is independently selected from the group consisting of $C_1$-$C_6$ alkyl, halo, $C_1$-$C_6$ haloalkyl, wherein m is 0, 1 or 2.

In another embodiment,

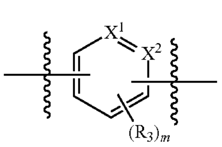

is

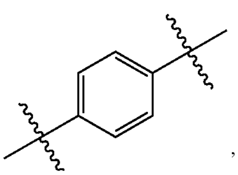

,

-continued

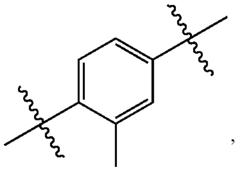
,
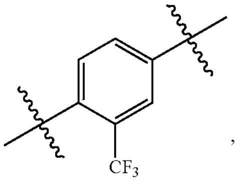
,
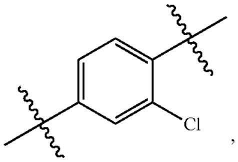
,
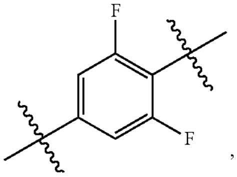
, or
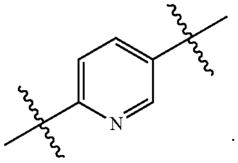
.

In another embodiment of a compound of formula I or IIA or a pharmaceutically acceptable salt thereof, CRR is selected from the group consisting of $CH_2CH(C_1\text{-}C_6$ alkyl), $C(C_1\text{-}C_6$ alkyl$)_2CH$—$COO(C_1\text{-}C_6$ alkyl) and CHCOOH.

In another embodiment, $CR_iR_{ii}$ is selected from the group consisting of $CH_2$, $CH(CH_3)$, CH(COOEt) and CH(COOH).

In another embodiment of a compound of formula I or IIA or a pharmaceutically acceptable salt thereof,

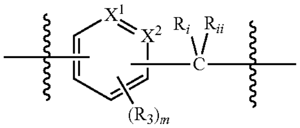

is selected from the group consisting of

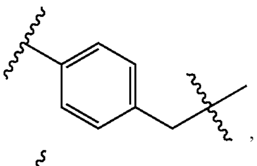
,
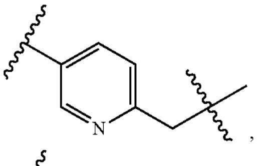
,
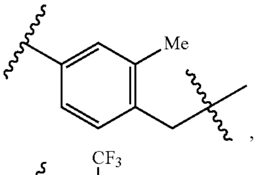
,
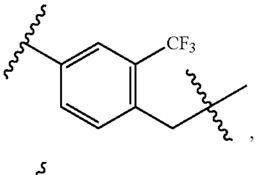
,
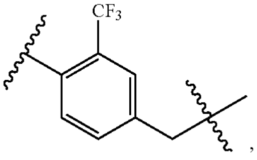
,
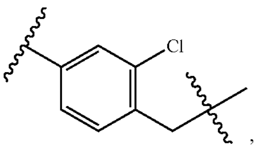
, -continued

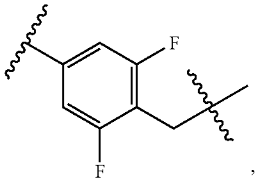
,
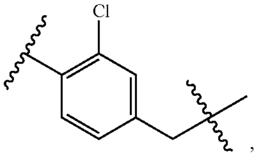
,
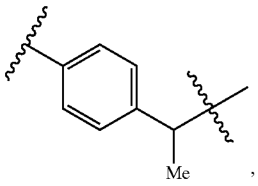
,
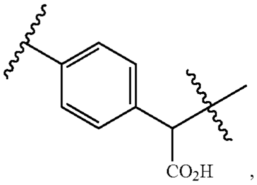
, and
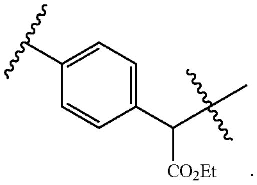
.

In another embodiment of a compound of formula I or IIA or a pharmaceutically acceptable salt thereof, ring B is a bicyclic heterocycloalkylene optionally substituted with up to three substituents selected from the group consisting of $C_1\text{-}C_6$ alkyl, $C_1\text{-}C_6$ alkoxy, halo, $C_1\text{-}C_6$ haloalkyl, OH, and $C_1\text{-}C_6$ hydroxyalkyl.

In another embodiment, ring B is a fused, spiro, or bridged bicyclic heterocycloalkylene containing up to 3 nitrogen atoms, wherein the fused, spiro, or bridged bicyclic heterocycloalkylene is optionally substituted with up to three substituents selected from the group consisting of $C_1\text{-}C_6$ alkyl, $C_1\text{-}C_6$ alkoxy, halo, $C_1\text{-}C_6$ haloalkyl, OH, and $C_1\text{-}C_6$ hydroxyalkyl.

In another embodiment, ring B is a fused bicyclic heterocycloalkylene containing up to two nitrogen atoms, wherein the fused bicyclic heterocycloalkylene is optionally substituted with $C_1\text{-}C_6$ alkyl or $C_1\text{-}C_6$ hydroxyalkyl.

In another embodiment, ring B is a spiro bicyclic heterocycloalkylene containing up to two nitrogen atoms.

In another embodiment, ring B is a bridged bicyclic heterocycloalkylene containing up to two nitrogen atoms.

In another embodiment, ring B is a bicyclic cycloalkylene optionally substituted with up to three substituents selected from the group consisting of $C_1\text{-}C_6$ alkyl, $C_1\text{-}C_6$ alkoxy, halo, $C_1\text{-}C_6$ haloalkyl, OH, and $C_1\text{-}C_6$ hydroxyalkyl.

In another embodiment, ring B is a fused, spiro, or bridged bicyclic cycloalkylene optionally substituted with up to two substituents selected from the group consisting of $C_1\text{-}C_6$ alkyl, $C_1\text{-}C_6$ alkoxy, halo, $C_1\text{-}C_6$ haloalkyl, OH, and $C_1\text{-}C_6$ hydroxyalkyl.

In another embodiment, ring B is a fused bicyclic cycloalkylene.

In another embodiment, ring B is a spiro bicyclic cycloalkylene.

In another embodiment, ring B is a bridged bicyclic cycloalkylene.

In another embodiment, ring B is selected from the group consisting of

-continued
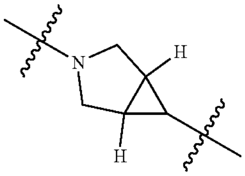
,
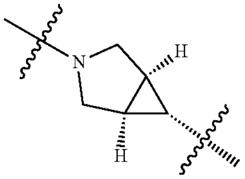
,
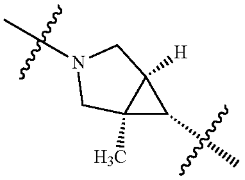
,
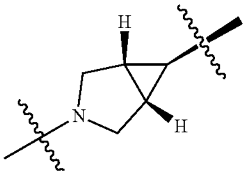
,
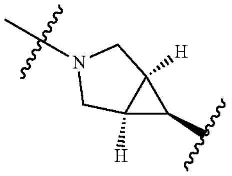
,
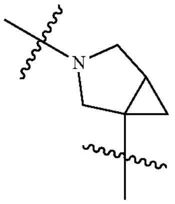
,
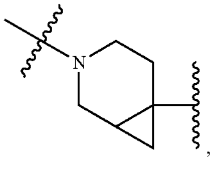
,
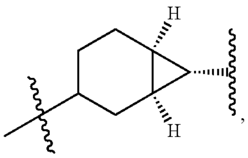
,
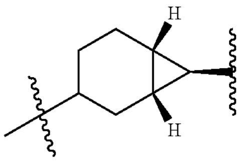
,
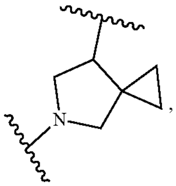
,
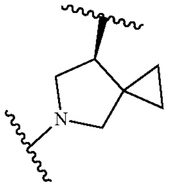
,
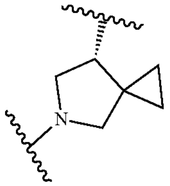
,
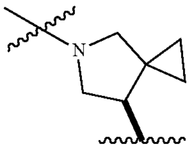
,
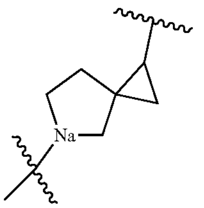
,
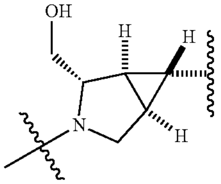
,
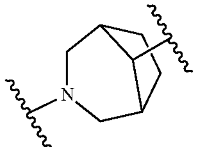
,
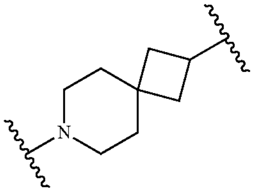
,
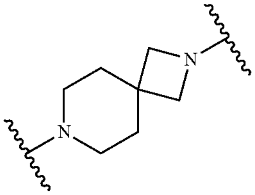
,
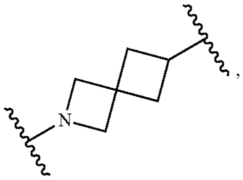
,
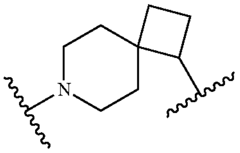
,
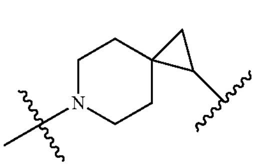
,
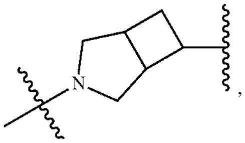
,
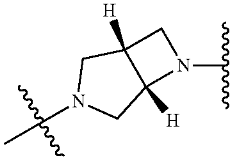
,
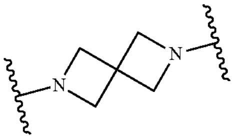
,
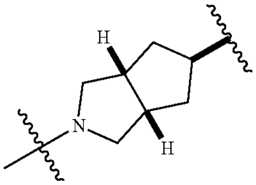
,
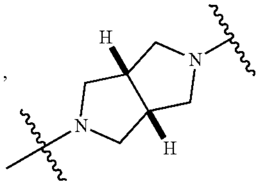
,
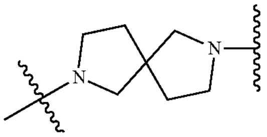
,
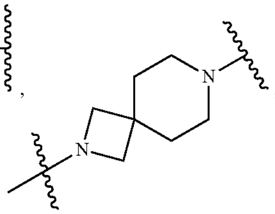
,
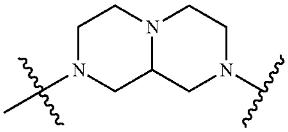
,
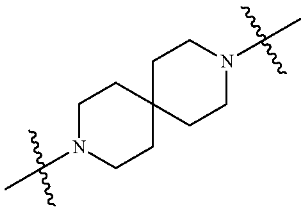
, -continued

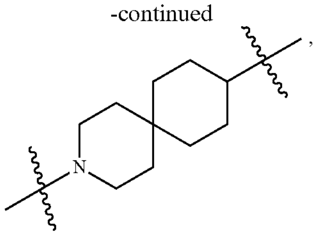

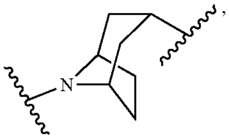

, and

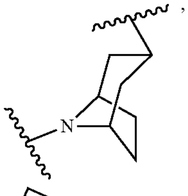

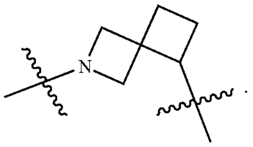

In another embodiment of a compound of formula I or IIA or a pharmaceutically acceptable salt thereof, L is absent.

In another embodiment, L is a linear or branched $C_1$-$C_6$ alkylene, wherein one carbon atom of the $C_1$-$C_6$ alkylene may be replaced with O, NH, (C═O), or N—($C_{1-6}$ alkyl).

In another embodiment, L is $CH_2CH(CH_3)$, or C═O.

In another embodiment of a compound of formula I or IIA or a pharmaceutically acceptable salt thereof, $R_1$ is H, $NH_2$ or NH($C_1$-$C_6$ alkyl).

In another embodiment, $R_1$ is H, $NH_2$ or $NHCH_3$.

In another embodiment of a compound of formula I or IIA or a pharmaceutically acceptable salt thereof,

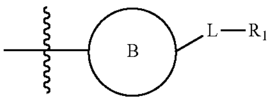

is selected from the group consisting of

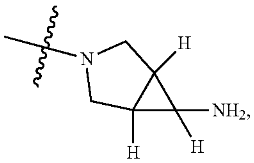

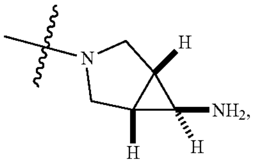

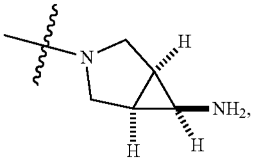

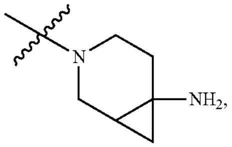

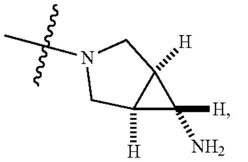

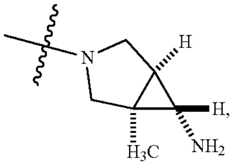

-continued

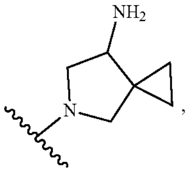

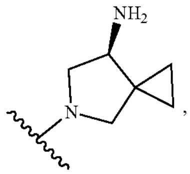

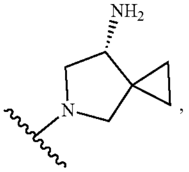

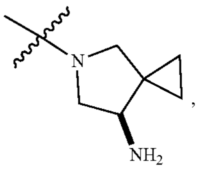

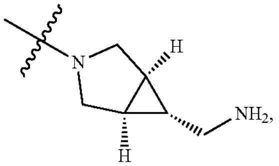

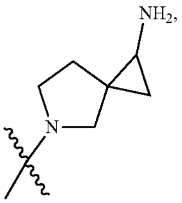

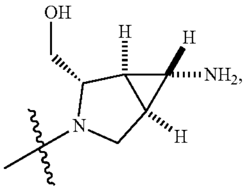

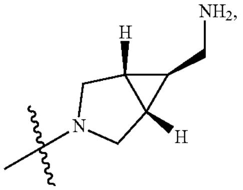

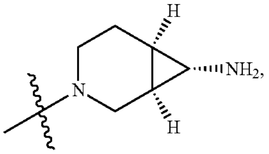

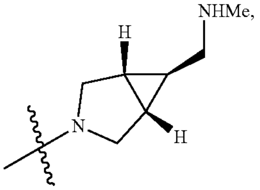

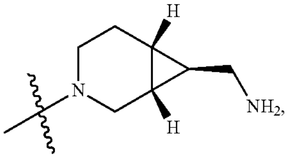

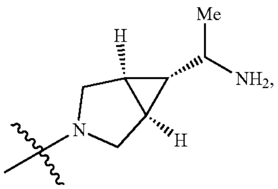

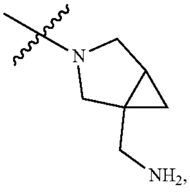

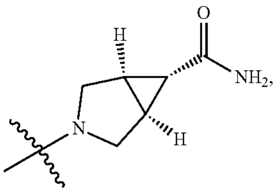

-continued

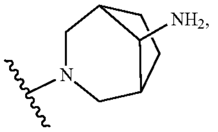

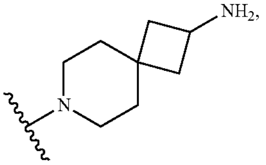

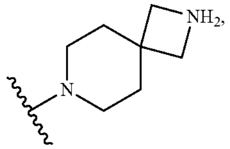

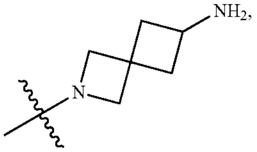

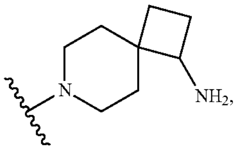

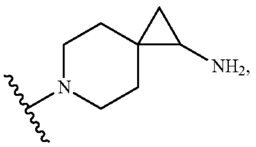

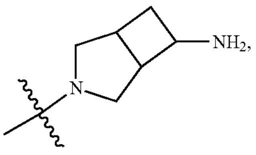

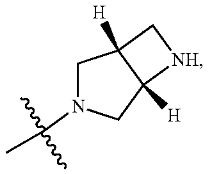

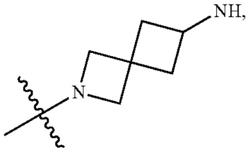

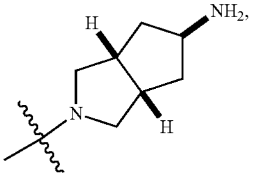

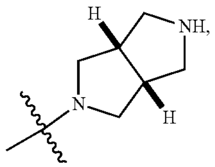

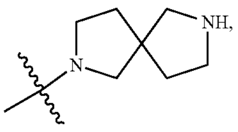

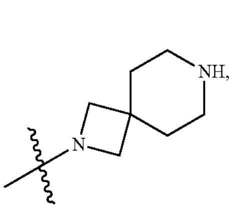

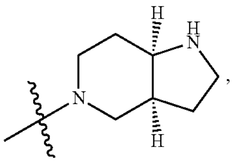

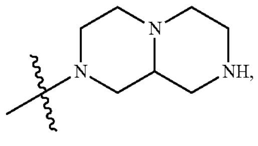

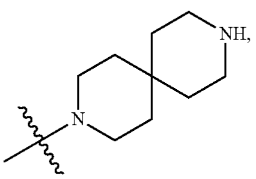

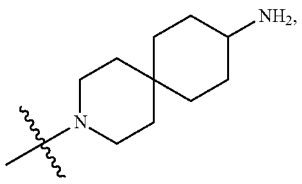

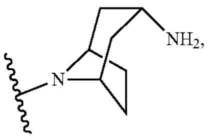

-continued

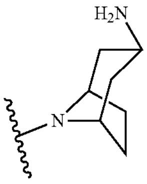

and

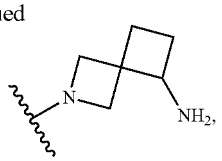

In another embodiment of a compound of formula I or IIA or a pharmaceutically acceptable salt thereof, $R_2$ and $R_3$ are each independently selected from the group consisting of $C_1$-$C_6$ alkyl, halo, $C_1$-$C_6$ haloalkyl, and $C_1$-$C_6$ alkoxy and m and n are each independently 0, 1 or 2.

In another embodiment, $R_2$ and $R_3$ are each independently selected from the group consisting of $C_1$-$C_6$ alkyl, halo, $C_1$-$C_6$ haloalkyl, and m and n are each independently 0 or 1.

In another embodiment of a compound of formula I or IIA or a pharmaceutically acceptable salt thereof, m is 1 or 2, and each $R_3$ is independently selected from the group consisting $CH_3C_1F$, $OCH_3CO_2H$, $CO_2Et$, and $CF_3$.

In another embodiment, the compound of formula I or IIA is a compound of formula IIA-1:

(IIA-1)

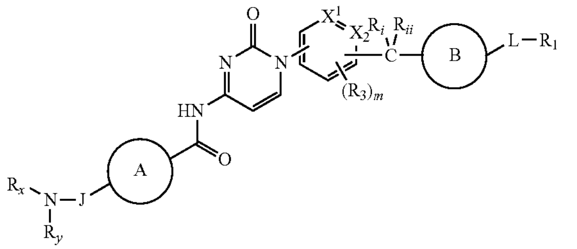

or a pharmaceutically acceptable salt thereof, wherein ring A, ring B, L, J, $X^1$, $X^2$, $R_1$, $R_3$, $R_i$, $R_{ii}$, $R_x$, $R_y$, and m are the same as defined herein.

In another embodiment, the compound of formula I or IIA is a compound of formula IIA-2:

(IIA-2)

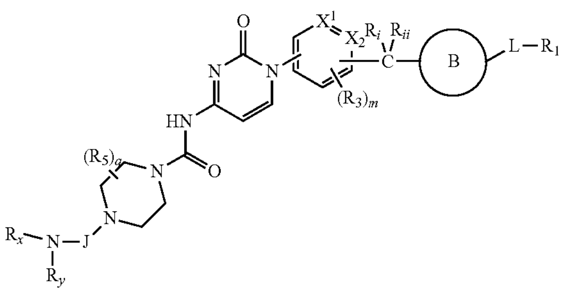

or a pharmaceutically acceptable salt thereof, wherein ring B, L, J, $X^1$, $X^2$, $R_1$, $R_3$, $R_i$, $R_{ii}$, $R_x$, $R_y$, and m are the same as defined herein; $R_5$ is selected from the group consisting of H, $C_1$-$C_6$ alkyl, $C_1$-$C_6$ alkoxy, halo, CN, $C_1$-$C_6$ haloalkyl, phenyl, OH, $NH_2$, and oxo; and q is 1, 2, or 3.

In another embodiment, the compound of formula I or IIA is a compound of formula IIA-3:

(IIA-3)

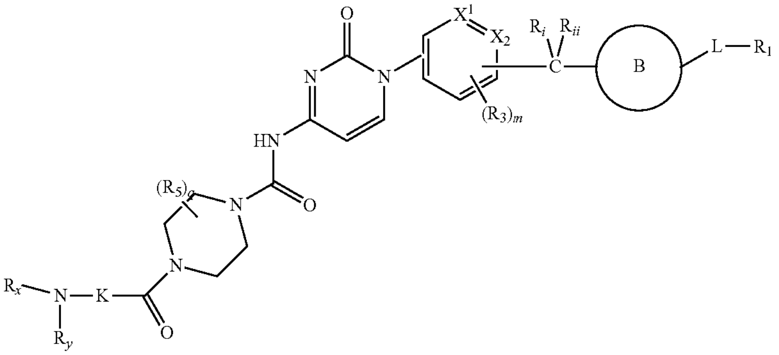

or a pharmaceutically acceptable salt thereof, wherein ring B, L, $X^1$, $X^2$, $R_1$, $R_3$, $R_5$, $R_i$, $R_{ii}$, $R_x$, $R_y$, q and m are the same as defined herein; K is $C_1$-$C_4$ alkylene optionally substituted with halo, $C_1$-$C_6$ alkoxy, $C_1$-$C_6$ haloalkyl, $NH_2CN$ or OH.

In another embodiment, the compound of formula I or IIA is a compound of formula IIA-4:

(IIA-4)

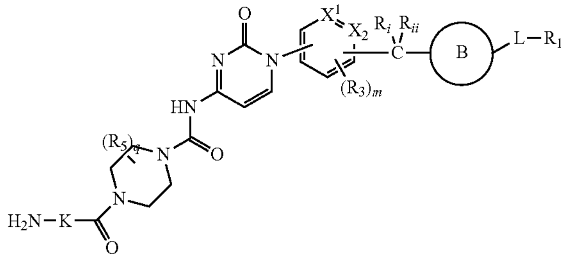

or a pharmaceutically acceptable salt thereof, wherein ring B, L, K, $X^1$, $X^2$, $R_1$, $R_3$, $R_5$, $R_i$, $R_{ii}$, q and m are the same as defined herein.

In another embodiment, the compound of formula I or IIA is a compound of formula IIA-4a or IA-4b:

(IIA-4a)

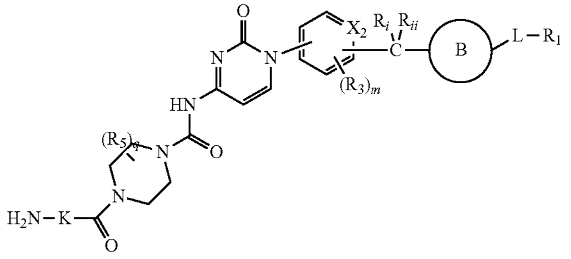

(IIA-4b)

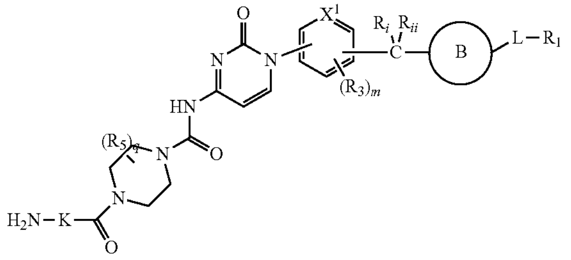

or a pharmaceutically acceptable salt thereof, wherein ring B, L, K, $X^1$, $X^2$, $R_1$, $R_3$, $R_i$, $R_{ii}$, and m are the same as defined herein.

In another embodiment, the compound of formula I or IIA is a compound of formula IIA-5:

(IIA-5)

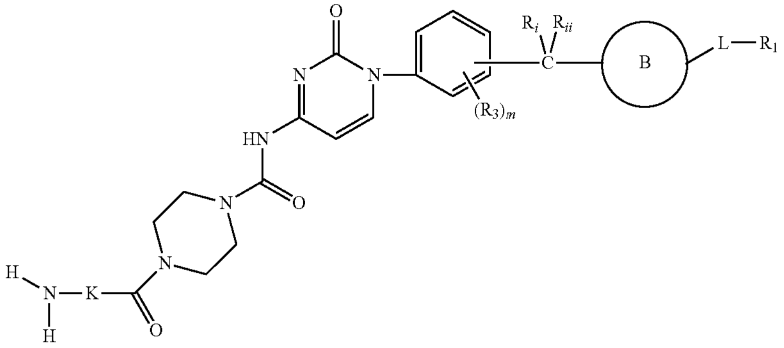

or a pharmaceutically acceptable salt thereof, wherein ring B, L, K, $R_1$, $R_i$, $R_{ii}$, and m are the same as defined herein; $R_3$ is selected from the group consisting of $C_1$-$C_6$ alkyl, halo, $C_1$-$C_6$ haloalkyl, and $C_1$-$C_6$ alkoxy, $CO_2H$, and $CO_2Et$; and m is 0, 1 or 2.

In another embodiment, the compound of formula I or IIA is a compound of formula IIA-6:

(IIA-6)

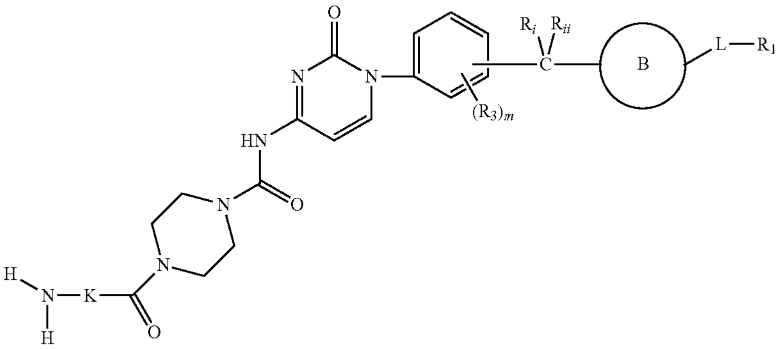

or a pharmaceutically acceptable salt thereof, wherein ring B, L, K, $R_1$, $R_3$, $R_i$, $R_{ii}$, and m are the same as defined herein.

In another embodiment, the compound of formula I or IIA is a compound of formula IIA-7:

(IIA-7)

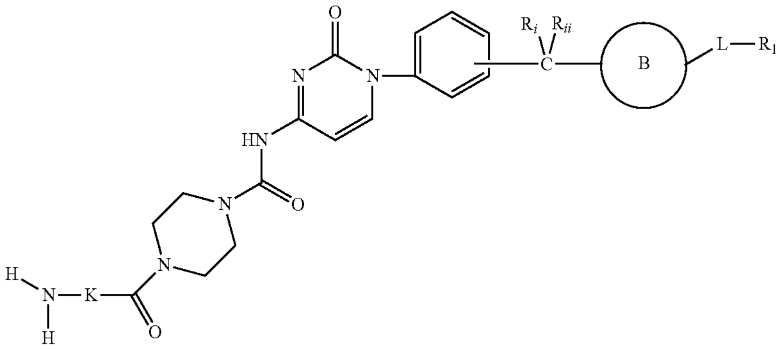

or a pharmaceutically acceptable salt thereof, wherein ring B, L, K, $R_1$, $R_i$, and $R_{ii}$ are the same as defined herein.

In another embodiment, the compound of formula I or IIA is a compound of formula IIA-8a or IIA-8b:

(IIA-8a)

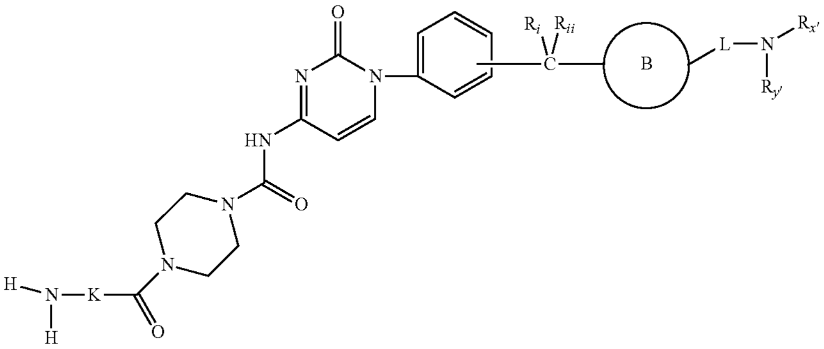

-continued (IIA-8b)

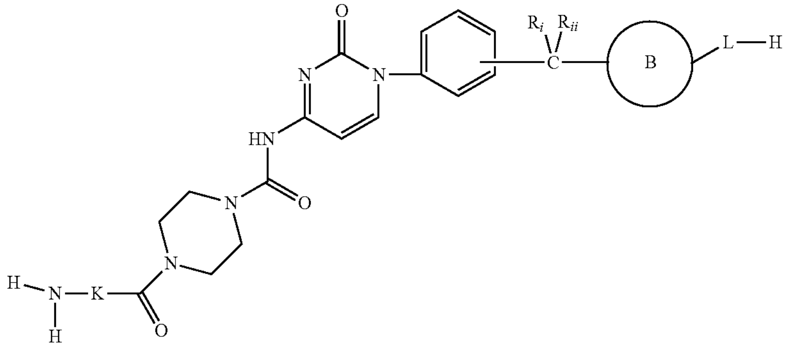

or a pharmaceutically acceptable salt thereof, wherein ring B, L, K, $R_{x'}$, $R_{y'}R_i$, and $R_{ii}$, are the same as defined herein.

In another embodiment, the compound of formula I or IIA is a compound of formula IIA-9:

IIA-9

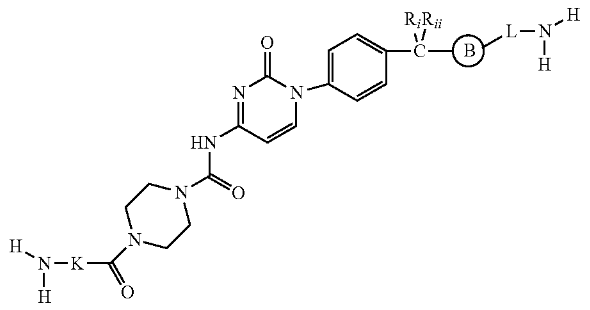

or a pharmaceutically acceptable salt thereof, wherein ring B, L, K, $R_i$ and $R_{ii}$ are the same as defined herein.

In another aspect, the disclosure provides a compound of formula IIB:

IIB

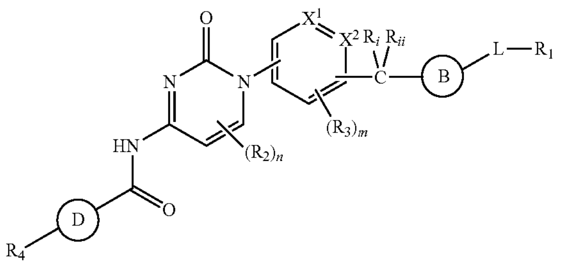

or a pharmaceutically acceptable salt thereof, wherein:

$R_1$, $R_2$, $R_3$, $X_1$, $X_2$, $R_i$, $R_j$, $Y_1$, ring B, L, m, and n are as defined in the preceding paragraphs; and ring D is a monocyclic heterocycloalkylene or bicyclic heterocycloalkylene, wherein the monocyclic heterocycloalkylene and bicyclic heterocycloalkylene are optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2NH(C_1$-$C_6$ alkyl), $N(C_1$-$C_6$ alkyl$)_2$, $COO(C_1$-$C_6$ alkyl), $COONH_2$, and oxo;

$R_4$ is H or $NR_{x''}R_{y''}$ wherein $R_{x''}$ and $R_{y''}$ are each independently H or $C_1$-$C_6$ alkyl.

In another embodiment, the compound of formula IIB is a compound of formula IIB-1:

IIB-1

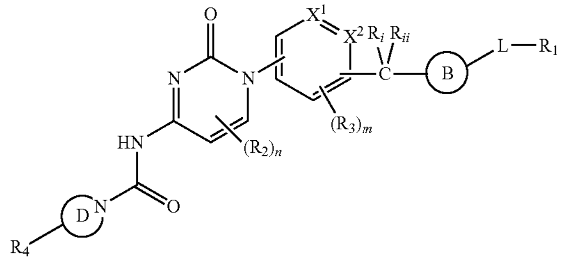

or a pharmaceutically acceptable salt thereof, wherein ring B, ring D, L, $X^1$, $X^2R_1$, $R_2$, $R_3$, $R_4$, $R_i$, $R_{ii}$, m, and n are the same as defined herein.

In another embodiment of a compound of formula IIB-1 or a pharmaceutically acceptable salt thereof,

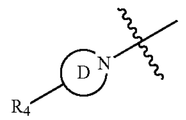

is

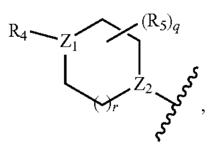

,

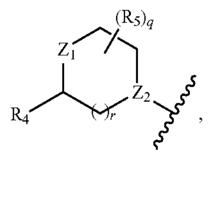

,

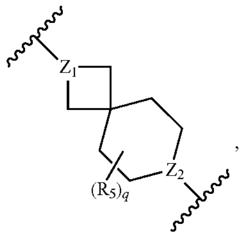

,

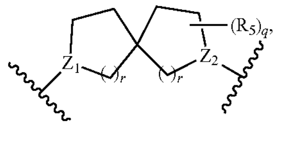

or

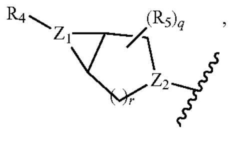

, wherein $Z_1$ and $Z_2$ are each independently selected from the group consisting of CH, $CH_2N$, NH and O; each $R_5$ is independently selected from the group consisting of $C_1$-$C_6$ alkyl, $C_1$-$C_6$ alkoxy, halo, CN, $C_1$-$C_6$ haloalkyl, phenyl, OH, $NH_2$, and oxo; q is 0, 1, 2 or 3, and r is 1 or 2.

In another embodiment,

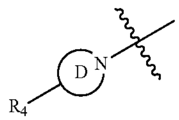

is selected from the group consisting of

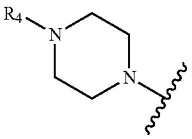,
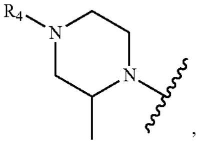,
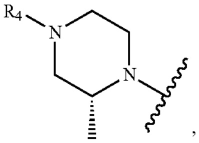,
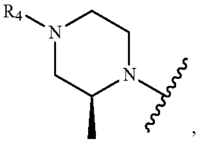,
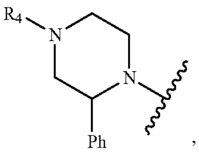,
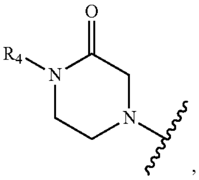,
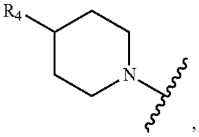,
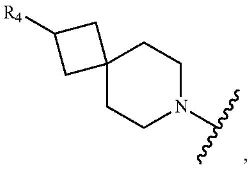,
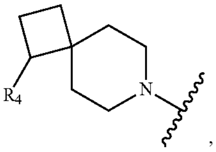,
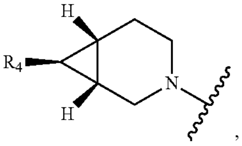,
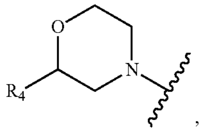,
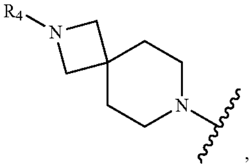,
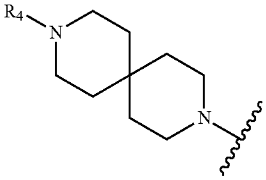,
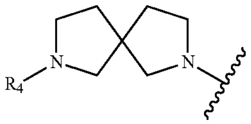,
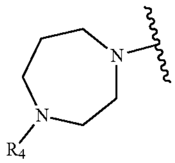, and
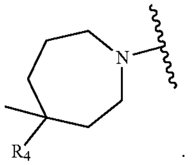.

In another aspect, the disclosure provides a compound of Formula IIIA:

IIIA

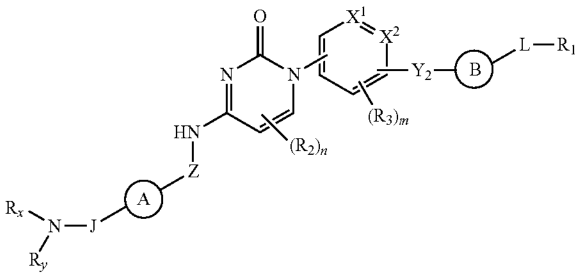

or a pharmaceutically acceptable salt thereof, wherein:

Z is —(C═O)—;

ring A is a monocyclic heterocycloalkylene or bicyclic heterocycloalkylene, wherein the monocyclic heterocycloalkylene and bicyclic heterocycloalkylene are optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2NH(C_1$-$C_6$ alkyl), $N(C_1$-$C_6$ alkyl$)_2$, —COO($C_1$-$C_6$ alkyl), —$COONH_2$, and oxo;

J is $C_1$-$C_6$ alkylene, $C_1$-$C_6$ alkylene-heterocycloalkylene or $C_1$-$C_6$ alkylene-cycloalkylene, any of which may be optionally substituted with halo, hydroxy, or alkoxy; and wherein one or two carbons of the $C_1$-$C_6$ alkylene may optionally be replaced with O, S, $SO_2$, C═O, or

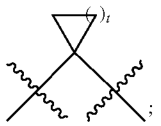 [SMILES: *C1(*)CC1];

and t is 1, 2, 3 or 4;

$R_x$ and $R_y$ are each independently H or $C_1$-$C_6$ alkyl;

$X^1$ and $X^2$ are each independently C—H or N;

$Y_2$ is a linear $C_2$ alkylene, optionally substituted with OH, $NH_2$, halo, $C_1$-$C_6$ alkyl, or $C_1$-$C_6$ alkoxy, and wherein one carbon atom of the $C_2$ alkylene may be replaced by O, NH, N—($C_1$-$C_6$ alkyl), N—($C_1$-$C_6$ hydroxyalkyl), N—($C_1$-$C_6$ haloalkyl), N—($C_1$-6 alkylene-cycloalkyl), NH(C═O), N—($C_{1-6}$ alkyl) (C═O), or (C═O);

ring B is a bicyclic heterocycloalkylene or bicyclic cycloalkylene, wherein the bicyclic heterocycloalkylene and bicyclic cycloalkylene are optionally substituted with up to three substituents selected from the group consisting of $C_1$-$C_6$ alkyl, $C_1$-$C_6$ alkoxy, halo, CN, $C_1$-$C_6$ haloalkyl, OH, —COO($C_1$-$C_6$ alkyl), —$COONH_2$, and $C_1$-$C_6$ hydroxyalkyl;

L is absent, or is a linear or branched $C_1$-$C_6$ alkylene, wherein up to two carbon atoms of the $C_1$-$C_6$ alkylene may be replaced with O, NH, (C═O), NH(C═O), N—($C_1$-6 alkyl)(C═O), (C═NH), NH(C═N), or N—($C_{1-6}$ alkyl);

$R_1$ is H or $NR_{x'}R_{y'}$, wherein $R_{x'}$ and $R_{y'}$ are each independently H or $C_1$-$C_6$ alkyl;

$R_2$ and $R_3$ are each independently selected from the group consisting of $C_1$-$C_6$ alkyl, halo, CN, OH, $NH_2NH(C_1$-$C_6$ alkyl), $N(C_1$-$C_6$ alkyl$)_2$, —COO($C_1$-$C_6$ alkyl), —$COONH_2C_1$-$C_6$ haloalkyl, and $C_1$-$C_6$ alkoxy; and m and n are each independently 0, 1, 2 or 3.

In another embodiment of a compound of formula IIIA or a pharmaceutically acceptable salt thereof, Z is —(C═O)—.

In another embodiment of a compound of formula I or IIIA or a pharmaceutically acceptable salt thereof, ring A is a monocyclic heterocycloalkylene or bicyclic heterocycloalkylene, wherein the monocyclic heterocycloalkylene and bicyclic heterocycloalkylene are optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, and oxo.

In another embodiment, ring A is a monocyclic heterocycloalkylene optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, and oxo.

In another embodiment, ring A is

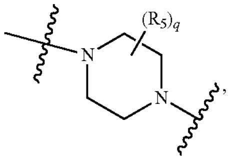, wherein each $R_5$ is independently selected from the group consisting of $C_1$-$C_6$ alkyl, $C_1$-$C_6$ alkoxy, halo, CN, $C_1$-$C_6$ haloalkyl, phenyl, OH, $NH_2$, and oxo; and q is 0, 1, 2 or 3.

In another embodiment, ring A is

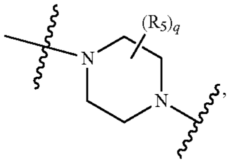, wherein $R_5$ is $C_1$-$C_6$ alkyl, and q is 1.

In another embodiment, ring A is

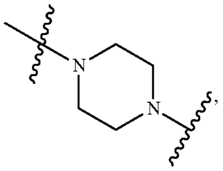, 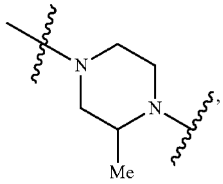, or

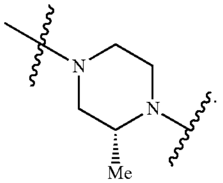.

In another embodiment of a compound of formula I or IIIA or a pharmaceutically acceptable salt thereof, J is $C_1$-$C_6$ alkylene.

In another embodiment, one of the $C_1$-$C_6$ alkylene carbons of J is —(C═O)—.

In another embodiment, J is optionally substituted with —OH.

In another embodiment, J is selected from the group consisting of

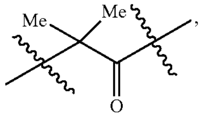, 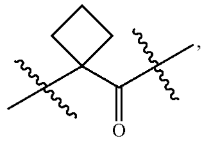,

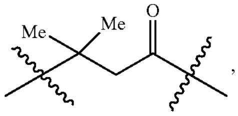, 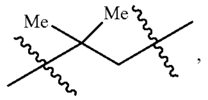,

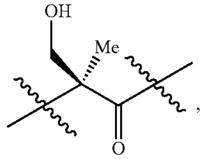, and 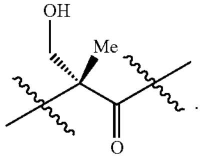.

In another embodiment of a compound of formula I or IIIA or a pharmaceutically acceptable salt thereof, $(R_xR_y)$N-J-is selected from the group consisting of

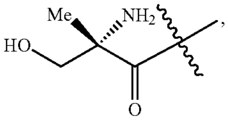, 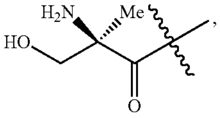,

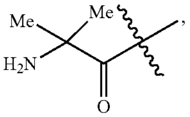, 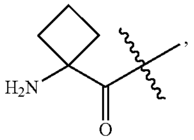, and

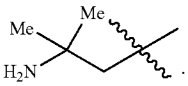.

In another embodiment of a compound of formula I or IIIA or a pharmaceutically acceptable salt thereof,

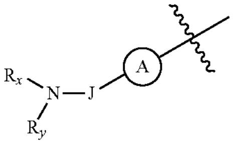 is 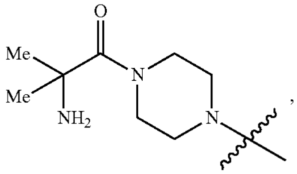,

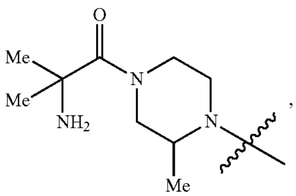,

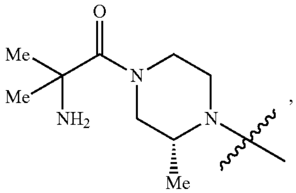,

-continued

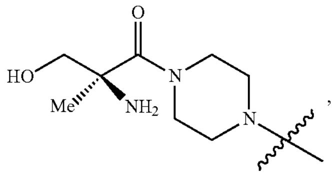

,

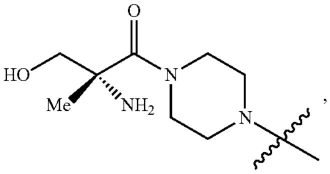

, or

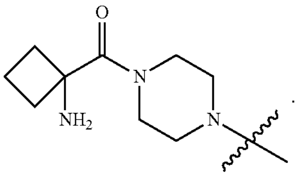

.

In another embodiment of a compound of formula I or IIIA or a pharmaceutically acceptable salt thereof,

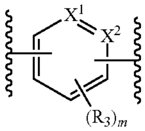

is

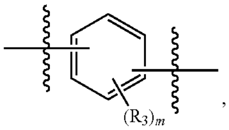

,

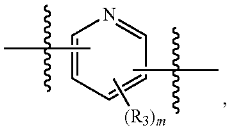

, or

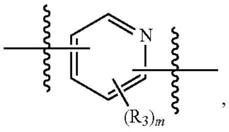

, wherein each $R_3$ is independently selected from the group consisting of $C_1$-$C_6$ alkyl, $C_1$-$C_6$ alkoxy, halo, and $C_1$-$C_6$ haloalkyl, and m is 0 or 1.

In another embodiment,

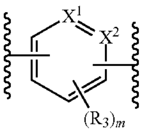

is

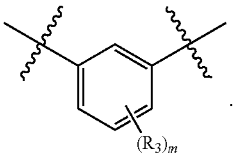

.

In another embodiment,

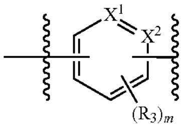

is

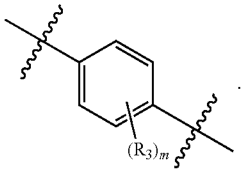

.

In another embodiment,

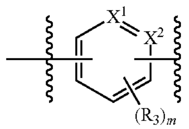

is

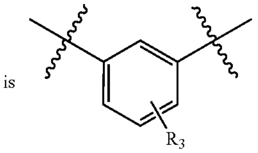

or

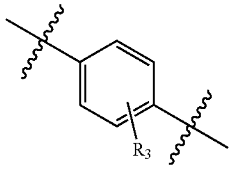

, wherein $R_3$ is selected from the group consisting of Me, OMe, halo, and $CF_3$.

In another embodiment,

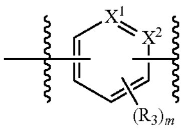

is selected from the group consisting of

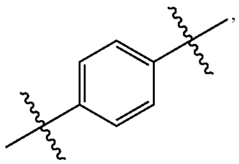

,

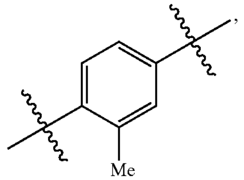

,

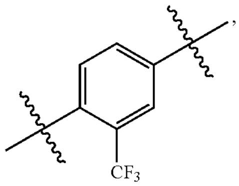

,

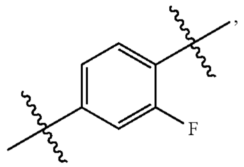

,

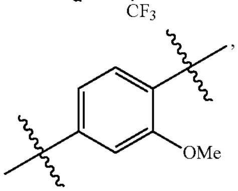

, and

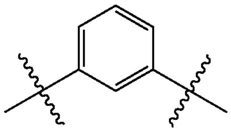

.

In another embodiment of a compound of formula I or IIIA or a pharmaceutically acceptable salt thereof, $Y_2$ is —$C(R_iR_j)$—$C(R_{i'}R_{j'})$—wherein $R_iR_jR_{i'}R_{j'}$ are each independently H or $C_1$-$C_6$ alkyl, wherein $C(R_iR_j)$ or $C(R_{i'}R_{j'})$ may be replaced with NH, N—($C_{1-6}$ alkyl), or (C═O).

In another embodiment, $Y_2$ is selected from the group consisting of

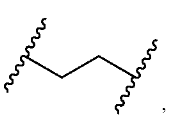

,

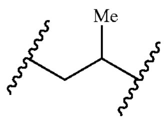

,

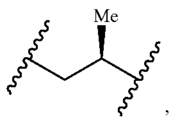

,

-continued
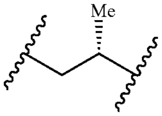, 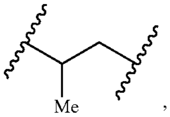, 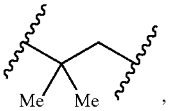,
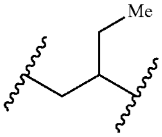, 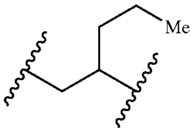, 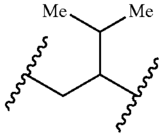,
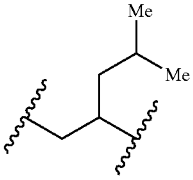, 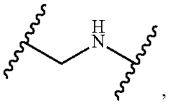, 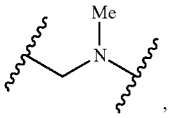,
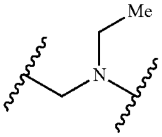, and 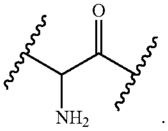.
In another embodiment of a compound of formula I or IIIA or a pharmaceutically acceptable salt thereof,
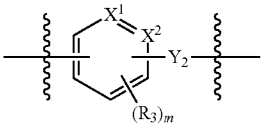
is selected from the group consisting of
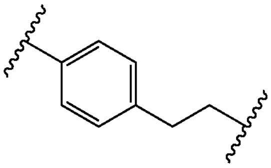,
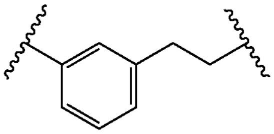,
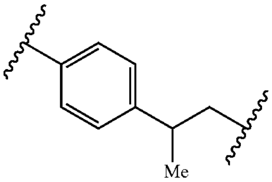,
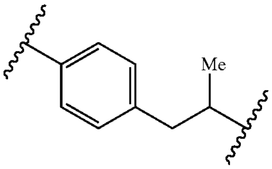,
-continued
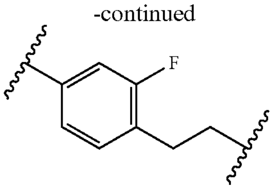,
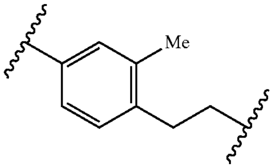,
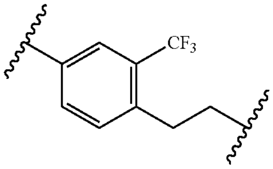,
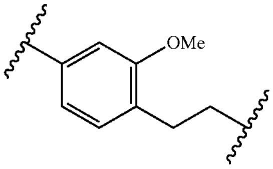,
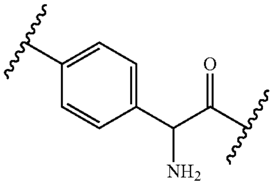,
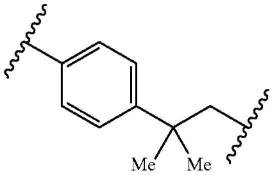,
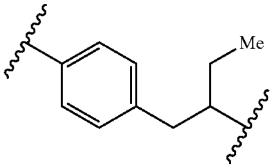,
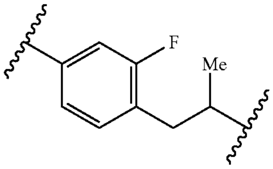,
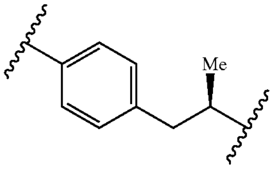,
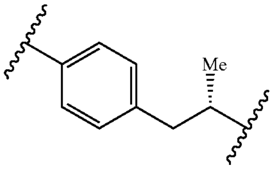, -continued

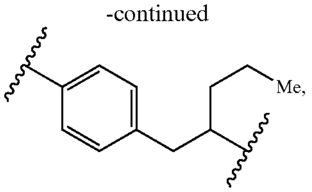

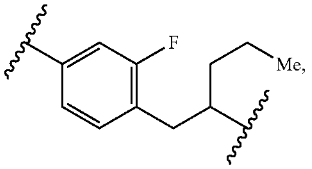

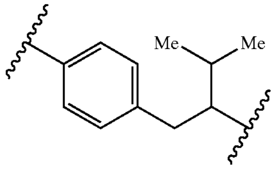

,

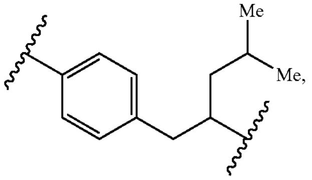

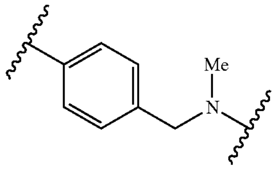

,

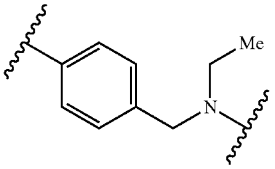

, and

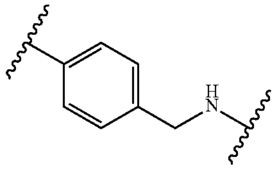

,

In another embodiment of a compound of formula I or IIIA or a pharmaceutically acceptable salt thereof, ring B is a bicyclic heterocycloalkylene optionally substituted with up to three substituents selected from the group consisting of $C_1$-$C_6$ alkyl, $C_1$-$C_6$ alkoxy, halo, $C_1$-$C_6$ haloalkyl, OH, and $C_1$-$C_6$ hydroxyalkyl.

In another embodiment, ring B is a fused, spiro, or bridged bicyclic heterocycloalkylene containing up to 3 nitrogen atoms, wherein the fused, spiro, or bridged bicyclic heterocycloalkylene is optionally substituted with up to three substituents selected from the group consisting of $C_1$-$C_6$ alkyl, $C_1$-$C_6$ alkoxy, halo, $C_1$-$C_6$ haloalkyl, OH, and $C_1$-$C_6$ hydroxyalkyl.

In another embodiment, ring B is a fused bicyclic heterocycloalkylene containing up to two nitrogen atoms, wherein the fused bicyclic heterocycloalkylene is optionally substituted with $C_1$-$C_6$ alkyl or $C_1$-$C_6$ hydroxyalkyl.

In another embodiment, ring B is a spiro bicyclic heterocycloalkylene containing up to two nitrogen atoms.

In another embodiment, ring B is a bridged bicyclic heterocycloalkylene containing up to two nitrogen atoms.

In another embodiment, ring B is a bicyclic cycloalkylene optionally substituted with up to three substituents selected from the group consisting of $C_1$-$C_6$ alkyl, $C_1$-$C_6$ alkoxy, halo, $C_1$-$C_6$ haloalkyl, OH, and $C_1$-$C_6$ hydroxyalkyl.

In another embodiment, ring B is a fused, spiro, or bridged bicyclic cycloalkylene.

In another embodiment, ring B is a fused bicyclic cycloalkylene.

In another embodiment, ring B is a spiro bicyclic cycloalkylene.

In another embodiment, ring B is a bridged bicyclic cycloalkylene.

In another embodiment, ring B is selected from the group consisting of

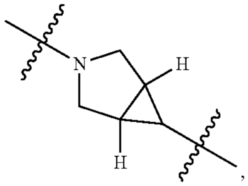

,

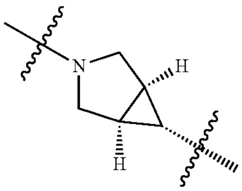

,

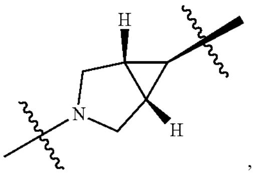

,

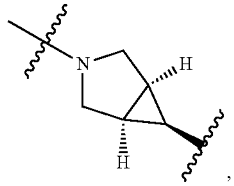

,

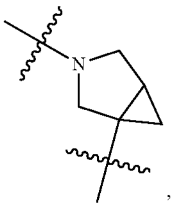

,

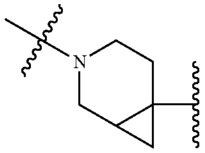

,

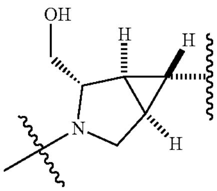

,

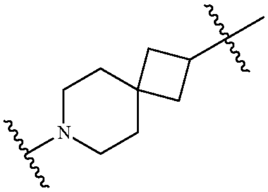

,

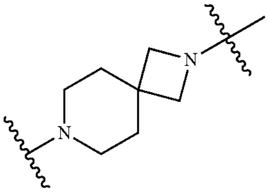

,

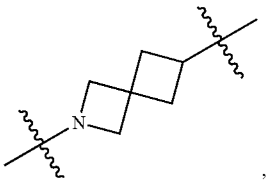

,

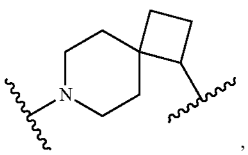

,

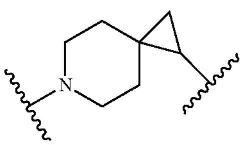

,

-continued

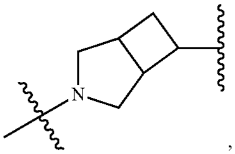
,
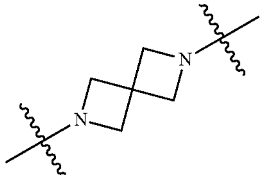
,
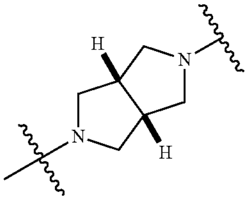
,
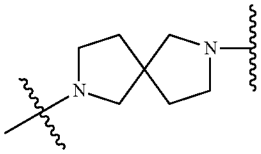
,
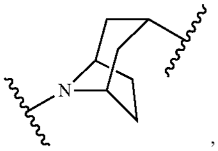
,
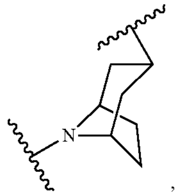
,
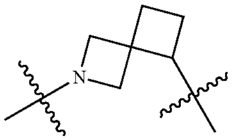
,
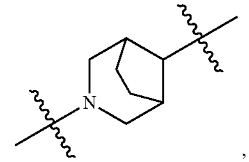
,
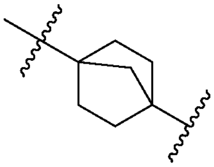
,
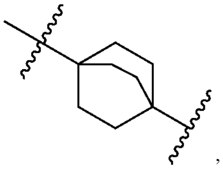
, and
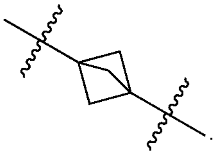

In another embodiment of a compound of formula I or IIIA or a pharmaceutically acceptable salt thereof, L is absent.

In another embodiment, L is a linear or branched $C_1$-$C_6$ alkylene, wherein one carbon atom of the $C_1$-$C_6$ alkylene may be replaced with O, NH, (C═O), or N—($C_{1-6}$ alkyl).

In another embodiment, L is $CH_2CH(CH_3)$, $CH(CH_2CH_3)$, or C═O.

In another embodiment of a compound of formula I or IIIA or a pharmaceutically acceptable salt thereof, $R_1$ is H, $NH_2$ or $NH(C_1$-$C_6$ alkyl).

In another embodiment, $R_1$ is H, $NH_2NHCH_3$.

In another embodiment of a compound of formula I or IIIA or a pharmaceutically acceptable salt thereof,

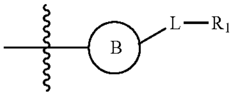

is selected from the group consisting of

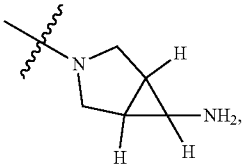
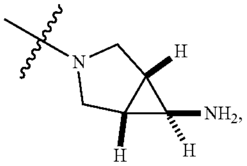
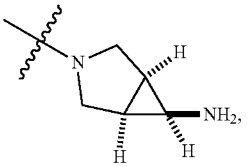
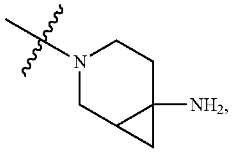
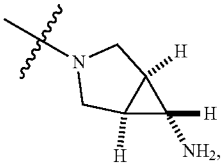
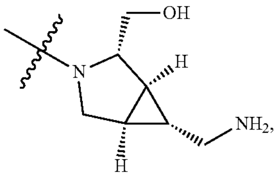
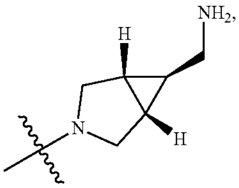
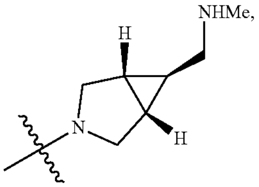
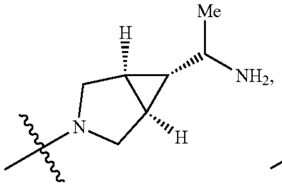
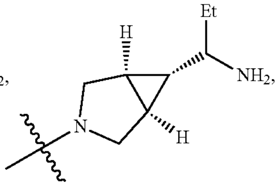
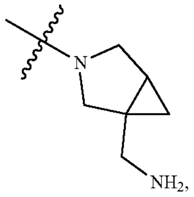
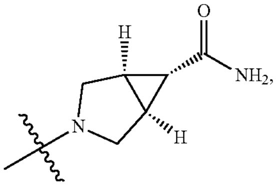
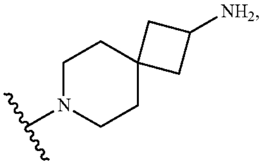
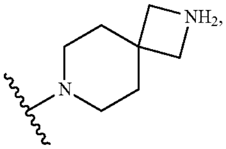
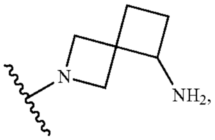
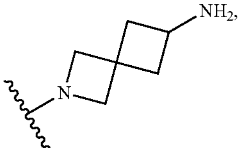

-continued

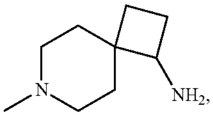

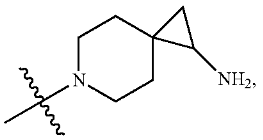

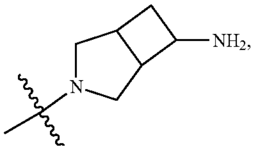

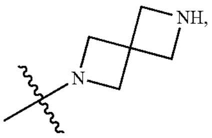

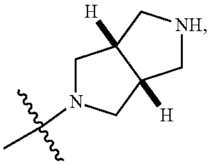

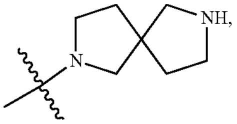

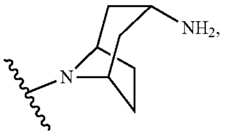

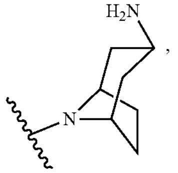

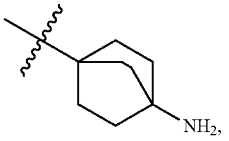

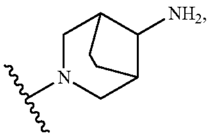

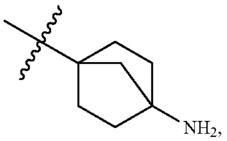

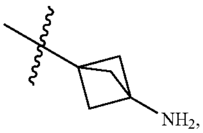

and

-continued

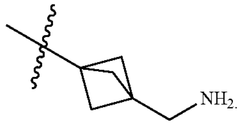

In another embodiment of a compound of formula I or IIIA or a pharmaceutically acceptable salt thereof, each $R_2$ and $R_3$ is independently selected from the group consisting of $C_1$-$C_6$ alkyl, halo, $C_1$-$C_6$ haloalkyl, and $C_1$-$C_6$ alkoxy and m and n are each independently 0, 1 or 2.

In another embodiment, $R_2$ and $R_3$ are each independently selected from the group consisting of $C_1$-$C_6$ alkyl, halo, $C_1$-$C_6$ alkoxy, and m and n are each independently 0 or 1.

In another embodiment of a compound of formula I or IIIA or a pharmaceutically acceptable salt thereof, m and n are each 0 or 1, and $R_2$ is Me and $R_3$ is selected from the group consisting of $CH_3F$, $OCH_3$, and $CF_3$.

In another embodiment, the compound of formula I or IIIA is a compound of formula IIIA-1:

IIIA-1

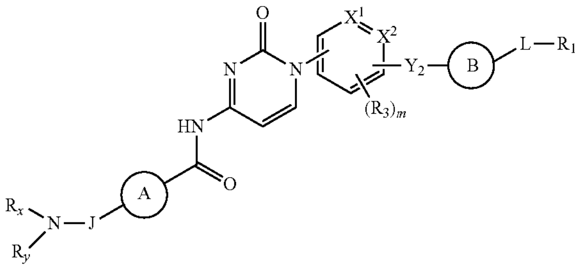

or a pharmaceutically acceptable salt thereof, wherein ring A, ring B, L, J, $Y_2$, $X^1$, $X^2$, $R_1$, $R_3$, $R_x$, $R_y$, and m are the same as defined herein.

In another embodiment, the compound of formula I or IIIA is a compound of formula IIIA-2:

III-A2

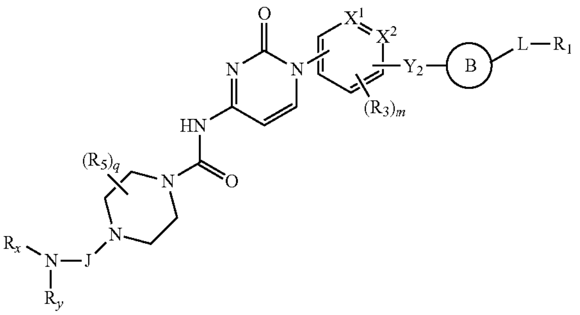

or a pharmaceutically acceptable salt thereof, wherein ring B, L, J, $Y_2$, $X^1$, $X^2R_1$, $R_3$, $R_x$, $R_y$, and m are the same as defined herein; $R_5$ is selected from the group consisting of $C_1$-$C_6$ alkyl, $C_1$-$C_6$ alkoxy, halo, CN, $C_1$-$C_6$ haloalkyl, phenyl, OH, $NH_2$, and oxo; and q is 0, 1 or 2.

In another embodiment, the compound of formula I or IIIA is a compound of formula IIIA-3:

IIIA-3

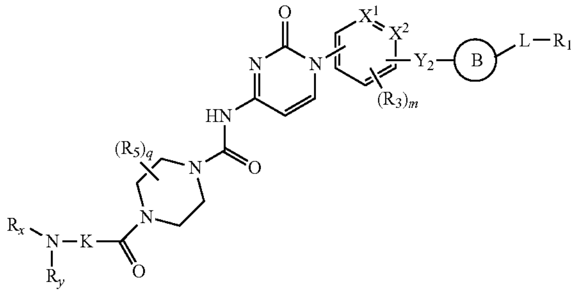

or a pharmaceutically acceptable salt thereof, wherein ring B, L, K, $Y_2$, $X^1$, $X^2$, $R_1$, $R_3$, $R_5$, $R_x$, $R_y$, q and m are the same as defined herein; K is $C_1$-$C_4$ alkylene optionally substituted with hydroxy or alkoxy.

In another embodiment, the compound of formula I or IIIA is a compound of formula IIIA-4:

IIIA-4

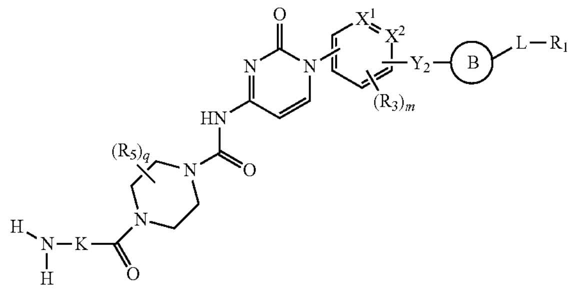

or a pharmaceutically acceptable salt thereof, wherein ring B, L, K, $Y_2$, $X^1$, $X^2$, $R_1$, $R_3$, $R_5$, q and m are the same as defined herein.

In another embodiment, the compound of formula I or IIIA is a compound of formula IIIA-4a or IIIA-4b:

IIIA-4a

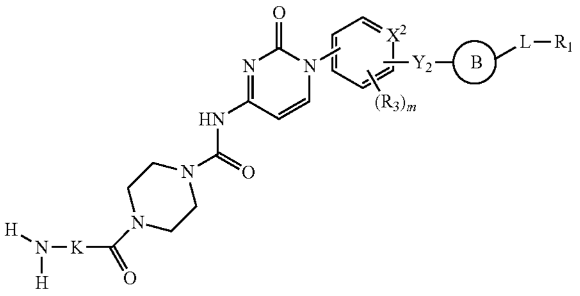

IIIA-4b

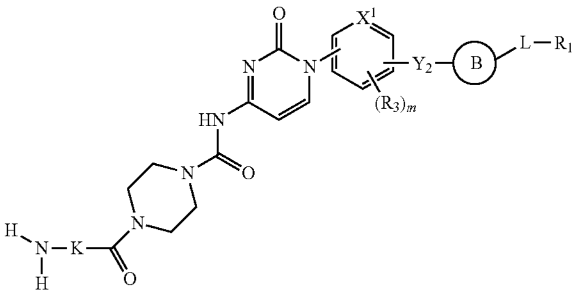

or a pharmaceutically acceptable salt thereof, wherein ring B, L, K, $Y_2$, $X^1$, $X^2$, $R_1$, $R_3$, and m are the same as defined herein.

In another embodiment, the compound of formula I or IIIA is a compound of formula IIIA-5:

IIIA-5

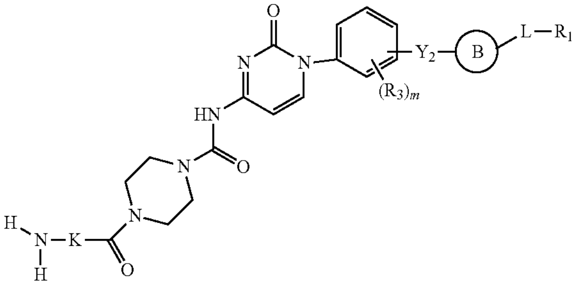

or a pharmaceutically acceptable salt thereof, wherein ring B, L, K, $Y_2$, and $R_1$ are the same as defined herein; $R_3$ is selected from the group consisting of $C_1$-$C_6$ alkyl, halo, $C_1$-$C_6$ haloalkyl, and $C_1$-$C_6$ alkoxy; and m is 0, 1 or 2.

In another embodiment, the compound of formula I or IIIA is a compound of formula IIIA-6:

IIIA-6

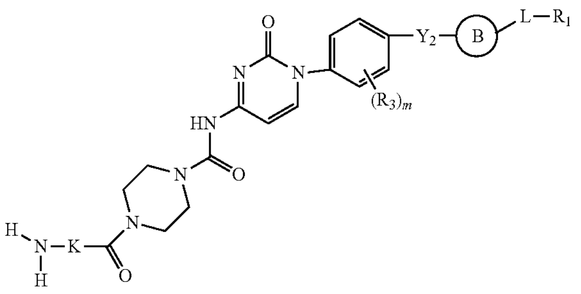

or a pharmaceutically acceptable salt thereof, wherein ring B, L, K, $Y_2$, $R_1$, $R_3$, and m are the same as defined herein.

In another embodiment, the compound of formula I or IIIA is a compound of formula IIIA-7:

IIIA-7

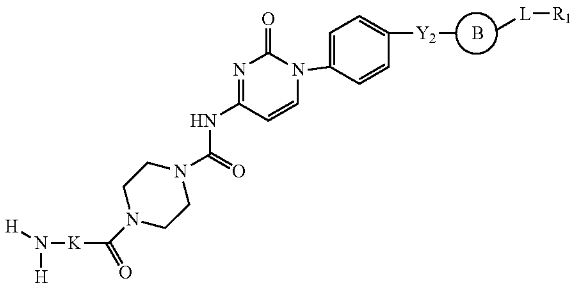

or a pharmaceutically acceptable salt thereof, wherein ring B, L, K, $Y_2$, and $R_1$ are the same as defined herein.

In another embodiment, the compound of formula I or IIIA is a compound of formula IIIA-8a or IIIA-8b:

IIIA-8a

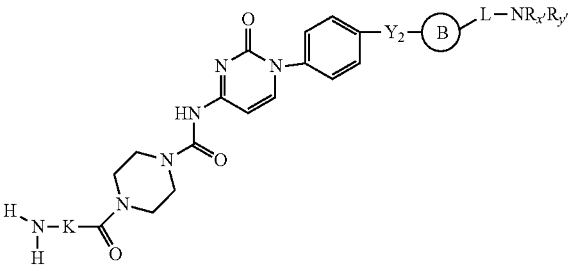

IIIA-8b

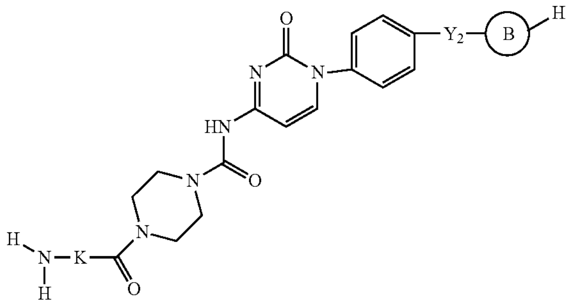

or a pharmaceutically acceptable salt thereof, wherein ring B, L, K, $Y_2$, $R_{x'}$, and $R_{y'}$ are the same as defined herein.

In another embodiment, the compound of formula I or IIIA is a compound of formula IIIA-9:

IIIA-9

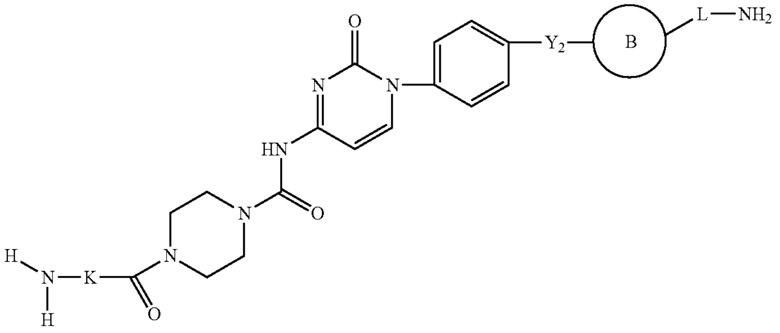

or a pharmaceutically acceptable salt thereof, wherein ring B, L, K, and $Y_2$ are the same as defined herein.

In another aspect, the disclosure provides a compound of formula IIIB:

IIIB

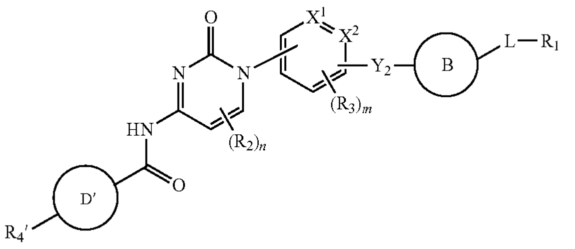

or a pharmaceutically acceptable salt thereof, wherein:

$R_1$, $R_2$, $R_3$, $X^1$, $X^2$, $Y_2$, B, L, m, and n are as defined herein; and ring D' is a monocyclic heterocycloalkylene or bicyclic heterocycloalkylene, wherein the monocyclic heterocycloalkylene and bicyclic heterocycloalkylene are optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2NH(C_1$-$C_6$ alkyl), $N(C_1$-$C_6$ alkyl$)_2$, COO($C_1$-$C_6$ alkyl), $COONH_2$, and oxo;

$R_{4'}$ is H or $NR_{x''}R_{y''}$ wherein $R_{x''}$ and $R_{y''}$ are each independently H or $C_1$-$C_6$ alkyl.

In another embodiment, the compound of formula I or IIIB is a compound of formula IIIB-1:

IIIB-1

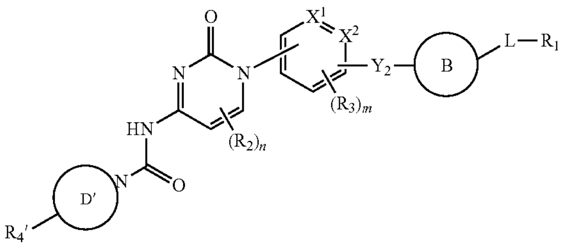

or a pharmaceutically acceptable salt thereof.

In another embodiment of a compound of formula IIIB or a pharmaceutically acceptable salt thereof, ring D' is selected from the group consisting of

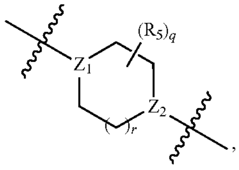,

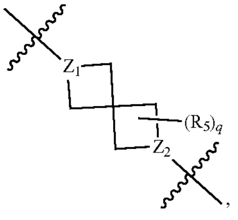,

-continued

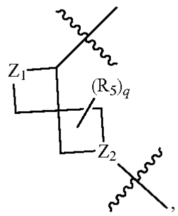,

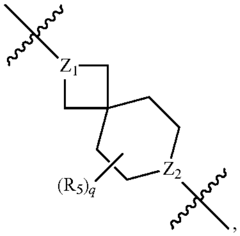, and

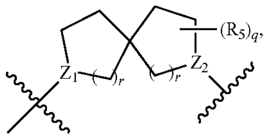

wherein $Z_1$ and $Z_2$ are each independently selected from the group consisting of CH, $CH_2N$, NH and O; each $R_5$ is independently selected from the group consisting of $C_1$-$C_6$ alkyl, $C_1$-$C_6$ alkoxy, halo, CN, $C_1$-$C_6$ haloalkyl, phenyl, OH, $NH_2$, and oxo; q is 0, 1, 2 or 3, and r is 1 or 2.

In another embodiment, ring D is

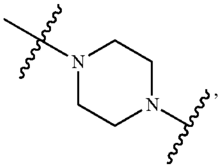,

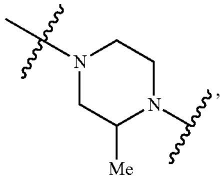,

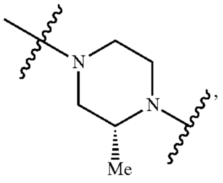,

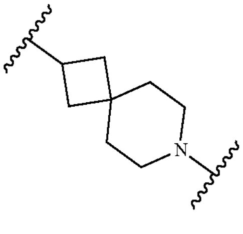,

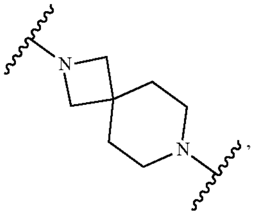,

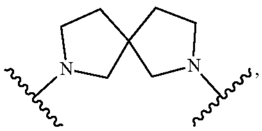,

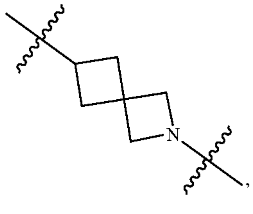, or

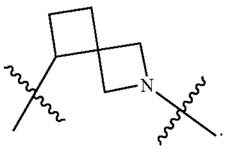.

In another embodiment of a compound of formula I or IIIB or a pharmaceutically acceptable salt thereof,

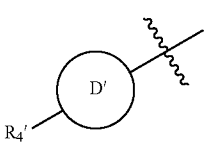 is 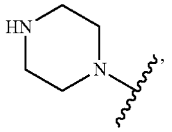, 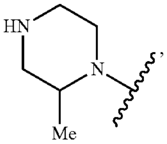, 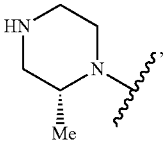, 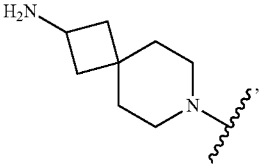, 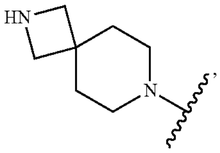, 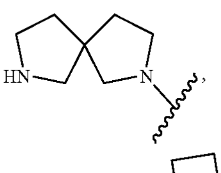, 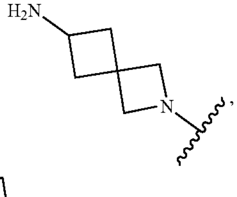, or 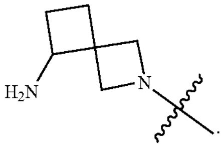.

In another aspect, the disclosure provides a compound of Formula IV:

IV

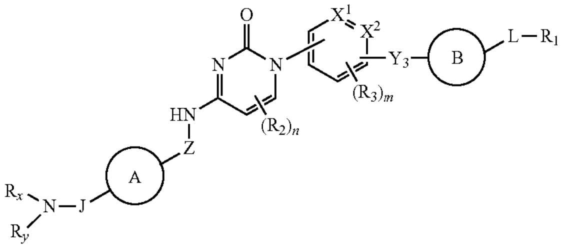

or a pharmaceutically acceptable salt thereof, wherein:

Z is —(C═O)—;

ring A is a monocyclic heterocycloalkylene or bicyclic heterocycloalkylene, wherein the monocyclic heterocycloalkylene and bicyclic heterocycloalkylene are optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2NH(C_1$-$C_6$ alkyl), $N(C_1$-$C_6$ alkyl$)_2$, —COO($C_1$-$C_6$ alkyl), —$COONH_2$, and oxo;

J is $C_1$-$C_6$ alkylene optionally substituted with halo, hydroxy, or alkoxy, wherein one or two carbons of the $C_1$-$C_6$ alkylene may optionally be replaced with O, S, $SO_2$ or C═O;

$R_x$ and $R_y$ are each independently H, $C_1$-$C_6$ alkyl, or a protecting group;

$X_1$ and $X_2$ are each independently C—H or N;

$Y_3$ is a linear $C_3$-$C_8$ alkylene, $C_3$-$C_8$ alkenylene, or $C_3$-$C_8$ alkynylene, any of which are optionally substituted with OH, $NH_2$, halo, $C_1$-$C_6$ alkyl, or $C_1$-$C_6$ alkoxy, and wherein up to two carbon atoms of the $C_3$-$C_8$ alkylene, $C_3$-$C_8$ alkenylene, or $C_3$-$C_8$ alkynylene may be independently replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-cycloalkyl), NH(C═O), N—($C_{1-6}$ alkyl) (C═O), or (C═O);

ring B is a bicyclic heterocycloalkylene or bicyclic cycloalkylene, wherein the bicyclic heterocycloalkylene and bicyclic cycloalkylene are optionally substituted with up to three substituents selected from the group consisting of $C_1$-$C_6$ alkyl, $C_1$-$C_6$ alkoxy, halo, CN, $C_1$-$C_6$ haloalkyl, OH, —COO($C_1$-$C_6$ alkyl), —$COONH_2$, and $C_1$-$C_6$ hydroxyalkyl;

L is absent, or is a $C_1$-$C_6$ alkylene, wherein up to two carbon atoms of the $C_1$-$C_6$ alkylene may be replaced with O, NH, (C═O), NH(C═O), N—($C_{1-6}$ alkyl) (C═O), (C═NH), NH(C═N), or N—($C_{1-6}$ alkyl);

$R_1$ is H or $NR_{x'}R_{y'}$, wherein $R_{x'}$ and $R_{y'}$ are each independently H, $C_1$-$C_6$ alkyl, or a protecting group;

$R_2$ and $R_3$ are each independently selected from the group consisting of $C_1$-$C_6$ alkyl, halo, CN, OH, $NH_2NH(C_1$-$C_6$ alkyl), $N(C_1$-$C_6$ alkyl$)_2$, —COO($C_1$-$C_6$ alkyl), —$COONH_2C_1$-$C_6$ haloalkyl, and $C_1$-$C_6$ alkoxy; and m and n are each independently 0, 1, 2 or 3.

In another embodiment of a compound of formula IV or a pharmaceutically acceptable salt thereof, Z is —(C═O)—.

In another embodiment of a compound of formula I or IV or a pharmaceutically acceptable salt thereof, ring A is a monocyclic heterocycloalkylene or bicyclic heterocycloalkylene, wherein the monocyclic heterocycloalkylene and bicyclic heterocycloalkylene are optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, and oxo.

In another embodiment, ring A is a monocyclic heterocycloalkylene optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, and oxo.

In another embodiment, ring A is a bicyclic heterocycloalkylene optionally substituted with up to three substituents selected from the group consisting of $C_1$-$C_6$ alkyl, $C_1$-$C_6$ alkoxy, halo, CN, $C_1$-$C_6$ haloalkyl, phenyl, OH, $NH_2$, and oxo.

In another embodiment, ring A is

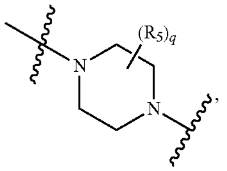

wherein each $R_5$ is independently selected from the group consisting of $C_1$-$C_6$ alkyl, $C_1$-$C_6$ alkoxy, halo, CN, $C_1$-$C_6$ haloalkyl, phenyl, OH, $NH_2$, and oxo, wherein q is 0, 1, 2 or 3.

In another embodiment, ring A is

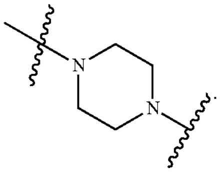 [SMILES: *N1CCN(*)CC1]

In another embodiment of a compound of formula I or IV or a pharmaceutically acceptable salt thereof, one of the $C_1$-$C_6$ alkylene carbons of J is —(C═O)—.

In another embodiment, J is optionally substituted with —OH.

In another embodiment, J is selected from the group consisting of

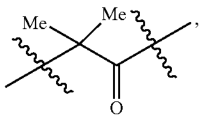, 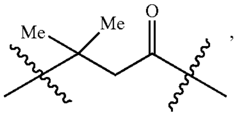,

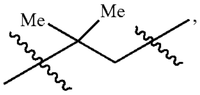, 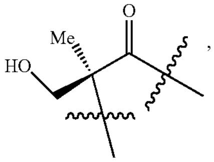, and

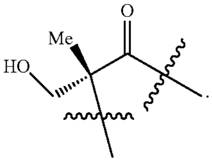.

In another embodiment of a compound of formula I or IV or a pharmaceutically acceptable salt thereof, $R_x$ and $R_y$ are each independently H.

In another embodiment of a compound of formula I or IV or a pharmaceutically acceptable salt thereof, ($R_x$ $R_y$)NJ is selected from the group consisting of

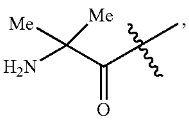, 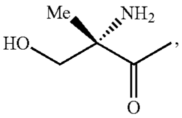,

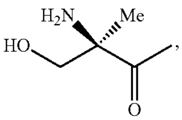, 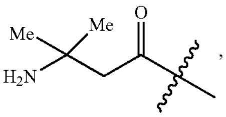, and

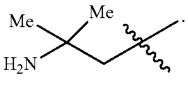.

In another embodiment of a compound of formula I or IV or a pharmaceutically acceptable salt thereof,

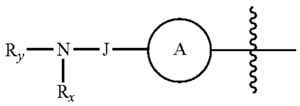 is

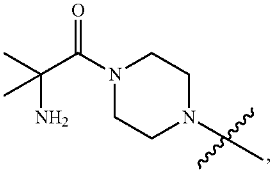,

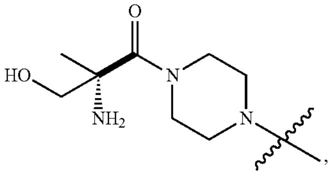, or

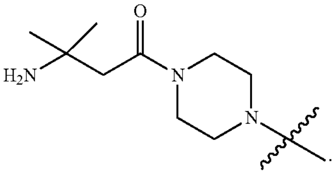.

In another embodiment of a compound of formula I or IV or a pharmaceutically acceptable salt thereof,

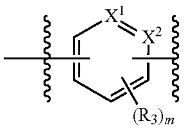 is 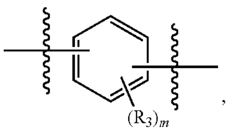,

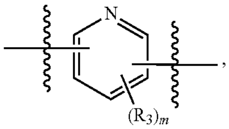, or 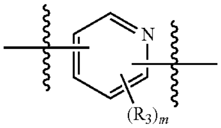, wherein each $R_4$ is independently selected from the group consisting of $C_1$-$C_6$ alkyl, halo, $C_1$-$C_6$ haloalkyl, and m is 0, 1 or 2.

In another embodiment,

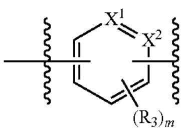 is 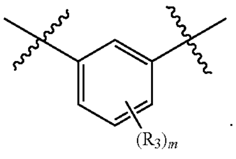.

In another embodiment,

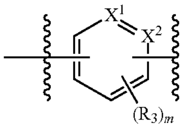 is 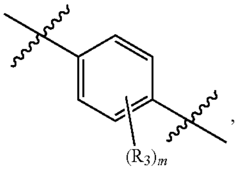, wherein each $R_3$ is independently selected from the group consisting of $C_1$-$C_6$ alkyl, halo, $C_1$-$C_6$ haloalkyl, wherein m is 0, 1 or 2.

In another embodiment,

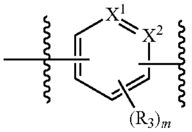

is

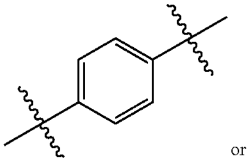

or

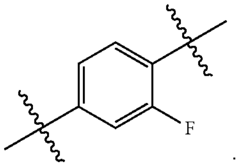

.

In another embodiment of a compound of formula I or IV or a pharmaceutically acceptable salt thereof, $Y_3$ is a linear $C_3$-$C_8$ alkylene, $C_3$-$C_8$ alkenylene, or $C_3$-$C_8$ alkynylene, any of which are optionally substituted with OH, $NH_2$, halo, $C_1$-$C_6$ alkyl, or $C_1$-$C_6$ alkoxy, and wherein one carbon atom of the $C_3$-$C_8$ alkylene, $C_3$-$C_8$ alkenylene, or $C_3$-$C_8$ alkynylene is replaced by O, NH, N—($C_1$-$C_6$ alkyl), N—($C_1$-$C_6$ hydroxyalkyl), N—($C_1$-$C_6$ haloalkyl), N—($C_1$-6 alkylene-cycloalkyl), NH(C═O), N—($C_{1-6}$ alkyl) (C═O), or (C═O).

In another embodiment, $Y_3$ is $C_3$-$C_8$ alkylene, or $C_3$-$C_8$ alkenylene, either of which is optionally substituted with OH, $NH_2$, halo, $C_1$-$C_6$ alkyl, or $C_1$-$C_6$ alkoxy, and wherein one carbon atom of the $C_3$-$C_8$ alkylene or $C_3$-$C_8$ alkenylene, is replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-cycloalkyl), NH(C═O), N—($C_{1-6}$ alkyl) (C═O), or (C═O). In another embodiment, $Y_3$ is

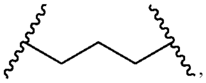

,

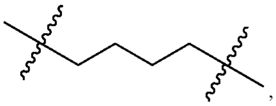

,

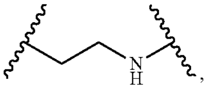

,

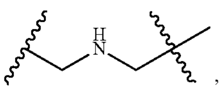

,

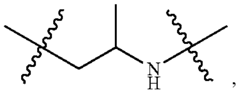

,

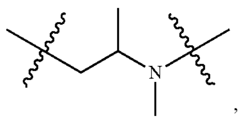

,

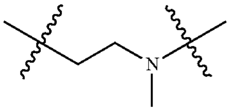

,

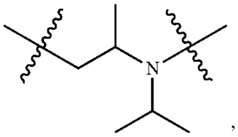

,

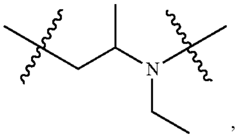

,

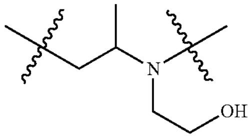

,

-continued

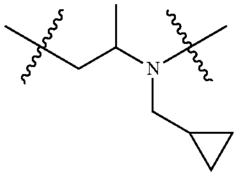

,

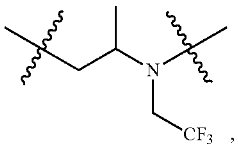

,

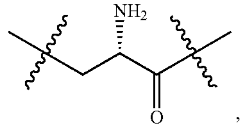

,

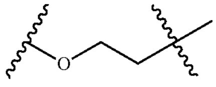

,

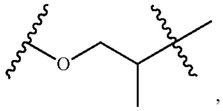

,

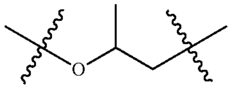

, or

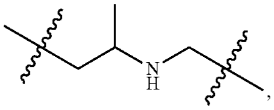

,

In another embodiment of a compound of formula I or IV or a pharmaceutically acceptable salt thereof,

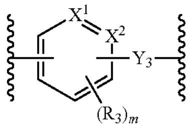

is

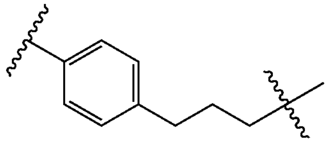

,

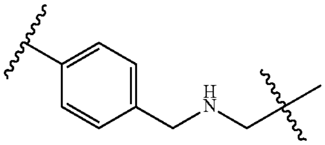

,

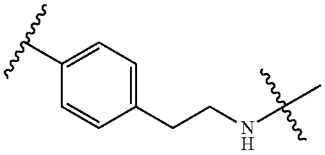

,

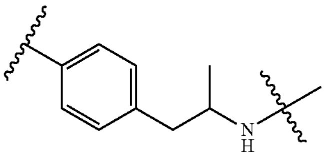

,

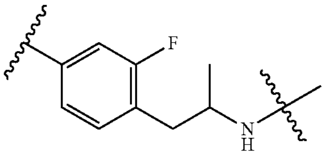

,

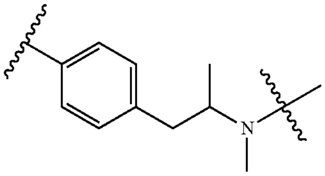

,

-continued

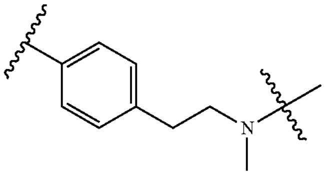

,

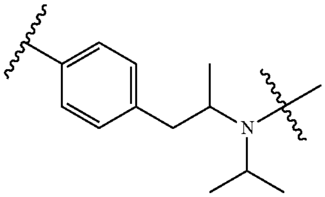

,

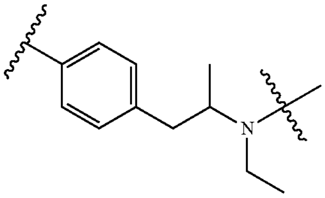

,

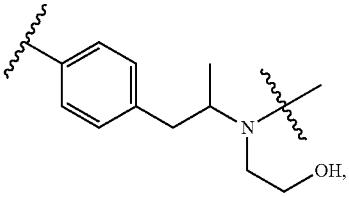

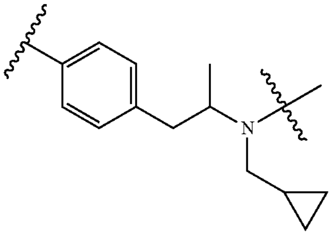

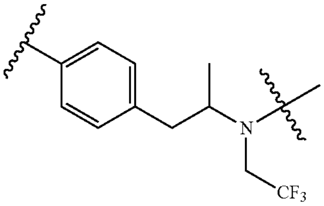

,

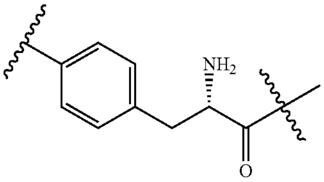

,

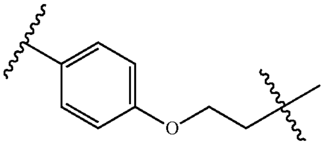

,

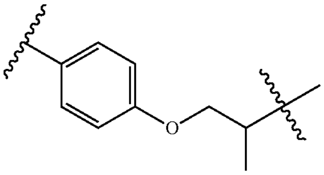

,

-continued

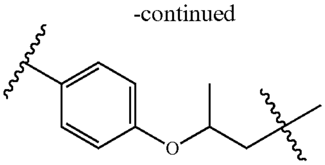

, or

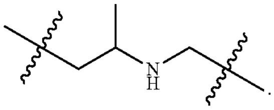

In another embodiment of a compound of formula I or IV or a pharmaceutically acceptable salt thereof, ring B is a bicyclic heterocycloalkylene optionally substituted with up to three substituents selected from the group consisting of $C_1$-$C_6$ alkyl, $C_1$-$C_6$ alkoxy, halo, $C_1$-$C_6$ haloalkyl, OH, and $C_1$-$C_6$ hydroxyalkyl.

In another embodiment, ring B is a fused, spiro, or bridged bicyclic heterocycloalkylene containing up to 3 nitrogen atoms, wherein the fused, spiro, or bridged bicyclic heterocycloalkylene is optionally substituted with up to three substituents selected from the group consisting of $C_1$-$C_6$ alkyl, $C_1$-$C_6$ alkoxy, halo, $C_1$-$C_6$ haloalkyl, OH, and $C_1$-$C_6$ hydroxyalkyl.

In another embodiment, ring B is a fused bicyclic heterocycloalkylene containing up to 2 nitrogen atoms.

In another embodiment, ring B is a spiro bicyclic heterocycloalkylene containing up to 2 nitrogen atoms.

In another embodiment, ring B is a bridged bicyclic heterocycloalkylene containing up to 2 nitrogen atoms.

In another embodiment, ring B is a bicyclic cycloalkylene optionally substituted with up to three substituents selected from the group consisting of $C_1$-$C_6$ alkyl, $C_1$-$C_6$ alkoxy, halo, $C_1$-$C_6$ haloalkyl, OH, and $C_1$-$C_6$ hydroxyalkyl.

In another embodiment, ring B is a fused, spiro, or bridged bicyclic cycloalkylene optionally substituted with up to two substituents selected from the group consisting of $C_1$-$C_6$ alkyl, $C_1$-$C_6$ alkoxy, halo, $C_1$-$C_6$ haloalkyl, OH, and $C_1$-$C_6$ hydroxyalkyl.

In another embodiment, ring B is a fused bicyclic cycloalkylene.

In another embodiment, ring B is a spiro bicyclic cycloalkylene.

In another embodiment, ring B is a bridged bicyclic cycloalkylene.

In another embodiment, ring B is

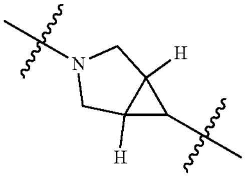

,

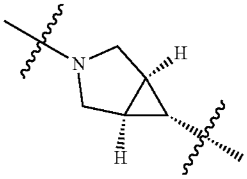

,

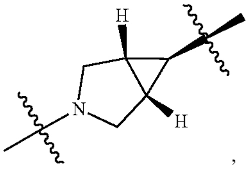

,

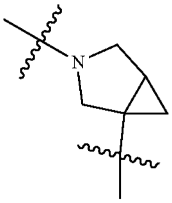

,

-continued

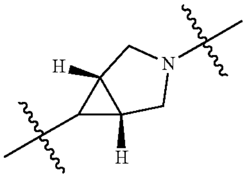,
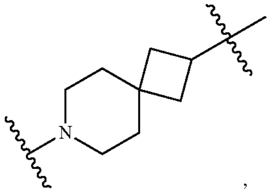,
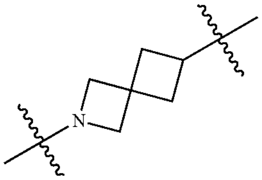,
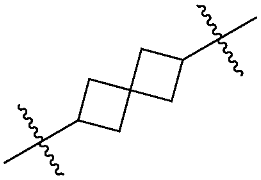, or
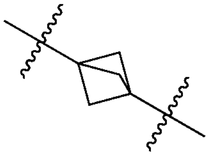.

In another embodiment of a compound of formula I or IV or a pharmaceutically acceptable salt thereof, L is absent.

In another embodiment, L is a linear or branched $C_1$-$C_6$ alkylene, wherein up to two carbon atoms of the $C_1$-$C_6$ alkylene may be replaced with O, NH, (C═O), NH(C═O), N—($C_1$-6 alkyl)(C═O), (C═NH), NH(C═N), or N—($C_1$-6 alkyl).

In another embodiment, L is —$CH_2$—.

In another embodiment of a compound of formula I or IV or a pharmaceutically acceptable salt thereof, $R_1$ is H, $NH_2$ or NH($C_1$-$C_6$ alkyl).

In another embodiment, $R_1$ is H or $NH_2$.

In another embodiment of a compound of formula I or IV or a pharmaceutically acceptable salt thereof,

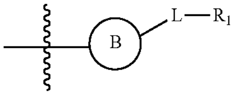

is selected from the group consisting of

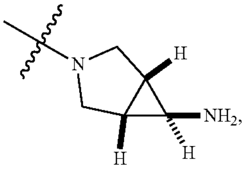
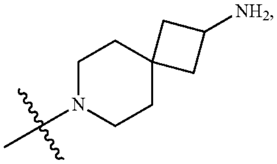
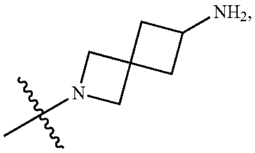
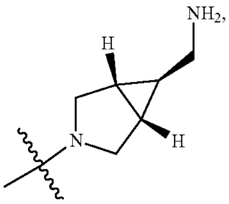

-continued

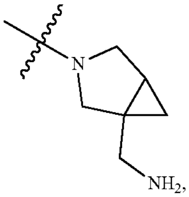
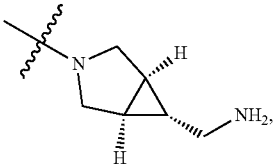
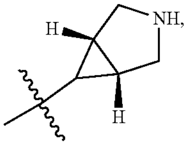
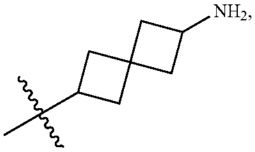
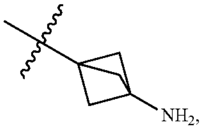 and
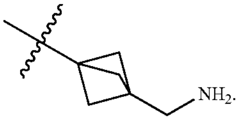

In another embodiment of a compound of formula I or IV or a pharmaceutically acceptable salt thereof, $R_2$ and $R_3$ are each independently selected from the group consisting of $C_1$-$C_6$ alkyl, halo, $C_1$-$C_6$ haloalkyl, and $C_1$-$C_6$ alkoxy and m and n are each independently 0, 1 or 2.

In another embodiment, $R_2$ and $R_3$ are each independently selected from the group consisting of $C_1$-$C_6$ alkyl, halo, $C_1$-$C_6$ alkoxy, and m and n are each independently 0 or 1.

In another embodiment, the compound of formula I or IV is a compound of formula IA:

or a pharmaceutically acceptable salt thereof.

In another embodiment, the compound of formula I or IV is a compound of formula IV-1:

IV-1

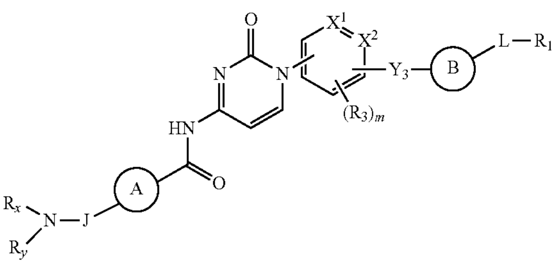

or a pharmaceutically acceptable salt thereof, wherein ring A, ring B, L, J, $Y_3$, $X^1$, $X^2$, $R_1$, $R_3$, $R_x$, $R_y$, and m are the same as defined herein.

In another embodiment, the compound of formula I or IV is a compound of formula IV-2:

IV-3

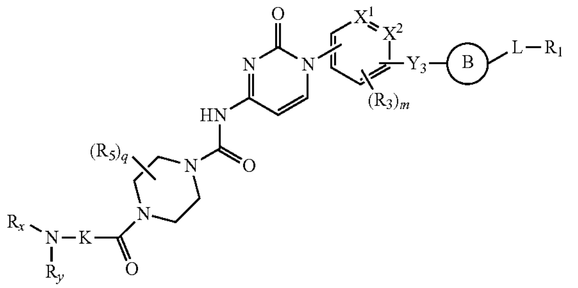

or a pharmaceutically acceptable salt thereof, wherein ring B, L, J, $Y_3$, $X^1$, $X^2$, $R_1$, $R_3$, $R_x$, $R_y$, and m are the same as defined herein; $R_5$ is selected from the group consisting of H, $C_1$-$C_6$ alkyl, $C_1$-$C_6$ alkoxy, halo, CN, $C_1$-$C_6$ haloalkyl, phenyl, OH, $NH_2$, and oxo; and q is 0, 1 or 2.

In another embodiment, the compound of formula I or IV is a compound of formula IV-3:

IV-3

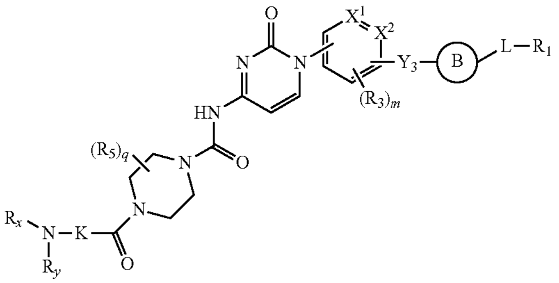

or a pharmaceutically acceptable salt thereof, wherein ring B, L, K, $Y_3$, $X^1$, $X^2$, $R_1$, $R_3$, $R_5$, $R_x$, $R_y$, q and m are the same as defined herein; K is $C_1$-$C_4$ alkylene optionally substituted with hydroxy or alkoxy.

In another embodiment, the compound of formula I or IV is a compound of formula IV-4:

IV-4

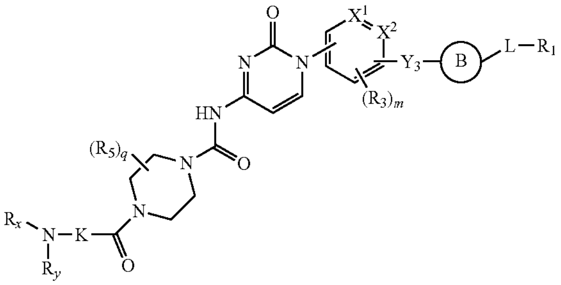

or a pharmaceutically acceptable salt thereof, wherein ring B, L, K, $Y_3$, $X^1$, $X^2$, $R_1$, $R_3$, $R_5$, q and m are the same as defined herein.

In another embodiment, the compound of formula I or IV is a compound of formula IV-4a or IIIA-4b:

IV-4a

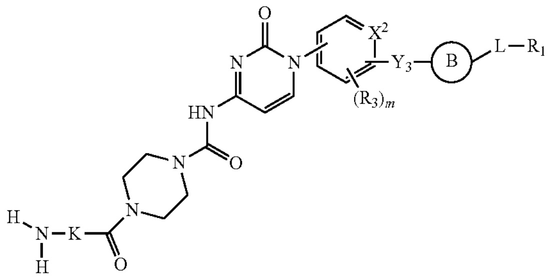

IV-4b

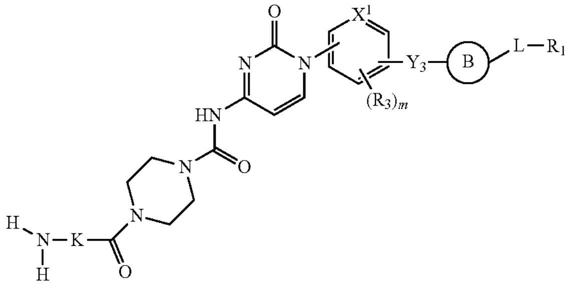

or a pharmaceutically acceptable salt thereof, wherein ring B, L, K, $Y_3$, $X^1$, $X^2$, $R_1$, $R_3$, and m are the same as defined herein.

In another embodiment, the compound of formula I or IV is a compound of formula IV-5:

IV-5

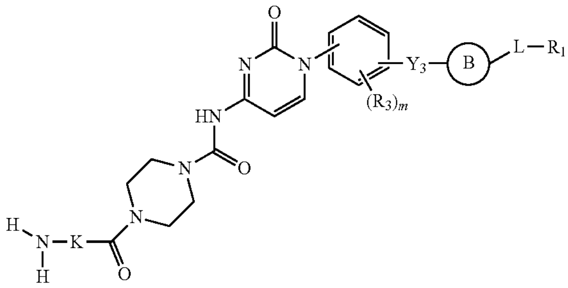

or a pharmaceutically acceptable salt thereof, wherein ring B, L, K, $Y_3$, and $R_1$ are the same as defined herein; $R_3$ is selected from the group consisting of $C_1$-$C_6$ alkyl, halo, $C_1$-$C_6$ haloalkyl, and $C_1$-$C_6$ alkoxy, wherein m is 0, 1 or 2.

In another embodiment, the compound of formula I or IV is a compound of formula IV-6:

IV-6

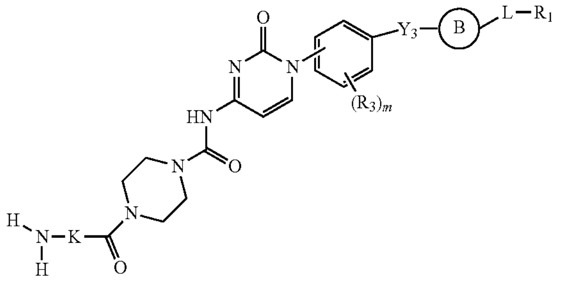

or a pharmaceutically acceptable salt thereof, wherein ring B, L, K, $Y_3$, $R_1$, $R_3$, and m are the same as defined herein.

In another embodiment, the compound of formula I or IV is a compound of formula IV-7:

IV-7

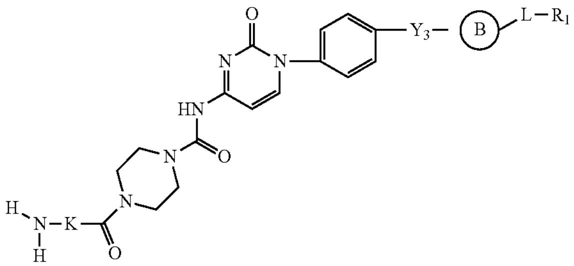

or a pharmaceutically acceptable salt thereof, wherein ring B, L, K, $Y_3$, and $R_1$ are the same as defined herein.

In another embodiment, the compound of formula I or IV is a compound of formula IV-8 or IV-9:

IV-8

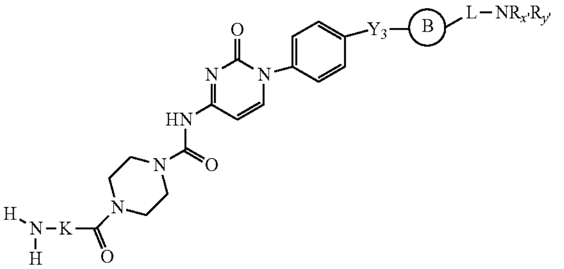

IV-9

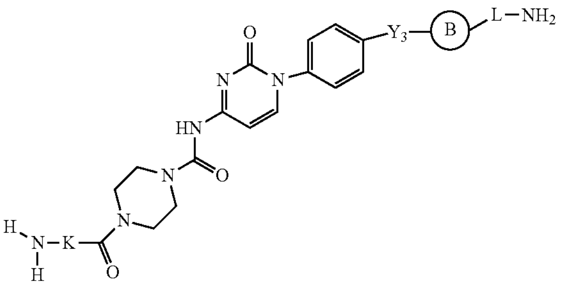

or a pharmaceutically acceptable salt thereof, wherein ring B, L, K, $Y_3$, $R_{x'}$ and $R_{y'}$ are the same as defined herein.

In another embodiment, the compound of formula I or IV is a compound of formula IV-10a, formula IV-10b, formula IV-10c, or formula IV-10 d:

IV-10a

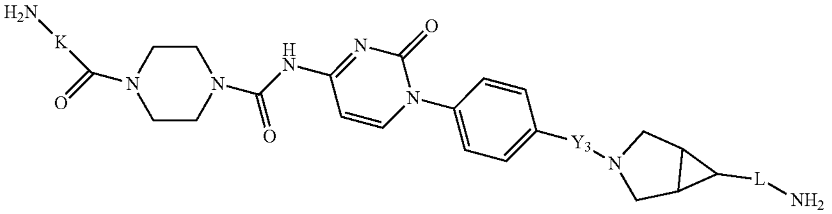

IV-10b

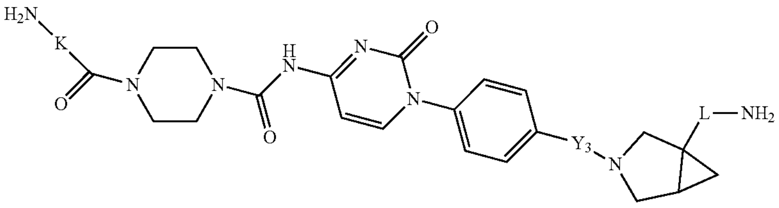

IV-10c

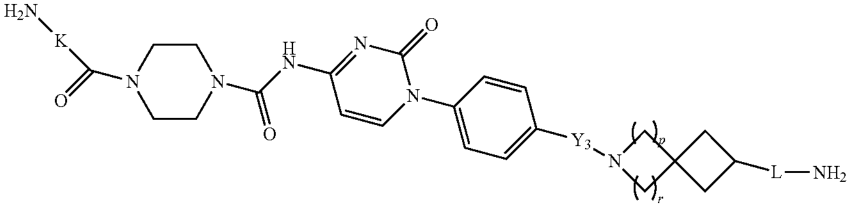

-continued

IV-10d

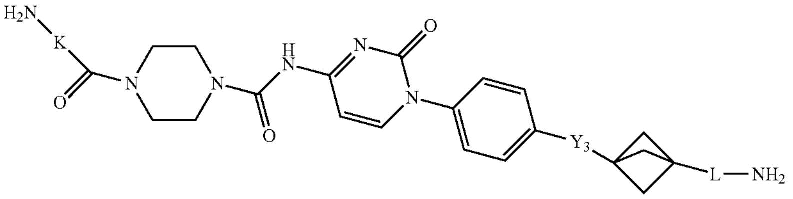

or a pharmaceutically acceptable salt thereof, wherein L, K, and $Y_3$ are the same as defined herein; p and r are each independently 1, 2 or 3.

In another embodiment, the compound of formula I or IV is a compound of formula IV-11:

IV-11

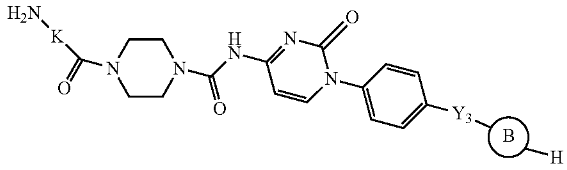

or a pharmaceutically acceptable salt thereof, wherein ring B, K, and $Y_3$ are the same as defined herein.

In another embodiment, the compound of formula I or IV is a compound of formula IV-12:

IV-12

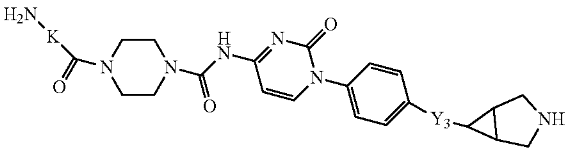

or a pharmaceutically acceptable salt thereof, wherein K and $Y_3$ are the same as defined herein.

In another aspect, the disclosure provides a compound or a pharmaceutically acceptable salt thereof which is depicted in Table 7. In Table 7a possible pharmaceutically acceptable salt and the free base is shown for each compound.

TABLE 7
| Compounds of Formula I | | |
|---|---|---|
| No. | Salt Structure | Free Base Structure |
| 1 | 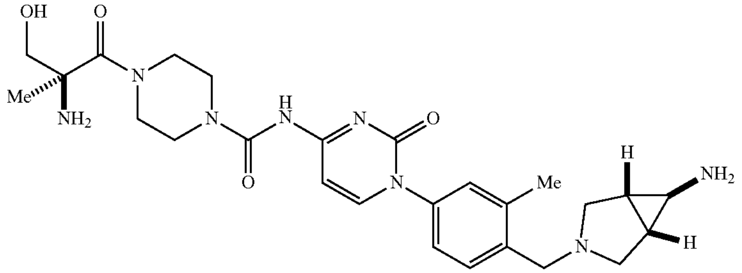 3 HCl | 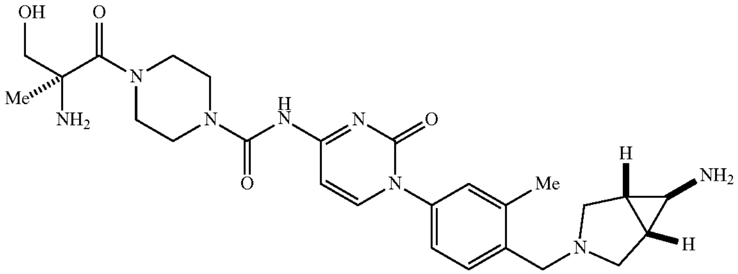 [SMILES: Cc1cc(-n2ccc(NC(=O)N3CCN(C(=O)[C@@](C)(N)CO)CC3)nc2=O)ccc1CN1C[C@@H]2[C@@H](N)[C@@H]2C1] |
| 2 | 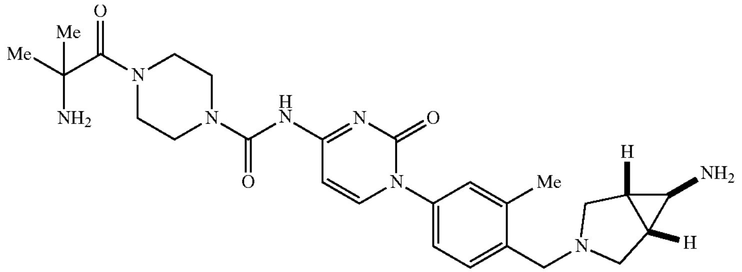 3 HCl | 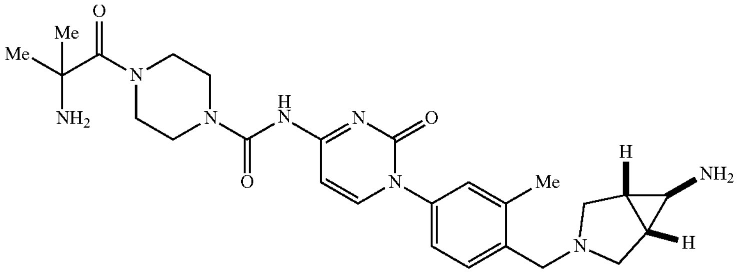 [SMILES: Cc1cc(-n2ccc(NC(=O)N3CCN(C(=O)C(C)(C)N)CC3)nc2=O)ccc1CN1C[C@@H]2[C@@H](N)[C@@H]2C1] |
| 3 | 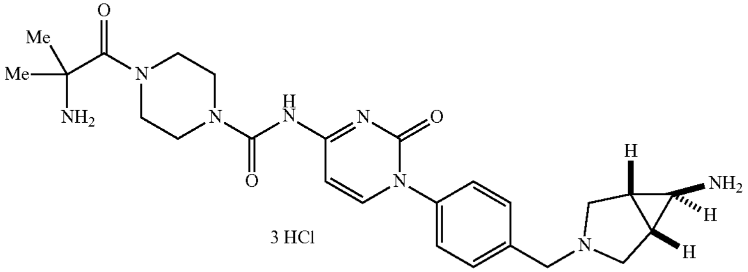 [SMILES: CC(C)(N)C(=O)N1CCN(C(=O)Nc2ccn(-c3ccc(CN4C[C@@H]5[C@@H](N)[C@@H]5C4)cc3)c(=O)n2)CC1] 3 HCl | 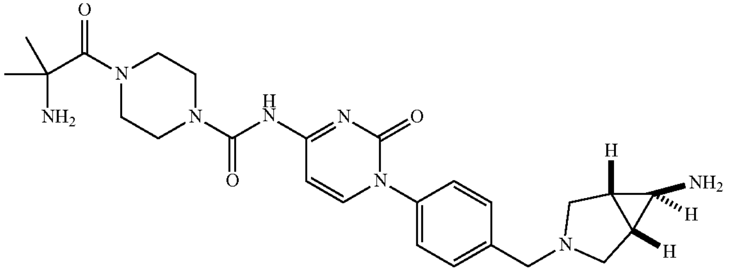 [SMILES: CC(C)(N)C(=O)N1CCN(C(=O)Nc2ccn(-c3ccc(CN4C[C@@H]5[C@@H](N)[C@@H]5C4)cc3)c(=O)n2)CC1] |

TABLE 7-continued
| Compounds of Formula I | | |
|---|---|---|
| No. | Salt Structure | Free Base Structure |
| 4 | 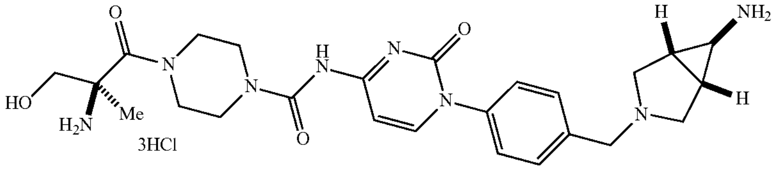 [SMILES: C[C@](N)(CO)C(=O)N1CCN(C(=O)Nc2ccn(-c3ccc(CN4C[C@@H]5[C@@H](N)[C@@H]5C4)cc3)c(=O)n2)CC1] 3HCl | 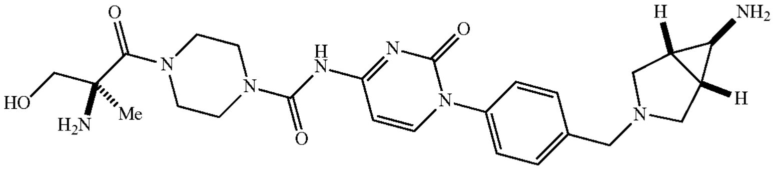 [SMILES: C[C@](N)(CO)C(=O)N1CCN(C(=O)Nc2ccn(-c3ccc(CN4C[C@@H]5[C@@H](N)[C@@H]5C4)cc3)c(=O)n2)CC1] |
| 5 | 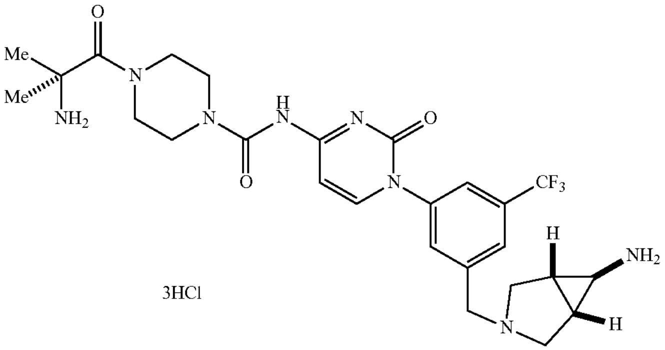 3HCl | 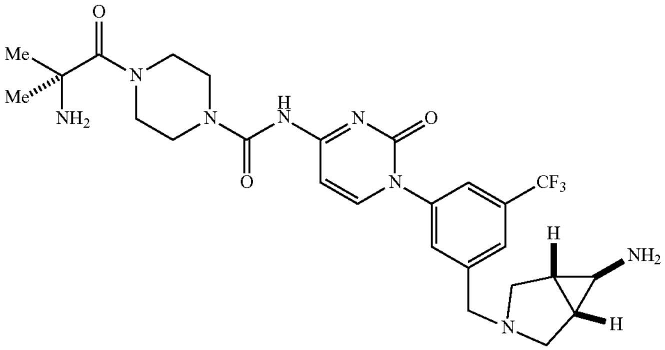 |
| 6 | 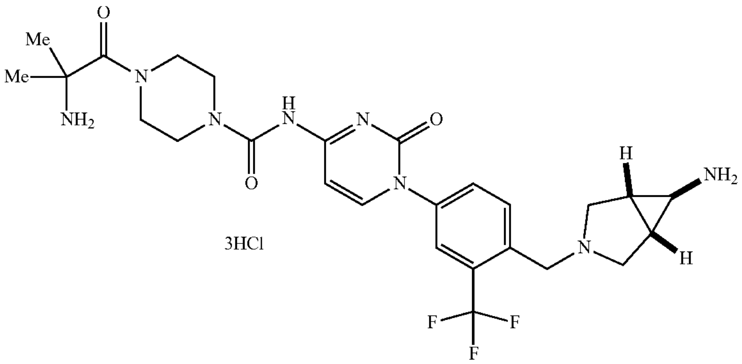 [SMILES: CC(C)(N)C(=O)N1CCN(C(=O)Nc2ccn(-c3ccc(CN4C[C@@H]5[C@@H](N)[C@@H]5C4)c(C(F)(F)F)c3)c(=O)n2)CC1] 3HCl | 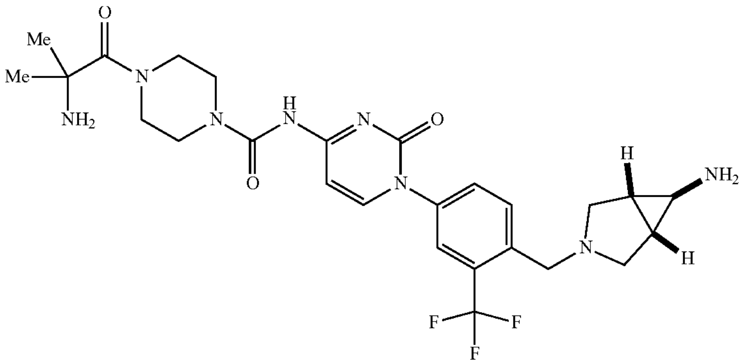 [SMILES: CC(C)(N)C(=O)N1CCN(C(=O)Nc2ccn(-c3ccc(CN4C[C@@H]5[C@@H](N)[C@@H]5C4)c(C(F)(F)F)c3)c(=O)n2)CC1] |

TABLE 7-continued
| Compounds of Formula I | | |
|---|---|---|
| No. | Salt Structure | Free Base Structure |
| 7 | 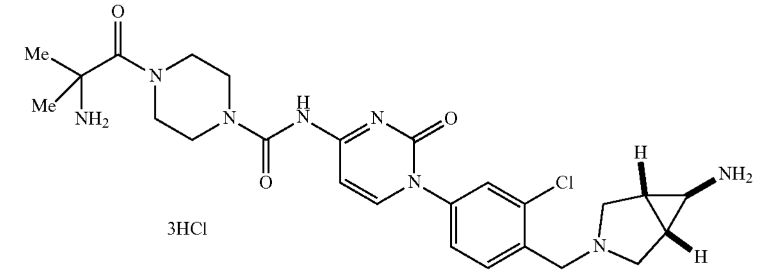 [SMILES: CC(C)(N)C(=O)N1CCN(C(=O)Nc2ccn(-c3ccc(CN4C[C@@H]5[C@@H](N)[C@@H]5C4)c(Cl)c3)c(=O)n2)CC1] 3HCl | 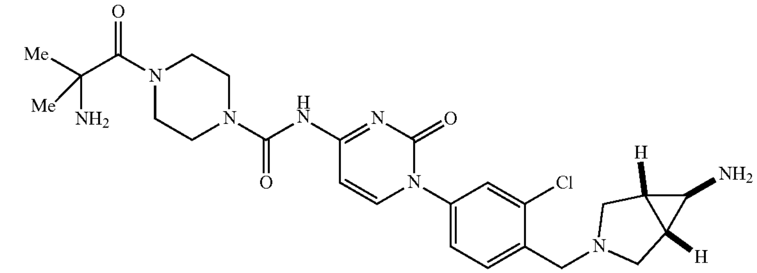 [SMILES: CC(C)(N)C(=O)N1CCN(C(=O)Nc2ccn(-c3ccc(CN4C[C@@H]5[C@@H](N)[C@@H]5C4)c(Cl)c3)c(=O)n2)CC1] |
| 8 | 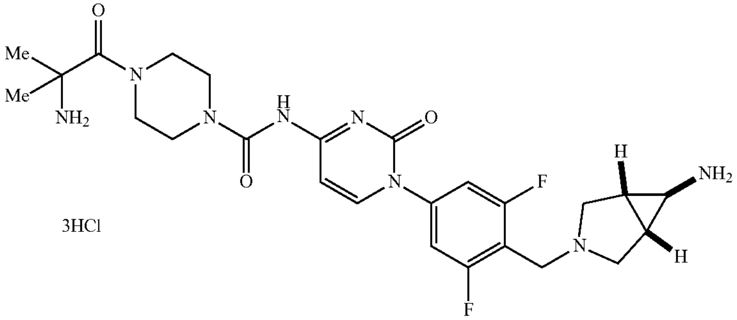 [SMILES: CC(C)(N)C(=O)N1CCN(C(=O)Nc2ccn(-c3cc(F)c(CN4C[C@@H]5[C@@H](N)[C@@H]5C4)c(F)c3)c(=O)n2)CC1] 3HCl | 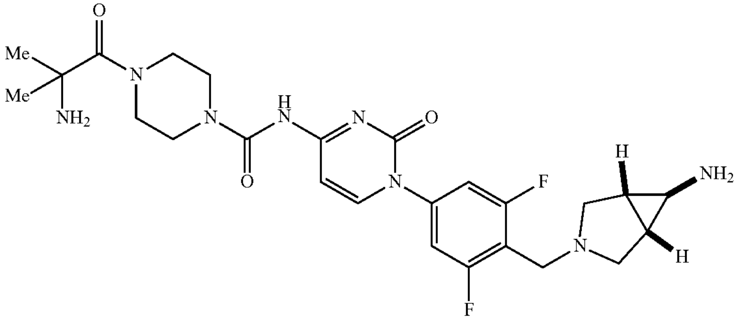 [SMILES: CC(C)(N)C(=O)N1CCN(C(=O)Nc2ccn(-c3cc(F)c(CN4C[C@@H]5[C@@H](N)[C@@H]5C4)c(F)c3)c(=O)n2)CC1] |
| 9 | 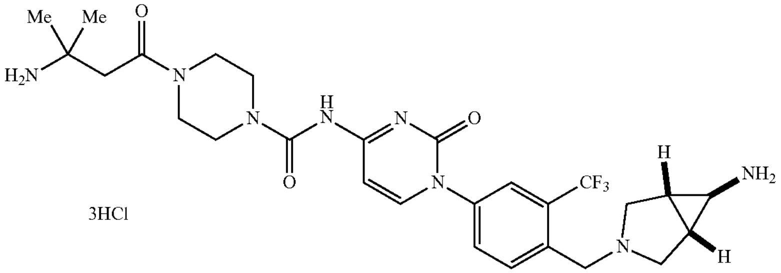 [SMILES: CC(C)(N)CC(=O)N1CCN(C(=O)Nc2ccn(-c3ccc(CN4C[C@@H]5[C@@H](N)[C@@H]5C4)c(C(F)(F)F)c3)c(=O)n2)CC1] 3HCl | 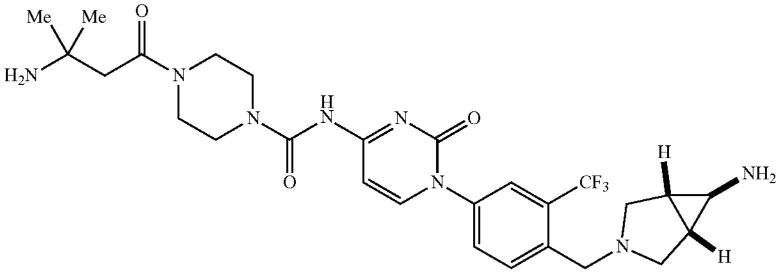 [SMILES: CC(C)(N)CC(=O)N1CCN(C(=O)Nc2ccn(-c3ccc(CN4C[C@@H]5[C@@H](N)[C@@H]5C4)c(C(F)(F)F)c3)c(=O)n2)CC1] |

TABLE 7-continued
| Compounds of Formula I | | |
|---|---|---|
| No. | Salt Structure | Free Base Structure |
| 10 | 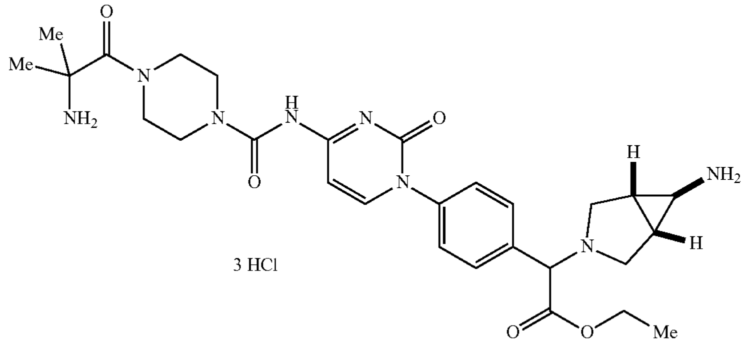 [SMILES: CCOC(=O)C(c1ccc(-n2ccc(NC(=O)N3CCN(C(=O)C(C)(C)N)CC3)nc2=O)cc1)N1C[C@@H]2[C@@H](N)[C@@H]2C1] 3 HCl | 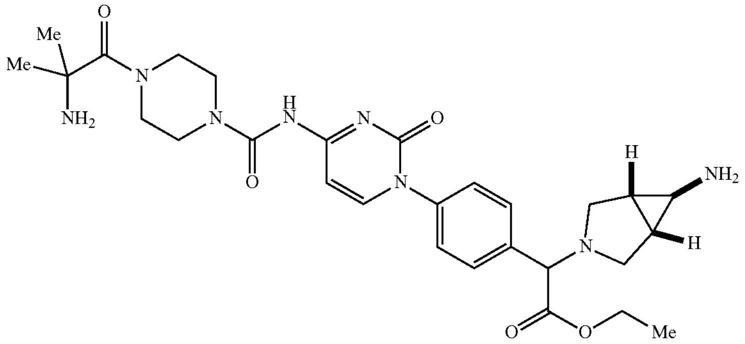 [SMILES: CCOC(=O)C(c1ccc(-n2ccc(NC(=O)N3CCN(C(=O)C(C)(C)N)CC3)nc2=O)cc1)N1C[C@@H]2[C@@H](N)[C@@H]2C1] |
| 11 | 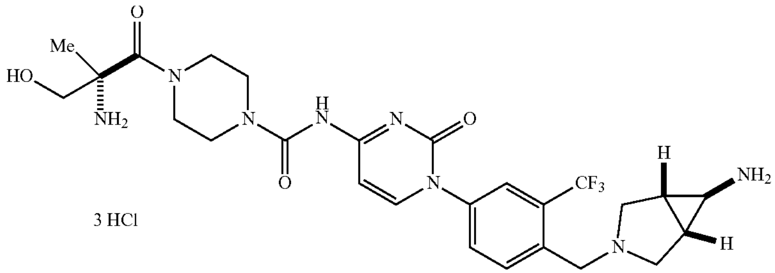 [SMILES: C[C@](N)(CO)C(=O)N1CCN(C(=O)Nc2ccn(-c3ccc(CN4C[C@@H]5[C@@H](N)[C@@H]5C4)c(C(F)(F)F)c3)c(=O)n2)CC1] 3 HCl | 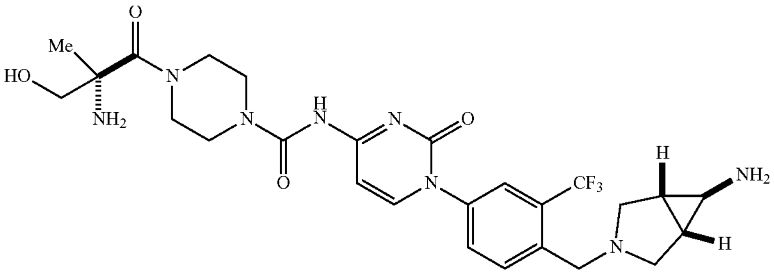 [SMILES: C[C@](N)(CO)C(=O)N1CCN(C(=O)Nc2ccn(-c3ccc(CN4C[C@@H]5[C@@H](N)[C@@H]5C4)c(C(F)(F)F)c3)c(=O)n2)CC1] |
| 12 | 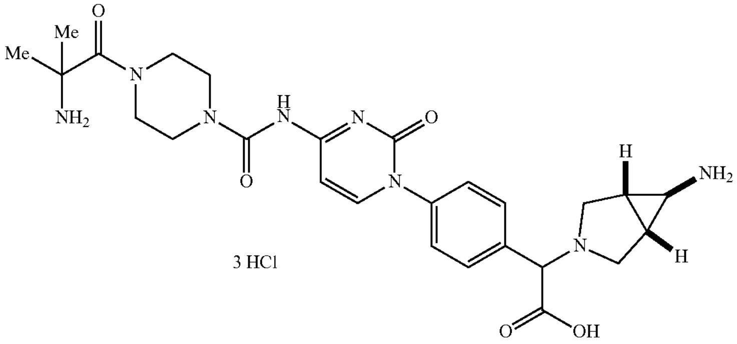 [SMILES: CC(C)(N)C(=O)N1CCN(C(=O)Nc2ccn(-c3ccc(C(C(=O)O)N4C[C@@H]5[C@@H](N)[C@@H]5C4)cc3)c(=O)n2)CC1] 3 HCl | 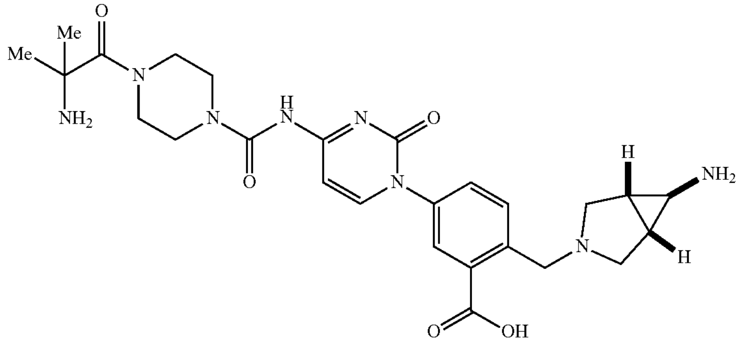 [SMILES: CC(C)(N)C(=O)N1CCN(C(=O)Nc2ccn(-c3ccc(CN4C[C@@H]5[C@@H](N)[C@@H]5C4)c(C(=O)O)c3)c(=O)n2)CC1] |

TABLE 7-continued
| Compounds of Formula I | | |
|---|---|---|
| No. | Salt Structure | Free Base Structure |
| 13 | 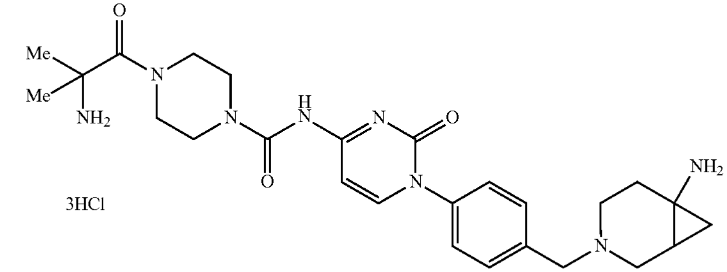 [SMILES: CC(C)(N)C(=O)N1CCN(C(=O)Nc2ccn(-c3ccc(CN4CCC5(N)CC5C4)cc3)c(=O)n2)CC1] 3HCl | 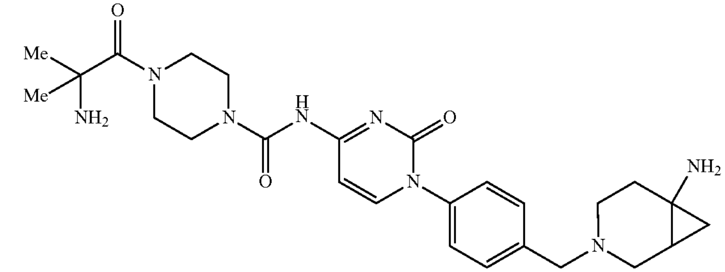 [SMILES: CC(C)(N)C(=O)N1CCN(C(=O)Nc2ccn(-c3ccc(CN4CCC5(N)CC5C4)cc3)c(=O)n2)CC1] |
| 14 | 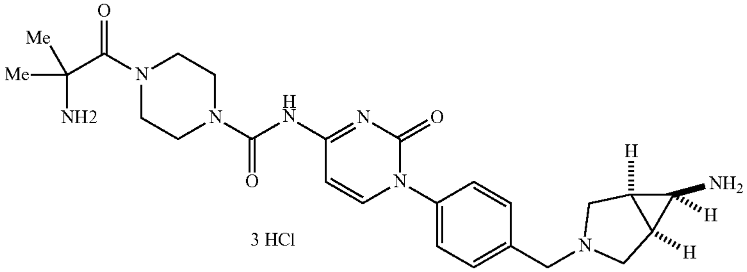 [SMILES: CC(C)(N)C(=O)N1CCN(C(=O)Nc2ccn(-c3ccc(CN4C[C@@H]5[C@H](N)[C@@H]5C4)cc3)c(=O)n2)CC1] 3 HCl | 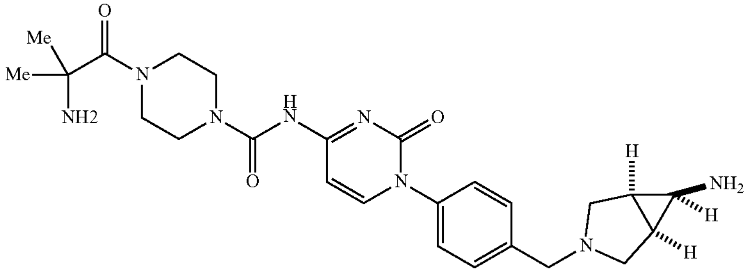 [SMILES: CC(C)(N)C(=O)N1CCN(C(=O)Nc2ccn(-c3ccc(CN4C[C@@H]5[C@H](N)[C@@H]5C4)cc3)c(=O)n2)CC1] |
| 15 | 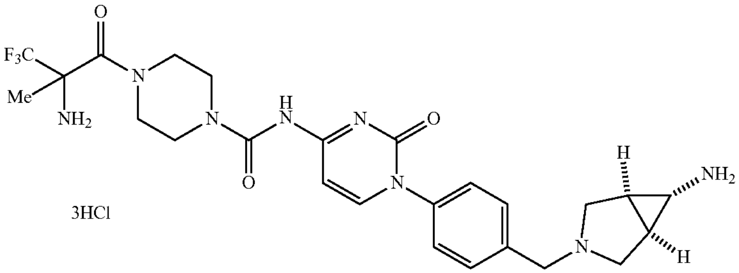 [SMILES: CC(N)(C(=O)N1CCN(C(=O)Nc2ccn(-c3ccc(CN4C[C@@H]5[C@@H](N)[C@@H]5C4)cc3)c(=O)n2)CC1)C(F)(F)F] 3HCl | 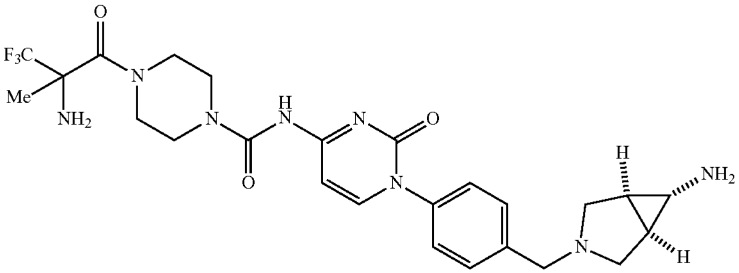 [SMILES: CC(N)(C(=O)N1CCN(C(=O)Nc2ccn(-c3ccc(CN4C[C@@H]5[C@@H](N)[C@@H]5C4)cc3)c(=O)n2)CC1)C(F)(F)F] |

TABLE 7-continued
| Compounds of Formula I | | |
|---|---|---|
| No. | Salt Structure | Free Base Structure |
| 16 | 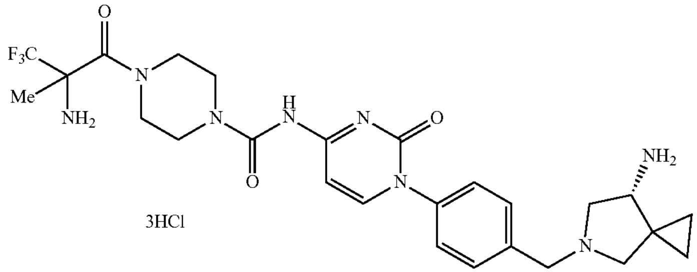 [SMILES: CC(N)(C(=O)N1CCN(C(=O)Nc2ccn(-c3ccc(CN4C[C@H](N)C5(CC5)C4)cc3)c(=O)n2)CC1)C(F)(F)F] 3HCl | 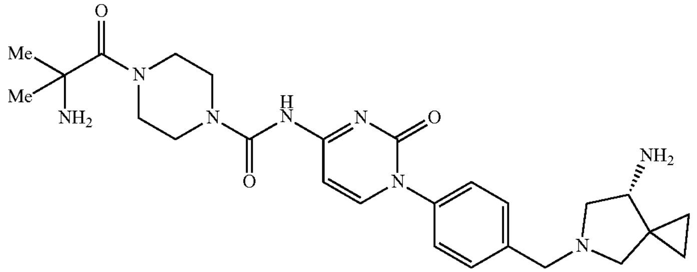 [SMILES: CC(C)(N)C(=O)N1CCN(C(=O)Nc2ccn(-c3ccc(CN4C[C@H](N)C5(CC5)C4)cc3)c(=O)n2)CC1] |
| 17 | 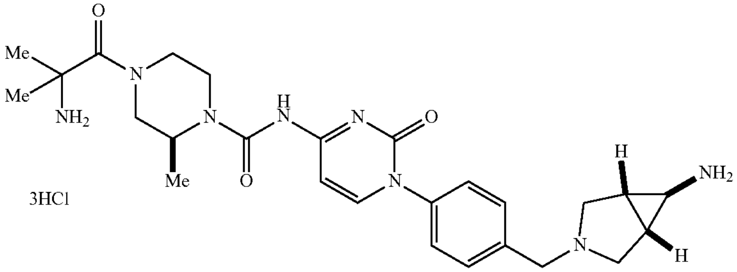 [SMILES: C[C@H]1CN(C(=O)C(C)(C)N)CCN1C(=O)Nc1ccn(-c2ccc(CN3C[C@@H]4[C@@H](N)[C@@H]4C3)cc2)c(=O)n1] 3HCl | 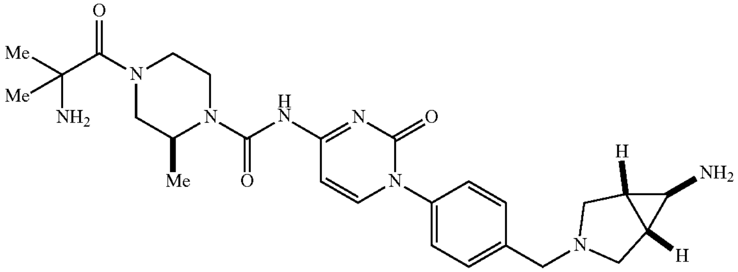 [SMILES: C[C@H]1CN(C(=O)C(C)(C)N)CCN1C(=O)Nc1ccn(-c2ccc(CN3C[C@@H]4[C@@H](N)[C@@H]4C3)cc2)c(=O)n1] |
| 18 | 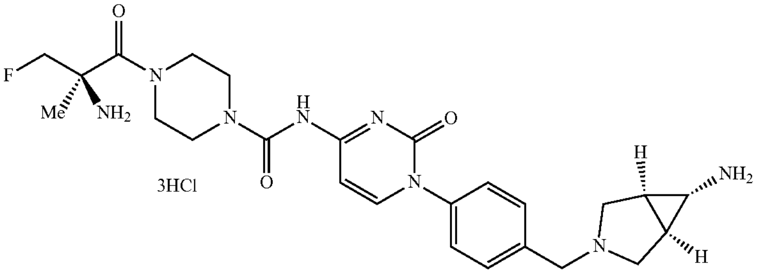 [SMILES: C[C@](N)(CF)C(=O)N1CCN(C(=O)Nc2ccn(-c3ccc(CN4C[C@@H]5[C@@H](N)[C@@H]5C4)cc3)c(=O)n2)CC1] 3HCl | 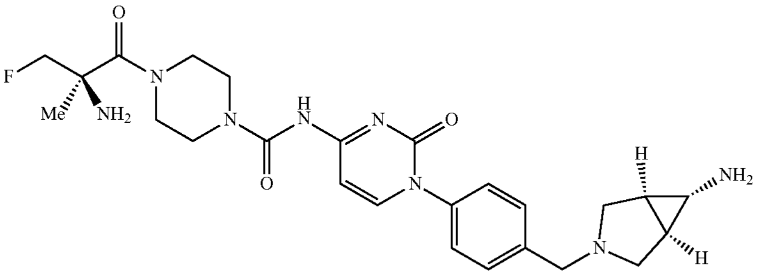 [SMILES: C[C@](N)(CF)C(=O)N1CCN(C(=O)Nc2ccn(-c3ccc(CN4C[C@@H]5[C@@H](N)[C@@H]5C4)cc3)c(=O)n2)CC1] |

TABLE 7-continued
| Compounds of Formula I | | |
|---|---|---|
| No. | Salt Structure | Free Base Structure |
| 19 | 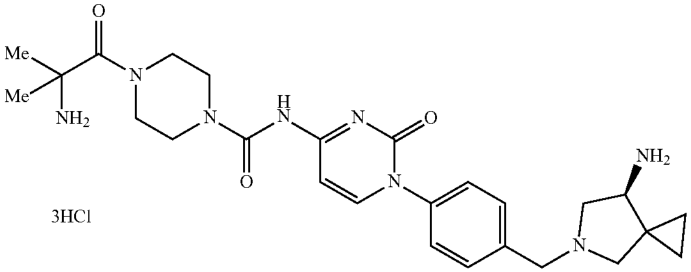 [SMILES: CC(C)(N)C(=O)N1CCN(C(=O)Nc2ccn(-c3ccc(CN4C[C@@H](N)C5(CC5)C4)cc3)c(=O)n2)CC1] 3HCl | 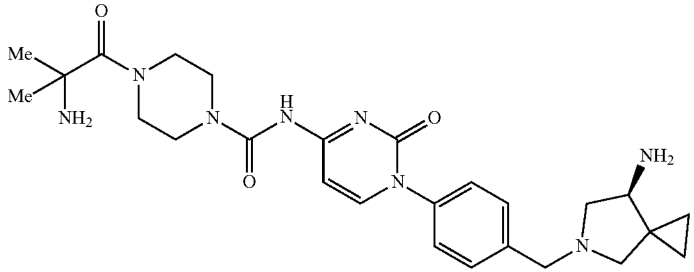 [SMILES: CC(C)(N)C(=O)N1CCN(C(=O)Nc2ccn(-c3ccc(CN4C[C@@H](N)C5(CC5)C4)cc3)c(=O)n2)CC1] |
| 20 | 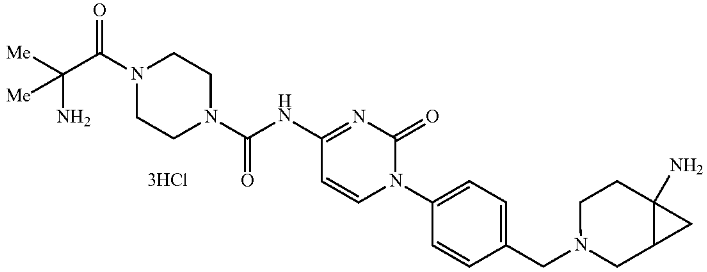 [SMILES: CC(C)(N)C(=O)N1CCN(C(=O)Nc2ccn(-c3ccc(CN4CCC5(N)CC5C4)cc3)c(=O)n2)CC1] 3HCl | 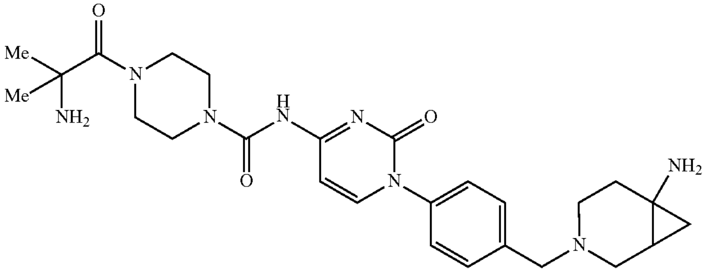 [SMILES: CC(C)(N)C(=O)N1CCN(C(=O)Nc2ccn(-c3ccc(CN4CCC5(N)CC5C4)cc3)c(=O)n2)CC1] |
| 21 | 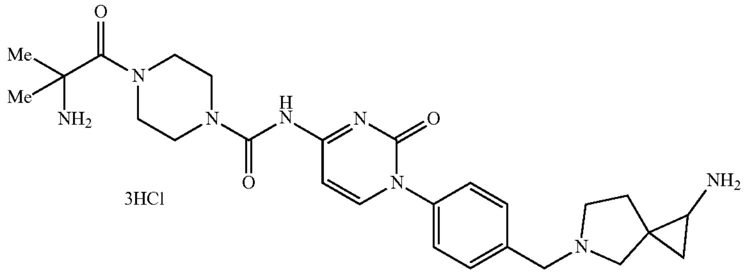 [SMILES: CC(C)(N)C(=O)N1CCN(C(=O)Nc2ccn(-c3ccc(CN4CCC5(CC5N)C4)cc3)c(=O)n2)CC1] 3HCl | 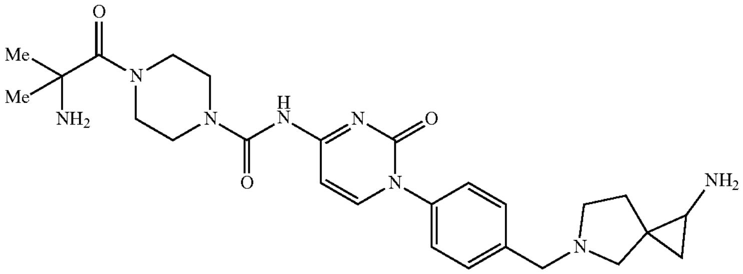 [SMILES: CC(C)(N)C(=O)N1CCN(C(=O)Nc2ccn(-c3ccc(CN4CCC5(CC5N)C4)cc3)c(=O)n2)CC1] |

TABLE 7-continued
| Compounds of Formula I | | |
|---|---|---|
| No. | Salt Structure | Free Base Structure |
| 22 | 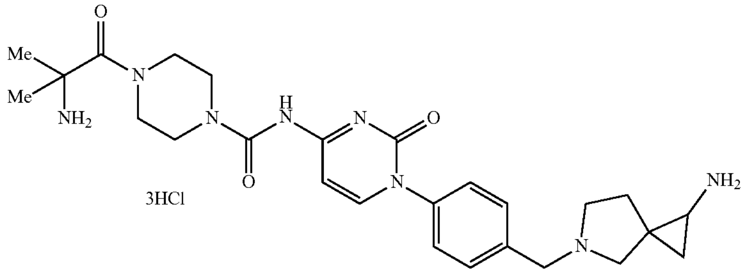 [SMILES: CC(C)(N)C(=O)N1CCN(C(=O)Nc2ccn(-c3ccc(CN4CCC5(CC5N)C4)cc3)c(=O)n2)CC1] 3HCl | 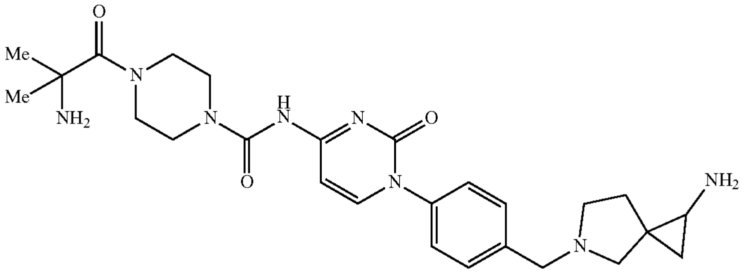 [SMILES: CC(C)(N)C(=O)N1CCN(C(=O)Nc2ccn(-c3ccc(CN4CCC5(CC5N)C4)cc3)c(=O)n2)CC1] |
| 23 | 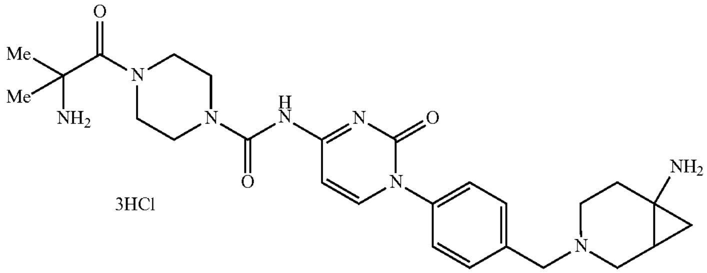 [SMILES: CC(C)(N)C(=O)N1CCN(C(=O)Nc2ccn(-c3ccc(CN4CCC5(N)CC5C4)cc3)c(=O)n2)CC1] 3HCl | 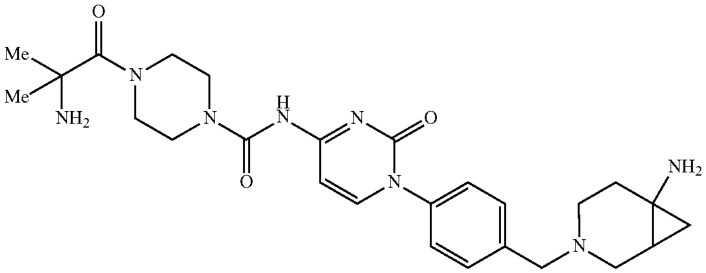 [SMILES: CC(C)(N)C(=O)N1CCN(C(=O)Nc2ccn(-c3ccc(CN4CCC5(N)CC5C4)cc3)c(=O)n2)CC1] |
| 24 | 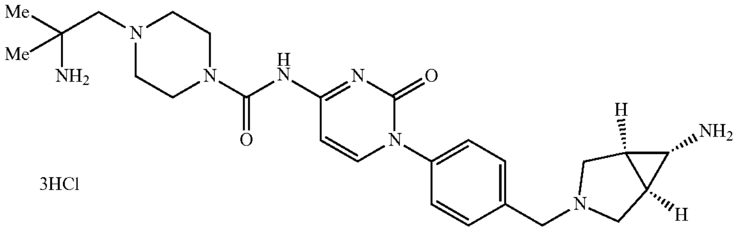 [SMILES: CC(C)(N)CN1CCN(C(=O)Nc2ccn(-c3ccc(CN4C[C@@H]5[C@@H](N)[C@@H]5C4)cc3)c(=O)n2)CC1] 3HCl | 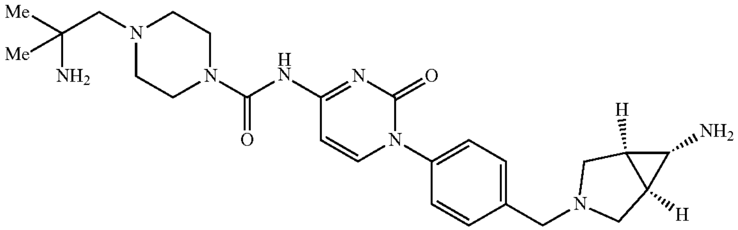 [SMILES: CC(C)(N)CN1CCN(C(=O)Nc2ccn(-c3ccc(CN4C[C@@H]5[C@@H](N)[C@@H]5C4)cc3)c(=O)n2)CC1] |

TABLE 7-continued
| Compounds of Formula I | | |
|---|---|---|
| No. | Salt Structure | Free Base Structure |
| 25 | 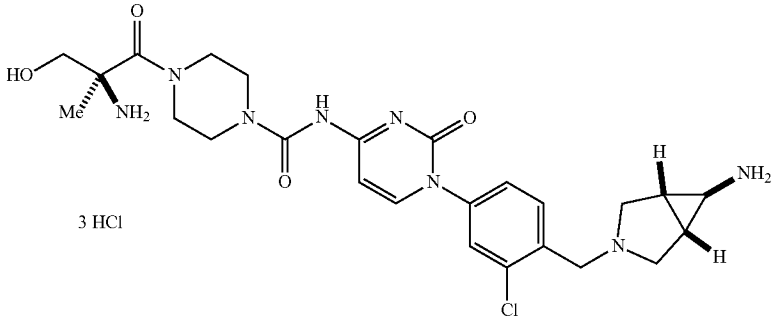 [SMILES: C[C@](N)(CO)C(=O)N1CCN(C(=O)Nc2ccn(-c3ccc(CN4C[C@@H]5[C@@H](N)[C@@H]5C4)c(Cl)c3)c(=O)n2)CC1] 3 HCl | 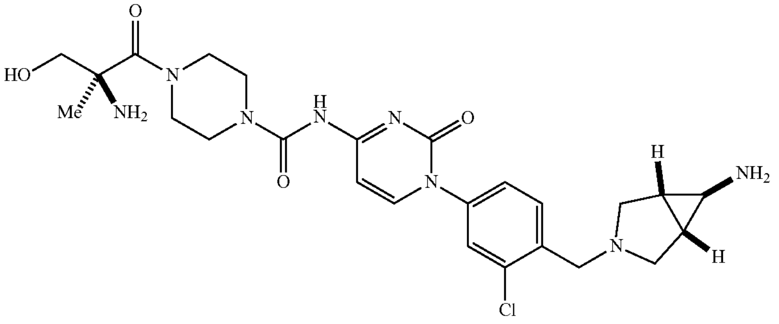 [SMILES: C[C@](N)(CO)C(=O)N1CCN(C(=O)Nc2ccn(-c3ccc(CN4C[C@@H]5[C@@H](N)[C@@H]5C4)c(Cl)c3)c(=O)n2)CC1] |
| 26 | 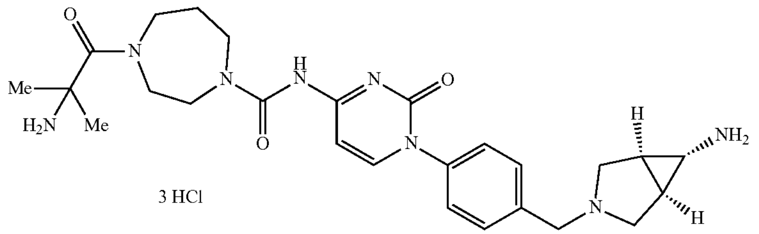 [SMILES: CC(C)(N)C(=O)N1CCCN(C(=O)Nc2ccn(-c3ccc(CN4C[C@@H]5[C@@H](N)[C@@H]5C4)cc3)c(=O)n2)CC1] 3 HCl | 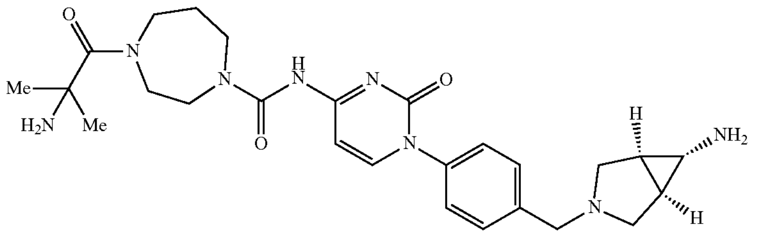 [SMILES: CC(C)(N)C(=O)N1CCCN(C(=O)Nc2ccn(-c3ccc(CN4C[C@@H]5[C@@H](N)[C@@H]5C4)cc3)c(=O)n2)CC1] |
| 27 | 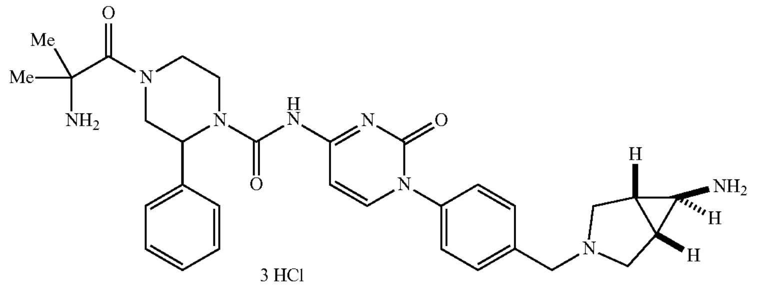 [SMILES: CC(C)(N)C(=O)N1CCN(C(=O)Nc2ccn(-c3ccc(CN4C[C@@H]5[C@@H](N)[C@@H]5C4)cc3)c(=O)n2)C(c2ccccc2)C1] 3 HCl | 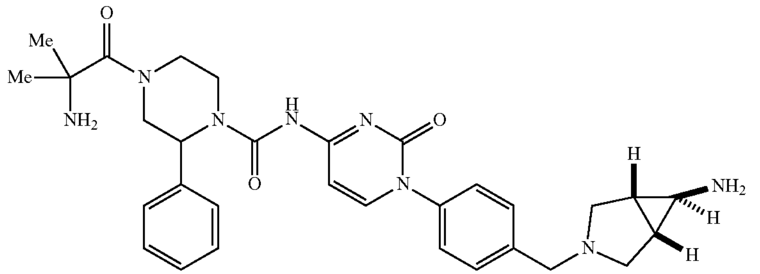 [SMILES: CC(C)(N)C(=O)N1CCN(C(=O)Nc2ccn(-c3ccc(CN4C[C@@H]5[C@@H](N)[C@@H]5C4)cc3)c(=O)n2)C(c2ccccc2)C1] |

TABLE 7-continued
| Compounds of Formula I | | |
|---|---|---|
| No. | Salt Structure | Free Base Structure |
| 28 | 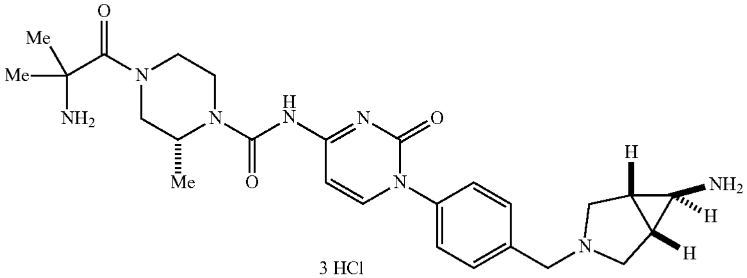 [SMILES: C[C@@H]1CN(C(=O)C(C)(C)N)CCN1C(=O)Nc1ccn(-c2ccc(CN3C[C@@H]4[C@@H](N)[C@@H]4C3)cc2)c(=O)n1] 3 HCl | 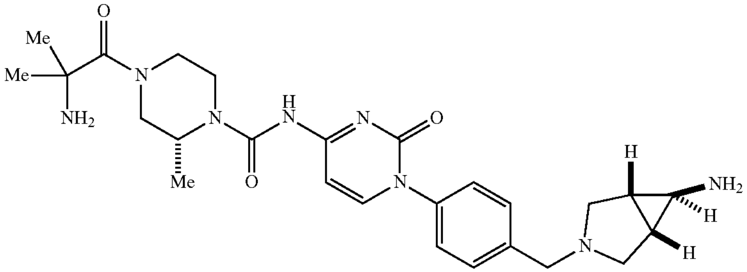 [SMILES: C[C@@H]1CN(C(=O)C(C)(C)N)CCN1C(=O)Nc1ccn(-c2ccc(CN3C[C@@H]4[C@@H](N)[C@@H]4C3)cc2)c(=O)n1] |
| 29 | 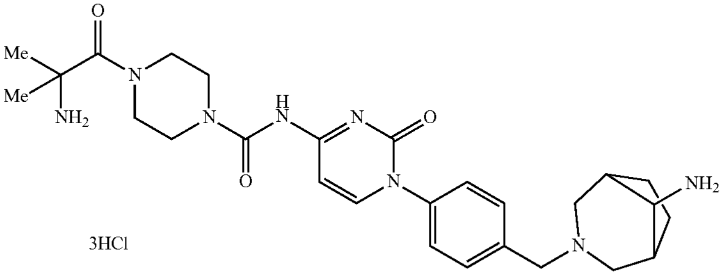 [SMILES: CC(C)(N)C(=O)N1CCN(C(=O)Nc2ccn(-c3ccc(CN4CC5CCC(C4)C5N)cc3)c(=O)n2)CC1] 3HCl | 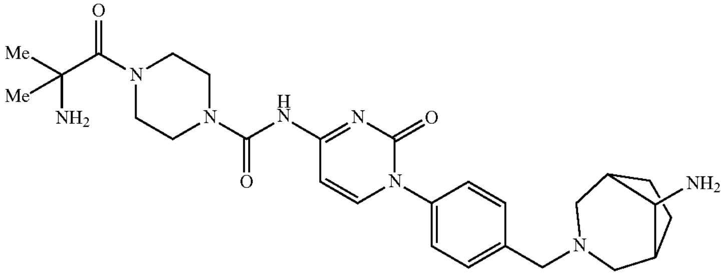 [SMILES: CC(C)(N)C(=O)N1CCN(C(=O)Nc2ccn(-c3ccc(CN4CC5CCC(C4)C5N)cc3)c(=O)n2)CC1] |
| 30 | 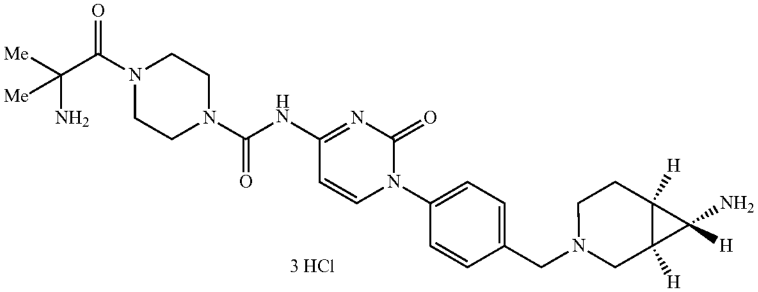 [SMILES: CC(C)(N)C(=O)N1CCN(C(=O)Nc2ccn(-c3ccc(CN4CC[C@H]5[C@H](N)[C@H]5C4)cc3)c(=O)n2)CC1] 3 HCl | 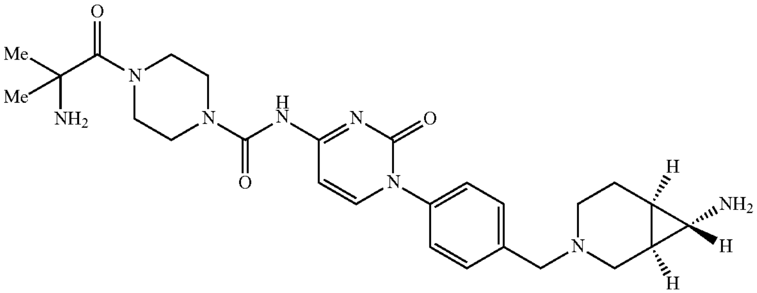 [SMILES: CC(C)(N)C(=O)N1CCN(C(=O)Nc2ccn(-c3ccc(CN4CC[C@H]5[C@H](N)[C@H]5C4)cc3)c(=O)n2)CC1] |

TABLE 7-continued
| Compounds of Formula I | | |
|---|---|---|
| No. | Salt Structure | Free Base Structure |
| 31 | 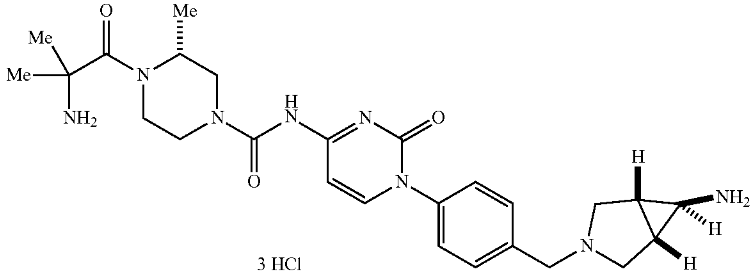 [SMILES: C[C@@H]1CN(C(=O)Nc2ccn(-c3ccc(CN4C[C@@H]5[C@@H](N)[C@@H]5C4)cc3)c(=O)n2)CCN1C(=O)C(C)(C)N] 3 HCl | 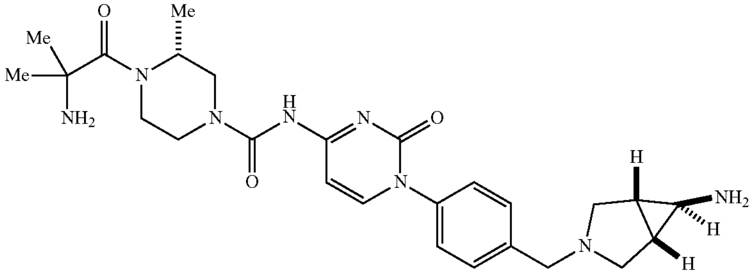 [SMILES: C[C@@H]1CN(C(=O)Nc2ccn(-c3ccc(CN4C[C@@H]5[C@@H](N)[C@@H]5C4)cc3)c(=O)n2)CCN1C(=O)C(C)(C)N] |
| 32 | 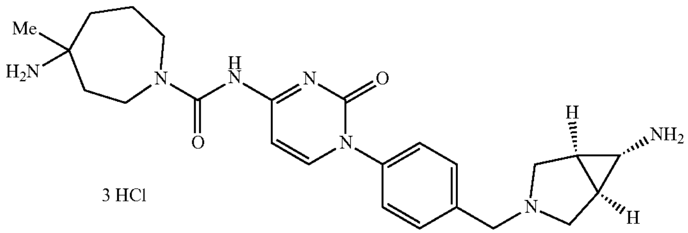 [SMILES: CC1(N)CCCN(C(=O)Nc2ccn(-c3ccc(CN4C[C@@H]5[C@@H](N)[C@@H]5C4)cc3)c(=O)n2)CC1] 3 HCl | 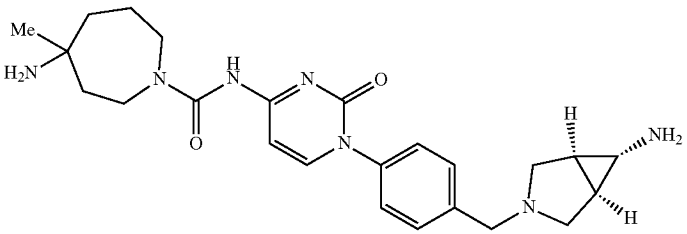 [SMILES: CC1(N)CCCN(C(=O)Nc2ccn(-c3ccc(CN4C[C@@H]5[C@@H](N)[C@@H]5C4)cc3)c(=O)n2)CC1] |
| 33 | 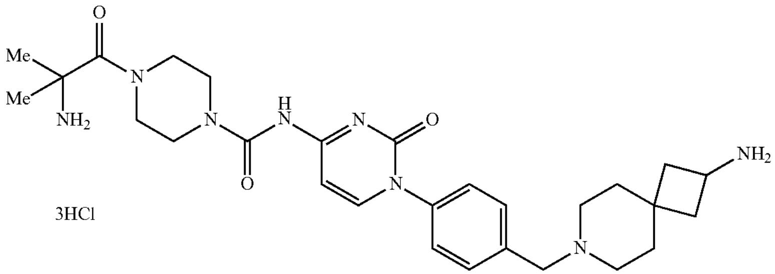 [SMILES: CC(C)(N)C(=O)N1CCN(C(=O)Nc2ccn(-c3ccc(CN4CCC5(CC4)CC(N)C5)cc3)c(=O)n2)CC1] 3HCl | 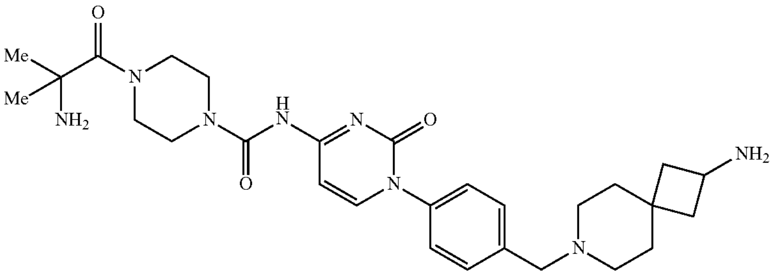 [SMILES: CC(C)(N)C(=O)N1CCN(C(=O)Nc2ccn(-c3ccc(CN4CCC5(CC4)CC(N)C5)cc3)c(=O)n2)CC1] |

TABLE 7-continued
| Compounds of Formula I | | |
|---|---|---|
| No. | Salt Structure | Free Base Structure |
| 34 | 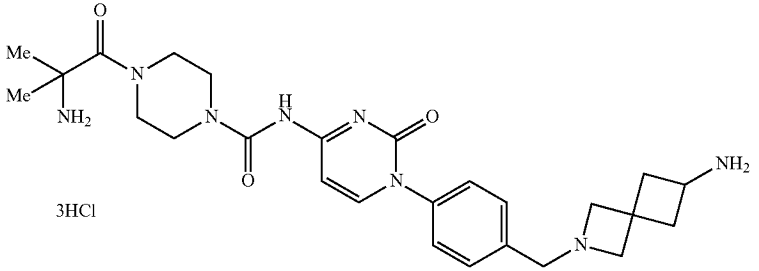 [SMILES: CC(C)(N)C(=O)N1CCN(C(=O)Nc2ccn(-c3ccc(CN4CC5(CC(N)C5)C4)cc3)c(=O)n2)CC1] 3HCl | 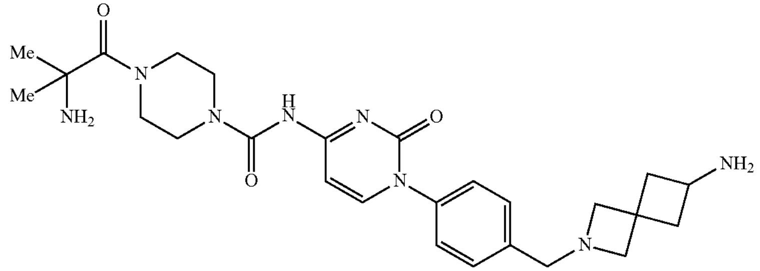 [SMILES: CC(C)(N)C(=O)N1CCN(C(=O)Nc2ccn(-c3ccc(CN4CC5(CC(N)C5)C4)cc3)c(=O)n2)CC1] |
| 35 | 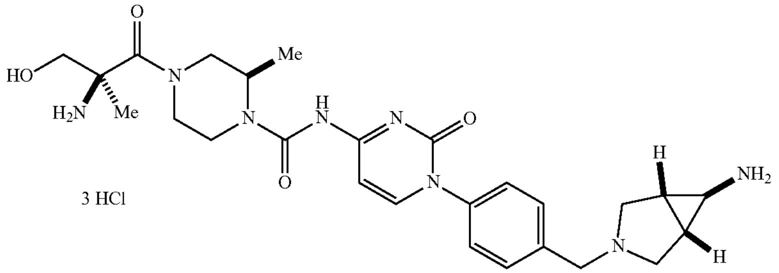 [SMILES: C[C@@H]1CN(C(=O)[C@@](C)(N)CO)CCN1C(=O)Nc1ccn(-c2ccc(CN3C[C@@H]4[C@@H](N)[C@@H]4C3)cc2)c(=O)n1] 3 HCl | 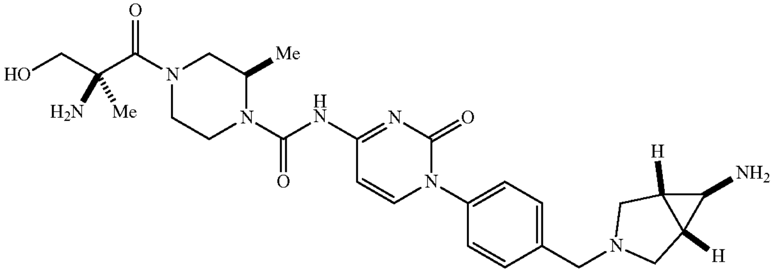 [SMILES: C[C@@H]1CN(C(=O)[C@@](C)(N)CO)CCN1C(=O)Nc1ccn(-c2ccc(CN3C[C@@H]4[C@@H](N)[C@@H]4C3)cc2)c(=O)n1] |
| 36 | 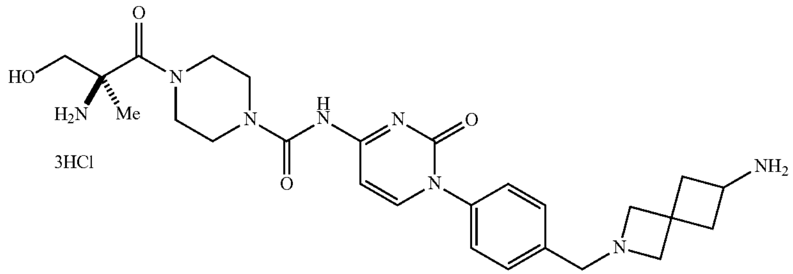 [SMILES: C[C@](N)(CO)C(=O)N1CCN(C(=O)Nc2ccn(-c3ccc(CN4CC5(CC(N)C5)C4)cc3)c(=O)n2)CC1] 3HCl | 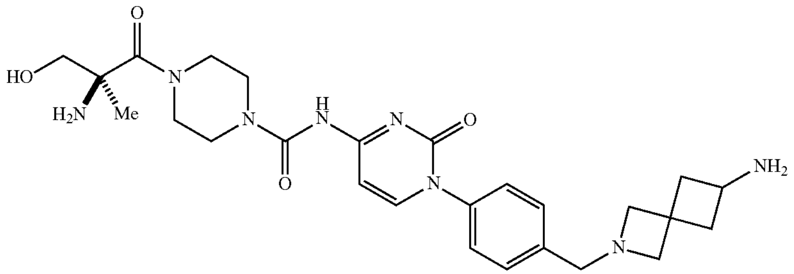 [SMILES: C[C@](N)(CO)C(=O)N1CCN(C(=O)Nc2ccn(-c3ccc(CN4CC5(CC(N)C5)C4)cc3)c(=O)n2)CC1] |

TABLE 7-continued
Compounds of Formula I
| No. | Salt Structure | Free Base Structure |
|---|---|---|
| 37 | 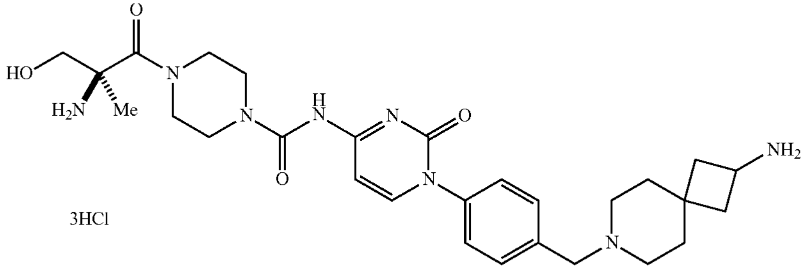 [SMILES: C[C@](N)(CO)C(=O)N1CCN(C(=O)Nc2ccn(-c3ccc(CN4CCC5(CC4)CC(N)C5)cc3)c(=O)n2)CC1] 3HCl | 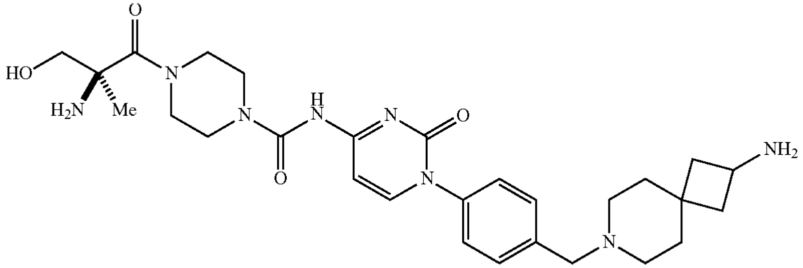 [SMILES: C[C@](N)(CO)C(=O)N1CCN(C(=O)Nc2ccn(-c3ccc(CN4CCC5(CC4)CC(N)C5)cc3)c(=O)n2)CC1] |
| 38 | 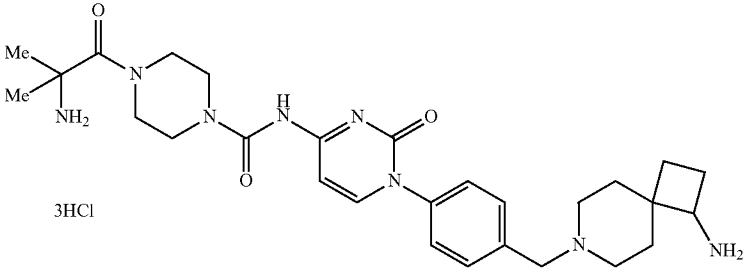 [SMILES: CC(C)(N)C(=O)N1CCN(C(=O)Nc2ccn(-c3ccc(CN4CCC5(CCC5N)CC4)cc3)c(=O)n2)CC1] 3HCl | 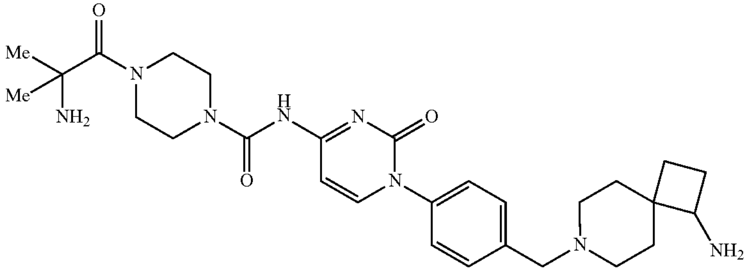 [SMILES: CC(C)(N)C(=O)N1CCN(C(=O)Nc2ccn(-c3ccc(CN4CCC5(CCC5N)CC4)cc3)c(=O)n2)CC1] |
| 39 | 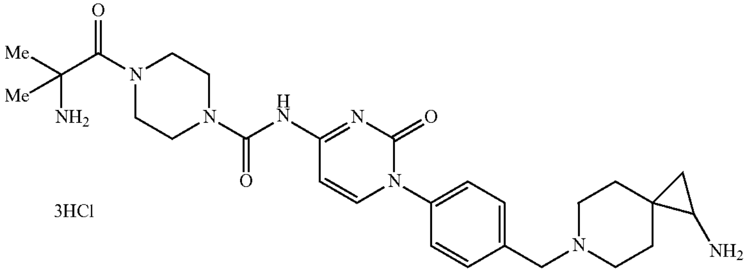 [SMILES: CC(C)(N)C(=O)N1CCN(C(=O)Nc2ccn(-c3ccc(CN4CCC5(CC4)CC5N)cc3)c(=O)n2)CC1] 3HCl | 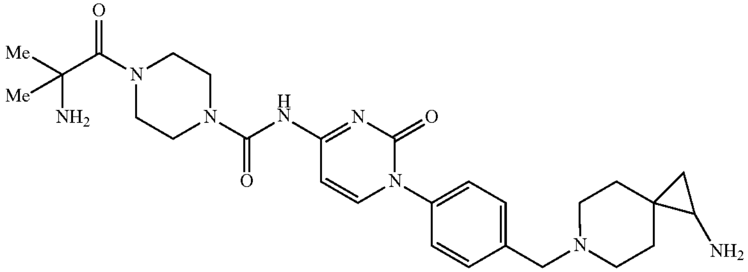 [SMILES: CC(C)(N)C(=O)N1CCN(C(=O)Nc2ccn(-c3ccc(CN4CCC5(CC4)CC5N)cc3)c(=O)n2)CC1] |

TABLE 7-continued
Compounds of Formula I
| No. | Salt Structure | Free Base Structure |
|---|---|---|
| 40 | 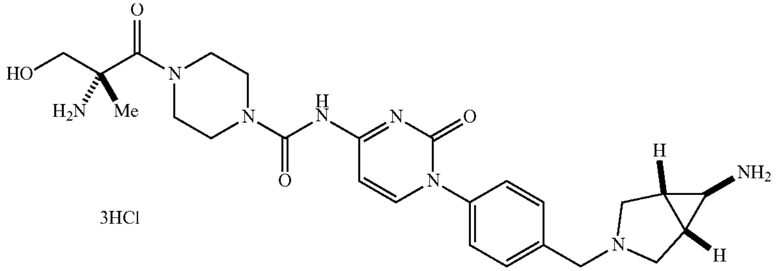 [SMILES: C[C@@](N)(CO)C(=O)N1CCN(C(=O)Nc2ccn(-c3ccc(CN4C[C@@H]5[C@@H](N)[C@@H]5C4)cc3)c(=O)n2)CC1] 3HCl | 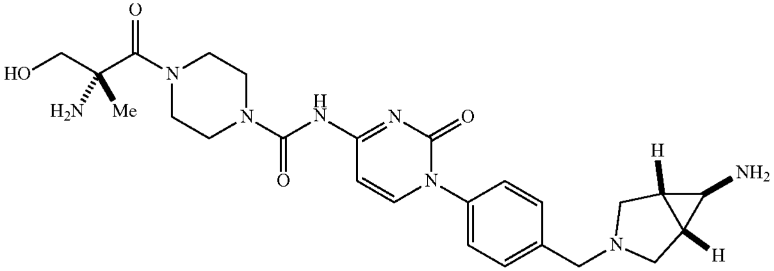 [SMILES: C[C@@](N)(CO)C(=O)N1CCN(C(=O)Nc2ccn(-c3ccc(CN4C[C@@H]5[C@@H](N)[C@@H]5C4)cc3)c(=O)n2)CC1] |
| 41 | 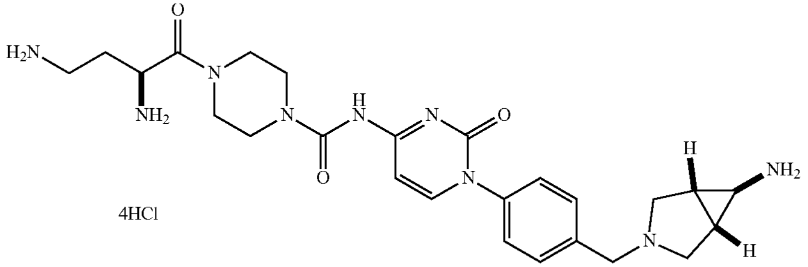 [SMILES: NCC[C@H](N)C(=O)N1CCN(C(=O)Nc2ccn(-c3ccc(CN4C[C@@H]5[C@@H](N)[C@@H]5C4)cc3)c(=O)n2)CC1] 4HCl | 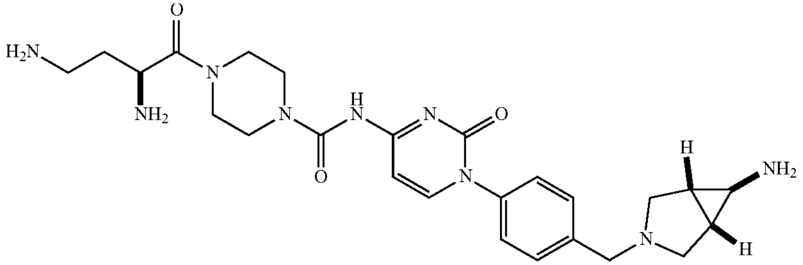 [SMILES: NCC[C@H](N)C(=O)N1CCN(C(=O)Nc2ccn(-c3ccc(CN4C[C@@H]5[C@@H](N)[C@@H]5C4)cc3)c(=O)n2)CC1] |
| 42 | 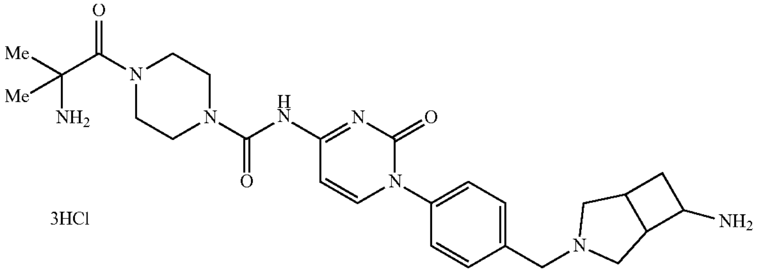 [SMILES: CC(C)(N)C(=O)N1CCN(C(=O)Nc2ccn(-c3ccc(CN4CC5CC(N)C5C4)cc3)c(=O)n2)CC1] 3HCl | 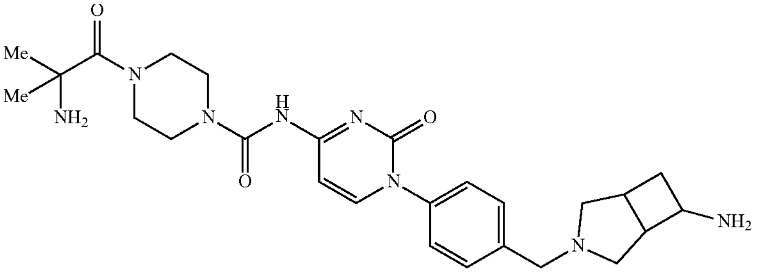 [SMILES: CC(C)(N)C(=O)N1CCN(C(=O)Nc2ccn(-c3ccc(CN4CC5CC(N)C5C4)cc3)c(=O)n2)CC1] |

TABLE 7-continued
| Compounds of Formula I | | |
|---|---|---|
| No. | Salt Structure | Free Base Structure |
| 43 | 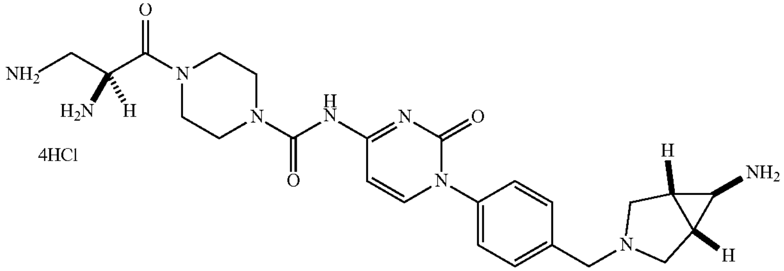 [SMILES: NC[C@H](N)C(=O)N1CCN(C(=O)Nc2ccn(-c3ccc(CN4C[C@@H]5[C@@H](N)[C@@H]5C4)cc3)c(=O)n2)CC1] 4HCl | 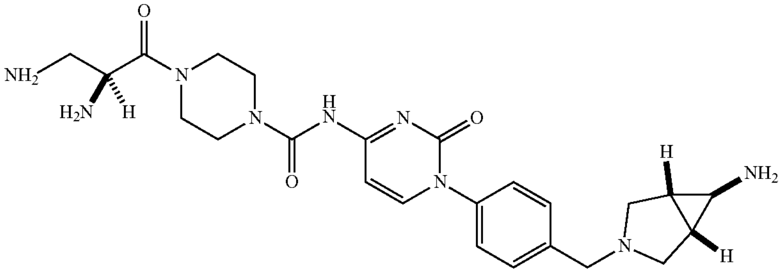 [SMILES: NC[C@H](N)C(=O)N1CCN(C(=O)Nc2ccn(-c3ccc(CN4C[C@@H]5[C@@H](N)[C@@H]5C4)cc3)c(=O)n2)CC1] |
| 44 | 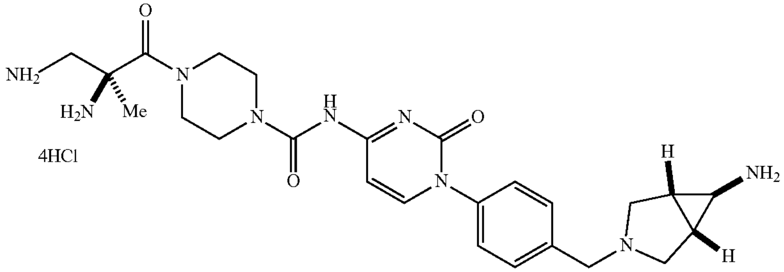 [SMILES: C[C@](N)(CN)C(=O)N1CCN(C(=O)Nc2ccn(-c3ccc(CN4C[C@@H]5[C@@H](N)[C@@H]5C4)cc3)c(=O)n2)CC1] 4HCl | 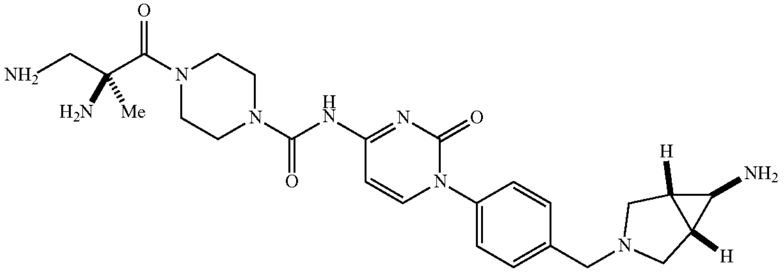 [SMILES: C[C@](N)(CN)C(=O)N1CCN(C(=O)Nc2ccn(-c3ccc(CN4C[C@@H]5[C@@H](N)[C@@H]5C4)cc3)c(=O)n2)CC1] |
| 45 | 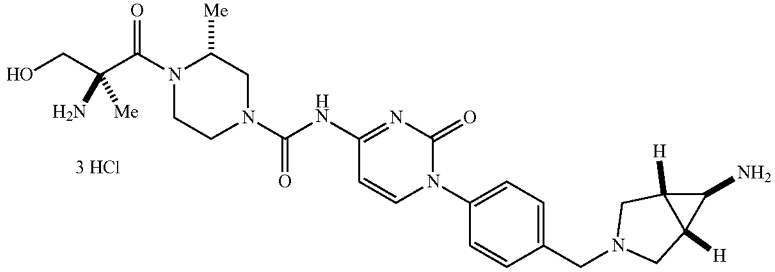 [SMILES: C[C@@H]1CN(C(=O)Nc2ccn(-c3ccc(CN4C[C@@H]5[C@@H](N)[C@@H]5C4)cc3)c(=O)n2)CCN1C(=O)[C@@](C)(N)CO] 3 HCl | 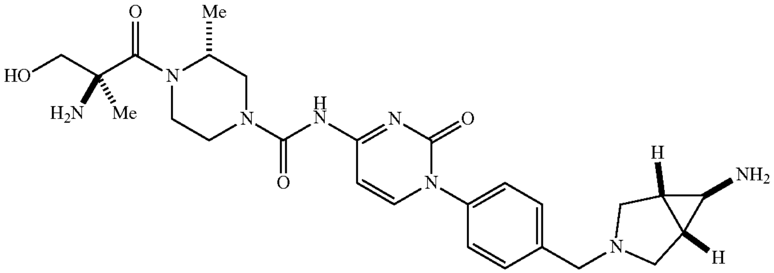 [SMILES: C[C@@H]1CN(C(=O)Nc2ccn(-c3ccc(CN4C[C@@H]5[C@@H](N)[C@@H]5C4)cc3)c(=O)n2)CCN1C(=O)[C@@](C)(N)CO] |

TABLE 7-continued
| Compounds of Formula I | | |
|---|---|---|
| No. | Salt Structure | Free Base Structure |
| 46 | 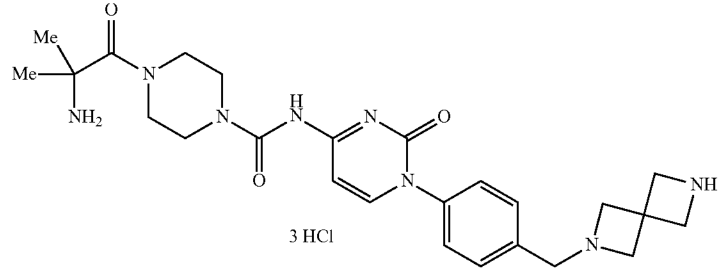 [SMILES: CC(C)(N)C(=O)N1CCN(C(=O)Nc2ccn(-c3ccc(CN4CC5(CNC5)C4)cc3)c(=O)n2)CC1] 3 HCl | 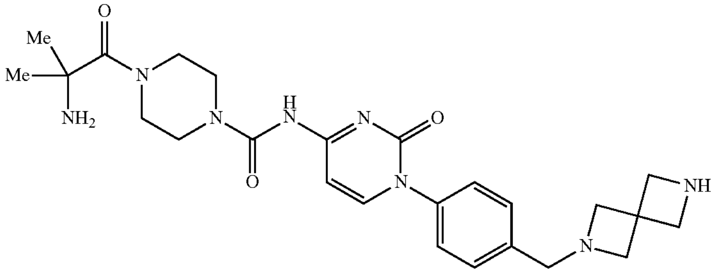 [SMILES: CC(C)(N)C(=O)N1CCN(C(=O)Nc2ccn(-c3ccc(CN4CC5(CNC5)C4)cc3)c(=O)n2)CC1] |
| 47 | 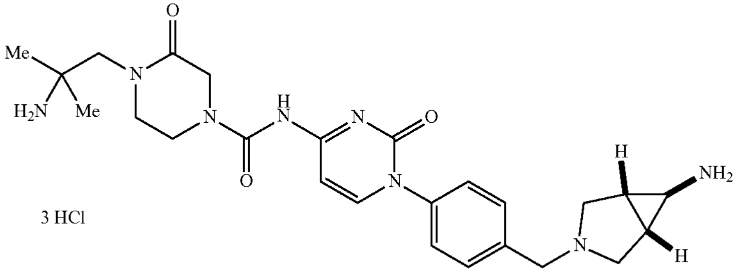 [SMILES: CC(C)(N)CN1CCN(C(=O)Nc2ccn(-c3ccc(CN4C[C@@H]5[C@@H](N)[C@@H]5C4)cc3)c(=O)n2)CC1=O] 3 HCl | 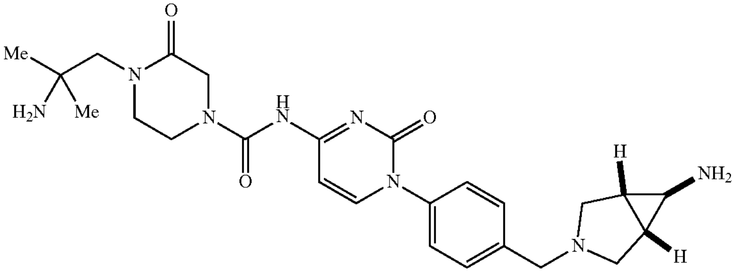 [SMILES: CC(C)(N)CN1CCN(C(=O)Nc2ccn(-c3ccc(CN4C[C@@H]5[C@@H](N)[C@@H]5C4)cc3)c(=O)n2)CC1=O] |
| 48 | 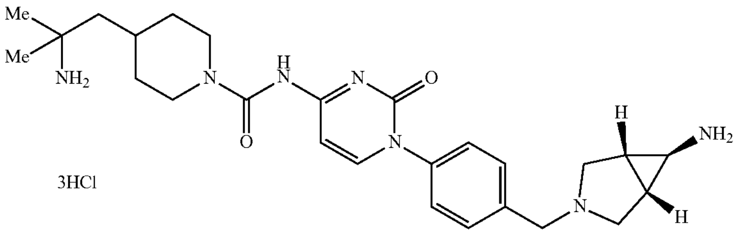 [SMILES: CC(C)(N)CC1CCN(C(=O)Nc2ccn(-c3ccc(CN4C[C@@H]5[C@@H](N)[C@@H]5C4)cc3)c(=O)n2)CC1] 3HCl | 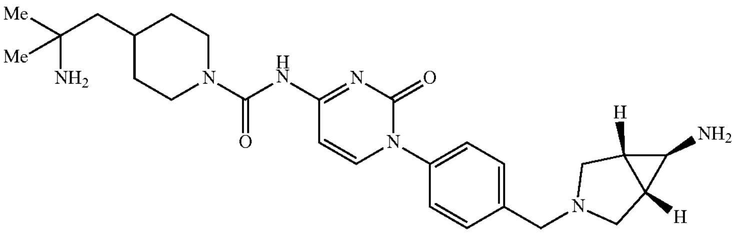 [SMILES: CC(C)(N)CC1CCN(C(=O)Nc2ccn(-c3ccc(CN4C[C@@H]5[C@@H](N)[C@@H]5C4)cc3)c(=O)n2)CC1] |

TABLE 7-continued
| Compounds of Formula I | | |
|---|---|---|
| No. | Salt Structure | Free Base Structure |
| 49 | 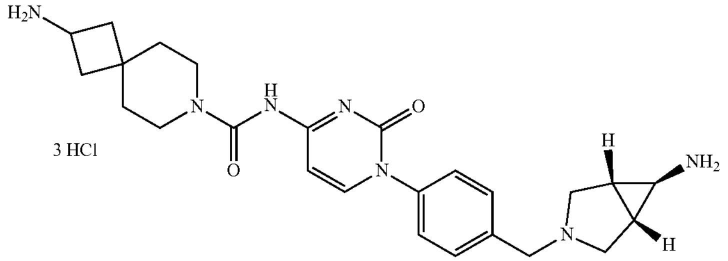 [SMILES: NC1CC2(CCN(C(=O)Nc3ccn(-c4ccc(CN5C[C@@H]6[C@@H](N)[C@@H]6C5)cc4)c(=O)n3)CC2)C1] 3 HCl | 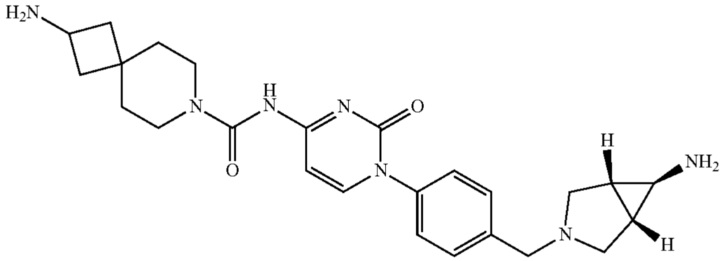 [SMILES: NC1CC2(CCN(C(=O)Nc3ccn(-c4ccc(CN5C[C@@H]6[C@@H](N)[C@@H]6C5)cc4)c(=O)n3)CC2)C1] |
| 50 | 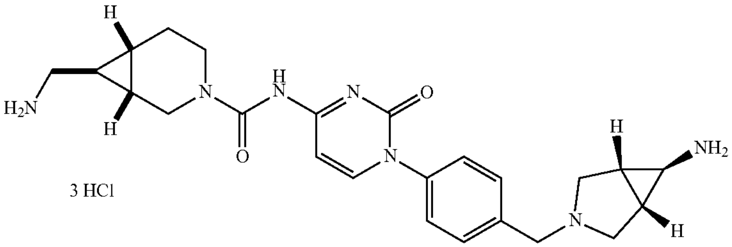 [SMILES: NC[C@H]1[C@@H]2CCN(C(=O)Nc3ccn(-c4ccc(CN5C[C@@H]6[C@@H](N)[C@@H]6C5)cc4)c(=O)n3)C[C@H]12] 3 HCl | 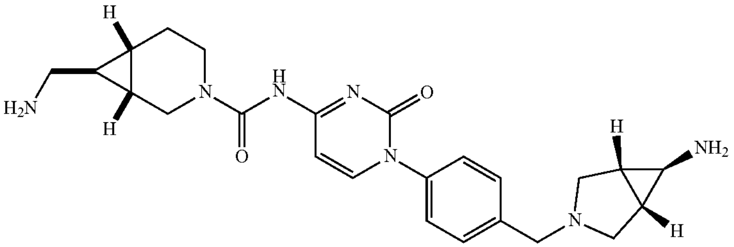 [SMILES: NC[C@H]1[C@@H]2CCN(C(=O)Nc3ccn(-c4ccc(CN5C[C@@H]6[C@@H](N)[C@@H]6C5)cc4)c(=O)n3)C[C@H]12] |
| 51 | 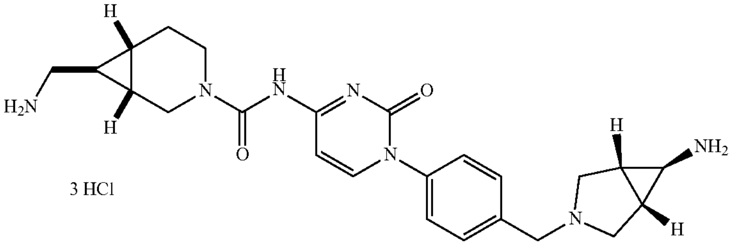 [SMILES: NC[C@H]1[C@@H]2CCN(C(=O)Nc3ccn(-c4ccc(CN5C[C@@H]6[C@@H](N)[C@@H]6C5)cc4)c(=O)n3)C[C@H]12] 3 HCl | 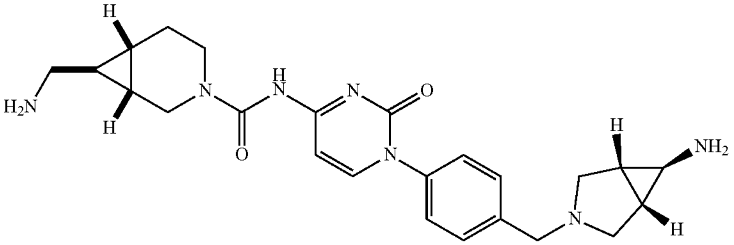 [SMILES: NC[C@H]1[C@@H]2CCN(C(=O)Nc3ccn(-c4ccc(CN5C[C@@H]6[C@@H](N)[C@@H]6C5)cc4)c(=O)n3)C[C@H]12] |

TABLE 7-continued
| Compounds of Formula I | | |
|---|---|---|
| No. | Salt Structure | Free Base Structure |
| 52 | 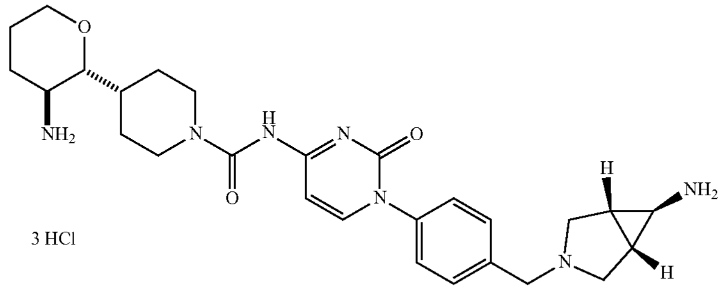 3 HCl | 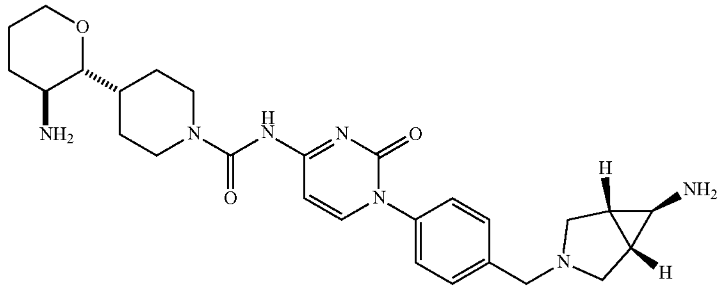 |
| 53 | 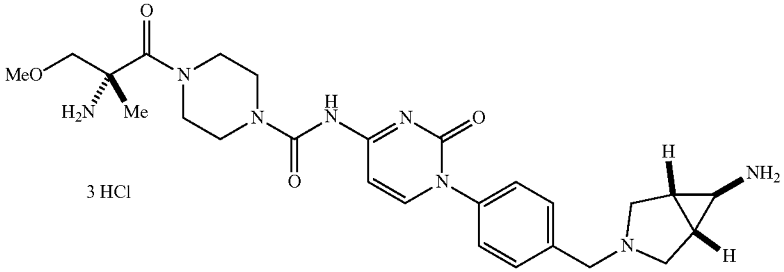 [SMILES: COC[C@@](C)(N)C(=O)N1CCN(C(=O)Nc2ccn(-c3ccc(CN4C[C@@H]5[C@@H](N)[C@@H]5C4)cc3)c(=O)n2)CC1] 3 HCl | 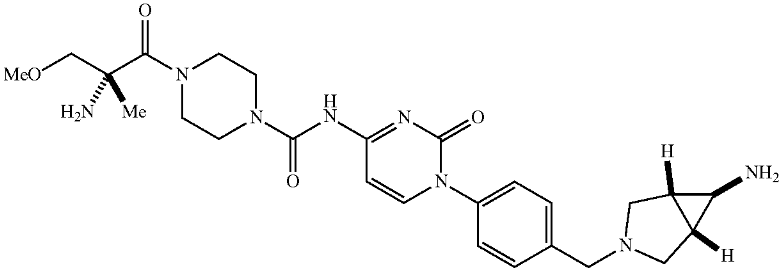 [SMILES: COC[C@@](C)(N)C(=O)N1CCN(C(=O)Nc2ccn(-c3ccc(CN4C[C@@H]5[C@@H](N)[C@@H]5C4)cc3)c(=O)n2)CC1] |
| 54 | 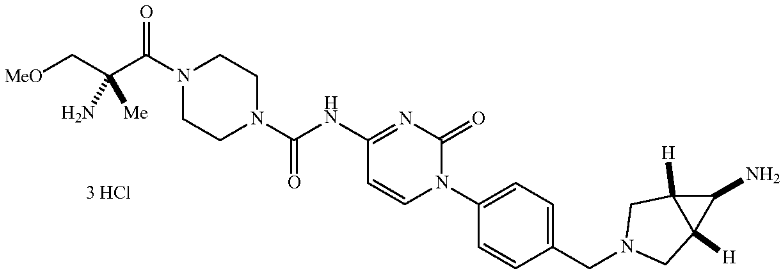 [SMILES: COC[C@@](C)(N)C(=O)N1CCN(C(=O)Nc2ccn(-c3ccc(CN4C[C@@H]5[C@@H](N)[C@@H]5C4)cc3)c(=O)n2)CC1] 3 HCl | 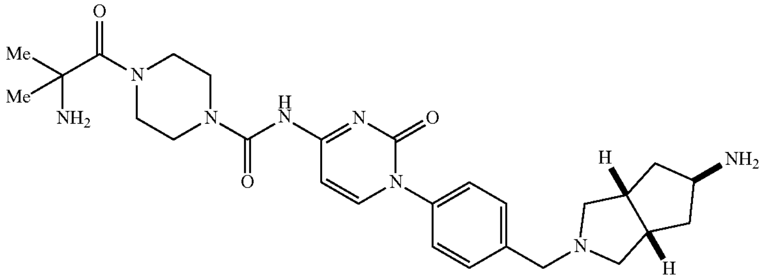 [SMILES: CC(C)(N)C(=O)N1CCN(C(=O)Nc2ccn(-c3ccc(CN4C[C@H]5C[C@H](N)C[C@H]5C4)cc3)c(=O)n2)CC1] |

TABLE 7-continued
| Compounds of Formula I | | |
|---|---|---|
| No. | Salt Structure | Free Base Structure |
| 55 | 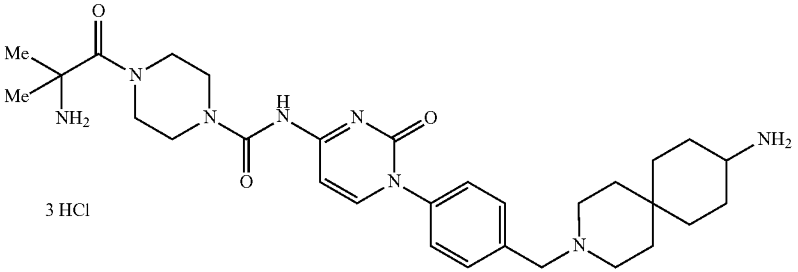 [SMILES: CC(C)(N)C(=O)N1CCN(C(=O)Nc2ccn(-c3ccc(CN4CCC5(CCC(N)CC5)CC4)cc3)c(=O)n2)CC1] 3 HCl | 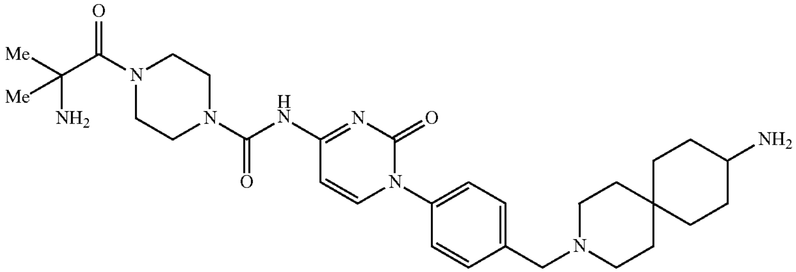 [SMILES: CC(C)(N)C(=O)N1CCN(C(=O)Nc2ccn(-c3ccc(CN4CCC5(CCC(N)CC5)CC4)cc3)c(=O)n2)CC1] |
| 56 | 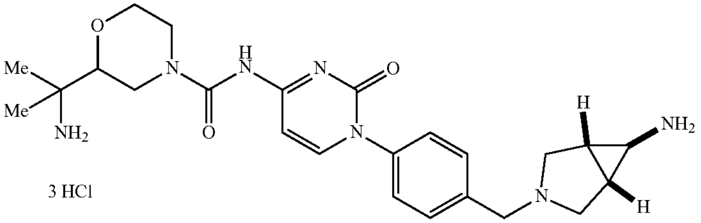 [SMILES: CC(C)(N)C1CN(C(=O)Nc2ccn(-c3ccc(CN4C[C@@H]5[C@@H](N)[C@@H]5C4)cc3)c(=O)n2)CCO1] 3 HCl | 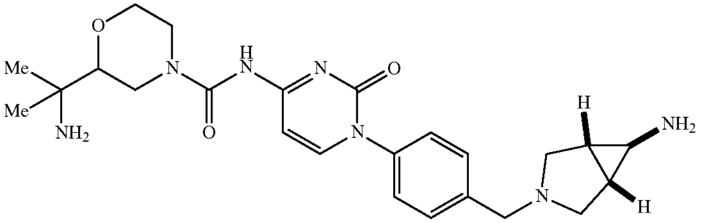 [SMILES: CC(C)(N)C1CN(C(=O)Nc2ccn(-c3ccc(CN4C[C@@H]5[C@@H](N)[C@@H]5C4)cc3)c(=O)n2)CCO1] |
| 57 | 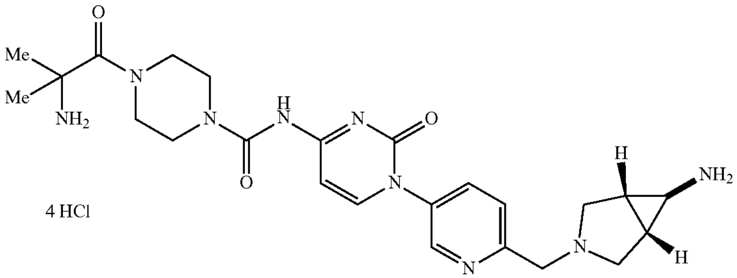 [SMILES: CC(C)(N)C(=O)N1CCN(C(=O)Nc2ccn(-c3ccc(CN4C[C@@H]5[C@@H](N)[C@@H]5C4)nc3)c(=O)n2)CC1] 4 HCl | 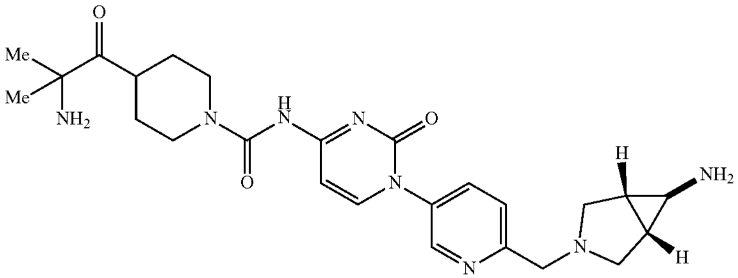 |

TABLE 7-continued
| Compounds of Formula I | | |
|---|---|---|
| No. | Salt Structure | Free Base Structure |
| 58 | 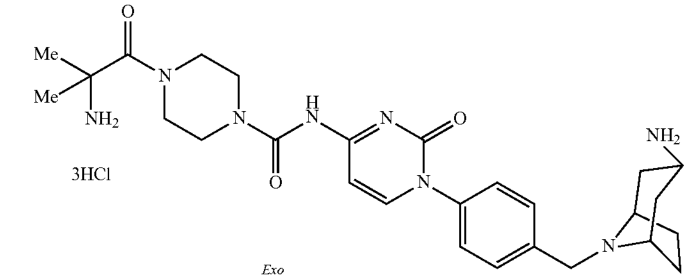 3HCl Exo | 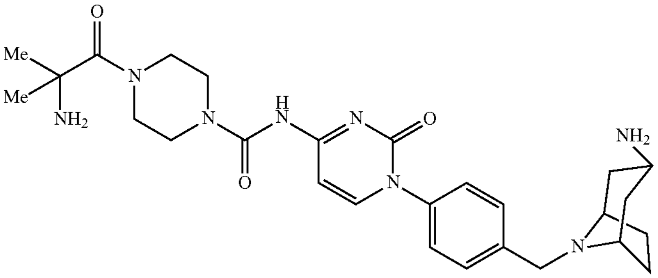 [SMILES: CC(C)(N)C(=O)N1CCN(C(=O)Nc2ccn(-c3ccc(CN4C5CCC4CC(N)C5)cc3)c(=O)n2)CC1] |
| 59 | 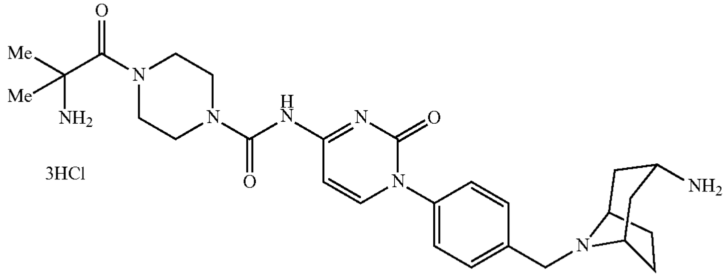 [SMILES: CC(C)(N)C(=O)N1CCN(C(=O)Nc2ccn(-c3ccc(CN4C5CCC4CC(N)C5)cc3)c(=O)n2)CC1] 3HCl | 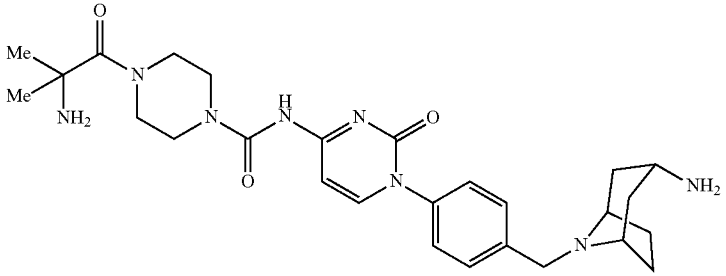 [SMILES: CC(C)(N)C(=O)N1CCN(C(=O)Nc2ccn(-c3ccc(CN4C5CCC4CC(N)C5)cc3)c(=O)n2)CC1] |
| 60 | 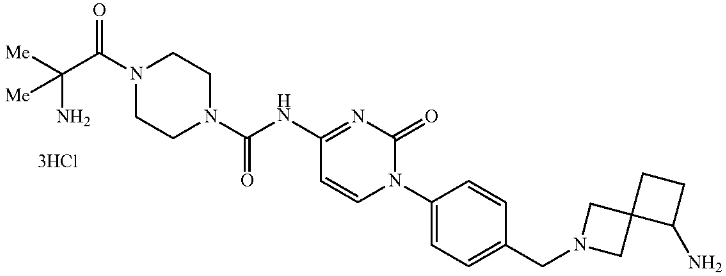 [SMILES: CC(C)(N)C(=O)N1CCN(C(=O)Nc2ccn(-c3ccc(CN4CC5(CCC5N)C4)cc3)c(=O)n2)CC1] 3HCl | 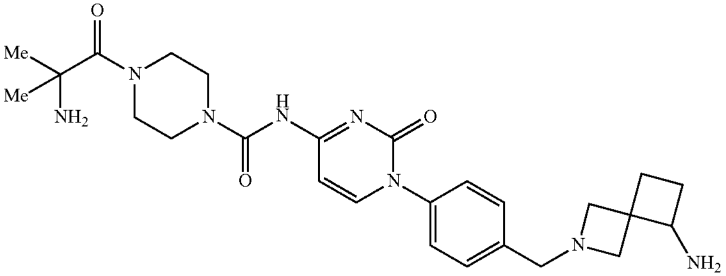 [SMILES: CC(C)(N)C(=O)N1CCN(C(=O)Nc2ccn(-c3ccc(CN4CC5(CCC5N)C4)cc3)c(=O)n2)CC1] |

TABLE 7-continued
| No. | Salt Structure | Free Base Structure |
|---|---|---|
| | Compounds of Formula I | |
| 61 | 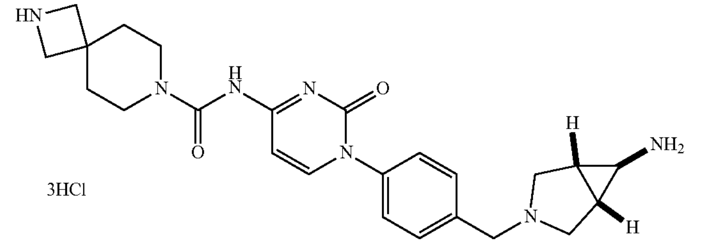 [SMILES: N[C@@H]1[C@H]2CN(Cc3ccc(-n4ccc(NC(=O)N5CCC6(CC5)CNC6)nc4=O)cc3)C[C@@H]12] 3HCl | 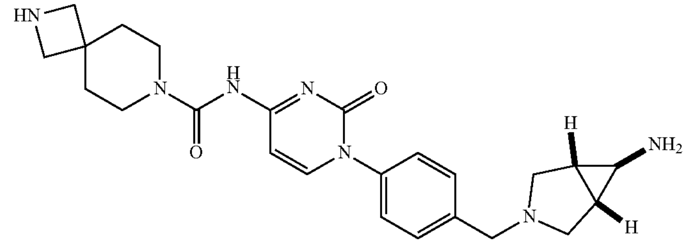 [SMILES: N[C@@H]1[C@H]2CN(Cc3ccc(-n4ccc(NC(=O)N5CCC6(CC5)CNC6)nc4=O)cc3)C[C@@H]12] |
| 62 | 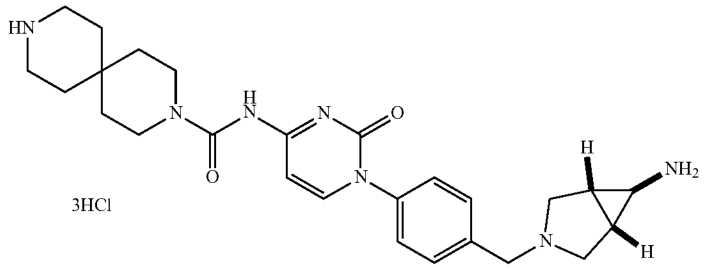 [SMILES: N[C@@H]1[C@H]2CN(Cc3ccc(-n4ccc(NC(=O)N5CCC6(CCNCC6)CC5)nc4=O)cc3)C[C@@H]12] 3HCl | 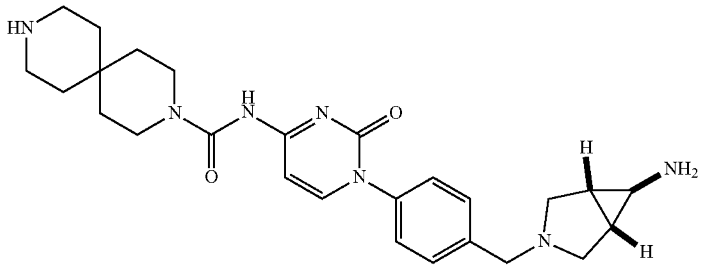 [SMILES: N[C@@H]1[C@H]2CN(Cc3ccc(-n4ccc(NC(=O)N5CCC6(CCNCC6)CC5)nc4=O)cc3)C[C@@H]12] |
| 63 | 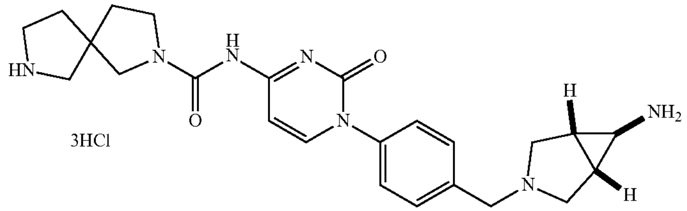 [SMILES: N[C@@H]1[C@H]2CN(Cc3ccc(-n4ccc(NC(=O)N5CCC6(CCNC6)C5)nc4=O)cc3)C[C@@H]12] 3HCl | 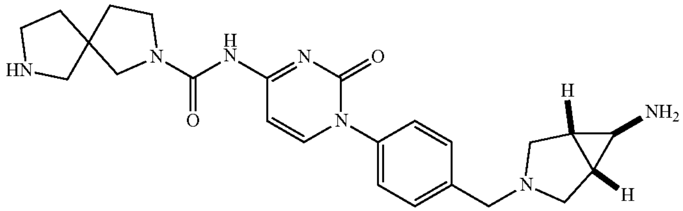 [SMILES: N[C@@H]1[C@H]2CN(Cc3ccc(-n4ccc(NC(=O)N5CCC6(CCNC6)C5)nc4=O)cc3)C[C@@H]12] |
| 64 | 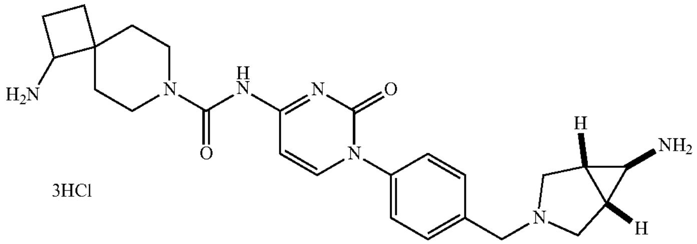 [SMILES: NC1CCC12CCN(C(=O)Nc1ccn(-c3ccc(CN4C[C@@H]5[C@@H](N)[C@@H]5C4)cc3)c(=O)n1)CC2] 3HCl | 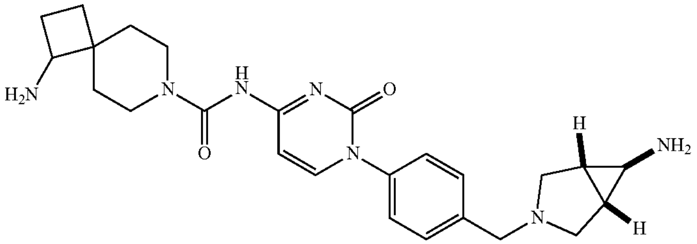 [SMILES: NC1CCC12CCN(C(=O)Nc1ccn(-c3ccc(CN4C[C@@H]5[C@@H](N)[C@@H]5C4)cc3)c(=O)n1)CC2] |

TABLE 7-continued
| Compounds of Formula I | | |
|---|---|---|
| No. | Salt Structure | Free Base Structure |
| 65 | 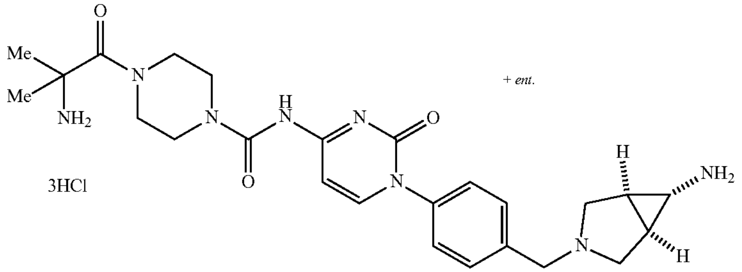 [SMILES: CC(C)(N)C(=O)N1CCN(C(=O)Nc2ccn(-c3ccc(CN4C[C@@H]5[C@@H](N)[C@@H]5C4)cc3)c(=O)n2)CC1] + ent. 3HCl | 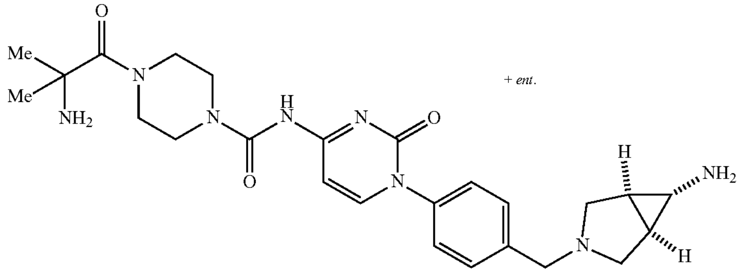 [SMILES: CC(C)(N)C(=O)N1CCN(C(=O)Nc2ccn(-c3ccc(CN4C[C@@H]5[C@@H](N)[C@@H]5C4)cc3)c(=O)n2)CC1] + ent. |
| 66 | 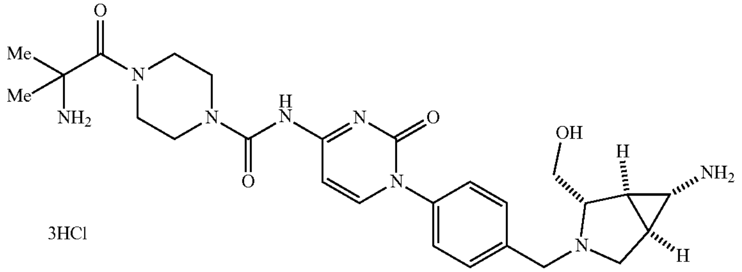 [SMILES: CC(C)(N)C(=O)N1CCN(C(=O)Nc2ccn(-c3ccc(CN4C[C@@H]5[C@@H](N)[C@@H]5[C@H]4CO)cc3)c(=O)n2)CC1] 3HCl | 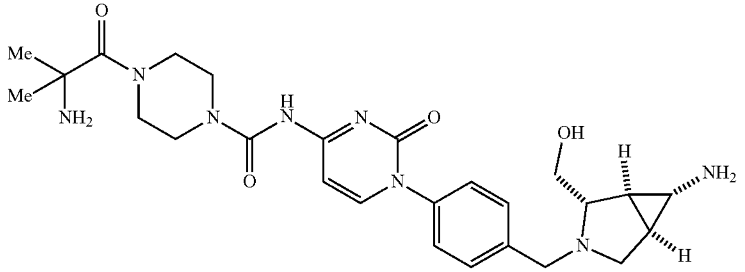 [SMILES: CC(C)(N)C(=O)N1CCN(C(=O)Nc2ccn(-c3ccc(CN4C[C@@H]5[C@@H](N)[C@@H]5[C@H]4CO)cc3)c(=O)n2)CC1] |
| 67 | 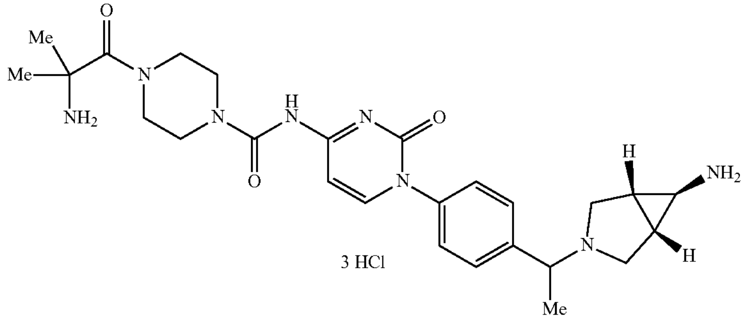 [SMILES: CC(c1ccc(-n2ccc(NC(=O)N3CCN(C(=O)C(C)(C)N)CC3)nc2=O)cc1)N1C[C@@H]2[C@@H](N)[C@@H]2C1] 3 HCl | 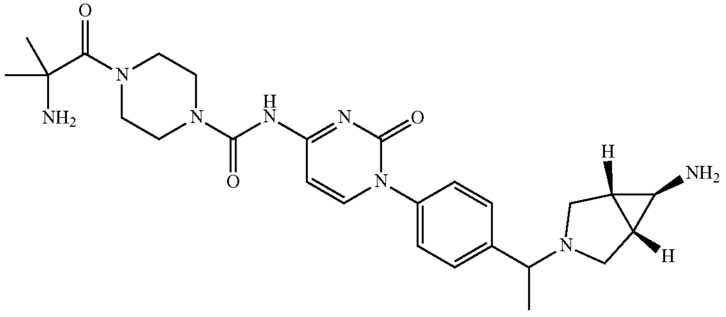 [SMILES: CC(c1ccc(-n2ccc(NC(=O)N3CCN(C(=O)C(C)(C)N)CC3)nc2=O)cc1)N1C[C@@H]2[C@@H](N)[C@@H]2C1] |

TABLE 7-continued
Compounds of Formula I
| No. | Salt Structure | Free Base Structure |
|---|---|---|
| 68 | 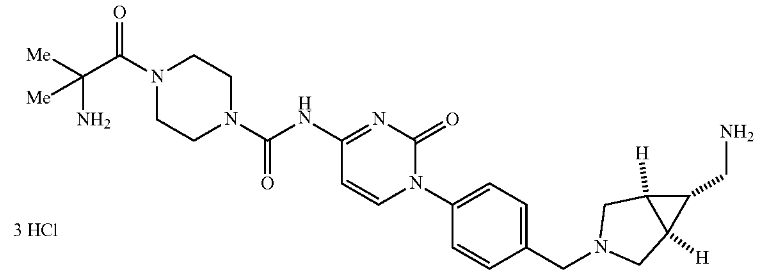 [SMILES: CC(C)(N)C(=O)N1CCN(C(=O)Nc2ccn(-c3ccc(CN4C[C@@H]5[C@@H](CN)[C@@H]5C4)cc3)c(=O)n2)CC1] 3 HCl | 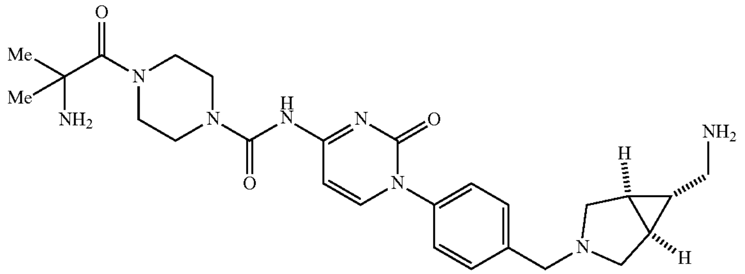 [SMILES: CC(C)(N)C(=O)N1CCN(C(=O)Nc2ccn(-c3ccc(CN4C[C@@H]5[C@@H](CN)[C@@H]5C4)cc3)c(=O)n2)CC1] |
| 69 | 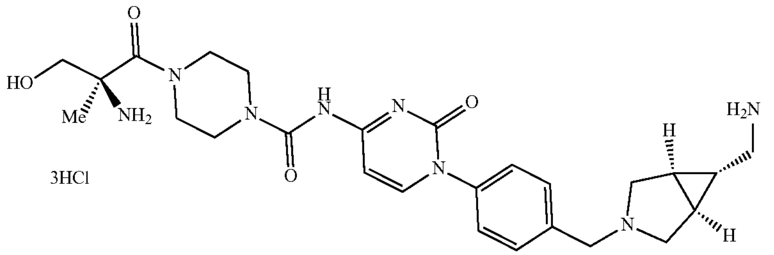 [SMILES: C[C@](N)(CO)C(=O)N1CCN(C(=O)Nc2ccn(-c3ccc(CN4C[C@@H]5[C@@H](CN)[C@@H]5C4)cc3)c(=O)n2)CC1] 3HCl | 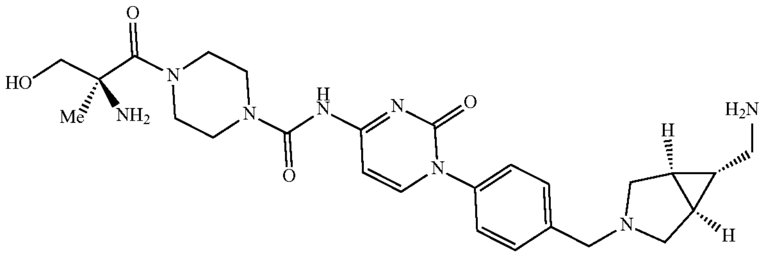 [SMILES: C[C@](N)(CO)C(=O)N1CCN(C(=O)Nc2ccn(-c3ccc(CN4C[C@@H]5[C@@H](CN)[C@@H]5C4)cc3)c(=O)n2)CC1] |
| 70 | 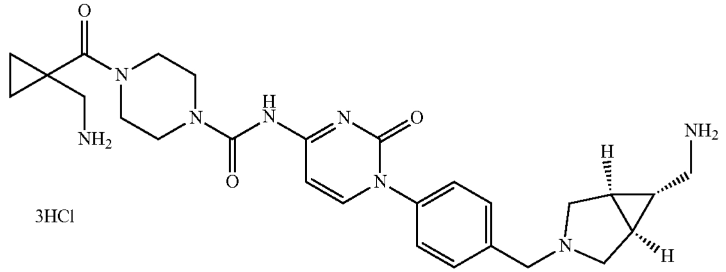 [SMILES: NC[C@@H]1[C@H]2CN(Cc3ccc(-n4ccc(NC(=O)N5CCN(C(=O)C6(CN)CC6)CC5)nc4=O)cc3)C[C@@H]12] 3HCl | 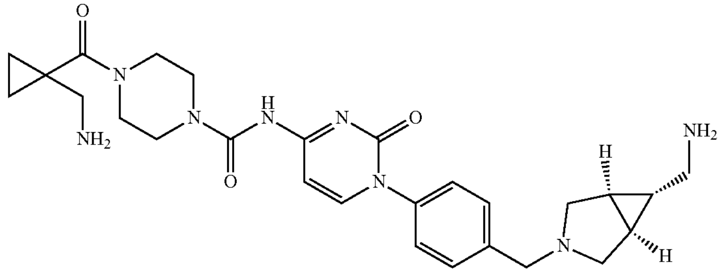 [SMILES: NC[C@@H]1[C@H]2CN(Cc3ccc(-n4ccc(NC(=O)N5CCN(C(=O)C6(CN)CC6)CC5)nc4=O)cc3)C[C@@H]12] |

TABLE 7-continued
| Compounds of Formula I | | |
|---|---|---|
| No. | Salt Structure | Free Base Structure |
| 71 | 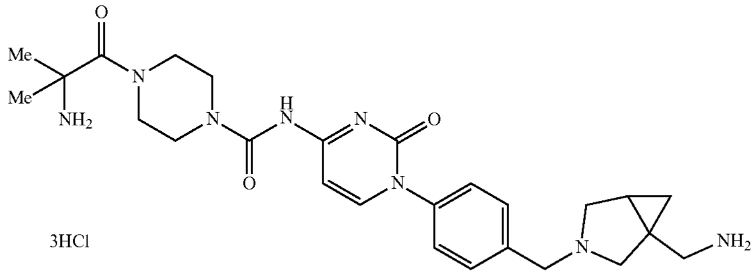 [SMILES: CC(C)(N)C(=O)N1CCN(C(=O)Nc2ccn(-c3ccc(CN4CC5CC5(CN)C4)cc3)c(=O)n2)CC1] 3HCl | 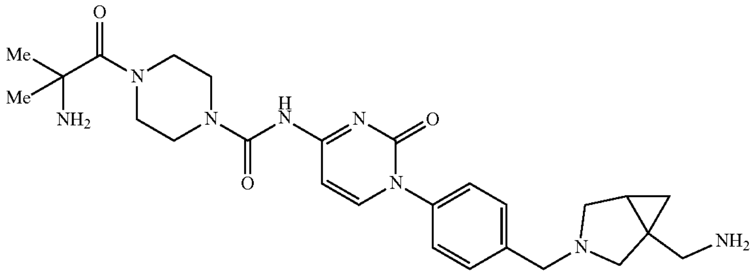 [SMILES: CC(C)(N)C(=O)N1CCN(C(=O)Nc2ccn(-c3ccc(CN4CC5CC5(CN)C4)cc3)c(=O)n2)CC1] |
| 72 | 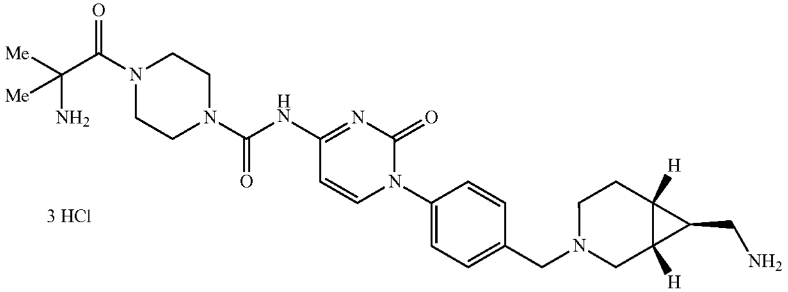 [SMILES: CC(C)(N)C(=O)N1CCN(C(=O)Nc2ccn(-c3ccc(CN4CC[C@@H]5[C@@H](CN)[C@@H]5C4)cc3)c(=O)n2)CC1] 3 HCl | 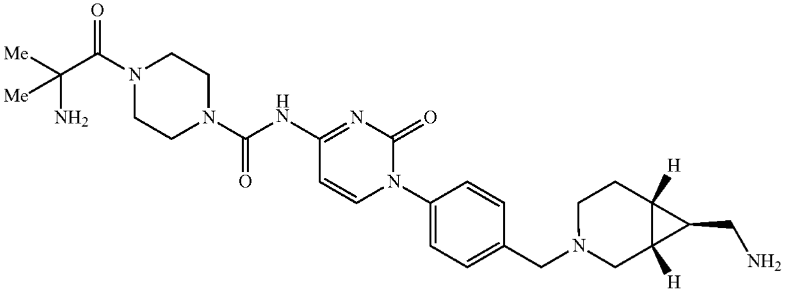 [SMILES: CC(C)(N)C(=O)N1CCN(C(=O)Nc2ccn(-c3ccc(CN4CC[C@@H]5[C@@H](CN)[C@@H]5C4)cc3)c(=O)n2)CC1] |
| 73 | 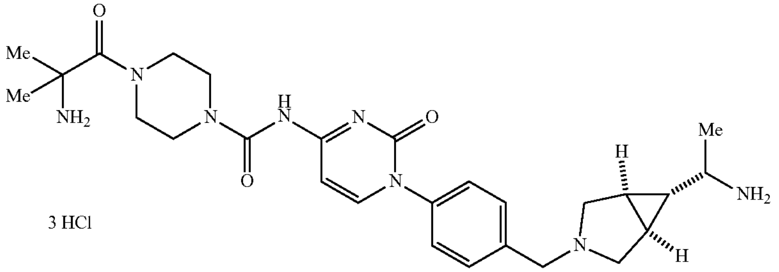 [SMILES: CC(N)[C@H]1[C@@H]2CN(Cc3ccc(-n4ccc(NC(=O)N5CCN(C(=O)C(C)(C)N)CC5)nc4=O)cc3)C[C@@H]21] 3 HCl | 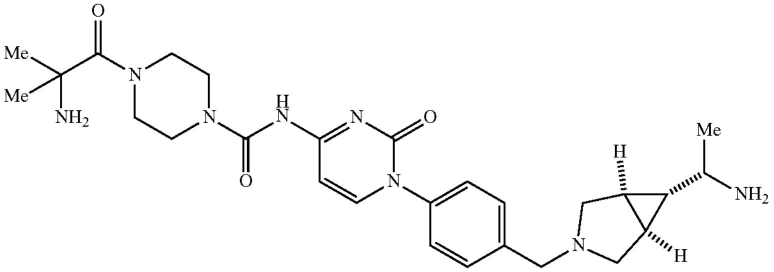 [SMILES: CC(N)[C@H]1[C@@H]2CN(Cc3ccc(-n4ccc(NC(=O)N5CCN(C(=O)C(C)(C)N)CC5)nc4=O)cc3)C[C@@H]21] |

TABLE 7-continued
| Compounds of Formula I | | |
|---|---|---|
| No. | Salt Structure | Free Base Structure |
| 74 | 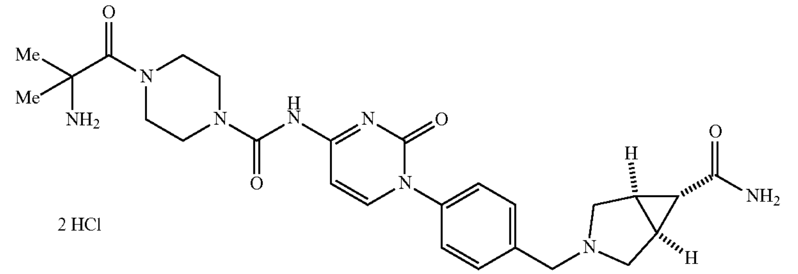 [SMILES: CC(C)(N)C(=O)N1CCN(C(=O)Nc2ccn(-c3ccc(CN4C[C@@H]5[C@H](C4)[C@H]5C(N)=O)cc3)c(=O)n2)CC1] 2 HCl | 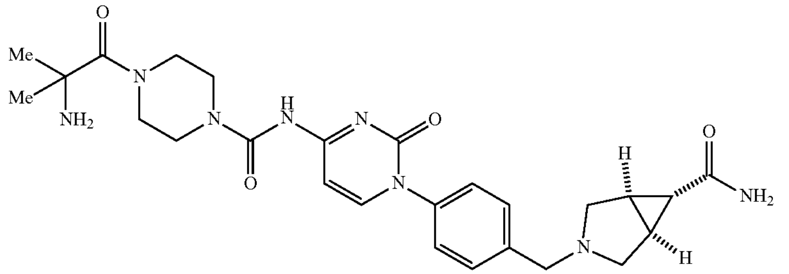 [SMILES: CC(C)(N)C(=O)N1CCN(C(=O)Nc2ccn(-c3ccc(CN4C[C@@H]5[C@H](C4)[C@H]5C(N)=O)cc3)c(=O)n2)CC1] |
| 75 | 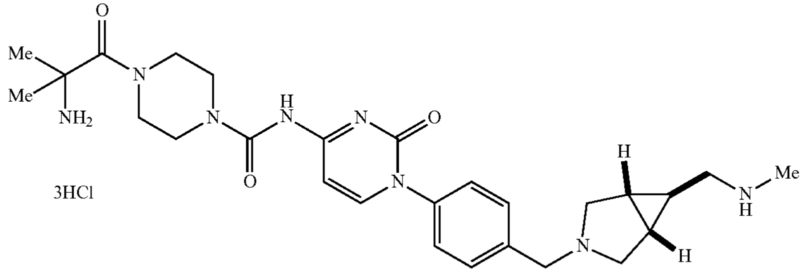 [SMILES: CNC[C@@H]1[C@H]2CN(Cc3ccc(-n4ccc(NC(=O)N5CCN(C(=O)C(C)(C)N)CC5)nc4=O)cc3)C[C@@H]12] 3HCl | 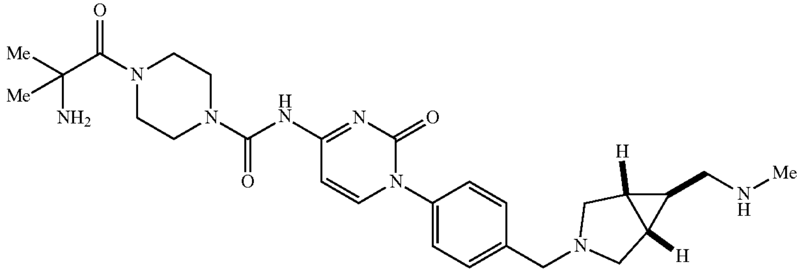 [SMILES: CNC[C@@H]1[C@H]2CN(Cc3ccc(-n4ccc(NC(=O)N5CCN(C(=O)C(C)(C)N)CC5)nc4=O)cc3)C[C@@H]12] |
| 76 | 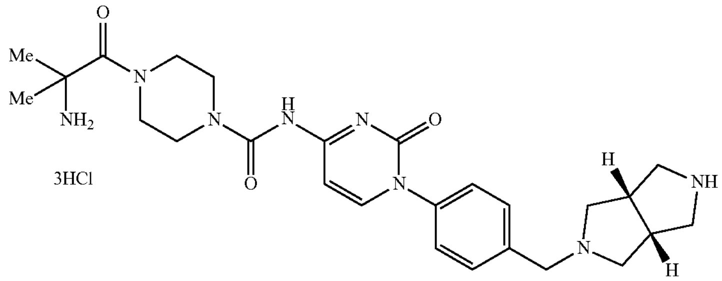 [SMILES: CC(C)(N)C(=O)N1CCN(C(=O)Nc2ccn(-c3ccc(CN4C[C@H]5CNC[C@H]5C4)cc3)c(=O)n2)CC1] 3HCl | 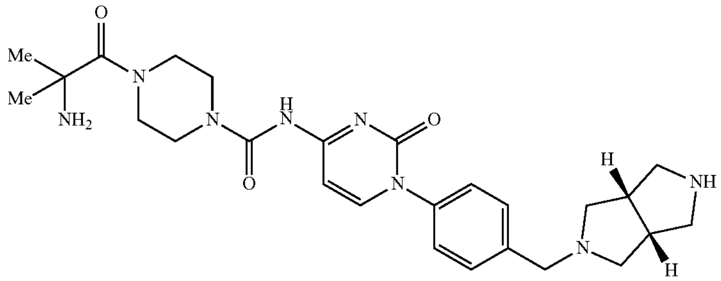 [SMILES: CC(C)(N)C(=O)N1CCN(C(=O)Nc2ccn(-c3ccc(CN4C[C@H]5CNC[C@H]5C4)cc3)c(=O)n2)CC1] |

TABLE 7-continued
| Compounds of Formula I | | |
|---|---|---|
| No. | Salt Structure | Free Base Structure |
| 77 | 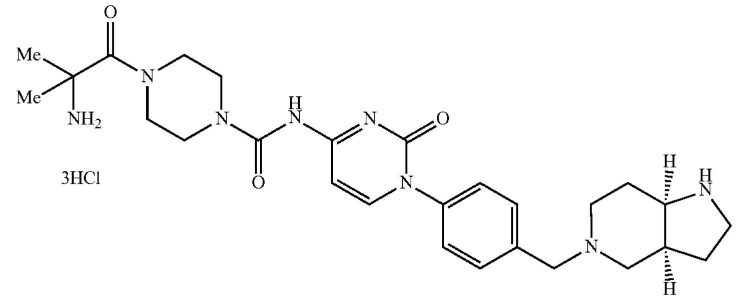 [SMILES: CC(C)(N)C(=O)N1CCN(C(=O)Nc2ccn(-c3ccc(CN4CC[C@H]5NCC[C@H]5C4)cc3)c(=O)n2)CC1] 3HCl | 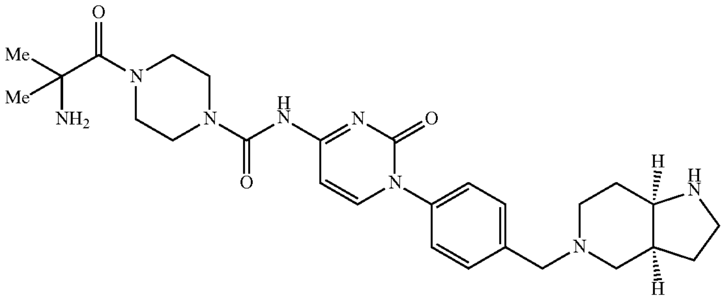 [SMILES: CC(C)(N)C(=O)N1CCN(C(=O)Nc2ccn(-c3ccc(CN4CC[C@H]5NCC[C@H]5C4)cc3)c(=O)n2)CC1] |
| 78 | 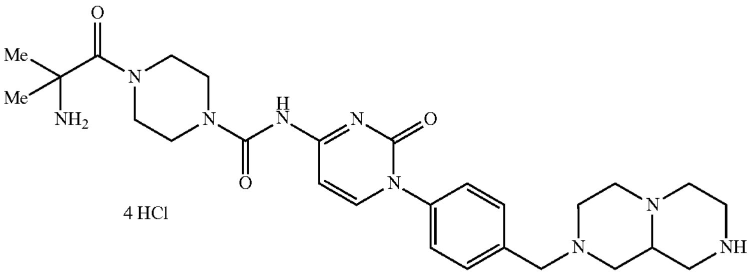 [SMILES: CC(C)(N)C(=O)N1CCN(C(=O)Nc2ccn(-c3ccc(CN4CCN5CCNCC5C4)cc3)c(=O)n2)CC1] 4 HCl | 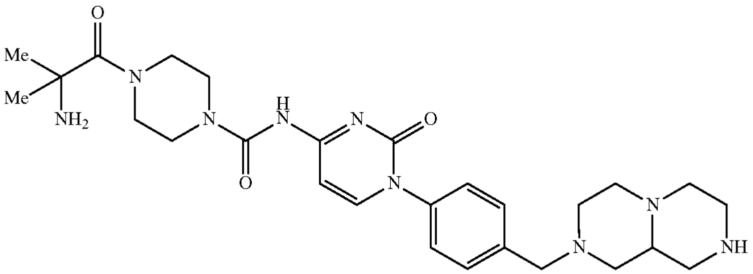 [SMILES: CC(C)(N)C(=O)N1CCN(C(=O)Nc2ccn(-c3ccc(CN4CCN5CCNCC5C4)cc3)c(=O)n2)CC1] |
| 79 | 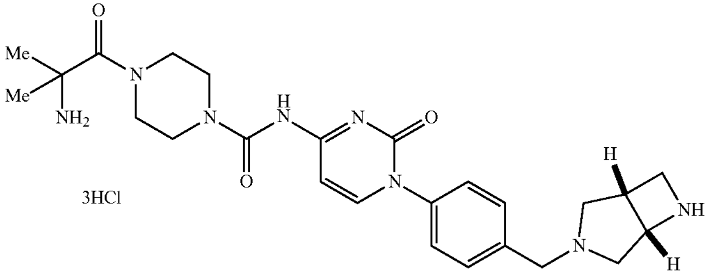 [SMILES: CC(C)(N)C(=O)N1CCN(C(=O)Nc2ccn(-c3ccc(CN4C[C@@H]5CN[C@@H]5C4)cc3)c(=O)n2)CC1] 3HCl | 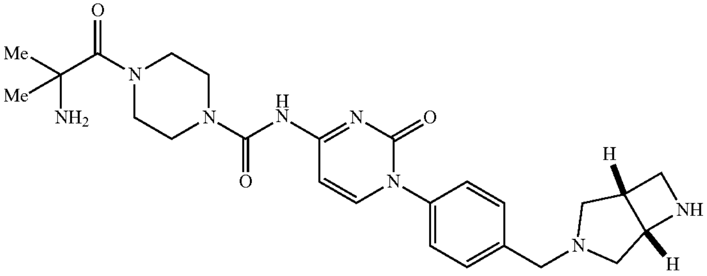 [SMILES: CC(C)(N)C(=O)N1CCN(C(=O)Nc2ccn(-c3ccc(CN4C[C@@H]5CN[C@@H]5C4)cc3)c(=O)n2)CC1] |

TABLE 7-continued
| No. | Compounds of Formula I Salt Structure | Free Base Structure |
|---|---|---|
| 80 | 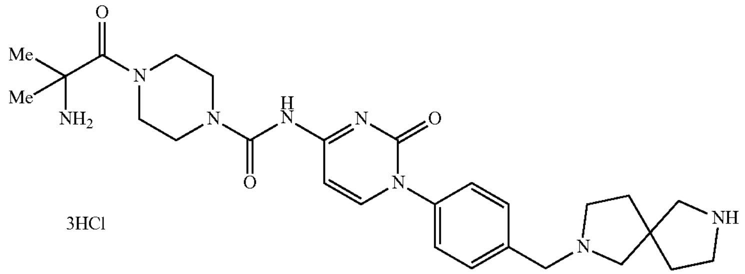 [SMILES: CC(C)(N)C(=O)N1CCN(C(=O)Nc2ccn(-c3ccc(CN4CCC5(CCNC5)C4)cc3)c(=O)n2)CC1] 3HCl | 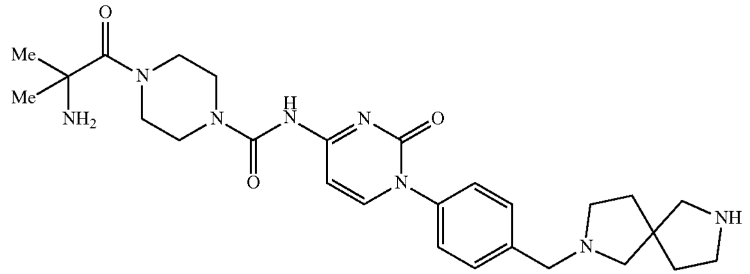 [SMILES: CC(C)(N)C(=O)N1CCN(C(=O)Nc2ccn(-c3ccc(CN4CCC5(CCNC5)C4)cc3)c(=O)n2)CC1] |
| 81 | 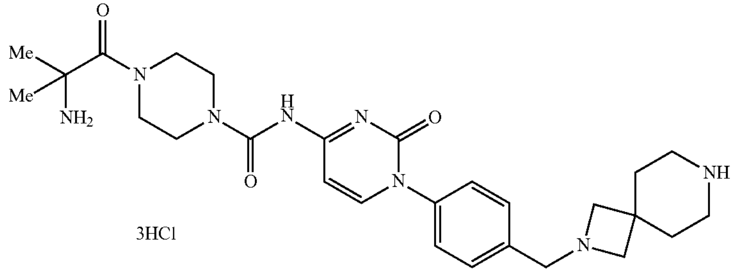 [SMILES: CC(C)(N)C(=O)N1CCN(C(=O)Nc2ccn(-c3ccc(CN4CC5(CCNCC5)C4)cc3)c(=O)n2)CC1] 3HCl | 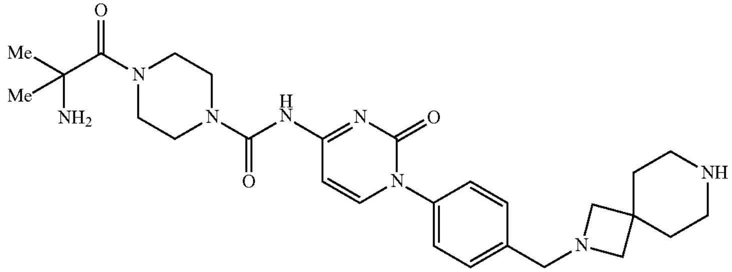 [SMILES: CC(C)(N)C(=O)N1CCN(C(=O)Nc2ccn(-c3ccc(CN4CC5(CCNCC5)C4)cc3)c(=O)n2)CC1] |
| 82 | 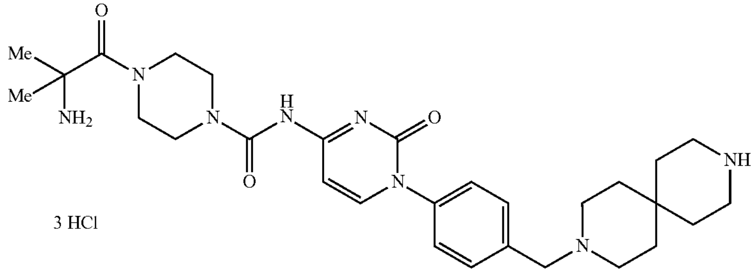 [SMILES: CC(C)(N)C(=O)N1CCN(C(=O)Nc2ccn(-c3ccc(CN4CCC5(CCNCC5)CC4)cc3)c(=O)n2)CC1] 3 HCl | 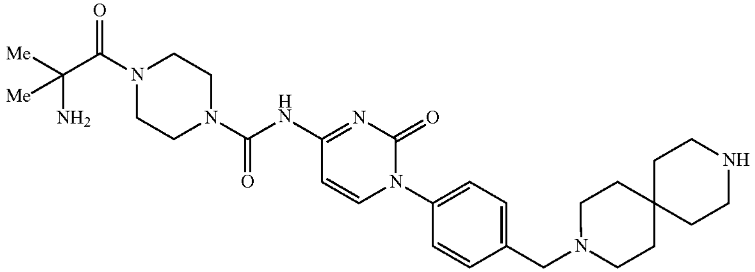 [SMILES: CC(C)(N)C(=O)N1CCN(C(=O)Nc2ccn(-c3ccc(CN4CCC5(CCNCC5)CC4)cc3)c(=O)n2)CC1] |

TABLE 7-continued
| Compounds of Formula I | | |
|---|---|---|
| No. | Salt Structure | Free Base Structure |
| 83 | 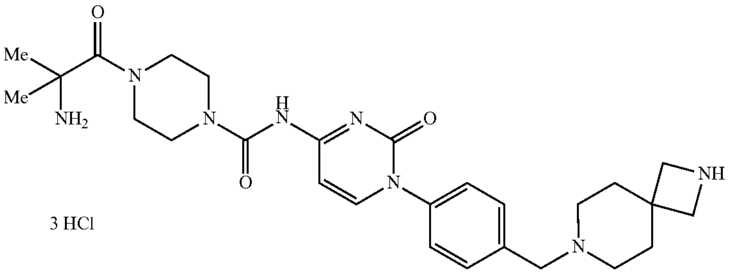 [SMILES: CC(C)(N)C(=O)N1CCN(C(=O)Nc2ccn(-c3ccc(CN4CCC5(CC4)CNC5)cc3)c(=O)n2)CC1] 3 HCl | 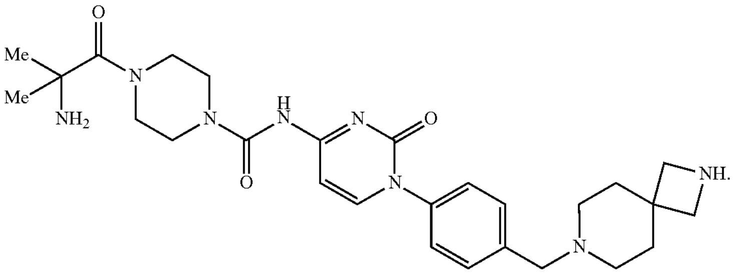 [SMILES: CC(C)(N)C(=O)N1CCN(C(=O)Nc2ccn(-c3ccc(CN4CCC5(CC4)CNC5)cc3)c(=O)n2)CC1] |

In another aspect, the disclosure provides a compound or a pharmaceutically acceptable salt thereof which is depicted in Table 8. In Table 8a possible pharmaceutically acceptable salt and the free base is shown for each compound.

TABLE 8
| Compounds of Formula I Continued | | |
|---|---|---|
| No. | Salt Structure | Free Base Structure |
| 84 | 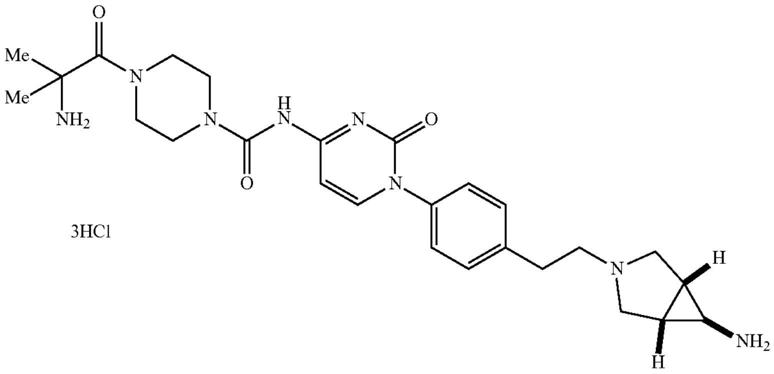 [SMILES: CC(C)(N)C(=O)N1CCN(C(=O)Nc2ccn(-c3ccc(CCN4C[C@@H]5[C@@H](N)[C@@H]5C4)cc3)c(=O)n2)CC1] 3HCl | 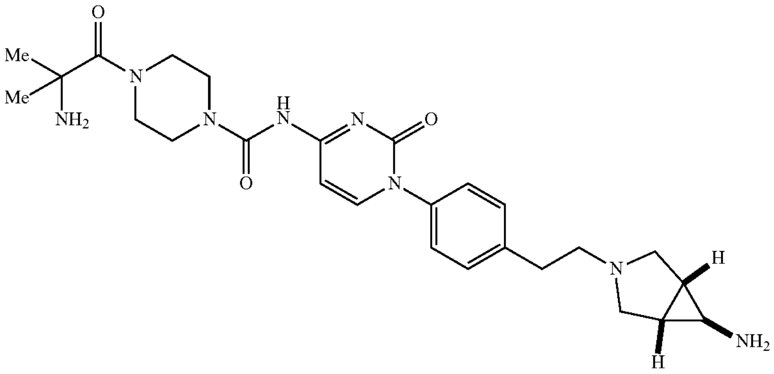 [SMILES: CC(C)(N)C(=O)N1CCN(C(=O)Nc2ccn(-c3ccc(CCN4C[C@@H]5[C@@H](N)[C@@H]5C4)cc3)c(=O)n2)CC1] |
| 85 | 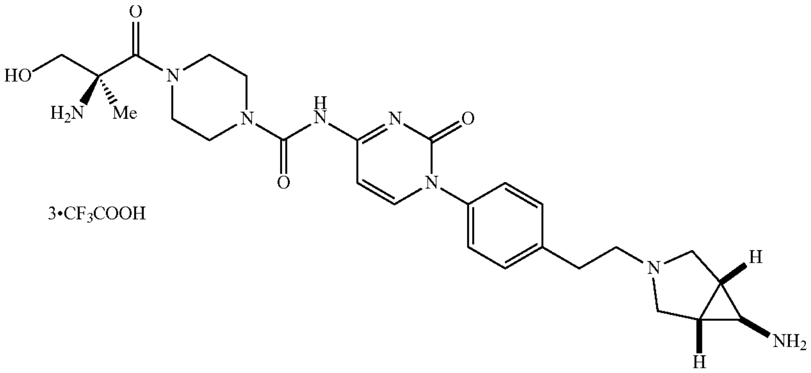 [SMILES: C[C@](N)(CO)C(=O)N1CCN(C(=O)Nc2ccn(-c3ccc(CCN4C[C@@H]5[C@@H](N)[C@@H]5C4)cc3)c(=O)n2)CC1] $3 \cdot CF_3COOH$ | 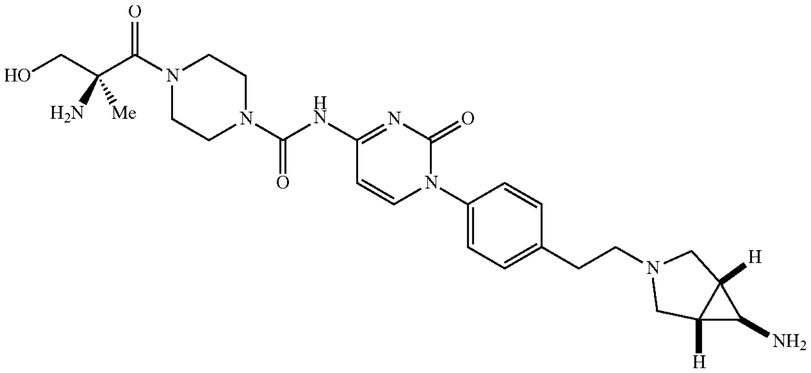 [SMILES: C[C@](N)(CO)C(=O)N1CCN(C(=O)Nc2ccn(-c3ccc(CCN4C[C@@H]5[C@@H](N)[C@@H]5C4)cc3)c(=O)n2)CC1] |

TABLE 8-continued
Compounds of Formula I Continued
| No. | Salt Structure | Free Base Structure |
|---|---|---|
| 86 | 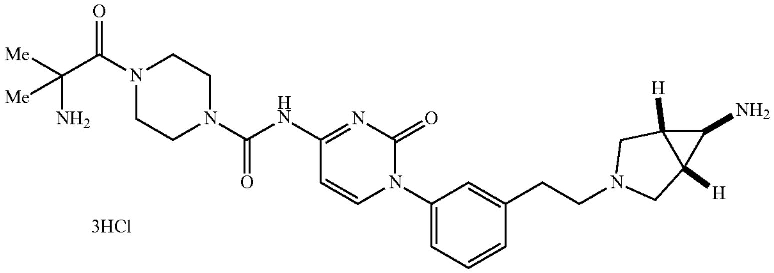 [SMILES: CC(C)(N)C(=O)N1CCN(C(=O)Nc2ccn(-c3cccc(CCN4C[C@@H]5[C@@H](N)[C@@H]5C4)c3)c(=O)n2)CC1] 3HCl | 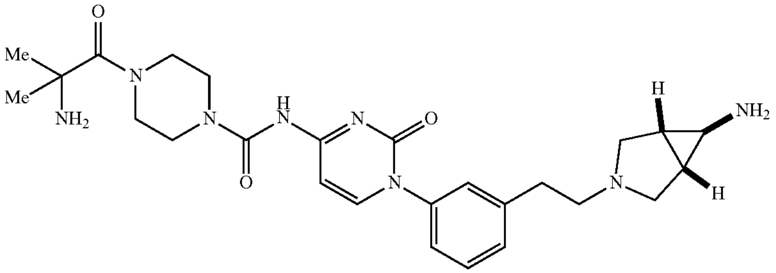 [SMILES: CC(C)(N)C(=O)N1CCN(C(=O)Nc2ccn(-c3cccc(CCN4C[C@@H]5[C@@H](N)[C@@H]5C4)c3)c(=O)n2)CC1] |
| 87 | 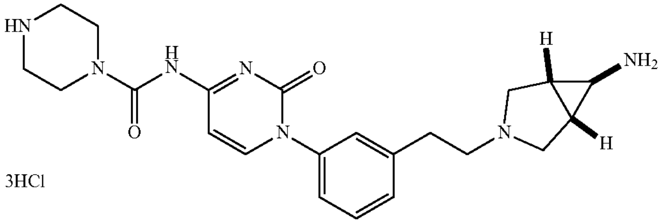 [SMILES: N[C@@H]1[C@H]2CN(CCc3cccc(-n4ccc(NC(=O)N5CCNCC5)nc4=O)c3)C[C@@H]12] 3HCl | 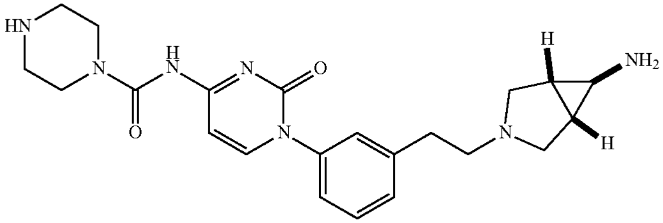 [SMILES: N[C@@H]1[C@H]2CN(CCc3cccc(-n4ccc(NC(=O)N5CCNCC5)nc4=O)c3)C[C@@H]12] |
| 88 | 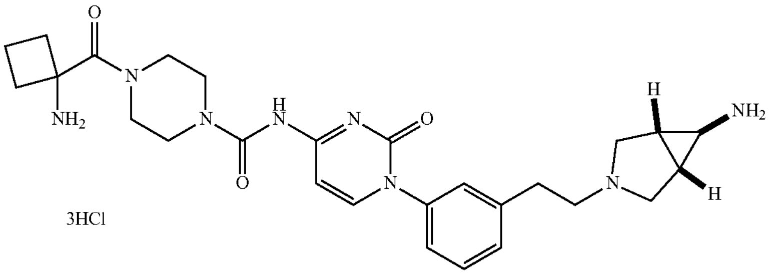 [SMILES: N[C@@H]1[C@H]2CN(CCc3cccc(-n4ccc(NC(=O)N5CCN(C(=O)C6(N)CCC6)CC5)nc4=O)c3)C[C@@H]12] 3HCl | 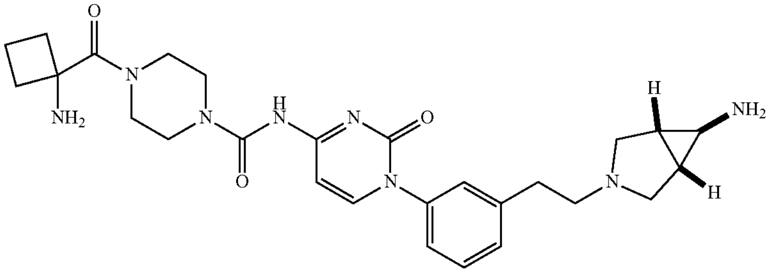 [SMILES: N[C@@H]1[C@H]2CN(CCc3cccc(-n4ccc(NC(=O)N5CCN(C(=O)C6(N)CCC6)CC5)nc4=O)c3)C[C@@H]12] |

TABLE 8-continued
| Compounds of Formula I Continued | | |
|---|---|---|
| No. | Salt Structure | Free Base Structure |
| 89 | 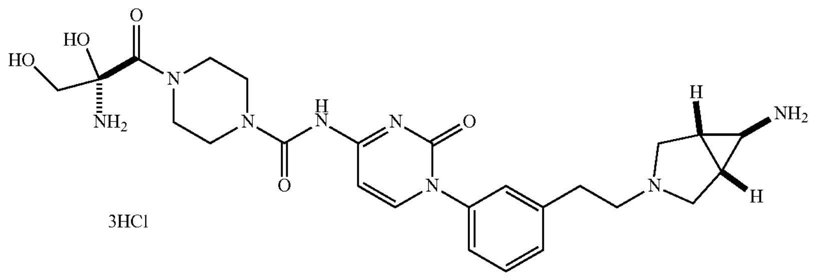 [SMILES: N[C@@H]1[C@H]2CN(CCc3cccc(-n4ccc(NC(=O)N5CCN(C(=O)[C@](N)(O)CO)CC5)nc4=O)c3)C[C@@H]12] 3HCl | 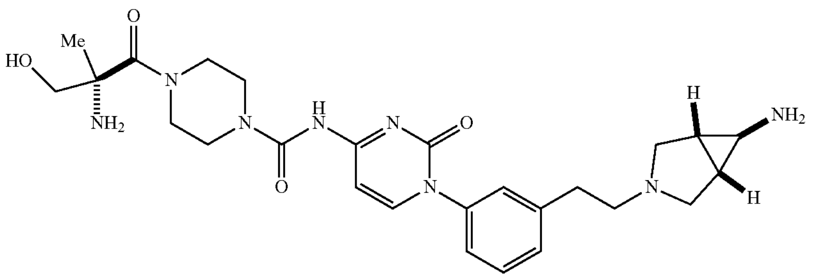 [SMILES: C[C@](N)(CO)C(=O)N1CCN(C(=O)Nc2ccn(-c3cccc(CCN4C[C@@H]5[C@@H](N)[C@@H]5C4)c3)c(=O)n2)CC1] |
| 90 | 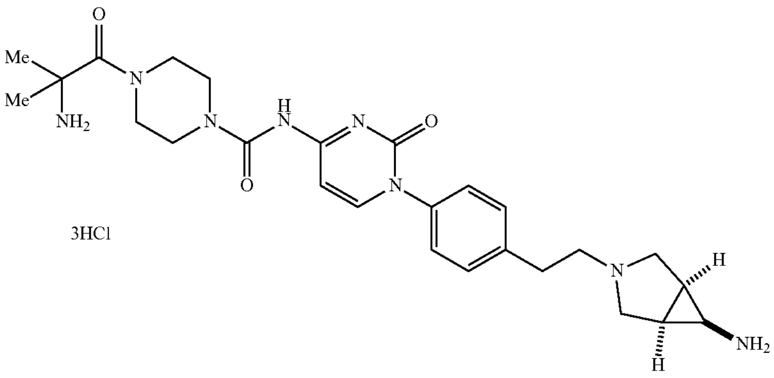 [SMILES: CC(C)(N)C(=O)N1CCN(C(=O)Nc2ccn(-c3ccc(CCN4C[C@@H]5[C@H](N)[C@@H]5C4)cc3)c(=O)n2)CC1] 3HCl | 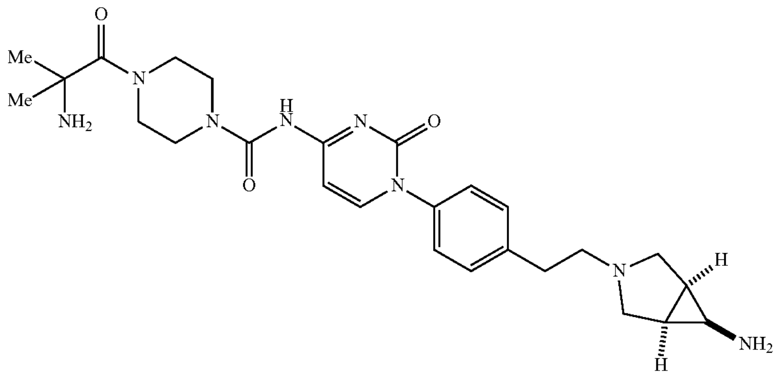 [SMILES: CC(C)(N)C(=O)N1CCN(C(=O)Nc2ccn(-c3ccc(CCN4C[C@@H]5[C@H](N)[C@@H]5C4)cc3)c(=O)n2)CC1] |

TABLE 8-continued
| Compounds of Formula I Continued | | |
|---|---|---|
| No. | Salt Structure | Free Base Structure |
| 91 | 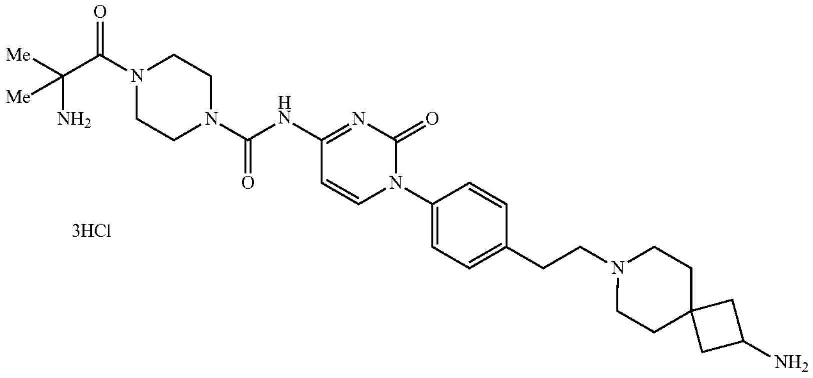 [SMILES: CC(C)(N)C(=O)N1CCN(C(=O)Nc2ccn(-c3ccc(CCN4CCC5(CC4)CC(N)C5)cc3)c(=O)n2)CC1] 3HCl | 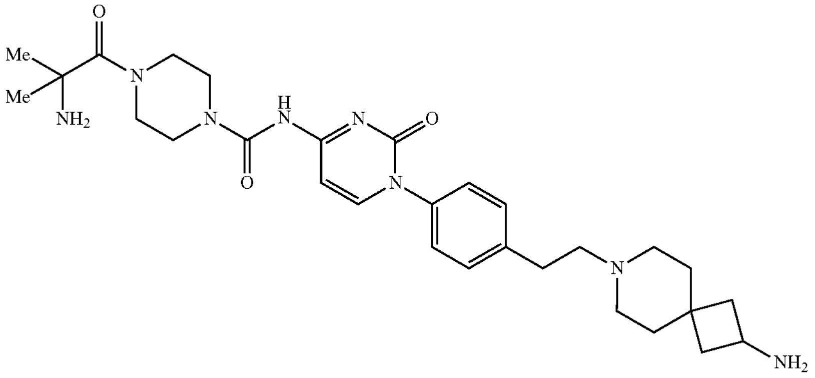 [SMILES: CC(C)(N)C(=O)N1CCN(C(=O)Nc2ccn(-c3ccc(CCN4CCC5(CC4)CC(N)C5)cc3)c(=O)n2)CC1] |
| 92 | 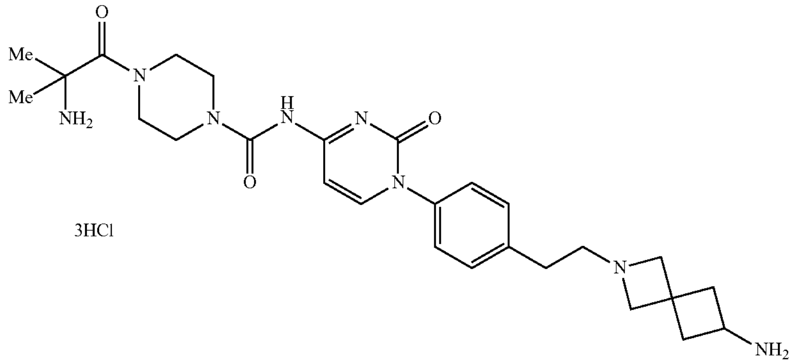 [SMILES: CC(C)(N)C(=O)N1CCN(C(=O)Nc2ccn(-c3ccc(CCN4CC5(CC(N)C5)C4)cc3)c(=O)n2)CC1] 3HCl | 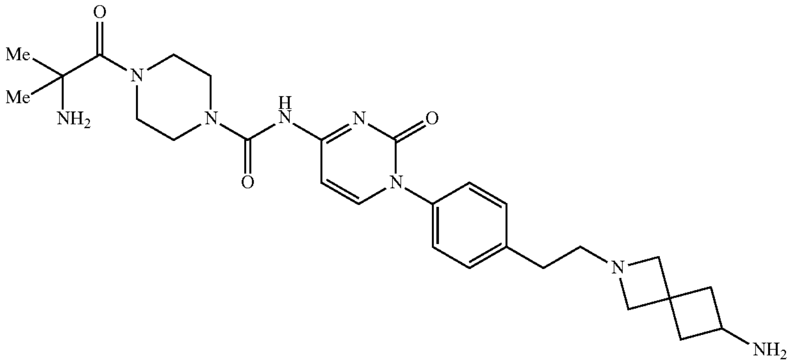 [SMILES: CC(C)(N)C(=O)N1CCN(C(=O)Nc2ccn(-c3ccc(CCN4CC5(CC(N)C5)C4)cc3)c(=O)n2)CC1] |

TABLE 8-continued
| Compounds of Formula I Continued | | |
|---|---|---|
| No. | Salt Structure | Free Base Structure |
| 93 | 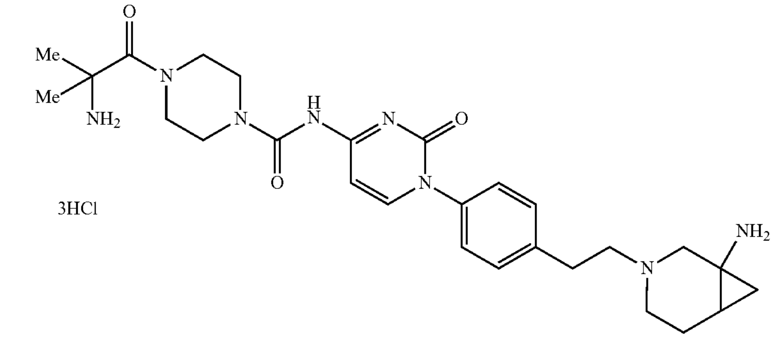 [SMILES: CC(C)(N)C(=O)N1CCN(C(=O)Nc2ccn(-c3ccc(CCN4CCC5CC5(N)C4)cc3)c(=O)n2)CC1] 3HCl | 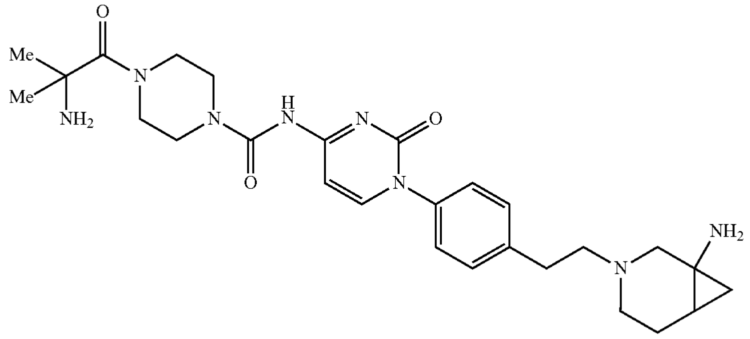 [SMILES: CC(C)(N)C(=O)N1CCN(C(=O)Nc2ccn(-c3ccc(CCN4CCC5CC5(N)C4)cc3)c(=O)n2)CC1] |
| 94 | 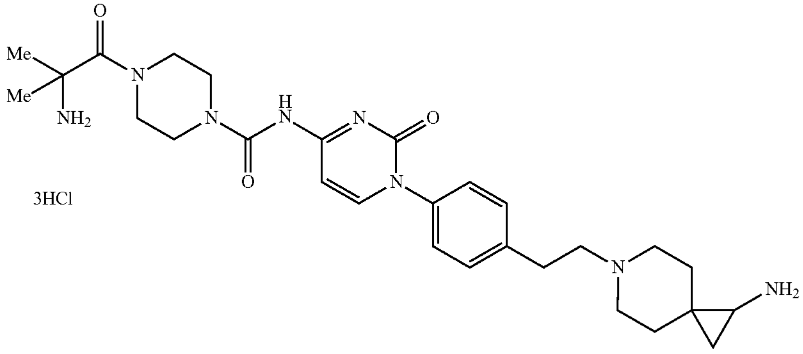 [SMILES: CC(C)(N)C(=O)N1CCN(C(=O)Nc2ccn(-c3ccc(CCN4CCC5(CC4)CC5N)cc3)c(=O)n2)CC1] 3HCl | 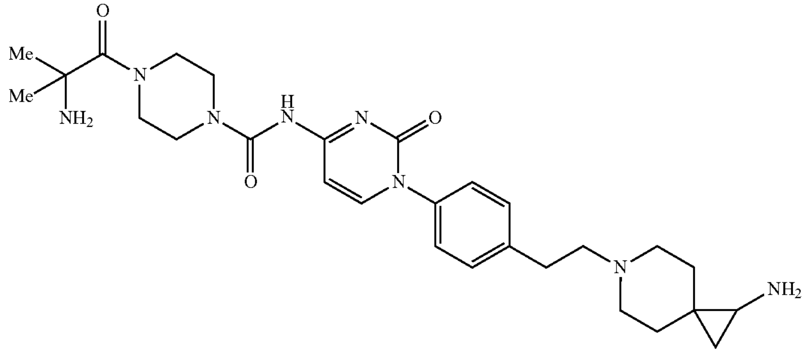 [SMILES: CC(C)(N)C(=O)N1CCN(C(=O)Nc2ccn(-c3ccc(CCN4CCC5(CC4)CC5N)cc3)c(=O)n2)CC1] |

TABLE 8-continued
| Compounds of Formula I Continued | | |
|---|---|---|
| No. | Salt Structure | Free Base Structure |
| 95 | 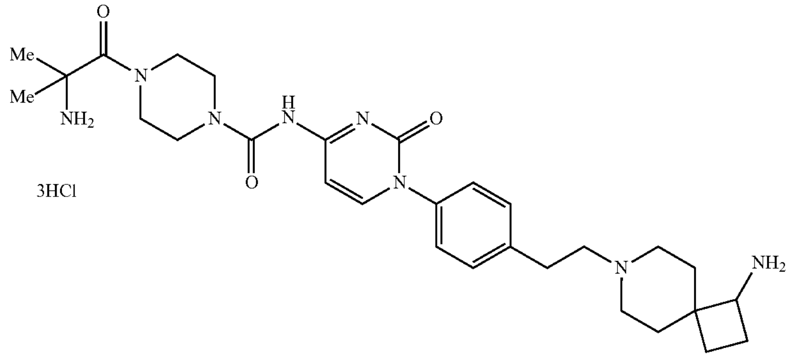 [SMILES: CC(C)(N)C(=O)N1CCN(C(=O)Nc2ccn(-c3ccc(CCN4CCC5(CCC5N)CC4)cc3)c(=O)n2)CC1] 3HCl | 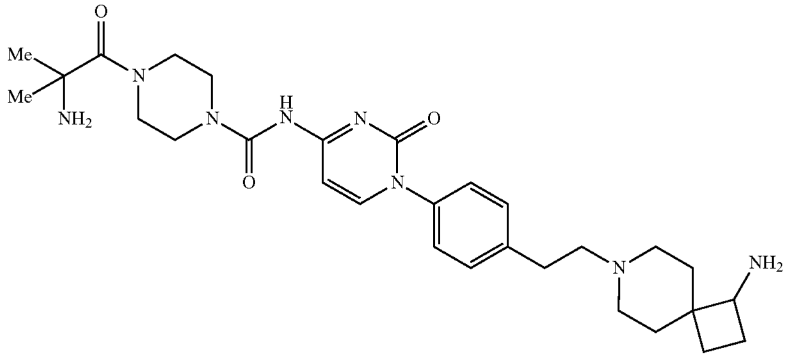 [SMILES: CC(C)(N)C(=O)N1CCN(C(=O)Nc2ccn(-c3ccc(CCN4CCC5(CCC5N)CC4)cc3)c(=O)n2)CC1] |
| 96 | 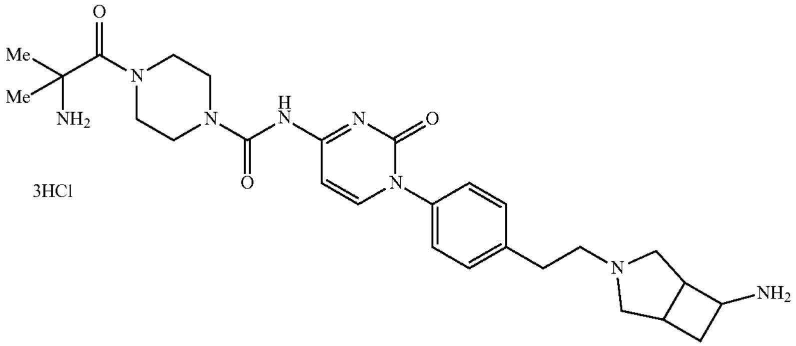 [SMILES: CC(C)(N)C(=O)N1CCN(C(=O)Nc2ccn(-c3ccc(CCN4CC5CC(N)C5C4)cc3)c(=O)n2)CC1] 3HCl | 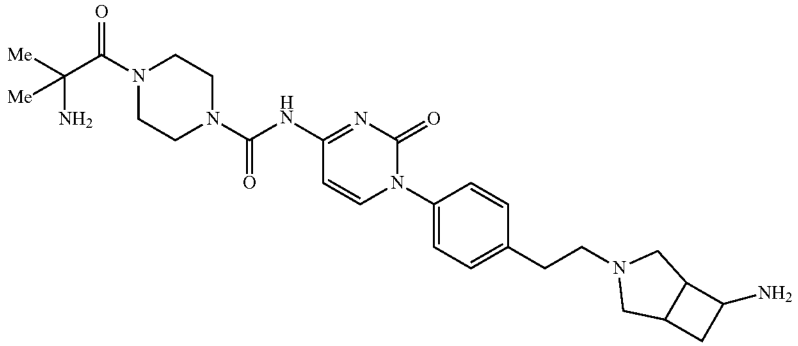 [SMILES: CC(C)(N)C(=O)N1CCN(C(=O)Nc2ccn(-c3ccc(CCN4CC5CC(N)C5C4)cc3)c(=O)n2)CC1] |

TABLE 8-continued
| Compounds of Formula I Continued | | |
|---|---|---|
| No. | Salt Structure | Free Base Structure |
| 97 | 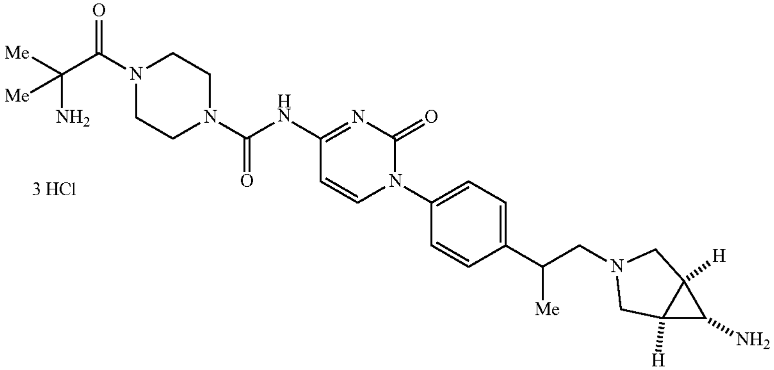 [SMILES: CC(CN1C[C@@H]2[C@@H](N)[C@@H]2C1)c1ccc(-n2ccc(NC(=O)N3CCN(C(=O)C(C)(C)N)CC3)nc2=O)cc1] 3 HCl | 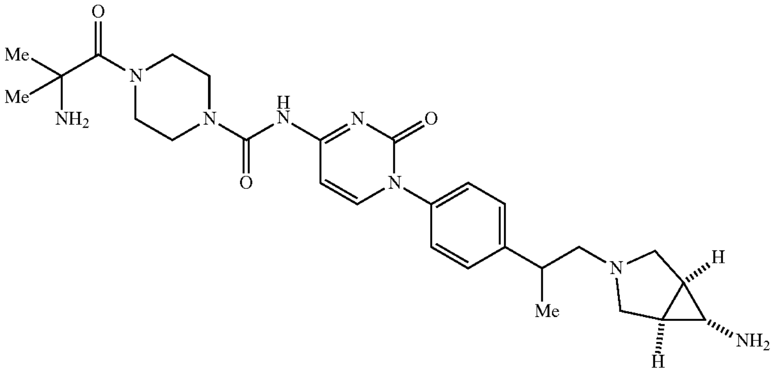 [SMILES: CC(CN1C[C@@H]2[C@@H](N)[C@@H]2C1)c1ccc(-n2ccc(NC(=O)N3CCN(C(=O)C(C)(C)N)CC3)nc2=O)cc1] |
| 98 | 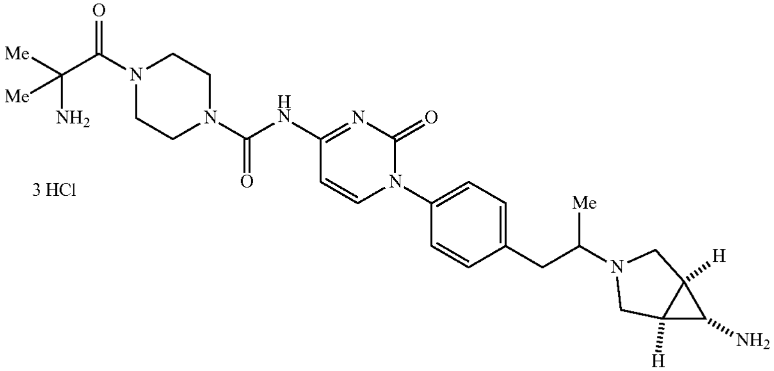 [SMILES: CC(Cc1ccc(-n2ccc(NC(=O)N3CCN(C(=O)C(C)(C)N)CC3)nc2=O)cc1)N1C[C@@H]2[C@@H](N)[C@@H]2C1] 3 HCl | 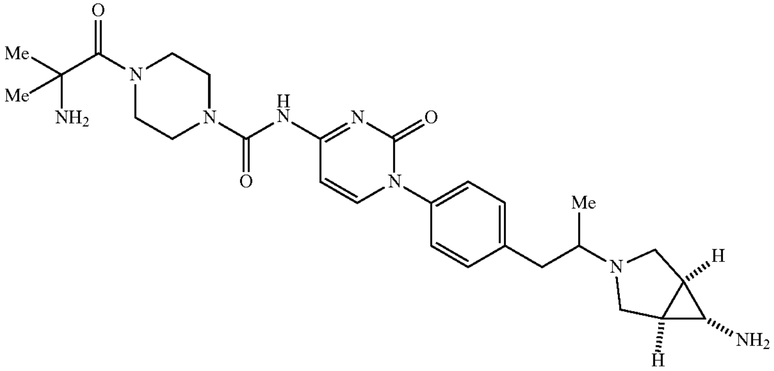 [SMILES: CC(Cc1ccc(-n2ccc(NC(=O)N3CCN(C(=O)C(C)(C)N)CC3)nc2=O)cc1)N1C[C@@H]2[C@@H](N)[C@@H]2C1] |

TABLE 8-continued
| Compounds of Formula I Continued | | |
|---|---|---|
| No. | Salt Structure | Free Base Structure |
| 99 | 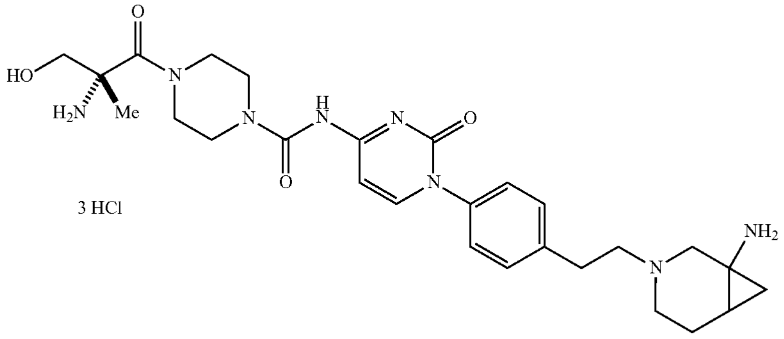 [SMILES: C[C@@](N)(CO)C(=O)N1CCN(C(=O)Nc2ccn(-c3ccc(CCN4CCC5CC5(N)C4)cc3)c(=O)n2)CC1] 3 HCl | 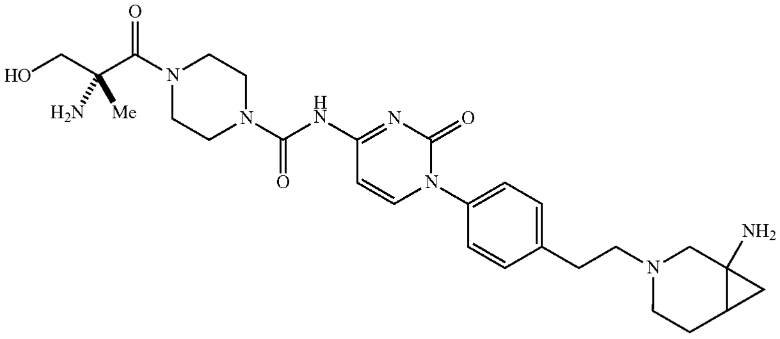 [SMILES: C[C@@](N)(CO)C(=O)N1CCN(C(=O)Nc2ccn(-c3ccc(CCN4CCC5CC5(N)C4)cc3)c(=O)n2)CC1] |
| 100 | 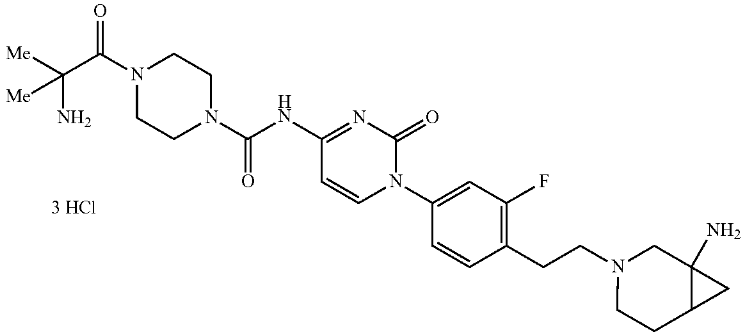 [SMILES: CC(C)(N)C(=O)N1CCN(C(=O)Nc2ccn(-c3ccc(CCN4CCC5CC5(N)C4)c(F)c3)c(=O)n2)CC1] 3 HCl | 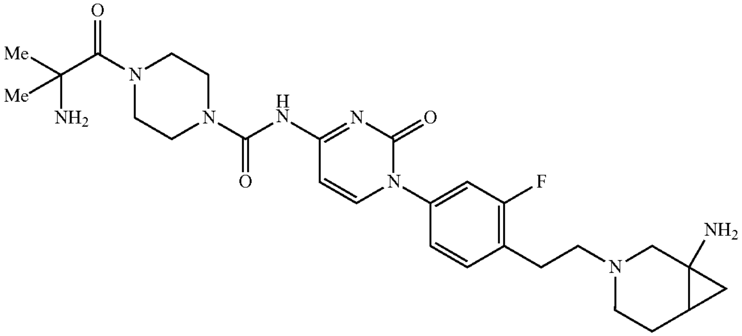 |
| 101 | 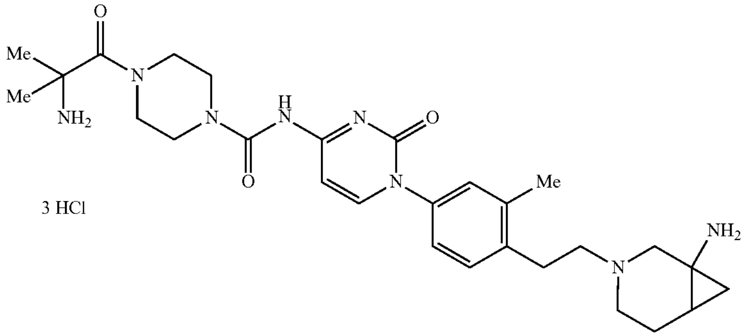 [SMILES: Cc1cc(-n2ccc(NC(=O)N3CCN(C(=O)C(C)(C)N)CC3)nc2=O)ccc1CCN1CCC2CC2(N)C1] 3 HCl | 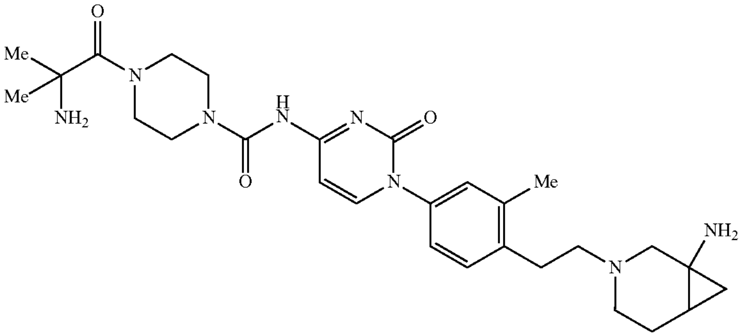 |

TABLE 8-continued
| Compounds of Formula I Continued | | |
| --- | --- | --- |
| No. | Salt Structure | Free Base Structure |
| 102 | 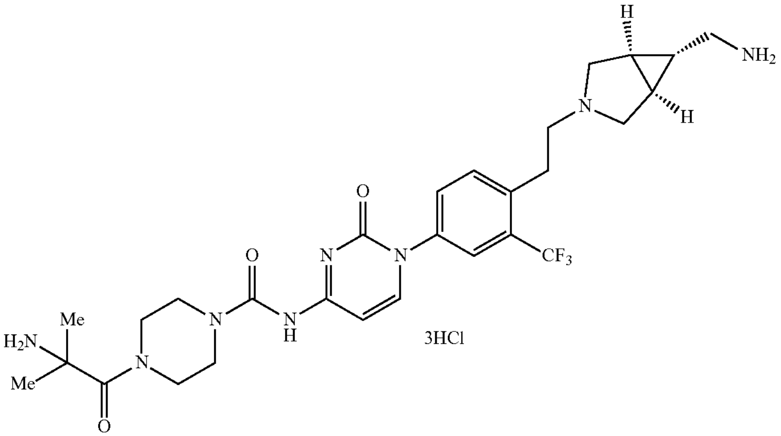 [SMILES: CC(C)(N)C(=O)N1CCN(C(=O)Nc2ccn(-c3ccc(CCN4C[C@@H]5[C@@H](CN)[C@@H]5C4)c(C(F)(F)F)c3)c(=O)n2)CC1] 3HCl | 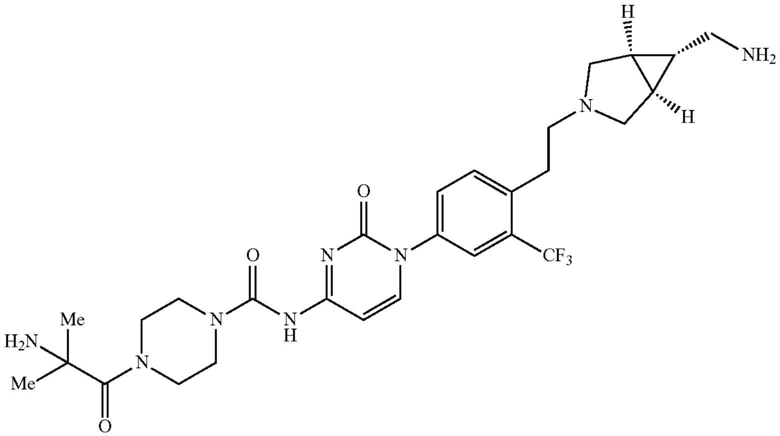 [SMILES: CC(C)(N)C(=O)N1CCN(C(=O)Nc2ccn(-c3ccc(CCN4C[C@@H]5[C@@H](CN)[C@@H]5C4)c(C(F)(F)F)c3)c(=O)n2)CC1] |
| 103 | 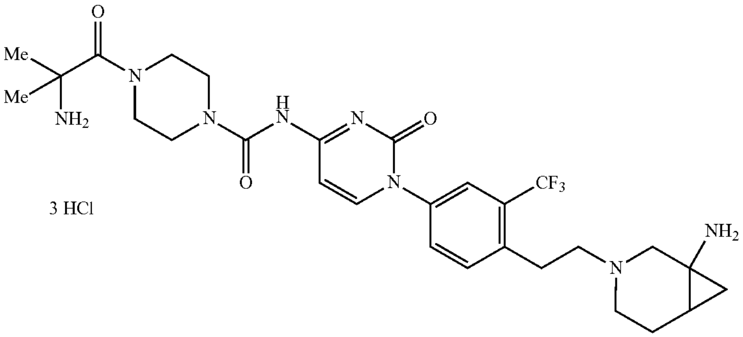 [SMILES: CC(C)(N)C(=O)N1CCN(C(=O)Nc2ccn(-c3ccc(CCN4CCC5CC5(N)C4)c(C(F)(F)F)c3)c(=O)n2)CC1] 3 HCl | 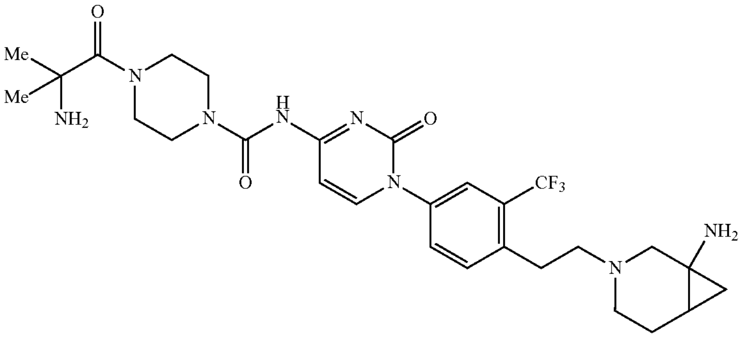 |

TABLE 8-continued
| Compounds of Formula I Continued | | |
|---|---|---|
| No. | Salt Structure | Free Base Structure |
| 104 | 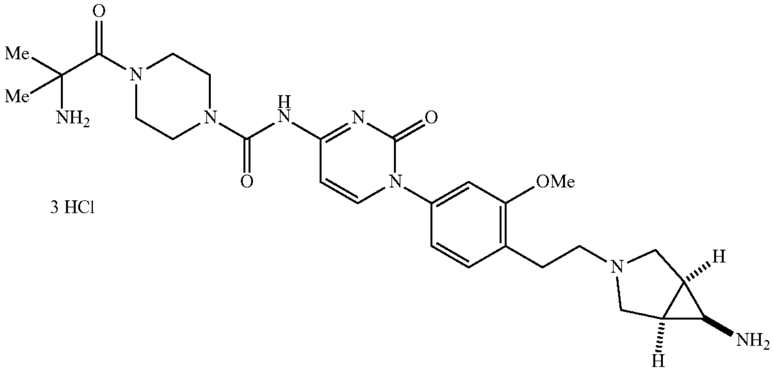 [SMILES: COc1cc(-n2ccc(NC(=O)N3CCN(C(=O)C(C)(C)N)CC3)nc2=O)ccc1CCN1C[C@@H]2[C@H](N)[C@@H]2C1] 3 HCl | 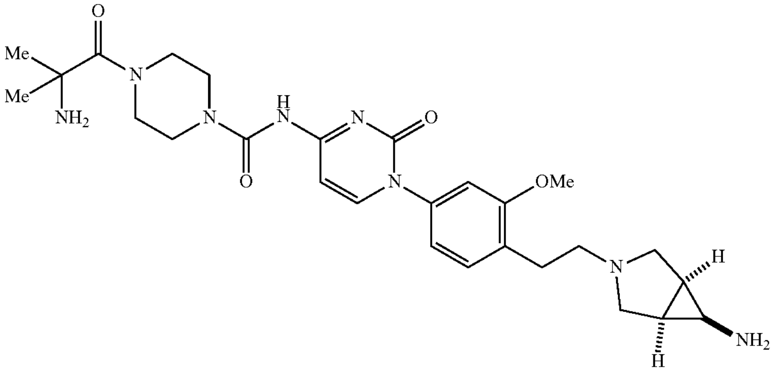 [SMILES: COc1cc(-n2ccc(NC(=O)N3CCN(C(=O)C(C)(C)N)CC3)nc2=O)ccc1CCN1C[C@@H]2[C@H](N)[C@@H]2C1] |
| 105 | 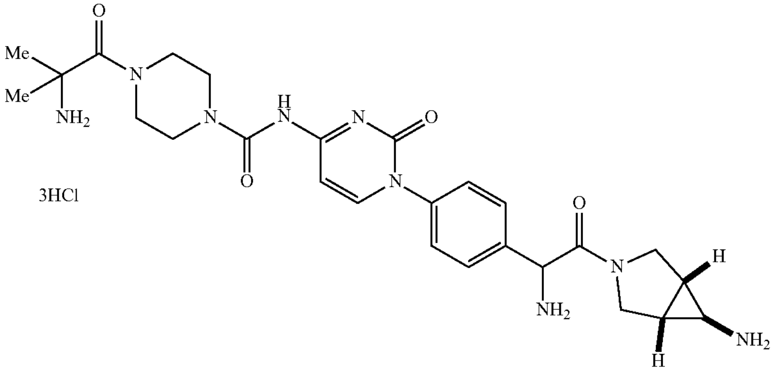 [SMILES: CC(C)(N)C(=O)N1CCN(C(=O)Nc2ccn(-c3ccc(C(N)C(=O)N4C[C@@H]5[C@@H](N)[C@@H]5C4)cc3)c(=O)n2)CC1] 3HCl | 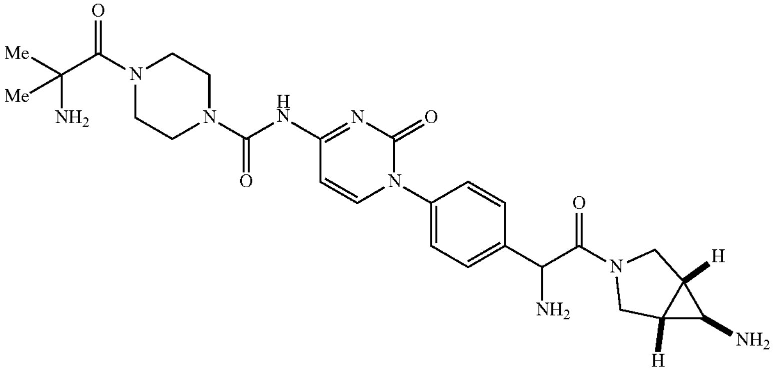 [SMILES: CC(C)(N)C(=O)N1CCN(C(=O)Nc2ccn(-c3ccc(C(N)C(=O)N4C[C@@H]5[C@@H](N)[C@@H]5C4)cc3)c(=O)n2)CC1] |

TABLE 8-continued
| Compounds of Formula I Continued | | |
|---|---|---|
| No. | Salt Structure | Free Base Structure |
| 106 | 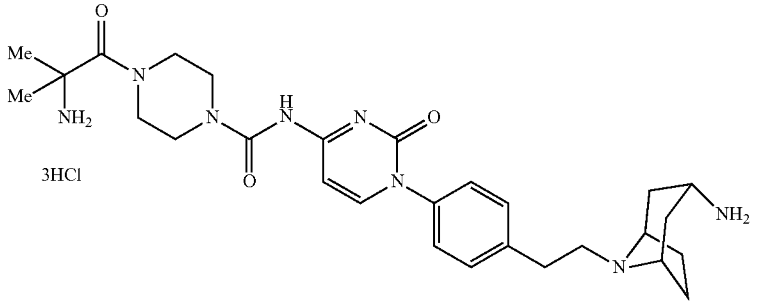 [SMILES: CC(C)(N)C(=O)N1CCN(C(=O)Nc2ccn(-c3ccc(CCN4C5CCC4CC(N)C5)cc3)c(=O)n2)CC1] 3HCl | 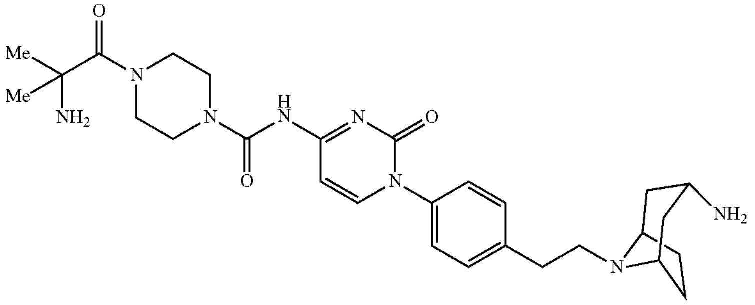 [SMILES: CC(C)(N)C(=O)N1CCN(C(=O)Nc2ccn(-c3ccc(CCN4C5CCC4CC(N)C5)cc3)c(=O)n2)CC1] |
| 107 | 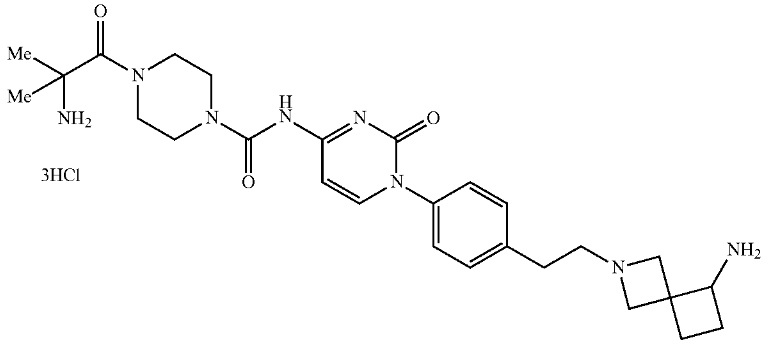 [SMILES: CC(C)(N)C(=O)N1CCN(C(=O)Nc2ccn(-c3ccc(CCN4CC5(CCC5N)C4)cc3)c(=O)n2)CC1] 3HCl | 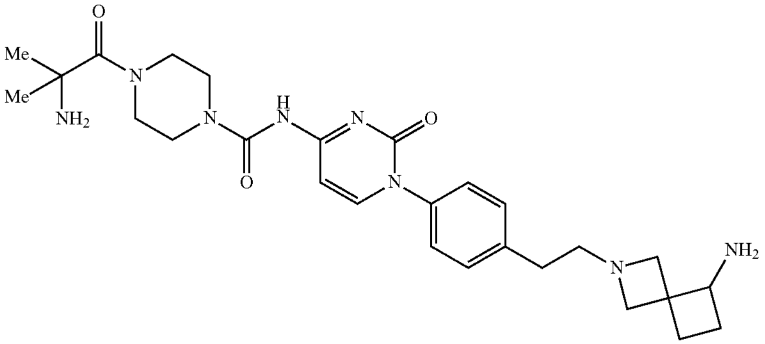 [SMILES: CC(C)(N)C(=O)N1CCN(C(=O)Nc2ccn(-c3ccc(CCN4CC5(CCC5N)C4)cc3)c(=O)n2)CC1] |
| 108 | 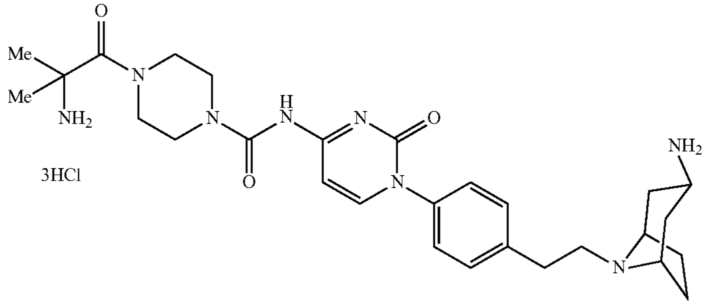 [SMILES: CC(C)(N)C(=O)N1CCN(C(=O)Nc2ccn(-c3ccc(CCN4C5CCC4CC(N)C5)cc3)c(=O)n2)CC1] 3HCl | 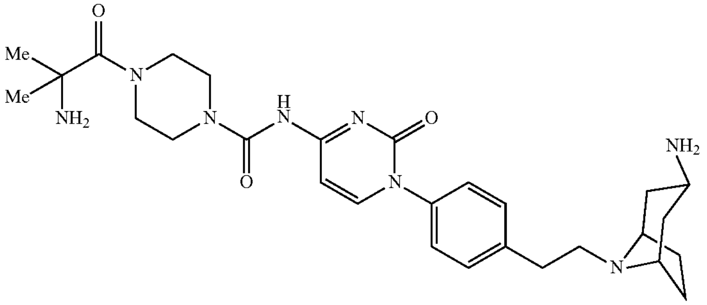 [SMILES: CC(C)(N)C(=O)N1CCN(C(=O)Nc2ccn(-c3ccc(CCN4C5CCC4CC(N)C5)cc3)c(=O)n2)CC1] |

TABLE 8-continued
| Compounds of Formula I Continued | | |
|---|---|---|
| No. | Salt Structure | Free Base Structure |
| 109 | 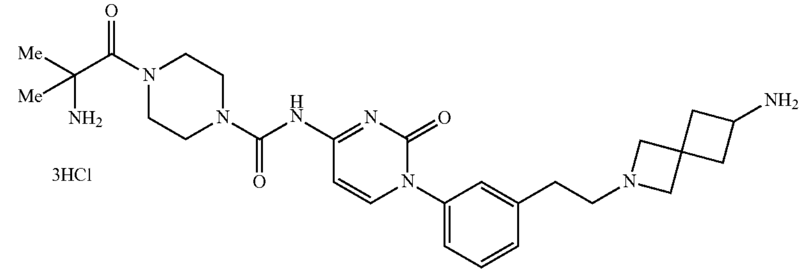 [SMILES: CC(C)(N)C(=O)N1CCN(C(=O)Nc2ccn(-c3cccc(CCN4CC5(CC(N)C5)C4)c3)c(=O)n2)CC1] 3HCl | 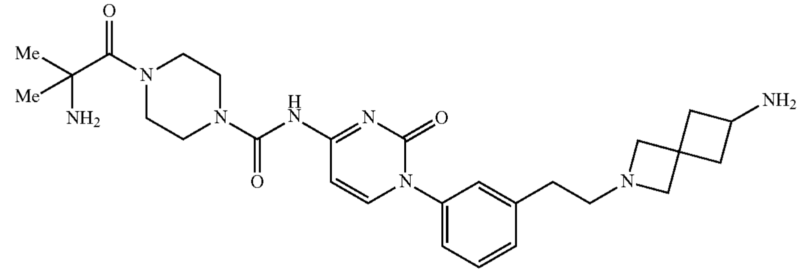 [SMILES: CC(C)(N)C(=O)N1CCN(C(=O)Nc2ccn(-c3cccc(CCN4CC5(CC(N)C5)C4)c3)c(=O)n2)CC1] |
| 110 | 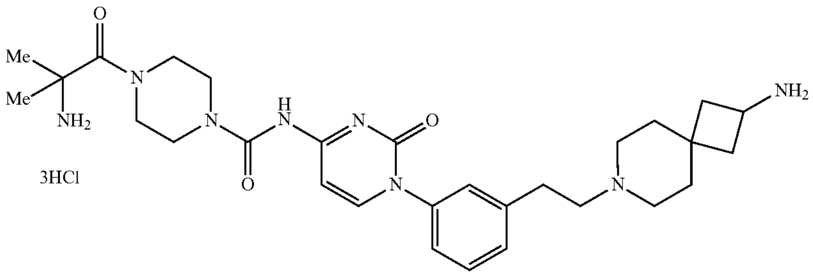 [SMILES: CC(C)(N)C(=O)N1CCN(C(=O)Nc2ccn(-c3cccc(CCN4CCC5(CC4)CC(N)C5)c3)c(=O)n2)CC1] 3HCl | 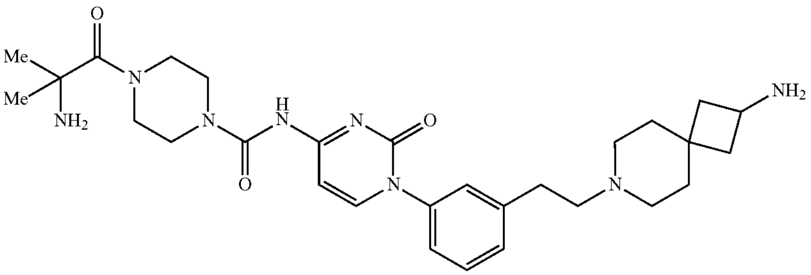 [SMILES: CC(C)(N)C(=O)N1CCN(C(=O)Nc2ccn(-c3cccc(CCN4CCC5(CC4)CC(N)C5)c3)c(=O)n2)CC1] |
| 111 | 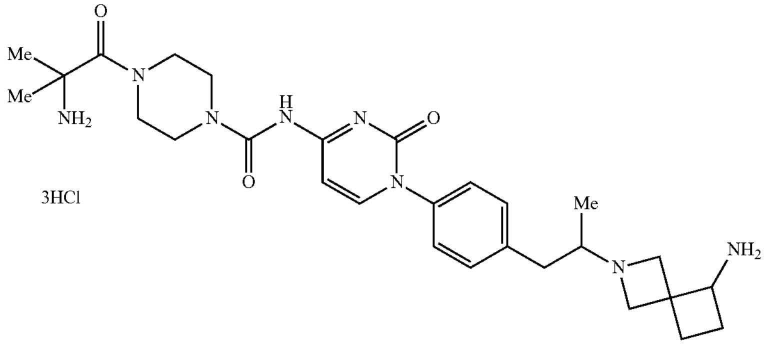 [SMILES: CC(Cc1ccc(-n2ccc(NC(=O)N3CCN(C(=O)C(C)(C)N)CC3)nc2=O)cc1)N1CC2(CCC2N)C1] 3HCl | 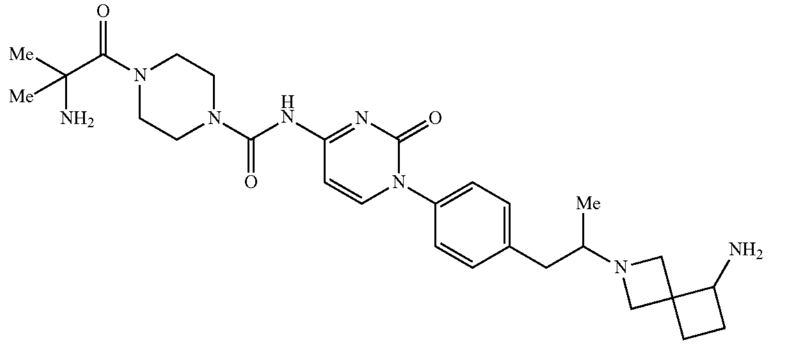 [SMILES: CC(Cc1ccc(-n2ccc(NC(=O)N3CCN(C(=O)C(C)(C)N)CC3)nc2=O)cc1)N1CC2(CCC2N)C1] |

TABLE 8-continued
| Compounds of Formula I Continued | | |
|---|---|---|
| No. | Salt Structure | Free Base Structure |
| 112 | 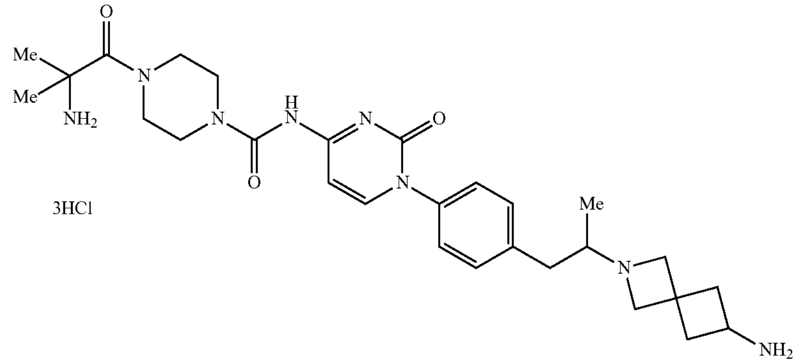 [SMILES: CC(Cc1ccc(-n2ccc(NC(=O)N3CCN(C(=O)C(C)(C)N)CC3)nc2=O)cc1)N1CC2(CC(N)C2)C1] 3HCl | 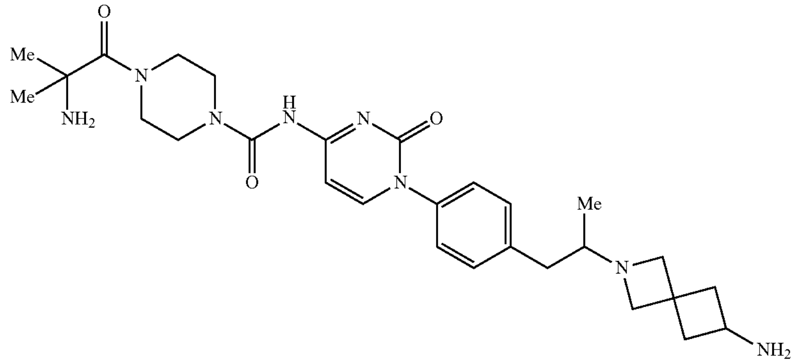 [SMILES: CC(Cc1ccc(-n2ccc(NC(=O)N3CCN(C(=O)C(C)(C)N)CC3)nc2=O)cc1)N1CC2(CC(N)C2)C1] |
| 113 | 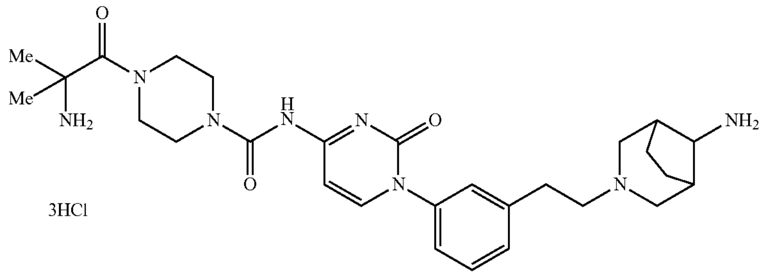 [SMILES: CC(C)(N)C(=O)N1CCN(C(=O)Nc2ccn(-c3cccc(CCN4CC5CCC(C4)C5N)c3)c(=O)n2)CC1] 3HCl | 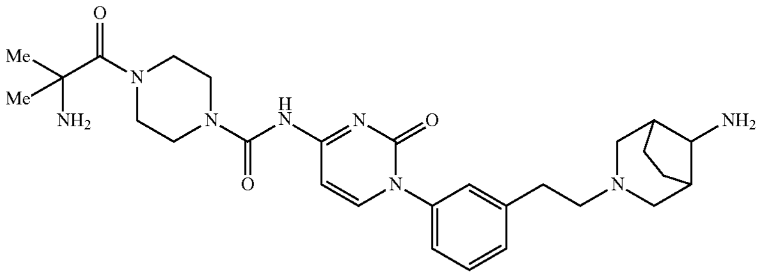 [SMILES: CC(C)(N)C(=O)N1CCN(C(=O)Nc2ccn(-c3cccc(CCN4CC5CCC(C4)C5N)c3)c(=O)n2)CC1] |
| 114 | 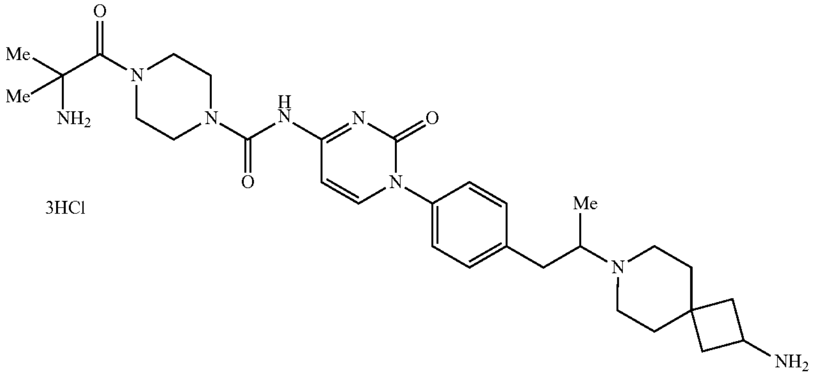 [SMILES: CC(Cc1ccc(-n2ccc(NC(=O)N3CCN(C(=O)C(C)(C)N)CC3)nc2=O)cc1)N1CCC2(CC1)CC(N)C2] 3HCl | 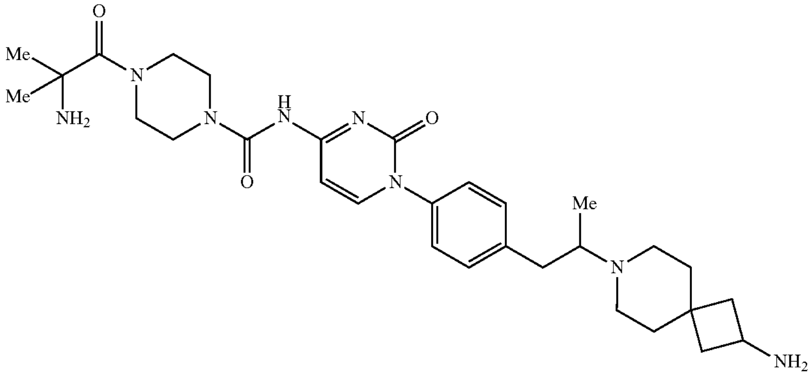 [SMILES: CC(Cc1ccc(-n2ccc(NC(=O)N3CCN(C(=O)C(C)(C)N)CC3)nc2=O)cc1)N1CCC2(CC1)CC(N)C2] |

TABLE 8-continued
| Compounds of Formula I Continued | | |
|---|---|---|
| No. | Salt Structure | Free Base Structure |
| 115 | 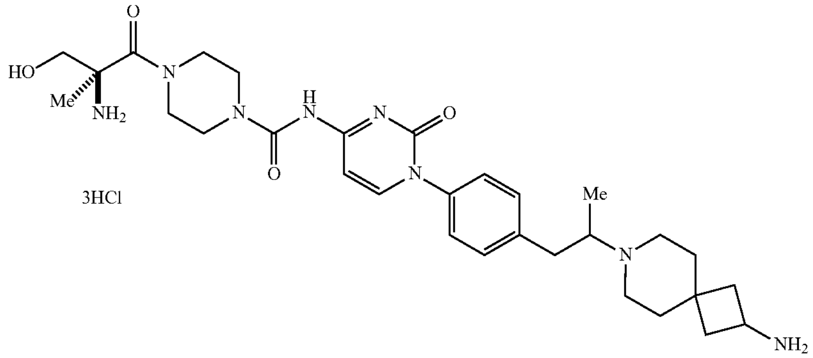 3HCl | 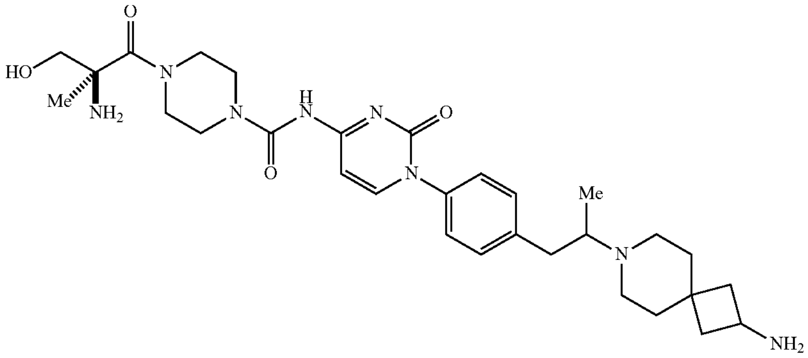 |
| 116 | 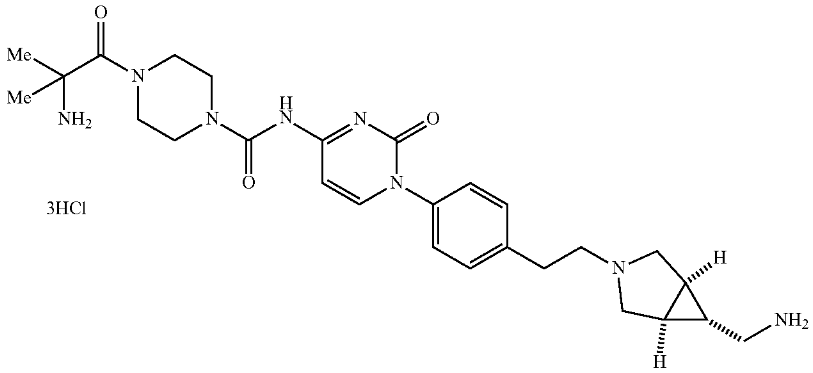 [SMILES: CC(C)(N)C(=O)N1CCN(C(=O)Nc2ccn(-c3ccc(CCN4C[C@@H]5[C@@H](CN)[C@@H]5C4)cc3)c(=O)n2)CC1] 3HCl | 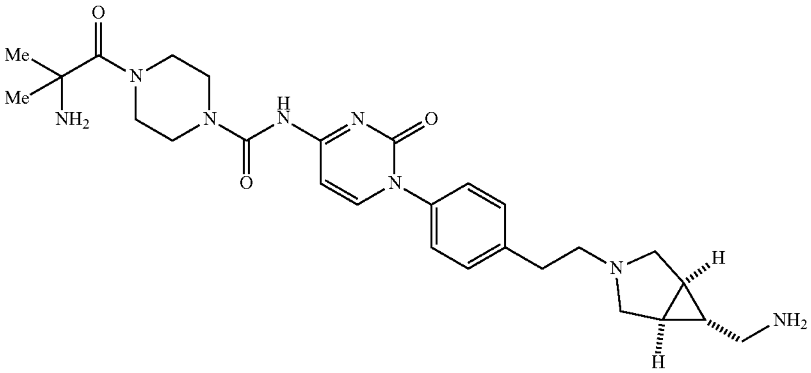 [SMILES: CC(C)(N)C(=O)N1CCN(C(=O)Nc2ccn(-c3ccc(CCN4C[C@@H]5[C@@H](CN)[C@@H]5C4)cc3)c(=O)n2)CC1] |

TABLE 8-continued
| Compounds of Formula I Continued | | |
|---|---|---|
| No. | Salt Structure | Free Base Structure |
| 117 | 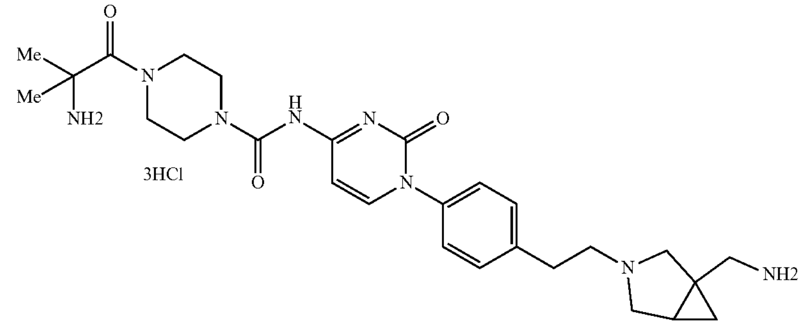 [SMILES: CC(C)(N)C(=O)N1CCN(C(=O)Nc2ccn(-c3ccc(CCN4CC5CC5(CN)C4)cc3)c(=O)n2)CC1] 3HCl | 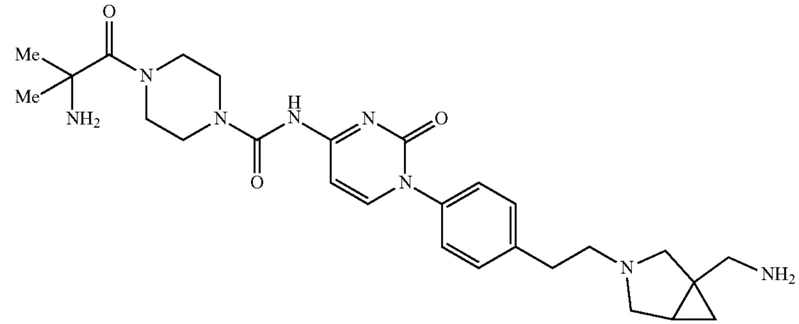 [SMILES: CC(C)(N)C(=O)N1CCN(C(=O)Nc2ccn(-c3ccc(CCN4CC5CC5(CN)C4)cc3)c(=O)n2)CC1] |
| 118 | 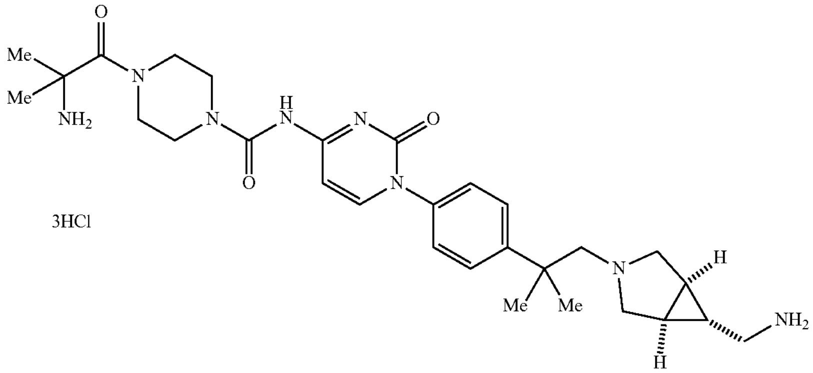 [SMILES: CC(C)(N)C(=O)N1CCN(C(=O)Nc2ccn(-c3ccc(C(C)(C)CN4C[C@@H]5[C@@H](CN)[C@@H]5C4)cc3)c(=O)n2)CC1] 3HCl | 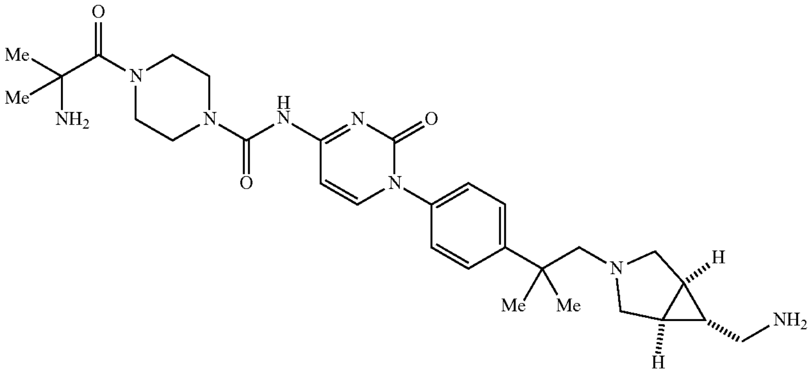 [SMILES: CC(C)(N)C(=O)N1CCN(C(=O)Nc2ccn(-c3ccc(C(C)(C)CN4C[C@@H]5[C@@H](CN)[C@@H]5C4)cc3)c(=O)n2)CC1] |
| 119 | 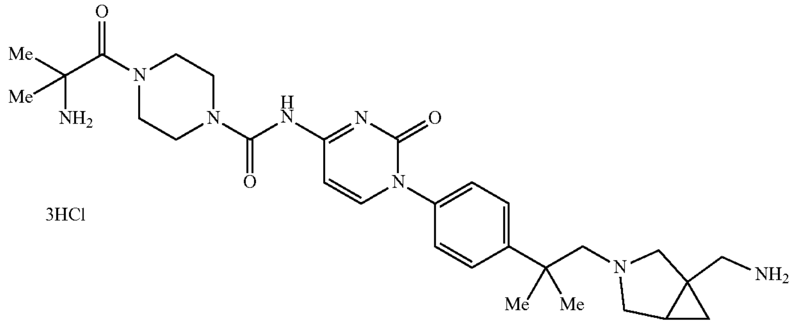 [SMILES: CC(C)(N)C(=O)N1CCN(C(=O)Nc2ccn(-c3ccc(C(C)(C)CN4CC5CC5(CN)C4)cc3)c(=O)n2)CC1] 3HCl | 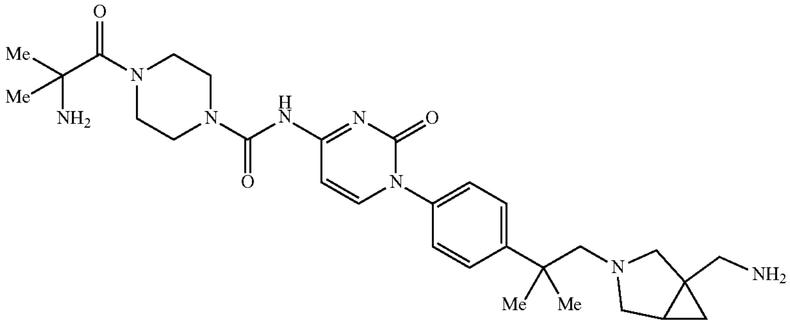 [SMILES: CC(C)(N)C(=O)N1CCN(C(=O)Nc2ccn(-c3ccc(C(C)(C)CN4CC5CC5(CN)C4)cc3)c(=O)n2)CC1] |

TABLE 8-continued
| Compounds of Formula I Continued | | |
|---|---|---|
| No. | Salt Structure | Free Base Structure |
| 120 | 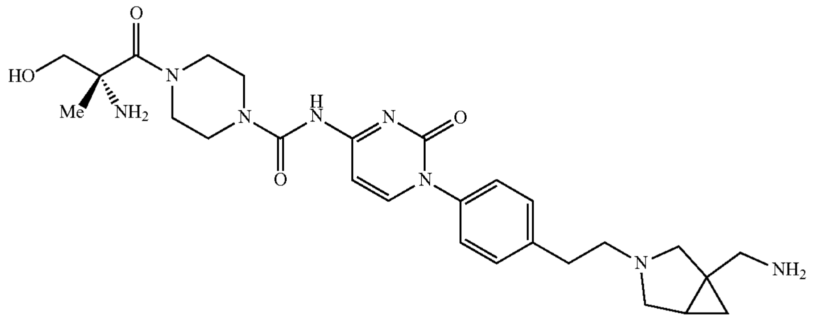 [SMILES: C[C@@](N)(CO)C(=O)N1CCN(C(=O)Nc2ccn(-c3ccc(CCN4CC5CC5(CN)C4)cc3)c(=O)n2)CC1] | 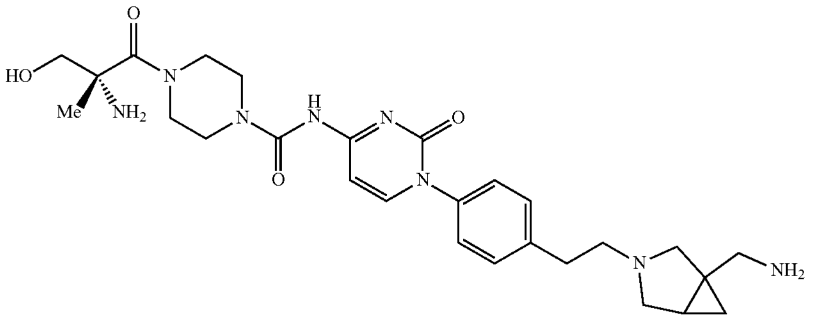 [SMILES: C[C@@](N)(CO)C(=O)N1CCN(C(=O)Nc2ccn(-c3ccc(CCN4CC5CC5(CN)C4)cc3)c(=O)n2)CC1] |
| 121 | 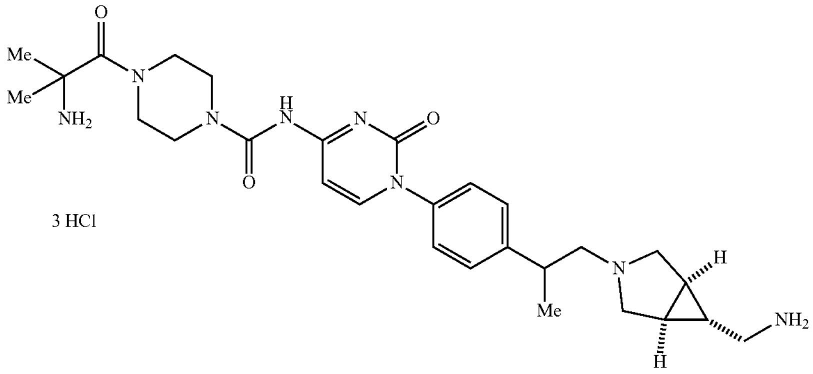 [SMILES: CC(CN1C[C@@H]2[C@@H](CN)[C@@H]2C1)c1ccc(-n2ccc(NC(=O)N3CCN(C(=O)C(C)(C)N)CC3)nc2=O)cc1] 3 HCl | 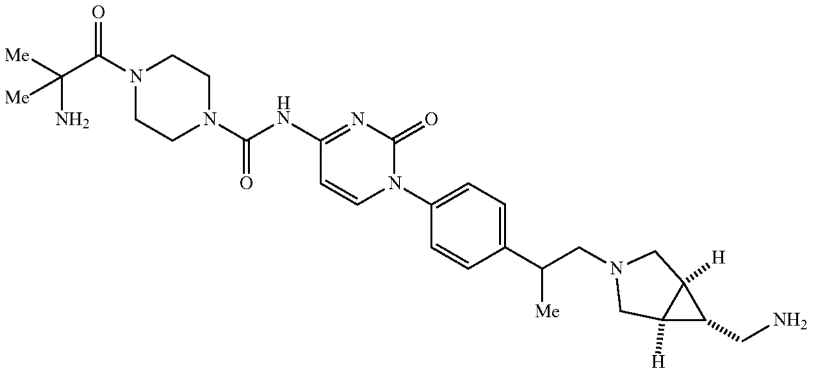 [SMILES: CC(CN1C[C@@H]2[C@@H](CN)[C@@H]2C1)c1ccc(-n2ccc(NC(=O)N3CCN(C(=O)C(C)(C)N)CC3)nc2=O)cc1] |

TABLE 8-continued
| Compounds of Formula I Continued | | |
|---|---|---|
| No. | Salt Structure | Free Base Structure |
| 122 | 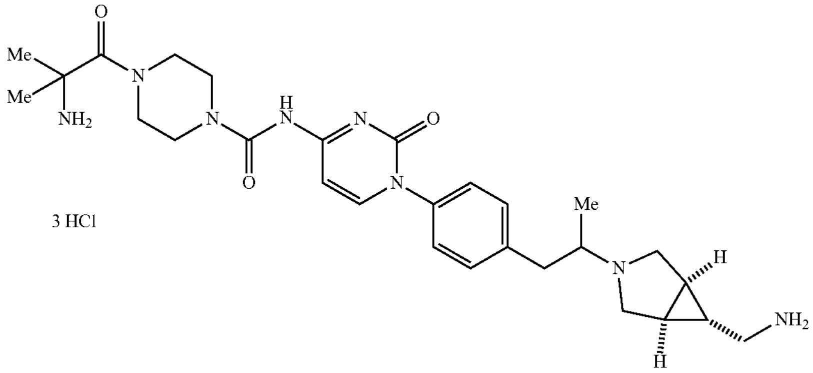 [SMILES: CC(Cc1ccc(-n2ccc(NC(=O)N3CCN(C(=O)C(C)(C)N)CC3)nc2=O)cc1)N1C[C@@H]2[C@@H](CN)[C@@H]2C1] 3 HCl | 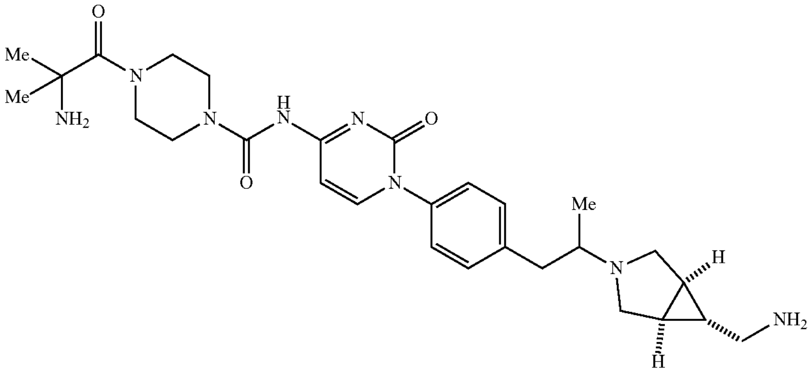 [SMILES: CC(Cc1ccc(-n2ccc(NC(=O)N3CCN(C(=O)C(C)(C)N)CC3)nc2=O)cc1)N1C[C@@H]2[C@@H](CN)[C@@H]2C1] |
| 123 | 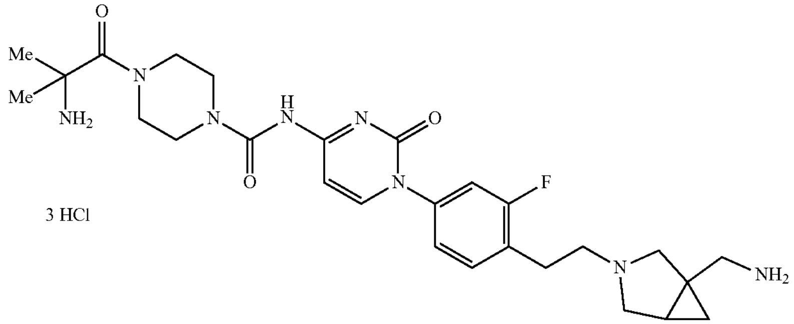 [SMILES: CC(C)(N)C(=O)N1CCN(C(=O)Nc2ccn(-c3ccc(CCN4CC5CC5(CN)C4)c(F)c3)c(=O)n2)CC1] 3 HCl | 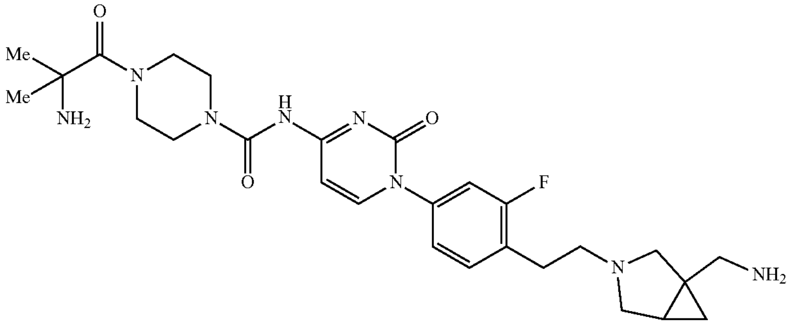 [SMILES: CC(C)(N)C(=O)N1CCN(C(=O)Nc2ccn(-c3ccc(CCN4CC5CC5(CN)C4)c(F)c3)c(=O)n2)CC1] |

TABLE 8-continued
| Compounds of Formula I Continued | | |
|---|---|---|
| No. | Salt Structure | Free Base Structure |
| 124 | 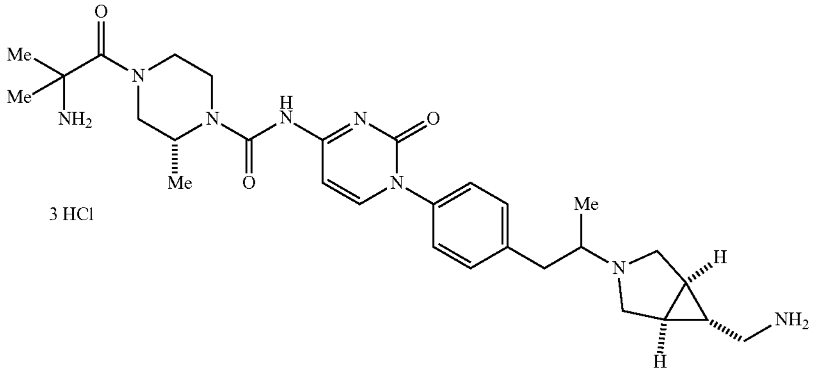 [SMILES: CC(Cc1ccc(-n2ccc(NC(=O)N3CCN(C(=O)C(C)(C)N)C[C@H]3C)nc2=O)cc1)N1C[C@@H]2[C@@H](CN)[C@@H]2C1] 3 HCl | 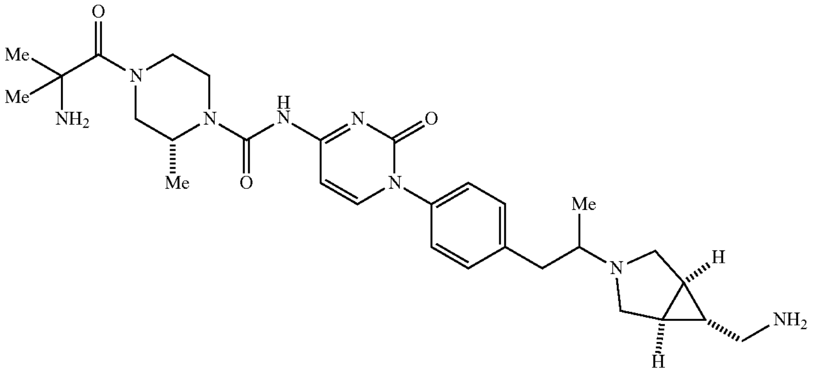 [SMILES: CC(Cc1ccc(-n2ccc(NC(=O)N3CCN(C(=O)C(C)(C)N)C[C@H]3C)nc2=O)cc1)N1C[C@@H]2[C@@H](CN)[C@@H]2C1] |
| 125 | 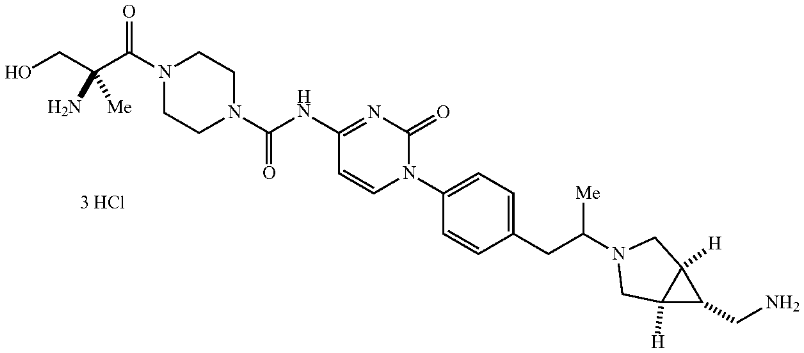 [SMILES: CC(Cc1ccc(-n2ccc(NC(=O)N3CCN(C(=O)[C@@](C)(N)CO)CC3)nc2=O)cc1)N1C[C@@H]2[C@@H](CN)[C@@H]2C1] 3 HCl | 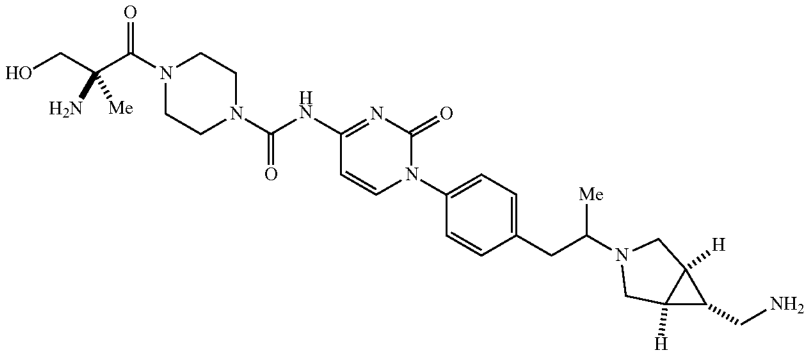 [SMILES: CC(Cc1ccc(-n2ccc(NC(=O)N3CCN(C(=O)[C@@](C)(N)CO)CC3)nc2=O)cc1)N1C[C@@H]2[C@@H](CN)[C@@H]2C1] |

TABLE 8-continued
| Compounds of Formula I Continued | | |
|---|---|---|
| No. | Salt Structure | Free Base Structure |
| 126 | 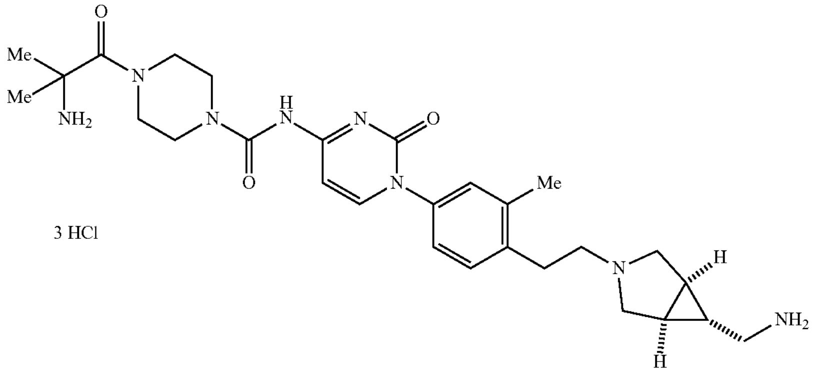 [SMILES: Cc1cc(-n2ccc(NC(=O)N3CCN(C(=O)C(C)(C)N)CC3)nc2=O)ccc1CCN1C[C@@H]2[C@@H](CN)[C@@H]2C1] 3 HCl | 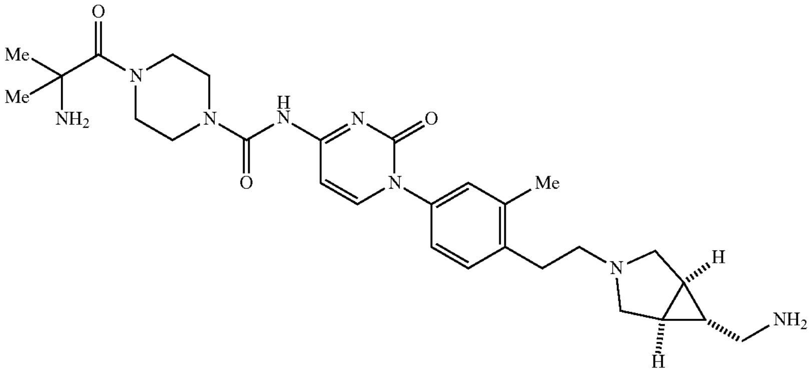 [SMILES: Cc1cc(-n2ccc(NC(=O)N3CCN(C(=O)C(C)(C)N)CC3)nc2=O)ccc1CCN1C[C@@H]2[C@@H](CN)[C@@H]2C1] |
| 127 | 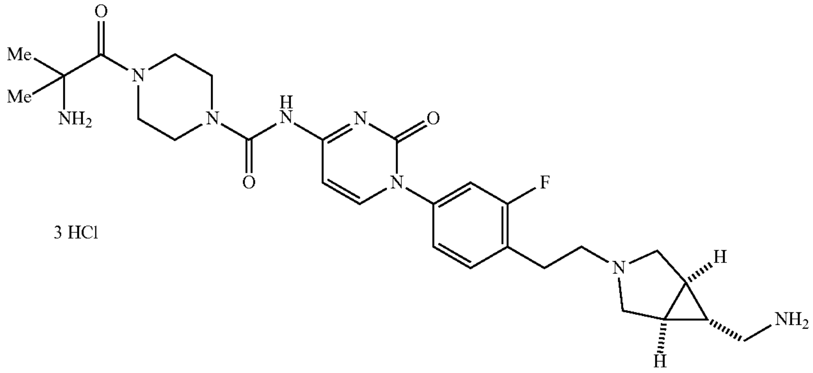 [SMILES: CC(C)(N)C(=O)N1CCN(C(=O)Nc2ccn(-c3ccc(CCN4C[C@@H]5[C@@H](CN)[C@@H]5C4)c(F)c3)c(=O)n2)CC1] 3 HCl | 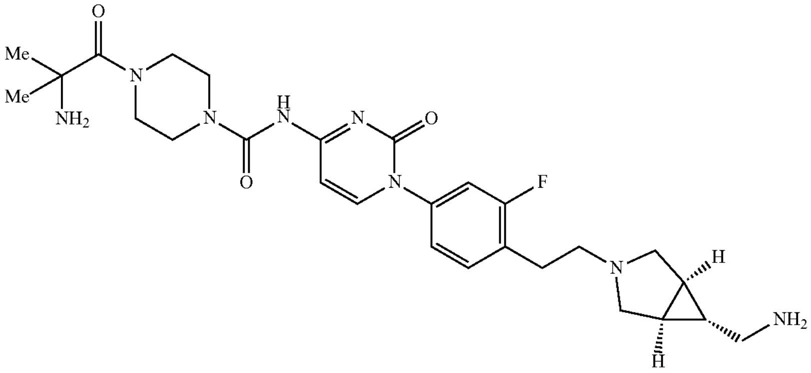 [SMILES: CC(C)(N)C(=O)N1CCN(C(=O)Nc2ccn(-c3ccc(CCN4C[C@@H]5[C@@H](CN)[C@@H]5C4)c(F)c3)c(=O)n2)CC1] |

TABLE 8-continued
| Compounds of Formula I Continued | | |
|---|---|---|
| No. | Salt Structure | Free Base Structure |
| 128 | 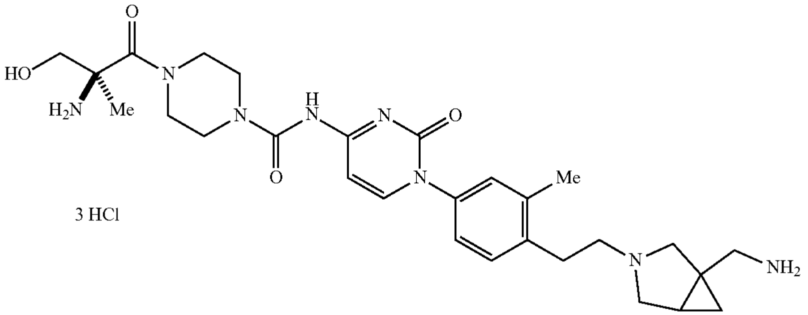 [SMILES: Cc1cc(-n2ccc(NC(=O)N3CCN(C(=O)[C@@](C)(N)CO)CC3)nc2=O)ccc1CCN1CC2CC2(CN)C1] 3 HCl | 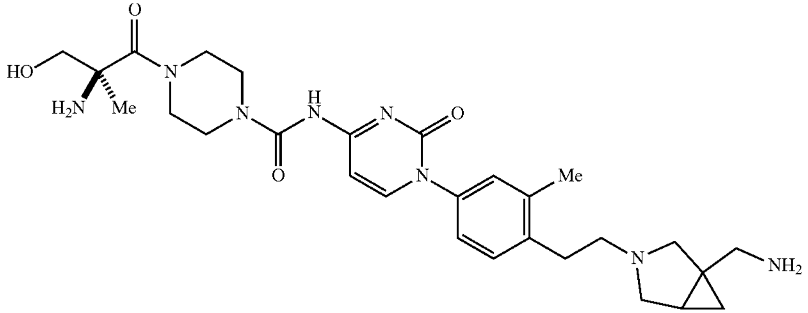 [SMILES: Cc1cc(-n2ccc(NC(=O)N3CCN(C(=O)[C@@](C)(N)CO)CC3)nc2=O)ccc1CCN1CC2CC2(CN)C1] |
| 129 | 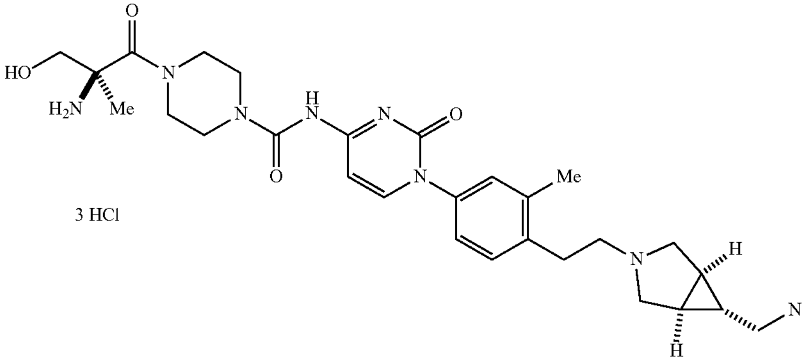 [SMILES: Cc1cc(-n2ccc(NC(=O)N3CCN(C(=O)[C@@](C)(N)CO)CC3)nc2=O)ccc1CCN1C[C@@H]2[C@@H](CN)[C@@H]2C1] 3 HCl | 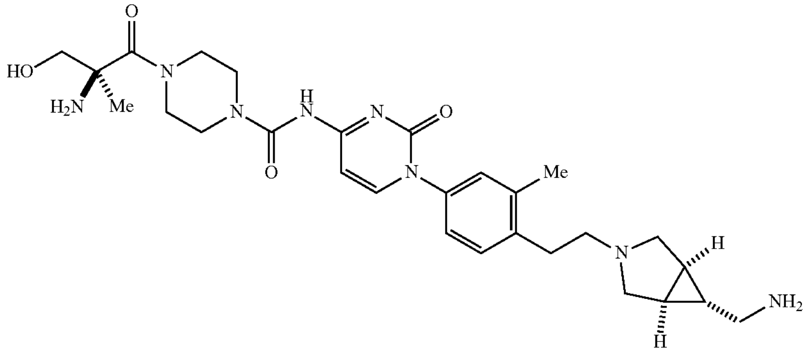 [SMILES: Cc1cc(-n2ccc(NC(=O)N3CCN(C(=O)[C@@](C)(N)CO)CC3)nc2=O)ccc1CCN1C[C@@H]2[C@@H](CN)[C@@H]2C1] |
| 130 | 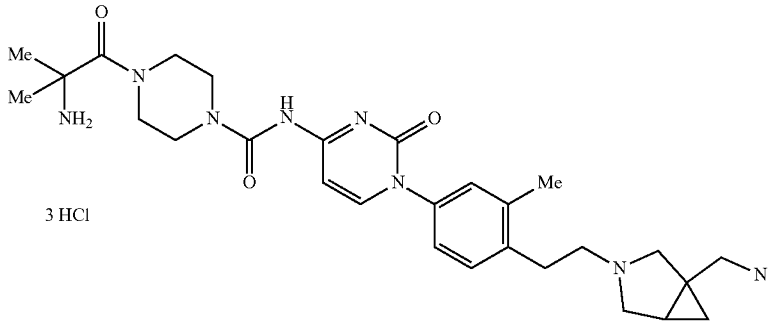 [SMILES: Cc1cc(-n2ccc(NC(=O)N3CCN(C(=O)C(C)(C)N)CC3)nc2=O)ccc1CCN1CC2CC2(CN)C1] 3 HCl | 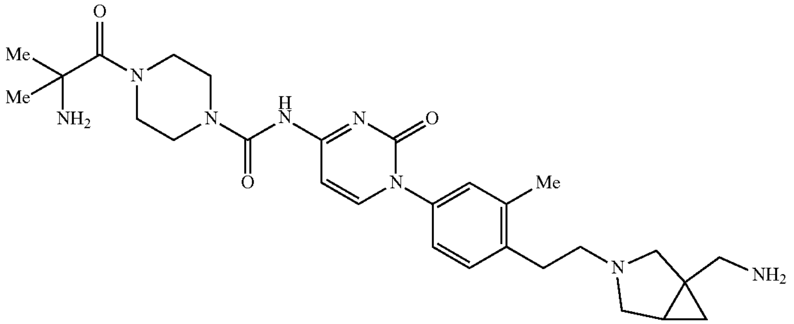 [SMILES: Cc1cc(-n2ccc(NC(=O)N3CCN(C(=O)C(C)(C)N)CC3)nc2=O)ccc1CCN1CC2CC2(CN)C1] |

TABLE 8-continued
| Compounds of Formula I Continued | | |
|---|---|---|
| No. | Salt Structure | Free Base Structure |
| 131 | 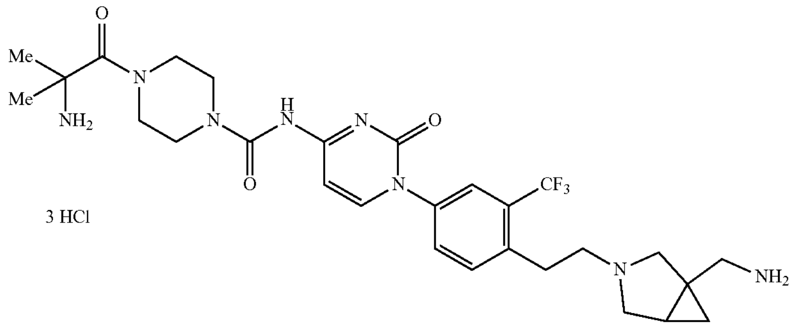 [SMILES: CC(C)(N)C(=O)N1CCN(C(=O)Nc2ccn(-c3ccc(CCN4CC5CC5(CN)C4)c(C(F)(F)F)c3)c(=O)n2)CC1] 3 HCl | 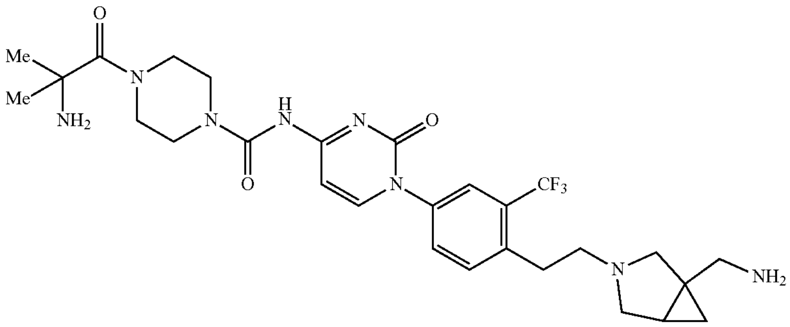 [SMILES: CC(C)(N)C(=O)N1CCN(C(=O)Nc2ccn(-c3ccc(CCN4CC5CC5(CN)C4)c(C(F)(F)F)c3)c(=O)n2)CC1] |
| 132 | 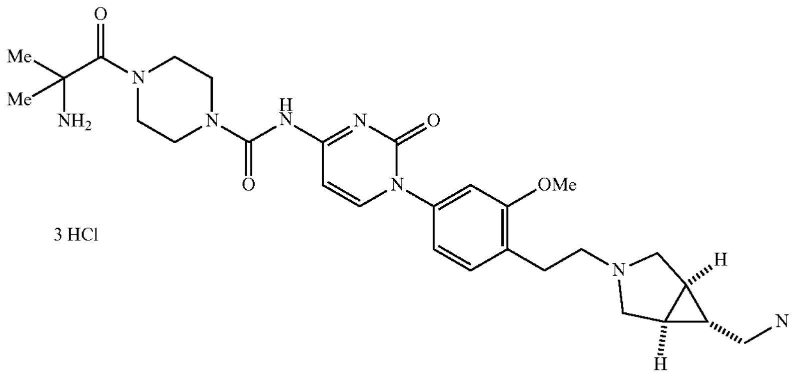 [SMILES: COc1cc(-n2ccc(NC(=O)N3CCN(C(=O)C(C)(C)N)CC3)nc2=O)ccc1CCN1C[C@@H]2[C@@H](CN)[C@@H]2C1] 3 HCl | 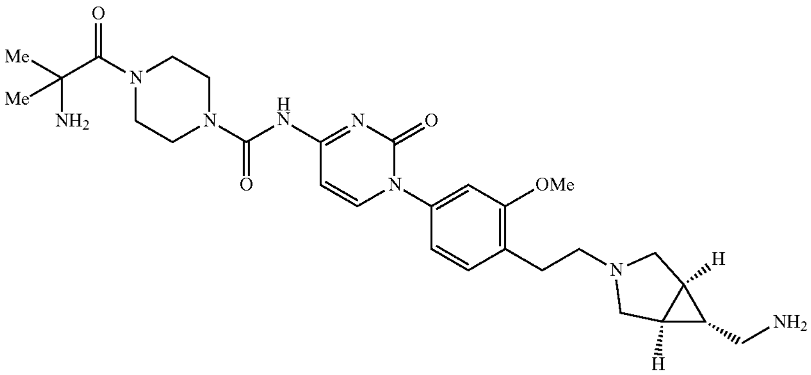 [SMILES: COc1cc(-n2ccc(NC(=O)N3CCN(C(=O)C(C)(C)N)CC3)nc2=O)ccc1CCN1C[C@@H]2[C@@H](CN)[C@@H]2C1] |

TABLE 8-continued
| Compounds of Formula I Continued | | |
|---|---|---|
| No. | Salt Structure | Free Base Structure |
| 133 | 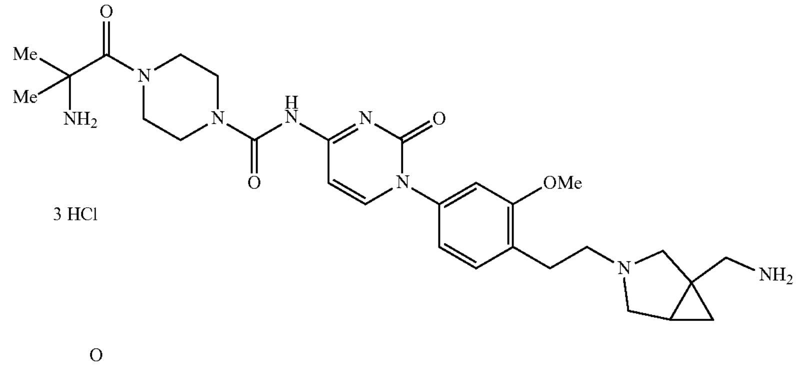 3 HCl | 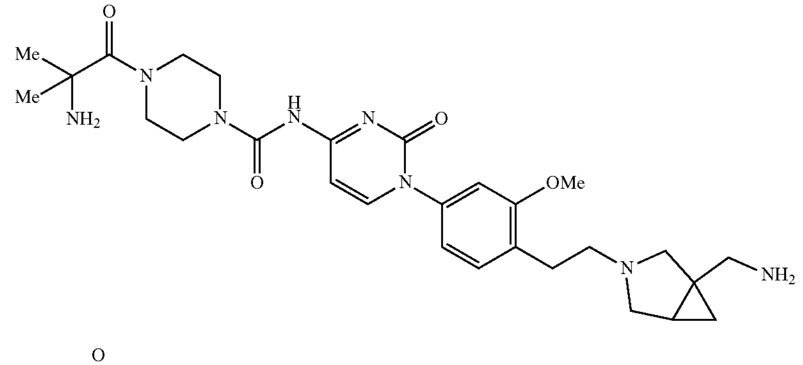 |
| 134 | 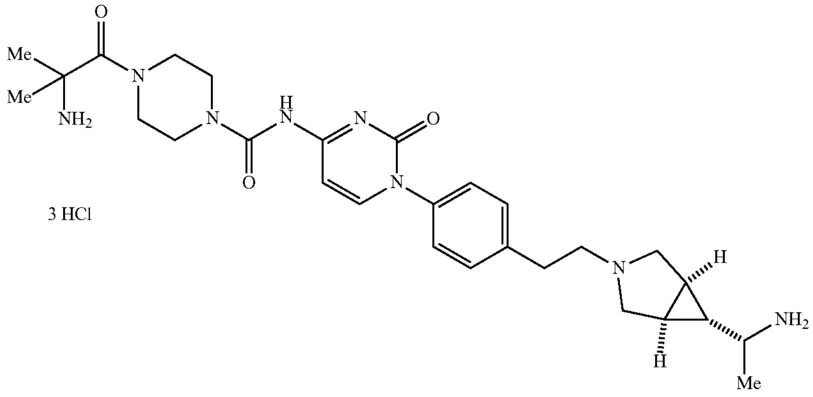 [SMILES: CC(N)[C@H]1[C@@H]2CN(CCc3ccc(-n4ccc(NC(=O)N5CCN(C(=O)C(C)(C)N)CC5)nc4=O)cc3)C[C@@H]21] 3 HCl | 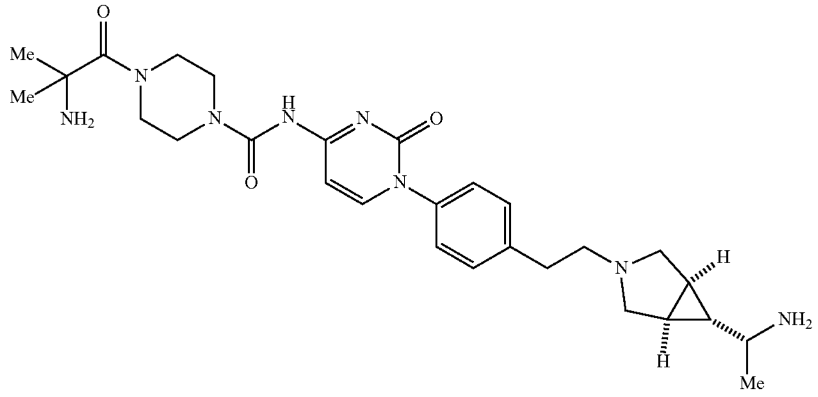 [SMILES: CC(N)[C@H]1[C@@H]2CN(CCc3ccc(-n4ccc(NC(=O)N5CCN(C(=O)C(C)(C)N)CC5)nc4=O)cc3)C[C@@H]21] |

TABLE 8-continued
| Compounds of Formula I Continued | | |
|---|---|---|
| No. | Salt Structure | Free Base Structure |
| 135 | 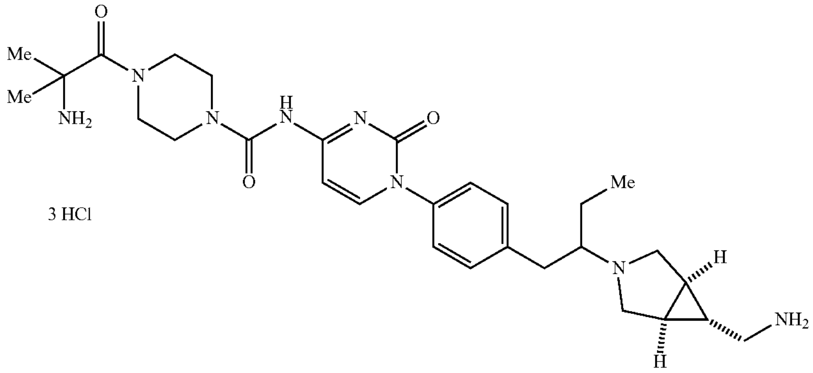 [SMILES: CCC(Cc1ccc(-n2ccc(NC(=O)N3CCN(C(=O)C(C)(C)N)CC3)nc2=O)cc1)N1C[C@@H]2[C@@H](CN)[C@@H]2C1] 3 HCl | 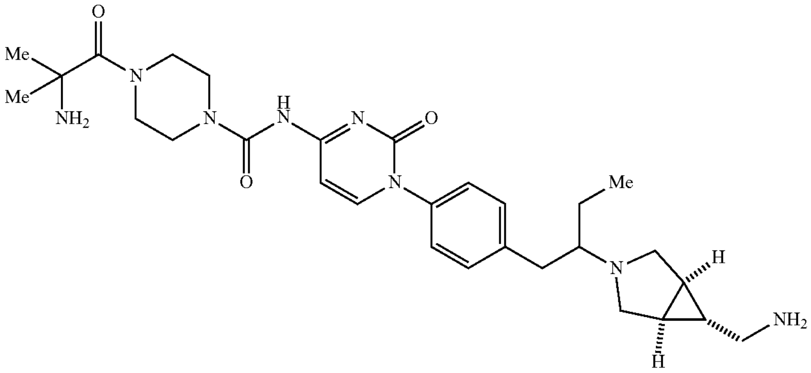 [SMILES: CCC(Cc1ccc(-n2ccc(NC(=O)N3CCN(C(=O)C(C)(C)N)CC3)nc2=O)cc1)N1C[C@@H]2[C@@H](CN)[C@@H]2C1] |
| 136 | 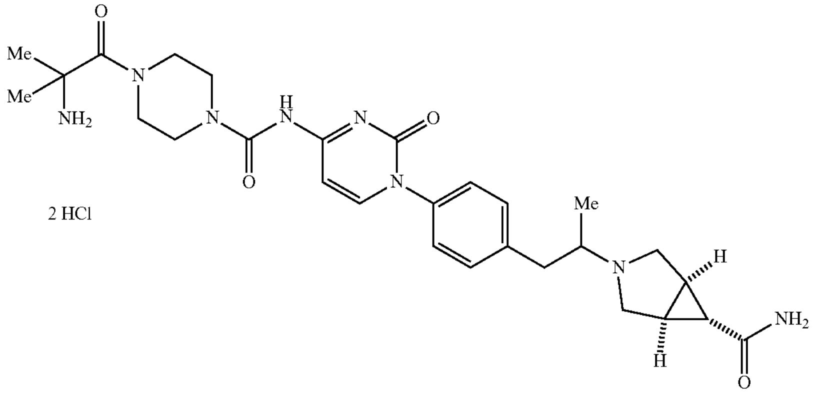 [SMILES: CC(Cc1ccc(-n2ccc(NC(=O)N3CCN(C(=O)C(C)(C)N)CC3)nc2=O)cc1)N1C[C@@H]2[C@H](C1)[C@H]2C(N)=O] 2 HCl | 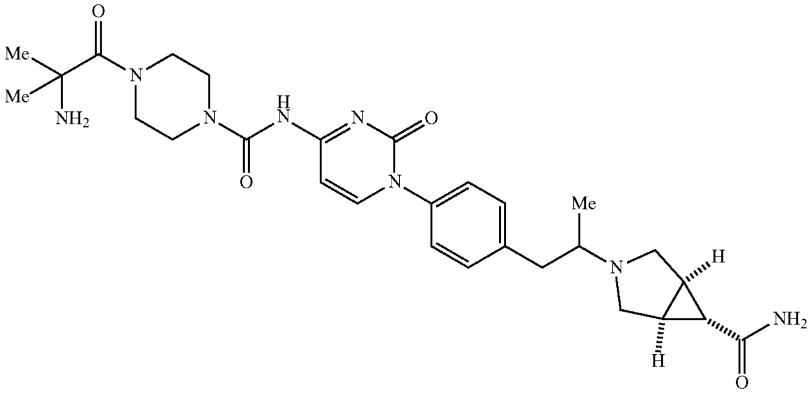 [SMILES: CC(Cc1ccc(-n2ccc(NC(=O)N3CCN(C(=O)C(C)(C)N)CC3)nc2=O)cc1)N1C[C@@H]2[C@H](C1)[C@H]2C(N)=O] |

TABLE 8-continued
| Compounds of Formula I Continued | | |
|---|---|---|
| No. | Salt Structure | Free Base Structure |
| 137 | 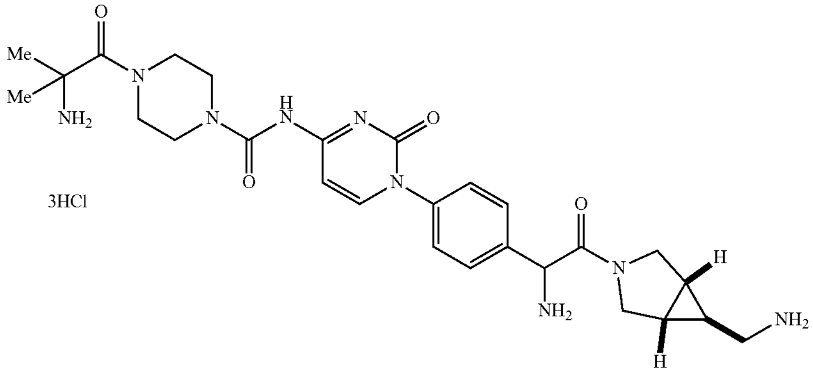 [SMILES: CC(C)(N)C(=O)N1CCN(C(=O)Nc2ccn(-c3ccc(C(N)C(=O)N4C[C@@H]5[C@@H](CN)[C@@H]5C4)cc3)c(=O)n2)CC1] 3HCl | 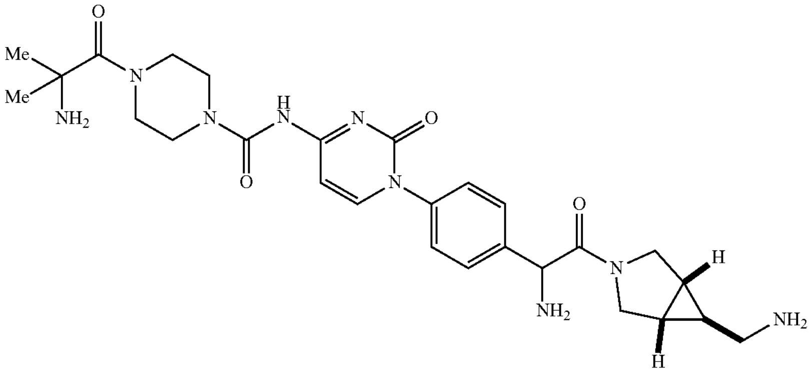 [SMILES: CC(C)(N)C(=O)N1CCN(C(=O)Nc2ccn(-c3ccc(C(N)C(=O)N4C[C@@H]5[C@@H](CN)[C@@H]5C4)cc3)c(=O)n2)CC1] |
| 138 | 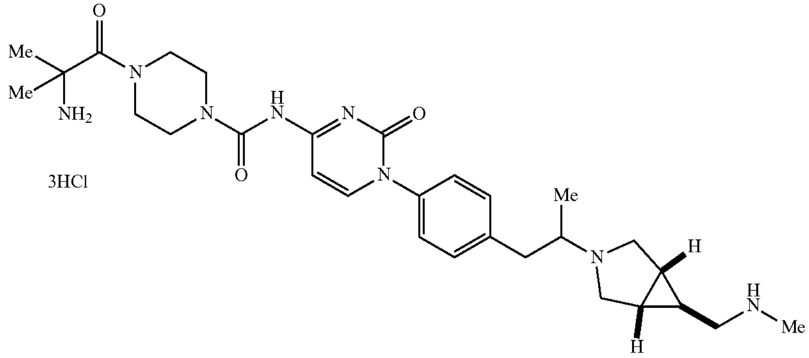 [SMILES: CNC[C@@H]1[C@H]2CN(C(C)Cc3ccc(-n4ccc(NC(=O)N5CCN(C(=O)C(C)(C)N)CC5)nc4=O)cc3)C[C@@H]12] 3HCl | 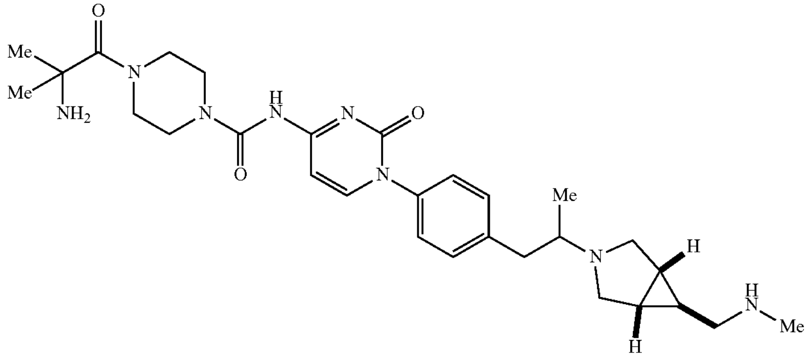 [SMILES: CNC[C@@H]1[C@H]2CN(C(C)Cc3ccc(-n4ccc(NC(=O)N5CCN(C(=O)C(C)(C)N)CC5)nc4=O)cc3)C[C@@H]12] |

TABLE 8-continued
| Compounds of Formula I Continued | | |
|---|---|---|
| No. | Salt Structure | Free Base Structure |
| 139 | 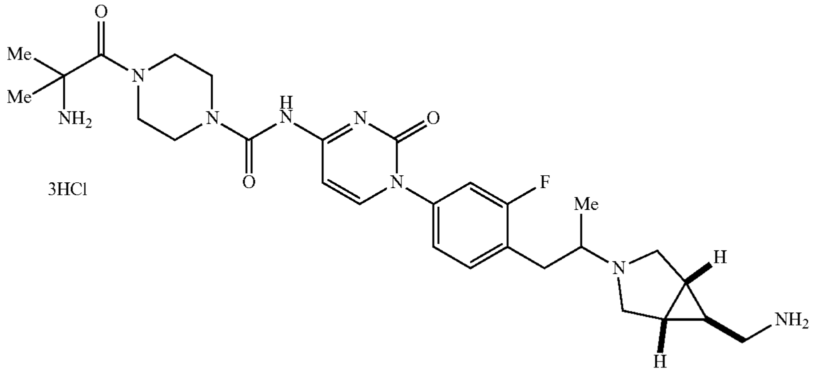 [SMILES: CC(Cc1ccc(-n2ccc(NC(=O)N3CCN(C(=O)C(C)(C)N)CC3)nc2=O)cc1F)N1C[C@@H]2[C@@H](CN)[C@@H]2C1] 3HCl | 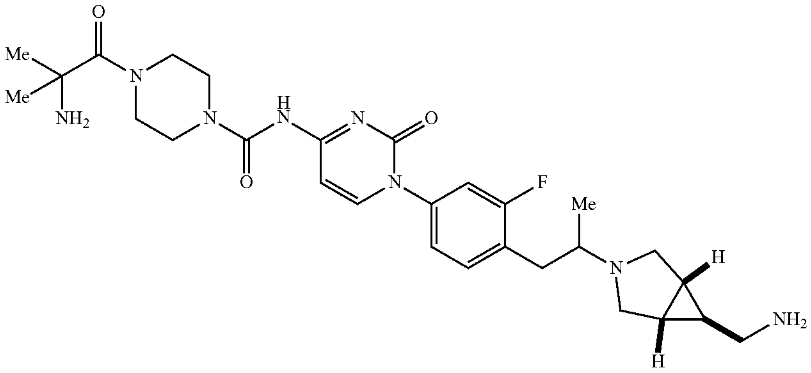 [SMILES: CC(Cc1ccc(-n2ccc(NC(=O)N3CCN(C(=O)C(C)(C)N)CC3)nc2=O)cc1F)N1C[C@@H]2[C@@H](CN)[C@@H]2C1] |
| 140 | 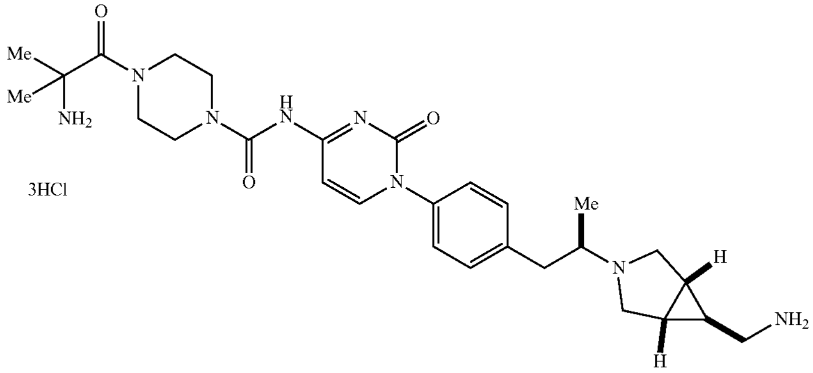 [SMILES: C[C@H](Cc1ccc(-n2ccc(NC(=O)N3CCN(C(=O)C(C)(C)N)CC3)nc2=O)cc1)N1C[C@@H]2[C@@H](CN)[C@@H]2C1] 3HCl | 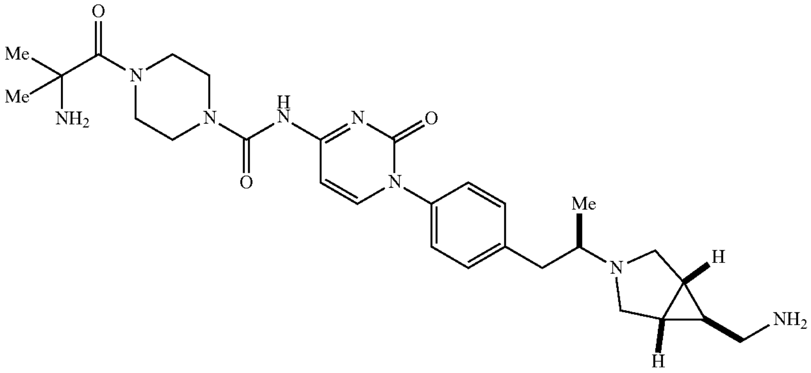 [SMILES: C[C@H](Cc1ccc(-n2ccc(NC(=O)N3CCN(C(=O)C(C)(C)N)CC3)nc2=O)cc1)N1C[C@@H]2[C@@H](CN)[C@@H]2C1] |

TABLE 8-continued
| Compounds of Formula I Continued | | |
|---|---|---|
| No. | Salt Structure | Free Base Structure |
| 141 | 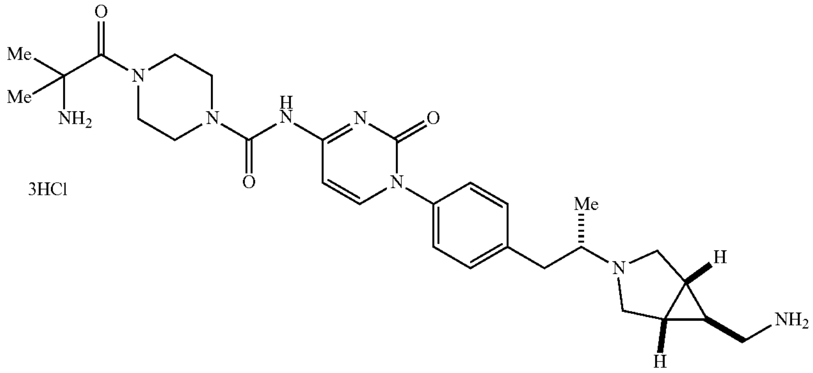 [SMILES: C[C@@H](Cc1ccc(-n2ccc(NC(=O)N3CCN(C(=O)C(C)(C)N)CC3)nc2=O)cc1)N1C[C@@H]2[C@@H](CN)[C@@H]2C1] 3HCl | 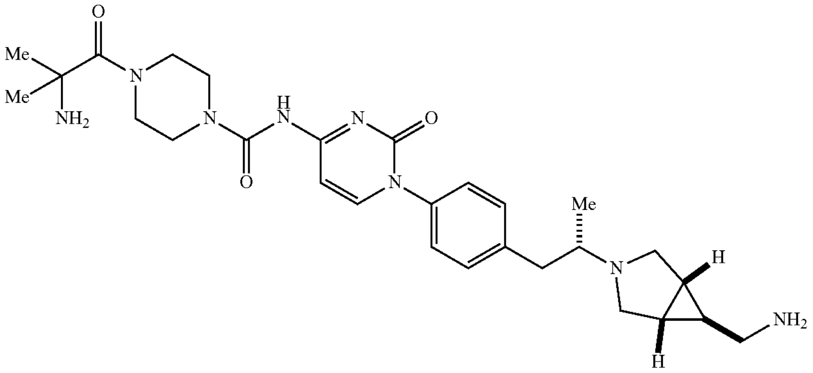 [SMILES: C[C@@H](Cc1ccc(-n2ccc(NC(=O)N3CCN(C(=O)C(C)(C)N)CC3)nc2=O)cc1)N1C[C@@H]2[C@@H](CN)[C@@H]2C1] |
| 142 | 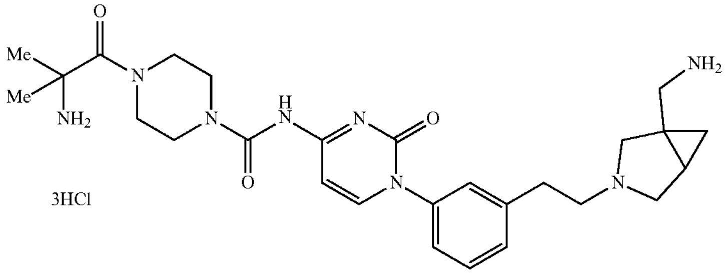 [SMILES: CC(C)(N)C(=O)N1CCN(C(=O)Nc2ccn(-c3cccc(CCN4CC5CC5(CN)C4)c3)c(=O)n2)CC1] 3HCl | 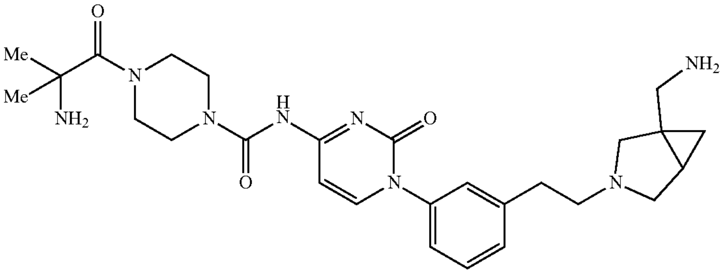 [SMILES: CC(C)(N)C(=O)N1CCN(C(=O)Nc2ccn(-c3cccc(CCN4CC5CC5(CN)C4)c3)c(=O)n2)CC1] |
| 143 | 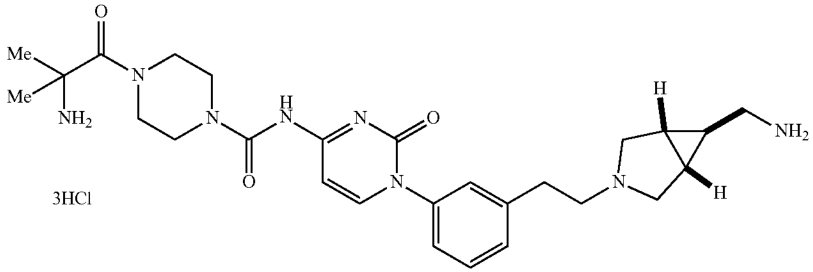 [SMILES: CC(C)(N)C(=O)N1CCN(C(=O)Nc2ccn(-c3cccc(CCN4C[C@@H]5[C@@H](CN)[C@@H]5C4)c3)c(=O)n2)CC1] 3HCl | 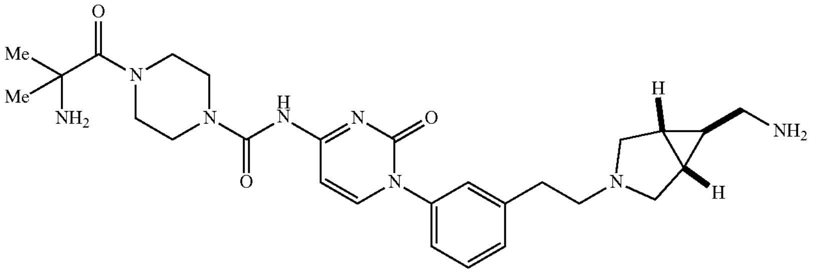 [SMILES: CC(C)(N)C(=O)N1CCN(C(=O)Nc2ccn(-c3cccc(CCN4C[C@@H]5[C@@H](CN)[C@@H]5C4)c3)c(=O)n2)CC1] |

TABLE 8-continued
| Compounds of Formula I Continued | | |
|---|---|---|
| No. | Salt Structure | Free Base Structure |
| 144 | 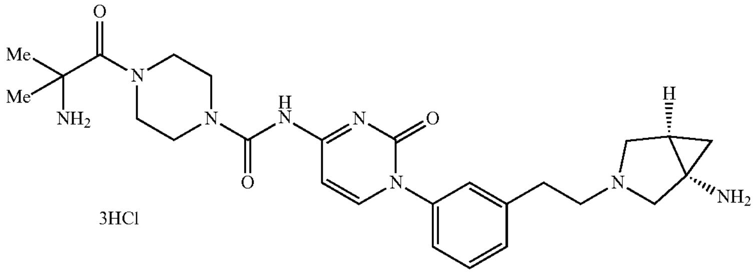 [SMILES: CC(C)(N)C(=O)N1CCN(C(=O)Nc2ccn(-c3cccc(CCN4C[C@H]5C[C@@]5(N)C4)c3)c(=O)n2)CC1] 3HCl | 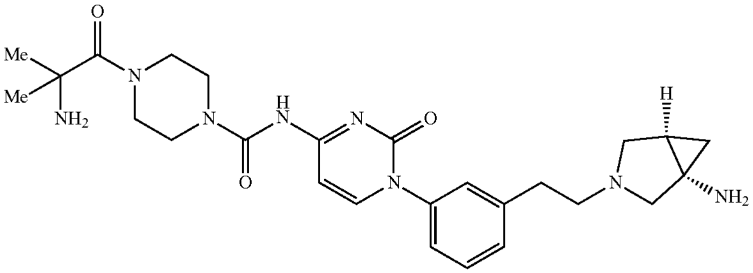 [SMILES: CC(C)(N)C(=O)N1CCN(C(=O)Nc2ccn(-c3cccc(CCN4C[C@H]5C[C@@]5(N)C4)c3)c(=O)n2)CC1] |
| 145 | 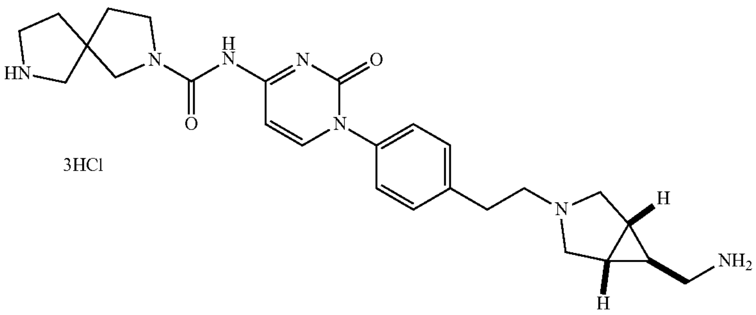 [SMILES: NC[C@@H]1[C@H]2CN(CCc3ccc(-n4ccc(NC(=O)N5CCC6(CCNC6)C5)nc4=O)cc3)C[C@@H]12] 3HCl | 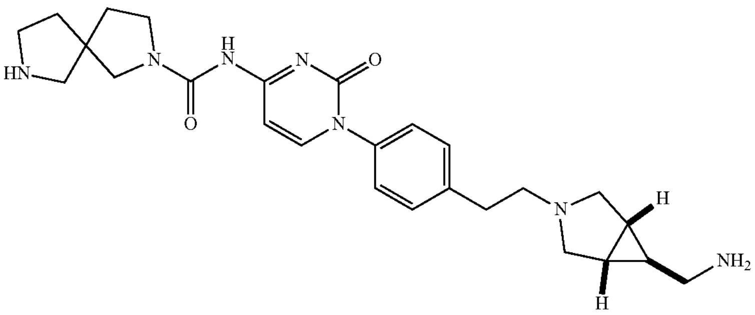 [SMILES: NC[C@@H]1[C@H]2CN(CCc3ccc(-n4ccc(NC(=O)N5CCC6(CCNC6)C5)nc4=O)cc3)C[C@@H]12] |
| 146 | 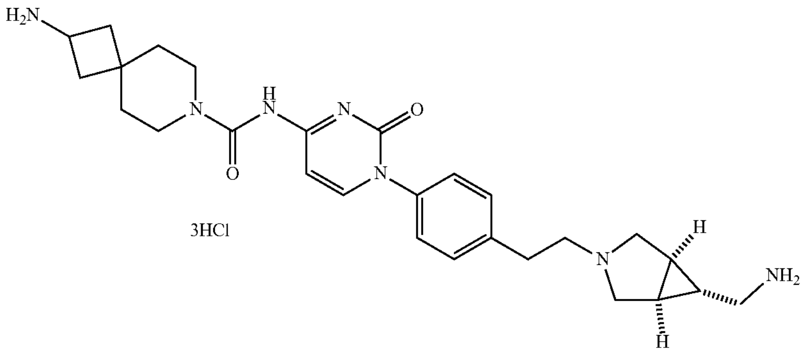 [SMILES: NC[C@@H]1[C@H]2CN(CCc3ccc(-n4ccc(NC(=O)N5CCC6(CC5)CC(N)C6)nc4=O)cc3)C[C@@H]12] 3HCl | 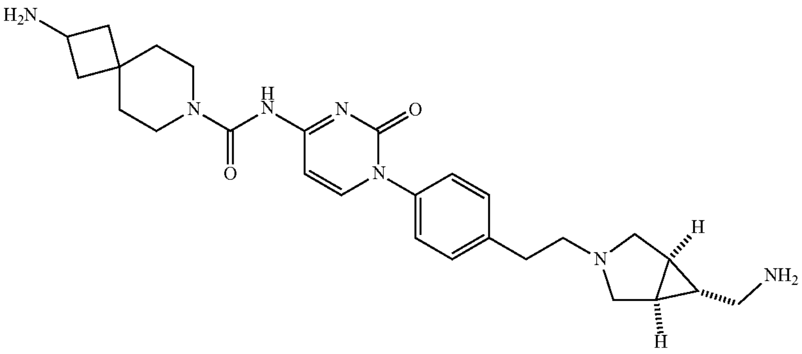 [SMILES: NC[C@@H]1[C@H]2CN(CCc3ccc(-n4ccc(NC(=O)N5CCC6(CC5)CC(N)C6)nc4=O)cc3)C[C@@H]12] |

TABLE 8-continued
| Compounds of Formula I Continued | | |
|---|---|---|
| No. | Salt Structure | Free Base Structure |
| 147 | 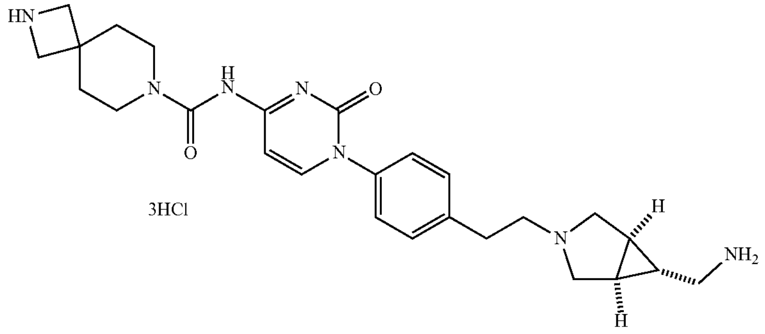 [SMILES: NC[C@@H]1[C@H]2CN(CCc3ccc(-n4ccc(NC(=O)N5CCC6(CC5)CNC6)nc4=O)cc3)C[C@@H]12] 3HCl | 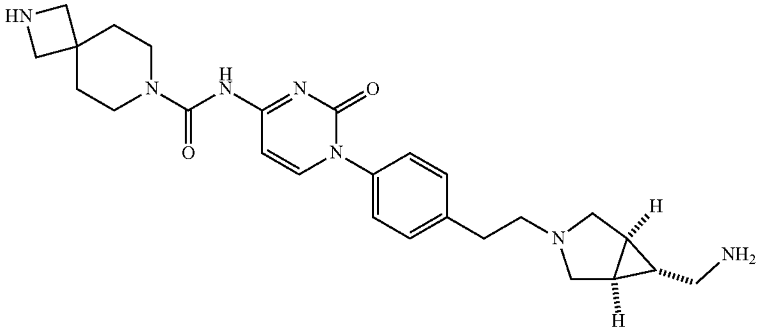 [SMILES: NC[C@@H]1[C@H]2CN(CCc3ccc(-n4ccc(NC(=O)N5CCC6(CC5)CNC6)nc4=O)cc3)C[C@@H]12] |
| 148 | 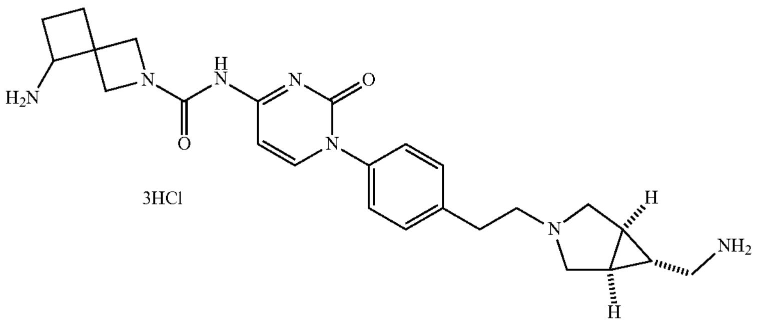 [SMILES: NC[C@@H]1[C@H]2CN(CCc3ccc(-n4ccc(NC(=O)N5CC6(CCC6N)C5)nc4=O)cc3)C[C@@H]12] 3HCl | 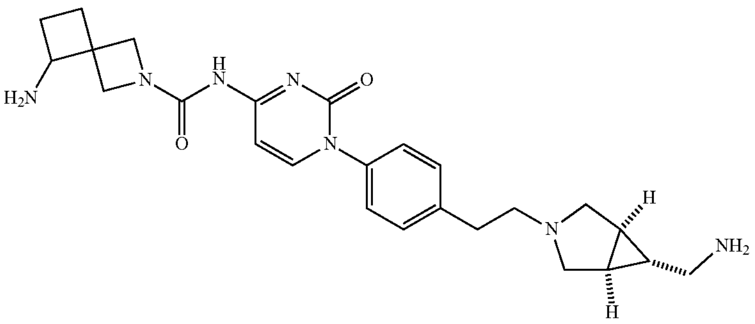 [SMILES: NC[C@@H]1[C@H]2CN(CCc3ccc(-n4ccc(NC(=O)N5CC6(CCC6N)C5)nc4=O)cc3)C[C@@H]12] |
| 149 | 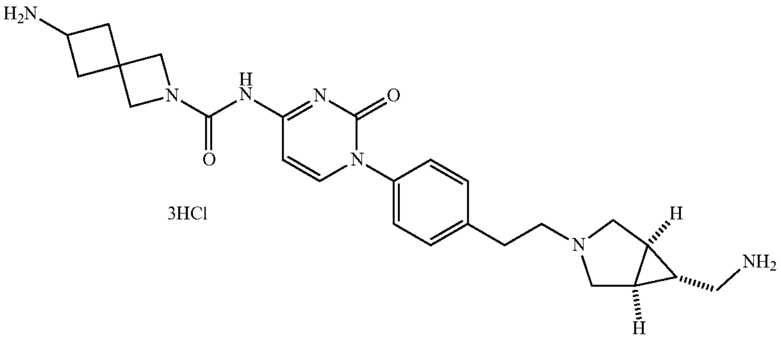 [SMILES: NC[C@@H]1[C@H]2CN(CCc3ccc(-n4ccc(NC(=O)N5CC6(CC(N)C6)C5)nc4=O)cc3)C[C@@H]12] 3HCl | 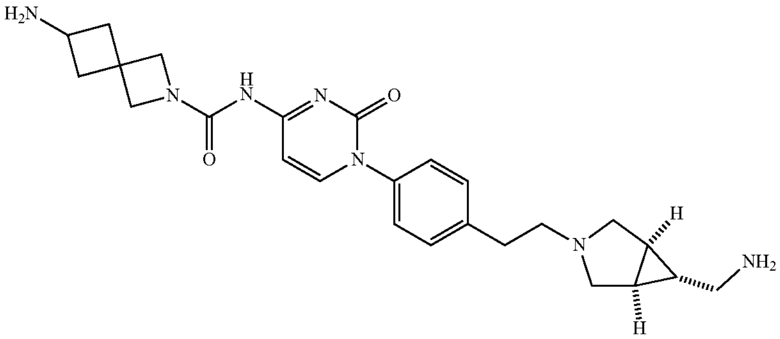 [SMILES: NC[C@@H]1[C@H]2CN(CCc3ccc(-n4ccc(NC(=O)N5CC6(CC(N)C6)C5)nc4=O)cc3)C[C@@H]12] |

TABLE 8-continued
| Compounds of Formula I Continued | | |
|---|---|---|
| No. | Salt Structure | Free Base Structure |
| 150 | 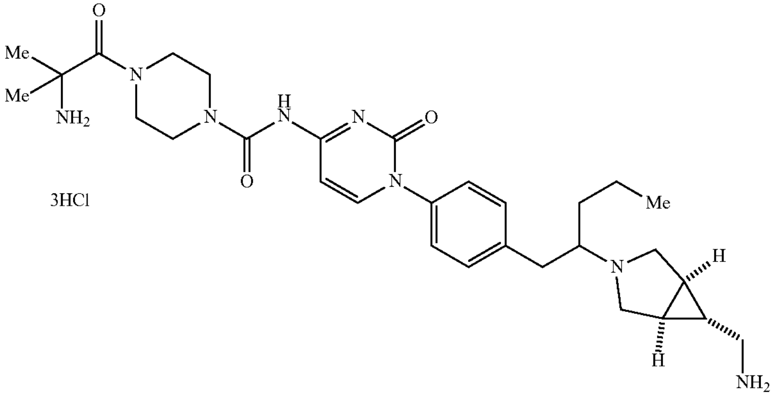 [SMILES: CCCC(Cc1ccc(-n2ccc(NC(=O)N3CCN(C(=O)C(C)(C)N)CC3)nc2=O)cc1)N1C[C@@H]2[C@@H](CN)[C@@H]2C1] 3HCl | 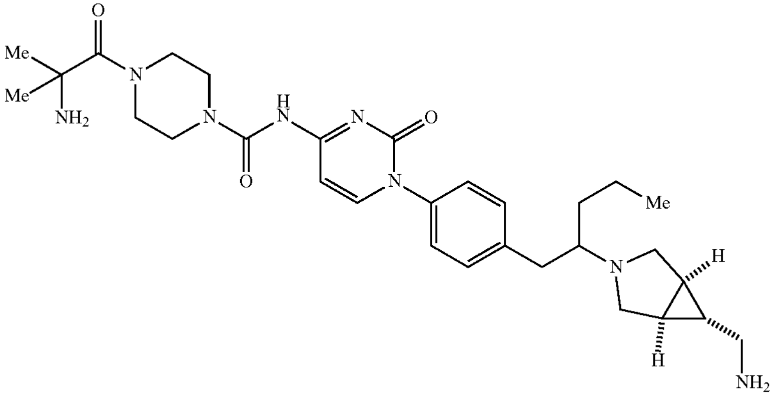 [SMILES: CCCC(Cc1ccc(-n2ccc(NC(=O)N3CCN(C(=O)C(C)(C)N)CC3)nc2=O)cc1)N1C[C@@H]2[C@@H](CN)[C@@H]2C1] |
| 151 | 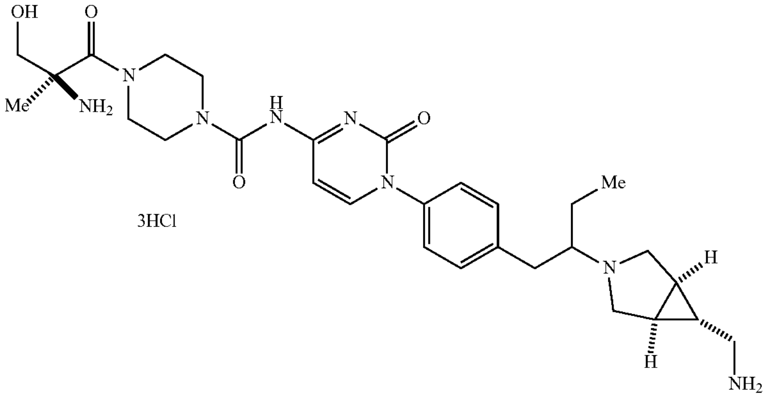 [SMILES: CCC(Cc1ccc(-n2ccc(NC(=O)N3CCN(C(=O)[C@@](C)(N)CO)CC3)nc2=O)cc1)N1C[C@@H]2[C@@H](CN)[C@@H]2C1] 3HCl | 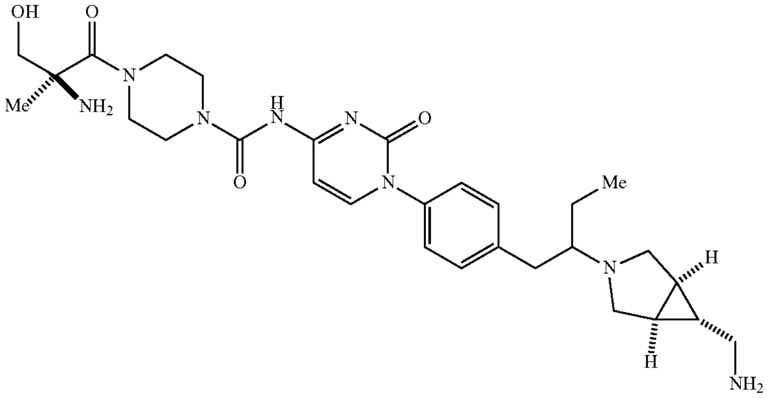 [SMILES: CCC(Cc1ccc(-n2ccc(NC(=O)N3CCN(C(=O)[C@@](C)(N)CO)CC3)nc2=O)cc1)N1C[C@@H]2[C@@H](CN)[C@@H]2C1] |

TABLE 8-continued
Compounds of Formula I Continued
| No. | Salt Structure | Free Base Structure |
|---|---|---|
| 152 | 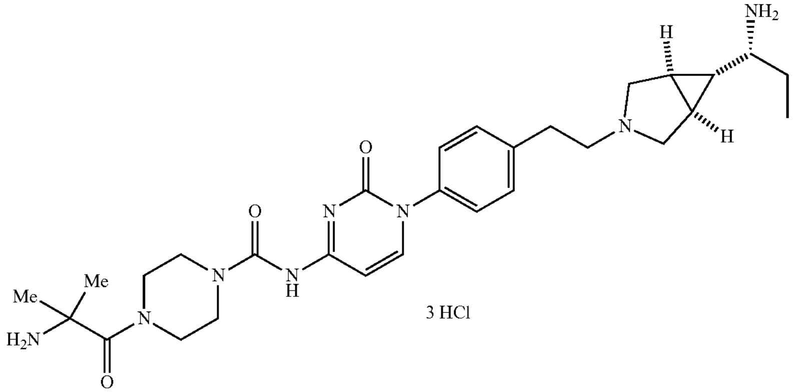 [SMILES: CC[C@@H](N)C1[C@H]2CN(CCc3ccc(-n4ccc(NC(=O)N5CCN(C(=O)C(C)(C)N)CC5)nc4=O)cc3)C[C@@H]12] 3 HCl | 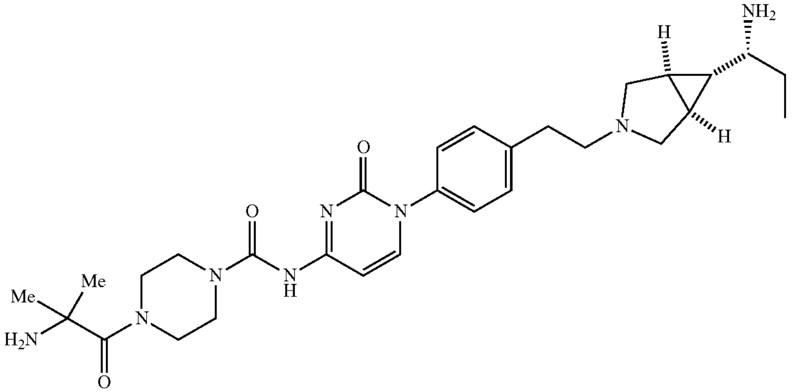 [SMILES: CC[C@@H](N)C1[C@H]2CN(CCc3ccc(-n4ccc(NC(=O)N5CCN(C(=O)C(C)(C)N)CC5)nc4=O)cc3)C[C@@H]12] |
| 153 | 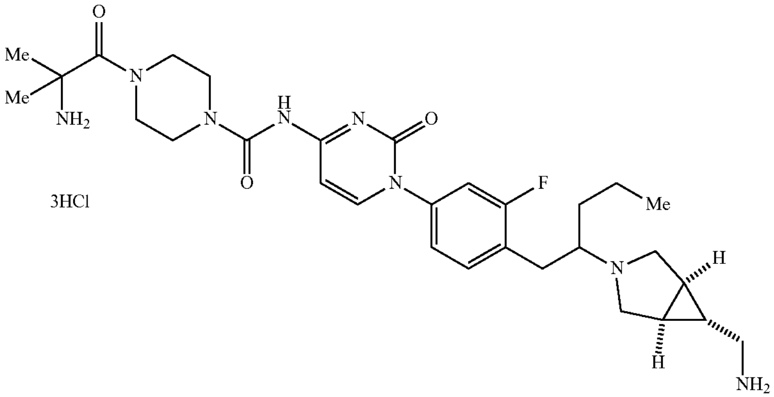 [SMILES: CCCC(Cc1ccc(-n2ccc(NC(=O)N3CCN(C(=O)C(C)(C)N)CC3)nc2=O)cc1F)N1C[C@@H]2[C@@H](CN)[C@@H]2C1] 3HCl | 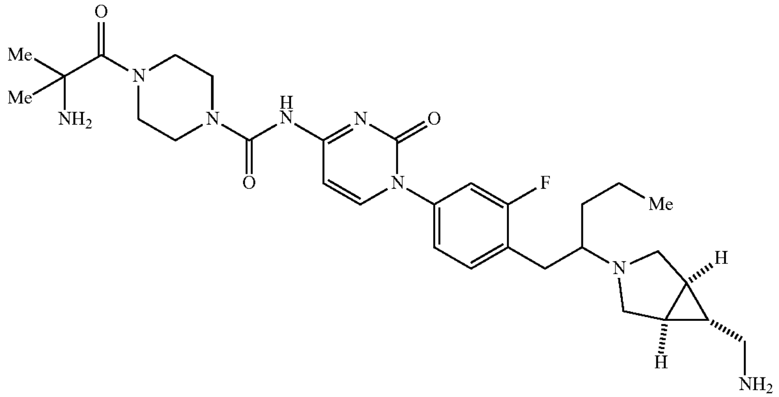 |

TABLE 8-continued
| Compounds of Formula I Continued | | |
|---|---|---|
| No. | Salt Structure | Free Base Structure |
| 154 | 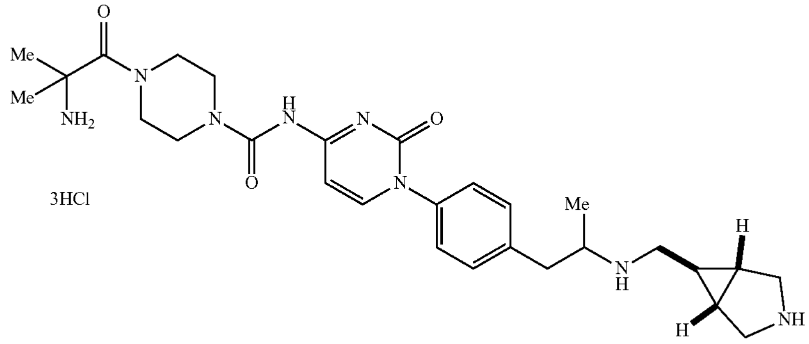 3HCl | 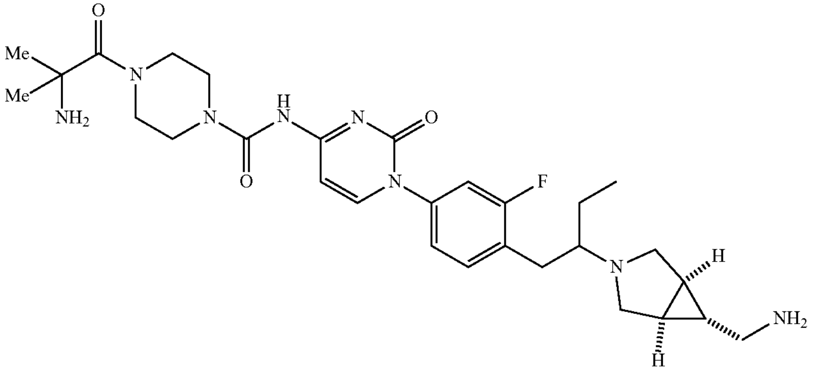 [SMILES: CCC(Cc1ccc(-n2ccc(NC(=O)N3CCN(C(=O)C(C)(C)N)CC3)nc2=O)cc1F)N1C[C@@H]2[C@@H](CN)[C@@H]2C1] |
| 155 | 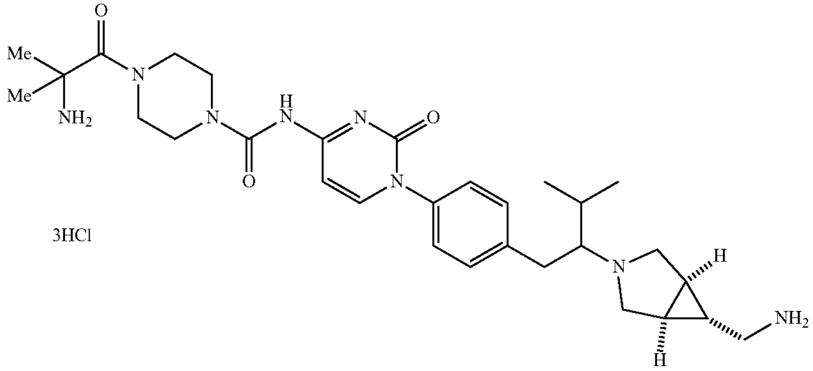 [SMILES: CC(C)C(Cc1ccc(-n2ccc(NC(=O)N3CCN(C(=O)C(C)(C)N)CC3)nc2=O)cc1)N1C[C@@H]2[C@@H](CN)[C@@H]2C1] 3HCl | 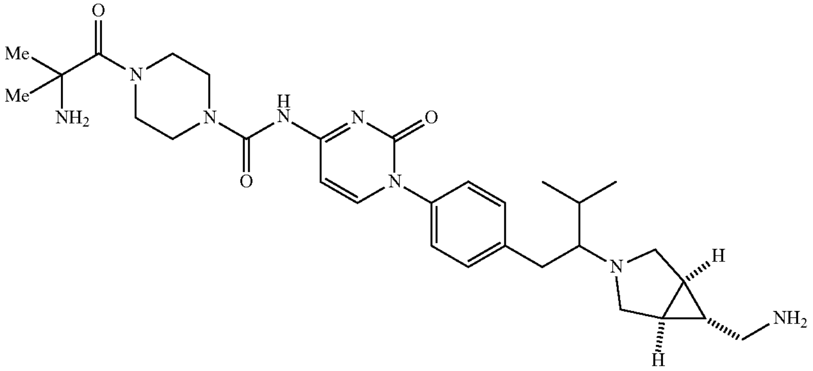 [SMILES: CC(C)C(Cc1ccc(-n2ccc(NC(=O)N3CCN(C(=O)C(C)(C)N)CC3)nc2=O)cc1)N1C[C@@H]2[C@@H](CN)[C@@H]2C1] |

TABLE 8-continued
| Compounds of Formula I Continued | | |
|---|---|---|
| No. | Salt Structure | Free Base Structure |
| 156 | 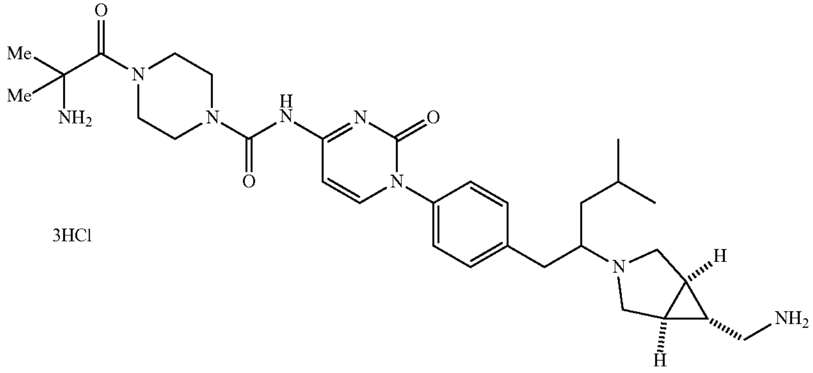 [SMILES: CC(C)CC(Cc1ccc(-n2ccc(NC(=O)N3CCN(C(=O)C(C)(C)N)CC3)nc2=O)cc1)N1C[C@@H]2[C@@H](CN)[C@@H]2C1] 3HCl | 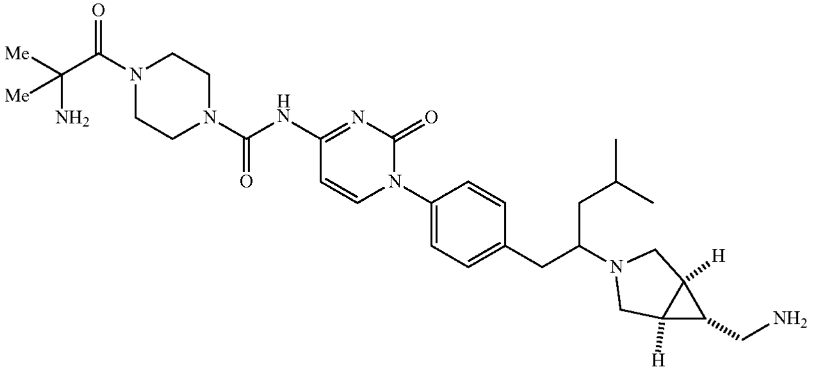 [SMILES: CC(C)CC(Cc1ccc(-n2ccc(NC(=O)N3CCN(C(=O)C(C)(C)N)CC3)nc2=O)cc1)N1C[C@@H]2[C@@H](CN)[C@@H]2C1] |
| 157 | 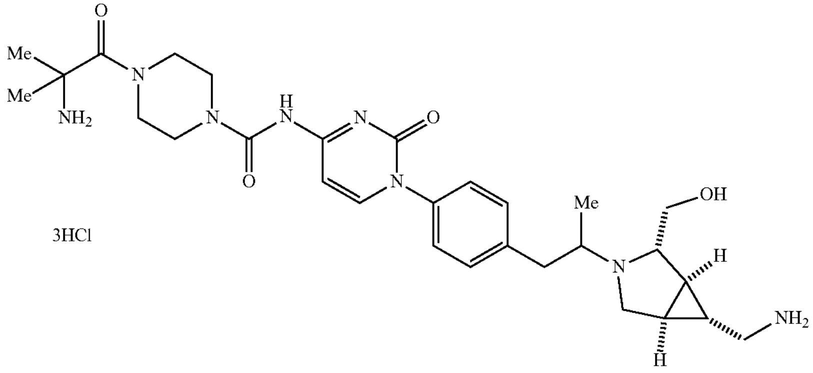 [SMILES: CC(Cc1ccc(-n2ccc(NC(=O)N3CCN(C(=O)C(C)(C)N)CC3)nc2=O)cc1)N1C[C@@H]2[C@@H](CN)[C@@H]2[C@H]1CO] 3HCl | 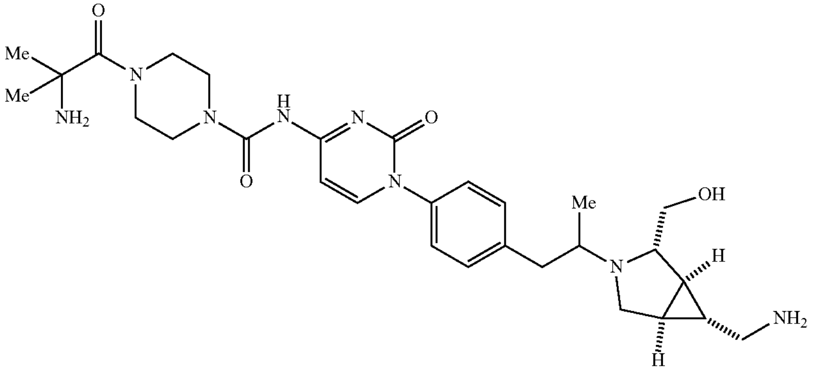 [SMILES: CC(Cc1ccc(-n2ccc(NC(=O)N3CCN(C(=O)C(C)(C)N)CC3)nc2=O)cc1)N1C[C@@H]2[C@@H](CN)[C@@H]2[C@H]1CO] |

TABLE 8-continued
| Compounds of Formula I Continued | | |
|---|---|---|
| No. | Salt Structure | Free Base Structure |
| 158 | 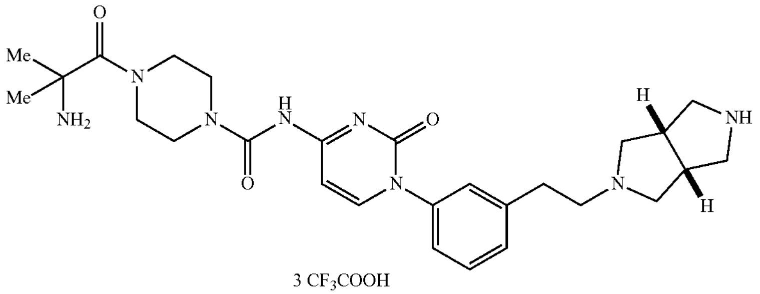 [SMILES: CC(C)(N)C(=O)N1CCN(C(=O)Nc2ccn(-c3cccc(CCN4C[C@H]5CNC[C@H]5C4)c3)c(=O)n2)CC1] 3 $CF_3COOH$ | 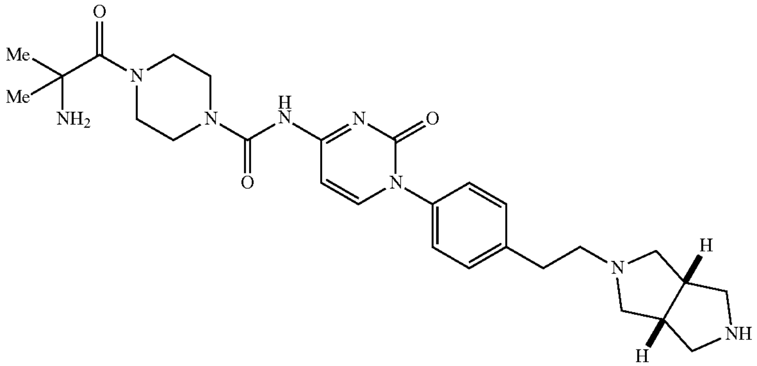 [SMILES: CC(C)(N)C(=O)N1CCN(C(=O)Nc2ccn(-c3ccc(CCN4C[C@H]5CNC[C@H]5C4)cc3)c(=O)n2)CC1] |
| 159 | 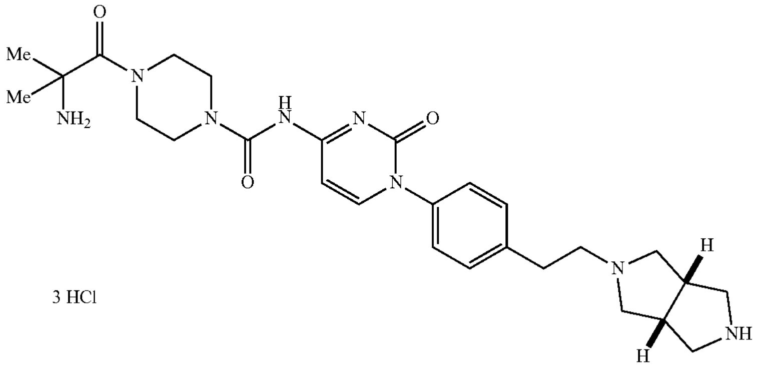 [SMILES: CC(C)(N)C(=O)N1CCN(C(=O)Nc2ccn(-c3ccc(CCN4C[C@H]5CNC[C@H]5C4)cc3)c(=O)n2)CC1] 3 HCl | 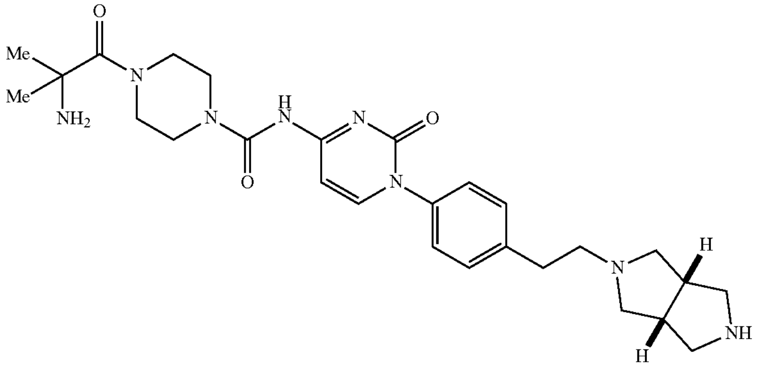 [SMILES: CC(C)(N)C(=O)N1CCN(C(=O)Nc2ccn(-c3ccc(CCN4C[C@H]5CNC[C@H]5C4)cc3)c(=O)n2)CC1] |

TABLE 8-continued
| Compounds of Formula I Continued | | |
|---|---|---|
| No. | Salt Structure | Free Base Structure |
| 160 | 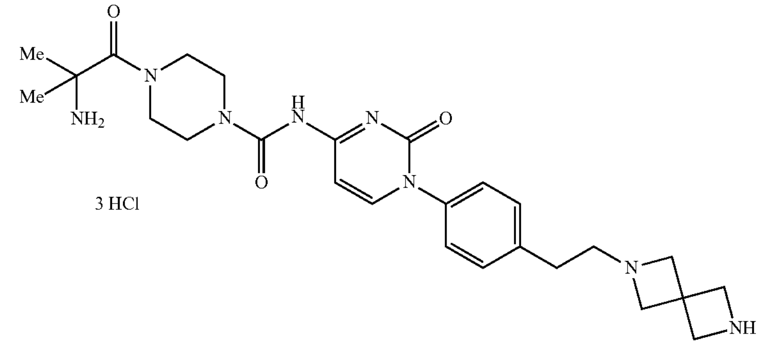 [SMILES: CC(C)(N)C(=O)N1CCN(C(=O)Nc2ccn(-c3ccc(CCN4CC5(CNC5)C4)cc3)c(=O)n2)CC1] 3 HCl | 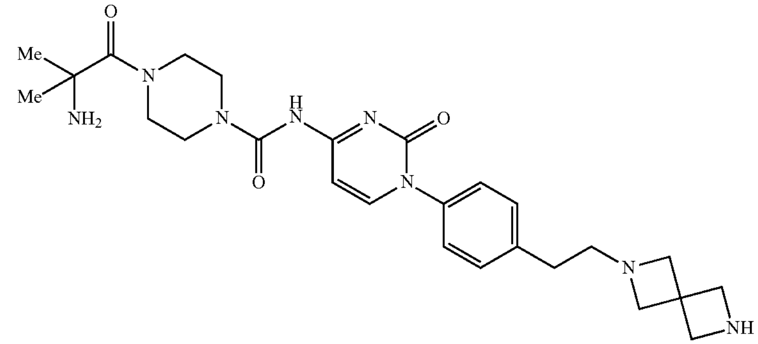 [SMILES: CC(C)(N)C(=O)N1CCN(C(=O)Nc2ccn(-c3ccc(CCN4CC5(CNC5)C4)cc3)c(=O)n2)CC1] |
| 161 | 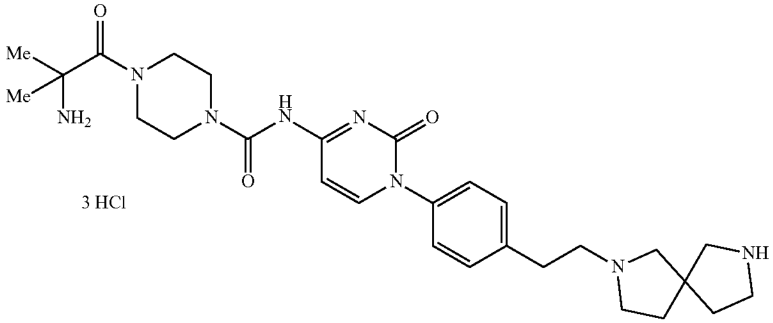 [SMILES: CC(C)(N)C(=O)N1CCN(C(=O)Nc2ccn(-c3ccc(CCN4CCC5(CCNC5)C4)cc3)c(=O)n2)CC1] 3 HCl | 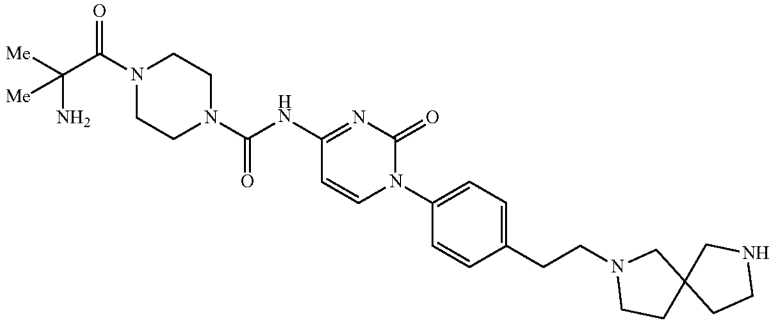 [SMILES: CC(C)(N)C(=O)N1CCN(C(=O)Nc2ccn(-c3ccc(CCN4CCC5(CCNC5)C4)cc3)c(=O)n2)CC1] |
| 162 | 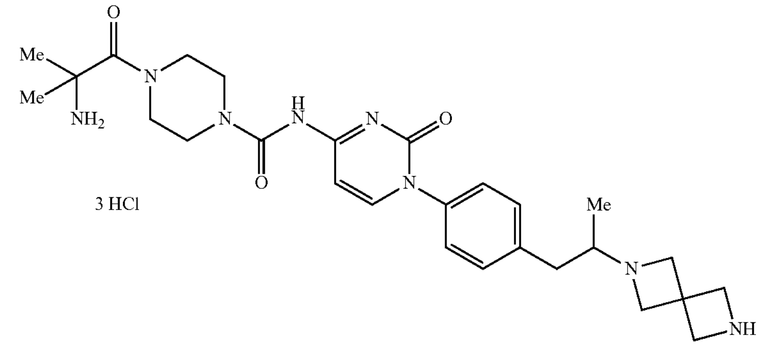 [SMILES: CC(Cc1ccc(-n2ccc(NC(=O)N3CCN(C(=O)C(C)(C)N)CC3)nc2=O)cc1)N1CC2(CNC2)C1] 3 HCl | 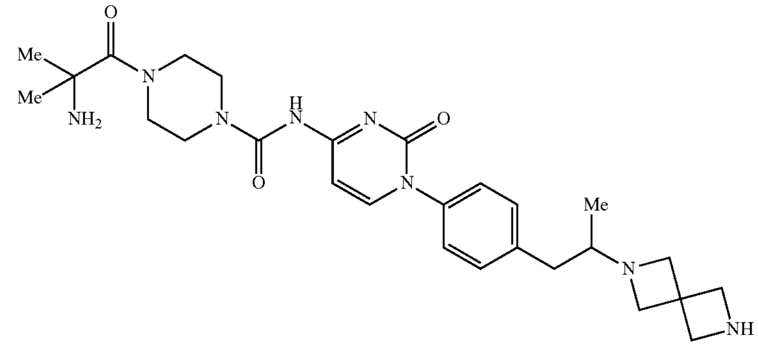 [SMILES: CC(Cc1ccc(-n2ccc(NC(=O)N3CCN(C(=O)C(C)(C)N)CC3)nc2=O)cc1)N1CC2(CNC2)C1] |

TABLE 8-continued
| Compounds of Formula I Continued | | |
|---|---|---|
| No. | Salt Structure | Free Base Structure |
| 163 | 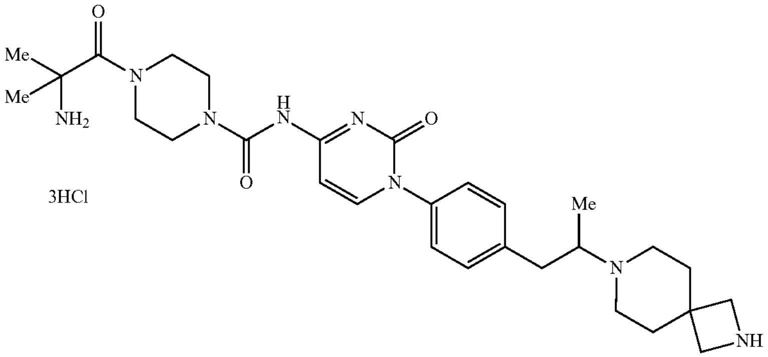 [SMILES: CC(Cc1ccc(-n2ccc(NC(=O)N3CCN(C(=O)C(C)(C)N)CC3)nc2=O)cc1)N1CCC2(CC1)CNC2] 3HCl | 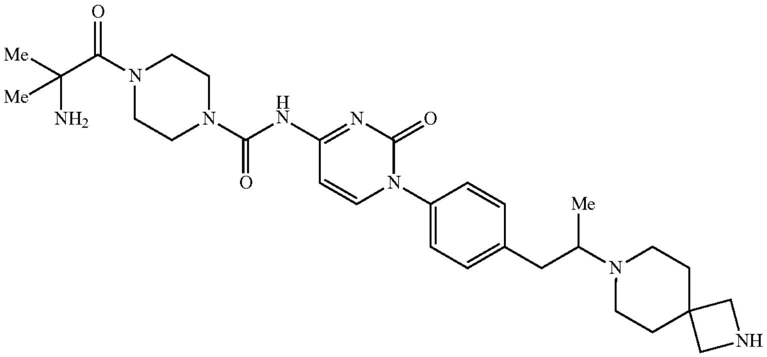 [SMILES: CC(Cc1ccc(-n2ccc(NC(=O)N3CCN(C(=O)C(C)(C)N)CC3)nc2=O)cc1)N1CCC2(CC1)CNC2] |
| 164 | 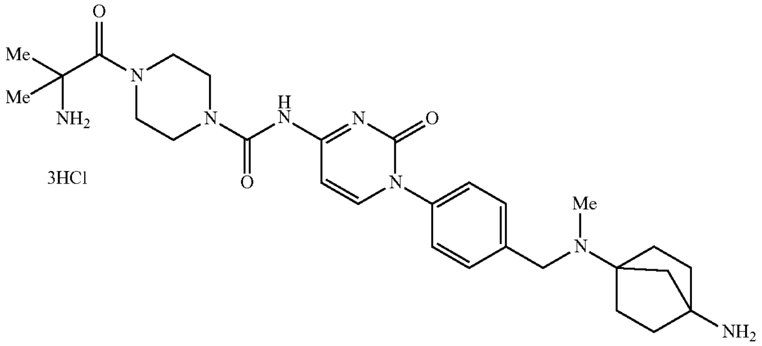 [SMILES: CN(Cc1ccc(-n2ccc(NC(=O)N3CCN(C(=O)C(C)(C)N)CC3)nc2=O)cc1)C12CCC(N)(CC1)C2] 3HCl | 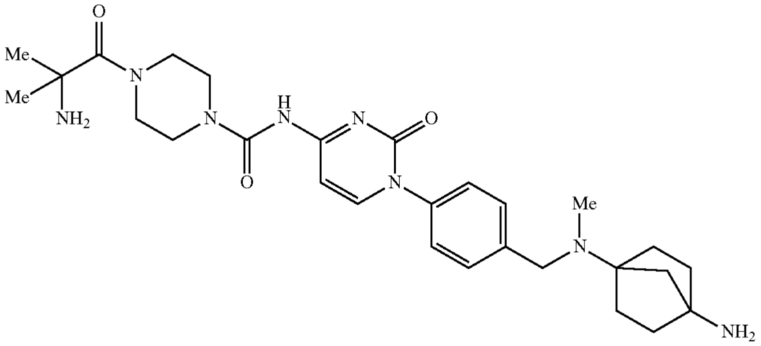 |

TABLE 8-continued
| Compounds of Formula I Continued | | |
|---|---|---|
| No. | Salt Structure | Free Base Structure |
| 165 | 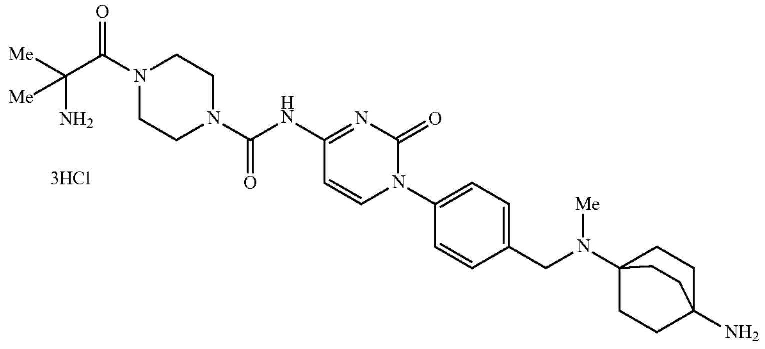 [SMILES: CN(Cc1ccc(-n2ccc(NC(=O)N3CCN(C(=O)C(C)(C)N)CC3)nc2=O)cc1)C12CCC(N)(CC1)CC2] 3HCl | 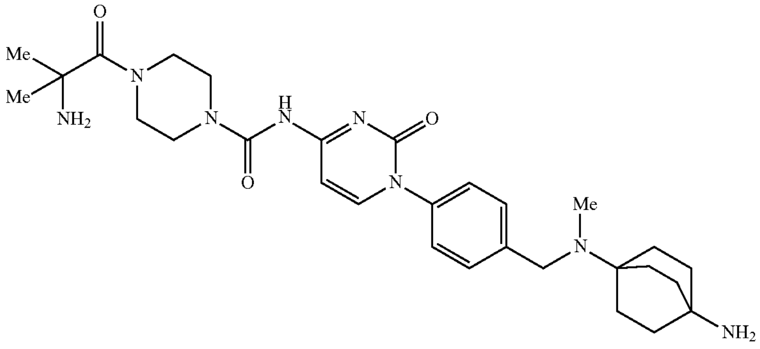 [SMILES: CN(Cc1ccc(-n2ccc(NC(=O)N3CCN(C(=O)C(C)(C)N)CC3)nc2=O)cc1)C12CCC(N)(CC1)CC2] |
| 166 | 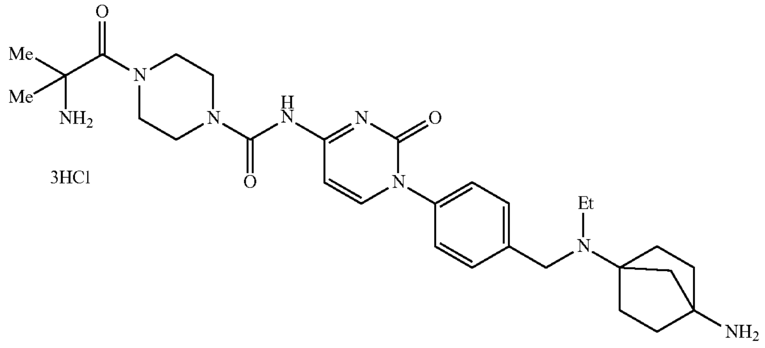 [SMILES: CCN(Cc1ccc(-n2ccc(NC(=O)N3CCN(C(=O)C(C)(C)N)CC3)nc2=O)cc1)C12CCC(N)(CC1)C2] 3HCl | 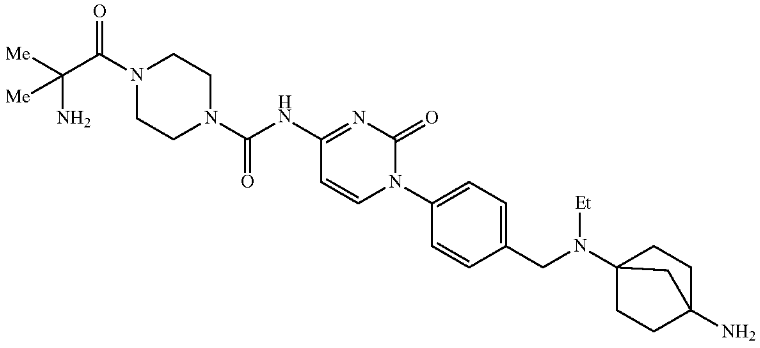 [SMILES: CCN(Cc1ccc(-n2ccc(NC(=O)N3CCN(C(=O)C(C)(C)N)CC3)nc2=O)cc1)C12CCC(N)(CC1)C2] |

TABLE 8-continued
| Compounds of Formula I Continued | | |
|---|---|---|
| No. | Salt Structure | Free Base Structure |
| 167 | 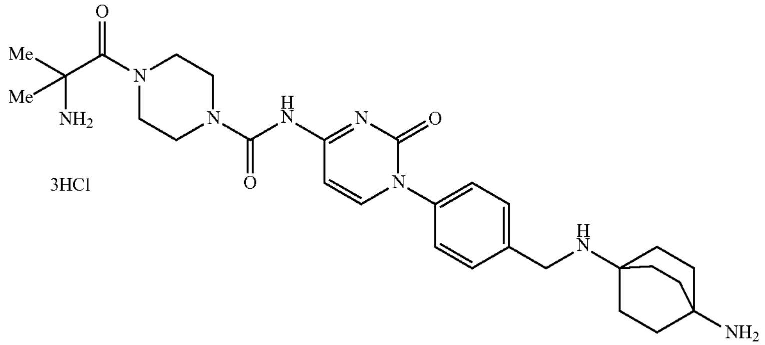 [SMILES: CC(C)(N)C(=O)N1CCN(C(=O)Nc2ccn(-c3ccc(CNC45CCC(N)(CC4)CC5)cc3)c(=O)n2)CC1] 3HCl | 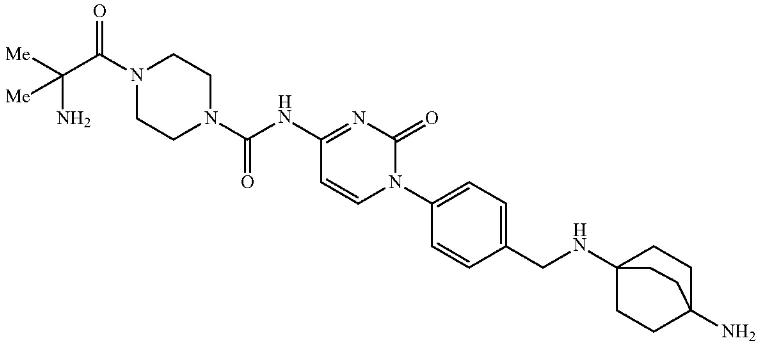 [SMILES: CC(C)(N)C(=O)N1CCN(C(=O)Nc2ccn(-c3ccc(CNC45CCC(N)(CC4)CC5)cc3)c(=O)n2)CC1] |
| 168 | 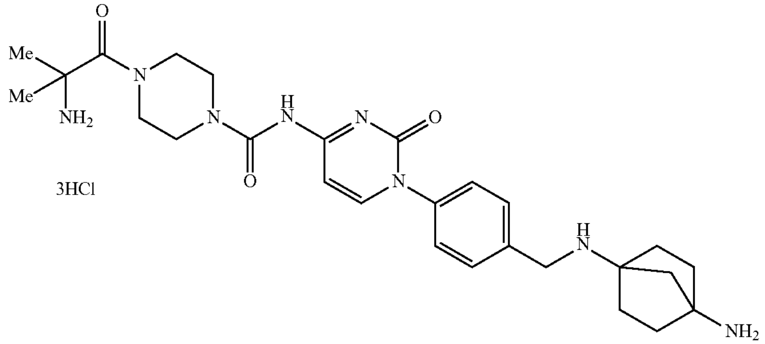 [SMILES: CC(C)(N)C(=O)N1CCN(C(=O)Nc2ccn(-c3ccc(CNC45CCC(N)(CC4)C5)cc3)c(=O)n2)CC1] 3HCl | 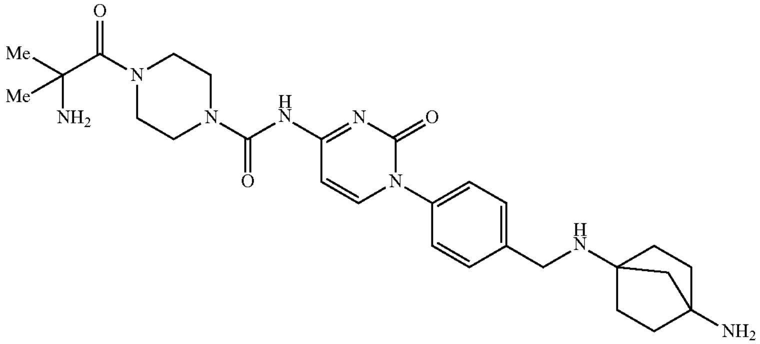 [SMILES: CC(C)(N)C(=O)N1CCN(C(=O)Nc2ccn(-c3ccc(CNC45CCC(N)(CC4)C5)cc3)c(=O)n2)CC1] |

TABLE 8-continued
Compounds of Formula I Continued
| No. | Salt Structure | Free Base Structure |
| --- | --- | --- |
| 169 | 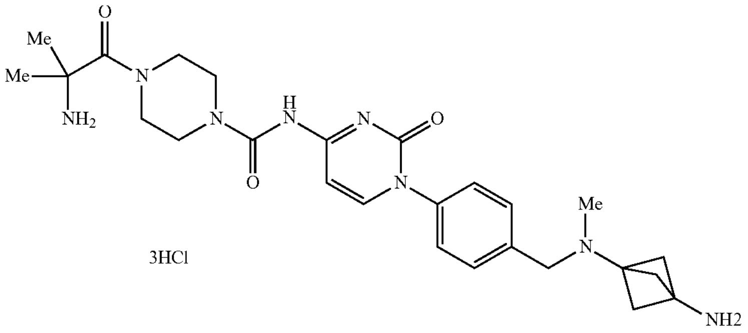 [SMILES: CN(Cc1ccc(-n2ccc(NC(=O)N3CCN(C(=O)C(C)(C)N)CC3)nc2=O)cc1)C12CC(N)(C1)C2] 3HCl | 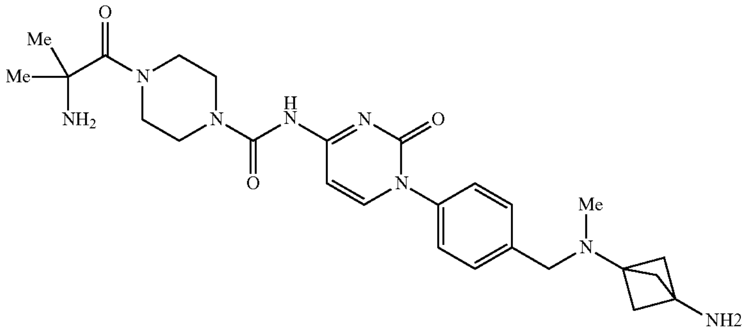 [SMILES: CN(Cc1ccc(-n2ccc(NC(=O)N3CCN(C(=O)C(C)(C)N)CC3)nc2=O)cc1)C12CC(N)(C1)C2] |
| 170 | 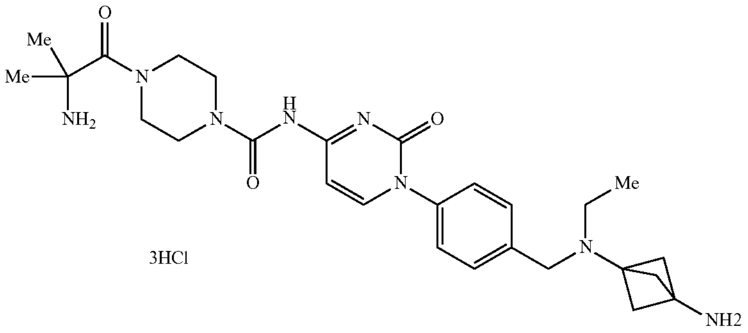 [SMILES: CCN(Cc1ccc(-n2ccc(NC(=O)N3CCN(C(=O)C(C)(C)N)CC3)nc2=O)cc1)C12CC(N)(C1)C2] 3HCl | 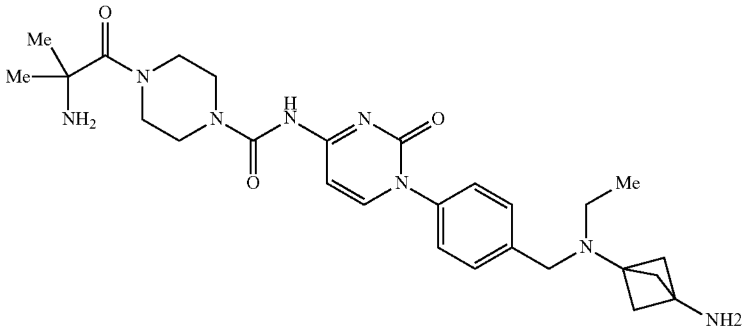 [SMILES: CCN(Cc1ccc(-n2ccc(NC(=O)N3CCN(C(=O)C(C)(C)N)CC3)nc2=O)cc1)C12CC(N)(C1)C2] |
| 171 | 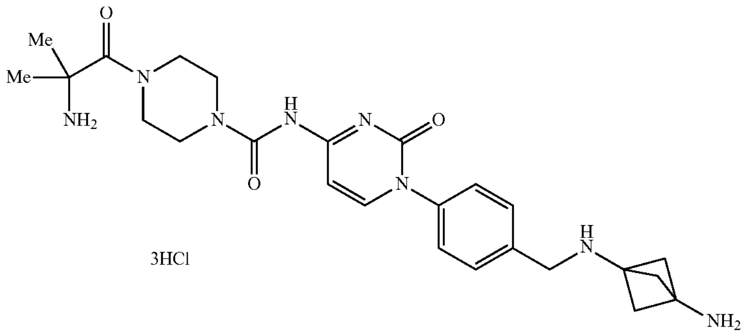 [SMILES: CC(C)(N)C(=O)N1CCN(C(=O)Nc2ccn(-c3ccc(CNC45CC(N)(C4)C5)cc3)c(=O)n2)CC1] 3HCl | 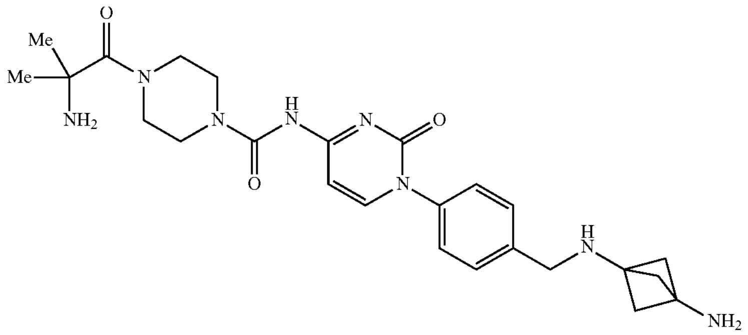 [SMILES: CC(C)(N)C(=O)N1CCN(C(=O)Nc2ccn(-c3ccc(CNC45CC(N)(C4)C5)cc3)c(=O)n2)CC1] |

TABLE 8-continued
| Compounds of Formula I Continued | | |
|---|---|---|
| No. | Salt Structure | Free Base Structure |
| 172 | 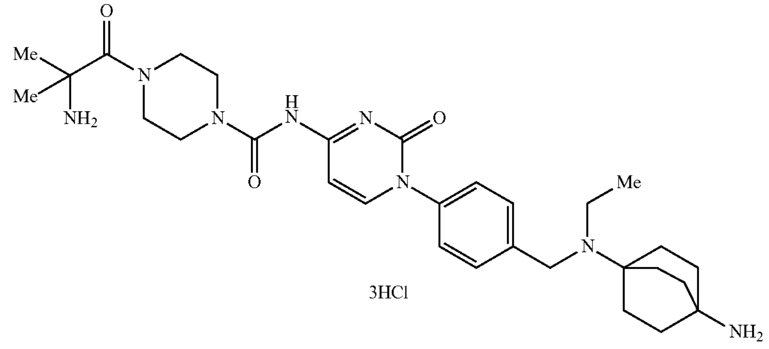 [SMILES: CCN(Cc1ccc(-n2ccc(NC(=O)N3CCN(C(=O)C(C)(C)N)CC3)nc2=O)cc1)C12CCC(N)(CC1)CC2] 3HCl | 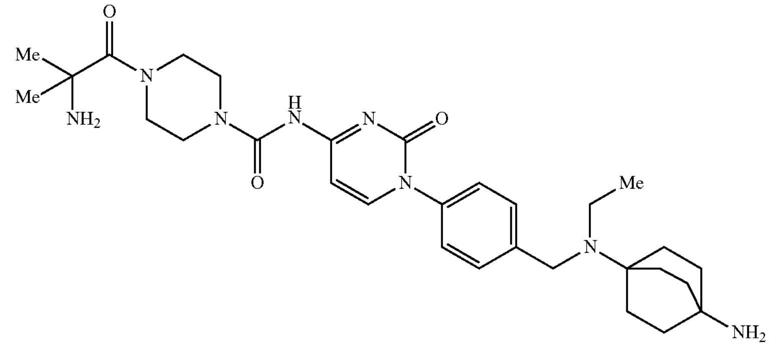 [SMILES: CCN(Cc1ccc(-n2ccc(NC(=O)N3CCN(C(=O)C(C)(C)N)CC3)nc2=O)cc1)C12CCC(N)(CC1)CC2] |
| 173 | 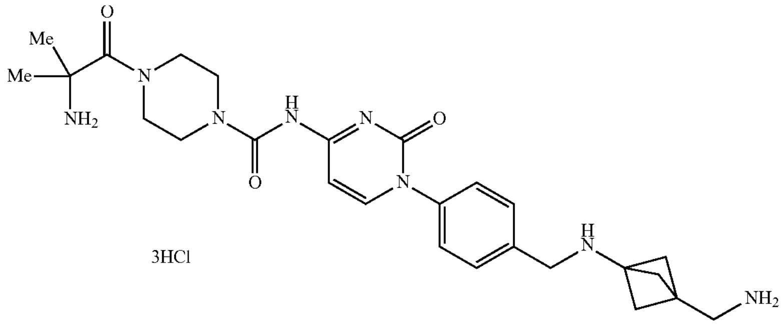 [SMILES: CC(C)(N)C(=O)N1CCN(C(=O)Nc2ccn(-c3ccc(CNC45CC(CN)(C4)C5)cc3)c(=O)n2)CC1] 3HCl | 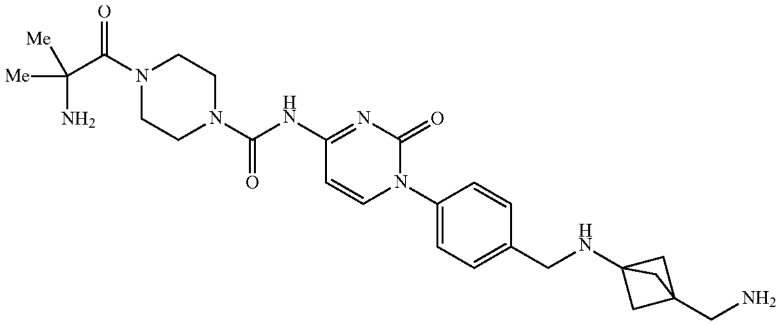 [SMILES: CC(C)(N)C(=O)N1CCN(C(=O)Nc2ccn(-c3ccc(CNC45CC(CN)(C4)C5)cc3)c(=O)n2)CC1] |
| 174 | 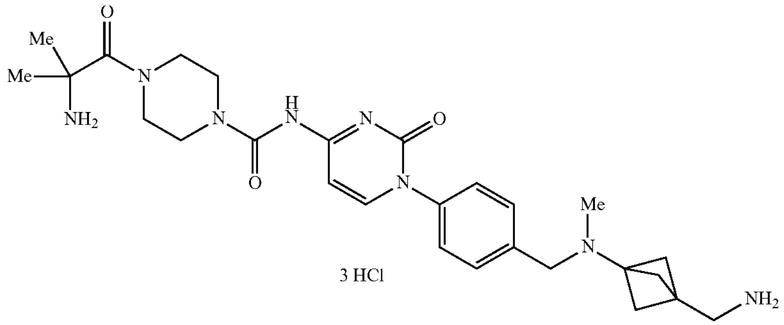 [SMILES: CN(Cc1ccc(-n2ccc(NC(=O)N3CCN(C(=O)C(C)(C)N)CC3)nc2=O)cc1)C12CC(CN)(C1)C2] 3 HCl | 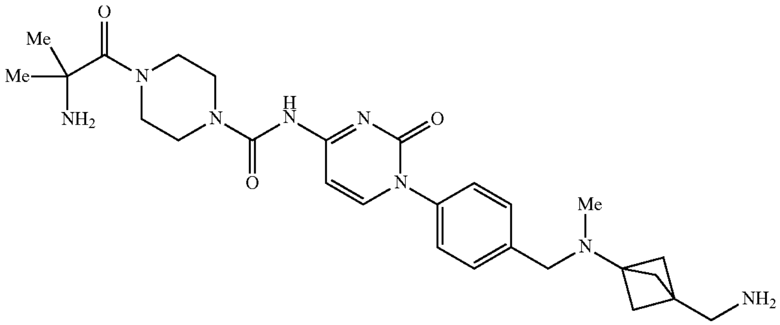 [SMILES: CN(Cc1ccc(-n2ccc(NC(=O)N3CCN(C(=O)C(C)(C)N)CC3)nc2=O)cc1)C12CC(CN)(C1)C2] |

TABLE 8-continued
| Compounds of Formula I Continued | | |
|---|---|---|
| No. | Salt Structure | Free Base Structure |
| 175 | 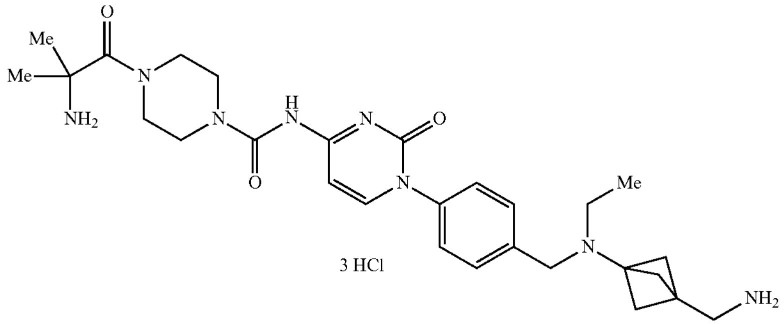 [SMILES: CCN(Cc1ccc(-n2ccc(NC(=O)N3CCN(C(=O)C(C)(C)N)CC3)nc2=O)cc1)C12CC(CN)(C1)C2] 3 HCl | 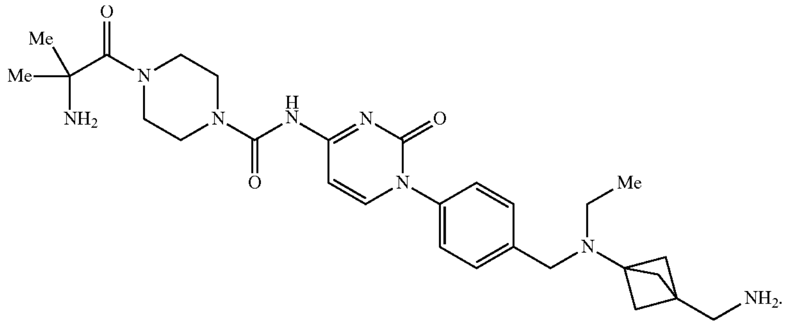 [SMILES: CCN(Cc1ccc(-n2ccc(NC(=O)N3CCN(C(=O)C(C)(C)N)CC3)nc2=O)cc1)C12CC(CN)(C1)C2] |

In another aspect, the disclosure provides a compound or a pharmaceutically acceptable salt thereof which is depicted in Table 9. In Table 9a possible pharmaceutically acceptable salt and the free base is shown for each compound.

TABLE 9
| Compounds of Formula I Continued | | |
|---|---|---|
| No. | Salt Structure | Free Base Structure |
| 176 | 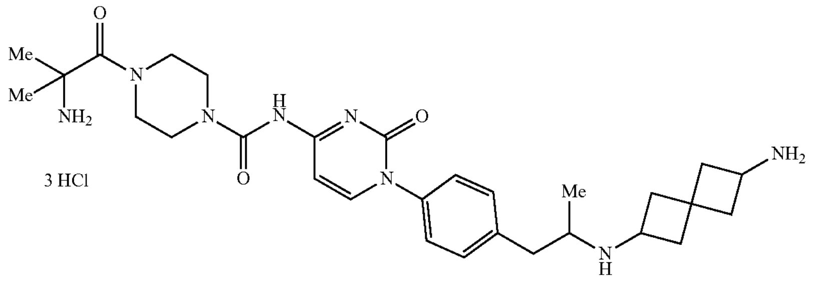 [SMILES: CC(Cc1ccc(-n2ccc(NC(=O)N3CCN(C(=O)C(C)(C)N)CC3)nc2=O)cc1)NC1CC2(CC(N)C2)C1] 3 HCl | 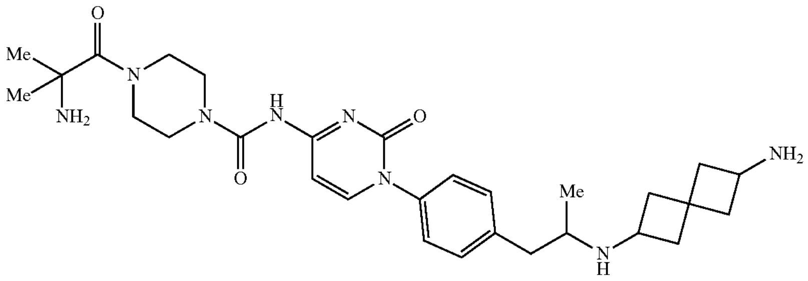 [SMILES: CC(Cc1ccc(-n2ccc(NC(=O)N3CCN(C(=O)C(C)(C)N)CC3)nc2=O)cc1)NC1CC2(CC(N)C2)C1] |
| 177 | 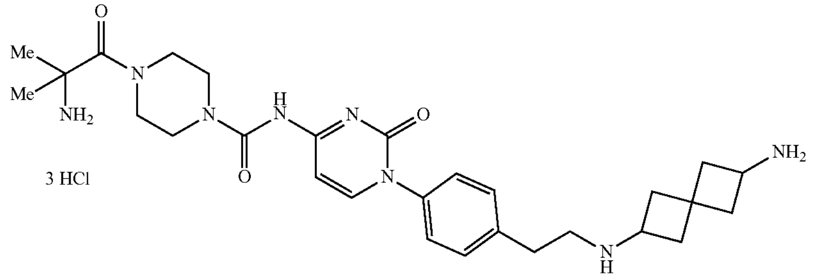 [SMILES: CC(C)(N)C(=O)N1CCN(C(=O)Nc2ccn(-c3ccc(CCNC4CC5(CC(N)C5)C4)cc3)c(=O)n2)CC1] 3 HCl | 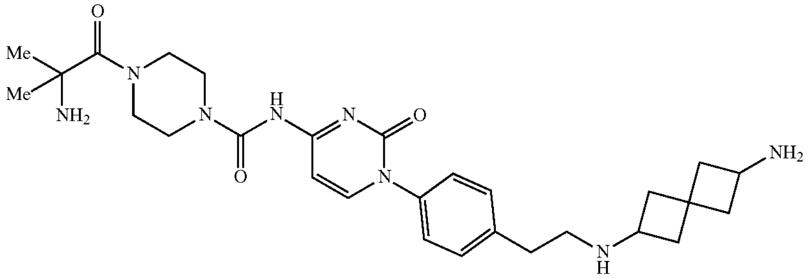 [SMILES: CC(C)(N)C(=O)N1CCN(C(=O)Nc2ccn(-c3ccc(CCNC4CC5(CC(N)C5)C4)cc3)c(=O)n2)CC1] |
| 178 | 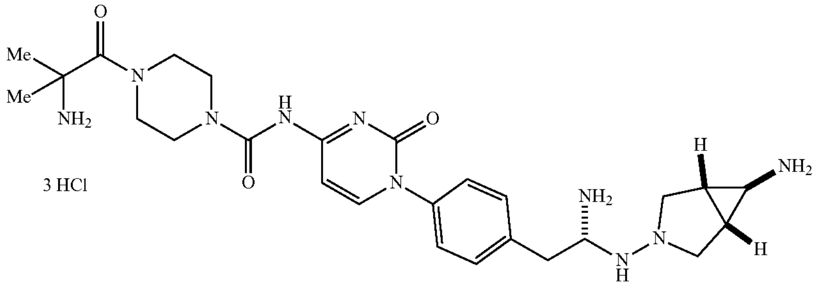 [SMILES: CC(C)(N)C(=O)N1CCN(C(=O)Nc2ccn(-c3ccc(C[C@H](N)NN4C[C@@H]5[C@@H](N)[C@@H]5C4)cc3)c(=O)n2)CC1] 3 HCl | 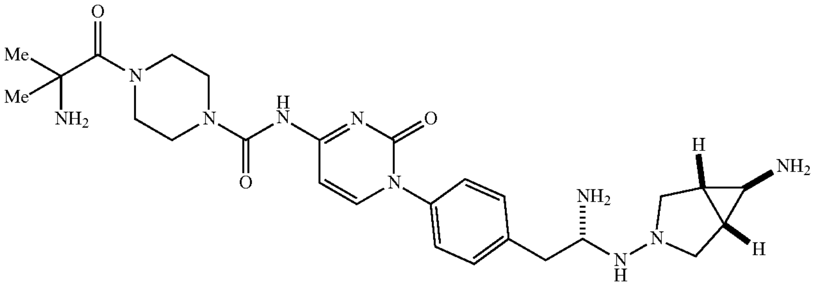 [SMILES: CC(C)(N)C(=O)N1CCN(C(=O)Nc2ccn(-c3ccc(C[C@H](N)NN4C[C@@H]5[C@@H](N)[C@@H]5C4)cc3)c(=O)n2)CC1] |

TABLE 9-continued
| Compounds of Formula I Continued | | |
|---|---|---|
| No. | Salt Structure | Free Base Structure |
| 179 | 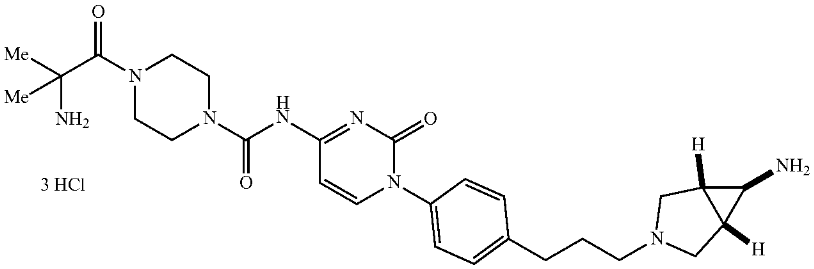 [SMILES: CC(C)(N)C(=O)N1CCN(C(=O)Nc2ccn(-c3ccc(CCCN4C[C@@H]5[C@@H](N)[C@@H]5C4)cc3)c(=O)n2)CC1] 3 HCl | 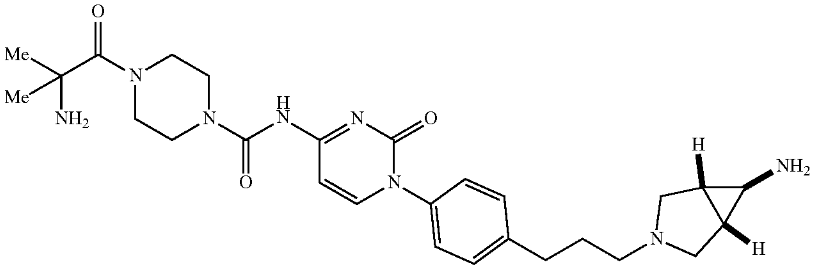 [SMILES: CC(C)(N)C(=O)N1CCN(C(=O)Nc2ccn(-c3ccc(CCCN4C[C@@H]5[C@@H](N)[C@@H]5C4)cc3)c(=O)n2)CC1] |
| 180 | 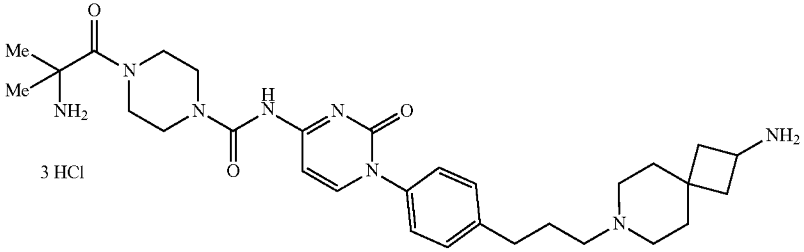 [SMILES: CC(C)(N)C(=O)N1CCN(C(=O)Nc2ccn(-c3ccc(CCCN4CCC5(CC4)CC(N)C5)cc3)c(=O)n2)CC1] 3 HCl | 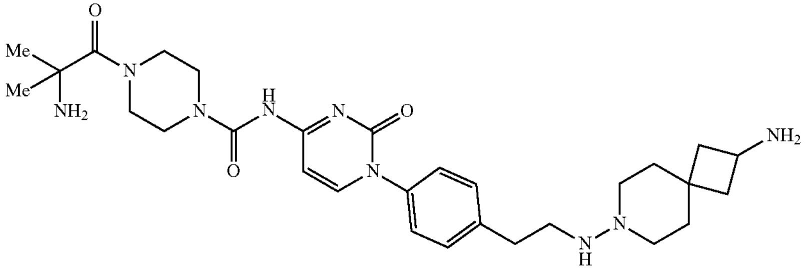 [SMILES: CC(C)(N)C(=O)N1CCN(C(=O)Nc2ccn(-c3ccc(CCNN4CCC5(CC4)CC(N)C5)cc3)c(=O)n2)CC1] |
| 181 | 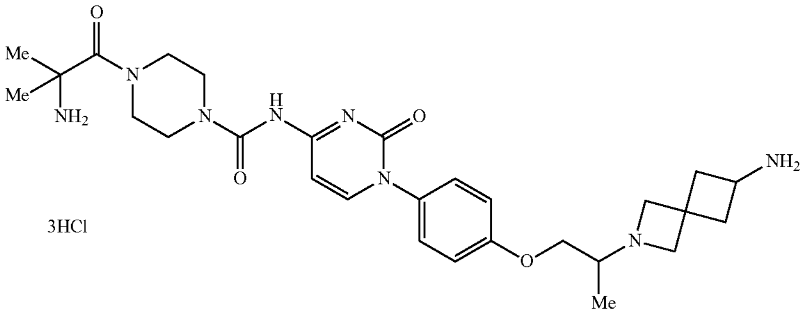 [SMILES: CC(COc1ccc(-n2ccc(NC(=O)N3CCN(C(=O)C(C)(C)N)CC3)nc2=O)cc1)N1CC2(CC(N)C2)C1] 3HCl | 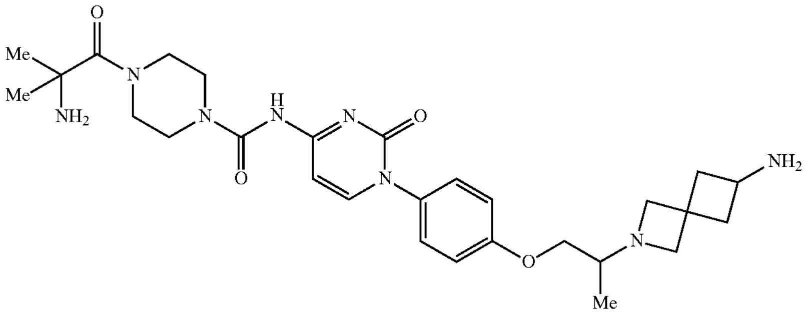 [SMILES: CC(COc1ccc(-n2ccc(NC(=O)N3CCN(C(=O)C(C)(C)N)CC3)nc2=O)cc1)N1CC2(CC(N)C2)C1] |

TABLE 9-continued
| Compounds of Formula I Continued | | |
|---|---|---|
| No. | Salt Structure | Free Base Structure |
| 182 | 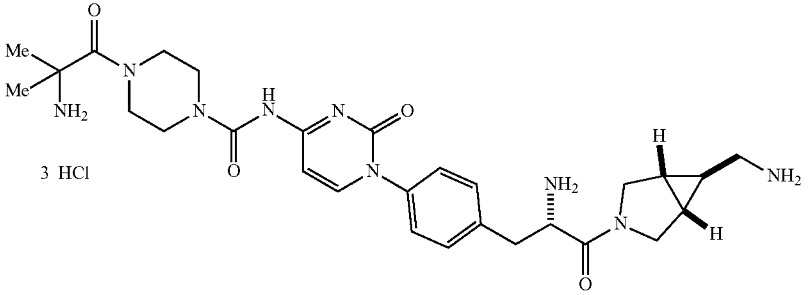 [SMILES: CC(C)(N)C(=O)N1CCN(C(=O)Nc2ccn(-c3ccc(C[C@H](N)C(=O)N4C[C@@H]5[C@@H](CN)[C@@H]5C4)cc3)c(=O)n2)CC1] 3 HCl | 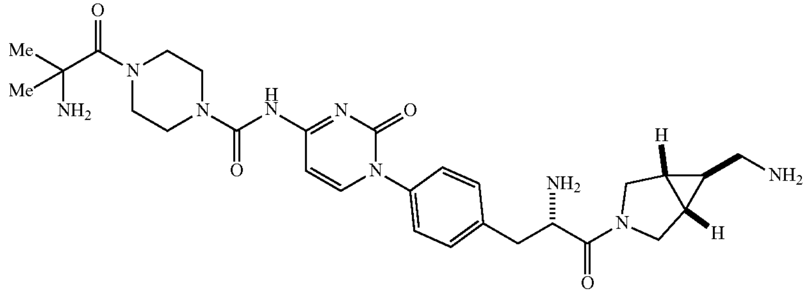 [SMILES: CC(C)(N)C(=O)N1CCN(C(=O)Nc2ccn(-c3ccc(C[C@H](N)C(=O)N4C[C@@H]5[C@@H](CN)[C@@H]5C4)cc3)c(=O)n2)CC1] |
| 183 | 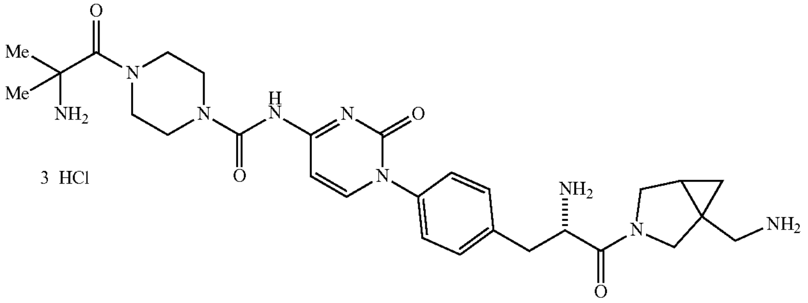 [SMILES: CC(C)(N)C(=O)N1CCN(C(=O)Nc2ccn(-c3ccc(C[C@H](N)C(=O)N4CC5CC5(CN)C4)cc3)c(=O)n2)CC1] 3 HCl | 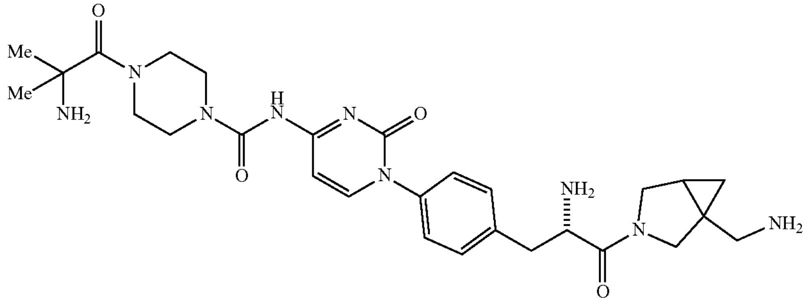 [SMILES: CC(C)(N)C(=O)N1CCN(C(=O)Nc2ccn(-c3ccc(C[C@H](N)C(=O)N4CC5CC5(CN)C4)cc3)c(=O)n2)CC1] |
| 184 | 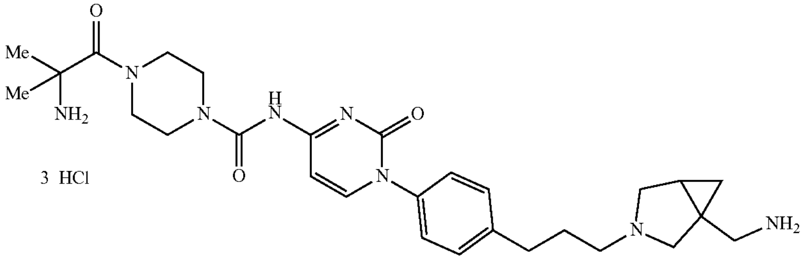 [SMILES: CC(C)(N)C(=O)N1CCN(C(=O)Nc2ccn(-c3ccc(CCCN4CC5CC5(CN)C4)cc3)c(=O)n2)CC1] 3 HCl | 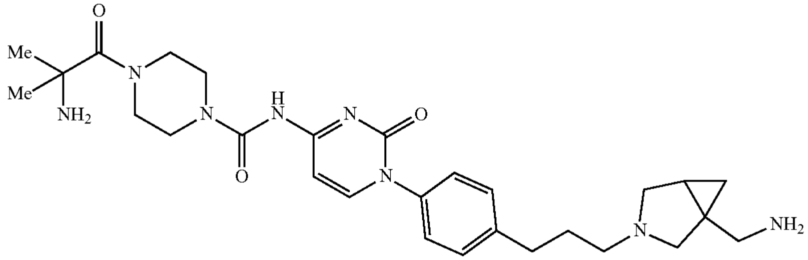 [SMILES: CC(C)(N)C(=O)N1CCN(C(=O)Nc2ccn(-c3ccc(CCCN4CC5CC5(CN)C4)cc3)c(=O)n2)CC1] |

TABLE 9-continued
| Compounds of Formula I Continued | | |
| --- | --- | --- |
| No. | Salt Structure | Free Base Structure |
| 185 | 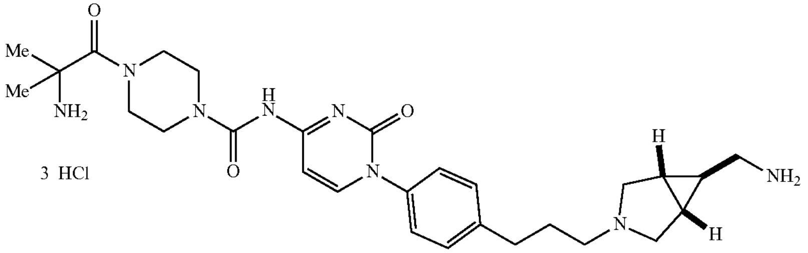 [SMILES: CC(C)(N)C(=O)N1CCN(C(=O)Nc2ccn(-c3ccc(CCCN4C[C@@H]5[C@@H](CN)[C@@H]5C4)cc3)c(=O)n2)CC1] 3 HCl | 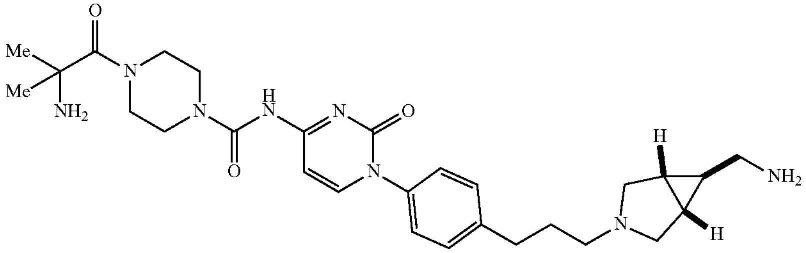 [SMILES: CC(C)(N)C(=O)N1CCN(C(=O)Nc2ccn(-c3ccc(CCCN4C[C@@H]5[C@@H](CN)[C@@H]5C4)cc3)c(=O)n2)CC1] |
| 186 | 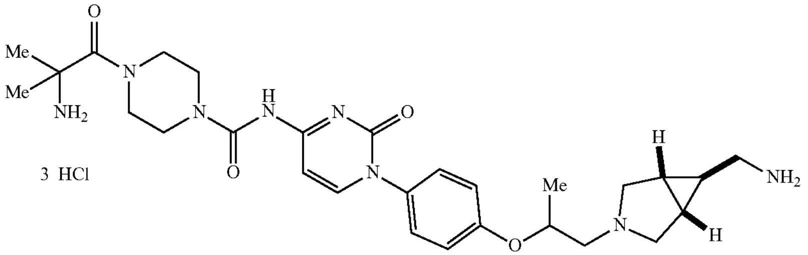 [SMILES: CC(CN1C[C@@H]2[C@@H](CN)[C@@H]2C1)Oc1ccc(-n2ccc(NC(=O)N3CCN(C(=O)C(C)(C)N)CC3)nc2=O)cc1] 3 HCl | 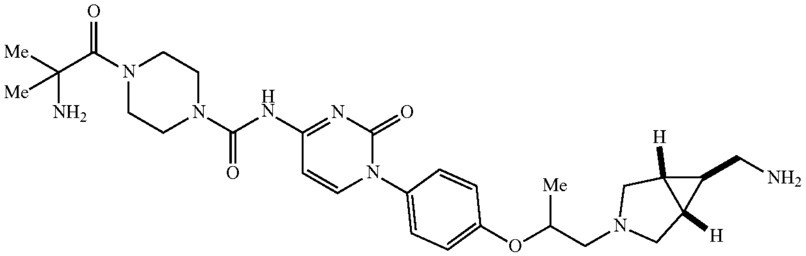 [SMILES: CC(CN1C[C@@H]2[C@@H](CN)[C@@H]2C1)Oc1ccc(-n2ccc(NC(=O)N3CCN(C(=O)C(C)(C)N)CC3)nc2=O)cc1] |
| 187 | 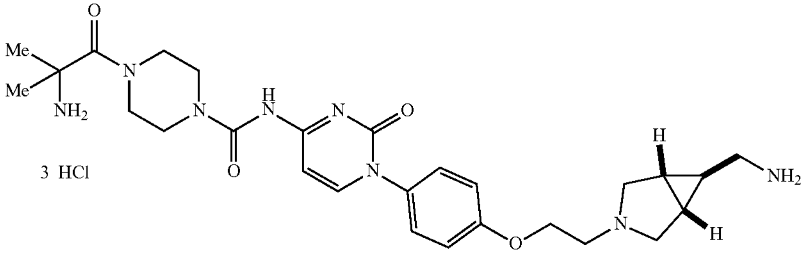 [SMILES: CC(C)(N)C(=O)N1CCN(C(=O)Nc2ccn(-c3ccc(OCCN4C[C@@H]5[C@@H](CN)[C@@H]5C4)cc3)c(=O)n2)CC1] 3 HCl | 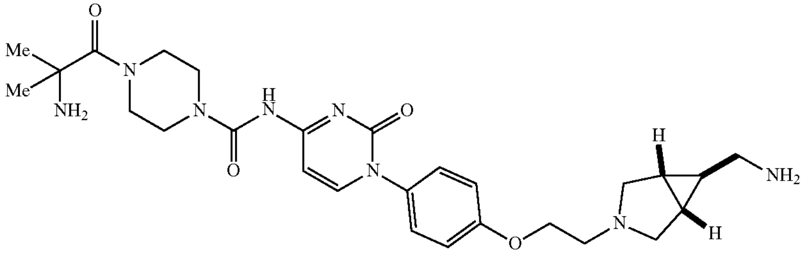 [SMILES: CC(C)(N)C(=O)N1CCN(C(=O)Nc2ccn(-c3ccc(OCCN4C[C@@H]5[C@@H](CN)[C@@H]5C4)cc3)c(=O)n2)CC1] |

TABLE 9-continued
| Compounds of Formula I Continued | | |
|---|---|---|
| No. | Salt Structure | Free Base Structure |
| 188 | 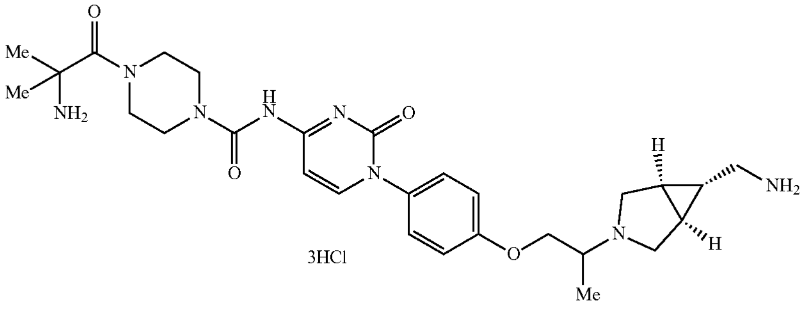 [SMILES: CC(COc1ccc(-n2ccc(NC(=O)N3CCN(C(=O)C(C)(C)N)CC3)nc2=O)cc1)N1C[C@@H]2[C@@H](CN)[C@@H]2C1] 3HCl | 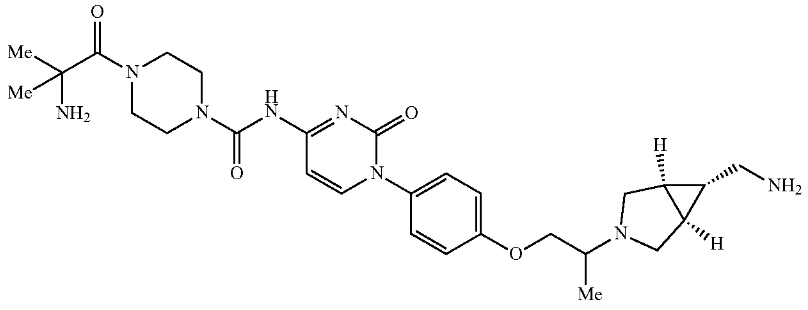 [SMILES: CC(COc1ccc(-n2ccc(NC(=O)N3CCN(C(=O)C(C)(C)N)CC3)nc2=O)cc1)N1C[C@@H]2[C@@H](CN)[C@@H]2C1] |
| 189 | 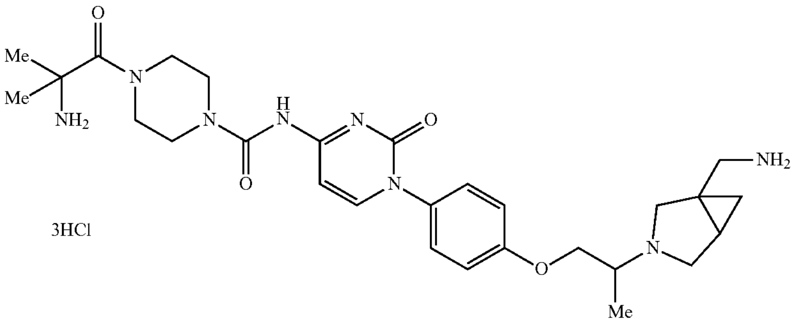 [SMILES: CC(COc1ccc(-n2ccc(NC(=O)N3CCN(C(=O)C(C)(C)N)CC3)nc2=O)cc1)N1CC2CC2(CN)C1] 3HCl | 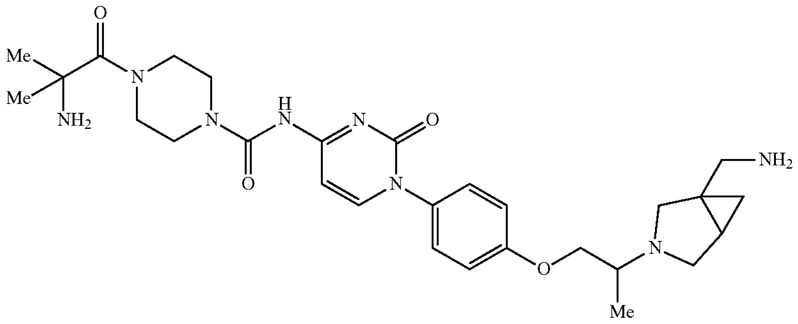 [SMILES: CC(COc1ccc(-n2ccc(NC(=O)N3CCN(C(=O)C(C)(C)N)CC3)nc2=O)cc1)N1CC2CC2(CN)C1] |
| 190 | 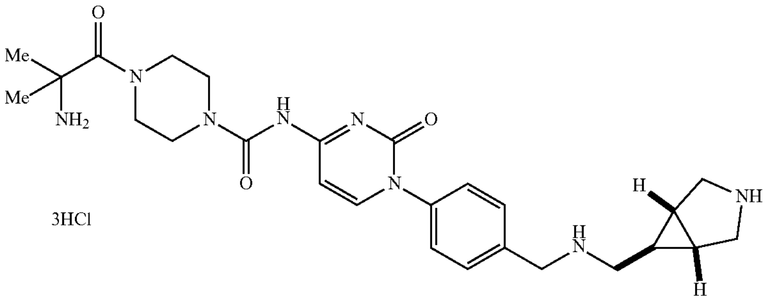 [SMILES: CC(C)(N)C(=O)N1CCN(C(=O)Nc2ccn(-c3ccc(CNC[C@@H]4[C@H]5CNC[C@@H]45)cc3)c(=O)n2)CC1] 3HCl | 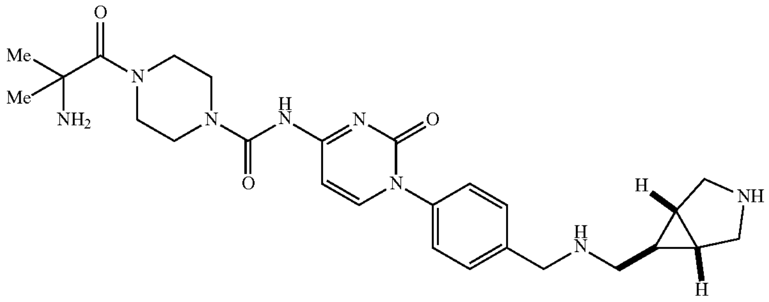 [SMILES: CC(C)(N)C(=O)N1CCN(C(=O)Nc2ccn(-c3ccc(CNC[C@@H]4[C@H]5CNC[C@@H]45)cc3)c(=O)n2)CC1] |

TABLE 9-continued
| Compounds of Formula I Continued | | |
|---|---|---|
| No. | Salt Structure | Free Base Structure |
| 191 | 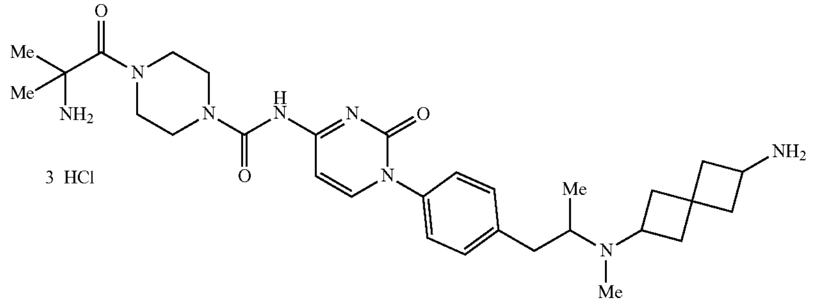 [SMILES: CC(Cc1ccc(-n2ccc(NC(=O)N3CCN(C(=O)C(C)(C)N)CC3)nc2=O)cc1)N(C)C1CC2(CC(N)C2)C1] 3 HCl | 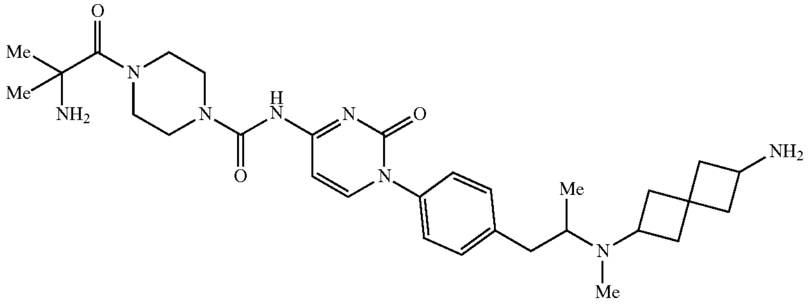 [SMILES: CC(Cc1ccc(-n2ccc(NC(=O)N3CCN(C(=O)C(C)(C)N)CC3)nc2=O)cc1)N(C)C1CC2(CC(N)C2)C1] |
| 192 | 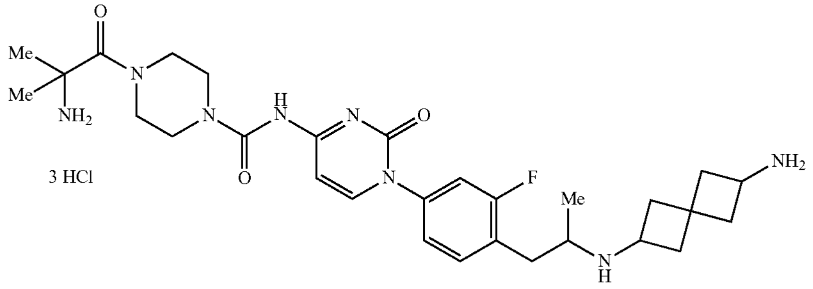 [SMILES: CC(Cc1ccc(-n2ccc(NC(=O)N3CCN(C(=O)C(C)(C)N)CC3)nc2=O)cc1F)NC1CC2(CC(N)C2)C1] 3 HCl | 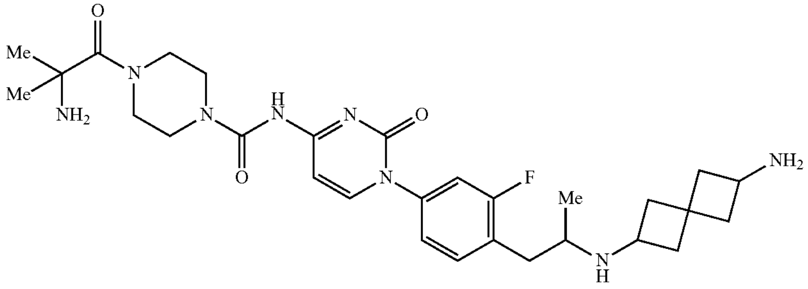 [SMILES: CC(Cc1ccc(-n2ccc(NC(=O)N3CCN(C(=O)C(C)(C)N)CC3)nc2=O)cc1F)NC1CC2(CC(N)C2)C1] |
| 193 | 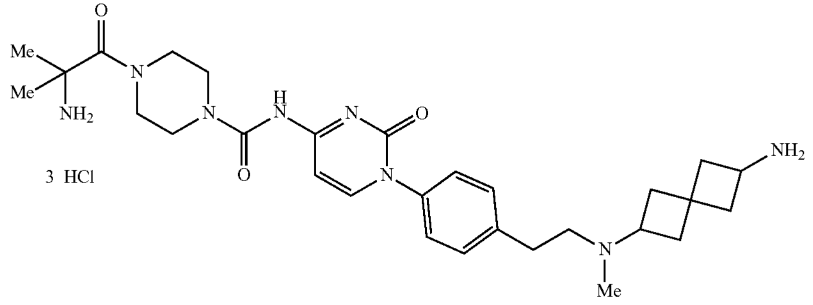 [SMILES: CN(CCc1ccc(-n2ccc(NC(=O)N3CCN(C(=O)C(C)(C)N)CC3)nc2=O)cc1)C1CC2(CC(N)C2)C1] 3 HCl | 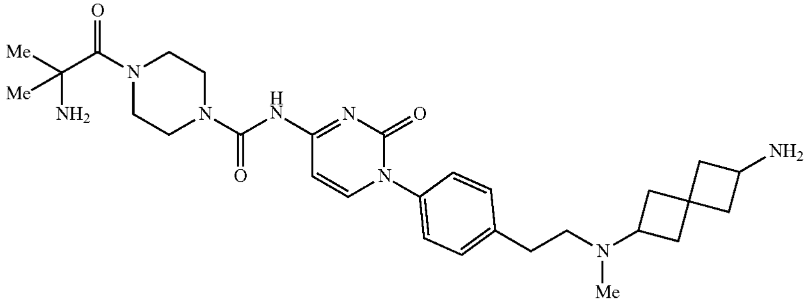 [SMILES: CN(CCc1ccc(-n2ccc(NC(=O)N3CCN(C(=O)C(C)(C)N)CC3)nc2=O)cc1)C1CC2(CC(N)C2)C1] |

TABLE 9-continued
| Compounds of Formula I Continued | | |
|---|---|---|
| No. | Salt Structure | Free Base Structure |
| 194 | 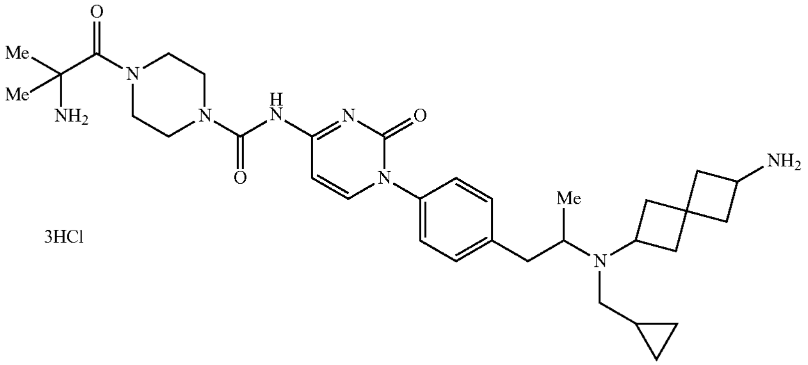 [SMILES: CC(Cc1ccc(-n2ccc(NC(=O)N3CCN(C(=O)C(C)(C)N)CC3)nc2=O)cc1)N(CC1CC1)C1CC2(CC(N)C2)C1] 3HCl | 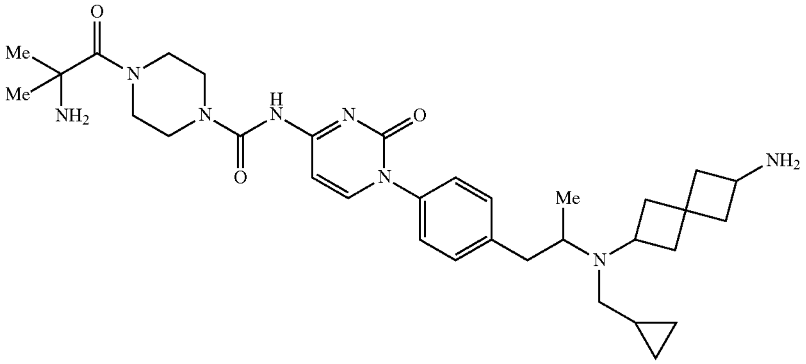 [SMILES: CC(Cc1ccc(-n2ccc(NC(=O)N3CCN(C(=O)C(C)(C)N)CC3)nc2=O)cc1)N(CC1CC1)C1CC2(CC(N)C2)C1] |
| 195 | 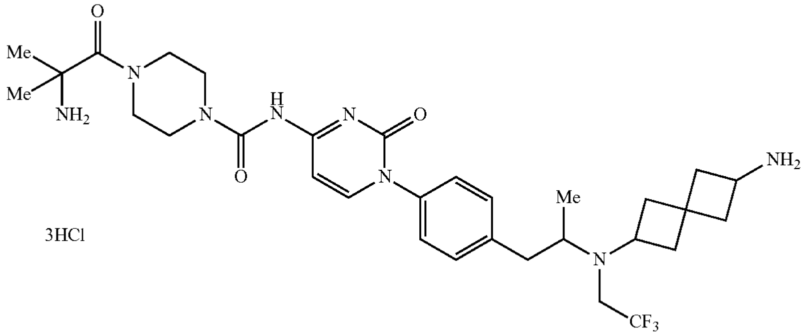 [SMILES: CC(Cc1ccc(-n2ccc(NC(=O)N3CCN(C(=O)C(C)(C)N)CC3)nc2=O)cc1)N(CC(F)(F)F)C1CC2(CC(N)C2)C1] 3HCl | 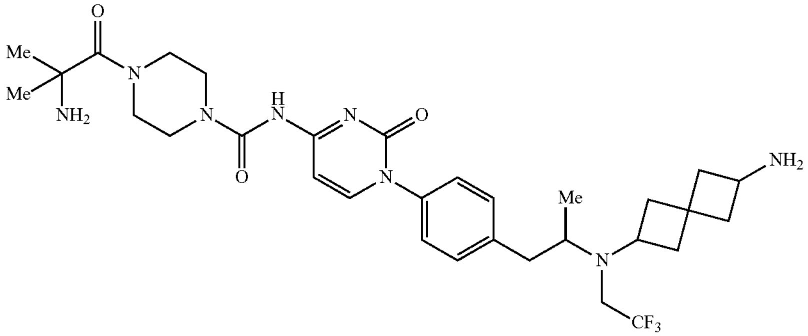 [SMILES: CC(Cc1ccc(-n2ccc(NC(=O)N3CCN(C(=O)C(C)(C)N)CC3)nc2=O)cc1)N(CC(F)(F)F)C1CC2(CC(N)C2)C1] |

TABLE 9-continued
| Compounds of Formula I Continued | | |
|---|---|---|
| No. | Salt Structure | Free Base Structure |
| 196 | 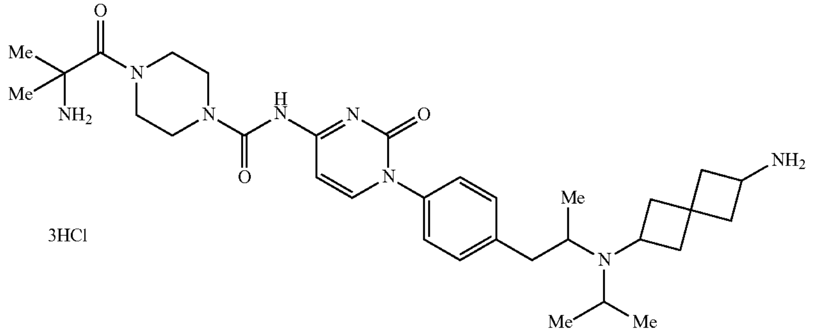 [SMILES: CC(C)N(C(C)Cc1ccc(-n2ccc(NC(=O)N3CCN(C(=O)C(C)(C)N)CC3)nc2=O)cc1)C1CC2(CC(N)C2)C1] 3HCl | 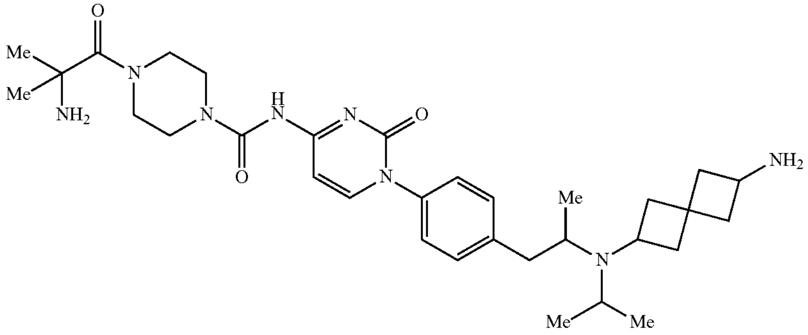 [SMILES: CC(C)N(C(C)Cc1ccc(-n2ccc(NC(=O)N3CCN(C(=O)C(C)(C)N)CC3)nc2=O)cc1)C1CC2(CC(N)C2)C1] |
| 197 | 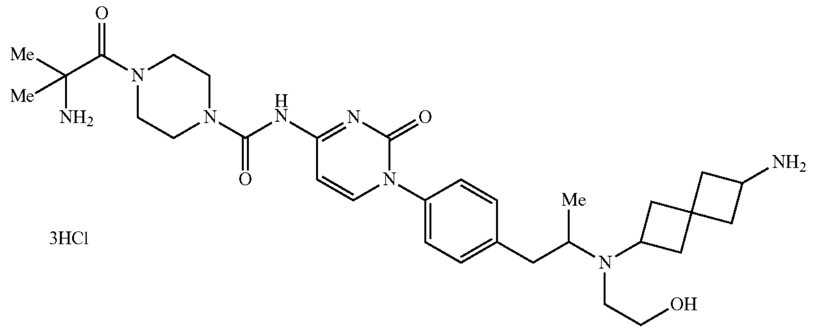 [SMILES: CC(Cc1ccc(-n2ccc(NC(=O)N3CCN(C(=O)C(C)(C)N)CC3)nc2=O)cc1)N(CCO)C1CC2(CC(N)C2)C1] 3HCl | 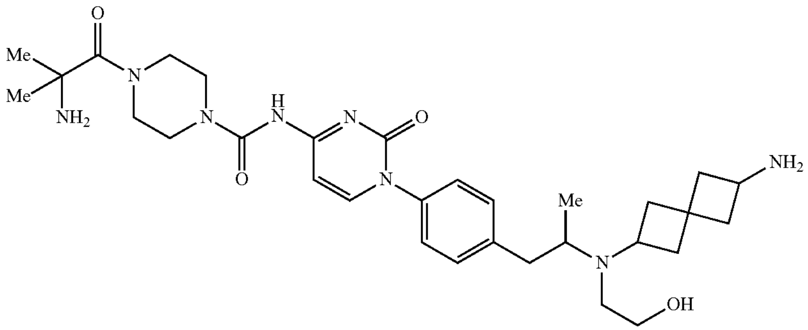 [SMILES: CC(Cc1ccc(-n2ccc(NC(=O)N3CCN(C(=O)C(C)(C)N)CC3)nc2=O)cc1)N(CCO)C1CC2(CC(N)C2)C1] |
| 198 | 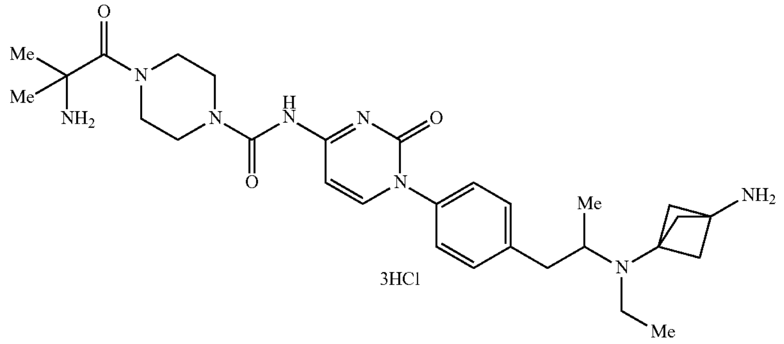 [SMILES: CCN(C(C)Cc1ccc(-n2ccc(NC(=O)N3CCN(C(=O)C(C)(C)N)CC3)nc2=O)cc1)C12CC(N)(C1)C2] 3HCl | 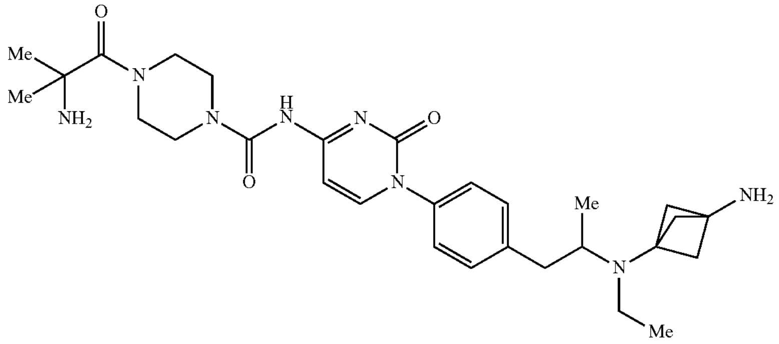 [SMILES: CCN(C(C)Cc1ccc(-n2ccc(NC(=O)N3CCN(C(=O)C(C)(C)N)CC3)nc2=O)cc1)C12CC(N)(C1)C2] |

TABLE 9-continued
Compounds of Formula I Continued
| No. | Salt Structure | Free Base Structure |
|---|---|---|
| 199 | 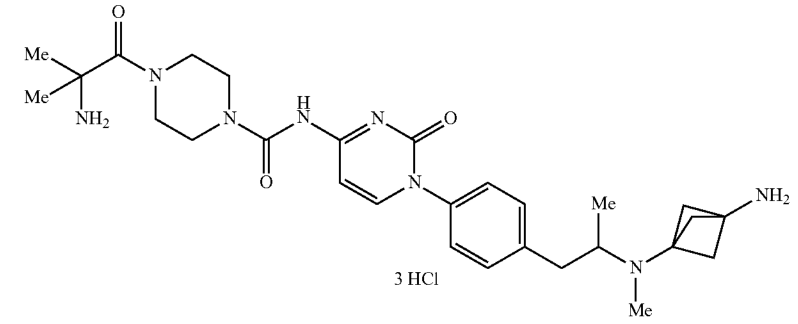 [SMILES: CC(Cc1ccc(-n2ccc(NC(=O)N3CCN(C(=O)C(C)(C)N)CC3)nc2=O)cc1)N(C)C12CC(N)(C1)C2] 3 HCl | 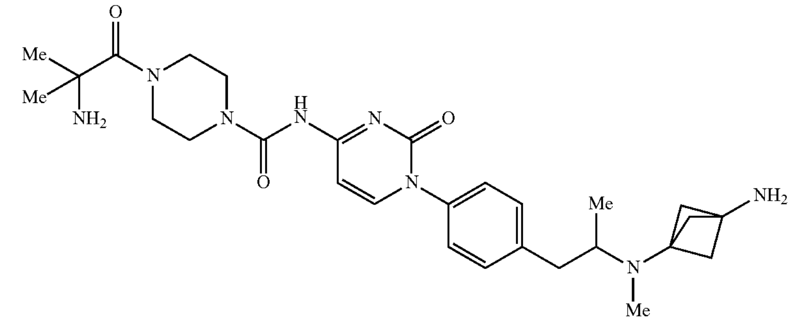 [SMILES: CC(Cc1ccc(-n2ccc(NC(=O)N3CCN(C(=O)C(C)(C)N)CC3)nc2=O)cc1)N(C)C12CC(N)(C1)C2] |
| 200 | 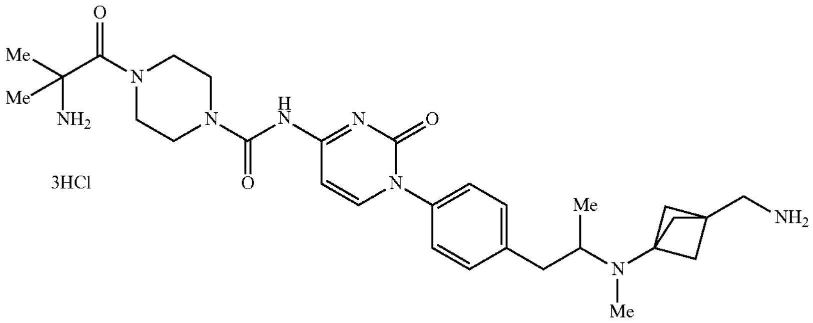 [SMILES: CC(Cc1ccc(-n2ccc(NC(=O)N3CCN(C(=O)C(C)(C)N)CC3)nc2=O)cc1)N(C)C12CC(CN)(C1)C2] 3HCl | 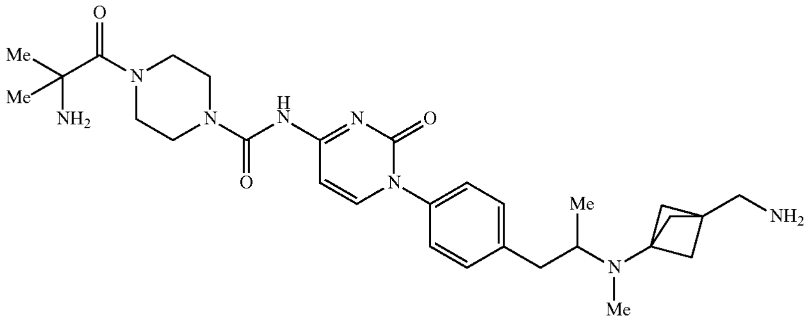 |
| 201 | 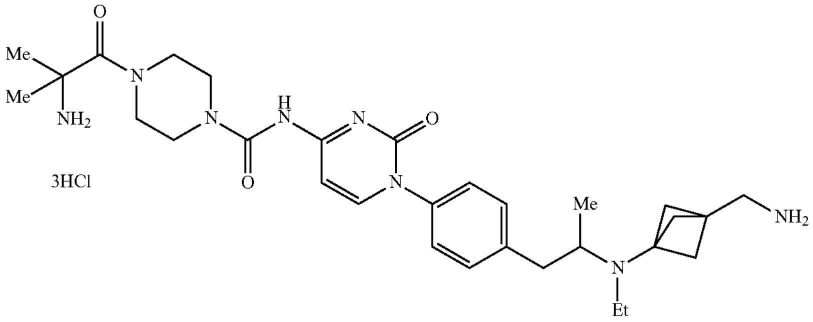 [SMILES: CCN(C(C)Cc1ccc(-n2ccc(NC(=O)N3CCN(C(=O)C(C)(C)N)CC3)nc2=O)cc1)C12CC(CN)(C1)C2] 3HCl | 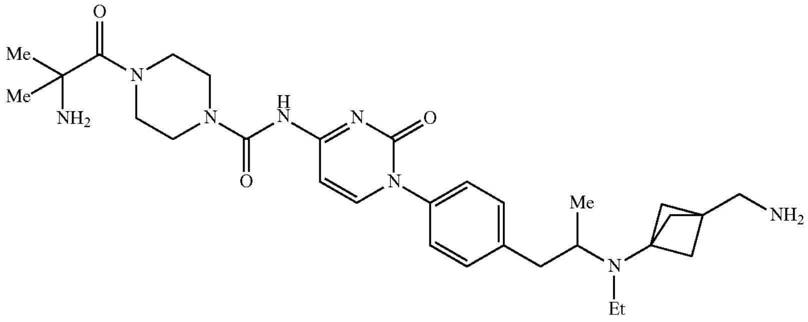 [SMILES: CCN(C(C)Cc1ccc(-n2ccc(NC(=O)N3CCN(C(=O)C(C)(C)N)CC3)nc2=O)cc1)C12CC(CN)(C1)C2] |

TABLE 9-continued
| Compounds of Formula I Continued | | |
|---|---|---|
| No. | Salt Structure | Free Base Structure |
| 202 | 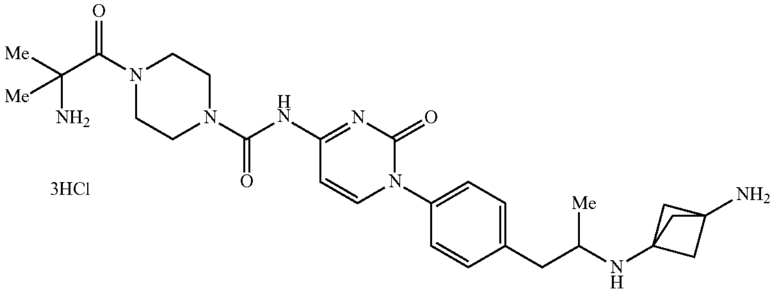 [SMILES: CC(Cc1ccc(-n2ccc(NC(=O)N3CCN(C(=O)C(C)(C)N)CC3)nc2=O)cc1)NC12CC(N)(C1)C2] 3HCl | 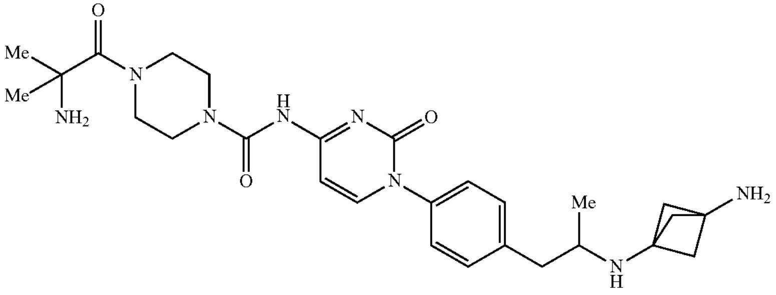 [SMILES: CC(Cc1ccc(-n2ccc(NC(=O)N3CCN(C(=O)C(C)(C)N)CC3)nc2=O)cc1)NC12CC(N)(C1)C2] |
| 203 | 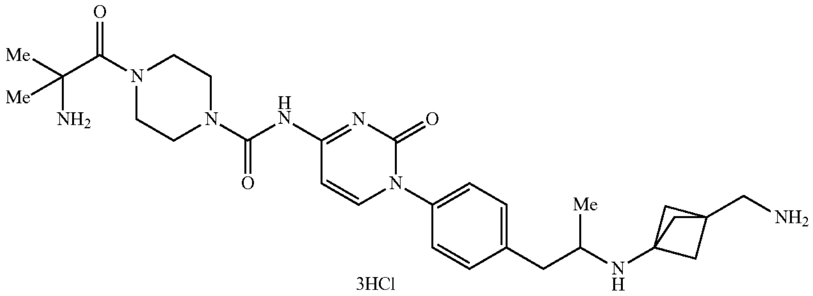 [SMILES: CC(Cc1ccc(-n2ccc(NC(=O)N3CCN(C(=O)C(C)(C)N)CC3)nc2=O)cc1)NC12CC(CN)(C1)C2] 3HCl | 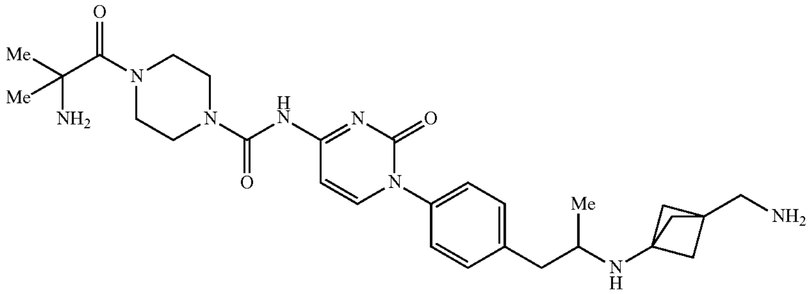 [SMILES: CC(Cc1ccc(-n2ccc(NC(=O)N3CCN(C(=O)C(C)(C)N)CC3)nc2=O)cc1)NC12CC(CN)(C1)C2] |
| 204 | 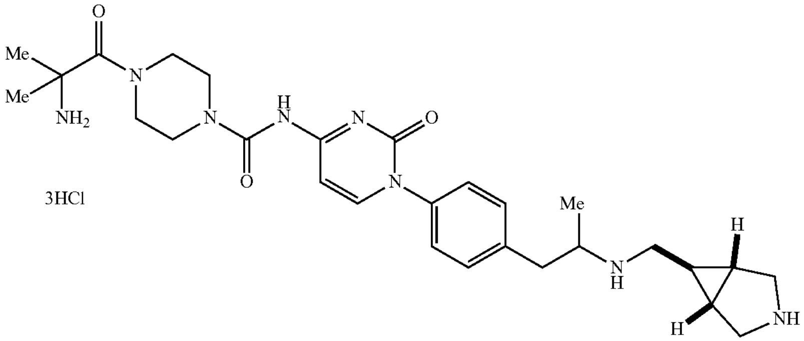 3HCl | 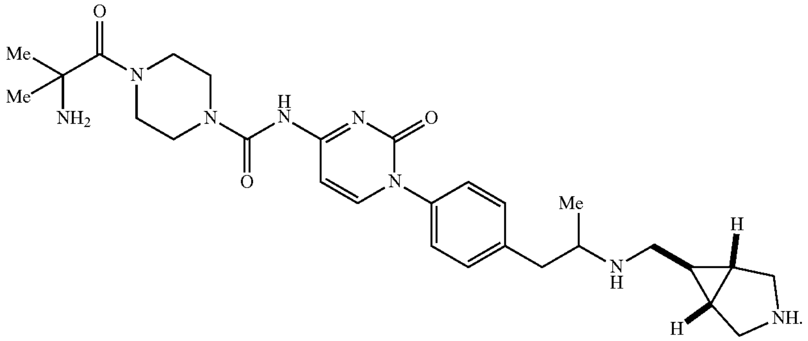 |

In another aspect, the disclosure provides a compound or a pharmaceutically acceptable salt thereof which is depicted in Table 10. In Table 10a possible pharmaceutically acceptable salt and the free base is shown for each compound.

TABLE 10
| Compounds of Formula I Continued | | |
|---|---|---|
| No. | Salt Structure | Free Base Structure |
| 205 | 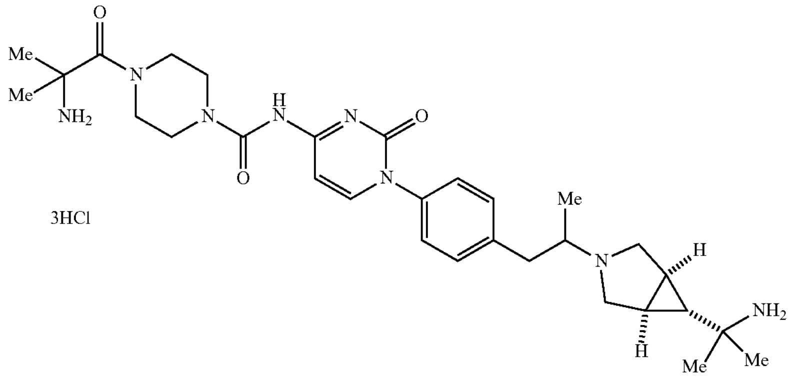 3HCl | 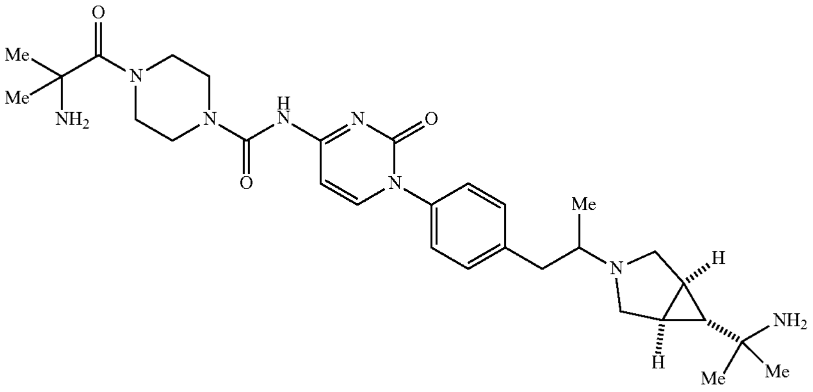 [SMILES: CC(Cc1ccc(-n2ccc(NC(=O)N3CCN(C(=O)C(C)(C)N)CC3)nc2=O)cc1)N1C[C@@H]2[C@H](C1)[C@H]2C(C)(C)N] |
| 206 | 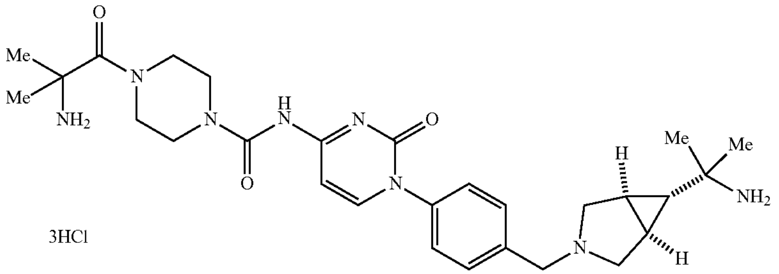 3HCl | 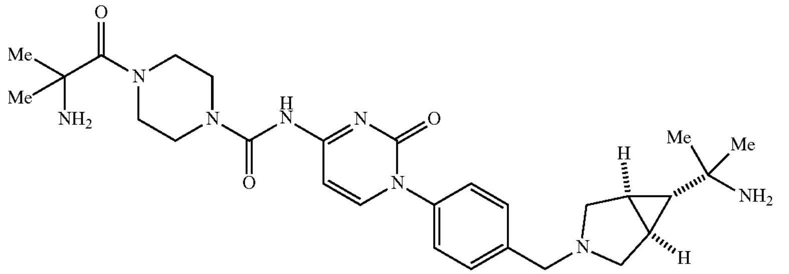 |
| 207 | 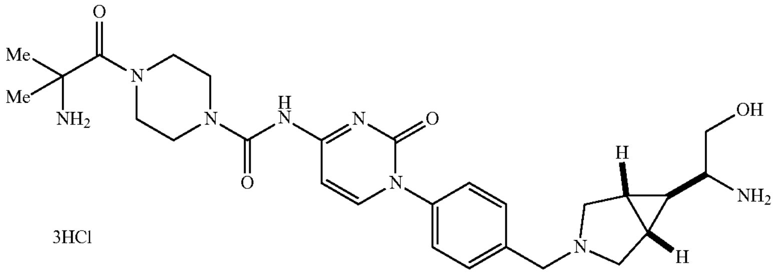 [SMILES: CC(C)(N)C(=O)N1CCN(C(=O)Nc2ccn(-c3ccc(CN4C[C@@H]5C([C@H](N)CO)[C@@H]5C4)cc3)c(=O)n2)CC1] 3HCl | 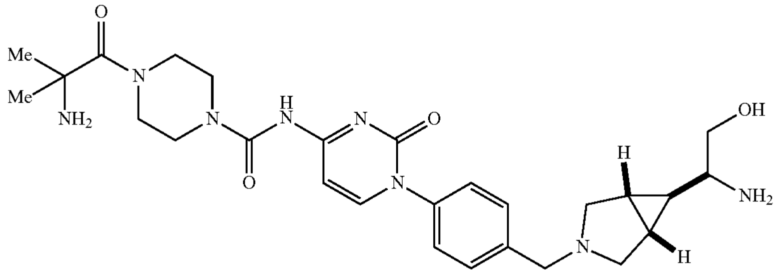 [SMILES: CC(C)(N)C(=O)N1CCN(C(=O)Nc2ccn(-c3ccc(CN4C[C@@H]5C([C@H](N)CO)[C@@H]5C4)cc3)c(=O)n2)CC1] |

TABLE 10-continued
| Compounds of Formula I Continued | | |
|---|---|---|
| No. | Salt Structure | Free Base Structure |
| 208 | 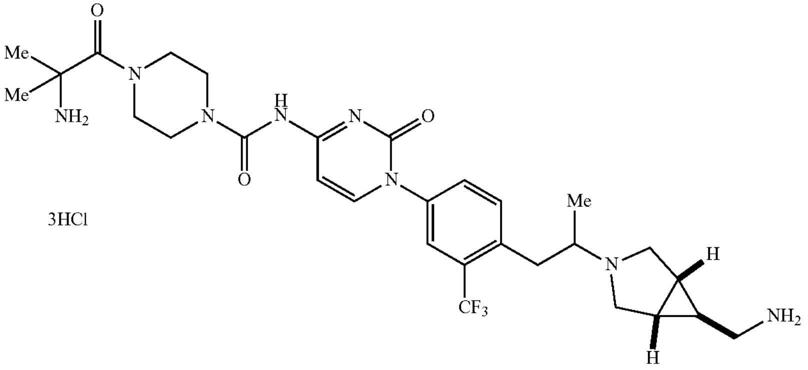 [SMILES: CC(Cc1ccc(-n2ccc(NC(=O)N3CCN(C(=O)C(C)(C)N)CC3)nc2=O)cc1C(F)(F)F)N1C[C@@H]2[C@@H](CN)[C@@H]2C1] 3HCl | 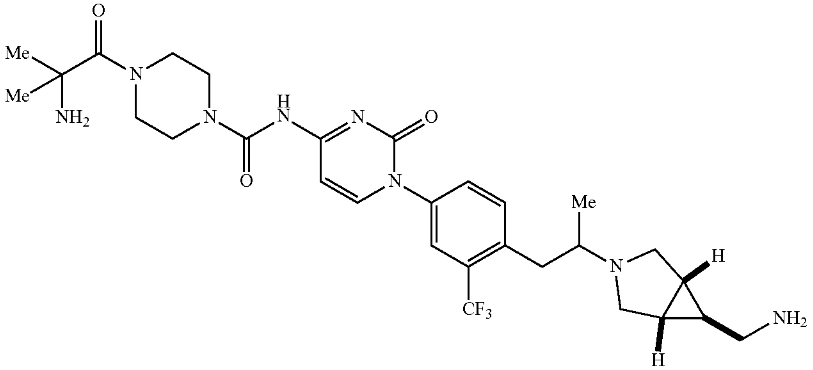 |
| 209 | 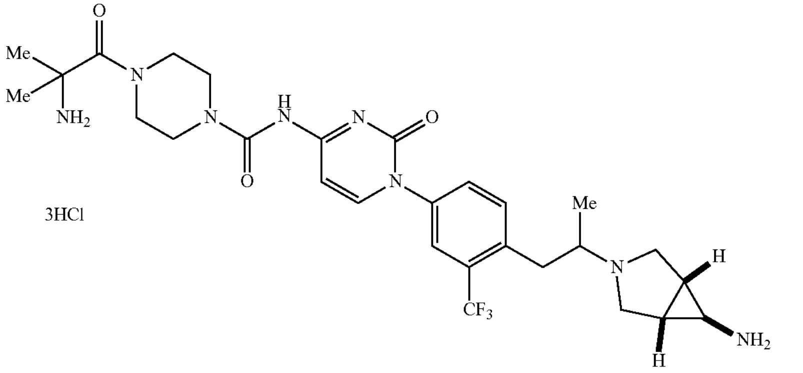 [SMILES: CC(Cc1ccc(-n2ccc(NC(=O)N3CCN(C(=O)C(C)(C)N)CC3)nc2=O)cc1C(F)(F)F)N1C[C@@H]2[C@@H](N)[C@@H]2C1] 3HCl | 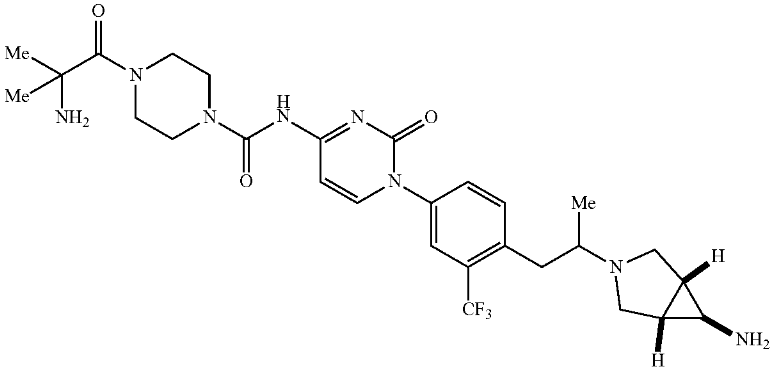 [SMILES: CC(Cc1ccc(-n2ccc(NC(=O)N3CCN(C(=O)C(C)(C)N)CC3)nc2=O)cc1C(F)(F)F)N1C[C@@H]2[C@@H](N)[C@@H]2C1] |

TABLE 10-continued
| Compounds of Formula I Continued | | |
|---|---|---|
| No. | Salt Structure | Free Base Structure |
| 210 | 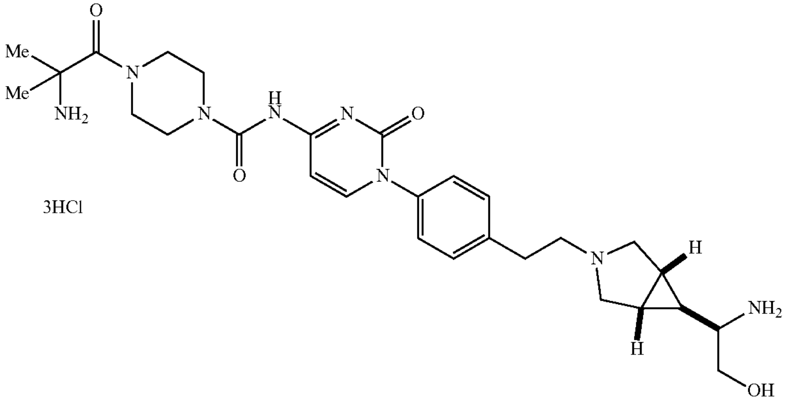 [SMILES: CC(C)(N)C(=O)N1CCN(C(=O)Nc2ccn(-c3ccc(CCN4C[C@@H]5[C@H](C4)[C@H]5C(N)CO)cc3)c(=O)n2)CC1] 3HCl | 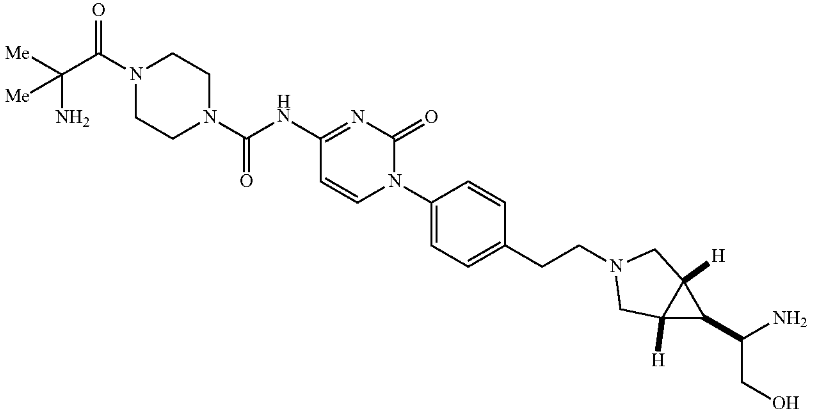 [SMILES: CC(C)(N)C(=O)N1CCN(C(=O)Nc2ccn(-c3ccc(CCN4C[C@@H]5[C@H](C4)[C@H]5C(N)CO)cc3)c(=O)n2)CC1] |
| 211 | 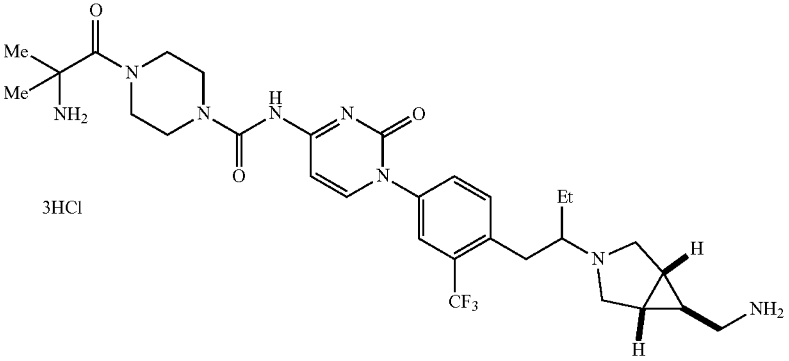 [SMILES: CCC(Cc1ccc(-n2ccc(NC(=O)N3CCN(C(=O)C(C)(C)N)CC3)nc2=O)cc1C(F)(F)F)N1C[C@@H]2[C@@H](CN)[C@@H]2C1] 3HCl | 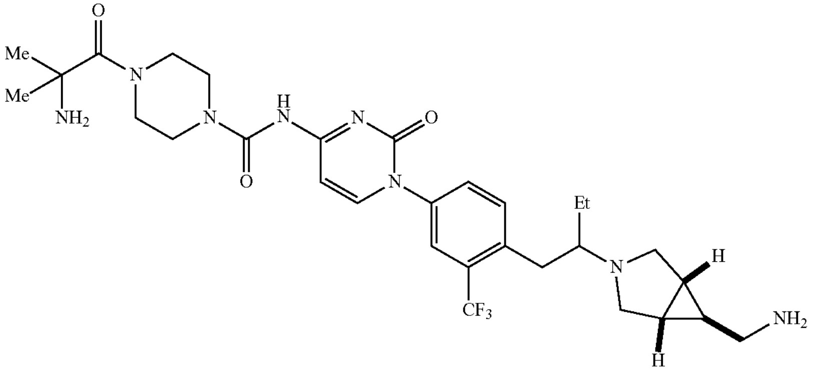 [SMILES: CCC(Cc1ccc(-n2ccc(NC(=O)N3CCN(C(=O)C(C)(C)N)CC3)nc2=O)cc1C(F)(F)F)N1C[C@@H]2[C@@H](CN)[C@@H]2C1] |

TABLE 10-continued
| Compounds of Formula I Continued | | |
|---|---|---|
| No. | Salt Structure | Free Base Structure |
| 212 | 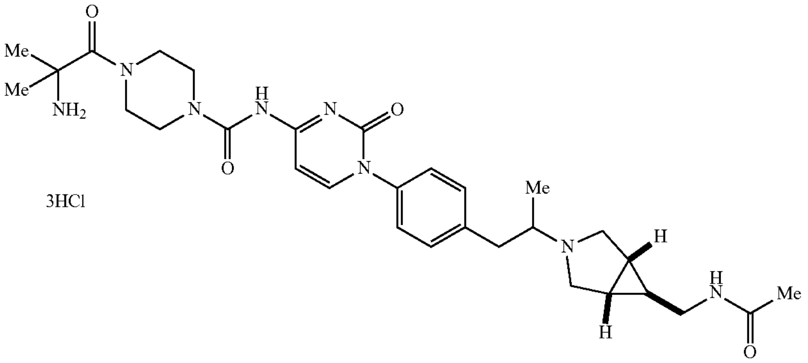 [SMILES: CC(=O)NC[C@@H]1[C@H]2CN(C(C)Cc3ccc(-n4ccc(NC(=O)N5CCN(C(=O)C(C)(C)N)CC5)nc4=O)cc3)C[C@@H]12] 3HCl | 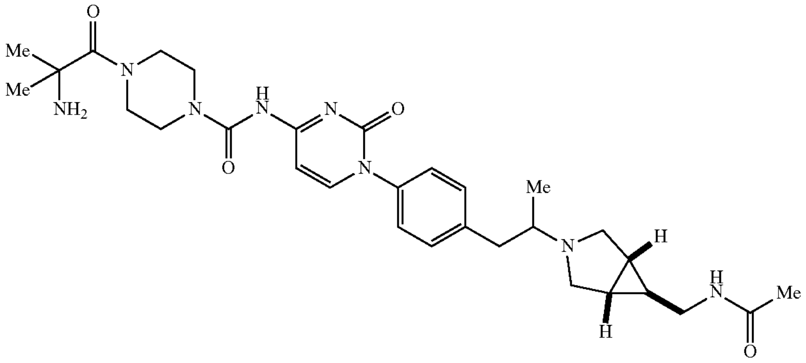 [SMILES: CC(=O)NC[C@@H]1[C@H]2CN(C(C)Cc3ccc(-n4ccc(NC(=O)N5CCN(C(=O)C(C)(C)N)CC5)nc4=O)cc3)C[C@@H]12] |
| 213 | 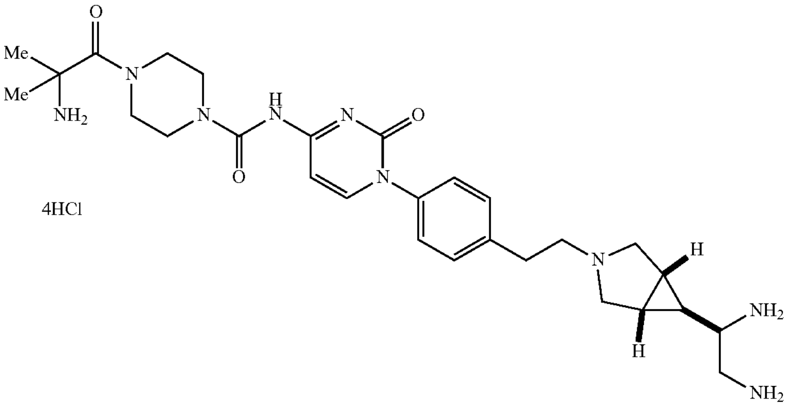 [SMILES: CC(C)(N)C(=O)N1CCN(C(=O)Nc2ccn(-c3ccc(CCN4C[C@@H]5[C@H](C4)[C@H]5C(N)CN)cc3)c(=O)n2)CC1] 4HCl | 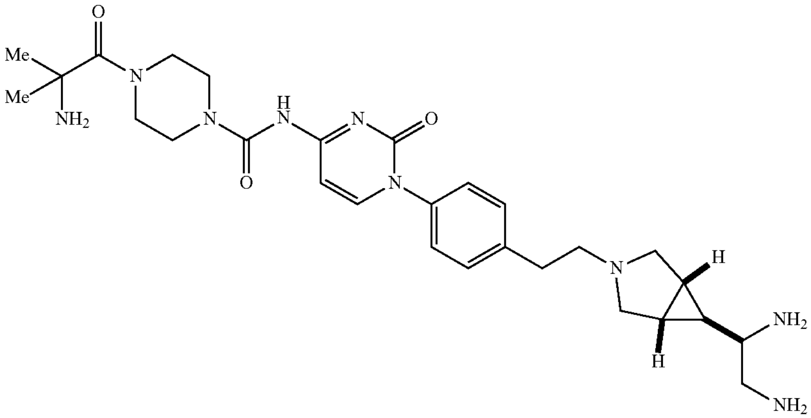 [SMILES: CC(C)(N)C(=O)N1CCN(C(=O)Nc2ccn(-c3ccc(CCN4C[C@@H]5[C@H](C4)[C@H]5C(N)CN)cc3)c(=O)n2)CC1] |

TABLE 10-continued
| Compounds of Formula I Continued | | |
|---|---|---|
| No. | Salt Structure | Free Base Structure |
| 214 | 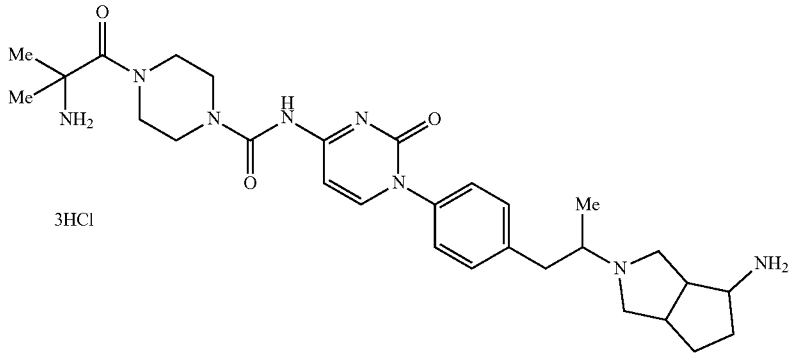 [SMILES: CC(Cc1ccc(-n2ccc(NC(=O)N3CCN(C(=O)C(C)(C)N)CC3)nc2=O)cc1)N1CC2CCC(N)C2C1] 3HCl | 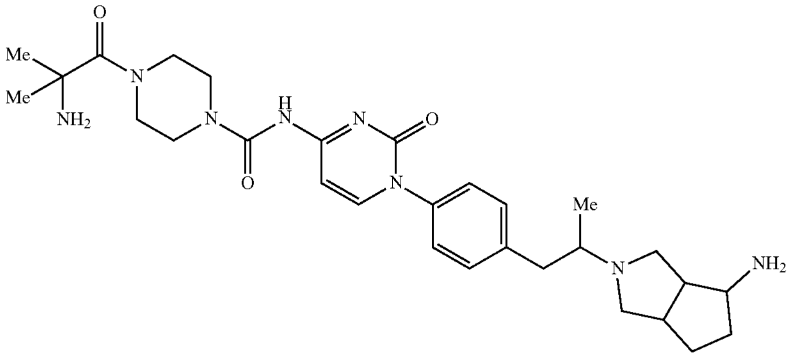 |
| 215 | 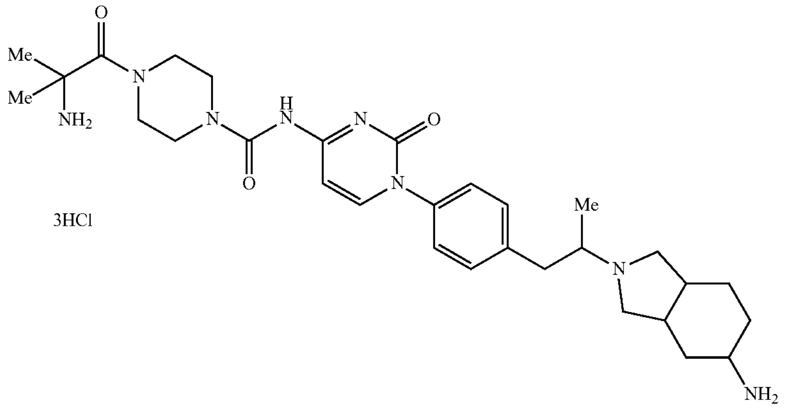 [SMILES: CC(Cc1ccc(-n2ccc(NC(=O)N3CCN(C(=O)C(C)(C)N)CC3)nc2=O)cc1)N1CC2CCC(N)CC2C1] 3HCl | 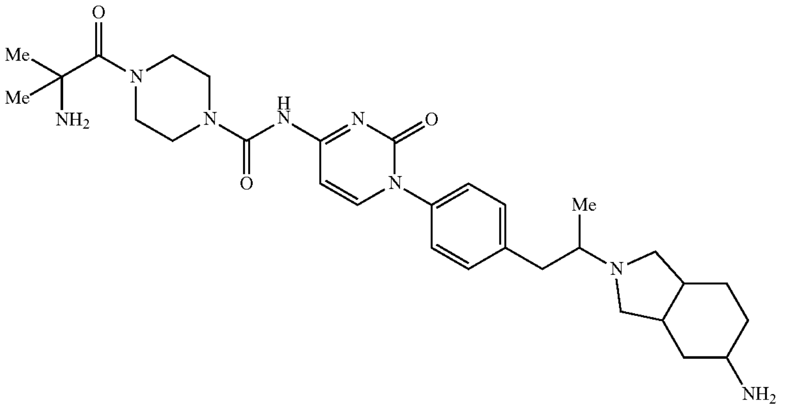 |

TABLE 10-continued
| Compounds of Formula I Continued | | |
|---|---|---|
| No. | Salt Structure | Free Base Structure |
| 216 | 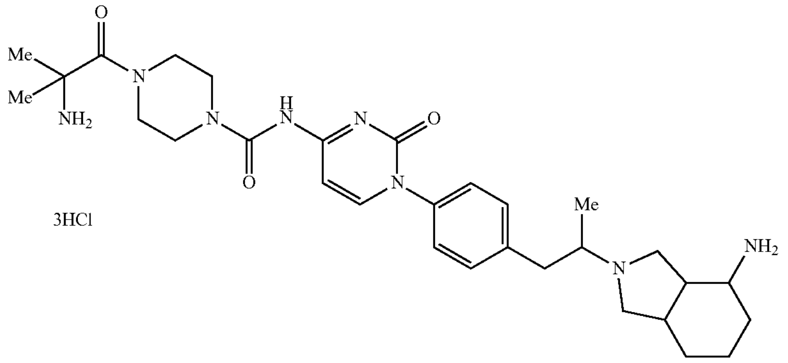 [SMILES: CC(Cc1ccc(-n2ccc(NC(=O)N3CCN(C(=O)C(C)(C)N)CC3)nc2=O)cc1)N1CC2CCCC(N)C2C1] 3HCl | 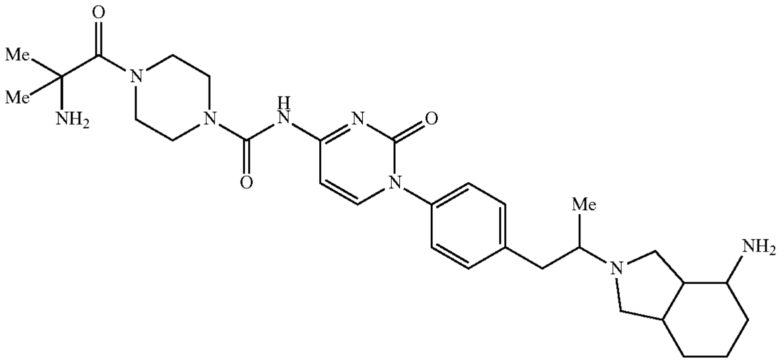 |
| 217 | 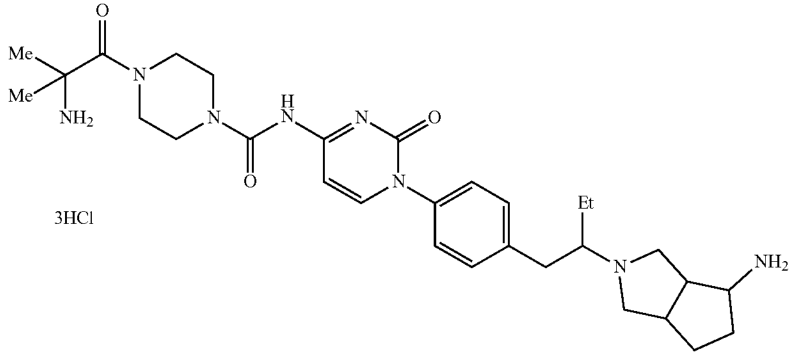 [SMILES: CCC(Cc1ccc(-n2ccc(NC(=O)N3CCN(C(=O)C(C)(C)N)CC3)nc2=O)cc1)N1CC2CCC(N)C2C1] 3HCl | 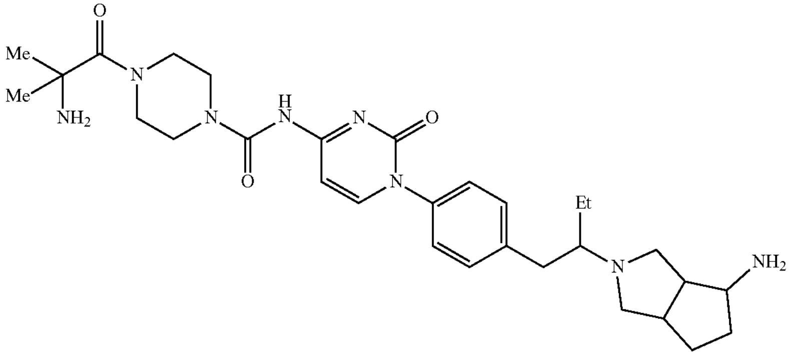 |

TABLE 10-continued
| Compounds of Formula I Continued | | |
|---|---|---|
| No. | Salt Structure | Free Base Structure |
| 218 | 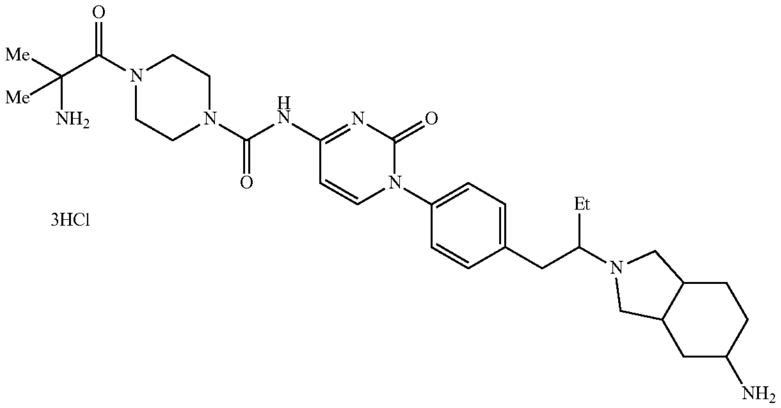 [SMILES: CCC(Cc1ccc(-n2ccc(NC(=O)N3CCN(C(=O)C(C)(C)N)CC3)nc2=O)cc1)N1CC2CCC(N)CC2C1] 3HCl | 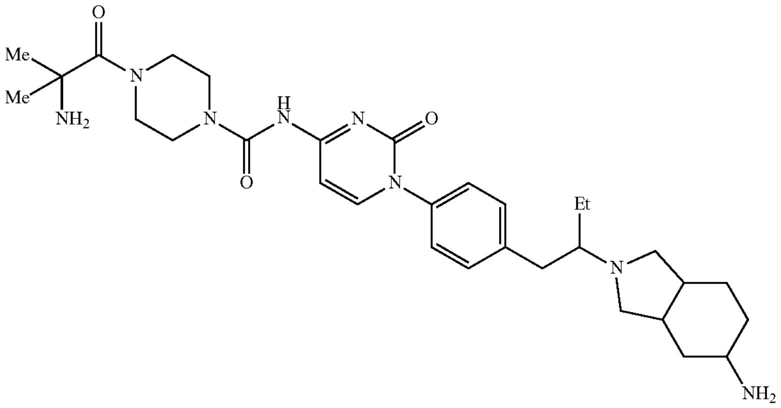 |
| 219 | 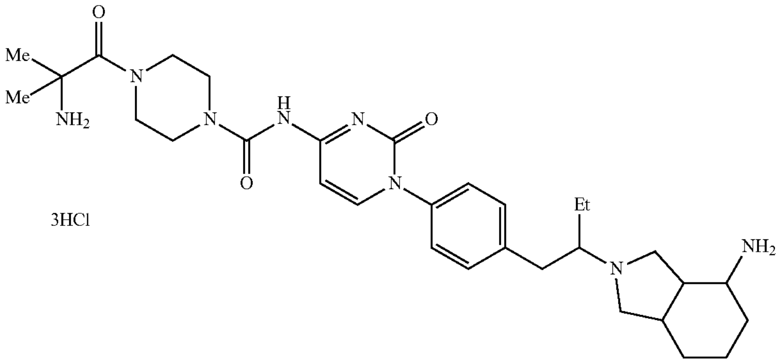 [SMILES: CCC(Cc1ccc(-n2ccc(NC(=O)N3CCN(C(=O)C(C)(C)N)CC3)nc2=O)cc1)N1CC2CCCC(N)C2C1] 3HCl | 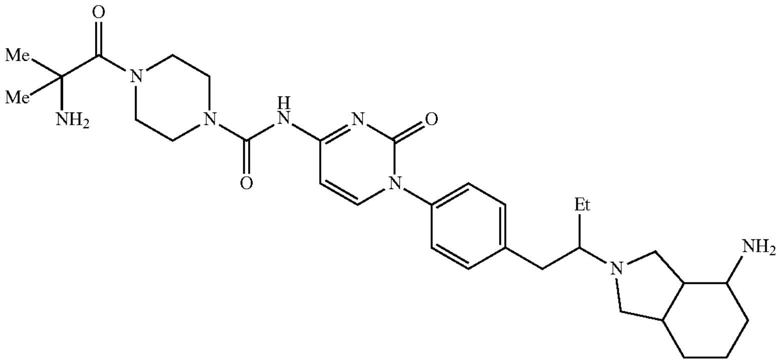 |

TABLE 10-continued
| Compounds of Formula I Continued | | |
|---|---|---|
| No. | Salt Structure | Free Base Structure |
| 220 | 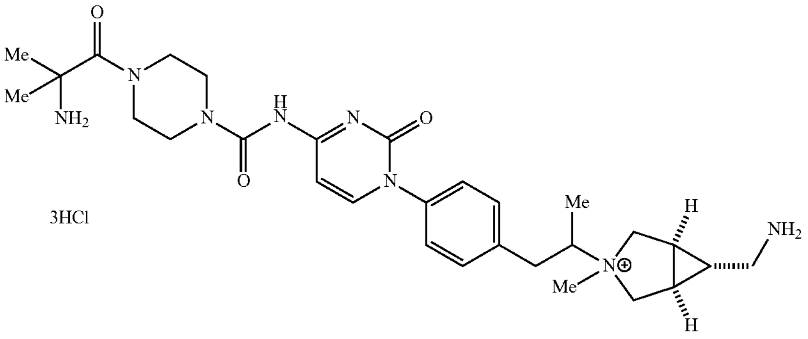 [SMILES: CC(Cc1ccc(-n2ccc(NC(=O)N3CCN(C(=O)C(C)(C)N)CC3)nc2=O)cc1)[N+]1(C)C[C@@H]2[C@@H](CN)[C@@H]2C1] 3HCl | 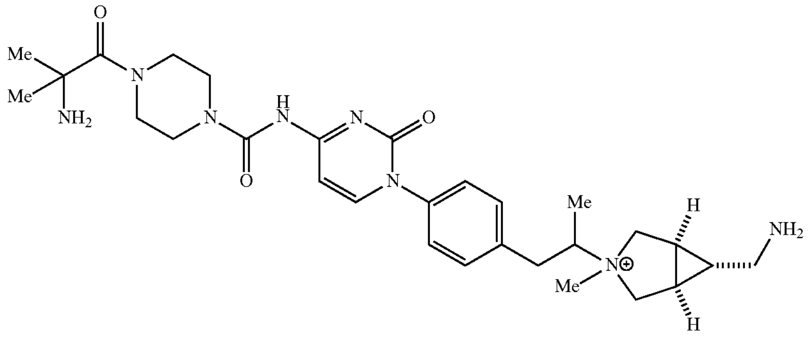 [SMILES: CC(Cc1ccc(-n2ccc(NC(=O)N3CCN(C(=O)C(C)(C)N)CC3)nc2=O)cc1)[N+]1(C)C[C@@H]2[C@@H](CN)[C@@H]2C1] |
| 221 | 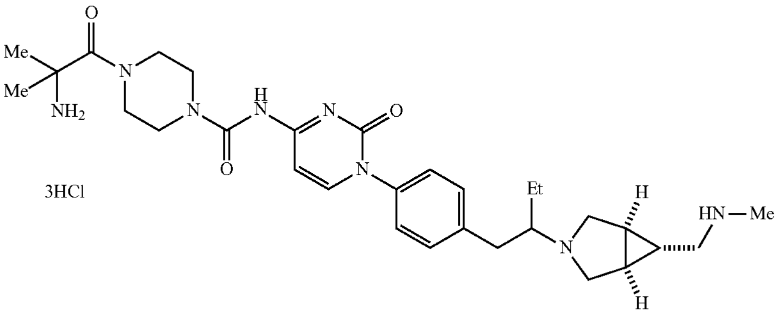 [SMILES: CCC(Cc1ccc(-n2ccc(NC(=O)N3CCN(C(=O)C(C)(C)N)CC3)nc2=O)cc1)N1C[C@@H]2[C@@H](CNC)[C@@H]2C1] 3HCl | 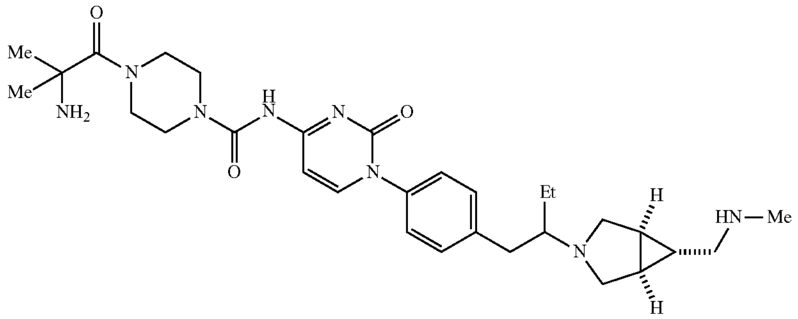 [SMILES: CCC(Cc1ccc(-n2ccc(NC(=O)N3CCN(C(=O)C(C)(C)N)CC3)nc2=O)cc1)N1C[C@@H]2[C@@H](CNC)[C@@H]2C1] |

TABLE 10-continued
| Compounds of Formula I Continued | | |
|---|---|---|
| No. | Salt Structure | Free Base Structure |
| 222 | 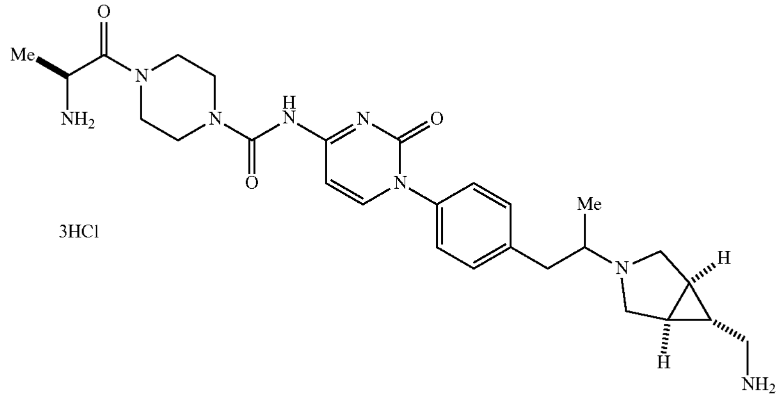 [SMILES: CC(Cc1ccc(-n2ccc(NC(=O)N3CCN(C(=O)[C@H](C)N)CC3)nc2=O)cc1)N1C[C@@H]2[C@@H](CN)[C@@H]2C1] 3HCl | 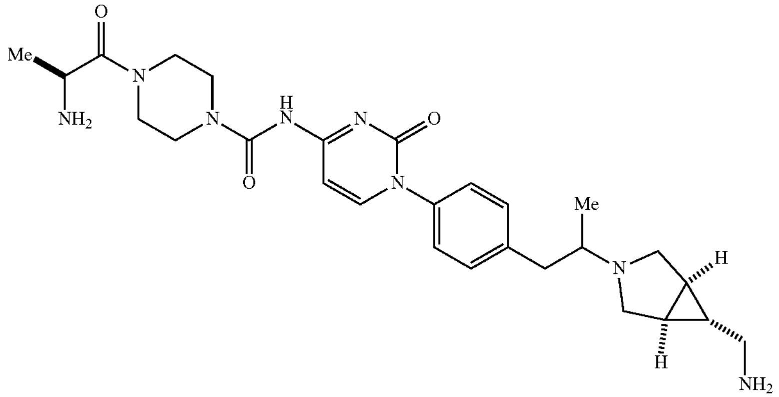 |
| 223 | 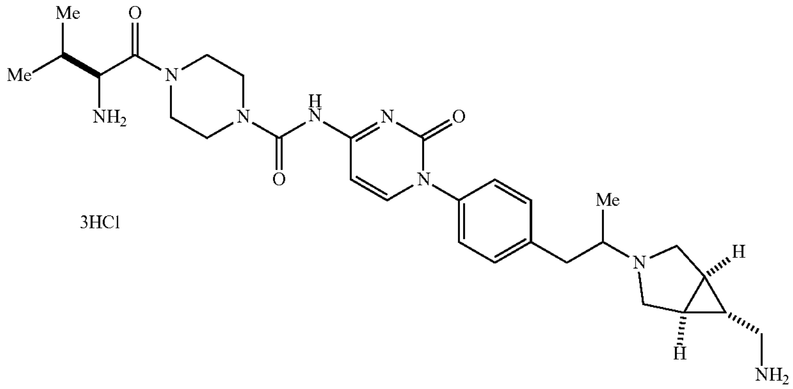 [SMILES: CC(C)[C@H](N)C(=O)N1CCN(C(=O)Nc2ccn(-c3ccc(CC(C)N4C[C@@H]5[C@@H](CN)[C@@H]5C4)cc3)c(=O)n2)CC1] 3HCl | 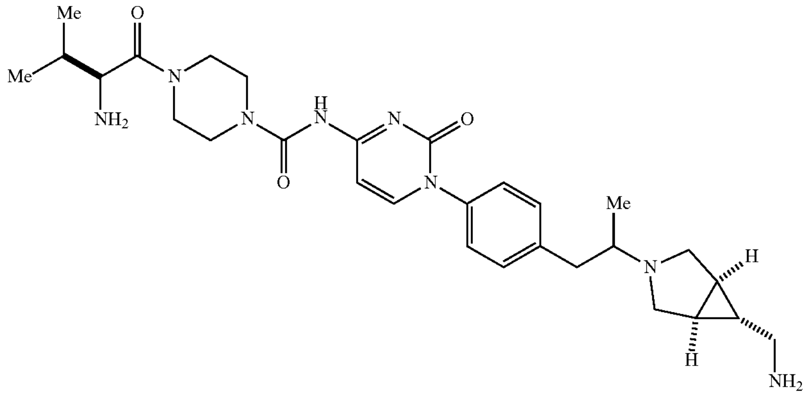 [SMILES: CC(C)[C@H](N)C(=O)N1CCN(C(=O)Nc2ccn(-c3ccc(CC(C)N4C[C@@H]5[C@@H](CN)[C@@H]5C4)cc3)c(=O)n2)CC1] |

TABLE 10-continued
| Compounds of Formula I Continued | | |
|---|---|---|
| No. | Salt Structure | Free Base Structure |
| 224 | 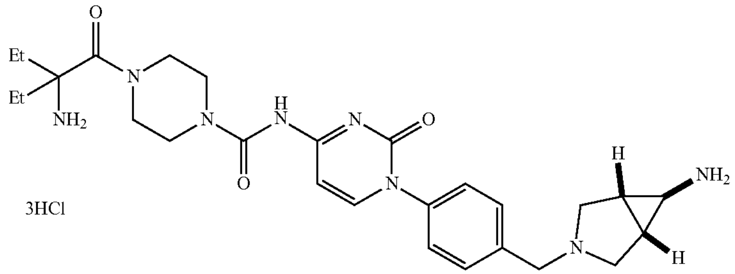 [SMILES: CCC(N)(CC)C(=O)N1CCN(C(=O)Nc2ccn(-c3ccc(CN4C[C@@H]5[C@@H](N)[C@@H]5C4)cc3)c(=O)n2)CC1] 3HCl | 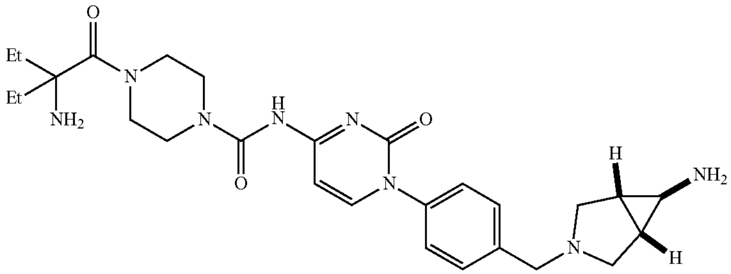 [SMILES: CCC(N)(CC)C(=O)N1CCN(C(=O)Nc2ccn(-c3ccc(CN4C[C@@H]5[C@@H](N)[C@@H]5C4)cc3)c(=O)n2)CC1] |
| 225 | 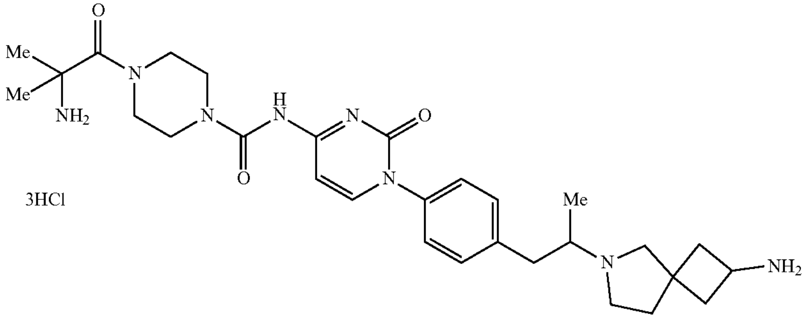 [SMILES: CC(Cc1ccc(-n2ccc(NC(=O)N3CCN(C(=O)C(C)(C)N)CC3)nc2=O)cc1)N1CCC2(CC(N)C2)C1] 3HCl | 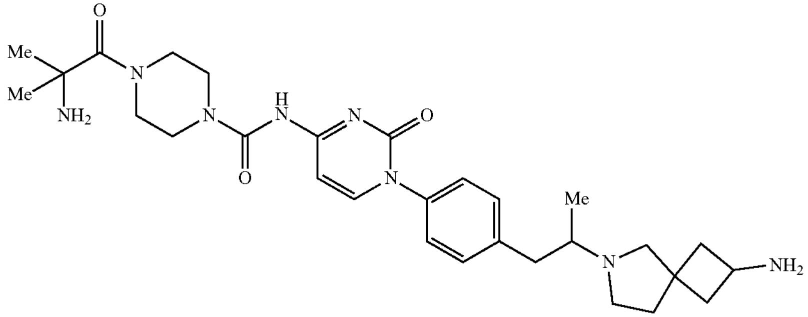 [SMILES: CC(Cc1ccc(-n2ccc(NC(=O)N3CCN(C(=O)C(C)(C)N)CC3)nc2=O)cc1)N1CCC2(CC(N)C2)C1] |
| 226 | 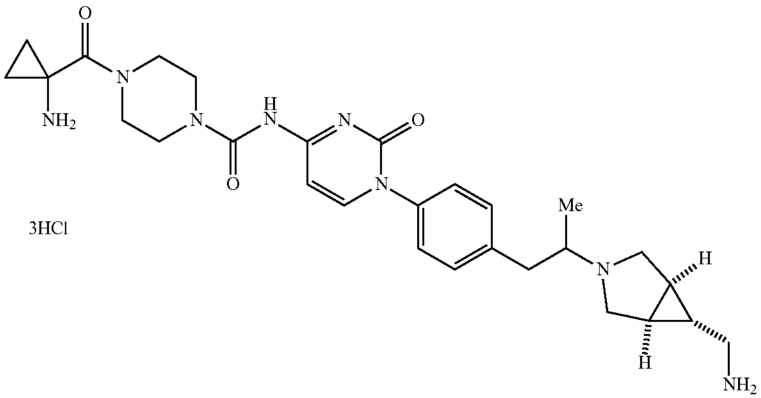 [SMILES: CC(Cc1ccc(-n2ccc(NC(=O)N3CCN(C(=O)C4(N)CC4)CC3)nc2=O)cc1)N1C[C@@H]2[C@@H](CN)[C@@H]2C1] 3HCl | 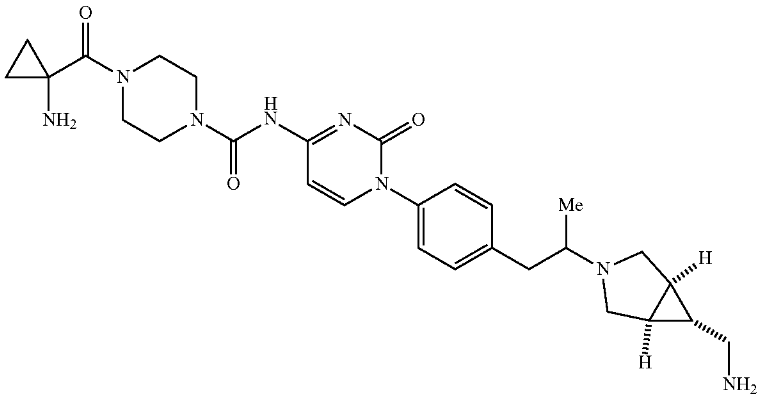 [SMILES: CC(Cc1ccc(-n2ccc(NC(=O)N3CCN(C(=O)C4(N)CC4)CC3)nc2=O)cc1)N1C[C@@H]2[C@@H](CN)[C@@H]2C1] |

TABLE 10-continued
| Compounds of Formula I Continued | | |
|---|---|---|
| No. | Salt Structure | Free Base Structure |
| 227 | 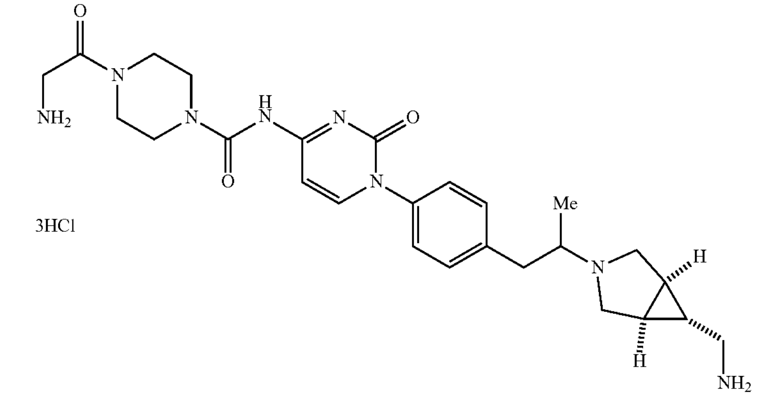 [SMILES: CC(Cc1ccc(-n2ccc(NC(=O)N3CCN(C(=O)CN)CC3)nc2=O)cc1)N1C[C@@H]2[C@@H](CN)[C@@H]2C1] 3HCl | 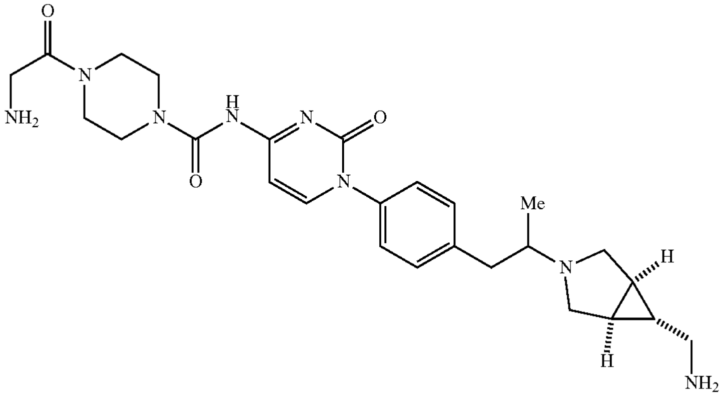 [SMILES: CC(Cc1ccc(-n2ccc(NC(=O)N3CCN(C(=O)CN)CC3)nc2=O)cc1)N1C[C@@H]2[C@@H](CN)[C@@H]2C1] |
| 228 | 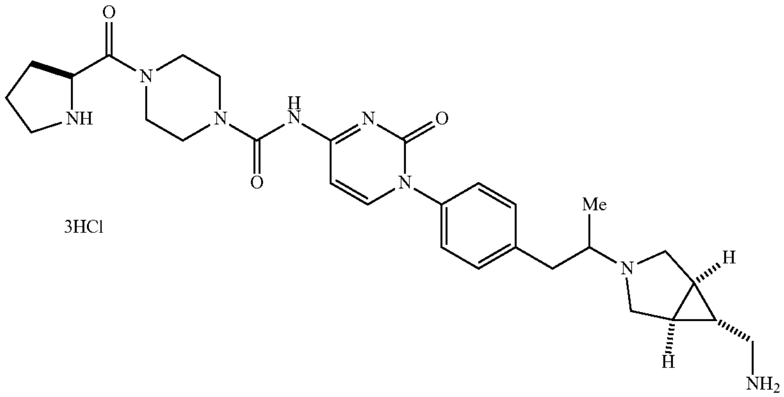 [SMILES: CC(Cc1ccc(-n2ccc(NC(=O)N3CCN(C(=O)[C@@H]4CCCN4)CC3)nc2=O)cc1)N1C[C@@H]2[C@@H](CN)[C@@H]2C1] 3HCl | 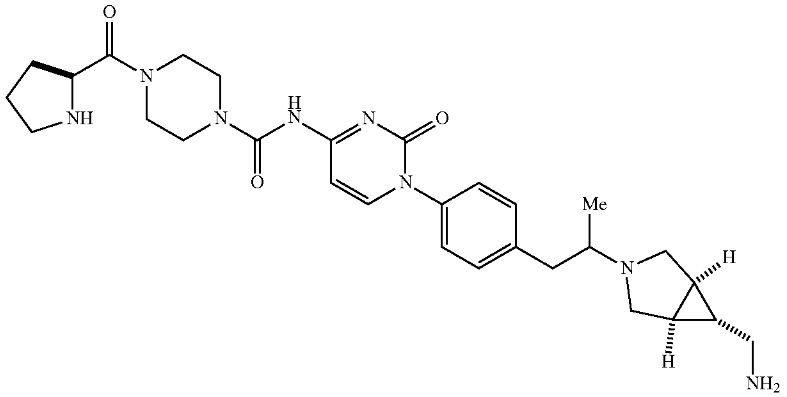 [SMILES: CC(Cc1ccc(-n2ccc(NC(=O)N3CCN(C(=O)[C@@H]4CCCN4)CC3)nc2=O)cc1)N1C[C@@H]2[C@@H](CN)[C@@H]2C1] |

TABLE 10-continued
| Compounds of Formula I Continued | | |
|---|---|---|
| No. | Salt Structure | Free Base Structure |
| 229 | 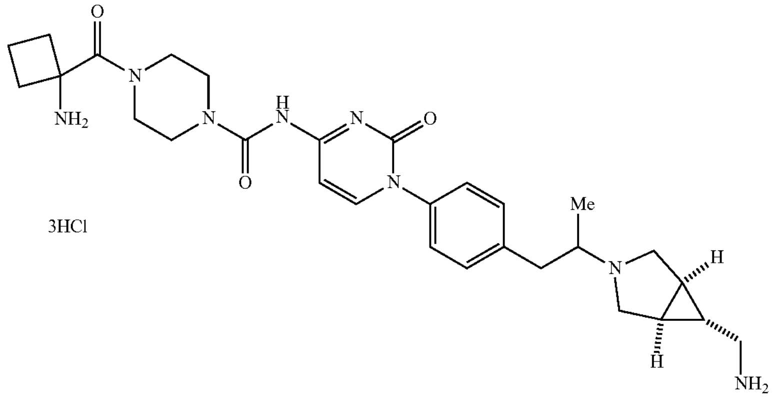 [SMILES: CC(Cc1ccc(-n2ccc(NC(=O)N3CCN(C(=O)C4(N)CCC4)CC3)nc2=O)cc1)N1C[C@@H]2[C@@H](CN)[C@@H]2C1] 3HCl | 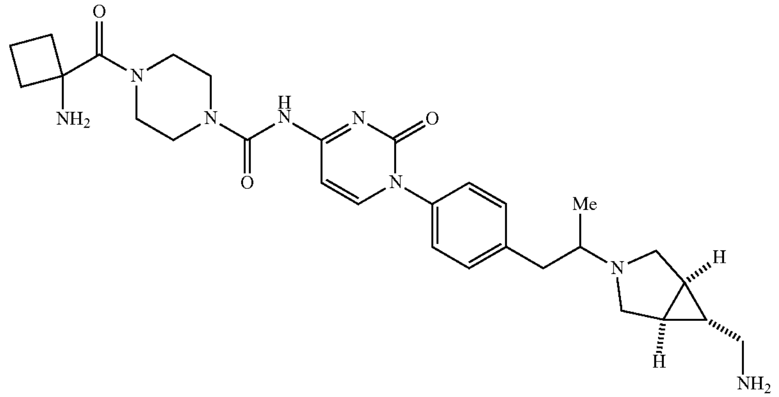 [SMILES: CC(Cc1ccc(-n2ccc(NC(=O)N3CCN(C(=O)C4(N)CCC4)CC3)nc2=O)cc1)N1C[C@@H]2[C@@H](CN)[C@@H]2C1] |
| 230 | 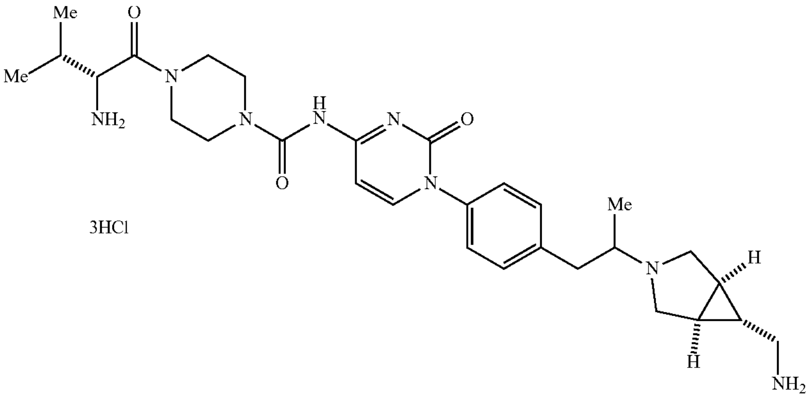 [SMILES: CC(C)[C@@H](N)C(=O)N1CCN(C(=O)Nc2ccn(-c3ccc(CC(C)N4C[C@@H]5[C@@H](CN)[C@@H]5C4)cc3)c(=O)n2)CC1] 3HCl | 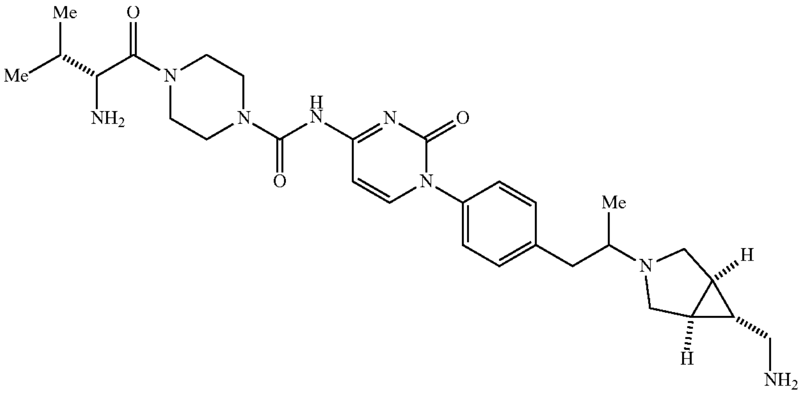 [SMILES: CC(C)[C@@H](N)C(=O)N1CCN(C(=O)Nc2ccn(-c3ccc(CC(C)N4C[C@@H]5[C@@H](CN)[C@@H]5C4)cc3)c(=O)n2)CC1] |

TABLE 10-continued
| Compounds of Formula I Continued | | |
|---|---|---|
| No. | Salt Structure | Free Base Structure |
| 231 | 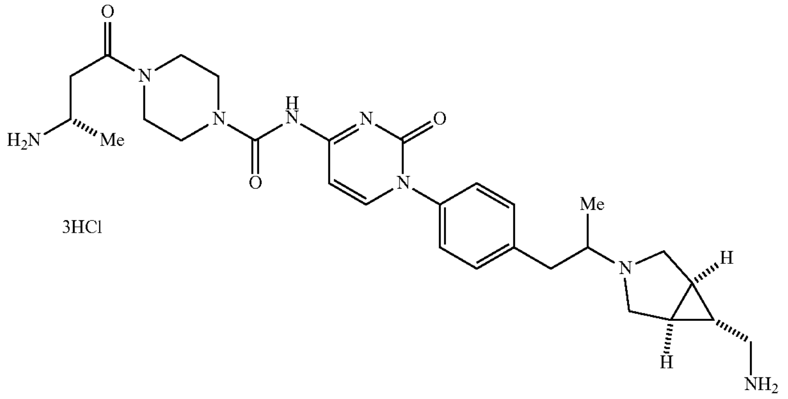 [SMILES: CC(Cc1ccc(-n2ccc(NC(=O)N3CCN(C(=O)C[C@H](C)N)CC3)nc2=O)cc1)N1C[C@@H]2[C@@H](CN)[C@@H]2C1] 3HCl | 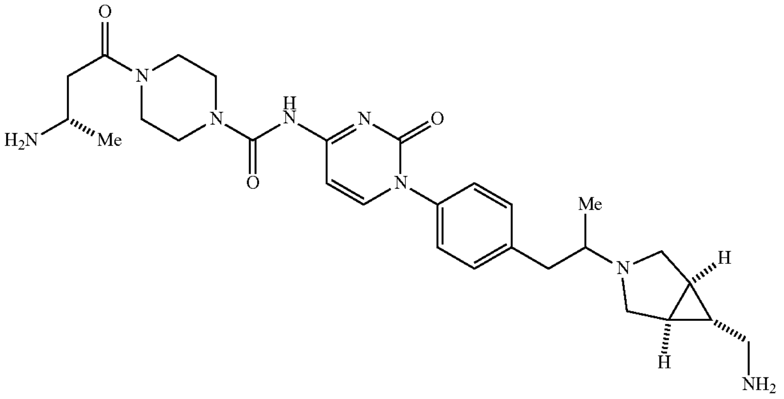 |
| 232 | 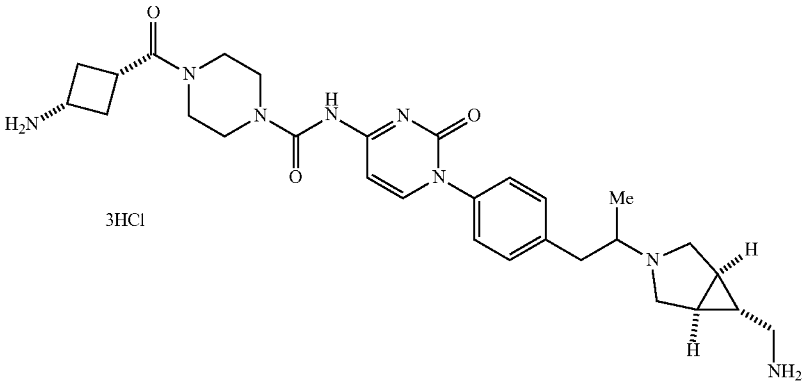 [SMILES: CC(Cc1ccc(-n2ccc(NC(=O)N3CCN(C(=O)[C@H]4C[C@@H](N)C4)CC3)nc2=O)cc1)N1C[C@@H]2[C@@H](CN)[C@@H]2C1] 3HCl | 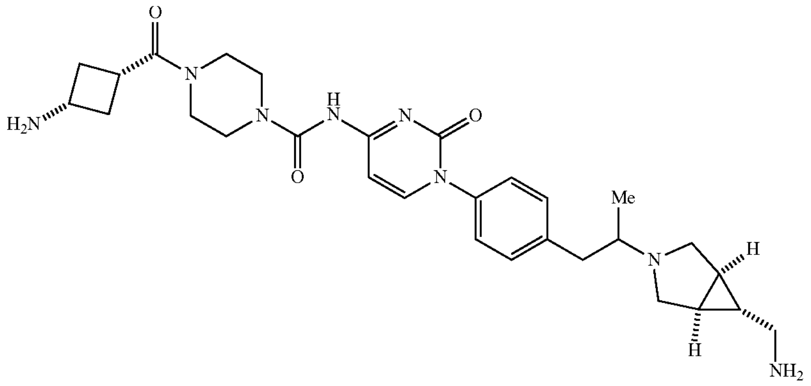 [SMILES: CC(Cc1ccc(-n2ccc(NC(=O)N3CCN(C(=O)[C@H]4C[C@@H](N)C4)CC3)nc2=O)cc1)N1C[C@@H]2[C@@H](CN)[C@@H]2C1] |

TABLE 10-continued
| Compounds of Formula I Continued | | |
|---|---|---|
| No. | Salt Structure | Free Base Structure |
| 233 | 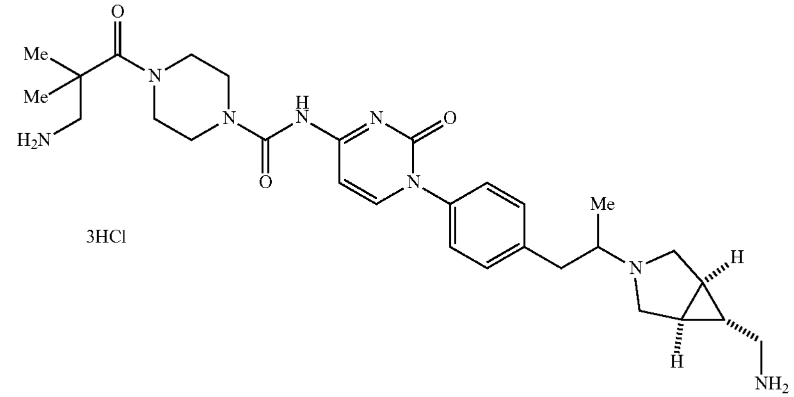 [SMILES: CC(Cc1ccc(-n2ccc(NC(=O)N3CCN(C(=O)C(C)(C)CN)CC3)nc2=O)cc1)N1C[C@@H]2[C@@H](CN)[C@@H]2C1] 3HCl | 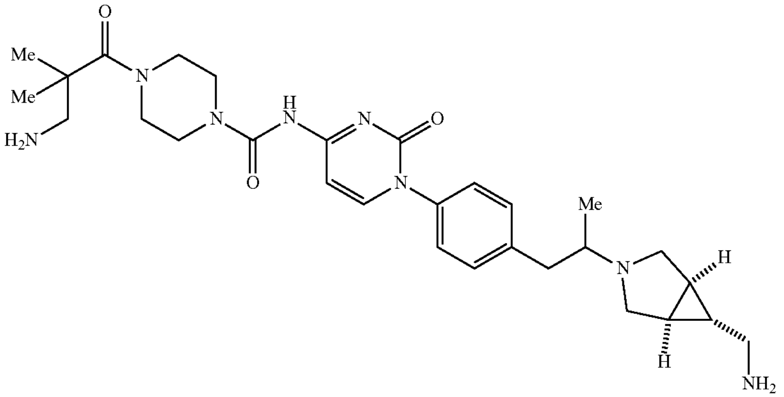 [SMILES: CC(Cc1ccc(-n2ccc(NC(=O)N3CCN(C(=O)C(C)(C)CN)CC3)nc2=O)cc1)N1C[C@@H]2[C@@H](CN)[C@@H]2C1] |
| 234 | 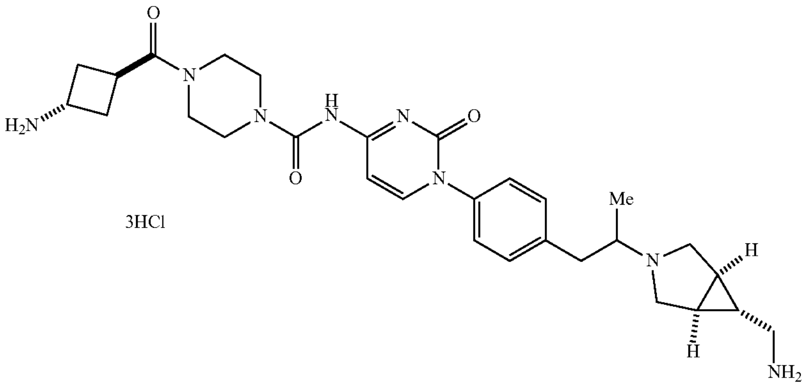 [SMILES: CC(Cc1ccc(-n2ccc(NC(=O)N3CCN(C(=O)[C@H]4C[C@H](N)C4)CC3)nc2=O)cc1)N1C[C@@H]2[C@@H](CN)[C@@H]2C1] 3HCl | 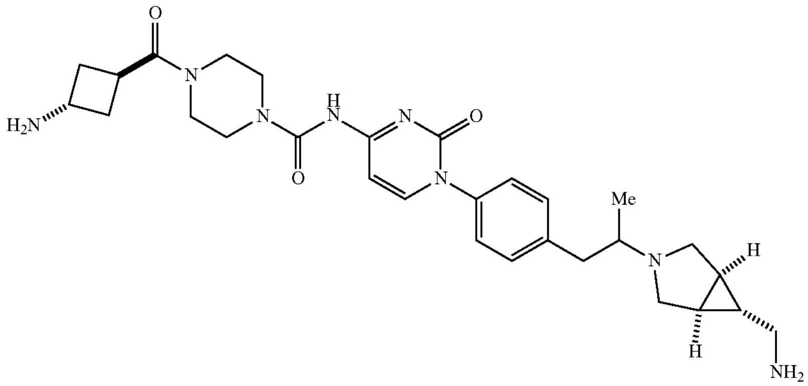 [SMILES: CC(Cc1ccc(-n2ccc(NC(=O)N3CCN(C(=O)[C@H]4C[C@H](N)C4)CC3)nc2=O)cc1)N1C[C@@H]2[C@@H](CN)[C@@H]2C1] |

TABLE 10-continued
| Compounds of Formula I Continued | | |
|---|---|---|
| No. | Salt Structure | Free Base Structure |
| 235 | 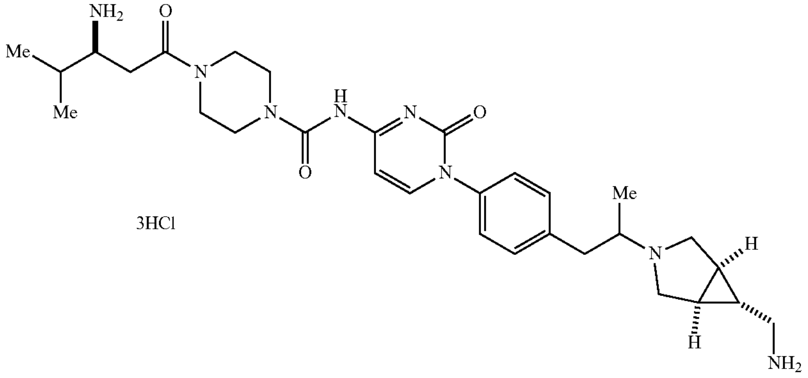 [SMILES: CC(C)[C@@H](N)CC(=O)N1CCN(C(=O)Nc2ccn(-c3ccc(CC(C)N4C[C@@H]5[C@@H](CN)[C@@H]5C4)cc3)c(=O)n2)CC1] 3HCl | 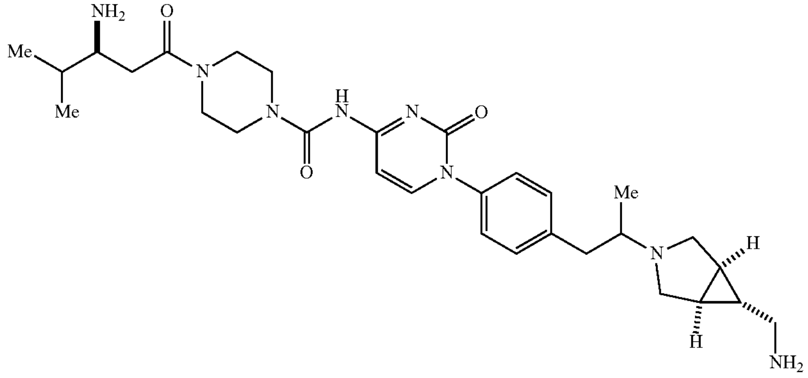 [SMILES: CC(C)[C@@H](N)CC(=O)N1CCN(C(=O)Nc2ccn(-c3ccc(CC(C)N4C[C@@H]5[C@@H](CN)[C@@H]5C4)cc3)c(=O)n2)CC1] |
| 236 | 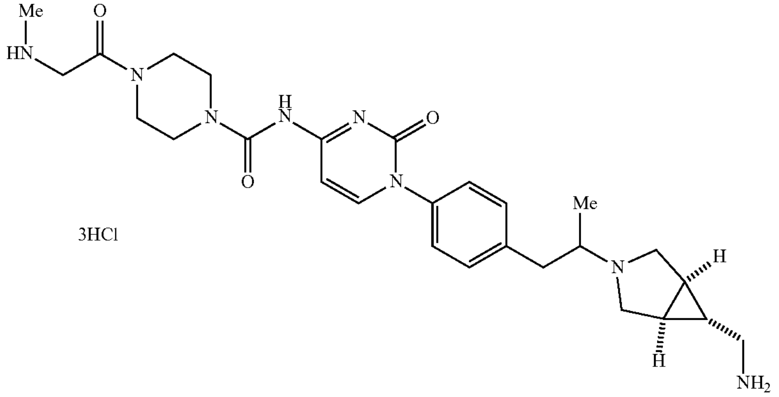 [SMILES: CNCC(=O)N1CCN(C(=O)Nc2ccn(-c3ccc(CC(C)N4C[C@@H]5[C@@H](CN)[C@@H]5C4)cc3)c(=O)n2)CC1] 3HCl | 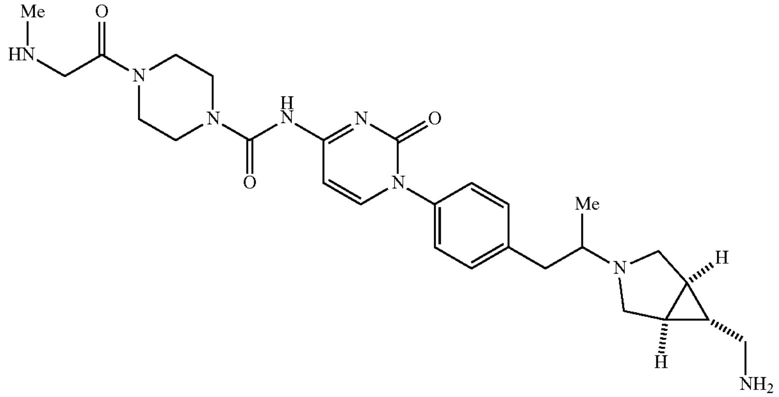 [SMILES: CNCC(=O)N1CCN(C(=O)Nc2ccn(-c3ccc(CC(C)N4C[C@@H]5[C@@H](CN)[C@@H]5C4)cc3)c(=O)n2)CC1] |

TABLE 10-continued
| Compounds of Formula I Continued | | |
|---|---|---|
| No. | Salt Structure | Free Base Structure |
| 237 | 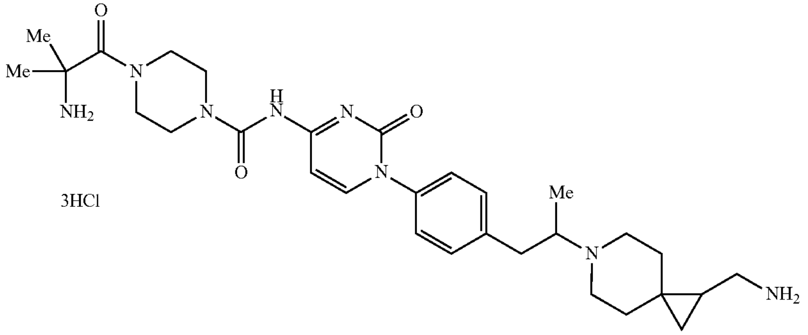 [SMILES: CC(Cc1ccc(-n2ccc(NC(=O)N3CCN(C(=O)C(C)(C)N)CC3)nc2=O)cc1)N1CCC2(CC1)CC2CN] 3HCl | 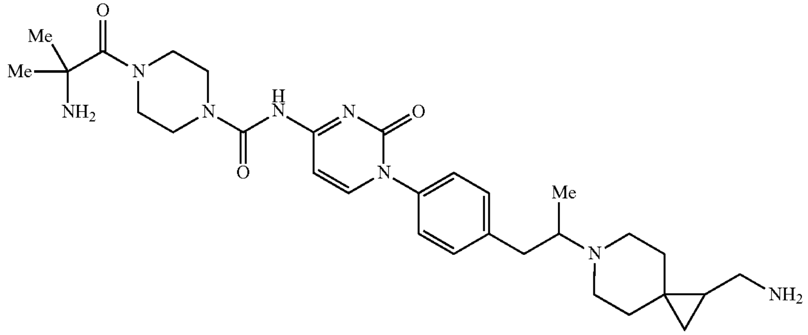 [SMILES: CC(Cc1ccc(-n2ccc(NC(=O)N3CCN(C(=O)C(C)(C)N)CC3)nc2=O)cc1)N1CCC2(CC1)CC2CN] |
| 238 | 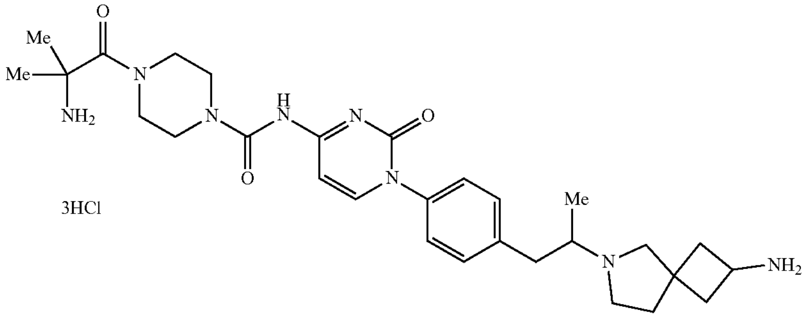 [SMILES: CC(Cc1ccc(-n2ccc(NC(=O)N3CCN(C(=O)C(C)(C)N)CC3)nc2=O)cc1)N1CCC2(CC(N)C2)C1] 3HCl | 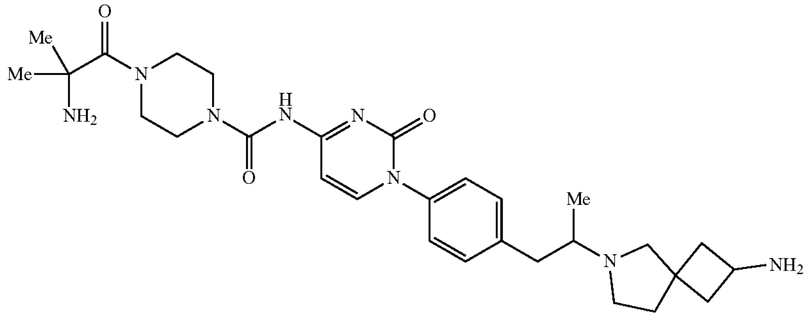 [SMILES: CC(Cc1ccc(-n2ccc(NC(=O)N3CCN(C(=O)C(C)(C)N)CC3)nc2=O)cc1)N1CCC2(CC(N)C2)C1] |
| 239 | 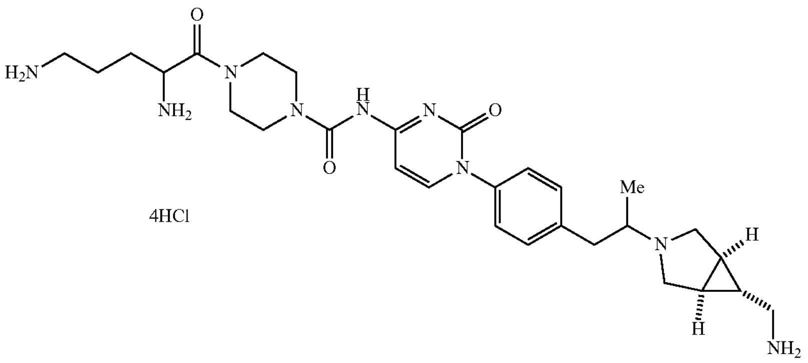 [SMILES: CC(Cc1ccc(-n2ccc(NC(=O)N3CCN(C(=O)C(N)CCCN)CC3)nc2=O)cc1)N1C[C@@H]2[C@@H](CN)[C@@H]2C1] 4HCl | 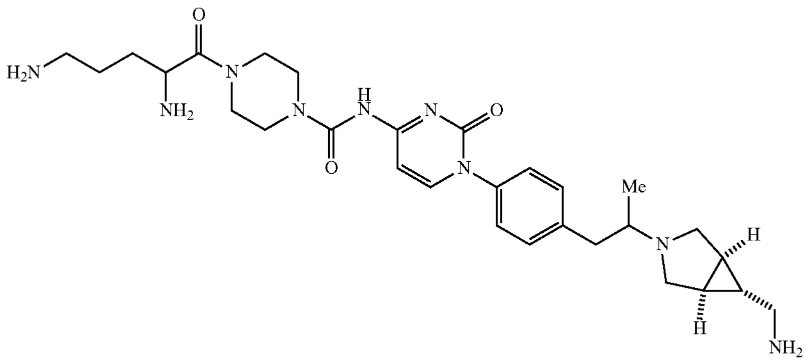 [SMILES: CC(Cc1ccc(-n2ccc(NC(=O)N3CCN(C(=O)C(N)CCCN)CC3)nc2=O)cc1)N1C[C@@H]2[C@@H](CN)[C@@H]2C1] |

TABLE 10-continued
| Compounds of Formula I Continued | | |
|---|---|---|
| No. | Salt Structure | Free Base Structure |
| 240 | 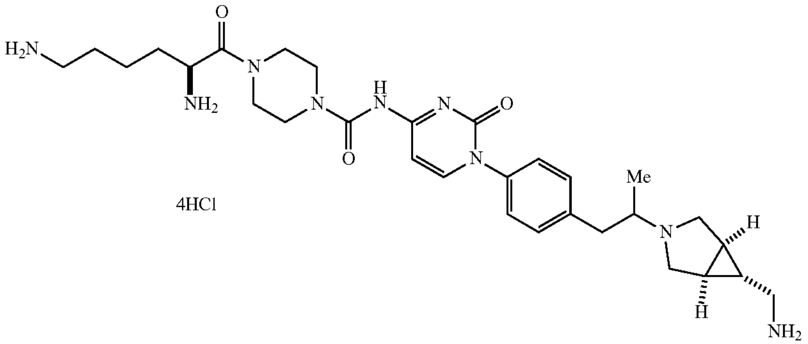 [SMILES: CC(Cc1ccc(-n2ccc(NC(=O)N3CCN(C(=O)[C@@H](N)CCCCN)CC3)nc2=O)cc1)N1C[C@@H]2[C@@H](CN)[C@@H]2C1] 4HCl | 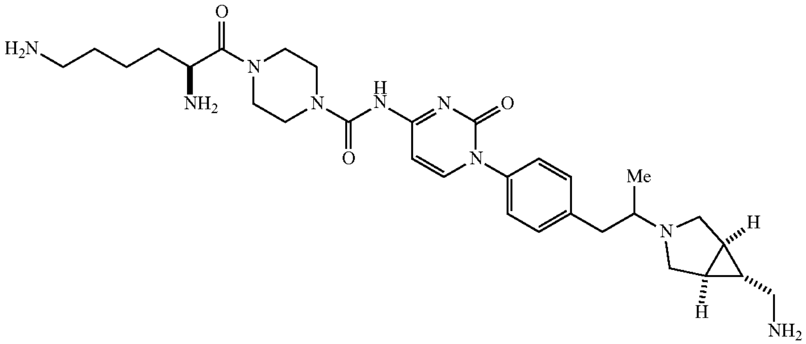 [SMILES: CC(Cc1ccc(-n2ccc(NC(=O)N3CCN(C(=O)[C@@H](N)CCCCN)CC3)nc2=O)cc1)N1C[C@@H]2[C@@H](CN)[C@@H]2C1] |
| 241 | 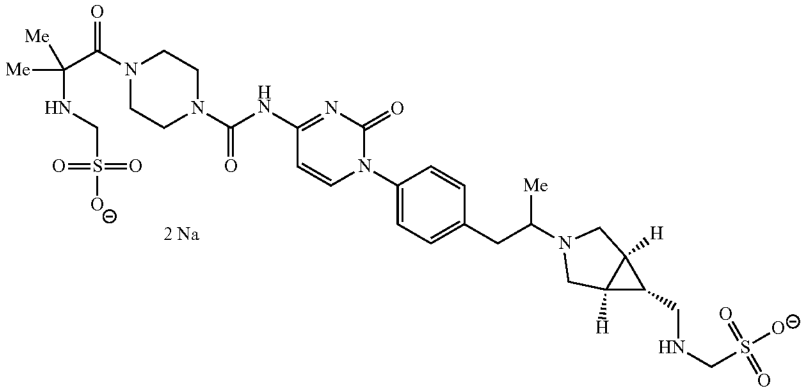 [SMILES: CC(Cc1ccc(-n2ccc(NC(=O)N3CCN(C(=O)C(C)(C)NCS(=O)(=O)[O-])CC3)nc2=O)cc1)N1C[C@@H]2[C@@H](CNCS(=O)(=O)[O-])[C@@H]2C1] 2 Na | 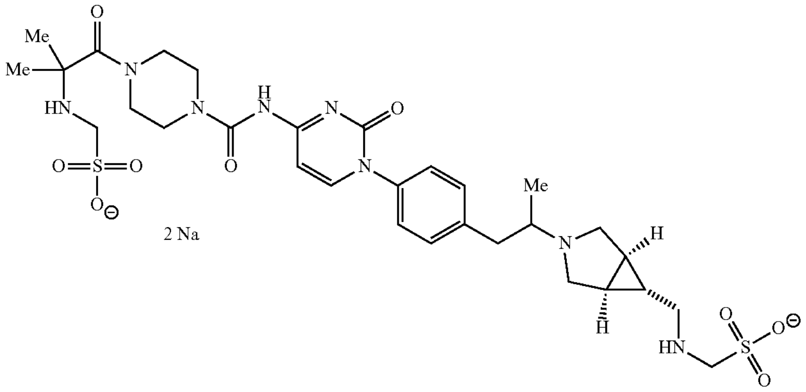 [SMILES: CC(Cc1ccc(-n2ccc(NC(=O)N3CCN(C(=O)C(C)(C)NCS(=O)(=O)[O-])CC3)nc2=O)cc1)N1C[C@@H]2[C@@H](CNCS(=O)(=O)[O-])[C@@H]2C1] 2 Na |

TABLE 10-continued
| Compounds of Formula I Continued | | |
|---|---|---|
| No. | Salt Structure | Free Base Structure |
| 242 | 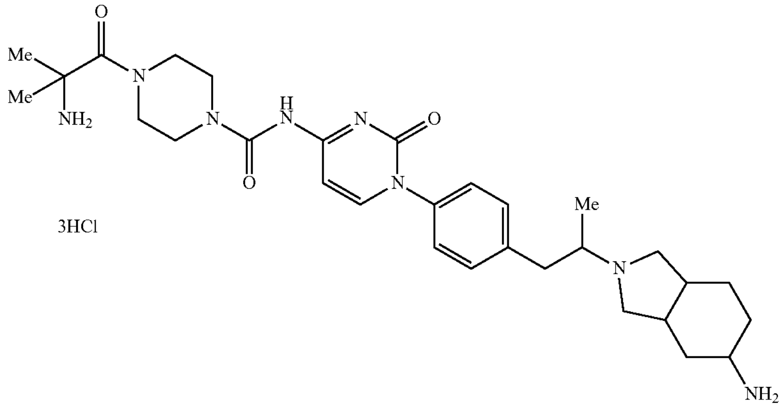 3HCl Diastereomer-1 | 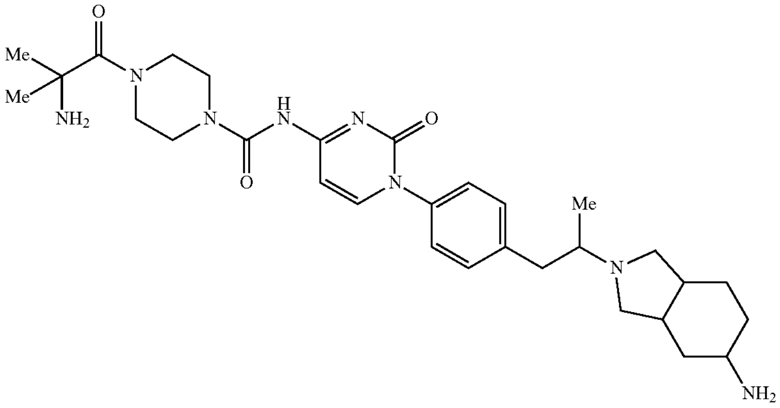 Diastereomer-1 |
| 243 | 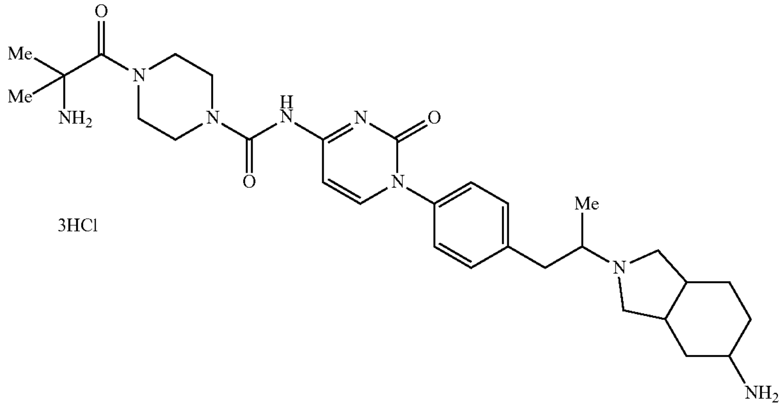 3HCl Diastereomer-2 | 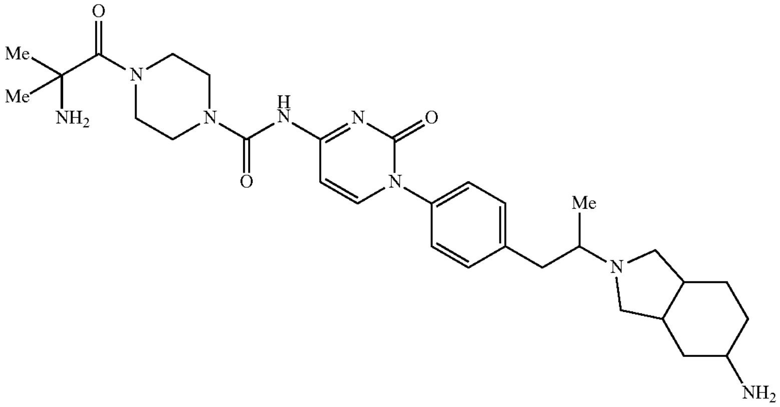 Diastereomer-2 |

TABLE 10-continued
| Compounds of Formula I Continued | | |
|---|---|---|
| No. | Salt Structure | Free Base Structure |
| 244 | 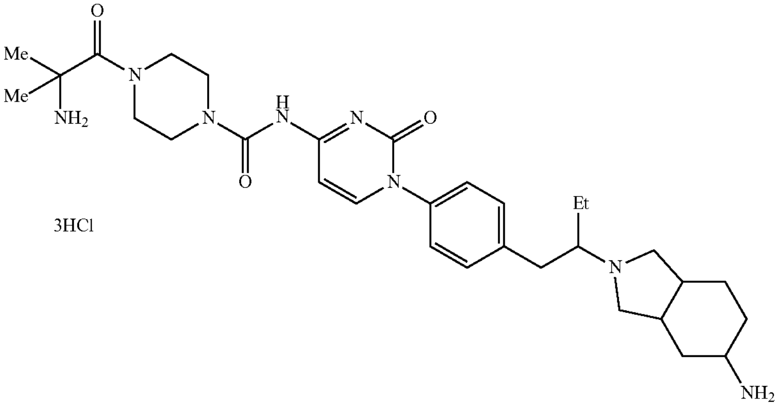 3HCl Diastereomer-1 | 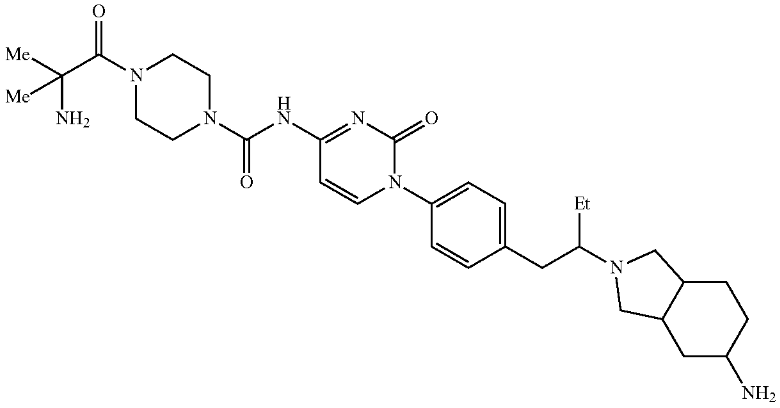 Diastereomer-1 |
| 245 | 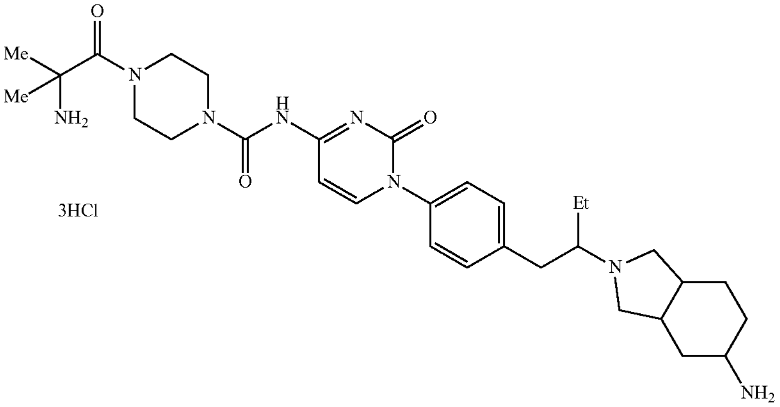 3HCl Diastereomer-2 | 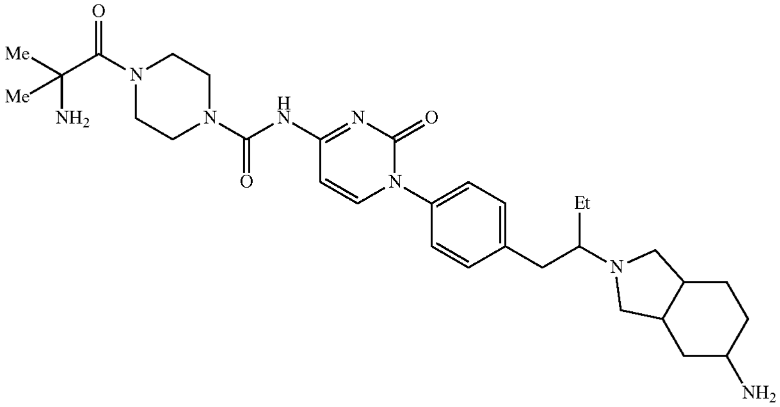 Diastereomer-2 |

TABLE 10-continued
| Compounds of Formula I Continued | | |
|---|---|---|
| No. | Salt Structure | Free Base Structure |
| 246 | 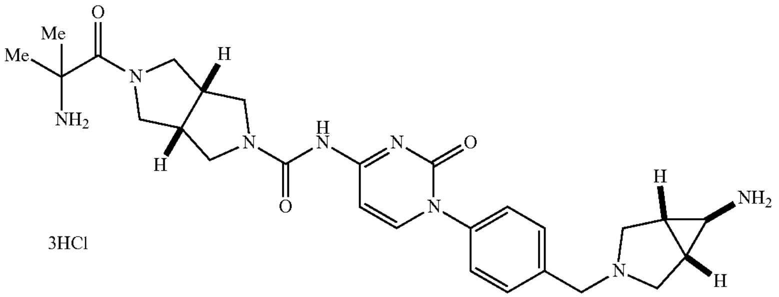 [SMILES: CC(C)(N)C(=O)N1C[C@H]2CN(C(=O)Nc3ccn(-c4ccc(CN5C[C@@H]6[C@@H](N)[C@@H]6C5)cc4)c(=O)n3)C[C@H]2C1] 3HCl | 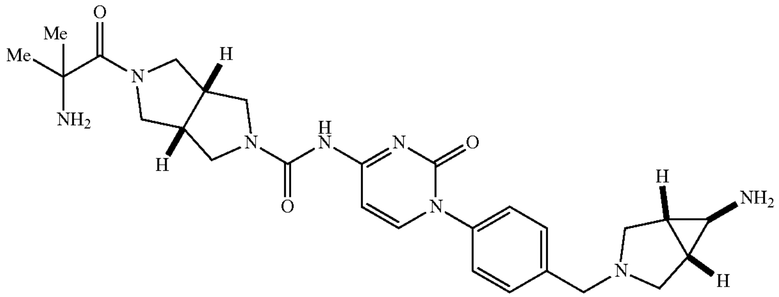 [SMILES: CC(C)(N)C(=O)N1C[C@H]2CN(C(=O)Nc3ccn(-c4ccc(CN5C[C@@H]6[C@@H](N)[C@@H]6C5)cc4)c(=O)n3)C[C@H]2C1] |
| 247 | 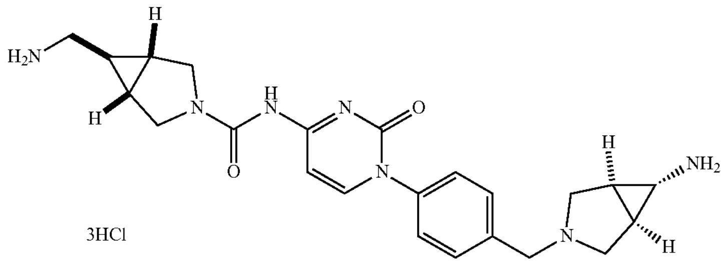 [SMILES: NC[C@@H]1[C@H]2CN(C(=O)Nc3ccn(-c4ccc(CN5C[C@@H]6[C@@H](N)[C@@H]6C5)cc4)c(=O)n3)C[C@@H]12] 3HCl | 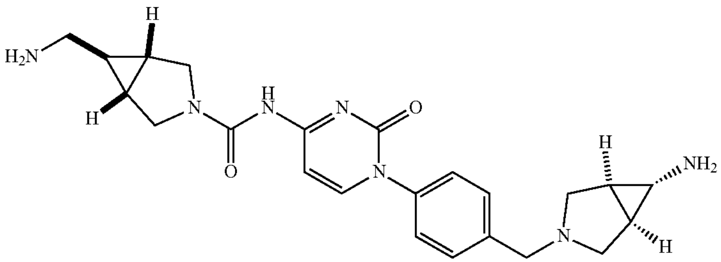 [SMILES: NC[C@@H]1[C@H]2CN(C(=O)Nc3ccn(-c4ccc(CN5C[C@@H]6[C@@H](N)[C@@H]6C5)cc4)c(=O)n3)C[C@@H]12] |
| 248 | 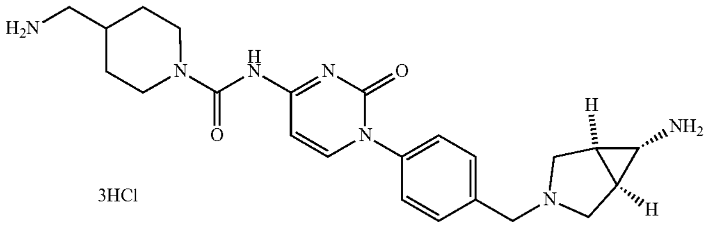 [SMILES: NCC1CCN(C(=O)Nc2ccn(-c3ccc(CN4C[C@@H]5[C@@H](N)[C@@H]5C4)cc3)c(=O)n2)CC1] 3HCl | 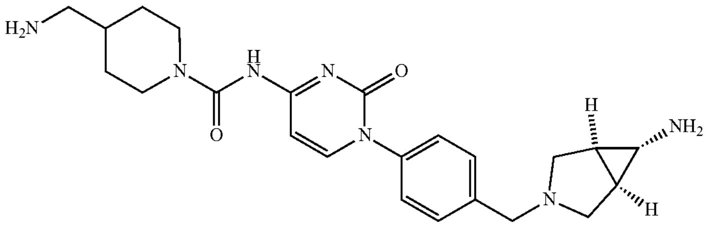 [SMILES: NCC1CCN(C(=O)Nc2ccn(-c3ccc(CN4C[C@@H]5[C@@H](N)[C@@H]5C4)cc3)c(=O)n2)CC1] |

TABLE 10-continued
| Compounds of Formula I Continued | | |
|---|---|---|
| No. | Salt Structure | Free Base Structure |
| 249 | 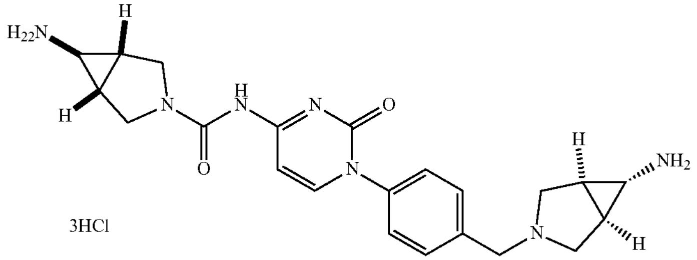 3HCl | 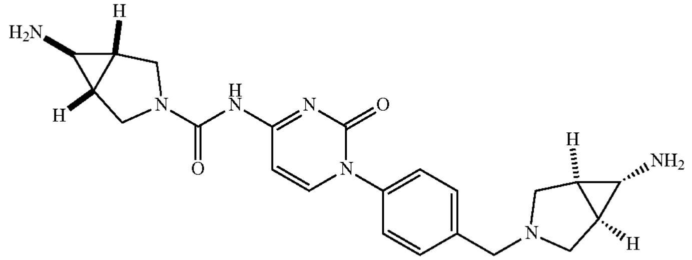 [SMILES: N[C@@H]1[C@H]2CN(Cc3ccc(-n4ccc(NC(=O)N5C[C@@H]6[C@@H](N)[C@@H]6C5)nc4=O)cc3)C[C@@H]12] |
| 250 | 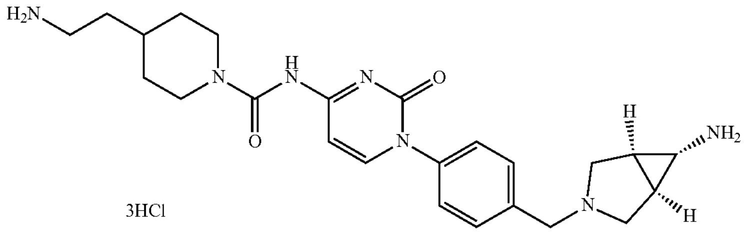 [SMILES: NCCC1CCN(C(=O)Nc2ccn(-c3ccc(CN4C[C@@H]5[C@@H](N)[C@@H]5C4)cc3)c(=O)n2)CC1] 3HCl | 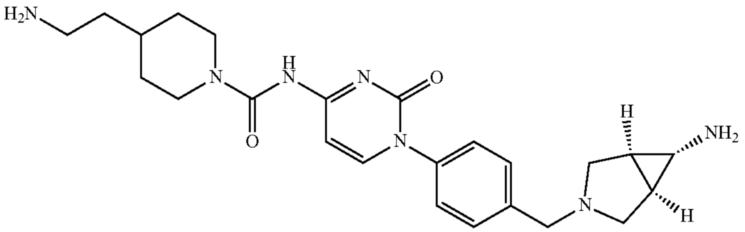 [SMILES: NCCC1CCN(C(=O)Nc2ccn(-c3ccc(CN4C[C@@H]5[C@@H](N)[C@@H]5C4)cc3)c(=O)n2)CC1] |
| 251 | 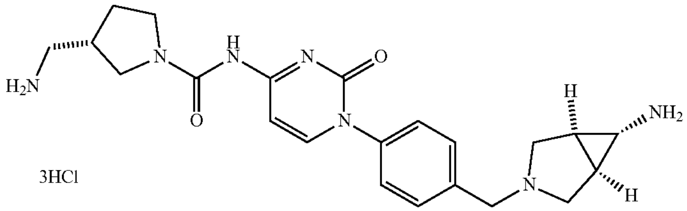 [SMILES: NC[C@@H]1CCN(C(=O)Nc2ccn(-c3ccc(CN4C[C@@H]5[C@@H](N)[C@@H]5C4)cc3)c(=O)n2)C1] 3HCl | 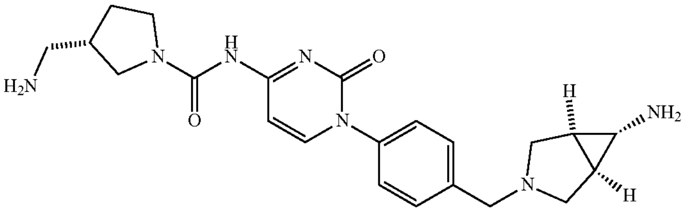 [SMILES: NC[C@@H]1CCN(C(=O)Nc2ccn(-c3ccc(CN4C[C@@H]5[C@@H](N)[C@@H]5C4)cc3)c(=O)n2)C1] |
| 252 | 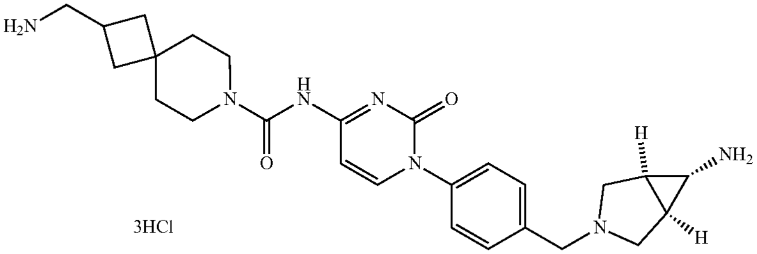 [SMILES: NCC1CC2(CCN(C(=O)Nc3ccn(-c4ccc(CN5C[C@@H]6[C@@H](N)[C@@H]6C5)cc4)c(=O)n3)CC2)C1] 3HCl | 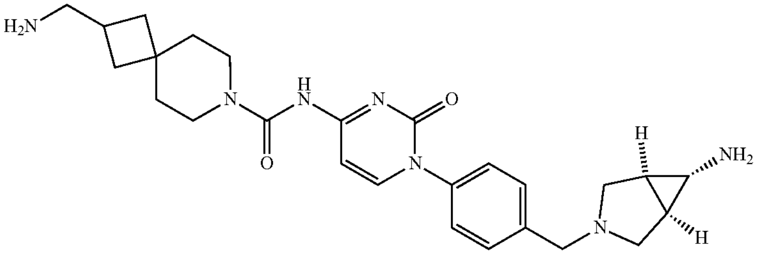 [SMILES: NCC1CC2(CCN(C(=O)Nc3ccn(-c4ccc(CN5C[C@@H]6[C@@H](N)[C@@H]6C5)cc4)c(=O)n3)CC2)C1] |

TABLE 10-continued
| Compounds of Formula I Continued | | |
|---|---|---|
| No. | Salt Structure | Free Base Structure |
| 253 | 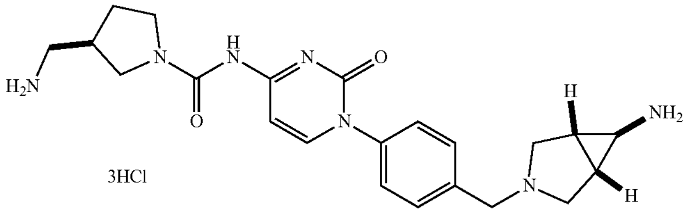 [SMILES: NC[C@H]1CCN(C(=O)Nc2ccn(-c3ccc(CN4C[C@@H]5[C@@H](N)[C@@H]5C4)cc3)c(=O)n2)C1] 3HCl | 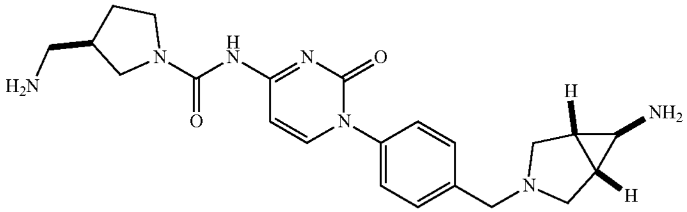 [SMILES: NC[C@H]1CCN(C(=O)Nc2ccn(-c3ccc(CN4C[C@@H]5[C@@H](N)[C@@H]5C4)cc3)c(=O)n2)C1] |
| 254 | 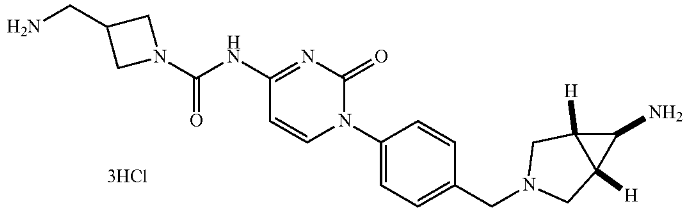 [SMILES: NCC1CN(C(=O)Nc2ccn(-c3ccc(CN4C[C@@H]5[C@@H](N)[C@@H]5C4)cc3)c(=O)n2)C1] 3HCl | 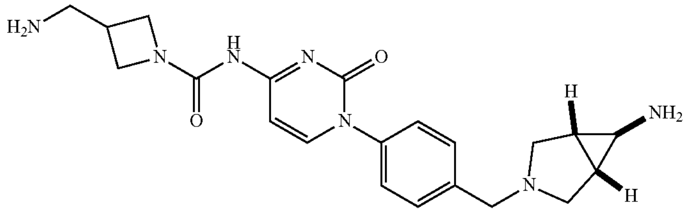 [SMILES: NCC1CN(C(=O)Nc2ccn(-c3ccc(CN4C[C@@H]5[C@@H](N)[C@@H]5C4)cc3)c(=O)n2)C1] |
| 255 | 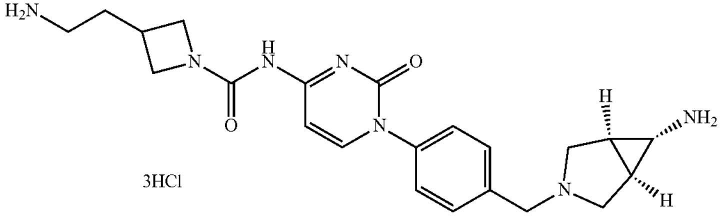 [SMILES: NCCC1CN(C(=O)Nc2ccn(-c3ccc(CN4C[C@@H]5[C@@H](N)[C@@H]5C4)cc3)c(=O)n2)C1] 3HCl | 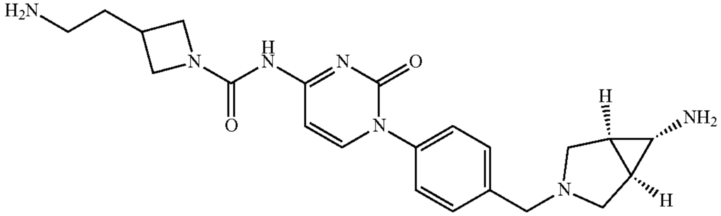 [SMILES: NCCC1CN(C(=O)Nc2ccn(-c3ccc(CN4C[C@@H]5[C@@H](N)[C@@H]5C4)cc3)c(=O)n2)C1] |

In another embodiment, the compound of formula I or a pharmaceutically acceptable salt thereof is selected from compounds listed in any one of Table 7, Table 8, table 9, and Table 10.

In another embodiment, the compound of formula IIA or IIB or a pharmaceutically acceptable salt thereof is selected from the compounds listed in Table 7.

In another embodiment, the compound of formula IIIA or IIIB or a pharmaceutically acceptable salt thereof is selected from the compounds listed in Table 8.

In another embodiment, the compound of formula IV or a pharmaceutically acceptable salt thereof is selected from the compounds listed in Table 9.

In another aspect, the disclosure provides a compound of formula V:

V

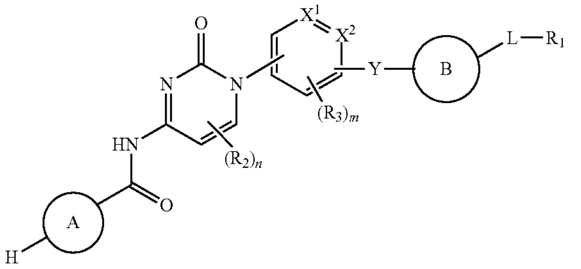

or a pharmaceutically acceptable salt thereof, wherein ring A, Z, $X^1$, $X^2$, $R_1R_2$, $R_3$, L, ring B, m, and n have the definitions as provided in the preceding paragraphs.

In another embodiment of the compound of formula V, ring A is

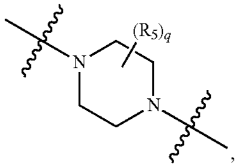

and $R_5$ and q have the definitions as provided in the preceding paragraphs.

In another embodiment, the compound of formula V is selected from the compounds as depicted in Table 11 below.

TABLE 11

| Compounds of Formula V |
|---|
| 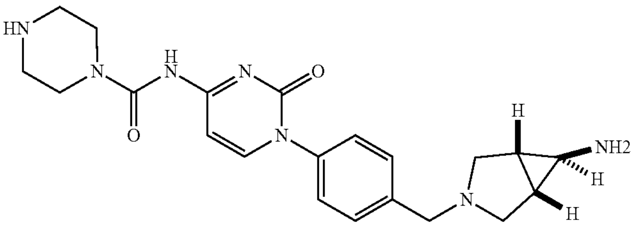 [SMILES: N[C@@H]1[C@H]2CN(Cc3ccc(-n4ccc(NC(=O)N5CCNCC5)nc4=O)cc3)C[C@@H]12] |
| 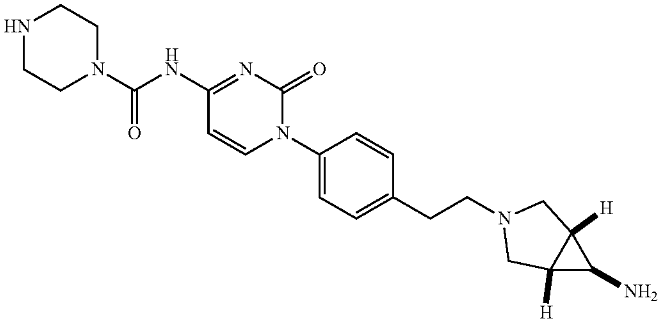 [SMILES: N[C@@H]1[C@H]2CN(CCc3ccc(-n4ccc(NC(=O)N5CCNCC5)nc4=O)cc3)C[C@@H]12] |
| 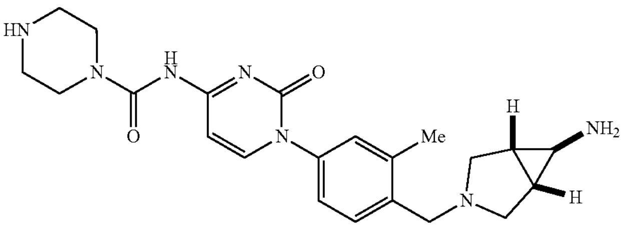 |

TABLE 11-continued
Compounds of Formula V
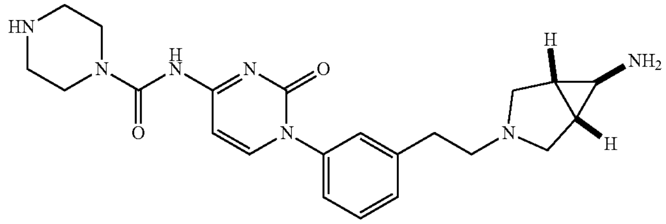 [SMILES: N[C@@H]1[C@H]2CN(CCc3cccc(-n4ccc(NC(=O)N5CCNCC5)nc4=O)c3)C[C@@H]12]
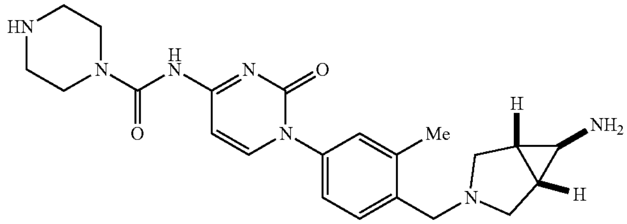 [SMILES: Cc1cc(-n2ccc(NC(=O)N3CCNCC3)nc2=O)ccc1CN1C[C@@H]2[C@@H](N)[C@@H]2C1]
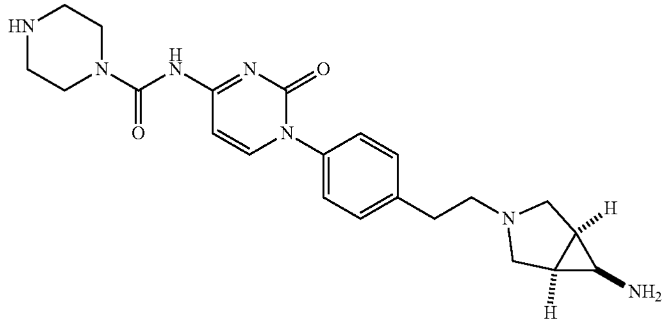 [SMILES: N[C@H]1[C@H]2CN(CCc3ccc(-n4ccc(NC(=O)N5CCNCC5)nc4=O)cc3)C[C@@H]12]
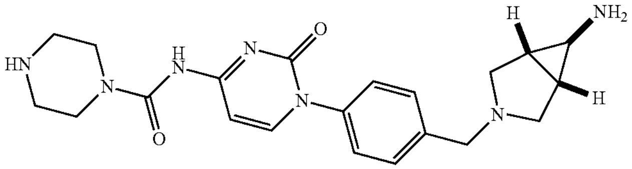 [SMILES: N[C@@H]1[C@H]2CN(Cc3ccc(-n4ccc(NC(=O)N5CCNCC5)nc4=O)cc3)C[C@@H]12]
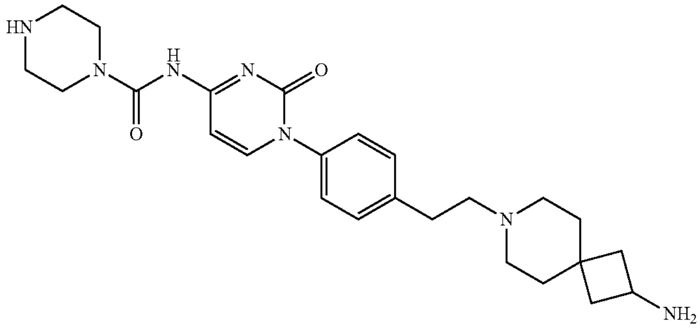 [SMILES: NC1CC2(CCN(CCc3ccc(-n4ccc(NC(=O)N5CCNCC5)nc4=O)cc3)CC2)C1]
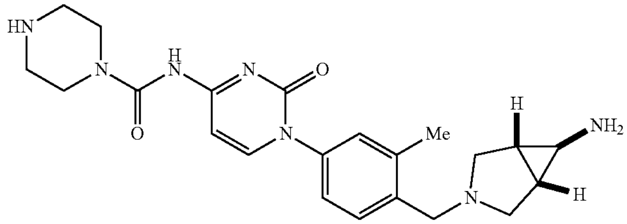 [SMILES: Cc1cc(-n2ccc(NC(=O)N3CCNCC3)nc2=O)ccc1CN1C[C@@H]2[C@@H](N)[C@@H]2C1]

TABLE 11-continued
| Compounds of Formula V |
|---|
| 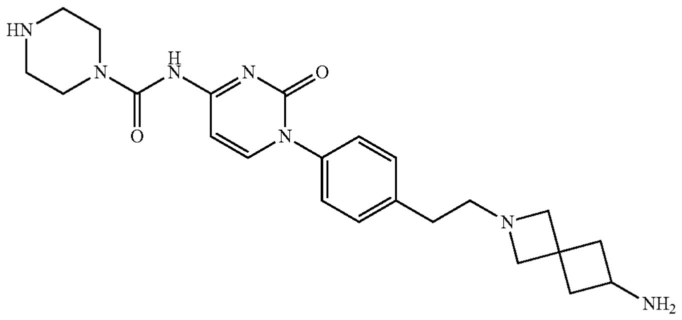 [SMILES: NC1CC2(C1)CN(CCc1ccc(-n3ccc(NC(=O)N4CCNCC4)nc3=O)cc1)C2] |
| 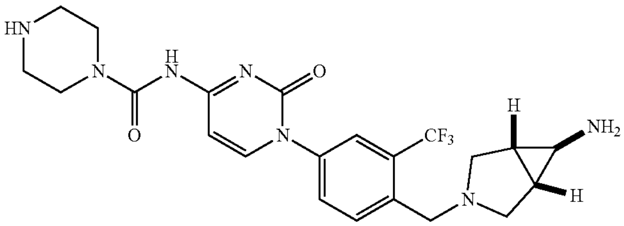 [SMILES: N[C@@H]1[C@H]2CN(Cc3ccc(-n4ccc(NC(=O)N5CCNCC5)nc4=O)cc3C(F)(F)F)C[C@@H]12] |
| 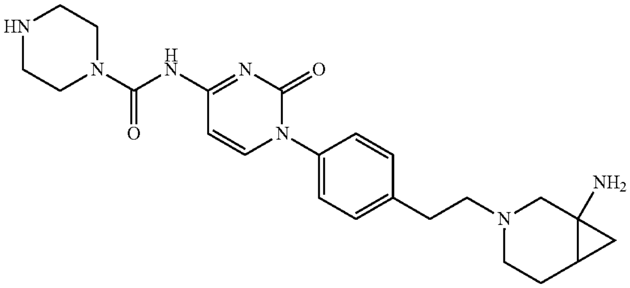 [SMILES: NC12CC1CCN(CCc1ccc(-n3ccc(NC(=O)N4CCNCC4)nc3=O)cc1)C2] |
| 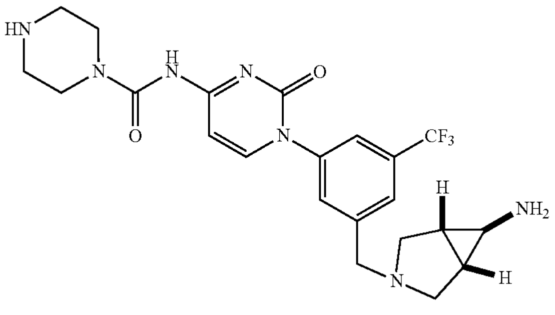 [SMILES: N[C@@H]1[C@H]2CN(Cc3cc(-n4ccc(NC(=O)N5CCNCC5)nc4=O)cc(C(F)(F)F)c3)C[C@@H]12] |
| 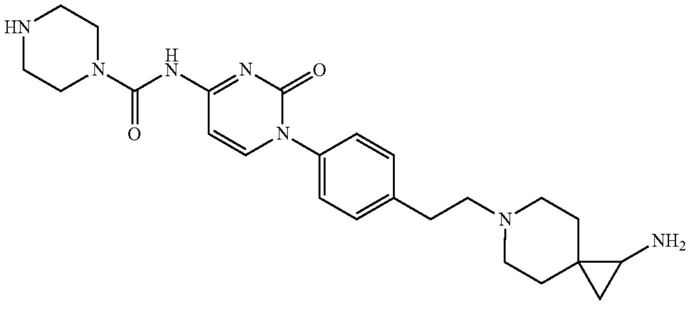 [SMILES: NC1CC12CCN(CCc1ccc(-n3ccc(NC(=O)N4CCNCC4)nc3=O)cc1)CC2] |

TABLE 11-continued
| Compounds of Formula V |
| --- |
| 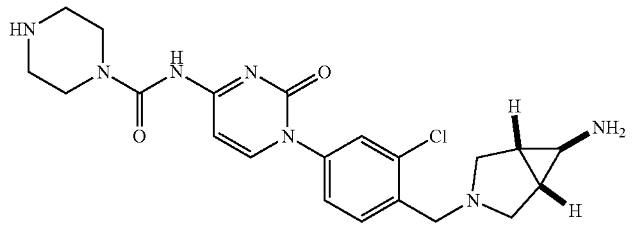 [SMILES: N[C@@H]1[C@H]2CN(Cc3ccc(-n4ccc(NC(=O)N5CCNCC5)nc4=O)cc3Cl)C[C@@H]12] |
| 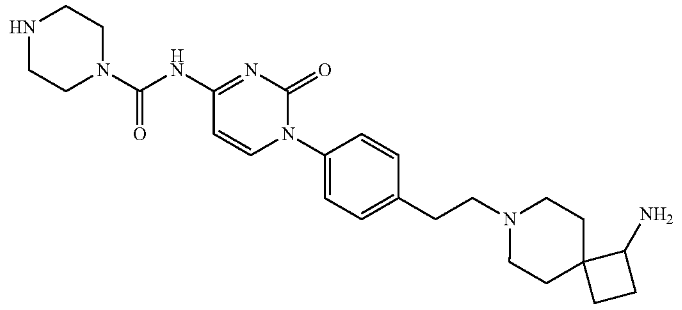 [SMILES: NC1CCC12CCN(CCc1ccc(-n3ccc(NC(=O)N4CCNCC4)nc3=O)cc1)CC2] |
| 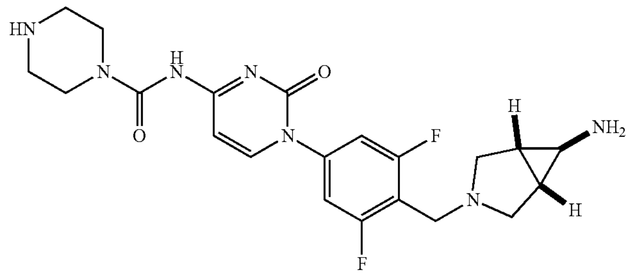 [SMILES: N[C@@H]1[C@H]2CN(Cc3c(F)cc(-n4ccc(NC(=O)N5CCNCC5)nc4=O)cc3F)C[C@@H]12] |
| 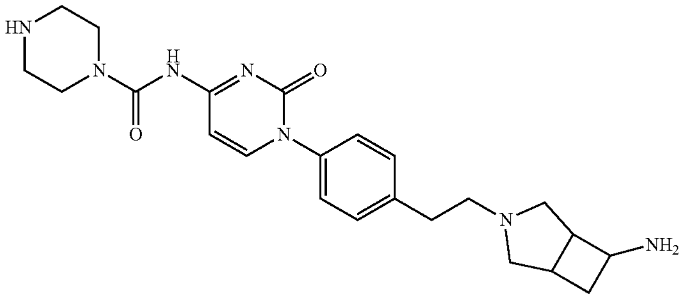 [SMILES: NC1CC2CN(CCc3ccc(-n4ccc(NC(=O)N5CCNCC5)nc4=O)cc3)CC12] |
| 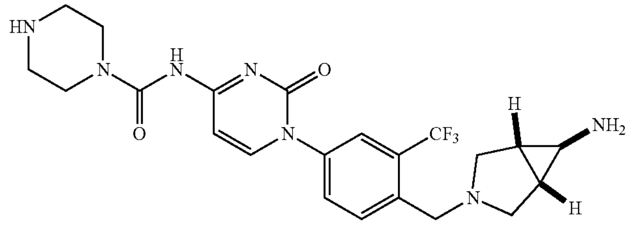 |

TABLE 11-continued
| Compounds of Formula V |
|---|
| 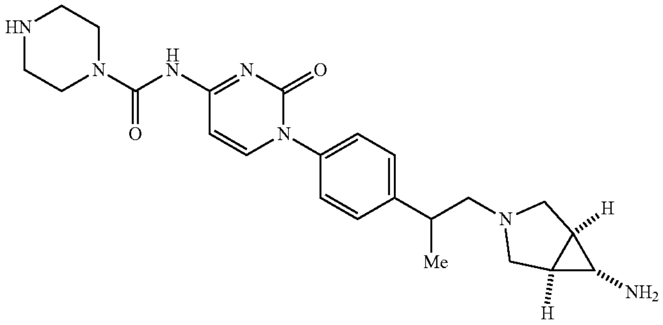 [SMILES: CC(CN1C[C@@H]2[C@@H](N)[C@@H]2C1)c1ccc(-n2ccc(NC(=O)N3CCNCC3)nc2=O)cc1] |
| 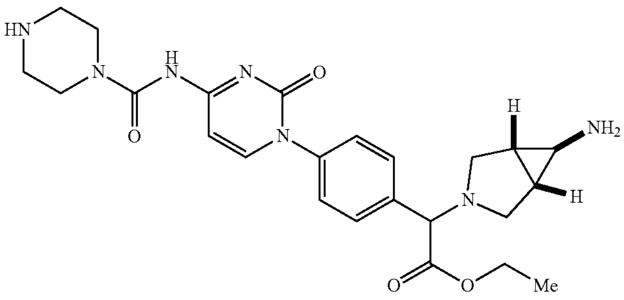 [SMILES: CCOC(=O)C(c1ccc(-n2ccc(NC(=O)N3CCNCC3)nc2=O)cc1)N1C[C@@H]2[C@@H](N)[C@@H]2C1] |
| 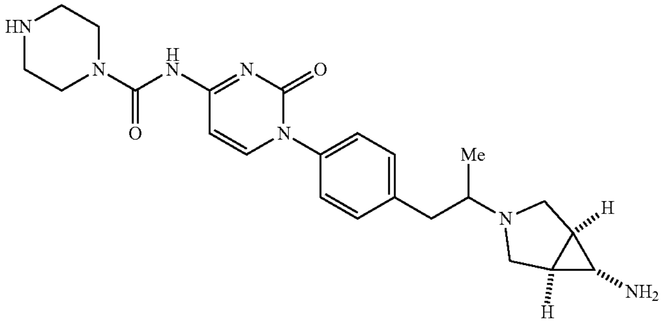 [SMILES: CC(Cc1ccc(-n2ccc(NC(=O)N3CCNCC3)nc2=O)cc1)N1C[C@@H]2[C@@H](N)[C@@H]2C1] |
| 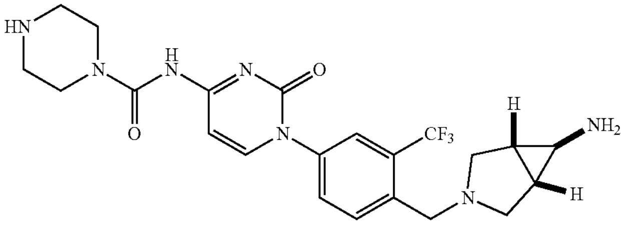 |
| 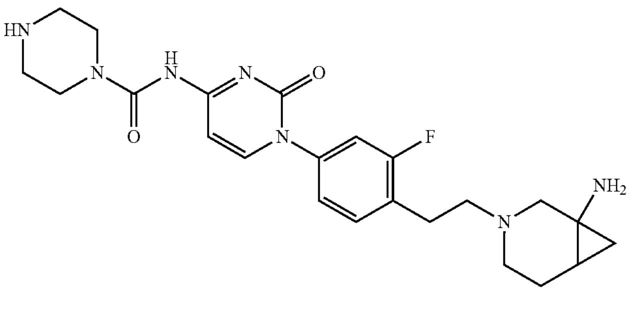 [SMILES: NC12CC1CCN(CCc1ccc(-n3ccc(NC(=O)N4CCNCC4)nc3=O)cc1F)C2] |

TABLE 11-continued
| Compounds of Formula V |
|---|
| 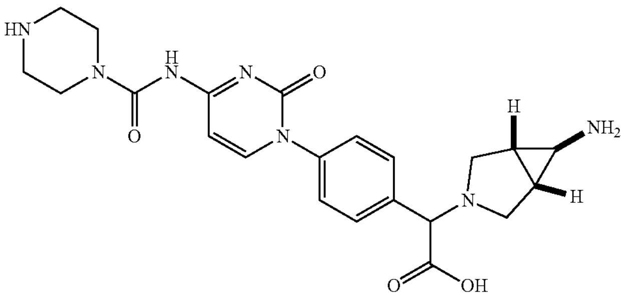 [SMILES: N[C@@H]1[C@H]2CN(C(C(=O)O)c3ccc(-n4ccc(NC(=O)N5CCNCC5)nc4=O)cc3)C[C@@H]12] |
| 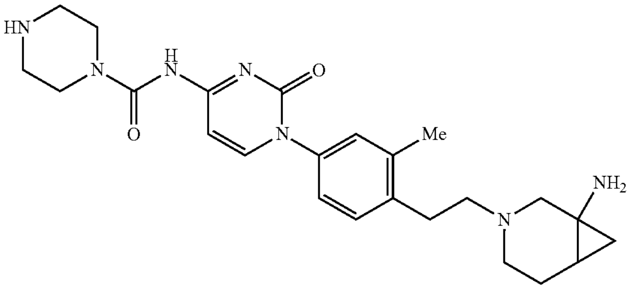 [SMILES: Cc1cc(-n2ccc(NC(=O)N3CCNCC3)nc2=O)ccc1CCN1CCC2CC2(N)C1] |
| 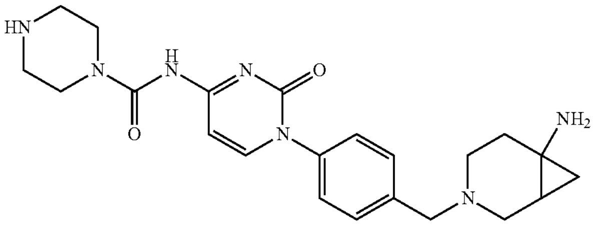 [SMILES: NC12CCN(Cc3ccc(-n4ccc(NC(=O)N5CCNCC5)nc4=O)cc3)CC1C2] |
| 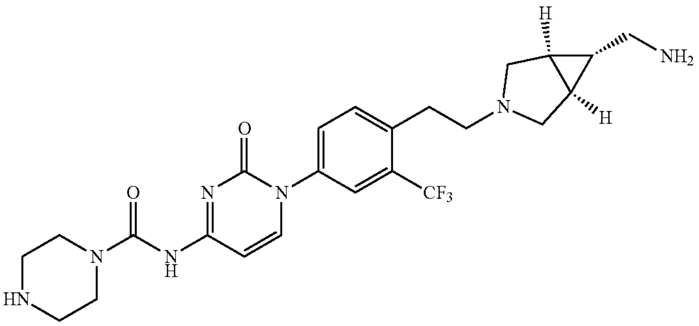 [SMILES: NC[C@@H]1[C@H]2CN(CCc3ccc(-n4ccc(NC(=O)N5CCNCC5)nc4=O)cc3C(F)(F)F)C[C@@H]12] |
| 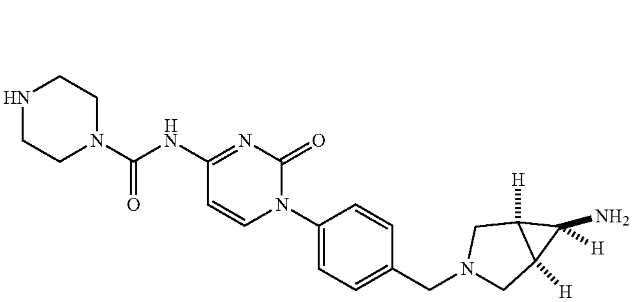 [SMILES: N[C@H]1[C@H]2CN(Cc3ccc(-n4ccc(NC(=O)N5CCNCC5)nc4=O)cc3)C[C@@H]12] |

TABLE 11-continued
Compounds of Formula V
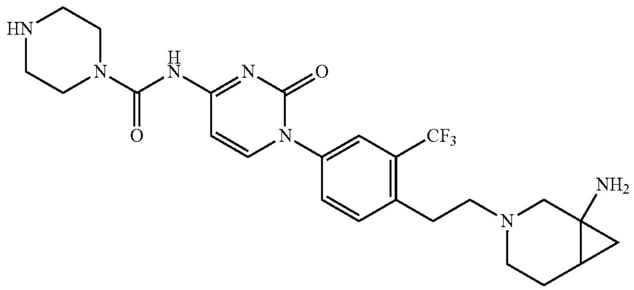 [SMILES: NC12CC1CCN(CCc1ccc(-n3ccc(NC(=O)N4CCNCC4)nc3=O)cc1C(F)(F)F)C2]
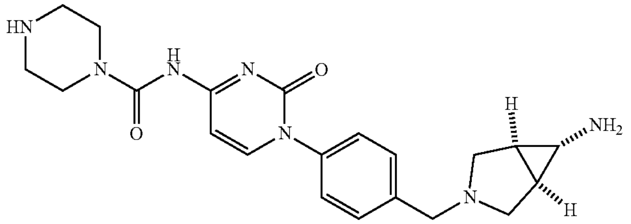 [SMILES: N[C@@H]1[C@H]2CN(Cc3ccc(-n4ccc(NC(=O)N5CCNCC5)nc4=O)cc3)C[C@@H]12]
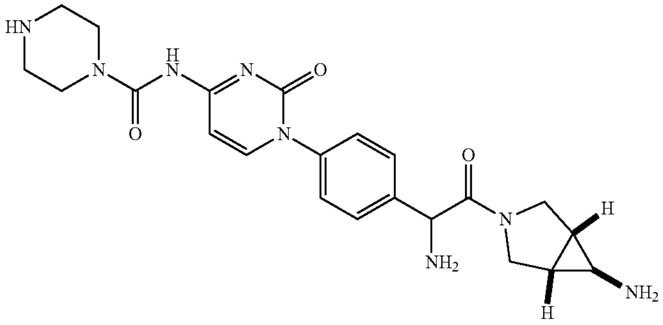 [SMILES: NC(C(=O)N1C[C@@H]2[C@@H](N)[C@@H]2C1)c1ccc(-n2ccc(NC(=O)N3CCNCC3)nc2=O)cc1]
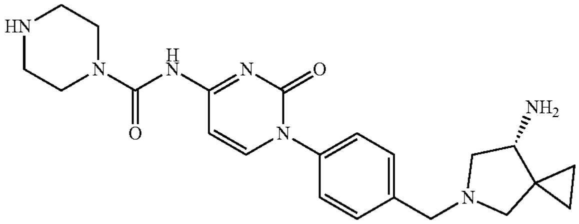 [SMILES: N[C@H]1CN(Cc2ccc(-n3ccc(NC(=O)N4CCNCC4)nc3=O)cc2)CC12CC2]
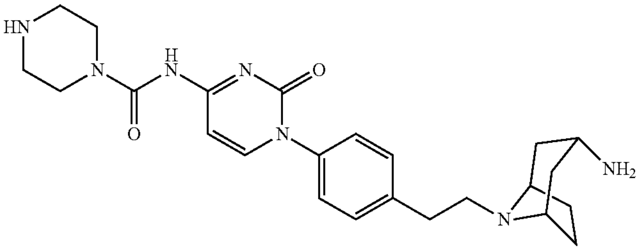 [SMILES: NC1CC2CCC(C1)N2CCc1ccc(-n2ccc(NC(=O)N3CCNCC3)nc2=O)cc1]
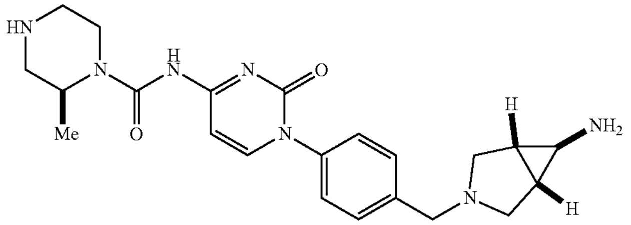 [SMILES: C[C@H]1CNCCN1C(=O)Nc1ccn(-c2ccc(CN3C[C@@H]4[C@@H](N)[C@@H]4C3)cc2)c(=O)n1]

TABLE 11-continued
| Compounds of Formula V |
| --- |
| 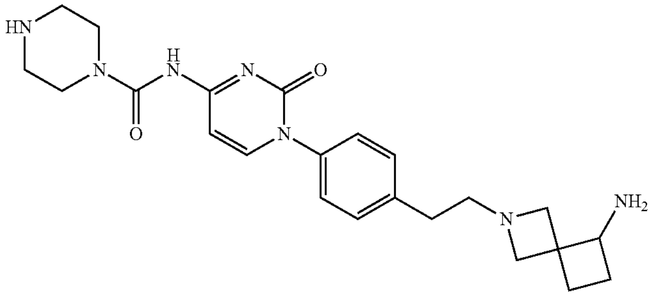 [SMILES: NC1CCC12CN(CCc1ccc(-n3ccc(NC(=O)N4CCNCC4)nc3=O)cc1)C2] |
| 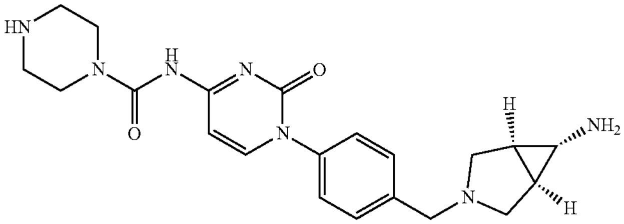 [SMILES: N[C@@H]1[C@H]2CN(Cc3ccc(-n4ccc(NC(=O)N5CCNCC5)nc4=O)cc3)C[C@@H]12] |
| 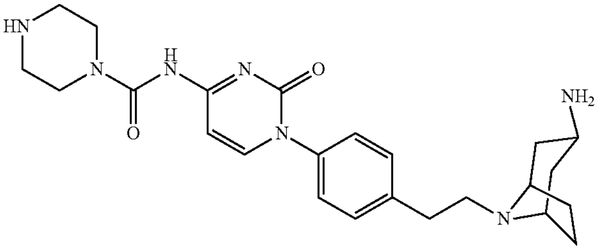 [SMILES: NC1CC2CCC(C1)N2CCc1ccc(-n2ccc(NC(=O)N3CCNCC3)nc2=O)cc1] |
| 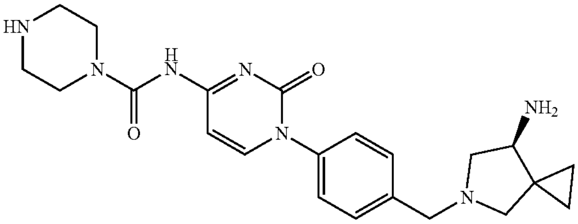 [SMILES: N[C@@H]1CN(Cc2ccc(-n3ccc(NC(=O)N4CCNCC4)nc3=O)cc2)CC12CC2] |
| 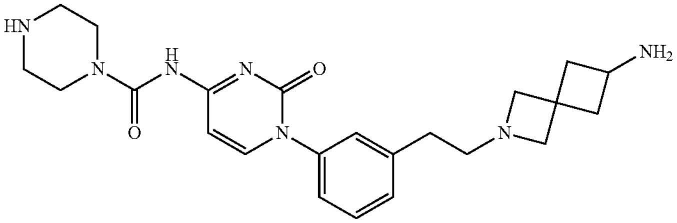 [SMILES: NC1CC2(C1)CN(CCc1cccc(-n3ccc(NC(=O)N4CCNCC4)nc3=O)c1)C2] |
| 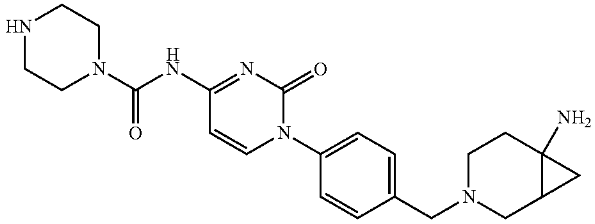 [SMILES: NC12CCN(Cc3ccc(-n4ccc(NC(=O)N5CCNCC5)nc4=O)cc3)CC1C2] |

TABLE 11-continued
Compounds of Formula V
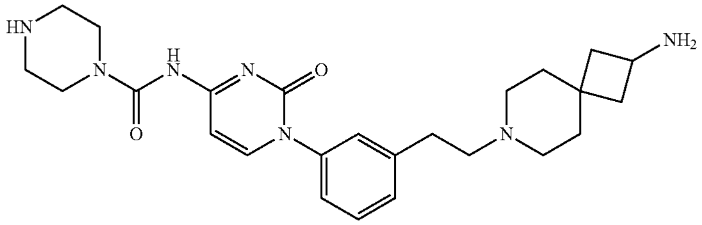 [SMILES: NC1CC2(CCN(CCc3cccc(-n4ccc(NC(=O)N5CCNCC5)nc4=O)c3)CC2)C1]
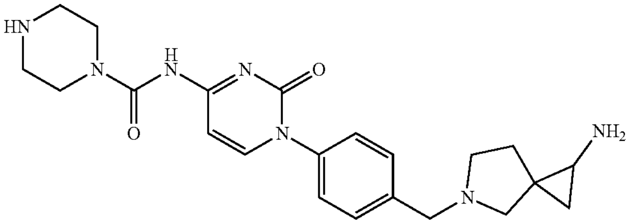 [SMILES: NC1CC12CCN(Cc1ccc(-n3ccc(NC(=O)N4CCNCC4)nc3=O)cc1)C2]
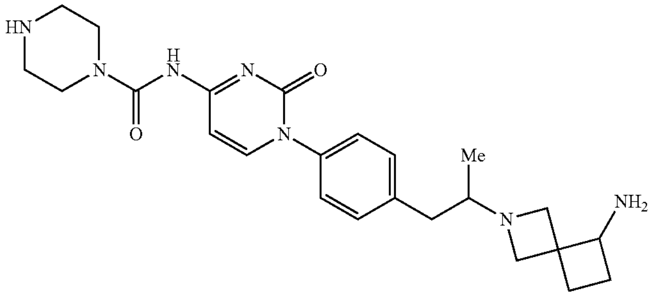 [SMILES: CC(Cc1ccc(-n2ccc(NC(=O)N3CCNCC3)nc2=O)cc1)N1CC2(CCC2N)C1]
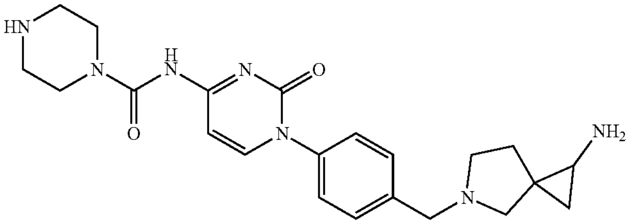 [SMILES: NC1CC12CCN(Cc1ccc(-n3ccc(NC(=O)N4CCNCC4)nc3=O)cc1)C2]
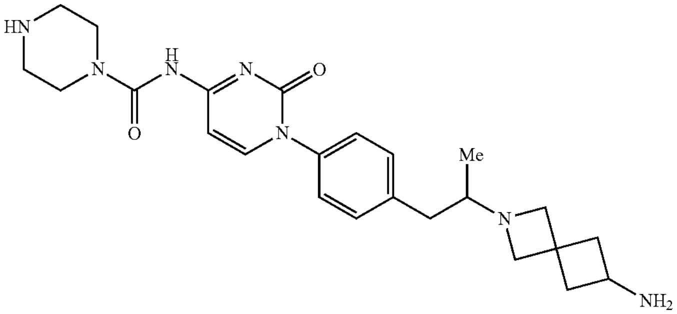 [SMILES: CC(Cc1ccc(-n2ccc(NC(=O)N3CCNCC3)nc2=O)cc1)N1CC2(CC(N)C2)C1]
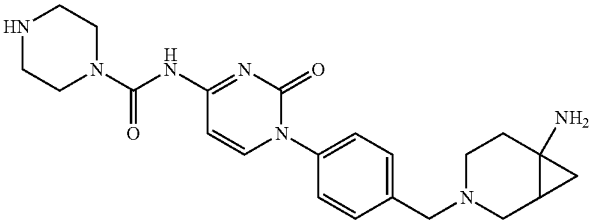 [SMILES: NC12CCN(Cc3ccc(-n4ccc(NC(=O)N5CCNCC5)nc4=O)cc3)CC1C2]

TABLE 11-continued
| Compounds of Formula V |
| --- |
| 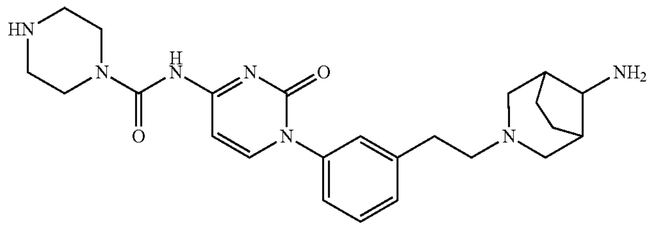 [SMILES: NC1C2CCC1CN(CCc1cccc(-n3ccc(NC(=O)N4CCNCC4)nc3=O)c1)C2] |
| 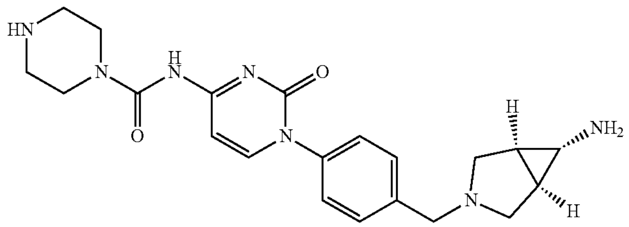 |
| 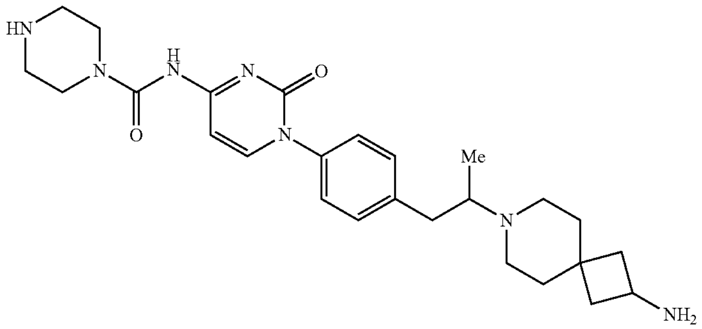 [SMILES: CC(Cc1ccc(-n2ccc(NC(=O)N3CCNCC3)nc2=O)cc1)N1CCC2(CC1)CC(N)C2] |
| 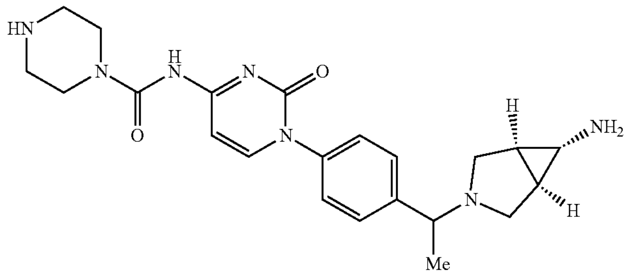 [SMILES: CC(c1ccc(-n2ccc(NC(=O)N3CCNCC3)nc2=O)cc1)N1C[C@@H]2[C@@H](N)[C@@H]2C1] |
| 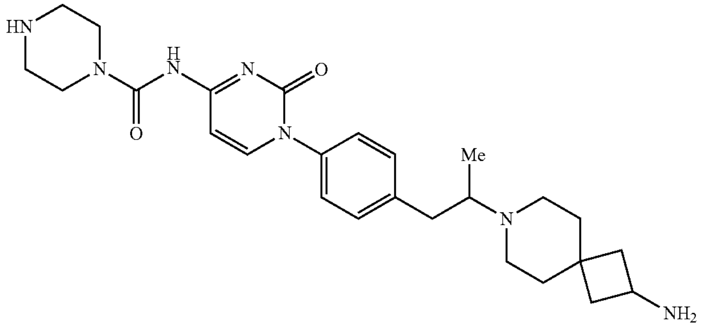 [SMILES: CC(Cc1ccc(-n2ccc(NC(=O)N3CCNCC3)nc2=O)cc1)N1CCC2(CC1)CC(N)C2] |

TABLE 11-continued
| Compounds of Formula V |
|---|
| 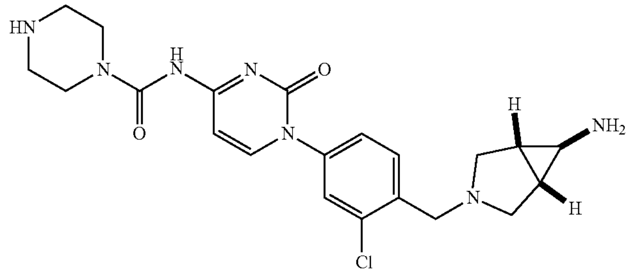 [SMILES: N[C@@H]1[C@H]2CN(Cc3ccc(-n4ccc(NC(=O)N5CCNCC5)nc4=O)cc3Cl)C[C@@H]12] |
| 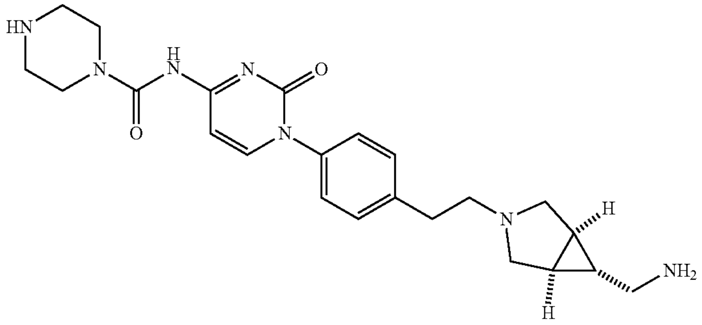 [SMILES: NC[C@@H]1[C@H]2CN(CCc3ccc(-n4ccc(NC(=O)N5CCNCC5)nc4=O)cc3)C[C@@H]12] |
| 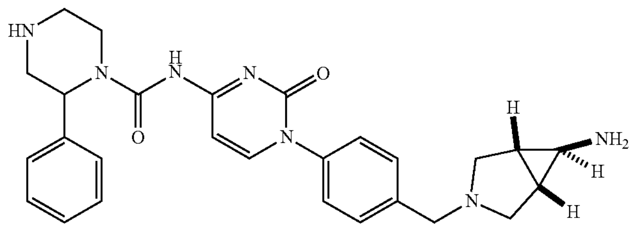 [SMILES: N[C@@H]1[C@H]2CN(Cc3ccc(-n4ccc(NC(=O)N5CCNCC5c5ccccc5)nc4=O)cc3)C[C@@H]12] |
| 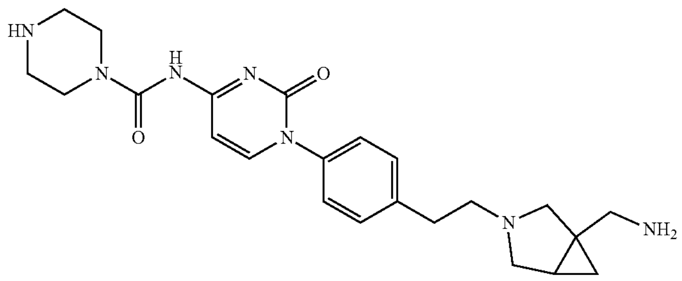 [SMILES: NCC12CC1CN(CCc1ccc(-n3ccc(NC(=O)N4CCNCC4)nc3=O)cc1)C2] |
| 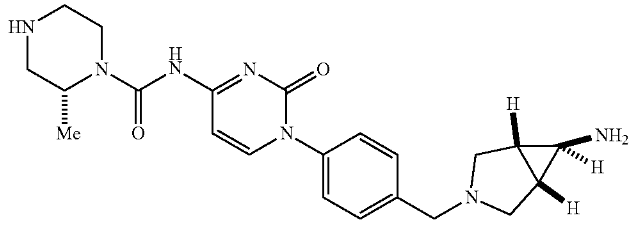 [SMILES: C[C@@H]1CNCCN1C(=O)Nc1ccn(-c2ccc(CN3C[C@@H]4[C@@H](N)[C@@H]4C3)cc2)c(=O)n1] |

TABLE 11-continued
| Compounds of Formula V |
| --- |
| 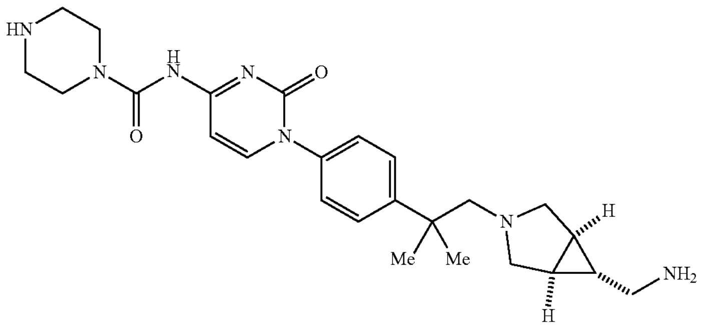 [SMILES: CC(C)(CN1C[C@@H]2[C@@H](CN)[C@@H]2C1)c1ccc(-n2ccc(NC(=O)N3CCNCC3)nc2=O)cc1] |
| 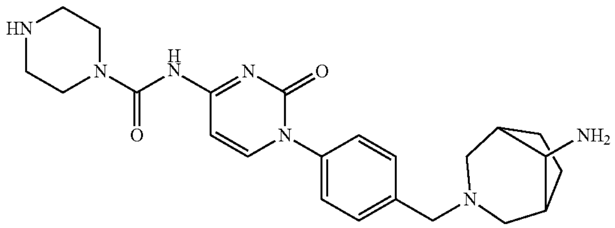 [SMILES: NC1C2CCC1CN(Cc1ccc(-n3ccc(NC(=O)N4CCNCC4)nc3=O)cc1)C2] |
| 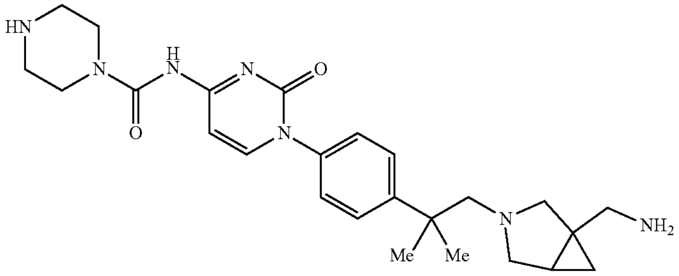 [SMILES: CC(C)(CN1CC2CC2(CN)C1)c1ccc(-n2ccc(NC(=O)N3CCNCC3)nc2=O)cc1] |
| 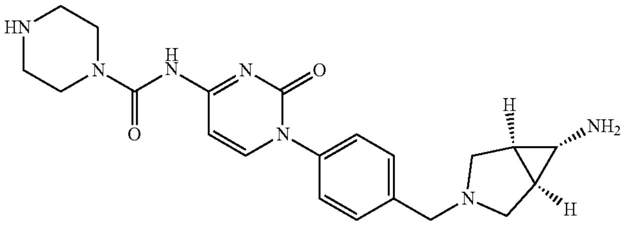 [SMILES: N[C@@H]1[C@H]2CN(Cc3ccc(-n4ccc(NC(=O)N5CCNCC5)nc4=O)cc3)C[C@@H]12] |
| 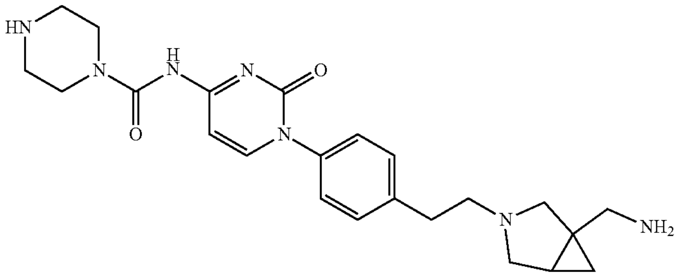 [SMILES: NCC12CC1CN(CCc1ccc(-n3ccc(NC(=O)N4CCNCC4)nc3=O)cc1)C2] |

TABLE 11-continued
Compounds of Formula V
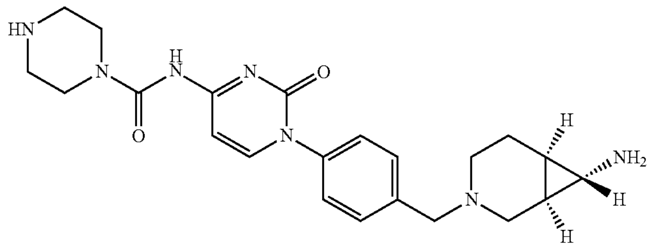 [SMILES: N[C@@H]1[C@H]2CN(Cc3ccc(-n4ccc(NC(=O)N5CCNCC5)nc4=O)cc3)CC[C@@H]12]
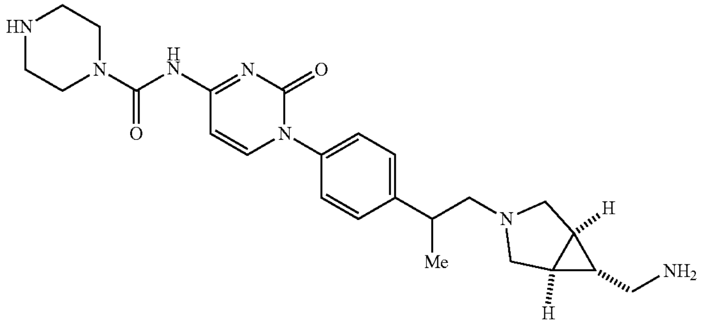 [SMILES: CC(CN1C[C@@H]2[C@@H](CN)[C@@H]2C1)c1ccc(-n2ccc(NC(=O)N3CCNCC3)nc2=O)cc1]
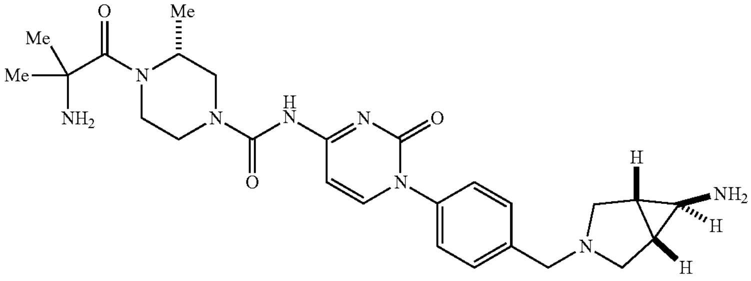 [SMILES: C[C@@H]1CN(C(=O)Nc2ccn(-c3ccc(CN4C[C@@H]5[C@@H](N)[C@@H]5C4)cc3)c(=O)n2)CCN1C(=O)C(C)(C)N]
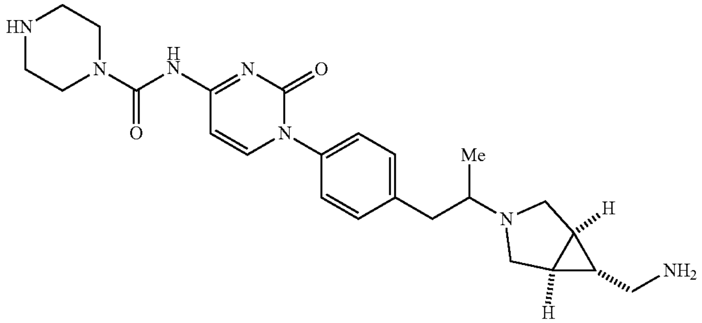 [SMILES: CC(Cc1ccc(-n2ccc(NC(=O)N3CCNCC3)nc2=O)cc1)N1C[C@@H]2[C@@H](CN)[C@@H]2C1]
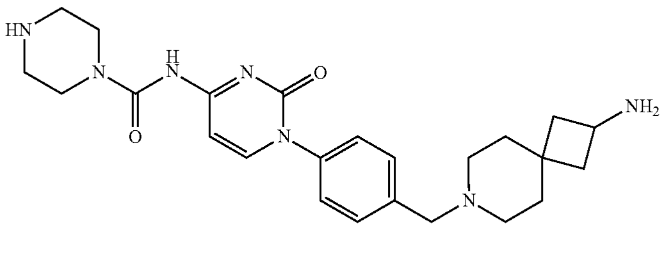 [SMILES: NC1CC2(CCN(Cc3ccc(-n4ccc(NC(=O)N5CCNCC5)nc4=O)cc3)CC2)C1]

TABLE 11-continued
| Compounds of Formula V |
| --- |
| 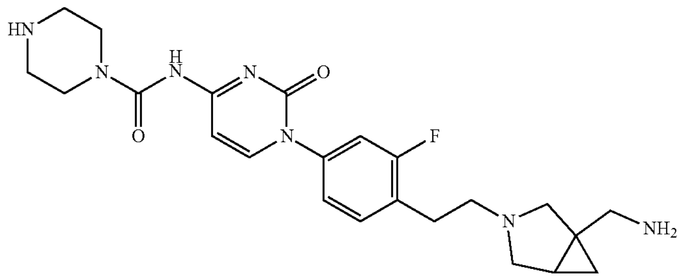 [SMILES: NCC12CC1CN(CCc1ccc(-n3ccc(NC(=O)N4CCNCC4)nc3=O)cc1F)C2] |
| 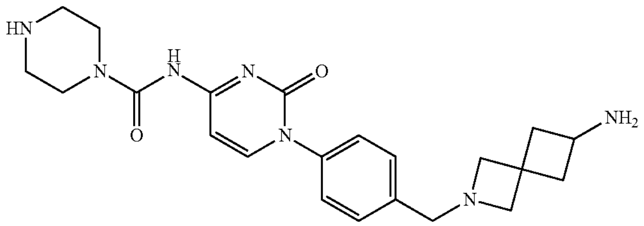 [SMILES: NC1CC2(C1)CN(Cc1ccc(-n3ccc(NC(=O)N4CCNCC4)nc3=O)cc1)C2] |
| 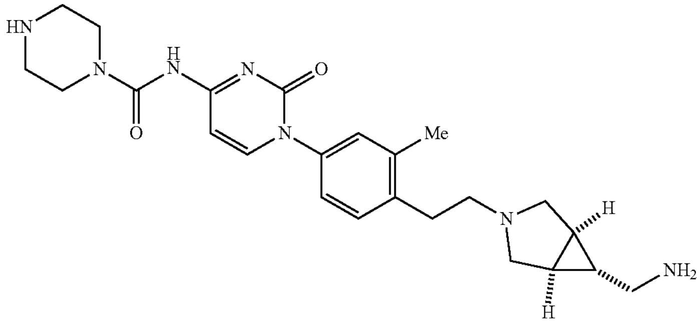 |
| 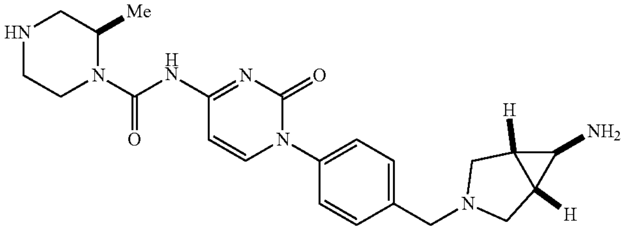 [SMILES: C[C@@H]1CNCCN1C(=O)Nc1ccn(-c2ccc(CN3C[C@@H]4[C@@H](N)[C@@H]4C3)cc2)c(=O)n1] |
| 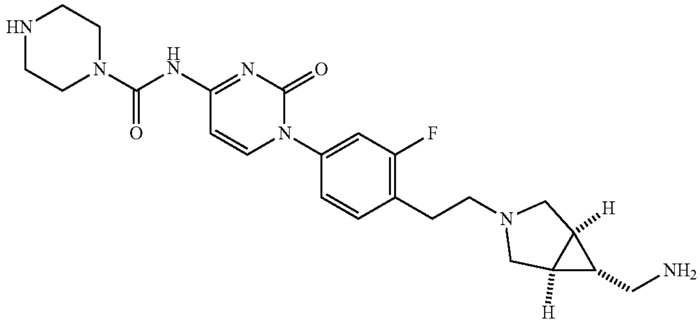 [SMILES: NC[C@@H]1[C@H]2CN(CCc3ccc(-n4ccc(NC(=O)N5CCNCC5)nc4=O)cc3F)C[C@@H]12] |

TABLE 11-continued
Compounds of Formula V
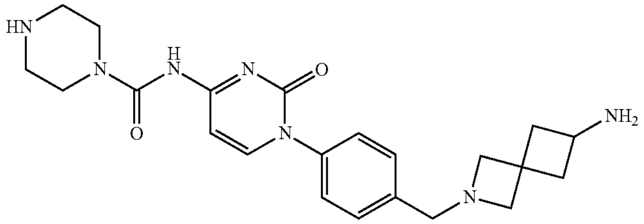 [SMILES: NC1CC2(C1)CN(Cc1ccc(-n3ccc(NC(=O)N4CCNCC4)nc3=O)cc1)C2]
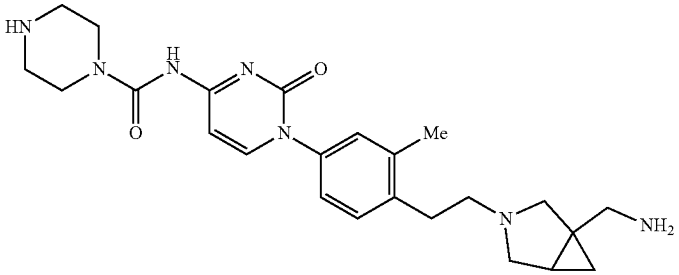 [SMILES: Cc1cc(-n2ccc(NC(=O)N3CCNCC3)nc2=O)ccc1CCN1CC2CC2(CN)C1]
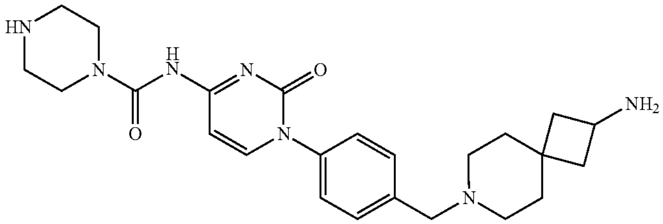 [SMILES: NC1CC2(CCN(Cc3ccc(-n4ccc(NC(=O)N5CCNCC5)nc4=O)cc3)CC2)C1]
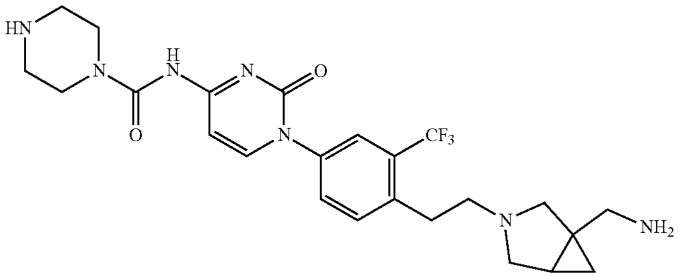 [SMILES: NCC12CC1CN(CCc1ccc(-n3ccc(NC(=O)N4CCNCC4)nc3=O)cc1C(F)(F)F)C2]
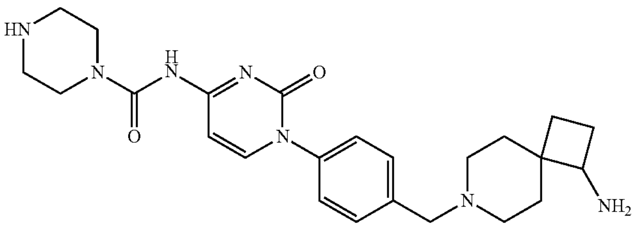 [SMILES: NC1CCC12CCN(Cc1ccc(-n3ccc(NC(=O)N4CCNCC4)nc3=O)cc1)CC2]
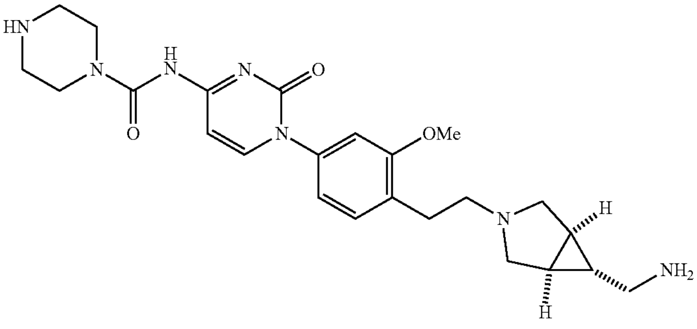 [SMILES: COc1cc(-n2ccc(NC(=O)N3CCNCC3)nc2=O)ccc1CCN1C[C@@H]2[C@@H](CN)[C@@H]2C1]

TABLE 11-continued
| Compounds of Formula V |
|---|
| 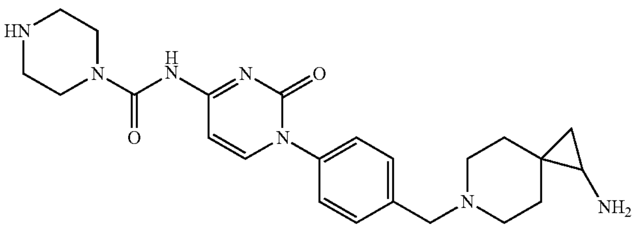 [SMILES: NC1CC12CCN(Cc1ccc(-n3ccc(NC(=O)N4CCNCC4)nc3=O)cc1)CC2] |
| 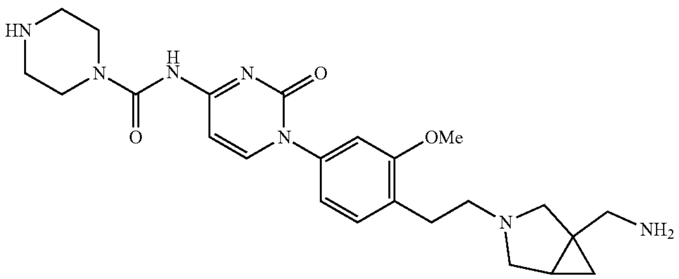 [SMILES: COc1cc(-n2ccc(NC(=O)N3CCNCC3)nc2=O)ccc1CCN1CC2CC2(CN)C1] |
| 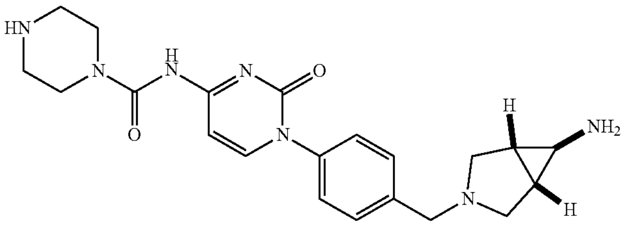 [SMILES: N[C@@H]1[C@H]2CN(Cc3ccc(-n4ccc(NC(=O)N5CCNCC5)nc4=O)cc3)C[C@@H]12] |
| 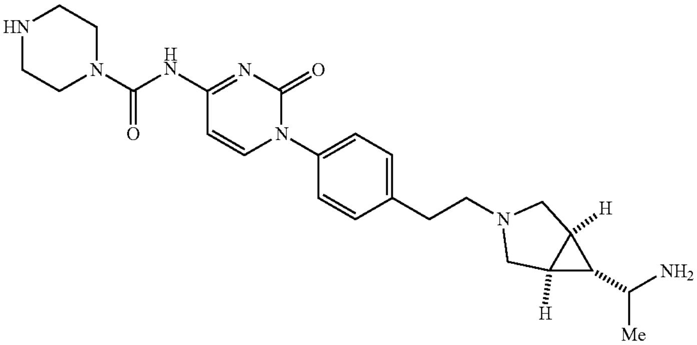 [SMILES: CC(N)[C@H]1[C@@H]2CN(CCc3ccc(-n4ccc(NC(=O)N5CCNCC5)nc4=O)cc3)C[C@@H]21] |
| 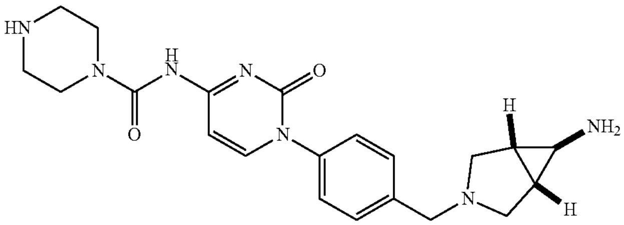 [SMILES: N[C@@H]1[C@H]2CN(Cc3ccc(-n4ccc(NC(=O)N5CCNCC5)nc4=O)cc3)C[C@@H]12] |

TABLE 11-continued
| Compounds of Formula V |
| --- |
| 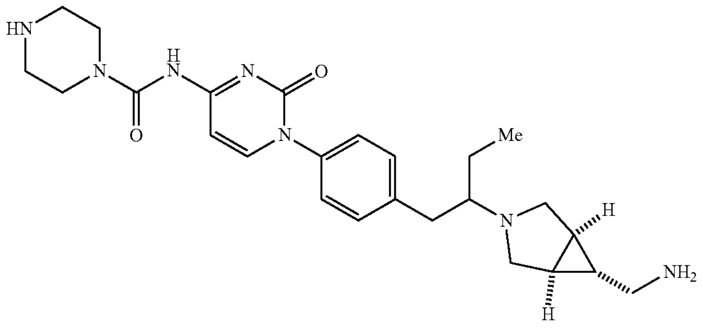 [SMILES: CCC(Cc1ccc(-n2ccc(NC(=O)N3CCNCC3)nc2=O)cc1)N1C[C@@H]2[C@@H](CN)[C@@H]2C1] |
| 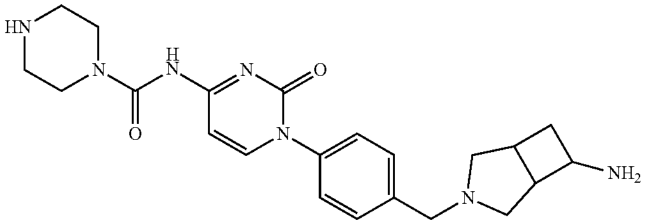 [SMILES: NC1CC2CN(Cc3ccc(-n4ccc(NC(=O)N5CCNCC5)nc4=O)cc3)CC12] |
| 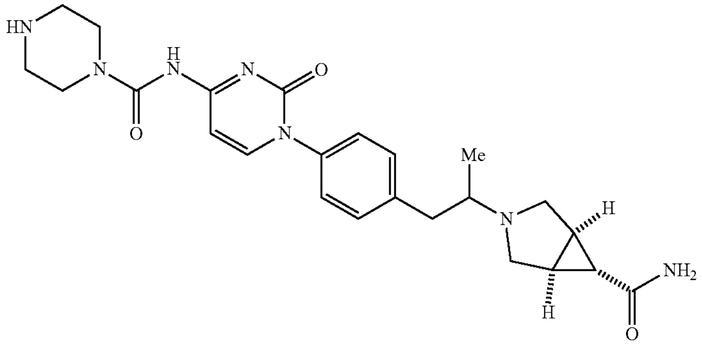 [SMILES: CC(Cc1ccc(-n2ccc(NC(=O)N3CCNCC3)nc2=O)cc1)N1C[C@@H]2[C@H](C1)[C@H]2C(N)=O] |
| 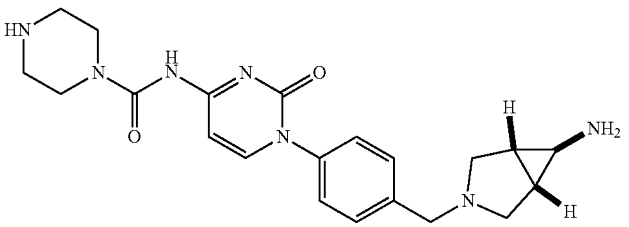 [SMILES: N[C@@H]1[C@H]2CN(Cc3ccc(-n4ccc(NC(=O)N5CCNCC5)nc4=O)cc3)C[C@@H]12] |
| 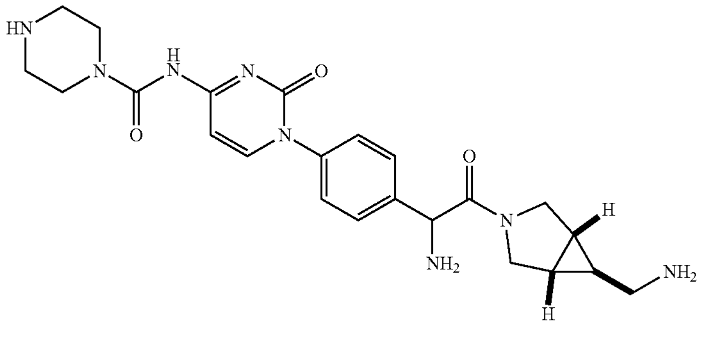 [SMILES: NC[C@@H]1[C@H]2CN(C(=O)C(N)c3ccc(-n4ccc(NC(=O)N5CCNCC5)nc4=O)cc3)C[C@@H]12] |

TABLE 11-continued
| Compounds of Formula V |
|---|
| 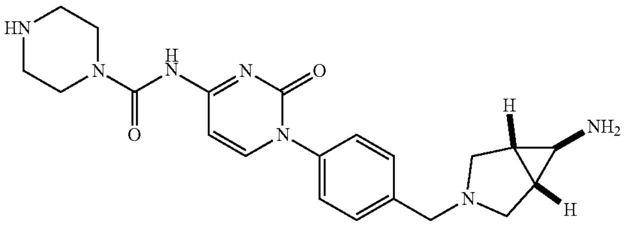 [SMILES: N[C@@H]1[C@H]2CN(Cc3ccc(-n4ccc(NC(=O)N5CCNCC5)nc4=O)cc3)C[C@@H]12] |
| 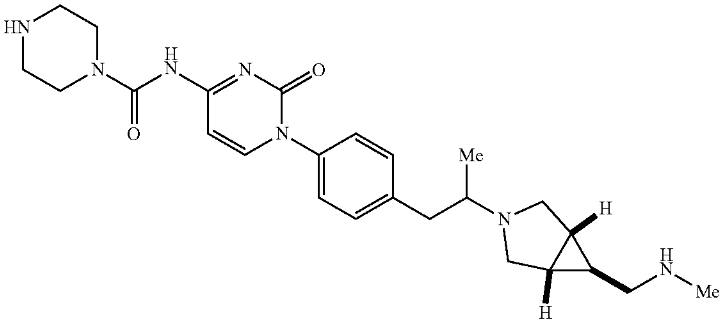 [SMILES: CNC[C@@H]1[C@H]2CN(C(C)Cc3ccc(-n4ccc(NC(=O)N5CCNCC5)nc4=O)cc3)C[C@@H]12] |
| 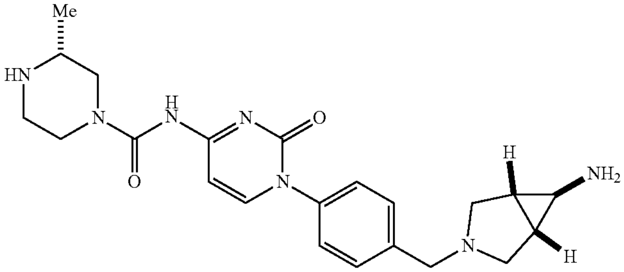 [SMILES: C[C@@H]1CN(C(=O)Nc2ccn(-c3ccc(CN4C[C@@H]5[C@@H](N)[C@@H]5C4)cc3)c(=O)n2)CCN1] |
| 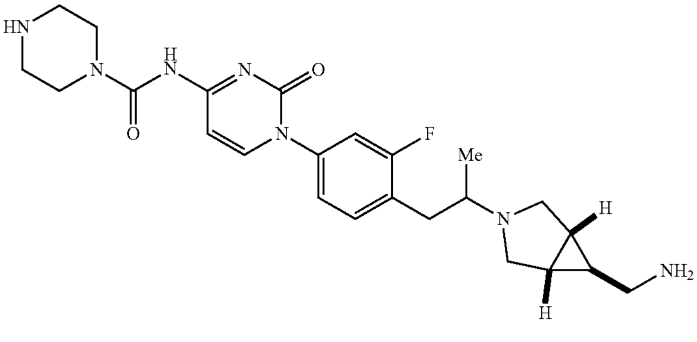 [SMILES: CC(Cc1ccc(-n2ccc(NC(=O)N3CCNCC3)nc2=O)cc1F)N1C[C@@H]2[C@@H](CN)[C@@H]2C1] |
| 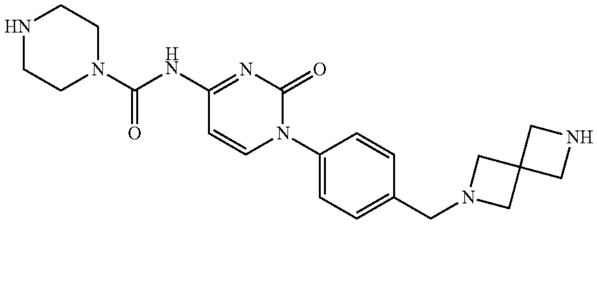 [SMILES: O=C(Nc1ccn(-c2ccc(CN3CC4(CNC4)C3)cc2)c(=O)n1)N1CCNCC1] |

TABLE 11-continued
| Compounds of Formula V |
|---|
| 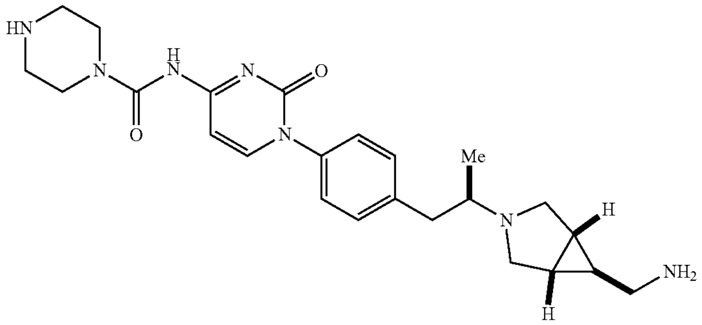 [SMILES: C[C@H](Cc1ccc(-n2ccc(NC(=O)N3CCNCC3)nc2=O)cc1)N1C[C@@H]2[C@@H](CN)[C@@H]2C1] |
| 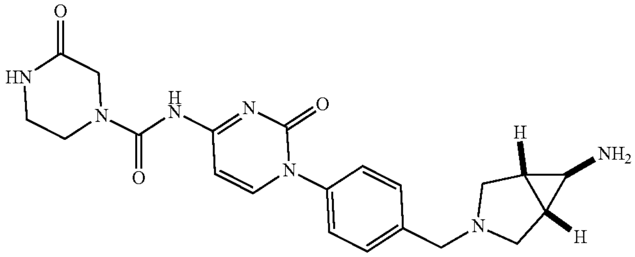 [SMILES: N[C@@H]1[C@H]2CN(Cc3ccc(-n4ccc(NC(=O)N5CCNC(=O)C5)nc4=O)cc3)C[C@@H]12] |
| 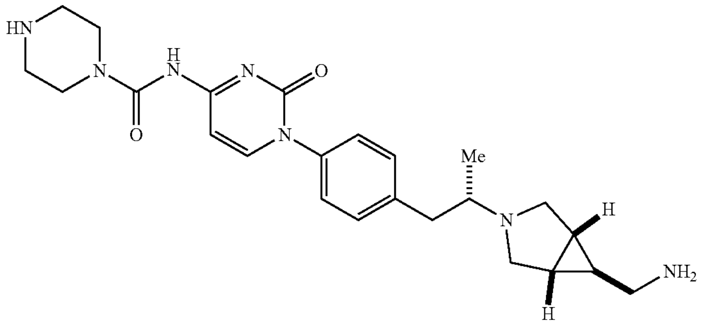 [SMILES: C[C@@H](Cc1ccc(-n2ccc(NC(=O)N3CCNCC3)nc2=O)cc1)N1C[C@@H]2[C@@H](CN)[C@@H]2C1] |
| 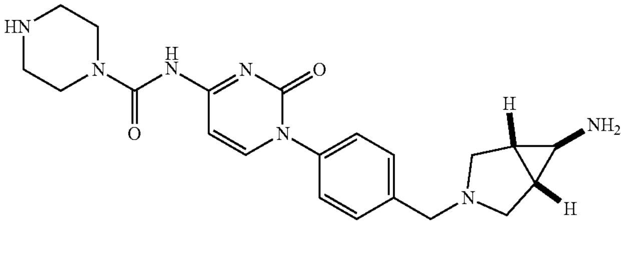 [SMILES: N[C@@H]1[C@H]2CN(Cc3ccc(-n4ccc(NC(=O)N5CCNCC5)nc4=O)cc3)C[C@@H]12] |
| 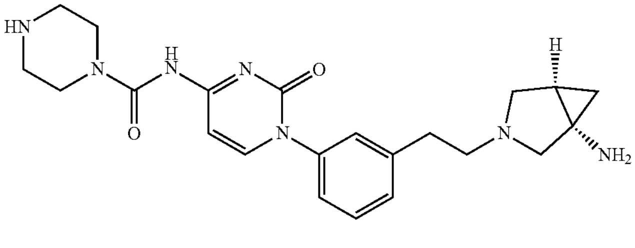 [SMILES: N[C@@]12C[C@@H]1CN(CCc1cccc(-n3ccc(NC(=O)N4CCNCC4)nc3=O)c1)C2] |

TABLE 11-continued
| Compounds of Formula V |
|---|
| 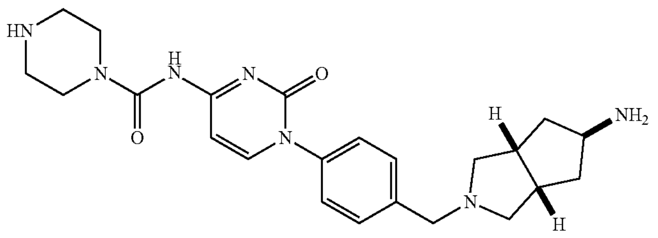 [SMILES: N[C@H]1C[C@@H]2CN(Cc3ccc(-n4ccc(NC(=O)N5CCNCC5)nc4=O)cc3)C[C@@H]2C1] |
| 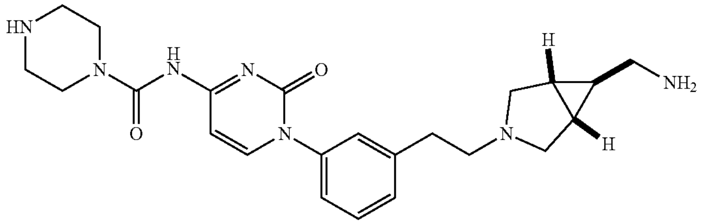 [SMILES: NC[C@@H]1[C@H]2CN(CCc3cccc(-n4ccc(NC(=O)N5CCNCC5)nc4=O)c3)C[C@@H]12] |
| 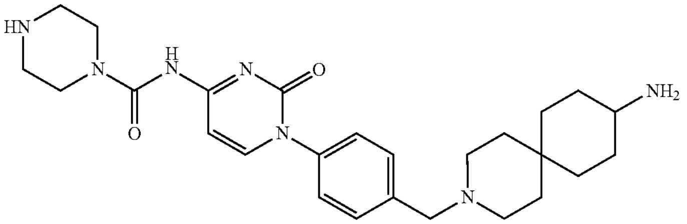 [SMILES: NC1CCC2(CC1)CCN(Cc1ccc(-n3ccc(NC(=O)N4CCNCC4)nc3=O)cc1)CC2] |
| 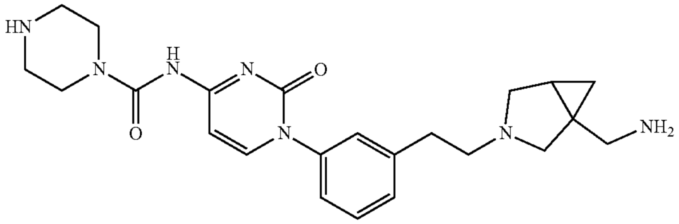 [SMILES: NCC12CC1CN(CCc1cccc(-n3ccc(NC(=O)N4CCNCC4)nc3=O)c1)C2] |
| 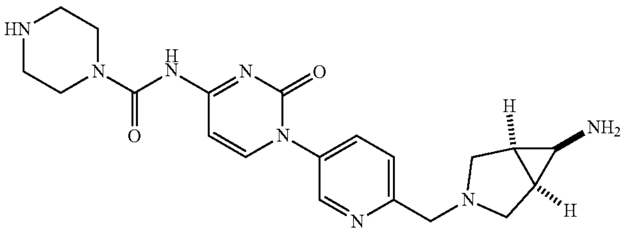 [SMILES: N[C@H]1[C@H]2CN(Cc3ccc(-n4ccc(NC(=O)N5CCNCC5)nc4=O)cn3)C[C@@H]12] |
| 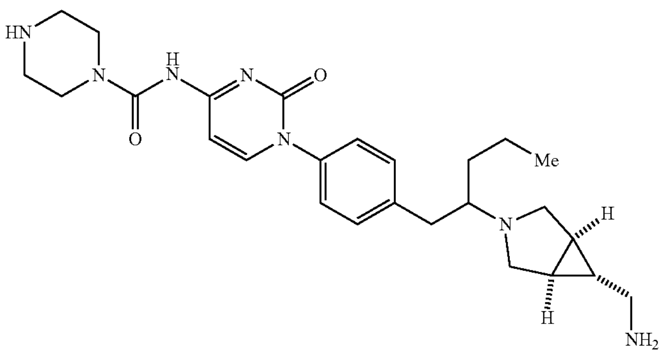 [SMILES: CCCC(Cc1ccc(-n2ccc(NC(=O)N3CCNCC3)nc2=O)cc1)N1C[C@@H]2[C@@H](CN)[C@@H]2C1] |

TABLE 11-continued
| Compounds of Formula V |
| --- |
| 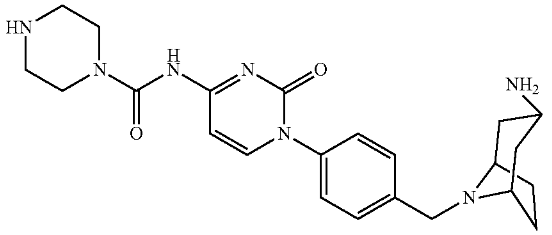 [SMILES: NC1CC2CCC(C1)N2Cc1ccc(-n2ccc(NC(=O)N3CCNCC3)nc2=O)cc1] |
| 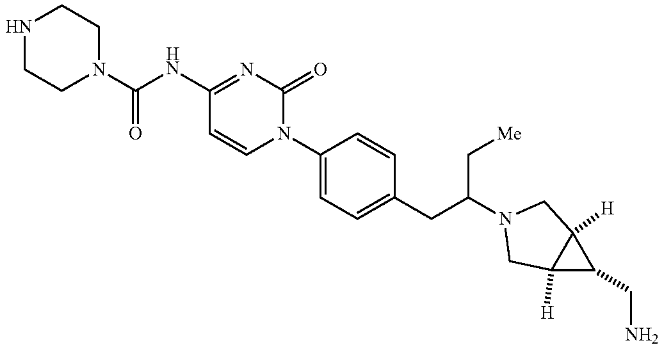 [SMILES: CCC(Cc1ccc(-n2ccc(NC(=O)N3CCNCC3)nc2=O)cc1)N1C[C@@H]2[C@@H](CN)[C@@H]2C1] |
| 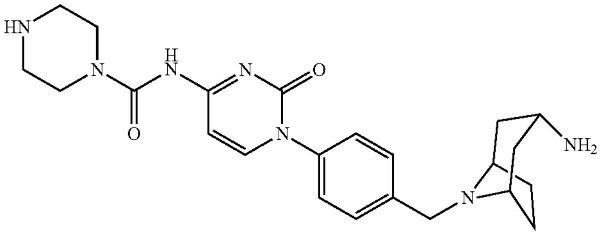 [SMILES: NC1CC2CCC(C1)N2Cc1ccc(-n2ccc(NC(=O)N3CCNCC3)nc2=O)cc1] |
| 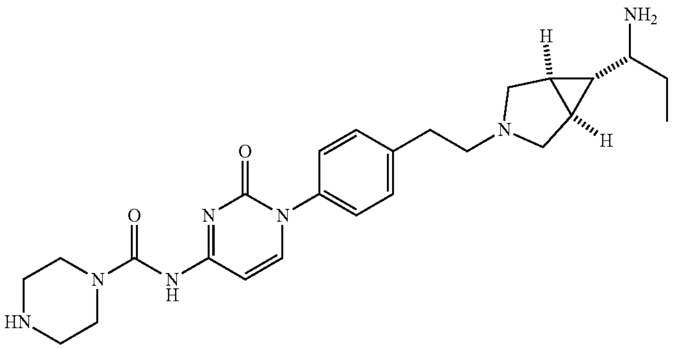 [SMILES: CC[C@@H](N)C1[C@H]2CN(CCc3ccc(-n4ccc(NC(=O)N5CCNCC5)nc4=O)cc3)C[C@@H]12] |
| 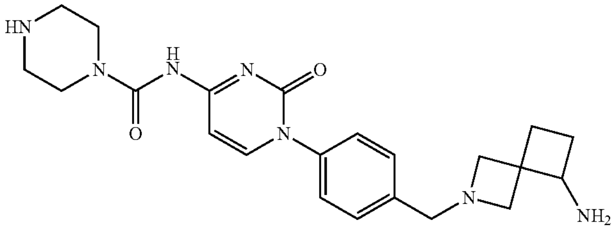 [SMILES: NC1CCC12CN(Cc1ccc(-n3ccc(NC(=O)N4CCNCC4)nc3=O)cc1)C2] |

TABLE 11-continued
| Compounds of Formula V |
| --- |
| 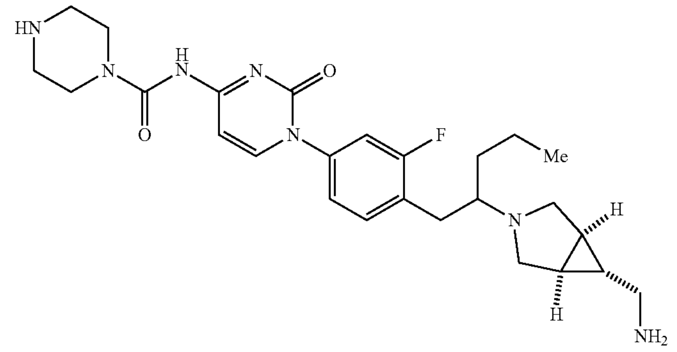 [SMILES: CCCC(Cc1ccc(-n2ccc(NC(=O)N3CCNCC3)nc2=O)cc1F)N1C[C@@H]2[C@@H](CN)[C@@H]2C1] |
| 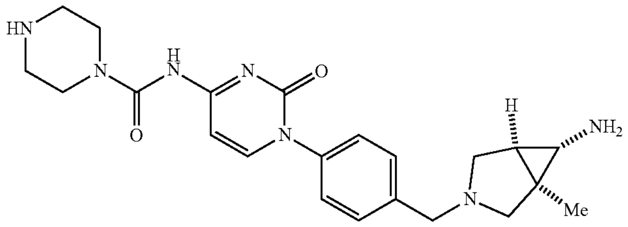 [SMILES: C[C@]12CN(Cc3ccc(-n4ccc(NC(=O)N5CCNCC5)nc4=O)cc3)C[C@H]1[C@@H]2N] |
| 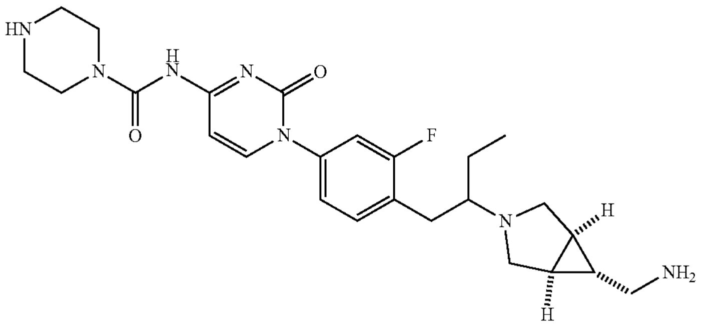 [SMILES: CCC(Cc1ccc(-n2ccc(NC(=O)N3CCNCC3)nc2=O)cc1F)N1C[C@@H]2[C@@H](CN)[C@@H]2C1] |
| 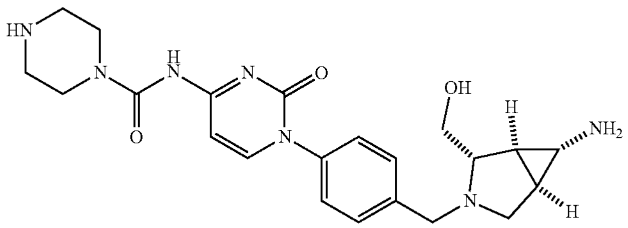 [SMILES: N[C@@H]1[C@H]2CN(Cc3ccc(-n4ccc(NC(=O)N5CCNCC5)nc4=O)cc3)[C@H](CO)[C@@H]12] |
| 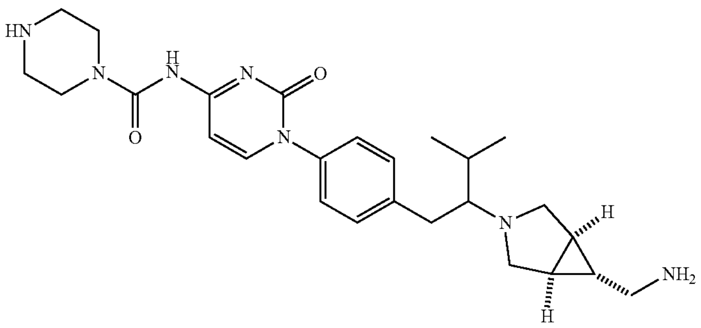 [SMILES: CC(C)C(Cc1ccc(-n2ccc(NC(=O)N3CCNCC3)nc2=O)cc1)N1C[C@@H]2[C@@H](CN)[C@@H]2C1] |

TABLE 11-continued
| Compounds of Formula V |
| --- |
| 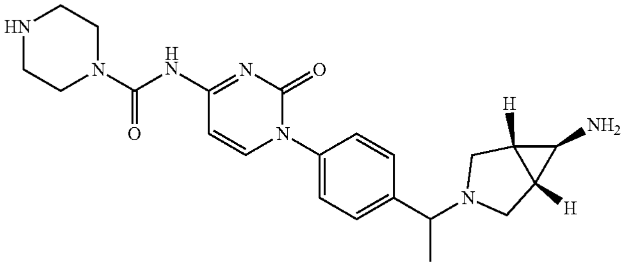 [SMILES: CC(c1ccc(-n2ccc(NC(=O)N3CCNCC3)nc2=O)cc1)N1C[C@@H]2[C@@H](N)[C@@H]2C1] |
| 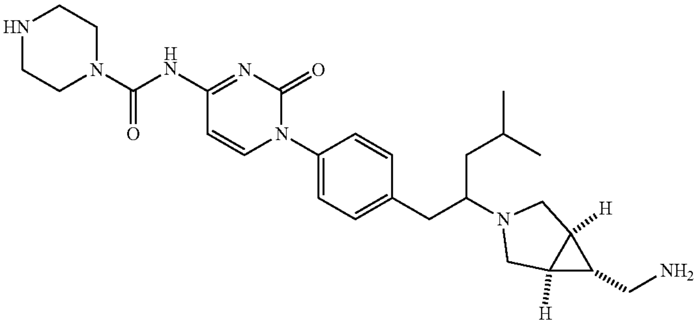 [SMILES: CC(C)CC(Cc1ccc(-n2ccc(NC(=O)N3CCNCC3)nc2=O)cc1)N1C[C@@H]2[C@@H](CN)[C@@H]2C1] |
| 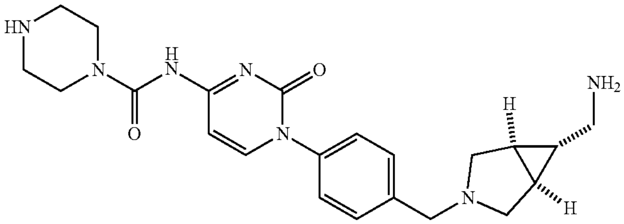 [SMILES: NC[C@@H]1[C@H]2CN(Cc3ccc(-n4ccc(NC(=O)N5CCNCC5)nc4=O)cc3)C[C@@H]12] |
| 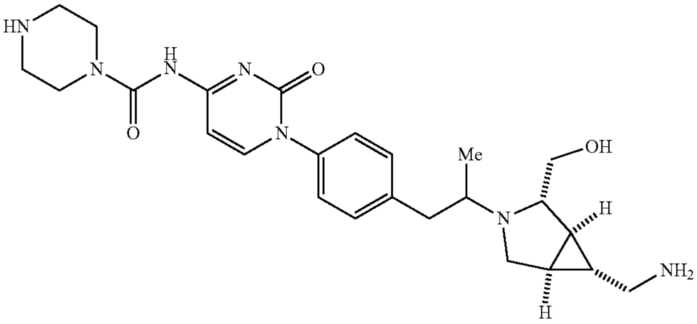 [SMILES: CC(Cc1ccc(-n2ccc(NC(=O)N3CCNCC3)nc2=O)cc1)N1C[C@@H]2[C@@H](CN)[C@@H]2[C@H]1CO] |
| 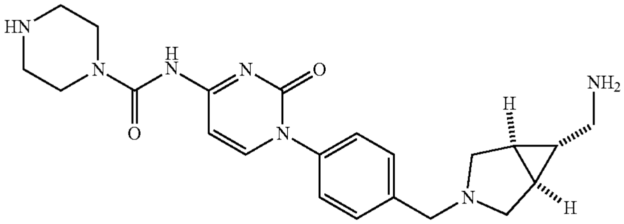 [SMILES: NC[C@@H]1[C@H]2CN(Cc3ccc(-n4ccc(NC(=O)N5CCNCC5)nc4=O)cc3)C[C@@H]12] |

TABLE 11-continued
| Compounds of Formula V |
|---|
| 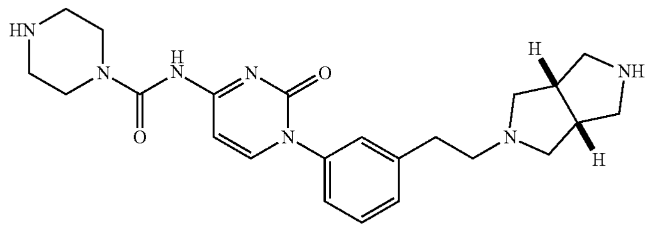 [SMILES: O=C(Nc1ccn(-c2cccc(CCN3C[C@H]4CNC[C@H]4C3)c2)c(=O)n1)N1CCNCC1] |
| 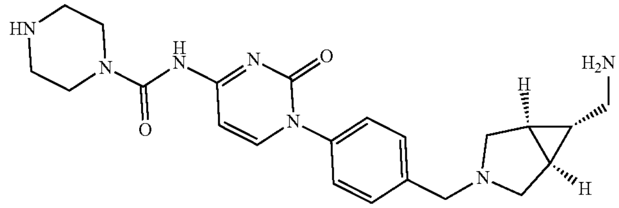 [SMILES: NC[C@@H]1[C@H]2CN(Cc3ccc(-n4ccc(NC(=O)N5CCNCC5)nc4=O)cc3)C[C@@H]12] |
| 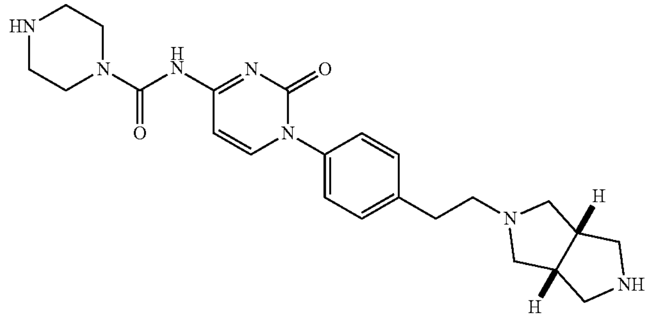 [SMILES: O=C(Nc1ccn(-c2ccc(CCN3C[C@H]4CNC[C@H]4C3)cc2)c(=O)n1)N1CCNCC1] |
| 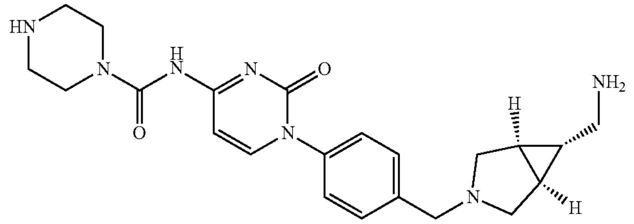 [SMILES: NC[C@@H]1[C@H]2CN(Cc3ccc(-n4ccc(NC(=O)N5CCNCC5)nc4=O)cc3)C[C@@H]12] |
| 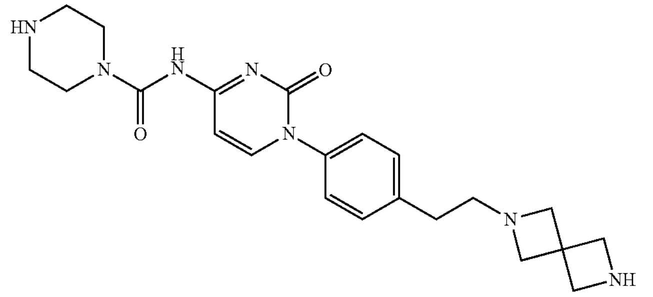 [SMILES: O=C(Nc1ccn(-c2ccc(CCN3CC4(CNC4)C3)cc2)c(=O)n1)N1CCNCC1] |
| 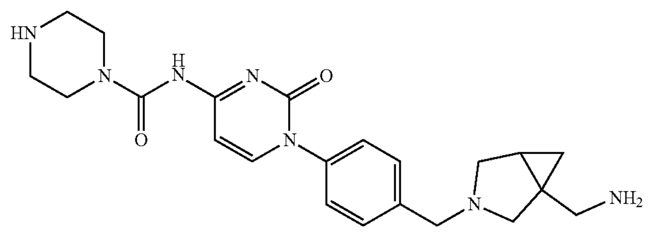 [SMILES: NCC12CC1CN(Cc1ccc(-n3ccc(NC(=O)N4CCNCC4)nc3=O)cc1)C2] |

TABLE 11-continued
| Compounds of Formula V |
| --- |
| 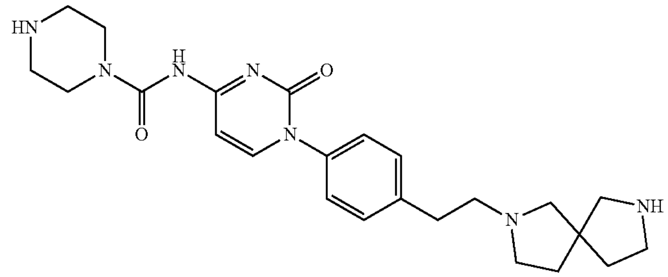 [SMILES: O=C(Nc1ccn(-c2ccc(CCN3CCC4(CCNC4)C3)cc2)c(=O)n1)N1CCNCC1] |
| 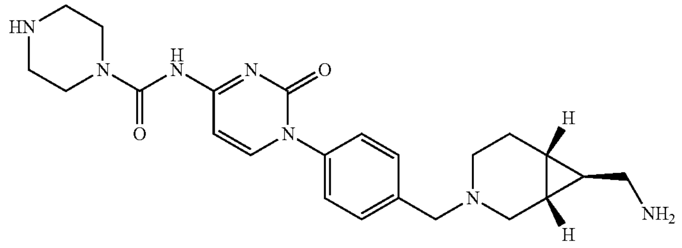 [SMILES: NC[C@@H]1[C@H]2CCN(Cc3ccc(-n4ccc(NC(=O)N5CCNCC5)nc4=O)cc3)C[C@@H]12] |
| 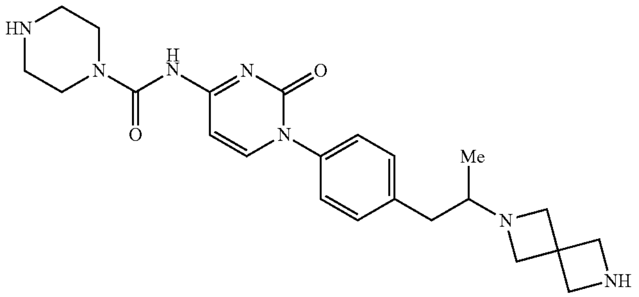 [SMILES: CC(Cc1ccc(-n2ccc(NC(=O)N3CCNCC3)nc2=O)cc1)N1CC2(CNC2)C1] |
| 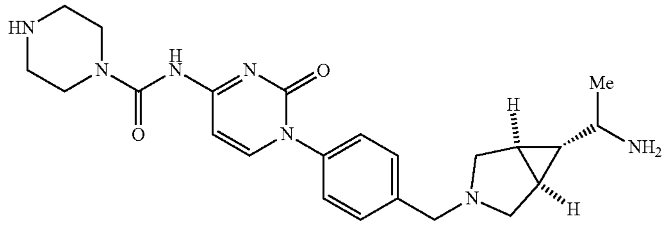 |
| 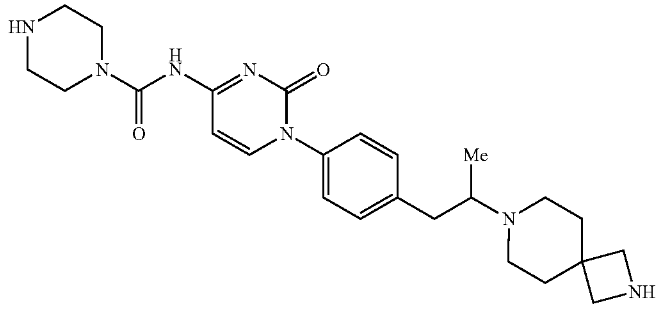 [SMILES: CC(Cc1ccc(-n2ccc(NC(=O)N3CCNCC3)nc2=O)cc1)N1CCC2(CC1)CNC2] |

TABLE 11-continued
Compounds of Formula V
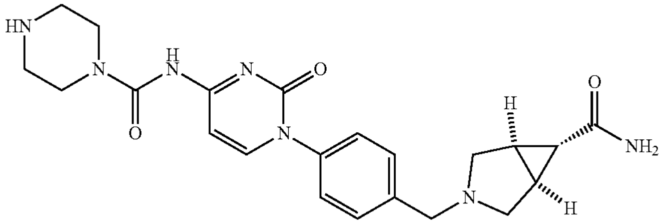
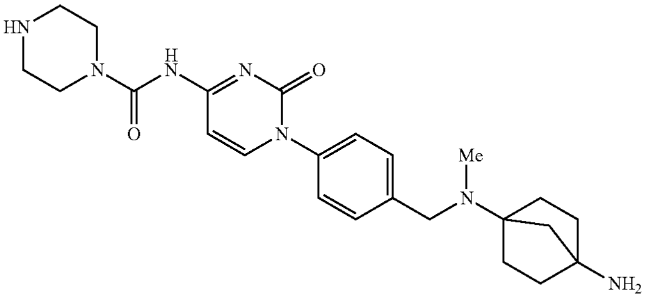
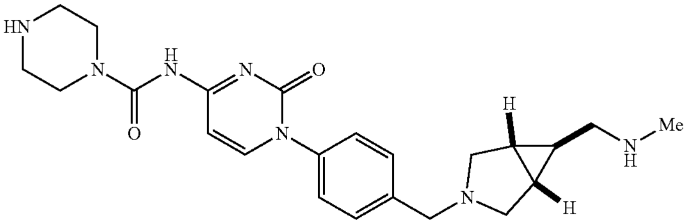 [SMILES: CNC[C@@H]1[C@H]2CN(Cc3ccc(-n4ccc(NC(=O)N5CCNCC5)nc4=O)cc3)C[C@@H]12]
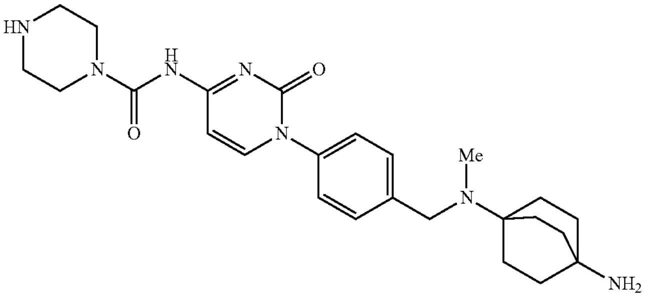 [SMILES: CN(Cc1ccc(-n2ccc(NC(=O)N3CCNCC3)nc2=O)cc1)C12CCC(N)(CC1)CC2]
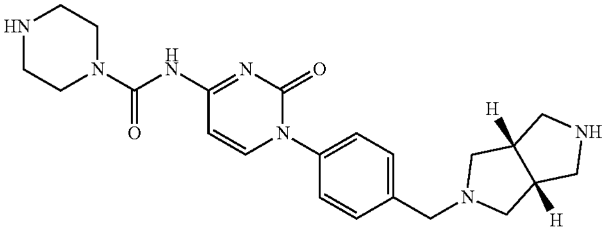 [SMILES: O=C(Nc1ccn(-c2ccc(CN3C[C@H]4CNC[C@H]4C3)cc2)c(=O)n1)N1CCNCC1]

TABLE 11-continued
| Compounds of Formula V |
| --- |
| 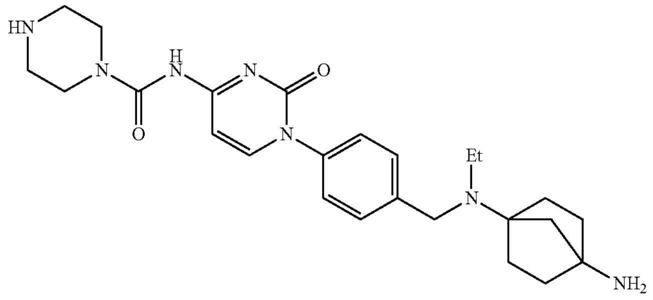 [SMILES: CCN(Cc1ccc(-n2ccc(NC(=O)N3CCNCC3)nc2=O)cc1)C12CCC(N)(CC1)C2] |
| 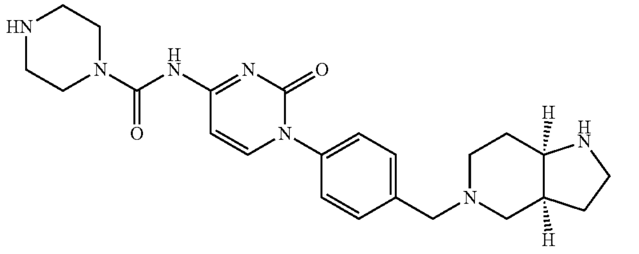 [SMILES: O=C(Nc1ccn(-c2ccc(CN3CC[C@H]4NCC[C@H]4C3)cc2)c(=O)n1)N1CCNCC1] |
| 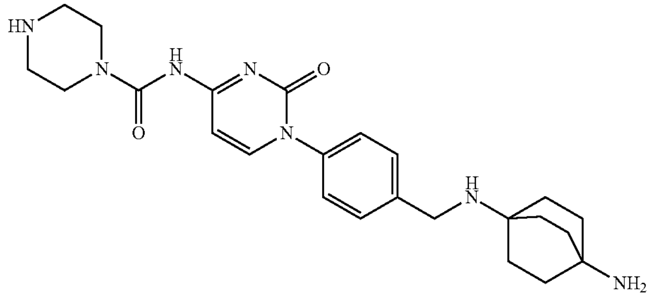 [SMILES: NC12CCC(NCc3ccc(-n4ccc(NC(=O)N5CCNCC5)nc4=O)cc3)(CC1)CC2] |
| 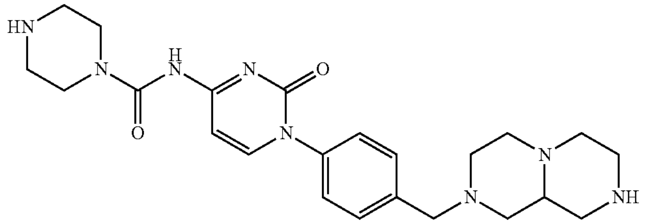 [SMILES: O=C(Nc1ccn(-c2ccc(CN3CCN4CCNCC4C3)cc2)c(=O)n1)N1CCNCC1] |
| 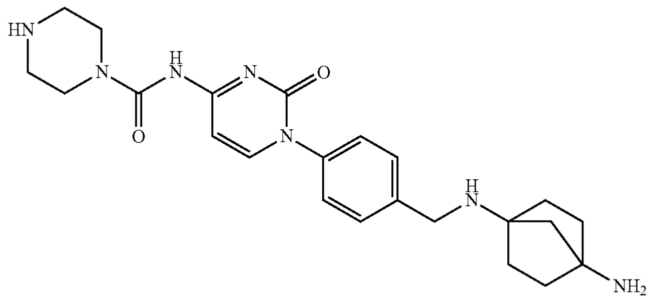 [SMILES: NC12CCC(NCc3ccc(-n4ccc(NC(=O)N5CCNCC5)nc4=O)cc3)(CC1)C2] |

TABLE 11-continued
| Compounds of Formula V |
| --- |
| 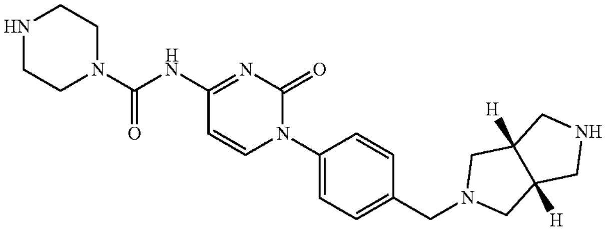 [SMILES: O=C(Nc1ccn(-c2ccc(CN3C[C@H]4CNC[C@H]4C3)cc2)c(=O)n1)N1CCNCC1] |
| 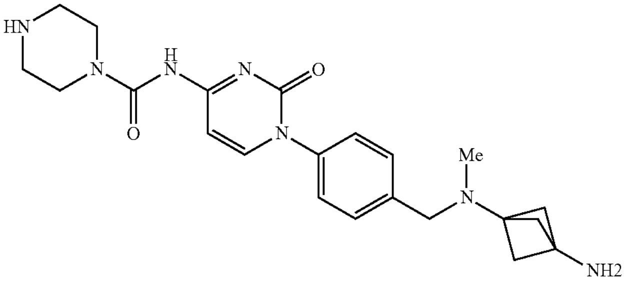 [SMILES: CN(Cc1ccc(-n2ccc(NC(=O)N3CCNCC3)nc2=O)cc1)C12CC(N)(C1)C2] |
| 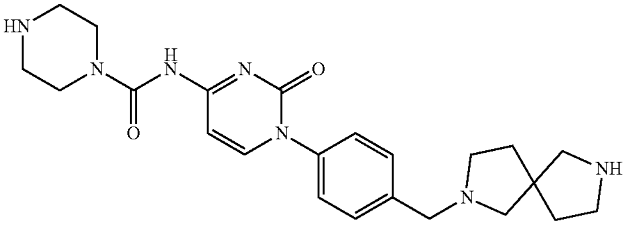 [SMILES: O=C(Nc1ccn(-c2ccc(CN3CCC4(CCNC4)C3)cc2)c(=O)n1)N1CCNCC1] |
| 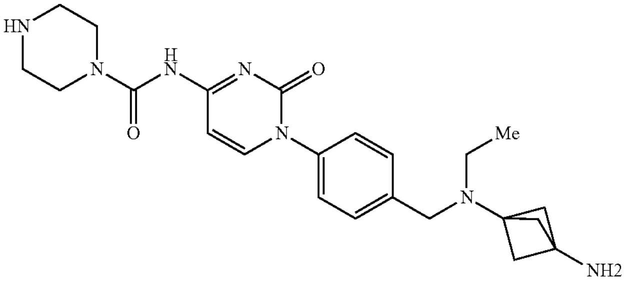 [SMILES: CCN(Cc1ccc(-n2ccc(NC(=O)N3CCNCC3)nc2=O)cc1)C12CC(N)(C1)C2] |
| 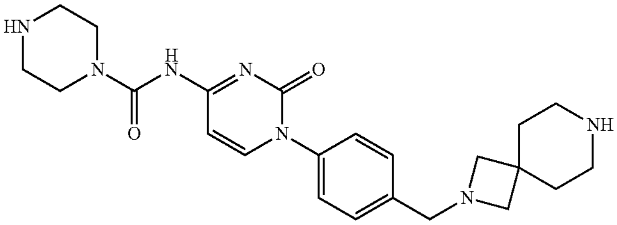 [SMILES: O=C(Nc1ccn(-c2ccc(CN3CC4(CCNCC4)C3)cc2)c(=O)n1)N1CCNCC1] |
| 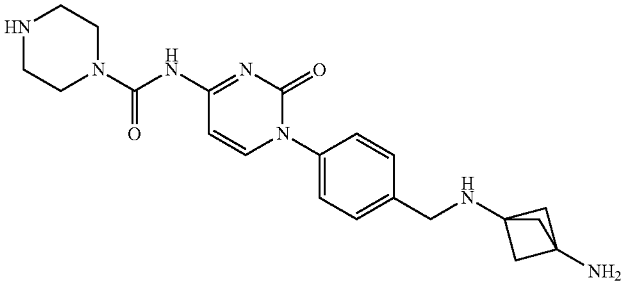 [SMILES: NC12CC(NCc3ccc(-n4ccc(NC(=O)N5CCNCC5)nc4=O)cc3)(C1)C2] |

TABLE 11-continued
| Compounds of Formula V |
| --- |
| 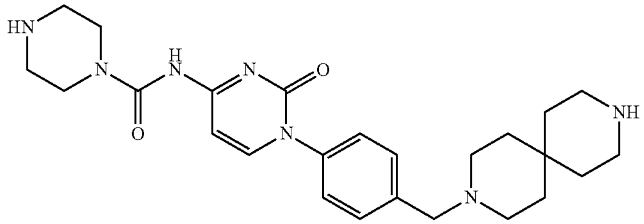 [SMILES: O=C(Nc1ccn(-c2ccc(CN3CCC4(CCNCC4)CC3)cc2)c(=O)n1)N1CCNCC1] |
| 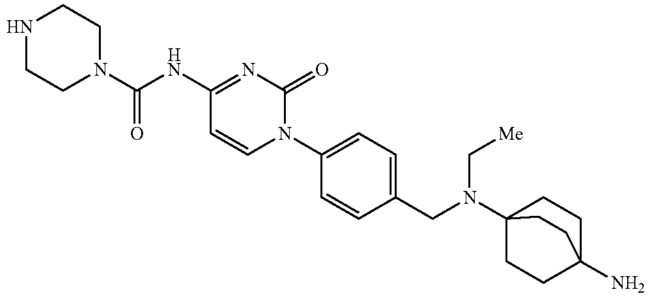 [SMILES: CCN(Cc1ccc(-n2ccc(NC(=O)N3CCNCC3)nc2=O)cc1)C12CCC(N)(CC1)CC2] |
| 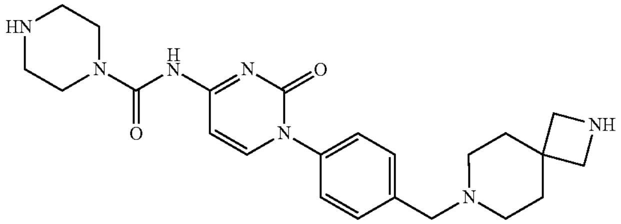 [SMILES: O=C(Nc1ccn(-c2ccc(CN3CCC4(CC3)CNC4)cc2)c(=O)n1)N1CCNCC1] |
| 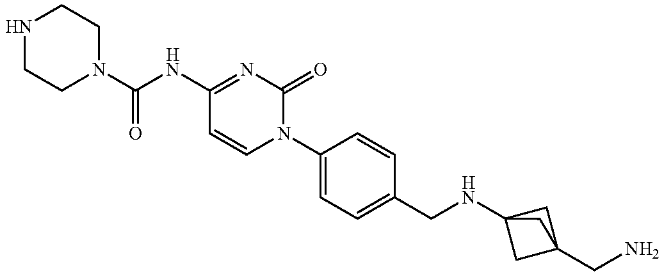 [SMILES: NCC12CC(NCc3ccc(-n4ccc(NC(=O)N5CCNCC5)nc4=O)cc3)(C1)C2] |
| 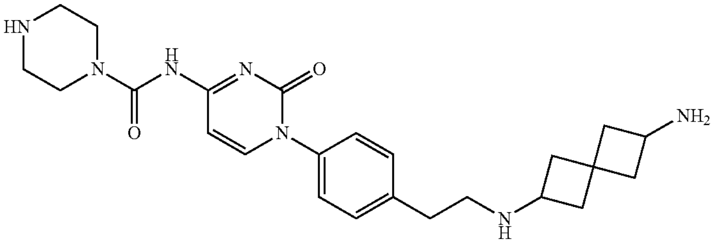 [SMILES: NC1CC2(C1)CC(NCCc1ccc(-n3ccc(NC(=O)N4CCNCC4)nc3=O)cc1)C2] |
| 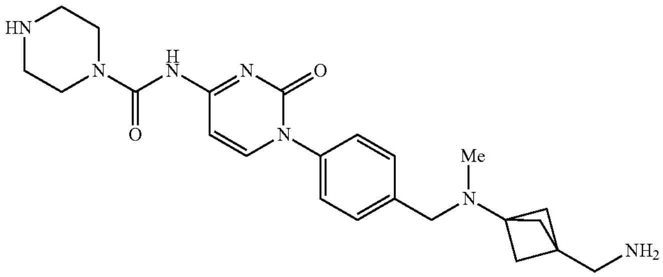 [SMILES: CN(Cc1ccc(-n2ccc(NC(=O)N3CCNCC3)nc2=O)cc1)C12CC(CN)(C1)C2] |

TABLE 11-continued
| Compounds of Formula V |
|---|
| 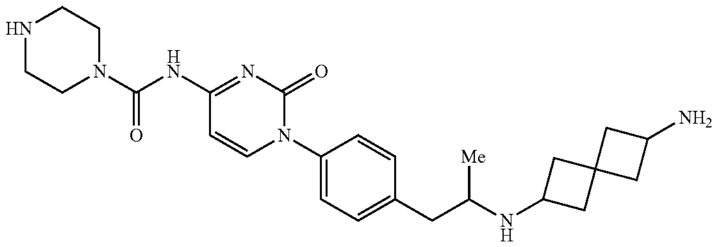 [SMILES: CC(Cc1ccc(-n2ccc(NC(=O)N3CCNCC3)nc2=O)cc1)NC1CC2(CC(N)C2)C1] |
| 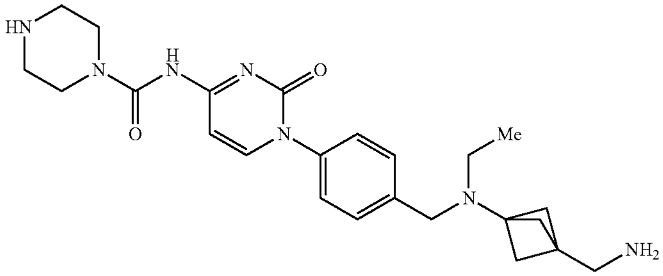 [SMILES: CCN(Cc1ccc(-n2ccc(NC(=O)N3CCNCC3)nc2=O)cc1)C12CC(CN)(C1)C2] |
| 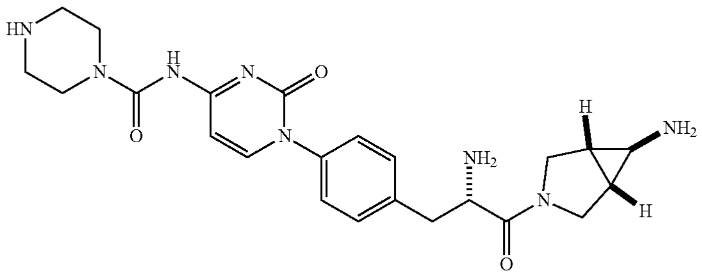 [SMILES: N[C@@H]1[C@H]2CN(C(=O)[C@@H](N)Cc3ccc(-n4ccc(NC(=O)N5CCNCC5)nc4=O)cc3)C[C@@H]12] |
| 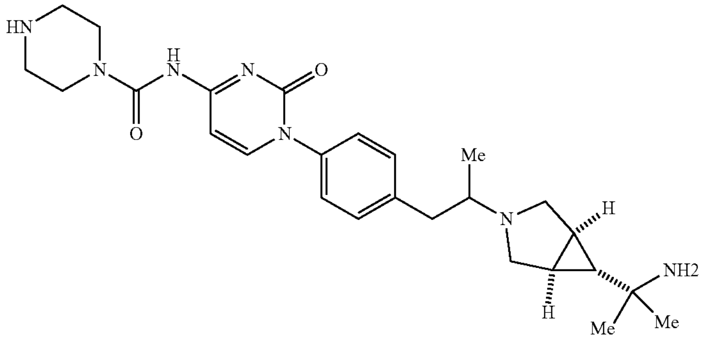 |
| 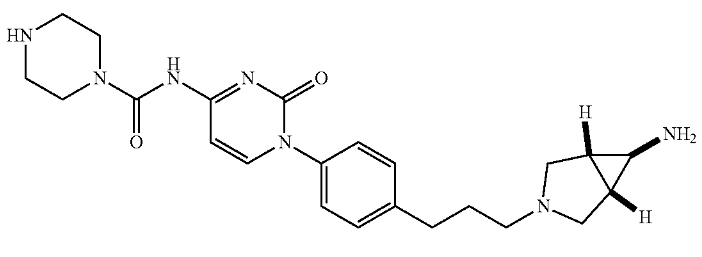 [SMILES: N[C@@H]1[C@H]2CN(CCCc3ccc(-n4ccc(NC(=O)N5CCNCC5)nc4=O)cc3)C[C@@H]12] |

TABLE 11-continued
Compounds of Formula V
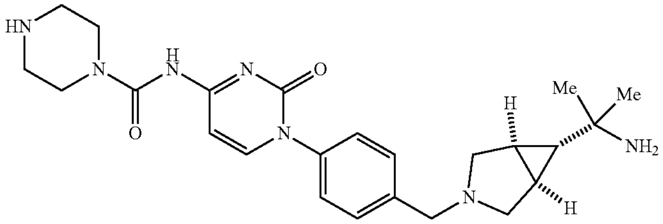
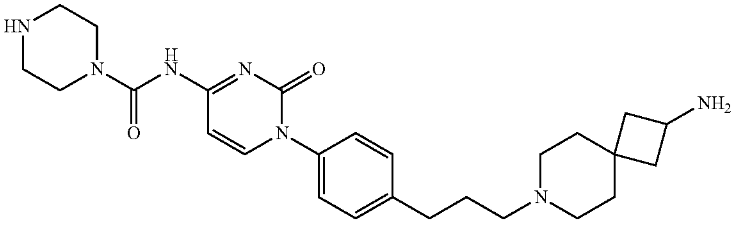 [SMILES: NC1CC2(CCN(CCCc3ccc(-n4ccc(NC(=O)N5CCNCC5)nc4=O)cc3)CC2)C1]
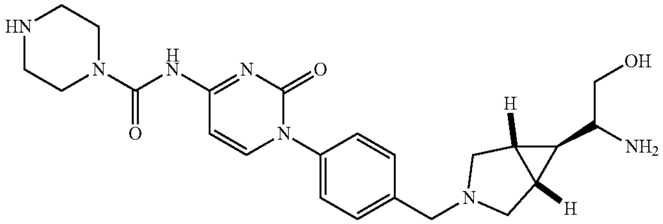 [SMILES: NC(CO)[C@H]1[C@@H]2CN(Cc3ccc(-n4ccc(NC(=O)N5CCNCC5)nc4=O)cc3)C[C@@H]21]
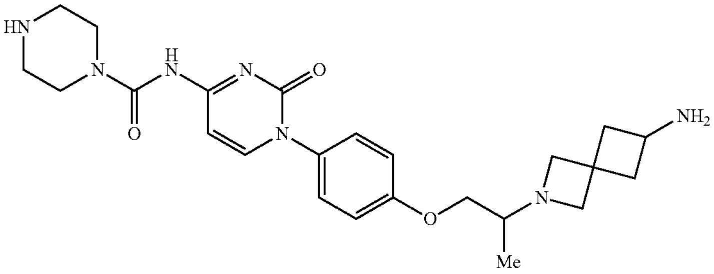 [SMILES: CC(COc1ccc(-n2ccc(NC(=O)N3CCNCC3)nc2=O)cc1)N1CC2(CC(N)C2)C1]
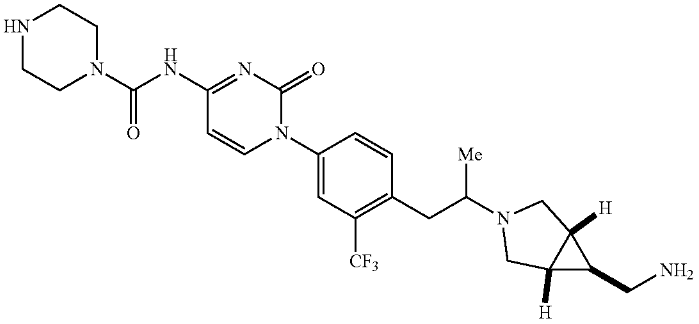
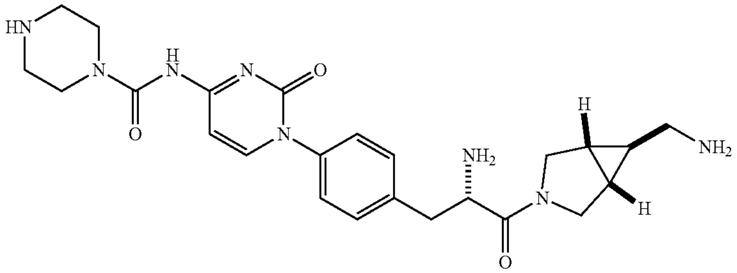 [SMILES: NC[C@@H]1[C@H]2CN(C(=O)[C@@H](N)Cc3ccc(-n4ccc(NC(=O)N5CCNCC5)nc4=O)cc3)C[C@@H]12]

TABLE 11-continued
| Compounds of Formula V |
| --- |
| 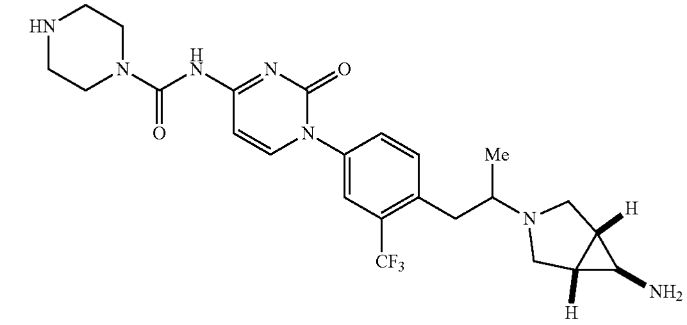 [SMILES: CC(Cc1ccc(-n2ccc(NC(=O)N3CCNCC3)nc2=O)cc1C(F)(F)F)N1C[C@@H]2[C@@H](N)[C@@H]2C1] |
| 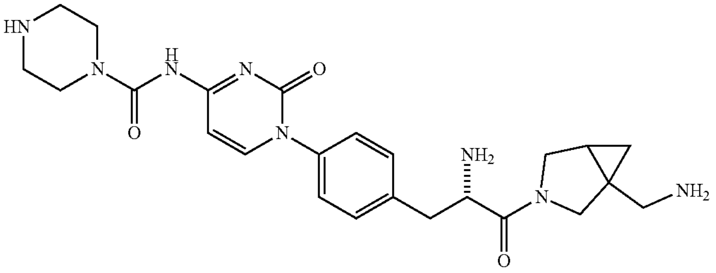 [SMILES: NCC12CC1CN(C(=O)[C@@H](N)Cc1ccc(-n3ccc(NC(=O)N4CCNCC4)nc3=O)cc1)C2] |
| 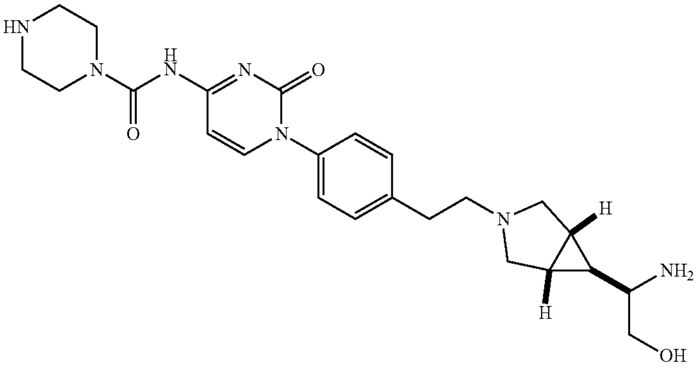 [SMILES: NC(CO)[C@H]1[C@@H]2CN(CCc3ccc(-n4ccc(NC(=O)N5CCNCC5)nc4=O)cc3)C[C@@H]21] |
| 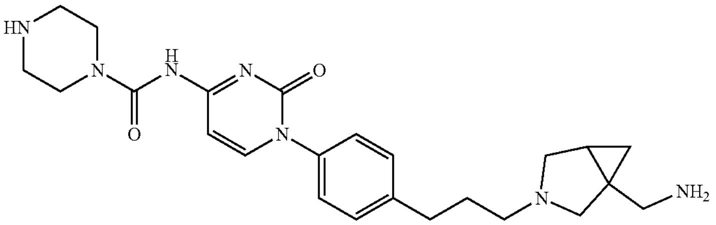 [SMILES: NCC12CC1CN(CCCc1ccc(-n3ccc(NC(=O)N4CCNCC4)nc3=O)cc1)C2] |
| 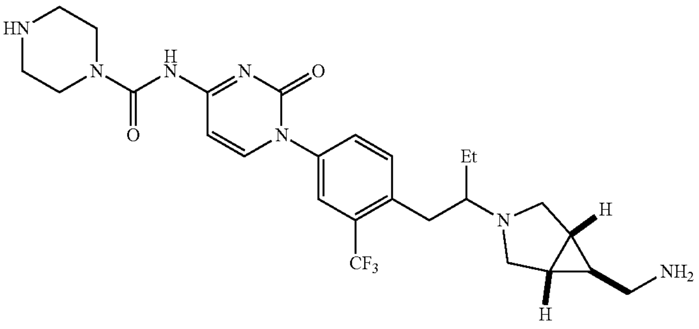 [SMILES: CCC(Cc1ccc(-n2ccc(NC(=O)N3CCNCC3)nc2=O)cc1C(F)(F)F)N1C[C@@H]2[C@@H](CN)[C@@H]2C1] |

TABLE 11-continued
| Compounds of Formula V |
| --- |
| 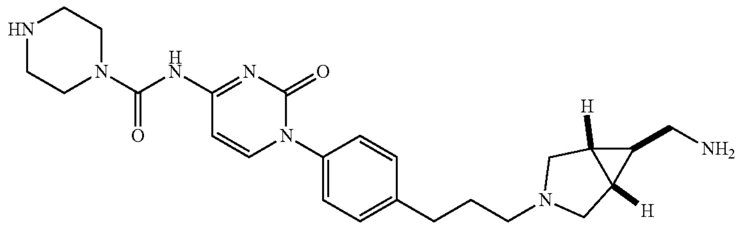 [SMILES: NC[C@@H]1[C@H]2CN(CCCc3ccc(-n4ccc(NC(=O)N5CCNCC5)nc4=O)cc3)C[C@@H]12] |
| 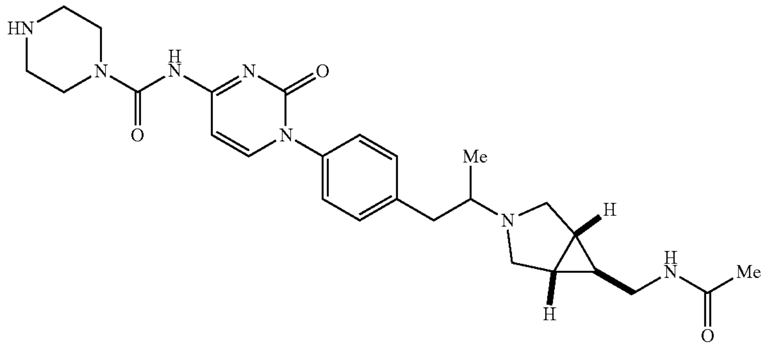 [SMILES: CC(=O)NC[C@@H]1[C@H]2CN(C(C)Cc3ccc(-n4ccc(NC(=O)N5CCNCC5)nc4=O)cc3)C[C@@H]12] |
| 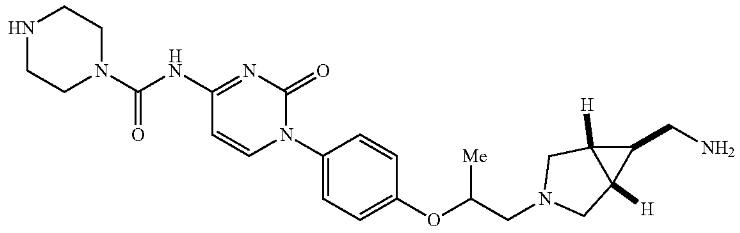 [SMILES: CC(CN1C[C@@H]2[C@@H](CN)[C@@H]2C1)Oc1ccc(-n2ccc(NC(=O)N3CCNCC3)nc2=O)cc1] |
| 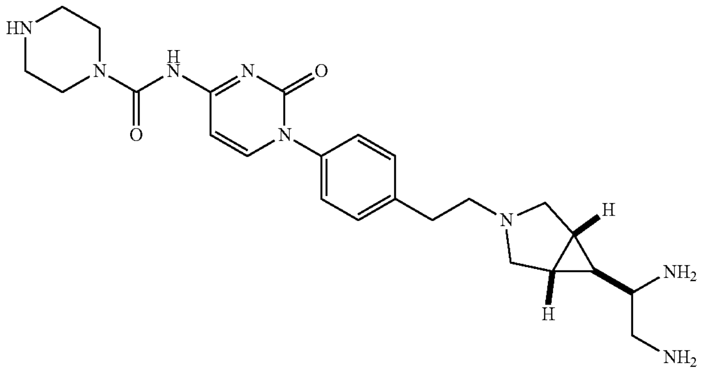 [SMILES: NCC(N)[C@H]1[C@@H]2CN(CCc3ccc(-n4ccc(NC(=O)N5CCNCC5)nc4=O)cc3)C[C@@H]21] |
| 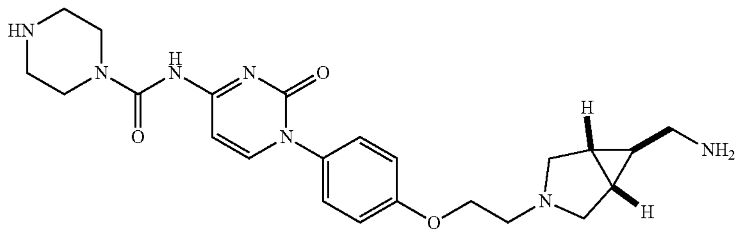 [SMILES: NC[C@@H]1[C@H]2CN(CCOc3ccc(-n4ccc(NC(=O)N5CCNCC5)nc4=O)cc3)C[C@@H]12] |

TABLE 11-continued
| Compounds of Formula V |
| --- |
| 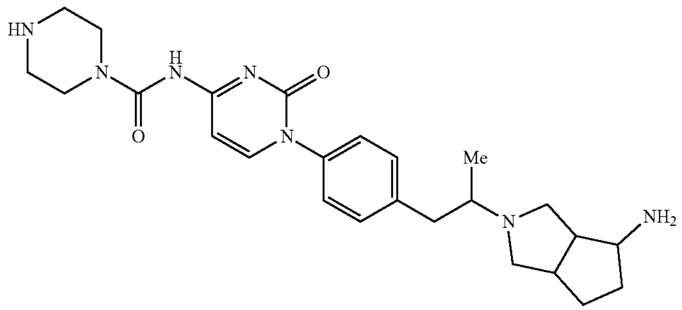 [SMILES: CC(Cc1ccc(-n2ccc(NC(=O)N3CCNCC3)nc2=O)cc1)N1CC2CCC(N)C2C1] |
| 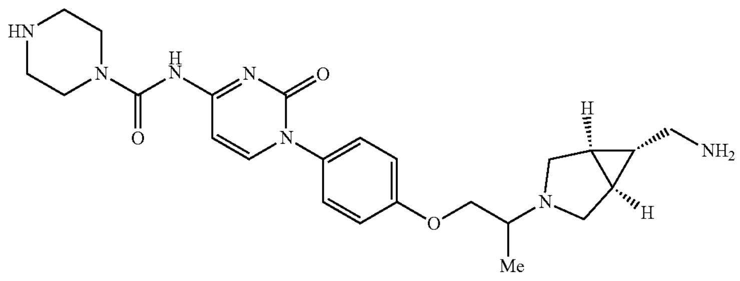 [SMILES: CC(COc1ccc(-n2ccc(NC(=O)N3CCNCC3)nc2=O)cc1)N1C[C@@H]2[C@@H](CN)[C@@H]2C1] |
| 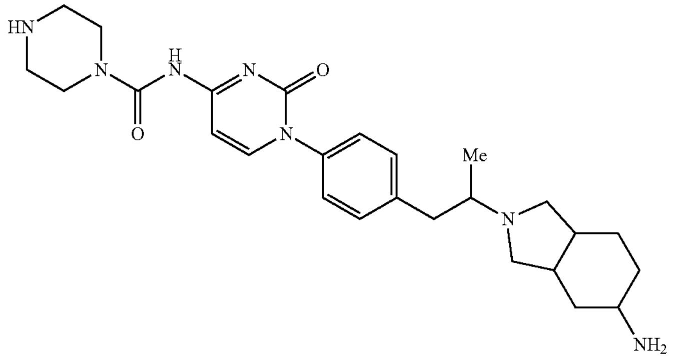 |
| 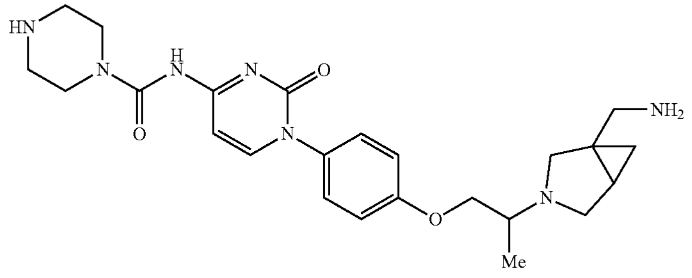 [SMILES: CC(COc1ccc(-n2ccc(NC(=O)N3CCNCC3)nc2=O)cc1)N1CC2CC2(CN)C1] |
| 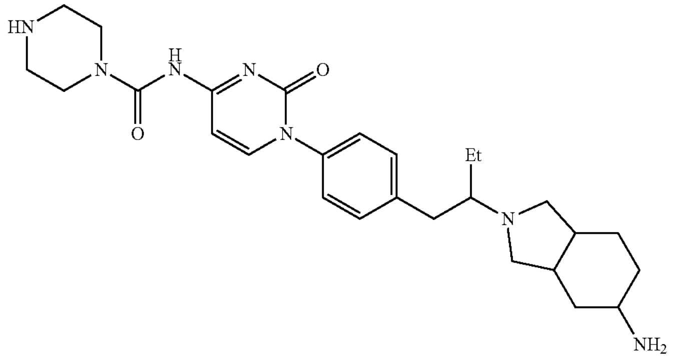 [SMILES: CCC(Cc1ccc(-n2ccc(NC(=O)N3CCNCC3)nc2=O)cc1)N1CC2CCC(N)CC2C1] |

TABLE 11-continued
| Compounds of Formula V |
|---|
| 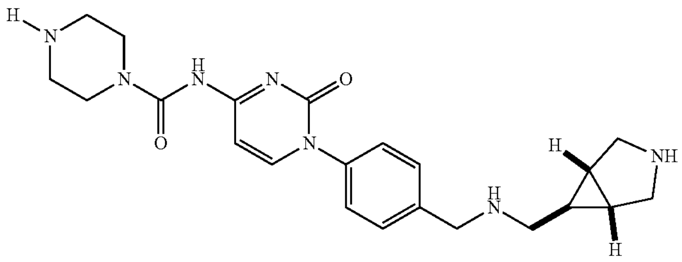 [SMILES: O=C(Nc1ccn(-c2ccc(CNC[C@@H]3[C@H]4CNC[C@@H]34)cc2)c(=O)n1)N1CCNCC1] |
| 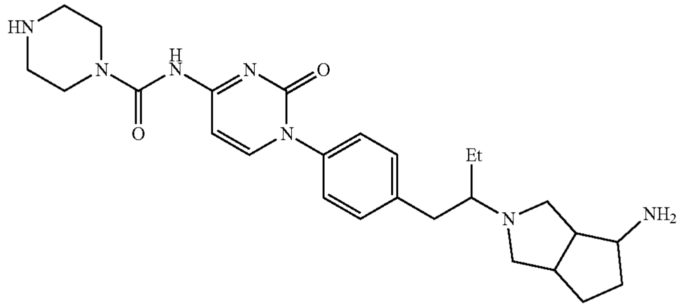 [SMILES: CCC(Cc1ccc(-n2ccc(NC(=O)N3CCNCC3)nc2=O)cc1)N1CC2CCC(N)C2C1] |
| 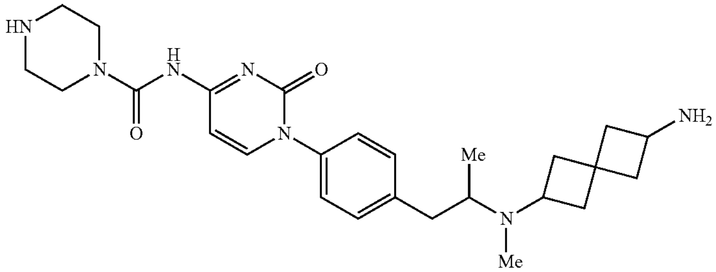 [SMILES: CC(Cc1ccc(-n2ccc(NC(=O)N3CCNCC3)nc2=O)cc1)N(C)C1CC2(CC(N)C2)C1] |
| 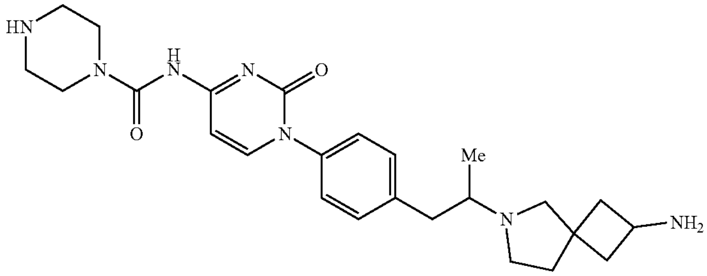 [SMILES: CC(Cc1ccc(-n2ccc(NC(=O)N3CCNCC3)nc2=O)cc1)N1CCC2(CC(N)C2)C1] |
| 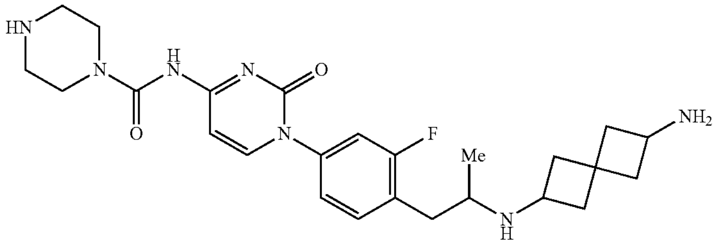 [SMILES: CC(Cc1ccc(-n2ccc(NC(=O)N3CCNCC3)nc2=O)cc1F)NC1CC2(CC(N)C2)C1] |

TABLE 11-continued
| Compounds of Formula V |
|---|
| 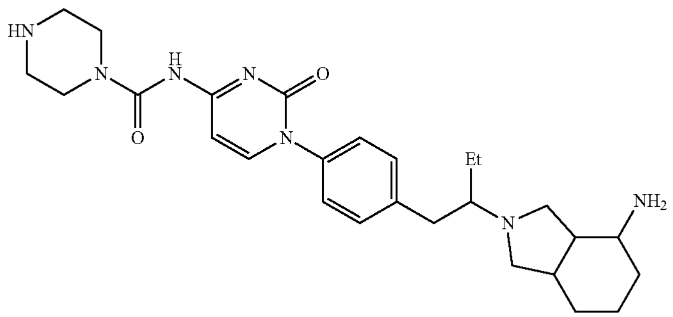 [SMILES: CCC(Cc1ccc(-n2ccc(NC(=O)N3CCNCC3)nc2=O)cc1)N1CC2CCCC(N)C2C1] |
| 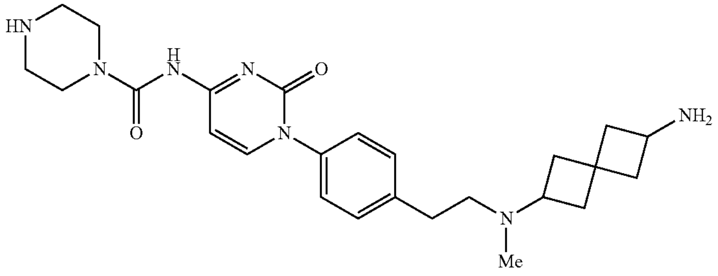 [SMILES: CN(CCc1ccc(-n2ccc(NC(=O)N3CCNCC3)nc2=O)cc1)C1CC2(CC(N)C2)C1] |
| 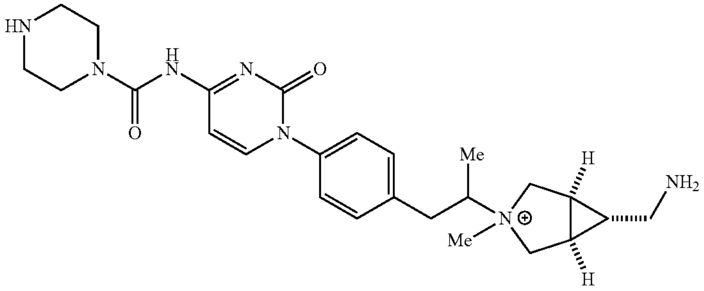 [SMILES: CC(Cc1ccc(-n2ccc(NC(=O)N3CCNCC3)nc2=O)cc1)[N+]1(C)C[C@@H]2[C@@H](CN)[C@@H]2C1] |
| 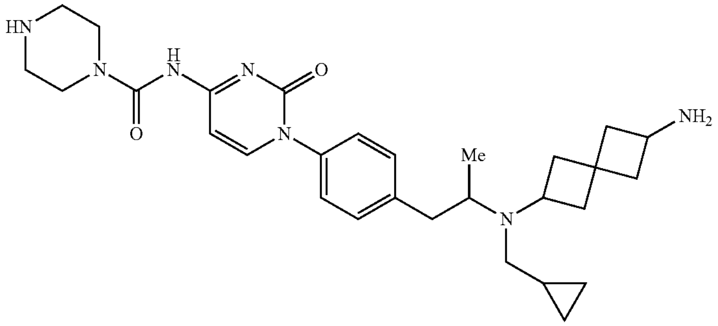 [SMILES: CC(Cc1ccc(-n2ccc(NC(=O)N3CCNCC3)nc2=O)cc1)N(CC1CC1)C1CC2(CC(N)C2)C1] |
| 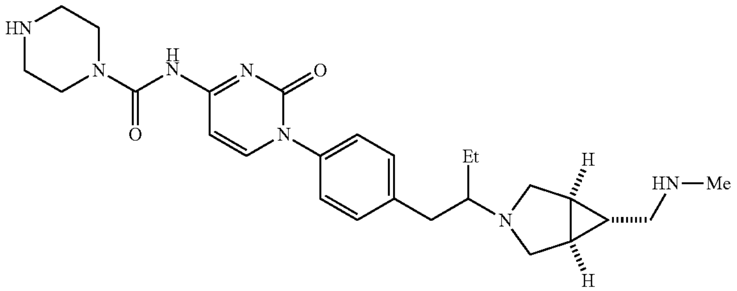 [SMILES: CCC(Cc1ccc(-n2ccc(NC(=O)N3CCNCC3)nc2=O)cc1)N1C[C@@H]2[C@@H](CNC)[C@@H]2C1] |

TABLE 11-continued
Compounds of Formula V
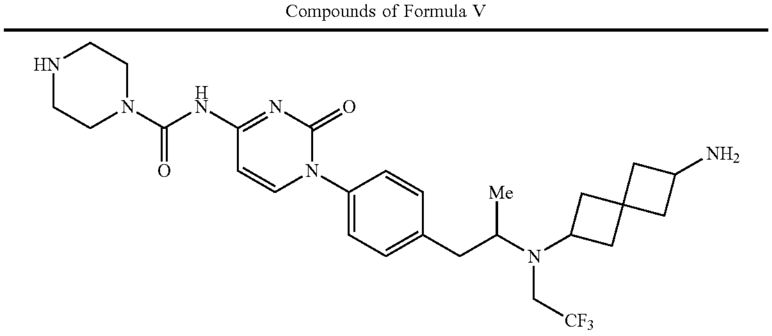
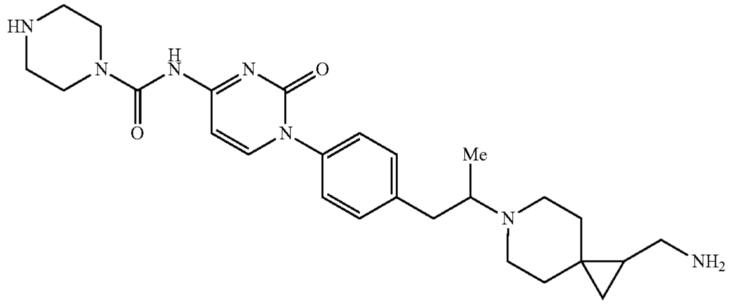 [SMILES: CC(Cc1ccc(-n2ccc(NC(=O)N3CCNCC3)nc2=O)cc1)N1CCC2(CC1)CC2CN]
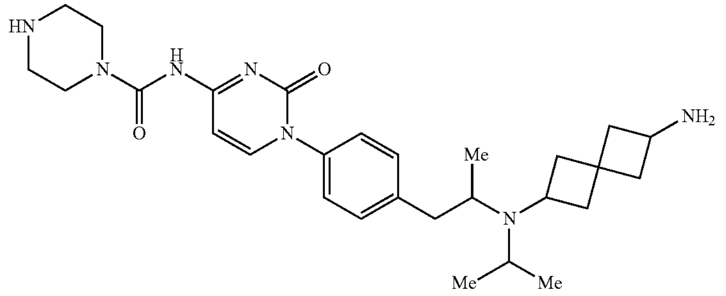 [SMILES: CC(C)N(C(C)Cc1ccc(-n2ccc(NC(=O)N3CCNCC3)nc2=O)cc1)C1CC2(CC(N)C2)C1]
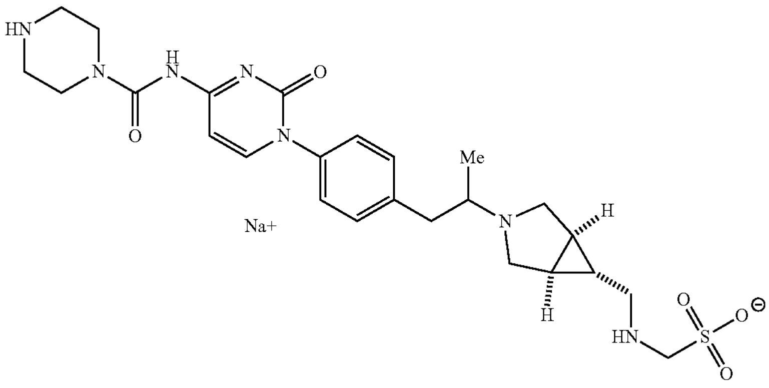 [SMILES: CC(Cc1ccc(-n2ccc(NC(=O)N3CCNCC3)nc2=O)cc1)N1C[C@@H]2[C@@H](CNCS(=O)(=O)[O-])[C@@H]2C1 ; [Na+]]
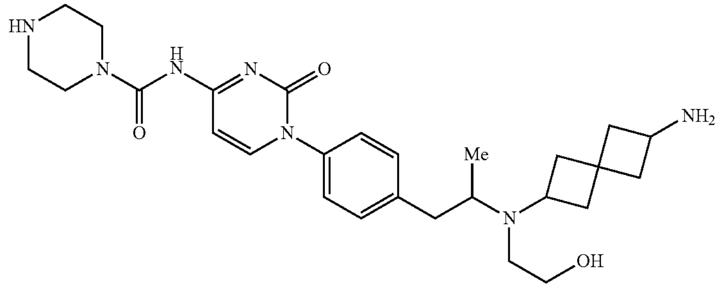 [SMILES: CC(Cc1ccc(-n2ccc(NC(=O)N3CCNCC3)nc2=O)cc1)N(CCO)C1CC2(CC(N)C2)C1]

TABLE 11-continued
Compounds of Formula V
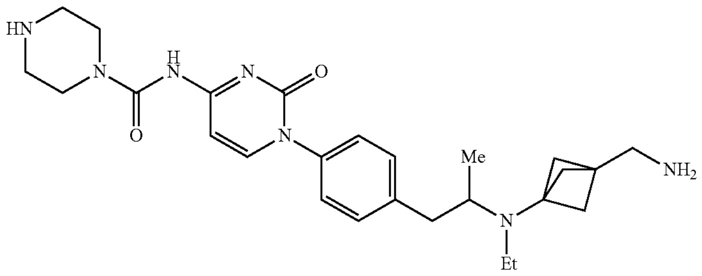 [SMILES: CCN(C(C)Cc1ccc(-n2ccc(NC(=O)N3CCNCC3)nc2=O)cc1)C12CC(CN)(C1)C2]
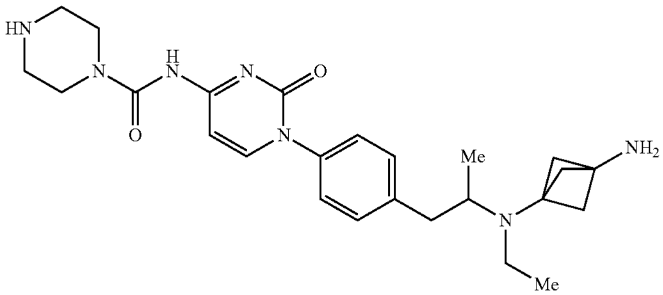 [SMILES: CCN(C(C)Cc1ccc(-n2ccc(NC(=O)N3CCNCC3)nc2=O)cc1)C12CC(N)(C1)C2]
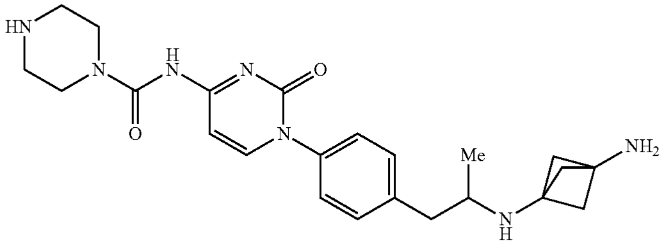 [SMILES: CC(Cc1ccc(-n2ccc(NC(=O)N3CCNCC3)nc2=O)cc1)NC12CC(N)(C1)C2]
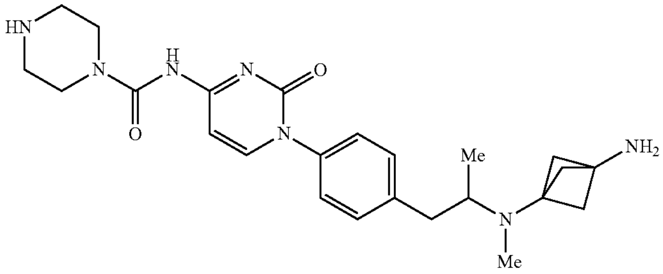 [SMILES: CC(Cc1ccc(-n2ccc(NC(=O)N3CCNCC3)nc2=O)cc1)N(C)C12CC(N)(C1)C2]
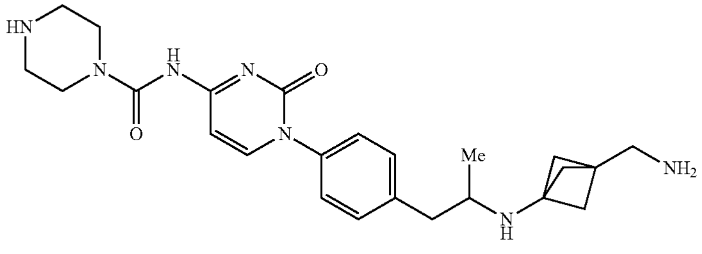 [SMILES: CC(Cc1ccc(-n2ccc(NC(=O)N3CCNCC3)nc2=O)cc1)NC12CC(CN)(C1)C2]

TABLE 11-continued

| Compounds of Formula V |
| --- |
| 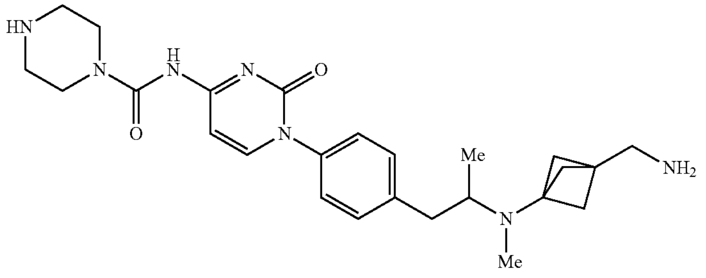 [SMILES: CC(Cc1ccc(-n2ccc(NC(=O)N3CCNCC3)nc2=O)cc1)N(C)C12CC(CN)(C1)C2] |
| 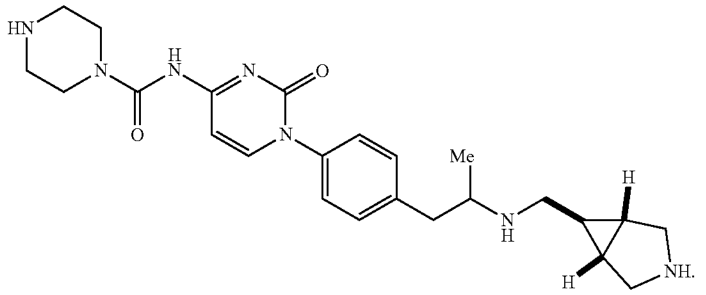 |

In another embodiment, the compound of formula I-5 is selected from the compounds as depicted in Table 11.

In another aspect, the disclosure provides a compound of formula VI:

VI

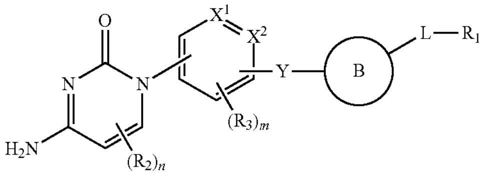

or a pharmaceutically acceptable salt thereof, wherein the variables have the definitions as disclosed herein.

In another embodiment, the compound of formula VI is selected from the compounds as depicted in Table 12 below.

TABLE 12

| Compounds of Formula VI |
| --- |
| Structure |
| 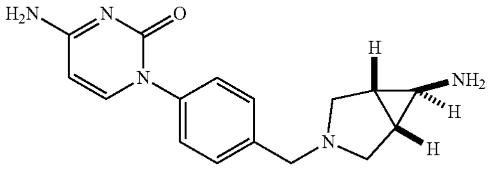 [SMILES: Nc1ccn(-c2ccc(CN3C[C@@H]4[C@@H](N)[C@@H]4C3)cc2)c(=O)n1] |

TABLE 12-continued
| Compounds of Formula VI |
| --- |
| Structure |
| 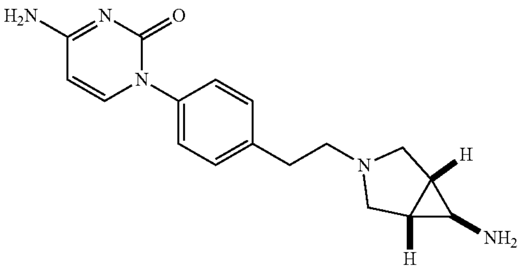 [SMILES: Nc1ccn(-c2ccc(CCN3C[C@@H]4[C@@H](N)[C@@H]4C3)cc2)c(=O)n1] |
| 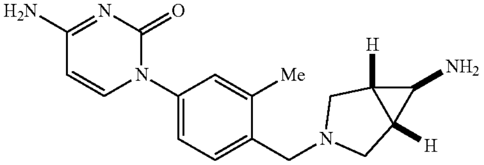 [SMILES: Cc1cc(-n2ccc(N)nc2=O)ccc1CN1C[C@@H]2[C@@H](N)[C@@H]2C1] |
| 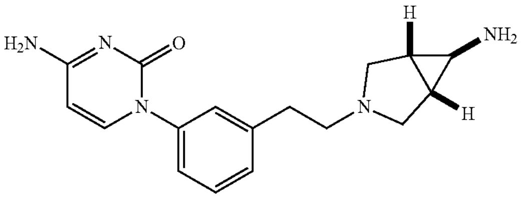 [SMILES: Nc1ccn(-c2cccc(CCN3C[C@@H]4[C@@H](N)[C@@H]4C3)c2)c(=O)n1] |
| 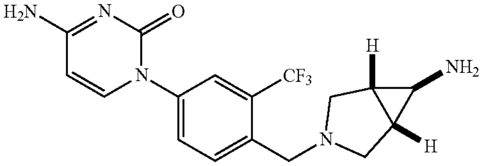 [SMILES: Nc1ccn(-c2ccc(CN3C[C@@H]4[C@@H](N)[C@@H]4C3)c(C(F)(F)F)c2)c(=O)n1] |
| 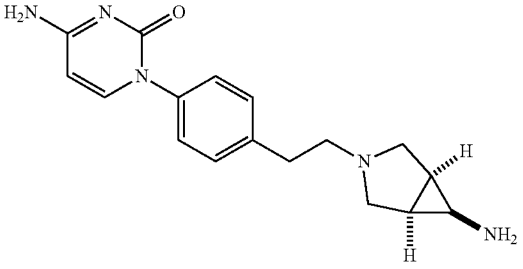 [SMILES: Nc1ccn(-c2ccc(CCN3C[C@@H]4[C@H](N)[C@@H]4C3)cc2)c(=O)n1] |
| 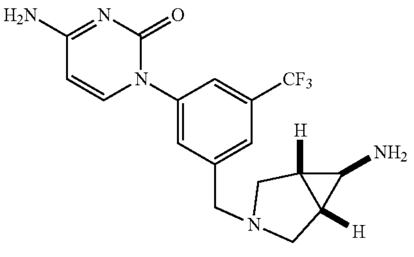 [SMILES: Nc1ccn(-c2cc(CN3C[C@@H]4[C@@H](N)[C@@H]4C3)cc(C(F)(F)F)c2)c(=O)n1] |

TABLE 12-continued
| Compounds of Formula VI |
|---|
| Structure |
| 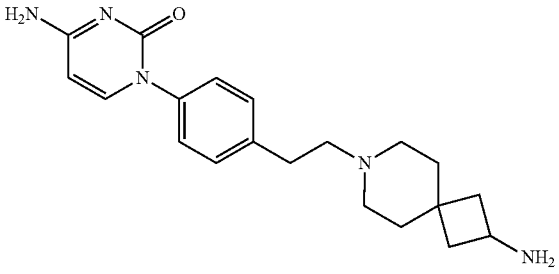 [SMILES: Nc1ccn(-c2ccc(CCN3CCC4(CC3)CC(N)C4)cc2)c(=O)n1] |
| 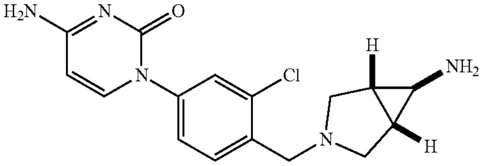 [SMILES: Nc1ccn(-c2ccc(CN3C[C@@H]4[C@@H](N)[C@@H]4C3)c(Cl)c2)c(=O)n1] |
| 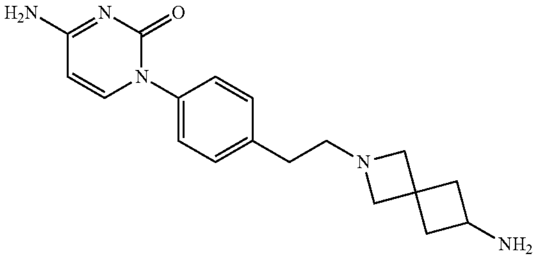 [SMILES: Nc1ccn(-c2ccc(CCN3CC4(CC(N)C4)C3)cc2)c(=O)n1] |
| 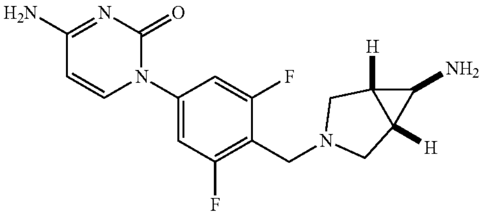 [SMILES: Nc1ccn(-c2cc(F)c(CN3C[C@@H]4[C@@H](N)[C@@H]4C3)c(F)c2)c(=O)n1] |
| 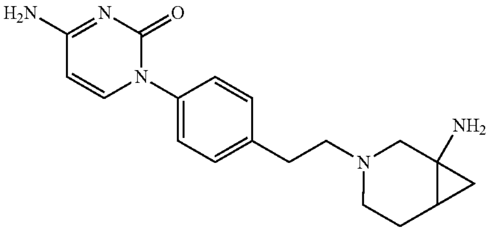 [SMILES: Nc1ccn(-c2ccc(CCN3CCC4CC4(N)C3)cc2)c(=O)n1] |
| 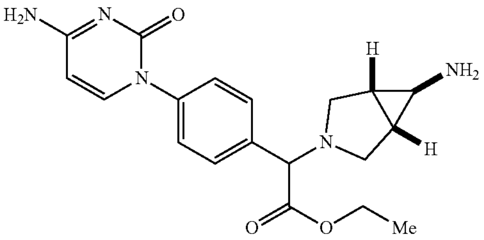 [SMILES: CCOC(=O)C(c1ccc(-n2ccc(N)nc2=O)cc1)N1C[C@@H]2[C@@H](N)[C@@H]2C1] |

TABLE 12-continued
| Compounds of Formula VI |
| --- |
| Structure |
| 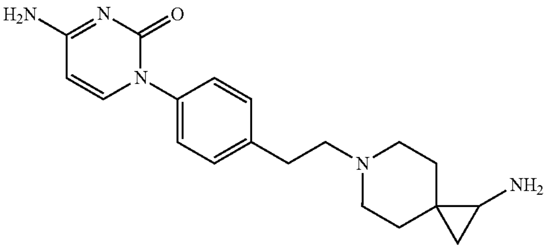 [SMILES: Nc1ccn(-c2ccc(CCN3CCC4(CC3)CC4N)cc2)c(=O)n1] |
| 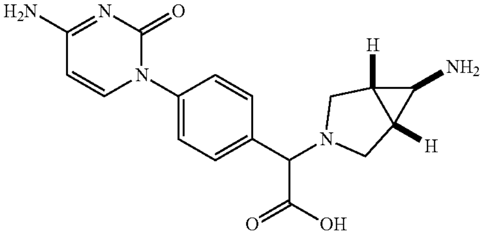 [SMILES: Nc1ccn(-c2ccc(C(C(=O)O)N3C[C@@H]4[C@@H](N)[C@@H]4C3)cc2)c(=O)n1] |
| 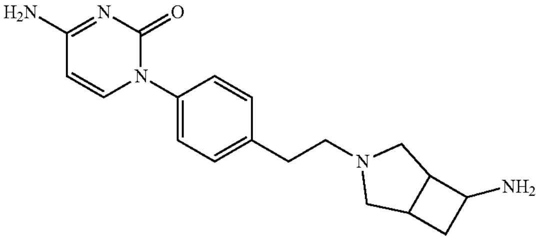 [SMILES: Nc1ccn(-c2ccc(CCN3CC4CC(N)C4C3)cc2)c(=O)n1] |
| 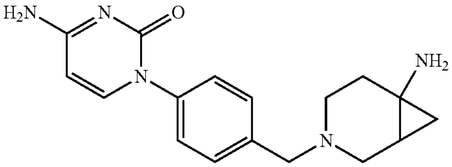 [SMILES: Nc1ccn(-c2ccc(CN3CCC4(N)CC4C3)cc2)c(=O)n1] |
| 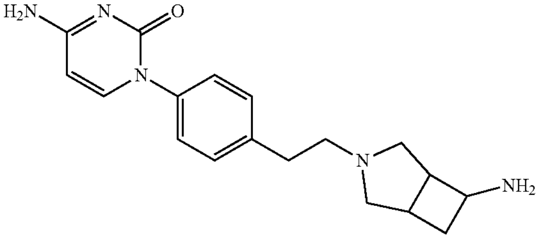 [SMILES: Nc1ccn(-c2ccc(CCN3CC4CC(N)C4C3)cc2)c(=O)n1] |
| 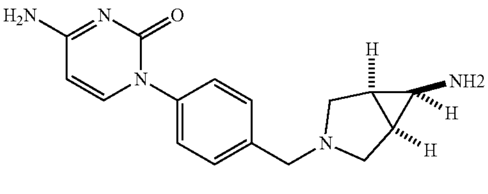 [SMILES: Nc1ccn(-c2ccc(CN3C[C@@H]4[C@H](N)[C@@H]4C3)cc2)c(=O)n1] |

TABLE 12-continued
| Compounds of Formula VI |
|---|
| Structure |
| 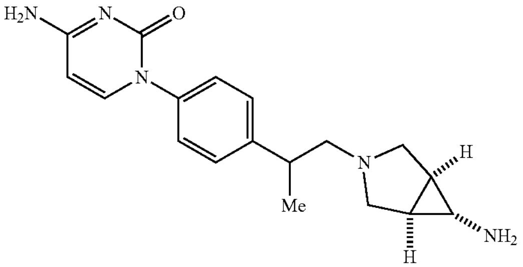 [SMILES: CC(CN1C[C@@H]2[C@@H](N)[C@@H]2C1)c1ccc(-n2ccc(N)nc2=O)cc1] |
| 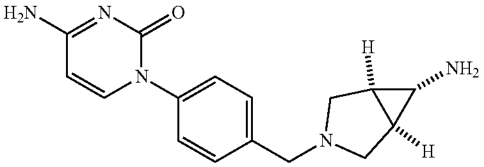 [SMILES: Nc1ccn(-c2ccc(CN3C[C@@H]4[C@@H](N)[C@@H]4C3)cc2)c(=O)n1] |
| 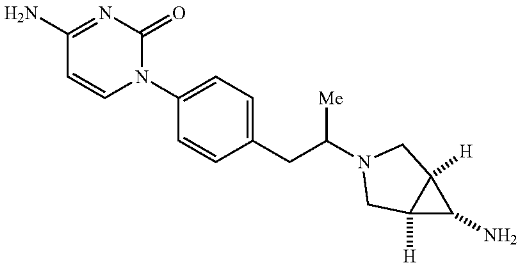 [SMILES: CC(Cc1ccc(-n2ccc(N)nc2=O)cc1)N1C[C@@H]2[C@@H](N)[C@@H]2C1] |
| 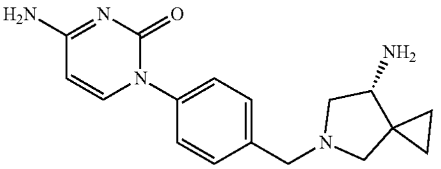 [SMILES: Nc1ccn(-c2ccc(CN3C[C@H](N)C4(CC4)C3)cc2)c(=O)n1] |
| 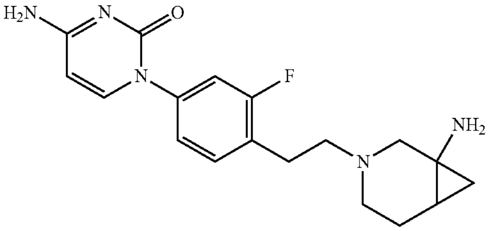 [SMILES: Nc1ccn(-c2ccc(CCN3CCC4CC4(N)C3)c(F)c2)c(=O)n1] |
| 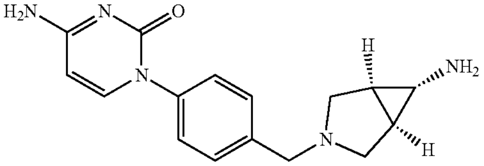 [SMILES: Nc1ccn(-c2ccc(CN3C[C@@H]4[C@@H](N)[C@@H]4C3)cc2)c(=O)n1] |
| 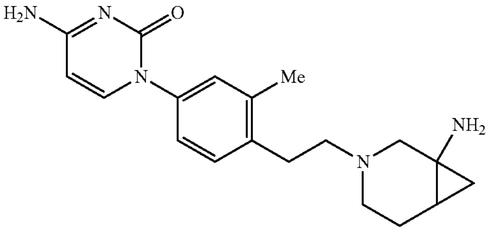 [SMILES: Cc1cc(-n2ccc(N)nc2=O)ccc1CCN1CCC2CC2(N)C1] |

TABLE 12-continued
| Compounds of Formula VI |
| --- |
| Structure |
| 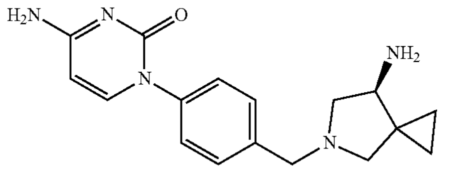 [SMILES: Nc1ccn(-c2ccc(CN3C[C@@H](N)C4(CC4)C3)cc2)c(=O)n1] |
| 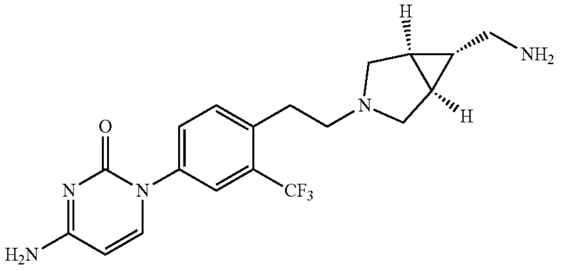 [SMILES: NC[C@@H]1[C@H]2CN(CCc3ccc(-n4ccc(N)nc4=O)cc3C(F)(F)F)C[C@@H]12] |
| 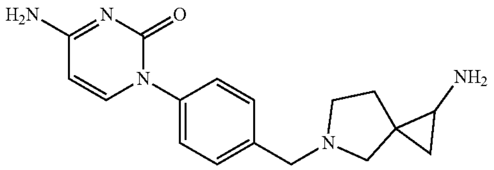 [SMILES: Nc1ccn(-c2ccc(CN3CCC4(CC4N)C3)cc2)c(=O)n1] |
| 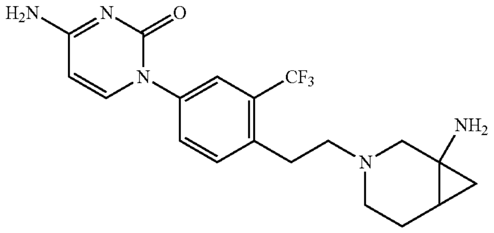 [SMILES: Nc1ccn(-c2ccc(CCN3CCC4CC4(N)C3)c(C(F)(F)F)c2)c(=O)n1] |
| 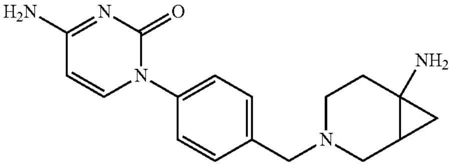 [SMILES: Nc1ccn(-c2ccc(CN3CCC4(N)CC4C3)cc2)c(=O)n1] |
| 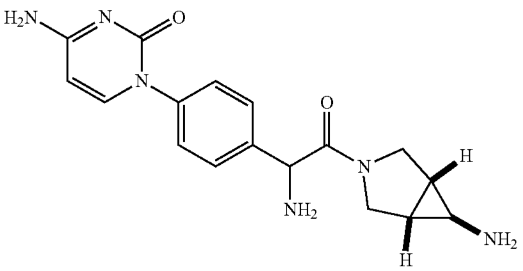 [SMILES: Nc1ccn(-c2ccc(C(N)C(=O)N3C[C@@H]4[C@@H](N)[C@@H]4C3)cc2)c(=O)n1] |
| 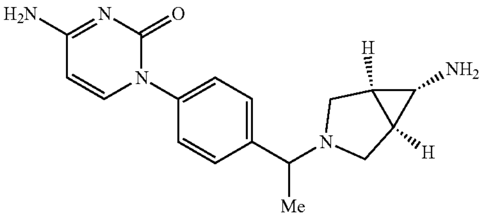 [SMILES: CC(c1ccc(-n2ccc(N)nc2=O)cc1)N1C[C@@H]2[C@@H](N)[C@@H]2C1] |

TABLE 12-continued
| Compounds of Formula VI |
| --- |
| Structure |
| 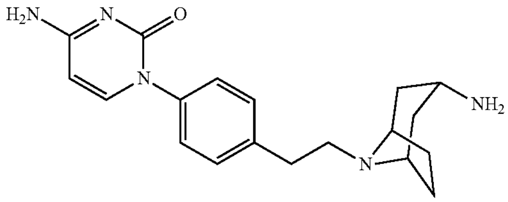 [SMILES: Nc1ccn(-c2ccc(CCN3C4CCC3CC(N)C4)cc2)c(=O)n1] |
| 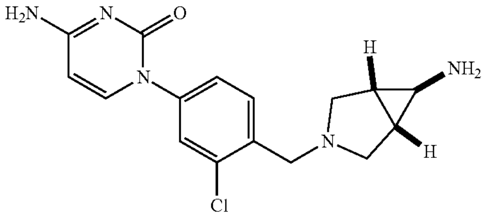 [SMILES: Nc1ccn(-c2ccc(CN3C[C@@H]4[C@@H](N)[C@@H]4C3)c(Cl)c2)c(=O)n1] |
| 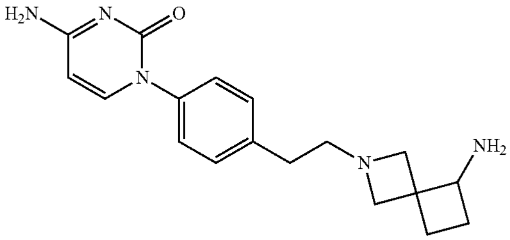 [SMILES: Nc1ccn(-c2ccc(CCN3CC4(CCC4N)C3)cc2)c(=O)n1] |
| 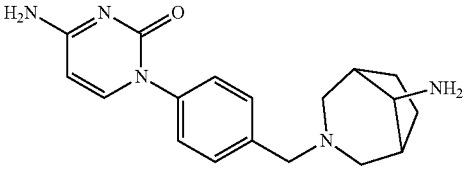 [SMILES: Nc1ccn(-c2ccc(CN3CC4CCC(C3)C4N)cc2)c(=O)n1] |
| 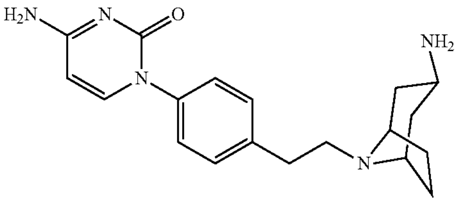 [SMILES: Nc1ccn(-c2ccc(CCN3C4CCC3CC(N)C4)cc2)c(=O)n1] |
| 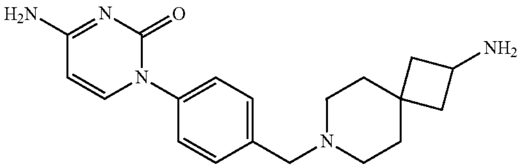 [SMILES: Nc1ccn(-c2ccc(CN3CCC4(CC3)CC(N)C4)cc2)c(=O)n1] |
| 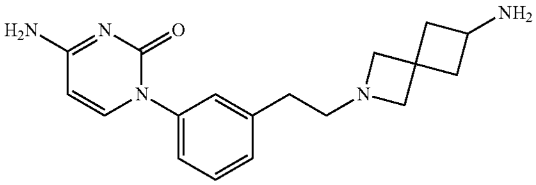 [SMILES: Nc1ccn(-c2cccc(CCN3CC4(CC(N)C4)C3)c2)c(=O)n1] |

TABLE 12-continued
| Compounds of Formula VI |
|---|
| Structure |
| 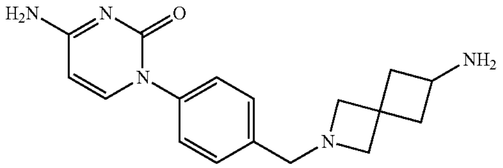 [SMILES: Nc1ccn(-c2ccc(CN3CC4(CC(N)C4)C3)cc2)c(=O)n1] |
| 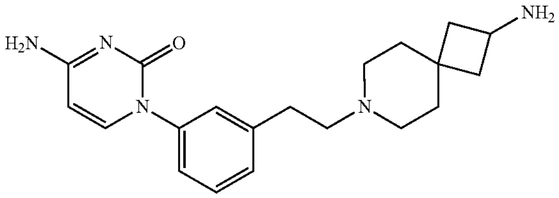 [SMILES: Nc1ccn(-c2cccc(CCN3CCC4(CC3)CC(N)C4)c2)c(=O)n1] |
| 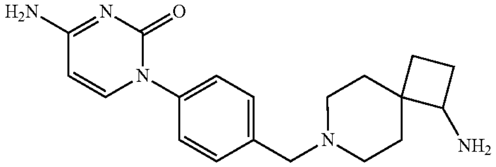 [SMILES: Nc1ccn(-c2ccc(CN3CCC4(CCC4N)CC3)cc2)c(=O)n1] |
| 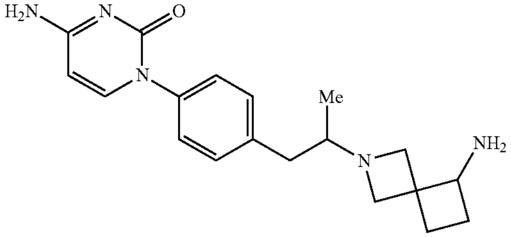 [SMILES: CC(Cc1ccc(-n2ccc(N)nc2=O)cc1)N1CC2(CCC2N)C1] |
| 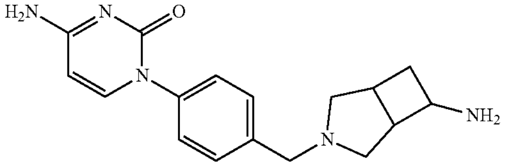 [SMILES: Nc1ccn(-c2ccc(CN3CC4CC(N)C4C3)cc2)c(=O)n1] |
| 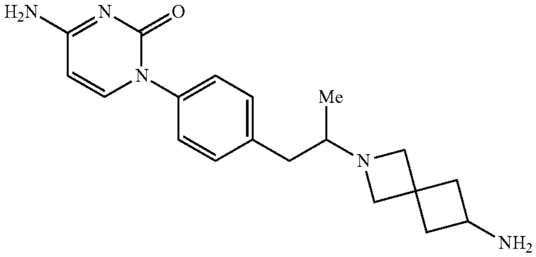 [SMILES: CC(Cc1ccc(-n2ccc(N)nc2=O)cc1)N1CC2(CC(N)C2)C1] |
| 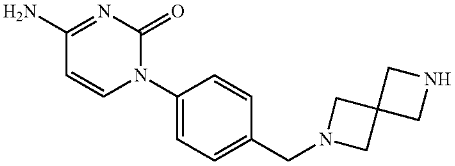 [SMILES: Nc1ccn(-c2ccc(CN3CC4(CNC4)C3)cc2)c(=O)n1] |

TABLE 12-continued
| Compounds of Formula VI |
| --- |
| Structure |
| 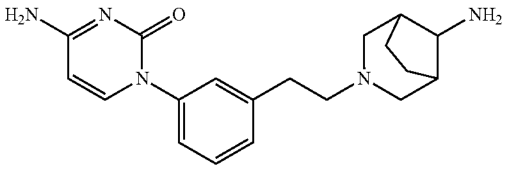 [SMILES: Nc1ccn(-c2cccc(CCN3CC4CCC(C3)C4N)c2)c(=O)n1] |
| 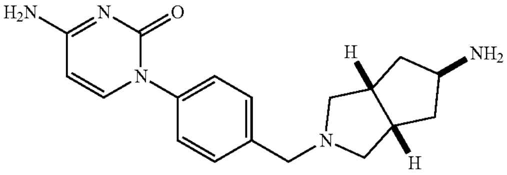 [SMILES: Nc1ccn(-c2ccc(CN3C[C@H]4C[C@H](N)C[C@H]4C3)cc2)c(=O)n1] |
| 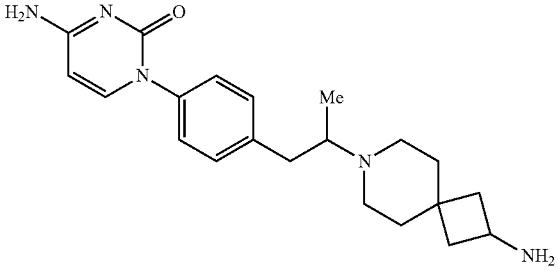 [SMILES: CC(Cc1ccc(-n2ccc(N)nc2=O)cc1)N1CCC2(CC1)CC(N)C2] |
| 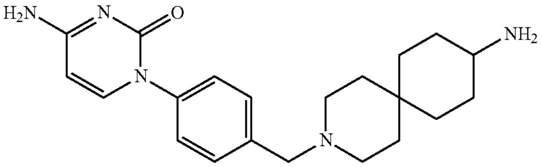 [SMILES: Nc1ccn(-c2ccc(CN3CCC4(CCC(N)CC4)CC3)cc2)c(=O)n1] |
| 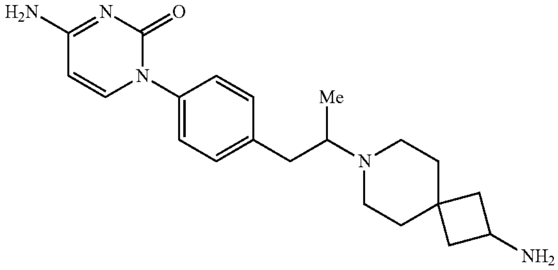 [SMILES: CC(Cc1ccc(-n2ccc(N)nc2=O)cc1)N1CCC2(CC1)CC(N)C2] |
| 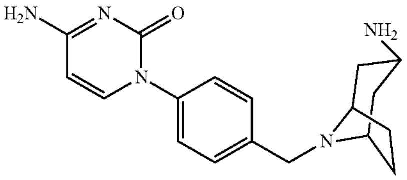 [SMILES: Nc1ccn(-c2ccc(CN3C4CCC3CC(N)C4)cc2)c(=O)n1] |
| 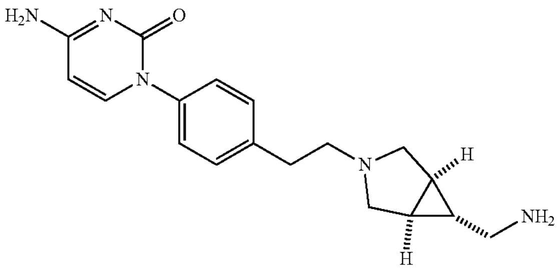 [SMILES: NC[C@@H]1[C@H]2CN(CCc3ccc(-n4ccc(N)nc4=O)cc3)C[C@@H]12] |

TABLE 12-continued
| Compounds of Formula VI |
|---|
| Structure |
| 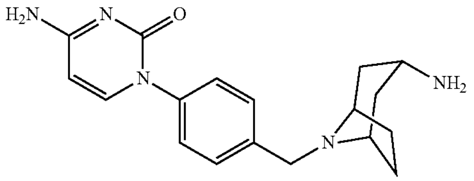 [SMILES: Nc1ccn(-c2ccc(CN3C4CCC3CC(N)C4)cc2)c(=O)n1] |
| 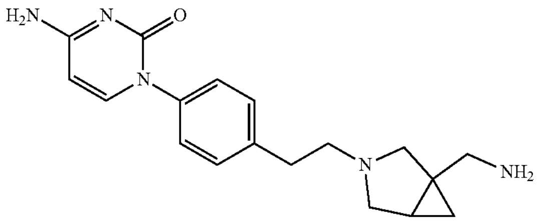 [SMILES: NCC12CC1CN(CCc1ccc(-n3ccc(N)nc3=O)cc1)C2] |
| 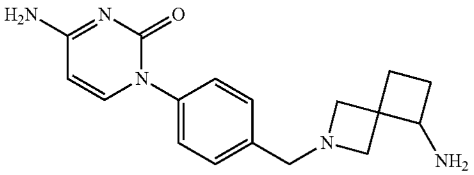 [SMILES: Nc1ccn(-c2ccc(CN3CC4(CCC4N)C3)cc2)c(=O)n1] |
| 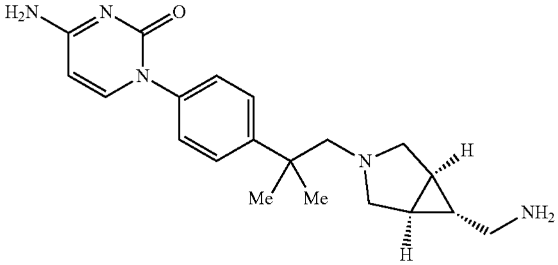 [SMILES: CC(C)(CN1C[C@@H]2[C@@H](CN)[C@@H]2C1)c1ccc(-n2ccc(N)nc2=O)cc1] |
| 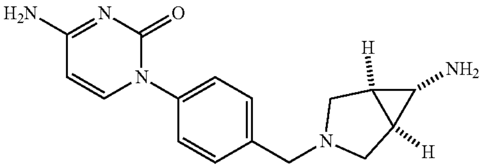 [SMILES: Nc1ccn(-c2ccc(CN3C[C@@H]4[C@@H](N)[C@@H]4C3)cc2)c(=O)n1] |
| 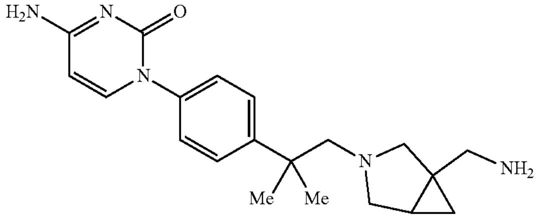 [SMILES: CC(C)(CN1CC2CC2(CN)C1)c1ccc(-n2ccc(N)nc2=O)cc1] |
| 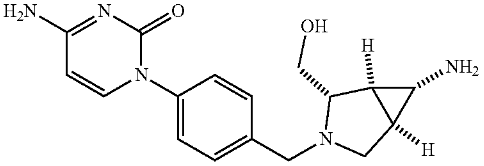 [SMILES: Nc1ccn(-c2ccc(CN3C[C@@H]4[C@@H](N)[C@@H]4[C@H]3CO)cc2)c(=O)n1] |

TABLE 12-continued
| Compounds of Formula VI |
|---|
| Structure |
| 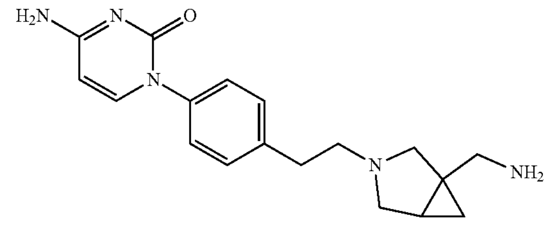 [SMILES: NCC12CC1CN(CCc1ccc(-n3ccc(N)nc3=O)cc1)C2] |
| 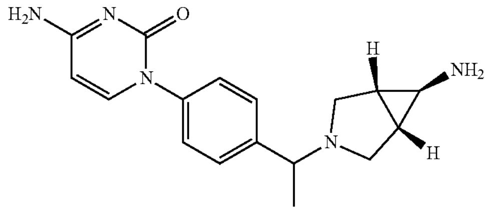 [SMILES: CC(c1ccc(-n2ccc(N)nc2=O)cc1)N1C[C@@H]2[C@@H](N)[C@@H]2C1] |
| 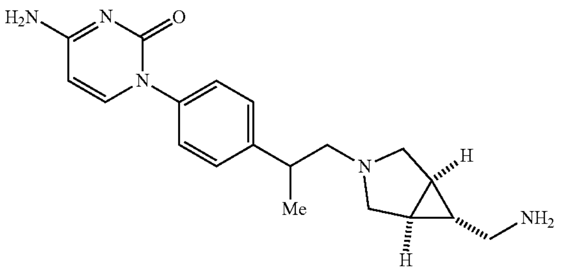 [SMILES: CC(CN1C[C@@H]2[C@@H](CN)[C@@H]2C1)c1ccc(-n2ccc(N)nc2=O)cc1] |
| 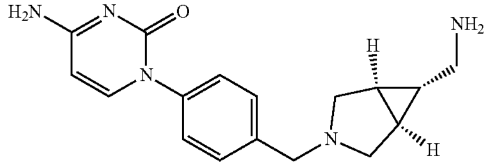 [SMILES: NC[C@@H]1[C@H]2CN(Cc3ccc(-n4ccc(N)nc4=O)cc3)C[C@@H]12] |
| 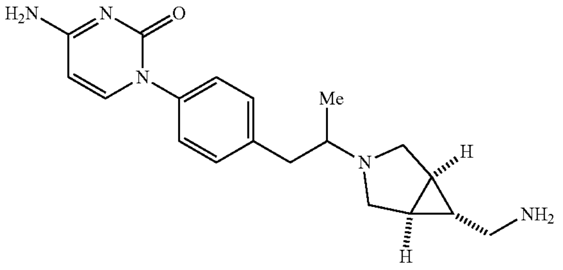 [SMILES: CC(Cc1ccc(-n2ccc(N)nc2=O)cc1)N1C[C@@H]2[C@@H](CN)[C@@H]2C1] |
| 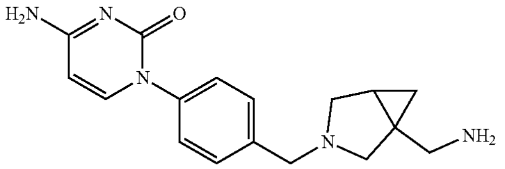 [SMILES: NCC12CC1CN(Cc1ccc(-n3ccc(N)nc3=O)cc1)C2] |

TABLE 12-continued
| Compounds of Formula VI |
| --- |
| Structure |
| 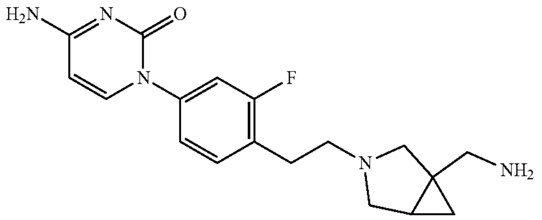 [SMILES: NCC12CC1CN(CCc1ccc(-n3ccc(N)nc3=O)cc1F)C2] |
| 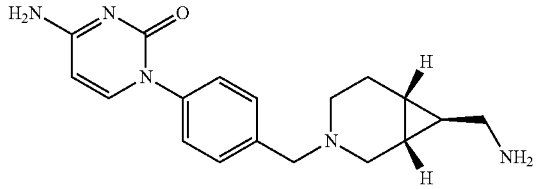 [SMILES: NC[C@@H]1[C@H]2CCN(Cc3ccc(-n4ccc(N)nc4=O)cc3)C[C@@H]12] |
| 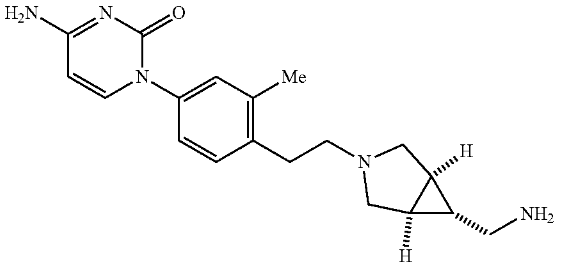 [SMILES: Cc1cc(-n2ccc(N)nc2=O)ccc1CCN1C[C@@H]2[C@@H](CN)[C@@H]2C1] |
| 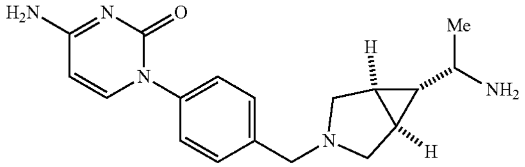 [SMILES: C[C@H](N)C1[C@H]2CN(Cc3ccc(-n4ccc(N)nc4=O)cc3)C[C@@H]12] |
| 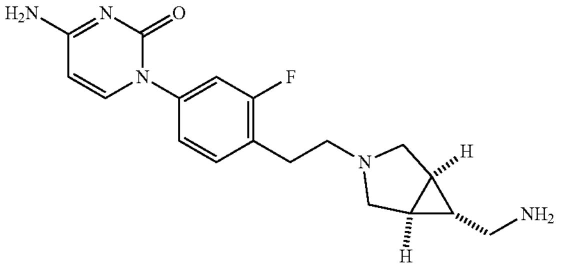 [SMILES: NC[C@@H]1[C@H]2CN(CCc3ccc(-n4ccc(N)nc4=O)cc3F)C[C@@H]12] |
| 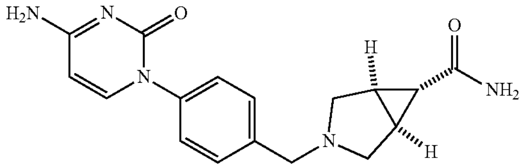 |
| 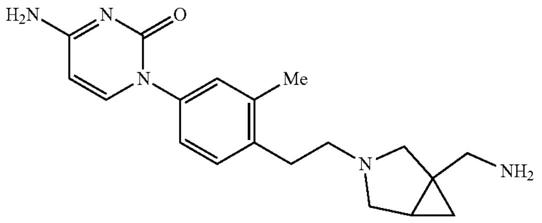 [SMILES: Cc1cc(-n2ccc(N)nc2=O)ccc1CCN1CC2CC2(CN)C1] |

TABLE 12-continued
| Compounds of Formula VI |
|---|
| Structure |
| 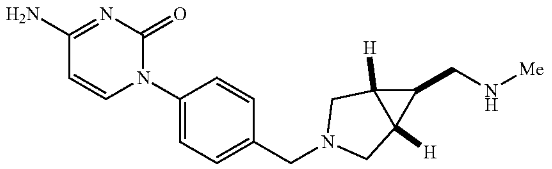 [SMILES: CNC[C@@H]1[C@H]2CN(Cc3ccc(-n4ccc(N)nc4=O)cc3)C[C@@H]12] |
| 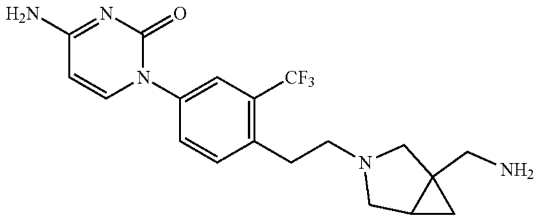 [SMILES: NCC12CC1CN(CCc1ccc(-n3ccc(N)nc3=O)cc1C(F)(F)F)C2] |
| 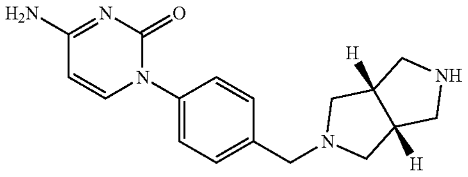 [SMILES: Nc1ccn(-c2ccc(CN3C[C@H]4CNC[C@H]4C3)cc2)c(=O)n1] |
| 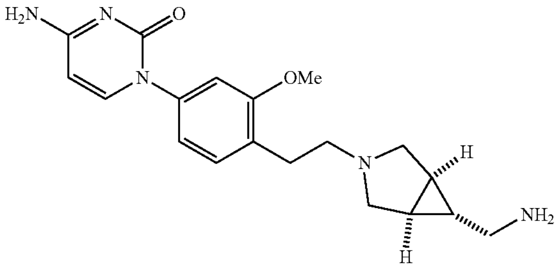 [SMILES: COc1cc(-n2ccc(N)nc2=O)ccc1CCN1C[C@@H]2[C@@H](CN)[C@@H]2C1] |
| 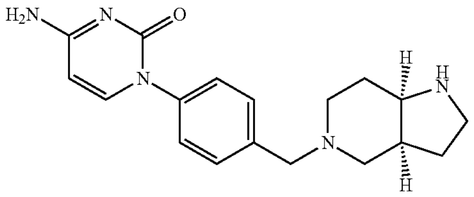 [SMILES: Nc1ccn(-c2ccc(CN3CC[C@H]4NCC[C@H]4C3)cc2)c(=O)n1] |
| 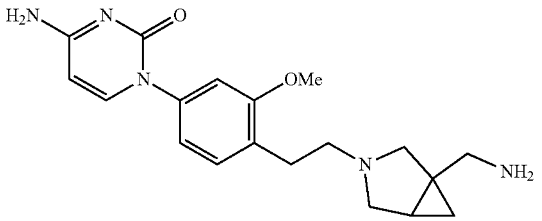 [SMILES: COc1cc(-n2ccc(N)nc2=O)ccc1CCN1CC2CC2(CN)C1] |
| 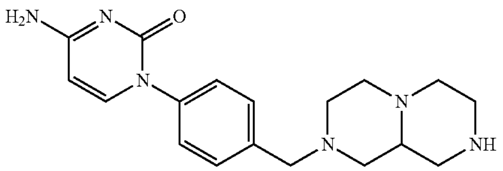 [SMILES: Nc1ccn(-c2ccc(CN3CCN4CCNCC4C3)cc2)c(=O)n1] |

TABLE 12-continued
| Compounds of Formula VI |
| --- |
| Structure |
| 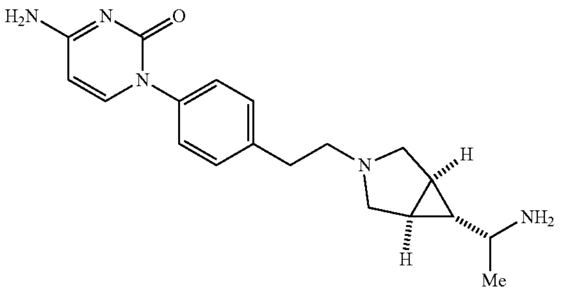 [SMILES: CC(N)[C@H]1[C@@H]2CN(CCc3ccc(-n4ccc(N)nc4=O)cc3)C[C@@H]21] |
| 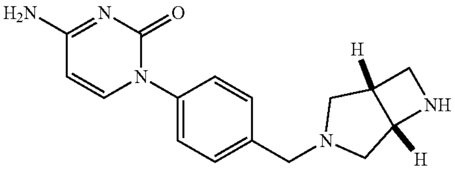 [SMILES: Nc1ccn(-c2ccc(CN3C[C@@H]4CN[C@@H]4C3)cc2)c(=O)n1] |
| 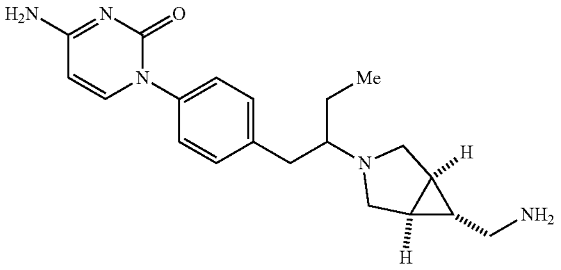 [SMILES: CCC(Cc1ccc(-n2ccc(N)nc2=O)cc1)N1C[C@@H]2[C@@H](CN)[C@@H]2C1] |
| 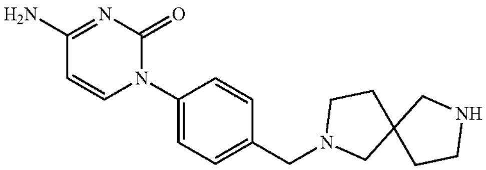 [SMILES: Nc1ccn(-c2ccc(CN3CCC4(CCNC4)C3)cc2)c(=O)n1] |
| 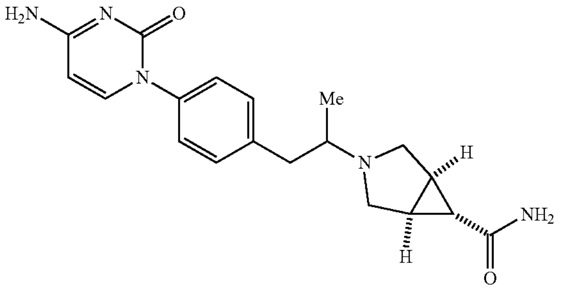 [SMILES: CC(Cc1ccc(-n2ccc(N)nc2=O)cc1)N1C[C@@H]2[C@H](C1)[C@H]2C(N)=O] |
| 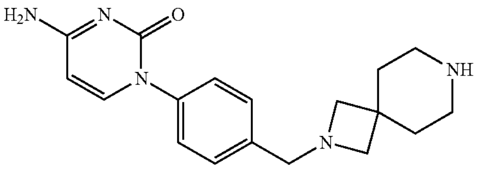 [SMILES: Nc1ccn(-c2ccc(CN3CC4(CCNCC4)C3)cc2)c(=O)n1] |

TABLE 12-continued
| Compounds of Formula VI |
| --- |
| Structure |
| 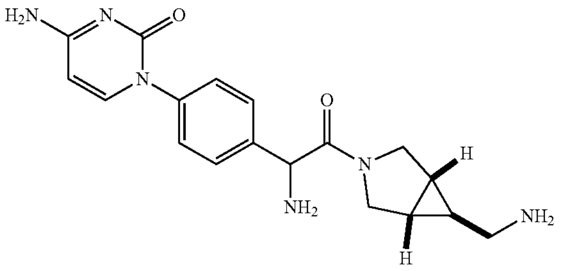 [SMILES: NC[C@@H]1[C@H]2CN(C(=O)C(N)c3ccc(-n4ccc(N)nc4=O)cc3)C[C@@H]12] |
| 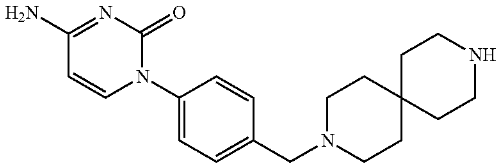 [SMILES: Nc1ccn(-c2ccc(CN3CCC4(CCNCC4)CC3)cc2)c(=O)n1] |
| 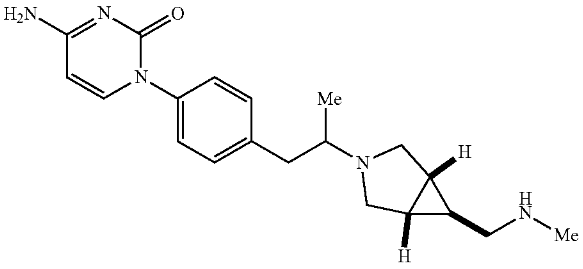 [SMILES: CNC[C@@H]1[C@H]2CN(C(C)Cc3ccc(-n4ccc(N)nc4=O)cc3)C[C@@H]12] |
| 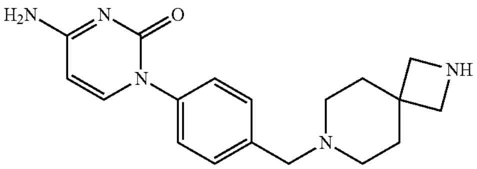 [SMILES: Nc1ccn(-c2ccc(CN3CCC4(CC3)CNC4)cc2)c(=O)n1] |
| 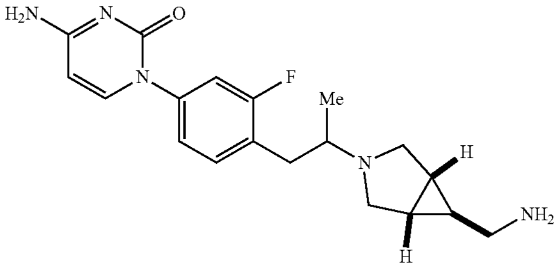 [SMILES: CC(Cc1ccc(-n2ccc(N)nc2=O)cc1F)N1C[C@@H]2[C@@H](CN)[C@@H]2C1] |
| 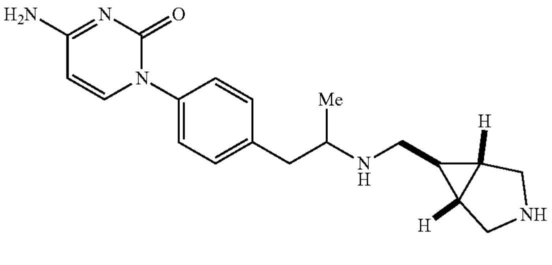 |

TABLE 12-continued
| Compounds of Formula VI |
| --- |
| Structure |
| 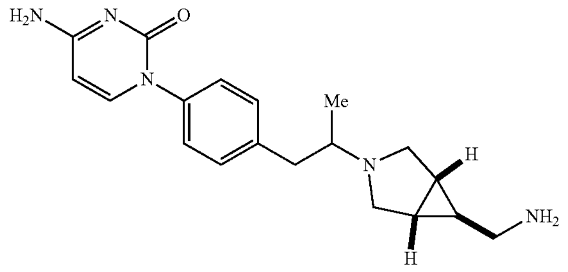 [SMILES: CC(Cc1ccc(-n2ccc(N)nc2=O)cc1)N1C[C@@H]2[C@@H](CN)[C@@H]2C1] |
| 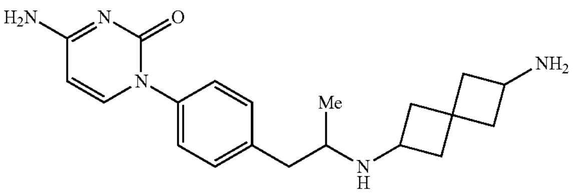 [SMILES: CC(Cc1ccc(-n2ccc(N)nc2=O)cc1)NC1CC2(CC(N)C2)C1] |
| 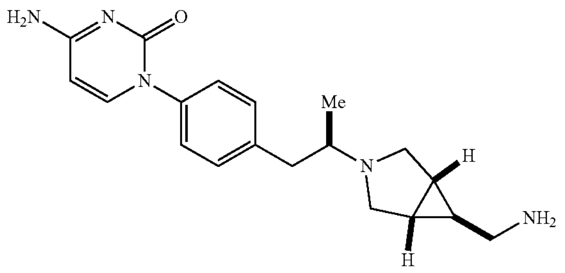 [SMILES: C[C@H](Cc1ccc(-n2ccc(N)nc2=O)cc1)N1C[C@@H]2[C@@H](CN)[C@@H]2C1] |
| 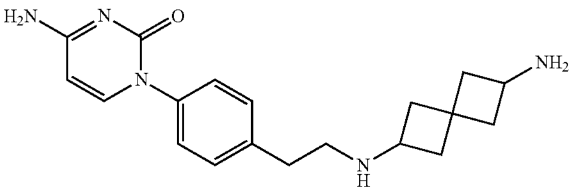 [SMILES: Nc1ccn(-c2ccc(CCNC3CC4(CC(N)C4)C3)cc2)c(=O)n1] |
| 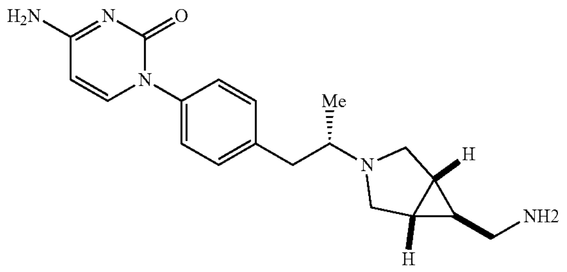 [SMILES: C[C@@H](Cc1ccc(-n2ccc(N)nc2=O)cc1)N1C[C@@H]2[C@@H](CN)[C@@H]2C1] |
| 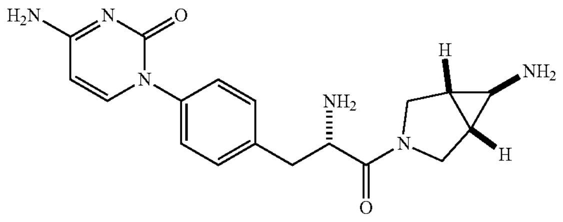 [SMILES: Nc1ccn(-c2ccc(C[C@H](N)C(=O)N3C[C@@H]4[C@@H](N)[C@@H]4C3)cc2)c(=O)n1] |

TABLE 12-continued
| Compounds of Formula VI |
|---|
| Structure |
| 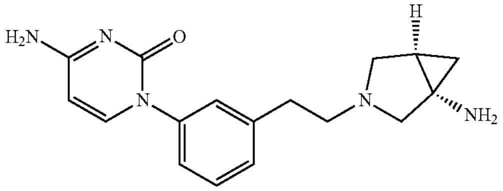 [SMILES: Nc1ccn(-c2cccc(CCN3C[C@H]4C[C@@]4(N)C3)c2)c(=O)n1] |
| 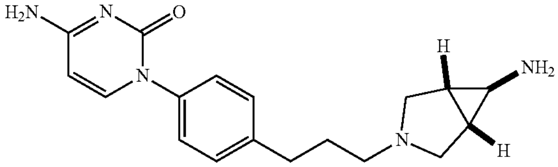 [SMILES: Nc1ccn(-c2ccc(CCCN3C[C@@H]4[C@@H](N)[C@@H]4C3)cc2)c(=O)n1] |
| 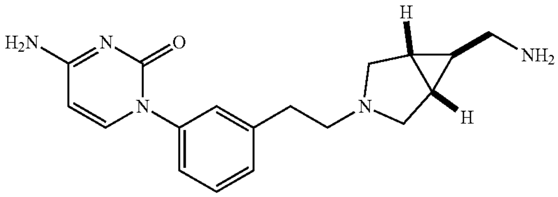 [SMILES: NC[C@@H]1[C@H]2CN(CCc3cccc(-n4ccc(N)nc4=O)c3)C[C@@H]12] |
| 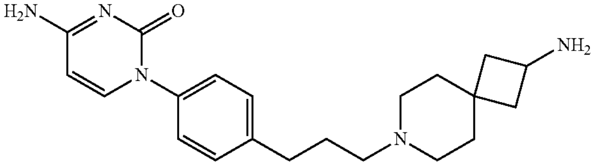 [SMILES: Nc1ccn(-c2ccc(CCCN3CCC4(CC3)CC(N)C4)cc2)c(=O)n1] |
| 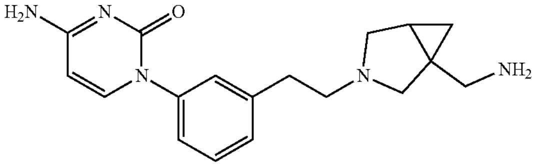 [SMILES: NCC12CC1CN(CCc1cccc(-n3ccc(N)nc3=O)c1)C2] |
| 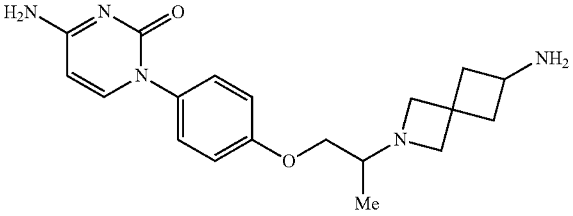 [SMILES: CC(COc1ccc(-n2ccc(N)nc2=O)cc1)N1CC2(CC(N)C2)C1] |
| 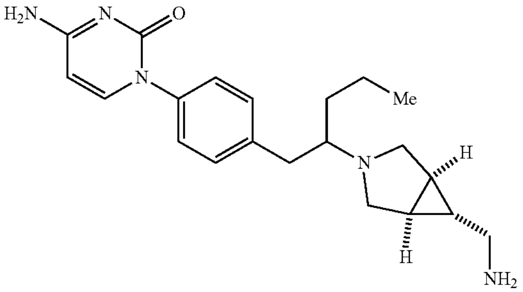 [SMILES: CCCC(Cc1ccc(-n2ccc(N)nc2=O)cc1)N1C[C@@H]2[C@@H](CN)[C@@H]2C1] |

TABLE 12-continued
| Compounds of Formula VI |
| --- |
| Structure |
| 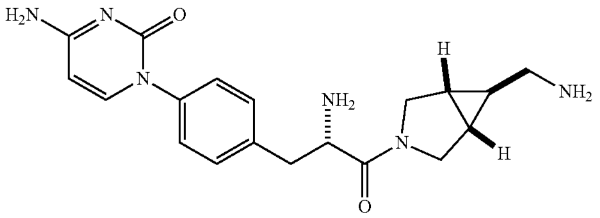 [SMILES: NC[C@@H]1[C@H]2CN(C(=O)[C@@H](N)Cc3ccc(-n4ccc(N)nc4=O)cc3)C[C@@H]12] |
| 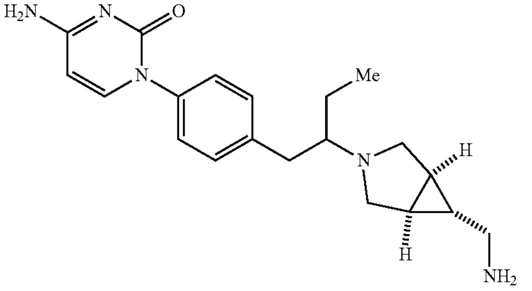 [SMILES: CCC(Cc1ccc(-n2ccc(N)nc2=O)cc1)N1C[C@@H]2[C@@H](CN)[C@@H]2C1] |
| 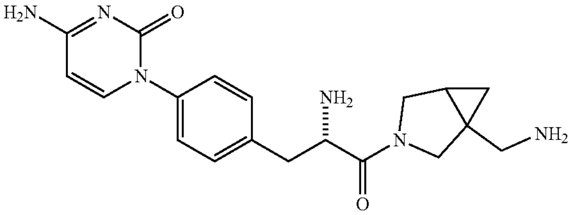 [SMILES: NCC12CC1CN(C(=O)[C@@H](N)Cc1ccc(-n3ccc(N)nc3=O)cc1)C2] |
| 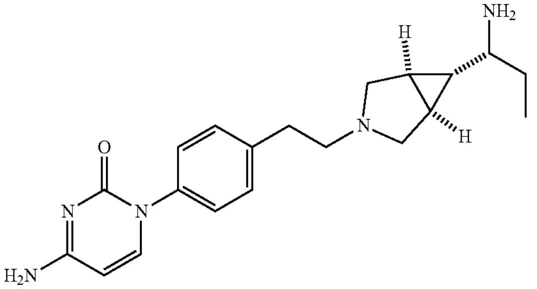 [SMILES: CC[C@@H](N)C1[C@H]2CN(CCc3ccc(-n4ccc(N)nc4=O)cc3)C[C@@H]12] |
| 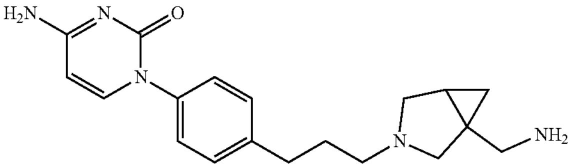 [SMILES: NCC12CC1CN(CCCc1ccc(-n3ccc(N)nc3=O)cc1)C2] |
| 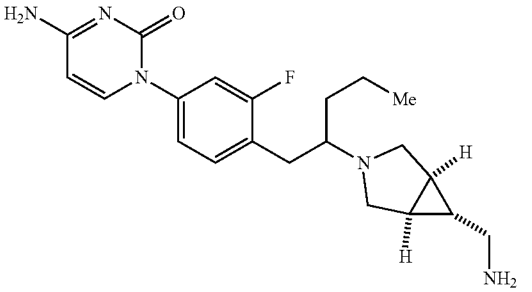 [SMILES: CCCC(Cc1ccc(-n2ccc(N)nc2=O)cc1F)N1C[C@@H]2[C@@H](CN)[C@@H]2C1] |

TABLE 12-continued
| Compounds of Formula VI |
|---|
| Structure |
| 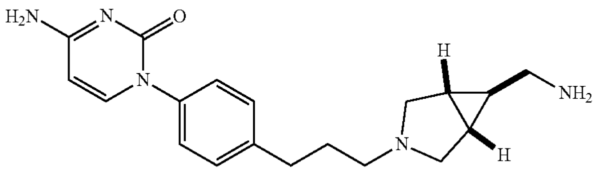 [SMILES: NC[C@@H]1[C@H]2CN(CCCc3ccc(-n4ccc(N)nc4=O)cc3)C[C@@H]12] |
| 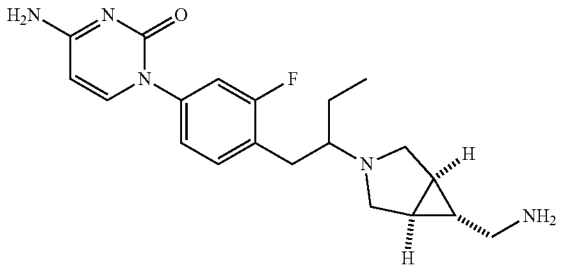 [SMILES: CCC(Cc1ccc(-n2ccc(N)nc2=O)cc1F)N1C[C@@H]2[C@@H](CN)[C@@H]2C1] |
| 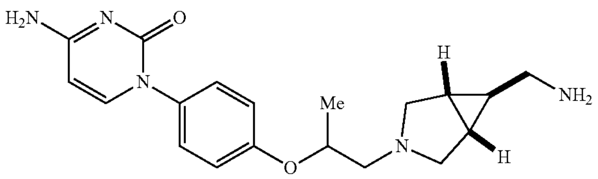 [SMILES: CC(CN1C[C@@H]2[C@@H](CN)[C@@H]2C1)Oc1ccc(-n2ccc(N)nc2=O)cc1] |
| 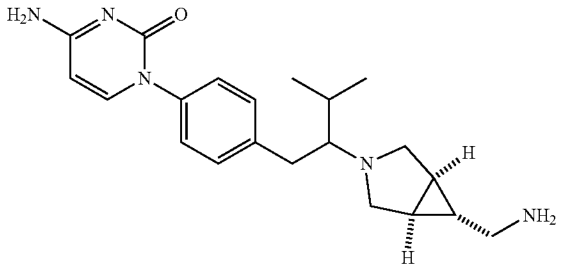 [SMILES: CC(C)C(Cc1ccc(-n2ccc(N)nc2=O)cc1)N1C[C@@H]2[C@@H](CN)[C@@H]2C1] |
| 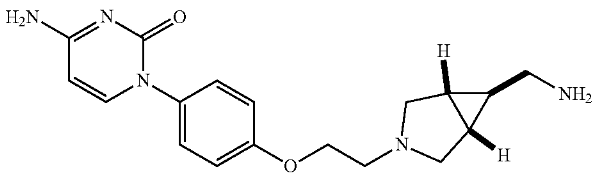 [SMILES: NC[C@@H]1[C@H]2CN(CCOc3ccc(-n4ccc(N)nc4=O)cc3)C[C@@H]12] |
| 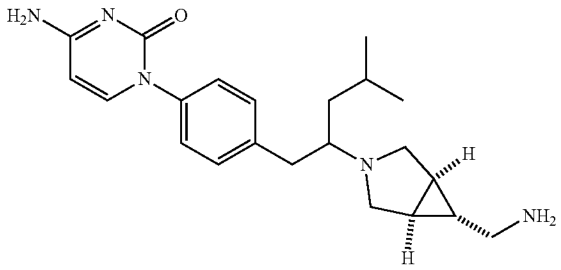 [SMILES: CC(C)CC(Cc1ccc(-n2ccc(N)nc2=O)cc1)N1C[C@@H]2[C@@H](CN)[C@@H]2C1] |

TABLE 12-continued
| Compounds of Formula VI |
| --- |
| Structure |
| 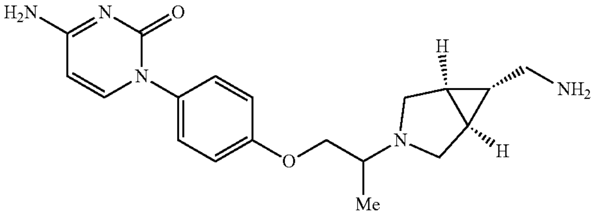 [SMILES: CC(COc1ccc(-n2ccc(N)nc2=O)cc1)N1C[C@@H]2[C@@H](CN)[C@@H]2C1] |
| 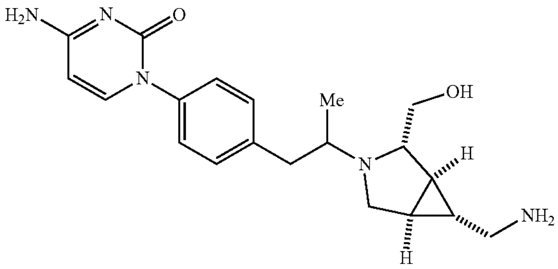 [SMILES: CC(Cc1ccc(-n2ccc(N)nc2=O)cc1)N1C[C@@H]2[C@@H](CN)[C@@H]2[C@H]1CO] |
| 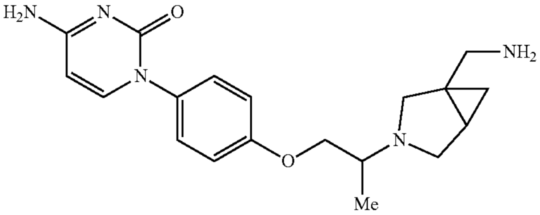 [SMILES: CC(COc1ccc(-n2ccc(N)nc2=O)cc1)N1CC2CC2(CN)C1] |
| 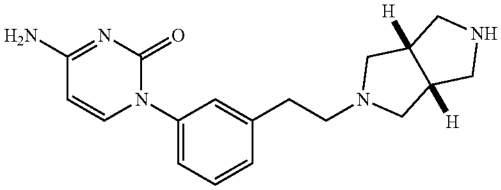 [SMILES: Nc1ccn(-c2cccc(CCN3C[C@H]4CNC[C@H]4C3)c2)c(=O)n1] |
| 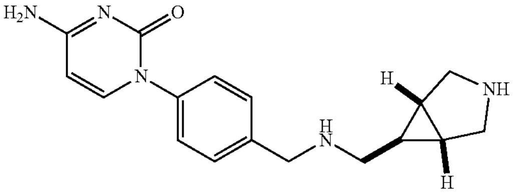 [SMILES: Nc1ccn(-c2ccc(CNC[C@@H]3[C@H]4CNC[C@@H]34)cc2)c(=O)n1] |
| 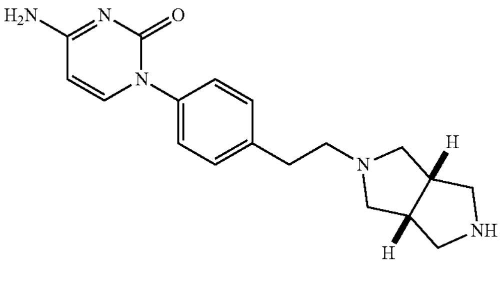 [SMILES: Nc1ccn(-c2ccc(CCN3C[C@H]4CNC[C@H]4C3)cc2)c(=O)n1] |

TABLE 12-continued
| Compounds of Formula VI |
| --- |
| Structure |
| 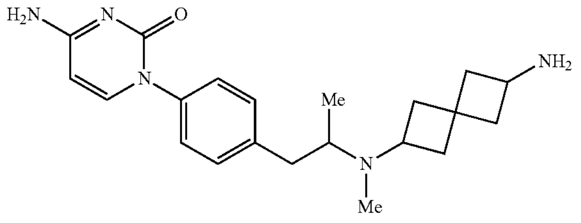 [SMILES: CC(Cc1ccc(-n2ccc(N)nc2=O)cc1)N(C)C1CC2(CC(N)C2)C1] |
| 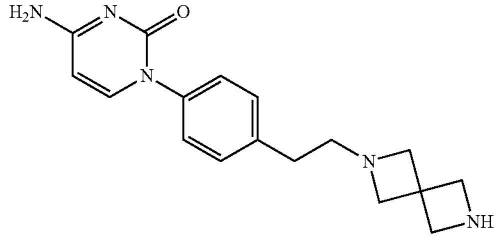 [SMILES: Nc1ccn(-c2ccc(CCN3CC4(CNC4)C3)cc2)c(=O)n1] |
| 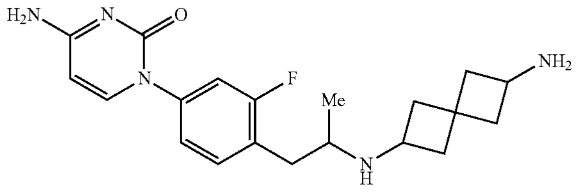 [SMILES: CC(Cc1ccc(-n2ccc(N)nc2=O)cc1F)NC1CC2(CC(N)C2)C1] |
| 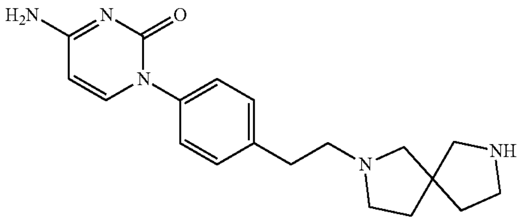 [SMILES: Nc1ccn(-c2ccc(CCN3CCC4(CCNC4)C3)cc2)c(=O)n1] |
| 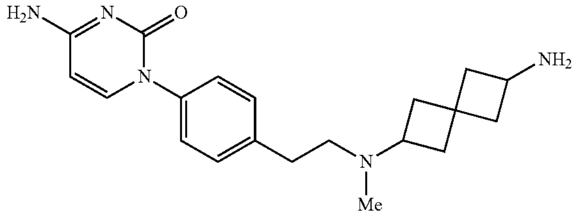 [SMILES: CN(CCc1ccc(-n2ccc(N)nc2=O)cc1)C1CC2(CC(N)C2)C1] |
| 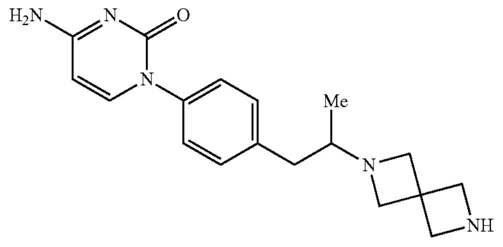 [SMILES: CC(Cc1ccc(-n2ccc(N)nc2=O)cc1)N1CC2(CNC2)C1] |

TABLE 12-continued
| Compounds of Formula VI |
|---|
| Structure |
| 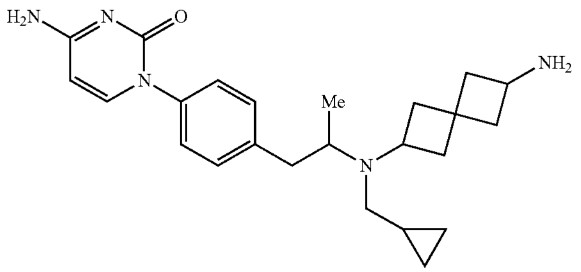 [SMILES: CC(Cc1ccc(-n2ccc(N)nc2=O)cc1)N(CC1CC1)C1CC2(CC(N)C2)C1] |
| 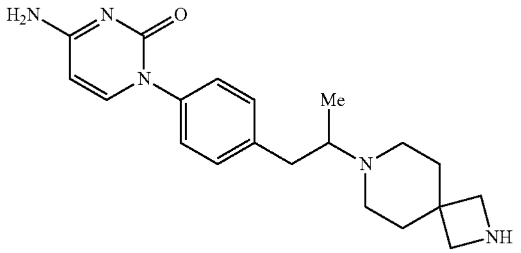 [SMILES: CC(Cc1ccc(-n2ccc(N)nc2=O)cc1)N1CCC2(CC1)CNC2] |
| 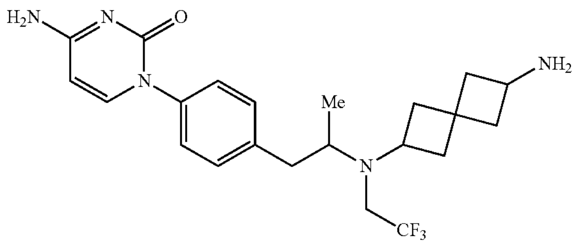 [SMILES: CC(Cc1ccc(-n2ccc(N)nc2=O)cc1)N(CC(F)(F)F)C1CC2(CC(N)C2)C1] |
| 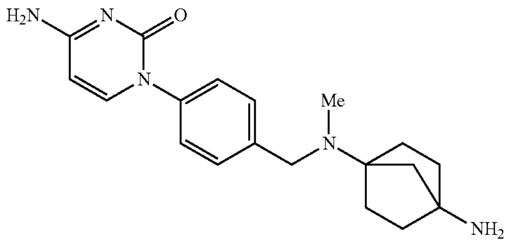 [SMILES: CN(Cc1ccc(-n2ccc(N)nc2=O)cc1)C12CCC(N)(CC1)C2] |
| 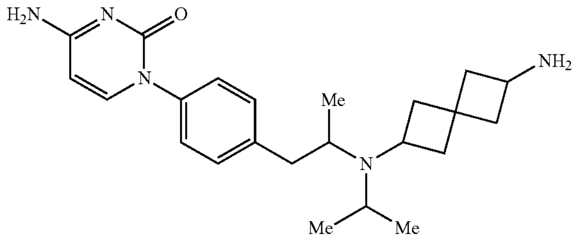 [SMILES: CC(C)N(C(C)Cc1ccc(-n2ccc(N)nc2=O)cc1)C1CC2(CC(N)C2)C1] |
| 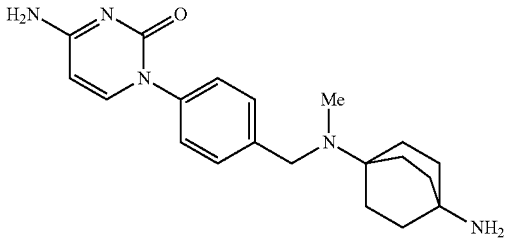 [SMILES: CN(Cc1ccc(-n2ccc(N)nc2=O)cc1)C12CCC(N)(CC1)CC2] |

TABLE 12-continued
| Compounds of Formula VI |
|---|
| Structure |
| 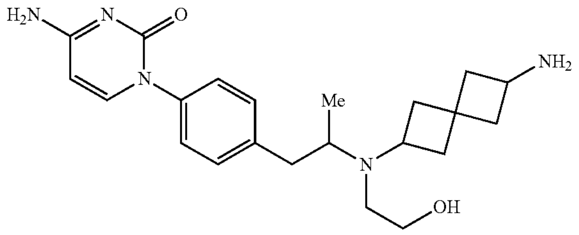 [SMILES: CC(Cc1ccc(-n2ccc(N)nc2=O)cc1)N(CCO)C1CC2(CC(N)C2)C1] |
| 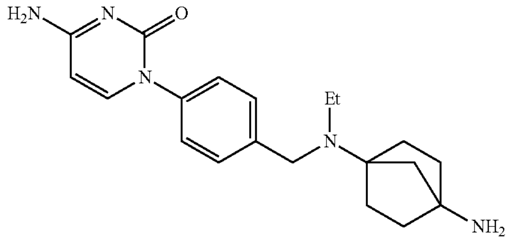 [SMILES: CCN(Cc1ccc(-n2ccc(N)nc2=O)cc1)C12CCC(N)(CC1)C2] |
| 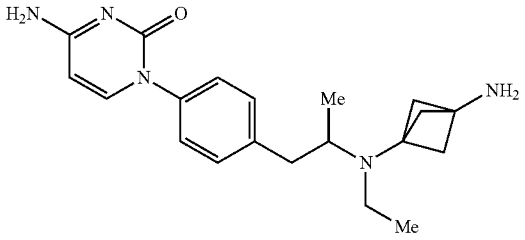 [SMILES: CCN(C(C)Cc1ccc(-n2ccc(N)nc2=O)cc1)C12CC(N)(C1)C2] |
| 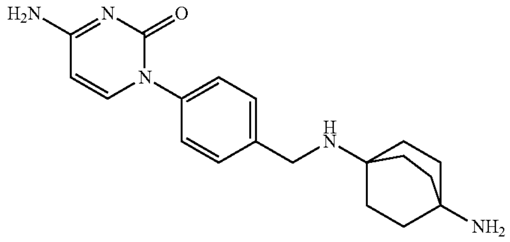 [SMILES: Nc1ccn(-c2ccc(CNC34CCC(N)(CC3)CC4)cc2)c(=O)n1] |
| 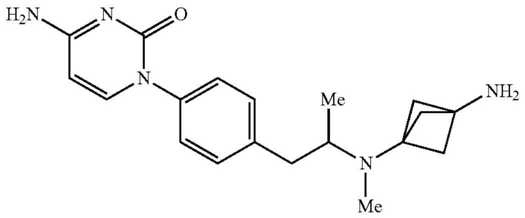 [SMILES: CC(Cc1ccc(-n2ccc(N)nc2=O)cc1)N(C)C12CC(N)(C1)C2] |
| 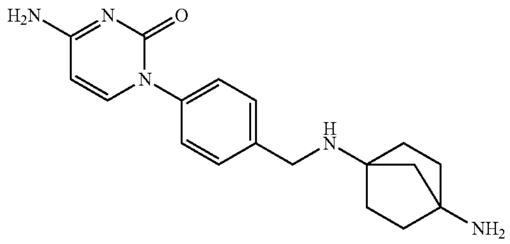 [SMILES: Nc1ccn(-c2ccc(CNC34CCC(N)(CC3)C4)cc2)c(=O)n1] |

TABLE 12-continued
| Compounds of Formula VI |
| --- |
| Structure |
| 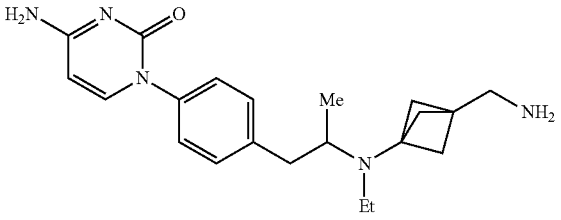 [SMILES: CCN(C(C)Cc1ccc(-n2ccc(N)nc2=O)cc1)C12CC(CN)(C1)C2] |
| 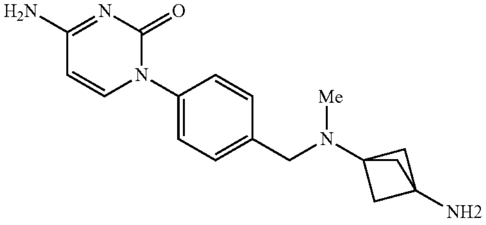 [SMILES: CN(Cc1ccc(-n2ccc(N)nc2=O)cc1)C12CC(N)(C1)C2] |
| 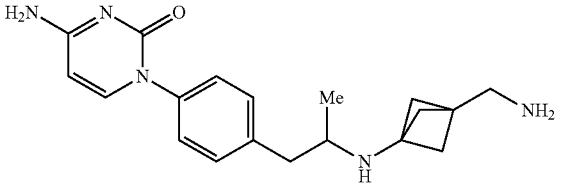 [SMILES: CC(Cc1ccc(-n2ccc(N)nc2=O)cc1)NC12CC(CN)(C1)C2] |
| 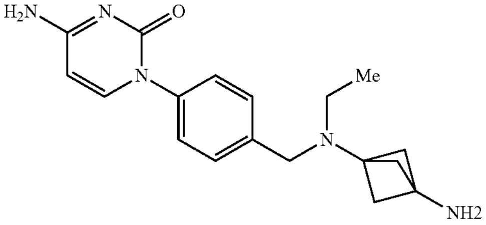 [SMILES: CCN(Cc1ccc(-n2ccc(N)nc2=O)cc1)C12CC(N)(C1)C2] |
| 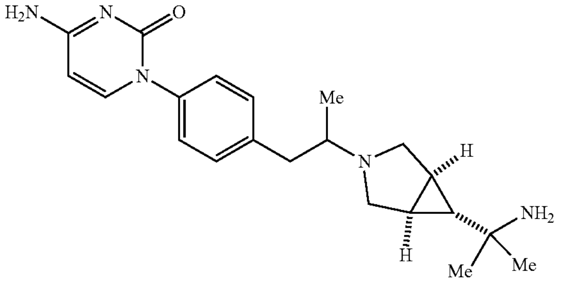 |
| 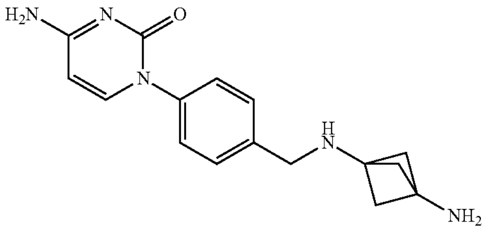 [SMILES: Nc1ccn(-c2ccc(CNC34CC(N)(C3)C4)cc2)c(=O)n1] |

TABLE 12-continued
| Compounds of Formula VI |
| --- |
| Structure |
| 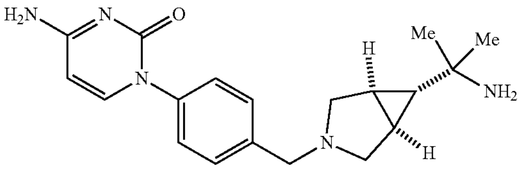 |
| 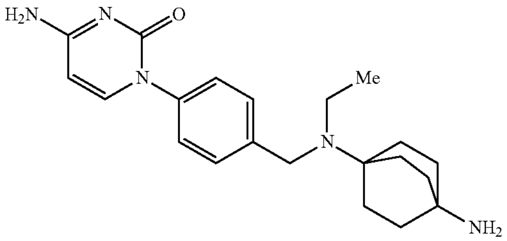 [SMILES: CCN(Cc1ccc(-n2ccc(N)nc2=O)cc1)C12CCC(N)(CC1)CC2] |
| 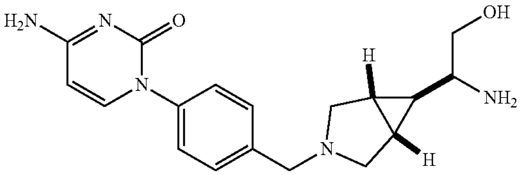 [SMILES: Nc1ccn(-c2ccc(CN3C[C@@H]4C([C@H](N)CO)[C@@H]4C3)cc2)c(=O)n1] |
| 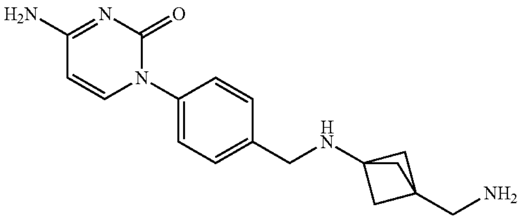 [SMILES: NCC12CC(NCc3ccc(-n4ccc(N)nc4=O)cc3)(C1)C2] |
| 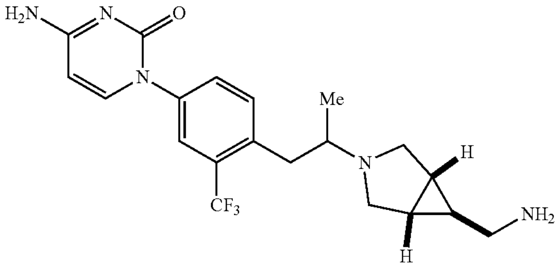 |
| 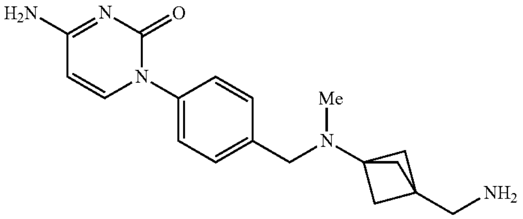 [SMILES: CN(Cc1ccc(-n2ccc(N)nc2=O)cc1)C12CC(CN)(C1)C2] |

TABLE 12-continued
| Compounds of Formula VI |
| --- |
| Structure |
| 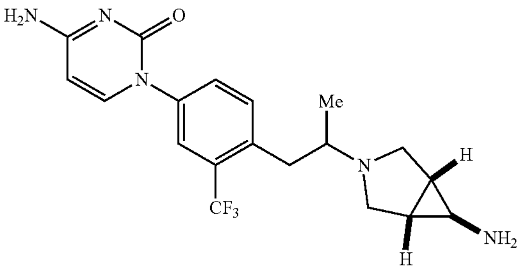 |
| 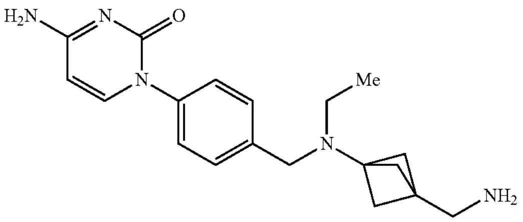 [SMILES: CCN(Cc1ccc(-n2ccc(N)nc2=O)cc1)C12CC(CN)(C1)C2] |
| 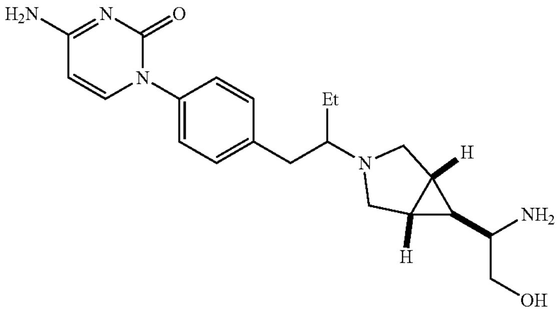 [SMILES: CCC(Cc1ccc(-n2ccc(N)nc2=O)cc1)N1C[C@@H]2C([C@@H](N)CO)[C@@H]2C1] |
| 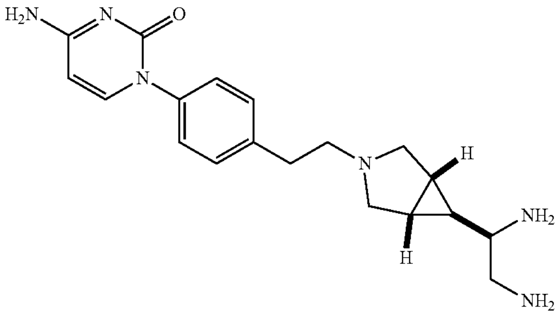 [SMILES: NC[C@H](N)C1[C@H]2CN(CCc3ccc(-n4ccc(N)nc4=O)cc3)C[C@@H]12] |
| 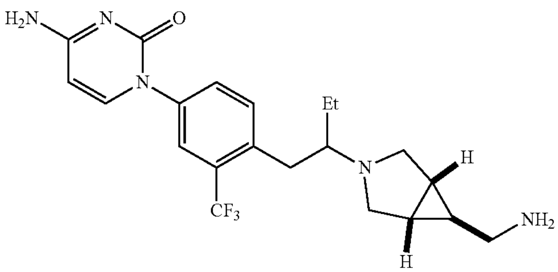 |

TABLE 12-continued
| Compounds of Formula VI |
| --- |
| Structure |
| 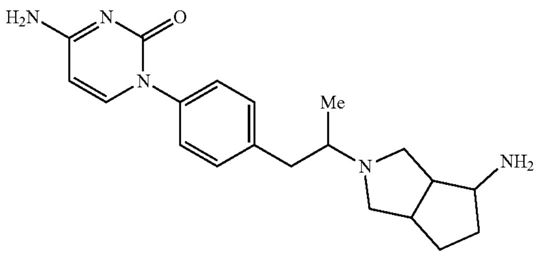 [SMILES: CC(Cc1ccc(-n2ccc(N)nc2=O)cc1)N1CC2CCC(N)C2C1] |
| 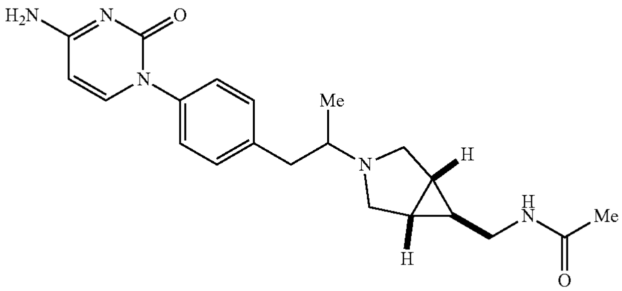 [SMILES: CC(=O)NC[C@@H]1[C@H]2CN(C(C)Cc3ccc(-n4ccc(N)nc4=O)cc3)C[C@@H]12] |
| 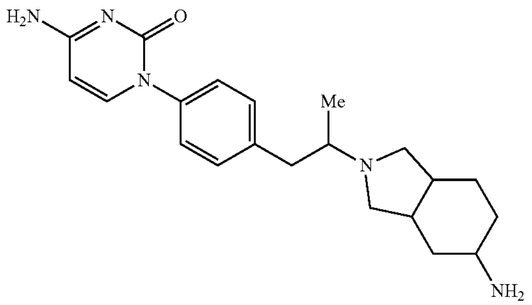 [SMILES: CCC(Cc1ccc(-n2ccc(N)nc2=O)cc1)N1CC2CCC(N)CC2C1] |
| 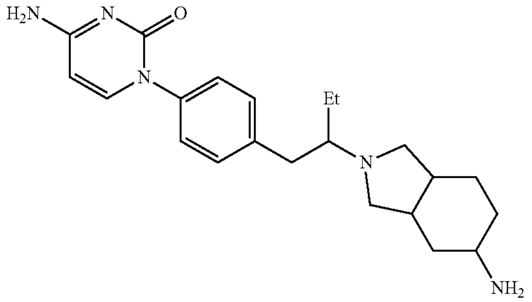 |
| 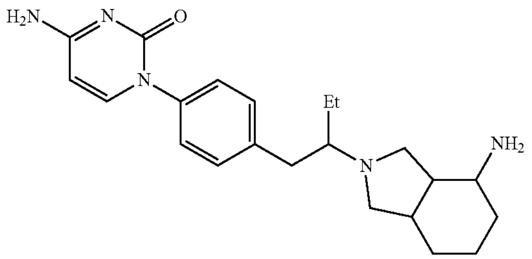 [SMILES: CCC(Cc1ccc(-n2ccc(N)nc2=O)cc1)N1CC2CCCC(N)C2C1] |

TABLE 12-continued
| Compounds of Formula VI |
| --- |
| Structure |
| 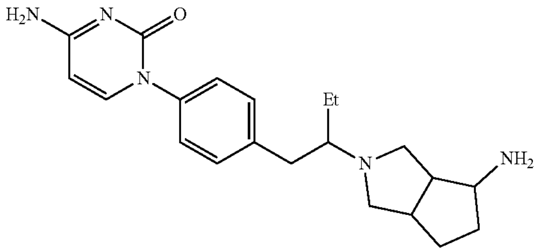 [SMILES: CCC(Cc1ccc(-n2ccc(N)nc2=O)cc1)N1CC2CCC(N)C2C1] |
| 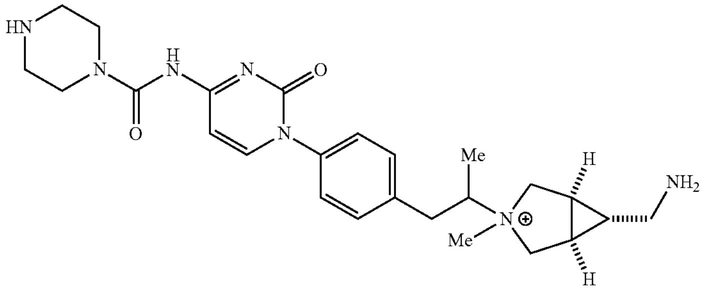 [SMILES: CC(Cc1ccc(-n2ccc(NC(=O)N3CCNCC3)nc2=O)cc1)[N+]1(C)C[C@@H]2[C@@H](CN)[C@@H]2C1] |
| 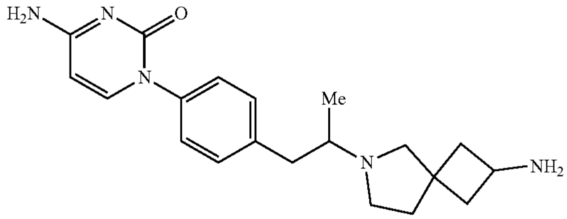 [SMILES: CC(Cc1ccc(-n2ccc(N)nc2=O)cc1)N1CCC2(CC(N)C2)C1] |
| 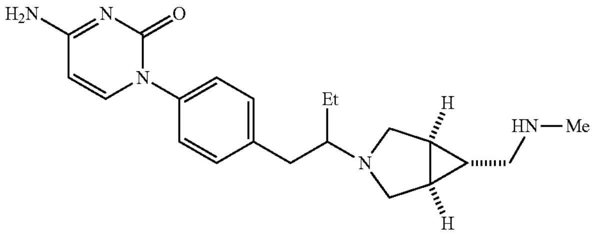 [SMILES: CCC(Cc1ccc(-n2ccc(N)nc2=O)cc1)N1C[C@@H]2[C@@H](CNC)[C@@H]2C1] |
| 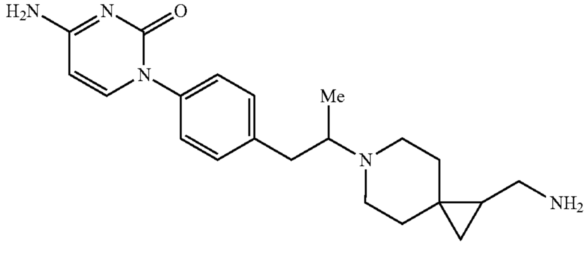 [SMILES: CC(Cc1ccc(-n2ccc(N)nc2=O)cc1)N1CCC2(CC1)CC2CN] |

TABLE 12-continued

| Compounds of Formula VI |
|---|
| Structure |
| 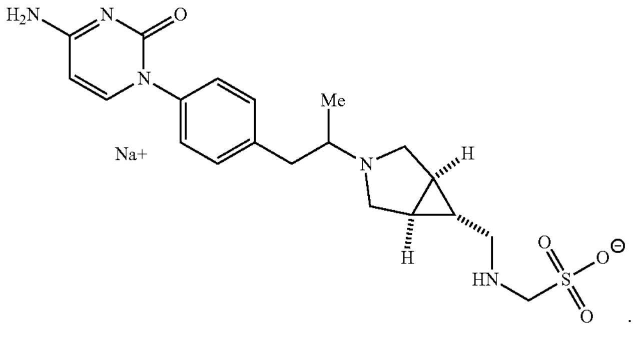 [SMILES: CC(Cc1ccc(-n2ccc(N)nc2=O)cc1)N1C[C@@H]2[C@@H](CNCS(=O)(=O)[O-])[C@@H]2C1 ; [Na+]] |

In another aspect, the disclosure provides a compound of formula E:

E

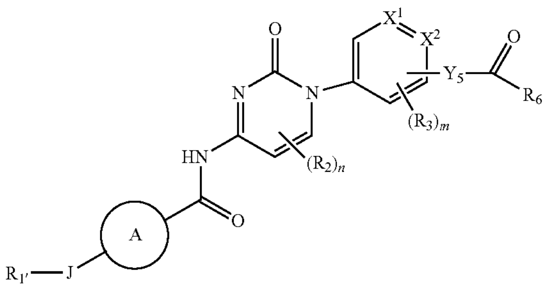

or a pharmaceutically acceptable salt thereof wherein ring A, ring B, J, $X^1$, $X^2R_{1'}$, $R_2$, $R_3$, $R_6$, m, and n have the same definitions in the preceding paragraphs; $Y_5$ is a bond or is a linear $C_1$-$C_7$ alkylene, $C_2$-$C_7$ alkenylene, or $C_2$-$C_7$ alkynylene, any of which are optionally substituted with OH, $NH_2CN$, halo, $C_1$-$C_6$ alkyl, $C_1$-$C_6$ haloalkyl, COO($C_1$-$C_6$ alkyl), COOH, $CONH_2$ or $C_1$-$C_6$ alkoxy; and $R_6$ is H or $C_1$-$C_6$ alkyl.

In another embodiment of the compound of formula E or a pharmaceutically acceptable salt, $Y_5$ is a bond or is a linear $C_1$-$C_3$ alkylene optionally substituted with OH, $NH_2$, halo, $C_1$-$C_6$ alkyl, or $C_1$-$C_6$ alkoxy.

In an embodiment, the compound of formula E or pharmaceutically acceptable salt thereof is selected from the compounds as depicted in Table 13 below.

TABLE 13

| Compound of formula E |
|---|
| 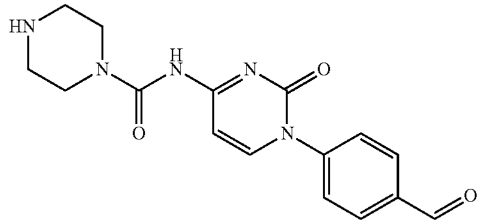 [SMILES: O=Cc1ccc(-n2ccc(NC(=O)N3CCNCC3)nc2=O)cc1] |

TABLE 13-continued

| Compound of formula E |
|---|
| 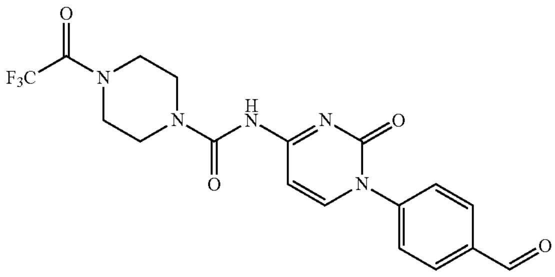 [SMILES: O=Cc1ccc(-n2ccc(NC(=O)N3CCN(C(=O)C(F)(F)F)CC3)nc2=O)cc1] |
| 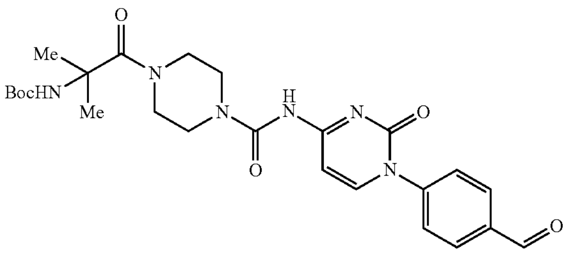 [SMILES: CC(C)(C)OC(=O)NC(C)(C)C(=O)N1CCN(C(=O)Nc2ccn(-c3ccc(C=O)cc3)c(=O)n2)CC1] |
| 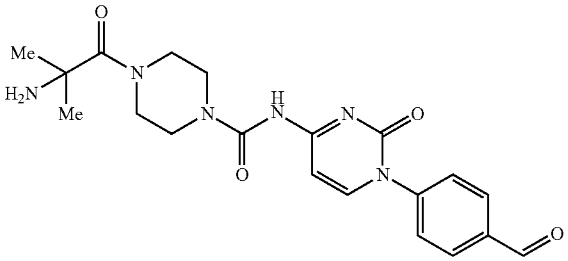 [SMILES: CC(C)(N)C(=O)N1CCN(C(=O)Nc2ccn(-c3ccc(C=O)cc3)c(=O)n2)CC1] |

TABLE 13-continued
| Compound of formula E |
|---|
| 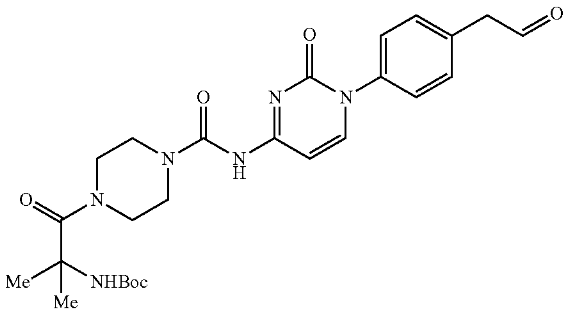 [SMILES: CC(C)(C)OC(=O)NC(C)(C)C(=O)N1CCN(C(=O)Nc2ccn(-c3ccc(CC=O)cc3)c(=O)n2)CC1] |
| 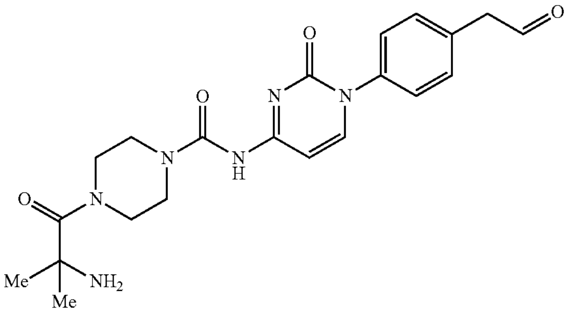 [SMILES: CC(C)(N)C(=O)N1CCN(C(=O)Nc2ccn(-c3ccc(CC=O)cc3)c(=O)n2)CC1] |
| 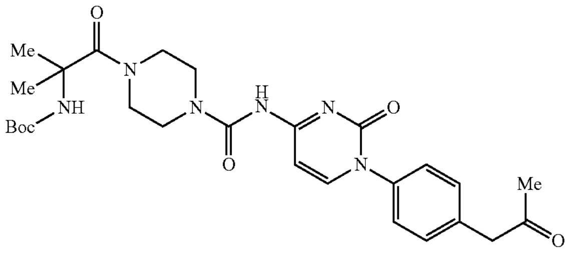 [SMILES: CC(=O)Cc1ccc(-n2ccc(NC(=O)N3CCN(C(=O)C(C)(C)NC(=O)OC(C)(C)C)CC3)nc2=O)cc1] |
| 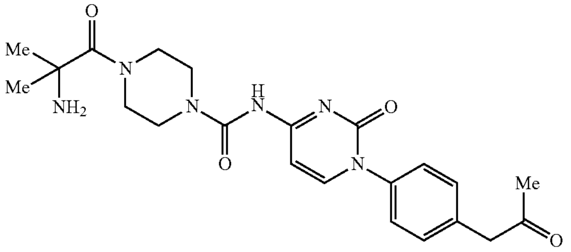 [SMILES: CC(=O)Cc1ccc(-n2ccc(NC(=O)N3CCN(C(=O)C(C)(C)N)CC3)nc2=O)cc1] |
| 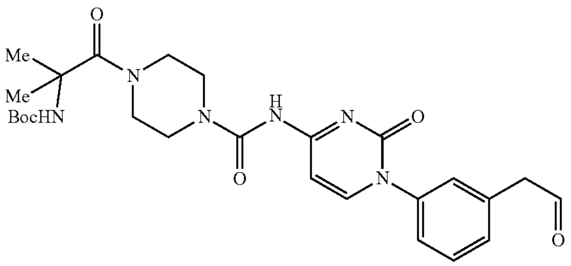 [SMILES: CC(C)(C)OC(=O)NC(C)(C)C(=O)N1CCN(C(=O)Nc2ccn(-c3cccc(CC=O)c3)c(=O)n2)CC1] |
TABLE 13-continued
| Compound of formula E |
|---|
| 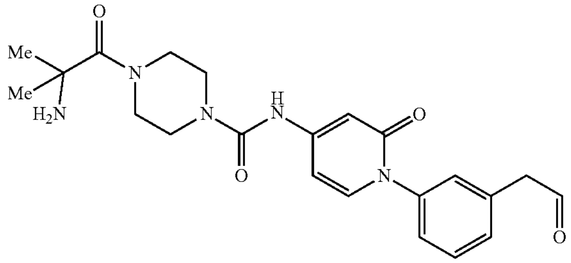 [SMILES: CC(C)(N)C(=O)N1CCN(C(=O)Nc2ccn(-c3cccc(CC=O)c3)c(=O)c2)CC1] |
| 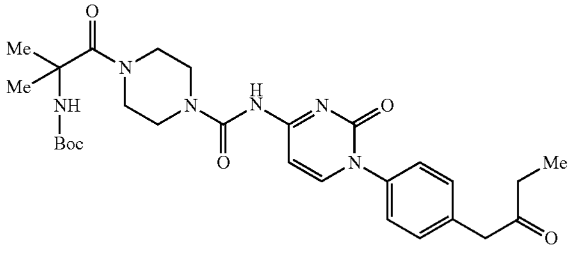 [SMILES: CCC(=O)Cc1ccc(-n2ccc(NC(=O)N3CCN(C(=O)C(C)(C)NC(=O)OC(C)(C)C)CC3)nc2=O)cc1] |
| 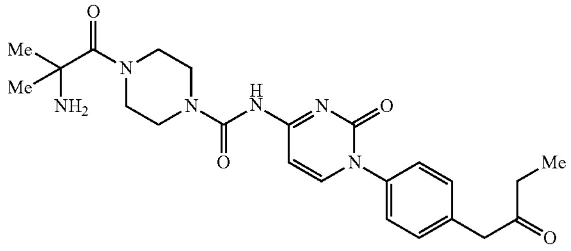 [SMILES: CCC(=O)Cc1ccc(-n2ccc(NC(=O)N3CCN(C(=O)C(C)(C)N)CC3)nc2=O)cc1] |
| 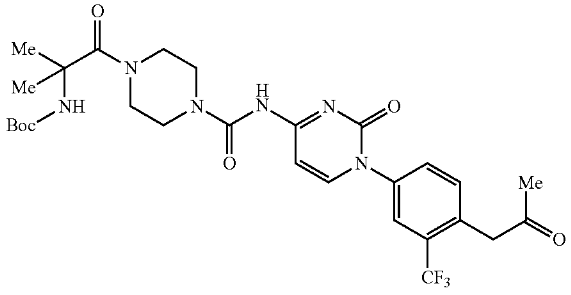 [SMILES: CC(=O)Cc1ccc(-n2ccc(NC(=O)N3CCN(C(=O)C(C)(C)NC(=O)OC(C)(C)C)CC3)nc2=O)cc1C(F)(F)F] |
| 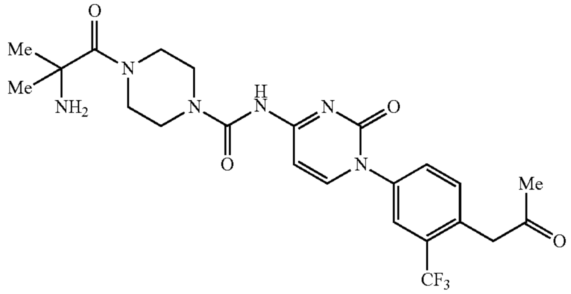 [SMILES: CC(=O)Cc1ccc(-n2ccc(NC(=O)N3CCN(C(=O)C(C)(C)N)CC3)nc2=O)cc1C(F)(F)F] |

TABLE 13-continued

| Compound of formula E |
| --- |
| 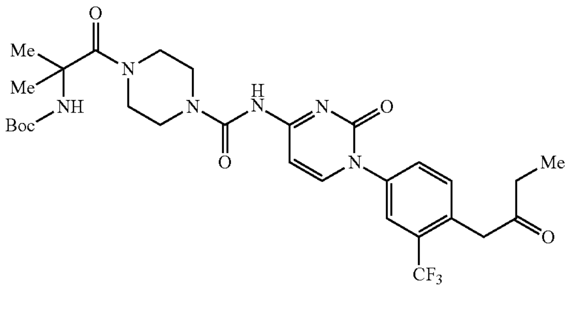 [SMILES: CCC(=O)Cc1ccc(-n2ccc(NC(=O)N3CCN(C(=O)C(C)(C)NC(=O)OC(C)(C)C)CC3)nc2=O)cc1C(F)(F)F] |
| 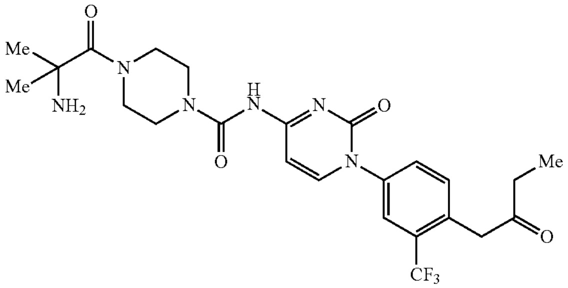 [SMILES: CCC(=O)Cc1ccc(-n2ccc(NC(=O)N3CCN(C(=O)C(C)(C)N)CC3)nc2=O)cc1C(F)(F)F] |
| 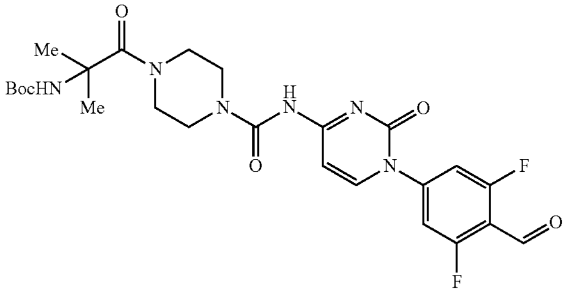 [SMILES: CC(C)(C)OC(=O)NC(C)(C)C(=O)N1CCN(C(=O)Nc2ccn(-c3cc(F)c(C=O)c(F)c3)c(=O)n2)CC1] |
| 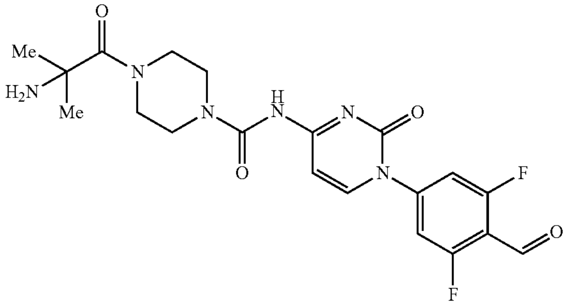 [SMILES: CC(C)(N)C(=O)N1CCN(C(=O)Nc2ccn(-c3cc(F)c(C=O)c(F)c3)c(=O)n2)CC1] |
| 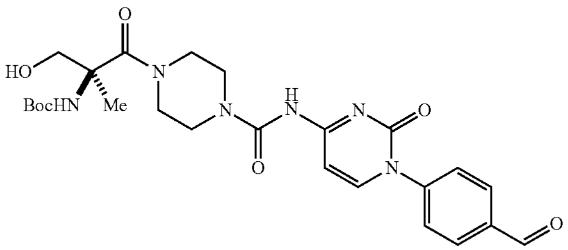 [SMILES: CC(C)(C)OC(=O)N[C@@](C)(CO)C(=O)N1CCN(C(=O)Nc2ccn(-c3ccc(C=O)cc3)c(=O)n2)CC1] |
| 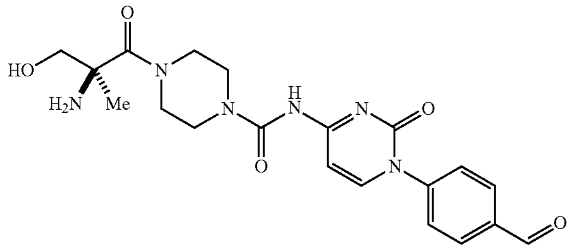 [SMILES: C[C@](N)(CO)C(=O)N1CCN(C(=O)Nc2ccn(-c3ccc(C=O)cc3)c(=O)n2)CC1] |
| 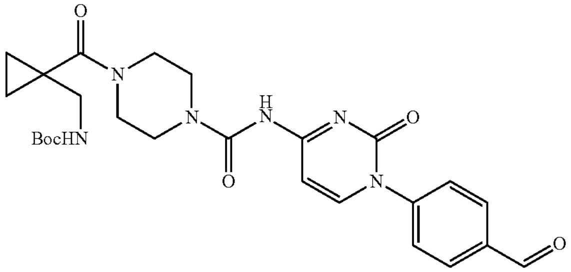 [SMILES: CC(C)(C)OC(=O)NCC1(C(=O)N2CCN(C(=O)Nc3ccn(-c4ccc(C=O)cc4)c(=O)n3)CC2)CC1] |
| 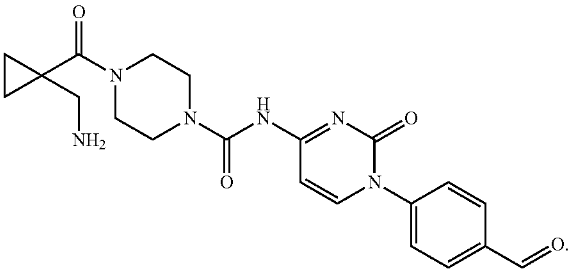 [SMILES: NCC1(C(=O)N2CCN(C(=O)Nc3ccn(-c4ccc(C=O)cc4)c(=O)n3)CC2)CC1] |

Pharmaceutical Compositions and Administration

The present invention provides pharmaceutical compositions comprising a compound of the present invention and a pharmaceutically acceptable excipient. In certain embodiments, the compound of the present invention is provided in an effective amount in the pharmaceutical composition. In certain embodiments, the effective amount is a therapeutically effective amount. In certain embodiments, the effective amount is a prophylactically effective amount.

Pharmaceutically acceptable excipients include any and all solvents, diluents, or other liquid vehicles, dispersions, suspension aids, surface active agents, isotonic agents, thickening or emulsifying agents, preservatives, solid binders, lubricants and the like, as suited to the particular dosage form desired. General considerations in formulation and/or manufacture of pharmaceutical compositions agents can be found, for example, in Remington's Pharmaceutical Sciences, Sixteenth Edition, E. W. Martin (Mack Publishing Co., Easton, Pa., 1980), and Remington: The Science and Practice of Pharmacy, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40]sorbitan monostearate [Span 60]sorbitan tristearate [Span 65]glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof: malic acid and salts and hydrates thereof: phosphoric acid and salts and hydrates thereof: and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662, Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460, and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

To practice the method of this invention, the above-described compound or its pharmaceutical composition can be administered orally, parenterally, by inhalation spray, topically, rectally, nasally, buccally, vaginally, rectally, or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually. Additional therapeutically active agents include antibiotic agents, e.g., antibiotics useful for treating tuberculosis. Exemplary antibiotics include, but are not limited to, isoniazid, rifampin, pyrazinamide, ethambutol, and streptomycin.

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Uses and Methods of Treatment

In another aspect, the invention provides a method of treating a bacterial infection in a patient in need of such treatment, comprising administering an effective amount of a compound of formula I or a pharmaceutically acceptable salt thereof or a composition comprising a compound of formula I or a pharmaceutically acceptable salt thereof. In certain embodiments, the effective amount is a therapeutically effective amount. In certain other embodiments, the effective amount is a prophylactically effective amount.

In some embodiments, the compounds of the invention can be active against a wide range of both Gram-positive and Gram-negative organisms. In these and other embodiments, the compounds of the invention can be used to treat infections and to inhibit microbial growth. Thus, the compounds of the invention can be used to treat humans and animals having a broad spectrum of bacterial infections such as impetigo, pneumonia, bronchitis, pharyngitis, endocarditis, urinary tract infections, diabetes foot ulcers, gastro-intestinal infections and bacteremia. These bacterial infections could be caused by any of the following bacteria—*Staphylococcus aureus*, coagulase negative staphylococci, methicillin-resistant *Staphylococcus aureus*, methicillin-resistant coagulase negative staphylococci, enterococci, beta-haemolytic streptococci, *viridans* group of streptococci, *Bacillus* mycobacterial infections due to multi-drug resistant *M. tuberculosis* and other atypical mycobacteria such as *M. intracellulare* and *M. avium*, as well as newly emerging Gram-negative pathogens such as *Chryseobacterium meningosepticum, Chryseobacterium indologense* and other Gram-negative pathogens such as *E. coli, Klebsiella, Proteus, Serratia, Citrobacter, Pseudomonas, Burkholderia, Brucella, Yersinia, Francisella, Coxiella, Chlamydia, Salmonella, Rickettsia, Shigella* and *Campylobacter.*

In one embodiment, the bacterial infection is tuberculosis. In certain embodiments, the tuberculosis infection is a *Mycobacterium tuberculosis* infection. In certain embodiments, the tuberculosis infection is multi-drug-resistant tuberculosis (MDR-TB) infection, e.g., resistant to first-line TB drugs rifampicin and/or isoniazid. In certain embodiments, the tuberculosis infection is extensively-drug-resistant tuberculosis (XDR-TB) infection, e.g., also resistant to three or more of the six classes of second-line drugs (see, e.g., Centers for Disease Control and Prevention (CDC) (2006). "Emergence of *Mycobacterium tuberculosis* with extensive resistance to second-line drugs worldwide, 2000-2004". MMWR Morb Mortal Wkly Rep 55 (11): 301-5).

Processes

In some aspects, the compounds and intermediates of the present disclosure can be prepared according to General Synthetic Schemes G-1 and G-2 below. In the general schemes, variables such as ring A, ring B, J, L, $X^1$, $X^2$Y, $R_1$, $R_{1'}$, $R_2$, $R_3$, $R_6$, m, and n have the same definitions in the preceding paragraphs; $Y_5$ is a bond or is a linear $C_1$-$C_7$ alkylene, $C_2$-$C_7$ alkenylene, or $C_2$-$C_7$ alkynylene, any of which are optionally substituted with OH, $NH_2$, halo, $C_1$-$C_6$ alkyl, or $C_1$-$C_6$ alkoxy; $R_6$ is H or $C_1$-$C_6$ alkyl; X is halo; and P is a hydroxyl protecting group.

General Synthetic Synthetic G-1
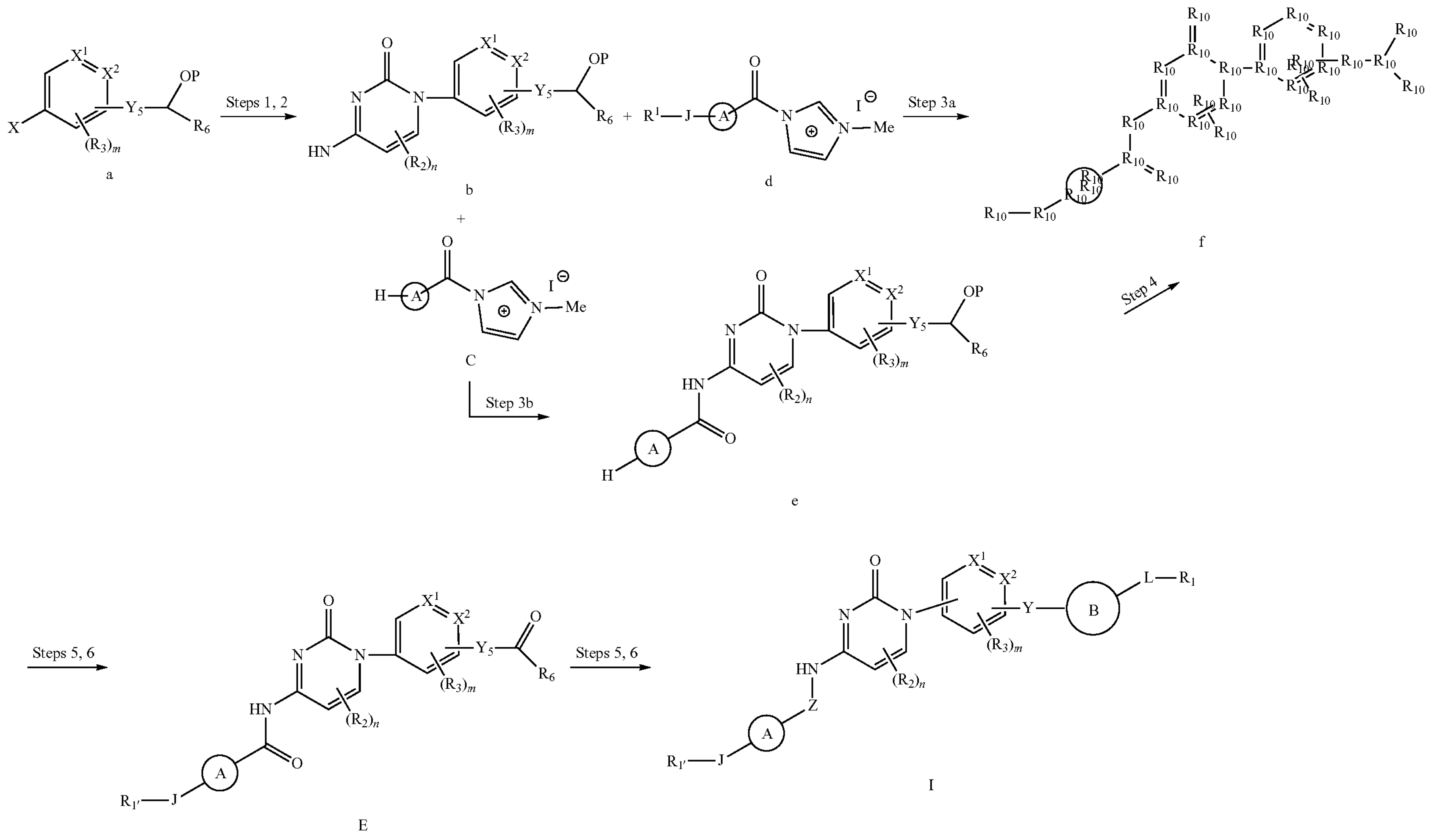

General Synthetic Scheme G-2

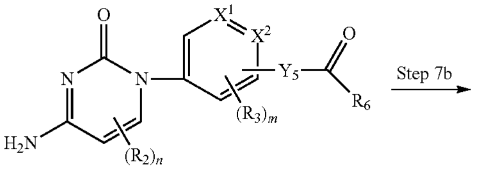

g

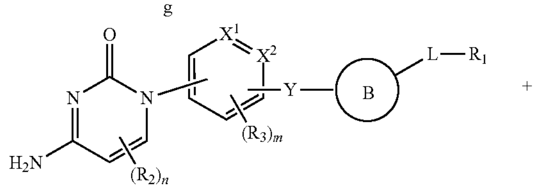

VI

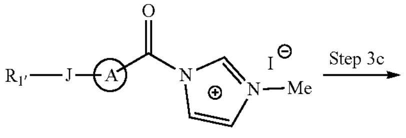

d

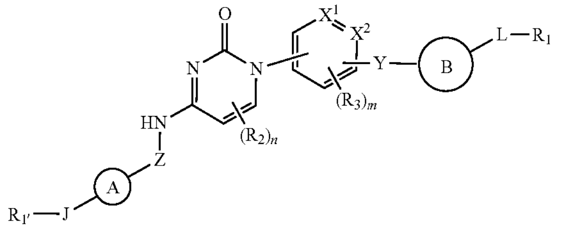

I

In step 1 of General Synthetic Scheme G-1, the protected alcohol (a) is reacted with a borate such as triisopropyl borate in the presence of a base such as butyl lithium to afford a boronate. In step 2, the boronate is cross-coupled with cytosine in the presence of a base such as a tertiary amine and a copper reagent such as a copper (II) reagent to afford the compound of formula (b).

In steps 3a, 3b, and 3c of General Synthetic Schemes G-1 and G-2, the compound of formula (b) or (VI) and the iodide (c) or (d) undergo an amide coupling to yield the intermediate (e) or (f), or the compound of formula I. In a typical procedure, 1.1 to 2.0 molar equivalents of the compound of formula (b) or (VI) are combined with 1 molar equivalent of the iodide (c) or (d) in a suitable solvent, such as a polar aprotic solvent. Polar aprotic solvents include solvents such as dichloromethane, dimethylformamide, acetonitrile, and the like. The mixture in the polar aprotic solvent are then allowed to undergo reaction at a temperature of from about 0° C. to 100° C. for a sufficient time. Typically, the temperature is from about 25° C. to 95° C. or from about 50° C. to 95° C. and the reaction time is from about 1 to 24 hours and more typically 2 to 20 hours or from about 5 to 18 hours.

In step 4 of General Synthetic Scheme G-1, the compound of formula (e) may conduct a further coupling to afford the compound of formula (0.

In steps 5 and 6 of General Synthetic Scheme G-1, the compound of formula (0 is deprotected to yield a free alcohol and then oxidized to a ketone, a compound of formula E.

In steps 7a and 7b of General Synthetic Scheme G-1 and G-2, the compound of formula E (or g) is reacted with an amine under a reductive amination condition to afford the compound of formula I (or VI). The reductive amination can be performed in the presence of a reducing agent and a suitable solvent. A suitable solvent includes protic solvents or aprotic solvents. Protic solvents include but is not limited to water and alcohols such as methanol, ethanol, propanol, and the like. Aprotic solvents include but is not limited to solvents such as dichloromethane, dimethylformamide, acetonitrile, and the like. The suitable solvent may also be a combination of two or three solvents. The reducing agent includes but is not limited to a borohydride reagent or a metal hydride reagent. Non-limiting examples are lithium borohydride, sodium borohydride, sodium cyanoborohydride and Sodium triacetoxyborohydride.

In one aspect, the disclosure provides a process for preparing a compound of formula I-2:

I-2

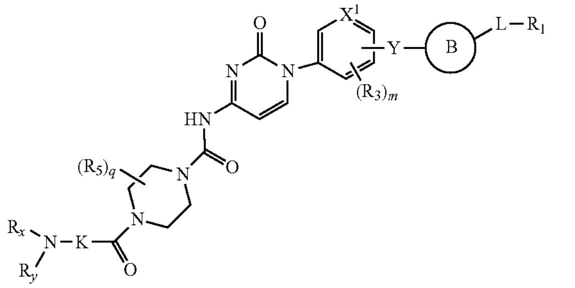

or a pharmaceutically acceptable salt thereof, the process comprising:

coupling a compound of formula A with a compound of formula B to provide a compound of formula I-2:

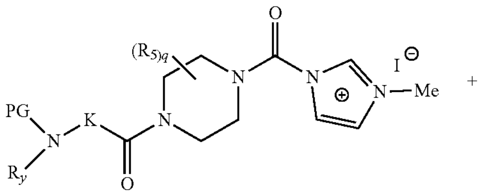

A

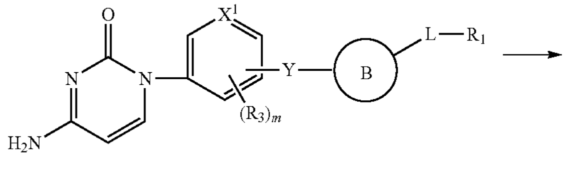

B

I-2 wherein ring B, K, L, Y, $R_1$, $R_x$, $R_y$, $R_5$, $X^1$, m, and q are as defined herein, and wherein PG is an amino protecting group.

Processes and conditions for performing the amide coupling of a compound of formula A to a compound of formula B are as in the general synthetic schemes Steps 3a, 3b, and 3c.

In one embodiment, the process further comprises the step of removing the amino protecting group PG.

In another embodiment, the compound of formula B is selected from the compounds as depicted in Table 12.

In another aspect, the disclosure provides a process for preparing a compound of formula I-6:

I-6

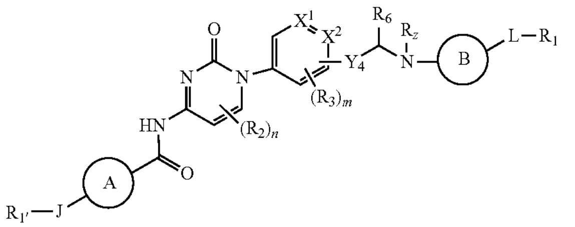

or a pharmaceutically acceptable salt thereof, the process comprising:

combining a compound of formula C with a compound of formula D under a reductive amination condition to provide a compound of formula I-6:

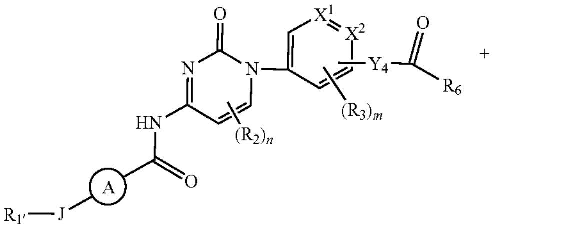

C

D

I-6, wherein ring A, ring B, J, L, $R_1$, $R_{1'}$, $R_2$, $R_3$, $X^1$, $X^2$, m, and n are as defined herein;

$Y_4$ is a bond or is a linear $C_1$-$C_6$ alkylene, $C_2$-$C_6$ alkenylene, or $C_2$-$C_6$ alkynylene, any of which are optionally substituted with OH, $NH_2$, halo, $C_1$-$C_6$ alkyl, or $C_1$-$C_6$ alkoxy;

$R_6$ is H or $C_1$-$C_6$ alkyl; and $R_7$ is H, $C_1$-$C_6$ alkyl, $C_1$-$C_6$ hydroxyalkyl, $C_1$-$C_6$ haloalkyl, or $C_1$-$C_6$ alkylene-$C_3$-$C_8$ cycloalkyl.

In another embodiment, the compound of formula C is selected from the compounds as depicted in Table 13.

In another aspect, the disclosure provides processes for preparing a compound of formula I-7:

I-7

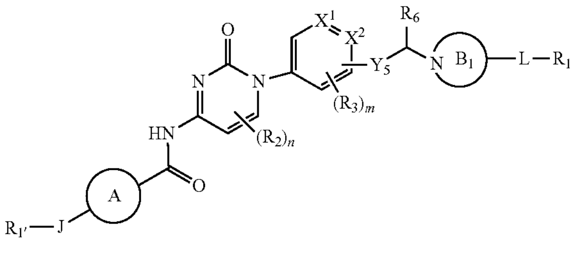

or a pharmaceutically acceptable salt thereof, the process comprising:

combining a compound of formula E with a compound of formula F under a reductive amination condition to provide a compound of formula I-7

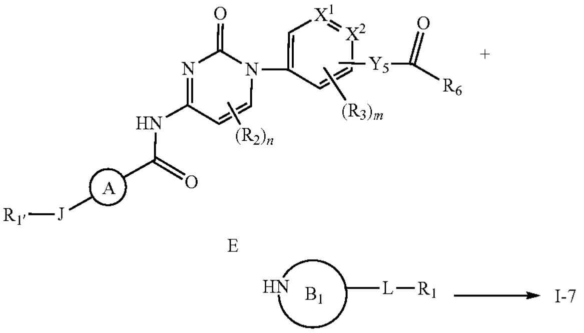

E

F

I-7 wherein ring A, ring B, J, L, $R_1$, $R_{1'}$, $R_2$, $R_3$, $X^1$, $X^2$, m, and n are as defined herein;

ring $B_1$ is a nitrogen containing bicyclic heterocycloalkylene optionally substituted with up to three substituents independently selected from the group consisting of $C_1$-$C_6$ alkyl, $C_1$-$C_6$ alkoxy, halo, CN, $C_1$-$C_6$ haloalkyl, OH, COO($C_1$-$C_6$ alkyl), $CONH_2$, and $C_1$-$C_6$ hydroxyalkyl;

$Y_5$ is a bond or is a linear $C_1$-$C_7$ alkylene, $C_2$-$C_7$ alkenylene, or $C_2$-$C_7$ alkynylene, any of which are optionally substituted with OH, $NH_2$, halo, $C_1$-$C_6$ alkyl, or $C_1$-$C_6$ alkoxy; and $R_6$ is H or $C_1$-$C_6$ alkyl.

The reductive amination between a compound of formula C and a compound of formula D or between a compound of formula E and a compound of formula F are as in general synthetic schemes Steps 7a and 7b. In a typical procedure, 1.1 to 2.0 molar equivalents of the compound of formula D (or F) are combined with 1 molar equivalent of a compound of formula C (or E) and 1.0 to 2.0 molar equivalents of the reducing agent in a suitable solvent. The mixture are then allowed to undergo reaction at a temperature of from about 0° C. to 100° C. for a sufficient time. Typically, the temperature is from about 10° C. to 95° C., or from about 10° C. to 50° C., or at room temperature, and the reaction time is from about 1 to 24 hours and more typically 2 to 20 hours or from about 5 to 18 hours. Work-up and purification as needed provides the compound of formula I-6 or 1-7.

In another embodiment, the compound of formula E is selected from the compounds listed in Table 13.

Compound Preparation

The preparation of starting materials that are commercially available, described in the literature, or readily obtainable by those skilled in the art is not described. It will be appreciated by the skilled person that where it is stated that compounds were prepared analogously to earlier examples or intermediates, the reaction time, number of equivalents of reagents, and temperature, can be modified for each specific reaction and that it may be necessary or desirable to employ different work-up or purification techniques. Where reactions are carried out using microwave irradiation, the microwave oven used was either a Biotage Initiator or in CEM Discover System Model 908005. The actual power supplied varies during the reaction in order to maintain a constant temperature.

General Methods

All reactions requiring anhydrous conditions were conducted in flame-dried glassware under a positive pressure of either nitrogen or argon. Commercially available reagents were used as received; otherwise, materials were purified according to *Purification of Laboratory Chemicals*, Dichloromethane ($CH_2Cl_2$), N,N'-dimethylformamide (DMF), toluene and tetrahydrofuran (THF) were degassed with nitrogen and passed through a solvent purification system (Innovative Technologies Pure Solv). Dry 1,4-dioxane was purchased from Acros Organics in an Acros Seal™ bottle. Triethylamine ($Et_3N$) N,N-diisopropylethylamine (DIPEA were distilled from $CaH_2$ immediately prior to use, stored over 4 Å molecular sieves or distilled over 4 Å molecular sieves prior to usage. Microwave reactions were done in CEM Discover System Model 908005. Reactions were monitored by TLC and visualized by a dual short wave/long wave UV lamp and/or stained with ethanolic solutions of either $KMnO_4$12-phosphomolybdic acid or other commonly used stains. Flash chromatography was performed on Merck silica gel Kieselgel 60 (230-400 mesh) from EM Science with the indicated HPLC grade solvent or an automated medium pressure column chromatography system (Teledyne ISCO CombiFlash RF75 or CombiFlash Rf+). Reverse phase HPLC was conducted on a Waters HPLC Semi Prep 150B system with Sunfire $C_{18}$ Prep Column or Atlantis T3 Prep Column with isocratic or gradient conditions with $H_2O$ (0.1% TFA) and 10% $H_2O$:90 $CH_3CN$ (0.1% TFA) as eluents Melting points were determined using Mel-Temp® Capillary Melting Point Apparatus. Infrared spectra were obtained using Nicolet 380-FT IR spectrometer fitted with a Smart Orbit sample system. Optical rotations were obtained at ambient temperature on a Perkin Elmer Model 343 polarimeter (Na D line) using a microcell with a 1 decimeter path length. Mass spectra determined by LCMS were collected on Thermo Scientific™ UltiMate™ 3000 UHPLC with electrochemical detector with a fluorescence detector monitored at either 214 or 254 nm, or a Waters Aquity UPLC HClass Series with photodiode array detector and QDa mass detector. $^1H$ NMR spectra were recorded at 500 MHz, 400 MHz, and 300 MHz, and $^{13}C$ at 125 MHz. Proton resonances were reported relative to the deuterated solvent peak: 7.27 ppm for $CDCl_3$3.31 ppm (center line signal) for $CD_3OD$, 2.50 for D6-DMSO and 4.79 for $D_2O$ using the following format: chemical shift (δ (ppm)) [multiplicity (s=singlet, br s=broad singlet, d=doublet, t=triplet, q=quartet, m=multiplet)]. Carbon resonances were reported as chemical shifts (δ) in parts per million, relative to the center line signal of the respective solvent peak: 77.23 ppm for $CDCl_3$ and 49.15 ppm for $CD_3OD$. Commercially available chemicals are purchased from multiple vendors including Sigma-Aldrich, Acros, Enamine, TCI America, Combi-Blocks, Alfa-Aesar, Angene, Ark Pharma, PharmaBlock, Strem Chemicals, Frontier Scientific, and AstaTech, Inc.

Liquid Chromatography-Mass Spectrometry Methods

Liquid Chromatography-Mass Spectrometry Method A

Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. [LC/MS-ES (+/−): analyses performed using an Acquity UPLC™ CSH, $C_{18}$ column (50×2.1 mm, 1.7 μm particle size), column temperature 40° C., mobile phase: A-water+0.1% HCOOH/B—$CH_3CN$+0.1% HCOOH, flow rate: 1.0 mL/min, runtime=2.0 min, gradient: t=0 min 3% B, t=1.5 min 99.9% B, t=1.9 min 99.9% B, t=2.0 min 3% B, stop time 2.0 min. Positive ES 100-1000, Negative ES 100-1000, UV detection DAD 210-350 nm.

Liquid Chromatography-Mass Spectrometry Method B

Total ion current (TIC) and DAD UV chromatographic traces together with MS and UV spectra associated with the peaks were taken on a UPLC/MS Acquity™ system equipped with PDA detector and coupled to a Waters single quadrupole mass spectrometer operating in alternated positive and negative electrospray ionization mode. [LC/MS-ES (+/−): analyses performed using an Acquity UPLC™ BEH, $C_{18}$ column (50×2.1 mm, 1.7 μm particle size), column temperature 40° C., mobile phase: A—0.1% v/v aqueous (aq) ammonia solution pH 10/B—$CH_3CN$, flow rate: 1.0 mL/min, runtime=2.0 min, gradient: t=0 min 3% B, t=1.5 min 99.9% B, t=1.9 min 99.9% B, t=2.0 min 3% B, stop time 2.0 min. Positive ES 100-1000, Negative ES 100-1000, UV detection DAD 210-350 nm.

Liquid Chromatography-Mass Spectrometry Method C

LC/MS-ES (+/−): analyses performed using an AQUITY with PDA detector and QDA Performance, $C_{18}$ column (50×2.1 mm, 1.6 μm particle size), column temperature 35° C., mobile phase: A—0.1% Formic acid in Milli Q water (pH=2.70)/B—0.1% Formic acid in water: $CH_3CN$ (10:90), flow rate: 0.8-1.0 mL/min, runtime=4.0 min, gradient: t=0 min 3% B, t=2.7 min 98% B, t=3.0 min 100% B, t=3.51 min 3% B, stop time 4.0 min.

Liquid Chromatography-Mass Spectrometry Method D

LC/MS-ES (+/−): analyses performed using AQUITY HClass with PDA detector and QDA, $C_{18}$ column (50×2.1 mm, 1.6 μm particle size), column temperature 35° C., mobile phase: A—0.1% Formic acid in Milli Q water (pH=2.70)/B—0.1% Formic acid in water: $CH_3CN$ (10:90), flow rate: 0.8-1.0 mL/min, runtime=4.0 min, gradient: t=0 min 3% B, t=2.7 min 98% B, t=3.0 min 100% B, t=3.51 min 3% B, stop time 4.0 min.

Liquid Chromatography-Mass Spectrometry Method E

LC/MS-ES (+/−): analyses performed using AQUITY HClass with PDA detector and QDA, $C_{18}$ column (50×2.1 mm, 1.6 μm particle size), column temperature 35° C., mobile phase: A—0.1% Formic acid in water (pH=2.70)/B—0.1% Formic acid in water: $CH_3CN$ (10:90), runtime=9.0 min, gradient: t=0 min 1% B, t=2.5 min 50% B, t=4.5 min 97.5% B, t=6.5 min 1% B, stop time 9.0 min.

Liquid Chromatography-Mass Spectrometry Method F

LC/MS-ES (+/−): analyses performed using Agilent Infinity II G6125C LCMS, $C_{18}$ column (50×4.6 mm, 3.5 μm particle size), column temperature 35° C., mobile phase: A—5 mM Ammonium Bicarbonate in Milli-Qwater (pH=7.35)/B—MeOH, runtime=7.0 min, gradient: t=0 min 8% B, t=3.0 min 70% B, t=3.7 min 95% B, t=4.2 min 100% B, t=5.21 min 8% B, stop time 7.0 min.

Liquid Chromatography-Mass Spectrometry Method G

LC/MS-ES (+/−): analyses performed using Waters Alliance 2690 and 996 PDA detector with Micromass ZQ, $C_{18}$ column (150×4.6 mm, 3.5 μm particle size), column temperature 35° C., mobile phase: A—5 mM Ammonium Acetate+0.1% FA in Water/B-MeOH, runtime=17.0 min, gradient: t=0 min 10% B, t=7.0 min 90% B, t=9.0 min 100% B, t=14.01 min 10% B, stop time 17.0 min.

Liquid Chromatography-Mass Spectrometry Method H

LC/MS-ES (+/−): analyses performed using AQUITY with PDA detector and QDA Performance, $C_{18}$ column (50×2.1 mm, 1.6 μm particle size), column temperature 35° C., mobile phase: A—0.1% Formic acid inMilli Q water (pH=2.70)/B—0.1% Formic acid in water: $CH_3CN$ (10:90), flow rate: 0.9 mL/min, runtime=3.0 min, gradient: t=0 min 5% B, t=1.8 min 98% B, t=2.0 min 100% B, t=2.51 min 5% B, stop time 17.0 min.

Analytical Methods

1H Nuclear magnetic resonance (NMR) spectroscopy was carried out using one of the following instruments: a Bruker Avance 400 instrument equipped with probe DUAL 400 MHz S1a Bruker Avance 400 instrument equipped with probe 6 S1 400 MHz 5 mm $^1H$-$^{13}C$ ID, a Bruker Avance III 400 instrument with nanobay equipped with probe Broadband BBFO 5 mm direct, a 400 MHz Agilent Direct Drive instrument with ID AUTO-X PFG probe, all operating at 400 MHz, or an Agilent VNMRS500 Direct Drive instrument equipped with a 5 mm Triple Resonance $^1H\{^{13}C/^{15}N\}$ cryoprobe operating at 500 MHz. The spectra were acquired in the stated solvent at around room temperature unless otherwise stated. In all cases, NMR data were consistent with the proposed structures. Characteristic chemical shifts (δ) are given in parts-per-million using conventional abbreviations for designation of major peaks: e.g. s, singlet; d, doublet; t, triplet; q, quartet; dd, doublet of doublets; dt, doublet of triplets; br, broad.

Thin layer chromatography (TLC) refers to silica gel TLC using silica gel F254 (Merck) plates. Column chromatography was performed using an automatic column chromatography (Biotage SP1 or Isolera) system over Biotage silica gel cartridges (KP-Sil or KP-NH) or in the case of reverse phase chromatography over Biotage $C_{18}$ cartridges (KP-$C_{18}$).

Prep HPLC were performed on Shimadzu LC-20AP, Waters 2545 and Agilent 1260 infinity. Purity was determined on Waters Alliance e2695-PDA detector 2998 and Agilent 1260 Infinity-II. (Mobile phase: 0.05% HCl in Water/MeOH in gradient elution method).

TABLE 14

Abbreviations and Names of Reagents

| Abbreviations/ Acronyms | Full Name/Description |
|---|---|
| AcOH | Acetic acid |
| aq. | aqueous |
| $CH_3CN$ | Acetonitrile |
| $B_2pin_2$ | Bis(pinacolato)diboron |
| $Boc_2O$ | Di-tert-butyl dicarbonate |
| $BH_3$•$SMe_2$ | Borane dimethyl sulfide complex |
| i-BuMgBr | Isobutyl magnesium bromide |
| n-BuLi | n-Butyllithium |
| $B(O\text{-}iPr)_3$• | Triisopropyl borate |
| CBzCl | Benzyl chloroformate |
| CDI | 1,1'-Carbonyldiimidazole |
| DAST | Diethylaminosulfur trifluoride |
| DCE | 1,2-Dichloethane |
| DCM | Dichloromethane |
| DIAD | Diisopropyl azodicarboxylate |
| DIPEA | N,N-Diisopropylethylamine |
| DMAP | N,N-dimethylaminopyridine |
| DMF | N,N'-dimethylformamide |
| DMP | Dess-Martin periodinane |
| DMSO | Dimethylsulfoxide |
| EDCI | 1-Ethyl-3-(3-dimethylaminopropyl)carbodiimide |
| DPPA | Diphenylphosphoryl azide |

TABLE 14-continued

Abbreviations and Names of Reagents

| Abbreviations/ Acronyms | Full Name/Description |
|---|---|
| $Et_2O$ | Diethyl ether |
| $Et_3N$ | Triethylamine |
| EtOAc | Ethyl acetate |
| EtOH | Ethanol |
| EtMgBr | Ethylmagnesium bromide |
| HATU | Hexafluorophosphate azabenzotriazole tetramethyl uronium |
| HPLC | High performance liquid chromatography |
| KHMDS | Potassium bis(trimethylsilyl)amide |
| LCMS | Liquid chromatography mass spectrometry |
| LDA | Lithium diisopropylamide |
| $Li(AlH)_4$ | Lithium aluminum hydride |
| $LiAlH(Ot\text{-}Bu)_3$ | Lithium tri-tert-butoxyaluminum hydride |
| LHMDS | Lithium bis(trimethylsilyl)amide |
| MeOH | Methanol |
| MeI | Methyl Iodide |
| min. | minutes |
| MsCl | Methane sulfonyl chloride |
| NMR | Nuclear magnetic resonance |
| rt | Room temperature |
| $NaBH_4$ | Sodium borohydride |
| $NaBH(Oac)_3$ | Sodium triacetoxyborohydride |
| NaOAc | Sodium acetate |
| $NaBH_3CN$ | Sodium cyanoborohydride |
| PCC | Pyridinium chlorochromate |
| $Pd(dba)_2$ | Bis(dibenzylideneacetone)palladium(0) |
| $Pd(dppf)Cl_2$ | [1,1'-Bis(diphenylphosphino)ferrocene]dichloro-palladium(II) |
| $PPh_3$ | Triphenylphosphine |
| sat. | Saturate |
| TBAF | Tetrabutlyammonium fluoride |
| TBSCl/TBDMSCl | t-butyldimethylsilyl chloride |
| Ti(O—iPr)$_4$ | Titanium isopropoxide |
| TEA | Triethylamine |
| TFA | Trifluoroacetic acid |
| TFAA | Trifluoroacetic anhydride |
| THF | Tetrahydrofuran |
| TMEDA | N,N,N',N'-Tetramethylethylenediamine |
| TMSCN | Trimethylsilyl cyanide |
| TsOH | p-Toluenesulfonic acid |

Intermediate Synthesis

Intermediate 1

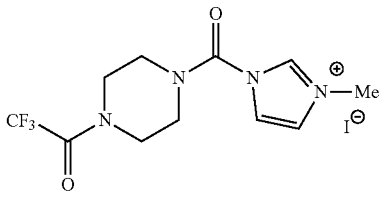

3-Methyl-1-(4-(2,2,2-trifluoroacetylpiperazine-1-carbonyl)-1H-imidazol-3-ium Iodide Scheme I-1

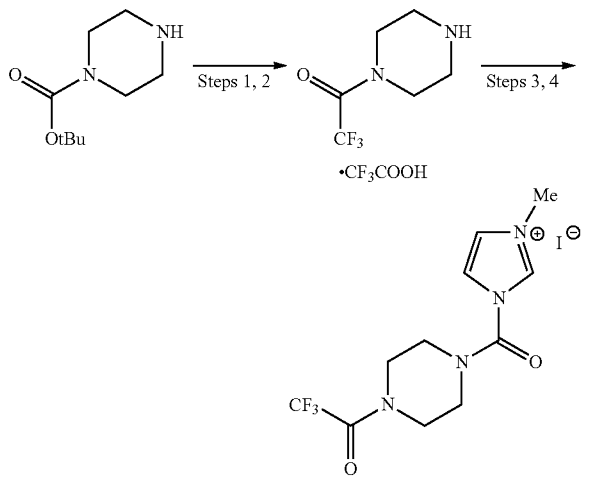

Reagents: a) TFAA, $CH_2Cl_2$, 0° C. to rt, 16 h b) TFA, $CH_2Cl_2$, rt, 1.5 h c) CDI, $CH_2Cl_2$, 16 h d) MeI, $CH_3CN$, rt, 16 h.

Step 1: tert-butyl 4-(2,2,2-trifluoroacetyl)piperazine-1-carboxylate. A solution of tert-butyl piperazine-1-carboxylate (20.0 g, 107 mmol) in dry $CH_2Cl_2$ (100 mL) was cooled to 0° C. under $N_2$. TFAA (15.0 ml, 107 mmol) was added dropwise over 10 min. The reaction was warmed to rt and stirred for 16 h. The reaction mixture was diluted with $CH_2Cl_2$ (1 L), and quenched with saturated $NaHCO_3$ (1 L). The organic layer was separated, dried over $Na_2SO_4$, filtered and concentrated under reduced pressure to afford the title compound as a pale orange solid (29.1 g, 96%).

Step 2: 2,2,2-trifluoro-1-(piperazin-1-yl)ethan-1-one trifluoroacetate salt. To a solution of TFA in $CH_2Cl_2$ (50 mL, 1:1) was added tert-butyl 4-(2,2,2-trifluoroacetyl) piperazine-1-carboxylate (29.1 g, 103 mmol). The reaction was stirred for 1.5 h at rt. The solvent and TFA were removed under reduced pressure. The crude reaction mixture was triturated with $Et_2O$ to yield a solid precipitate. The solid was filtered and washed with $Et_2O$ to yield the title compound as a white solid (29.5 g, 97%).

Step 3: 1-(4-(1H-imidazole-1-carbonyl)piperazin-1-yl)-2,2,2-trifluoroethan-1-one. To suspension of 2,2,2-trifluoro-1-(piperazin-1-yl)ethan-1-one trifluoroacetate salt (26.0 g, 88 mmol) in $CH_2Cl_2$ (100 mL) was added CDI (17.1 g, 105 mmol). The reaction mixture was stirred for 16 h at rt. The reaction was concentrated under reduced pressure and the crude reaction mixture was purified by column chromatography to afford the desire product as a white solid (18 g, 76%).

Step 4: 3-methyl-1-(4-(2,2,2-trifluoroacetylpiperazine-1-carbonyl)-1H-imidazol-3-ium iodide. To a solution of 1-(4-(1H-imidazole-1-carbonyl)piperazin-1-yl)-2,2,2-trifluoroethan-1-one (10.8 g, 39.1 mmol) in dry $CH_3CN$ (80 mL) was added MeI (15.0 mL, 235 mmol). The reaction was stirred for 24 h at rt. The solvent and excess MeI were removed under reduced pressure to yield the title compound as a light yellow solid (27.6 g, 98%).

Intermediate 2

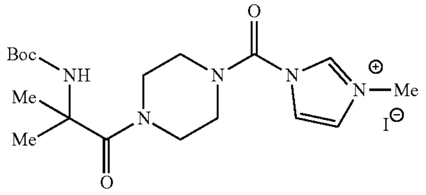

1-(4-(2-((tert-butoxycarbonyl)amino)-2-methylpropanoyl)piperazine-1-carbonyl)-3-methyl-1H-imidazol-3-ium Iodide Scheme I-2

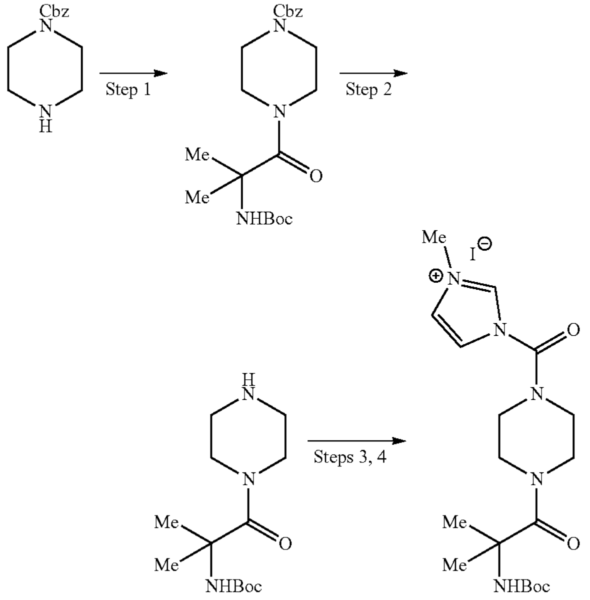

Reagents: 1) HATU, DIPEA, DMF, rt, 16 h 2) 10% Pd/C, MeOH, rt, 16 h 3) CDI, $CH_2Cl_2$, rt, 16 h 4) MeI, $CH_3CN$, rt, 16 h.

Step 1: benzyl 4-(2-((t-butoxycarbonyl) amino)-2-methylpropanoyl) piperazine-1-carboxylate. To a stirred solution of 2-((t-butoxycarbonyl) amino)-2-methylpropanoic acid (35.5 g, 174.8 mmol) in DMF (350 mL) were added DIPEA (51.24 g, 397.2 mmol) and HATU (90.62 g, 238.3 mmol) at 0° C. The reaction mixture was stirred at 0° C. for 45 min. Benzyl piperazine-1-carboxylate (35 g, 158.9 mmol) was added to the reaction mixture at 0° C. and stirred at rt for 16 h. The reaction mixture was poured into $H_2O$ (1500 mL) and extracted with EtOAc (3x700 mL) and the combined organics were dried over $Na_2SO_4$, filtered and concentrated under reduced pressure. The resulting crude material was purified by column chromatography (20-30% Hexane: EtOAc) to afford the title compound (36.0 g, 55%) as an off-white solid. LCMS [M+H] 406.

Step 2: t-butyl (2-methyl-1-oxo-1(piperazn-1-yl) propan-2-yl)carbamate. To a stirred solution of benzyl 4-(2-((t-butoxycarbonyl) amino)-2-methylpropanoyl) piperazine-1-carboxylate (35.0 g, 86.4 mmol) in MeOH (500 mL) was added 10% Pd/C (3.5 g). The reaction mixture was stirred under $H_2$ at rt for 16 h. The reaction mixture was filtered through Celite® and washed with MeOH (1500 mL). The filtrate was concentrated under reduced pressure and dried to afford the title compound (25.0 g, Quant.) as a viscous oil. LCMS [M+H] 272.

Step 3: t-butyl (1-(4-1H-imidazole-1-carbonyl) piperazin-1-yl)-2-methyl-1-oxopropan-2-yl) carbamate. To a stirred solution of t-butyl (2-methyl-1-oxo-1(piperazn-1-yl) propan-2-yl) carbamate (25.0 g, 92.2 mmol) in $CH_2Cl_2$ (300 mL) was added CDI (17.78 g, 109.7 mmol) at rt. The reaction mixture was stirred at rt for 16 h. The reaction mixture was concentrated under reduced pressure and the crude material was purified by column chromatography (4-5% MeOH in $CH_2Cl_2$) to afford the title compound (30.0 g, 89%) as an off-white solid. $^1H$ NMR (DMSO-$d_6$400 MHz): δ 8.04 (s, 1H), 7.48 (s, 1H), 7.36 (s, 1H), 7.03 (s, 1H), 3.65-3.52 (m, 4H), 3.51-3.40 (m, 4H), 1.38 (s, 6H), 1.30 (s, 9H). LCMS [M+H] 366.3.

Step 4: 1-(4-(2-((t-butoxycarbonyl) amino)-2-methylpropanoyl) piperazine-1-carbonyl)-3-methyl-1H-imidazol-3-ium iodide. To a stirred solution of t-butyl (1-(4-1H-imidazole-1-carbonyl)piperazin-1-yl)-2-methyl-1-oxopropan-2-yl)carbamate (20.0 g, 54.8 mmol) in $CH_3CN$ (250 mL) was added MeI (46.66 g, 20.8 ml, 328.7 mmol) at 0° C. The reaction mixture was stirred at rt for 16 h. The reaction mixture was concentrated under reduced pressure to afford the title compound (30.0 g, Quant.) as a pale yellow solid. $^1H$ NMR (DMSO-$d_6$400 MHz): δ 9.57 9 s, 1H), 8.05 (s, 1H), 7.87 (t, 1H), 7.40 (s, 1H), 3.93 (s, 3H), 3.78-3.65 (m, 4H), 3.59-3.45 (m, 4H), 1.40 (s, 6H), 1.32 (S, 9H). LCMS [M+H] 380.2 (−iodide).

Intermediate 3

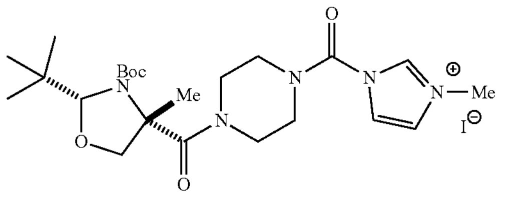

1-(4-((2R,4S)-3-(tert-Butoxycarbonyl)-2-(tert-butyl)-4-methyloxazolidine-4-carbonyl)piperazine-1-carbonyl)-3-methyl-1H-imidazol-3-ium Iodide Prepared in a similar fashion to Scheme 1-2 from (2R, 4S)-3-(tert-butoxycarbonyl)-2-(tert-butyl)oxazolidine-4-carboxylic acid and 1-Cbz-piperazine to afford the title compound as a yellow solid.

Intermediate 4

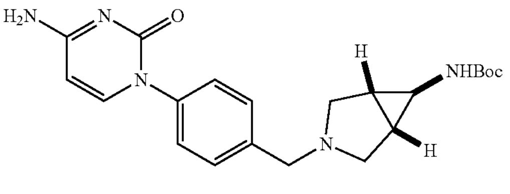

tert-Butyl N-[exo-3-{[4-(4-amino-2-oxo-1,2-dihydropyrimidin-1-yl)phenyl]methyl}-3-azabicyclo[3.1.0]hexan-6-yl]carbamate Scheme I-3

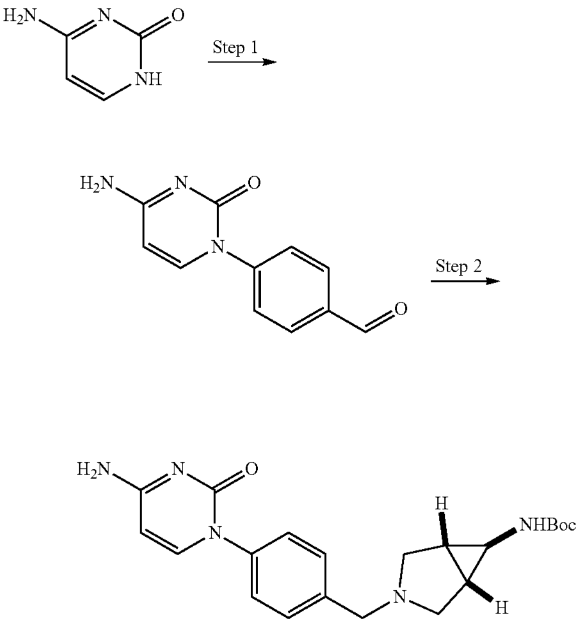

Reagents: Step 1) 4-Formylphenylboronic acid, TMEDA, $Cu(OAc)_2 \cdot H_2O$, MeOH:$H_2O$, rt, 16 h 2) tert-Butyl (exo-3-azabicyclo[3.1.0]hexan-6-yl)carbamate, $NaBH(OAc)_3$, DCE:$CH_3CN$, rt, 16 h Step 1:) Step 1: 4-(4-amino-2-oxopyrimidin-1 (2H)-yl) benzaldehyde: A suspension of cytosine (2.60 g, 24.0 mmol) and 4-formylphenylboronic acid (3.53 g 24 mmol) in a mixture of 4:1 MeOH:$H_2O$ (25 ml), was stirred at rt in open air. After 30 min. TMEDA (6.70 ml, 28.0 mmol) and $Cu(OAc)_2H_2O$ (4.70 g 24.0 mmol) were added. The reaction was stirred open to air for 16 h at rt. The MeOH was evaporated under reduced pressure, and ice was added to the remaining mixture and stirred for 10 min. The reaction mixture was was filtered and the solid was washed with $H_2O$ to yield the title compound (3.5 g, 69%) as a white solid.

Step 2: tert-butyl (exo-3-(4-(4-amino-2-oxopyrimidin-1 (2H)-yl)benzyl)-3-azabicyclo[3.1.0]hexan-6-yl)carbamate: tert-Butyl N-[exo-3-azabicyclo[3.1.0]hexan-6-yl]carbamate (2.07 g, 10.5 mmol) and AcOH (0.5 mL) were added to a suspension of 4-(4-amino-2-oxo-1,2-dihydropyrimidin-1-yl)benzaldehyde (1.5 g, 6.97 mmol) in DCE (80 mL). The reaction was stirred at rt for 15 min and $NaBH(OAc)_3$ (3.7 g, 17.5 mmol) was added. After 2 h the reaction was diluted with $CH_2Cl_2$ and washed with sat. $NaHCO_3$ solution. The organic portion was concentrated under reduced pressure. The crude product was triturated with a mixture of EtOAc, MeOH and cyclohexane. The solid was filtered and dried to afford the title compound (3.26 g, 85%). $^1H$ NMR (400 MHz, DMSO-$d_6$) δ 7.62 (d, 1H), 7.35-7.12 (m, 6H), 6.95-6.82 (m, 1H), 5.78 (d, 1H), 3.61-3.54 (m, 2H), 2.93 (d, 2H), 2.76-2.65 (m, 1H), 2.35 (d, 2H), 1.44 (br. s, 2H), 1.37 (s, 9H). LCMS [M+H] 398.4.

Intermediate 5

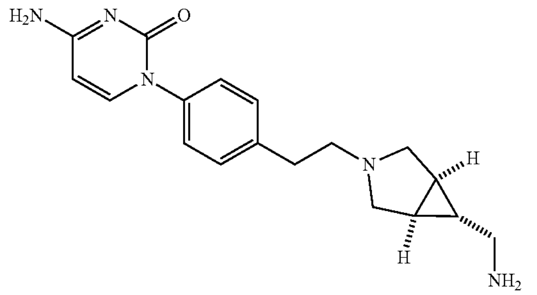

tert-Butyl ((exo-3-(4-(4-amino-2-oxopyrimidin-1(2H)-yl)phenethyl)-3-azabicyclo[3.1.0]hexan-6-yl)methyl)carbamate Scheme I-4

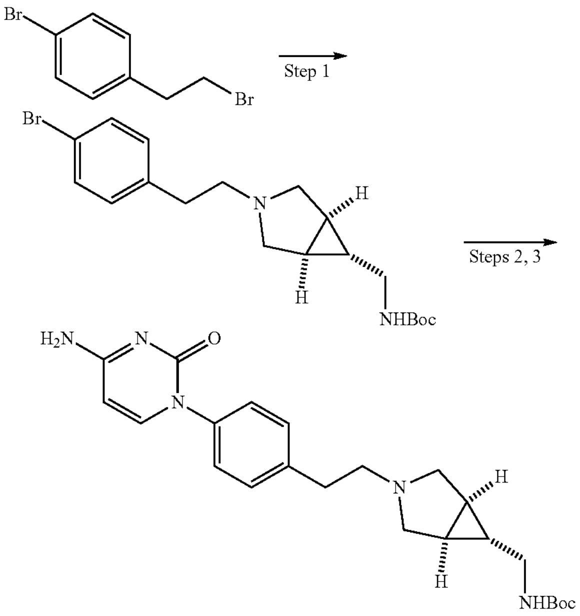

Reagents: Step 1) tert-butyl ((exo-3-azabicyclo[3.1.0]hexan-6-yl)methyl)carbamate, $K_2CO_3$, THF, 85° C., 48 h 2) $Pd(dppf)Cl_2$, KOAc, 1,4-dioxane, 90° C., 16 h 3) TMEDA, $Cu(OAc)_2 \cdot H_2O$, $CH_3OH$:$H_2O$ (4:1), $O_2$, rt, 48 h.

Step 1: t-butyl ((exo-3-(4-bromophenethyl)-3-azabicyclo[3.1.0]hexan-6-yl)methyl)carbamate. A mixture of 1-bromo-4-(2-bromoethyl)benzene (0.9 g, 3.40 mmol), t-butyl ((exo-3-azabicyclo[3.1.0]hexan-6-yl)methyl)carbamate (0.7 g, 3.4 mmol), and $K_2CO_3$ (1.41 mL, 10.2 mmol) in THF (10 mL) was stirred at 85° C. for 48 h. It was cooled, poured into $H_2O$ (50 mL), and extracted with $CH_2Cl_2$ (3×20 mL). The extracts were dried over $Na_2SO_4$, filtered, concentrated under reduced pressure, and the residue was purified by column chromatography on silica gel ($CH_3OH/CH_2Cl_2$) to afford the title compound. LCMS [M+H] 395.1.

Step 2: t-butyl ((exo-3-(4-(4,4,5,5-tetramethyl-1,3,2-dioxaborolan-2-yl)phenethyl)-3-azabicyclo[3.1.0]hexan-6-yl)methyl)carbamate. A mixture of tert-butyl ((exo-3-(4-bromophenethyl)-3-azabicyclo[3.1.0]hexan-6-yl)methyl)carbamate (0.85 g, 2.15 mmol), bis(pinacolato)diboron (1.1 g, 4.31 mmol), and KOAc (0.8 g, 8.62 mmol) in 1,4-dioxane (20 mL) was purged with $N_2$ for 15 min. $Pd(dppf)C_{12}$ (0.088 g, 0.10 mmol) was added and the mixture was stirred at 90° C. for 16 h, cooled, poured into $H_2O$ (100 mL), and extracted with EtOAc (2×100 mL). The extracts were dried ($Na_2SO_4$), filtered, and concentrated under reduced pressure to afford the title compound. LCMS [M+H] 443.3.

Step 3: t-butyl ((exo-3-(4-(4-amino-2-oxopyrimidin-1(2H)-yl)phenethyl)-3-azabicyclo[3.1.0]hexan-6-yl)methyl)carbamate. A mixture of tert-butyl ((exo-3-(4-(4,4,5,5-tetramethyl-1,3,2-dioxaborolan-2-yl)phenethyl)-3-azabicyclo[3.1.0]hexan-6-yl)methyl)carbamate (1.9 g, 4.29 mmol) and cytosine (0.58 g, 5.27 mmol) in $CH_3OH$:$H_2O$ (4:1, 50 mL) was stirred at rt open to air for 30 min. TMEDA (0.9 mL, 6.33 mmol) and $Cu(OAc)_2 \cdot H_2O$ (0.98 g, 5.27 mmol) were added, and the mixture was stirred at rt open to air for 48 h. It was poured into $H_2O$ (150 mL) and extracted with $CH_2Cl_2$ (2×100 mL). The extracts were dried ($Na_2SO_4$), filtered, and concentrated under reduced pressure, and the residue was triturated with $Et_2O$ (10 mL) to afford the title compound. LCMS [M+H] 426.3.

Intermediate 6

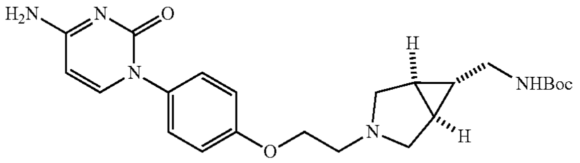

tert-Butyl ((exo-3-(4-(4-amino-2-oxopyrimidin-1(2H)-yl)phenethyl)-3-azabicyclo[3.1.0]hexan-6-yl)methyl)carbamate Scheme I-5

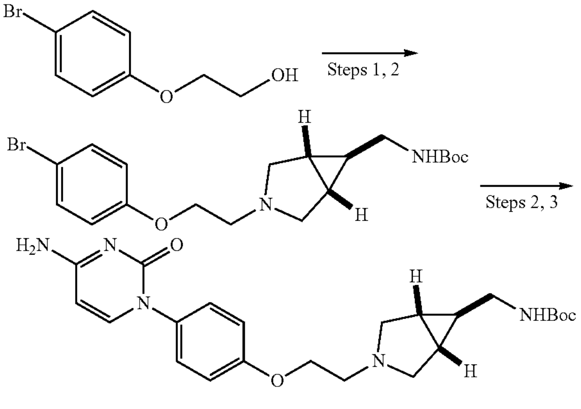

Reagents: 1) MsCl, $Et_3N$, $CH_2Cl_2$, 1 h 2) tert-butyl ((exo-3-azabicyclo[3.1.0]hexan-6-yl)methyl)carbamate, $K_2CO_3NaI$, $CH_3CN$, reflux, 4 h 3)$B_2pin_2Cl_2$ $Pd(dppf).CH_2Cl_2$, KOAc, dioxane, 100° C., 16 h 4) Cytosine, $Cu(OAc)_2 \cdot H_2O$, TMEDA, MeOH, $H_2O$, air, 72 h.

Step 1: 2-(4-bromophenoxy)ethyl methanesulfonate. MsCl (2.2 mL, 28.4 mmol) was added dropwise to a solution of 2-(4-bromophenoxy)ethanol (5.11 g, 23.6 mmol) and $NEt_3$ (4.9 mL, 35.2 mmol) in $CH_2Cl_2$ (120 mL). The mixture was stirred at rt under $N_2$ for 1 h, poured into sat. aq. $NaHCO_3$ (250 mL) and extracted with $CH_2Cl_2$ (2×200 mL). The extracts were dried ($Na_2SO_4$), filtered, and concentrated under reduced pressure to afford the title compound.

Step 2: tert-butyl ((exo-3-(2-(4-bromophenoxy)ethyl)-3-azabicyclo[3.1.0]hexan-6-yl)methyl)carbamate. A mixture of 2-(4-bromophenoxy)ethyl methanesulfonate (2.23 g, 7.55 mmol), tert-butyl ((exo-3-azabicyclo[3.1.0]hexan-6-yl) methyl)carbamate (1.76 g, 8.27 mmol), $K_2CO_3$ (2.10 g, 15.20 mmol), and NaI (1.22 g, 8.16 mmol) in $CH_3CN$ (50 mL) was stirred at reflux under $N_2$ for 4 h. It was cooled, diluted with EtOAc (250 mL), washed with sat. aq. $NaHCO_3$ (2×150 mL) followed by brine (1×150 mL), dried ($Na_2SO_4$), filtered and concentrated under reduced pressure to afford the title compound. The product was used in the next step without further purification.

Step 3: tert-butyl ((exo-3-(2-(4-(4,4,5,5-tetramethyl-1,3,2-dioxaborolan-2-yl)phenoxy)ethyl)-3-azabicyclo[3.1.0]hexan-6-yl)methyl)carbamate. A mixture of tert-butyl ((exo-3-(2-(4-bromophenoxy)ethyl)-3-azabicyclo[3.1.0]hexan-6-yl)methyl)carbamate (2.99 g, 7.26 mmol), bis(pinacolato) diboron (3.69 g, 14.53 mmol), $Cl_2Pd(dppf)\cdot CH_2Cl_2$ (296 mg, 0.362 mmol), and KOAc (1.45 g, 14.74 mmol) in dry dioxane (35 mL) was placed under an $N_2$ atmosphere and purged with $N_2$ for 20 min and then stirred at 100° C. for 16 h, cooled, diluted with EtOAc (100 mL), and filtered through Celite® rinsing with additional EtOAc (50 mL). The filtrate was concentrated under reduced pressure and purified by column chromatography on silica gel (MeOH/EtOAc/hexanes) to afford the title compound.

Step 4: tert-butyl ((exo-3-(2-(4-(4-amino-2-oxopyrimidin-1 (2H)-yl)phenoxy)ethyl)-3-azabicyclo[3.1.0]hexan-6-yl)methyl)carbamate. A mixture of tert-butyl ((exo-3-(2-(4-(4,4,5,5-tetramethyl-1,3,2-dioxaborolan-2-yl)phenoxy) ethyl)-3-azabicyclo[3.1.0]hexan-6-yl)methyl)carbamate (3.27 g, 7.13 mmol) and cytosine (796 mg, 7.16 mmol) in MeOH (32 mL) and $H_2O$ (8 mL) was stirred for 20 min. $Cu(OAc)_2\cdot H_2O$ (1.42 g, 7.1 mmol) and TMEDA (1.28 mL, 8.54 mmol) were added and the mixture was stirred open to the air for 72 h. The reaction mixture was concentrated under reduced pressure to remove most of the MeOH. $H_2O$ and ice were added to the residue, and the precipitate was collected by vacuum filtration. The solid was dissolved in $CH_2Cl_2$ and MeOH, dry-loaded onto Celite®, and purified by column chromatography on silica gel ($CH_2Cl_2$/MeOH/$NH_4OH$) to afford the title compound.

Intermediate 7

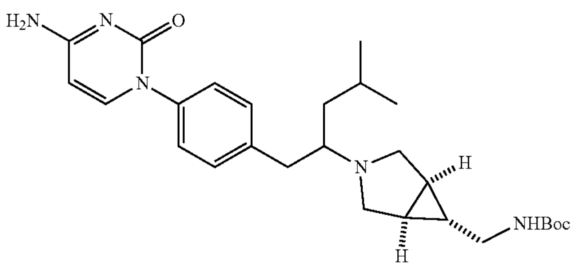

tert-Butyl ((exo-3-(1-(4-(4-amino-2-oxopyrimidin-1 (2H)-yl)phenyl)-4-methylpentan-2-yl)-3-azabicyclo[3.1.0] hexan-6-yl)methyl)carbamate Scheme I-6

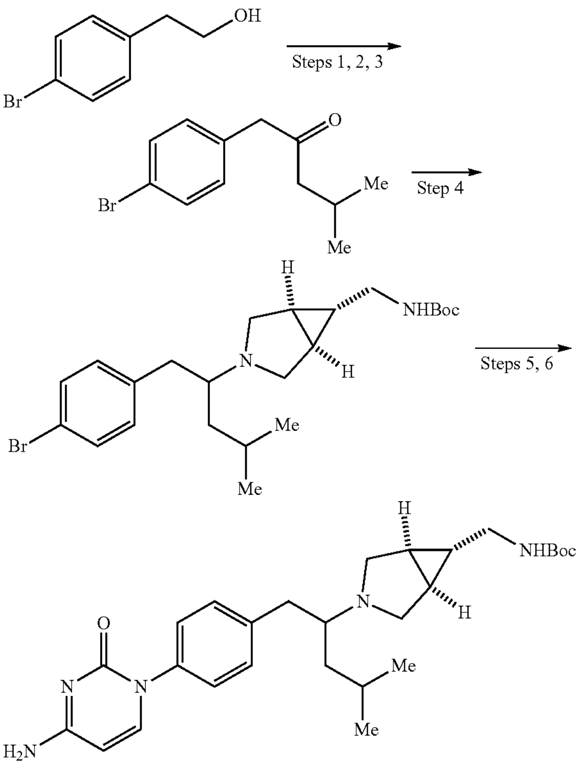

Reagents: 1) DMP, $CH_2Cl_2$, rt, 16 h 2) i-BuMgBr, THF −78° C., 2 h 3) DMP, $CH_2Cl_2$, rt, 16 h 4) tert-butyl ((exo-3-azabicyclo[3.1.0]hexan-6-yl)methyl)carbamate, $Ti(O\text{-}iPr)_4$70° C. to rt 16 h; $NaBH_4$, MeOH, 16 h 5) $B_2pin_2Cl_2Pd(dppf).CH_2Cl_2$, KOAc, dioxane, 100° C., 16 h 6) Cytosine, $Cu(OAc)_2\cdot H_2O$, TMEDA, MeOH, $H_2O$, air, 72 h.

Step 1: 2-(4-bromophenyl)acetaldehyde. To a solution of 2-(4-bromophenyl)ethan-1-ol (1.3 g, 6.47 mmol) in $CH_2Cl_2$ (100 mL) was added DMP (4.0 g, 9.43 mmol). The solution was stirred for 16 h. The crude reaction mixture was extracted with a 1:1 mixture of $NaHCO_3$ and $Na_2S_2O_3$ (3×300 mL). The organic layer was dried over $Na_2SO_4$ and concentrated under reduced pressure to afford the title compound as a yellow solid.

Step 2: 1-(4-bromophenyl)-4-methylpentan-2-ol. A solution of 2-(4-bromophenyl)acetaldehyde (1.0 g, 5.02 mmol) in THF (50 mL) was cooled to −78° C. To this was added isobutyl magnesium bromide (4.2 ml, 8.53 mmol) over the span of 30 min. The solution was stirred for 2 h and subsequently quenched with 1N HCl (10 mL). The crude rxn mixture was partitioned between EtOAc (100 mL) and 1N HCl (100 mL). The organic layer was dried over $Na_2SO_4$, concentrated under reduced pressure, and purified by column chromatography (Hex:EtOAc) to afford the title compound as a yellow semi-solid.

Step 3: 1-(4-bromophenyl)-4-methylpentan-2-one. To a solution of 1-(4-bromophenyl)-4-methylpentan-2-ol (520 mg, 2.02 mmol) in $CH_2Cl_2$ (50 mL) was added DMP (1.4 g, 3.30 mmol). The solution was stirred for 16 h. The crude reaction mixture was extracted with a 1:1 mixture of $NaHCO_3$ and $Na_2S_2O_3$ (3×300 mL). The organic layer was dried over $Na_2SO_4$ and concentrated under reduced pressure to afford the title compound as a yellow solid. The product was used in the next step without further purification.

Step 4: tert-butyl ((exo-3-(1-(4-bromophenyl)-4-methylpentan-2-yl)-3-azabicyclo[3.1.0]hexan-6-yl)methyl)carbamate. To a flask containing 1-(4-bromophenyl)-4-methylpentan-2-one (400 mg, 1.57 mmol) and tert-butyl ((exo-3-azabicyclo[3.1.0]hexan-6-yl)methyl)carbamate (489 mg, 2.30 mmol) was added neat $Ti(i\text{-}OPr)_4$ (4 mL). The rxn mixture was heated to 70° C. for 3 h, cooled to rt and stirred for 16 h. $NaBH_4$ (597 mg, 15.7 mmol) in MeOH (50 mL) was added portionwise over 30 min. The rxn mixture was stirred for an additional 16 h at which point the solution became a milky slurry. 1-2 mL of $H_2O$ was added and the slurry was filtered through Celite® and rinsed with EtOAc, this step was repeated as upon filtration more titanium salts had crashed out. The combined organics were concentrated under reduced pressure and partitioned between $CH_2Cl_2$ (100 mL) and 1N NaOH (100 mL), the aqueous layer was washed again with $CH_2Cl_2$ (2×50 mL). The combined organics were dried over $Na_2SO_4$, concentrated under reduced pressure, and purified by column chromatography (Hex:EtOAc) to afford the title compound as an off-white solid.

Step 5: tert-butyl ((exo-3-(4-methyl-1-(4-(4,4,5,5-tetramethyl-1,3,2-dioxaborolan-2-yl)phenyl)pentan-2-yl)-3-azabicyclo[3.1.0]hexan-6-yl)methyl)carbamate. A suspension of tert-butyl ((exo-3-(1-(4-bromophenyl)-4-methylpentan-2-yl)-3-azabicyclo[3.1.0]hexan-6-yl)methyl)carbamate (500 mg, 1.11 mmol), $B_2pin_2$ (421 mg, 1.66 mmol), $Pd(dppf)Cl_2(CH_2Cl_2)$ (27 mg, 0.03 mmol), and KOAc (271 mg, 2.78 mmol) in dioxane (50 mL) was degassed and heated to 100° C. for 16 h. The crude reaction mixture was filtered through Celite® and concentrated under reduced pressure. Purification by column chromatography (EtOAc:Hex) afforded the title compound.

Step 6: tert-butyl ((exo-3-(1-(4-(4-amino-2-oxopyrimidin-1 (2H)-yl)phenyl)-4-methylpentan-2-yl)-3-azabicyclo [3.1.0]hexan-6-yl)methyl)carbamate. A suspension of cytosine (116 mg, 1.05 mmol) and tert-butyl ((exo-3-(4-methyl-1-(4-(4,4,5,5-tetramethyl-1,3,2-dioxaborolan-2-yl)phenyl) pentan-2-yl)-3-azabicyclo[3.1.0]hexan-6-yl)methyl) carbamate (524 mg, 1.05 mmol) in 4:1 $MeOH:H_2O$ (100 mL) was stirred at rt in open air for 30 min. TMEDA (0.18 mL, 1.16 mmol) and $Cu(OAc)_2$—$H_2O$ (208 mg, 1.05 mmol) were added and the reaction was stirred in open air for 72 h at rt. The reaction mixture was concentrated under reduced pressure and $H_2O$ (50 mL) was added. The aqueous phase was extracted with $CHCl_3$ (4×15 mL) and the combined organics were concentrated under reduced pressure. The crude reaction mixture was purified by column chromatography ($MeOH:CHCl_3$) to afford the title compound.

Intermediate 8

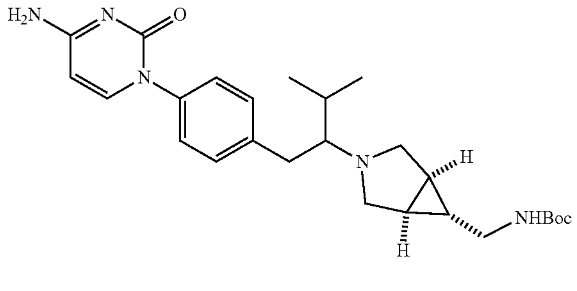

tert-Butyl ((exo-3-(1-(4-(4-amino-2-oxopyrimidin-1 (2H)-yl)phenyl)-3-methylbutan-2-yl)-3-azabicyclo [3.1.0]hexan-6-yl)methyl)carbamate Prepared in a similar fashion to Scheme 1-6 from 1-(4-bromophenyl)-3-methylbutan-2-one and tert-butyl ((exo-3-azabicyclo[3.1.0]hexan-6-yl)methyl)carbamate.

Intermediate 9

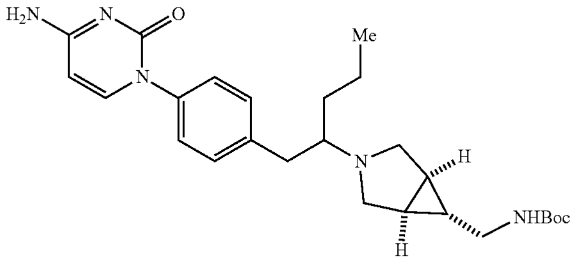

tert-Butyl ((exo-3-(1-(4-(4-amino-2-oxopyrimidin-1 (2H)-yl)phenyl)pentan-2-yl)-3-azabicyclo[3.1.0] hexan-6-yl)methyl)carbamate Prepared in a similar fashion to Scheme 1-6 from 1-(4-bromophenyl)pentan-2-one and tert-butyl ((exo-3-azabicyclo[3.1.0]hexan-6-yl)methyl)carbamate.

Intermediate 10

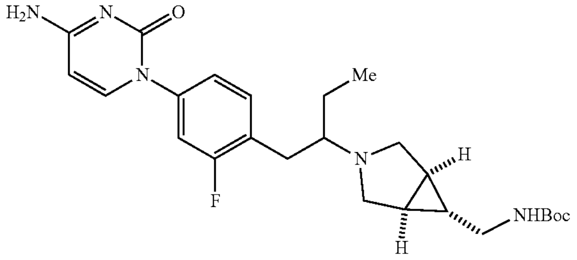

tert-Butyl ((exo-3-(1-(4-(4-amino-2-oxopyrimidin-1 (2H)-yl)-2-fluorophenyl)butan-2-yl)-3-azabicyclo [3.1.0]hexan-6-yl)methyl)carbamate Scheme I-7

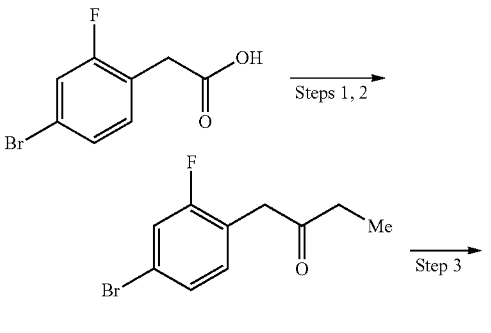

-continued

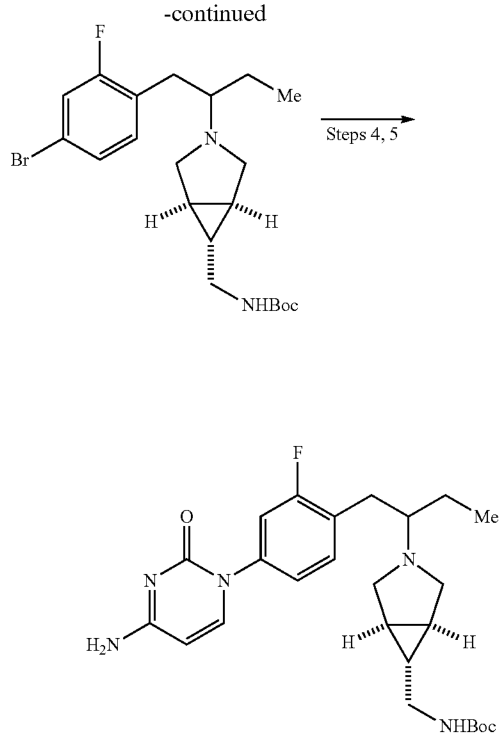

Reagents: 1) N,O-Dimethylhydroxylamine, EDCl·HCl, $NEt_3$, DMAP, $CH_2Cl_2$16 h 2) EtMgBr, THF, −78° C., 4 h 3) tert-butyl ((exo-3-azabicyclo[3.1.0]hexan-6-yl)methyl)carbamate, $NaCNBH_3$, MeOH, 16 h 4) $B_2pin_2Pd(dppf)_2$, KOAc, dioxane, 100° C., 16 h 5) cytosine, TMEDA, $Cu(OAc)_2$—$H_2O$, 4:1 MeOH:$H_2O$, 48 h.

Step 1: 2-(4-bromo-2-fluorophenyl)-N-methoxy-N-methylacetamide. To a solution of 2-(4-bromo-2-fluorophenyl)acetic acid (1.51 g, 6.51 mmol) in $CH_2Cl_2$ (50 mL) was added N,O-Dimethylhydroxylamine (0.96 g, 9.76 mmol), EDCl·HCl (1.86 g, 9.76 mmol), $NEt_3$ (3.60 mL, 26.04 mmol), and DMAP (0.10 g). The solution was stirred for 16 h. The reaction mixture was washed with sat. aq. aq. $NaHCO_3$ (1×50 mL), 2N HCl (1×50 mL), sat. aq. aq. $NaHCO_3$ (1×50 mL), and 2N HCl (1×50 mL). The organic extract was dried over $Na_2SO_4$, filtered, and the solvent was removed under reduced pressure to afford the title compound.

Step 2: 1-(4-bromo-2-fluorophenyl)butan-2-one. A solution of 2-(4-bromo-2-fluorophenyl)-N-methoxy-N-methylacetamide (1.60 g, 5.80 mmol) in THF (100 mL) was cooled to −78° C. EtMgBr (2.51 mL, 7.54 mmol) was added dropwise over the span of 25 min. The solution was stirred for an additional 4 h. The crude reaction mixture was quenched with $H_2O$ (5 mL) and combined solvents were removed under reduced pressure. The crude mixture was purified by column chromatography (Hexanes:EtOAc) to afford the title compound.

Step 3: tert-butyl ((exo-3-(1-(4-bromo-2-fluorophenyl) butan-2-yl)-3-azabicyclo[3.1.0]hexan-6-yl)methyl)carbamate. To a solution of 1-(4-bromo-2-fluorophenyl)butan-2-one (840 mg, 3.44 mmol) in MeOH (50 mL) was added tert-butyl ((exo-3-azabicyclo[3.1.0]hexan-6-yl)methyl)carbamate (877 mg, 4.14 mmol) followed by $NaCNBH_3$ (854 mg, 13.76 mmol). The solution was stirred for 16 h. The excess MeOH was removed and the crude solid was partitioned between EtOAc (100 mL) and 1N NaOH (100 mL). The aqueous layer was washed an additional time with EtOAc (1×50 mL). The combined organic extracts were dried over $Na_2SO_4$, filtered, and the solvent was removed under pressure. The crude mixture was purified by column chromatography (Hexanes:EtOAc) to afford the title compound.

Step 4: tert-butyl ((exo-3-(1-(2-fluoro-4-(4,4,5,5-tetramethyl-1,3,2-dioxaborolan-2-yl)phenyl)butan-2-yl)-3-azabicyclo[3.1.0]hexan-6-yl)methyl)carbamate. A mixture of tert-butyl ((exo-3-(1-(4-bromo-2-fluorophenyl)butan-2-yl)-3-azabicyclo[3.1.0]hexan-6-yl)methyl)carbamate (380 mg, 0.87 mmol), $B_2pin_2$ (329 mg, 1.30 mmol), KOAc (212 mg, 2.17 mmol), and $Pd(dppf)_2$ (21 mg, 0.03 mmol) were evacuated and pressurized under $N_2$ three times over the course of 30 min. Dioxane (30 mL) was added and the reaction was purged with $N_2$ by bubbling for 20 min. The reaction was heated to 100° C. and stirred overnight. The solvent was removed to afford a brown goo which was purified by column chromatography (Hexanes:EtOAc) to afford the title compound.

Step 5: tert-butyl ((exo-3-(1-(4-(4-amino-2-oxopyrimidin-1 (2H)-yl)-2-fluorophenyl)butan-2-yl)-3-azabicyclo [3.1.0]hexan-6-yl)methyl)carbamate. A suspension of cytosine (70 mg, 0.63 mmol) and tert-butyl ((exo-3-(1-(2-fluoro-4-(4,4,5,5-tetramethyl-1,3,2-dioxaborolan-2-yl)phenyl) butan-2-yl)-3-azabicyclo[3.1.0]hexan-6-yl)methyl) carbamate (306 mg, 0.63 mmol), in MeOH:$H_2O$ (4:1, 36 ml) was stirred at rt in open air for 30 min. TMEDA (0.10 mL, 0.69 mmol) and $Cu(OAc)_2 \cdot H_2O$ (125 mg, 0.63 mmol) were added and the reaction was stirred in open air for 48H at rt. The reaction mixture was concentrated under reduced pressure, and cold $H_2O$ (100 mL) was added. The solid was filtered and washed with $H_2O$ (5×50 mL), $Et_2O$ (3×30 mL), and $H_2O$ (2×30 mL) to afford the title compound.

Intermediate 11

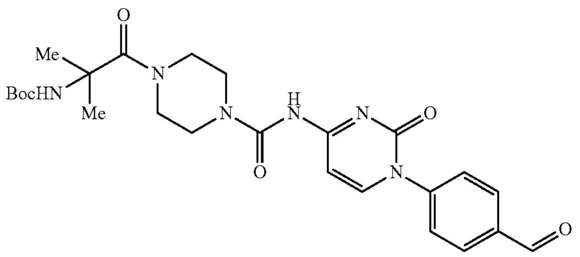

tert-Butyl N-[1-(4-{[1-(4-formylphenyl)-2-oxo-1,2-dihydropyrimidin-4-yl]carbamoyl}piperazin-1-yl)-2-methyl-1-oxopropan-2-yl]carbamate Scheme I-8

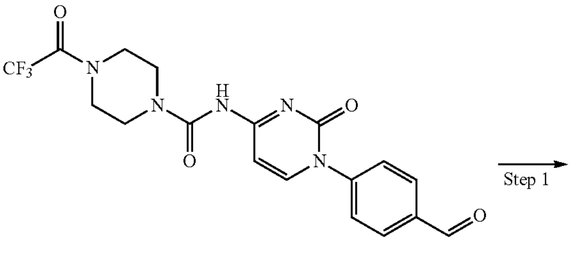

-continued

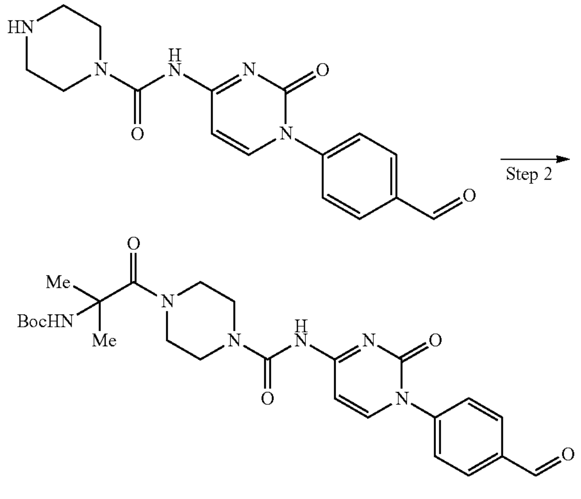

Reagents: 1) $K_2CO_3$, MeOH; 2)N-Boc-AIB-OH, HATU, DIPEA, $CH_3CN$.

Step 1: N-[1-(4-formylphenyl)-2-oxo-1,2-dihydropyrimidin-4-yl]piperazine-1-carboxamide. $K_2CO_3$ (653 mg, 4.72 mmol) was added to a suspension of N-[1-(4-formylphenyl)-2-oxo-1,2-dihydropyrimidin-4-yl]-4-(trifluoroacetyl)piperazine-1-carboxamide (1.0 g, 2.36 mmol) in MeOH (30 mL) and the resulting mixture was stirred at rt for 2 h. Volatiles were removed under reduced pressure to afford the crude product which was directly used in the next step. LCMS (Method A): m/z=328.0 [M+1-1]+0.30 min.

Step 2: tert-Butyl N-[1-(4-{[1-(4-formylphenyl)-2-oxo-1,2-dihydropyrimidin-4-yl]carbamoyl}piperazin-1-yl)-2-methyl-1-oxopropan-2-yl]carbamate. N-Boc-α-Methylalanine (576 mg, 2.83 mmol), HATU (1.35 g, 3.54 mmol) and DIPEA (822 μL, 4.72 mmol) were sequentially added to a solution of N-[1-(4-formylphenyl)-2-oxo-1,2-dihydropyrimidin-4-yl]piperazine-1-carboxamide (2.36 mmol theoretical) in $CH_3CN$ (50 mL). The resulting mixture was stirred at rt for 16 h. Volatiles were removed under reduced pressure. The crude residue was dissolved in $H_2O$ and the aqueous portion was extracted with EtOAc (2×50 mL). The combined organic portions were washed with brine, dried ($Na_2SO_4$), filtered and concentrated under reduced pressure. The crude product was purified by column chromatography ($CH_2Cl_2$-MeOH, 95:5) to afford the title compound (650 mg, 54% over two steps). $^1H$ NMR (400 MHz, $CDCl_3$) δ 13.01 (br. s., 1H), 10.07 (s, 1H), 8.01 (d, 2H), 7.58 (d, 2H), 7.31 (d, 1H), 5.90 (d, 1H), 4.95-4.72 (m, 1H), 3.95-3.57 (m, 8H), 1.52 (s, 6H), 1.44 (s, 9H).

Intermediate 12

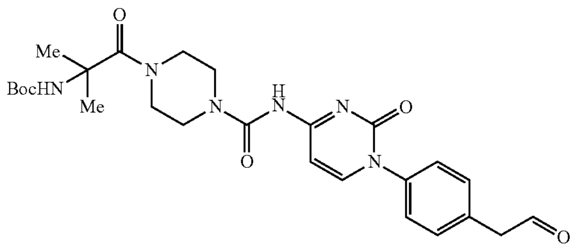

tert-Butyl (2-methyl-1-oxo-1-(4-(2-oxo-1-(4-(2-oxoethyl)phenyl)-1,2-dihydropyrimidin-4-yl)carbamoyl)piperazin-1-yl)propan-2-yl)carbamate Scheme I-9

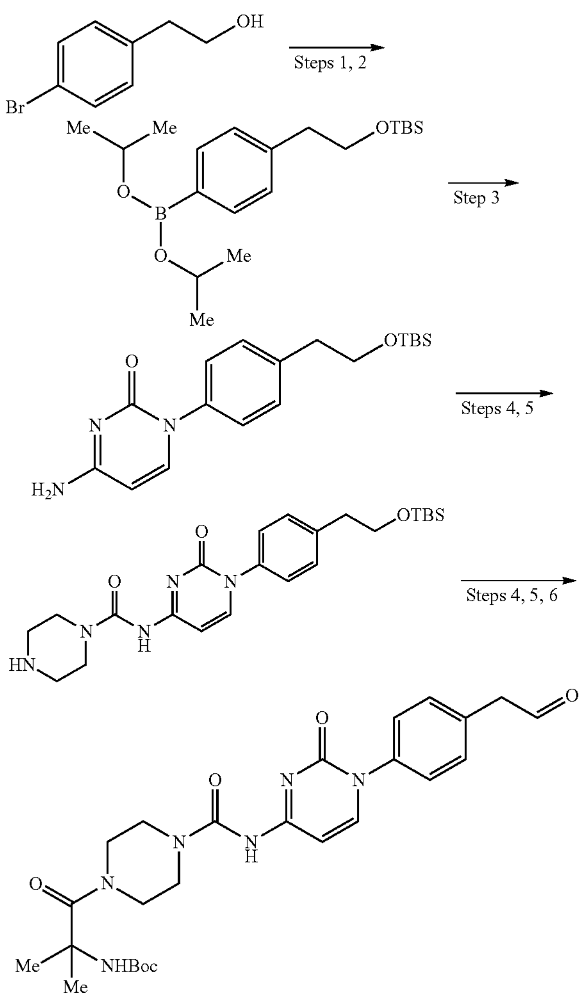

Reagents: 1) TBSCl, imidazole, DMF, rt, 16 h 2) n-BuLi, THF, −78° C. $(iPrO)_3B$, 2N HCl 4 h 3) cytosine, TMEDA, $Cu(OAc)_2 \cdot H_2O$, 4:1 $MeOH:H_2O$, rt, 48 h. 4) 3-methyl-1-(4-(2,2,2-trifluoroacetyl)piperazine-1-carbonyl)-1H-imidazol-3-ium iodide, $CH_3CN$, 85° C., 16 h 5) $K_2CO_3$, MeOH, 3 h 6) Boc-aminoisobutyric acid, HATU, DIPEA, DMF, 8 h 7) TBAF, THF 0° C. to rt 8) DMP, 100:1 $CH_2Cl_2:H_2O$, 1 h.

Step 1: (4-bromophenethoxy)(tert-butyl)dimethylsilane. To a stirring solution of 2-(4-bromophenyl)ethan-1-ol (7.0 mL, 49.7 mmol) in DMF (50 mL) was added imidazole (5.1 g, 74.6 mmol) and TBSCl (9.0 g, 60.0 mmol). The solution was stirred for 16 h. The reaction mixture was dissolved in EtOAc (100 mL) and extracted with aqueous LiCl (3×50 mL). The organic layer was dried over $Na_2SO_4$ and concentrated under reduced pressure to give an oily residue, which was purified by silica gel column chromatography (Hexanes: EtOAc) to afford the title compound.

Step 2: bisisopropyl (4-(2-((tert-butyldimethylsilyl)oxy)ethyl)phenyl)boronate. A stirred solution of (4-bromophenethoxy)(tert-butyl)dimethylsilane (9.0 g, 28.0 mmol)

in THF (100 mL) was cooled to −78° C. n-BuLi (28.0 mL, 1 M in hexanes, 71.4 mmol) was added dropwise over 30 min. and the temperature maintained below −60° C. After 25 min $(iPrO)_3B$ (10.0 mL, 42.0 mmol) was added dropwise over 30 min. The reaction mixture was warmed to rt and stirred for 15 min. 2N HCl (50 mL) was added and the reaction was stirred for 30 min. The mixture was separated and the aq. layer washed with $CH_2Cl_2$ (2×50 mL). The combined organics were dried over $Na_2SO_4$ and concentrated under reduced pressure afford the title compound.

Step 3: 4-amino-1-(4-(2-((tert-butyldimethylsilyl)oxy)ethyl)phenyl)pyrimidin-2 (1H)-one. A suspension of cytosine (10.5 g, 95 mmol) and diisopropyl (4-(2-((tert-butyldimethylsilyl)oxy)ethyl)phenyl)boronate (26.6 g, 95 mmol), in MeOH:$H_2O$ (4:1, 600 ml) was stirred at rt in open air for 30 min. TMEDA (17.0 ml, 114.0 mmol) and $Cu(OAc)_2$ $H_2O$ (19.0 g, 95 mmol) were added and the reaction was stirred in open air for 48 h at rt. The reaction mixture was concentrated under reduced pressure, and cold $H_2O$ (100 mL) was added. The reaction mixture was filtered and the solid was washed with with $H_2O$ (5×50 mL), $Et_2O$ (3×30 mL), and $H_2O$ (2×30 mL) to afford the title compound. LCMS [M+H] 346.2.

Step 4: N-(1-(4-(2-((tert-butyldimethylsilyl)oxy)ethyl)phenyl)-2-oxo-1,2-dihydropyrimidin-4-yl)-4-(2,2,2-trifluoroacetyl)piperazine-1-carboxamide. To a stirred solution of 4-amino-1-(4-(2-((tert-butyldimethylsilyl)oxy)ethyl)phenyl)pyrimidin-2 (1H)-one (2.41 g, 7.0 mmol) in $CH_3CN$ (50 mL) was added 3-methyl-1-(4-(2,2,2-trifluoroacetyl)piperazine-1-carbonyl)-1H-imidazol-3-ium iodide (3.79 g, 8.4 mmol). The vessel was flushed with nitrogen and heated to 85° C. and refluxed for 16 h. The reaction mixture was concentrated under reduced pressure and purified by column chromatography ($CH_2Cl_2$:MeOH:$NH_4OH$) to afford the title compound. LCMS [M+H] 554.3.

Step 5: N-(1-(4-(2-((tert-butyldimethylsilyl)oxy)ethyl)phenyl)-2-oxo-1,2-dihydropyrimidin-4-yl)piperazine-1-carboxamide. N-(1-(4-(2-((tert-butyldimethylsilyl)oxy)ethyl)phenyl)-2-oxo-1,2-dihydropyrimidin-4-yl)-4-(2,2,2-trifluoroacetyl)piperazine-1-carboxamide (4.5 g, 8.1 mmol) and $K_2CO_3$ (3.36 g, 24.3 mmol) were dissolved in MeOH (200 mL), and stirred at rt for 3 h. The reaction mixture was concentrated under reduced pressure to give a solid residue and purified by column chromatography ($CH_2Cl_2$:MeOH:$NH_4OH$) to afford the title compound.

Step 6: tert-butyl (1-(4-((1-(4-(2-((tert-butyldimethylsilyl)oxy)ethyl)phenyl)-2-oxo-1,2-dihydropyrimidin-4-yl)carbamoyl)piperazin-1-yl)-2-methyl-1-oxopropan-2-yl)carbamate. To a stirring solution of N-(1-(4-(2-((tert-butyldimethylsilyl)oxy)ethyl)phenyl)-2-oxo-1,2-dihydropyrimidin-4-yl)piperazine-1-carboxamide (3.66 g, 8.1 mmol) in DMF (30 mL) was added 2-((tert-butoxycarbonyl)amino)-2-methylpropanoic acid (1.63 g, 8.1 mmol) followed by DIPEA (3.36 mL, 24.2 mmol). The solution stirred for 5 min. and HATU (5.51 g, 14.5 mmol) was added and the solution was stirred for 8 h. The crude reaction mixture was dissolved in EtOAc (50 mL) and washed with aqueous LiCl (3×30 mL). The organic layer was dried over $Na_2SO_4$, concentrated under reduced pressure and purified by column chromatography ($CH_2Cl_2$:MeOH:$NH_4OH$) to afford the title compound. LCMS [M+H] 643.4.

Step 7: tert-butyl (1-(4-((1-(4-(2-hydroxyethyl)phenyl)-2-oxo-1,2-dihydropyrimidin-4-yl)carbamoyl)piperazin-1-yl)-2-methyl-1-oxopropan-2-yl)carbamate. To a stirred solution of tert-butyl (1-(4-((1-(4-(2-((tert-butyldimethylsilyl)oxy)ethyl)phenyl)-2-oxo-1,2-dihydropyrimidin-4-yl)carbamoyl)piperazin-1-yl)-2-methyl-1-oxopropan-2-yl)carbamate (1.0 g, 1.63 mmol) in THF (30 mL) at 0° C. was added 2M TBAF in THF (3.27 mL) over the span of 20 min. The solution was stirred for 16 h. The crude reaction mixture was concentrated under reduced pressure to give an oily residue, which was purified by column chromatography ($CH_2Cl_2$:MeOH) to afford the title compound. LCMS [M+H] 529.4.

Step 8: tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate. To a stirred solution of tert-butyl (1-(4-((1-(4-(2-hydroxyethyl)phenyl)-2-oxo-1,2-dihydropyrimidin-4-yl)carbamoyl)piperazin-1-yl)-2-methyl-1-oxopropan-2-yl)carbamate (150 mg, 0.28 mmol) in $CH_2Cl_2$:$H_2O$ (100:1, 10 mL) was added DMP (361 mg, 0.85 mmol). The solution was stirred for 1 h. The crude reaction mixture was dissolved in additional $CH_2Cl_2$ (50 mL) and washed with aq. $NaHCO_3$/$Na_2S_2O_3$ (1×50 mL). The aq. layer was extracted with $CH_2Cl_2$ (1×10 mL). The combined organic layers were dried over $Na_2SO_4$ and concentrated under reduced pressure to give the title compound.

Intermediate 13

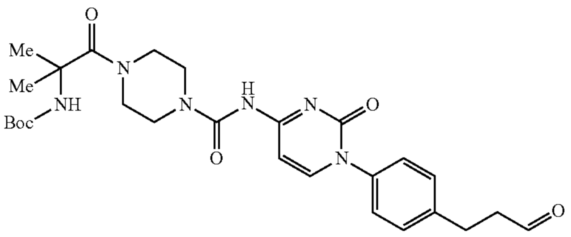

tert-Butyl (2-methyl-1-oxo-1-(4-((2-oxo-1-(4-(3-oxopropyl)phenyl)-1,2-dihydropyrimidin-4-yl)carbamoyl)piperazin-1-yl)propan-2-yl)carbamate Prepared in a similar fashion to Scheme 1-9 from 3-(4-bromophenyl)propan-1-ol.

Intermediate 14

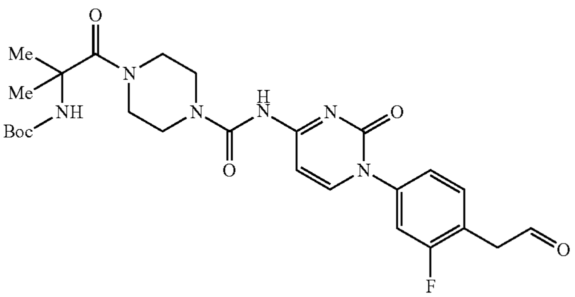

tert-Butyl (1-(4-((1-(3-fluoro-4-(2-oxoethyl)phenyl)-2-oxo-1,2-dihydropyrimidin-4-yl)carbamoyl)piperazin-1-yl)-2-methyl-1-oxopropan-2-yl)carbamate Prepared in a similar fashion to Scheme 1-9 from 2-(4-bromo-2-fluorophenyl)ethan-1-ol.

Intermediate 15

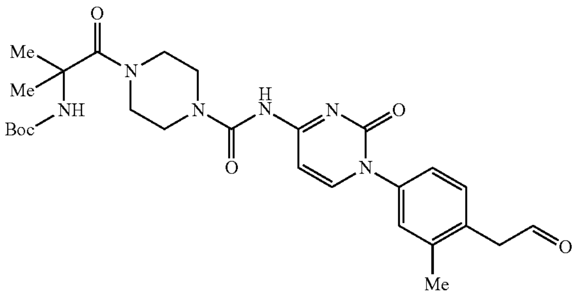

tert-Butyl (2-methyl-1-(4-((1-(3-methyl-4-(2-oxoethyl)phenyl)-2-oxo-1,2-dihydropyrimidin-4-yl)carbamoyl)piperazin-1-yl)-1-oxopropan-2-yl)carbamate Prepared in a similar fashion to Scheme 1-9 from 2-(4-bromo-2-methylphenyl)ethan-1-ol.

Intermediate 16

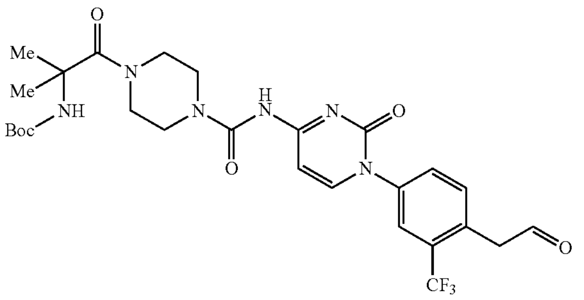

tert-Butyl (2-methyl-1-oxo-1-(4-((2-oxo-1-(4-(2-oxoethyl)-3-(trifluoromethyl)phenyl)-1,2-dihydropyrimidin-4-yl)carbamoyl)piperazin-1-yl)propan-2-yl) carbamate Prepared in a similar fashion to Scheme 1-9 from 2-(4-bromo-2-(trifluoromethyl)phenyl)ethan-1-ol.

Intermediate 17

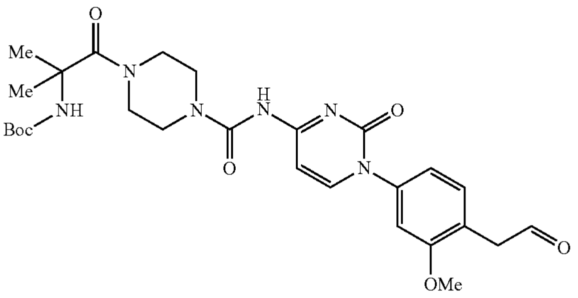

tert-Butyl (1-(4-((1-(3-methoxy-4-(2-oxoethyl)phenyl)-2-oxo-1,2-dihydropyrimidin-4-yl)carbamoyl)piperazin-1-yl)-2-methyl-1-oxopropan-2-yl)carbamate Prepared in a similar fashion to Scheme 1-9 from 2-(4-bromo-2-methoxyphenyl)ethan-1-ol.

Intermediate 18

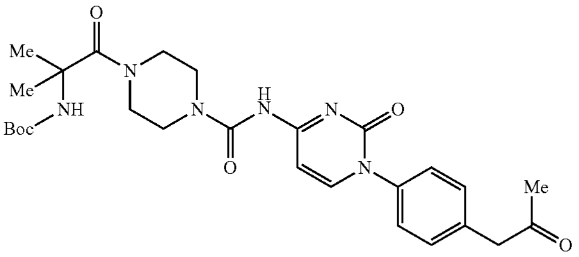

tert-Butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate Scheme I-10

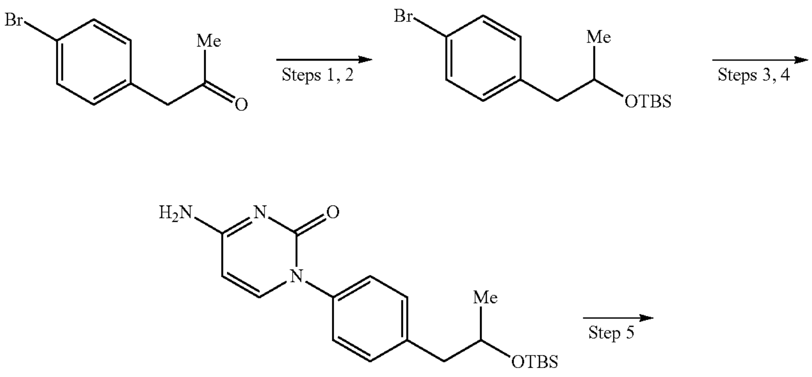

-continued

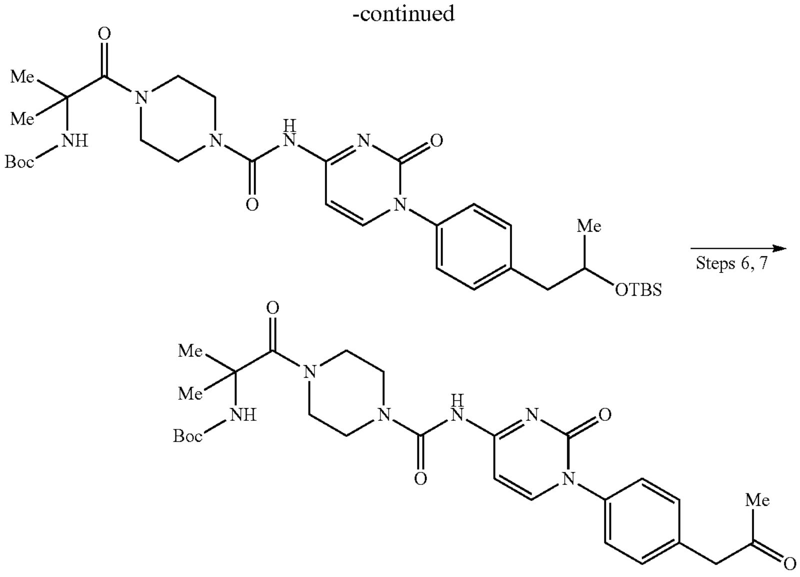

Reagents: 1) $NaBH_4$, MeOH, rt, 3 h 2) TBDMSCl, Imidazole, $CH_2Cl_2$, rt, 16 h 3) n-BuLi, $B(OiPr)_3$, THF, −78° C.-rt, 3 h 4) Cytosine, TMEDA, $Cu(OAc)_2$ $H_2O$, MeOH:$H_2O$ (4:1), $O_2$, rt, 16 h 5) 1-(4-(2-((t-butoxycarbonyl)amino)-2-methylpropanoyl)piperazine-1-carbonyl)-3-methyl-1H-imidazol-3-ium iodide, $CH_3CN$, 90° C., 16 h 6) TBAF, THF, rt, 16 h 7) DMP, $CH_2Cl_2$, rt, 3 h.

Step 1: 1-(4-bromophenyl) propan-2-ol. To a stirred solution of 1-(4-bromophenyl) propan-2-one (30.0 g, 140.8 mmol) in MeOH (150 mL) was added $NaBH_4$ (13.3 g, 351.9 mmol) at 0° C. The reaction mixture was stirred at rt for 3 h. The reaction mixture was poured into $H_2O$ (500 mL) and extracted with EtOAc (3×200 mL). The combined organics were dried over $Na_2SO_4$, filtered and concentrated under reduced pressure to afford the title compound (29.0 g, 95%) as a colorless oil. $^1H$ NMR (DMSO-$d_6$400 MHz): δ 7.43 (d, 2H), 7.15 (d, 2H), 4.58 (d, 1H), 3.82-3.73 (m, 1H), 2.64-2.48 (m, 2H), 1.01 (d, 3H).

Step 2: ((1-(4-bromophenyl) propan-2-yl)oxy)(-butyl)dimethylsilane. To a stirred solution of 1-(4-bromophenyl) propan-2-ol (29.0 g, 134.9 mmol) in $CH_2Cl_2$ (300 mL) were added imidazole (13.8 g, 202.3 mmol) and TBSCl (24.4 g, 161.8 mmol) at 0° C. The reaction mixture was stirred at rt for 16 h. The reaction mixture was poured into $H_2O$ (500 mL) and extracted with $CH_2Cl_2$ (3×700 mL). The combined organics were dried over $Na_2SO_4$, filtered and concentrated under reduced pressure to afford the title compound (40.0 g, 90%) as a yellow oil. $^1H$ NMR (DMSO-$d_6$400 MHz): δ 7.43 (d, 2H), 7.13 (d, 2H), 3.98-3.90 (m, 1H), 2.68-2.64 (m, 1H), 2.56-2.48 (m, 1H), 1.09 (d, 3H), 0.76 (s, 9H), 0.10 (s, 3H), −0.27 (s, 3H).

Step 3: diisopropyl (4-(2-((t-butyldimethylsilyl)oxy)propyl)phenyl)boronate. To a stirred solution of ((1-(4bromophenyl) propan-2-yl)oxy)(t-butyl) dimethylsilane (20.0 g, 60.8 mmol) in THF (300 mL) at −78° C., was added 1.6 M solution of n-BuLi in THF (94 mL, 152.0 mmol). The reaction mixture was stirred −78° C. for 30 min. $B(iPrO)_3$ (21.17 mL, 91.2 mmol) was added at −78° C. The reaction mixture was warmed to rt and stirred for 3 h. The reaction mixture was poured into $NH_4C_1$ solution (100 mL) and extracted with EtOAc (3×300 ml). The combined organics were dried over $Na_2SO_4$, filtered and concentrated under reduced pressure to afford the title compound (20.0 g, 86%).

Step 4: 4-amino-1-(4-(2-((t-butyldimethylsilyl)oxy)propyl)phenyl)pyrimidin-2 (1H)-one. To a solution of diisopropyl (3-(2-((isopropyldimethylsilyl)oxy)ethyl)phenyl) boronate (20.0 g, 52.91 mmol) and cytosine (5.87 g, 52.9 mmol) in MeOH:$H_2O$ (300 mL, 4:1) was stirred at rt in open air for 30 min. TMEDA (9.58 mL, 63.5 mmol) and $Cu(OAc)_2 \cdot H_2O$ (9.6 g, 52.9 mmol) were added and the reaction mixture stirred in open air at rt for 48 h. The reaction mixture was concentrated under reduced pressure and cold $H_2O$ (100 mL) was added into the mixture. The solid was filtered off and washed with $H_2O$ (5×100 mL) and $Et_2O$ (2×60 mL) under reduced pressure. The resulting solid was dried to afford the title compound (9.2 g, 48%) as a white solid. $^1H$ NMR (DMSO-$d_6$400 MHz): δ 7.52 (d, 1H), 7.25-7.22 (m, 6H), 5.80 (bs, 1H), 4.00-3.99 (m, 1H), 2.70-2.65 (m, 2H), 1.10 (d, 3H), 0.79 (s, 9H), −0.55 (s, 3H), −0.178 (s, 3H). LCMS [M+H] 360.3.

Step 5: t-butyl (1-(4-((1-(4 (2-hydroxypropyl)phenyl)-2-oxo-1,2-dihydropyrimidine-4-yl)carbamoyl)piperazin-1-yl)-2-methyl-1-oxopropan-2-yl)carbamate. To a stirred solution of 4-amino-1-(4-(2-((t-butyldimethylsilyl)oxy)propyl) phenyl) pyrimidin-2 (1H)-one (3.0 g, 8.3 mmol) and 1-(4-(2-((t-butoxycarbonyl)amino)-2-methylpropanoyl) piperazine-1-carbonyl)-3-methyl-1H-imidazol-3-ium iodide (6.35 g, 12.5 mmol) in $CH_3CN$ (45 mL) was heated at 90° C. for 16 h. The reaction mixture was concentrated under reduced pressure and the crude material was purified by column chromatography ($CH_3OH/CH_2Cl_2$) to afford the title compound. LCMS [M+H] 357.2.

Step 6: t-butyl (1-(4-((1-(4-(2-hydroxypropyl)phenyl)-2-oxo-1,2-dihydropyrimidin-4-yl)carbamoyl)piperazin-1-yl)-2-methyl-1-oxopropan-2-yl)carbamate. To a stirred solution of t-butyl(1-4-(−2-((t-butyldimethylsilyl)oxy)propyl)phenyl)-2-oxo-1,2-dihydropyrimidin-4-yl)piperazin-1-yl)-2-methyl-1-oxopropan-2-yl)carbamate (3.1 g, 4.72 mmol) in THF (40 mL) was added TBAF (1.0 M in THF) (18.9 mL, 18.9 mmol) at 0° C. The reaction mixture was stirred at rt for 16 h. The reaction mixture was poured in to sat. aq. aq. $NaHCO_3$ (25 mL) and extracted with $CH_2Cl_2$:MeOH (9:1, 3×100 mL). The combined organics were dried over $Na_2SO_4$, filtered and concentrated under reduced pressure. The crude material was purified by column chromatography (4-5% MeOH in $CH_2Cl_2$) to afford the title compound as an off-white solid (2.4 g, 93%). LCMS [M+H] 543.2.

Step 7: t-butyl (2-methyl-1-oxo-1-(4-((2-oxo-1-(4-(2-oxopropyl)phenyl)-1,2-dihydropyrimidin-4-yl)carbamoyl) piperazin-1-yl)propan-2-yl)carbamate. To a stirred solution of t-butyl (1-(4-((1-(4 (2-hdroxypropyl)phenyl)-2-oxo-1,2-dihydropyrimidine-4-yl)carbamoyl)piperazin-1-yl)-2-methyl-1-oxopropan-2-yl)carbamate (0.5 g, 0.92 mmol) in $CH_2Cl_2$ (5 mL) was added DMP (0.78 g, 1.84 mmol) at 0° C. The reaction mixture was stirred at rt for 3 h. The reaction mixture was poured in to $NaHCO_3$ solution (20 mL) and extracted with $CH_2Cl_2$ (3×50 mL). The combined organics were dried over $Na_2SO_4$, filtered and concentrated under reduced pressure at low temperature (30-35° C.) to afford the title compound (0.7 g, Quant.) as an off-white solid. LCMS [M+H] 541.0.

Intermediate 19

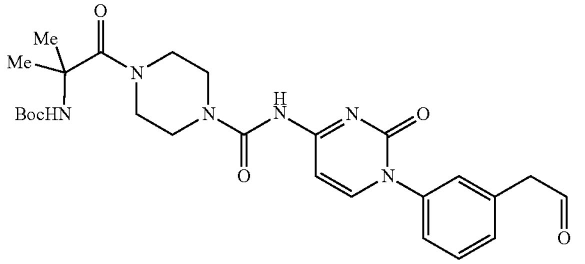

tert-Butyl (2-methyl-1-oxo-1-(4-((2-oxo-1-(3-(2-oxoethyl)phenyl)-1,2-dihydropyrimidin-4-yl)carbamoyl)piperazin-1-yl)propan-2-yl)carbamate Scheme I-11

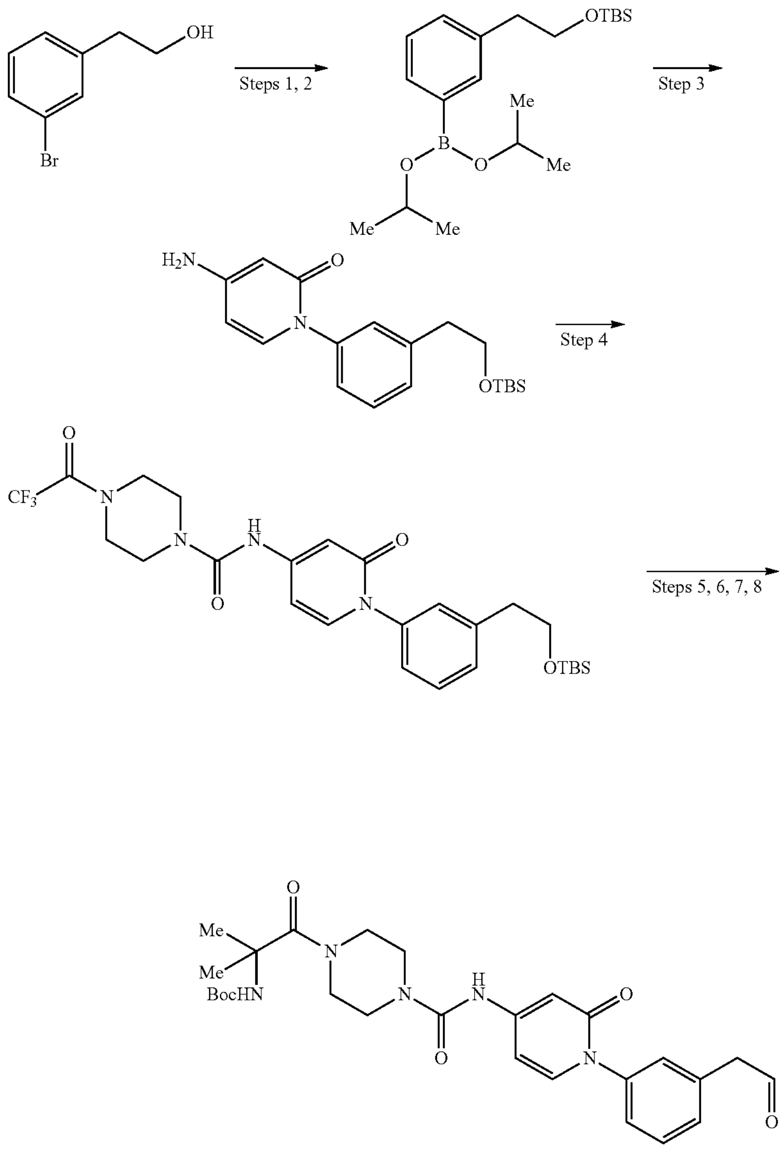

Reagents: Step: 1) TBSCl, Imidazole, $CH_2Cl_2$, rt, 16 h. 2) n-BuLi, $B(OiPr)_3$, THF, −78° C. to rt, 2 h. 3) Cytosine, TMEDA, $Cu(OAc)_2$ $H_2O$, MeOH:$H_2O$ (4:1), $O_2$, rt, 48 h. 4) $CH_3CN$, 85° C., 16 h, 5) $K_2CO_3$, MeOH, rt, 3 h. 6) 2-((t-butoxycarbonyl)amino-2-methylpropanoic acid, HATU, DIPEA, DMF, rt, 16 h. 7) TBAF, THF, rt, 16 h. 8) DMP, $CH_2Cl_2$, rt, 1 h.

Step 1: (3-bromophenethoxy)(t-butyl)dimethylsilane. To a stirred solution of 2-(3-bromophenyl)ethan-1-ol (30.0 g, 149.2 mmol) in DMF (150 mL) was added imidazole (15.24 g, 223.8 mmol) and TBSCl (26.99 g, 179.0 mmol) at rt. The reaction mixture was stirred at rt for 16 h. The reaction mixture was neutralized by saturated LiCl solution (500 mL) and extracted with EtOAc (3×200 mL). The combined organics were dried over $Na_2SO_4$, filtered, concentrated under reduced pressure and purified by column chromatography (5% EtOAc in hexane) to afford the title compound (45.0 g, 95%) as a colorless oil. $^1$H NMR (400 Mz, DMSO-$d_6$): δ 7.46-7.36 (m, 2H), 7.25-7.21 (m, 2H), 3.75 (t, 2H), 2.73 (t, 2H), 0.80 (s, 9H), −0.08 (s, 6H).

Step 2: diisopropyl (3-(2-((t-butyldimethylsilyl)oxy) ethyl) phenyl)boronate. To a stirred solution of (3-bromophenethoxy)(t-butyl)dimethylsilane (10.0 g, 31.7 mmol) in THF (100 mL) was added 2.5 M n-BuLi in hexane (31.71 mL, 79.3 mmol) drop wise at −78° C. over 30 min. During addition of n-BuLi, the temperature of the reaction mixture was maintained below −60° C. After 30 min $B(OiPr)_3$ (9.7 mL, 47.6 mmol) was added drop wise over 30 min at −78° C. The reaction mixture was stirred at −78° C. for 1 h. The reaction mixture was quenched with saturated $NH_4C_1$ solution (500 mL) and extracted with EtOAc (4×100 mL) and combined organics were dried over $Na_2SO_4$, filtered and concentrated under reduced pressure to yield the title compound (17.0 g) as a colorless oil.

Step 3: 4-amino-1-(3-(2-((t-butyldimethylsilyl)oxy) ethyl)phenyl) pyrimidin-2 (1H)-one. A solution of diisopropyl (3-(2-((t-butyldimethylsilyl)oxy)ethyl)phenyl)boronate (17.0 g, 46.9 mmol) and cytosine (5.22 g, 46.9 mmmol) in MeOH:$H_2O$ (375 mL, 4:1) was stirred in open air for 30 min. TMEDA (7.18 mL, 56.3 mmol) and $Cu(OAc)_2$ $H_2O$ (8.53 g, 46.9 mmol) were added and the reaction stirred in open air for 48 h at rt. The reaction mixture was concentrated under reduce pressure and cold $H_2O$ (100 mL) was added to the mixture. The resulting solid was filtered and washed with $H_2O$ (5×50 mL), hexane (3×30 mL) and again with $H_2O$ (2×30 mL) to afford the title compound (9.0 g, 82%) as a white solid. $^1$H NMR (400 Mz, DMSO-$d_6$): δ 7.55 (d, 1H), 7.33 (t, 1H), 7.21-7.15 (m, 5H), 5.76 (d, 1H), 3.77 (t, 2H), 2.77 (t, 2H), 0.82 (s, 9H), −0.036 (s, 6H). LCMS [M+H] 346.1.

Step 4: N-(1-(3-(2-((t-butyldimethylsilyl)oxy)ethyl)phenyl)-2-oxo-1,2-dihydropyrimidin-4-yl)-4-(2,2,2-trifluoroacetyl) piperazine-1-carboxamide. To a stirred solution of 4-amino-1-(3-(2-((t-butyldimethylsilyl)oxy) ethyl)phenyl) pyrimidin-2 (1H)-one (1.0 g, 2.9 mmol) in $CH_3CN$ (25 mL) was added 3-methyl-1-(4-(2,2,2-trifluoroacetyl)piperazine-1-carbonyl)-1H-imidazol-3-ium iodide (1.6 g, 3.7 mmol) at rt. The reaction mixture was heated at 85° C. for 16 h. The reaction mixture was concentrated under reduced pressure and purified by column chromatography (2-3% MeOH: $CH_2Cl_2$) to afford the title compound (2.0 g, 62%) as a brown sticky solid. LCMS [M+H] 554.03.

Step 5: N-(1-(3-(2-((t-butyldimethylsilyl)oxy)ethyl)phenyl)-2-oxo-1,2-dihydropyrimidin-4-yl)piperazine-1-carboxamide. To a stirred solution of N-(1-(3-(2-((t-butyldimethylsilyl)oxy)ethyl)phenyl)-2-oxo-1,2-dihydropyrimidin-4-yl)-4-(2,2,2-trifluoroacetyl) piperazine-1-carboxamide (2.0 g, 3.6 mmol) in MeOH (50 mL) was added $K_2CO_3$ (1.5 g, 10.8 mmol). The reaction mixture was stirred at rt for 3 h. The reaction mixture was poured into $H_2O$ (50 mL) and extracted with EtOAc (3×30 mL). The combined organics were dried over $Na_2SO_4$, filtered and concentrated under reduced pressure to afford the title compound (1.7 g, Quant.) as a brown, sticky solid. $^1$H NMR (400 Mz, DMSO-$d_6$): δ 7.73 (d, 1H), 7.38 (t, 1H), 7.28-7.24 (m, 3H), 6.71 (bs, 1H), 4.05-3.99 (m, 2H), 3.78 (t, 2H), 3.40-3.38 (m, 4H), 2.79 (t, 2H), 2.66-2.62 (m, 4H), 0.82 (s, 9H), −0.036 (s, 6H). LCMS [M+H] 458.21.

Step 6: t-butyl (1-(4-((1-(3-(2-((t-butyldimethylsilyl)oxy) ethyl)phenyl)-2-oxo-1,2-dihydropyrimidin-4-yl)carbamoyl) piperazin-1-yl)-2-methyl-1-oxopropan-2-yl)carbamate. To a stirred solution of N-(1-(3-(2-((t-butyldimethylsilyl)oxy) ethyl)phenyl)-2-oxo-1,2-dihydropyrimidin-4-yl)piperazine-1-carboxamide (1.7 g, 3.7 mmol) in DMF (10 mL) were added 2-((t-butoxycarbonyl)amino-2-methylpropanoic acid (0.75 g, 3.7 mmol) and DIPEA (1.44 g, 11.14 mL) at 0° C. and stirred for 10 min. HATU (2.8 g, 7.42 mL) was added and the reaction mixture was stirred at rt for 16 h. The reaction mixture was poured into $H_2O$ (50 mL) and resulting solid was filtered and dried to afford the title compound (1.7 g, 70%) as a white solid. LCMS [M+H] 643.2.

Step 7: t-butyl (1-(4-((1-(3-(2-hydroxyethyl)phenyl)-2-oxo-1,2-dihydropyrimidin-4-yl)carbamoyl)piperazin-1-yl)-2-methyl-1-oxopropan-2-yl)carbamate. To a stirred solution of t-butyl (1-(4-((1-(3-(2-((t-butyldimethylsilyl) oxy)ethyl) phenyl)-2-oxo-1,2-dihydropyrimidin-4-yl)carbamoyl)piperazin-1-yl)-2-methyl-1-oxopropan-2-yl)carbamate (1.7 g, 2.64 mmol) in THF (60 mL) was added TBAF (1M in THF) (5.3 mL, 10.6 mmol) at rt. The reaction mixture was stirred at rt for 16 h. The reaction mixture was neutralized with saturated $NaHCO_3$ solution (50 mL) and extracted with EtOAc (3×30 mL). The combined organics were dried over $Na_2SO_4$, filtered and concentrated under reduced pressure to afford the title compound (1.5 g, 72%) as an off-white solid. LCMS [M+H] 529.1.

Step 8: tert-butyl (2-methyl-1-oxo-1-(4-((2-oxo-1-(3-(2-oxoethyl)phenyl)-1,2-dihydropyridin-4-yl)carbamoyl)piperazin-1-yl)propan-2-yl)carbamate. To a stirred solution of t-butyl (1-(4-((1-(3-(2-hydroxyethyl)phenyl)-2-oxo-1,2-dihydropyrimidin-4-yl)carbamoyl)piperazin-1-yl)-2-methyl-1-oxopropan-2-yl)carbamate (0.2 g, 0.37 mmol) in DCE (20 mL) was added DMP (0.64 g, 1.51 mmol) at rt. The reaction mixture was stirred at rt for 1 h. The reaction mixture was neutralized with saturated $NaHCO_3$ solution (30 mL) and extracted with DCE (2×20 mL). The combined organics were dried over $Na_2SO_4$, filtered to afford a solution of the title compound.

Intermediate 20

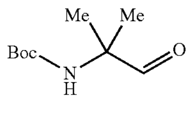

tert-Butyl N-(2-methyl-1-oxopropan-2-yl)carbamate

Scheme I-12

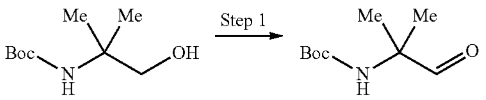

Reagents: DMP, $CH_2Cl_2$, 0° C. to rt. 1 h

Step 1: tert-butyl N-(2-methyl-1-oxopropan-2-yl)carbamate. DMP (1.68 g, 3.97 mmol) was added portionwise to a solution of N-Boc2-amino-2-methyl-1-propanol (500 mg, 2.64 mmol) in $CH_2Cl_2$ (16 mL) at 0° C. The mixture was stirred at 0° C. for 10 min, warmed to rt and stirred for 1 h. A 1:1 mixture of sat. $Na_2S_2O_3$:$NaHCO_3$ was added and the mixture was vigorously stirred for 20 min. The layers were separated and the organic portion was washed twice with sat. aq. aq. $NaHCO_3$, dried ($Na_2SO_4$), filtered and concentrated under reduced pressure to afford the title compound (490 mg) as a white solid. $^1$H NMR (400 MHz, $CDCl_3$) δ 9.45 (s, 1H), 4.99 (br.s., 1H), 1.46 (s, 9H), 1.35 (s, 6H).

Intermediate 21

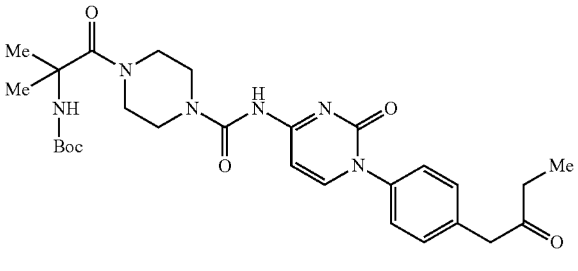

tert-Butyl (2-methyl-1-oxo-1-(4-((2-oxo-1-(4-(2-oxobutyl)phenyl)-1,2-dihydropyrimidin-4-yl)carbamoyl)piperazin-1-yl)propan-2-yl)carbamate Scheme I-13

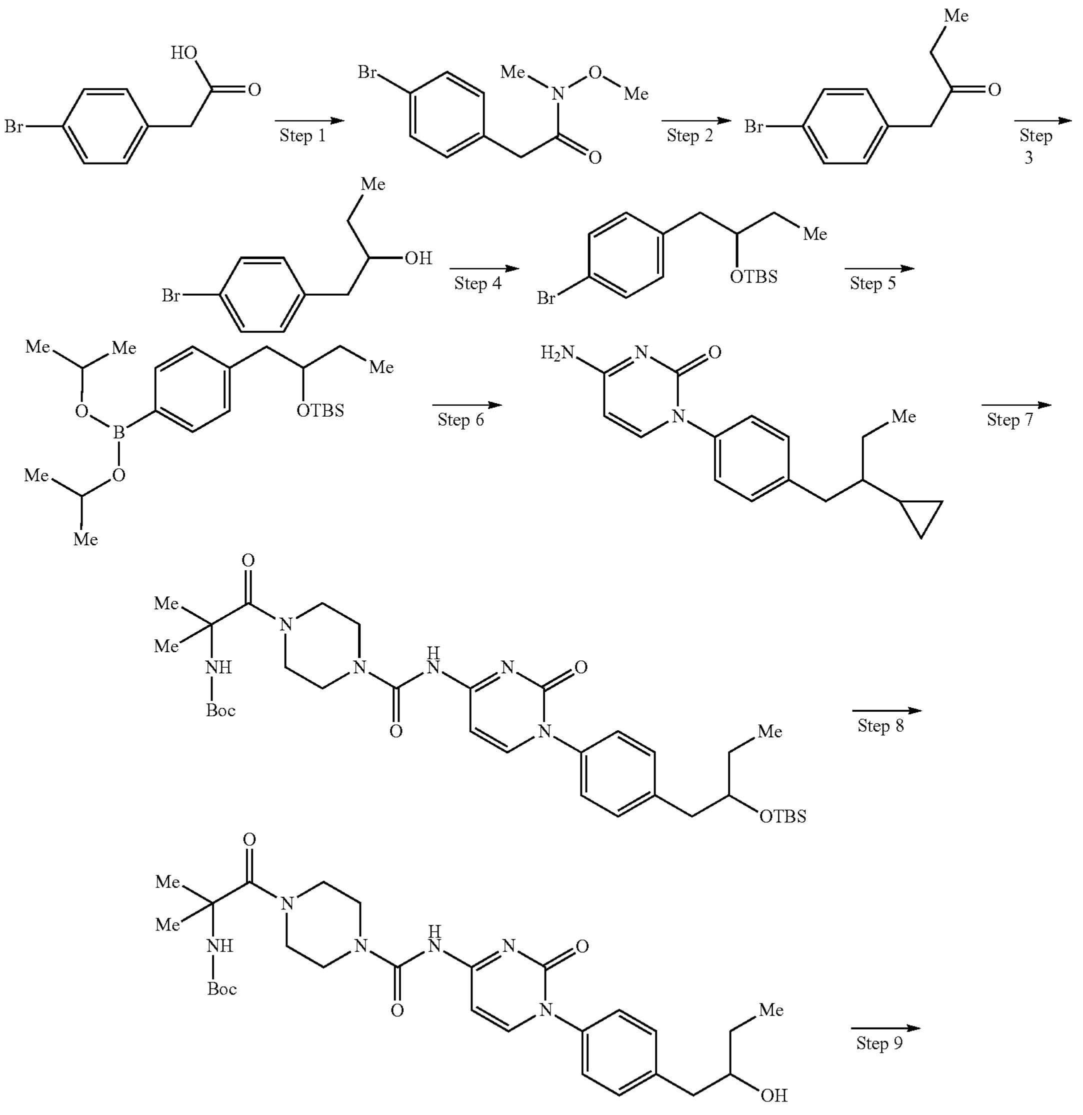

-continued

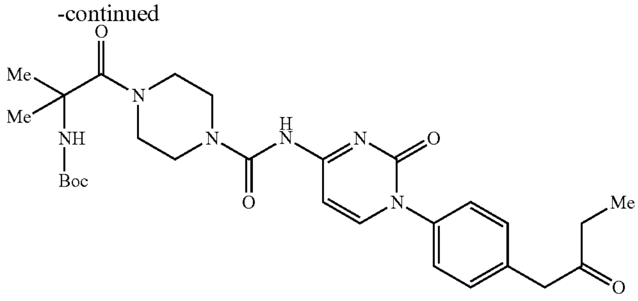

Reagents: Step 1) EDCI, TEA, DMAP, N,O-dimethylhydroxylamine HCl, $CH_2Cl_2$, 0° C. to rt, 16 h 2) EtMgBr, THF, −78° C. to rt, 3 h. 3) $NaBH_4$, MeOH, 0° C. to rt, 8 h 4) TBDMSCl, imidazole, $CH_2Cl_2$, rt, 16 h 5) n-BuLi, $B(OiPr)_3$, THF, −78° C.-rt, 2 h 6) Cytosine, TMEDA, $Cu(OAc)_2$ $H_2O$, MeOH:$H_2O$ (4:1), $O_2$, rt, 24 h 7) 1-(4-(2-((tert-butoxycarbonyl)amino)-2-methylpropanoyl)piperazine-1-carbonyl)-3-methyl-1H-imidazol-3-ium iodide, $CH_3CN$, 90° C., 16 h 8) TBAF, THF, 50° C., 16 h 9) DMP, $CH_2Cl_2$, rt, 3 h.

Step 1: 2-(4-bromophenyl)-N-methoxy-N-methylacetamide. To a stirred solution of N, O-dimethylhydroxylamine hydrochloride (17.1 g, 175.3 mmol) in $CH_2Cl_2$ (650 mL) was added TEA (23.3 mL, 175.3 mmol) at 0° C. The reaction mixture was stirred at 0° C. for 10 min. 2-(4-bromophenyl) acetic acid (25 g, 116.9 mmol), EDCI (24.63 g, 128.5 mmol) and DMAP (2.85 g, 23.4 mmol) were added at 0° C. into the reaction mixture. The reaction mixture was stirred at rt for 16 h. The reaction mixture was concentrated under reduce pressure and purified by column chromatography (Hex: EtOAc, 1:1) to afford the title compound (50.0 g, 83%) as white solid. $^1$H NMR (400 MHz, DMSO-$d_6$): δ 7.49 (d, 2H), 7.19 (d, 2H), 3.72 (s, 2H), 3.68 (s, 3H), 3.10 (s, 3H). LCMS[M+H] 257.9

Step 2: 1-(4-bromophenyl)butan-2-one. To a stirred a solution of 2-(4-bromophenyl)-N-methoxy-N-methylacetamide (6.0 g, 23.4 mmol) in THF (150 mL) was added 3M EtMgBr in $Et_2O$ (77 mL, 233.5 mmol) at −78° C. The reaction mixture was stirred at rt for 3 h. The reaction mixture was quenched with sat. $NH_4C_1$ solution (500 mL) and extracted with EtOAc (3×200 mL). The combined organics were dried over $Na_2SO_4$, filtered, concentrated under reduced pressure and purified by column chromatography (Hex:EtOAc, 85:15) to afford the title compound (2.5 g, 31%) as light yellow oil. $^1$H NMR (400 MHz, DMSO-$d_6$): δ 7.38-7.34 (m, 2H), 7.00 (d, 2H), 3.57 (s, 2H), 2.43-2.38 (m, 2H), 0.96 (t, 3H).

Step-3: 1-(4-bromophenyl)butan-2-ol. To a stirred solution of 1-(4-bromophenyl)butan-2-one (13.5 g, 59.8 mmol) in MeOH (150 mL) was added $NaBH_4$ (6.8 g, 179.3 mmol) at 0° C. The reaction mixture was warmed to rt and stirred for 8 h. The reaction mixture was poured into $H_2O$ (50 mL) and extracted with $CH_2Cl_2$ (3×30 mL). The combined organics were dried over $Na_2SO_4$, filtered and concentrated under reduced pressure to afford the title compound (13.0 g, 96%) as off white solid. $^1$H NMR (400 MHz, DMSO-$d_6$): δ 7.46-7.42 (m, 2H), 7.16 (d, 2H), 4.38 (d, 1H), 3.53-3.49 (m, 1H), 2.65-2.53 (m, 1H), 1.40-1.24 (m, 2H), 0.86 (t, 3H).

Step 4: ((1-(4-bromophenyl)butan-2-yl)oxy)(tert-butyl) dimethylsilane. To a stirred a solution of 1-(4-bromophenyl) butan-2-ol (6.0 g, 26.3 mmol) in $CH_2Cl_2$ (120 mL) were added imidazole (7.16 g, 105.3 mmol) and TBSCl (15.9 g, 105.3 mmol) at 0° C. The reaction mixture was stirred at rt for 16 h. The reaction mixture was poured into $H_2O$ (500 mL) and extracted with $CH_2Cl_2$ (3×300 mL). The combined organics were dried over $Na_2SO_4$, filtered, concentrated under reduced pressure and purified by column chromatography (Hex:EtOAc, 19:1) to afford the title compound (8.3 g, 93%) as colorless oil. $^1$H NMR (400 MHz, DMSO-$d_6$): δ 7.45 (d, 2H), 7.14 (d, 2H), 3.78-3.75 (m, 1H), 2.71-2.54 (m, 2H), 1.41-1.36 (m, 2H), 0.86 (t, 3H), 0.72 (s, 9H), −0.07 (s, 3H), −0.26 (s, 3H).

Step 5: diisopropyl (4-(2-((tert-butyldimethylsilyl)oxy) butyl)phenyl)boronate. To a stirred solution of ((1-(4-bromophenyl)butan-2-yl)oxy)(tert-butyl)dimethylsilane (5.0 g, 14.6 mmol) in THF (100 mL) at −78° C., was added 2.5 M solution of n-BuLi in THF (30 mL, 73.1 mmol). The reaction mixture was stirred −78° C. for 30 min. $B(OiPr)_3$ (10.7 mL, 43.9 mmol) was added at −78° C. The reaction mixture was warmed to rt and stirred for 2 h. The reaction mixture was poured into $NH_4C_1$ solution (200 mL) and extracted with EtOAc (3×100 ml). The combined organics were dried over $Na_2SO_4$, filtered and concentrated under reduced pressure to afford the title compound (11.0 g).

Step 6: 4-amino-1-(4-(2-((tert-butyldimethylsilyl)oxy) butyl)phenyl)pyrimidin-2 (1H)-one. A solution of diisopropyl (4-(2-((tert-butyldimethylsilyl)oxy)butyl)phenyl)boronate (11.0 g, 28.1 mmol) and cytosine (3.1 g, 28.1 mmol) in MeOH:$H_2O$ (100 mL, 4:1) was stirred at rt in open air for 30 min. TMEDA (4.2 mL, 30.9 mmol) and $Cu(OAc)_2\cdot H_2O$ (5.09 g, 28.1 mmol) were added and the reaction mixture was stirred in open air at rt for 48 h. The reaction mixture was concentrated under reduced pressure and cold $H_2O$ (50 mL) was added. The reaction was filtered and the solid was washed with $H_2O$ (5×50 mL) and hexane (2×20 mL) to afford the title compound (2.3 g, 31%) as white solid. $^1$H NMR (400 MHz, DMSO-$d_6$): δ 7.54 (d, 1H), 7.26-7.20 (m, 6H), 5.77 (d, 1H), 3.81 (t, 1H), 2.75-2.64 (m, 2H), 1.42-1.33 (m, 2H), 0.87 (t, 3H), 0.82 (s, 9H), −0.02 (s, 3H), −0.15 (s, 3H). LCMS[M+H] 374.2.

Step 7: 4-(2-amino-2-methylpropanoyl)-N-(1-(4-(2-((tert-butyldimethylsilyl) oxy)butyl) phenyl)-2-oxo-1,2-dihydropyrimidin-4-yl)piperazine-1-carboxamide. A stirred solution of 4-amino-1-(4-(2-((tert-butyldimethylsilyl) oxy)butyl) phenyl) pyrimidin-2 (1H)-one (1.0 g, 2.7 mmol) and 1-(4-(2-((tert-butoxycarbonyl)amino)-2-methylpropanoyl)piperazine-1-carbonyl)-3-methyl-1H-imidazol-3-ium iodide (2.0 g, 4.0 mmol) in $CH_3CN$ (25 mL) was heated at 90° C. for 16 h. The reaction mixture was concentrated under reduced pressure and purified by reverse phase chromatography ($CH_3CN$:$H_2O$, 80:20) to afford the title compound (1.2 g, 60%) as white solid. $^1$H NMR (400 MHz, DMSO-$d_6$): δ 11.99 (s, 1H), 7.61 (s, 1H), 7.31 (m, 5H), 6.92 (s, 1H), 6.32 (s, 1H), 3.95-3.8 (m, 1H), 3.57 (d, 9H), 2.81-2.70 (m, 2H), 2.53 (s, 1H), 1.61-1.44 (m, 3H), 1.38 (d, 15H), 0.91 (t, 3H), 0.86 (s, 9H), 0.01 (s, 3H), 0.10 (s, 3H). LCMS[M+H] 671.2.

Step 8: tert-butyl (1-(4-((1-(4-(2-hydroxybutyl)phenyl)-2-oxo-1,2-dihydropyrimidin-4-yl)carbamoyl)piperazin-1-yl)-2-methyl-1-oxopropan-2-yl)carbamate. To a stirred solution of tert-butyl (1-(4-((1-(4-(2-((tert-butyldimethylsilyl) oxy) butyl)phenyl)-2-oxo-1,2-dihydropyrimidin-4-yl)carbamoyl) piperazin-1-yl)-2-methyl-1-oxopropan-2-yl)carbamate (0.87 g, 1.3 mmol) in THF (40 mL) was added TBAF (1.0 M in THF) (1.42 mL, 1.4 mmol) at 0° C. The reaction mixture was stirred at 50° C. for 16 h. The reaction mixture was poured into sat. aq. aq. $NaHCO_3$ solution (25 mL) and extracted with $CH_2Cl_2$:MeOH (9:1, 3×100 mL). The combined organics were dried over $Na_2SO_4$, filtered, concentrated under reduced pressure and purified by column chromatography (4-5% MeOH in $CH_2Cl_2$) to afford the title compound (1.3 g, 60%) as an off white solid. LCMS[M+H] 557.3.

Step 9: tert-butyl (2-methyl-1-oxo-1-(4-((2-oxo-1-(4-(2-oxobutyl)phenyl)-1,2-dihydropyrimidin-4-yl)carbamoyl) piperazin-1-yl)propan-2-yl)carbamate. To a stirred solution of tert-butyl (1-(4-((1-(4-(2-hydroxybutyl)phenyl)-2-oxo-1,2-dihydropyrimidin-4-yl)carbamoyl)piperazin-1-yl)-2-methyl-1-oxopropan-2-yl)carbamate (0.25 g, 0.6 mmol) in $CH_2Cl_2$ (15 mL) was added DMP (3.81 g, 0.9 mmol) at 0° C. The reaction was stirred at rt for 3 h. The reaction mixture was poured into sat. aq. $NaHCO_3$ (100 mL) and extracted with $CH_2Cl_2$ (3×50 mL). The combined organics were dried over $Na_2SO_4$, filtered and concentrated under reduced pressure at low temperature (35° C.) to afford the title compound (0.22 g, 88%) as off white solid. LCMS[M+H] 555.

Intermediate 22

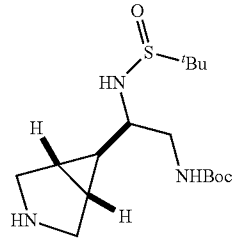

tert-Butyl ((2R)-2-(exo-3-azabicyclo[3.1.0]hexan-6-yl)-2-((tert-butylsulfinyl)amino)ethyl)carbamate Scheme I-14

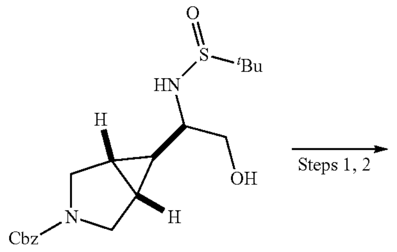

-continued

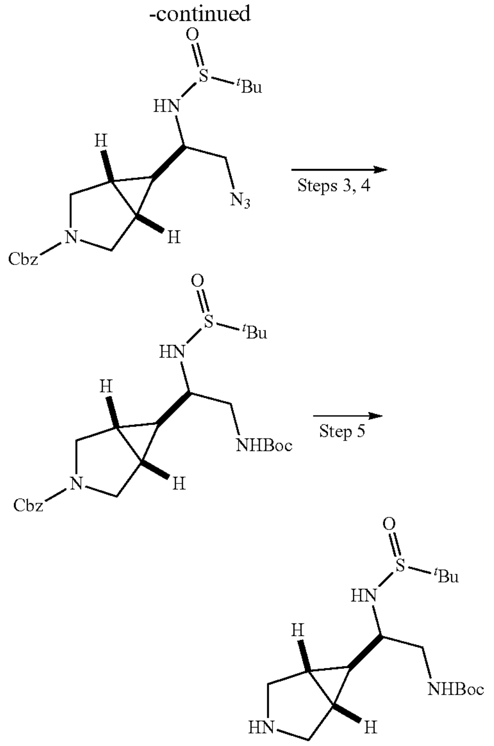

Reagents: Step 1) MsCl, $Et_3N$, $CH_2Cl_2$, 0° C. to rt, 3 h 2) $NaN_3$ DMF, 50° C., 16 h 3) $PPh_3$, THF: $H_2O$ (1:1), 60° C., 16 h 4) $(Boc)_2O$, TEA, $CH_2Cl_2$, rt, 16 h 5) 20 wt. % $Pd(OH)_2H_2$, MeOH, rt, 16 h.

Step 1: benzyl exo-6-((1R)-1-((tert-butylsulfinyl)amino)-2-((methylsulfonyl)oxy)ethyl)-3-azabicyclo[3.1.0]hexane-3-carboxylate. To a solution of Benzyl exo-6-((1R)-1-((tert-butylsulfinyl)amino)-2-hydroxyethyl)-3-azabicyclo[3.1.0] hexane-3-carboxylate (0.35 g, 0.92 mmol), and $Et_3N$ (0.19 g, 1.84 mmol) in $CH_2Cl_2$ (15 mL) at 0° C. was added MsCl (0.16 g, 1.38 mmol) slowly dropwise. The reaction mixture was warmed to rt and stirred for 3 h. The reaction mixture diluted with $CH_2Cl_2$ (15 mL) and washed with sat. $NaHCO_3H_2O$, brine, dried over $Na_2SO_4$, filtered, and concentrated under reduced pressure. The residue was purified by flash column chromatography to give title compound (0.42 g, Quant.) as a colorless sticky solid.

Step 2: benzyl exo-6-((1R)-2-azido-1-((tert-butylsulfinyl) amino)ethyl)-3-azabicyclo[3.1.0]hexane-3-carboxylate. To a solution of benzyl exo-6-((1R)-1-((tert-butylsulfinyl) amino)-2-((methylsulfonyl)oxy)ethyl)-3-azabicyclo[3.1.0] hexane-3-carboxylate (0.42 g, 0.92 mmol), in $CH_2Cl_2$ (15 mL) at rt was added $NaN_3$ (0.15 g, 2.30 mmol), and stirred for 16 h at 60° C. The reaction mixture was quenched with sat. LiCl, and the compound was extracted with EtOAc (2×15 mL). The combined organics were dried over $Na_2SO_4$, filtered, and concentrated under reduced pressure. The residue was purified by column chromatography to give title compound (0.22 g, 60%) as a colorless solid.

Step 3: benzyl exo-6-((1R)-2-amino-1-((tert-butylsulfinyl)amino)ethyl)-3-azabicyclo[3.1.0]hexane-3-carboxylate. To a solution of Benzyl exo-6-((1R)-2-azido-1-((tert-butylsulfinyl)amino)ethyl)-3-azabicyclo[3.1.0]hexane-3-carboxylate (0.22 g, 0.54 mmol) THF:$H_2O$ (2:1, 10 mL) at rt was added $PPh_3$ (0.22 g, 0.82 mmol), and stirred for 16 h at 60° C. The reaction mixture was diluted with $H_2O$, and the compound was extracted with EtOAc (2×15 mL). The combined organics were dried over $Na_2SO_4$, filtered, and concentrated under reduced pressure. The residue was purified by flash column chromatography to give the title compound (0.14 g, 68%) as a colorless sticky solid.

Step 4: benzyl exo-6-((1R)-2-((tert-butoxycarbonyl) amino)-1-((tert-butylsulfinyl)amino)ethyl)-3-azabicyclo[3.1.0]hexane-3-carboxylate. To a solution of Benzyl exo-6-((1R)-2-amino-1-((tert-butylsulfinyl)amino)ethyl)-3-azabicyclo[3.1.0]hexane-3-carboxylate (0.14 g, 0.36 mmol), and $Et_3N$ (0.11 g, 1.08 mmol) in $CH_2Cl_2$ (10 mL) at rt, was added $Boc_2O$ (0.12 g, 0.54 mmol), and stirred for 16 h. The reaction mixture was diluted with $CH_2Cl_2$ (15 mL) and washed with saturated $NaHCO_3H_2O$, brine, dried over $Na_2SO_4$, filtered, and concentrated under reduced pressure. The residue was purified by column chromatography to give the title compound (0.12 g, 70%) as a sticky solid.

Step 5: tert-Butyl ((2R)-2-(exo-3-azabicyclo[3.1.0]hexan-6-yl)-2-((tert-butylsulfinyl)amino)ethyl)carbamate. To a degassed solution of benzyl exo-6-((1R)-2-((tert-butoxycarbonyl)amino)-1-((tert-butylsulfinyl)amino)ethyl)-3-azabicyclo[3.1.0]hexane-3-carboxylate (0.12 g, 0.25 mmol) in MeOH (15 mL), was added $Pd(OH)_2/C$ (0.03 g, 20 wt. %). The mixture stirred under an atmosphere of $H_2$ for 16 h. The mixture was filtered through Celite®, and the filtrate was concentrated in vacuum to afford the title compound (0.07 g, 82%) as a sticky solid.

Compound Synthesis

Compound 3

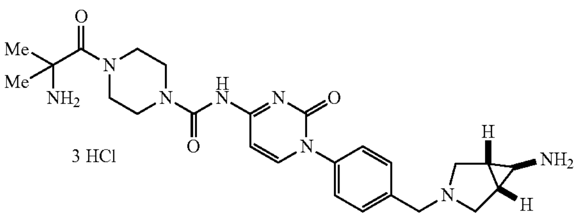

4-(2-Amino-2-methylpropanoyl)-N-(1-(4-((exo-6-amino-3-azabicyclo[3.1.0]hexan-3-yl)methyl)phenyl)-2-oxo-1,2-dihydropyrimidin-4-yl)piperazine-1-carboxamide Hydrochloride Salt Scheme C-1

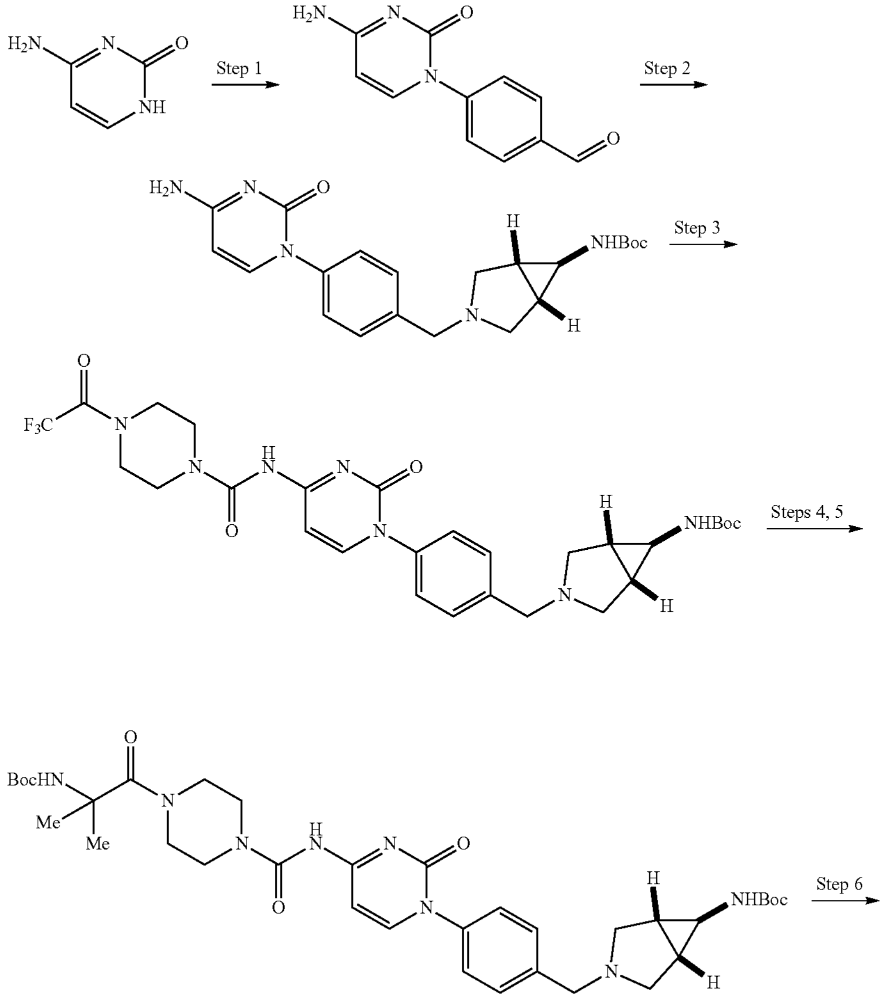

-continued

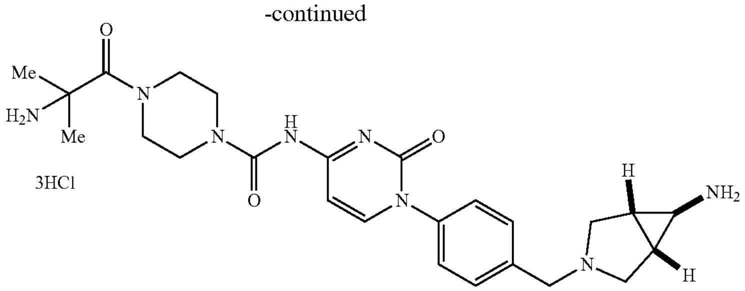

1) 4-Formylphenylboronic acid, TMEDA, $Cu(OAc)_2 \cdot H_2O$, $MeOH:H_2O$, rt, 16 h 2) tert-Butyl (exo-3-azabicyclo[3.1.0]hexan-6-yl)carbamate, $NaBH(OAc)_3$, $DCE:CH_3CN$, rt, 16 h 3) 3-Methyl-1-(4-(2,2,2-trifluoro-acetylpiperazine-1-carbonyl)-1H-imidazol-3-ium iodide, $CH_3CN$, 70° C., 16 h 4) $K_2CO_3$, MeOH, 2 h, rt 5) Boc-α-methylalanine, HATU, DIPEA, $CH_2Cl_2$, rt, 16 h 6) HCl, MeOH, rt, 4 h.

Step 1: 4-(4-amino-2-oxopyrimidin-1 (2H)-yl)benzaldehyde: A suspension of cytosine (2.60 g, 24.0 mmol) and 4-formylphenylboronic acid (3.53 g 24.0 mmol) in MeOH: $H_2O$ (4:1, 25 mL), was stirred at rt in open air. After 30 min, TMEDA (6.70 ml, 28.0 mmol) and $Cu(OAc)_2H_2O$ (4.70 g 24.0 mmol) were added. The reaction was stirred in open air for 16 h at rt. The MeOH was removed under reduced pressure, and ice was added to the remaining mixture and stirred for 10 min. The reaction was filtered and the solid was washed with $H_2O$ to yield the title compound (3.5 g, 69%) as a white solid.

Step 2: tert-butyl (exo-3-(4-(4-amino-2-oxopyrimidin-1 (2H)-yl)benzyl)-3-azabicyclo[3.1.0]hexan-6-yl)carbamate: To a stirred suspension of 4-(4-amino-2-oxopyrimidin-1 (2H)-yl)benzaldehyde (1.00 g 4.6 mmol) and tert-butyl ((exo)-3-azabicyclo[3.1.0]hexan-6-yl)carbamate (1.39 g, 7.0 mmol) in $DCE:CH_3CN$ (1:1, 25 mL) was added DIPEA (1.61 mL, 9.20 mmol) and $NaBH(OAc)_3$ (1.97 g, 9.30 mmol). The reaction was stirred for 16 h at rt. The solvent was evaporated under reduced pressure, the residue dissolved in $CHCl_3$ and washed with 10% NaOH. Purification by column chromatography ($CHCl_3$:MeOH) yielded the title compound as a white solid (1.40 g, 76%).

Step 3: tert-butyl (exo-3-(4-(2-oxo-4-(4-(2,2,2-trifluoroacetyl)piperazine-1-carboxamido)pyrimidin-1 (2H)-yl)benzyl)-3-azabicyclo[3.1.0]hexan-6-yl)carbamate: To a round bottom flask containing 3-methyl-1-(4-(2,2,2-trifluoroacetylpiperazine-1-carbonyl)-1H-imidazol-3-ium iodide (100 mg, 0.25 mmol) and tert-butyl (exo-3-(4-(4-amino-2-oxopyrimidin-1 (2H)-yl)benzyl)-3-azabicyclo[3.1.0]hexan-6-yl)carbamate (112 mg, 0.28 mmol) was added dry $CH_3CN$ (12 mL). The reaction was heated to 85° C. for 8 h. The solvent was removed under reduced pressure and the crude reaction mixture was partitioned between $CHCl_3$ (50 mL) and $H_2O$ (50 mL). The organic layer was separated and concentrated under reduced pressure. Purification by column chromatography ($CHCl_3$:MeOH) afforded the title compound as a pale white solid (136 mg, 92%).

Step 4: tert-butyl (exo-3-(4-(2-oxo-4-(piperazine-1-carboxamido)pyrimidin-1 (2H)-yl)benzyl)-3-azabicyclo[3.1.0]hexan-6-yl)carbamate: To tert-butyl (exo-3-(4-(2-oxo-4-(4-(2,2,2-trifluoroacetyl)piperazine-1-carboxamido)pyrimidin-1 (2H)-yl)benzyl)-3-azabicyclo[3.1.0]hexan-6-yl)carbamate (135 mg, 0.23 mmol) and $K_2CO_3$ (126 mg, 0.91 mmol) was added MeOH (5 mL), and stirred at rt for 2 h. The solvent was evaporated under reduced pressure and the residue was dissolved in $H_2O$. The aqueous phase was extracted with $CHCl_3$ (3×20 mL). The organic layers were combined, dried over $Na_2SO_4$, filtered and concentrated under reduced pressure to afford the title compound as a pale yellow solid (85 mg, 91%).

Step 5: tert-butyl (exo-3-(4-(4-(4-(2-((tert-butoxycarbonyl)amino)-2-methylpropanoyl)piperazine-1-carboxamido)-2-oxopyrimidin-1 (2H)-yl)benzyl)-3-azabicyclo[3.1.0]hexan-6-yl)carbamate: To a suspension of Boc-α-methylalanine (52 mg, 0.26 mmol) in $CH_2Cl_2$ (2 mL) was added HATU (100 mg, 0.26 mmol), DIPEA (0.054 mL, 0.31 mmol). To the suspension was added solid tert-butyl (exo-3-(4-(2-oxo-4-(piperazine-1-carboxamido)pyrimidin-1 (2H)-yl)benzyl)-3-azabicyclo[3.1.0]hexan-6-yl)carbamate (85 mg, 0.26 mmol) and the mixture stirred at rt for 16 h. The solution was diluted with $CH_2Cl_2$ (5 mL) and washed once with $H_2O$. The organic layer was concentrated under reduced pressure. Purification by column chromatography ($CHCl_3$:MeOH) yielded the title compound (140 mg, 80%) as a white solid.

Step 6: 4-(2-amino-2-methylpropanoyl)-N-(1-(4-((exo-6-amino-3-azabicyclo[3.1.0]hexan-3-yl)methyl)phenyl)-2-oxo-1,2-dihydropyrimidin-4-yl)piperazine-1-carboxamide: To tert-butyl (exo-3-(4-(4-(4-(2-((tert-butoxycarbonyl)amino)-2-methylpropanoyl)piperazine-1-carboxamido)-2-oxopyrimidin-1 (2H)-yl)benzyl)-3-azabicyclo[3.1.0]hexan-6-yl)carbamate (100 mg, 0.14 mmol) was added HCl in MeOH (2N, 15 mL) and stirred at rt for 4 h. The solvent was evaporated under reduced pressure. Purification by column chromatography ($CHCl_3$:MeOH:$NH_4OH$/8:2:0.2) afforded the title compound (65 mg, 76%) as a light yellow solid. $^1H$ NMR (500 MHz, $CD_3OD$): δ 7.70 (d, 1H), 7.41 (d, 2H), 7.35 (d, 2H), 6.62 (d, 1H), 3.82 (s, 4H), 3.67 (s, 4H), 3.60 (s, 2H), 2.96 (d, 2H), 2.57 (s, 1H), 2.44 (d, 2H), 1.43 (s, 6H), 1.41-1.40 (m, 2H). LCMS[M+H] 495.3.

Compound 2

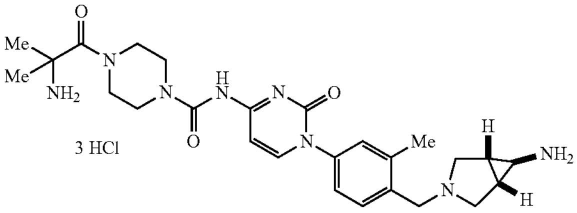

4-(2-Amino-2-methylpropanoyl)-N-(1-(4-((exo-6-amino-3-azabicyclo[3.1.0]hexan-3-yl)methyl)-3-methylphenyl)-2-oxo-1,2-dihydropyrimidin-4-yl) piperazine-1-carboxamide Hydrochloride Salt Prepared in a similar fashion to Scheme C-1 from N-(1-(4-((exo-6-amino-3-azabicyclo[3.1.0]hexan-3-yl)methyl)-3-methylphenyl)-2-oxo-1,2-dihydropyrimidin-4-yl)piperazine-1-carboxamide and 2-((tert-butoxy carbonyl)amino)-2-methylpropanoic acid. $^1H$ NMR (500 MHz, $CD_3OD$): δ 8.40 (s, 1H), 7.92 (d, 2H), 7.53 (s, 1H), 7.51 (t, 1H), 6.89 (s, 1H), 4.60 (s, 2H), 3.89-3.72 (m, 12H), 2.59 (s, 3H), 2.39 (s, 2H), 1.74 (s, 6H). LCMS [M+H] 509.5.

Compound 4

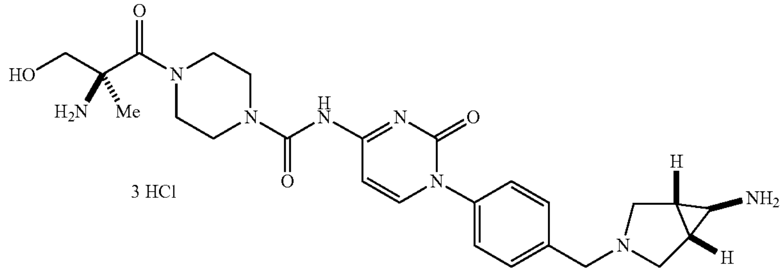

N-(1-(4-((exo-6-Amino-3-azabicyclo[3.1.0]hexan-3-yl)methyl)phenyl)-2-oxo-1,2-dihydropyrimidin-4-yl)-4-((S)-2-amino-3-hydroxy-2-methylpropanoyl) piperazine-1-carboxamide Hydrochloride Salt Prepared in a similar fashion to Scheme C-1 from N-(1-(4-((exo-6-amino-3-azabicyclo[3.1.0]hexan-3-yl)methyl) phenyl)-2-oxo-1,2-dihydropyrimidin-4-yl)piperazine-1-carboxamide and (2R,4S)-3-(tert-butoxycarbonyl)-2-(tert-butyl)-4-methyloxazolidine-4-carboxylic acid. $^{1}H$ NMR (500 MHz, $D_2O$) δ 8.06 (d, 1H), 7.70 (d, 2H), 7.59 (d, 2H), 6.86 (d, 1H), 4.95 (s, 2H), 4.18 (d, 1H), 3.93 (d, 1H), 3.90-3.60 (m, 12H), 2.95 (s, 1H), 2.46 (s, 2H), 1.71 (s, 3H). LCMS [M+H] 511.29.

Compound 5

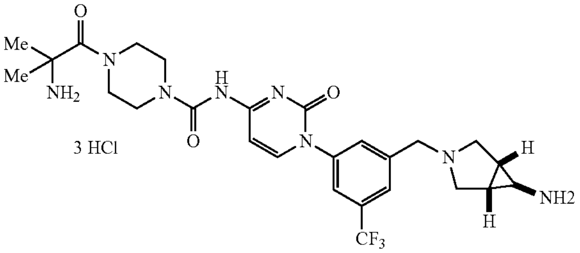

4-(2-Amino-2-methylpropanoyl)-N-(1-(3-((exo-6-amino-3-azabicyclo[3.1.0]hexan-3-yl)methyl)-5-(trifluoromethyl)phenyl)-2-oxo-1,2-dihydropyrimidin-4-yl)piperazine-1-carboxamide Hydrochloride Salt Prepared in a similar fashion to Scheme C-1 from N-(1-(3-((exo-6-amino-3-azabicyclo[3.1.0]hexan-3-yl)methyl)-5-(trifluoromethyl)phenyl)-2-oxo-1,2-dihydropyrimidin-4-yl) piperazine-1-carboxamide and 2-((tert-butoxycarbonyl) amino)-2-methylpropanoic acid. LCMS[M+H] 563.29.

Compound 6

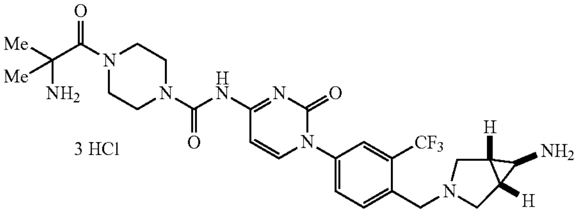

4-(2-Amino-2-methylpropanoyl)-N-(1-(4-((exo-6-amino-3-azabicyclo[3.1.0]hexan-3-yl)methyl)-3-(trifluoromethyl)phenyl)-2-oxo-1,2-dihydropyrimidin-4-yl)piperazine-1-carboxamide Hydrochloride Salt Prepared in a similar fashion to Scheme C-1 from tert-butyl (exo-3-(4-(2-oxo-4-(piperazine-1-carboxamido)pyrimidin-1 (2H)-yl)-2-(trifluoromethyl)benzyl)-3-azabicyclo [3.1.0]hexan-6-yl)carbamate and 2-((tert-butoxycarbonyl) amino)-2-methylpropanoic acid.

Compound 9

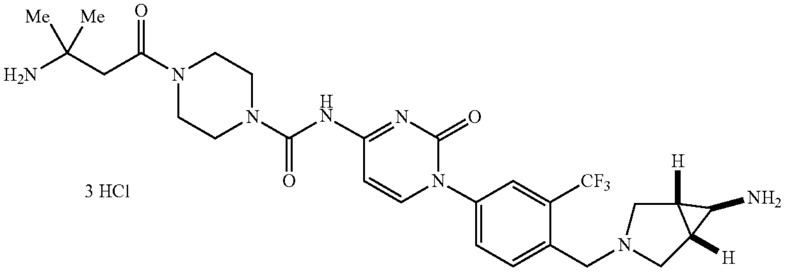

N-(1-(4-((exo-6-Amino-3-azabicyclo[3.1.0]hexan-3-yl)methyl)-3-(trifluoromethyl)phenyl)-2-oxo-1,2-dihydropyrimidin-4-yl)-4-(3-amino-3-methylbutanoyl)piperazine-1-carboxamide Hydrochloride Salt Prepared in a similar fashion to a similar fashion to Scheme C-1 from tert-butyl (exo-3-(4-(2-oxo-4-(piperazine-1-carboxamido)pyrimidin-1 (2H)-yl)-2-(trifluoromethyl) benzyl)-3-azabicyclo[3.1.0]hexan-6-yl)carbamate and 3-((tert-butoxycarbonyl)amino)-3-methylbutanoic acid. $^1H$ NMR (400 MHz, $D_2O$) δ 7.91-7.61 (m, 4H), 6.71 (d, 1H), 4.53 (s, 2H), 3.74 (br. s., 2H), 3.55 (br.s, 8H), 3.46 (s, 2H), 2.93 (s, 1H), 2.70 (s, 2H), 2.33 (s, 2H), 1.27 (d, 6H). LCMS[M+H] 577.31.

Compound 10

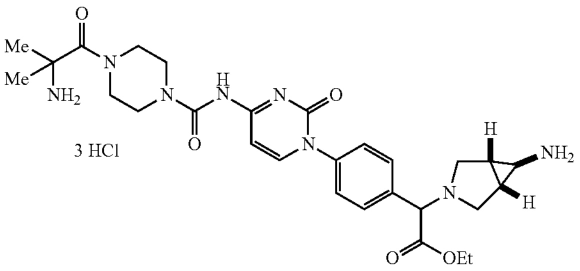

Ethyl 2-(4-(4-(4-(2-amino-2-methylpropanoyl)piperazine-1-carboxamido)-2-oxopyrimidin-1 (2H)-yl) phenyl)-2-(exo-6-amino-3-azabicyclo[3.1.0]hexan-3-yl)acetate Hydrochloride Salt Prepared in a similar fashion to Scheme C-1 from ethyl 2-(exo-6-amino-3-azabicyclo[3.1.0]hexan-3-yl)-2-(4-(2-oxo-4-(piperazine-1-carboxamido)pyrimidin-1 (2H)-yl)phenyl)acetate and 2-((tert-butoxycarbonyl)amino)-2-methylpropanoic acid. $^1H$ NMR (500 MHz, $CD_3OD$): δ 8.18 (s, 1H), 7.73 (d, 2H), 7.64 (d, 2H), 6.74 (s, 1H), 5.45 (s, 1H), 4.30-4.15 (m, 2H), 3.77-3.62 (m, 8H), 2.33 (s, 2H), 1.65 (s, 6H), 1.16-1.12 (m, 3H). LCMS [M+H] 567.4.

Compound 12

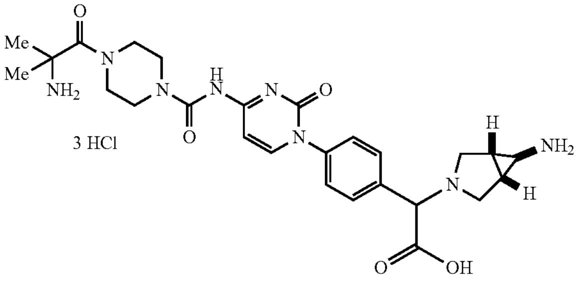

2-(4-(4-(4-(2-Amino-2-methyl propanoyl)piperazine-1-carboxamido)-2-oxopyrimidin-1 (2H)-yl) phenyl)-2-(exo-6-amino-3-azabicyclo[3.1.0]hexan-3-yl)acetic Acid Hydrochloride Salt Prepared in a similar fashion to Scheme C-1 from ethyl 2-(exo-6-amino-3-azabicyclo[3.1.0]hexan-3-yl)-2-(4-(2-oxo-4-(piperazine-1-carboxamido)pyrimidin-1 (2H)-yl)phenyl)acetate and 2-((tert-butoxycarbonyl)amino)-2-methylpropanoic acid. $^1H$ NMR (500 MHz, $CD_3OD$): δ 8.44 (s, 1H), 7.86 (s, 2H), 7.74 (s, 2H), 6.93 (s, 1H), 5.52 (s, 1H), 3.87-3.72 (m, 8H), 3.34 (s, 5H), 2.43 (s, 2H), 1.71 (s, 6H). LCMS [M+H] 539.3.

Compound 31

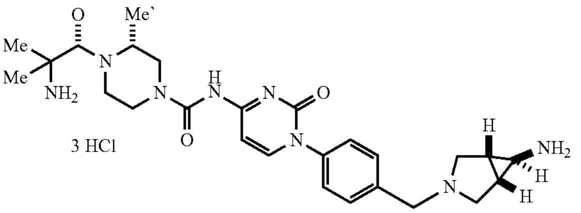

(R)-4-(2-Amino-2-methylpropanoyl)-N-(1-(4-((exo-6-amino-3-azabicyclo[3.1.0]hexan-3-yl)methyl)phenyl)-2-oxo-1,2-dihydropyrimidin-4-yl)-3-methylpiperazine-1-carboxamide Hydrochloride Salt Prepared in a similar fashion to Scheme C-1 from tert-butyl (exo-3-(4-(4-((R)-3-methylpiperazine-1-carboxamido)-2-oxopyrimidin-1 (2H)-yl)benzyl)-3-azabicyclo [3.1.0]hexan-6-yl)carbamate and 2-((tert-butoxycarbonyl) amino)-2-methylpropanoic acid. $^1H$ NMR (400 MHz, $D_2O$) δ 8.09 (d, 1H), 7.70 (d, 2H), 7.59 (d, 2H), 6.81 (d, 1H), 4.50 (s, 2H), 4.18 (s, 1H), 4.03 (s, 2H), 3.74 (s, 4H), 3.35 (s, 2H), 2.93 (s, 1H), 2.45 (s, 2H), 2.00 (s, 1H), 1.87-1.62 (m, 6H), 1.26 (s, 4H). LCMS [M+H]509.2.

Compound 45

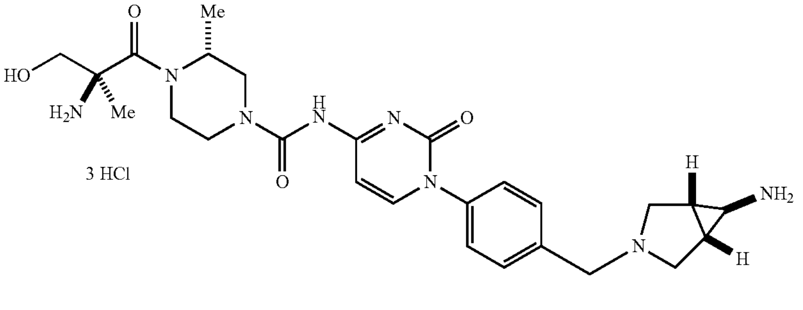

(R)—N-(1-(4-((exo-6-Amino-3-azabicyclo[3.1.0]hexan-3-yl)methyl)phenyl)-2-oxo-1,2-dihydropyrimidin-4-yl)-4-((S)-2-amino-3-hydroxy-2-methylpropanoyl)-3-methylpiperazine-1-carboxamide Hydrochloride Salt Prepared in a similar fashion to Scheme C-1 from tert-butyl (exo-3-(4-(4-((R)-3-methylpiperazine-1-carboxamido)-2-oxopyrimidin-1 (2H)-yl)benzyl)-3-azabicyclo[3.1.0]hexan-6-yl)carbamate and (2R,4S)-3-(tert-butoxycarbonyl)-2-(tert-butyl)-4-methyloxazolidine-4-carboxylic acid. $^1H$ NMR (400 MHz, $D_2O$) δ 7.94 (d, 1H), 7.68 (d, 2H), 7.57 (d, 2H), 6.87 (d, 1H), 4.48 (s, 2H), 4.25-4.10 (m, 3H), 4.03 (s, 1H), 3.93 (d, 1H), 3.73 (s, 4H), 3.48-3.15 (m, 3H), 2.92 (s, 1H), 2.45 (s, 2H), 2.09 (s, 1H), 1.71 (s, 3H), 1.43-1.19 (m, 3H). LCMS [M+H] 525.1.

Compound 111

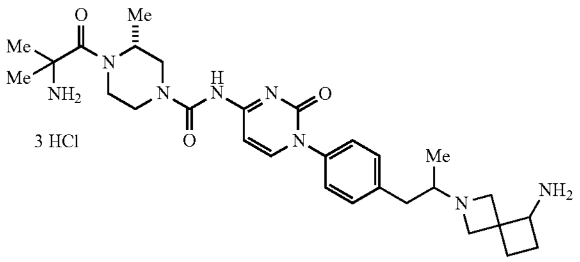

N-(1-(4-(2-(5-Amino-2-azaspiro[3.3] heptan-2-yl)propyl)phenyl)-2-oxo-1,2-dihydropyrimidin-4-yl)-4-(2-amino-2-methylpropanoyl)piperazine-1-carboxamide Hydrochloride Salt Scheme C-2

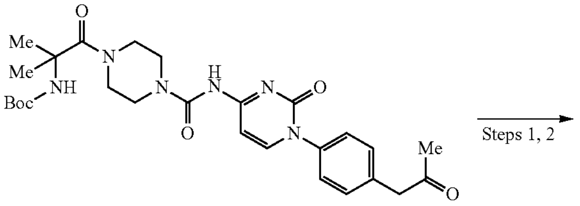

-continued

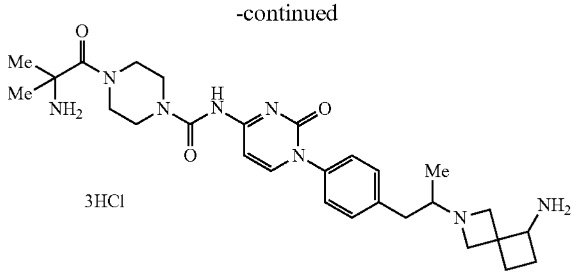

Reagents: 1) tert-butyl (2-azaspiro[3.3]heptan-5-yl)carbamate, NaH(OAc)$_3$ DIPEA, DCE, rt, 4 h 2) 2N HCl in MeOH, rt, 16 h.

Step 1: t-butyl (2-(1-(4-(4-(4-(2-((t-butoxycarbonyl)amino)-2-methylpropanoyl)piperazine-1-carboxamido)-2-oxopyrimidin-1 (2H)-yl)phenyl)propan-2-yl)-2-azaspiro[3.3]heptan-5-yl)carbamate. To a stirred solution t-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate (0.23 g, 0.42 mmol) and t-butyl (2-azaspiro[3.3]heptan-5-yl)carbamate (0.108 g, 0.51 mmol) in DCE (5.0 mL) were added DIPEA (0.2 mL, 1.27 mmol) and NaBH(OAc)$_3$ (0.180 g, 0.85 mmol) at 0° C. atmosphere. The reaction mixture was stirred at rt for 4 h. The reaction mixture was poured in to 1N NaOH (2.0 mL) and extracted with $CH_2Cl_2$ (3×50 mL). The combined organics were dried over $Na_2SO_4$, filtered and concentrated under reduced pressure. The crude material was purified by column chromatography (5-7% MeOH in $CH_2Cl_2$) to afford the title compound as a solid (0.12 g, 38%). Alternatively, this reaction can be carried out in MeOH with $NaBH_3CN$ (1.5 equiv). LCMS [M+H] 736.9.

Step 2: N-(1-(4-(2-(5-amino-2-azaspiro[3.3]heptan-2-yl)propyl)phenyl)-2-oxo-1,2-dihydropyrimidin-4-yl)-4-(2-amino-2-methylpropanoyl)piperazine-1-carboxamide hydrochloride salt. To a stirred solution of t-butyl (2-(1-(4-(4-(4-(2-((t-butoxycarbonyl)amino)-2-methylpropanoyl)piperazine-1-carboxamido)-2-oxopyrimidin-1 (2H)-yl)phenyl)propan-2-yl)-2-azaspiro[3.3]heptan-5-yl)carbamate (0.12 g, 0.16 mmol) in MeOH (3.0 mL) was added 4 M HCl in Dioxane (8.0 mL) at rt. The reaction mixture was stirred at rt for 16 h. The reaction mixture was concentrated under reduced pressure and triturated by $Et_2O$ (10 mL). The resulting solid was purified by Prep HPLC to afford the title compound (0.027 g, 25%) as an off-white solid. $^1H$ NMR (400 MHz, $D_2O$): Mixture of rotamers, δ 7.78-7.75 (m, 1H), 7.36-7.29 (m, 4H), 6.72-6.70 (m, 1H), 4.25-3.96 (m, 4H), 3.92-3.88 (m, 1H), 3.80-3.73 (m, 1H), 3.63-3.48 (m, 8H), 2.99-2.91 (m, 1H), 2.78-2.68 (m, 1H), 2.28-2.12 (m, 3H), 1.93-1.85 (m, 1H), 1.59 (s, 6H), 1.10-1.04 (m, 3H). LCMS [(M+2H)/2] 269.0.

Compound 112

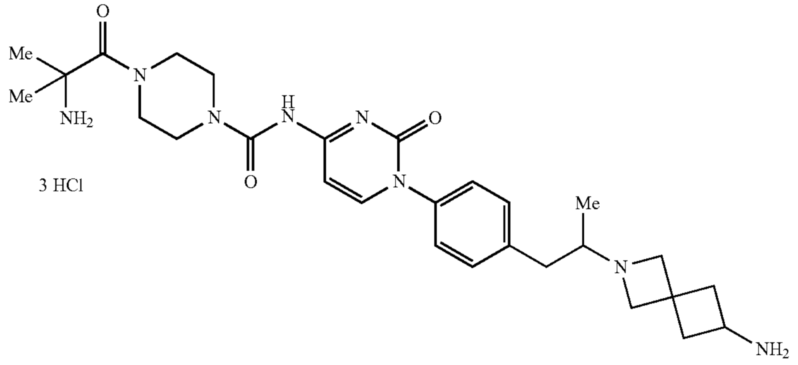

N-(1-(4-(2-(6-Amino-2-azaspiro[3.3]heptan-2-yl)propyl)phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-2 from t-butyl N-(2-azaspiro[3.3]heptan-6-yl)carbamate and t-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate. $^1$H NMR (400 MHz, $D_2O$): Mixture of rotamers, δ 7.82 (dd, 1H), 7.33-7.28 (m, 4H), 6.69 (d, 1H), 4.19-3.93 (m, 5H), 3.69-3.50 (m, 9H), 2.96-2.90 (m, 1H), 2.73-2.64 (m, 2H), 2.54-2.25 (m, 3H), 1.59 (s, 6H), 1.05-1.02 (m, 3H). LCMS [(M+2H)/2] 269.0.

Compound 98

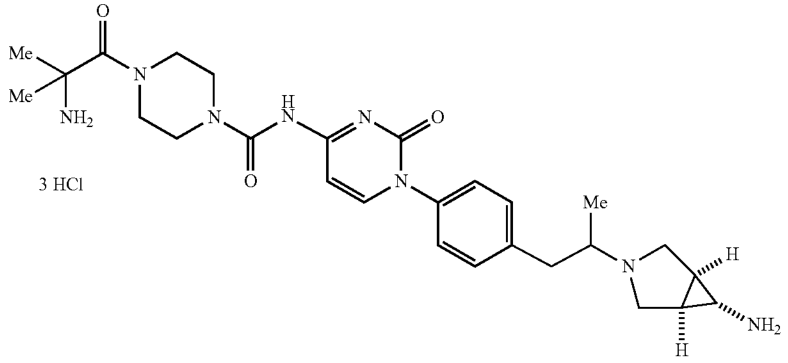

4-(2-Amino-2-methylpropanoyl)-N-(1-(4-(2-(exo-6-amino-3-azabicyclo[3.1.0]hexan-3-yl)propyl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-(2-oxo-1-(4-(2-oxopropyl)phenyl)-1,2-dihydropyrimidin-4-yl)carbamoyl)piperazin-1-yl)propan-2-yl)carbamate and tert-butyl exo-3-azabicyclo[3.1.0]hexan-6-ylcarbamate. $^{1}H$ NMR (400 MHz, $D_2O$) δ 7.95 (d, 1H), 7.44-7.37 (m, 4H), 6.78 (d, 1H), 3.94 (d, 1H), 3.88 (d, 1H), 3.78-3.59 (m 10H), 3.30 (s, 1H), 2.80 (t, 2H), 2.38 (s, 2H), 1.68 (s, 7H), 1.21 (d, 3H). LCMS [M+H] 523.3.

Compound 162

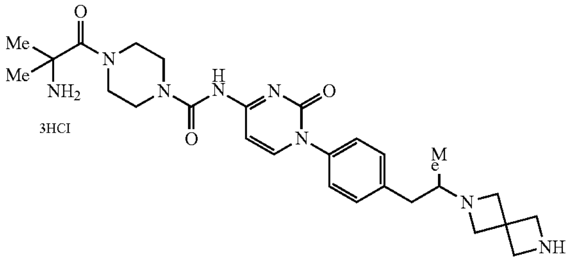

N-(1-(4-(2-(2,6-Diazaspiro[3.3]heptan-2-yl)propyl)phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-2 using t-butyl 2,6-diazaspiro[3.3]heptane-2-carboxylate hydrochloride and t-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate. $^{1}H$ NMR (400 MHz, $D_2O$): Mixture of rotamers, δ 7.76 (d, 1H), 7.33-7.31 (m, 4H), 6.71 (d, 1H), 4.63-4.34 (m, 2H), 4.32 (s, 2H), 4.20 (s, 2H), 4.19 (s, 2H), 3.63-3.57 (m, 8H), 2.97-2.92 (m, 1H), 2.75-2.70 (m, 1H), 1.59 (s, 6H), 1.06 (d, 3H). LCMS [(M+2H)/2] 263.3.

Compound 163

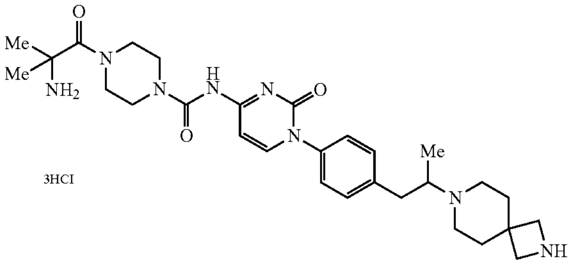

N-(1-(4-(2-(2,7-Diazaspiro[3.5]nonan-7-yl)propyl)phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-2 using t-butyl 2,7-diazaspiro[3.5]nonane-2-carboxylate and t-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate. $^{1}H$ NMR (400 MHz, $D_2O$): Mixture of rotamers, δ 7.72 (d, 1H), 7.32-7.26 (m, 4H), 6.70 (d, 1H), 3.94 (s, 2H), 3.83 (s, 2H), 3.62-3.56 (m, 9H), 3.44 (t, 3H), 3.19-3.15 (m, 2H), 3.01 (t, 3H), 2.78-2.72 (m, 2H), 2.27 (d, 3H), 1.96 (t, 3H), 1.58 (s, 6H), 1.09 (d, 3H). LCMS [(M+2H)/2] 276.1.

Compound 85

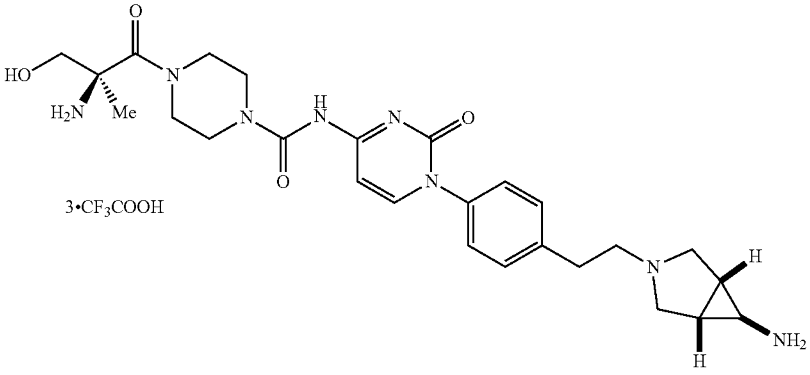

N-(1-(4-(2-(exo-6-amino-3-azabicyclo[3.1.0]hexan-3-yl)ethyl)phenyl)-2-oxo-1,2-dihydropyrimidin-4-yl)-4-((S)-2-amino-3-hydroxy-2-methylpropanoyl) piperazine-1-carboxamide Trifluoroacetetate Salt Prepared in a similar fashion to Scheme C-2 from tert-butyl (2S,4S)-2-(tert-butyl)-4-methyl-4-(4-((2-oxo-1-(4-(2-oxoethyl)phenyl)-1,2-dihydropyrimidin-4-yl)carbamoyl) piperazine-1-carbonyl)oxazolidine-3-carboxylate and tert-butyl (exo-3-azabicyclo[3.1.0]hexan-6-yl)carbamate to afford the title compound. $^1$H NMR (500 MHz, $D_2O$) δ 7.90 (d, 1H), 7.52 (d, 2H), 7.47 (d, 2H), 6.89 (d, 1H), 4.20 (d, 1H), 4.00-3.92 (m, 3H), 3.84-3.73 (m, 8H), 3.65-3.55 (m, 4H), 3.17 (t, 2H) 2.87 (s, 1H), 2.47 (s, 2H), 1.73 (s, 3H). LCMS [M+H] 525.4.

Compound 86

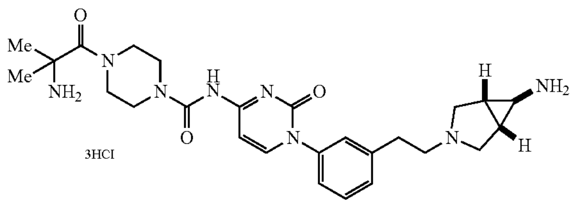

4-(2-Amino-2-methylpropanoyl)-N-(1-(3-(2-(exo-6-amino-3-azabicyclo[3.1.0]hexan-3-yl)ethyl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(3-(2-oxoethyl)phenyl)-1,2-dihydropyrimidin-4-yl)carbamoyl)piperazin-1-yl) propan-2-yl)carbamate and tert-butyl (exo-3-azabicyclo [3.1.0]hexan-6-yl)carbamate. $^1$H NMR (500 MHz, $D_2O$) δ 8.05 (d, 1H), 7.63 (t, 1H), 7.52 (d, 1H), 7.46-7.42 (m, 2H), 6.88 (d, 1H), 3.99-3.94 (m, 2H), 3.86-3.75 (m, 8H), 3.66-3.56 (m, 3H), 3.21-3.06 (m, 3H), 2.87 (s, 1H), 2.46 (s, 2H), 1.78 (s, 6H). LCMS [M+H] 509.4.

Compound 89

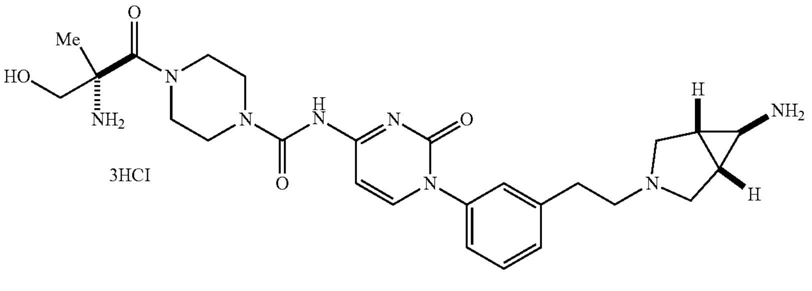

N-(1-(3-(2-(exo-6-Amino-3-azabicyclo[3.1.0]hexan-3-yl)ethyl)phenyl)-2-oxo-1,2-dihydropyrimidin-4-yl)-4-((S)-2-amino-3-hydroxy-2-methylpropanoyl) piperazine-1-carboxamide Hydrochloride Salt Prepared in a similar fashion to Scheme C-2 from tert-butyl (2S,4S)-2-(tert-butyl)-4-methyl-4-(4-((2-oxo-1-(3-(2-oxoethyl)phenyl)-1,2-dihydropyrimidin-4-yl)carbamoyl) piperazine-1-carbonyl)oxazolidine-3-carboxylate and tert-butyl (exo-3-azabicyclo[3.1.0]hexan-6-yl)carbamate. $^1$H NMR (500 MHz, $D_2O$) δ 7.89 (d, 1H), 7.59 (t, 1H), 7.47 (d, 1H), 7.40-7.37 (m, 2H), 6.87 (d, 1H), 4.17 (d, 1H), 3.92 (d, 3H), 3.83-3.72 (m, 10H), 3.13 (t, 4H), 2.82 (s, 1H), 2.43 (s, 2H), 1.70 (s, 3H). LCMS [M+H] 525.4.

Compound 90

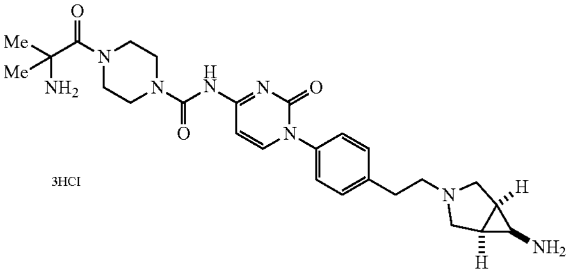

4-(2-Amino-2-methylpropanoyl)-N-(1-(4-(2-(endo-6-amino-3-azabicyclo[3.1.0]hexan-3-yl)ethyl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl (endo-3-azabicyclo[3.1.0]hexan-6-yl)carbamate. $^1$H NMR (500 MHz, $D_2O$) δ 8.00 (d, 1H), 7.49 (d, 2H), 7.45 (d, 2H), 6.83 (d, 1H), 3.94 (d, 1H), 3.85-3.72 (m, 8H), 3.63-3.54 (m, 4H), 3.20-3.01 (m, 3H), 2.84 (s, 1H), 2.42 (s, 2H), 1.75 (s, 6H). LCMS [M+H] 509.3.

Compound 91

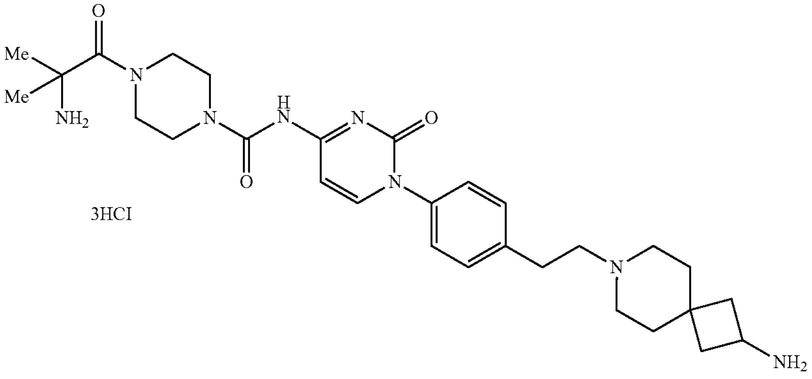

4-(2-Amino-2-methylpropanoyl)-N-(1-(4-(2-(2-amino-7-azaspiro[3.5]nonan-7-yl)ethyl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl (7-azaspiro[3.5]nonan-2-yl)carbamate. $^1$H NMR (500 MHz, $D_2O$) δ 7.94 (d, 1H), 7.50 (d, 2H), 7.44 (d, 2H), 6.85 (d, 1H), 3.92-3.86 (m, 1H), 3.83-3.68 (m, 8H), 3.64-3.52 (m, 2H), 3.44 (t, 2H), 3.18 (t, 2H), 3.13-2.97 (m, 2H), 2.56-2.47 (m, 2H), 2.37-2.29 (m, 2H), 2.15-2.00 (m, 2H), 1.94-1.84 (m, 2H), 1.75 (s, 6H). LCMS [M+H] 551.3.

Compound 92

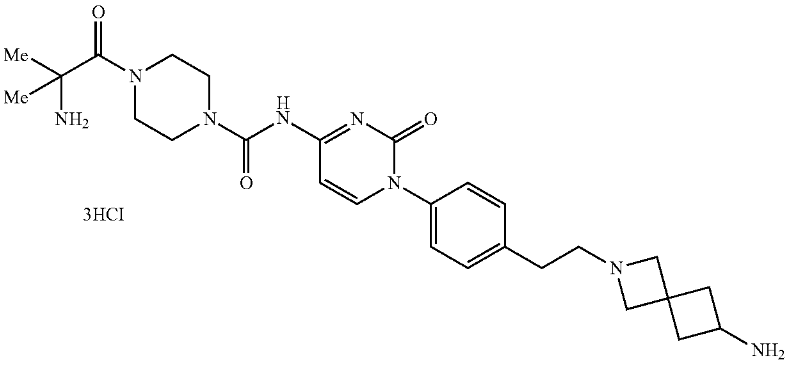

N-(1-(4-(2-(6-Amino-2-azaspiro[3.3]heptan-2-yl)ethyl)phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-2 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl (2-azaspiro[3.3]heptan-6-yl)carbamate. $^1$H NMR (500 MHz, $D_2O$) δ 7.93 (d, 1H), 7.46 (d, 2H), 7.42 (d, 2H), 6.83 (d, 1H), 4.32 (d, 1H), 4.24-4.10 (m, 3H), 3.82-3.69 (m, 8H), 3.54 (t, 2H), 3.01 (t, 2H), 2.81-2.65 (m, 3H), 2.53-2.42 (m, 2H), 1.72 (s, 6H) LCMS [M+H] 523.4.

Compound 93

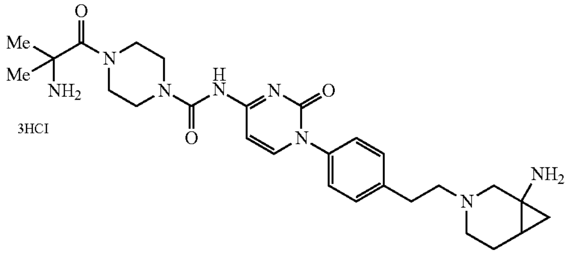

4-(2-Amino-2-methylpropanoyl)-N-(1-(4-(2-(1-amino-3-azabicyclo[4.1.0]heptan-3-yl)ethyl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl (3-azabicyclo[4.1.0]heptan-1-yl)carbamate. $^1$H NMR (500 MHz, $D_2O$) δ 7.89 (d, 1H), 7.46 (d, 2H), 7.40 (d, 2H), 6.81 (d, 1H), 3.79-3.65 (m, 8H), 3.64-3.49 (m, 2H), 3.45-3.34 (m, 1H), 3.19-3.08 (m, 2H), 2.93-2.84 (m, 1H), 2.63-2.41 (m, 3H), 1.85-1.78 (m, 1H), 1.71 (s, 6H) LCMS [M+H] 523.2.

Compound 94

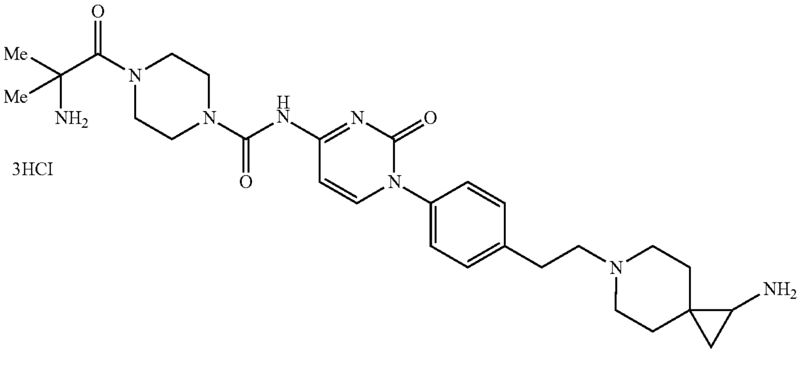

4-(2-Amino-2-methylpropanoyl)-N-(1-(4-(2-(1-amino-6-azaspiro[2.5] octan-6-yl)ethyl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl 6-azaspiro[2.5]octan-1-ylcarbamate. $^1$H NMR (400 MHz, $D_2O$) δ 7.89 (d, 1H), 7.52 (d, 2H), 7.45 (d, 2H), 6.86 (d, 1H), 3.79 (s, 2H), 3.73 (s, 7H), 3.52 (t, 2H), 3.31-3.15 (m, 4H), 2.73 (s, 1H), 2.29 (d, 1H), 1.75 (s, 6H), 1.35 (d, 4H), 1.17-1.12 (m, 1H), 0.97-0.93 (m, 1H). LCMS [M+H] 537.2.

Compound 95

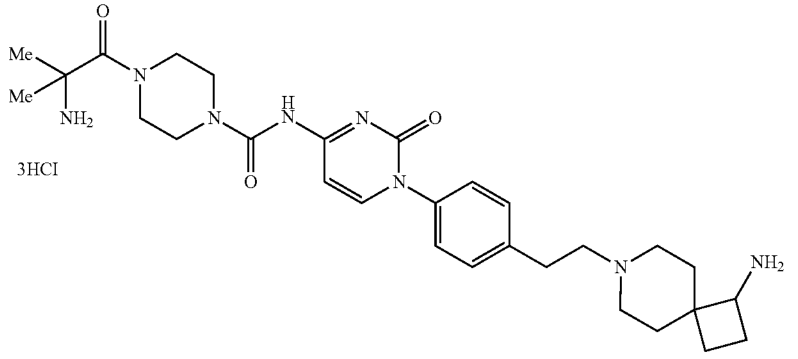

4-(2-Amino-2-methylpropanoyl)-N-(1-(4-(2-(1-amino-7-azaspiro[3.5]nonan-7-yl)ethyl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and 2,2,2-trifluoro-N-(7-azaspiro[3.5]nonan-1-yl)acetamide trifluoroacetate salt. $^1$H NMR (400 MHz, $D_2O$) δ 7.89 (d, 1H), 7.50 (d, 2H), 7.44 (d, 2H), 6.86 (d, 1H), 3.78 (s, 3H), 3.71 (d, 7H), 3.58 (d, 1H), 3.50-3.42 (m, 2H), 3.19 (d, 3H), 3.02 (s, 1H), 2.38 (d, 1H), 2.25-1.83 (m, 7H), 1.75 (s, 6H). LCMS [M+H] 551.2.

Compound 96

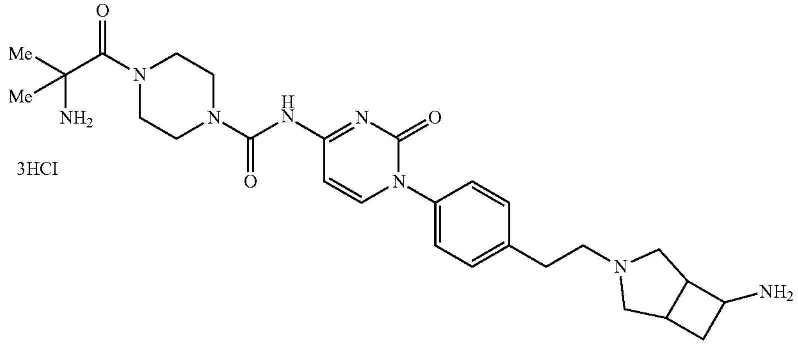

4-(2-Amino-2-methylpropanoyl)-N-(1-(4-(2-(6-amino-3-azabicyclo[3.2.0]heptan-3-yl)ethyl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl 3-azabicyclo[3.2.0]heptan-6-ylcarbamate. $^1$H NMR (400 MHz, $D_2O$) δ 8.00 (d, 1H), 7.55 (d, 2H), 7.47 (d, 2H), 6.84 (d, 1H), 4.18-3.94 (m, 2H), 3.93-3.48 (m, 12H), 3.38-3.13 (m, 4H), 2.73 (s, 1H), 2.04-1.93 (m, 1H), 1.73 (s, 6H), 1.71 (d, 1H). LCMS [M+H] 523.2.

Coumpound 97

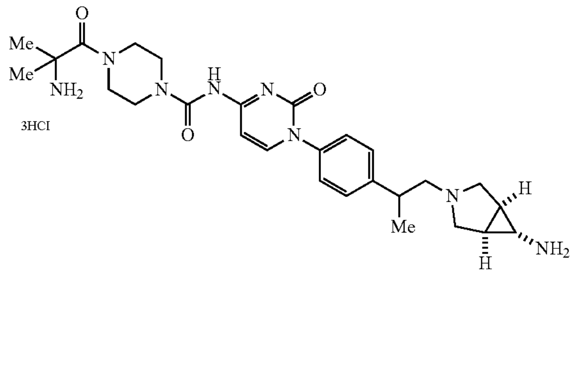

4-(2-Amino-2-methylpropanoyl)-N-(1-(4-(1-(exo-6-amino-3-azabicyclo[3.1.0]hexan-3-yl)propan-2-yl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(1-oxopropan-2-yl)phenyl)-1,2-dihydropyrimidin-4-yl)carbamoyl)piperazin-1-yl)propan-2-yl)carbamate and tert-butyl (endo-3-azabicyclo[3.1.0]hexan-6-yl)carbamate. $^1$H NMR (400 MHz, $D_2O$) δ 7.95 (d, 1H), 7.53 (d, 2H), 7.46 (d, 2H), 6.82 (d, 1H), 3.82-3.69 (m, 8H), 3.68-3.48 (m, 4H), 3.44-3.23 (m, 2H), 3.13-2.88 (m, 1H), 2.80 (s, 1H), 2.40-2.27 (m, 2H), 1.72 (s, 6H), 1.32 (d, 3H). LCMS [M+H] 523.3.

4-(2-Amino-2-methylpropanoyl)-N-(1-(4-(2-(1-amino-3-azabicyclo[4.1.0]heptan-3-yl)ethyl)-3-fluorophenyl)-2-oxo-1,2-dihydropyrimidin-4-yl)piperazine-1-carboxamide Hydrochloride Salt Prepared in a similar fashion to Scheme C-2 from tert-butyl (1-(4-((1-(3-fluoro-4-(2-oxoethyl)phenyl)-2-oxo-1,2-dihydropyrimidin-4-yl)carbamoyl)piperazin-1-yl)-2-methyl-1-oxopropan-2-yl)carbamate and t-butyl (3-azabicyclo[4.1.0]heptan-1-yl)carbamate. $^1$H NMR 7.88 (d, 1H), 7.51 (t, 1H), 7.32 (d, 1H), 7.27 (d, 1H), 6.84 (d, 1H), 4.18-4.07 (m, 1H), 3.81-3.68 (m, 8H), 3.46-3.37 (m, 2H), 3.20 (t, 2H), 3.17-3.06 (m, 1H), 2.97-2.87 (m, 1H), 2.67-2.57 (m, 1H), 2.54-2.45 (m, 1H), 1.89-1.82 (m, 1H), 1.73 (s, 6H), 1.48 (t, 1H), 1.32-1.20 (m, 1H). LCMS [M+H] 541.3.

Compound 99

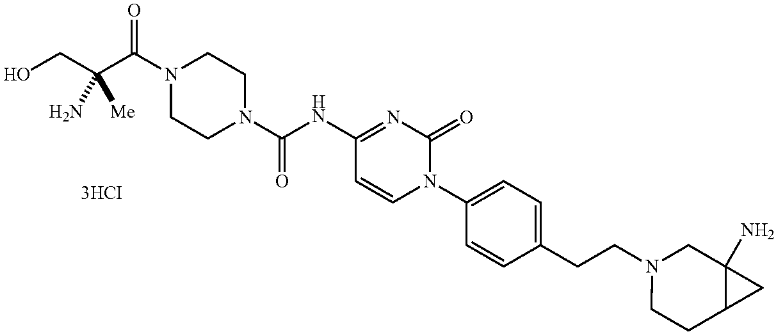

N-(1-(4-(2-(1-Amino-3-azabicyclo[4.1.0]heptan-3-yl)ethyl)phenyl)-2-oxo-1,2-dihydropyrimidin-4-yl)-4-((R)-2-amino-3-hydroxy-2-methylpropanoyl)piperazine-1-carboxamide Hydrochloride Salt Prepared in a similar fashion to Scheme C-2 from tert-butyl (2S,4R)-4-(4-((1-(4-((6-((tert-butoxycarbonyl)amino)-7-azaspiro[3.5]nonan-7-yl)methyl)phenyl)-2-oxo-1,2-dihydropyrimidin-4-yl)carbamoyl)piperazine-1-carbonyl)-2-(tert-butyl)-4-methyloxazolidine-3-carboxylate and tert-butyl (3-azabicyclo[4.1.0]heptan-1-yl)carbamate. $^1$H NMR (500 MHz, $D_2O$) δ 7.90 (d, 1H), 7.50 (d, 2H), 7.44 (d, 2H), 6.83 (d, 1H), 4.16 (d, 1H), 3.90 (d, 1H), 3.82-3.67 (m, 8H), 3.66-3.34 (m, 4H), 3.19 (t, 2H), 2.97-2.83 (m, 2H), 2.67-2.45 (m, 3H), 1.90-1.80 (m, 2H), 1.68 (s, 3H). LCMS [M+H] 539.2.

Compound 101

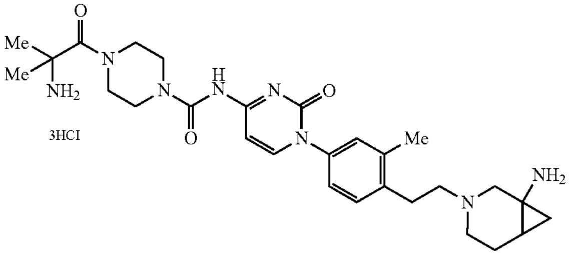

Compound 101

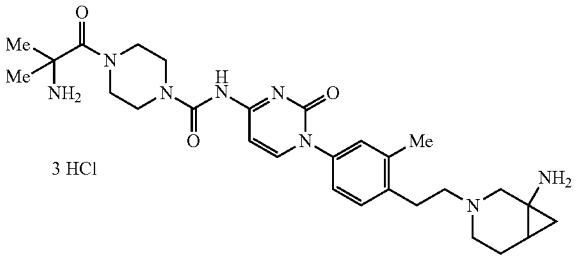

4-(2-Amino-2-methylpropanoyl)-N-(1-(4-(2-(1-amino-3-azabicyclo[4.1.0]heptan-3-yl)ethyl)-3-methylphenyl)-2-oxo-1,2-dihydropyrimidin-4-yl)piperazine-1-carboxamide Hydrochloride Salt Prepared in a similar fashion to Scheme C-2 from t-butyl (2-methyl-1-(4-((1-(3-methyl-4-(2-oxoethyl)phenyl)-2-oxo- 1,2-dihydropyrimidin-4-yl)carbamoyl)piperazin-1-yl)-1-oxopropan-2-yl)carbamate and t-butyl (3-azabicyclo[4.1.0]heptan-1-yl)carbamate. $^1$H NMR (400 MHz, $D_2O$) δ 7.98 (d, 1H), 7.37 (d, 1H), 7.29 (s, 1H), 7.24 (d, 1H), 6.77 (d, 1H), 4.21-4.08 (m, 1H), 3.86-3.58 (m, 9H), 3.44 (s, 1H), 3.30 (d, 2H), 3.18-3.07 (m, 2H), 2.96-2.82 (m, 1H), 2.60 (d, 1H), 2.55-2.40 (m, 1H), 2.36 (s, 3H), 1.89-1.79 (m, 1H), 1.70 (s, 6H), 1.46 (t, 1H), 1.22 (t, 1H). LCMS[M+H] 537.2.

Compound 102

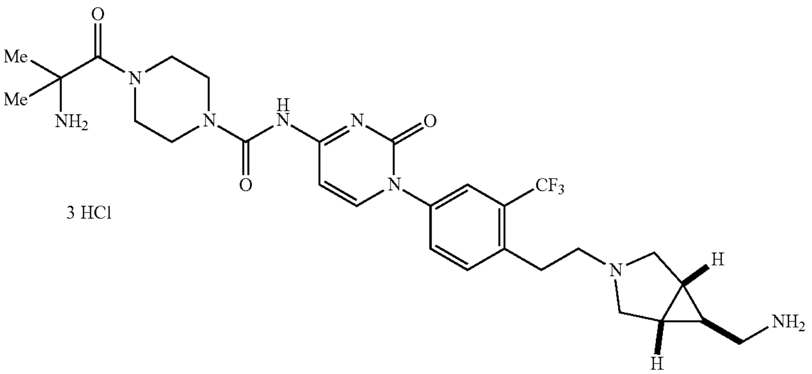

3 HCl 4-(2-Amino-2-methylpropanoyl)-N-(1-(4-(2-(exo-6-(aminomethyl)-3-azabicyclo[3.1.0]hexan-3-yl)ethyl)-3-(trifluoromethyl)phenyl)-2-oxo-1,2-dihydropyrimidin-4-yl)piperazine-1-carboxamide Hydrochloride Salt Prepared in a similar fashion to Scheme C-2 from t-butyl (2-methyl-1-oxo-1-(4-(2-oxo-1-(4-(2-oxoethyl)-3-(trifluoromethyl)phenyl)-1,2-dihydropyrimidin-4-yl)carbamoyl)piperazin-1-yl)propan-2-yl)carbamate and t-butyl ((exo-3-azabicyclo[3.1.0]hexan-6-yl)methyl)carbamate. $^1$H NMR (400 MHz, $D_2O$) δ 7.90 (d, 1H), 7.84 (s, 1H), 7.70-7.60 (m, 2H), 6.81 (d, 1H), 3.88 (d, 2H), 3.74 (s, 2H), 3.69 (s, 6H), 3.48 (t, 4H), 3.30-3.21 (m, 2H), 2.96 (d, 2H), 2.00 (s, 2H), 1.70 (s, 6H), 1.40-1.32 (m, 1H). LCMS[M+H] 591.3

Compound 103

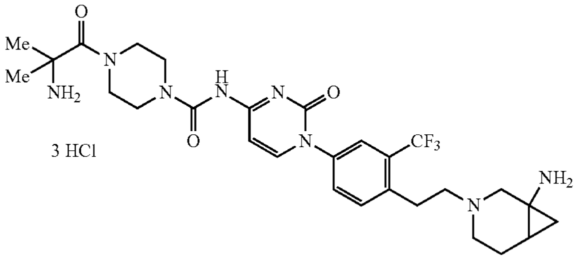

3 HCl 4-(2-amino-2-methylpropanoyl)-N-(1-(4-(2-(1-amino-3-azabicyclo[4.1.0]heptan-3-yl)ethyl)-3-(trifluoromethyl)phenyl)-2-oxo-1,2-dihydropyrimidin-4-yl)piperazine-1-carboxamide Hydrochloride Salt Prepared in a similar fashion to Scheme C-2 from t-butyl (2-methyl-1-oxo-1-(4-(2-oxo-1-(4-(2-oxoethyl)-3-(trifluoromethyl)phenyl)-1,2-dihydropyrimidin-4-yl)carbamoyl)piperazin-1-yl)propan-2-yl)carbamate and t-butyl (3-azabicyclo[4.1.0]heptan-1-yl)carbamate. $^1$H NMR (400 MHz, $D_2O$) δ 7.87 (d, 2H), 7.70-7.61 (m, 2H), 6.83 (d, 1H), 4.15 (s, 1H), 3.74 (s, 2H), 3.69 (s, 7H), 3.32 (s, 3H), 3.15 (s, 1H), 2.91 (s, 1H), 2.59 (s, 1H), 2.49 (t, 2H), 1.91-1.72 (m, 1H), 1.70 (s, 6H), 1.50-1.42 (m, 1H), 1.21 (s, 1H). LCMS[M+H] 591.4

Compound 104

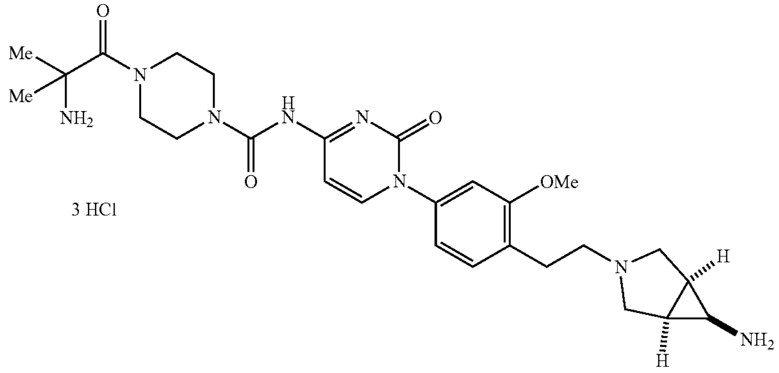

4-(2-Amino-2-methylpropanoyl)-N-(1-(4-(2-(endo-6-amino-3-azabicyclo[3.1.0]hexan-3-yl)ethyl)-3-methoxyphenyl)-2-oxo-1,2-dihydropyrimidin-4-yl) piperazine-1-carboxamide Hydrochloride Salt Prepared in a similar fashion to Scheme C-2 from tert-butyl (1-(4-((1-(3-methoxy-4-(2-oxoethyl)phenyl)-2-oxo-1,2-dihydropyrimidin-4-yl)carbamoyl)piperazin-1-yl)-2-methyl-1-oxopropan-2-yl)carbamate and tert-butyl (endo-3-azabicyclo[3.1.0]hexan-6-yl)carbamate $^1$H NMR 8.07 (d, 1H), 7.37 (d, 1H), 7.10 (s, 1H), 7.01 (d, 1H), 6.78 (d, 1H), 3.91 (d, 1H), 3.86 (s, 3H), 3.81-3.68 (m, 8H), 3.58-3.43 (m, 4H), 3.10-3.00 (m, 3H), 2.80 (s, 1H), 2.48-2.37 (m, 2H), 1.71 (s, 6H). LCMS [M+H] 539.3.

Compound 116

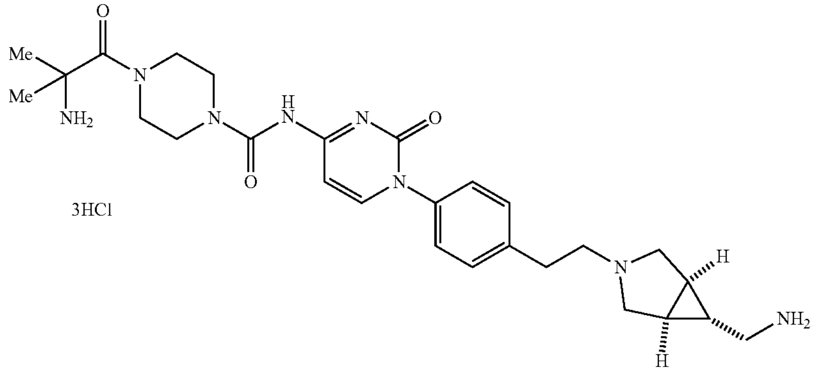

4-(2-Amino-2-methylpropanoyl)-N-(1-(4-(2-(exo-6-(aminomethyl)-3-azabicyclo[3.1.0]hexan-3-yl)ethyl) phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(2-oxoethyl)phenyl)-1,2-dihydropyrimidin-4-yl)carbamoyl)piperazin-1-yl) propan-2-yl)carbamate and tert-butyl ((exo-3-azabicyclo [3.1.0]hexan-6-yl)methyl)carbamate. $^1$H NMR (500 MHz, $D_2O$) δ 8.10 (d, 1H), 7.53 (d, 2H), 7.48 (d, 2H), 6.85 (d, 1H), 3.88 (d, 1H), 3.82-3.77 (m, 8H), 3.57-3.48 (m, 4H), 3.17 (t, 2H), 3.04-2.98 (m, 2H), 2.05 (s, 2H), 1.77 (s, 6H), 1.41-1.35 (m, 2H). LCMS[M+H] 523.28

Compound 117

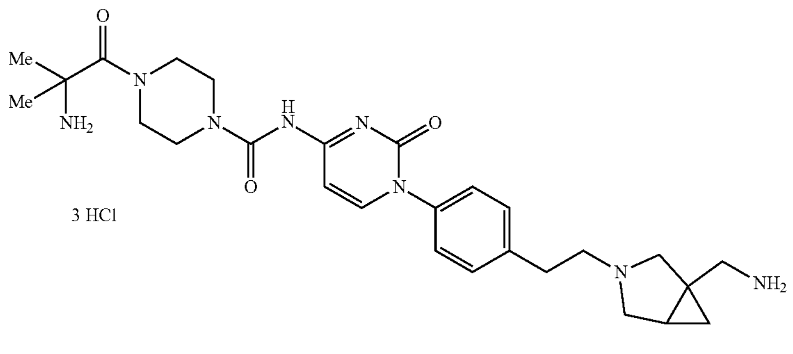

4-(2-Amino-2-methylpropanoyl)-N-(1-(4-(2-(1-(aminomethyl)-3-azabicyclo[3.1.0]hexan-3-yl)ethyl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl ((3-azabicyclo[3.1.0]hexan-1-yl)methyl)carbamate. $^{1}H$ NMR (400 MHz, $D_2O$) δ 8.18 (d, 1H), 7.56 (d, 2H), 7.51 (d, 2H), 6.85 (d, 1H), 4.00 (d, 1H), 3.88-3.75 (m, 8H), 3.65-3.53 (m, 5H), 3.23-3.16 (m, 3H), 2.11-2.06 (m, 1H), 1.79 (s, 6H), 1.40-1.37 (m, 1H), 1.20 (t, 1H), 1.09 (t, 1H). LCMS [M+H] 523.3.

Compound 118

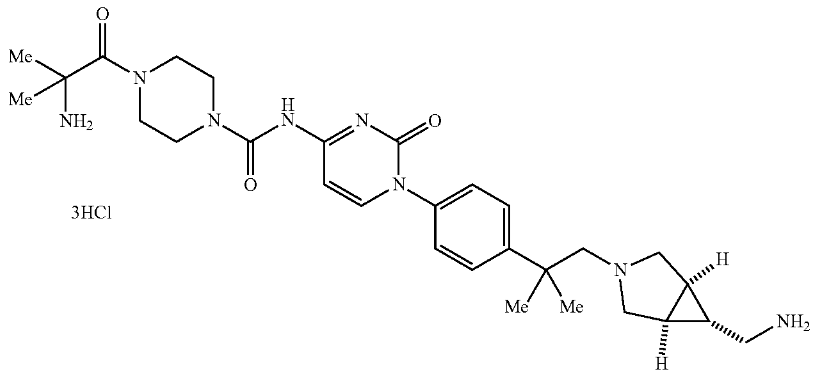

4-(2-Amino-2-methylpropanoyl)-N-(1-(4-(1-(exo-6-(aminomethyl)-3-azabicyclo[3.1.0]hexan-3-yl)-2-methylpropan-2-yl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-(4-((1-(4-(2-methyl-1-oxopropan-2-yl)phenyl)-2-oxo-1,2-dihydropyrimidin-4-yl)carbamoyl)piperazin-1-yl)-1-oxopropan-2-yl)carbamate and tert-butyl ((exo-3-azabicyclo[3.1.0]hexan-6-yl)methyl)carbamate. $^{1}H$ NMR (500 MHz, $D_2O$) δ 8.11 (d, 1H), 7.67 (d, 2H), 7.50 (d, 2H), 6.79 (d, 1H), 3.82-3.71 (m, 8H), 3.65 (s, 2H), 3.55-3.48 (m, 2H), 3.16 (d, 1H), 2.85 (t, 2H), 2.73-2.65 (m, 1H), 1.92-1.88 (m, 1H), 1.83-1.79 (m, 2H), 1.71 (s, 6H), 1.47 (s, 6H) LCMS [M+H] 551.2.

Compound 119

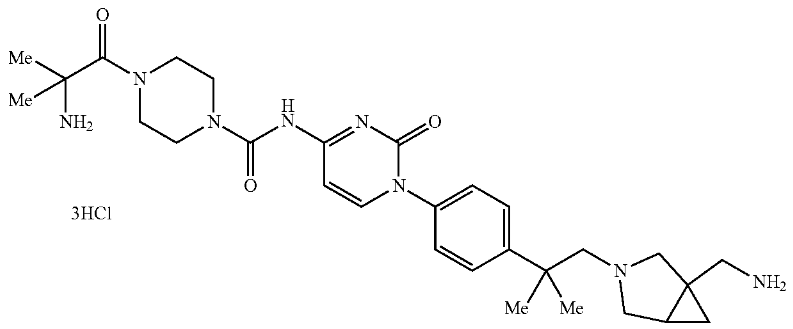

4-(2-Amino-2-methylpropanoyl)-N-(1-(4-(1-(1-(aminomethyl)-3-azabicyclo[3.1.0]hexan-3-yl)-2-methylpropan-2-yl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-(4-((1-(4-(2-methyl-1-oxopropan-2-yl)phenyl)-2-oxo-1,2-dihydropyrimidin-4-yl)carbamoyl)piperazin-1-yl)-1-oxopropan-2-yl)carbamate and tert-butyl ((3-azabicyclo[3.1.0]hexan-1-yl)methyl)carbamate. $^{1}$H NMR (500 MHz, $D_2O$) δ 8.03 (d, 1H), 7.67 (d, 2H), 7.49 (d, 2H), 6.82 (d, 1H), 3.81-3.65 (m, 12H), 3.57 (s, 1H), 3.45 (d, 1H), 3.21 (t, 1H), 2.98 (d, 1H), 1.84-1.78 (m, 1H), 1.71 (s, 6H), 1.48 (s, 6H) LCMS [M+H] 551.2.

Compound 120

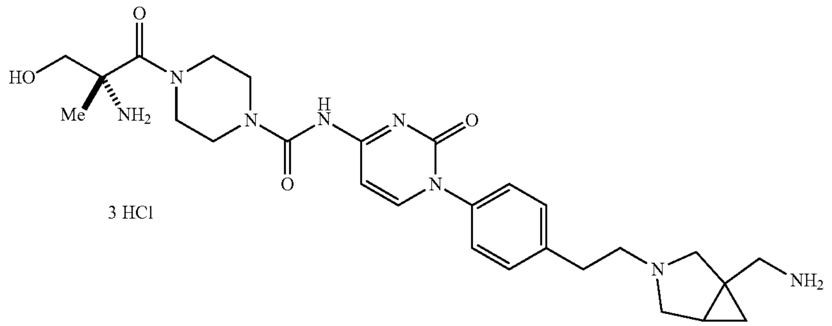

4-((R)-2-Amino-3-hydroxy-2-methylpropanoyl)-N-(1-(4-(2-(1-(aminomethyl)-3-azabicyclo[3.1.0]hexan-3-yl)ethyl)phenyl)-2-oxo-1,2-dihydropyrimidin-4-yl)piperazine-1-carboxamide Hydrochloride Salt Prepared in a similar fashion to Scheme C-2 from tert-butyl (2S,4R)-2-(tert-butyl)-4-methyl-4-(4-((2-oxo-1-(4-(2-oxoethyl)phenyl)-1,2-dihydropyrimidin-4-yl)carbamoyl)piperazine-1-carbonyl)oxazolidine-3-carboxylate and tert-butyl ((3-azabicyclo[3.1.0]hexan-1-yl)methyl)carbamate. $^{1}$H NMR (500 MHz, $D_2O$) δ 8.08 (d, 1H), 7.48 (d, 2H), 7.44 (d, 2H), 6.79 (d, 1H), 4.14 (d, 1H), 3.96-3.87 (m, 2H), 3.82-3.70 (m, 8H), 3.59-3.45 (m, 5H), 3.17-3.09 (m, 3H), 2.04-1.99 (m, 1H), 1.67 (s, 3H), 1.34-1.31 (m, 1H), 1.14 (t, 1H), 1.02 (t, 1H) LCMS [M+H] 539.3.

Compound 121

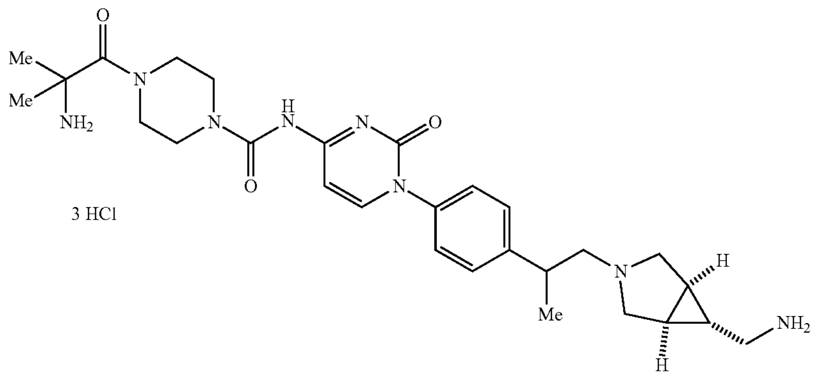

4-(2-Amino-2-methylpropanoyl)-N-(1-(4-(1-(exo-6-(aminomethyl)-3-azabicyclo[3.1.0]hexan-3-yl)propan-2-yl)phenyl)-2-oxo-1,2-dihydropyrimidin-4-yl) piperazine-1-carboxamide Hydrochloride Salt Prepared in a similar fashion to Scheme C-2 from tert-butyl (2-methyl-1-oxo-1-(4-((2-oxo-1-(4-(1-oxopropan-2-yl)phenyl)-1,2-dihydropyrimidin-4-yl)carbamoyl)piperazin-1-yl)propan-2-yl)carbamate and tert-butyl ((exo-3-azabicyclo[3.1.0]hexan-6-yl)methyl)carbamate $^1H$ NMR (500 MHz, $D_2O$) δ 8.08 (d, 1H), 7.55 (d, 2H), 7.48 (d, 2H), 6.81 (d, 1H), 3.84-3.71 (m, 8H), 3.60-3.48 (m, 4H), 3.34-3.26 (m, 2H), 2.91 (d, 2H), 2.03-1.89 (m, 3H), 1.73 (s, 6H), 1.35-1.26 (m, 4H) LCMS [M+H] 537.2.

Compound 123

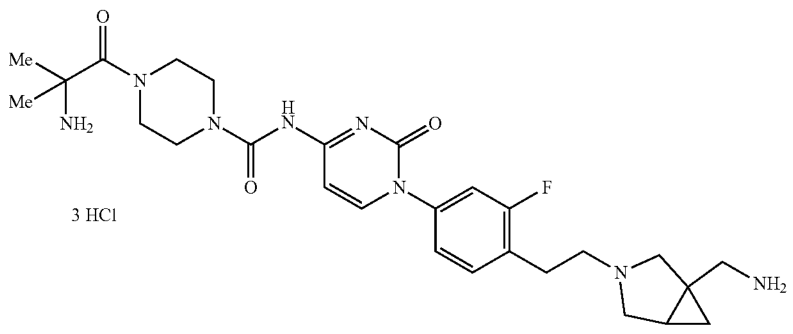

4-(2-Amino-2-methylpropanoyl)-N-(1-(4-(2-(1-(aminomethyl)-3-azabicyclo[3.1.0]hexan-3-yl)ethyl)-3-fluorophenyl)-2-oxo-1,2-dihydropyrimidin-4-yl) piperazine-1-carboxamide Hydrochloride Salt Prepared in a similar fashion to Scheme C-2 from 4-(2-amino-2-methylpropanoyl)-N-(1-(3-fluoro-4-(2-oxoethyl) phenyl)-2-oxo-1,2-dihydropyrimidin-4-yl)piperazine-1-carboxamide and t-butyl ((3-azabicyclo[3.1.0]hexan-1-yl) methyl)carbamate. $^1H$ NMR 7.97 (d, 1H), 7.52 (t, 1H), 7.33 (d, 1H), 7.28 (d, 1H), 6.82 (d, 1H), 3.97 (d, 2H), 3.83 (d, 2H), 3.81-3.67 (m, 8H), 3.59-3.54 (m, 2H), 3.50 (t, 2H), 3.23-3.10 (m, 2H), 1.73 (s, 6H), 1.12 (t, 1H), 1.00 (t, 1H), 0.89 (t, 1H). LCMS [M+H] 541.3.

Compound 126

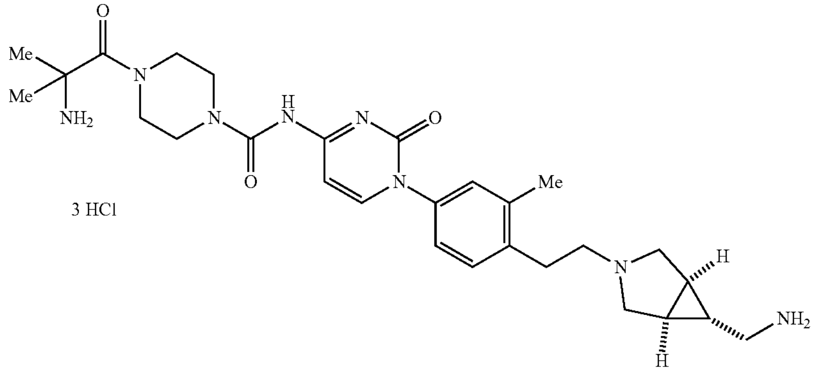

4-(2-Amino-2-methylpropanoyl)-N-(1-(4-(2-(exo-6-(aminomethyl)-3-azabicyclo[3.1.0]hexan-3-yl)ethyl)-3-methylphenyl)-2-oxo-1,2-dihydropyrimidin-4-yl)piperazine-1-carboxamide Hydrochloride Salt Prepared in a similar fashion to in Scheme C-2 rom t-butyl (2-methyl-1-(4-((1-(3-methyl-4-(2-oxoethyl)phenyl)-2-oxo-1,2-dihydropyrimidin-4-yl)carbamoyl)piperazin-1-yl)-1-oxopropan-2-yl)carbamate and t-butyl ((exo-3-azabicyclo[3.1.0]hexan-6-yl)methyl)carbamate. $^1$H NMR (400 MHz, $D_2O$) δ 7.98 (d, 1H), 7.36 (d, 1H), 7.29 (s, 1H), 7.24 (d, 1H), 6.77 (d, 1H), 3.86 (d, 2H), 3.75 (s, 2H), 3.71 (s, 6H), 3.49 (d, 2H), 3.46-3.38 (m, 2H), 3.12-3.05 (m, 2H), 2.96 (d, 2H), 2.35 (s, 3H), 2.00 (s, 2H), 1.70 (s, 6H), 1.39-1.29 (m, 1H). LCMS[M+H]537.4

Compound 127

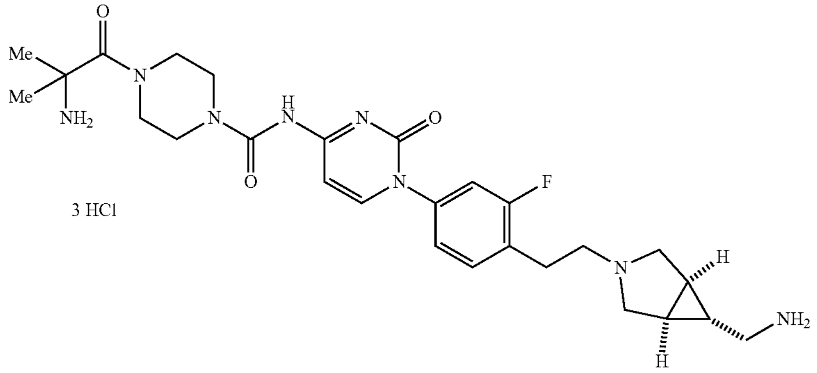

4-(2-Amino-2-methylpropanoyl)-N-(1-(4-(2-(exo-6-(aminomethyl)-3-azabicyclo[3.1.0]hexan-3-yl)ethyl)-3-fluorophenyl)-2-oxo-1,2-dihydropyrimidin-4-yl)piperazine-1-carboxamide Hydrochloride Salt Prepared in a similar fashion as in Scheme C-2 from 4-(2-amino-2-methylpropanoyl)-N-(1-(3-fluoro-4-(2-oxoethyl)phenyl)-2-oxo-1,2-dihydropyrimidin-4-yl)piperazine-1-carboxamide and t-butyl ((exo-3-azabicyclo[3.1.0]hexan-6-yl)methyl)carbamate. $^1$H NMR 7.86 (d, 1H), 7.50 (t, 1H), 7.30 (d, 1H), 7.26 (d, 1H), 6.84 (d, 1H), 3.86 (d, 2H), 3.81-3.66 (m, 8H), 3.54-3.48 (m, 4H), 3.17 (t, 2H), 3.00-2.95 (m, 2H), 2.13-1.97 (m, 2H), 1.73 (s, 6H), 1.38-1.29 (m, 1H). LCMS [M+H] 541.3.

Compound 128

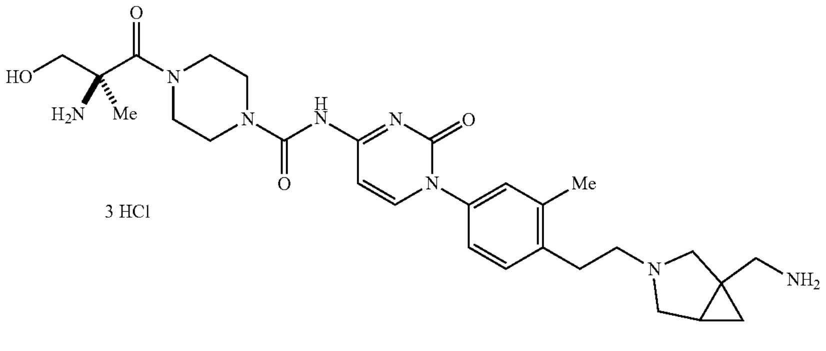

4-((S)-2-amino-3-hydroxy-2-methylpropanoyl)-N-(1-(4-(2-(1-(aminomethyl)-3-azabicyclo[3.1.0]hexan-3-yl)ethyl)-3-methylphenyl)-2-oxo-1,2-dihydropyrimidin-4-yl)piperazine-1-carboxamide Hydrochloride Salt Prepared in a similar fashion to Scheme C-2 from 4-((2R,4S)-2-(t-butyl)-4-methyloxazolidine-4-carbonyl)-N-(1-(3-methyl-4-(2-oxoethyl)phenyl)-2-oxo-1,2-dihydropyrimidin-4-yl)piperazine-1-carboxamide and t-butyl ((3-azabicyclo[3.1.0]hexan-1-yl)methyl)carbamate. $^1$H NMR (400 MHz, $d_2o$) δ 7.89 (d, 1H), 7.36 (d, 1H), 7.28 (s, 1H), 7.23 (d, 1H), 6.79 (d, 1H), 4.13 (d, 1H), 3.96 (d, 1H), 3.87 (d, 1H), 3.83 (d, 1H), 3.76 (s, 4H), 3.70 (s, 4H), 3.57-3.41 (m, 5H), 3.15-3.06 (m, 3H), 2.35 (s, 3H), 2.05-1.98 (m, 1H), 1.65 (s, 3H), 1.18-0.99 (m, 2H). LCMS[M+H] 553.3.

Compound 129

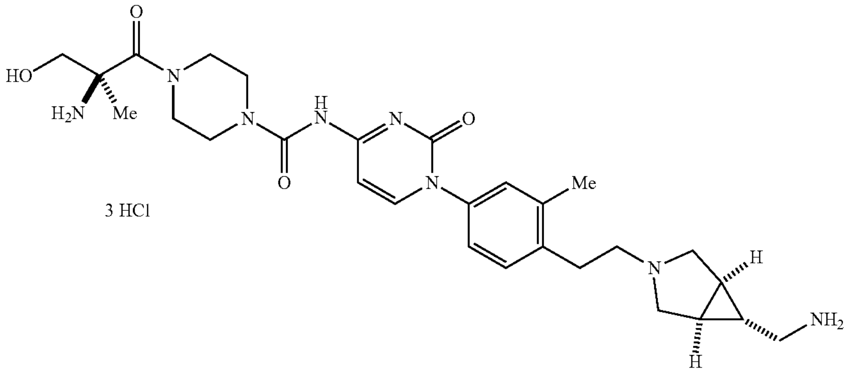

4-((S)-2-Amino-3-hydroxy-2-methylpropanoyl)-N-(1-(4-(2-(exo-6-(aminomethyl)-3-azabicyclo[3.1.0]hexan-3-yl)ethyl)-3-methylphenyl)-2-oxo-1,2-dihydropyrimidin-4-yl)piperazine-1-carboxamide Hydrochloride Salt Prepared in a similar fashion to Scheme C-2 from 4-((2R,4S)-2-(t-butyl)-4-methyloxazolidine-4-carbonyl)-N-(1-(3-methyl-4-(2-oxoethyl)phenyl)-2-oxo-1,2-dihydropyrimidin-4-yl)piperazine-1-carboxamide and t-butyl ((exo-3-azabicyclo[3.1.0]hexan-6-yl)methyl)carbamate. LCMS[M+H] 553.1.

Compound 130

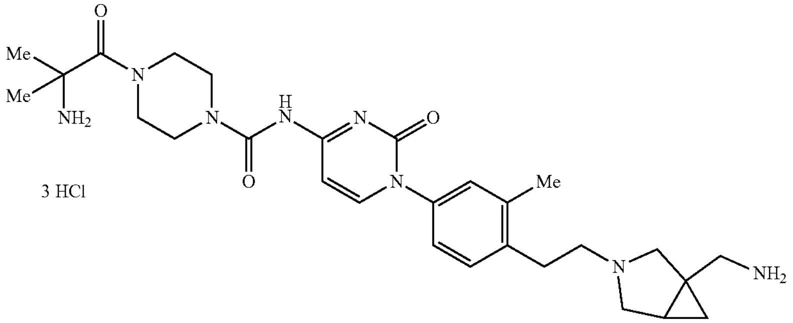

4-(2-Amino-2-methylpropanoyl)-N-(1-(4-(2-(1-(aminomethyl)-3-azabicyclo[3.1.0]hexan-3-yl)ethyl)-3-methylphenyl)-2-oxo-1,2-dihydropyrimidin-4-yl) piperazine-1-carboxamide Hydrochloride Salt Prepared in a similar fashion to Scheme C-2 from t-butyl (2-methyl-1-(4-((1-(3-methyl-4-(2-oxoethyl)phenyl)-2-oxo-1,2-dihydropyrimidin-4-yl)carbamoyl)piperazin-1-yl)-1-oxopropan-2-yl)carbamate and t-butyl ((3-azabicyclo[3.1.0] hexan-1-yl)methyl)carbamate. $^{1}$H NMR (400 MHz, $D_2O$) δ 7.93 (d, 1H), 7.36 (d, 1H), 7.28 (s, 1H), 7.23 (d, 1H), 6.78 (d, 1H), 3.96 (d, 1H), 3.82 (d, 1H), 3.75 (s, 2H), 3.70 (s, 6H), 3.57-3.41 (m, 5H), 3.17-3.03 (m, 3H), 2.35 (s, 3H), 2.06-1.97 (m, 1H), 1.69 (s, 6H), 1.13 (t, 1H), 1.03 (d, 1H). LCMS[M+H] 537.4.

Compound 131

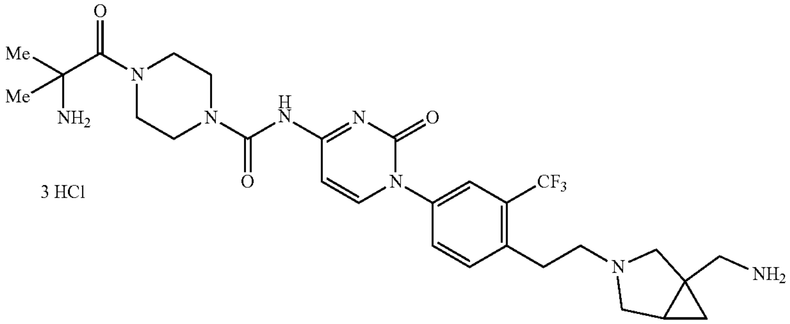

4-(2-Amino-2-methylpropanoyl)-N-(1-(4-(2-(1-(aminomethyl)-3-azabicyclo[3.1.0]hexan-3-yl)ethyl)-3-(trifluoromethyl)phenyl)-2-oxo-1,2-dihydropyrimidin-4-yl)piperazine-1-carboxamide Hydrochloride Salt Prepared in a similar fashion to Scheme C-2 from t-butyl (2-methyl-1-oxo-1-(4-(2-oxo-1-(4-(2-oxoethyl)-3-(trifluoromethyl)phenyl)-1,2-dihydropyrimidin-4-yl)carbamoyl) piperazin-1-yl)propan-2-yl)carbamate and t-butyl ((3-azabicyclo[3.1.0]hexan-1-yl)methyl)carbamate. $^{1}$H NMR (400 MHz, $D_2O$) δ 7.94-7.89 (m, 1H), 7.84 (s, 1H), 7.71-7.60 (m, 2H), 6.81 (d, 1H), 3.98 (d, 1H), 3.84 (d, 1H), 3.74 (s, 2H), 3.69 (s, 6H), 3.59-3.44 (m, 5H), 3.32-3.22 (m, 3H), 3.11 (d, 1H), 2.01 (s, 1H), 1.69 (s, 6H), 1.67 (s, 1H). LCMS[M+H] 591.4.

Compound 132

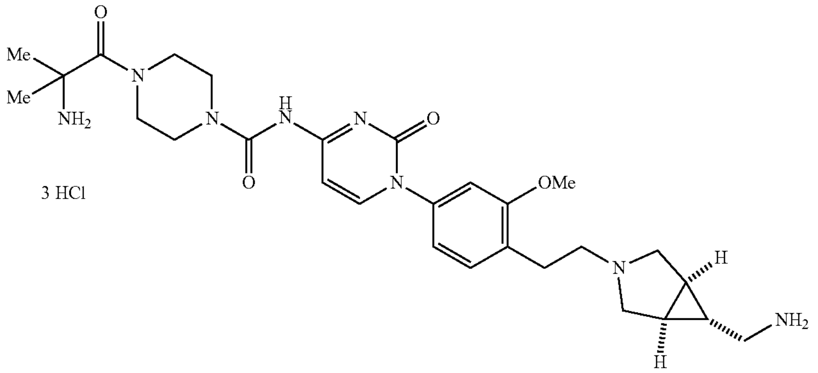

4-(2-Amino-2-methylpropanoyl)-N-(1-(4-(2-(exo-6-(aminomethyl)-3-azabicyclo[3.1.0]hexan-3-yl)ethyl)-3-methoxyphenyl)-2-oxo-1,2-dihydropyrimidin-4-yl)piperazine-1-carboxamide Hydrochloride Salt Prepared in a similar fashion to Scheme C-2 from tert-butyl (1-(4-((1-(3-methoxy-4-(2-oxoethyl)phenyl)-2-oxo-1,2-dihydropyrimidin-4-yl)carbamoyl)piperazin-1-yl)-2-methyl-1-oxopropan-2-yl)carbamate and and t-butyl ((exo-3-azabicyclo[3.1.0]hexan-6-yl)methyl)carbamate. $^1$H NMR 8.03 (d, 1H), 7.38 (d, 1H), 7.10 (s, 1H), 7.01 (d, 1H), 6.79 (d, 1H), 3.86 (s, 3H), 3.85-3.80 (m, 2H), 3.80-3.68 (m, 8H), 3.48-3.41 (m, 3H), 3.07 (t, 2H), 2.98-2.91 (m, 3H), 2.01-1.95 (m, 2H), 1.72 (s, 6H), 1.35-1.29 (m, 1H). LCMS [M+H] 553.3.

Compound 133

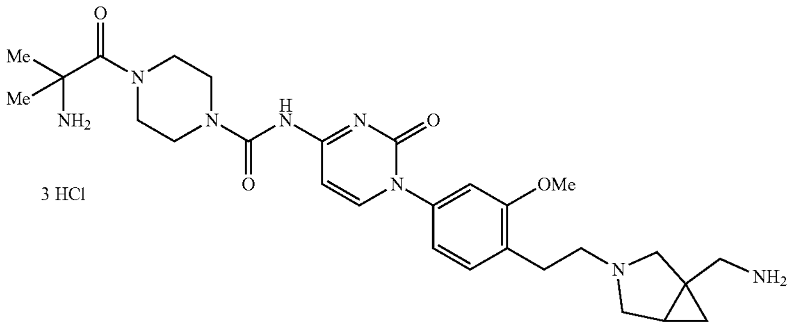

4-(2-Amino-2-methylpropanoyl)-N-(1-(4-(2-(1-(aminomethyl)-3-azabicyclo[3.1.0]hexan-3-yl)ethyl)-3-methoxyphenyl)-2-oxo-1,2-dihydropyrimidin-4-yl)piperazine-1-carboxamide Hydrochloride Salt Prepared in a similar fashion to Scheme C-2 from tert-butyl (1-(4-((1-(3-methoxy-4-(2-oxoethyl)phenyl)-2-oxo-1,2-dihydropyrimidin-4-yl)carbamoyl)piperazin-1-yl)-2-methyl-1-oxopropan-2-yl)carbamate and t-butyl ((3-azabicyclo[3.1.0]hexan-1-yl)methyl)carbamate. $^1$H NMR 8.03 (d, 1H), 7.39 (d, 1H), 7.11 (s, 1H), 7.02 (d, 1H), 6.80 (d, 1H), 3.94 (d, 1H), 3.87 (s, 3H), 3.82-3.70 (m, 9H), 3.53-3.44 (m, 5H), 3.12-3.05 (m, 3H), 2.03-1.98 (m, 1H), 1.72 (s, 6H), 1.13 (t, 1H), 1.01 (t, 1H). LCMS [M+H] 553.3.

Compound 84

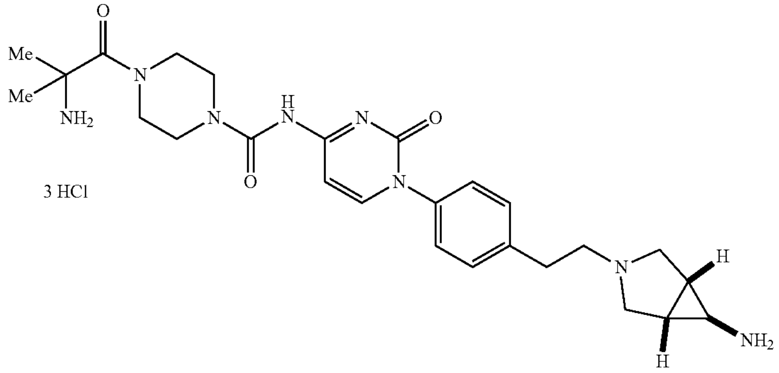

4-(2-Amino-2-methylpropanoyl)-N-(1-(4-(2-(exo-6-amino-3-azabicyclo[3.1.0]hexan-3-yl)ethyl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl (exo-3-azabicyclo[3.1.0]hexan-6-yl)carbamate. $^1$H NMR (500 MHz, $D_2O$) δ 7.97 (d, 1H), 7.47 (d, 2H), 7.42 (d, 2H), 6.81 (d, 1H), 3.91 (d, 2H), 3.80-3.66 (m, 8H), 3.60-3.50 (m, 4H), 3.14-3.10 (m, 2H), 2.82 (s, 1H), 2.39 (s, 2H), 1.71 (s, 6H). LCMS [M+H] 509.5.

Compound 152

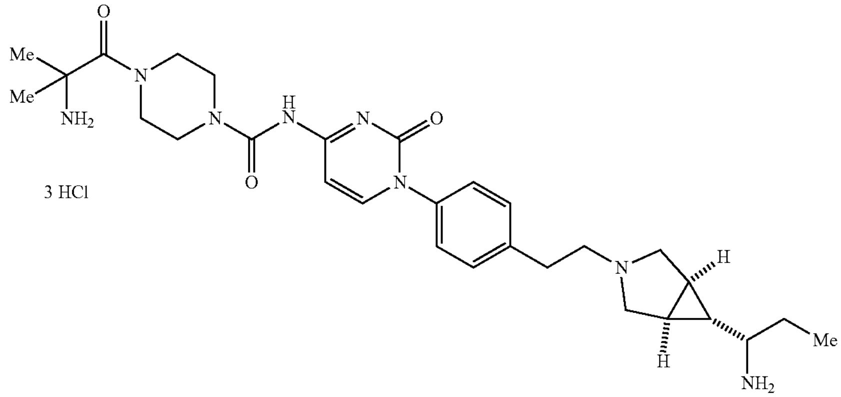

4-(2-Amino-2-methylpropanoyl)-N-(1-(4-(2-(exo-6-((S)-1-aminopropyl)-3-azabicyclo[3.1.0]hexan-3-yl)ethyl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl ((S)-1-(exo-3-azabicyclo[3.1.0]hexan-6-yl)propyl)carbamate LCMS[M+H] 551.2.

Compound 158

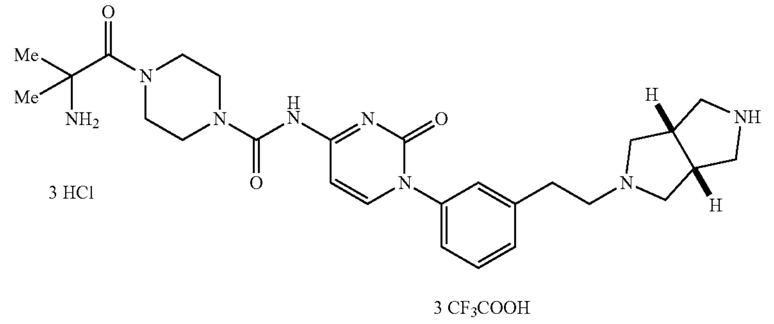

4-(2-Amino-2-methylpropanoyl)-N-(1-(3-(2-((3aR, 6aS)-hexahydropyrrolo[3,4-c]pyrrol-2 (1H)-yl)ethyl) phenyl)-2-oxo-1,2-dihydropyrimidin-4-yl)piperazine-1-carboxamide tri-trifluoroacetetate Salt Prepared in a similar fashion to Scheme C-2 from tert-butyl (2-methyl-1-oxo-1-(4-((2-oxo-1-(3-(2-oxoethyl)phenyl)-1,2-dihydropyrimidin-4-yl)carbamoyl)piperazin-1-yl) propan-2-yl)carbamate and tert-butyl (3aR,6aS)-hexahydropyrrolo[3,4-c]pyrrole-2 (1H)-carboxylate. $^{1}H$ NMR (500 MHz, $D_2O$) δ 8.02 (d, 1H), 7.61 (t, 1H), 7.51 (d, 1H), 7.44 (s, 1H), 7.41 (d, 1H), 6.85 (d, 1H), 4.14-4.02 (m, 1H), 3.86-3.71 (m, 10H), 3.66-3.38 (m, 8H), 3.19 (t, 2H), 3.09 (bs, 1H), 1.75 (s, 6H). LCMS [M+H] 523.2.

Compound 159

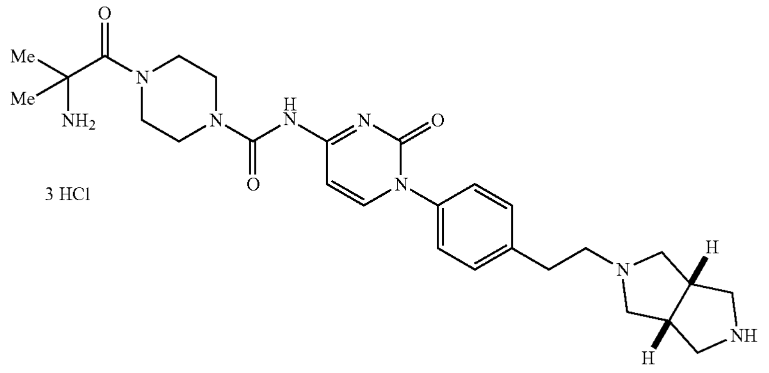

4-(2-Amino-2-methylpropanoyl)-N-(1-(4-(2-((3aR, 6aS)-hexahydropyrrolo[3,4-c]pyrrol-2 (1H)-yl)ethyl) phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(2-oxoethyl)phenyl)-1,2-dihydropyrimidin-4-yl)carbamoyl)piperazin-1-yl) propan-2-yl)carbamate and tert-butyl (3aR,6aS)-hexahydropyrrolo[3,4-c]pyrrole-2 (1H)-carboxylate. $^{1}H$ NMR (500 MHz, $D_2O$) δ 8.24 (d, 1H), 7.54 (d, 2H), 7.48 (d, 2H), 6.79 (d, 1H), 4.09-4.05 (m, 1H), 3.83-3.73 (m, 10H), 3.65-3.58 (m 2H), 3.56-3.46 (m, 4H), 3.43-3.36 (m, 2H), 3.25-3.16 (m, 2H), 3.14-3.08 (m, 1H), 1.73 (s, 6H). LCMS [M+H] 523.4.

Compound 160

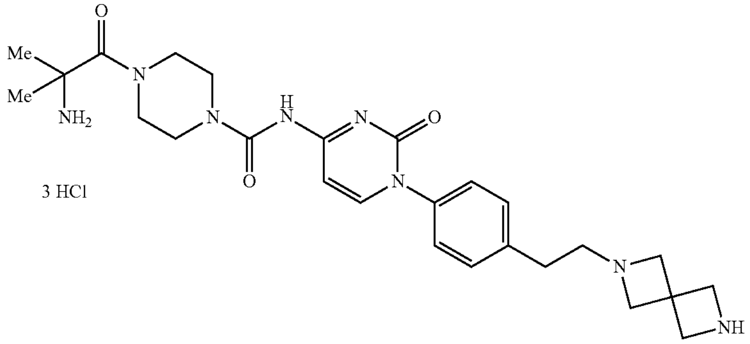

N-(1-(4-(2-(2,6-Diazaspiro[3.3]heptan-2-yl)ethyl) phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-2 from tert-butyl (2-methyl-1-oxo-1-(4-((2-oxo-1-(4-(2-oxoethyl)phenyl)-1,2-dihydropyrimidin-4-yl)carbamoyl)piperazin-1-yl) propan-2-yl)carbamate and tert-butyl 2,6-diazaspiro[3.3] heptane-2-carboxylate. $^{1}$H NMR (500 MHz, $D_2O$) δ 7.95 (d, 1H), 7.47 (d, 2H), 7.44 (d, 2H), 6.83 (d, 1H), 4.52 (s, 1H), 4.49 (s, 1H), 4.42-4.33 (m, 6H), 3.80-3.68 (m, 8H), 3.57 (t, 2H), 3.03 (t, 2H), 1.73 (s, 6H). LCMS [M+H] 509.3.

Compound 161

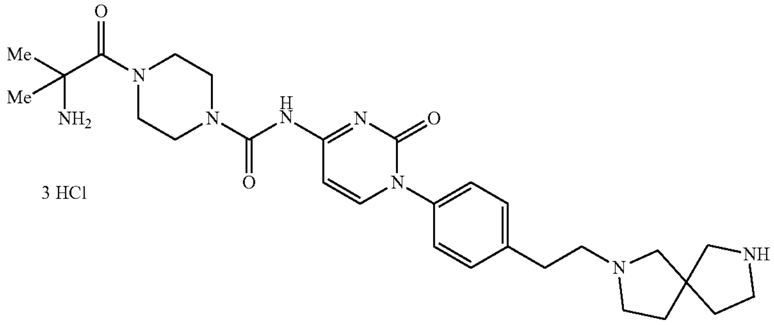

N-(1-(4-(2-(2,7-Diazaspiro[4.4]nonan-2-yl)ethyl) phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-2 from tert-butyl (2-methyl-1-oxo-1-(4-((2-oxo-1-(4-(2-oxoethyl)phenyl)-1,2-dihydropyrimidin-4-yl)carbamoyl)piperazin-1-yl) propan-2-yl)carbamate and tert-butyl 2,7-diazaspiro[4.4] nonane-2-carboxylate. $^{1}$H NMR (500 MHz, $D_2O$) δ 7.98 (d, 1H), 7.50 (d, 2H), 7.44 (d, 2H), 6.82 (d, 1H), 3.87-3.69 (m, 10H), 3.64-3.57 (m, 3H), 3.52-3.45 (m, 2H), 3.43-3.35 (m, 2H), 3.21-3.12 (m, 4H), 2.37-2.12 (m, 3H), 1.73 (s, 6H). LCMS [M+H] 537.4.

Compound 173

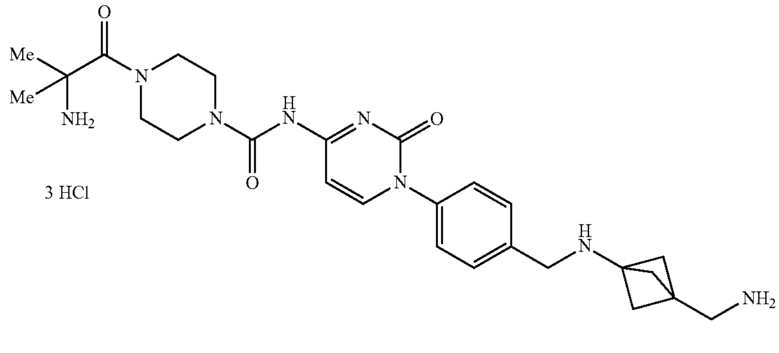

4-(2-Amino-2-methylpropanoyl)-N-(1-(4-(3-(aminomethyl)bicyclo[1.1.1]pentan-1-yl)amino)methyl)phenyl)-2-oxo-1,2-dihydropyrimidin-4-yl)piperazine-1-carboxamide Hydrochloride Salt Prepared in a similar fashion to Scheme C-2 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and t-butyl ((3-aminobicyclo[1.1.1]pentan-1-yl)methyl) carbamate. $^1$H NMR (400 Mz, $D_2O$): δ 7.80 (d, 1H), 7.47 (d, 2H), 7.37 (d, 2H), 6.68 (d, 2H), 4.16 (s, 2H), 3.75-3.51 (m, 8H), 3.15 (s, 2H), 2.08 (s, 6H), 1.56 (s, 6H). LCMS [M+H] 509.2.

Compound 14

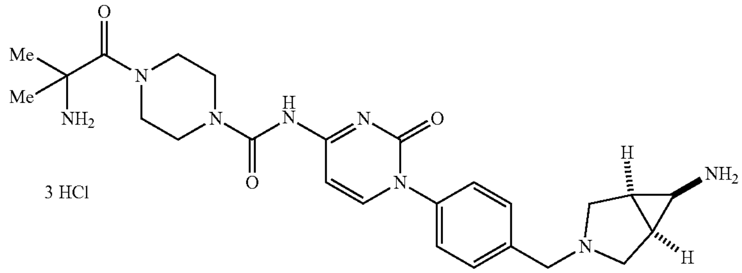

4-(2-Amino-2-methylpropanoyl)-N-(1-(4-((endo-6-amino-3-azabicyclo[3.1.0]hexan-3-yl)methyl)phenyl)-2-oxo-1,2-dihydropyrimidin-4-yl)piperazine-1-carboxamide Hydrochloride Salt Prepared in a similar fashion to Scheme C-2 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (endo-3-azabicyclo[3.1.0]hexan-6-yl)carbamate. $^1$H NMR (400 MHz, $CD_3OD$) δ 8.35 (d, 1H), 7.88 (d, 2H), 7.65 (d, 2H), 6.86 (d, 1H), 4.52 (s, 2H), 3.78 (br. s, 8H), 3.75-3.63 (m, 3H), 3.37 (d, 2H), 2.36 (s, 2H), 1.72 (d 6H). $^1$H NMR (500 MHz, $D_2O$) δ 7.86 (d, 1H), 7.55 (d, 2H), 7.44 (d, 2H), 6.72 (d, 1H), 4.28-4.40 (m, 2H), 3.42-3.84 (m, 12H), 2.71-2.83 (m, 1H), 2.24-2.35 (m, 2H), 1.60 (s, 6H). LCMS[M+H] 495.2

Compound 46

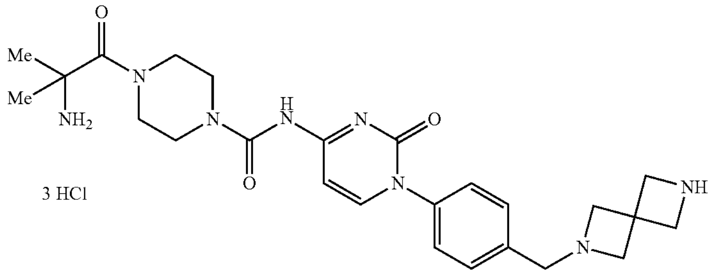

N-(1-(4-((2,6-Diazaspiro[3.3]heptan-2-yl)methyl) phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-2 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl 2,6-diazaspiro[3.3]heptane-2-carboxylate. $^1$H NMR (500 MHz, $D_2O$) δ 7.96 (d, 1H), 7.63 (d, 2H), 7.56 (d, 2H), 6.84 (d, 1H), 4.53-4.48 (m, 4H), 4.45 (d, 4H), 4.37 (s, 2H), 3.82-3.68 (m, 8H), 1.73 (s, 6H). LCMS [M+H] 495.3.

Compound 79

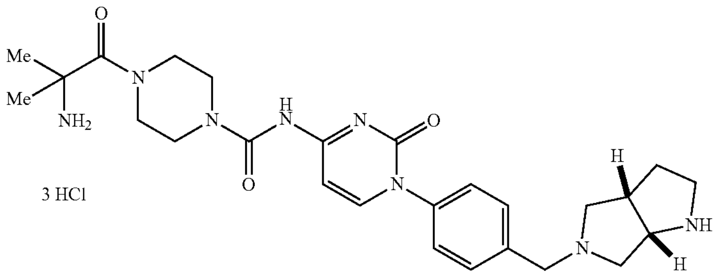

N-(1-(4-(((1S,5S)-3,6-Diazabicyclo[3.2.0]heptan-3-yl)methyl)phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-2 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (1R,5S)-3,6-diazabicyclo [3.2.0]heptane-6-carboxylate. $^1$H NMR (500 MHz, $D_2O$) δ 8.04 (d, 1H), 7.78 (d, 2H), 7.61 (d, 2H), 6.85 (d, 1H), 5.25 (t, 1H), 4.74 (d, 1H), 4.63 (d, 1H), 4.37 (t, 1H), 4.17 (d, 1H), 4.04-3.97 (m, 2H), 3.89-3.72 (m, 10H), 3.65-3.55 (m, 1H), 1.73 (s, 6H). LCMS [M+H] 495.3.

Compound 80

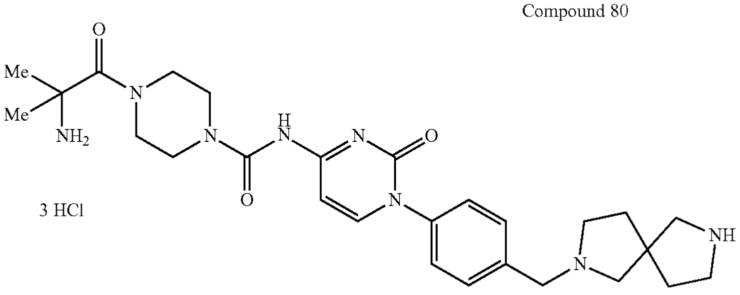 [SMILES: CC(C)(N)C(=O)N1CCN(C(=O)Nc2ccn(-c3ccc(CN4CCC5(CCNC5)C4)cc3)c(=O)n2)CC1]

N-(1-(4-((2,7-Diazaspiro[4.4]nonan-2-yl)methyl) phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-2 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl 2,7-diazaspiro[4.4]nonane-2-carboxylate. $^1$H NMR (500 MHz, $D_2O$) δ 8.00 (d, 1H), 7.70 (d, 2H), 7.57 (d, 2H), 6.84 (d, 1H), 4.55 (s 2H), 3.83-3.60 (m, 8H), 3.58-3.35 (m, 6H), 2.40-2.13 (m, 4H), 1.73 (s, 6H). LCMS [M+H] 522.3.

Compound 33

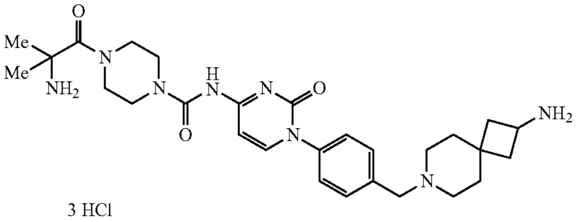

4-(2-Amino-2-methylpropanoyl)-N-(1-(4-((2-amino-7-azaspiro[3.5]nonan-7-yl)methyl)phenyl)-2-oxo-1,2-dihydropyrimidin-4-yl)piperazine-1-carboxamide Hydrochloride Salt Prepared in a similar fashion to Scheme C-2 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl 7-azaspiro[3.5]nonan-2-ylcarbamate. $^1$H NMR (400 MHz, $D_2O$) δ 8.08 (d, 1H), 7.69 (d, 2H), 7.59 (d, 2H), 6.85 (d, 1H), 4.39 (s, 2H), 3.92-3.84 (m, 1H), 3.80 (s, 2H), 3.76 (s, 6H), 3.54-3.39 (m, 2H), 3.23-2.95 (m, 2H), 2.41 (d, 2H), 2.16-1.99 (m, 3H), 1.99-1.81 (m, 3H), 1.74 (s, 6H). LCMS [M+H] 537.2.

Compound 34

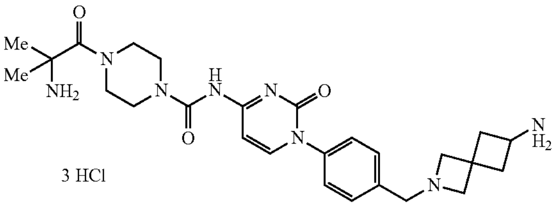

N-(1-(4-((6-amino-2-azaspiro[3.3]heptan-2-yl) methyl)phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-2 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl 2-azaspiro[3.3]heptan-6-ylcarbamate. $^1$H NMR (400 MHz, $D_2O$) δ 8.02 (d, 1H), 7.64 (d, 2H), 7.58 (d, 2H), 6.86 (d, 1H), 4.46 (s, 2H), 4.32 (d, 4H), 4.22 (d, 1H), 3.88-3.62 (m, 8H), 2.87-2.69 (m, 2H), 2.58-2.47 (m, 2H), 1.75 (s, 6H). LCMS [M+H] 509.1.

Compound 38

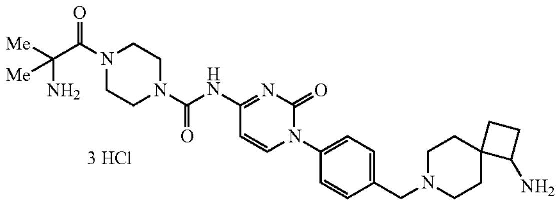

4-(2-Amino-2-methylpropanoyl)-N-(1-(4-((1-amino-7-azaspiro[3.5]nonan-7-yl)methyl)phenyl)-2-oxo-1,2-dihydropyrimidin-4-yl)piperazine-1-carboxamide Hydrochloride Salt Prepared in a similar fashion to Scheme C-2 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl (7-azaspiro[3.5]nonan-1-yl) carbamate NMR (400 MHz, $D_2O$) δ 7.90 (d, 3H), 7.68 (d, 2H), 7.57 (d, 2H), 6.89 (d, 1H), 4.41 (s, 2H), 3.78 (s, 2H), 3.71 (s, 6H), 3.65-3.45 (m, 2H), 3.26-3.16 (m, 1H), 3.11-3.01 (m, 1H), 2.45-2.34 (m, 1H), 2.24 (s, 1H), 2.21-1.78 (m, 7H), 1.74 (d, 6H). LCMS [M+H] 537.2.

Compound 39

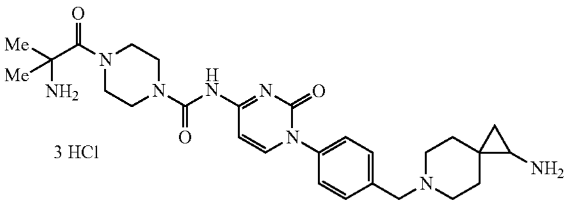

4-(2-Amino-2-methylpropanoyl)-N-(1-(4-((1-amino-6-azaspiro[2.5]octan-6-yl)methyl)phenyl)-2-oxo-1,2-dihydropyrimidin-4-yl)piperazine-1-carboxamide Hydrochloride Salt Prepared in a similar fashion to Scheme C-2 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl 6-azaspiro[2.5]octan-1-ylcarbamate $^1$H NMR (400 MHz, $D_2O$) δ 7.96 (d, 1H), 7.71 (d, 2H), 7.59 (d, 2H), 6.86 (d, 1H), 4.46 (s, 2H), 3.79 (s, 2H), 3.73 (s, 6H), 3.59 (d, 1H), 3.37-3.16 (m, 2H), 2.72 (d, 1H), 2.33-2.16 (m, 1H), 1.74 (d, 6H), 1.34 (m, 4H), 1.15-1.07 (m, 1H), 0.97-0.92 (m, 1H). LCMS [M+H] 523.2.

Compound 42

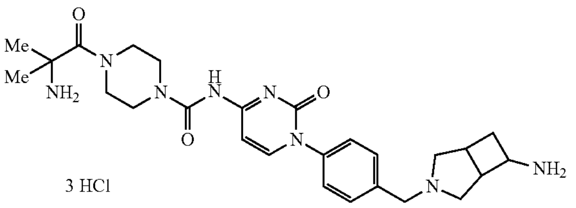

4-(2-Amino-2-methylpropanoyl)-N-(1-(4-((6-amino-3-azabicyclo[3.2.0]heptan-3-yl)methyl)phenyl)-2-oxo-1,2-dihydropyrimidin-4-yl)piperazine-1-carboxamide Hydrochloride Salt Prepared in a similar fashion to Scheme C-2 from tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate and tert-butyl 3-azabicyclo[3.2.0]heptan-6-ylcarbamate $^1$H NMR (400 MHz, $D_2O$) δ 8.00 (d, 1H), 7.76 (d, 2H), 7.59 (d, 2H), 6.85 (d, 1H), 4.62 (s, 2H), 4.08 (q, 1H), 3.98-3.55 (m, 11H), 3.40 (s, 1H), 3.28 (s, 1H), 2.71 (s, 1H), 1.99 (s, 1H), 1.73 (s, 6H), 1.71 (d, 1H). LCMS [M+H] 509.3.

Compound 57

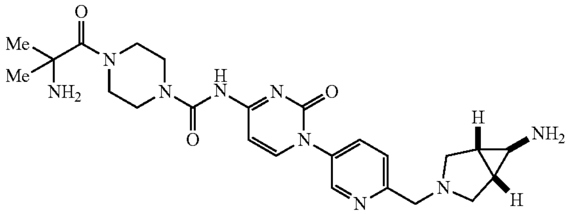

4-(2-Amino-2-methylpropanoyl)-N-(1-(6-((exo-6-amino-3-azabicyclo[3.1.0]hexan-3-yl)methyl)pyridin-3-yl)-2-oxo-1,2-dihydropyrimidin-4-yl)piperazine-1-carboxamide Hydrochloride Salt Prepared in a similar fashion to Scheme C-2 from tert-butyl (1-(4-((1-(6-formylpyridin-3-yl)-2-oxo-1,2-dihydropyrimidin-4-yl)carbamoyl)piperazin-1-yl)-2-methyl-1-oxopropan-2-yl)carbamate and tert-butyl (exo-3-azabicyclo [3.1.0]hexan-6-yl)carbamate. $^1$H NMR (400 MHz, $D_2O$) δ 8.54 (d, 1H), 7.86-7.81 (m, 1H), 7.71 (d, 1H), 7.50 (d, 1H), 6.70 (d, 1H), 4.45 (s, 2H), 3.68 (s, 2H), 3.64-3.47 (m, 10H), 2.80 (s, 1H), 2.28 (s, 2H), 1.53 (s, 6H). LCMS[M+H] 496.2.

Compound 58

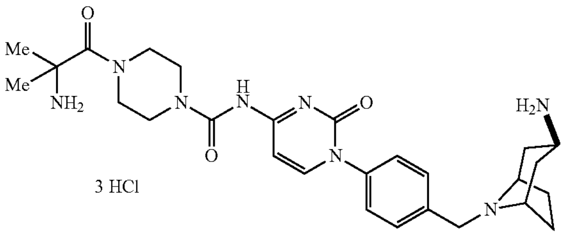

4-(2-Amino-2-methylpropanoyl)-N-(1-(4-((exo-3-amino-8-azabicyclo[3.2.1]octan-8-yl)methyl)phenyl)-2-oxo-1,2-dihydropyrimidin-4-yl)piperazine-1-carboxamide Hydrochloride Salt Prepared in a similar fashion to Scheme C-2 from t-butyl (1-(4-((1-(4-((exo-3-((t-butoxycarbonyl)amino)-8-azabicyclo[3.2.1]octan-8-yl)methyl)phenyl)-2-oxo-1,2-dihydropyrimidin-4-yl)carbamoyl)piperazin-1-yl)-2-methyl-1-oxopropan-2-yl)carbamate. $^1$H NMR (400 MHz, $D_2O$) δ 8.15 (d, 1H), 7.74 (d, 2H), 7.61 (d, 2H), 6.85 (d, 1H), 4.36 (s, 2H), 4.11 (br s, 2H), 3.82-3.75 (m, 11H), 2.66-2.57 (m, 4H), 2.26-2.20 (m, 4H), 1.74 (s, 6H). LCMS [M+H] 523.4.

Compound 59

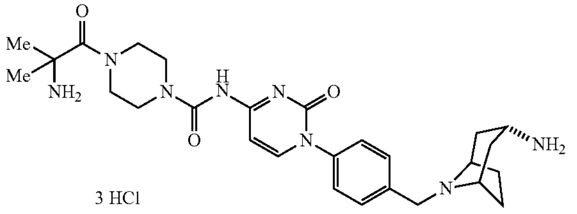

4-(2-Amino-2-methylpropanoyl)-N-(1-(4-((endo-3-amino-8-azabicyclo[3.2.1] octan-8-yl)methyl)phenyl)-2-oxo-1,2-dihydropyrimidin-4-yl)piperazine-1-carboxamide Hydrochloride Salt Prepared in a similar fashion to Scheme C-2 from t-butyl (1-(4-((1-(4-((endo-3-((t-butoxycarbonyl)amino)-8-azabicyclo[3.2.1]octan-8-yl)methyl)phenyl)-2-oxo-1,2-dihydropyrimidin-4-yl)carbamoyl)piperazin-1-yl)-2-methyl-1-oxopropan-2-yl)carbamate. $^1$H NMR (400 MHz, $D_2O$) δ 8.08 (d, 1H), 7.75 (d, 2H), 7.61 (d, 2H), 6.85 (d, 1H), 4.35 (s, 2H), 4.18 (br s, 2H), 3.83-3.74 (m, 11H), 2.56-2.51 (m, 2H), 2.34-2.28 (m, 2H), 2.17 (d, 2H), 2.07 (t, 2H), 1.74 (s, 6H). LCMS [M+H] 523.4.

Compound 60

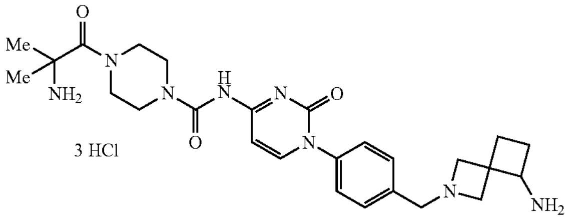

N-(1-(4-((5-Amino-2-azaspiro[3.3]heptan-2-yl) methyl)phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-2 from tert-butyl N-[1-(4-{[1-(4-formylphenyl)-2-oxo-1,2-dihydropyrimidin-4-yl]carbamoyl}piperazin-1-yl)-2-methyl-1-oxopropan-2-yl]carbamate and tert-butyl (2-azaspiro[3.3] heptan-5-yl)carbamate. $^1$H NMR (400 MHz, $D_2O$) δ 8.17 (d, 1H), 7.67 (d, 2H), 7.59 (d, 2H), 6.82 (d, 1H), 4.49 (s, 2H), 4.38 (d, 2H), 4.28 (d, 2H), 4.02-4.00 (m, 1H), 3.80-3.74 (m, 8H), 2.45-2.37 (m, 1H), 2.35-2.29 (m, 2H), 2.06-2.00 (m, 1H), 1.73 (s, 6H). LCMS [M+H] 509.2.

Compound 76

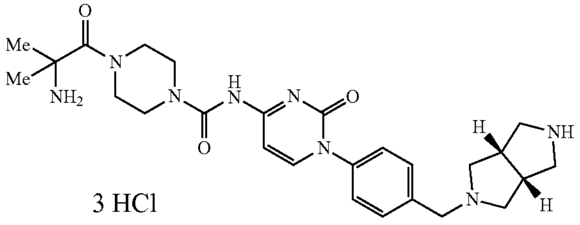

N-(1-{4-[(cis)-Octahydropyrrolo[3,4-c]pyrrol-2-ylmethyl]phenyl}-2-oxo-1,2-dihydropyrimidin-4-yl)-4-(2-amino-2-methylpropanoyl)piperazine-1-carboxamide Hydrochloride Salt Step 1: tert-butyl (cis)-5-{[4-(4-{[4-(2-{[(tert-butoxy)carbonyl]amino}-2-methylpropanoyl)piperazine-1-carbonyl] amino}-2-oxo-1,2-dihydropyrimidin-1-yl)phenyl]methyl}-octahydropyrrolo[3,4-c]pyrrole-2-carboxylate. Prepared in a similar fashion to Scheme C-2 from tert-butyl N-[1-(4-{[1-(4-formylphenyl)-2-oxo-1,2-dihydropyrimidin-4-yl] carbamoyl}piperazin-1-yl)-2-methyl-1-oxopropan-2-yl]carbamate (50.0 mg, 0.098 mmol) and tert-butyl (cis)-octahydropyrrolo[3,4-c]pyrrole-2-carboxylate (25.0 mg, 0.118 mmol) to afford the desired product (52.0 mg, 74%). LCMS [M+H] 709.7.

Step 2: N-(1-{4-[(cis)-octahydropyrrolo[3,4-c]pyrrol-2-ylmethyl]phenyl}-2-oxo-1,2-dihydropyrimidin-4-yl)-4-(2-amino-2-methylpropanoyl)piperazine-1-carboxamide hydrochloride salt. Prepared from tert-butyl (cis)-5-{[4-(4-{[4-(2-{[(tert-butoxy)carbonyl]amino}-2-methylpropanoyl) piperazine-1-carbonyl]amino}-2-oxo-1,2-dihydropyrimidin-1-yl)phenyl]methyl}-octahydropyrrolo[3,4-c]pyrrole-2-carboxylate (52.0 mg, 0.074 mmol) to give the title compound (38.6 mg, 84%) as a white solid. $^1$H NMR (400 MHz, $D_2O$) δ 7.84 (d, 1H), 7.63 (d, 2H), 7.51 (d, 2H), 6.81 (d, 1H), 4.47 (s, 2H), 3.76-3.62 (m, 8H), 3.97-2.96 (m, 10H), 1.68 (s, 6H). LCMS[M+H] 509.4.

Compound 16

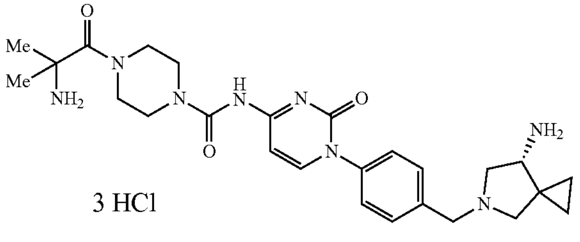

4-(2-Amino-2-methylpropanoyl)-N-[1-(4-{[(7R)-7-amino-5-azaspiro[2.4]heptan-5-yl]methyl}phenyl)-2-oxo-1,2-dihydropyrimidin-4-yl]piperazine-1-carboxamide Hydrochloride Salt Step 1: tert-butyl N-[(7R)-5-{[4-(4-{[4-(2-{[(tert-butoxy) carbonyl]amino}-2-methylpropanoyl)piperazine-1-carbonyl]amino}-2-oxo-1,2-dihydropyrimidin-1-yl)phenyl] methyl}-5-azaspiro[2.4]heptan-7-yl]carbamate. Prepared in a similar fashion to Scheme C-2 from tert-butyl N-[1-(4-{ [1-(4-formylphenyl)-2-oxo-1,2-dihydropyrimidin-4-yl] carbamoyl}piperazin-1-yl)-2-methyl-1-oxopropan-2-yl]carbamate (43.0 mg, 0.084 mmol) and tert-butyl N-[(7R)-5-azaspiro[2.4]heptan-7-yl]carbamate (26.7 mg, 0.126 mmol) to afford the title compound. (43.0 mg, 72%). $^1$H NMR (400 MHz, $CDCl_3$) δ 12.94 (br. s., 1H), 7.45 (d, 2H), 7.34-7.24 (m, 3H), 5.84 (d, 1H), 5.04-4.44 (m, 2H), 3.98-3.54 (m, 11H), 3.03-2.86 (m, 1H), 2.71 (d, 2H), 2.37 (d, 1H), 1.54 (s, 6H), 1.46 (s, 9H), 1.45 (s, 9H), 0.89-0.70 (m, 2H), 0.67-0.59 (m, 1H), 0.52-0.44 (m, 1H). LCMS [M+H] 709.7.

Step 2: 4-(2-Amino-2-methylpropanoyl)-N-[1-(4-{[(7R)-7-amino-5-azaspiro[2.4]heptan-5-yl]methyl}phenyl)-2-oxo-1,2-dihydropyrimidin-4-yl]piperazine-1-carboxamide hydrochloride salt. Prepared from tert-butyl N-{[(7R)-1-{ [4-(4-{[4-(2-{[(tert-butoxy)carbonyl]amino}-2-methylpropanoyl)piperazine-1-carbonyl]amino}-2-oxo-1,2-dihydropyrimidin-1-yl)phenyl]methyl}pyrrolidin-3-yl] methyl}carbamate (43.0 mg, 0.06 mmol) to afford the title compound (30.0 mg, 81%) as a pale yellow solid. $^1$H NMR (400 MHz, $D_2O$) δ 7.86 (d, 1H), 7.66 (d, 2H), 7.52 (d, 2H), 6.81 (d, 1H), 4.61 (d, 1H), 4.54 (d, 1H), 4.32-4.16 (m, 1H), 3.91-3.54 (m, 11H), 3.32-3.19 (m, 1H), 1.68 (s, 6H), 1.18-1.05 (m, 1H), 1.03-0.85 (m, 3H). LCMS [M+H] 509.4.

Compound 19

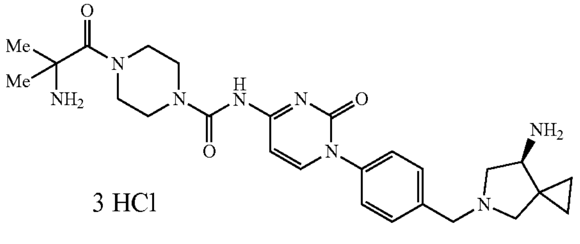

4-(2-Amino-2-methylpropanoyl)-N-[1-(4-{[(7S)-7-amino-5-azaspiro[2.4]heptan-5-yl]methyl}phenyl)-2-oxo-1,2-dihydropyrimidin-4-yl]piperazine-1-carboxamide Hydrochloride Salt Step 1: tert-butyl N-[(7S)-5-{[4-(4{[4-(2-{[(tert-butoxy)carbonyl]amino}-2-methylpropanoyl)piperazine-1-carbonyl]amino}-2-oxo-1,2-dihydropyrimidin-1-yl)phenyl]methyl}-5-azaspiro[2.4]heptan-7-yl]carbamate. Prepared in a similar fashion to Scheme C-2 from tertbutyl N-[1-(4-{[1-(4-formylphenyl)-2-oxo-1,2-dihydropyrimidin-4-yl]carbamoyl}piperazin-1-yl)-2-methyl-1-oxopropan-2-yl]carbamate (50.0 mg, 0.098 mmol) and tert-butyl N-[(7S)-5-azaspiro[2.4]heptan-7-yl]carbamate (26.7 mg, 0.147 mmol) to afford the title compound (54.0 mg, 78%)'H NMR (400 MHz, $CDCl_3$) δ 12.95 (br. s., 1H), 7.45 (d, 2H), 7.34-7.24 (m, 3H), 5.84 (d, 1H), 4.98-4.44 (m, 2H), 4.00-3.53 (m, 11H), 3.04-2.88 (m, 1H), 2.76-2.54 (m, 2H), 2.37 (d, 1H), 1.54 (s, 6H), 1.46 (s, 9H), 1.45 (s, 9H), 0.88-0.70 (m, 2H), 0.66-0.56 (m, 1H), 0.52-0.44 (m, 1H). LCMS [M+H] 709.7.

Step 2: 4-(2-Amino-2-methylpropanoyl)-N-[1-(4-{[(7S)-7-amino-5-azaspiro[2.4] heptan-5-yl]methyl}phenyl)-2-oxo-1,2-dihydropyrimidin-4-yl] piperazine-1-carboxamide hydrochloride salt. Prepared from tert-butyl N-{[(7S)-1-{[4-(4-{[4-(2-{[(tert-butoxy)carbonyl]amino}-2-methylpropanoyl)piperazine-1-carbonyl]amino}-2-oxo-1,2-dihydropyrimidin-1-yl)phenyl]methyl}pyrrolidin-3-yl]methyl}carbamate (54.0 mg, 0.076 mmol) to afford the title compound as its hydrochloride salt (41.3 mg, 88%) as a yellow solid. $^1$H NMR (400 MHz, $D_2O$) δ 7.86 (d, 1H), 7.65 (d, 2H), 7.51 (d, 2H), 6.80 (d, 1H), 4.60 (d, 1H), 4.53 (d, 1H), 4.29-4.11 (m, 1H), 3.87-3.50 (m, 11H), 3.30-3.19 (m, 1H), 1.67 (s, 6H), 1.17-1.05 (m, 1H), 1.01-0.88 (m, 3H). LCMS [M+H] 509.4.

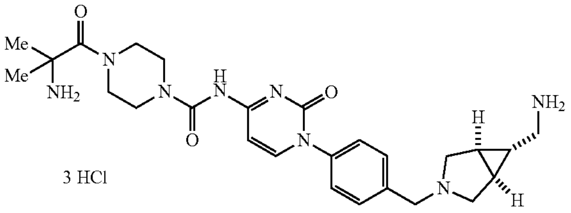 [SMILES: CC(C)(N)C(=O)N1CCN(C(=O)Nc2ccn(-c3ccc(CN4C[C@@H]5[C@@H](CN)[C@@H]5C4)cc3)c(=O)n2)CC1]

3 HCl 4-(2-Amino-2-methylpropanoyl)-N-[1-(4-{[(exo)-6-(aminomethyl)-3-azabicyclo[3.1.0]hexan-3-yl]methyl}phenyl)-2-oxo-1,2-dihydropyrimidin-4-yl]piperazine-1-carboxamide Hydrochloride Salt Step 1: tert-Butyl N-{[(exo)-3-{[444{[442{[(tert-butoxy)carbonyl]amino}-2-methylpropanoyl)piperazine-1-carbonyl]amino}-2-oxo-1,2-dihydropyrimidin-1-yl)phenyl]methyl}-3-azabicyclo[3.1.0]hexan-6-yl]methyl}carbamate. Prepared in a similar fashion to Scheme C-2 from tert-butyl N-[1-(4-{[1-(4-formylphenyl)-2-oxo-1,2-dihydropyrimidin-4-yl]carbamoyl}piperazin-1-yl)-2-methyl-1-oxopropan-2-yl]carbamate to afford the title compound (50.0 mg, 0.098 mmol) and tert-butyl N-[exo-3-azabicyclo[3.1.0]hexan-6-ylmethyl]carbamate (31.1 mg, 0.147 mmol) to (53.0 mg, 76%). $^1$H NMR (400 MHz, $CDCl_3$) δ 12.94 (br. s., 1H), 7.38 (d, 2H), 7.31-7.25 (m, 3H), 5.83 (d, 1H), 4.87 (br. s., 1H), 4.58 (br. s., 1H), 3.95-3.52 (m, 10H), 3.05-2.94 (m, 4H), 2.36 (d, 2H), 1.54 (s, 6H), 1.50-1.38 (m, 19H), 1.33-1.25 (m, 2H). LCMS [M+H] 709.7.

Step 2: 4-(2-Amino-2-methylpropanoyl)-N-[1-(4-{[exo-6-(aminomethyl)-3-azabicyclo[3.1.0]hexan-3-yl]methyl}phenyl)-2-oxo-1,2-dihydropyrimidin-4-yl]piperazine-1-carboxamide hydrochloride salt. Prepared as from tert-butyl N-{[exo-3-{[4-(4-{[4-(2-{[(tert-butoxy)carbonyl]amino}-2-methylpropanoyl)piperazine-1-carbonyl]amino}-2-oxo-1,2-dihydropyrimidin-1-yl)phenyl]methyl}-3-azabicyclo[3.1.0]hexan-6-yl]methyl}carbamate (53.0 mg, 0.075 mmol) to afford the title compound (40.4 mg, 87%) as a pale yellow solid. $^1$H NMR (400 MHz, $D_2O$) δ 7.86 (d, 1H), 7.67-7.55 (m, 2H), 7.50 (d, 2H), 6.81 (d, 1H), 4.47-4.28 (m, 2H), 3.99-3.49 (m, 12H), 3.06-2.87 (m, 2H), 2.07-1.93 (m, 2H), 1.69 (s, 6H), 1.41-1.28 (m, 1H). LCMS [M+H] 509.4.

Compound 77

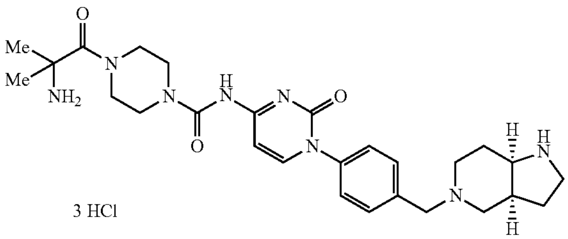

3 HCl 4-(2-Amino-2-methylpropanoyl)-N-(1-(4-4 (3aS,7aR)-octahydro-5H-pyrrolo[3,2-c]pyridin-5-yl)methyl)phenyl)-2-oxo-1,2-dihydropyrimidin-4-yl)piperazine-1-carboxamide Hydrochloride Salt Step 1: tert-butyl (3aS,7aR)-rel-5-{[4-(4-{[4-(2-{[(tert-butoxy)carbonyl]amino}-2-methylpropanoyl)piperazine-1-carbonyl]amino}-2-oxo-1,2-dihydropyrimidin-1-yl)phenyl]methyl}-octahydro-1H-pyrrolo[3,2-c]pyridine-1-carboxylate. Prepared in a similar fashion to Scheme C-2 from tert-butyl N-[1-(4-{[1-(4-formylphenyl)-2-oxo-1,2-dihydropyrimidin-4-yl]carbamoyl}piperazin-1-yl)-2-methyl-1-oxopropan-2-yl]carbamate (50.0 mg, 0.098 mmol) and cis-1-N-Boc-octahydropyrrolo[3,2-c]pyridine (33.1 mg, 0.147 mmol) to afford the title compound (44.0 mg, 62%). $^1$H NMR (400 MHz, $CDCl_3$) δ 12.95 (br. s., 1H), 7.45 (d, 2H), 7.34-7.24 (m, 3H), 5.84 (d, 1H), 4.97-4.46 (m, 1H), 4.03-3.19 (m, 14H), 2.85-2.58 (m, 2H), 2.45-2.15 (m, 3H), 2.14-1.91 (m, 2H), 1.87-1.59 (m, 1H), 1.53 (s, 6H), 1.47 (s, 9H), 1.46 (s, 9H). LCMS [M+H] 723.8.

Step 2: N 4-(2-amino-2-methylpropanoyl)-N-(1-(4-4 (3aS,7aR)-octahydro-5H-pyrrolo[3,2-c]pyridin-5-yl)methyl)phenyl)-2-oxo-1,2-dihydropyrimidin-4-yl)piperazine-1-carboxamide hydrochloride salt. Prepared from tert-butyl (3aS,7aR)-rel-5-{[4-(4-{[4-(2-{[(tert-butoxy)carbonyl]amino}-2-methylpropanoyl)piperazine-1-carbonyl]amino}-2-oxo-1,2-dihydropyrimidin-1-yl)phenyl]methyl}-octahydro-1H-pyrrolo[3,2-c]pyridine-1-carboxylate (44.0 mg, 0.061 mmol) to afford the title compound (33.2 mg, 86%) as a pale yellow solid. $^1$H NMR (400 MHz, $D_2O$) δ 7.91 (d, 1H), 7.70 (d, 2H), 7.57 (d, 2H), 6.87 (d, 1H), 4.47 (br. s., 2H), 4.14-3.07 (m, 15H), 2.92-2.76 (m, 1H), 2.51-1.81 (m, 4H), 1.73 (s, 6H). LCMS [M+H] 523.4.

Compound 71

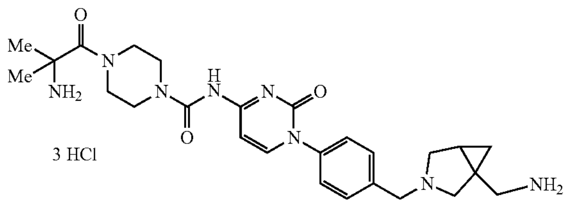

4-(2-Amino-2-methylpropanoyl)-N-[1-(4-{[1-(aminomethyl)-3-azabicyclo[3.1.0]hexan-3-yl] methyl}phenyl)-2-oxo-1,2-dihydropyrimidin-4-yl] piperazine-1-carboxamide Hydrochloride Salt Step 1: tert-butyl (1-(4-((1-(4-((1-(((tert-butoxycarbonyl) amino)methyl)-3-azabicyclo[3.1.0]hexan-3-yl)methyl)phenyl)-2-oxo-1,2-dihydropyrimidin-4-yl)carbamoyl)piperazin-1-yl)-2-methyl-1-oxopropan-2-yl)carbamate. Prepared in a similar fashion to Scheme C-2 from tert-butyl N-[1-(4-{[1-(4-formylphenyl)-2-oxo-1,2-dihydropyrimidin-4-yl] carbamoyl}piperazin-1-yl)-2-methyl-1-oxopropan-2-yl]carbamate (30.0 mg, 0.058 mmol) and tert-butyl N-{3-azabicyclo[3.1.0]hexan-1-ylmethyl}carbamate (15.0 mg, 0.070 mmol) to afford (9.0 mg, 29%). LCMS [M+H] 709.7.

Step 2: 4-(2-Amino-2-methylpropanoyl)-N-[1-(4-{[1-(aminomethyl)-3-azabicyclo[3.1.0]hexan-3-yl] methyl}phenyl)-2-oxo-1,2-dihydropyrimidin-4-yl]piperazine-1-carboxamide hydrochloride salt. Prepared from tert-butyl (1-(4-((1-(4-((1-(((tert-butoxycarbonyl)amino) methyl)-3-azabicyclo[3.1.0]hexan-3-yl)methyl)phenyl)-2-oxo-1,2-dihydropyrimidin-4-yl)carbamoyl)piperazin-1-yl)-2-methyl-1-oxopropan-2-yl)carbamate (9.0 mg, 0.017 mmol) to afford the title compound (4.2 mg, 40%) as a colorless wax. $^1$H NMR (400 MHz, $D_2O$) δ 7.88 (d, 1H), 7.63 (d, 2H), 7.51 (d, 2H), 6.81 (d, 1H), 4.45 (br. s., 2H), 3.85-3.51 (m, 12H), 3.49-3.39 (m, 1H), 3.15-3.00 (m, 1H), 2.05-1.92 (m, 1H), 1.68 (s, 6H), 1.15-0.95 (m, 2H). LCMS [M+H] 509.5.

Compound 74

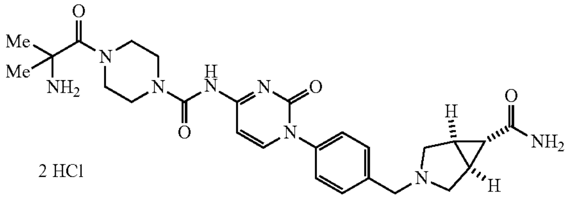

Exo-3-(4-(4-(4-(2-Amino-2-methylpropanoyl)piperazine-1-carboxamido)-2-oxopyrimidin-1 (2H)-yl) benzyl)-3-azabicyclo[3.1.0]hexane-6-carboxamide Hydrochloride Salt Prepared in a similar fashion to Scheme C-2 from t-butyl (1-(4-((1-(4-formylphenyl)-2-oxo-1,2-dihydropyrimidin-4-yl)carbamoyl)piperazin-1-yl)-2-methyl-1-oxopropan-2-yl) carbamate and exo-3-azabicyclo[3.1.0]hexane-6-carboxamide. $^1$H NMR (400 MHz, $D_2O$) δ 8.08 (d, 1H), 7.69 (d, 2H), 7.56 (d, 2H), 6.81 (d, 1H), 4.48 (s, 2H), 3.90-3.59 (m, 12H), 2.30 (s, 2H), 1.90 (d, 1H), 1.72 (s, 6H). LCMS[M+H] 523.2.

Compound 81

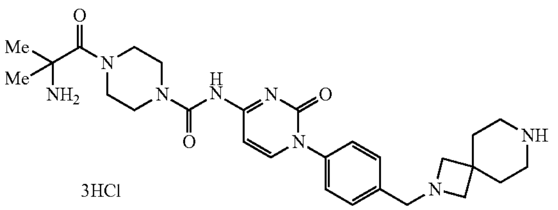

N-(1-(4-((2,7-Diazaspiro[3.5]nonan-2-yl)methyl) phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-2 from tert-butyl 2-(4-(4-(4-(2-((tert-butoxycarbonyl)amino)-2-methylpropanoyl)piperazine-1-carboxamido)-2-oxopyrimidin-1 (2H)-yl)benzyl)-2,7-diazaspiro[3.5]nonane-7-carboxylate. $^1$H NMR (500 MHz, $D_2O$) δ 8.08 (d, 1H), 7.77 (d, 2H), 7.68 (d, 2H), 6.95 (d, 1H), 4.65 (s, 2H), 4.31-4.25 (m, 4H), 3.94-3.88 (m, 4H), 3.87-3.80 (m, 4H), 3.36 (t, 2H), 3.32 (t, 2H), 2.30-2.25 (m, 4H), 1.85 (s, 6H). LCMS [M+H] 523.3.

Compound 168

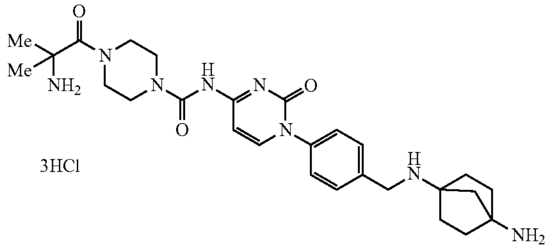

4-(2-Amino-2-methylpropanoyl)-N-(1-(4-(((4-aminobicyclo[2.2.1]heptan-1-yl)amino)methyl)phenyl)-2-oxo-1,2-dihydropyrimidin-4-yl)piperazine-1-carboxamide Hydrochloride Salt Prepared in a similar fashion to Scheme C-2 using t-butyl (1-(4-((1-(4-formylphenyl)-2-oxo-1,2-dihydropyrimidin-4-yl)carbamoyl)piperazin-1-yl)-2-methyl-1-oxopropan-2-yl) carbamate and t-butyl (4-aminobicyclo[2.2.1]heptan-1-yl) carbamate. LCMS [(M+2H)/2] 262.0.

Compound 167

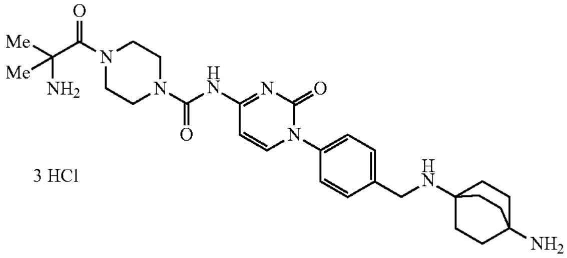

4-(2-Amino-2-methylpropanoyl)-N-(1-(4-(((4-aminobicyclo[2.2.2]octan-1-yl)amino)methyl)phenyl)-2-oxo-1,2-dihydropyrimidin-4-yl)piperazine-1-carboxamide Hydrochloride Salt Prepared in a similar fashion to Scheme C-2 using t-butyl (1-(4-((1-(4-formylphenyl)-2-oxo-1,2-dihydropyrimidin-4-yl)carbamoyl)piperazin-1-yl)-2-methyl-1-oxopropan-2-yl) carbamate and t-butyl (4-aminobicyclo[2.2.2]octan-1-yl) carbamate. $^1$H NMR (400 MHz, $D_2O$) δ 8.00 (d, 1H), 7.66 (d, 2H), 7.56 (d, 2H), 6.88 (d, 1H), 4.32 (s, 2H), 3.89-3.58 (m, 8H), 2.25-2.05 (m, 12H), 1.76 (s, 6H). LCMS [M+H] 537.2.

Compound 171

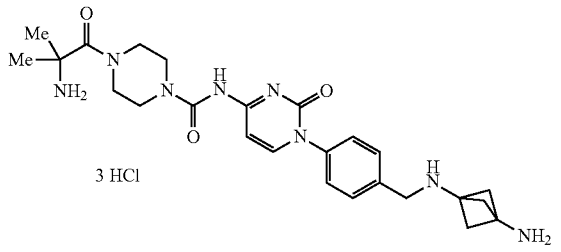

4-(2-Amino-2-methylpropanoyl)-N-(1-(4-(((3-aminobicyclo[1.1.1]pentan-1-yl)amino)methyl)phenyl)-2-oxo-1,2-dihydropyrimidin-4-yl)piperazine-1-carboxamide Hydrochloride Salt Prepared in a similar fashion to Scheme C-2 using t-butyl (1-(4-((1-(4-formylphenyl)-2-oxo-1,2-dihydropyrimidin-4-yl)carbamoyl)piperazin-1-yl)-2-methyl-1-oxopropan-2-yl) carbamate and t-butyl (3-aminobicyclo[1.1.1]pentan-1-yl) carbamate. $^1$H NMR (400 MHz, $D_2O$) δ 7.71 (d, 1H), 7.44 (d, 2H), 7.33 (d, 2H), 6.71 (m, 1H), 4.06 (s, 2H), 3.68-3.55 (m, 8H), 2.27 (s, 6H), 1.56 (s, 6H). LCMS [M+H] 495.1.

Compound 1

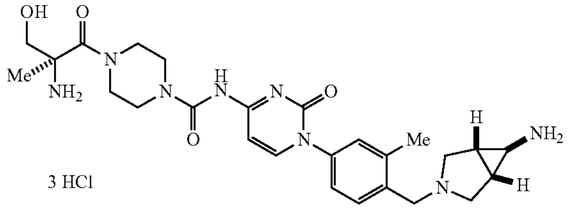

N-(1-(4-((exo-6-Amino-3-azabicyclo[3.1.0]hexan-3-yl)methyl)-3-methylphenyl)-2-oxo-1,2-dihydropyrimidin-4-yl)-4-((S)-2-amino-3-hydroxy-2-methylpropanoyl)piperazine-1-carboxamide Hydrochloride Salt Prepared in a similar fashion to Scheme C-2 from tert-butyl (2R,4S)-2-(tert-butyl)-4-(4-((1-(4-formyl-3-methylphenyl)-2-oxo-1,2-dihydropyrimidin-4-yl)carbamoyl)piperazine-1-carbonyl)-4-methyloxazolidine-3-carboxylate and tert-butyl (exo-3-azabicyclo[3.1.0]hexan-6-yl)carbamate. $^1$H NMR (500 MHz, $CD_3OD$): δ 7.72 (d, 1H), 7.62 (d, 1H), 7.38 (s 1H), 7.34 (d, 1H), 6.61 (s, 1H), 4.43 (s, 2H), 4.07 (d, 1H), 3.70 (d, 1H), 3.74-3.67 (m, 12H), 3.12 (s, 1H), 2.49 (s, 3H), 2.32 (s, 2H), 1.61 (s, 3H). LCMS [M+H] 525.3.

Compound 11

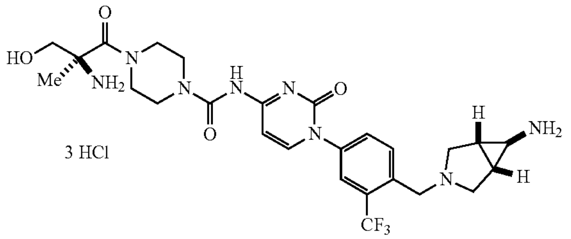

N-(1-(4-((exo-6-Amino-3-azabicyclo[3.1.0]hexan-3-yl)methyl)-3-(trifluoromethyl)phenyl)-2-oxo-1,2-dihydropyrimidin-4-yl)-4-((S)-2-amino-3-hydroxy-2-methylpropanoyl)piperazine-1-carboxamide Hydrochloride Salt Prepared in a similar fashion to Scheme C-2 from 4-4S, 4S)-2-(tert-butyl)-4-methyloxazolidine-4-carbonyl)-N-(1-(4-formyl-3-(trifluoromethyl)phenyl)-2-oxo-1,2-dihydropyrimidin-4-yl)piperazine-1-carboxamide and tert-butyl exo-3-azabicyclo[3.1.0]hexan-6-ylcarbamate.

Compound 142

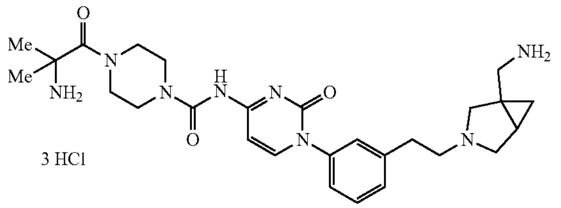

4-(2-Amino-2-methylpropanoyl)-N-(1-(3-(2-(1-(aminomethyl)-3-azabicyclo[3.1.0]hexan-3-yl)ethyl)phenyl)-2-oxo-1,2-dihydropyrimidin-4-yl)piperazine-1-carboxamide Hydrochloride Salt Prepared in a similar fashion to Scheme C-2 using tert-butyl (2-methyl-1-oxo-1-(4-((2-oxo-1-(3-(2-oxoethyl)phenyl)-1,2-dihydropyrimidin-4-yl)carbamoyl)piperazin-1-yl) propan-2-yl)carbamate and t-butyl ((3-azabicyclo[3.1.0] hexan-1-yl)methyl)carbamate. $^1$H NMR (400 MHz, $D_2O$) δ 7.82 (d, 1H), 7.42 (t, 1H), 7.32 (d, 1H), 7.25-7.22 (m, 2H), 6.69 (d, 1H), 3.78 (d, 1H), 3.66-3.58 (m, 10H), 3.43-3.31 (m, 5H), 3.00-2.95 (m, 2H), 1.90-1.84 (m, 1H), 1.58 (s, 6H), 0.98 (t, 1H), 0.87-0.84 (m, 1H). LCMS [(M+2H)/2] 262.1.

Compound 143

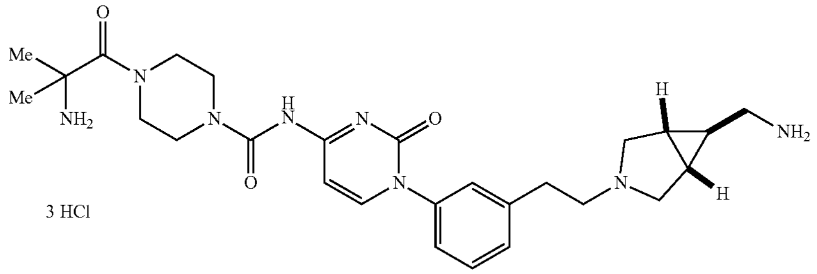

4-(2-Amino-2-methylpropanoyl)-N-(1-(3-(2-(exo-6-(aminomethyl)-3-azabicyclo[3.1.0]hexan-3-yl)ethyl)phenyl)-2-oxo-1,2-dihydropyrimidin-4-yl)piperazine-1-carboxamide Hydrochloride Salt Prepared in a similar fashion to Scheme C-2 using tert-butyl (2-methyl-1-oxo-1-(4-((2-oxo-1-(3-(2-oxoethyl)phenyl)-1,2-dihydropyrimidin-4-yl)carbamoyl)piperazin-1-yl)propan-2-yl)carbamate and exo-t-butyl ((3-azabicyclo[3.1.0]hexan-6-yl)methyl)carbamate. $^1$H NMR (400 MHz, $D_2O$) δ 7.79 (d, 1H), 7.42 (t, 1H), 7.31 (d, 1H), 7.28-7.20 (m, 2H), 6.70 (d, 1H), 3.69-3.57 (m, 10H), 3.39-3.32 (m, 4H), 2.99-2.93 (m, 2H), 2.81 (d, 2H), 1.92-1.81 (m, 2H), 1.58 (s, 6H), 1.19-1.15 (m, 1H). LCMS [M+H] 523.0.

Compound 144

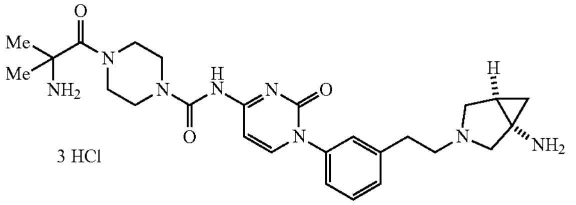

Cis-4-(2-Amino-2-methylpropanoyl)-N-(1-(3-(2-(1-amino-3-azabicyclo[3.1.0]hexan-3-yl)ethyl)phenyl)-2-oxo-1,2-dihydropyrimidin-4-yl)piperazine-1-carboxamide Hydrochloride Salt Prepared in a similar fashion to Scheme C-2 using tert-butyl (2-methyl-1-oxo-1-(4-((2-oxo-1-(3-(2-oxoethyl)phenyl)-1,2-dihydropyrimidin-4-yl)carbamoyl)piperazin-1-yl)propan-2-yl)carbamate and cis-t-butyl (3-azabicyclo[3.1.0]hexan-1-yl)carbamate. $^1$H NMR (400 MHz, $D_2O$): δ 7.80 (d, 1H), 7.43 (t, 1H), 7.39-7.31 (m, 1H), 7.29-7.22 (m, 2H), 6.70 (d, 1H), 4.10-3.91 (m, 1H), 3.63-3.48 (m, 13H), 3.00 (t, 2H), 2.24-2.15 (m, 1H), 1.59 (s, 6H) 1.45-1.35 (m, 1H), 1.19-1.13 (s, 1H). LCMS [M+H] 509.4.

Compound 109

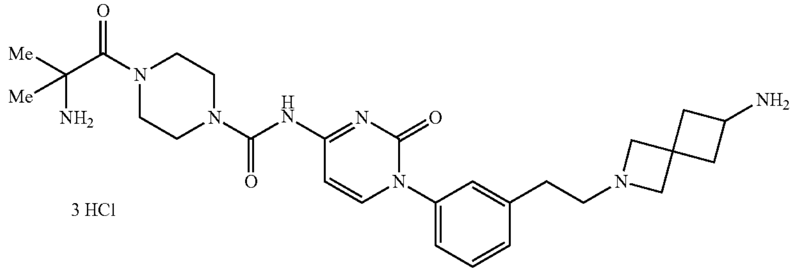

N-(1-(3-(2-(6-Amino-2-azaspiro[3.3]heptan-2-yl)ethyl)phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-2 using tert-butyl (2-methyl-1-oxo-1-(4-((2-oxo-1-(3-(2-oxoethyl)phenyl)-1,2-dihydropyrimidin-4-yl)carbamoyl)piperazin-1-yl)propan-2-yl)carbamate and t-butyl N-(2-azaspiro[3.3]heptan-6-yl). $^1$H NMR (400 MHz, $D_2O$): δ 7.78 (d, 1H), 7.43 (t, 1H), 7.30 (d, 1H), 7.26-7.21 (m, 2H), 6.71 (d, 1H), 4.29-3.95 (m, 4H), 3.65-3.51 (m, 8H), 3.39 (t, 2H), 2.86 (t, 2H), 2.65-2.60 (m, 1H), 2.57-2.50 (m, 1H), 2.35-2.30 (m, 2H), 1.589 (s, 6H), 1.18 (d, 1H). LCMS [(M+2H)/2] 261.2.

Compound 110

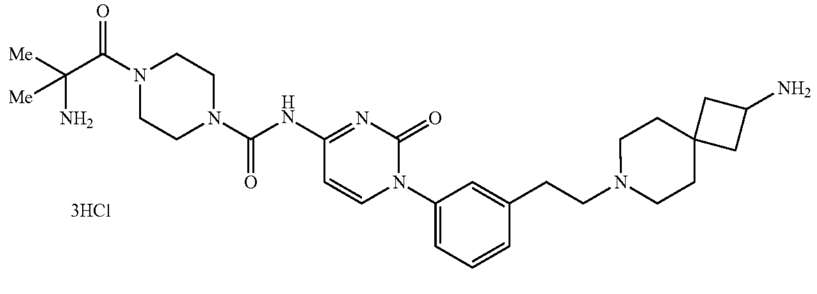

4-(2-Amino-2-methylpropanoyl)-N-(1-(3-(2-(2-amino-7-azaspiro[3.5]nonan-7-yl)ethyl)phenyl)-2-oxo-1,2-dihydropyrimidin-4-yl)piperazine-1-carboxamide Hydrochloride Salt Prepared in a similar fashion to Scheme C-2 using tert-butyl (2-methyl-1-oxo-1-(4-((2-oxo-1-(3-(2-oxoethyl)phenyl)-1,2-dihydropyrimidin-4-yl)carbamoyl)piperazin-1-yl)propan-2-yl)carbamate and t-butyl (7-azaspiro[3.5]nonan-2-yl)carbamate. $^1$H NMR (400 MHz, $D_2O$): δ 7.76 (d, 1H), 7.42 (t, 1H), 7.32 (d, 1H), 6.78-6.70 (m, 2H), 6.71 (d, 1H), 3.81-3.71 (m, 1H), 3.62-3.57 (m, 8H), 3.44-3.36 (m, 2H), 3.31-3.21 (m, 2H), 3.01 (t, 2H), 2.99-2.85 (m, 2H), 2.35-2.32 (m, 1H), 2.16-2.13 (m, 1H), 1.97-1.91 (m, 3H), 1.88-1.71 (m, 3H), 1.58 (s, 6H). LCMS [M+H] 551.1.

Compound 113

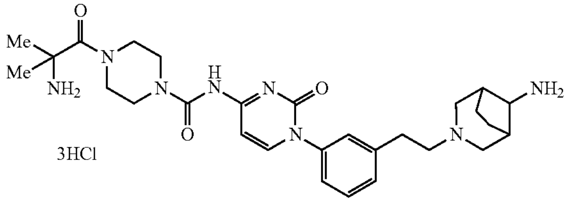

4-(2-Amino-2-methylpropanoyl)-N-(1-(3-(2-(8-amino-3-azabicyclo[3.2.1]octan-3-yl)ethyl)phenyl)-2-oxo-1,2-dihydropyrimidin-4-yl)piperazine-1-carboxamide Hydrochloride Salt Prepared in a similar fashion to Scheme C-2 using tert-butyl (2-methyl-1-oxo-1-(4-((2-oxo-1-(3-(2-oxoethyl)phenyl)-1,2-dihydropyrimidin-4-yl)carbamoyl)piperazin-1-yl)propan-2-yl)carbamate and t-butyl (3-azabicyclo[3.2.1]octan-8-yl) carbamate. $^1$H NMR (400 MHz, $D_2O$): Mixture of rotamers, δ 7.80 (d, 1H), 7.42 (t, 1H), 7.31 (d, 1H), 7.28-7.20 (m, 2H), 6.70 (d, 1H), 3.61-3.53 (m, 9H), 3.30-3.26 (m, 2H), 3.18 (d, 2H), 3.07-2.98 (m, 2H), 2.65-2.50 (m, 2H), 2.01-1.98 (m, 2H), 1.89-1.81 (m, 2H), 1.59 (s, 6H), 1.78 (d, 4H). LCMS [M+H] 537.4.

Compound 106

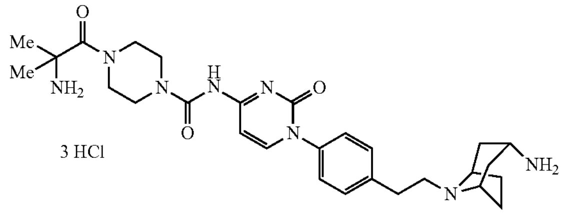

4-(2-Amino-2-methylpropanoyl)-N-(1-(4-(2-(endo-3-amino-8-azabicyclo[3.2.1]octan-8-yl)ethyl)phenyl)-2-oxo-1,2-dihydropyrimidin-4-yl)piperazine-1-carboxamide Hydrochloride Salt Prepared in a similar fashion to Scheme C-2 from t-butyl (2-methyl-1-oxo-1-(4-(2-oxo-1-(4-(2-oxoethyl)phenyl)-1,2-dihydropyrimidin-4-yl)carbamoyl)piperazin-1-yl)propan-2-yl)carbamate and t-butyl (endo-8-azabicyclo[3.2.1]octan-3-yl)carbamate. $^1$H NMR (400 MHz, $D_2O$) δ 8.01 (d, 1H), 7.51 (d, 2H), 7.45 (d, 2H), 6.83 (d, 1H), 4.19 (s, 2H), 3.80 (s, 4H), 3.74 (s, 4H), 3.65-3.59 (m, 1H), 3.42-3.34 (m, 2H), 3.24-3.16 (m, 2H), 2.75-2.62 (m, 2H), 2.56-2.47 (m, 2H), 2.31-2.15 (m, 4H), 1.74 (s, 6H). LCMS[M+H] 537.3

Compound 107

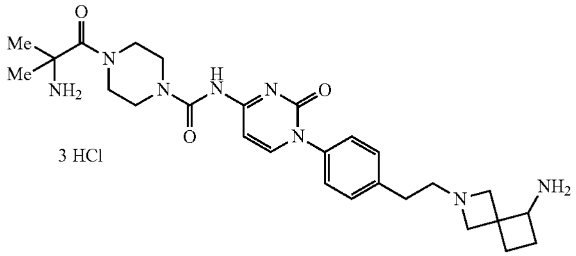

N-(1-(4-(2-(5-Amino-2-azaspiro[3.3]heptan-2-yl)ethyl)phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-2 using t-butyl (2-methyl-1-oxo-1-(4-(2-oxo-1-(4-(2-oxoethyl)phenyl)-1,2-dihydropyrimidin-4-yl)carbamoyl)piperazin-1-yl)propan-2-yl)carbamate and tert-butyl (2-azaspiro[3.3]heptan-5-yl)carbamate. $^1$H NMR 7.95 (d, 1H), 7.48 (d, 2H), 7.44 (d, 2H), 6.83 (d, 1H), 4.63-4.39 (m, 1H), 4.32-4.10 (m, 3H), 4.01-3.87 (m, 1H), 3.82-3.69 (m, 8H), 3.58 (t, 2H), 3.03 (t, 2H), 2.39 (t, 1H), 2.33-2.25 (m, 2H), 2.06-1.94 (m, 1H), 1.73 (s, 6H). LCMS[M+H] 523.3.

Compound 108

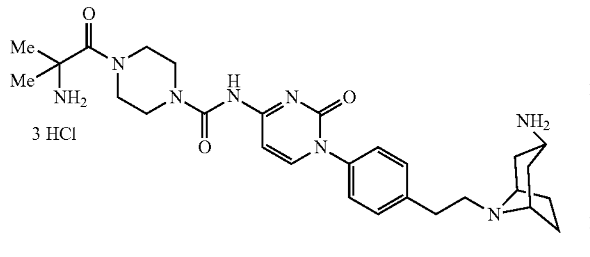

4-(2-Amino-2-methylpropanoyl)-N-(1-(4-(2-(exo-3-amino-8-azabicyclo[3.2.1]octan-8-yl)ethyl)phenyl)-2-oxo-1,2-dihydropyrimidin-4-yl)piperazine-1-carboxamide Hydrochloride Salt Prepared in a similar fashion to Scheme C-2 using t-butyl (2-methyl-1-oxo-1-(4-(2-oxo-1-(4-(2-oxoethyl)phenyl)-1,2-dihydropyrimidin-4-yl)carbamoyl)piperazin-1-yl)propan-2-yl)carbamate and t-butyl (exo-8-azabicyclo[3.2.1]octan-3-yl)carbamate. $^1$H NMR 7.93 (d, 1H), 7.50-7.39 (m, 4H), 6.82 (d, 1H), 4.28-4.17 (m, 2H), 3.85-3.66 (m, 9H), 3.38-3.33 (m, 2H), 3.23-3.17 (m, 2H), 2.40-2.29 (m, 4H), 2.18-2.05 (m, 4H), 1.73 (s, 6H). LCMS[M+H] 537.34

Compound 136

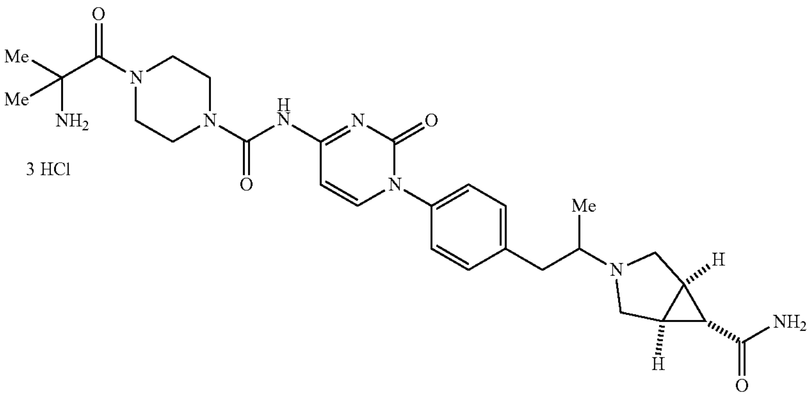

Exo-3-(1-(4-(4-(4-(2-Amino-2-methylpropanoyl) piperazine-1-carboxamido)-2-oxopyrimidin-1 (2H)-yl)phenyl)propan-2-yl)-3-azabicyclo[3.1.0]hexane-6-carboxamide Hydrochloride Salt Prepared in a similar fashion to Scheme C-2 from t-butyl (2-methyl-1-oxo-1-(4-(2-oxo-1-(4-(2-oxopropyl)phenyl)-1,2-dihydropyrimidin-4-yl)carbamoyl)piperazin-1-yl)propan-2-yl)carbamate and exo-3-azabicyclo[3.1.0]hexane-6-carboxamide. $^1$H NMR (400 MHz, $D_2O$) δ 8.01 (d, 1H), 7.51-7.40 (m, 4H), 6.80 (d, 1H), 3.95-3.60 (m, 13H), 3.37 (d, 1H), 2.90-2.78 (m, 1H), 2.33 (s, 2H), 1.88 (s, 1H), 1.72 (s, 6H), 1.25 (d, 3H). LCMS[M+H] 551.2.

Compound 114

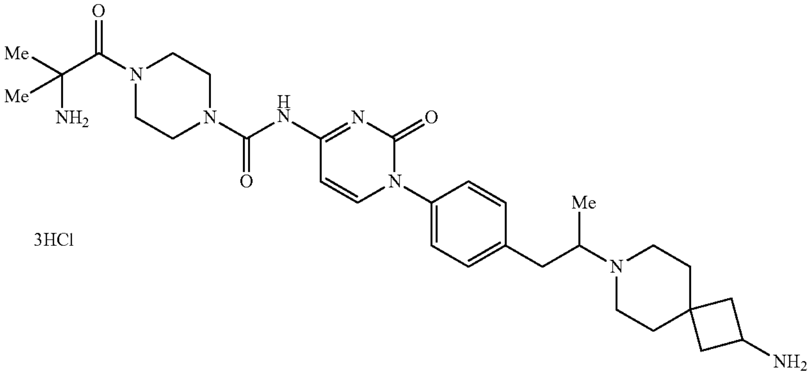

4-(2-Amino-2-methylpropanoyl)-N-(1-(4-(2-(2-amino-7-azaspiro[3.5]nonan-7-yl)propyl)phenyl)-2-oxo-1,2-dihydropyrimidin-4-yl)piperazine-1-carboxamide Hydrochloride Salt This compound was prepared as in scheme C-2 from tert-butyl (2-methyl-1-oxo-1-(4-((2-oxo-1-(4-(2-oxopropyl) phenyl)-1,2-dihydropyrimidin-4-yl)carbamoyl)piperazin-1-yl)propan-2-yl)carbamate and tert-butyl (7-azaspiro[3.5] nonan-2-yl)carbamate. $^1$H NMR (400 MHz, $D_2O$) δ 7.99-7.85 (m, 1H), 7.49 (d, 2H), 7.46 (d, 2H), 6.85 (d, 1H), 3.97-3.84 (m, 1H), 3.79 (s, 3H), 3.74 (s, 6H), 3.57-3.44 (m, 2H), 3.32 (d, 1H), 3.25-3.06 (m, 2H), 2.92 (t, 1H), 2.60-2.49 (m, 1H), 2.40-2.28 (m, 1H), 2.22-1.88 (m, 6H), 1.75 (s, 6H), 1.27 (d, 3H). LCMS[M+H] 565.4.

Compound 177

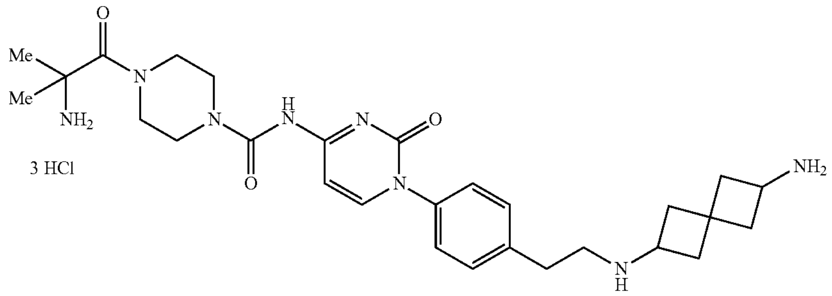

4-(2-amino-2-methylpropanoyl)-N-(1-(4-(2-((6-aminospiro[3.3]heptan-2-yl)amino)ethyl)phenyl)-2-oxo-1,2-dihydropyrimidin-4-yl)piperazine-1-carboxamide Hydrochloride Salt Prepares as in Scheme C-2 from using t-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate and tert-butyl (6-aminospiro[3.3]heptan-2-yl) carbamate. $^1$H NMR (500 MHz, $D_2O$) δ 8.12 (d, 1H), 7.50 (d, 2H), 7.46 (d, 2H), 6.81 (d, 1H), 3.84-3.71 (m, 10H), 3.25 (t, 2H), 3.08 (t, 2H), 2.59-2.53 (m, 2H), 2.45-2.39 (m, 2H), 2.30-2.22 (m, 4H), 1.73 (s, 6H). LCMS[M+H] 537.4.

Compound 176

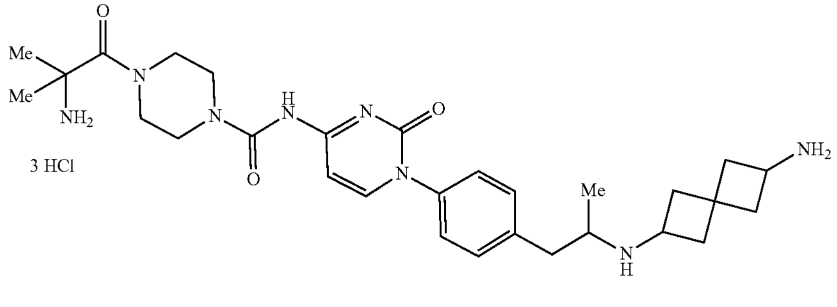

4-(2-Amino-2-methylpropanoyl)-N-(1-(4-(2-((6-aminospiro[3.3]heptan-2-yl)amino)propyl)phenyl)-2-oxo-1,2-dihydropyrimidin-4-yl)piperazine-1-carboxamide Hydrochloride Salt Prepared in a similar fashion to Scheme C-2 from tert-butyl tert-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate and tert-butyl (6-aminospiro[3.3]heptan-2-yl)carbamate. $^1$H NMR (400 MHz, $D_2O$) δ 7.93 (d, 1H), 7.45 (s, 4H), 6.85 (d, 1H), 3.92 (s, 1H), 3.78 (s, 4H), 3.73 (s, 5H), 3.57 (s, 1H), 3.19 (d, 1H), 2.88 (t, 1H), 2.59 (s, 2H), 2.44 (s, 2H), 2.38-2.22 (m, 4H), 1.74 (s, 6H), 1.23 (d, 3H). LCMS[M+H] 551.4.

Compound 190

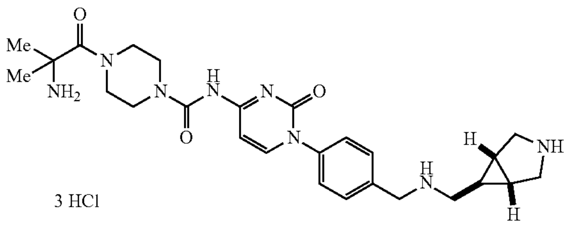

N-(1-(4-4((exo-3-Azabicyclo[3.1.0]hexan-6-yl) methyl)amino)methyl)phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-2 from t-butyl (1-(4-((1-(4-formylphenyl)-2-oxo-1,2-dihydropyrimidin-4-yl)carbamoyl)piperazin-1-yl)-2-methyl-1-oxopropan-2-yl) carbamate and t-butyl exo-6-(aminomethyl)-3-azabicyclo [3.1.0]hexane-3-carboxylate. $^1$H NMR (400 MHz, $D_2O$) δ 7.96 (d, 1H), 7.65 (d, 2H), 7.54 (d, 2H), 6.85 (d, 1H), 4.34 (s, 2H), 3.77 (s, 3H), 3.72 (s, 5H), 3.50 (s, 4H), 3.12 (d, 2H), 1.99 (s, 2H), 1.72 (s, 6H), 1.21 (s, 1H). LCMS [M+H] 509.2.

Compound 204

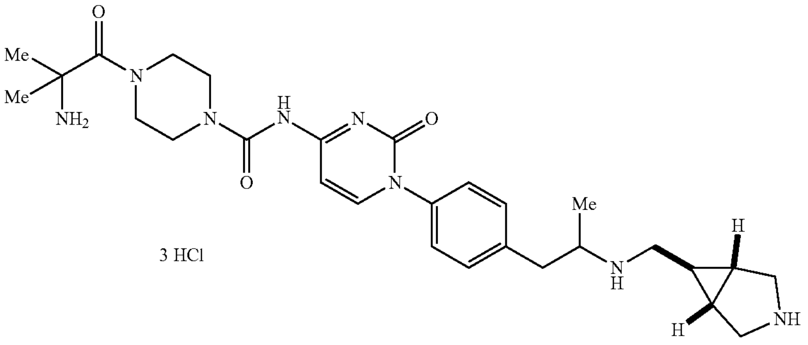

N-(1-(4-(2-(((exo-3-Azabicyclo[3.1.0]hexan-6-yl) methyl)amino)propyl)phenyl)-2-oxo-1,2-dihydropyrimidin-4-yl)-4-(2-amino-2-methyl propanoyl)piperazine-1-carboxamide Hydrochloride Salt Prepared in a similar fashion to Scheme C-2 from t-butyl (2-methyl-1-oxo-1-(4-(2-oxo-1-(4-(2-oxopropyl)phenyl)-1,2-dihydropyrimidin-4-yl)carbamoyl)piperazin-1-yl)propan-2-yl)carbamate and t-butyl exo-6-(aminomethyl)-3-azabicyclo[3.1.0]hexane-3-carboxylate. $^1$H NMR (400 MHz, $D_2O$) δ 7.97 (d, 1H), 7.51-7.39 (m, 4H), 6.83 (d, 1H), 3.85-3.60 (m, 9H), 3.50 (s, 4H), 3.28-3.19 (m, 1H), 3.13 (d, 2H), 2.97-2.86 (m, 1H), 1.99 (s, 2H), 1.72 (s, 6H), 1.26 (d, 3H), 1.19 (s, 1H). LCMS[M+H] 537.4.

Compound 192

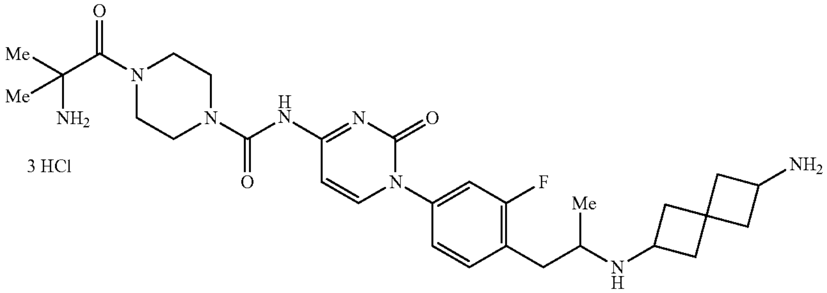

4-(2-Amino-2-methylpropanoyl)-N-(1-(4-(2-((6-aminospiro[3.3]heptan-2-yl)amino)propyl)-3-fluorophenyl)-2-oxo-1,2-dihydropyrimidin-4-yl)piperazine-1-carboxamide Hydrochloride Salt Prepared in a similar fashion to Scheme C-2 from tert-butyl (1-(4-((1-(3-fluoro-4-(2-oxopropyl)phenyl)-2-oxo-1,2-dihydropyrimidin-4-yl)carbamoyl)piperazin-1-yl)-2-methyl-1-oxopropan-2-yl)carbamate and tert-butyl (6-aminospiro[3.3]heptan-2-yl)carbamate. $^1$H NMR (500 MHz, $D_2O$) δ 7.95 (d, 1H), 7.50 (t, 1H), 7.36-7.27 (m, 2H), 6.84 (d, 1H), 4.01-3.89 (m, 1H), 3.84-3.68 (m, 8H), 3.62-3.55 (m, 1H), 3.26-3.21 (m, 1H), 2.91 (t, 2H), 2.65-2.57 (m, 2H), 2.51-2.39 (m, 2H), 2.37-2.23 (m, 4H), 1.73 (s, 6H), 1.23 (d, 3H). LCMS[M+H]569.3.

Compound 202

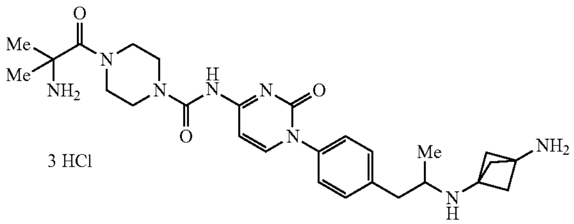

4-(2-Amino-2-methylpropanoyl)-N-(1-(4-(2-((3-aminobicyclo[1.1.1]pentan-1-yl)amino)propyl)phenyl)-2-oxo-1,2-dihydropyrimidin-4-yl)piperazine-1-carboxamide Hydrochloride Salt Prepared in a similar fashion to Scheme C-2 using tert-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate and t-butyl (3-aminobicyclo[1.1.1]pentan-1-yl)carbamate. $^1$H NMR ($D_2O$, 400 MHz): δ 7.74 (d, 1H), 7.31-7.26 (m, 4H), 6.69 (d, 1H), 3.65-3.51 (m, 8H), 3.13-3.01 (m, 1H) 2.79-2.73 (m, 2H), 2.43 (s, 6H), 1.56 (s, 6H), 1.13 (d, 3H). LCMS [M+H] 523.2.

Compound 203

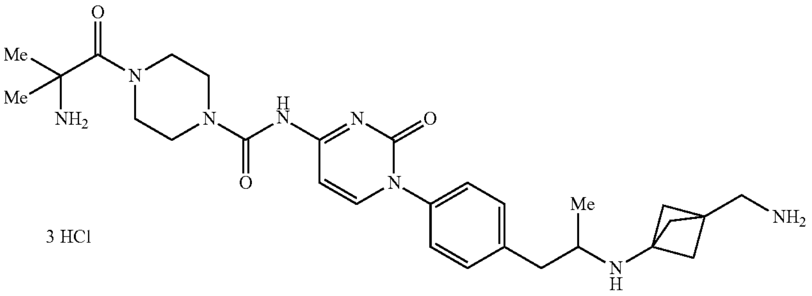

4-(2-Amino-2-methylpropanoyl)-N-(1-(4-(2-((3-(aminomethyl)bicyclo [1.1.1]pentan-1-yl)amino)propyl)phenyl)-2-oxo-1,2-dihydropyrimidin-4-yl)piperazine-1-carboxamide hydrochloride salt Prepared in a similar fashion to Scheme C-2 using tert-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate and t-butyl ((3-aminobicyclo [1.1.1]pentan-1-yl)methyl)carbamate. $^1$H NMR (400 MHz, $D_2O$): δ 7.77 (d, 1H), 7.35-7.29 (m, 4H), 6.72 (d, 1H), 3.69-3.58 (m, 9H), 3.18 (s, 2H), 3.15-3.11 (m, 1H), 2.81-2.75 (m, 1H), 2.16 (s, 6H), 1.60 (s, 6H), 1.16 (d, 3H). LCMS [M+H] 537.2.

Compound 179

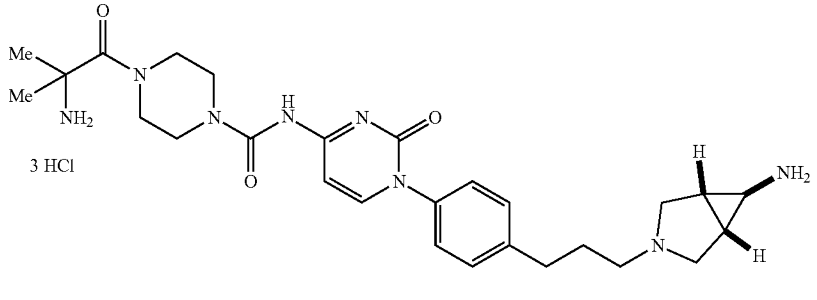

4-(2-Amino-2-methylpropanoyl)-N-(1-(4-(3-(exo-6-amino-3-azabicyclo[3.1.0]hexan-3-yl)propyl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(3-oxopropyl)phenyl)-1,2-dihydropyrimidin-4-yl)carbamoyl)piperazin-1-yl)propan-2-yl)carbamate and tert-butyl (exo-3-azabicyclo[3.1.0]hexan-6-yl)carbamate. $^{1}$H NMR 8.08 (d, 1H), 7.44 (d, 2H), 7.40 (d, 2H), 6.79 (d, 1H), 3.88 (d, 2H), 3.83-3.70 (m, 8), 3.47 (d, 2H), 3.24-3.18 (m, 2H), 2.81-2.74 (m, 3H), 2.36 (s, 2H), 2.10-1.94 (m, 2H), 1.72 (s, 6H). [M+H] 523.2.

Compound 180

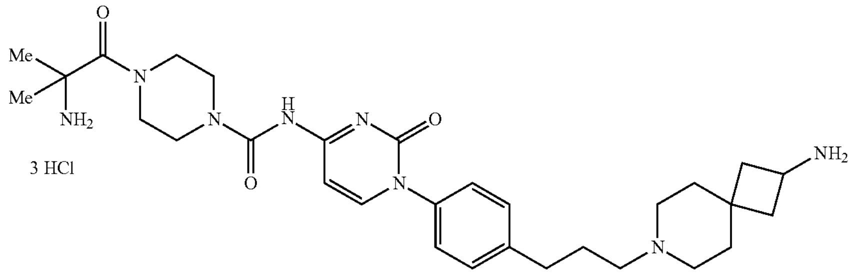

4-(2-Amino-2-methylpropanoyl)-N-(1-(4-(3-(2-amino-7-azaspiro[3.5]nonan-7-yl)propyl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(3-oxopropyl)phenyl)-1,2-dihydropyrimidin-4-yl)carbamoyl)piperazin-1-yl)propan-2-yl)carbamate and tert-butyl (7-azaspiro[3.5]nonan-2-yl)carbamate. $^{1}$H NMR 8.04 (d, 1H), 7.44 (d, 2H), 7.39 (d, 2H), 6.79 (d, 1H), 3.88-3.64 (m, 9H), 3.50-3.39 (m, 2H), 3.11-3.05 (m, 2H), 2.97-2.84 (m, 2H), 2.78 (t, 2H), 2.48-2.42 (m, 1H), 2.31-2.24 (m, 1H), 2.11-1.95 (m, 5H), 1.92-1.77 (m, 3H), 1.71 (s, 6H). [M+H] 565.4.

Compound 184

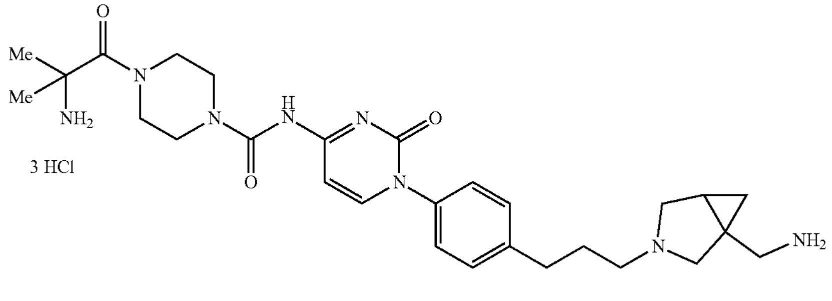

4-(2-Amino-2-methylpropanoyl)-N-(1-(4-(3-(1-(aminomethyl)-3-azabicyclo[3.1.0]hexan-3-yl)propyl) phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(3-oxopropyl)phenyl)-1,2-dihydropyrimidin-4-yl)carbamoyl)piperazin-1-yl) propan-2-yl)carbamate and tert-butyl ((3-azabicyclo[3.1.0] hexan-1-yl)methyl)carbamate. $^1$H NMR 8.14 (d, 1H), 7.45 (d, 2H), 7.41 (d, 2H), 6.79 (d, 1H), 3.88 (d, 1H), 3.85-3.71 (m, 9H), 3.47-3.36 (m, 3H), 3.26-3.19 (m, 2H), 3.11 (d, 1H), 2.79 (t, 2H), 2.10-1.95 (m, 3H), 1.72 (s, 6H), 1.12 (t, 1H), 0.99 (t, 1H). [M+H] 537.4.

Compound 185

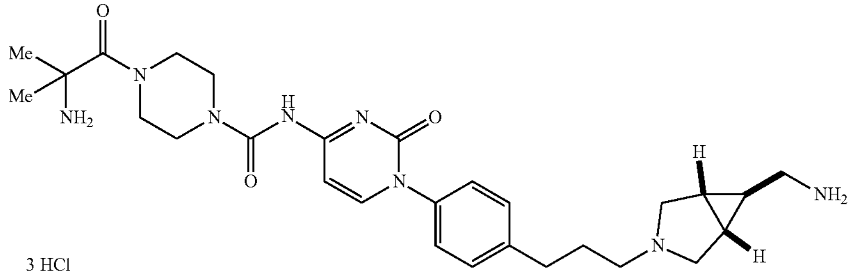

3 HCl 4-(2-Amino-2-methylpropanoyl)-N-(1-(4-(3-(exo-6-(aminomethyl)-3-azabicyclo[3.1.0]hexan-3-yl)propyl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(3-oxopropyl)phenyl)-1,2-dihydropyrimidin-4-yl)carbamoyl)piperazin-1-yl) propan-2-yl)carbamate and exo-1-butyl ((3-azabicyclo [3.1.0]hexan-6-yl)methyl)carbamate. $^1$H NMR 8.15 (d, 1H), 7.44 (d, 2H), 7.40 (d, 2H), 6.78 (d, 1H), 3.82-3.70 (m, 10H), 3.36 (d, 2H), 3.17 (t, 2H), 2.94 (d, 2H), 2.78 (t, 2H), 2.08-1.95 (m, 4H), 1.72 (s, 6H), 1.32-1.27 (m, 1H). [M+H] 537.3.

Compound 212

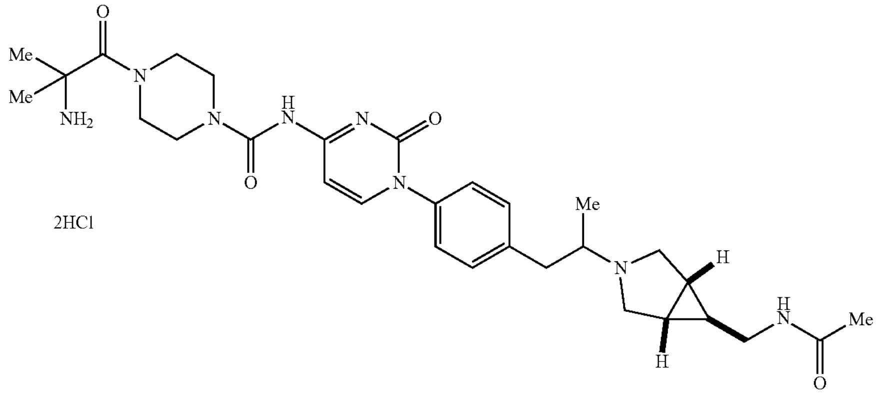

2HCl

N-(1-(4-(2-((exo)-6-(Acetamidomethyl)-3-azabicyclo[3.1.0]hexan-3-yl)propyl)phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-2 from tert-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate and N-((exo-3-azabicyclo[3.1.0]hexan-6-yl)methyl)acetamide. $^1H$ NMR (400 MHz, $D_2O$) δ 8.05 (d, 1H), 7.45 (d, 4H), 6.82 (d, 1H), 3.87-3.67 (m, 10H), 3.67-3.56 (m, 1H), 3.56-3.48 (m, 1H), 3.41-3.34 (m, 1H), 3.14 (d, 2H), 2.88-2.76 (m, 1H), 2.00 (s, 3H), 1.88 (d, 2H), 1.74 (s, 6H), 1.28-1.15 (m, 4H). LCMS[M+H] 579.5

Compound 213

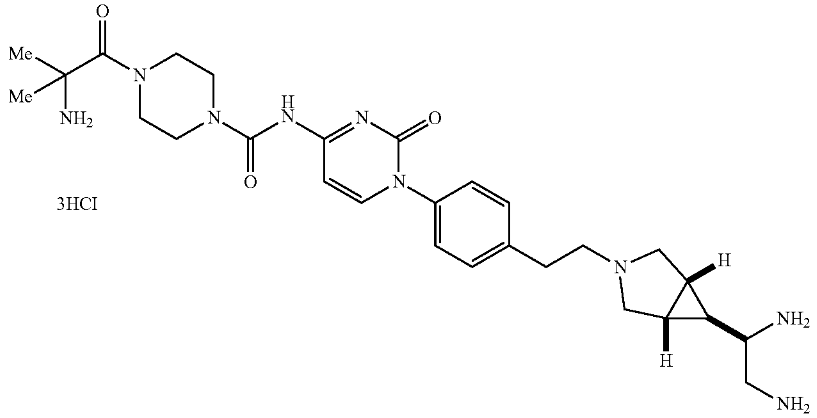

4-(2-Amino-2-methylpropanoyl)-N-(1-(4-(2-(exo-6-(1,2-diaminoethyl)-3-azabicyclo[3.1.0]hexan-3-yl)ethyl)phenyl)-2-oxo-1,2-dihydropyrimidin-4-yl)piperazine-1-carboxamide Hydrochloride Salt Prepared in a similar fashion to Scheme C-2 using tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate (0.10 g, 0.19 mmol), and tert-butyl (2-(exo-3-azabicyclo[3.1.0]hexan-6-yl)-2-((tert-butylsulfinyl)amino)ethyl)carbamate (0.07 g, 0.19 mmol). $^1H$ NMR (500 MHz, $D_2O$): δ 8.09 (d, 1H), 7.53 (d, 2H), 7.48 (d, 2H), 6.84 (d, 1H), 3.97 (d, 1H), 3.92 (d, 1H), 3.83-3.75 (m, 8H), 3.61-3.56 (m, 4H), 3.50 (d, 2H), 3.20-3.08 (m, 3H), 2.35-2.23 (m, 2H), 1.76 (s, 6H), 1.46-1.42 (m, 1H). LCMS [M+H] 552.3.

Compounds 242 and 243 diastereomer 1

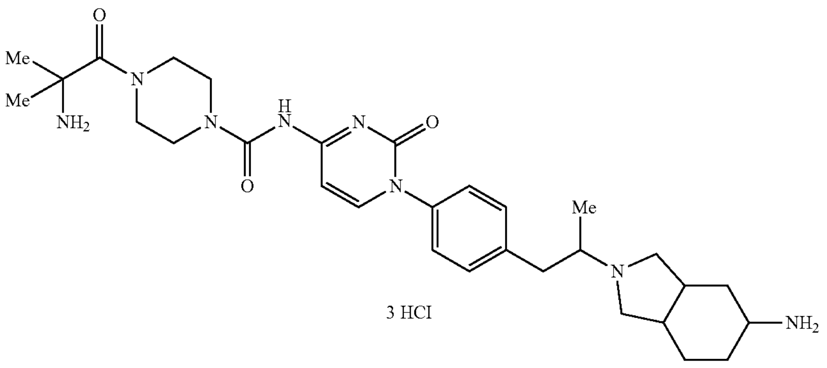

-continued diastereomer 2

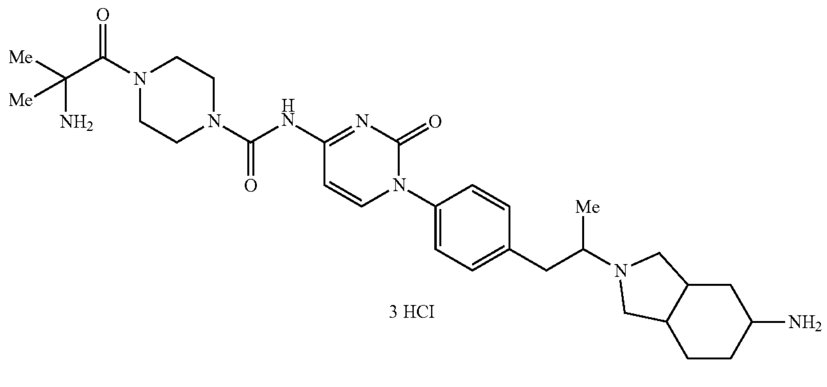

3 HCl 4-(2-Amino-2-methylpropanoyl)-N-(1-(4-(2-(5-aminooctahydro-2H-isoindol-2-yl)propyl)phenyl)-2-oxo-1,2-dihydropyrimidin-4-yl)piperazine-1-carboxamide Hydrochloride Salt Step 1: tert-butyl (2-(1-(4-(4-(4-(2-((tert-butoxycarbonyl)amino)-2-methylpropanoyl)piperazine-1-carboxamido)-2-oxopyrimidin-1 (2H)-yl)phenyl)propan-2-yl)octahydro-1H-isoindol-5-yl)carbamate. To a stirred solution tert-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate (0.2 g, 0.4 mmol) and tert-butyl (octahydro-1H-isoindol-5-yl)carbamate (0.11 g, 0.4 mmol) in MeOH (5.0 mL) were added $NaBH_3CN$ (0.05 g, 0.7 mmol) at 0° C. under $N_2$ atmosphere. The reaction mixture was stirred at rt for 48 h. The reaction mixture concentrated under reduced pressure and purified by column chromatography (7% MeOH in DCM) to afford the title compound as white solid (0.26 g, 90%). The mixture of diastereomers were separated by semipreparative HPLC on an YMC CHIRALART CELLULOSE-SC, 250×20 mm, 5 nm with isocratic conditions (A:B)=87-13 with mobile phases (A) 0.1% Diethyl amine in methyl tert butyl ether and (B) MeOH. $^1H$ NMR (400 MHz, $D_2O$): Mixture of rotamers, 7.82 (d, 1H), 7.42-7.25 (m, 4H), 6.70 (d, 1H), 3.49-3.40 (m, 9H), 3.34-3.22 (m, 6H), 2.76 (bs, 2H), 2.35 (bs, 1H), 2.04-2.01 (m, 1H), 1.92 (s, 2H), 1.78 (s, 1H), 1.67 (s, 6H), 1.36 (s, 2H), 1.12 (s, 3H). LCMS[M+2H/2] 383.7

Step 2: 4-(2-amino-2-methylpropanoyl)-N-(1-(4-(2-(5-aminooctahydro-2H-isoindol-2-yl)propyl)phenyl)-2-oxo-1,2-dihydropyrimidin-4-yl)piperazine-1-carboxamide hydrochloride salt. To a stirred solution of tert-butyl (2-(1-(4-(4-(4-(2-((tert-butoxycarbonyl)amino)-2-methylpropanoyl)piperazine-1-carboxamido)-2-oxopyrimidin-1 (2H)-yl)phenyl)propan-2-yl)octahydro-1H-isoindol-5-yl)carbamate (Isomer-1) (0.02 g, 0.02 mmol) in dioxane (2.0 mL) was added 4 M HCl in dioxane (2.0 mL) at 0° C. The reaction mixture was stirred at rt for 5 h. The reaction mixture was concentrated under reduced pressure to afford diastereomer 1 of the title compound (0.02 g, 77%) as off white solid. NMR (400 MHz, $D_2O$): Mixture of rotamers, 7.82 (d, 1H), 7.42-7.25 (m, 4H), 6.70 (d, 1H), 3.49-3.40 (m, 9H), 3.34-3.22 (m, 6H), 2.76 (bs, 2H), 2.35 (bs, 1H), 2.04-2.01 (m, 1H), 1.92 (s, 2H), 1.78 (s, 1H), 1.67 (s, 6H), 1.36 (s, 2H), 1.12 (s, 3H). LCMS[M+H] 565.4. LCMS[M+2H/2] 283.4.

Isomer-2 was prepared in a similar fashion to afford diastereomer 2. LCMS[M+2H/2] 283.3.

Compound 238

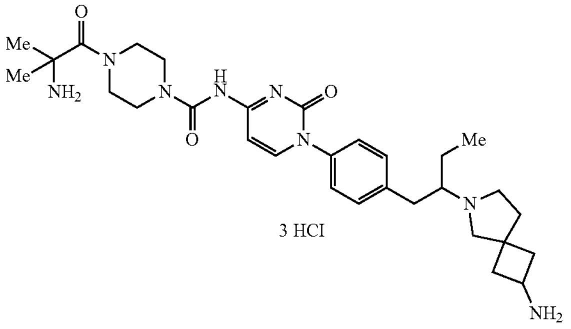

3 HCl 4-(2-Amino-2-methylpropanoyl)-N-(1-(4-(2-(2-amino-6-azaspiro[3.4]octan-6-yl)butyl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(2-oxobutyl)phenyl)-1,2-dihydropyrimidin-4-yl)carbamoyl)piperazin-1-yl)propan-2-yl)carbamate and tert-butyl (6-azaspiro[3.4]octan-2-yl)carbamate. $^1H$ NMR (400 MHz, $D_2O$): δ 7.82 (d, 1H), 7.38-7.34 (m, 4H), 6.73 (d, 1H), 3.78-3.54 (m, 10H), 3.55-3.28 (m, 3H), 3.11-2.98 (m, 3H), 2.49-2.37 (m, 3H), 2.27-2.19 (m, 3H), 2.11-1.92 (m, 2H), 1.62 (s, 6H), 0.86 (s, 3H). LCMS[M+H] 565.5.

Compound 214

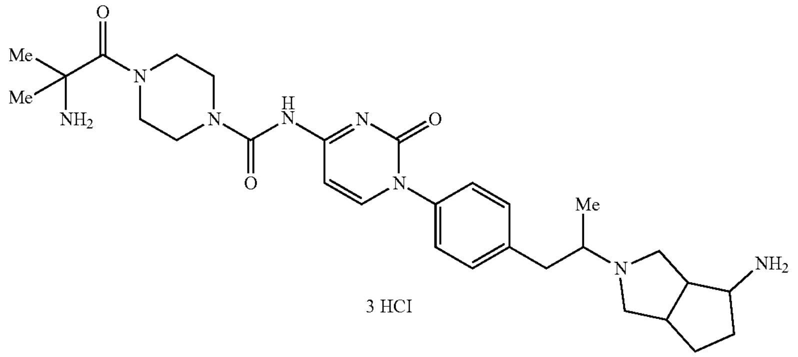

3 HCl 4-(2-Amino-2-methylpropanoyl)-N-(1-(4-(2-(4-aminohexahydrocyclopenta[c]pyrrol-2 (1H)-yl)propyl) phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(2-oxopropyl)phenyl)-1,2-dihydropyrimidin-4-yl)carbamoyl)piperazin-1-yl) propan-2-yl)carbamate and tert-butyl (octahydrocyclopenta [c]pyrrol-4-yl)carbamate. $^1$H NMR (400 MHz, $D_2O$): 7.87 (d, 1H), 7.39-7.29 (m, 4H), 6.67 (d, 1H), 3.96-3.86 (m, 1H), 3.75-3.71 (m, 1H), 3.65-3.51 (m, 4H), 3.58-3.50 (m, 7H), 3.44-3.42 (m, 1H), 3.27-3.25 (m, 2H), 3.05-3.01 (m, 1H), 2.99-2.86 (m, 1H), 2.83-2.71 (m, 2H), 2.09-1.99 (m, 1H), 1.83-1.71 (m, 1H), 1.58 (s, 6H), 1.15 (d, 3H). LCMS[M+H] 551.2.

Compound 215

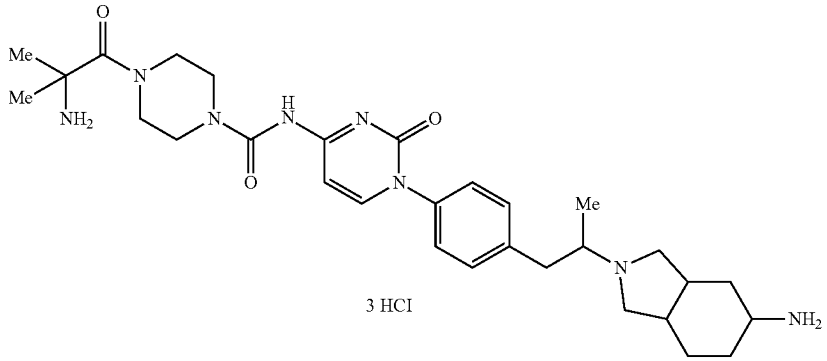

3 HCl 4-(2-Amino-2-methylpropanoyl)-N-(1-(4-(2-(5-aminooctahydro-2H-isoindol-2-yl)propyl)phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(2-oxopropyl)phenyl)-1,2-dihydropyrimidin-4-yl)carbamoyl)piperazin-1-yl) propan-2-yl)carbamate and tert-butyl (octahydro-1H-isoindol-5-yl)carbamate. $^1$H NMR (400 MHz, $D_2O$): Mixture of rotamers, 7.82 (d, 1H), 7.42-7.25 (m, 4H), 6.70 (d, 1H), 3.49-3.40 (m, 9H), 3.34-3.22 (m, 6H), 2.76 (bs, 2H), 2.35 (bs, 1H), 2.04-2.01 (m, 1H), 1.92 (s, 2H), 1.78 (s, 1H), 1.67 (s, 6H), 1.36 (s, 2H), 1.12 (s, 3H). LCMS[M+H] 565.4.

Compound 216

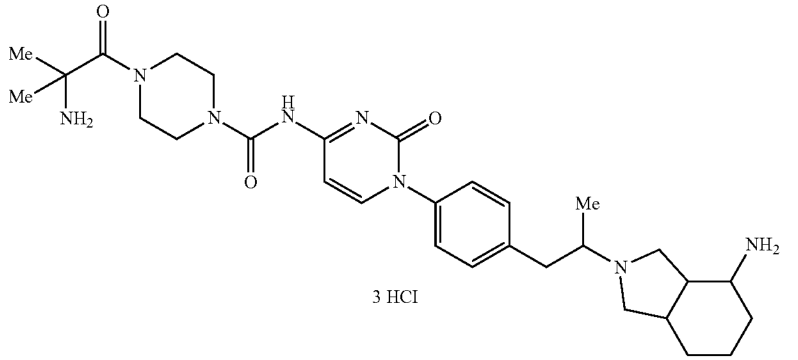

3 HCl 4-(2-Amino-2-methylpropanoyl)-N-(1-(4-(2-(4-aminooctahydro-2H-isoindol-2-yl)propyl) phenyl)-2-oxo-1,2-dihydropyrimidin-4-yl)piperazine-1-carboxamide Hydrochloride Salt Prepared in a similar fashion to Scheme C-2 from tert-butyl (2-methyl-1-oxo-1-(4-((2-oxo-1-(4-(2-oxopropyl)phenyl)-1,2-dihydropyrimidin-4-yl)carbamoyl)piperazin-1-yl) propan-2-yl)carbamate and tert-butyl (octahydro-1H-isoindol-4-yl)carbamate. $^1$H NMR ($D_2O$, 400 MHz): Mixture of rotamers, 7.82 (d, 1H), 7.36-7.29 (m, 4H), 6.69 (d, 1H), 3.76-3.74 (m, 4H), 3.63-3.59 (m, 6H), 3.51-3.48 (m, 1H), 3.46-3.37 (m, 1H), 3.34-3.18 (m, 2H), 2.80-2.67 (m, 2H), 2.49 (bs, 1H), 1.79-1.76 (m, 2H), 1.59 (s, 6H), 1.43-1.39 (m, 2H), 1.29-1.26 (m, 1H), 1.19-1.13 (m, 3H). LCMS [M+H] 565.2.

Compounds 13, 20 and 23

Racemate

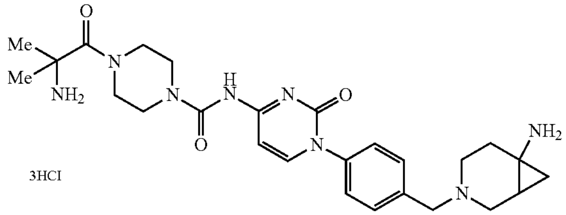

3HCl

Enantiomer 1

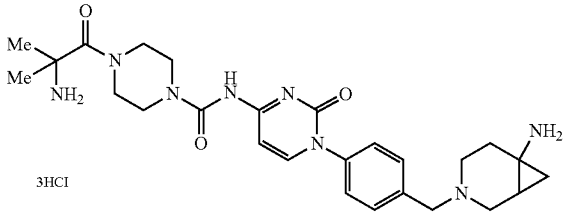

3HCl

-continued

Enantiomer 2

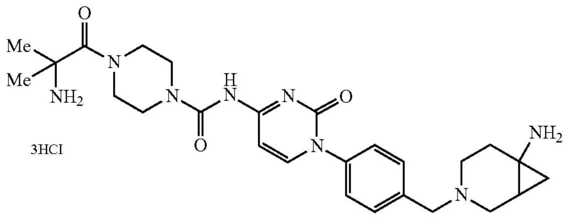

3HCl 4-(2-Amino-2-methylpropanoyl)-N-{1[4-({6-amino-3-azabicyclo [4.1.0] heptan-3-yl}methyl)phenyl]-2-oxo-1,2-dihydropyrimidin-4-yl}piperazine-1-carboxamide Hydrochloride Salt Step 1: tert-butyl N-(3-{[4-(4-{[4-(2-{[(tert-butoxy)carbonyl]amino}-2-methylpropanoyl)piperazine-1-carbonyl] amino}-2-oxo-1,2-dihydropyrimidin-1-yl)phenyl]methyl}-3-azabicyclo [4.1.0] heptan-6-yl)carbamate. Prepared in a similar fashion to Scheme C-2 from tert-butyl N-[1-(4-{[1-(4-formylphenyl)-2-oxo-1,2-dihydropyrimidin-4-yl] carbamoyl}piperazin-1-yl)-2-methyl-1-oxopropan-2-yl]carbamate (50.0 mg, 0.098 mmol) and tert-butyl N-{3-azabicyclo[4.1.0]heptan-6-yl}carbamate (prepared according to procedures reported in WO2015148597, 31.2 mg, 0.147 mmol) to afford the title compound (61.0 mg, 88%) as a white solid. $^1$H NMR (400 MHz, $CDCl_3$) δ 12.94 (br. s., 1H), 7.42 (d, 2H), 7.32-7.24 (m, 3H), 5.83 (d, 1H), 5.10-4.73 (m, 2H), 4.01-3.37 (m, 10H), 2.88-2.65 (m, 2H), 2.43-1.94 (m, 4H), 1.72-1.20 (m, 25H), 0.91-0.74 (m, 2H). LCMS (Method A): m/z=709.7 $[M+H]^+$0.63 min.

The crude racemate (80.0 mg, 0.156 mmol) was resolved by chiral HPLC on a Chiralpak AD-H (25×2.0 cm), 5 μm column using a mobile phase of n-hexane/(ethanol+0.1% isopropylamine) 30/70% v/v and a flow rate of 17 mL/min to afford the two separated enantiomers of the title compound. First eluting (Enantiomer 1): (24.1 mg, 22%). $^1$H NMR (400 MHz, $CDCl_3$) δ 7.42 (d, 2H), 7.33-7.24 (m, 3H), 5.83 (d, 1H), 5.11-4.70 (m, 2H), 4.00-3.58 (m, 8H), 3.56-3.41 (m, 2H), 2.79-2.65 (m, 2H), 2.43-2.11 (m, 3H), 2.10-1.95 (m, 1H), 1.72-1.18 (m, 25H), 0.90-0.75 (m, 2H). (LCMS (Method A): m/z=709.7 $[M+H]^+$ 0.63 min. Second eluting, (Enantiomer 2): (21.2 mg, 19%). $^1$H NMR (400 MHz, $CDCl_3$) δ 7.42 (d, 2H), 7.33-7.24 (m, 3H), 5.83 (d, 1H), 5.11-4.70 (m, 2H), 4.00-3.58 (m, 8H), 3.56-3.41 (m, 2H), 2.79-2.65 (m, 2H), 2.43-2.11 (m, 3H), 2.10-1.95 (m, 1H), 1.72-1.18 (m, 25H), 0.90-0.75 (m, 2H). (Note: exchangeable urea NH not identified). LCMS [M+H] 709.7

Steps 2: 4-(2-Amino-2-methylpropanoyl)-N-{1-[4-({6-amino-3-azabicyclo[4.1.0]heptan-3-yl}methyl)phenyl]-2-oxo-1,2-dihydropyrimidin-4-yl}piperazine-1-carboxamide hydrochloride salt. Prepared in a similar fashion to Scheme AD from tert-butyl N-(3-{[4-(4-{[4-(2-{[(tert-butoxy)carbonyl]amino}-2-methylpropanoyl)piperazine-1-carbonyl]amino}-2-oxo-1,2-dihydropyrimidin-1-yl)phenyl]methyl}-3-azabicyclo[4.1.0]heptan-6-yl)carbamate (racemate, 58.0 mg, 0.082 mmol) to afford the title compound as its trihydrochloride salt (43.0 mg, 85%) as an off-white solid. $^1$H NMR (400 MHz, $D_2O$) δ 7.90 (d, 1H), 7.65 (d, 2H), 7.55 (d, 2H), 6.84 (d, 1H), 4.49-4.16 (m, 2H), 4.06-2.74 (m, 12H), 2.67-2.18 (m, 2H), 1.86-1.62 (m, 7H), 1.45 (dd, 1H), 1.28-1.03 (m, 1H). LCMS $[M+H]^+$ 509.2.

Enantiomerically pure isomers of the title compound were prepared by running the Boc-deprotection on to the single enantiomers of tert-butyl N-(3-{[4-(4-{[4-(2-{[(tert-butoxy)carbonyl]amino}-2-methylpropanoyl)piperazine-1-carbonyl]amino}-2-oxo-1,2-dihydropyrimidin-1-yl)phenyl]methyl}-3-azabicyclo[4.1.0]heptan-6-yl)carbamate according to the procedure described in Scheme AD. Enantiomer 1 (85%) as a yellow solid. $^1$H NMR (400 MHz, $D_2O$) δ 7.82 (d, 1H), 7.59 (d, 2H), 7.48 (d, 2H), 6.78 (d, 1H), 4.40-4.18 (m, 2H), 3.93-2.72 (m, 12H), 2.60-2.27 (m, 2H), 1.77-1.58 (m, 7H), 1.38 (dd, 7.9 Hz, 1H), 1.20-1.04 (m, 1H). LCMS[M+H] 509.5 Enantiomer 2 (74%) as a yellow solid. $^1$H NMR (400 MHz, $D_2O$) δ 7.80 (d, 1H), 7.57 (d, 2H), 7.46 (d, 2H), 6.76 (d, 1H), 4.40-4.18 (m, 2H), 3.93-2.70 (m, 12H), 2.55-2.26 (m, 2H), 1.77-1.56 (m, 7H), 1.36 (dd, 7.8 Hz, 1H), 1.17-1.01 (m, 1H). LCMS[M+H] 509.5.

Compound 21 and 22

Diastereomer 1

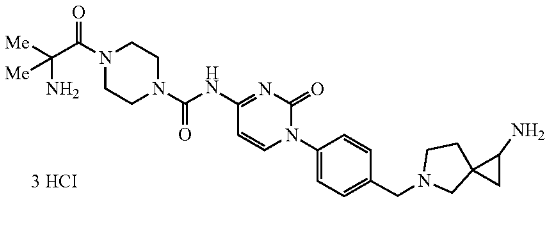

3 HCl

Diastereomer 2

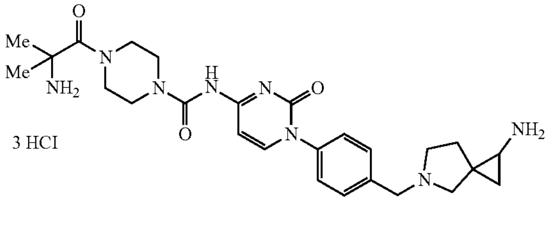

3 HCl 4-(2-Amino-2-methylpropanoyl)-N-{1-[4-({1-amino-5-azaspiro[2.4]heptan-5-yl}methyl)phenyl]-2-oxo-1,2-dihydropyrimidin-4-yl}piperazine-1-carboxamide Hydrochloride Salt Step 1: tert-butyl N-{1-[4-({1-[4-({1-amino-5-azaspiro[2.4]heptan-5-yl}methyl)phenyl]-2-oxo-1,2-dihydropyrimidin-4-yl}carbamoyl)piperazin-1-yl]-2-methyl-1-oxopropan-2-yl}carbamate. Prepared in a similar fashion to Scheme C-2 from tert-butyl N-[1-(4-{[1-(4-formylphenyl)-2-oxo-1,2-dihydropyrimidin-4-yl]carbamoyl}piperazin-1-yl)-2-methyl-1-oxopropan-2-yl]carbamate (200 mg, 0.390 mmol) and tert-butyl N-{5-azaspiro[2.4]heptan-1-yl}carbamate (124 mg, 0.585 mmol) to afford the title compound (174 mg, 63%). The mixture of diastereoisomers was separated by semipreparative HPLC on an XSelect CSH Prep. $C_{18}$ (30×100 mm), 5 μm column using a mobile phase of A: ($H_2O$+0.1% HCOOH)/B: $CH_3CN$, flow rate: 40 mL/min, runtime=15.0 min, gradient: t=0 min 3% B, t=2 min 25% B, t=10 min 25% B, t=10.5 min 100% B, t=14.5 min 100% B, t=15 min 3% B, stop time: 16 min, to afford the two separated isomers: First eluting isomer, Isomer 1 (30.0 mg, 11%). LCMS $[M+I-1]^+$709.6 Second eluting isomer, Isomer 2 (6.2 mg, 2%). LCMS $[M+H]^+$ 709.6.

Step 2: 4-(2-amino-2-methylpropanoyl)-N-{1-[4-({1-amino-5-azaspiro[2.4]heptan-5-yl}methyl)phenyl]-2-oxo-1,2-dihydropyrimidin-4-yl}piperazine-1-carboxamide hydrochloride salt. Prepared from single isomers of tert-butyl N-{1-{4-({1-[4-({1-amino-5-azaspiro[2.4]heptan-5-yl}methyl)phenyl]-2-oxo-1,2-dihydropyrimidin-4-yl}carbamoyl) piperazin-1-yl}-2-methyl-1-oxopropan-2-yl}carbamate. Diastereoisomer 1: (86%) as a yellow solid. $^1$H NMR (400 MHz, $D_2O$) δ 7.83 (d, 1H), 7.63 (d, 2H), 7.49 (d, 2H), 6.79 (d, 1H), 4.51 (s, 2H), 3.88-3.25 (m, 12H), 2.99-2.73 (m, 1H), 2.32-1.87 (m, 2H), 1.65 (s, 6H), 1.46-1.17 (m, 1H), 1.10 (br. s., 1H). LCMS $[M+H]^+$ 509.6. Diastereoisomer 2 (77%) as a yellow solid. $^1$H NMR (400 MHz, $D_2O$) δ 7.79 (d, 1H), 7.57 (d, 2H), 7.44 (d, 2H), 6.74 (d, 1H), 4.51-4.30 (m, 2H), 3.88-3.13 (m, 12H), 2.90-2.66 (m, 1H), 2.41-1.95 (m, 2H), 1.61 (s, 6H), 1.38-0.88 (m, 2H). LCMS $[M+H]^+$ 509.5.

Compound 30

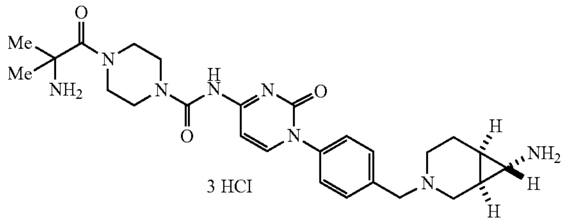

3 HCl 4-(2-Amino-2-methylpropanoyl)-N-(1-(4-(((1R,6R,7S)-7-amino-3-azabicyclo[4.1.0]heptan-3-yl)methyl)phenyl)-2-oxo-1,2-dihydropyrimidin-4-yl)piperazine-1-carboxamide Hydrochloride Salt Prepared in a similar fashion to Scheme C-2 from tert-butyl N-[1-(4-{[1-(4-formylphenyl)-2-oxo-1,2-dihydropyrimidin-4-yl]carbamoyl}piperazin-1-yl)-2-methyl-1-oxopropan-2-yl]carbamate and tert-butyl ((1R,6R,7S)-3-azabicyclo[4.1.0]heptan-7-yl)carbamate.

Compound 217
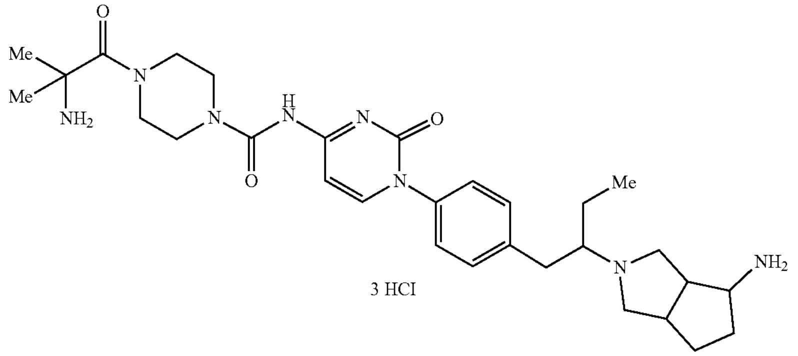
4-(2-Amino-2-methylpropanoyl)-N-(1-(4-(2-(4-aminohexahydrocyclopenta[c] pyrrol-2 (1H)-yl)butyl) phenyl)-2-oxo-1,2-dihydropyrimidin-4-yl)piperazine-1-carboxamide Hydrochloride Salt
Scheme C-3
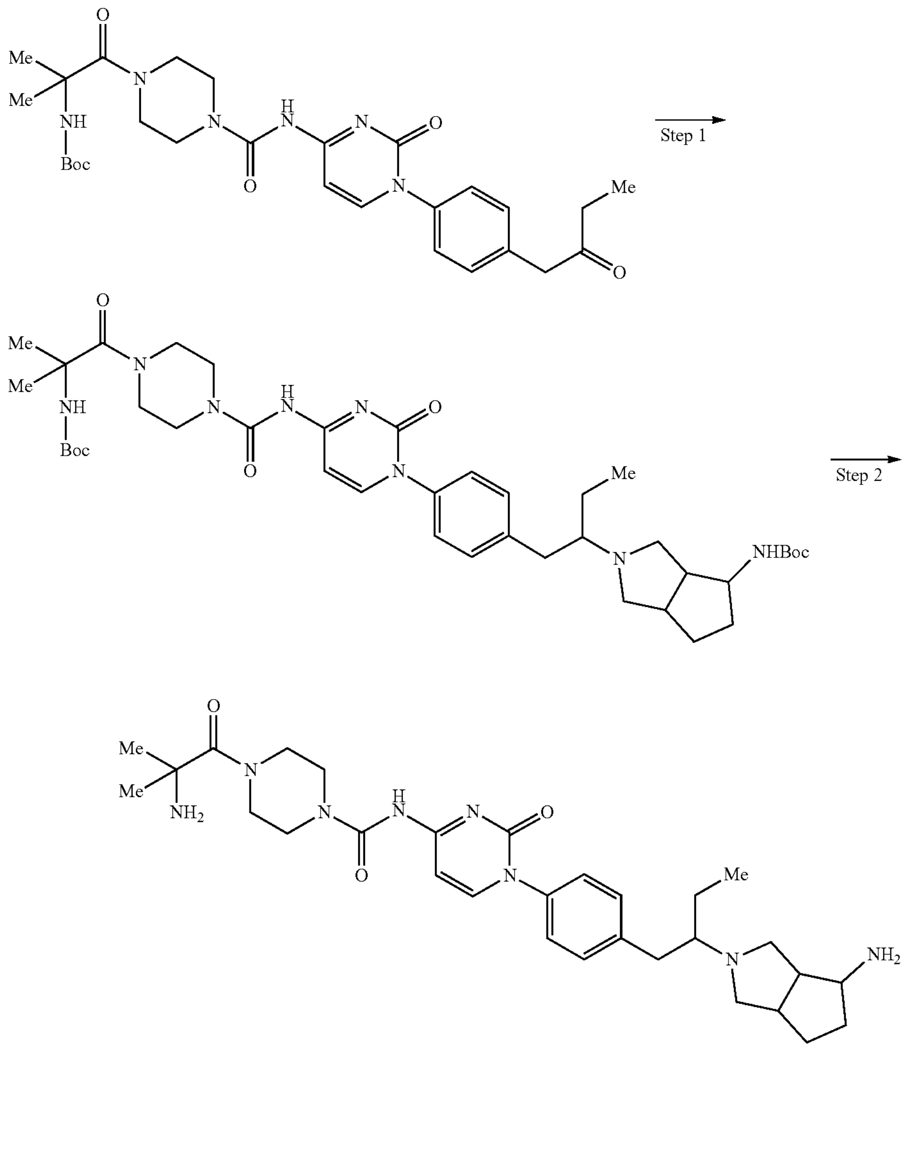

Reagents: 1) tert-butyl (octahydrocyclopenta[c]pyrrol-4-yl)carbamate, $NaBH_3CN$, 4 Å MS, DCE, rt, 48 h 2) 4M HCl in dioxane, rt, 4 h.

Step 1: tert-butyl (2-(1-(4-(4-(4-(2-((tert-butoxycarbonyl) amino)-2-methylpropanoyl) piperazine-1-carboxamido)-2-oxopyrimidin-1 (2H)-yl)phenyl)butan-2-yl)octahydro-1H-isoindol-4-yl)carbamate. To a stirred solution of tert-butyl (2-methyl-1-oxo-1-(4-((2-oxo-1-(4-(2-oxobutyl)phenyl)-1, 2-dihydropyrimidin-4-yl)carbamoyl)piperazin-1-yl)propan-2-yl)carbamate (0.25 g, 0.5 mmol) and tert-butyl (octahydro-1H-isoindol-4-yl)carbamate (0.13 g, 0.5 mmol) in DCE (5.0 mL), were added $NaBH_3CN$ (0.06 g, 0.9 mmol) at 0° C. atmosphere. The reaction mixture was stirred at rt for 48 h. The reaction mixture concentrated under reduced pressure and purified by column chromatography (7% MeOH in $CH_2Cl_2$) to afford the title compound as white solid (0.22 g). LCMS[M+H] 779.5.

Step 2: 4-(2-Amino-2-methylpropanoyl)-N-(1-(4-(2-(4-aminohexahydrocyclopenta [c]pyrrol-2 (1H)-yl)butyl)phenyl)-2-oxo-1,2-dihydropyrimidin-4-yl)piperazine-1-carboxamide hydrochloride salt. To a stirred solution of tert-butyl (2-(1-(4-(4-(4-(2-((tert-butoxycarbonyl)amino)-2-methylpropanoyl)piperazine-1-carboxamido)-2-oxopyrimidin-1 (2H)-yl)phenyl)butan-2-yl)octahydro-1H-isoindol-4-yl)carbamate (0.22 g, 0.3 mmol) in dioxane (2.0 mL) was added 4 M HCl in dioxane (3.0 mL) at 0° C. The reaction mixture was stirred at rt for 4 h. The reaction mixture was concentrated under reduced pressure and purified by Prep HPLC to afford the title compound (0.03 g, 20%) as an off white solid. LCMS[M+H] 565.3.

Compound 218

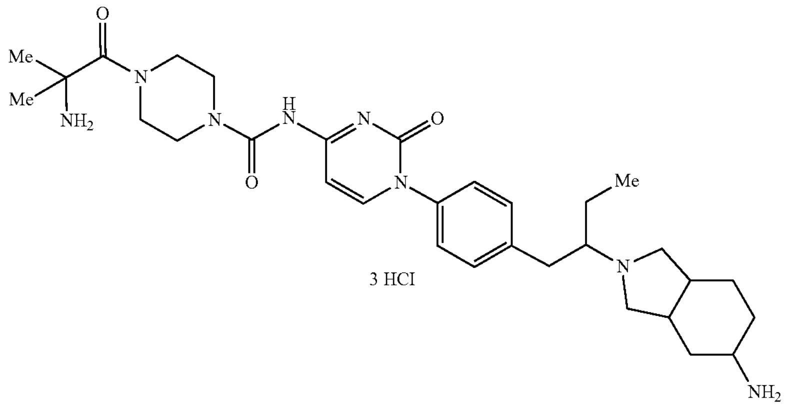

3 HCl

-

4-(2-Amino-2-methylpropanoyl)-N-(1-(4-(2-(5-aminooctahydro-2H-isoindol-2-yl)butyl)phenyl)-2-oxo-1,2-dihydropyrimidin-4-yl)piperazine-1-carboxamide Hydrochloride Salt Prepared in a similar fashion to Scheme C-3 from tert-butyl (2-methyl-1-oxo-1-(4-((2-oxo-1-(4-(2-oxobutyl)phenyl)-1,2-dihydropyrimidin-4-yl)carbamoyl)piperazin-1-yl) propan-2-yl)carbamate and tert-butyl (octahydro-1H-isoindol-5-yl)carbamate. $^1H$ NMR (400 MHz, $D_2O$): δ 7.75 (d, 1H), 7.36 (d, 2H), 7.29 (d, 2H), 6.70 (d, 1H), 3.70-3.57 (m, 7H), 3.49-3.35 (m, 2H), 3.29-3.20 (m, 2H), 3.12-3.05 (m, 2H), 2.97-2.95 (m, 2H), 2.80-2.74 (m, 1H), 2.55-2.50 (m, 2H), 2.40-2.31 (m, 1H), 2.10-1.99 (m, 1H), 1.90-1.85 (m, 1H), 1.80-1.79 (m, 1H), 1.71-1.62 (m, 2H), 1.59 (s, 6H), 1.40-1.31 (m, 2H), 0.85-0.78 (m, 3H). LCMS[(M+2H)/2] 290.2

Compound 219

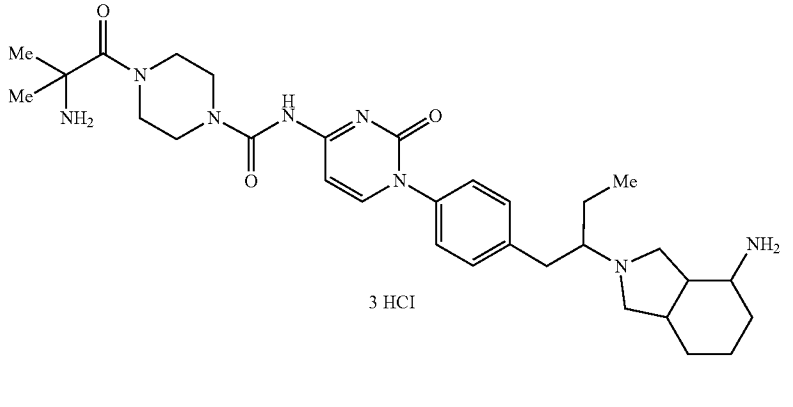

3 HCl 4-(2-Amino-2-methylpropanoyl)-N-(1-(4-(2-(4-aminooctahydro-2H-isoindol-2-yl)butyl)phenyl)-2-oxo-1,2-dihydropyrimidin-4-yl) piperazine-1 carboxamide Hydrochloride Salt Prepared in a similar fashion to Scheme C-3 from tert-butyl (2-methyl-1-oxo-1-(4-((2-oxo-1-(4-(2-oxobutyl)phenyl)-1,2-dihydropyrimidin-4-yl)carbamoyl)piperazin-1-yl)propan-2-yl)carbamate and tert-butyl (octahydro-1H-isoindol-4-yl)carbamate. $^1$H NMR (400 MHz, $D_2O$): δ 7.93 (d, 2H), 7.51-7.37 (m, 2H), 7.32 (d, 2H), 6.67 (d, 1H), 3.71-3.59 (m, 8H), 3.46-3.38 (m, 2H), 3.21-3.14 (m, 2H), 3.04-2.98 (m, 1H), 2.79-2.60 (m, 1H), 2.52-2.36 (m, 1H), 1.85-1.74 (m, 2H), 1.58 (s, 6H), 1.49-1.42 (m, 2H), 1.25-1.23 (m, 1H), 0.85-0.76 (m, 3H). LCMS[M+H] 579.3.

(10.0 mL) were added $NaBH_3CN$ (0.11 g, 1.8 mmol) at 0° C. under $N_2$ atm. The reaction mixture was stirred at rt for 24 h. The reaction mixture poured into $H_2O$ (70 mL) and extracted with DCM (4×30 mL). The combined organic phase was dried over $Na_2SO_4$, concentrated under reduced pressure and purified by column chromatography (7% MeOH in DCM) to afford the title compound as white solid (0.35 g, 50%). LCMS[M+H] 779.6. The mixture of diastereomers were separated by semipreparative HPLC on an YMC CHIRALART CELLULOSE-SC, 250×20 mm, 5 µm with isocratic conditions (A:B)=85-15 with mobile phases (A) methyl tert butyl ether and (B) 0.1% diethyl amine in MeOH and flow rate 20 ml/min. Isomer-1: 90 mg. Isomer-2: 180 mg.

Compound 244 and 245

Diastereomer 1

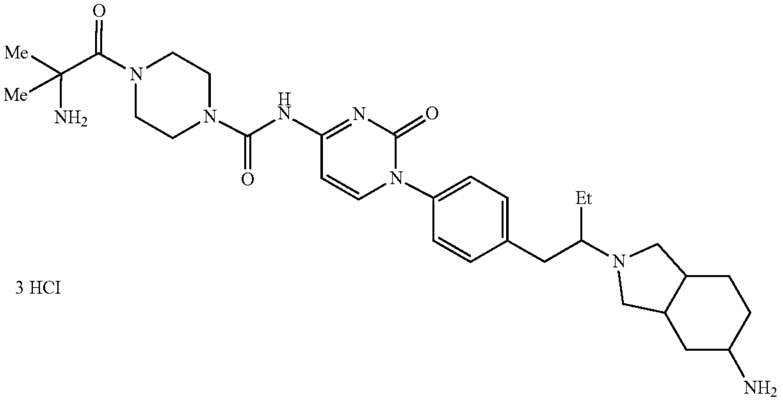

3 HCl

Diastereomer 2

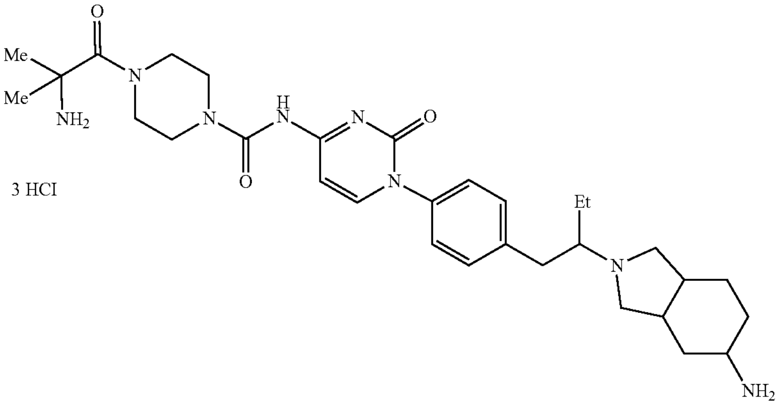

3 HCl 4-(2-Amino-2-methylpropanoyl)-N-(1-(4-(2-(5-aminooctahydro-2H-isoindol-2-yl)butyl)phenyl)-2-oxo-1,2-dihydropyrimidin-4-yl)piperazine-1-carboxamide Hydrochloride Salt Step 1: tert-butyl (2-(1-(4-(4-(4-(2-((tert-butoxycarbonyl)amino)-2-methylpropanoyl) piperazine-1-carboxamido)-2-oxopyrimidin-1 (2H)-yl)phenyl)butan-2-yl)octahydro-1H-isoindol-5-yl)carbamate. To a stirred solution tert-butyl (2-methyl-1-oxo-1-(4-((2-oxo-1-(4-(2-oxobutyl)phenyl)-1,2-dihydropyrimidin-4-yl)carbamoyl)piperazin-1-yl)propan-2-yl) carbamate (0.5 g, 0.9 mmol) and tert-butyl (octahydro-1H-isoindol-5-yl)carbamate (0.26 g, 1.1 mmol) in DCE Step 2: 4-(2-amino-2-methylpropanoyl)-N-(1-(4-(2-(5-aminooctahydro-2H-isoindol-2-yl)butyl) phenyl)-2-oxo-1,2-dihydropyrimidin-4-yl)piperazine-1-carboxamide hydrochloride salt. To a stirred solution of tert-butyl (2-(1-(4-(4-(4-(2-((tert-butoxy carbonyl)amino)-2-methylpropanoyl) piperazine-1-carboxamido)-2-oxopyrimidin-1 (2H)-yl)phenyl)butan-2-yl)octahydro-1H-isoindol-5-yl)carbamate (Isomer-1) (0.09 g, 0.1 mmol) in dioxane (2.0 mL) was added 4 M HCl in dioxane (2.0 mL) at 0° C. The reaction mixture was stirred at rt for 5 h. The reaction mixture was concentrated under reduced pressure and purified by Prep HPLC to afford the title compound (0.028 g, 35%) as off white solid. Isomer:1 LCMS[M+H] 579.6.

Isomer-2 was prepared in a similar fashion to afford diastereomer 2 LCMS[M+H] 579.6.
Compound 208
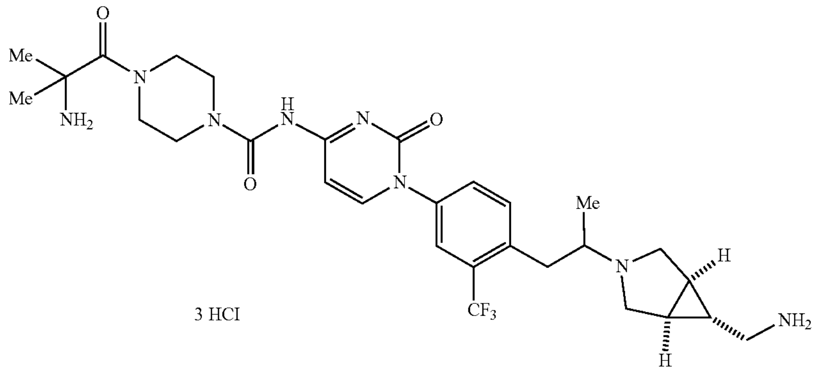
3 HCl
Exo-4-(2-Amino-2-methylpropanoyl)-N-(1-(4-(2-(6-(aminomethyl)-3-azabicyclo[3.1.0]hexan-3-yl)propyl)-3-(trifluoromethyl)phenyl)-2-oxo-1,2-dihydropyrimidin-4-yl)piperazine-1-carboxamide Hydrochloride Salt
Scheme C-4
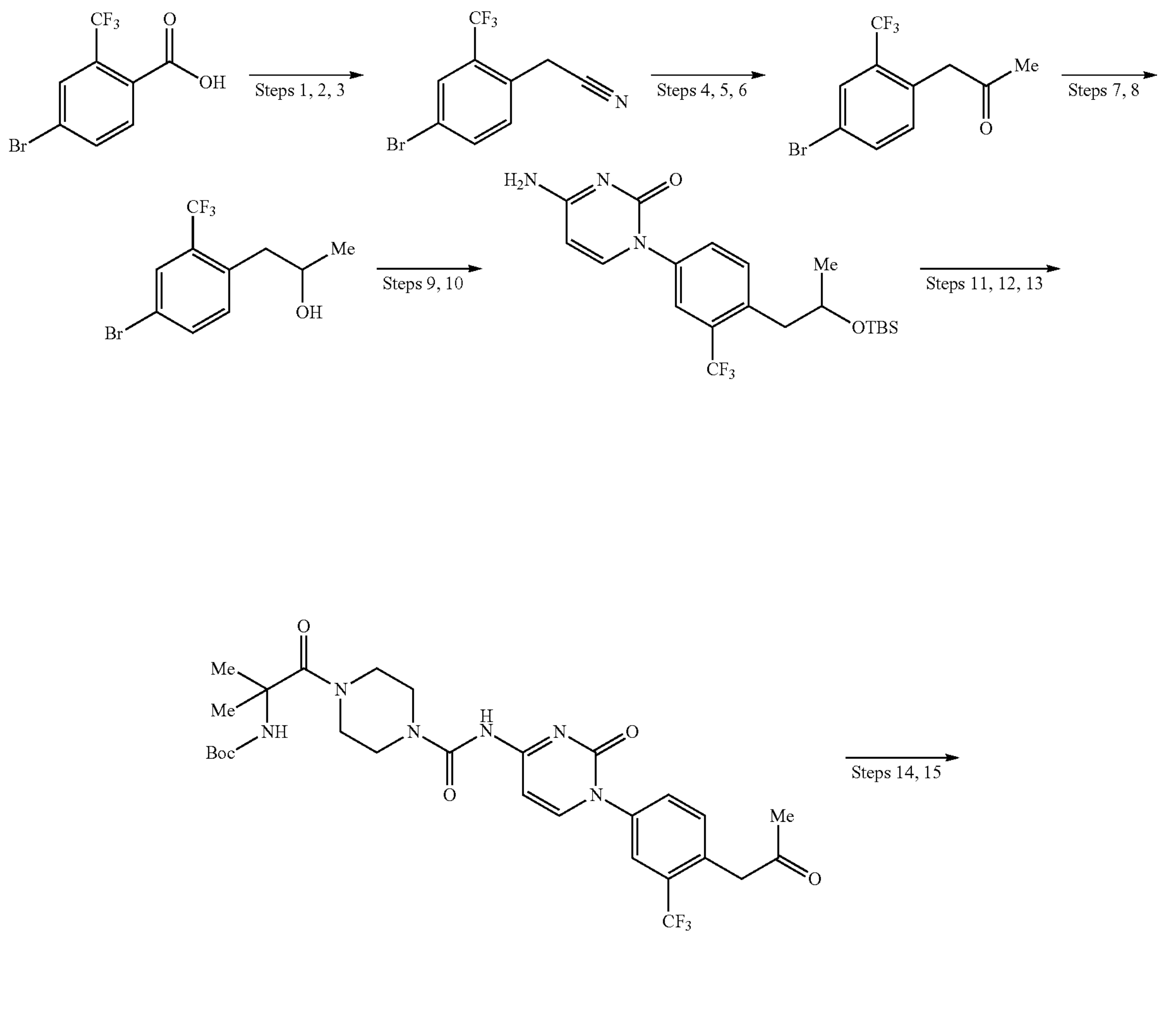

-continued

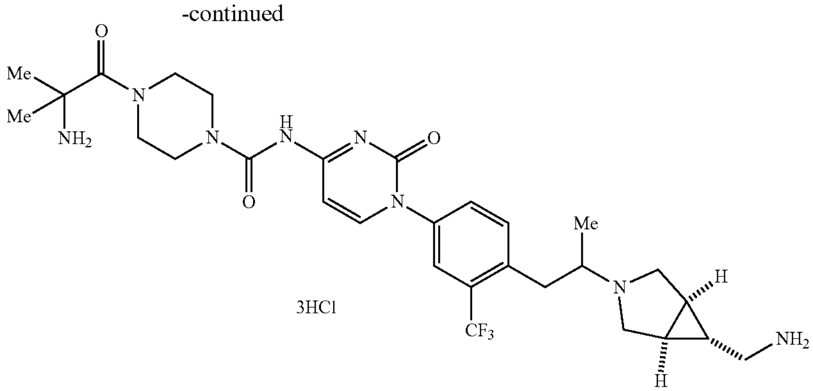

3HCl

Reagents: Step 1) $BH_3$·THF, THF, 80° C., 3 h 2) $CBr_4$ $PPh_3$, THF, rt, 2 h 3) TMSCN, TBAF, rt, 1 h 4) LiOH, $H_2O$, 100° C., 16 h 5) EDCI, TEA, N,O-Dimethyl hydroxylamine, HCl, DMAP, $CH_2Cl_2$, rt, 16 h 6) MeMgBr, THF, 0° C., 30 min 7) $NaBH_4$, MeOH, rt, 3 h 8) TBSCl, Imidazole, $CH_2Cl_2$, rt, 16 h 9) n-BuLi, $B(OiPr)_3$, THF, −78° C., rt, 4 h 10) Cytosine, TMEDA, $Cu(OAc)_2$·$H_2O$, MeOH:$H_2O$ (4:1), $O_2$, rt, 48 h 11) 1-(4-(2-((tert-butoxycarbonyl)amino)-2-methylpropanoyl)piperazine-1-carbonyl)-3-methyl-1H-imidazol-3-ium iodide, $CH_3CN$, 90° C., 16 h 12) TBAF, THF, rt, 16 h 13) DMP, $CH_2Cl_2$, rt, 3 h 14) exo-tert-butyl ((3-azabicyclo [3.1.0]hexan-6-yl)methyl)carbamate, $NaBH_3CN$, MeOH, rt, 5 d. 15) 4M HCl in dioxane, MeOH, rt, 4 h.

Step 1: 4-bromo-2-(trifluoromethyl)phenyl)methanol. To a stirred solution of 4-bromo-2-(trifluoromethyl)benzoic acid (100.0 g, 371.7 mmol) in THF (3.0 L), was added $BH_3$·THF (742.0 ml, 742.0 mmol) at 0° C. The reaction mixture was heated at 80° C. for 3 h. The reaction mixture was poured in to 2N HCl (3.0 L) and extracted with EtOAc (3×1.0 L). The combined organics were dried over $Na_2SO_4$, filtered, concentrated under reduced pressure and purified by column chromatography (25% EtOAc in Hexane) to afford the title compound (70.0 g, 74%) as an off white solid. $^1H$ NMR (400 MHz, DMSO-$d_6$): δ 7.89 (d, 1H), 7.83 (s, 1H), 7.77-7.68 (m, 1H), 5.59 (t, 1H), 4.62 (d, 2H).

Step 2: 4-Bromo-1-(bromomethyl)-2-(trifluoromethyl) benzene. To a stirred a solution of 4-bromo-2-(trifluoromethyl)phenyl)methanol (50.0 g, 196.1 mmol) in THF (800 mL) were added $PPh_3$ (77.2 g, 294.1 mmol) and $CBr_4$ (78.0 g, 235.3 mmol) at 0° C. The reaction mixture was warmed to rt and stirred for 2 h. The reaction mixture was poured into $H_2O$ (500 mL) and extracted with EtOAc (3×1000 mL). The combined organics were dried over $Na_2SO_4$, filtered and concentrated under reduced pressure and purified by column chromatography (10% EtOAc in Hexane) to afford the title compound (56.0 g, 88%) as yellow oil. $^1H$ NMR (400 MHz, DMSO-$d_6$): 7.95-7-91 (m, 2H), 7.69 (d, 1H), 4.76 (s, 2H).

Step 3: 2-(4-bromo-2-(trifluoromethyl) phenyl) acetonitrile. To a stirred solution of 4-bromo-1-(bromomethyl)-2-(trifluoromethyl)benzene (50.0 g, 157.7 mmol) in $CH_3CN$ (600 mL) at 0° C. 1M solution of TBAF in THF (252 mL, 252.4 mmol) and TMSCN (32.0 mL, 252.4 mmol) were added to reaction mixture at 0° C. and stirred at rt for 1 h. The reaction mixture was poured into $H_2O$ (500 mL) and extracted with EtOAc (3×500 mL). The combined organics were dried over $Na_2SO_4$, filtered, concentrated under reduced pressure and purified by column chromatography (15% EtOAc in Hexane) to afford the title compound (26.0 g, 62%) as an off white solid. $^1H$ NMR (400 MHz, DMSO-$d_6$): δ 8.04-7.83 (m, 2H), 7.57 (d, 1H), 4.14 (s, 2H).

Step 4: 2-(4-bromo-2-(trifluoromethyl)phenyl)acetic acid. To a solution of 2-(4-bromo-2-(trifluoromethyl) phenyl) acetonitrile (25.0 g, 94.7 mmol) and LiOH (40.0 g, 946.9 mmol) in $H_2O$ (300 mL) was stirred at 100° C. in for 16 h. The reaction mixture was extracted with $Et_2O$ (3×200 mL). The aqueous layer was acidified with 1N HCl (500 mL) and extracted with EtOAc (3×500 mL). The combined organics were dried over $Na_2SO_4$, filtered, concentrated under reduced pressure to afford the title compound (18.0 g, 67%) as an off white solid. $^1H$ NMR (400 MHz, DMSO-$d_6$): δ 12.63 (s, 1H), 7.86-7.85 (m, 2H), 7.48-7.46 (m, 1H), 3.77 (s, 2H).

Step 5: 2-(4-bromo-2-(trifluoromethyl)phenyl)-N-methoxy-N-methylacetamide. To a stirred solution of N,O-dimethyl hydroxylamine HCl (7.75 g, 79.5 mmol) and $Et_3N$ (11.2 ml, 79.5 mmol) in $CH_2Cl_2$ (500 mL), were added EDCI (11.2 g, 58.3 mmol), 2-(4-bromo-2-(trifluoromethyl) phenyl)acetic acid (15.0 g, 53.0 mmol) and DMAP (1.3 g, 10.6 mmol) at 0° C. The reaction mixture was stirred rt for 16 h. The reaction mixture was poured into $H_2O$ (500 mL) and extracted with $CH_2Cl_2$ (3×300 mL). The combined organics were dried over $Na_2SO_4$, filtered, concentrated under reduced pressure and crude was purified by column chromatography (25% EtOAc in Hexane) to afford the title compound (14.6 g, 85%) as a pale yellow oil. $^1H$ NMR (400 MHz, DMSO-$d_6$): δ 7.85 (d, 2H), 7.41 (d, 1H), 3.95 (s, 2H), 3.71 (s, 3H), 3.11 (s, 3H). LCMS [M+H] 326.

Step 6: 1-(4-bromo-2-(trifluoromethyl) phenyl) propan-2-one. To a stirred solution 2-(4-bromo-2-(trifluoromethyl) phenyl)-N-methoxy-N-methylacetamide (5.0 g, 15.4 mmol) in THF (250 mL) was added MeMgBr (2.0 M in THF) (77.0 mL, 153.8 mmol) at 0° C. The reaction mixture was stirred at 0° C. for 30 min. The reaction mixture was quenched with saturated $NH_4C_1$ solution (250 mL) and extracted with EtOAc (3×100 mL). The combined organics were dried over $Na_2SO_4$, filtered, concentrated under reduced pressure and purified by column chromatography (15% EtOAc in Hexane) to afford the title compound (2.7 g, 57%) as yellow oil. $^1H$ NMR (400 MHz, DMSO-$d_6$): δ 7.86 (d, 2H), 7.36 (d, 1H), 4.01 (s, 2H), 2.19 (s, 3H).

Step 7: 1-(4-bromo-2-(trifluoromethyl)phenyl)propan-2-ol. To a stirred solution of 1-(4-bromo-2-(trifluoromethyl) phenyl) propan-2-one (2.7 g, 9.6 mmol) in MeOH (30 mL) were added $NaBH_4$ (0.91 g, 24.0 mmol) at 0° C. The reaction mixture was stirred at rt for 3 h. The reaction mixture was poured into $H_2O$ (100 mL) and extracted with $CH_2Cl_2$ (3×50 mL). The combined organics were dried over $Na_2SO_4$, filtered, concentrated under reduced pressure to afford the title compound (2.6 g, 95%) as off white solid. $^1$H NMR (400 MHz, DMSO-$d_6$): δ 7.81 (d, 2H), 7.49 (d, 1H), 4.74 (d, 1H), 3.85-3.82 (m, 1H), 2.76 (d, 2H), 1.09 (d, 3H).

Step 8: 41-(4-bromo-2-(trifluoromethyl)phenyl)propan-2-yl)oxy)(tert-butyl) dimethylsilane. To a stirred a solution of 1-(4-bromo-2-(trifluoromethyl) phenyl) propan-2-ol (2.6 g, 9.2 mmol) in $CH_2Cl_2$ (30 mL) were added imidazole (4.6 g, 68.9 mmol) and TBS-$C_1$ (9.0 g, 59.7 mmol) at 0° C. The reaction mixture was stirred at rt for 16 h. The reaction mixture was poured into $H_2O$ (200 mL) and extracted with $CH_2Cl_2$ (3×100 mL). The combined organics were dried over $Na_2SO_4$, filtered, concentrated under reduced pressure and purified by column chromatography (5% EtOAc in Hex) to afford the title compound (3.1 g, 90%) as yellow oil. $^1$H NMR (400 MHz, DMSO-$d_6$): δ 7.84-7.82 (m, 2H), 7.45 (d, 1H), 4.04-3.99 (m, 1H), 2.85-2.84 (m, 1H), 2.79-2.77 (m, 1H), 1.18 (d, 3H), 0.85 (s, 6H), 0.75 (s, 9H).

Step 9: diisopropyl (4-(2-((tert-butyldimethylsilyl) oxy) propyl)-3-(trifluoromethyl) phenyl) boronate. To a stirred solution of ((1-(4-bromo-2-(trifluoromethyl)phenyl)propan-2-yl)oxy)(tert-butyl)dimethylsilane (2.6 g, 6.5 mmol) in THF (100 mL) at −78° C., was added n-BuLi in THF (1.6 M, 40.93 mL, 65.5 mmol). The reaction mixture was stirred −78° C. for 30 min. $B(iPrO)_3$ (7.6 mL, 32.8 mmol) was added at −78° C. The reaction mixture was warmed to rt and stirred for 4 h. The reaction mixture was quenched with saturated $NH_4C_1$ solution (100 mL) and extracted with EtOAc (3×100 mL). The combined organics were dried over $Na_2SO_4$, filtered, concentrated under reduced pressure to afford the title compound (3.5 g, 92%) as yellow oil.

Step 10: 4-amino-1-(4-(2-((tert-butyldimethylsilyl) oxy) propyl)-3-(trifluoromethyl) phenyl) pyrimidin-2 (1H)-one. To a solution of diisopropyl (4-(2-((tert-butyldimethylsilyl) oxy) propyl)-3-(trifluoromethyl) phenyl) boronate (3.5 g, 7.5 mmol) and cytosine (0.87 g, 7.9 mmol) in MeOH:$H_2O$ (50 mL, 4:1) was stirred at rt in open air for 30 min. TMEDA (1.42 mL, 9.4 mmol) and $Cu(OAc)_2 \cdot H_2O$ (1.43 g, 7.9 mmol) were added and the reaction mixture was stirred in open air at rt for 48 h. The reaction mixture was concentrated under reduced pressure and poured into $H_2O$ (100 mL). The reaction mixture was extracted with $CH_2Cl_2$ (3×100 mL). The combined organics were dried over $Na_2SO_4$, filtered, concentrated under reduced pressure. Hexane (100 mL) was added and the crude mixture was filtered. The solid was washed with hexane (2×60 mL) and dried under reduced pressure to afford the title compound (1.2 g, 36%) as white solid. $^1$H NMR (400 MHz, DMSO-$d_6$): δ 7.66 (d, 1H), 7.61-7.51 (m, 3H), 7.34 (d, 2H), 5.80 (d, 1H), 4.04-4.02 (m, 1H), 2.90-2.80 (m, 2H), 1.15 (d, 3H), 0.76 (s, 9H), −0.10 (s, 3H), −0.29 (s, 3H). LCMS[M+H] 428.2.

Step 11: tert-butyl(1-(4-((1-(4-(2-((tert-butyldimethylsilyl)oxy)propyl)-3-(trifluoromethyl)phenyl)-2-oxo-1,2-dihydropyrimidin-4-yl)carbamoyl)piperazin-1-yl)-2-methyl-1-oxopropan-2-yl)carbamate. A solution of 4-amino-1-(4-(2-((tert-butyl dimethylsilyl)oxy)propyl)-3-(trifluoromethyl) phenyl)pyrimidin-2 (1H)-one (1.0 g, 2.4 mmol) and 1-(4-(2-((tert-butoxycarbonyl)amino)-2-methylpropanoyl) piperazine-1-carbonyl)-3-methyl-1H-imidazol-3-ium iodide (1.8 g, 3.5 mmol) in $CH_3CN$ (15 mL) was heated to 90° C. for 16 h. The reaction mixture was concentrated under reduced pressure and the crude residue was purified by column chromatography (2.5% MeOH in $CH_2Cl_2$) to afford the title compound (1.1 g, 64%) as a pale yellow solid. $^1$H NMR (400 MHz, DMSO-$d_6$): δ 10.24 (bs, 1H), 7.79 (d, 1H), 7.68-7.65 (m, 1H), 7.58 (d, 1H), 7.39 (s, 1H), 7.06-6.93 (m, 1H), 4.10-4.02 (m, 1H), 3.59-3.42 (m, 8H), 2.88-2.84 (m, 2H), 1.37 (s, 6H), 1.29 (s, 9H), 1.16 (d, 3H), 0.76 (s, 9H), −0.10 (s, 3H), −0.29 (s, 3H). LCMS[M+23] 747.3.

Step 12: tert-butyl(1-(4-((1-(4-(2-hydroxypropyl)-3-(trifluoromethyl)phenyl)-2-oxo-1,2-dihydropyrimidin-4-yl)carbamoyl)piperazin-1-yl)-2-methyl-1-oxopropan-2-yl)carbamate. To a stirred solution of tert-butyl (1-(4-((1-(4-(2-((tert-butyldimethyl silyl)oxy)propyl)-3-(trifluoromethyl) phenyl)-2-oxo-1,2-dihydropyrimidin-4-yl)carbamoyl) piperazin-1-yl)-2-methyl-1-oxopropan-2-yl)carbamate (1.1 g, 1.5 mmol) in THF (10 mL) was added TBAF (1.0 M in THF) (4.5 mL, 4.6 mmol) at 0° C. The reaction mixture was stirred at rt for 16 h. The reaction mixture was poured in to aq. $NaHCO_3$ solution (25 mL) and extracted with $CH_2Cl_2$: MeOH (9:1, 3×100 mL). The combined organics were dried over $Na_2SO_4$, filtered, concentrated under reduced pressure and purified by column chromatography (5% MeOH in $CH_2Cl_2$) to afford the title compound (0.9 g, 90%) as an off white solid. $^1$H NMR (400 MHz, DMSO-$d_6$): δ 7.77 (d, 1H), 7.67-7.61 (m, 2H), 7.40 (s, 1H), 7.09-6.95 (m, 1H), 4.77 (d, 1H), 3.90-3.84 (m, 1H), 3.70-3.42 (m, 8H), 2.81 (d, 2H), 1.37 (s, 6H), 1.29 (s, 9H), 1.11 (d, 3H). LCMS[M+H] 611.

Step 13: tert-butyl(2-methyl-1-oxo-1-(4-((2-oxo-1-(4-(2-oxopropyl)-3-(trifluoromethyl) phenyl)-1,2-dihydropyrimidin-4-yl)carbamoyl)piperazin-1-yl)propan-2-yl)carbamate. To a stirred solution of tert-butyl (1-(4-((1-(4-(2-hydroxypropyl)-3-(trifluoromethyl) phenyl)-2-oxo-1,2-dihydropyrimidin-4-yl) carbamoyl) piperazin-1-yl)-2-methyl-1-oxopropan-2-yl) carbamate (0.85 g, 1.4 mmol) in $CH_2Cl_2$ (15 mL), was added DMP (2.4 g, 5.6 mmol) at 0° C. The reaction mixture was stirred at rt for 3 h. The reaction mixture was poured into $NaHCO_3$ solution (100 mL) and extracted with $CH_2Cl_2$ (3×50 mL). The combined organics were dried over $Na_2SO_4$, filtered, concentrated under reduced pressure at low temperature (35° C.) to afford the title compound (0.87 g, quantitative) as an off white solid. LCMS[M+H]-100 509.2.

Step 14: exo-tert-butyl (1-(4-((1-(4-(2-(6-(((tert-butoxycarbonyl)amino)methyl)-3-azabicyclo[3.1.0]hexan-3-yl) propyl)-3-(trifluoromethyl)phenyl)-2-oxo-1,2-dihydro pyrimidin-4-yl)carbamoyl)piperazin-1-yl)-2-methyl-1-oxopropan-2-yl)carbamate. To a stirred solution tert-butyl (2-methyl-1-oxo-1-(4-((2-oxo-1-(4-(2-oxopropyl)-3-(trifluoro methyl)phenyl)-1,2-dihydropyrimidin-4-yl)carbamoyl)piperazin-1-yl)propan-2-yl)carbamate (0.4 g, 0.7 mmol) and exo-tert-butyl ((3-azabicyclo[3.1.0]hexan-6-yl)methyl) carbamate (0.348 g, 1.7 mmol) in MeOH (5.0 mL), was added $NaBH_3CN$ (0.180 g, 0.9 mmol) at 0° C. The reaction mixture was stirred at rt for 5 d. The reaction mixture was concentrated under reduced pressure and the crude material was purified by column chromatography (7% MeOH in $CH_2Cl_2$) to afford the title compound (0.7 g) as an off-white solid LCMS[M+H]-100 705.2.

Step 15: exo-4-(2-Amino-2-methylpropanoyl)-N-(1-(4-(2-(6-(aminomethyl)-3-azabicyclo[3.1.0]hexan-3-yl)propyl)-3-(trifluoromethyl)phenyl)-2-oxo-1,2-dihydropyrimidin-4-yl)piperazine-1-carboxamide hydrochloride salt. To a stirred solution of exo-tert-butyl (1-(4-((1-(4-(2-(6-(((tert-butoxycarbonyl)amino)methyl)-3-azabicyclo[3.1.0]hexan-3-yl)propyl)-3-(trifluoromethyl)phenyl)-2-oxo-1,2-dihydropyrimidin-4-yl) carbamoyl) piperazin-1-yl)-2-methyl-1-oxopropan-2-yl)carbamate (0.6 g, 0.8 mmol) in dioxane (6.0 mL) was added 4 M HCl in dioxane (6.0 mL) at 0° C. The reaction mixture was stirred at rt for 4 h. The reaction mixture was concentrated under reduced pressure. The solid was purified by Prep HPLC to afford the title compound as solid (0.1 g, 21%) as off white solid. $^1$H NMR (400 MHz, $D_2O$): δ 7.75-7.71 (m, 2H), 7.55-7.46 (m, 2H), 6.68 (m, 1H), 3.78-3.75 (m, 3H), 3.70-3.55 (m, 8H), 3.50-3.37 (m, 3H), 2.91-2.79 (m, 4H), 1.90-1.87 (m, 2H), 1.56 (s, 6H), 1.24-1.20 (m, 1H), 1.08 (d, 3H). LCMS[M+H] 605.2.

Compound 209

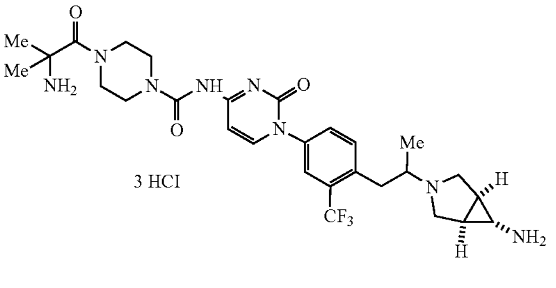

3 HCl

Exo-4-(2-Amino-2-methylpropanoyl)-N-(1-(4-(2-(6-amino-3-azabicyclo[3.1.0]hexan-3-yl)propyl)-3-(trifluoromethyl)phenyl)-2-oxo-1,2-dihydropyrimidin-4-yl)piperazine-1-carboxamide Hydrochloride Salt Prepared in a similar fashion to Scheme C-4 from tert-butyl (2-methyl-1-oxo-1-(4-((2-oxo-1-(4-(2-oxopropyl)-3-(trifluoromethyl)phenyl)-1,2-dihydropyrimidin-4-yl)carbamoyl)piperazin-1-yl)propan-2-yl)carbamate and exo-tert-butyl(3-azabicyclo[3.1.0]hexan-6-yl)carbamate. $^1$H NMR (400 MHz, $D_2O$) δ 7.82 (d, 1H), 7.74 (s, 1H), 7.57-7.48 (m, 2H), 6.68 (d, 1H), 3.89-3.78 (m, 2H), 3.61-3.57 (m, 9H), 3.42-3.34 (m, 2H), 2.93-2.87 (m, 2H), 2.73 (s, 1H), 2.29 (s, 2H), 1.57 (s, 6H), 1.09 (d, 3H). LCMS[M+H] 591.3.

Compound 211

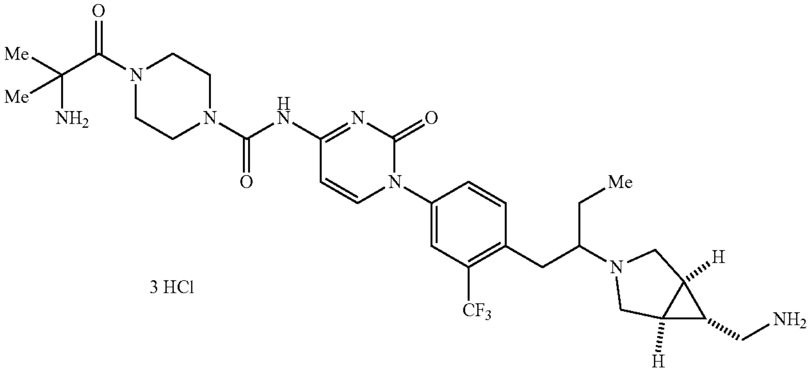

3 HCl

Exo-4-(2-Amino-2-methylpropanoyl)-N-(1-(4-(2-(6-(aminomethyl)-3-azabicyclo[3.1.0]hexan-3-yl)butyl)-3-(trifluoromethyl)phenyl)-2-oxo-1,2-dihydropyrimidin-4-yl)piperazine-1-carboxamide Hydrochloride Salt Scheme C-5

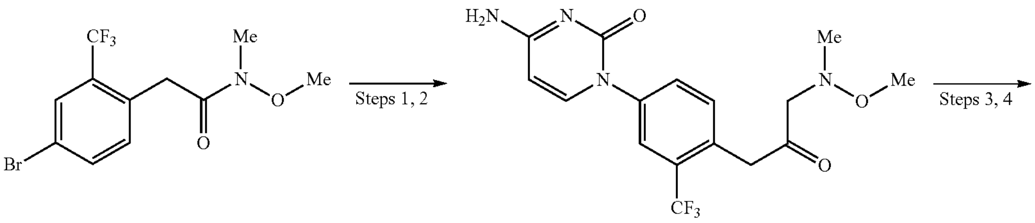

-continued

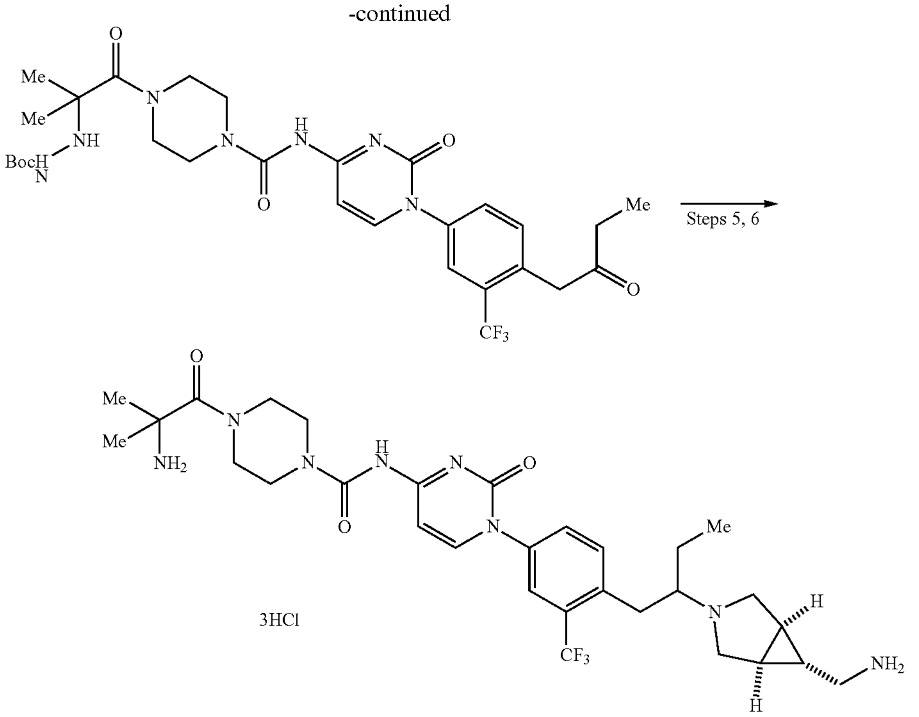

Reagents: Step 1) $B_2pin_2$ $PdCl_2(dppf)$, $K_2CO_3$ dioxane, 80° C., 15 h 2) Cytosine, TMEDA, $Cu(OAc)_2 \cdot H_2O$, MeOH: $H_2O$ (4:1), $O_2$, rt, 16 h 3) 1-(4-(2-((tert-butoxycarbonyl)amino)-2-methylpropanoyl)piperazine-1-carbonyl)-3-methyl-1H-imidazol-3-ium, $CH_3CN$, 80° C., 16 h 4) EtMgBr, 2-Me-THF, rt, 2 5) tert-butyl ((3-azabicyclo[3.1.0]hexan-6-yl)methyl)carbamate, $NaBH_3CN$, MeOH, 4 Å MS, rt, 18 h 6) 4M HCl in dioxane, MeOH, rt, 4 h.

Step 1: N-Methoxy-N-methyl-2-(4-(4,4,5,5-tetramethyl-1,3,2-dioxaborolan-2-yl)-2-(trifluoromethyl) phenyl)acetamide. To a stirred solution of 2-(4-bromo-2-(trifluoromethyl)phenyl)-N-methoxy-N-methylacetamide (1.0 g, 3.1 mmol) in dioxane (10 mL) were added 4,4,4',4',5,5,5',5'-octamethyl-2,2'-bi(1,3,2-dioxaborolane) (1.17 g, 4.6 mmol) and KOAc (0.75 g, 7.7 mmol) at rt and degassed with $N_2$ for 15 min. $PdCl_2(dppf)$ (0.1 g, 10%) was added and reaction mixture was heated at 80° C. for 16 h. The reaction mixture was quenched with sat. aq. $NH_4C_1$ (50 mL) and extracted with EtOAc (3×20 mL). The combined organics were dried over $Na_2SO_4$, filtered, concentrated under reduced pressure and purified by column chromatography (5% MeOH in $CH_2Cl_2$) to afford the title compound (1.2 g, quantitative) as an off white solid. $^1H$ NMR (400 MHz, DMSO-$d_6$) δ 7.94-7.85 (m, 2H), 7.46 (d, 1H), 3.98 (s, 1H), 3.69 (s, 2H), 3.10 (s, 2H), 2.49 (t, 2H), 1.29 (s, 9H), 1.14 (d, 3H), 1.05 (s, 1H). LCMS[M+H] 374.1.

Step 2: 2-(4-(4-amino-2-oxopyrimidin-1 (2H)-yl)-2-(trifluoromethyl)phenyl)-N-methoxy-N-methylacetamide. To a stirred a solution of (N-methoxy-N-methyl-2-(4-(4,4,5,5-tetramethyl-1,3,2-dioxaborolan-2-yl)-2-(trifluoromethyl) phenyl)acetamide (12.0 g, 32.2 mmol) in MeOH:$H_2O$ (25: 100 mL) were added cytosine (3.6 g, 32.2 mmol) at rt. The reaction mixture was stirred at rt for 30 min. TMEDA (5.8 ml, 38.6 mmol) and $Cu(OAc)_2$ (5.85 g, 32.2 mmol) added at rt. The reaction mixture was stirred open to air at rt for 16 h. The reaction mixture was concentrated under reduced pressure $H_2O$ (500 mL). The solid was filtered to afford the title compound (4.5 g, 39%) as an off white solid. $^1H$ NMR (400 MHz, DMSO-$d_6$) δ 7.71-7.69 (m, 2H), 7.60 (d, 1H), 7.50 (d, 1H), 7.34 (d, 2H), 5.80 (d, 1H), 3.99 (s, 2H), 3.73 (s, 3H), 3.12 (s, 3H). LCMS[M+H] 357.0.

Step 3: tert-butyl (1-(4-((1-(4-(2-(methoxy(methyl)amino)-2-oxoethyl)-3-(trifluoro methyl)phenyl)-2-oxo-1,2-dihydropyrimidin-4-yl)carbamoyl)piperazin-1-yl)-2-methyl-1-oxopropan-2-yl)carbamate. A solution of 2-(4-(4-amino-2-oxopyrimidin-1 (2H)-yl)-2-(trifluoromethyl) phenyl)-N-methoxy-N-methylacetamide (1.0 g, 2.8 mmol) and 1-(4-(2-((tert-butoxycarbonyl)amino)-2-methylpropanoyl)piperazine-1-carbonyl)-3-iodo-1H-imidazol-3-ium (2.13 g, 4.2 mmol) in $CH_3CN$ (12 mL) was heated at 85° C. for 16 h. The reaction mixture was concentrated under reduced pressure and purified by column chromatography (5% MeOH in MDC) to afford the title compound (1.2 g, 65%) as an off white solid. $^1H$ NMR (400 MHz, DMSO-$d_6$) δ 7.82 (d, 1H), 7.71-7.68 (m, 1H), 7.56 (d, 1H), 7.37 (d, 1H), 7.19-6.80 (m, 1H), 5.74 (s, 1H), 4.01 (s, 1H), 3.73 (s, 3H), 3.67-3.32 (m, 7H), 3.21-3.08 (m, 4H), 1.37 (s, 6H), 1.29 (s, 9H). LCMS[M+H] 654.

Step 4: tert-butyl (2-methyl-1-oxo-1-(4-((2-oxo-1-(4-(2-oxobutyl)-3-(trifluoro methyl) phenyl)-1,2-dihydropyrimidin-4-yl)carbamoyl)piperazin-1-yl)propan-2-yl)carbamate. To a solution of tert-butyl (1-(4-((1-(4-(2-(methoxy(methyl)amino)-2-oxoethyl)-3-(trifluoro methyl)phenyl)-2-oxo-1,2-dihydropyrimidin-4-yl)carbamoyl)piperazin-1-yl)-2-methyl-1-oxopropan-2-yl)carbamate (0.1 g, 0.2 mmol) in 2-methyl THF (10 mL), was added EtMgBr (0.36 ml, 1.2 mmol) at rt. The reaction mixture was stirred at rt for 2 h. The reaction mixture was quenched with sat. aq. aq. $NH_4C_1$ (100 mL) and extracted with EtOAc (10×40 mL). The combined organics were dried over $Na_2SO_4$, filtered, concentrated under reduced pressure and purified by reversed phase column chromatography ($CH_3CN$:$H_2O$, 30:70) to afford the title compound (0.01 g, 10%) as a viscous oil. $^1H$ NMR (400 MHz, DMSO-$d_6$) δ 10.34 (s, 2H), 8.25-8.06 (m, 1H), 7.82 (s, 1H), 7.69 (d, 1H), 7.50 (d, 1H), 7.40 (s, 1H), 4.05 (s, 2H), 3.85-3.33 (m, 8H), 2.49 (s, 3H), 1.37 (s, 6H), 1.29 (s, 9H), 0.95 (t, 3H). LCMS[M+H] 623.3.

Step 5: tert-butyl ((exo-3-(1-(4-(4-(4-(2-((tert-butoxycarbonyl)amino)-2-methylpropanoyl)piperazine-1-carboxamido)-2-oxopyrimidin-1 (2H)-yl)-2-(trifluoromethyl)phenyl)butan-2-yl)-3-azabicyclo[3.1.0]hexan-6-yl)methyl) carbamate. To a suspension of 4 Å molecular sieves and tert-butyl (2-methyl-1-oxo-1-(4-((2-oxo-1-(4-(2-oxobutyl)-3-(trifluoromethyl)phenyl)-1,2-dihydropyrimidin-4-yl)carbamoyl)piperazin-1-yl)propan-2-yl)carbamate (0.1 g, 0.2 mmol) was added exo-tert-butyl ((3-azabicyclo[3.1.0] hexan-6-yl)methyl)carbamate (0.085 g, 0.4 mmol) and the reaction mixture stirred at rt for 2 h. $NaCNBH_3$ (0.05 g, 0.8 mmol) was added and the reaction mixture was stirred at rt for 16 h. The reaction mixture was filtered and organic layer was concentrated under reduced pressure. The crude material was triturated with $CH_2Cl_2$:MeOH (30 mL, 1:1) and solid was dried under reduced pressure to afford the title compound (0.085 g, 3%) as a viscous oil. LCMS[M+H] 819.3.

Step 6: exo-4-(2-amino-2-methylpropanoyl)-N-(1-(4-(2-(6-(aminomethyl)-3-azabicyclo[3.1.0]hexan-3-yl)butyl)-3-(trifluoromethyl)phenyl)-2-oxo-1,2-dihydropyrimidin-4-yl) piperazine-1-carboxamide hydrochloride salt. To a stirred solution of tert-butyl ((exo-3-(1-(4-(4-(4-(2-((tert-butoxycarbonyl)amino)-2-methylpropanoyl)piperazine-1-carboxamido)-2-oxopyrimidin-1 (2H)-yl)-2-(trifluoromethyl)phenyl)butan-2-yl)-3-azabicyclo[3.1.0]hexan-6-yl)methyl) carbamate (0.075 g, 0.1 mmol) in dioxane (3 mL) was added 6N HCl in dioxane (1 mL) at 0° C. The reaction mixture was warmed to rt and stirred 5 h. The reaction mixture was concentrated under reduced pressure and purified by prep HPLC to afford the title compound (0.004 g, 3%) as an off white solid. $^1H$ NMR (400 MHz, $D_2O$) δ 7.83 (s, 2H), 7.63 (s, 2H), 6.79 (d, 1H), 3.80-3.60 (m, 14H), 3.52-3.49 (m, 2H), 3.39-3.36 (m, 2H), 3.23-3.20 (m, 1H), 2.91 (br s, 2H) 1.96 (br s, 2H), 1.67 (s, 9H), 1.34 (br s, 1H), 0.95-0.84 (m, 3H). LCMS[M+H] 619.4.

Compound 8

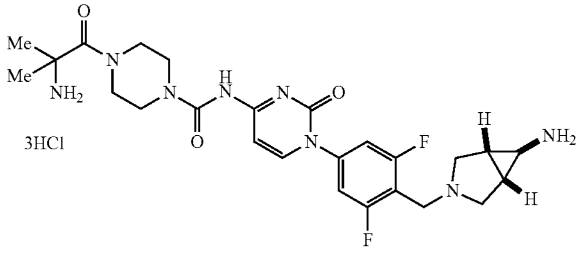

4-(2-Amino-2-methylpropanoyl)-N-(1-(4-((exo-6-amino-3-azabicyclo[3.1.0]hexan-3-yl)methyl)-3,5-difluorophenyl)-2-oxo-1,2-dihydropyrimidin-4-yl) piperazine-1-carboxamide Hydrochloride Salt Scheme C-6

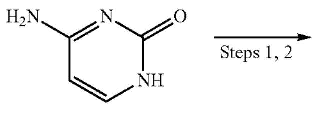

-continued

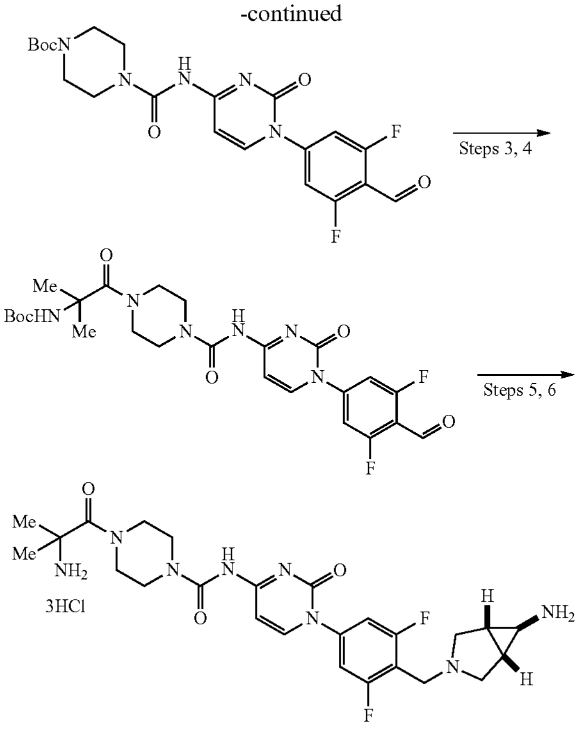

Reagents: 1) (3,5-Difluoro-4-formylphenyl)boronic acid, TMEDA, $Cu(OAc)_2 \cdot H_2O$, MeOH:$H_2O$, rt, 16 h 2) 1-(4-(tert-Butoxycarbonyl)piperazine-1-carbonyl)-3-methyl-1H-imidazol-3-ium-4-ide, $CH_3CN$, reflux, 16 h 3) TFA, $CH_2Cl_2$1.5 h 4) 2-((tert-butoxycarbonyl)amino)-2-methylpropanoic acid, HATU, DIPEA, $CH_2Cl_2$, rt, 16 h 5) tert-Butyl (exo-3-azabicyclo[3.1.0]hexan-6-yl)carbamate, DIPEA, $Na(OAc)_3BH$, DCE:$CH_3CN$, rt, 16 h 6)HCl, MeOH, rt, 4 h Step 1: 4-(4-amino-2-oxopyrimidin-1 (2H)-yl)-2,6-difluorobenzaldehye. A suspension of cytosine (207 mg, 1.9 mmol) and (3,5-difluoro-4-formylphenyl)boronic acid (500 mg 1.9 mmol), in a mixture of MeOH:$H_2O$ (4:1, 25 ml) was stirred for at rt in an open atmosphere. After 30 min TMEDA (0.514 mL, 2.2 mmol) and $Cu(OAc)_2 \cdot H_2O$ (373 mg, 1.9 mmol) were added. The reaction was stirred in an open atmosphere at rt for 16 h. The MeOH was evaporated under reduced pressure, and the remaining mixture was diluted with $H_2O$ (25 mL) and stirred at 0° C. for 15 min. The mixture was filtered and the solid was washed with $H_2O$ (1×25 mL) and $Et_2O$ (1×25 mL) to afford the title compound as a white solid (50%).

Step 2: tert-butyl 44 (1-(3,5-difluoro-4-formylphenyl)-2-oxo-1,2-dihydropyrimidin-4-yl)carbamoyl)piperazine-1-carboxylate. 1-(4-(tert-Butoxycarbonyl)piperazine-1-carbonyl)-3-methyl-1H-imidazol-3-ium iodide (241 mg, 0.59 mmol) and 4-(4-amino-2-oxopyrimidin-1 (2H)-yl)-2,6-difluorobenzaldehyde (135 mg, 0.53 mmol) were dissolved in $CH_3CN$ (12 mL). The solution was heated to reflux for 16 h. The solvent was removed under reduced pressure and the crude reaction mixture was partitioned between $CHCl_3$ (50 mL) and $H_2O$ (50 mL). The organic layer was concentrated and purified by column chromatography to afford the title compound as a white solid (85%).

Step 3: N-(1-(3,5-difluoro-4-formylphenyl)-2-oxo-1,2-dihydropyrimidin-4-yl)piperazine-1-carboxamide trifluoroacetate salt. tert-Butyl 4-((1-(3,5-difluoro-4-formylphenyl)-2-oxo-1,2-dihydropyrimidin-4-yl)carbamoyl)piperazine-1-carboxylate (205 mg, 0.45 mmol) was dissolved in a solution of TFA:$CH_2Cl_2$ (1:1, 10 mL). The reaction was stirred for 1.5 h at rt. The volatiles were removed reduced pressure. The crude residue was triturated with $Et_2O$. The precipitate was filtered and washed with $Et_2O$ (1×10 mL) to afford the title compound as a white solid (92%).

Step 4: tert-butyl (1-(4-((1-(3,5-difluoro-4-formylphenyl)-2-oxo-1,2-dihydropyrimidin-4-yl)carbamoyl)piperazin-1-yl)-2-methyl-1-oxopropan-2-yl)carbamate. To a suspension of 2-((tert-butoxycarbonyl)amino)-2-methylpropanoic acid (63 mg, 0.31 mmol) and HATU (118 mg, 0.31 mmol) in $CH_2Cl_2$ DIPEA (0.12 mL, 0.68 mmol) was added. The suspension was stirred for 10 min. N-(1-(3,5-difluoro-4-formylphenyl)-2-oxo-1,2-dihydropyrimidin-4-yl)piperazine-1-carboxamide trifluoroacetate salt (124 mg, 0.31 mmol) was added and the solution was stirred at rt for 16 h. The solution was diluted with $CH_2Cl_2$ (25 mL) and washed with $H_2O$ (1×25 mL). The organic layer was concentrated and purified by column chromatography to afford the title compound as a white solid (72%).

Step 5: tert-butyl (exo-3-(4-(4-(4-(2-((tert-butoxycarbonyl)amino)-2-methylpropanoyl)piperazine-1-carboxamido)-2-oxopyrimidin-1 (2H)-yl)-2,6-difluorobenzyl)-3-azabicyclo[3.1.0]hexan-6-yl)carbamate. To stirring suspension of tert-butyl (1-(4-((1-(3,5-difluoro-4-formylphenyl)-2-oxo-1,2-dihydropyrimidin-4-yl)carbamoyl)piperazin-1-yl)-2-methyl-1-oxopropan-2-yl)carbamate (40 mg, 0.07 mmol) and tert-butyl (exo-3-azabicyclo[3.1.0]hexan-6-yl)carbamate (21.7 mg, 0.11 mmol) in DCE:$CH_3CN$ (1:1, 25 mL), were added DIPEA (0.03 mL, 0.15 mmol) and $Na(OAc)_3BH$ (0.30 g, 0.15 mmol). The reaction was stirred at rt for 16 h, and the solvent was removed reduced pressure. The crude residue was dissolved in $CHCl_3$ (50 mL) and washed with 10% NaOH (50 mL). Purification by column chromatography afforded the title compound as a white solid (84%).

Step 6: 4-(2-Amino-2-methylpropanoyl)-N-(1-(4-((exo-6-amino-3-azabicyclo[3.1.0]hexan-3-yl)methyl)-3,5-difluorophenyl)-2-oxo-1,2-dihydropyrimidin-4-yl)piperazine-1-carboxamide hydrochloride salt. tert-butyl (exo-3-(4-(4-(4-(2-((tert-butoxycarbonyl)amino)-2-methylpropanoyl)piperazine-1-carboxamido)-2-oxopyrimidin-1 (2H)-yl)-2,6-difluorobenzyl)-3-azabicyclo[3.1.0]hexan-6-yl)carbamate (55 mg, 0.07) was treated with HCl in MeOH (2N, 10 mL) and stirred at rt for 4 h. The reaction mixture was concentrated under reduced pressure and the solid was triturated with $Et_2O$ to afford the title compound as a light yellow solid. $^1H$ NMR (500 MHz, $D_2O$) δ 7.87 (br s, 1H), 7.23 (d, 2H), 6.86 (br s, 1H), 3.92 (s, 2H), 3.86-3.66 (m, 10H), 3.11 (d, 2H), 2.76 (s, 1H), 1.93 (s, 2H), 1.73 (s, 6H). LCMS [M+H] 531.33

Compound 7

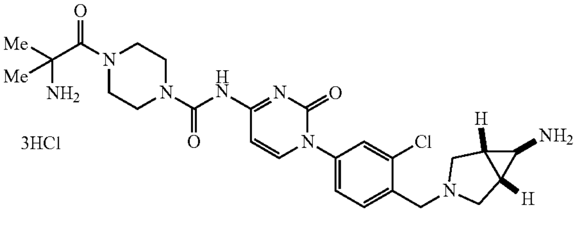

4-(2-Amino-2-methylpropanoyl)-N-(1-(4-((exo-6-amino-3-azabicyclo[3.1.0]hexan-3-yl)methyl)-3-chlorophenyl)-2-oxo-1,2-dihydropyrimidin-4-yl)piperazine-1-carboxamide Hydrochloride Salt Prepared in a similar fashion to Scheme C-6 from tert-butyl (1-(4-((1-(3-chloro-4-formylphenyl)-2-oxo-1,2-dihydropyrimidin-4-yl)carbamoyl)piperazin-1-yl)-2-methyl-1-oxopropan-2-yl)carbamate and tert-butyl (exo-3-azabicyclo[3.1.0]hexan-6-yl)carbamate. $^1H$ NMR (400 MHz, $D_2O$) δ 8.03 (d, 1H), 7.87-7.72 (m, 2H), 7.57 (d, 1H), 6.87 (d, 1H), 4.67 (s, 2H), 4.15-3.57 (m, 12H), 3.08 (s, 1H), 2.49 (s, 2H), 1.76 (s, 6H). LCMS [M+H] 529.23

Compound 15

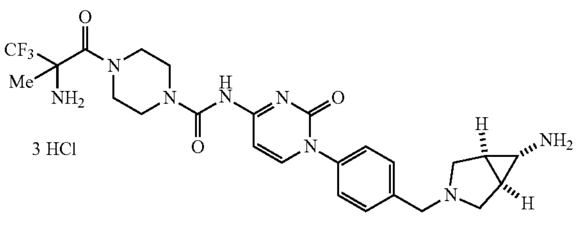

4-(2-Amino-3,3,3-trifluoro-2-methylpropanoyl)-N-[1-(4-{[(exo)-6-amino-3-azabicyclo[3.1.0]hexan-3-yl]methyl}phenyl)-2-oxo-1,2-dihydropyrimidin-4-yl]piperazine-1-carboxamide Hydrochloride Salt Scheme C-7

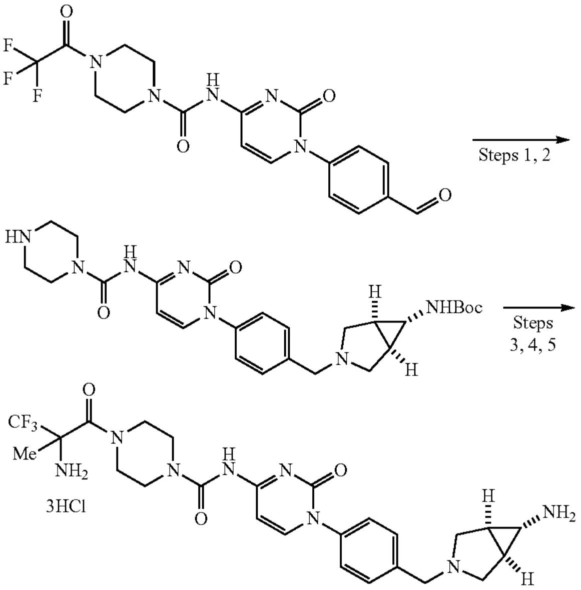

Reagents: 1) tert-Butyl N-[exo-3-azabicyclo[3.1.0]hexan-6-yl]carbamate, $NaBH(OAc)_3CH_2Cl_2$ rt, 16 h, 2) $K_2CO_3$, MeOH, rt, 2 h 3) 2-{[(benzyloxy)carbonyl]amino}-3,3,3-trifluoro-2-methylpropanoic acid, HATU, DIPEA, $CH_3CN$, rt, 2 h, 4) $H_2$Pd/C, EtOH, rt, 2.5 h 5) 3M HCl MeOH, rt, 4 h Step 1: tert-butyl N-[(exo)-3-{[4-(2-oxo-4-{[4-(trifluoroacetyl)piperazine-1-carbonyl]amino}-1,2-dihydropyrimidin-1-yl)phenyl]methyl}-3-azabicyclo[3.1.0]hexan-6-yl]carbamate. tert-Butyl N-[exo-3-azabicyclo[3.1.0]hexan-6-yl]carbamate (140 mg, 0.708 mmol) was added to a suspension of N-[1-(4-formylphenyl)-2-oxo-1,2-dihydropyrimidin-4-yl]-4-(trifluoroacetyl)piperazine-1-carboxamide (200 mg, 0.472 mmol) in $CH_2Cl_2$ (10 mL) and the reaction mixture was stirred at rt for 15 min. $NaBH(OAc)_3$ (250 mg, 1.18 mmol) was added and the reaction was stirred for 16 h, diluted with $CH_2Cl_2$ and washed with sat. $NaHCO_3$ solution. The organic portion was dried ($Na_2SO_4$), filtered, and concentrated under reduced pressure. The crude product was purified by column chromatography ($CH_2Cl_2$:MeOH, 95:5) to afford the title compound (260 mg, 80%). LCMS[M+H] 606.5

Step 2: tert-butyl N-[(exo)-3-[(4-{2-oxo-4-[(piperazine-1-carbonyl)amino]-1,2-dihydropyrimidin-1-yl}phenyl) methyl]-3-azabicyclo[3.1.0]hexan-6-yl]carbamate. $K_2CO_3$ (120 mg, 0.860 mmol) was added to a suspension of tert-butyl N-[exo-3-{[4-(2-oxo-4-{[4-(trifluoroacetyl)piperazine-1-carbonyl]amino}-1,2-dihydropyrimidin-1-yl)phenyl]methyl}-3-azabicyclo[3.1.0]hexan-6-yl]carbamate (260 mg, 0.430 mmol) in MeOH (10 mL). The reaction was stirred at rt for 2 h and concentrated under reduced pressure. The crude product was purified by column chromatography (KP-NH, EtOAc-MeOH, 80:20) to afford the title compound (195 mg, 89%). $^1H$ NMR (400 MHz, $CDCl_3$) δ 7.37 (d, 2H), 7.30-7.19 (m, 3H), 5.83 (d, 1H), 4.80-4.59 (m, 1H), 3.92-3.81 (m, 2H), 3.68-3.52 (m, 4H), 3.09 (d, 2H), 2.97-2.82 (m, 5H), 2.42 (d, 2H), 1.53 (br.s., 2H), 1.46 (s, 9H). LCMS [M+H] 510.6

Step 3: benzyl N-[3-(4-{[1-(4-{[exo-6-{[(tert-butoxy)carbonyl]amino}-3-azabicyclo[3.1.0]hexan-3-yl] methyl}phenyl)-2-oxo-1,2-dihydropyrimidin-4-yl] carbamoyl}piperazin-1-yl)-1,1,1-trifluoro-2-methyl-3-oxopropan-2-yl]carbamate. N-2-{[(Benzyloxy)carbonyl] amino}-3,3,3-trifluoro-2-methylpropanoic acid (69.3 mg, 0.238 mmol), HATU (113 mg, 0.297 mmol) and DIPEA (69 μL, 0.396 mmol) were sequentially added to a solution of tert-butyl N-[exo-3-[(4-{2-oxo-4-[(piperazine-1-carbonyl) amino]-1,2-dihydropyrimidin-1-yl}phenyl)methyl]-3-azabicyclo[3.1.0]hexan-6-yl]carbamate (101 mg, 0.198 mmol) in $CH_3CN$ (5 mL). The reaction mixture was stirred at rt for 2 h, diluted with $H_2O$ and extracted twice with EtOAc. The combined organics were washed with $H_2O$, dried ($Na_2SO_4$), filtered, concentrated under reduced pressure. The crude product was purified by column chromatography ($CH_2Cl_2$: MeOH, 90:10) to afford the title compound (96.0 mg, 59%). $^1H$ NMR (400 MHz, $CDCl_3$) δ 12.95 (s, 1H), 7.41-7.35 (m, 6H), 7.30-7.26 (s, 4H), 5.83 (d, 1H), 5.30-5.20 (m, 1H), 5.15 (s, 2H), 4.67-4.55 (m, 1H), 3.91-3.35 (m, 10H), 3.10 (d, 2H), 2.95-2.87 (m, 1H), 2.43 (d, 2H), 1.75 (s, 3H), 1.54 (br.s., 2H), 1.46 (s, 9H). LCMS[M+H] 783.7

Step 4: tert-butyl N-[exo-3-{[4-(4-{[4-(2-amino-3,3,3-trifluoro-2-methylpropanoyl)piperazine-1-carbonyl]amino}-2-oxo-1,2-dihydropyrimidin-1-yl)phenyl]methyl}-3-azabicyclo[3.1.0]hexan-6-yl]carbamate. Pd/C (10% wt, Degussa type, 3 mg) was added to a solution of benzyl N-[3-(4-{[1-(4-{[exo-6-{[(tert-butoxy)carbonyl]amino}-3-azabicyclo [3.1.0]hexan-3-yl]methyl}phenyl)-2-oxo-1,2-dihydropyrimidin-4-yl]carbamoyl}piperazin-1-yl)-1,1,1-trifluoro-2-methyl-3-oxopropan-2-yl]carbamate (20.0 mg, 0.026 mmol) in EtOH (3 mL) and the reaction was stirred under $H_2$ atmosphere for 3.5 h. The reaction was filtered from the catalyst and the organic portion was concentrated under reduced pressure. The crude product was purified by column chromatography (KP-NH, EtOAc-MeOH, 95:5) to afford the title compound (10.0 mg, 58%). $^1H$ NMR (400 MHz, $CDCl_3$) δ 12.93 (s, 1H), 7.38 (d, 2H), 7.31-7.24 (m, 3H), 5.84 (d, 1H), 4.70-4.52 (m, 1H), 4.05-3.56 (m, 10H), 3.10 (d, 2H), 2.91 (br. s., 1H), 2.42 (d, 2H), 1.82 (s, 2H), 1.61 (s, 3H), 1.53 (br.s., 2H), 1.46 (s, 9H). LCMS [M+H] 649.6

Step 5: 4-(2-amino-3,3,3-trifluoro-2-methylpropanoyl)-N-[1-(4-{[(exo)-6-amino-3-azabicyclo[3.1.0]hexan-3-yl] methyl}phenyl)-2-oxo-1,2-dihydropyrimidin-4-yl]piperazine-1-carboxamide. A solution of tert-butyl N-[exo-3-{[4-(4-{[4-(2-amino-3,3,3-trifluoro-2-methylpropanoyl) piperazine-1-carbonyl]amino}-2-oxo-1,2-dihydropyrimidin-1-yl)phenyl]methyl}-3-azabicyclo[3.1.0] hexan-6-yl]carbamate (9.0 mg, 0.013 mmol) in 3M HCl in MeOH (1 mL) was stirred at rt for 4 h. Volatiles were removed under reduced pressure. The residue was dissolved in MeOH and precipitated with $Et_2O$. The solid was filtered and dried to afford the title compound as its trihydrochloride salt (4.7 mg, 55%) as a white solid. $^1H$ NMR (400 MHz, $D_2O$) δ 7.82 (d, 1H), 7.61 (d, 2H), 7.52-7.47 (m, 2H), 6.81 (d, 1H), 4.41 (br. s., 2H), 4.00-3.51 (m, 12H), 3.01-2.78 (m, 1H), 2.38 (br. s., 2H), 1.90 (s, 3H). LCMS [M+H] 549.4

Compound 18

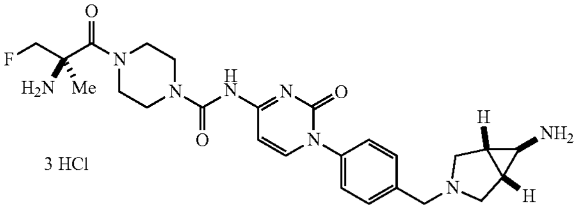

N-(1-(4-((exo-6-Amino-3-azabicyclo[3.1.0]hexan-3-yl)methyl)phenyl)-2-oxo-1,2-dihydropyrimidin-4-yl)-4-((R)-2-amino-3-fluoro-2-methylpropanoyl) piperazine-1-carboxamide Hydrochloride Salt Scheme C-8

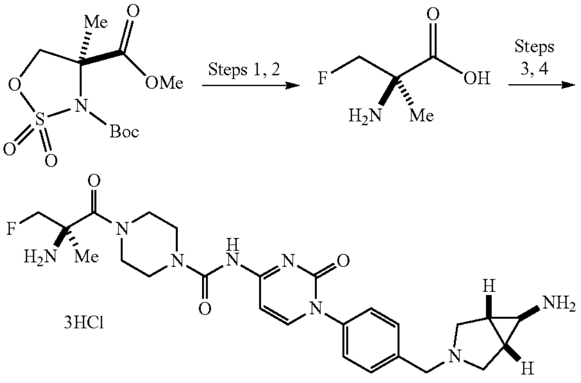

Reagents: 1) TBAF, $CH_3CN$, rt, 16 h, 2) $LiOH{\cdot}H_2O$, THF:$H_2O$; 3) tert-Butyl (exo-3-(4-(2-oxo-4-(piperazine-1-carboxamido)pyrimidin-1 (2H)-yl)benzyl)-3-azabicyclo [3.1.0]hexan-6-yl)carbamate, HATU, DIPEA, $CH_3CN$, rt, 2 h 4) 3M HCl-MeOH, 4 h, rt Step 1: Methyl (2R)-2-{[(tert-butoxy)carbonyl]amino}-3-fluoro-2-methylpropanoate. Tetrabutylammonium fluoride (1M solution in THF, 2.8 mL, 2.8 mmol) was added to a solution of 3-tert-butyl 4-methyl (4S)-4-methyl-2,2-dioxo-1,2λ,$^6$,3-oxathiazolidine-3,4-dicarboxylate (prepared according to procedures reported in *J. Med. Chem.* 2010, 53, 876-886, 275 mg, 0.93 mmol) in $CH_3CN$ (10 mL). The reaction was stirred at rt for 16 h and concentrated under reduced pressure. The crude product was dissolved in $H_2O$ and the aqueous portion was extracted with EtOAc. The organic portion was dried over $Na_2SO_4$, filtered and concentrated under reduced pressure to afford the title compound (185 mg, 85%). $^1$H NMR (400 MHz, $CDCl_3$) δ 5.29 (br. s., 1H), 4.78 (dd, 8.4 Hz, 1H), 4.70 (dd, 7.5 Hz, 1H), 3.81 (s, 3H), 1.53 (d, 3H), 1.47 (s, 9H). LCMS[M+H] 236.2

Step 2: (2R)-2-{[(tert-butoxy)carbonyl]amino}-3-fluoro-2-methylpropanoic acid. $LiOH{\cdot}H_2O$ (32.1 mg, 0.765 mmol) was added to a solution of methyl (2R)-2-{[(tert-butoxy)carbonyl]amino}-3-fluoro-2-methylpropanoate (60.0 mg, 0.255 mmol) in THF:$H_2O$ (3:1, 4 mL). The reaction was stirred at rt for 3 h and concentrated under reduced pressure. The crude product was dissolved in $H_2O$. The aqueous portion was acidified with 1M HCl and extracted with EtOAc. The organic portion was dried over $Na_2SO_4$, filtered and concentrated under reduced pressure to afford the crude product (53 mg). $^1$H NMR (400 MHz, $CDCl_3$) δ 5.32 (br.s., 1H), 4.80 (br.s., 1H), 4.69 (br.s., 1H), 1.59 (d, 3H), 1.48 (s, 9H). LCMS[+H] 222.1

Step 3: tert-butyl N-[(2R)-1-(4-{[1-(4-{[(exo)-6-{[(tert-butoxy)carbonyl]amino}-3-azabicyclo[3.1.0]hexan-3-yl]methyl}phenyl)-2-oxo-1,2-dihydropyrimidin-4-yl]carbamoyl}piperazin-1-yl)-3-fluoro-2-methyl-1-oxopropan-2-yl]carbamate. (2R)-2-{[(tert-butoxy)carbonyl]amino}-3-fluoro-2-methylpropanoic acid (52.9 mg, 0.239 mmol), HATU (105 mg, 0.276 mmol) and DIPEA (64 μL, 0.368 mmol) were sequentially added to a solution of tert-butyl N-[(exo)-3-[(4-{2-oxo-4-[(piperazine-1-carbonyl)amino]-1,2-dihydropyrimidin-1-yl}phenyl)methyl]-3-azabicyclo[3.1.0]hexan-6-yl]carbamate (94 mg, 0.184 mmol) in $CH_3CN$ (5 mL). The resulting mixture was stirred at rt for 2 h. Volatiles were removed under reduced pressure. The residue was dissolved in EtOAc and the organic portion was washed with $H_2O$, dried over $Na_2SO_4$, filtered and concentrated under reduced pressure. The crude product was purified by column chromatography ($CH_2Cl_2$:MeOH, 95:5 gradient to 85:15) to afford the title compound (55 mg, 42%). $^1$H NMR (400 MHz, $CDCl_3$) δ 12.92 (br. s., 1H), 7.37 (d, 2H), 7.28-7.25 (m, 3H), 5.84 (d, 1H), 5.03-4.78 (m, 2H), 4.72-4.51 (m, 2H), 3.60 (s, 2H), 4.04-3.48 (m, 8H), 3.10 (d, 2H), 2.91 (br.s., 1H), 2.42 (d, 2H), 1.53 (br.s., 5H), 1.49-1.43 (m, 18H). LCMS[M+H] 713.8

Step 4: N-(1-(4-((exo-6-Amino-3-azabicyclo[3.1.0]hexan-3-yl)methyl)phenyl)-2-oxo-1,2-dihydropyrimidin-4-yl)-4-((R)-2-amino-3-fluoro-2-methylpropanoyl)piperazine-1-carboxamide hydrochloride salt. A solution of tert-butyl N-[(2R)-1-(4-{[1-(4-{[exo-6-{amino}-3-azabicyclo[3.1.0]hexan-3-yl]methyl}phenyl)-2-oxo-1,2-dihydropyrimidin-4-yl]carbamoyl}piperazin-1-yl)-3-fluoro-2-methyl-1-oxopropan-2-yl]carbamate (55.0 mg, 0.077 mmol) in 3M HCl in MeOH (5 mL) was stirred at rt for 8 h. Volatiles were removed under reduced pressure. The residue was dissolved in MeOH and precipitated with $Et_2O$. The solid was filtered and dried to afford the title compound as its trihydrochloride salt (41.3 mg, 86%) as a pale yellow solid. $^1$H NMR (400 MHz, $D_2O$) δ 7.89 (d, 1H), 7.64 (d, 2H), 7.53 (d, 2H), 6.83 (d, 1H), 5.12-4.80 (m, 2H), 4.45 (br.s., 2H), 3.94-3.64 (m, 12H), 2.89 (br. s., 1H), 2.41 (br. s., 2H), 1.73 (s, 3H). LCMS [M+H] 513.5

Compound 69

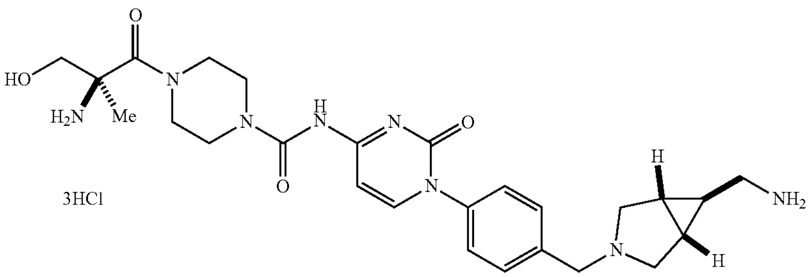

4-[(2S)-2-Amino-3-hydroxy-2-methylpropanoyl]-N-[1-(4-{[(exo)-6-(aminomethyl)-3-azabicyclo[3.1.0]hexan-3-yl]methyl}phenyl)-2-oxo-1,2-dihydropyrimidin-4-yl] piperazine-1-carboxamide Hydrochloride Salt Scheme C-9

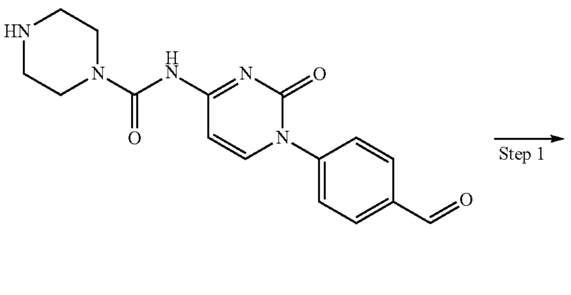

-continued

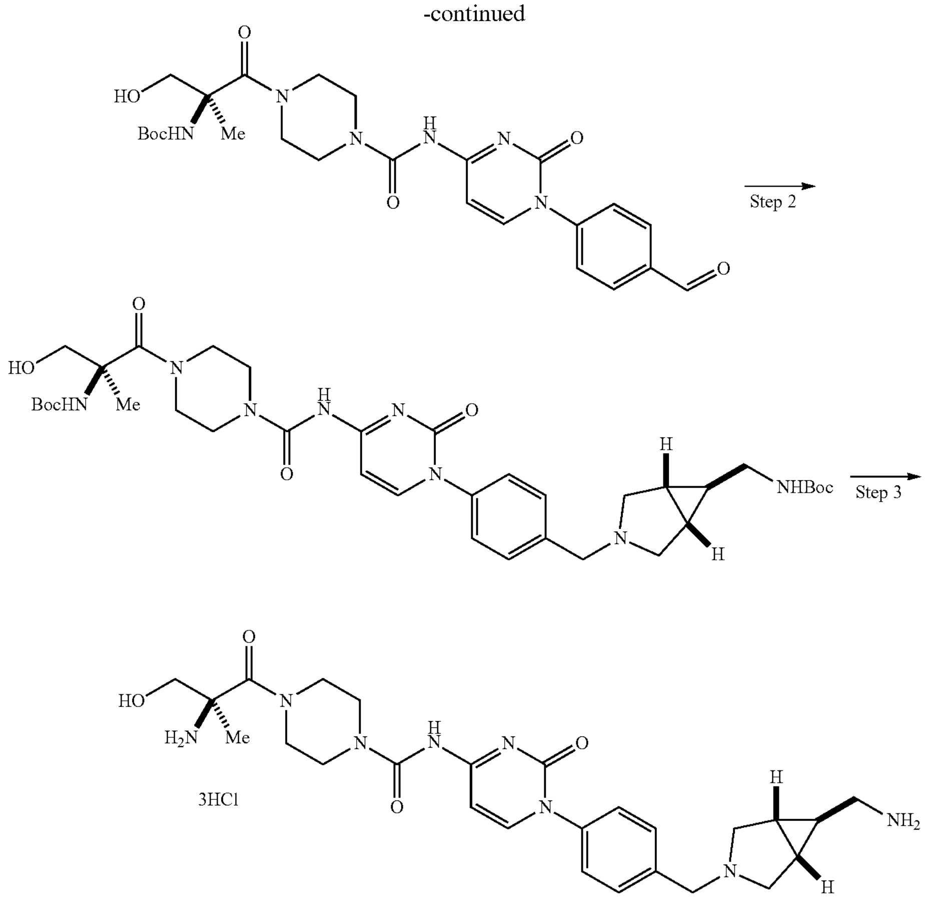

Reagents:1) (2S)-2-{[(tert-Butoxy)carbonyl]amino}-3-hydroxy-2-methylpropanoic acid, HATU, DIPEA, $CH_3CN$, rt, 16 h 2) tert-butyl N-[exo-3-azabicyclo[3.1.0]hexan-6-ylmethyl]carbamate, $NaBH(OAc)_3CH_2Cl_2$, rt, 16 h 3) 3M HCl in MeOH, rt, 4 h Step 1: tert-butyl N-[(2S)-1-(4-{[1-(4-formylphenyl)-2-oxo-1,2-dihydropyrimidin-4-yl] carbamoyl}piperazin-1-yl)-3-hydroxy-2-methyl-1-oxopropan-2-yl]carbamate. (2S)-2-{[(tert-butoxy)carbonyl]amino}-3-hydroxy-2-methylpropanoic acid (62.0 mg, 0.283 mmol), HATU (135 mg, 0.354 mmol) and DIPEA (82 μL, 0.472 mmol) were sequentially added to a solution of N-[1-(4-formylphenyl)-2-oxo-1,2-dihydropyrimidin-4-yl]piperazine-1-carboxamide (0.236 mmol) in $CH_3CN$ (7 mL). The reaction mixture was stirred at rt for 16 h. Volatiles were removed under reduced pressure. The residue was dissolved in EtOAc and the organic portion was washed with sat. aq. NaCl, dried over $Na_2SO_4$, filtered and concentrated under reduced pressure. The crude product was purified by column chromatography ($CH_2Cl_2$:MeOH, 95:5) to afford the title compound (20.0 mg, 16%). LCMS[M+H] 529.5

Step 2: tert-butyl N-{[exo-3-({4-[4-({4-[(2S)-2-{[(tert-butoxy)carbonyl]amino}-3-hydroxy-2-methylpropanoyl] piperazine-1-carbonyl}amino)-2-oxo-1,2-dihydropyrimidin-1-yl]phenyl}methyl)-3-azabicyclo[3.1.0]hexan-6-yl] methyl}carbamate. tert-Butyl N-[exo-3-azabicyclo[3.1.0] hexan-6-ylmethyl]carbamate (12.1 mg, 0.057 mmol) was added to a mixture of tert-butyl N-[(2S)-1-(4-{[1-(4-formylphenyl)-2-oxo-1,2-dihydropyrimidin-4-yl] carbamoyl}piperazin-1-yl)-3-hydroxy-2-methyl-1-oxopropan-2-yl]carbamate (20.0 mg, 0.038 mmol) in $CH_2Cl_2$ (3 mL) and the reaction mixture was stirred at rt for 10 min. $NaBH(OAc)_3$ (16.1 mg, 0.076 mmol) was added and the reaction was stirred at room temperature for 16 h and concentrated under reduced pressure. The crude product was purified by column chromatography (EtOAc:MeOH, 90:10) to afford the title compound (15.0 mg, 55%). $^1H$ NMR (400 MHz, $CDCl_3$) δ 12.93 (br. s., 1H), 7.39 (d, 2H), 7.32-7.24 (m, 3H), 5.84 (d, 1H), 4.78 (br. s., 1H), 4.59 (br. s., 1H), 4.19 (d, 1H), 4.02-3.50 (m, 10H), 3.43-3.32 (m, 1H), 3.08-2.90 (m, 4H), 2.44-2.30 (m, 2H), 1.55 (s, 3H), 1.52-1.37 (m, 19H), 1.30 (br.s., 2H). LCMS [M+H] 725.7

Step 3: 4-[(2S)-2-Amino-3-hydroxy-2-methylpropanoyl]-N-[1-(4-{[(exo)-6-(aminomethyl)-3-azabicyclo[3.1.0] hexan-3-yl]methyl}phenyl)-2-oxo-1,2-dihydropyrimidin-4-yl]piperazine-1-carboxamide hydrochloride salt. A solution of tert-butyl N-{[exo-3-({4-[4-({4-[(2S)-2-{[(tert-butoxy) carbonyl]amino}-3-hydroxy-2-methylpropanoyl]piperazine-1-carbonyl}amino)-2-oxo-1,2-dihydropyrimidin-1-yl] phenyl}methyl)-3-azabicyclo[3.1.0]hexan-6-yl] methyl}carbamate (15.0 mg, 0.021 mmol) in 3M HCl in MeOH (3 mL) was stirred at rt for 8 h. Volatiles were removed under reduced pressure. The residue was dissolved in MeOH and precipitated with $Et_2O$. The solid was filtered and dried to afford the title compound as its trihydrochloride salt (6.6 mg, 49%) as a colorless wax. $^1H$ NMR (400 MHz, $D_2O$) δ 7.83 (d, 1H), 7.65-7.55 (m, 2H), 7.49 (d, 2H), 6.80 (d, 1H), 4.41 (s, 2H), 4.10 (d, 1H), 3.84 (d, 1H), 3.79-3.19 (m, 12H), 2.89 (d, 2H), 2.05-1.91 (m, 2H), 1.63 (s, 3H), 1.38-1.29 (m, 1H). LCMS [M+H] 525.5

Compound 70
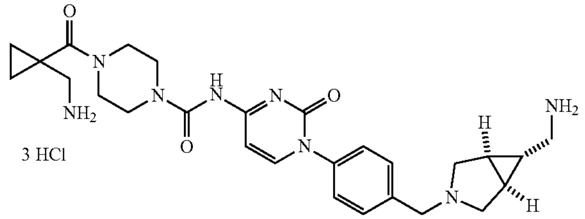
N-[1-(4{[(exo)-6-(Aminomethyl)-3-azabicyclo [3.1.0]hexan-3-yl]methyl}phenyl)-2-oxo-1,2-dihydropyrimidin-4-yl]-4-[1-(aminomethyl)cyclopropanecarbonyl] piperazine-1-Carboxamide Hydrochloride Salt
Scheme C-10
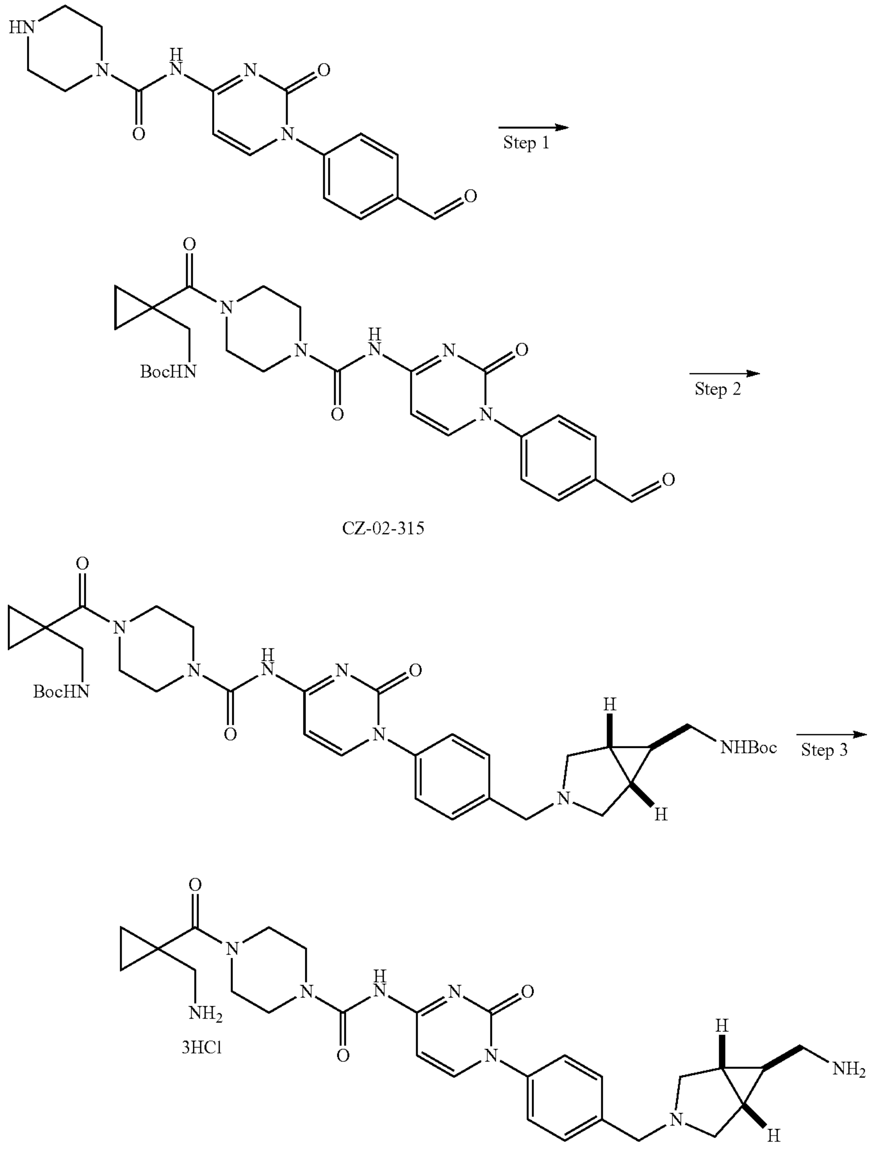
CZ-02-315

Reagents: 1) 1-({[(tert-butoxy)carbonyl]amino}methyl) cyclopropane-1-carboxylic acid, HATU, DIPEA, $CH_3CN$, rt, 4 h 2) tert-butyl N-[exo-3-azabicyclo[3.1.0]hexan-6-yl-methyl]carbamate, $NaBH(OAc)_3CH_2Cl_2$, rt, 16 h 3) 3M HCl in MeOH, rt, 8 h Step 1: tert-butyl N-{[1-(4-{[1-(4-formylphenyl)-2-oxo-1,2-dihydropyrimidin-4-yl]carbamoyl}piperazine-1-carbonyl)cyclopropyl]methyl}carbamate. 1-({[(tert-Butoxy)carbonyl]amino}methyl)cyclopropane-1-carboxylic acid (61 mg, 0.283 mmol), HATU (135 mg, 0.354 mmol) and DIPEA (82 μL, 0.472 mmol) were sequentially added to a solution of N-[1-(4-formylphenyl)-2-oxo-1,2-dihydropyrimidin-4-yl]piperazine-1-carboxamide (0.236 mmol) in $CH_3CN$ (7 mL). The resulting mixture was stirred at rt for 4 h. Volatiles were removed under reduced pressure. The crude product was purified by column chromatography (EtOAc:MeOH, 80:20) to afford the title compound (87 mg, 70%). $^1H$ NMR (400 MHz, $CDCl_3$) δ 13.02 (br. s., 1H), 10.09 (s, 1H), 8.03 (d, 2H), 7.60 (d, 2H), 7.32 (d, 1H), 5.92 (d, 1H), 4.96-4.83 (m, 1H), 4.01-3.88 (m, 2H), 3.70 (br. s., 6H), 3.29 (d, 2H), 1.45 (s, 9H), 1.03-0.97 (m, 2H), 0.82-0.76 (m, 2H). LCMS (Method A): m/z=525.4 $[M+H]^+$.

Step 2: tert-butyl N-{[(exo)-3-({4-[4-({4-[1-({[(tert-butoxy)carbonyl]amino}methyl)cyclopropanecarbonyl]piperazine-1-carbonyl}amino)-2-oxo-1,2-dihydropyrimidin-1-yl]phenyl}methyl)-3-azabicyclo[3.1.0]hexan-6-yl] methyl}carbamate. tert-Butyl N-[exo-3-azabicyclo[3.1.0] hexan-6-ylmethyl]carbamate (52.9 mg, 0.249 mmol) was added to a mixture tert-butyl N-{[1-(4-{[1-(4-formylphenyl)-2-oxo-1,2-dihydropyrimidin-4-yl] carbamoyl}piperazine-1-carbonyl)cyclopropyl] methyl}carbamate (87.0 mg, 0.166 mmol) in $CH_2Cl_2$ (5 mL) and the mixture was stirred at rt for 10 min. $NaBH(OAc)_3$ (88.0 mg, 0.415 mmol) was added; the reaction was stirred at rt for 16 h, diluted with $CH_2Cl_2$ and washed with sat. $NaHCO_3$. The organic portion was dried ($Na_2SO_4$), filtered and concentrated under reduced pressure. The crude product was purified by column chromatography (EtOAc:MeOH, 90:10) to afford the title compound (105 mg, 88%). $^1H$ NMR (400 MHz, $CDCl_3$) δ 12.94 (br. s., 1H), 7.39 (d, 2H), 7.33-7.24 (m, 3H), 5.83 (d, 1H), 4.90 (br. s., 1H), 4.59 (br. s., 1H), 4.02-3.85 (m, 2H), 3.76-3.56 (m, 8H), 3.29 (d, 2H), 3.05-2.95 (m, 4H), 2.43-2.32 (m, 2H), 1.52-1.37 (m, 19H), 1.30 (br.s., 2H), 1.02-0.96 (m, 2H), 0.82-0.75 (m, 2H). LCMS[M+H] 721.8

Step 3: N-[1-(4-{[(exo)-6-(aminomethyl)-3-azabicyclo [3.1.0]hexan-3-yl]methyl}phenyl)-2-oxo-1,2-dihydropyrimidin-4-yl]-4-[1-(aminomethyl)cyclopropane carbonyl] piperazine-1-carboxamide. A solution of tert-butyl N-{[(exo)-3-({4-[4-({4-[1-({[(tert-butoxy)carbonyl] amino}methyl)cyclopropanecarbonyl]piperazine-1-carbonyl}amino)-2-oxo-1,2-dihydropyrimidin-1-yl] phenyl}methyl)-3-azabicyclo[3.1.0]hexan-6-yl] methyl}carbamate (50.0 mg, 0.069 mmol) in 3M HCl in MeOH (6 mL) was stirred at room temperature for 8 h. Volatiles were removed under reduced pressure. The residue was dissolved in MeOH and precipitated with $Et_2O$. The solid was filtered and dried to afford the title compound as its trihydrochloride salt (39.8 mg, 91%) as a pale yellow solid. $^1H$ NMR (400 MHz, $D_2O$) δ 7.87 (d, 1H), 7.70-7.54 (m, 2H), 7.49 (d, 2H), 6.80 (d, 1H), 4.41 (s, 2H), 3.99-3.44 (m, 12H), 3.12 (s, 2H), 2.89 (d, 2H), 2.06-1.91 (m, 2H), 1.34 (br. s., 1H), 1.21-1.09 (m, 2H), 1.05-0.97 (m, 2H). LCMS [M+H] 521.5

Compound 24

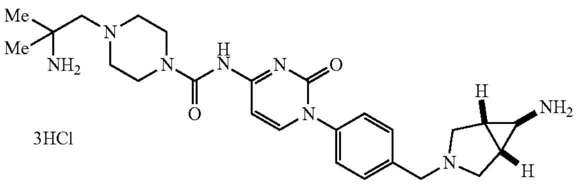

4-(2-amino-2-methylpropyl)-N-(1-(4-(exo-6-amino-3-azabicyclo[3.1.0]hexan-3-yl)methyl)phenyl)-2-oxo-1,2-dihydropyrimidin-4-yl)piperazine-1-carboxamide Hydrochloride Salt Scheme C-11

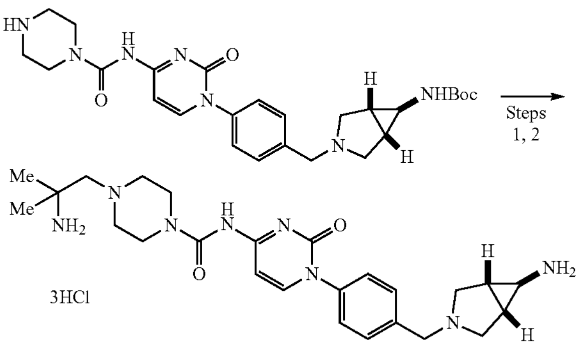

Reagents: 1) $NaBH_3CN$, tert-Butyl N-(2-methyl-1-oxopropan-2-yl)carbamate, MeOH; $NaBH(OAc)_3CH_3CN$, rt, 32 h 2) 3M HCl-MeOH, rt, 16 h Step 1: tert-butyl N-[(exo)-3-{[4-(4-{[4-(2-{[(tert-butoxy)carbonyl]amino}-2-methylpropyl)piperazine-1-carbonyl]amino}-2-oxo-1,2-dihydropyrimidin-1-yl)phenyl] methyl}-3-azabicyclo[3.1.0]hexan-6-yl]carbamate. A mixture of tert-butyl N-[(exo)-3-[(4-{2-oxo-4-[(piperazine-1-carbonyl)amino]-1,2-dihydropyrimidin-1-yl}phenyl) methyl]-3-azabicyclo[3.1.0]hexan-6-yl]carbamate (34.0 mg, 0.066 mmol) and tert-butyl N-(2-methyl-1-oxopropan-2-yl) carbamate (25.0 mg, 0.133 mmol) in MeOH (3 mL) was stirred at rt for 1 h. $NaBH_3CN$ (8.0 mg, 0.133 mmol) was added; the reaction was stirred at rt for 1 h, and concentrated under reduced pressure. The residue was dissolved in $CH_3CN$ and tert-butyl N-(2-methyl-1-oxopropan-2-yl)carbamate (60.0 mg, 0.319 mmol) was added. After 16 h at rt, $NaBH(OAc)_3$ (40.0 mg) was added and the reaction was stirred for an additional 16 h. Volatiles were removed under reduced pressure. The crude residue containing the title compound was pooled together with the crude and fractions containing the title compound obtained from two other preparations run under similar conditions. The mixture was purified by column chromatography ($CH_2Cl_2$:MeOH, 90:10) and subsequently by reverse phase chromatography ($H_2O$:$CH_3CN$, gradient 100:0 to 0:100) to afford the title compound (3.5 mg). LCMS [M+H] 681.6

Step 2: 4-(2-amino-2-methylpropyl)-N-[1-(4-{[(exo)-6-amino-3-azabicyclo[3.1.0]hexan-3-yl]methyl}phenyl)-2-oxo-1,2-dihydropyrimidin-4-1]piperazine-1-carboxamide hydrochloride salt. A solution of tert-Butyl N-[(exo)-3-{[4-(4-{[4-(2-{[(tert-butoxy)carbonyl]amino}-2-methylpropyl)

piperazine-1-carbonyl]amino}-2-oxo-1,2-dihydropyrimidin-1-yl)phenyl]methyl}-3-azabicyclo[3.1.0]hexan-6-yl] carbamate (3.5 mg, 0.0047 mmol) in 3M HCl in MeOH (3 mL) was stirred at rt overnight. Volatiles were removed under reduced pressure. The residue was dissolved in MeOH and precipitated with $Et_2O$. The solid was filtered and dried to afford the title compound (3.1 mg, 97%) as a colorless wax. $^1H$ NMR (400 MHz, $D_2O$) δ 7.82 (d, 1H), 7.61 (d, 2H), 7.50 (d, 2H), 6.80 (d, 1H), 4.46-4.34 (m, 2H), 3.79-3.57 (m, 8H), 2.96-2.83 (m, 5H), 2.81-2.76 (m, 2H), 2.40-2.36 (m, 2H), 1.35 (s, 6H). LCMS[M+H] 481.4

Compound 26

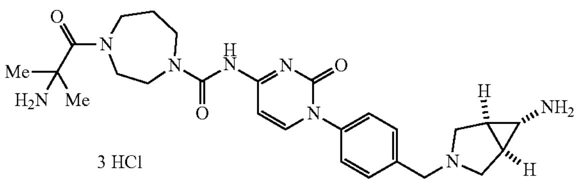

4-(2-Amino-2-methylpropanoyl)-N-(1-(4-((exo-6-amino-3-azabicyclo[3.1.0]hexan-3-yl)methyl)phenyl)-2-oxo-1,2-dihydropyrimidin-4-yl)-1,4-diazepane-1-carboxamide Hydrochloride Salt Scheme C-12

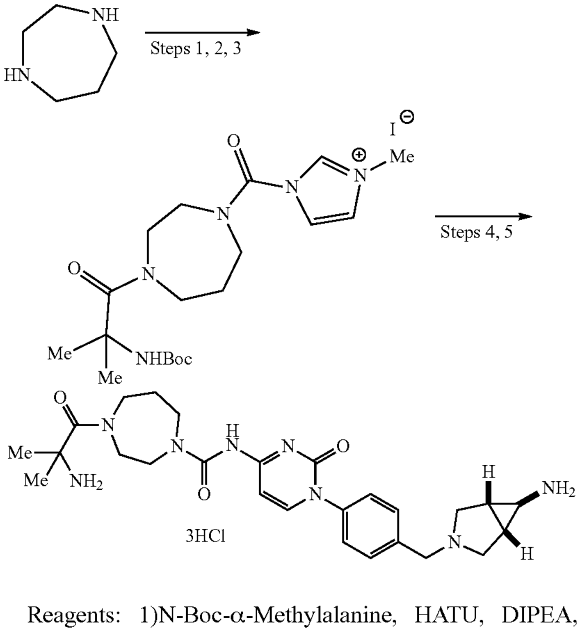

Reagents: 1)N-Boc-α-Methylalanine, HATU, DIPEA, $CH_2Cl_2$, rt, 1 h 2) CDI, DIPEA, THF, reflux, 2 h 3) MeI, $CH_3CN$, 80° C., 22 h 4) tert-butyl N-[exo-3-{[4-(4-amino-2-oxo-1,2-dihydropyrimidin-1-1)phenyl]methyl}-3-azabicyclo[3.1.0]hexan-6-yl] carbamate, $CH_3CN$, reflux, 6 h, 5) 3M HCl-MeOH, rt, 6 h.

Step 1: tert-butyl N-[1-(1,4-diazepan-1-yl)-2-methyl-1-oxopropan-2-yl]carbamate. 1,4-Diazepane (200 mg, 2.0 mmol) was added to a solution of 2-{[(tert-butoxy)carbonyl]amino}-2-methylpropanoic acid (203 mg, 1.0 mmol), HATU (456 mg, 1.2 mmol) and DIPEA (350 μL, 2.0 mmol) in $CH_2Cl_2$ (10 mL), which had been stirred for 20 min. The reaction was stirred at rt for 1 h, diluted with $CH_2Cl_2$ and washed twice with $H_2O$. The organic portion was dried ($Na_2SO_4$), filtered and concentrated under reduced pressure to afford the crude tert-butyl N-[1-(1,4-diazepan-1-yl)-2-methyl-1-oxopropan-2-yl]carbamate (390 mg). LCMS [M+H] 286.3

Step 2: tert-butyl N-{1-[4-(1H-imidazole-1-carbonyl)-1,4-diazepan-1-yl]-2-methyl-1-oxopropan-2-yl}carbamate. CDI (443 mg, 2.73 mmol) and DIPEA (480 μL, 2.76 mmol) were added to a solution of tert-butyl N-[1-(1,4-diazepan-1-yl)-2-methyl-1-oxopropan-2-yl]carbamate (390 mg) in THF (15 mL). The reaction was heated to reflux and stirred for 2 h. EtOAc was added and the organic portion was washed twice with $H_2O$, dried over $Na_2SO_4$, filtered and concentrated under reduced pressure. The crude product was purified by reverse phase chromatography ($H_2O$:$CH_3CN$, gradient 100:0 to 0:100) to afford the title compound (200 mg, 52% over two steps). LCMS [M+H] 380.4

Step 3: 1-[4-(2-{[(tert-butoxy)carbonyl]amino}-2-methylpropanoyl)-1,4-diazepane-1-carbonyl]-3-methyl-1H-imidazol-3-ium iodide. Iodomethane (200 μL, 3.21 mmol) was added to a solution of tert-butyl N-[1-[4-(1H-imidazole-1-carbonyl)-1,4-diazepan-1-yl]-2-methyl-1-oxopropan-2-yl] carbamate (200 mg, 0.526 mmol) in $CH_3CN$ (20 mL) and the reaction was heated to 80° C. for 6 h. Additional iodomethane (200 μL, 3.21 mmol) was added and the reaction was stirred at 75° C. for 16 h. Volatiles were removed under reduced pressure to afford the crude 1-[4-(2-{[(tert-butoxy)carbonyl]amino}-2-methylpropanoyl)-1,4-diazepane-1-carbonyl]-3-methyl-1H-imidazol-3-ium iodide. LCMS $[M]^+$ 394.4

Step 4: tert-butyl N-[exo-3-{[4-(4-{[4-(2-{[(tert-butoxy)carbonyl]amino}-2-methylpropanoyl)-1,4-diazepane-1-carbonyl]amino}-2-oxo-1,2-dihydropyrimidin-1-yl)phenyl]methyl}-3-azabicyclo[3.1.0]hexan-6-yl]carbamate. A mixture of tert-butyl N-[exo-3-{[4-(4-amino-2-oxo-1,2-dihydropyrimidin-1-yl)phenyl]methyl}-3-azabicyclo[3.1.0]hexan-6-yl]carbamate (300 mg, 0.756 mmol) and 1-[4-(2-{[(tert-butoxy)carbonyl]amino}-2-methylpropanoyl)-1,4-diazepane-1-carbonyl]-3-methyl-1H-imidazol-3-ium iodide in $CH_3CN$ (20 mL) was refluxed for 6 h. Volatiles were removed under reduced pressure and the crude product was purified first by column chromatography (EtOAc:MeOH, gradient 100:0 to 80:20) and then by reverse phase chromatography ($H_2O$:$CH_3CN$, gradient 100:0 to 0:100) to afford the title compound (13.4 mg, 4% over two steps) as a colorless wax. LCMS[M+H] 709.7

Step 5: 4-(2-amino-2-methylpropanoyl)-N-[1-(4-{[exo-6-amino-3-azabicyclo[3.1.0]hexan-3-yl]methyl}phenyl)-2-oxo-1,2-dihydropyrimidin-4-yl]-1,4-diazepane-1-carboxamide hydrochloride salt. tert-butyl N-[exo-3-{[4-(4-{[4-(2-{[(tert-butoxy)carbonyl]amino}-2-methylpropanoyl)-1,4-diazepane-1-carbonyl]amino}-2-oxo-1,2-dihydropyrimidin-1-yl)phenyl]methyl}-3-azabicyclo[3.1.0]hexan-6-yl] carbamate (8.0 mg, 0.011 mmol) was dissolved in a 3M solution of HCl in MeOH (3 mL) and the reaction was stirred at rt for 6 h. Volatiles were removed under reduced pressure. The crude product was washed with $Et_2O$, dissolved in $H_2O$ and concentrated under reduced pressure to afford the title compound (6.0 mg, 86%) as a colorless wax. $^1H$ NMR (400 MHz, $D_2O$) δ 7.83 (d, 1H), 7.61 (d, 2H), 7.52-7.46 (m, 2H), 6.90-6.80 (m, 1H), 4.41 (br.s., 2H), 3.94-3.46 (m, 13H), 2.48-2.31 (m, 2H), 1.95-1.82 (m, 2H), 1.65 (s, 6H). LCMS[M+H] 509.5

Compound 67

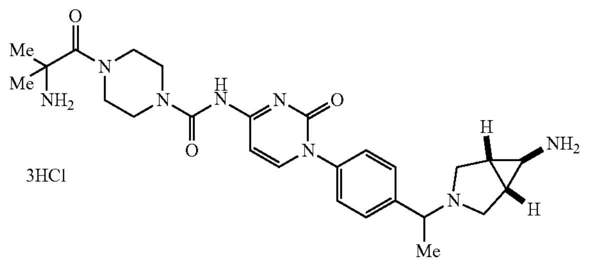

4-(2-Amino-2-methylpropanoyl)-N-(1-(4-(1-(exo-6-amino-3-azabicyclo[3.1.0]hexan-3-yl)ethyl)phenyl)-2-oxo-1,2-dihydropyrimidin-4-yl)piperazine-1-carboxamide Hydrochloride Salt Scheme C-13

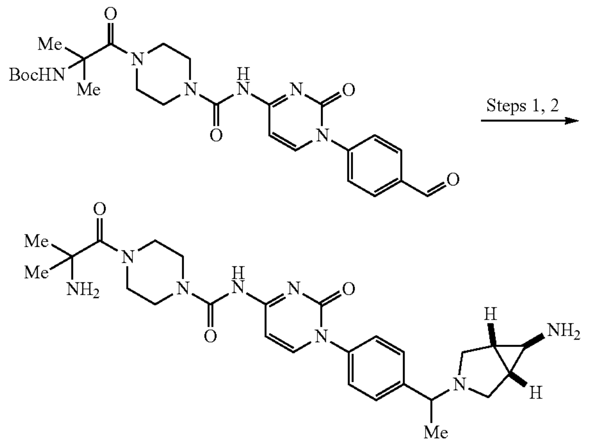

Reagents: a) tert-butyl 3-azabicyclo (3.1.0) hexan-6-ylcarbamate, $CH_2Cl_2$, rt, 16 h; MeMgBr 0° C. to rt, 2 h b) 3M HCl-MeOH.

Step 1: tert-butyl N-[exo-3-{1-[4-(4-{[4-(2-{[(tert-butoxy)carbonyl]amino}-2-methylpropanoyl)piperazine-1-carbonyl]amino}-2-oxo-1,2-dihydropyrimidin-1-yl)phenyl]ethyl}-3-azabicyclo[3.1.0]hexan-6-yl]carbamate. tert-Butyl 3-azabicyclo (3.1.0) hexan-6-ylcarbamate (23.0 mg, 0.117 mmol) was added to a solution of tert-butyl N-[1-(4-{[1-(4-formylphenyl)-2-oxo-1,2-dihydropyrimidin-4-yl]carbamoyl}piperazin-1-yl)-2-methyl-1-oxopropan-2-yl]carbamate (40.0 mg, 0.078 mmol) in $CH_2Cl_2$ and the reaction was stirred at rt for 16 h. The solution was cooled to 0° C. and MeMgBr (3M solution in THF, 52 μL, 0.156 mmol) was added. After 1 h at rt, additional MeMgBr (3M solution in THF, 78 μL, 0.234 mmol) was added the reaction was stirred for 1 h. The reaction was diluted with $CH_2Cl_2$ and washed with $H_2O$. The organic portion was dried over $Na_2SO_4$, filtered and concentrated under reduced pressure. The crude product was purified by column chromatography to afford (EtOAc:MeOH, 100:0 to 80:20) to afford the title compound (4.0 mg, 7%). LCMS[M+H] 709.7

Step 2: 4-(2-amino-2-methylpropanoyl)-N-(1-(4-(1-(exo-6-amino-3-azabicyclo[3.1.0]hexan-3-yl)ethyl)phenyl)-2-oxo-1,2-dihydropyrimidin-4-yl)piperazine-1-carboxamide. Prepared from tert-butyl N-[exo-3-{1-[4-(4-{[4-(2-{[(tert-butoxy)carbonyl]amino}-2-methylpropanoyl)piperazine-1-carbonyl]amino}-2-oxo-1,2-dihydropyrimidin-1-yl)phenyl]ethyl}-3-azabicyclo[3.1.0]hexan-6-yl] carbamate (4.0 mg, 0.0056 mmol) to afford the title compound as its trihydrochloride salt (0.5 mg, 14%) as a colorless wax. $^1H$ NMR (400 MHz, $D_2O$) δ 7.81 (d, 1H), 7.60 (d, 2H), 7.50 (d, 2H), 6.81 (d, 1H), 4.07-3.19 (m, 13H), 2.96-2.73 (m, 1H), 2.48-2.15 (m, 2H), 1.68 (s, 9H). LCMS[M+H] 509.7

Alternatively, this compound can be prepared from 1-(4-bromophenyl)ethan-1-ol and tert-butyl (exo-3-azabicyclo[3.1.0]hexan-6-yl)carbamate. $^1H$ NMR (500 MHz, $D_2O$) δ 7.96-8.02 (m, 1H), 7.62-7.72 (m, 2H), 7.56 (d, 2H), 6.79-6.85 (m, 1H), 4.43-4.54 (m, 1H), 3.98-4.10 (m, 1H), 3.63-3.84 (m, 8H), 3.45-3.56 (m, 1H), 3.36-3.41 (m, 1H), 3.29-3.35 (m, 1H), 2.86-2.95 (m, 1H), 2.35-2.45 (m, 1H), 2.25-2.35 (m, 1H), 1.66-1.77 (m, 9H). LCMS[M+H] 509.4.

Compound 17

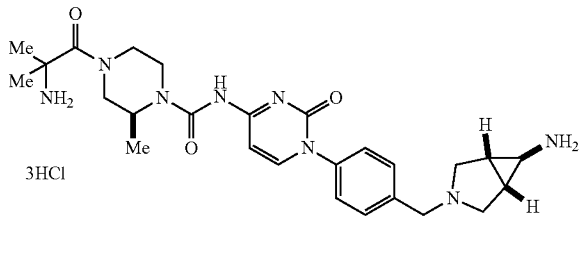

(S)-4-(2-Amino-2-methylpropanoyl)-N-(1-(4-((exo-6-amino-3-azabicyclo[3.1.0]hexan-3-yl)methyl)phenyl)-2-oxo-1,2-dihydropyrimidin-4-yl)-2-methylpiperazine-1-carboxamide Hydrochloride Salt Scheme C-14

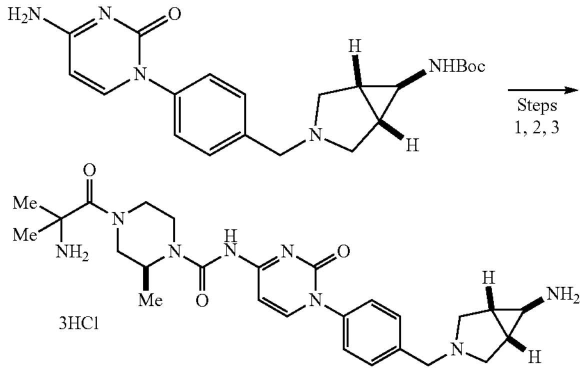

Reagents: 1) CDI, $CH_2Cl_2$, rt, 16 h 2) $CH_3CN$, tert-butyl (S)-(2-methyl-1-(3-methylpiperazin-1-yl)-1-oxopropan-2-yl)carbamate, 85° C. 2 h. 3) HCl, MeOH, rt, 4 h.

Step 1: tert-butyl (exo-3-(4-(4-(1H-imidazole-1-carboxamido)-2-oxopyrimidin-1 (2H)-yl)benzyl)-3-azabicyclo[3.1.0]hexan-6-yl)carbamate. A suspension of tert-butyl (exo-3-(4-(4-amino-2-oxopyrimidin-1 (2H)-yl)benzyl)-3-azabicyclo[3.1.0]hexan-6-yl)carbamate (2.50 g, 6.90 mmol) and CDI (1.63 g, 9.72 mmol) in $CH_2Cl_2$ was stirred for 16 h at rt. The solvent was removed under reduced pressure, and the solid was triturated with EtOAc to afford the title compound.

Step 2: tert-butyl (1-((S)-4-((1-(4-((exo-6-((tert-butoxycarbonyl)amino)-3-azabicyclo[3.1.0]hexan-3-yl)methyl)phenyl)-2-oxo-1,2-dihydropyrimidin-4-yl)carbamoyl)-3-methylpiperazin-1-yl)-2-methyl-1-oxopropan-2-yl)carbamate. To a solution of tert-butyl (exo-3-(4-(4-(1H-imidazole-1-carboxamido)-2-oxopyrimidin-1 (2H)-yl)benzyl)-3-azabicyclo[3.1.0]hexan-6-yl)carbamate in $CH_3CN$ (10 mL) was added tert-butyl (S)-(2-methyl-1-(3-methylpiperazin-1-yl)-1-oxopropan-2-yl)carbamate. The reaction was heated to 85° C. for 2 h. The reaction mixture was concentrated under reduced pressure, dissolved in EtOAc (50 mL), and washed with $H_2O$ (3×50 mL). The organic layer was dried over $Na_2SO_4$ and purified by column chromatography ($MeOH:CH_2Cl_2$) to afford the desired compound.

Step 3: (S)-4-(2-amino-2-methylpropanoyl)-N-(1-(4-((exo-6-amino-3-azabicyclo[3.1.0]hexan-3-yl)methyl)phenyl)-2-oxo-1,2-dihydropyrimidin-4-yl)-2-methylpiperazine-1-carboxamide hydrochloride salt. Tert-butyl (1-((S)-4-((1-(4-((exo-6-((tert-butoxycarbonyl)amino)-3-azabicyclo[3.1.0]hexan-3-yl)methyl)phenyl)-2-oxo-1,2-dihydropyrimidin-4-yl)carbamoyl)-3-methylpiperazin-1-yl)-2-methyl-1-oxopropan-2-yl)carbamate was dissolved in a solution of HCl in MeOH (2N, 5 mL) and stirred for 4 h. The volatiles were removed under reduced pressure and the crude solid was purified by reversed phase HPLC ($H_2O$:$CH_3CN$:TFA) and concentrated under reduced pressure. Addition and evaporation under reduced pressure with HCl in MeOH (2N, 2N, 3×15 mL) afforded the title compound. $^1H$ NMR (400 MHz, $CD_3OD$) δ 8.35 (d, 1H), 7.88 (d, 2H), 7.65 (d, 2H), 6.89 (d, 1H), 4.66 (s, 1H), 4.52 (s, 2H), 4.36-4.18 (m, 3H), 3.72 (q, 3H), 3.49-3.20 (m, 5H), 2.36 (s, 2H), 1.75 (s, 3H), 1.73 (s, 3H), 1.31 (d, 3H). LCMS[M+H] 509.3

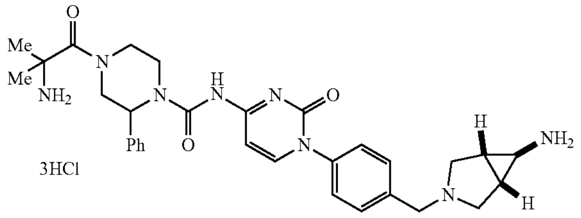 [SMILES: CC(C)(N)C(=O)N1CCN(C(=O)Nc2ccn(-c3ccc(CN4C[C@@H]5[C@@H](N)[C@@H]5C4)cc3)c(=O)n2)C(c2ccccc2)C1]

4-(2-Amino-2-methylpropanoyl)-N-(1-(4-((exo-6-amino-3-azabicyclo[3.1.0]hexan-3-yl)methyl)phenyl)-2-oxo-1,2-dihydropyrimidin-4-yl)-2-phenylpiperazine-1-carboxamide Hydrochloride Salt Prepared in a similar fashion as in Scheme C-14 from tert-butyl (exo-3-(4-(4-(1H-imidazole-1-carboxamido)-2-oxopyrimidin-1 (2H)-yl)benzyl)-3-azabicyclo[3.1.0]hexan-6-yl)carbamate and tert-butyl (2-methyl-1-oxo-1-(3-phenylpiperazin-1-yl)propan-2-yl)carbamate. $^1H$ NMR (400 MHz, $D_2O$) δ 7.82 (s, 1H), 7.67 (d, 2H), 7.53 (d, 2H), 7.50-7.34 (m, 5H), 6.68 (s, 1H), 4.48 (s, 2H), 4.19 (s, 2H), 4.03 (s, 1H), 3.74 (s, 5H), 3.36 (s, 1H), 3.21 (q, 1H), 2.92 (s, 1H), 2.43 (d, 2H), 1.81-1.43 (m, 6H), 1.29 (t, 1H).

Compound 28

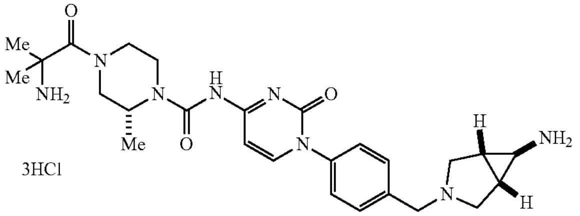

(R)-4-(2-Amino-2-methylpropanoyl)-N-(1-(4-((exo-6-amino-3-azabicyclo[3.1.0]hexan-3-yl)methyl)phenyl)-2-oxo-1,2-dihydropyrimidin-4-yl)-2-methylpiperazine-1-carboxamide Hydrochloride Salt Prepared in a similar fashion to Scheme C-14 from tert-butyl (exo-3-(4-(4-(1H-imidazole-1-carboxamido)-2-oxopyrimidin-1 (2H)-yl)benzyl)-3-azabicyclo[3.1.0]hexan-6-yl)carbamate and (R)-tert-butyl (2-methyl-1-(3-methylpiperazin-1-yl)-1-oxopropan-2-yl)carbamate. $^1H$ NMR (400 MHz, $D_2O$) δ 8.00 (d, 1H), 7.55 (d, 2H), 7.44 (d, 2H), 6.68 (d, 1H), 4.38 (d, 2H), 4.07 (d, 1H), 3.94 (d, 1H), 3.61 (s, 4H), 3.35 (s, 2H), 2.77 (s, 1H), 2.29 (s, 2H), 1.84 (s, 1H), 1.59 (t, 6H), 1.13 (s, 3H). LC-MS [M+H] 509.2.

Compound 35

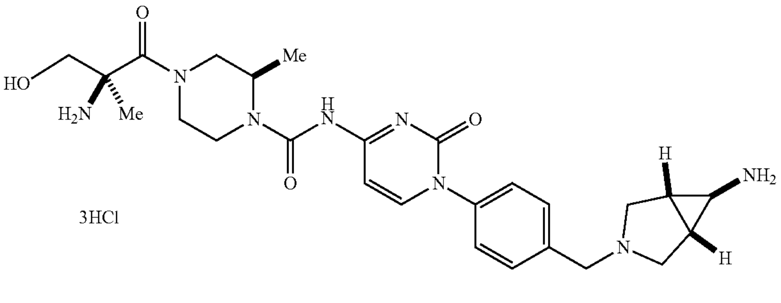

(R)—N-(1-(4-((exo-6-Amino-3-azabicyclo[3.1.0]hexan-3-yl)methyl)phenyl)-2-oxo-1,2-dihydropyrimidin-4-yl)-4-((S)-2-amino-3-hydroxy-2-methylpropanoyl)-2-methylpiperazine-1-carboxamide Hydrochloride Salt Prepared in a similar fashion to Scheme C-14 from tert-butyl (exo-3-(4-(4-(1H-imidazole-1-carboxamido)-2-oxopyrimidin-1 (2H)-yl)benzyl)-3-azabicyclo[3.1.0]hexan-6-yl)carbamate and (2R,4S)-tert-butyl 2-(tert-butyl)-4-methyl-4-((R)-3-methylpiperazine-1-carbonyl)oxazolidine-3-carboxylate. $^{1}H$ NMR (400 MHz, $D_2O$) δ 7.92 (d, 1H), 7.68 (d, 2H), 7.57 (d, 2H), 6.84 (d, 1H), 4.57 (s, 1H), 4.48 (s, 2H), 4.22 (d, 1H), 4.18 (d, 1H), 4.09 (d, 1H), 3.92 (d, 1H), 3.75 (s, 3H), 3.53-3.30 (m, 3H), 2.92 (s, 1H), 2.45 (s, 2H), 1.70 (d, 3H), 1.28 (d, 3H). LCMS [M+H] 525.4.

-continued

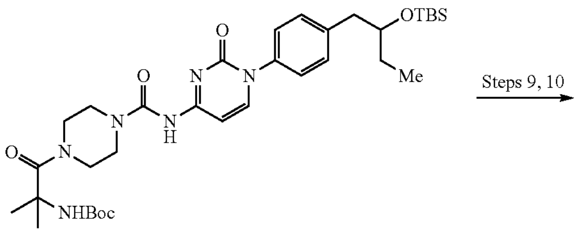

Compound 135

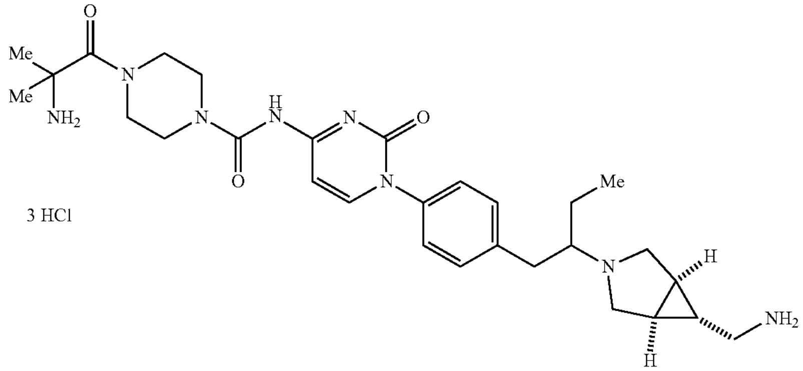

4-(2-Amino-2-methylpropanoyl)-N-(1-(4-(2-(exo-6-(aminomethyl)-3-azabicyclo[3.1.0]hexan-3-yl)butyl)phenyl)-2-oxo-1,2-dihydropyrimidin-4-yl)piperazine-1-carboxamide Hydrochloride Salt Scheme C-15

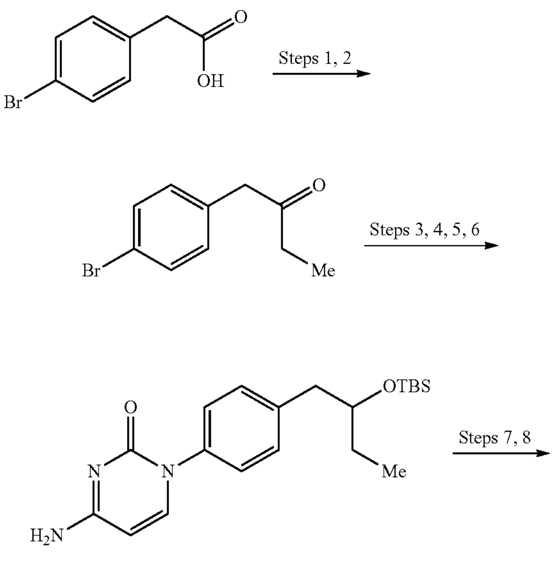

-continued

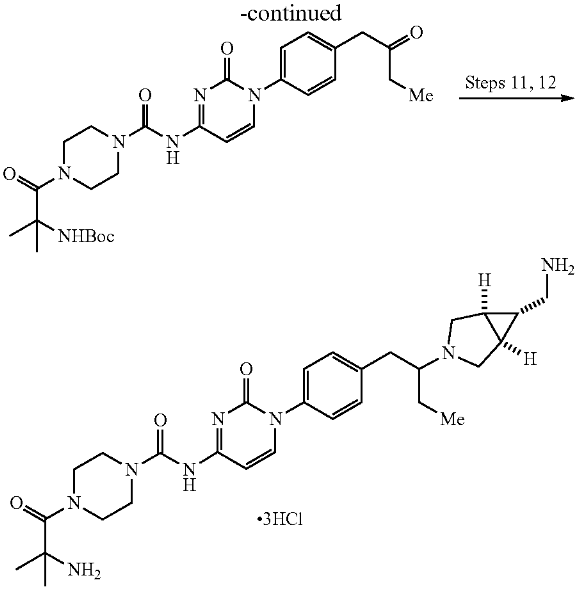

Reagents: 1) HN(OMe)Me·HCl, EDCI·HCl, $NEt_3$, DMAP, $CH_2Cl_2$, rt, 16 h, 2) EtMgBr, THF, −78° C. to rt, 16 h, 3) $NaBH_4$, MeOH, 0° C., 8 h, 4) TBSCl, imidazole, $CH_2Cl_2$16 h, 5) BuLi, THF, −78° C. $(iPrO)_3B$, 2N HCl, 4 h, 6) cytosine, TMEDA, $Cu(OAc)_2 \cdot H_2O$, 4:1 $MeOH:H_2O$, 48 h, 7) CDI, $CH_2Cl_2$, 48 h, 8) tert-butyl (2-methyl-1-oxo-1-

(piperazin-1-yl)propan-2-yl)carbamate, $CH_3CN$, 80° C., 2 h, 9) TsOH, MeOH, 1 h, 10) DMP, $CH_2Cl_2$, 2 h 11) tert-butyl ((exo-3-azabicyclo[3.1.0]hexan-6-yl)methyl)carbamate, $NaCNBH_3$, MeOH, 16 days 12) HCl in MeOH, Step 1: 2-(4-bromophenyl)-N-methoxy-N-methylacetamide. To a solution of 2-(4-bromophenyl)acetic acid (15.0 g, 64.67 mmol) acid in $CH_2Cl_2$ (750 mL) was added N,O-Dimethylhydroxylamine hydrochloride (9.5 g, 97.0 mmol), followed by EDCI HCl (18.6 g, 97.0 mmol). To this solution was added a catalytic amount of DMAP and $Et_3N$ (36.0 mL). The solution was stirred for 16 h. The crude reaction mixture was the extracted with 2N HCl (1×500 mL) followed by $NaHCO_3$ (1×500 mL) and again by 2N HCl (1×500 mL) and $NaHCO_3$ (1×500 mL). The organic layer was dried over $Na_2SO_4$, concentrated under reduced pressure to afford the title compound as a white solid.

Step 2: 1-(4-bromophenyl)butan-2-one. To a solution of 2-(4-bromophenyl)-N-methoxy-N-methylacetamide (18.0 g, 69.8 mmol) in THF (500 mL) at −78° C., was added EtMgBr (30.0 mL, 90.7 mmol) and the solution was slowly warmed to rt and stirred for 16 h. 2N HCl (1×200 mL) was added and the solution was partitioned between $H_2O$ (500 mL) and EtOAc (1000 mL). The organic layer was dried over $Na_2SO_4$, concentrated under reduced pressure, and purified by column chromatography (Hex:EtOAc) to afford the title compound.

Step 3: 1-(4-bromophenyl)butan-2-ol. A solution of 1-(4-bromophenyl)butan-2-one (6.0 g, 26.4 mmol) in MeOH (100 mL) was cooled to 0° C. To this was added $NaBH_4$ (4.0 g, 105.2 mmol) portionwise over the span of 30 min. The solution was warmed and stirred for 8 h. The reaction mixture was concentrated and partitioned between EtOAc (500 mL) and 1N NaOH (500 mL). The organic layer was collected and the aqueous layer was washed again with EtOAc (1×500 mL). The combined organics were dried over $Na_2SO_4$ and concentrated under reduced pressure to afford the title compound as a white solid. The product was used in the next step without further purification.

Step 4: ((1-(4-bromophenyl)butan-2-yl)oxy)(tert-butyl)dimethylsilane. To a solution of 1-(4-bromophenyl)butan-2-ol (26.4 mmol) in $CH_2Cl_2$ (200 mL) was added imidazole (3.5 g, 51.5 mmol) and TBSCl (5.5 g, 36.6 mmol). The reaction was stirred for 16 h. The crude reaction mixture was concentrated under reduced pressure to give an oily residue, which was purified by column chromatography (Hexanes: EtOAc) to afford the title compound.

Step 5: tert-butyldimethyl((1-(4-(4,4,5,5-tetramethyl-1,3,2-dioxaborolan-2-yl)phenyl)butan-2-yl)oxy)silane. A stirred solution of ((1-(4-bromophenyl)butan-2-yl)oxy)(tert-butyl)dimethylsilane (9.0 g, 26.2 mmol) in THF (300 mL) was cooled to −78° C. n-BuLi in Hexanes (1.0 M, 26.0 mL, 65.5 mmol) was added dropwise over 30 min maintaining the temperature below −60° C. After 25 min, $B(iPrO)_3$ (9.0 mL, 39.3 mmol) was added dropwise over 30 min. The reaction mixture was warmed to rt and stirred for 15 min. 2N HCl (200 mL) was added and the reaction was stirred for 30 min. The biphasic mixture was separated and the aq. layer extracted with $CH_2Cl_2$ (2××500 mL). The combined organics were dried over $Na_2SO_4$ and concentrated under reduced pressure to afford the title compound.

Step 6: 4-amino-1-(4-(2-((tert-butyldimethylsilyl)oxy)butyl)phenyl)pyrimidin-2 (1H)-one. A suspension of cytosine (2.9 g, 26.2 mmol) and tert-butyldimethyl((1-(4-(4,4,5,5-tetramethyl-1,3,2-dioxaborolan-2-yl)phenyl)butan-2-yl)oxy)silane (26.2 mmol), in MeOH:$H_2O$ (4:1, 300 mL) was stirred at rt in open air for 30 min. TMEDA (4.7 ml, 31.4 mmol) and $Cu(OAc)_{2+120}$ (5.21 g, 26.2 mmol) were added and the reaction was stirred in open air for 48 h at rt. The reaction mixture was concentrated under reduced pressure, and cold $H_2O$ (150 mL) was added. The solid was filtered and washed with $H_2O$ (5×50 mL), $Et_2O$ (3×30 mL), and $H_2O$ (2×30 mL) to the title compound as an off white solid.

Step 7: N-(1-(4-(2-((tert-butyldimethylsilyl)oxy)butyl)phenyl)-2-oxo-1,2-dihydropyrimidin-4-yl)-1H-imidazole-1-carboxamide. A suspension of 4-amino-1-(4-(2-((tert-butyldimethylsilyl)oxy)butyl)phenyl)pyrimidin-2 (1H)-one (5.3 mg, 14.2 mmol) and CDI (3.9 g 24.1) in $CH_2Cl_2$ (250 mL) was stirred at rt for 48 h. The solvent was removed under reduced pressure to afford the title compound.

Step 8: tert-butyl (1-(4-((1-(4-(2-((tert-butyldimethylsilyl)oxy)butyl)phenyl)-2-oxo-1,2-dihydropyrimidin-4-yl)carbamoyl)piperazin-1-yl)-2-methyl-1-oxopropan-2-yl)carbamate. N-(1-(4-(2-((tert-butyldimethylsilyl)oxy)butyl)phenyl)-2-oxo-1,2-dihydropyrimidin-4-yl)-1H-imidazole-1-carboxamide (14.2 mmol) and tert-butyl (2-methyl-1-oxo-1-(piperazin-1-yl)propan-2-yl)carbamate as prepared in Scheme 2 (4.4 g, 16.2 mmol) were dissolved in $CH_3CN$ (300 mL) and heated to reflux for 2 h. The reaction mixture was concentrated under reduced pressure and purified by column chromatography (Hexanes:EtOAc) to afford the title compound.

Step 9: tert-butyl (1-(4-((1-(4-(2-hydroxybutyl)phenyl)-2-oxo-1,2-dihydropyrimidin-4-yl)carbamoyl)piperazin-1-yl)-2-methyl-1-oxopropan-2-yl)carbamate. To a solution of tert-butyl (1-(4-((1-(4-(2-((tert-butyldimethylsilyl)oxy)butyl)phenyl)-2-oxo-1,2-dihydropyrimidin-4-yl)carbamoyl)piperazin-1-yl)-2-methyl-1-oxopropan-2-yl)carbamate (2.0 g, 3.0 mmol) in MeOH (150 mL) was added p-toluenesulfonic acid (1.0 g, 3.0 mmol) and stirred for 60 min. The reaction mixture was concentrated under reduced pressure and partitioned between $CH_2Cl_2$ (250 mL) and sat. aq. aq. $NaHCO_3$ (250 mL). The organic layer was collected and the aqueous layer was extracted with $CH_2Cl_2$ (1×250 mL). The organic layers were combined, dried over $Na_2SO_4$ and concentrated under reduced pressure to afford the title compound as an off white solid.

Step 10: tert-butyl (2-methyl-1-oxo-1-(4-((2-oxo-1-(4-(2-oxobutyl)phenyl)-1,2-dihydropyrimidin-4-yl)carbamoyl)piperazin-1-yl)propan-2-yl)carbamate. To a stirred solution of tert-butyl (1-(4-((1-(4-(2-hydroxybutyl)phenyl)-2-oxo-1,2-dihydropyrimidin-4-yl)carbamoyl)piperazin-1-yl)-2-methyl-1-oxopropan-2-yl)carbamate (1.6 g, 3.0 mmol) in $CH_2Cl_2$ (250 mL) was added DMP (1.9 g, 4.5 mmol). The solution was stirred for 2.5 h. The crude reaction mixture was diluted with $CH_2Cl_2$ (250 mL) and washed with aq. $NaHCO_3/Na_2S_2O_3$ (1×500 mL). The organic layer was dried over $Na_2SO_4$ and concentrated under reduced pressure. The crude solid was purified by column chromatography (MeOH:$CHCl_3$) afford the title compound.

Step 11: tert-butyl (1-(4-((1-(4-(2-(exo-6-(((tert-butoxycarbonyl)amino)methyl)-3-azabicyclo[3.1.0]hexan-3-yl)butyl)phenyl)-2-oxo-1,2-dihydropyrimidin-4-yl)carbamoyl)piperazin-1-yl)-2-methyl-1-oxopropan-2-yl)carbamate. To a stirred tert-butyl (2-methyl-1-oxo-1-(4-((2-oxo-1-(4-(2-oxobutyl)phenyl)-1,2-dihydropyrimidin-4-yl)carbamoyl)piperazin-1-yl)propan-2-yl)carbamate (1.2 g, 2.1 mmol) was added tert-butyl ((exo-3-azabicyclo[3.1.0]hexan-6-yl)methyl)carbamate (530 mg, 2.4 mmol) followed by $NaCNBH_3$ (260 mg, 4.2 mmol) and 4 Å molecular sieves (5 g). The reaction was stirred for 16 d. The reaction mixture was filtered and concentrated under reduced pressure. The solid was partitioned between $CHCl_3$ (125 mL) and aq. $NaHCO_3$ (125 mL). The layers were separated, and the aqueous layer was extracted with $CHCl_3$ (1×125 mL). The combined organics were dried over $Na_2SO_4$ and concentrated under reduced pressure to afford the title compound.

Step 12: 4-(2-amino-2-methylpropanoyl)-N-(1-(4-(2-(exo-6-(aminomethyl)-3-azabicyclo[3.1.0]hexan-3-yl)butyl)phenyl)-2-oxo-1,2-dihydropyrimidin-4-yl)piperazine-1-carboxamide hydrochloride salt. tert-butyl (1-(4-((1-(4-(2-(exo-6-(((tert-butoxycarbonyl)amino)methyl)-3-azabicyclo[3.1.0]hexan-3-yl)butyl)phenyl)-2-oxo-1,2-dihydropyrimidin-4-yl)carbamoyl)piperazin-1-yl)-2-methyl-1-oxopropan-2-yl)carbamate (1.0 g, 1.3 mmol) was dissolved in a solution of HCl in MeOH (2N, 150 mL) and stirred for 4 h. The HCl/MeOH was evaporated and the crude solid was purified by column chromatography ($NH_4OH$:MeOH:$CHCl_3$). Addition and evaporation of HCl in MeOH (2N, 2×50 mL) afforded the desired compound. $^1H$ NMR (400 MHz, $D_2O$) δ 8.00 (d, 1H), 7.51 (d, 2H), 7.46 (d, 2H), 6.84 (d, 1H), 3.86 (d, 1H), 3.83 (d, 1H), 3.79 (s, 3H), 3.75 (s, 5H), 3.68-3.56 (m, 3H), 3.29-3.22 (m, 1H), 3.16-3.03 (m, 1H), 2.99 (d, 2H), 2.07 (s 2H), 1.83-1.67 (m, 8H), 1.40 (s, 1H), 0.95 (t, 3H). LCMS[M+H] 551.2.

Compound 139

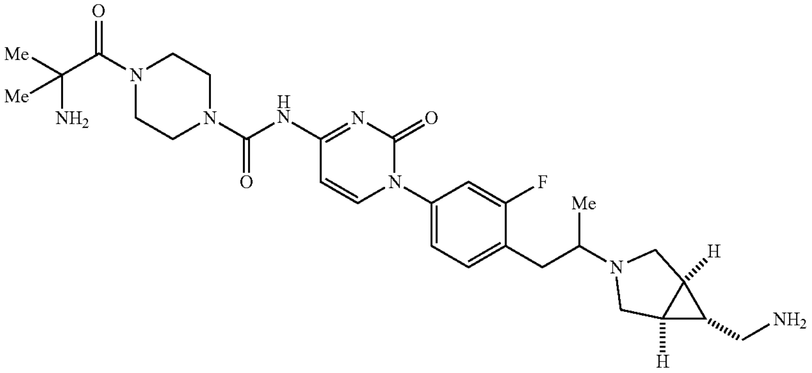

4-(2-Amino-2-methylpropanoyl)-N-(1-(4-(2-(exo-6-(aminomethyl)-3-azabicyclo[3.1.0]hexan-3-yl)propyl)-3-fluorophenyl)-2-oxo-1,2-dihydropyrimidin-4-yl)piperazine-1-carboxamide Hydrochloride Salt Prepared in a similar fashion as in Scheme C-15 from tert-butyl (1-(4-((1-(3-fluoro-4-(2-oxopropyl)phenyl)-2-oxo-1,2-dihydropyrimidin-4-yl)carbamoyl)piperazin-1-yl)-2-methyl-1-oxopropan-2-yl)carbamate and tert-butyl ((exo-3-azabicyclo[3.1.0]hexan-6-yl)methyl)carbamate. $^1H$ NMR (500 MHz, $D_2O$) δ 7.99 (d, 1H), 7.50 (t, 1H), 7.35-7.27 (m, 2H), 6.82 (d, 1H), 3.94 (d, 1H), 3.85-3.69 (m, 9H), 3.68-3.64 (m, 2H), 3.60-3.56 (m, 1H), 3.40-3.35 (m, 1H), 3.01-2.95 (m, 2H), 2.94-2.87 (m, 1H), 2.07-2.01 (m, 2H), 1.73 (s, 6H), 1.39-1.34 (m, 1H), 1.27 (d, 3H). LCMS[M+H]555.3.

Compound 122

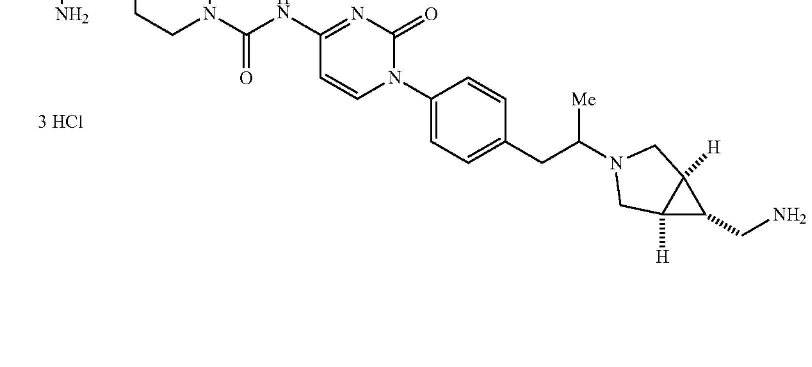

4-(2-Amino-2-methylpropanoyl)-N-(1-(4-(2-(exo-6-(aminomethyl)-3-azabicyclo[3.1.0]hexan-3-yl)propyl)phenyl)-2-oxo-1,2-dihydropyrimidin-4-yl)piperazine-1-carboxamide Hydrochloride Salt
Scheme C-16
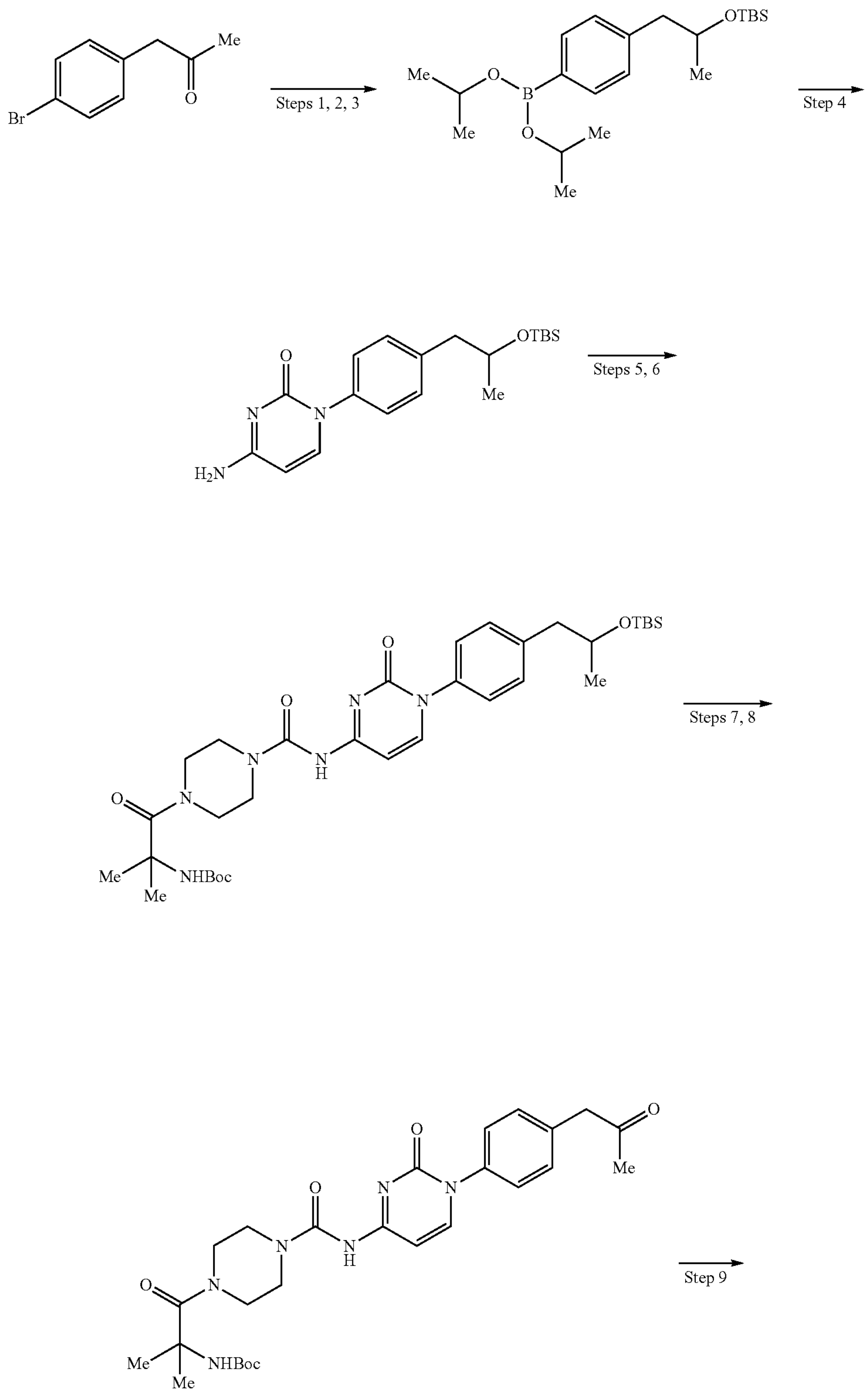

-continued

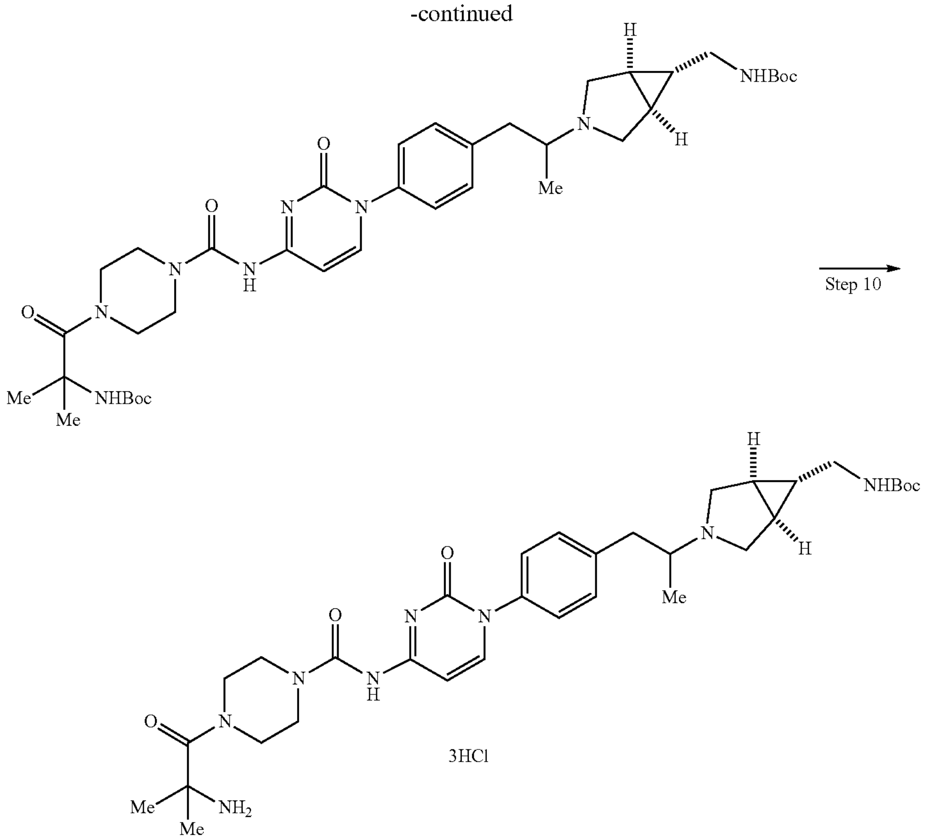

3HCl

Reagents: 1) $NaBH_4$, MeOH, 0° C. to rt, 16 h 2) TBSCl, imidazole, $CH_2Cl_2$16 h 3) n-BuLi, THF, −78° C. $(iPrO)_3B$, 2N HCl 4) cytosine, TMEDA, $Cu(OAc)_2{\cdot}H_2O$, 4:1 MeOH: $H_2O$ rt. 48 h 5) CDI, $CH_2Cl_2$, rt. 4 h 6) t-butyl (2-methyl-1-oxo-1-(piperazin-1-yl)propan-2-yl)carbamate $CH_3CN$, 85° C., 3 h 7) TBAF, THF 0° C. to rt, 16 h 8) DMP, $CH_2Cl_2$15 min 9) t-butyl ((exo-3-azabicyclo[3.1.0]hexan-6-yl)methyl)carbamate, $NaBH_3CN$, MeOH, rt, 16 h 10)HCl in MeOH, rt, 4 h Step 1: 1-(4-bromophenyl)propan-2-ol. To a solution of 1-(4-bromophenyl)propan-2-one (10.0 g, 47.0 mmol) in MeOH (250 mL) stirred at 0° C., was added $NaBH_4$ (1.78 g, 47.0 mmol). The solution was warmed to rt and stirred for 6 h. The reaction mixture was concentrated under reduced pressure, dissolved in $CHCl_3$ (500 mL) and washed with 10% aq. NaOH solution (1×500 mL). The organic layer was dried over $Na_2SO_4$ and concentrated under reduced pressure to afford the title compound.

Step 2: ((1-(4-bromophenyl)propan-2-yl)oxy)(t-butyl)dimethylsilane. To a solution of 1-(4-bromophenyl)propan-2-ol (10 g, 46.5 mmol) in $CH_2Cl_2$ (150 mL) was added imidazole (4.79 g, 70.5 mmol) and TBSCl (10.57 g, 70.5 mmol). The solution was stirred at rt for 16 h The reaction mixture was concentrated under reduced pressure and the residue was dissolved in EtOAc (250 mL) and washed with $H_2O$ (1×250 mL). The organic layer was dried over $Na_2SO_4$, concentrated under reduced pressure and purified by column chromatography (Hexanes:EtOAc) to afford the title compound.

Step 3: diisopropyl (4-(2-((t-butyldimethylsilyl)oxy)propyl)phenyl)boronate. To a solution of ((1-(4-bromophenyl) propan-2-yl)oxy)(t-butyl)dimethylsilane (15.1 g, 46.0 mmol) in THF (150 mL) at −78° C., was added n-buLi in hexanes (2.5 M, 58.5 mL, 146 mmol) was added dropwise over 30 min, maintaining the temperature below −60° C. The reaction was stirred for an additional 25 min, after which $B(iPrO)_3$ (16.9 mL, 73.0 mmol) was added dropwise over 30 min. The reaction mixture was warmed to rt and stirred for 15 min. 2N HCl (250 mL) was added and the reaction stirred for 30 min. The biphasic mixture was separated, and the aqueous layer extracted with $CH_2Cl_2$ (2×50 mL). The combined organics were dried over $Na_2SO_4$ and concentrated under reduced pressure to afford the desired product.

Step 4: 4-amino-1-(4-(2-((t-butyldimethylsilyl)oxy)propyl)phenyl)pyrimidin-2 (1H)-one. A suspension of cytosine (5.20 g, 46.0 mmol) and diisopropyl (4-(2-((t-butyldimethylsilyl)oxy)propyl)phenyl)boronate (2.3 g, 460.0 mmol), in $MeOH{:}H_2O$ (4:1, 500 mL) was stirred at rt in open air for 30 min. TMEDA (13.1 mL, 13.1 mmol) and $Cu(OAc)_2{\cdot}H_2O$ (1.33 g, 6.67 mmol) were added and the reaction was stirred in open air at rt for 48 h. The reaction mixture was concentrated under reduced pressure and cold $H_2O$ (350 mL) was added. The precipitate was filtered and washed with $H_2O$ (2×50 mL) and $Et_2O$ (3×50 mL) to afford the title compound.

Step 5: N-(1-(4-(2-((t-butyldimethylsilyl)oxy)propyl)phenyl)-2-oxo-1,2-dihydropyrimidin-4-yl)-1H-imidazole-1-carboxamide. A suspension of 4-amino-1-(4-(2-((t-butyldimethylsilyl)oxy)propyl)phenyl)pyrimidin-2 (1H)-one (2.50 g, 6.90 mmol) and CDI (1.63 g, 9.72 mmol) in $CH_2Cl_2$ was stirred at rt for 16 h. The solvent was removed reduced pressure and the solid was triturated with EtOAc to afford the title compound.

Step 6: t-butyl (1-(4-((1-(4-(2-((t-butyldimethylsilyl)oxy) propyl)phenyl)-2-oxo-1,2-dihydropyrimidin-4-yl)carbamoyl)piperazin-1-yl)-2-methyl-1-oxopropan-2-yl)carbamate. N-(1-(4-(2-((t-butyldimethylsilyl)oxy)propyl)phenyl)-2-oxo-1,2-dihydropyrimidin-4-yl)-1H-imidazole-1-carboxamide (2.49 g, 5.50 mmol) and t-butyl (2-methyl-1-oxo-1-(piperazin-1-yl)propan-2-yl)carbamate (1.5 mg, 5.50 mmol) were dissolved in $CH_3CN$ (60 mL) and heated to reflux for 2 h. The reaction mixture was concentrated under reduced pressure, dissolved in EtOAc (100 mL) and washed with $H_2O$ (3×100 mL). The crude material was purified by column chromatography (Hexanes:EtOAc) to afford the title compound.

Step 7: t-butyl (1-(4-((1-(4-(2-hydroxypropyl)phenyl)-2-oxo-1,2-dihydropyrimidin-4-yl)carbamoyl)piperazin-1-yl)-2-methyl-1-oxopropan-2-yl)carbamate. To a solution of t-butyl (1-(4-((1-(4-(2-((t-butyldimethylsilyl)oxy)propyl)phenyl)-2-oxo-1,2-dihydropyrimidin-4-yl)carbamoyl)piperazin-1-yl)-2-methyl-1-oxopropan-2-yl)carbamate (2.75 g, 4.19 mmol) in THF (50 mL) at 0° C. was added TBAF in THF (1 M, 8.40 mL, 8.40 mL) dropwise over the span of 5 min. The solution was warmed to rt and stirred for 16 h. The crude reaction mixture was concentrated under reduced pressure and purified by column chromatography (MeOH: $CHCl_3$) to afford the title compound.

Step 8: t-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate. To a stirred solution of t-butyl (1-(4-((1-(4-(2-hydroxypropyl)phenyl)-2-oxo-1,2-dihydropyrimidin-4-yl)carbamoyl)piperazin-1-yl)-2-methyl-1-oxopropan-2-yl)carbamate (1.00 g, 1.84 mmol) in $CH_2Cl_2$:$H_2O$ (1000:1, 50 mL) was added DMP (1.52 g, 3.69 mmol). The solution was stirred for 1 h. The crude reaction mixture was dissolved in additional $CH_2Cl_2$ (50 mL) and washed with aq. $NaHCO_3/Na_2S_2O_3$ (1×100 mL). The aq. layer was extracted with $CH_2Cl_2$ (1×50 mL). The combined organic layers were dried over $Na_2SO_4$ and concentrated under reduced pressure to give the title compound.

Step 9: t-butyl (1-(4-((1-(4-(2-(exo-6-(((t-butoxycarbonyl)amino)methyl)-3-azabicyclo[3.1.0]hexan-3-yl)propyl)phenyl)-2-oxo-1,2-dihydropyrimidin-4-yl)carbamoyl)piperazin-1-yl)-2-methyl-1-oxopropan-2-yl)carbamate. To a stirred solution of t-butyl (2-methyl-1-oxo-1-(4-((2-oxo-1-(4-(2-oxopropyl)phenyl)-1,2-dihydropyrimidin-4-yl)carbamoyl)piperazin-1-yl)propan-2-yl)carbamate (500 mg, 0.942 mmol) in MeOH, was added t-butyl ((exo-3-azabicyclo[3.1.0]hexan-6-yl)methyl)carbamate (275 mg, 1.38 mmol) and $NaBH_3CN$ (116 mg, 1.84 mmol). The reaction mixture was stirred for 16 h at rt. The reaction mixture was concentrated under reduced pressure, dissolved in $CHCl_3$ (100 mL) and washed with 10% aq. NaOH solution (1×100 mL). The crude reaction mixture was the purified by column chromatography (MeOH:$CHCl_3$) to afford the title compound.

Step 10: 4-(2-amino-2-methylpropanoyl)-N-(1-(4-(2-(exo-6-(aminomethyl)-3-azabicyclo[3.1.0]hexan-3-yl)propyl)phenyl)-2-oxo-1,2-dihydropyrimidin-4-yl)piperazine-1-carboxamide hydrochloride salt. tert-butyl (1-(4-((1-(4-(2-(exo-6-(((t-butoxycarbonyl)amino)methyl)-3-azabicyclo[3.1.0]hexan-3-yl)propyl)phenyl)-2-oxo-1,2-dihydropyrimidin-4-yl)carbamoyl)piperazin-1-yl)-2-methyl-1-oxopropan-2-yl)carbamate was dissolved in a solution of HCl in MeOH (2N, 2N, 10 mL) and stirred for 4 h. The reaction mixture was concentrated under reduced pressure and the crude solid was purified by column chromatography ($NH_4OH$:MeOH:$CHCl_3$) and concentrated under reduced pressure. Addition of HCl/MeOH and evaporation under reduced pressure afforded the title compound. $^1H$ NMR (400 MHz, $D_2O$) δ 7.97 (d, 1H), 7.48-7.32 (m, 4H), 6.78 (d, 1H), 3.88-3.65 (m, 10H), 3.65-3.49 (m, 3H), 3.45 (s, 1H), 2.95-2.89 (m, 2H), 2.84-2.72 (m, 1H), 2.04-1.96 (m, 2H), 1.69 (s, 6H), 1.37-1.30 (m, 1H), 1.24 (d, 3H). LCMS [M+H] 537.3.

Compound 124

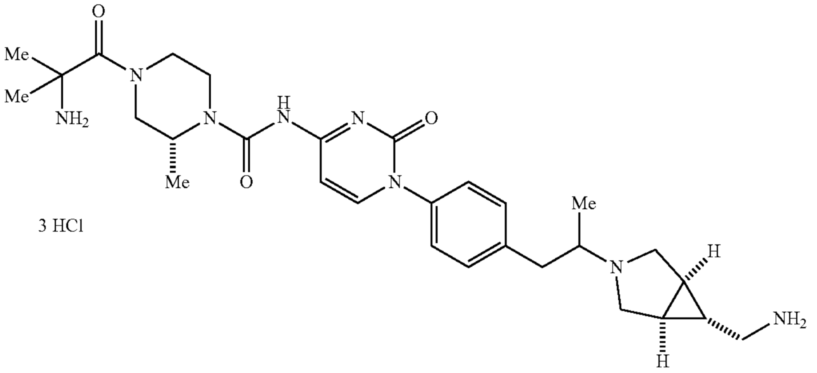

(2R)-4-(2-Amino-2-methylpropanoyl)-N-(1-(4-(2-(exo-6-(aminomethyl)-3-azabicyclo[3.1.0]hexan-3-yl)propyl)phenyl)-2-oxo-1,2-dihydropyrimidin-4-yl)-2-methylpiperazine-1-carboxamide Hydrochloride Salt Prepared in a similar fashion to Scheme C-16 from tert-butyl (R)-(2-methyl-1-(3-methyl-4-((2-oxo-1-(4-(2-oxopropyl)phenyl)-1,2-dihydropyrimidin-4-yl)carbamoyl)piperazin-1-yl)-1-oxopropan-2-yl)carbamate and tert-butyl (((1R,5S)-3-azabicyclo[3.1.0]hexan-6-yl)methyl)carbamate NMR (400 MHz, $D_2O$) δ 8.01 (d, 1H), 7.47-7.40 (m, 4H), 6.78 (d, 1H), 4.53 (s, 1H), 4.23-4.00 (m, 2H), 3.89-3.75 (m, 2H), 3.74-3.13 (m, 8H), 3.01-2.75 (m, 3H), 1.98 (d, 2H), 1.70 (s, 6H), 1.31 (d, 3H), 1.24-1.19 (m, 4H). LCMS[M+H] 551.4.

Compound 125

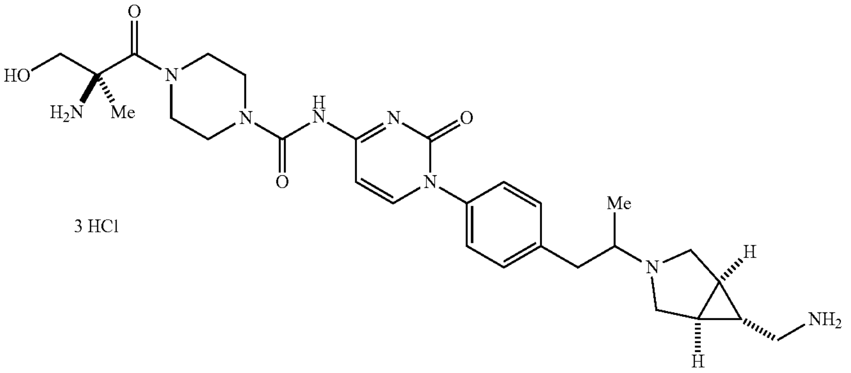

4-((S)-2-amino-3-hydroxy-2-methylpropanoyl)-N-(1-(4-(2-(exo-6-(aminomethyl)-3-azabicyclo[3.1.0]hexan-3-yl)propyl)phenyl)-2-oxo-1,2-dihydropyrimidin-4-yl)piperazine-1-carboxamide Hydrochloride Salt Prepared in a similar fashion to Scheme C-16 from tert-butyl (2R,4S)-2-(tert-butyl)-4-methyl-4-(4-((2-oxo-1-(4-(2-oxopropyl)phenyl)-1,2-dihydropyrimidin-4-yl)carbamoyl)piperazine-1-carbonyl)oxazolidine-3-carboxylate and tert-butyl (41R,5S)-3-azabicyclo[3.1.0]hexan-6-yl) methyl)carbamate $^1$H NMR (400 MHz, $D_2O$) δ 7.98 (d, 1H), 7.42 (s, 4H), 6.79 (d, 1H), 4.13 (d, 1H), 3.87 (d, 1H), 3.84-3.52 (m, 11H), 3.35 (d, 1H), 2.96 (d, 2H), 2.87-2.76 (m, 1H), 2.01 (s, 2H), 1.65 (s, 6H), 1.41-1.13 (m, 4H). LCMS [M+H] 553.3

Compound 187

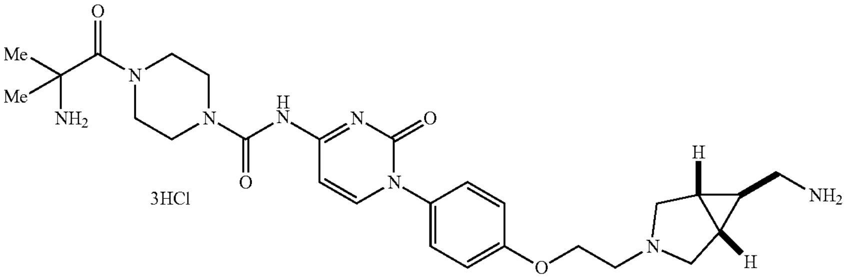

4-(2-amino-2-methylpropanoyl)-N-(1-(4-(2-(exo-6-(aminomethyl)-3-azabicyclo[3.1.0]hexan-3-yl)ethoxy)phenyl)-2-oxo-1,2-dihydropyrimidin-4-yl)piperazine-1-carboxamide Hydrochloride Salt Scheme C-17

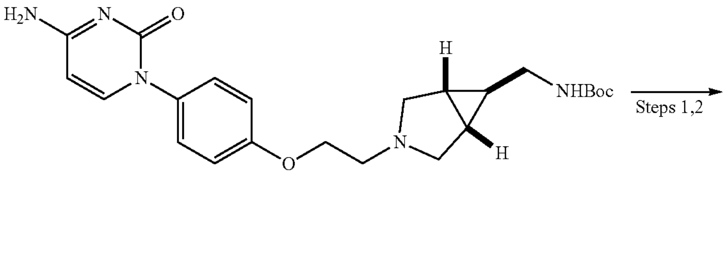

-continued

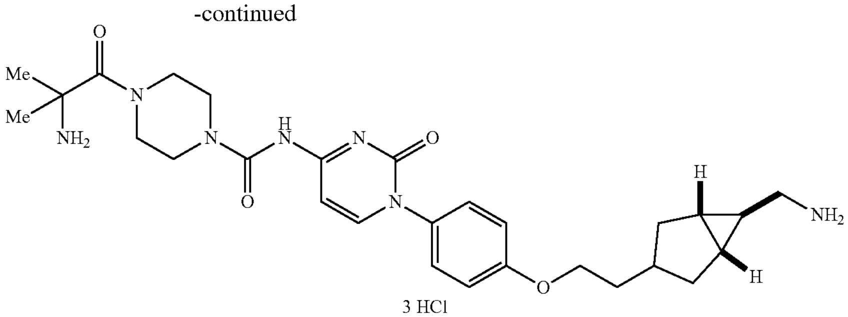

3 HCl

Reagents: 1) 1-(4-(2-((tert-Butoxycarbonyl)amino)-2-methylpropanoyl)piperazine-1-carbonyl)-3-methyl-1H-imidazol-3-ium iodide, $CH_3CN$, reflux, 22 h 2) HCl, MeOH, 21 h Step 1: tert-butyl ((exo-3-(2-(4-(4-(4-(2-((tert-butoxycarbonyl)amino)-2-methylpropanoyl)piperazine-1-carboxamido)-2-oxopyrimidin-1 (2H)-yl)phenoxy)ethyl)-3-azabicyclo[3.1.0]hexan-6-yl)methyl)carbamate. A mixture of tert-butyl ((exo-3-(2-(4-(4-amino-2-oxopyrimidin-1 (2H)-yl) phenoxy)ethyl)-3-azabicyclo[3.1.0]hexan-6-yl)methyl) carbamate (944 mg, 2.14 mmol) and 1-(4-(2-((tert-Butoxycarbonyl)amino)-2-methylpropanoyl)piperazine-1-carbonyl)-3-methyl-1H-imidazol-3-ium iodide (1.639 g, 2.58 mmol) in $CH_3CN$ was stirred at reflux for 22 h. The reaction mixture was cooled and concentrated under reduced pressure. The residue was dissolved $CH_2Cl_2$ poured into sat. aq. $NaHCO_3$ (100 mL) and extracted with $CH_2Cl_2$ (2×100 mL). The combined extracts were dried over $Na_2SO_4$, filtered and concentrated under reduced pressure. The residue was purified by column chromatography on silica gel (MeOH/EtOAc/Hexanes) to afford the title compound.

Step 2: 4-(2-amino-2-methylpropanoyl)-N-(1-(4-(2-(exo-6-(aminomethyl)-3-azabicyclo[3.1.0]hexan-3-yl)ethoxy) phenyl)-2-oxo-1,2-dihydropyrimidin-4-yl)piperazine-1-carboxamide hydrochloride salt. A mixture of tert-butyl ((exo-3-(2-(4-(4-(4-(2-((tert-butoxycarbonyl)amino)-2-methylpropanoyl)piperazine-1-carboxamido)-2-oxopyrimidin-1 (2H)-yl)phenoxy)ethyl)-3-azabicyclo [3.1.0]hexan-6-yl)methyl)carbamate (1.219 g, 1.485 mmol) and 2.0 M HCl in MeOH (45 mL, 90.0 mmol) was stirred at rt for 21 h then concentrated to dryness. The residue was dissolved in MeOH, made basic with $NH_4OH$ (2 mL), dry-loaded onto Celite® and purified by column chromatography on silica gel ($CH_2Cl_2$/MeOH/$NH_4OH$). Pure fractions were combined, concentrated under reduced pressure, converted into the HCl salt with 2.0 M HCl in MeOH, concentrated, dissolved in $H_2O$, and lyophilized to give the target compound. $^1H$ NMR (500 MHz, $D_2O+K_2CO_3$) δ 7.68 (d, 1H), 7.22 (d, 2H), 6.97 (d, 2H), 6.66 (d, 1H), 4.05-4.14 (m, 2H), 3.44-3.71 (m, 8H), 3.17 (d, 2H), 2.96-3.05 (m, 2H), 2.85 (d, 2H), 2.75 (d, 2H), 1.57-1.63 (m, 2H), 1.54 (s, 6H), 1.15-1.24 (m, 1H). LCMS[M+H] 539.0.

Compound 150

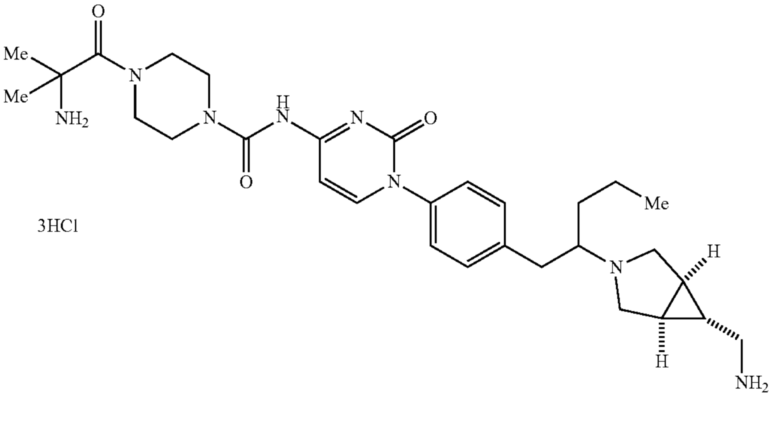

3HCl 4-(2-amino-2-methylpropanoyl)-N-(1-(4-(2-(exo-6-(aminomethyl)-3-azabicyclo[3.1.0]hexan-3-yl)pentyl)phenyl)-2-oxo-1,2-dihydropyrimidin-4-yl)piperazine-1-carboxamide Hydrochloride Salt Prepared in a similar fashion to scheme C-17 from tert-butyl ((exo-3-(1-(4-(4-($^1H$-imidazole-1-carboxamido)-2-oxopyrimidin-1 (2H)-yl)phenyl)pentan-2-yl)-3-azabicyclo[3.1.0]hexan-6-yl)methyl)carbamate and tert-butyl (2-methyl-1-oxo-1-(piperazin-1-yl)propan-2-yl)carbamate. $^1H$ NMR (500 MHz, $D_2O$) δ 8.05 (d, 1H), 7.51 (d, 2H), 7.46 (d, 2H), 6.83 (d, 1H), 3.86-3.70 (m, 9H), 3.70-3.56 (m, 3H), 3.29-3.23 (m, 1H), 3.13-3.04 (m, 2H), 3.01-2.91 (m, 2H), 2.12-2.00 (m, 2H), 1.75 (s, 6H), 1.72-1.57 (m, 2H), 1.43-1.20 (m, 3H), 0.84 (t, 3H). LCMS[M+H]565.4

Compound 151

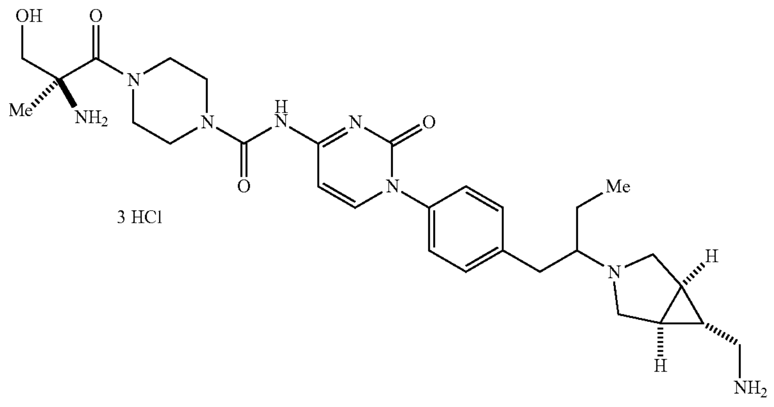

3 HCl 4-((S)-2-amino-3-hydroxy-2-methylpropanoyl)-N-(1-(4-(2-(exo-6-(aminomethyl)-3-azabicyclo[3.1.0]hexan-3-yl)butyl)phenyl)-2-oxo-1,2-dihydropyrimidin-4-yl)piperazine-1-carboxamide Hydrochloride Salt Prepared in a similar fashion to Scheme C-17 from 1-(4-((2R,4S)-3-(tert-butoxycarbonyl)-2-(tert-butyl)-4-methyloxazolidine-4-carbonyl)piperazine-1-carbonyl)-3-methyl-1H-imidazol-3-ium iodide and tert-butyl ((exo-3-(1-(4-(4-amino-2-oxopyrimidin-1 (2H)-yl)phenyl)butan-2-yl)-3-azabicyclo[3.1.0]hexan-6-yl)methyl)carbamate $^1$H NMR (500 MHz, $D_2O$) δ 8.03 (d, 1H), 7.51 (d, 2H), 7.46 (d, 2H), 6.83 (d, 1H), 4.26-4.09 (m, 2H), 3.92 (d, 1H), 3.88-3.70 (m, 8H), 3.69-3.57 (m, 4H), 3.29-3.23 (m, 2H), 3.17-2.94 (m, 4H), 2.24 (s, 1H), 2.13-2.00 (m, 2H), 1.82-1.58 (m, 8H), 1-(4-1.37 (m, 1H) 0.96 (t, 3H). LCMS[M+H]: 567.3

4-((S)-2-amino-3-hydroxy-2-methylpropanoyl)-N-(1-(4-(2-(2-amino-7-azaspiro[3.5]nonan-7-yl)propyl)phenyl)-2-oxo-1,2-dihydropyrimidin-4-yl)piperazine-1-carboxamide Hydrochloride Salt Prepared in a similar fashion to Scheme C-17 from 1-(4-((2R,4S)-3-(tert-butoxycarbonyl)-2-(tert-butyl)-4-methyloxazolidine-4-carbonyl)piperazine-1-carbonyl)-3-methyl-1H-imidazol-3-ium iodide and tert-butyl (7-(1-(4-(4-amino-2-oxopyrimidin-1 (2H)-yl)phenyl)propan-2-yl)-7-azaspiro[3.5]nonan-2-yl)carbamate. $^1$H NMR (400 MHz, $D_2O$) δ 7.95 (d, 1H), 7.49 (d, 2H), 7.45 (d, 2H), 6.85 (d, 1H), 4.17 (d, 1H), 3.92 (d, 1H), 3.83-3.64 (m, 12H), 3.60-3.43 (m, 2H), 3.34 (d, 1H), 3.24-3.07 (m, 2H), 2.98-2.88 (m, 1H), 2.59-2.49 (m, 1H), 2.40-2.29 (m, 1H), 2.21-1.88 (m, 4H), 1.70 (s, 3H), 1.27 (d, 3H). LCMS[M+H] 581.2.

Compound 115

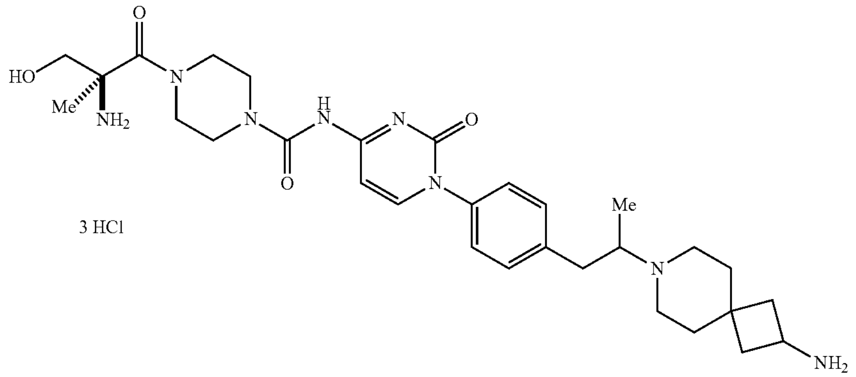

3 HCl

Compound 153

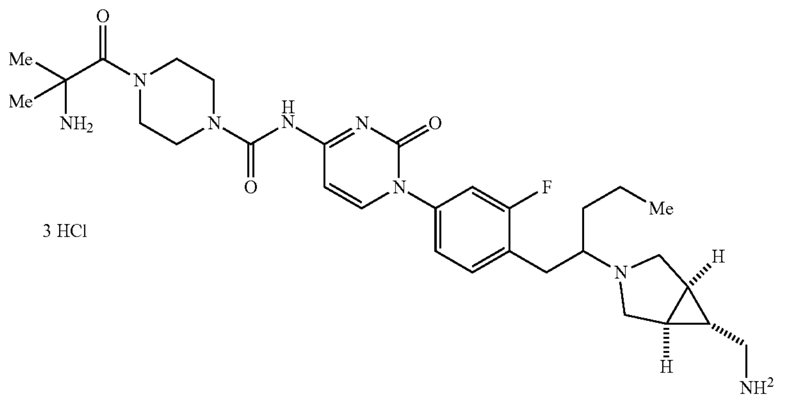

4-(2-amino-2-methylpropanoyl)-N-(1-(4-(2-(exo-6-(aminomethyl)-3-azabicyclo[3.1.0]hexan-3-yl)pentyl)-3-fluorophenyl)-2-oxo-1,2-dihydropyrimidin-4-yl)piperazine-1-carboxamide Hydrochloride Salt Prepared in a similar fashion to Scheme C-17 from tert-butyl ((exo-3-(1-(4-(4-(1H-imidazole-1-carboxamido)-2-oxopyrimidin-1 (2H)-yl)-2-fluorophenyl)pentan-2-yl)-3-azabicyclo[3.1.0]hexan-6-yl)methyl)carbamate and tert-butyl (2-methyl-1-oxo-1-(piperazin-1-yl)propan-2-yl) carbamate. $^{1}H$ NMR (500 MHz, $D_2O$) δ 7.99 (d, 1H), 7.55 (t, 1H), 7.37-7.28 (m, 2H), 6.83 (d, 1H), 3.86 (t, 2H), 3.82-3.71 (m, 8H), 3.70-3.59 (m, 2H), 3.32-3.26 (m, 2H), 3.16-3.06 (m, 2H), 3.01-2.95 (m, 2H), 2.04 (s, 2H), 1.75 (s, 6H), 1-(4-1.36 (m, 2H), 1.33-1.19 (m, 2H), 0.85 (t, 3H). LCMS[M+H]583.3

4-(2-amino-2-methylpropanoyl)-N-(1-(4-(2-(exo-6-(aminomethyl)-3-azabicyclo[3.1.0]hexan-3-yl) butyl)-3-fluorophenyl)-2-oxo-1,2-dihydropyrimidin-4-yl)piperazine-1-carboxamide Hydrochloride Salt Prepared in a similar fashion to Scheme C-17 from tert-butyl ((exo-3-(1-(4-(4-($^{1}H$-imidazole-1-carboxamido)-2-oxopyrimidin-1 (2H)-yl)-2-fluorophenyl)butan-2-yl)-3-azabicyclo[3.1.0]hexan-6-yl)methyl)carbamate and tert-butyl (2-methyl-1-oxo-1-(piperazin-1-yl)propan-2-yl) carbamate. $^{1}H$ NMR (500 MHz, $D_2O$) δ 8.05 (d, 1H), 7.55 (t, 1H), 7.39-7.29 (m, 2H), 6.82 (d, 1H), 3.91-3.82 (m, 2H), 3.82-3.71 (m, 8H), 3.70-3.59 (m, 3H), 3.31-3.06 (m, 2H), 3.01-2.96 (m, 2H), 2.04 (s, 2H), 1.84-1.75 (m, 1H), 1.74 (s, 6H), 1.45-1.38 (m, 2H), 0.96 (t, 3H). LCMS[M+H]569.3

Compound 154

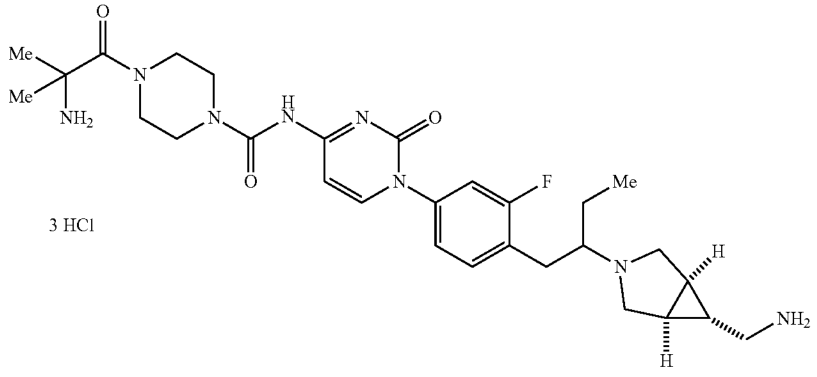

Compound 155

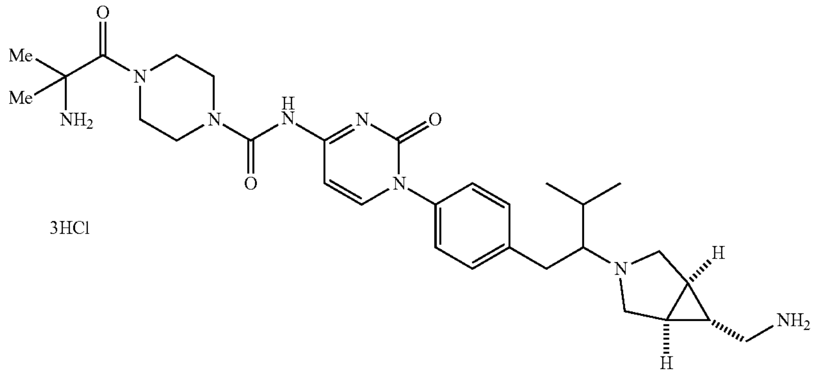

4-(2-amino-2-methylpropanoyl)-N-(1-(4-(2-(exo-6-(aminomethyl)-3-azabicyclo[3.1.0]hexan-3-yl)-3-methylbutyl)phenyl)-2-oxo-1,2-dihydropyrimidin-4-yl)piperazine-1-carboxamide Hydrochloride Salt Prepared in a similar fashion to Scheme C-17 from 1-(4-(2-((tert-butoxycarbonyl)amino)-2-methylpropanoyl) piperazine-1-carbonyl)-3-methyl-1H-imidazol-3-ium iodide and tert-butyl ((exo-3-(1-(4-(4-amino-2-oxopyrimidin-1 (2H)-yl)phenyl)propan-2-yl)-3-azabicyclo[3.1.0]hexan-6-yl)methyl)carbamate. $^1$H NMR (400 MHz, $D_2O$) δ 8.04-7.96 (m, 1H), 7.55-7.43 (m, 4H), 6.91-6.80 (m, 1H), 3.95-3.58 (m, 12H), 3.38-3.25 (m, 2H), 3.25-3.15 (m, 1H), 3.09-2.84 (m, 2H), 2.44-2.25 (m, 1H), 2.09-1.92 (m, 1H), 1.92-1.83 (m, 1H), 1.74 (d, 6H), 1.51-1.37 (m, 1H), 1.15-0.99 (m, 6H). LCMS[M+H] 565.4

4-(2-amino-2-methylpropanoyl)-N-(1-(4-(2-(exo-6-(aminomethyl)-3-azabicyclo[3.1.0]hexan-3-yl)-4-methylpentyl)phenyl)-2-oxo-1,2-dihydropyrimidin-4-yl)piperazine-1-carboxamide Hydrochloride Salt Prepared in a similar fashion to Scheme C-17 from 1-(4-(2-((tert-butoxycarbonyl)amino)-2-methylpropanoyl) piperazine-1-carbonyl)-3-methyl-1H-imidazol-3-ium iodide and tert-butyl ((exo-3-(1-(4-(4-amino-2-oxopyrimidin-1 (2H)-yl)phenyl)-4-methylpentan-2-yl)-3-azabicyclo[3.1.0] hexan-6-yl)methyl)carbamate. $^1$H NMR (500 MHz, $D_2O$) δ 8.20 (d, 1H), 7.54 (d, 2H), 7.48 (d, 2H), 6.80 (d, 1H), 3.85-3.71 (m, 9H), 3.70-3.53 (m, 3H), 3.31-3.25 (m, 2H), 3.12-2.94 (m, 3H), 2.08-1.99 (m, 2H), 1.74 (s, 6H), 1.72-1.54 (m, 2H), 1.40-1.32 (m, 2H), 0.83 (d, 3H), 0.73 (d, 3H). LCMS[M+H]579.4

Compound 156

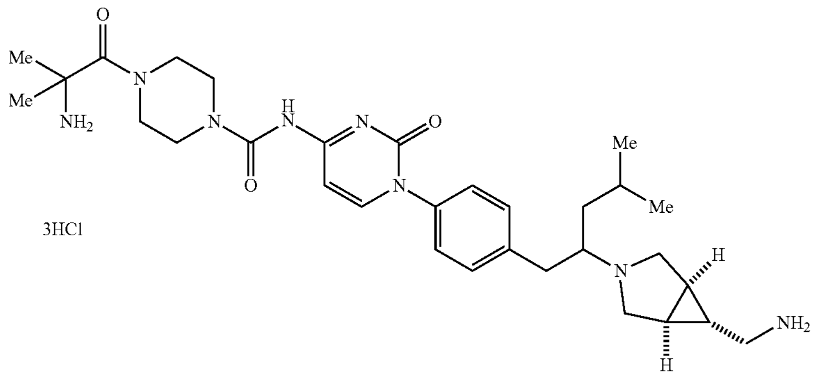

Compound 188
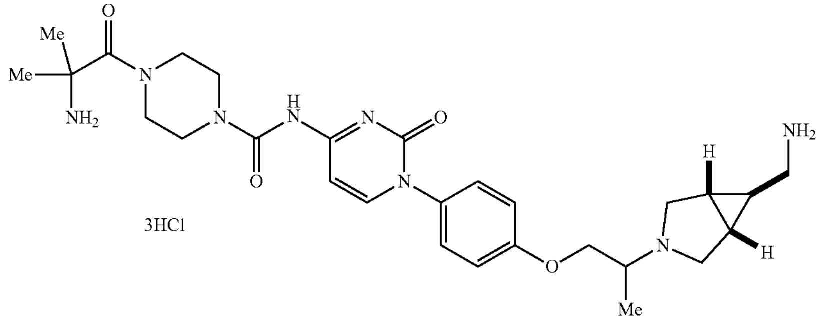
4-(2-Amino-2-methylpropanoyl)-N-(1-(4-(2-(exo-6-(aminomethyl)-3-azabicyclo[3.1.0]hexan-3-yl) propoxy)phenyl)-2-oxo-1,2-dihydropyrimidin-4-yl) piperazine-1-carboxamide Hydrochloride Salt
Scheme C-18
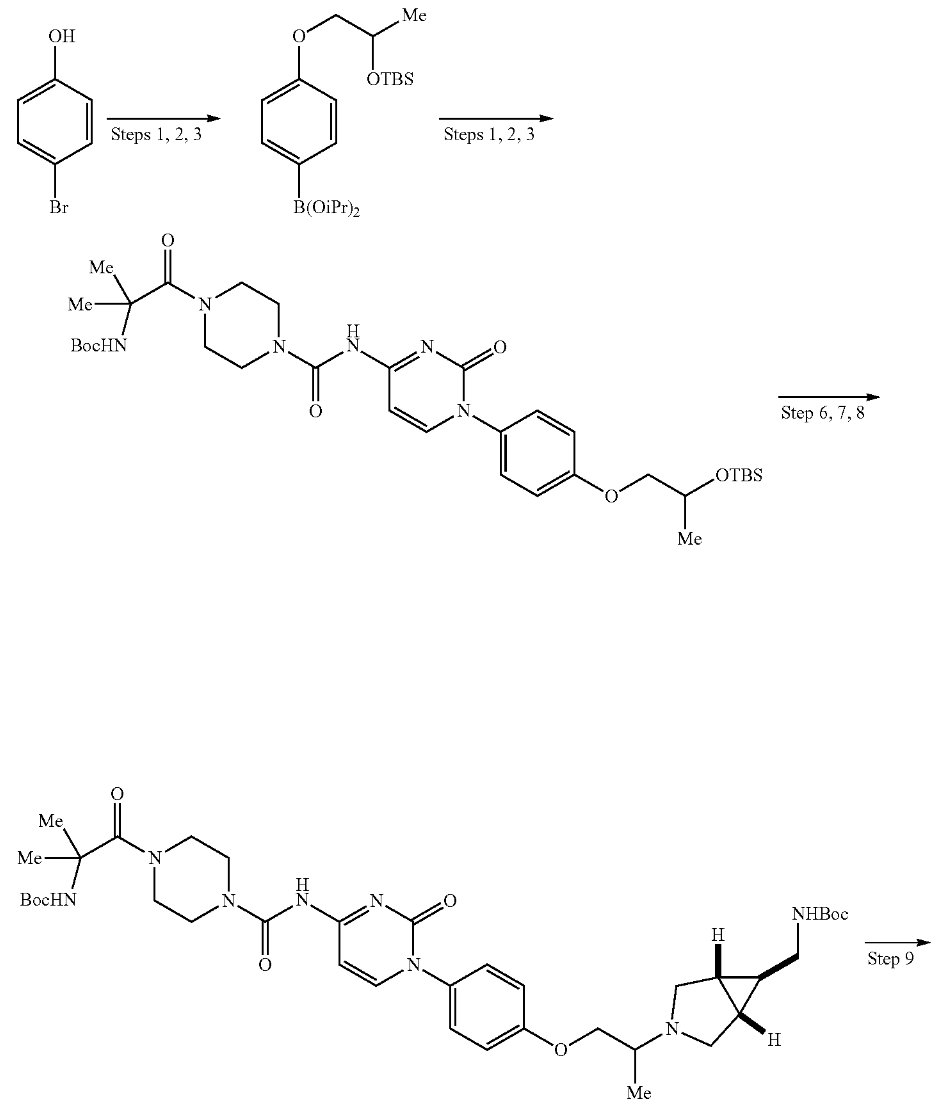

-continued

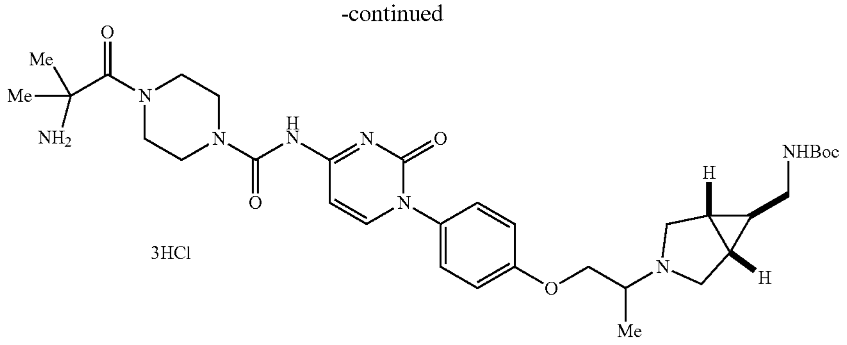

3HCl

Reagents: Step 1) $K_2CO_3$ Diethyl carbonate, 110° C., 8 days 2) TBDMSCl, Imidazole, $CH_2Cl_2$, rt, 16 h 3) nBuLi, $B(OiPr)_3$, THF, −78° C. to rt, 3 h 4) Cytosine, TMEDA, $Cu(OAc)_2 \cdot H_2O$, $CH_3OH$:$H_2O$ (4:1), $O_2$, rt, 16 h 5) $CH_3CN$, 90° C., 16 h 6) TBAF, THF, rt, 16 h 7) DMP, $CH_2Cl_2$, rt, 3 h 8) $NaBH_3CN$, 4 Å MS, MeOH, rt, 16 h 9) 4.0 M HCl in dioxane, dioxane, rt, 4 h.

Step 1: 1-(4-Bromophenoxy)propan-2-ol. A mixture of 4-bromophenol (25.0 g, 144.5 mmol), propane-1,2-diol (32.94 g, 433.5 mmol), and $K_2CO_3$ (2.0 g, 14.45 mmol) in diethyl carbonate (25.0 mL, 202.3 mmol) was stirred at 110° C. for 8 days. The reaction mixture was poured into 1 N NaOH (200 mL) and extracted with EtOAc (3×200 mL). The extracts were dried ($Na_2SO_4$), filtered, and concentrated under reduced pressure to afford the title compound. $^1H$ NMR (400 MHz, DMSO-$d_6$) δ 7.44-7.39 (m, 2H), 6.91-6.87 (m, 2H), 4.89 (d, 1H), 3.95-3.90 (m, 1H), 3.81-3.73 (m, 2H), 1.14 (d, 3H).

Step 2: ((1-(4-Bromophenoxy)propan-2-yl)oxy)(t-butyl) dimethylsilane. To a stirred solution of 1-(4-bromophenoxy) propan-2-ol (18.0 g, 77.9 mmol) in $CH_2Cl_2$ (200 mL) at 0° C. was added imidazole (7.94 g, 116.9 mmol) and TBSCl (14.11 g, 93.5 mmol). The reaction mixture was stirred at rt for 16 h then poured into $H_2O$ (200 mL) and extracted with $CH_2Cl_2$ (3×200 mL). The extracts were dried ($Na_2SO_4$), filtered, and concentrated under reduced pressure to afford the title compound. $^1H$ NMR (400 MHz, DMSO-$d_6$) δ 7.44-7.40 (m, 2H), 6.89-6.86 (m, 2H), 4.13-4.08 (m, 1H), 3.86-3.66 (m, 2H), 1.14 (d, 3H), 0.84 (s, 9H), 0.059 (s, 3H), 0.022 (s, 3H).

Step 3: Diisopropyl (4-(2-((t-butyldimethylsilyl) oxy) propoxy) phenyl) boronate. To a stirred solution of ((1-(4-bromophenoxy)propan-2-yl)oxy)(t-butyl)dimethylsilane (5.0 g, 14.5 mmol) in THF (300 mL) at −78° C. under $N_2$ was added n-BuLi (1.6 M in THF, 22.64 mL, 36.2 mmol) dropwise. The reaction mixture was stirred at that temperature for 30 min. and $B(iPrO)_3$ (5.04 mL, 21.7 mmol) was added dropwise. The reaction mixture was warmed to rt and stirred for 3 h. The reaction mixture was poured into saturated aqueous $NH_4C_1$ (400 mL) and extracted with EtOAc (3×1000 mL). The combined organic phases were dried ($Na_2SO_4$), filtered, and concentrated under reduced pressure to afford the title compound.

Step 4: 4-Amino-1-(4-(2-((t-butyldimethylsilyl)oxy) propoxy)phenyl)pyrimidin-2 (1H)-one. A mixture of diisopropyl (4-(2-((t-butyldimethylsilyl)oxy)propoxy) phenyl) boronate (6.5 g, 16.5 mmol) and cytosine (1.8 g, 16.5 mmol) in $CH_3OH$:$H_2O$ (50 mL; 4:1) was stirred at rt open to air for 30 min. TMEDA (2.3 mL, 19.8 mmol) and $Cu(OAc)_{2+120}$ (2.3 g, 16.5 mmol) were added and the mixture was stirred at rt open to air for 48 h. It was concentrated under reduced pressure to remove the $CH_3OH$, and cold $H_2O$ (100 mL) was added. The precipitate was collected by filtration, washed with $H_2O$ (5×50 mL) and $Et_2O$ (2×20 mL), and dried to yield the title compound. $^1H$ NMR (400 MHz, DMSO-$d_6$) δ 7.57 (d, 1H), 7.21 (d, 2H), 6.94 (d, 2H), 5.73 (d, 1H), 4.13-4.08 (m, 1H), 3.87-3.86 (m, 1H), 3.81-3.80 (m, 1H), 1.17 (d, 3H), 0.86 (s, 9H), 0.09 (s, 3H), 0.05 (s, 3H). LCMS [M+H] 376.1.

Step 5: t-Butyl (1-(4-((1-(4-(2-((t-butyldimethylsily-Doxy)propoxy)phenyl)-2-oxo-1,2-dihydropyrimidin-4-yl) carbamoyl)piperazin-1-yl)-2-methyl-1-oxopropan-2-yl)carbamate. A mixture of 4-amino-1-(4-(2-((t-butyldimethylsilyl)oxy)propoxy)phenyl) pyrimidin-2 (1H)-one (0.5 g, 1.33 mmol) and 1-(4-(2-((t-butoxycarbonyl) amino)-2-methylpropanoyl)piperazine-1-carbonyl)-3-methyl-1H-imidazol-3-ium iodide (1.01 g, 2.0 mmol) in $CH_3CN$ (15 mL) was stirred at 90° C. for 16 h. The reaction mixture was concentrated under reduced pressure and the residue was purified by column chromatography on silica gel ($CH_2Cl_2$:MeOH) to afford the title compound. LCMS [M+H] 673.1.

Step 6: t-Butyl (1-(4-((1-(4-(2-hydroxypropoxy)phenyl)-2-oxo-1,2-dihydropyrimidin-4-yl)carbamoyl)piperazin-1-yl)-2-methyl-1-oxopropan-2-yl)carbamate. To a stirred solution of t-butyl (1-(4-((1-(4-(2-((t-butyldimethylsilyl)oxy) propoxy)phenyl)-2-oxo-1,2-dihydropyrimidin-4-yl)carbamoyl)piperazin-1-yl)-2-methyl-1-oxopropan-2-yl)carbamate (0.4 g, 0.59 mmol) in THF (10 mL) at 0° C. was added TBAF (1.0 M in THF, 2.4 mL, 2.38 mmol). The reaction mixture was warmed to rt and stirred for 16 h. The reaction mixture was poured into saturated aqueous $NaHCO_3$ (10 mL) and extracted with $CH_2Cl_2$:MeOH (9:1, 3×50 mL). The extracts were dried ($Na_2SO_4$), filtered, and concentrated under reduced pressure, and the residue purified by column chromatography on silica gel ($CH_2Cl_2$:MeOH) to afford the title compound. LCMS [M+H] 559.1.

Step 7: t-Butyl (2-methyl-1-oxo-1-(4-((2-oxo-1-(4-(2-oxopropoxy)phenyl)-1,2-dihydropyrimidin-4-yl)carbamoyl)piperazin-1-yl)propan-2-yl)carbamate. To a stirred solution of t-butyl (1-(4-((1-(4-(2-hydroxypropoxy)phenyl)-2-oxo-1,2-dihydropyrimidin-4-yl)carbamoyl)piperazin-1-yl)-2-methyl-1-oxopropan-2-yl)carbamate (0.3 g, 0.53 mmol) in $CH_2Cl_2$ (5.0 mL) at 0° C. was added DMP (1.36 g, 3.22 mmol). The reaction mixture was stirred at rt for 3 h, then poured into saturated aqueous $NaHCO_3$ (20 mL) and extracted with $CH_2Cl_2$ (3×50 mL). The extracts were dried ($Na_2SO_4$), filtered, and concentrated under reduced pressure at <35° C. to afford the title compound. LCMS [M+H] 557.1.

Step 8: t-Butyl ((exo-3-(1-(4-(4-(4-(2-((t-butoxycarbonyl) amino)-2-methylpropanoyl)piperazine-1-carboxamido)-2-oxopyrimidin-1 (2H)-yl)phenoxy)propan-2-yl)-3-azabicyclo[3.1.0]hexan-6-yl)methyl)carbamate. To a stirred solution of t-butyl (2-methyl-1-oxo-1-(4-((2-oxo-1-(4-(2-oxopropoxy)phenyl)-1,2-dihydropyrimidin-4-yl)carbamoyl)piperazin-1-yl)propan-2-yl)carbamate (0.3 g, 0.53 mmol) and t-butyl ((exo-3-azabicyclo[3.1.0]hexan-6-yl)methyl)carbamate (0.137 g, 0.64 mmol) in MeOH (10 mL) at 0° C., was added activated 4 Å molecular sieves followed by $NaBH_3CN$ (0.67 g, 1.07 mmol). The mixture was stirred at rt for 16 h and concentrated under reduced pressure. The residue was purified by column chromatography on silica gel ($CH_2Cl_2$:MeOH) to afford the title compound. LCMS [M+H] 753.3.

Step 9: 4-(2-amino-2-methylpropanoyl)-N-(1-(4-(2-(exo-6-(aminomethyl)-3-azabicyclo[3.1.0]hexan-3-yl)propoxy)phenyl)-2-oxo-1,2-dihydropyrimidin-4-yl)piperazine-1-carboxamide hydrochloride salt. To a stirred solution of t-butyl ((exo-3-(1-(4-(4-(4-(2-((t-butoxycarbonyl)amino)-2-methylpropanoyl)piperazine-1-carboxamido)-2-oxopyrimidin-1(2H)-yl)phenoxy)propan-2-yl)-3-azabicyclo[3.1.0]hexan-6-yl)methyl)carbamate (0.2 g, 0.26 mmol) in dioxane (3 mL) was added 4 M HCl in Dioxane (5 mL, 20 mmol). The mixture was stirred at rt for 3 h, concentrated under reduced pressure, and triturated with $Et_2O$ (10 mL). The residue was purified by prep HPLC to afford the title compound. $^1H$ NMR (400 MHz, $D_2O$, 80° C.) mixture of rotamers, δ 8.40 (d, 1H), 7.99 (d, 2H), 7.74 (d, 2H), 7.31 (d, 1H), 4.97-4.90 (m, 1H), 4.85-4.81 (m, 1H), 4.51-4.45 (m, 1H), 4.40-4.29 (m, 14H), 3.57 (d, 2H), 2.65 (s, 2H), 2.31 (s, 6H), 2.10-2.0 (m, 4H). LCMS [M+H] 553.3.

Compound 181

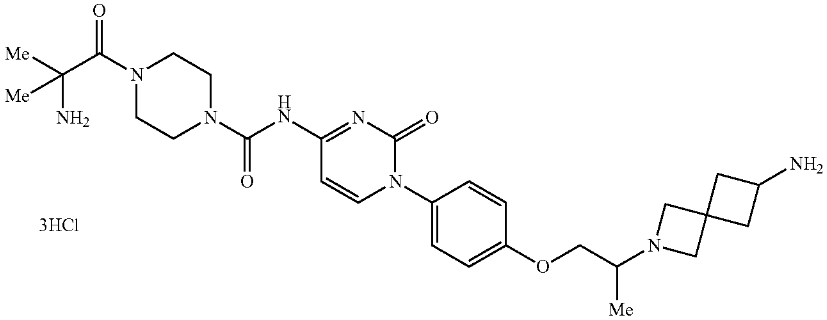

3HCl

N-(1-(4-(2-(6-Amino-2-azaspiro[3.3]heptan-2-yl)propoxy)phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-18 using: t-Butyl (2-methyl-1-oxo-1-(4-((2-oxo-1-(4-(2-oxopropoxy)phenyl)-1,2-dihydropyrimidin-4-yl)carbamoyl)piperazin-1-yl)propan-2-yl)carbamate and t-butyl N-(2-azaspiro[3.3]heptan-6-yl)carbamate. $^1H$ NMR (400 MHz, $D_2O$) mixture of rotamers, δ 7.83 (d, 1H), 7.28 (d, 2H), 7.01 (d, 2H), 6.60 (d, 1H), 4.42-4.15 (m, 4H), 4.14-4.01 (m, 2H), 3.71-3.55 (m, 10H), 2.76-2.66 (m, 1H), 2.61-2.51 (m, 1H), 2.48-2.31 (m, 2H), 1.60 (s, 6H), 1.21 (d, 3H). LCMS [M+H] 553.2.

Compound 189

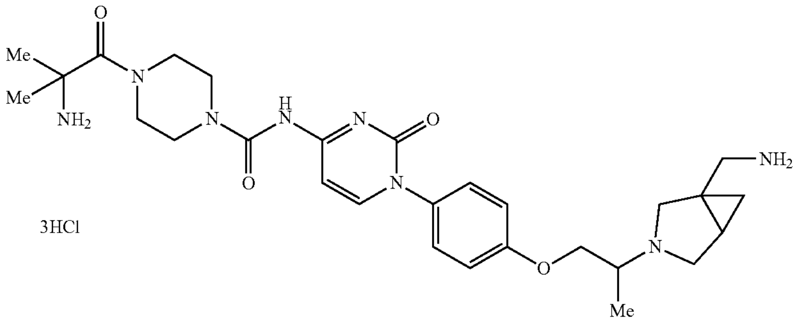

3HCl 4-(2-Amino-2-methylpropanoyl)-N-(1-(4-(2-(1-(aminomethyl)-3-azabicyclo[3.1.0]hexan-3-yl)propoxy) phenyl)-2-oxo-1,2-dihydropyrimidin-4-yl)piperazine-1-carboxamide Hydrochloride Salt Prepared in a similar fashion to Scheme C-18 using: t-Butyl (2-methyl-1-oxo-1-(4-((2-oxo-1-(4-(2-oxopropoxy) phenyl)-1,2-dihydropyrimidin-4-yl)carbamoyl)piperazin-1-yl)propan-2-yl)carbamate and t-butyl ((3-azabicyclo[3.1.0] hexan-1-yl)methyl)carbamate. $^1$H NMR (400 MHz, $D_2O$) mixture of rotamers, δ 7.75 (d, 1H), 7.27 (d, 2H), 7.02 (d, 2H), 6.70 (d, 1H), 4.32-4.14 (m, 2H), 3.85-3.50 (m, 11H), 3.42-3.35 (m, 1H), 3.05-2.95 (m, 1H), 1.98-1.90 (m, 1H), 1.60 (s, 6H), 1.45-1.35 (m, 3H), 1.06-0.93 (m, 2H). LCMS [M+H] 553.2.

Compound 65

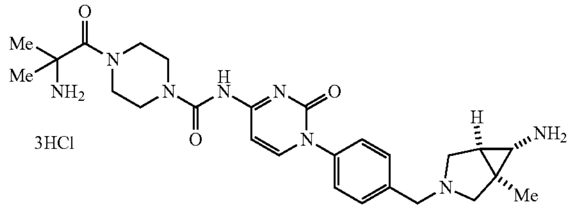

N-(1-(4-((exo-6-Amino-1-methyl-3-azabicyclo [3.1.0]hexan-3-yl)methyl)phenyl)-2-oxo-1,2-dihydropyrimidin-4-yl)-4-(2-amino-2-methylpropanoyl) piperazine-1-carboxamide Hydrochloride Salt Scheme C-19

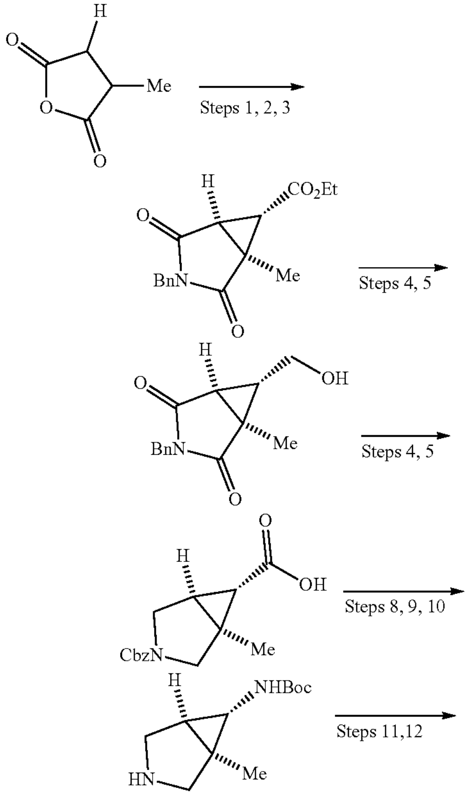

-continued

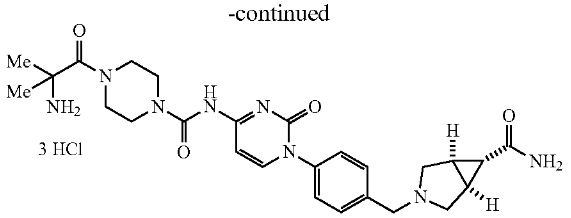

Reagents: 1) Benzylamine, Neat, 120° C., 16 h. 2) Ethyl Diazoacetate, THF, 66° C., 24 h. 3) Heat, 170° C. 3 h. 4) $Li(AlH_4)$, THF, 66° C., 16 h. 5) $Pd(OH)_2/C$, $H_2$ MeOH, rt. 16 h. 6) $Cb_2Cl$, $NEt_3CH_2Cl_2$, 0° C. to rt, 16 h. 7) $CrO_3H_2SO_4$, 0° C., 2 h. 8) ethyl chloroformate, $NaN_3$ acetone, $H_2O$, 0° C., 2.5 h. 9) BuOH, PPTS, toluene, 100° C., 16 h. 10) $Pd(OH)_2/C$, $H_2$ MeOH, rt. 16 h. 11) tert-butyl (1-(4-((1-(4-formylphenyl)-2-oxo-1,2-dihydropyrimidin-4-yl)carbamoyl)piperazin-1-yl)-2-methyl-1-oxopropan-2-yl) carbamate, $Na(OAc)_3BH$, DIPEA, DCE, 16 h. 12) HCl/ MeOH, rt, 4 h.

Step 1: 1-benzyl-3-methyl-1H-pyrrole-2,5-dione. To 3-methylfuran-2,5-dione (6.0 mL, 55 mmol) at 0° C., was added benzylamine (6.0 mL, 55 mmol) dropwise and the mixture was heated to 120° C. for 16 h. The reaction was cooled to rt and purified by column chromatography (Hexanes:EtOAc) to afford the title compound.

Step 2: ethyl 5-benzyl-6a-methyl-4,6-dioxo-1,3a,4,5,6,6a-hexahydropyrrolo[3,4-c]pyrazole-3-carboxylate. To a stirred solution of 1-benzyl-3-methyl-1H-pyrrole-2,5-dione (5.0 g, 25 mmol) in THF (120 mL) at rt was added ethyl diazoacetate (3.9 mL, 28 mmol). The solution was heated to 66° C. for 24 h. The reaction mixture was concentrated under reduced pressure and purified by column chromatography (Hexanes:EtOAc) to afford the title compound.

Step 3: exo-ethyl 3-benzyl-1-methyl-2,4-dioxo-3-azabicyclo[3.1.0]hexane-6-carboxylate. Ethyl 5-benzyl-6a-methyl-4,6-dioxo-1,3a,4,5,6,6a-hexahydropyrrolo[3,4-c] pyrazole-3-carboxylate (3.5 g, 11 mmol) was heated to 170° C. for 3 h. The crude reaction mixture was cooled and purified by column chromatography (Hexanes:EtOAc) to afford the title compound.

Step 4: exo-(3-benzyl-1-methyl-3-azabicyclo[3.1.0] hexan-6-yl)methanol. To a stirred suspension of $LiAlH_4$ (280 mg, 7.0 mmol) in THF (50 mL) at 0° C., was added a solution of exo-ethyl 3-benzyl-1-methyl-2,4-dioxo-3-azabicyclo[3.1.0]hexane-6-carboxylate (500 mg, 1.79 mmol) in THF (10 mL) dropwise. The reaction was heated to 66° C. for 16 h. The reaction was cooled to 0° C. and quenched upon dropwise addition of sat. aq. $NH_4C_1$ (1.0 mL). The reaction mixture was diluted with EtOAc (50 mL), $Na_2SO_4$ (2.0 g) was added and the suspension was stirred at rt for 1 h. The crude reaction mixture was filtered through Celite® and concentrated under reduced pressure. The crude solid was purified by column chromatography (Hexanes:EtOAc) to afford the title compound.

Step 5: exo-(1-methyl-3-azabicyclo[3.1.0]hexan-6-yl) methanol. To a stirred solution of exo-(3-benzyl-1-methyl-3-azabicyclo[3.1.0]hexan-6-yl)methanol (275 mg, 1.3 mmol) in MeOH (15 mL), was added $Pd(OH)_2/C$ (28 mg, 0.20 mmol). The suspension was stirred under a $H_2$ atmosphere (1 atm) for 16 h. The reaction mixture was filtered through Celite® and concentrated under reduced pressure to afford the crude title compound.

Step 6: exo-benzyl 6-(hydroxymethyl)-1-methyl-3-azabicyclo[3.1.0]hexane-3-carboxylate. To a solution of exo-(1-methyl-3-azabicyclo[3.1.0]hexan-6-yl)methanol (160 mg, 1.25 mmol) and $NEt_3$ (0.35 mL, 2.5 mmol) in $CH_2Cl_2$ (15 mL) at 0° C., was added benzyl chloroformate (0.36 mL, 2.5 mmol). The solution was warmed to rt and stirred for 16 h. The reaction was diluted with $CH_2Cl_2$ (50 mL) and washed with sat. aq. $NaHCO_3$ (1×50 mL). The organic layer was concentrated under reduced pressure and purified by column chromatography (Hexanes:EtOAc) to afford the title compound.

Step 7: exo-3-((benzyloxy)carbonyl)-1-methyl-3-azabicyclo[3.1.0]hexane-6-carboxylic acid. To a solution of $CrO_3$ (275 mg, 2.8 mmol) in $H_2O$ (0.5 mL), was added $H_2SO_4$ (0.15 mL) dropwise and stirred for 10 min. This solution was added dropwise to exo-benzyl 6-(hydroxymethyl)-1-methyl-3-azabicyclo[3.1.0]hexane-3-carboxylate in acetone (15 mL) at 0° C. and was stirred for 2 h. The reaction was quenched upon addition of iPrOH (2 mL) and diluted with $H_2O$. The aqueous layer was extracted with $Et_{20}$ (2×50 mL), and the combined organics were washed with sat. aq. NaCl (1×75 mL), dried over $Na_2SO_4$ and concentrated under reduced pressure to afford the crude title compound.

Step 8: exo-benzyl 6-(azidocarbonyl)-1-methyl-3-azabicyclo[3.1.0]hexane-3-carboxylate. To a solution of exo-3-((benzyloxy)carbonyl)-1-methyl-3-azabicyclo[3.1.0]hexane-6-carboxylic acid (55 mg, 0.20 mmol) and $NEt_3$ (0.03 mL, 0.25 mmol) in acetone (10 mL) at 0° C., ethyl chloroformate (0.024 mL, 0.25 mmol) was added dropwise. The solution was stirred at 0° C. for 30 min, after which a solution of sodium azide (130 mg, 2.0 mmol) in $H_2O$ (1 mL) was added dropwise. The solution was warmed to rt and stirred for 2.5 h. The reaction mixture was the diluted with $H_2O$ (15 mL) and extracted with $Et_2O$ (1×30 mL). The organic layer was washed with sat. aq. NaCl (1×15 mL), dried with $Na_2SO_4$ and concentrated reduced pressure to afford the title compound.

Step 9: exo-benzyl 6-((tert-butoxycarbonyl)amino)-1-methyl-3-azabicyclo[3.1.0]hexane-3-carboxylate. To a solution of exo-benzyl 6-(azidocarbonyl)-1-methyl-3-azabicyclo[3.1.0]hexane-3-carboxylate (60 mg, 0.19 mmol) in toluene was added, tert-butanol (1.05 mL) and pyridinium tosylate (1.0 mg 0.004 mmol). The reaction mixture was heated to 100° C. for 12 h. The crude reaction mixture was concentrated under reduced pressure and purified by column chromatography (EtOAc:Hex) to afford the title compound.

Step 10: exo-tert-butyl (1-methyl-3-azabicyclo[3.1.0]hexan-6-yl)carbamate. To a solution of exo-benzyl 6-((tert-butoxycarbonyl)amino)-1-methyl-3-azabicyclo[3.1.0]hexane-3-carboxylate 40 mg, 0.15 mmol) in MeOH (15 mL), was added $Pd(OH)_2/C$ (4 mg, 0.03 mmol). The suspension was stirred under a $H_2$ atmosphere (1 atm) for 16 h. The reaction mixture was filtered through Celite® and concentrated under reduced pressure to afford the title compound. The product was used in the next step without further purification.

Step 11: tert-butyl (1-(4-((1-(4-((6-((tert-butoxycarbonyl)amino)-1-methyl-3-azabicyclo[3.1.0]hexan-3-yl)methyl)phenyl)-2-oxo-1,2-dihydropyrimidin-4-yl)carbamoyl)piperazin-1-yl)-2-methyl-1-oxopropan-2-yl)carbamate. To a stirred solution of tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate as prepared in Scheme 1 (50 mg, 0.10 mmol) in DCE (10 mL) was added exo-tert-butyl (1-methyl-3-azabicyclo[3.1.0]hexan-6-yl)carbamate (31 mg, 0.15 mmol), $Na(OAc)_3BH$ (42 mg, 0.20 mmol) and DIPEA (0.035 mL, 0.20 mmol) and was stirred at rt for 16 h. The reaction mixture was treated with 10% NaOH (10 mL) and the aqueous layer was extracted with $CH_2Cl_2$ (2×10 mL). The combined organics were dried over $Na_2SO_4$ and concentrated under reduced pressure to afford the crude title compound.

Step 12: N-(1-(4-((6-amino-1-methyl-3-azabicyclo[3.1.0]hexan-3-yl)methyl)phenyl)-2-oxo-1,2-dihydropyrimidin-4-yl)-4-(2-amino-2-methylpropanoyl)piperazine-1-carboxamide hydrochloride salt. Tert-butyl (1-(4-((1-(4-((6-((tert-butoxycarbonyl)amino)-1-methyl-3-azabicyclo[3.1.0]hexan-3-yl)methyl)phenyl)-2-oxo-1,2-dihydropyrimidin-4-yl)carbamoyl)piperazin-1-yl)-2-methyl-1-oxopropan-2-yl)carbamate was dissolved in a solution of HCl in MeOH (2N, 5 mL) and stirred for 4 h. The volatiles were removed under reduced pressure and purified by reverse phase HPLC ($H_2O$: $CH_3CN$ with 0.1% TFA). Addition of HCl in MeOH (2N, 3×15 mL) and evaporation under reduced pressure afforded the title compound. $^1H$ NMR (400 MHz, $D_2O$) δ 8.03 (d, 1H), 7.70 (d, 2H), 7.58 (d, 2H), 6.86 (d, 1H), 4.49 (s, 2H), 3.79 (s, 5H), 3.75 (s, 6H), 3.61 (s, 1H), 2.91 (s, 1H), 2.14 (s, 1H), 1.75 (s, 6H), 1.47 (s, 3H). LCMS[M+H] 509.3.

Compound 66

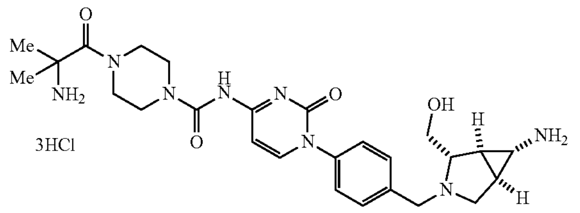

N-(1-(4-(((1R,2S,5R,6R)-6-Amino-2-(hydroxymethyl)-3-azabicyclo[3.1.0]hexan-3-yl)methyl)phenyl)-2-oxo-1,2-dihydropyrimidin-4-yl)-4-(2-amino-2-methylpropanoyl)piperazine-1-carboxamide Hydrochloride Salt Scheme C-20

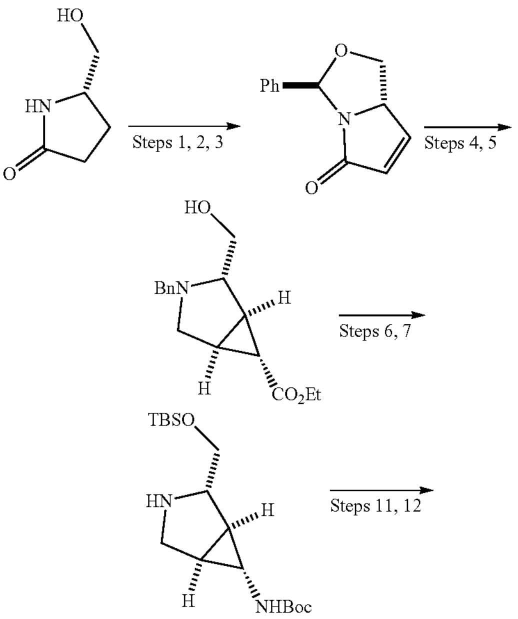

-continued

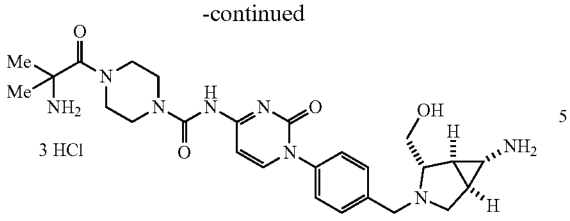

Reagents: 1) benzaldehyde, TsOH, PhMe 120° C., 16 h. 2) KHMDS, TMSCl, PhSeCl, −78° C. to rt, 16 h. 3) $H_2O_2$ EtOAc, 0° C., 30 min. 4) ethyl (dimethylsulfuranylidene) acetate, DMSO, rt, 24 h 5) $BH_3$·THF, THF, 66° C., 2 h. 6) TBSCl, imidazole $CH_2Cl_2$, rt, 16 h. 7) Li(OH), THF:$H_2O$, rt, 72 h. 8) ethyl chloroformate, $NaN_3$ acetone, $H_2O$, 0° C., 2.5 h. 9) t-BuOH, pyridinium tosylate, toluene, 100° C., 16 h. 10) $Pd(OH)_2$/C, $H_2$, MeOH, rt. 16 h. 11) tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate, $NaBH_3CN$, MeOH, 16 h. 12) HCFMeOH, rt, 4 h.

Step 1: (3R,7aS)-3-phenyltetrahydro-3H,5H-pyrrolo[1,2-c]oxazol-5-one. To a suspension of (S)-5-(hydroxymethyl) pyrrolidin-2-one (5.0 g, 4.3 mmol) in toluene (100 mL) at rt, was added benzaldehyde (5.3 mL, 5.2 mmol) and TsOH (35 mg, 0.24 mmol). The suspension was heated to reflux with a Dean-Stark trap for 16 h. The reaction mixture was cooled to rt and quenched upon the addition of sat. aq. $NaHCO_3$ (100 mL). The layers were separated, and the aqueous phase was extracted with EtOAc (2×100 mL). The combined organics were dried over $Na_2SO_4$ and concentrated under reduced pressure. Purification by column chromatography (Hexanes:EtOAc) afforded the title compound.

Step 2: (3R,7aS)-3-phenyl-6-(phenylselanyl)tetrahydro-3H,5H-pyrrolo[1,2-c]oxazol-5-one. To a solution of 0.5 M KHMDS (36 mL, 18 mmol) in THF at −78° C., was added (3R,7aS)-3-phenyltetrahydro-3H,5H-pyrrolo[1,2-c]oxazol-5-one (3.6 g, 17 mmol) in THF (60 mL) dropwise over the span of 30 min. The reaction was maintained at −78° C. for 30 min. TMSC1 (2.2 mL, 18 mmol) in THF (15 mL) was added dropwise. The reaction was warmed to 0° C. over 1 h and maintained at 0° C. for 3 h. A solution of PhSeCl (3.2 g, 17 mmol) in THF was added dropwise at 0° C. The solution was warmed to rt and stirred for 16 h. The reaction mixture was quenched upon the addition of sat. aq. $NaHCO_3$ (100 mL). The layers were separated, and the aqueous phase was extracted with EtOAc (2×100 mL). The combined organics were dried over $Na_2SO_4$ and concentrated under reduced pressure to afford the title compound.

Step 3: (3R,7aS)-3-phenyl-1,7a-dihydro-3H,5H-pyrrolo [1,2-c]oxazol-5-one. To a solution of (3R,7aS)-3-phenyl-6-(phenylselanyl)tetrahydro-3H,5H-pyrrolo[1,2-c]oxazol-5-one (14 mmol) in EtOAc (30 mL) at 0° C., was added 30% aqueous $H_2O_2$ (7.5 mL) and was stirred at 0° C. for 30 min. The reaction was partitioned between $H_2O$ (100 mL) and EtOAc (80 mL). The organic layer was washed with sat. aq. NaCl (1×100 mL) and concentrated under reduced pressure. Purification by column chromatography (Hexanes:EtOAc) afforded the title compound.

Step 4: ethyl (3R,5aS,6S,6aR,6bS)-5-oxo-3-phenylhexahydro-3H-cyclopropa[3,4]pyrrolo[1,2-c]oxazole-6-carboxylate. To a solution of (3R,7aS)-3-phenyl-1,7a-dihydro-3H,5H-pyrrolo[1,2-c]oxazol-5-one (980 mg, 4.8 mmol) in DMSO (2.5 mL) was added ethyl 2-(dimethyl-14-sulfaneylidene)acetate (2.1 g, 14 mmol) the reaction mixture was stirred for 24 h. The reaction mixture was diluted with $H_2O$ (50 mL) and extracted with $Et_2O$ (2×50 mL). The combined organics were washed with sat. aq. NaCl (1×50 mL) and concentrated under reduced pressure. Purification by column chromatography (Hexanes:EtOAc) afforded the title compound.

Step 5: ethyl (1R,2S,5S,6R)-3-benzyl-2-(hydroxymethyl)-3-azabicyclo[3.1.0]hexane-6-carboxylate. To a solution of ethyl (3R,5aS,6S,6aR,6bS)-5-oxo-3-phenylhexahydro-3H-cyclopropa[3,4]pyrrolo[1,2-c]oxazole-6-carboxylate (820 mg, 3.0 mmol) in THF (12 mL) at 0° C., was added 1.0 M $BH_3$·THF (4.8 mL, 4.8 mmol) dropwise. The solution was heated to 66° C. for 1 h. The reaction mixture was cooled to rt and concentrated under reduced pressure. The crude solid was dissolved in 2N HCl in MeOH and heated to reflux for 2 h. The reaction was cooled to rt and concentrated under reduced pressure. The crude solid was dissolved in $CHCl_3$ (50 mL) and washed with 20% $K_2CO_3$ (1×50 mL). The aqueous layer was extracted with $CHCl_3$ (2×50 mL) and the combined organics were dried over $Na_2SO_4$ and concentrated under reduced pressure. Purification by column chromatography (Hexanes:EtOAc) afforded the title compound.

Step 6: ethyl (1R,2S,5S,6R)-3-benzyl-2-(((tert-butyldimethylsilyl)oxy)methyl)-3-azabicyclo[3.1.0]hexane-6-carboxylate. To a solution of ethyl (1R,2S,5S,6R)-3-benzyl-2-(hydroxymethyl)-3-azabicyclo[3.1.0]hexane-6-carboxylate (340 mg, 1.3 mmol) in $CH_2Cl_2$ (10 mL) was added imidazole (130 mg, 2.0 mmol) and TBSCl (230 mg, 1.6 mmol) the reaction mixture was stirred for 16 h. The crude mixture was concentrated under reduced pressure and the solid was dissolved in EtOAc (50 mL) and washed with $H_2O$ (1×50 mL). The organic layer was dried over $Na_2SO_4$ and concentrated under reduced pressure. Purification by column chromatography (Hexanes:EtOAc) afforded the title compound.

Step 7: (1R,2S,5S,6R)-3-benzyl-2-(((tert-butyldimethylsilyl)oxy)methyl)-3-azabicyclo[3.1.0]hexane-6-carboxylic acid. To a suspension of ethyl (1R,2S,5S,6R)-3-benzyl-2-(((tert-butyldimethylsilyl)oxy)methyl)-3-azabicyclo[3.1.0] hexane-6-carboxylate (420 mg, 1.1 mmol) in THF/$H_2O$ (8 mL/4 mL) at rt, was added Li(OH) (270 mg, 11 mmol) and was stirred for 72 h. The reaction mixture was concentrated under reduced pressure and diluted with $H_2O$ (25 mL). The aqueous layer was washed with $Et_2O$ (1×25 mL) and was acidified to pH 2 with 2N HCl. The aqueous layer was extracted with $CH_2Cl_2$ (3×25 mL). The combined organics were dried over $Na_2SO_4$ and concentrated under reduced pressure to afford the title compound.

Step 8: (1R,2S,5S,6R)-3-benzyl-2-(((tert-butyldimethylsilyl)oxy)methyl)-3-azabicyclo[3.1.0]hexane-6-carbonyl azide. To a solution of (1R,2S,5S,6R)-3-benzyl-2-(((tert-butyldimethylsilyl)oxy)methyl)-3-azabicyclo[3.1.0]hexane-6-carboxylic acid (130 mg, 0.36 mmol) and $NEt_3$ (0.06 mL, 0.43 mmol) in acetone (10 mL) at 0° C., ethyl chloroformate (0.04 mL, 0.43 mmol) was added dropwise. The solution was stirred at 0° C. for 30 min, and a solution of sodium azide (230 mg, 3.6 mmol) in $H_2O$ (1.5 mL) was added dropwise. The solution was warmed to rt and stirred for 2.5 h. The reaction mixture was the diluted with $H_2O$ (25 mL) and extracted with $Et_2O$ (1×30 mL). The organic layer was washed with saturated aqueous NaCl, dried with $Na_2SO_4$ and concentrated reduced pressure to afford the crude title compound.

Step 9: tert-butyl ((1R,2S,5R,6R)-3-benzyl-2-(((tert-butyldimethylsilyl)oxy)methyl)-3-azabicyclo[3.1.0]hexan-6-yl)carbamate. To a solution of (1R,2S,5S,6R)-3-benzyl-2-(((tert-butyldimethylsilyl)oxy)methyl)-3-azabicyclo[3.1.0]hexane-6-carbonyl azide (125 mg, 0.34 mmol) in toluene was added, tert-butanol (1.5 mL) and pyridinium tosylate (2.0 mg 0.008 mmol). The reaction mixture was heated to 100° C. for 12 h. The crude reaction mixture was concentrated under reduced pressure and purified by column chromatography (EtOAc/Hex) to afford the title compound.

Step 10: tert-butyl ((1R,2S,5R,6R)-2-(((tert-butyldimethylsilyl)oxy)methyl)-3-azabicyclo[3.1.0]hexan-6-yl)carbamate. To a solution of tert-butyl ((1R,2S,5R,6R)-3-benzyl-2-(((tert-butyldimethylsilyl)oxy)methyl)-3-azabicyclo[3.1.0]

Step 12: N-(1-(4-((1R,2S,5R,6R)-6-amino-2-(hydroxymethyl)-3-azabicyclo[3.1.0]hexan-3-yl)methyl)phenyl)-2-oxo-1,2-dihydropyrimidin-4-yl)-4-(2-amino-2-methylpropanoyl)piperazine-1-carboxamide hydrochloride salt. Tert-butyl (1-(4-((1-(4-(((1R,2S,5R,6R)-6-((tert-butoxycarbonyl)amino)-2-(((tert-butyldimethylsilyl)oxy)methyl)-3-azabicyclo[3.1.0]hexan-3-yl)methyl)phenyl)-2-oxo-1,2-dihydropyrimidin-4-yl)carbamoyl)piperazin-1-yl)-2-methyl-1-oxopropan-2-yl)carbamate was dissolved in a solution of HCl in MeOH (2N, 5 mL) and stirred for 4 h. The volatiles were removed under reduced pressure and the crude solid was purified by reversed phase HPLC ($H_2O$: $CH_3CN$:TFA) and concentrated under reduced pressure. Addition of HCl in MeOH (2N, 3×15 mL) and evaporation under reduced pressure afforded the title compound. $^1H$ NMR (500 MHz, $D_2O$) δ 7.97 (d, 1H), 7.72 (d, 2H), 7.62 (d, 2H), 6.92 (d, 1H), 4.69-4.61 (m, 1H), 4.45 (s, 1H), 4.14 (s, 2H), 4.07-3.94 (m, 1H), 3.83 (br s, 4H), 3.78 (br s, 5H), 3.40-3.35 (m, 1H), 3.20 (s, 1H), 2.53-2.41 (m, 2H), 1.80 (s, 6H). LCMS[M+H] 525.3.

Compound 157

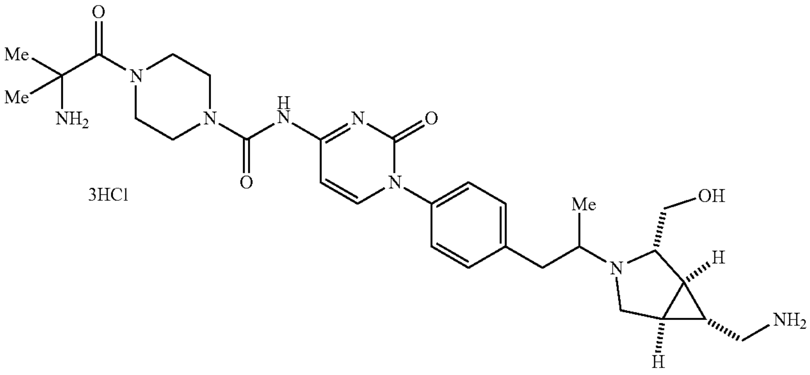

3HCl hexan-6-yl)carbamate (44 mg, 0.15 mmol) in MeOH (15 mL), was added $Pd(OH)_2/C$ (4 mg, 0.03 mmol). The suspension was stirred under a $H_2$ atmosphere (1 atm) for 16 h. The reaction mixture was filtered through Celite® and concentrated under reduced pressure to afford the title compound.

Step 11: tert-butyl (1-(4-((1-(4-(((1R,2S,5R,6R)-6-((tert-butoxycarbonyl)amino)-2-(((tert-butyldimethylsilyl)oxy)methyl)-3-azabicyclo[3.1.0]hexan-3-yl)methyl)phenyl)-2-oxo-1,2-dihydropyrimidin-4-yl)carbamoyl)piperazin-1-yl)-2-methyl-1-oxopropan-2-yl)carbamate. To a solution of tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate (44 mg, 0.09 mmol) in MeOH (10 mL) was added tert-butyl ((1R,2S,5R,6R)-2-(((tert-butyldimethylsilyl)oxy)methyl)-3-azabicyclo[3.1.0]hexan-6-yl)carbamate (37 mg, 0.10 mmol), $NaBH_3CN$ (11 mg, 0.17 mmol). The solution was stirred at rt for 16 h. The reaction mixture was concentrated under reduced pressure and dissolved in $CHCl_3$ (10 mL). The solution was washed with sat. aq. $NaHCO_3$ (10 mL) and the aqueous layer extracted with $CH_2Cl_2$ (2×10 mL). The combined organics were dried over $Na_2SO_4$ and concentrated under reduced pressure to afford the crude title compound.

4-(2-Amino-2-methylpropanoyl)-N-(1-(4-(2-((1S,2S,5R,6R)-6-(aminomethyl)-2-(hydroxymethyl)-3-azabicyclo[3.1.0]hexan-3-yl)propyl)phenyl)-2-oxo-1,2-dihydropyrimidin-4-yl)piperazine-1-carboxamide Hydrochloride Salt Scheme C-21

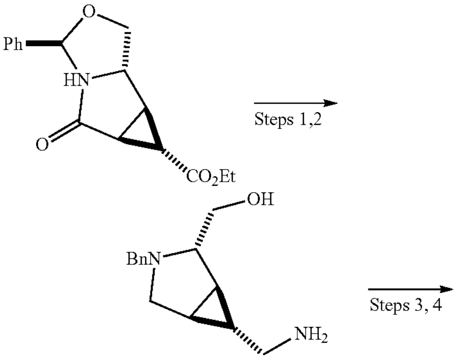

-continued

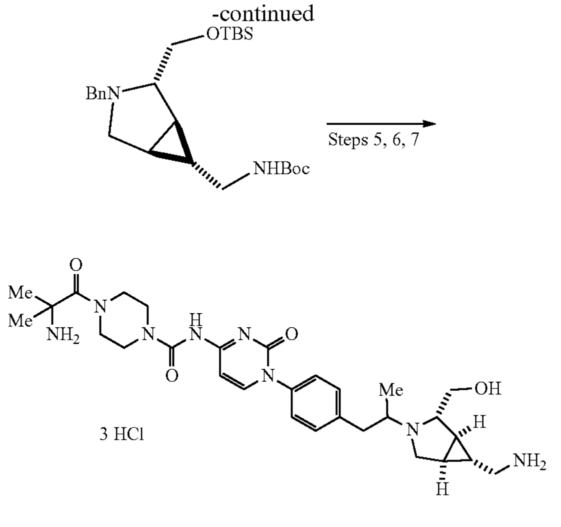

Reagents: 1) $NH_3$, MeOH, rt, 24 h. 2) $LiAlH_4$ THF, 66° C., 16 h. 3) $Boc_2O$, $Et_3N$, $CH_2Cl_2$, rt, 16 h. 4) TBSCl, Imidazole, $CH_2Cl_2$, rt, 16 h. 5) $Pd(OH)_2/C$, Hz, MeOH, rt 6) $NaBH_3CN$, MeOH, 16 h. 7) HCl/MeOH, rt, 4 h.

Step 1: (3R,5aS,6S,6aS,6bS)-5-oxo-3-phenylhexahydro-3H-cyclopropa[3,4]pyrrolo[1,2-c]oxazole-6-carboxamide. To a solution of ethyl (3R,5aS,6S,6aR,6bS)-5-oxo-3-phenylhexahydro-3H-cyclopropa[3,4]pyrrolo[1,2-c]oxazole-6-carboxylate (100 mg, 0.36 mmol) in MeOH (10 mL) at rt, was added 7 N $NH_3$ (5 mL). The solution was stirred at rt for 24 h. The reaction mixture was concentrated under reduced pressure and purified by column chromatography (EtOAc: MeOH) to afford the title compound.

Step 2: ((1S,2S,5R,6R)-6-(aminomethyl)-3-benzyl-3-azabicyclo[3.1.0]hexan-2-yl)methanol. To a stirred suspension of $LiAlH_4$ (50 mg, 1.2 mmol) in THF (10 mL) at 0° C., was added a solution of (3R,5aS,6S,6aS,6bS)-5-oxo-3-phenylhexahydro-3H-cyclopropa[3,4]pyrrolo[1,2-c]oxazole-6-carboxamide (80 mg, 0.33 mmol) in THF (2 mL) dropwise. The reaction was heated to 66° C. for 16 h. The reaction mixture was cooled to 0° C. and quenched upon addition of sat. aq. aqueous $Na_2SO_4$ (0.5 mL). The suspension was diluted with EtOAc (50 mL) and filtered through Celite®. The filtrate was concentrated under reduced pressure and was purified by flash chromatography ($CHCl_3$:MeOH) to afford the title compound.

Step 3: tert-butyl ((1S,2S,5R,6R)-3-benzyl-2-(hydroxymethyl)-3-azabicyclo[3.1.0]hexan-6-yl)methyl)carbamate. To a solution of 41S,2S,5R,6R)-6-(aminomethyl)-3-benzyl-3-azabicyclo[3.1.0]hexan-2-yl)methanol (45 mg, 0.19 mmol) in $CH_2Cl_2$ at rt was added $Et_3N$ (0.04 mL 0.29 mmol) and di-tert-butyl dicarbonate (50 mg, 0.23 mmol). The reaction mixture was stirred for 2 h and was concentrated under reduced pressure. The solid was dissolved in EtOAc (30 mL) and washed with saturated $NaHCO_3$ (1×30 mL). The organic layer was concentrated under reduced pressure and purified by flash chromatography (Hex:EtOAc) to afford the title compound.

Step 4: tert-butyl ((1S,2S,5R,6R)-3-benzyl-2-(((tert-butyldimethylsilyl)oxy)methyl)-3-azabicyclo[3.1.0]hexan-6-yl)methyl)carbamate. To a solution of tert-butyl (((1S,2S,5R,6R)-3-benzyl-2-(hydroxymethyl)-3-azabicyclo[3.1.0]hexan-6-yl)methyl)carbamate (60 mg, 0.18 mmol) in $CH_2Cl_2$ (10 mL) at rt, was added imidazole (20 mg, 0.30 mmol) and TBSCl (45 mg, 0.30 mmol) and the solution was stirred at rt for 16 h. The reaction mixture was concentrated under reduced pressure, dissolved in EtOAc (50 mL) and washed with $H_2O$ (1×50 mL). The organic layer was dried over $Na_2SO_4$ and concentrated under reduced pressure. Purification by flash chromatography (Hexanes:EtOAc) afforded the title compound.

Step 5: tert-butyl ((1R,2S,5R,6R)-2-(((tert-butyldimethylsilyl)oxy)methyl)-3-azabicyclo[3.1.0]hexan-6-yl)methyl) carbamate. To a solution of tert-butyl (((1S,2S,5R,6R)-3-benzyl-2-(((tert-butyldimethylsilyl)oxy)methyl)-3-azabicyclo[3.1.0]hexan-6-yl)methyl)carbamate (50 mg, 0.13 mmol) in MeOH (15 mL), was added $Pd(OH)_2/C$ (5 mg, 0.04 mmol). The suspension was stirred under a $H_2$ atmosphere (1 atm) for 16 h. The reaction mixture was filtered through Celite® and concentrated under reduced pressure to afford the title compound.

Step 6: tert-butyl (1-(4-((1-(4-(2-01S,2S,5R,6R)-6-(((tert-butoxycarbonyl)amino)methyl)-2-(((tert-butyldimethylsilyl)oxy)methyl)-3-azabicyclo[3.1.0]hexan-3-yl)propyl)phenyl)-2-oxo-1,2-dihydropyrimidin-4-yl)carbamoyl) piperazin-1-yl)-2-methyl-1-oxopropan-2-yl)carbamate. To a solution of tert-butyl (2-methyl-1-oxo-1-(4-((2-oxo-1-(4-(2-oxopropyl)phenyl)-1,2-dihydropyrimidin-4-yl)carbamoyl) piperazin-1-yl)propan-2-yl)carbamate (48 mg, 0.09 mmol) in MeOH (10 mL) was added tert-butyl (((1R,2S,5R,6R)-2-(((tert-butyldimethylsilyl)oxy)methyl)-3-azabicyclo[3.1.0] hexan-6-yl)methyl)carbamate (41 mg, 0.12 mmol), $NaBH_3CN$ (11 mg, 0.18 mmol). The solution was stirred at rt for 16 h. The reaction mixture was concentrated under reduced pressure, dissolved in $CHCl_3$ washed with sat. aq. aqueous $NaHCO_3$ (10 mL) and the aqueous layer extracted with $CH_2Cl_2$ (2×10 mL). The combined organics were dried over $Na_2SO_4$ and concentrated under reduced pressure to afford the title compound.

Step 7: 4-(2-amino-2-methylpropanoyl)-N-(1-(4-(2-((1S,2S,5R,6R)-6-(aminomethyl)-2-(hydroxymethyl)-3-azabicyclo[3.1.0]hexan-3-yl)propyl)phenyl)-2-oxo-1,2-dihydropyrimidin-4-yl)piperazine-1-carboxamide hydrochloride salt. Tert-butyl (1-(4-((1-(4-(2-((1S,2S,5R,6R)-6-(((tert-butoxycarbonyl)amino)methyl)-2-(((tert-butyldimethylsilyl)oxy) methyl)-3-azabicyclo[3.1.0]hexan-3-yl)propyl)phenyl)-2-oxo-1,2-dihydropyrimidin-4-yl)carbamoyl)piperazin-1-yl)-2-methyl-1-oxopropan-2-yl)carbamate was dissolved in a 2N solution of HCl in MeOH (5 mL) and stirred for 4 h. The volatiles were removed under reduced pressure and the crude solid was purified by reversed phase HPLC ($H_2O$: $CH_3CN$:TFA) and concentrated under reduced pressure. Addition of HCl in MeOH (2N, 3×15 mL) and evaporation under reduced pressure afforded the title compound. $^1H$ NMR (400 MHz, $D_2O$) δ 7.97-7.92 (m, 1H), 7.53-7.42 (m, 4H), 6.85 (d, 1H), 4.30 (s, 1H), 4.17-3.96 (m, 3H), 3.89-3.68 (m, 10H), 3.39-3.32 (m, 1H), 3.08-2.76 (m, 3H), 2.18-2.05 (m, 1H), 2.05-1.95 (m, 1H), 1.75 (s, 6H), 1.72-1.56 (m, 1H), 1.34-1.20 (m, 3H). LCMS[M+H]: 567.3.

Compound 73

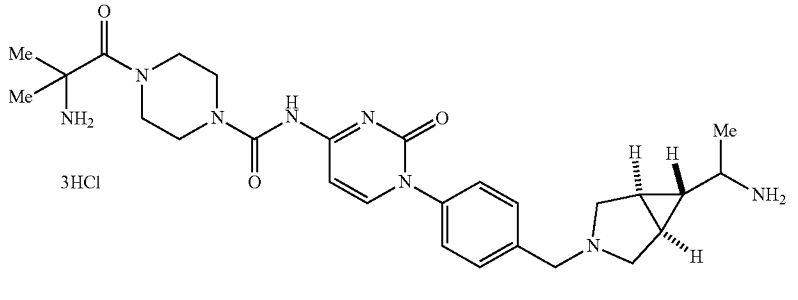

4-(2-Amino-2-methylpropanoyl)-N-(1-(4-((exo-6-(1-aminoethyl)-3-azabicyclo[3.1.0]hexan-3-yl)methyl) phenyl)-2-oxo-1,2-dihydropyrimidin-4-yl)piperazine-1-carboxamide Hydrochloride Salt Scheme C-22

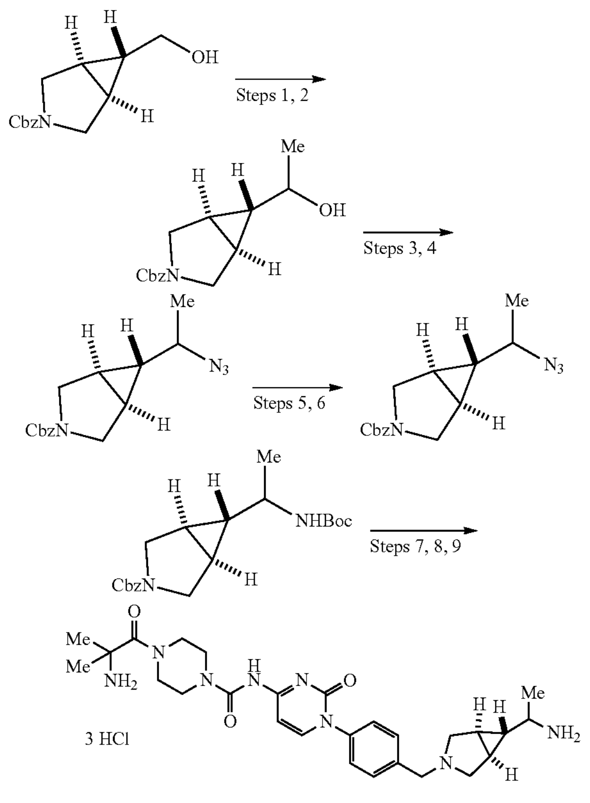

Reagents: DMP, $CH_2Cl_2$ rt, 4 h 2) MeMgCl, THF, −78° C. to rt, 16 h 3) MsCl, $NEt_3CH_2Cl_2$, 0° C., 4 h 4) $NaN_3$ DMF, 80° C. 5) $PPh_3$, THF, $H_2O$, 45° C. 16 h 6) $Boc_2O$, $CH_2Cl_2$ rt, 16 h 7) Hz, $Pd(OH)_2$, MeOH rt, 16 h 8) tert-Butyl (1-(4-((1-(4-formylphenyl)-2-oxo-1,2-dihydropyrimidin-4-yl)carbamoyl)piperazin-1-yl)-2-methyl-1-oxopropan-2-yl) carbamate, $CH_3CN$, $NaBH(OAc)_3$, rt. 16 h 9) HCl/MeOH, rt. 4 h.

Step 1: benzyl exo-6-formyl-3-azabicyclo[3.1.0]hexane-3-carboxylate. To a solution of benzyl exo-6-(hydroxymethyl)-3-azabicyclo[3.1.0]hexane-3-carboxylate (500 mg, 2.02 mmol) in $CH_2Cl_2$ (100 mL) was added DMP (1.37 g, 3.23 mmol). The solution was stirred for 4 h. The reaction mixture was washed with $NaHCO_3$:$Na_2S_2O_3$ (1×100 mL) solution and the organic layer was dried over $Na_2SO_4$, concentrated under reduced pressure, and purified by column chromatography (Hex:EtOAc) to afford the title compound.

Step 2: benzyl exo-6-(1-hydroxyethyl)-3-azabicyclo [3.1.0]hexane-3-carboxylate. To a solution of benzyl exo-6-formyl-3-azabicyclo[3.1.0]hexane-3-carboxylate (370 mg, 1.5 mmol) in THF (15 mL) at −78° C., was added 3M MeMgCl (1.00 mL, 3.0 mmol) dropwise over the span of 30 min. The solution was warmed to rt and stirred for 16 h. The organic layer was washed with sat. aq. citric acid (1×15 mL) and the organic layer was dried over $Na_2SO_4$, concentrated under reduced pressure to afford the crude title compound.

Step 3: benzyl exo-6-(1-((methylsulfonyl)oxy)ethyl)-3-azabicyclo[3.1.0]hexane-3-carboxylate. A solution of benzyl exo-6-(1-hydroxyethyl)-3-azabicyclo[3.1.0]hexane-3-carboxylate (260 mg, 1.0 mmol) in $Et_3N$ (0.4 mL, 3.0 mmol) and $CH_2Cl_2$ (10 mL) at 0° C., was added MsCl (0.14 mL, 2.0 mmol) dropwise over the span of 5 min. The solution was stirred for 4 h and then washed with $NaHCO_3$ (1×20 mL). The aqueous layer was extracted with $CH_2Cl_2$ (1×20 mL). The combined organics were dried over $Na_2SO_4$ and concentrated under reduced pressure to afford the crude title compound which was used immediately in the next step.

Step 4: benzyl exo-6-(1-azidoethyl)-3-azabicyclo[3.1.0] hexane-3-carboxylate. To a solution of benzyl exo-6-(1-((methylsulfonyl)oxy)ethyl)-3-azabicyclo[3.1.0]hexane-3-carboxylate (assuming 1.0 mmol) in DMF (12 mL) was added $NaN_3$ (325 mg, 5.0 mmol). The solution was warmed to 80° C. and stirred for 16 h. EtOAc (50 mL) was added and the solution washed with sat. aq. LiCl (4×20 mL). The organics layer was dried over $Na_2SO_4$ and concentrated under reduced pressure and purified by column chromatography (Hex:EtOAc) to afford the title compound.

Step 5: benzyl exo-6-(1-aminoethyl)-3-azabicyclo[3.1.0] hexane-3-carboxylate. To a solution of benzyl exo-6-(1-azidoethyl)-3-azabicyclo[3.1.0]hexane-3-carboxylate (220 mg, 0.8 mmol) in THF:$H_2O$ (15:2 mL) was added PPh3 (403 mg, 1.60 mmol). The solution was warmed to 45° C. and stirred for 16 h. The solution was concentrated under reduced pressure and purified by column chromatography (Hex:EtOAc then EtOAc:MeOH:$NH_4OH$) to afford the title compound.

Step 6: benzyl exo-6-(1-((t-butoxycarbonyl)amino)ethyl)-3-azabicyclo[3.1.0]hexane-3-carboxylate. To a solution of benzyl exo-6-(1-aminoethyl)-3-azabicyclo[3.1.0]hexane-3-carboxylate (37 mg, 0.14 mmol) in $CH_2Cl_2$ (10 mL) was added $Boc_2O$ (37 mg, 0.17 mmol) and $NEt_3$ (0.04 mL, 0.3 mmol). The solution was stirred for 16 h. The solution was concentrated under reduced pressure and purified by column chromatography (Hex:EtOAc) to afford the title compound.

Step 7: t-butyl (1-(exo-3-azabicyclo[3.1.0]hexan-6-yl) ethyl)carbamate. To a degassed solution of benzyl exo-6-(1-((t-butoxycarbonyl)amino)ethyl)-3-azabicyclo[3.1.0] hexane-3-carboxylate (42 mg, 0.11 mmol) in MeOH (10 mL) was added $Pd(OH)_2$ (4 mg, 0.04 mmol). The reaction was stirred at rt for 16 h under $H_2$ atmosphere. The reaction mixture was filtered through a pad of Celite® and washed with MeOH (5×20 mL). The combined organics were concentrated under reduced pressure to afford the title compound.

Step 8: tert-butyl (1-(exo-3-(4-(4-(4-(2-((tert-butoxycarbonyl)amino)-2-methylpropanoyl)piperazine-1-carboxamido)-2-oxopyrimidin-1 (2H)-yl)benzyl)-3-azabicyclo [3.1.0]hexan-6-yl)ethyl)carbamate. To a solution of tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate (20 mg, 0.05 mmol) in MeOH (10 mL) was added t-butyl (1-(exo-3-azabicyclo [3.1.0]hexan-6-yl)ethyl)carbamate (21 mg, 0.05 mmol), $NaBH_3CN$ (5 mg, 0.10 mmol). The solution was stirred at rt for 16 h. The reaction mixture was concentrated under reduced pressure, and the crude solid was dissolved in $CHCl_3$. The solution was washed with sat. aq. aqueous $NaHCO_3$ (10 mL) and the aqueous layer was extracted with $CH_2Cl_2$ (2×10 mL). The combined organics were dried over $Na_2SO_4$ and concentrated under reduced pressure to afford the title compound.

Step 9: 4-(2-amino-2-methylpropanoyl)-N-(1-(4-((exo-6-(1-aminoethyl)-3-azabicyclo[3.1.0]hexan-3-yl)methyl)phenyl)-2-oxo-1,2-dihydropyrimidin-4-yl)piperazine-1-carboxamide hydrochloride. tert-butyl (1-(exo-3-(4-(4-(4-(2-((tert-butoxycarbonyl)amino)-2-methylpropanoyl)piperazine-1-carboxamido)-2-oxopyrimidin-1 (2H)-yl)benzyl)-3-azabicyclo[3.1.0]hexan-6-yl)ethyl)carbamate salt was dissolved in a 2N solution of HCl in MeOH (5 mL) and stirred for 4 h. The volatiles were removed under reduced pressure and purified by reversed phase HPLC ($H_2O$: $CH_3CN$:TFA). Addition of HCl in MeOH (2N, 3×15 mL) and evaporation under reduced pressure afforded the title compound. $^1H$ NMR (400 MHz, $D_2O$) δ 7.92 (d, 1H), 7.64 (d, 2H), 7.52 (d, 2H), 6.82 (d, 1H), 4.44 (s, 2H), 3.81-3.54 (m, 12H), 2.83 (s, 1H), 2.11-1.97 (m, 2H), 1.70 (s, 6H), 1.32 (d, 3H), 1.29-1.22 (m, 1H). LCMS [M+H]523.3.

Compound 134

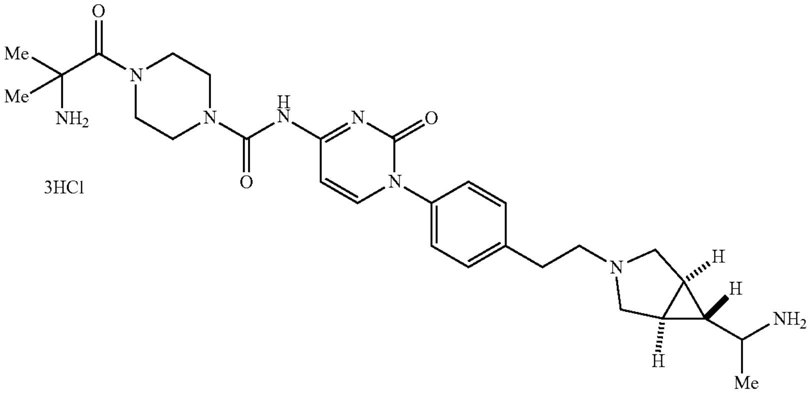

3HCl 4-(2-Amino-2-methylpropanoyl)-N-(1-(4-(2-(exo-6-(1-aminoethyl)-3-azabicyclo[3.1.0]hexan-3-yl)ethyl) phenyl)-2-oxo-1,2-dihydropyrimidin-4-yl)piperazine-1-carboxamide Hydrochloride Salt Prepared in a similar fashion to Scheme C-22 from tert-butyl (2-methyl-1-oxo-1-(4-((2-oxo-1-(4-(2-oxoethyl) phenyl)-1,2-dihydropyrimidin-4-yl)carbamoyl)piperazin-1-yl)propan-2-yl)carbamate and afford t-butyl (1-(3-azabicyclo[3.1.0]hexan-6-yl)ethyl)carbamate $^1H$ NMR (400 MHz, $D_2O$) δ 7.85 (d, 1H), 7.44 (d, 2H), 7.39 (d, 2H), 6.82 (d, 1H), 3.83-3.64 (m, 10H), 3.57-3.42 (m, 4H), 3.09 (d, 2H), 2.86 (s, 1H), 2.08-1.94 (m, 2H), 1.70 (s, 6H), 1.35 (d, 3H), 1.22-1.16 (m, 1H). LCMS[M+H] 537.5.

Compound 75

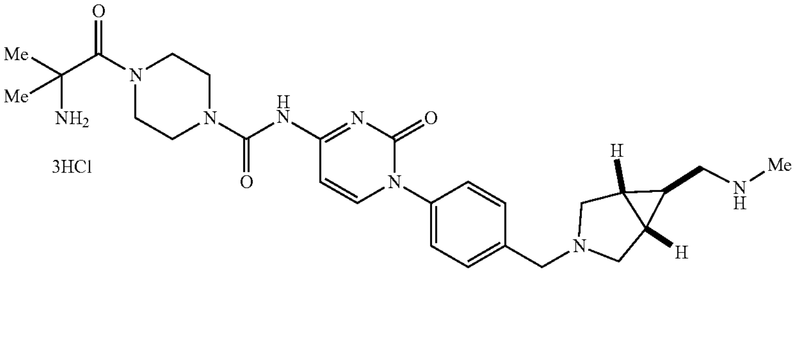

3HCl 4-(2-Amino-2-methylpropanoyl)-N-(1-(4-((exo-6-((methylamino)methyl)-3-azabicyclo[3.1.0]hexan-3-yl)methyl)phenyl)-2-oxo-1,2-dihydropyrimidin-4-yl) piperazine-1-carboxamide Hydrochloride Salt Scheme C-23

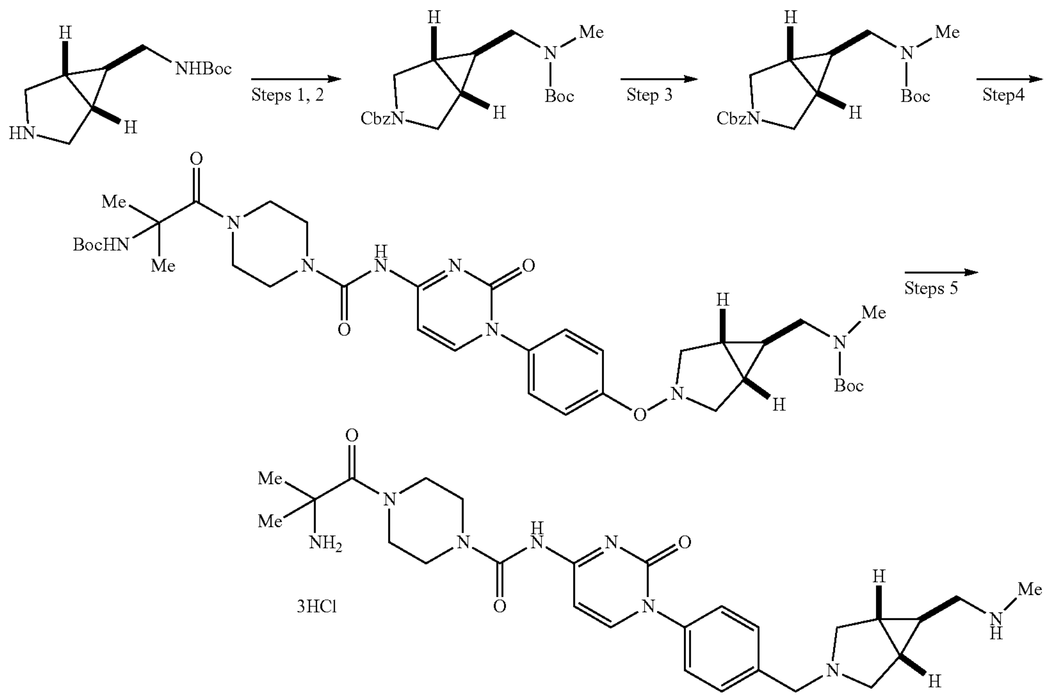

Reagents: 1) $Cb_2Cl$, $Et_3N$, $CH_2Cl_2$, 0° C. to rt, 16 h 2) NaH, MeI, THF, 0° C., 3 h 3) $H_2$, Pd/C, MeOH, rt, 16 h 4) $NaBH(OAc)_3$, 4) tert-Butyl (1-(4-((1-(4-formylphenyl)-2-oxo-1,2-dihydropyrimidin-4-yl)carbamoyl)piperazin-1-yl)-2-methyl-1-oxopropan-2-yl)carbamate, MeCN, NaBH $(OAc)_3$, rt. 16 h 5) HCl/MeOH, rt. 4 h.

Step 1: benzyl exo-6-(((t-butoxycarbonyl)amino)methyl)-3-azabicyclo[3.1.0]hexane-3-carboxylate. To a solution of t-butyl ((exo-3-azabicyclo[3.1.0]hexan-6-yl)methyl)carbamate (212 mg, 1.00 mmol) in $CH_2Cl_2$ (10 mL) at 0° C., was added $Et_3N$ (0.21 mL, 1.5 mmol) and benzyl carbonochloridate (0.17 mL, 1.2 mmol). The reaction was warmed to rt and stirred for 16 h. The reaction mixture was diluted with $CH_2Cl_2$ (50 mL), washed with $H_2O$ (1×50 mL) and the organic layer dried over $Na_2SO_4$ and concentrated under reduced pressure to afford the title compound Step 2: benzyl exo-6-(((t-butoxycarbonyl)(methyl)amino) methyl)-3-azabicyclo[3.1.0]hexane-3-carboxylate. To a solution of benzyl exo-6-(((t-butoxycarbonyl)amino) methyl)-3-azabicyclo[3.1.0]hexane-3-carboxylate (290 mg, 0.85 mmol) in THF (10 mL) at 0° C. was added NaH dispersion in mineral oil (44 mg 1.1 mmol). The reaction was stirred at 0° C. for 1 h after which MeI (0.11 mL, 1.7 mmol) was added. The reaction mixture was stirred for an additional 3 h at rt. Sat. aq. $NH_4C_1$ solution (10 mL) was added to the reaction and the biphasic reaction was separated. The aqueous layer was diluted with $H_2O$ (30 mL) and extracted with EtOAc (2×50 mL). The combined organics were dried over $Na_2SO_4$ and concentrated under reduced pressure to afford the desired compound.

Step 3: t-butyl ((exo-3-azabicyclo[3.1.0]hexan-6-yl) methyl)(methyl)carbamate. To a solution of benzyl exo-6-(((t-butoxycarbonyl)(methyl)amino)methyl)-3-azabicyclo [3.1.0]hexane-3-carboxylate (250 mg, 0.70 mmol), was added a Pd/C (25 mg, 0.24 mmol). The atmosphere was evacuated and replaced with $H_2$. The reaction mixture stirred under 1 atm $H_2$ at rt for 16 h. The reaction mixture was filtered through Celite® and concentrated to afford the title compound.

Step 4: tert-butyl ((1R,5S,6 s)-3-(4-(4-(4-(2-((tert-butoxycarbonyl)amino)-2-methylpropanoyl)piperazine-1-carboxamido)-2-oxopyrimidin-1 (2H)-yl)benzyl)-3-azabicyclo [3.1.0]hexan-6-yl)(methyl)carbamate. To a solution of tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate (18 mg, 0.05 mmol) in MeOH (10 mL) was added t-butyl ((exo-3-azabicyclo[3.1.0] hexan-6-yl)methyl)(methyl)carbamate (20 mg, 0.05 mmol) and $NaBH_3CN$ (4 mg, 0.08 mmol). The solution was stirred at rt for 16 h. The reaction mixture was concentrated under reduced pressure and dissolved in $CHCl_3$. The solution was washed with sat. aq. aqueous $NaHCO_3$ (10 mL) and the aqueous layer was extracted with $CH_2Cl_2$ (2×10 mL). The combined organics were dried over $Na_2SO_4$ and concentrated to afford the title compound.

Step 5: 4-(2-amino-2-methylpropanoyl)-N-(1-(4-((exo-6-((methylamino)methyl)-3-azabicyclo[3.1.0]hexan-3-yl) methyl)phenyl)-2-oxo-1,2-dihydropyrimidin-4-yl)piperazine-1-carboxamide hydrochloride salt. was dissolved in a 2N solution of HCl in MeOH (5 mL) and stirred for 4 h. The volatiles were removed under reduced pressure and the crude solid was purified by reversed phase HPLC ($H_2O$: $CH_3CN$:TFA) and concentrated under reduced pressure. Addition of HCl in MeOH (2N, 3×15 mL) and evaporation under reduced pressure afforded the title compounA. LCMS [M+H]523.2.

Compound 138

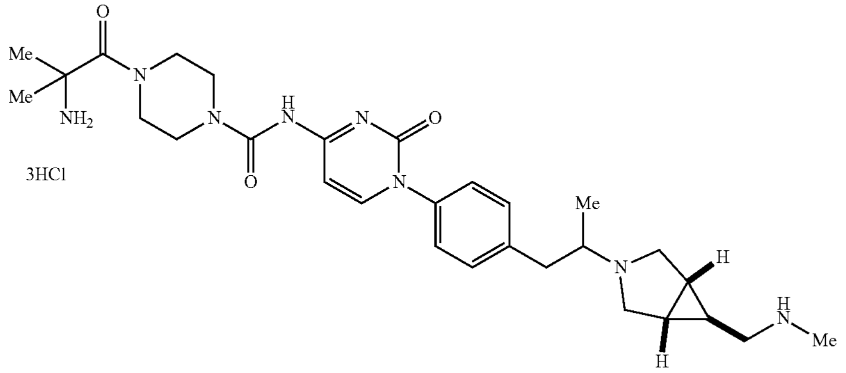

4-(2-Amino-2-methylpropanoyl)-N-(1-(4-(2-(exo-6-((methylamino)methyl)-3-azabicyclo[3.1.0]hexan-3-yl)propyl)phenyl)-2-oxo-1,2-dihydropyrimidin-4-yl) piperazine-1-carboxamide Hydrochloride Salt Prepared in a similar fashion to Scheme C-23 from tert-butyl (2-methyl-1-oxo-1-(4-((2-oxo-1-(4-(2-oxopropyl) phenyl)-1,2-dihydropyrimidin-4-yl)carbamoyl)piperazin-1-yl)propan-2-yl)carbamate and t-butyl ((exo-3-azabicyclo [3.1.0]hexan-6-yl)methyl)(methyl)carbamate. $^1$H NMR (400 MHz, $D_2O$) δ 8.04 (s, 1H), 7.46 (d, 4H), 6.83 (d, 1H), 3.96-3.63 (m, 12H), 3.62-3.37 (m, 2H), 3.06 (d, 2H), 2.86 (t, 1H), 2.75 (s, 3H), 2.08 (s, 2H), 1.75 (s, 6H), 1.45-1.21 (m, 4H). LCMS[M+H]551.4.

Compound 221

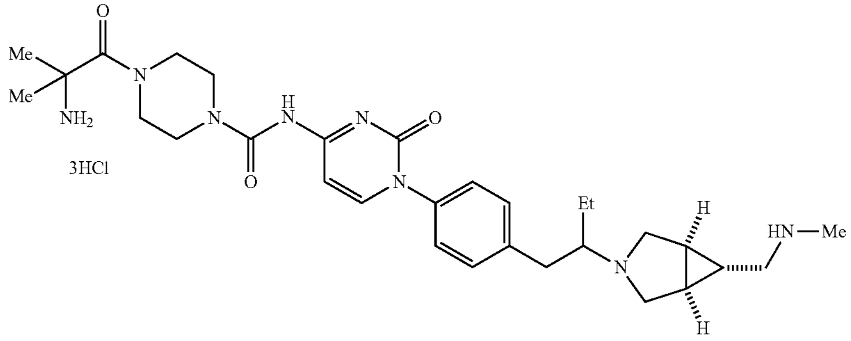

4-(2-Amino-2-methyl propanoyl)-N-(1-(4-(2-((exo)-6-((methylamino)methyl)-3-azabicyclo[3.1.0]hexan-3-yl)butyl)phenyl)-2-oxo-1,2-dihydropyrimidin-4-yl) piperazine-1-carboxamide Prepared in a similar fashion to Scheme C-23 from tert-butyl (2-methyl-1-oxo-1-(4-((2-oxo-1-(4-(2-oxobutyl) phenyl)-1,2-dihydropyrimidin-4-yl)carbamoyl)piperazin-1-yl)propan-2-yl)carbamate and tert-butyl ((exo-3-azabicyclo [3.1.0]hexan-6-yl)methyl)(methyl)carbamate. $^1$H NMR (400 MHz, $D_2O$) δ 7.95 (d, 1H), 7.50 (d, 2H), 7.45 (d, 2H), 6.85 (d, 1H), 3.89-3.70 (m, 10H), 3.69-3.57 (m, 3H), 3.29-3.21 (m, 1H), 3.17-3.07 (m, 1H), 3.04 (d, 2H), 2.74 (s, 3H), 2.05 (s, 2H), 1.83-1.70 (m, 2H), 1.75 (s, 6H), 1.41 (s, 1H), 0.96 (t, 3H). LCMS[M+H] 565.4.

Compound 237

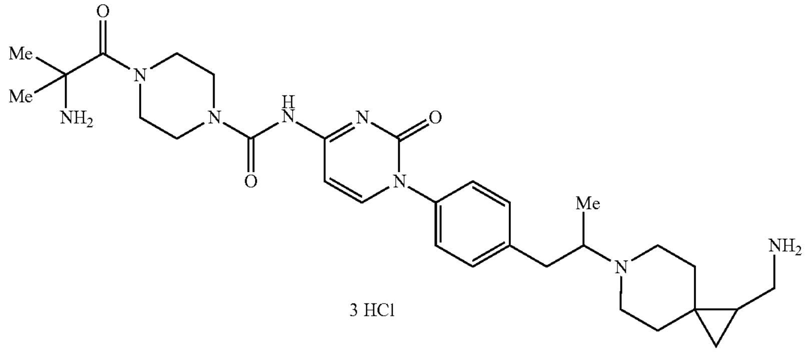

4-(2-Amino-2-methylpropanoyl)-N-(1-(4-(2-(1-(aminomethyl)-6-azaspiro[2.5]octan-6-yl)propyl)phenyl)-2-oxo-1,2-dihydropyrimidin-4-yl)piperazine-1-carboxamide Hydrochloride Salt Scheme C-24

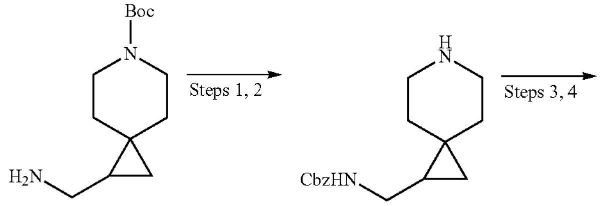

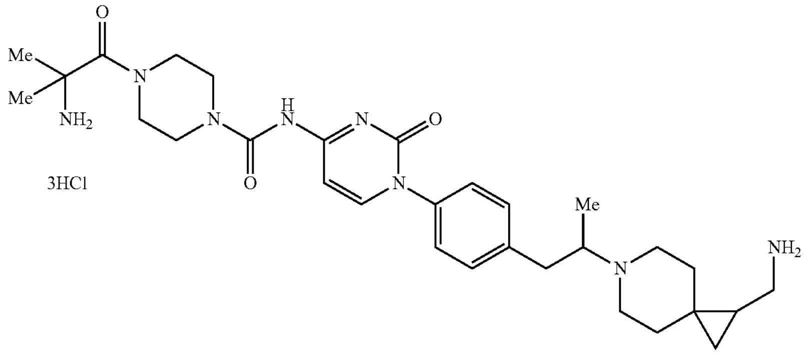

Reagents: Steps: 1) $CB_2Cl$, TEA, $CH_2Cl_2$, rt, 16 h 2) 4M HCl in dioxane, rt, 3 h. 3) tert-butyl(2-methyl-1-oxo-1-(4-((2-oxo-1-(4-(2-oxopropyl)-3-(trifluoromethyl)phenyl)-1,2-dihydropyrimidin-4-yl)carbamoyl)piperazin-1-yl)propan-2-yl)carbamate, $NaBH_3CN$, MeOH, rt, 36 d 4) conc. HCl, rt, 3 h.

Step 1: tert-butyl 1-((((benzyloxy)carbonyl)amino)methyl)-6-azaspiro[2.5]octane-6-carboxylate. To a stirred solution of tert-butyl 1-(aminomethyl)-6-azaspiro[2.5]octane-6-carboxylate (0.25 g, 1.1 mmol) in $CH_2Cl_2$ (5 mL) were added TEA (0.3 mL, 2.1 mmol) and $CB_2Cl$ (0.6 mL, 4.2 mmol) at 0° C. The reaction mixture was stirred at rt for 16 h. The reaction mixture was poured in to $H_2O$ (100 mL) and extracted with $CH_2Cl_2$ (3x30 mL). The combined organics were dried over $Na_2SO_4$, concentrated under reduced pressure and purified by column chromatography (Hexane: EtOAc 85:15) to afford the title compound (0.2 g, 64%). LCMS[M+H]-100 275.1.

Step 2: Benzyl ((6-azaspiro[2.5]octan-1-yl)methyl)carbamate. To a stirred solution of tert-butyl 1-((((benzyloxy)carbonyl)amino)methyl)-6-azaspiro[2.5]octane-6-carboxylate (0.2 g, 0.5 mmol) in dioxane (5 mL) was added 4M HCl in dioxane (5 mL) at 0° C. The reaction mixture was stirred at rt for 3 h. The reaction mixture was concentrated under reduced pressure and purified by reverse phase chromatography ($H_2O$:$CH_3CN$, 70:30) to afford the title compound (0.18 g, quantitative). LCMS[M+H] 275.2.

Step 3: tert-butyl(1-(4-((1-(4-(2-(1-((((benzyloxy)carbonyl)amino)methyl)-6-azaspiro[2.5]octan-6-yl)propyl)phenyl)-2-oxo-1,2-dihydropyrimidin-4-yl)carbamoyl) piperazin-1-yl)-2-methyl-1-oxopropan-2-yl)carbamate. To a stirred solution of tert-butyl (2-methyl-1-oxo-1-(4-((2-oxo-1-(4-(2-oxopropyl)phenyl)-1,2-dihydropyrimidin-4-yl)carbamoyl) piperazin-1-yl)propan-2-yl)carbamate (0.25 g, 0.5 mmol) and benzyl ((6-azaspiro[2.5]octan-1-yl)methyl)carbamate (0.15 g, 0.6 mmol) in MeOH (5.0 mL) were added activated 4 Å molecular sieves (1.5 g) and $NaBH_3CN$ (0.06 g, 0.9 mmol) at 0° C. The reaction mixture was stirred at rt for 36 d. The reaction mixture was concentrated under reduced pressure and purified by column chromatography ($CH_2Cl_2$:MeOH, 93:7) to afford the title compound (0.2 g, quantitative) as off white solid. LCMS[M+H] 799.8.

Step 4: 4-(2-Amino-2-methylpropanoyl)-N-(1-(4-(2-(1-(aminomethyl)-6-azaspiro[2.5]octan-6-yl)propyl)phenyl)-2-oxo-1,2-dihydropyrimidin-4-yl)piperazine-1-carboxamide hydrochloride salt. Concentrated HCl (5 mL) was added in to tert-butyl (1-(4-((1-(4-(2-(1-((((benzyloxy)carbonyl) amino)methyl)-6-azaspiro[2.5]octan-6-yl)propyl) phenyl)-2-oxo-1,2-dihydropyrimidin-4-yl)carbamoyl)piperazin-1-yl)-2-methyl-1-oxopropan-2-yl)carbamate (0.2 g, 0.3 mmol) at 0° C. The reaction mixture was stirred at rt for 3 h. The reaction mixture was concentrated under reduced pressure and purified by Prep HPLC to afford the title compound (0.02 g, 10%) as off white solid. $^1H$ NMR (400 MHz, $D_2O$): Mixture of rotamers, δ 7.82 (d, 1H), 7.32.7.27 (m, 4H), 6.67 (d, 1H), 3.71-3.50 (m, 8H), 3.49-3.39 (m, 3H), 3.21-3.07 (m, 4H), 2.78-2.76 (m, 2H), 2.19-2.12 (m, 2H), 1.57 (s, 6H), 1.40 (d, 1H), 1.12 (d, 3H), 1.25-1.03 (m, 1H), 0.74-0.73 (m, 1H), 0.50-0.38 (m, 1H). LCMS[M+H] 565.5.

Compound 225

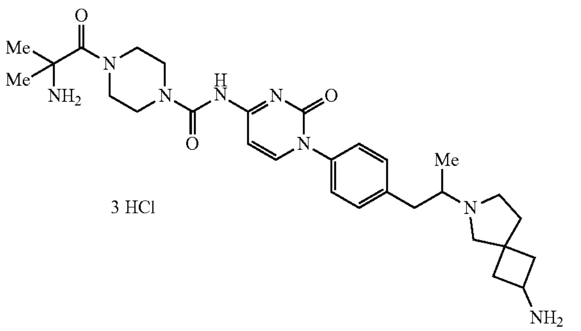

3 HCl 4-(2-Amino-2-methylpropanoyl)-N-(1-(4-(2-(2-amino-6-azaspiro[3.4]octan-6-yl)propyl)phenyl)-2-oxo-1,2-dihydropyrimidin-4-yl)piperazine-1-carboxamide Hydrochloride Salt Prepared in a similar fashion to Scheme C-24 from tert-butyl (2-methyl-1-oxo-1-(4-((2-oxo-1-(4-(2-oxopropyl) phenyl)-1,2-dihydropyrimidin-4-yl)carbamoyl)piperazin-1-yl)propan-2-yl)carbamate and tert-butyl 2-amino-6-azaspiro [3.4]octane-6-carboxylate. $^1H$ NMR (400 MHz, $D_2O$) δ 7.87 (d, 1H), 7.32-7.27 (m, 4H), 6.65 (d, 1H), 3.78-3.70 (m, 2H), 3.67-3.57 (m, 11H), 3.30-3.14 (m, 4H), 2.71 (t, 1H), 2.46-2.44 (m, 1H), 2.35-2.32 (m, 2H), 2.26-2.14 (m, 3H), 2.04-2.02 (m, 1H), 1.56 (s, 6H), 1.09 (d, 3H). LCMS[M+H] 591.3.

Compound 191

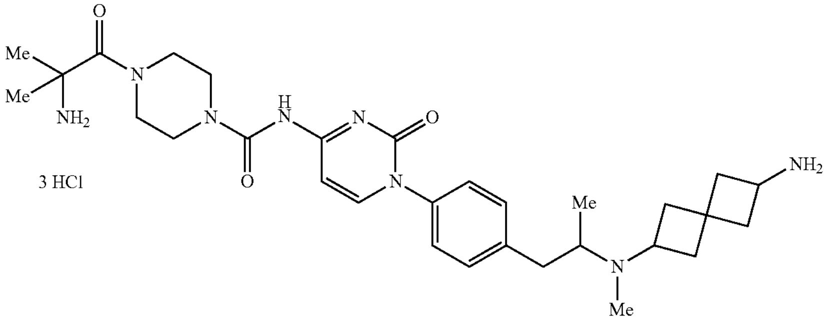

3 HCl 4-(2-Amino-2-methylpropanoyl)-N-(1-(4-(2-((6-aminospiro[3.3]heptan-2-yl)(methyl)amino)propyl) phenyl)-2-oxo-1,2-dihydropyrimidin-4-yl)piperazine-1-carboxamide Hydrochloride Salt Scheme C-25

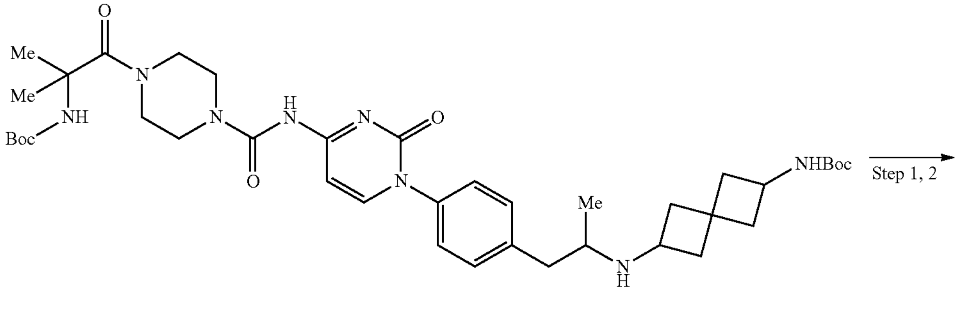

-continued

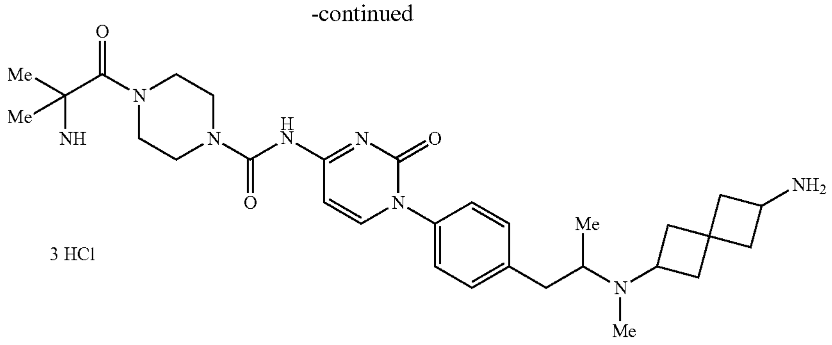

Reagents: Step 1) Formalin, $NaBH_3CN$, 4 Å molecular sieves, MeOH, 16 h, rt. 2) HCl in MeOH, 4 h rt.

Step 1: tert-butyl (1-(4-((1-(4-(2-((6-((tert-butoxycarbonyl)amino)spiro [3.3] heptan-2-yl)(methyl)amino)propyl) phenyl)-2-oxo-1,2-dihydropyrimidin-4-yl)carbamoyl)piperazin-1-yl)-2-methyl-1-oxopropan-2-yl)carbamate. To a solution of tert-butyl (1-(4-((1-(4-(2-((6-((tert-butoxycarbonyl)amino)spiro[3.3]heptan-2-yl)amino)propyl)phenyl)-2-oxo-1,2-dihydropyrimidin-4-yl)carbamoyl)piperazin-1-yl)-2-methyl-1-oxopropan-2-yl)carbamate (30 mg, 0.04 mmol) in MeOH (5 mL), was added formalin (0.04 mL, 0.4 mmol), 4 Å molecular sieves (200 mg) and $NaBH_3CN$ (5 mg, 0.08 mmol). The reaction was stirred at rt for 16 h. The reaction mixture was filtered through Celite® and concentrated under reduced pressure, dissolved in $CHCl_3$ (10 mL) and washed with 10% aqueous NaOH solution (1×15 mL). The organic layer was dried over $Na_2SO_4$ and concentrated under reduced pressure to afford the title compound.

Alternatively, This compound can be prepared from the corresponding alkyl-halide Step 1: tert-butyl (1-(4-((1-(4-(2-((6-((tert-butoxycarbonyl)amino)spiro[3.3]heptan-2-yl)(methyl)amino)propyl)phenyl)-2-oxo-1,2-dihydropyrimidin-4-yl)carbamoyl)piperazin-1-yl)-2-methyl-1-oxopropan-2-yl)carbamate. To a suspension of tert-butyl (1-(4-((1-(4-(2-((6-((tert-butoxycarbonyl)amino)spiro[3.3]heptan-2-yl)amino)propyl)phenyl)-2-oxo-1,2-dihydropyrimidin-4-yl)carbamoyl)piperazin-1-yl)-2-methyl-1-oxopropan-2-yl)carbamate (30 mg, 0.04 mmol) and $K_2CO_3$ (11 mg, 0.08 mmol) in DMF (0.2 mL) at rt, was added 2-bromopropane (0.010 mL, 0.08 mmol). The reaction was heated at 85° C. for 16 h. The reaction mixture was cooled to rt, diluted with EtOAc (10 mL) and washed with sat. aq. aqueous LiCl (2×10 mL). The organic layer was dried over $Na_2SO_4$ and concentrated under reduced pressure to afford the title compound.

Step 2: 4-(2-amino-2-methylpropanoyl)-N-(1-(4-(2-((6-aminospiro[3.3]heptan-2-yl)(methyl)amino)propyl)phenyl)-2-oxo-1,2-dihydropyrimidin-4-yl)piperazine-1-carboxamide hydrochloride salt. Tert-butyl (1-(4-((1-(4-(2-((6-((tert-butoxycarbonyl)amino)spiro[3.3]heptan-2-yl)(methyl)amino)propyl)phenyl)-2-oxo-1,2-dihydropyrimidin-4-yl)carbamoyl)piperazin-1-yl)-2-methyl-1-oxopropan-2-yl)carbamate was dissolved in a solution of HCl in MeOH (2N, 5 mL) and stirred for at rt for 4 h. The reaction mixture was concentrated under reduced pressure and the crude solid was purified by reverse phase HPLC ($H_2O$:$CH_3CN$:TFA). Addition of HCl/MeOH and evaporation under reduced pressure afforded the title compound. $^1H$ NMR (400 MHz, $D_2O$) δ 8.10 (d, 1H), 7.53-7.42 (m, 4H), 6.81 (d, 1H), 4.03-3.87 (m, 1H), 3.79 (s, 4H), 3.75 (s, 6H), 3.29-3.13 (m, 1H), 2.99 (t, 1H), 2.77-2.69 (m, 3H), 2.69-2.53 (m, 2H), 2.53-2.24 (m, 6H), 1.74 (s, 6H), 1.30-1.14 (m, 3H). LCMS[M+H] 565.4.

Compound 174

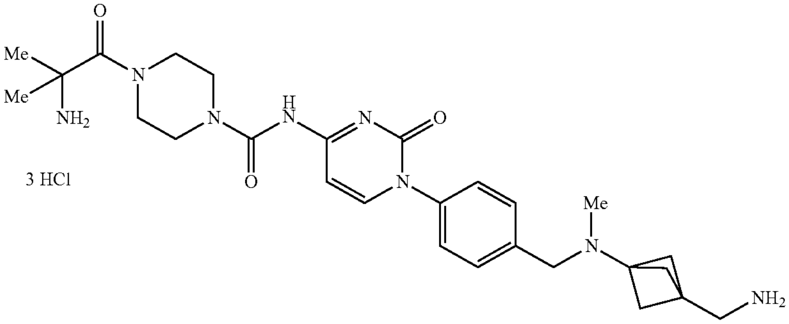

4-(2-Amino-2-methylpropanoyl)-N-(1-(4-(((3-(aminomethyl)bicyclo[1.1.1]pentan-1-yl)(methyl)amino)methyl)phenyl)-2-oxo-1,2-dihydropyrimidin-4-yl)piperazine-1-carboxamide Hydrochloride Salt Prepared in a similar fashion to Scheme C-25 from tert-butyl (1-(4-((1-(4-(((3-(((tert-butoxycarbonyl)amino)methyl)bicyclo[1.1.1]pentan-1-yl)amino)methyl)phenyl)-2-oxo-1,2-dihydropyrimidin-4-yl)carbamoyl)piperazin-1-yl)-2-methyl-1-oxopropan-2-yl)carbamate and formaldehyde. $^1H$ NMR (400 Mz, $D_2O$): Mixture of rotamers, δ 7.83 (d, 1H), 7.56 (d, 2H), 7.46 (d, 2H), 6.65 (d, 1H), 4.41-4.21 (m, 2H), 3.61 (m, 8H), 3.24 (s, 2H), 2.62 (s, 3H), 2.17 (s, 6H), 1.62 (s, 6H). LCMS [M+H] 523.4.

Compound 175

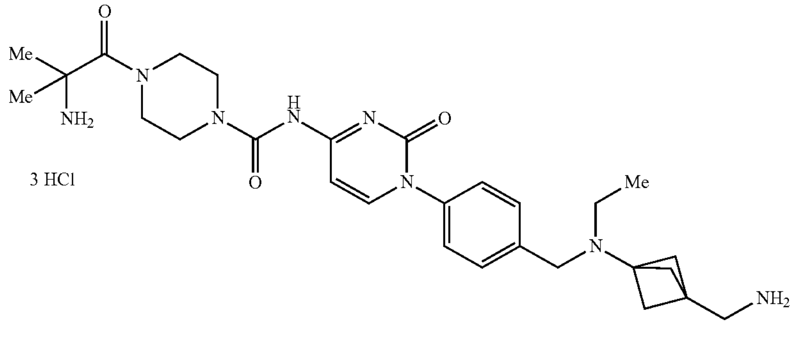

4-(2-Amino-2-methylpropanoyl)-N-(1-(4-(((3-(aminomethyl)bicyclo[1.1.1]pentan-1-yl)(ethyl)amino)methyl)phenyl)-2-oxo-1,2-dihydropyrimidin-4-yl)piperazine-1-carboxamide Hydrochloride Salt Prepared in a similar fashion to Scheme C-25 from tert-butyl (1-(4-((1-(4-(((3-(((tert-butoxycarbonyl)amino)methyl)bicyclo[1.1.1]pentan-1-yl)amino)methyl)phenyl)-2-oxo-1,2-dihydropyrimidin-4-yl)carbamoyl)piperazin-1-yl)-2-methyl-1-oxopropan-2-yl)carbamate and acetaldehyde. $^1$H NMR (400 Mz, $D_2O$): Mixture of rotamers, δ 7.79 (d, 1H), 7.56 (d, 2H), 7.44 (d, 2H), 6.75 (d, 1H), 4.40-4.30 (m, 2H), 3.69-3.55 (m, 8H), 3.25-3.14 (m, 4H), 2.17 (s, 6H), 1.60 (s, 6H), 1.18 (t, 3H). LCMS [M+23] 559.3.

Compound 164

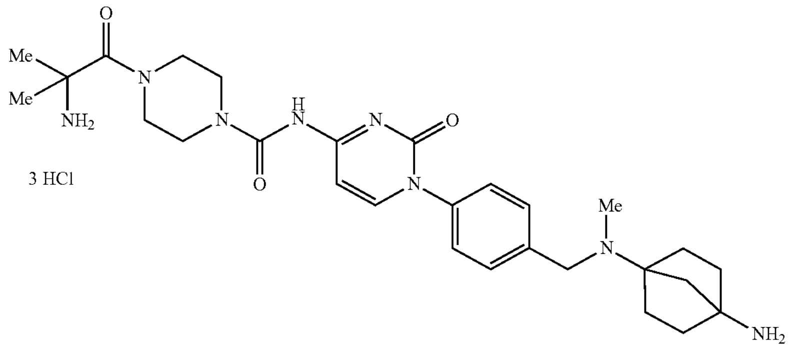

4-(2-Amino-2-methylpropanoyl)-N-(1-(4-(((4-aminobicyclo[2.2.1]heptan-1-yl)(methyl)amino)methyl)phenyl)-2-oxo-1,2-dihydropyrimidin-4-yl)piperazine-1-carboxamide Hydrochloride Salt Prepared in a similar fashion to Scheme C_25 using tert-butyl (1-(4-((1-(4-(((4-((tert-butoxycarbonyl)amino)bicyclo[2.2.1]heptan-1-yl)amino)methyl)phenyl)-2-oxo-1,2-dihydropyrimidin-4-yl)carbamoyl)piperazin-1-yl)-2-methyl-1-oxopropan-2-yl)carbamate. $^1$H NMR (400 MHz, $D_2O$): Mixture of rotamers, δ 7.72 (d, 1H), 7.46 (d, 2H), 7.35 (d, 2H), 6.63 (d, 1H), 4.45 (m, 1H), 4.05-3.95 (m, 1H), 3.65-3.45 (m, 8H), 2.56 (s, 3H), 2.20-1.80 (m, 10H), 1.50 (s, 6H). LCMS [(M+2H)/2] 269.11.

Compound 166

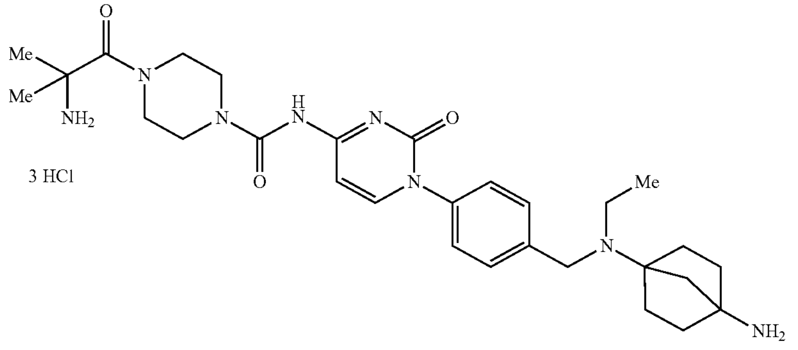

4-(2-Amino-2-methylpropanoyl)-N-(1-(4-(((4-aminobicyclo[2.2.1]heptan-1-yl)(ethyl)amino)methyl)phenyl)-2-oxo-1,2-dihydropyrimidin-4-yl)piperazine-1-carboxamide Hydrochloride Salt Prepared in a similar fashion to Scheme C-25 using tert-butyl (1-(4-((1-(4-(((4-((tert-butoxycarbonyl)amino)bicyclo[2.2.1]heptan-1-yl)amino)methyl)phenyl)-2-oxo-1,2-dihydropyrimidin-4-yl)carbamoyl)piperazin-1-yl)-2-methyl-1-oxopropan-2-yl)carbamate e and acetaldehyde. $^1$H NMR (400 MHz, $D_2O$) mixture of rotamers, δ 7.77 (d, 1H), 7.56 (d, 2H), 7.41 (d, 2H), 6.70 (d, 1H), 4.55-4.45 (m, 1H), 4.29-4.21 (m, 1H), 3.70-3.50 (m, 8H), 3.38-3.20 (m, 2H), 2.20-1.85 (m, 10H), 1.56 (s, 6H), 0.98 (t, 3H). LCMS [M+H] 551.2.

Compound 165

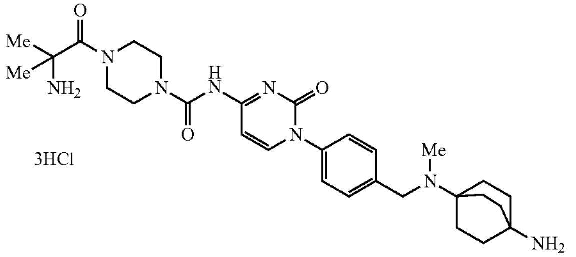

4-(2-Amino-2-methylpropanoyl)-N-(1-(4-(((4-aminobicyclo[2.2.2]octan-1-yl)(methyl)amino)methyl)phenyl)-2-oxo-1,2-dihydropyrimidin-4-yl)piperazine-1-carboxamide Hydrochloride Salt Prepared in a similar fashion to Scheme C-25 using tert-butyl (1-(4-((1-(4-(((4-((tert-butoxycarbonyl)amino)bicyclo[2.2.2]octan-1-yl)amino)methyl)phenyl)-2-oxo-1,2-dihydropyrimidin-4-yl)carbamoyl)piperazin-1-yl)-2-methyl-1-oxopropan-2-yl)carbamate and formaldehyde. $^1$H NMR (400 MHz, $D_2O$) mixture of rotamers, δ 7.86 (d, 1H), 7.50 (d, 2H), 7.41 (d, 2H), 6.68 (d, 1H), 4.67 (m, 1H), 3.90-3.80 (m, 1H), 3.70-3.55 (m, 8H), 2.53 (s, 3H), 2.15-2.02 (m, 6H) 1.95-1.89 (m, 6H), 1.56 (s, 6H). LCMS[M+H] 551.35

Compound 172

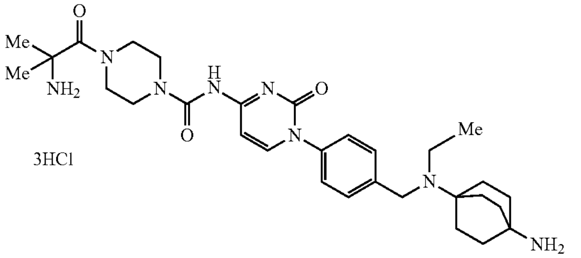

4-(2-Amino-2-methylpropanoyl)-N-(1-(4-(((4-aminobicyclo[2.2.2]octan-1-yl)(ethyl)amino)methyl)phenyl)-2-oxo-1,2-dihydropyrimidin-4-yl)piperazine-1-carboxamide Hydrochloride Salt Prepared in a similar fashion to Scheme C-25 using tert-butyl (1-(4-((1-(4-))(4-((tert-butoxycarbonyl)amino)bicyclo[2.2.2]octan-1-yl)amino)methyl)phenyl)-2-oxo-1,2-dihydropyrimidin-4-yl)carbamoyl)piperazin-1-yl)-2-methyl-1-oxopropan-2-yl)carbamate and acetaldehyde. $^1$H NMR (400 MHz, $D_2O$) mixture of rotamers, δ 8.39 (d, 1H), 8.26 (d, 2H), 8.12 (d, 2H), 7.33 (d, 1H), 4.63-4.58 (m, 1H), 4.15-4.05 (m, 1H), 3.68-3.55 (m, 8H), 3.45-3.35 (m, 1H), 3.12-3.07 (m, 1H), 2.21-2.05 (m, 6H), 2.00-1.85 (m, 6H), 1.57 (s, 6H), 0.88 (t, 3H). LCMS [(M+2H)/2] 283.3.

Compound 169

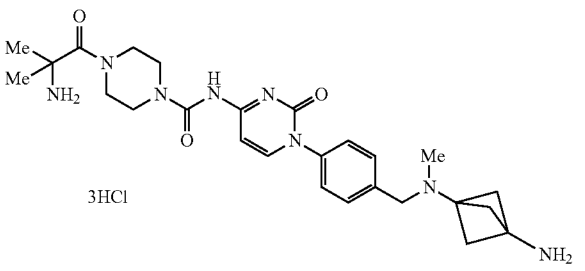

4-(2-Amino-2-methylpropanoyl)-N-(1-(4-(((3-aminobicyclo[1.1.1]pentan-1-yl)(methyl)amino)methyl)phenyl)-2-oxo-1,2-dihydropyrimidin-4-yl)piperazine-1-carboxamide Hydrochloride Salt Prepared in a similar fashion to Scheme C-25 using tert-butyl (1-(4-((1-(4-(((3-aminobicyclo[1.1.1]pentan-1-yl)amino)methyl)phenyl)-2-oxo-1,2-dihydropyrimidin-4-yl)carbamoyl)piperazin-1-yl)-2-methyl-1-oxopropan-2-yl)carbamate and formaldehyde. $^1H$ NMR (400 MHz, $D_2O$) mixture of rotamers, δ 7.76 (d, 1H), 7.52 (d, 2H), 7.42 (d, 2H), 6.71 (d, 1H), 4.31 (s, 2H), 3.68-3.57 (m, 8H), 2.64 (s, 3H), 2.45 (s, 6H), 1.57 (s, 6H). LCMS [M+H] 509.2.

Compound 170

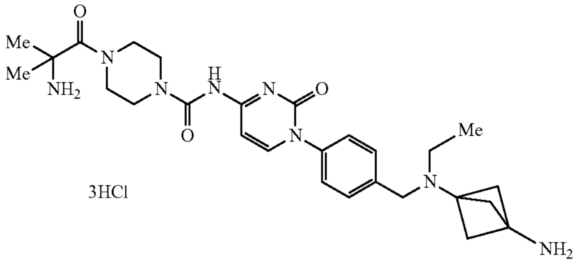

4-(2-Amino-2-methylpropanoyl)-N-(1-(4-(((3-aminobicyclo[1.1.1]pentan-1-yl)(ethyl)amino)methyl)phenyl)-2-oxo-1,2-dihydropyrimidin-4-yl)piperazine-1-carboxamide Hydrochloride Salt Prepared in a similar fashion to Scheme C-25 using tert-butyl (1-(4-((1-(4-(((3-aminobicyclo[1.1.1]pentan-1-yl)amino)methyl)phenyl)-2-oxo-1,2-dihydropyrimidin-4-yl)carbamoyl)piperazin-1-yl)-2-methyl-1-oxopropan-2-yl)carbamate and acetaldehyde. $^1H$ NMR (400 MHz, $D_2O$) mixture of rotamers, δ 7.73 (d, 1H), 7.52 (d, 2H), 7.40 (d, 2H), 6.71 (d, 1H), 4.35 (s, 2H), 3.68-3.55 (m, 8H), 3.18-3.14 (m, 2H), 3.44 (s, 6H), 1.57 (s, 6H), 1.15 (t, 3H). LCMS [M+H] 523.2.

Compound 193

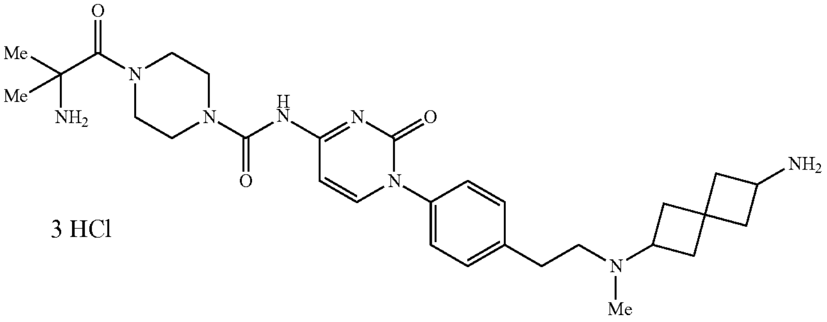

4-(2-Amino-2-methylpropanoyl)-N-(1-(4-(2-((6-aminospiro[3.3]heptan-2-yl)(methyl)amino)ethyl)phenyl)-2-oxo-1,2-dihydropyrimidin-4-yl)piperazine-1-carboxamide Hydrochloride Salt Prepared in a similar fashion to Scheme C-25 from tert-butyl (1-(4-((1-(4-(2-((6-((tert-butoxycarbonyl)amino)spiro[3.3]heptan-2-yl)amino)ethyl)phenyl)-2-oxo-1,2-dihydropyrimidin-4-yl)carbamoyl)piperazin-1-yl)-2-methyl-1-oxopropan-2-yl)carbamate and formaldehyde. $^1H$ NMR (500 MHz, $D_2O$) δ 7.99 (d, 1H), 7.49 (d, 2H), 7.44 (d, 2H), 6.83 (d, 1H), 3.84-3.70 (m, 8H), 3.50-3.40 (m, 1H), 3.29-3.15 (m, 2H), 3.13-3.03 (m, 1H), 2.81 (d, 3H), 2.65-2.52 (m, 2H), 2.50-2.38 (m, 2H), 2.33-2.24 (m, 4H), 1.73 (s, 6H). LCMS[M+H]: 551.3.

Compound 194

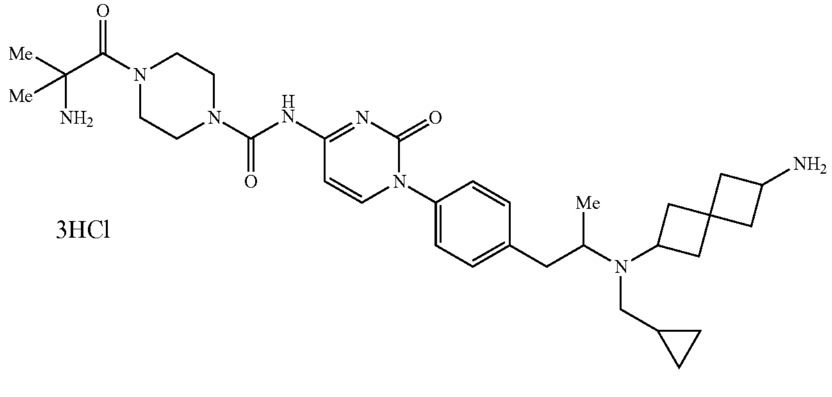

3HCl 4-(2-Amino-2-methylpropanoyl)-N-(1-(4-(2-((6-aminospiro[3.3]heptan-2-yl)(cyclopropylmethyl)amino)propyl)phenyl)-2-oxo-1,2-dihydropyrimidin-4-yl)piperazine-1-carboxamide Hydrochloride Salt Prepared in a similar fashion to Scheme C-25 from tert-butyl (1-(4-((1-(4-(2-((6-((tert-butoxycarbonyl)amino)spiro[3.3]heptan-2-yl)amino)propyl)phenyl)-2-oxo-1,2-dihydropyrimidin-4-yl)carbamoyl)piperazin-1-yl)-2-methyl-1-oxopropan-2-yl)carbamate and cyclopropanecarbaldehyde. $^1H$ NMR (400 MHz, $D_2O$) δ 7.93 (d, 1H), 7.47 (d, 2H), 7.45 (d, 2H), 6.85 (d, 1H), 4.10-3.95 (m, 1H), 3.91-3.68 (m, 10H), 3.33-3.22 (m, 1H), 3.21-3.02 (m, 2H), 3.02-2.81 (m, 1H), 2.77-2.65 (m, 1H), 2.62-2.41 (m, 4H), 2.36-2.27 (m, 2H), 1.75 (s, 6H), 1.34-1.24 (m, 2H), 1.24-1.19 (m, 2H), 1.19-1.08 (m, 1H), 0.88-0.73 (m, 2H), 0.51-0.35 (m, 2H). LCMS [M+H] 605.4.

Compound 195

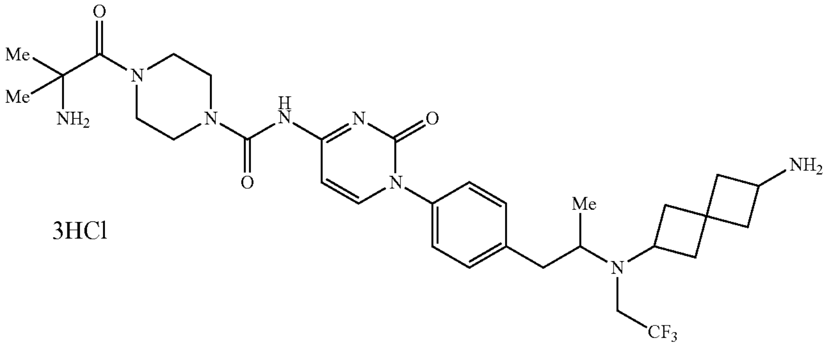

3HCl 4-(2-Amino-2-methylpropanoyl)-N-(1-(4-(2-((6-aminospiro[3.3]heptan-2-yl)(2,2,2-trifluoroethyl)amino)propyl)phenyl)-2-oxo-1,2-dihydropyrimidin-4-yl)piperazine-1-carboxamide Hydrochloride Salt Prepared in a similar fashion to Scheme C-25 from tert-butyl (1-(4-((1-(4-(2-((6-((tert-butoxycarbonyl)amino)spiro[3.3]heptan-2-yl)amino)propyl)phenyl)-2-oxo-1,2-dihydropyrimidin-4-yl)carbamoyl)piperazin-1-yl)-2-methyl-1-oxopropan-2-yl)carbamate and 2,2,2-trifluoroethyl trifluoromethanesulfonate. $^1H$ NMR (400 MHz, $D_2O$) δ 7.47-7.31 (m, 5H), 6.13 (d, 1H), 4.95-4.87 (m, 2H), 3.87-3.56 (m, 8H), 3.43-3.26 (m, 2H), 3.04-2.93 (m, 1H), 2.84-2.75 (m, 1H), 2.70-2.61 (m, 1H), 2.45-2.28 (m, 2H), 2.28-2.07 (m, 3H), 1.95-1.70 (m, 2H), 1.70-1.61 (m, 1H), 1.43 (s, 6H), 1.00 (d, 3H). LCMS[M+H] 633.4.

Compound 196

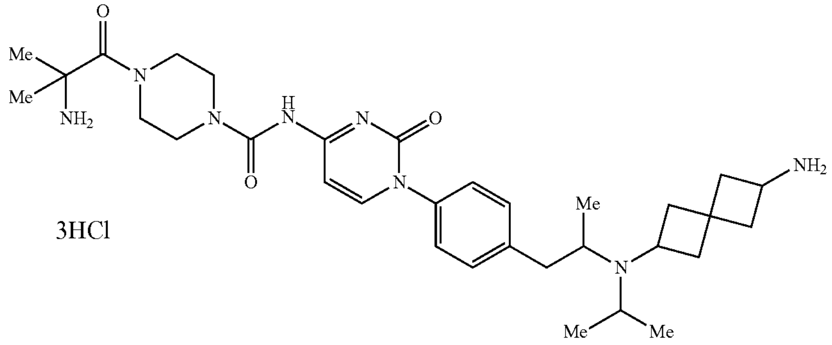

4-(2-Amino-2-methylpropanoyl)-N-(1-(4-(2-((6-aminospiro[3.3]heptan-2-yl)(isopropyl)amino)propyl)phenyl)-2-oxo-1,2-dihydropyrimidin-4-yl)piperazine-1-carboxamide Hydrochloride Salt Prepared in a similar fashion to Scheme C-25 from tert-butyl (1-(4-((1-(4-(2-((6-((tert-butoxycarbonyl)amino)spiro[3.3]heptan-2-yl)amino)propyl)phenyl)-2-oxo-1,2-dihydropyrimidin-4-yl)carbamoyl)piperazin-1-yl)-2-methyl-1-oxopropan-2-yl)carbamate and 2-bromopropane. $^{1}$H NMR (400 MHz, $D_2O$) δ 7.44 (d, 2H), 7.39 (d, 2H), 7.34 (d, 1H), 6.02 (d, 1H), 5.35-5.25 (m, 1H), 3.98-3.87 (m, 1H), 3.87-3.62 (m, 9H), 3.62-3.52 (m, 1H), 3.24-3.16 (m, 1H), 2.91-2.82 (m, 1H), 2.59 (s, 2H), 2.53-2.40 (m, 2H), 2.39-2.23 (m, 4H), 1.74 (s, 6H), 1.49 (d, 6H), 1.23 (d, 3H). LCMS[M+H] 593.5.

Compound 197

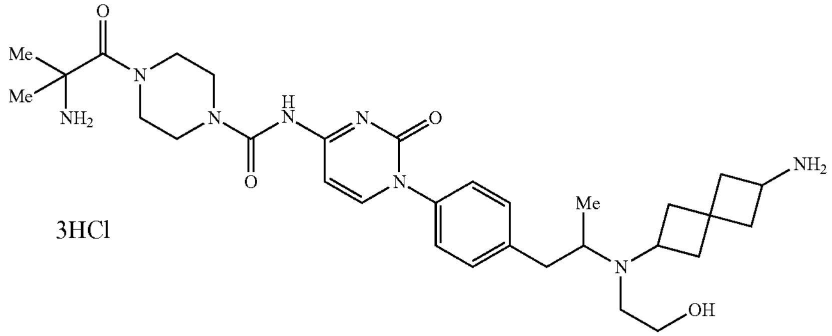

4-(2-Amino-2-methylpropanoyl)-N-(1-(4-(2-((6-aminospiro[3.3]heptan-2-yl)(2-hydroxyethyl)amino)propyl)phenyl)-2-oxo-1,2-dihydropyrimidin-4-yl)piperazine-1-carboxamide Hydrochloride Salt Prepared in a similar fashion to Scheme C-25 from tert-butyl (1-(4-((1-(4-(2-((6-((tert-butoxycarbonyl)amino)spiro[3.3]heptan-2-yl)amino)propyl)phenyl)-2-oxo-1,2-dihydropyrimidin-4-yl)carbamoyl)piperazin-1-yl)-2-methyl-1-oxopropan-2-yl)carbamate and 2-((tert-butyldimethylsilyl)oxy)acetaldehyde. LCMS[M+H]595.3.

Compound 199

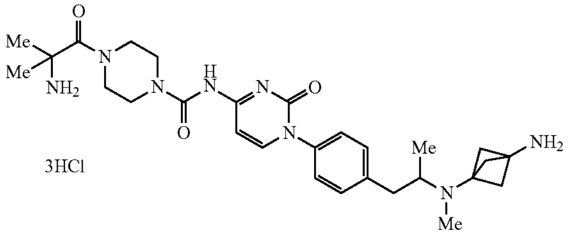

4-(2-Amino-2-methylpropanoyl)-N-(1-(4-(2-((3-aminobicyclo[1.1.1]pentan-1-yl)(methyl)amino)propyl)phenyl)-2-oxo-1,2-dihydropyrimidin-4-yl)piperazine-1-carboxamide Hydrochloride Salt Prepared in a similar fashion to Scheme C-25 using tert-butyl (1-(4-((1-(4-(2-((3-((tert-butoxycarbonyl)amino)bicyclo[1.1.1]pentan-1-yl)amino)propyl)phenyl)-2-oxo-1,2-dihydropyrimidin-4-yl)carbamoyl)piperazin-1-yl)-2-methyl-1-oxopropan-2-yl)carbamate and formaldehyde. NMR ($D_2O$, 400 MHz): δ 7.88 (d, 1H), 7.37-7.31 (m, 4H), 6.70 (d, 1H), 3.83-3.80 (m, 1H), 3.65-3.60 (m, 8H), 3.18-3.11 (m, 1H), 2.90-2.82 (m, 1H), 2.78 (s, 3H), 2.54 (s, 6H), 1.60 (s, 6H), 1.14 (d, 3H). LCMS [(M+2H)/2] 269.5.

Compound 198

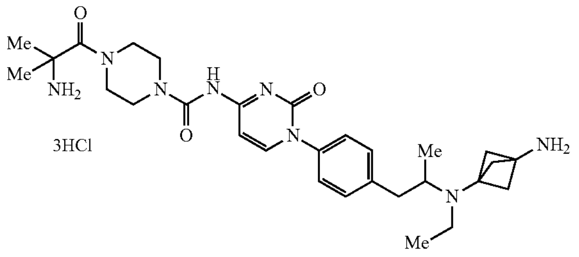

4-(2-Amino-2-methylpropanoyl)-N-(1-(4-(2-((3-aminobicyclo[1.1.1]pentan-1-yl)(ethyl)amino)propyl)phenyl)-2-oxo-1,2-dihydropyrimidin-4-yl)piperazine-1-carboxamide Hydrochloride Salt Prepared in a similar fashion to Scheme C-25 using tert-butyl (1-(4-((1-(4-(2-((3-((tert-butoxycarbonyl)amino)bicyclo[1.1.1]pentan-1-yl)amino)propyl)phenyl)-2-oxo-1,2-dihydropyrimidin-4-yl)carbamoyl)piperazin-1-yl)-2-methyl-1-oxopropan-2-yl)carbamate and acetaldehyde. $^1$H NMR ($D_2O$, 400 MHz): δ 7.79 (d, 1H), 7.34-7.27 (m, 4H), 6.68 (d, 1H), 3.82-3.75 (m, 1H), 3.52-3.68 (m, 8H), 3.35-3.22 (m, 2H), 3.20-3.10 (m, 1H), 2.86 (t, 1H), 2.58 (s, 6H), 1.57 (s, 6H), 1.25 (t, 3H), 1.14 (d, 3H). LCMS [M+H] 551.0.

Compound 200

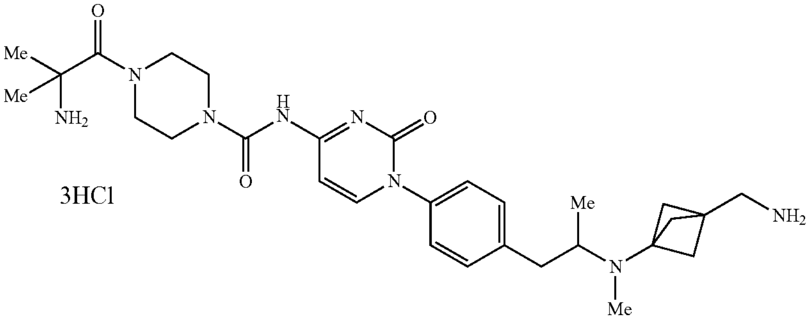

4-(2-Amino-2-methylpropanoyl)-N-(1-(4-(2-((3-(aminomethyl)bicyclo[1.1.1]pentan-1-yl)(methyl)amino)propyl)phenyl)-2-oxo-1,2-dihydropyrimidin-4-yl)piperazine-1-carboxamide Hydrochloride Salt Prepared in a similar fashion to Scheme C-25 using tert-butyl (1-(4-((1-(4-(2-((3-(((tert-butoxycarbonyl)amino)methyl)bicyclo[1.1.1]pentan-1-yl)amino)propyl)phenyl)-2-oxo-1,2-dihydropyrimidin-4-yl)carbamoyl)piperazin-1-yl)-2-methyl-1-oxopropan-2-yl)carbamate and formaldehyde. $^1$H NMR (400 MHz, $D_2O$): Mixture of rotamers, δ 7.81 (d, 1H), 7.35-7.28 (m, 4H), 6.68 (d, 1H), 3.86-3.76 (m, 1H), 3.63-3.58 (m, 8H), 3.20 (s, 2H), 3.18-3.08 (m, 1H), 2.88-2.75 (m, 1H), 2.71 (s, 3H), 2.20 (s, 6H), 1.58 (s, 6H), 1.11 (d, 3H). LCMS [(M+2H)/2] 276.2.

Compound 201

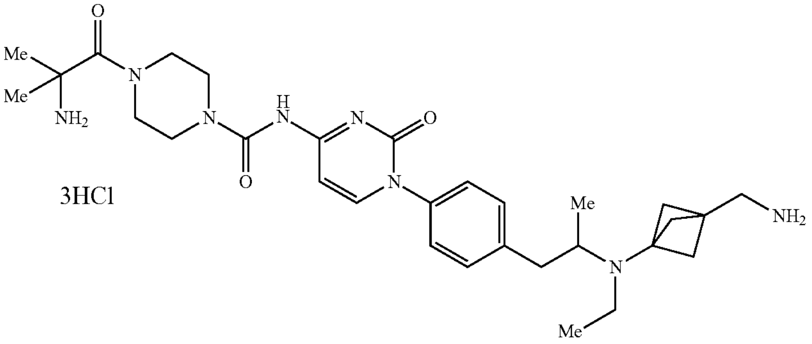

4-(2-Amino-2-methylpropanoyl)-N-(1-(4-(2-((3-(aminomethyl)bicyclo[1.1.1]pentan-1-yl)(ethyl)amino)propyl)phenyl)-2-oxo-1,2-dihydropyrimidin-4-yl)piperazine-1-carboxamide Hydrochloride Salt Prepared in a similar fashion to Scheme C-25 using tert-butyl (1-(4-((1-(4-(2-((3-(((tert-butoxycarbonyl)amino)methyl)bicyclo[1.1.1]pentan-1-yl)amino)propyl)phenyl)-2-oxo-1,2-dihydropyrimidin-4-yl)carbamoyl)piperazin-1-yl)-2-methyl-1-oxopropan-2-yl)carbamate and acetaldehyde. $^{1}$H NMR (400 MHz, $D_2O$): Mixture of rotamers, δ 7.87 (d, 1H), 7.35-7.28 (m, 4H), 6.66 (d, 1H), 3.79-3.71 (m, 1H), 3.74-3.58 (m, 8H), 3.45-3.12 (m, 5H), 2.92-2.81 (m, 1H), 2.40-2.20 (m, 6H), 1.57 (s, 6H), 1.24 (t, 3H), 1.19-1.09 (m, 3H). LCMS [M+H] 565.2.

Compound 140

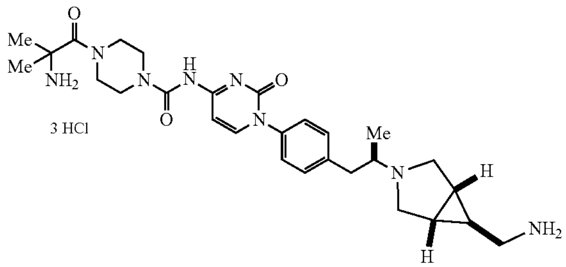

4-(2-Amino-2-methylpropanoyl)-N-(1-(4-((R)-2-(exo-6-(aminomethyl)-3-azabicyclo[3.1.0]hexan-3-yl)propyl)phenyl)-2-oxo-1,2-dihydropyrimidin-4-yl)piperazine-1-carboxamide Scheme C-26

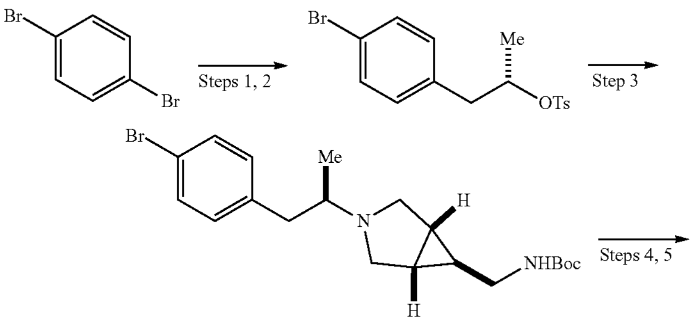

-continued

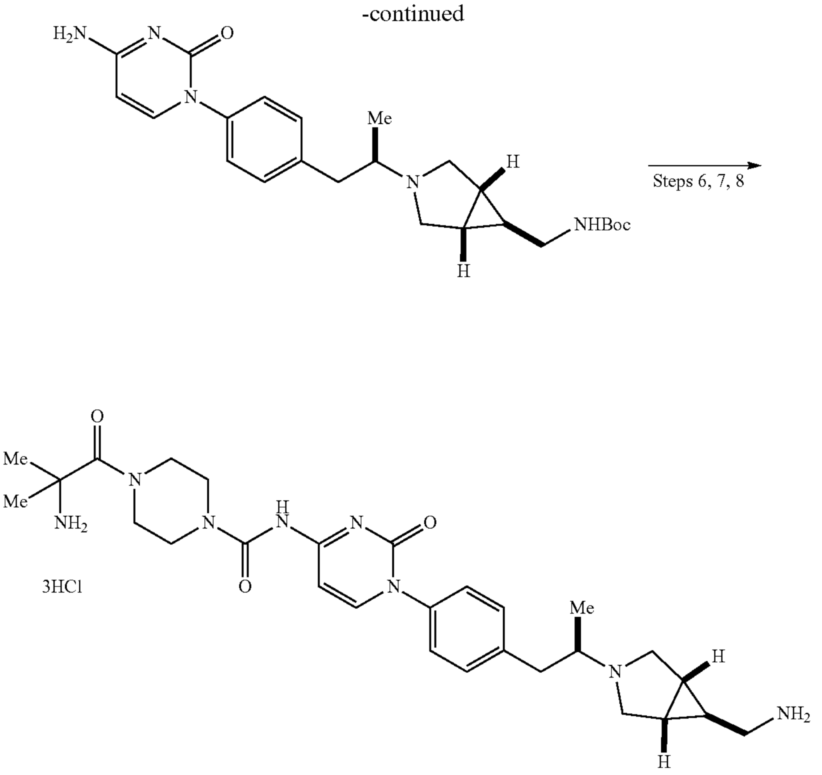

Reagents: 1) BuLi, (S)-propylene oxide, $BF_3 \cdot OEt_2$ THF, −78° C., 5 h. 2) TsCl, DMAP $NEt_3CH_2Cl_2$, rt, 24 h. 3) tert-butyl ((exo-3-azabicyclo[3.1.0]hexan-6-yl)methyl)carbamate, $NEt_3$ DMA, 85° C., 24 h. 4) $B_2pin_2Pd(dppf)Cl_2 \cdot CH_2Cl_2$, KOAc, dioxane, 100° C., 16 h. 5) cytosine, TMEDA, $Cu(OAc)_2 \cdot H_2O$, 4:1 $MeOH:H_2O$, rt, 16 h. 6) CDI, $CH_2Cl_2$, rt, 4 h. 7) tert-butyl (2-methyl-1-oxo-1-(piperazin-1-yl)propan-2-yl)carbamate $CH_3CN$, 85° C., 3 h. 8) HCl/MeOH, rt, 4 h.

Step 1: (S)-1-(4-bromophenyl)propan-2-ol. To a solution of 1,4-dibromobenzene (2.4 g, 10 mmol) in THF (120 mL) at −78° C., was added 2.5 M BuLi solution in hexanes (3.6 mL, 9.0 mmol) dropwise over the span of 30 min. The reaction was stirred at −78° C. for 30 min, after which (S)-propylene oxide (0.78 mL, 12 mmol) and $BF_3 \cdot OEt_2$ (1.5 mL, 12 mmol) were added simultaneously over the span of 30 min. The solution was stirred at −78° C. for an additional 4 h. The reaction was quenched upon addition of 2N HCl (50 mL) and was warmed to rt. The reaction mixture was diluted with EtOAc (250 mL) and washed with $H_2O$ (2×250 mL). The organic layer was concentrated under reduced pressure and purified by column chromatography (Hexanes:EtOAc) to afford the title compound.

Step 2: (S)-1-(4-bromophenyl)propan-2-yl 4-methylbenzenesulfonate. To a solution of (S)-1-(4-bromophenyl)propan-2-ol (1.6 g, 7.6 mmol) in $CH_2Cl_2$ (100 mL) was added, TsCl (1.3 g, 6.8 mmol), DMAP (37 mg, 0.30 mmol) and $NEt_3$ (1.3 mL, 9.1 mmol). The solution was stirred at rt for 24 h. The reaction was diluted with $CH_2Cl_2$ (100 mL) and washed with sat. aq. $NaHCO_3$ (1×200 mL). The organic layer was concentrated under reduced pressure and purified by column chromatography (Hexanes:EtOAc) to afford the title compound.

Step 3: tert-butyl ((exo-3-((R)-1-(4-bromophenyl)propan-2-yl)-3-azabicyclo[3.1.0]hexan-6-yl)methyl)carbamate. To a solution of (S)-1-(4-bromophenyl)propan-2-yl 4-methylbenzenesulfonate (880 mg, 2.3 mmol) in DMA (12 mL), was added tert-butyl ((exo-3-azabicyclo[3.1.0]hexan-6-yl)methyl)carbamate (580 mg, 2.7 mmol) and $NEt_3$ (0.36 mL, 4.6 mmol). The reaction was heated at 85° C. for 24 h and the DMA was removed by distillation. The crude reaction mixture was dissolved in EtOAc (100 mL) and washed with sat. aq. LiCl (2×100 mL). The organic layer was concentrated under reduced pressure and purified by column chromatography (Hexanes:EtOAc) to afford the title compound.

Step 4: tert-butyl ((exo-3-((R)-1-(4-(4,4,5,5-tetramethyl-1,3,2-dioxaborolan-2-yl)phenyl)propan-2-yl)-3-azabicyclo[3.1.0]hexan-6-yl)methyl)carbamate. A suspension of tert-butyl ((exo-3-((R)-1-(4-bromophenyl)propan-2-yl)-3-azabicyclo[3.1.0]hexan-6-yl)methyl)carbamate (150 mg, 0.37 mmol), $B_2pin_2$ (110 mg, 0.44 mmol), Pd(dppf)$Cl_2 \cdot CH_2Cl_2$ (8 mg, 0.01 mmol), and KOAc (100 mg, 1.1 mmol) in dioxane was degassed and heated to 100° C. for 16 h. The crude reaction mixture was filtered through Celite® and concentrated under reduced pressure. Purification by column chromatography (Hexanes: EtOAc) afforded the title compound.

Step 5: tert-butyl ((exo-3-((R)-1-(4-(4-amino-2-oxopyrimidin-1 (2H)-yl)phenyl)propan-2-yl)-3-azabicyclo[3.1.0]hexan-6-yl)methyl)carbamate. A suspension of cytosine (11 mg, 0.10 mmol) and tert-butyl ((exo-3-((R)-1-(4-(4,4,5,5-tetramethyl-1,3,2-dioxaborolan-2-yl)phenyl)propan-2-yl)-3-azabicyclo[3.1.0]hexan-6-yl)methyl)carbamate (45 mg, 0.10 mmol), in $MeOH:H_2O$ (4:1, 100 mL) was stirred at rt in open air for 30 min. TMEDA (0.012 mL, 0.12 mmol) and $Cu(OAc)_2 \cdot H_2O$ (20 mg, 0.10 mmol) were added and the reaction was stirred in open air for 24 h at rt. The reaction mixture was concentrated under reduced pressure and $H_2O$ (10 mL) was added. The aqueous phase was extracted with $CHCl_3$ (3×15 mL), and the combined organics were concentrated under reduced pressure. The crude reaction mixture was purified by column chromatography (MeOH: $CHCl_3$) to afford the title compound.

Step 6: tert-butyl ((exo-3-((R)-1-(4-(4-(1H-imidazole-1-carboxamido)-2-oxopyrimidin-1 (2H)-yl)phenyl)propan-2-yl)-3-azabicyclo[3.1.0]hexan-6-yl)methyl)carbamate. A suspension of tert-butyl ((exo-3-((R)-1-(4-(4-amino-2-oxopyrimidin-1 (2H)-yl)phenyl)propan-2-yl)-3-azabicyclo [3.1.0]hexan-6-yl)methyl)carbamate (99 mg, 0.23 mmol) and CDI (57 mg, 0.34 mmol) in $CH_2Cl_2$ (12 mL) was stirred for 16 h at rt. The solvent was removed reduced pressure, and the solid was triturated with EtOAc (10 mL). The solid was collected to afford the crude title compound.

Step 7: tert-butyl (1-(4-((1-(4-((R)-2-(exo-6-(((tert-butoxycarbonyl)amino)methyl)-3-azabicyclo[3.1.0]hexan-3-yl)propyl)phenyl)-2-oxo-1,2-dihydropyrimidin-4-yl)carbamoyl)piperazin-1-yl)-2-methyl-1-oxopropan-2-yl) carbamate. Tert-butyl ((exo-3-((R)-1-(4-(4-(1H-imidazole-1-carboxamido)-2-oxopyrimidin-1 (2H)-yl)phenyl)propan-2-yl)-3-azabicyclo[3.1.0]hexan-6-yl)methyl)carbamate (120 mg, 0.23 mmol) and tert-butyl (2-methyl-1-oxo-1-(piperazin-1-yl)propan-2-yl)carbamate (91 mg, 0.34 mmol) were dissolved in $CH_3CN$ (5 mL) and heated to reflux for 2 h. The reaction mixture was concentrated under reduced pressure and the crude reaction mixture was dissolved in EtOAc (25 mL) and washed with $H_2O$ (3×20 mL). The reaction mixture was purified by column chromatography (MeOH:$CHCl_3$) to afford the title compound.

Step 8: 4-(2-amino-2-methylpropanoyl)-N-(1-(4-((R)-2-(exo-6-(aminomethyl)-3-azabicyclo[3.1.0]hexan-3-yl)propyl)phenyl)-2-oxo-1,2-dihydropyrimidin-4-yl)piperazine-1-carboxamide hydrochloride salt. Tert-butyl (1-(4-((1-(4-((R)-2-(exo-6-(((tert-butoxycarbonyl)amino)methyl)-3-azabicyclo[3.1.0]hexan-3-yl)propyl)phenyl)-2-oxo-1,2-dihydropyrimidin-4-yl)carbamoyl)piperazin-1-yl)-2-methyl-1-oxopropan-2-yl)carbamate dissolved in a solution of HCl in MeOH (2N, 5 mL) and stirred for 4 h at rt. The reaction mixture was concentrated under reduced pressure and the crude solid was purified by reversed phase HPLC ($H_2O$:$CH_3CN$:TFA) and concentrated under reduced pressure. Addition of HCl in MeOH (2N, 3×10 mL) and evaporation under reduced pressure afforded the title compound. $^1$H NMR (400 MHz, $D_2O$) δ 7.96-7.93 (m, 1H), 7.50-7.40 (m, 4H), 6.84 (d, 1H), 3.92-3.70 (m, 10H), 3.70-3.55 (m, 3H), 3.38 (d, 1H), 3.00 (d, 2H), 2.85 (t, 1H), 2.05 (s, 2H), 1.75 (s, 6H), 1.36 (s, 1H), 1.26 (d, 3H). LCMS[M+H] 537.2.

Compound 141

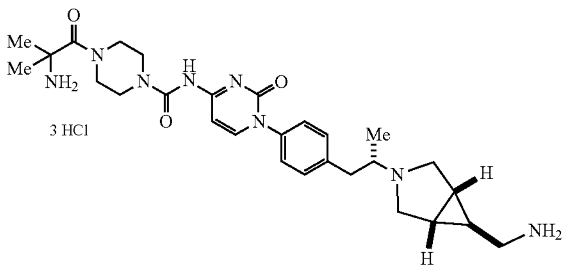

4-(2-Amino-2-methylpropanoyl)-N-(1-(4-((S)-2-(exo-6-(aminomethyl)-3-azabicyclo[3.1.0]hexan-3-yl)propyl)phenyl)-2-oxo-1,2-dihydropyrimidin-4-yl) piperazine-1-carboxamide Hydrochloride Salt Prepared in a similar fashion to Scheme C-26 using (S)-propylene oxide and 1,4-dibromobenzene. $^1$H NMR (400 MHz, $D_2O$) δ 7.91 (d, 1H), 7.49-7.39 (m, 4H), 6.85 (d, 1H), 3.93-3.70 (m, 10H), 3.70-3.55 (m, 3H), 3.39 (d, 1H), 3.00 (d, 2H), 2.85 (t, 1H), 2.05 (s, 2H), 1.75 (s, 6H), 1.41-1.34 (m, 1H), 1.27 (d, 3H). LCMS[M+H] 537.3

Compound 146

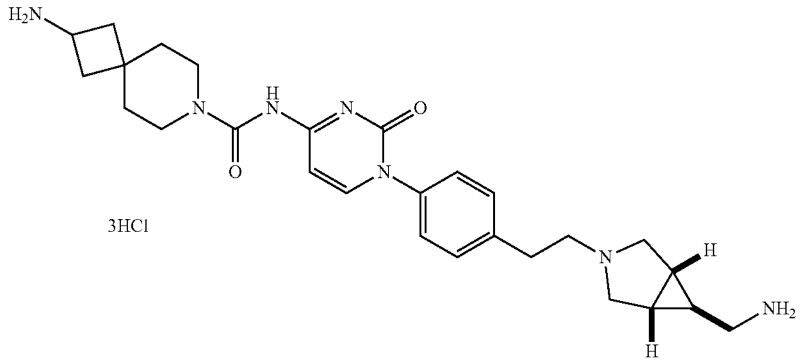

2-Amino-N-(1-(4-(2-(exo-6-(aminomethyl)-3-azabicyclo[3.1.0]hexan-3-yl)ethyl)phenyl)-2-oxo-1,2-dihydropyrimidin-4-yl)-7-azaspiro[3.5] nonane-7-carboxamide hydrochloride Salt Scheme C-27

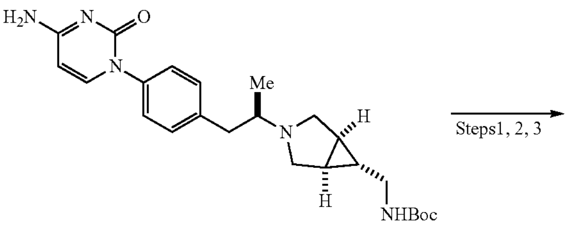

-continued

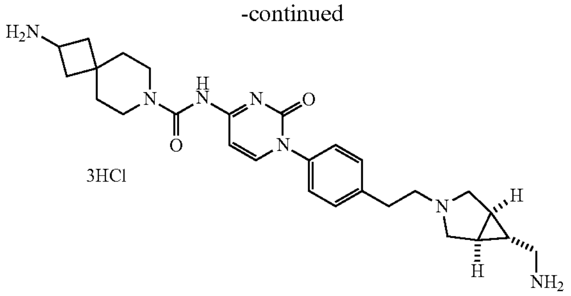

Reagents: 1) CDI, $CH_2Cl_2$, rt, 6 h 2) $CH_3CN$, 85° C., 16 h 3) 4 M HCl in dioxane, 1,4-dioxane, rt, 16 h.

Step 1: t-butyl ((exo-3-(4-(4-(1H-imidazole-1-carboxamido)-2-oxopyrimidin-1 (2H)-yl)phenethyl)-3-azabicyclo[3.1.0]hexan-6-yl)methyl)carbamate. To a stirred solution of t-butyl ((exo-3-(4-(4-amino-2-oxopyrimidin-1 (2H)-yl)phenethyl)-3-azabicyclo[3.1.0]hexan-6-yl)methyl)carbamate (0.2 g, 0.47 mmol) in $CH_2Cl_2$ (50 mL) was added CDI (0.46 g, 2.82 mmol), and the mixture was stirred at rt for 6 h. The reaction mixture was concentrated under reduced pressure to afford the title compound.

Step 2: t-butyl ((exo-3-(4-(4-(2-((t-butoxycarbonyl)amino)-7-azaspiro[3.5]nonane-7-carboxamido)-2-oxopyrimidin-1 (2H)-yl)phenethyl)-3-azabicyclo[3.1.0]hexan-6-yl)methyl)carbamate. A mixture of t-butyl ((exo-3-(4-(4-(1H-imidazole-1-carboxamido)-2-oxopyrimidin-1 (2H)-yl)phenethyl)-3-azabicyclo[3.1.0]hexan-6-yl)methyl)carbamate (0.2 g, 0.38 mmol) and t-butyl (7-azaspiro[3.5]nonan-2-yl)carbamate (0.2 g, 0.77 mmol) in $CH_3CN$ (7 mL) was stirred at 85° C. for 16 h and concentrated under reduced pressure. The residue was purified by column chromatography on silica gel ($CH_3OH/CH_2Cl_2$) to afford the title compound. LCMS [M+H] 692.1.

Step 3: 2-amino-N-(1-(4-(2-(exo-6-(aminomethyl)-3-azabicyclo[3.1.0]hexan-3-yl)ethyl)phenyl)-2-oxo-1,2-dihydropyrimidin-4-yl)-7-azaspiro[3.5]nonane-7-carboxamide hydrochloride salt. A mixture of t-butyl ((exo-3-(4-(4-(2-((t-butoxycarbonyl)amino)-7-azaspiro[3.5]nonane-7-carboxamido)-2-oxopyrimidin-1 (2H)-yl)phenethyl)-3-azabicyclo[3.1.0]hexan-6-yl)methyl)carbamate (0.4 g, 0.57 mmol) and 4 M HCl in dioxane (2 mL, 8.0 mmol) in dioxane (2.0 mL) was stirred at rt for 16 h and concentrated under reduced pressure. The residue was purified by HPLC to afford the title compound. $^1$H NMR (400 MHz, $D_2O$) δ 7.83 (d, 1H), 7.34-7.27 (m, 4H), 6.66 (d, 1H), 3.76-3.68 (m, 3H), 3.45-3.30 (m, 8H), 2.96 (t, 2H), 2.93 (d, 2H), 2.24 (t, 2H), 1.93-1.81 (m, 4H), 1.61-1.54 (m, 4H), 1.19-1.18 (m, 1H). LCMS [M+H] 491.9.

Compound 148

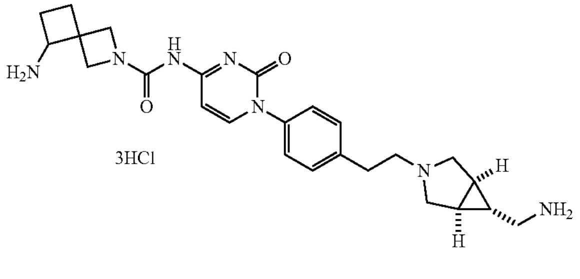

5-Amino-N-(1-(4-(2-(exo-6-(aminomethyl)-3-azabicyclo[3.1.0]hexan-3-yl)ethyl)phenyl)-2-oxo-1,2-dihydropyrimidin-4-yl)-2-azaspiro[3.3]heptane-2-carboxamide Hydrochloride Salt Prepared in a similar fashion to Scheme C-27 using t-butyl ((exo-3-(4-(4-(1H-imidazole-1-carboxamido)-2-oxopyrimidin-1 (2H)-yl)phenethyl)-3-azabicyclo[3.1.0]hexan-6-yl)methyl)carbamate and t-butyl (2-azaspiro[3.3]heptan-5-yl)carbamate. $^1$H NMR (400 MHz, $D_2O$) δ 7.95 (d, 1H), 7.38-7.28 (m, 4H), 6.90 (d, 1H), 4.41-4.30 (m, 1H), 4.21-4.01 (m, 2H), 3.82 (t, 1H), 3.71 (d, 2H), 3.42-3.36 (m, 4H), 3.10 (t, 2H), 2.85 (d, 2H), 2.21-2.10 (m, 3H), 1.88-1.85 (m, 3H), 1.23-1.21 (m, 1H). LCMS [M+H] 464.1.

Compound 149

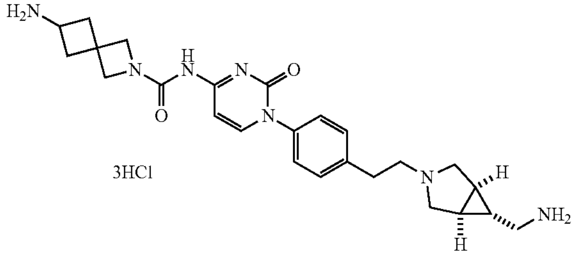

6-Amino-N-(1-(4-(2-(exo-6-(aminomethyl)-3-azabicyclo[3.1.0]hexan-3-yl)ethyl)phenyl)-2-oxo-1,2-dihydropyrimidin-4-yl)-2-azaspiro[3.3]heptane-2-carboxamide hydrochloride Salt Prepared in a similar fashion to Scheme DA using using t-butyl ((exo-3-(4-(4-(1H-imidazole-1-carboxamido)-2-oxopyrimidin-1 (2H)-yl)phenethyl)-3-azabicyclo[3.1.0]hexan-6-yl)methyl)carbamate and t-butyl N-(2-azaspiro[3.3]heptan-6-yl)carbamate. LCMS [(M+2H)/2] 232.6.

Compound 63

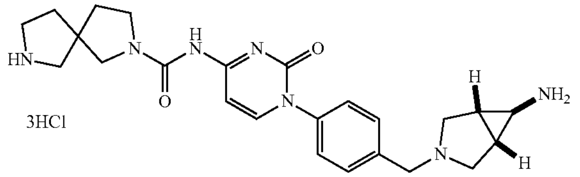

N-(1-(4-((exo-6-Amino-3-azabicyclo[3.1.0]hexan-3-yl)methyl)phenyl)-2-oxo-1,2-dihydropyrimidin-4-yl)-2,7-diazaspiro[4.4]nonane-2-carboxamide Hydrochloride Salt Prepared in a similar fashion to Scheme C-27 from tert-butyl (exo-3-(4-(4-(1H-imidazole-1-carboxamido)-2-oxopyrimidin-1 (2H)-yl)benzyl)-3-azabicyclo[3.1.0]hexan-6-yl)carbamate and tert-butyl 2,7-diazaspiro[4.4]nonane-2-carboxylate. $^1$H NMR (500 MHz, $D_2O$) δ 8.09 (d, 1H), 7.63 (d, 2H), 7.52 (d, 2H), 7.00 (d, 1H), 4.43 (s, 2H), 3.78-3.53 (m, 6H), 2.48-2.38 (m, 3H), 2.36-2.23 (m, 3H), 2.83-3.77 (m, 1H), 2.37 (br s, 2H), 2.18-1.96 (m, 4H). LCMS [M+H] 450.3.

Compound 64

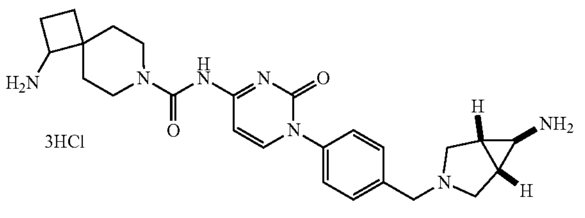

1-Amino-N-(1-(4-((exo-6-amino-3-azabicyclo[3.1.0]hexan-3-yl)methyl)phenyl)-2-oxo-1,2-dihydropyrimidin-4-yl)-7-azaspiro[3.5]nonane-7-carboxamide Hydrochloride Salt Prepared in a similar fashion to Scheme C-27 from tert-butyl (exo-3-(4-(4-(1H-imidazole-1-carboxamido)-2-oxopyrimidin-1 (2H)-yl)benzyl)-3-azabicyclo[3.1.0]hexan-6-yl)carbamate and tert-butyl (7-azaspiro[3.5]nonan-1-yl) carbamate. $^{1}$H NMR (400 MHz, $D_2O$) δ 8.11 (d, 1H), 7.68 (d, 2H), 7.59 (d, 2H), 6.81 (d, 1H), 4.43 (s, 2H), 4.21-3.97 (m, 2H), 3.60-3.52 (m, 4H), 3.21-2.96 (m, 3H), 2.83-2.77 (m, 1H), 2.44 (br s, 2H), 2.43-2.33 (m, 2H), 2.18-2.02 (m, 2H), 1.86-1.72 (m, 4H). LCMS [M+H] 464.3.

Compound 247

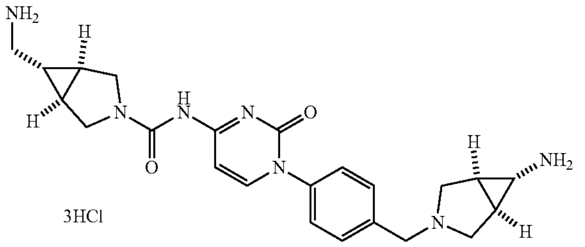

Exo-N-(1-(4-((exo-6-Amino-3-azabicyclo[3.1.0]hexan-3-yl)methyl)phenyl)-2-oxo-1,2-dihydropyrimidin-4-yl)-6-(aminomethyl)-3-azabicyclo[3.1.0]hexane-3-carboxamide Hydrochloride Salt Prepared in a similar fashion to Scheme C-27 from tert-butyl (exo-3-(4-(4-(1H-imidazole-1-carboxamido)-2-oxopyrimidin-1 (2H)-yl)benzyl)-3-azabicyclo[3.1.0]hexan-6-yl)carbamate and exo-6-(boc-aminomethyl)-3-azabicyclo[3.1.0]hexane. $^{1}$H NMR (400 MHz, $D_2O$): δ 7.91 (d, 1H), 7.52 (d, 2H), 7.40 (d, 2H), 6.84 (d, 1H), 4.32 (bs, 1H) 3.52-3.51 (m, 7H), 2.85-2.74 (m, 4H), 2.266 (s, 2H), 1.70 (d, 2H), 0.88-0.843 (m, 1H). LCMS[M+H] 436.0.

Compound 249

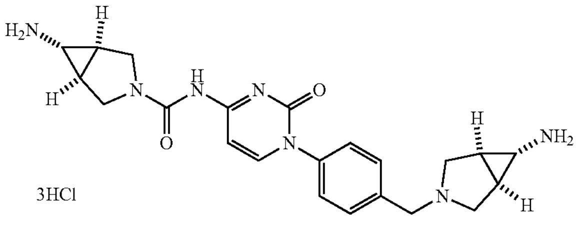

Exo-6-Amino-N-(1-(4-((exo-6-amino-3-azabicyclo[3.1.0]hexan-3-yl)methyl)phenyl)-2-oxo-1,2-dihydropyrimidin-4-yl)-3-azabicyclo[3.1.0]hexane-3-carboxamide Hydrochloride Salt Prepared in a similar fashion to Scheme C-27 from tert-butyl (exo-3-(4-(4-(1H-imidazole-1-carboxamido)-2-oxopyrimidin-1 (2H)-yl)benzyl)-3-azabicyclo[3.1.0]hexan-6-yl)carbamate and rac-tert-butyl (3-azabicyclo[3.1.0]hexan-6-yl)carbamate. $^{1}$H NMR (400 MHz, $D_2O$): δ 7.91 (d, 1H), 7.52 (d, 2H), 7.42 (d, 2H), 6.819 (d, 1H), 4.33 (bs, 2H), 3.94 (s, 1H), 3.72 (d, 2H), 3.60-3.51 (m, 6H), 3.02 (bs, 1H), 2.76 (bs, 1H), 2.40 (d, 1H), 2.28 (s, 2H), 2.07 (s, 2H). LCMS[M+H] 422.6.

Compound 252

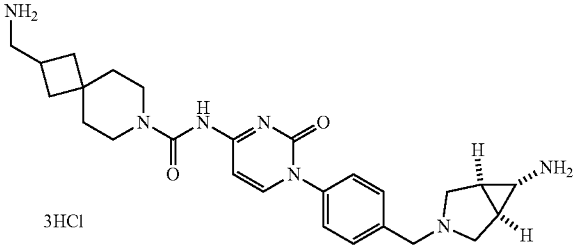

N-(1-(4-((exo-6-Amino-3-azabicyclo[3.1.0]hexan-3-yl)methyl)phenyl)-2-oxo-1,2-dihydropyrimidin-4-yl)-2-(aminomethyl)-7-azaspiro[3.5]nonane-7-carboxamide Hydrochloride Salt Prepared in a similar fashion to Scheme C-27 tert-butyl (exo-3-(4-(4-(1H-imidazole-1-carboxamido)-2-oxopyrimidin-1 (2H)-yl)benzyl)-3-azabicyclo[3.1.0]hexan-6-yl)carbamate and benzyl ((7-azaspiro[3.5]nonan-2-yl)methyl)carbamate. $^{1}$H NMR (400 MHz, $D_2O$): δ 7.81 (d, 1H), 7.518 (d, 2H), 7.419 (d, 2H), 6.61 (d, 1H), 4.328 (s, 1H), 3.88 (bs, 1H), 3.59 (bs, 3H), 3.41 (s, 2H), 3.32 (s, 2H), 2.92 (d, 2H), 2.74 (s, 1H), 2.48-2.42 (m, 1H), 2.27 (s, 2H), 1.95 (t, 3H), 1.59 (s, 2H), 1.44 (t, 4H). LCMS[M+H] 478.3.

Compound 250

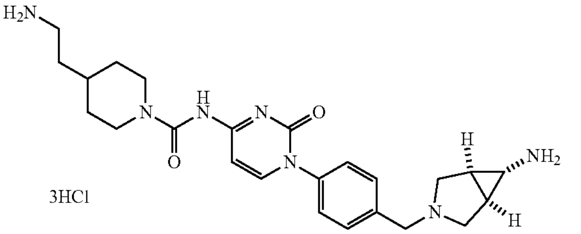

N-(1-(4-((exo-6-Amino-3-azabicyclo[3.1.0]hexan-3-yl)methyl)phenyl)-2-oxo-1,2-dihydropyrimidin-4-yl)-4-(2-aminoethyl)piperidine-1-carboxamide Hydrochloride Salt Prepared in a similar fashion to Scheme C-27 from tert-butyl (exo-3-(4-(4-(1H-imidazole-1-carboxamido)-2-oxopyrimidin-1 (2H)-yl)benzyl)-3-azabicyclo[3.1.0]hexan-6-yl)carbamate and 4-(2-boc-aminoethyl)piperidine. $^{1}$H NMR (400 MHz, $D_2O$): δ 7.81 (d, 1H), 7.51 (d, 2H), 7.41 (d, 2H), 6.61 (d, 1H), 4.34 (s, 2H), 4.02 (s, 2H), 3.60 (bs, 3H), 2.93 (s, 4H), 2.29 (s, 2H), 1.70 (d, 2H), 1.58-1.51 (m, 3H), 1.17-1.09 (m, 2H). LCMS[M+H] 452.3.

Compound 248

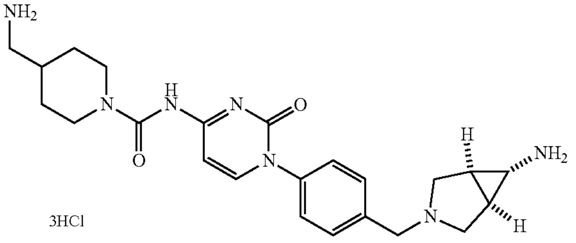

N-(1-(4-((exo-6-Amino-3-azabicyclo[3.1.0]hexan-3-yl)methyl)phenyl)-2-oxo-1,2-dihydropyrimidin-4-yl)-4-(aminomethyl)piperidine-1-carboxamide Hydrochloride Salt Prepared in a similar fashion to Scheme C-27 tert-butyl (exo-3-(4-(4-(1H-imidazole-1-carboxamido)-2-oxopyrimidin-1 (2H)-yl)benzyl)-3-azabicyclo[3.1.0]hexan-6-yl)carbamate and 4-(Boc-Aminomethyl)piperidine. $^1$H NMR (400 MHz, $D_2O$): δ 7.97 (d, 1H), 7.53 (s, 2H), 7.42 (d, 2H), 6.65 (d, 1H), 4.33 (s, 2H), 4.07 (s, 2H), 3.58 (d, 2H), 2.92 (d, 2H), 2.81-2.75 (m, 3H), 2.27 (s, 2H), 1.89-1.84 (m, 1H), 1.74 (d, 2H), 1.22-1.14 (m, 2H). LCMS[M+H] 438.2.

Compound 253

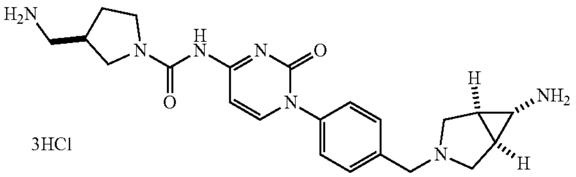

(R)—N-(1-(4-((exo-6-Amino-3-azabicyclo[3.1.0]hexan-3-yl)methyl)phenyl)-2-oxo-1,2-dihydropyrimidin-4-yl)-3-(aminomethyl)pyrrolidine-1-carboxamide Hydrochloride Salt Prepared in a similar fashion to Scheme C-27 tert-butyl (exo-3-(4-(4-(1H-imidazole-1-carboxamido)-2-oxopyrimidin-1 (2H)-yl)benzyl)-3-azabicyclo[3.1.0]hexan-6-yl)carbamate and (S)-3-N-boc-aminomethyl pyrrolidine. $^1$H NMR (400 MHz, $D_2O$): δ 7.97 (d, 1H), 7.55 (d, 2H), 7.44 (d, 2H), 6.92 (d, 1H), 4.35 (s, 2H), 3.76-3.52 (m, 5H), 3.41 (s, 1H), 3.15 (t, 1H), 2.98 (d, 3H), 2.77 (s, 1H), 2.52 (bs, 1H), 2.30 (s, 2H), 2.16 (bs, 1H), 1.74-1.72 (m, 1H). LCMS[M+H] 424.6.

Compound 251

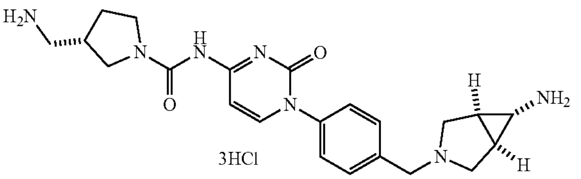

(S)—N-(1-(4-((exo-6-Amino-3-azabicyclo[3.1.0]hexan-3-yl)methyl)phenyl)-2-oxo-1,2-dihydropyrimidin-4-yl)-3-(aminomethyl)pyrrolidine-1-carboxamide Hydrochloride Salt Prepared in a similar fashion to Scheme C-27 from tert-butyl (exo-3-(4-(4-(1H-imidazole-1-carboxamido)-2-oxopyrimidin-1 (2H)-yl)benzyl)-3-azabicyclo[3.1.0]hexan-6-yl)carbamate and (R)-3-N-boc-aminomethyl pyrrolidine. $^1$H NMR (400 MHz, $D_2O$): δ 7.98 (d, 1H), 7.54 (d, 2H), 7.43 (d, 2H), 6.87 (d, 1H), 4.34 (s, 2H), 3.75-3.49 (m, 7H), 3.40-3.43 (m, 1H), 2.97 (t, 3H), 2.76 (s, 1H), 2.52-2.51 (m, 1H), 2.28 (s, 2H), 2.15 (s, 1H), 1.78-1.73 (m, 1H). LCMS [M+H] 424.6.

Compound 254

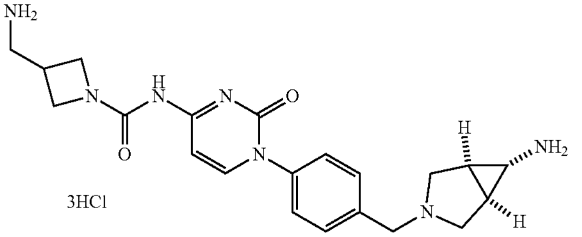

N-(1-(4-((exo-6-Amino-3-azabicyclo[3.1.0]hexan-3-yl)methyl)phenyl)-2-oxo-1,2-dihydropyrimidin-4-yl)-3-(aminomethyl)azetidine-1-carboxamide Hydrochloride Salt Prepared in a similar fashion to Scheme C-27 tert-butyl (exo-3-(4-(4-(1H-imidazole-1-carboxamido)-2-oxopyrimidin-1 (2H)-yl)benzyl)-3-azabicyclo[3.1.0]hexan-6-yl)carbamate and 3-Boc-aminomethylazetidine. $^1$H NMR (400 MHz, $D_2O$): δ 7.89 (d, 1H), 7.51 (d, 2H), 7.39 (d, 2H), 6.95 (d, 1H), 4.32 (s, 4H), 3.87 (bs, 3H), 3.59 (bs, 3H), 3.19 (d, 2H), 2.95-2.91 (m, 1H), 2.74 (s, 1H), 2.26 (s, 2H). LCMS [M+H] 410.6.

Compound 255

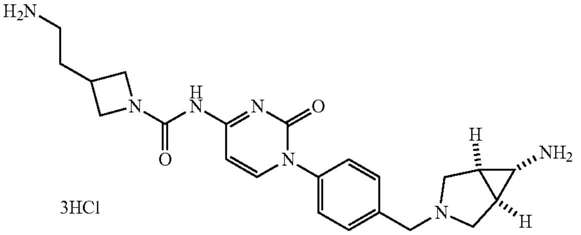

N-(1-(4-((exo-6-Amino-3-azabicyclo[3.1.0]hexan-3-yl)methyl)phenyl)-2-oxo-1,2-dihydropyrimidin-4-yl)-3-(2-aminoethyl)azetidine-1-carboxamide Hydrochloride Salt Prepared in a similar fashion to Scheme C-27 from tert-butyl (exo-3-(4-(4-(1H-imidazole-1-carboxamido)-2-oxopyrimidin-1 (2H)-yl)benzyl)-3-azabicyclo[3.1.0]hexan-6-yl)carbamate mate and 3-(2-N-boc-aminoethyl)azitidine; hydrochloride. $^1$H NMR (400 MHz, $D_2O$): δ 7.94 (d, 1H), 7.56 (d, 2H), 7.45 (d, 2H), 6.98 (d, 1H), 4.36 (s, 3H), 3.84 (bs, 1H), 3.64-3.62 (m, 4H), 3.02 (bs, 1H), 2.89 (t, 2H), 2.80 (s, 1H), 2.72-2.68 (t, 1H), 2.32 (s, 2H), 1.94 (dd, 2H). LCMS[M+H] 424.6.

Compound 49

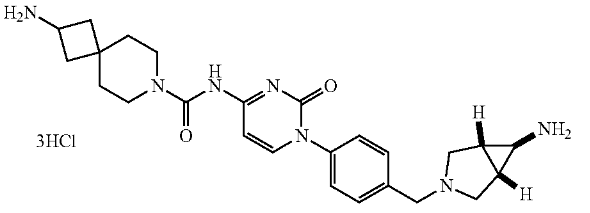

2-Amino-N-(1-(4-((exo-6-amino-3-azabicyclo[3.1.0]hexan-3-yl)methyl)phenyl)-2-oxo-1,2-dihydropyrimidin-4-yl)-7-azaspiro[3.5]nonane-7-carboxamide Hydrochloride Salt Scheme C-28

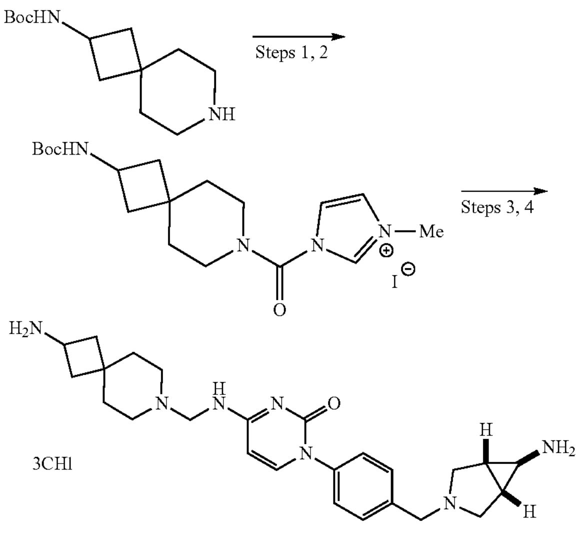

Reagents: 1) CDI, $CH_2Cl_2$, 2 h 2) $CH_3CN$, MeI, rt, 16 h 3) tert-butyl (exo-3-(4-(4-amino-2-oxopyrimidin-1 (2H)-yl)benzyl)-3-azabicyclo[3.1.0]hexan-6-yl)carbamate, $CH_3CN$, reflux, 16 h 4) HCl, MeOH rt, 4 h.

Step 1: tert-butyl (7-(1H-imidazole-1-carbonyl)-7-azaspiro[3.5]nonan-2-yl)carbamate. To a solution of tert-butyl (7-azaspiro[3.5]nonan-2-yl)carbamate (0.24 g, 1.0 mmol) in $CH_2Cl_2$ (10 mL) was added CDI (0.18 g, 1.1 mmol) and the solution was stirred at rt for 2 h. The reaction mixture was concentrated under reduced pressure and the residue was dissolved in EtOAc (15 mL) and washed with $H_2O$ (3×10 mL). The organic layer was dried over $Na_2SO_4$, filtered and concentrated under reduced pressure to give the title compound (0.32 g, 96%) as a while solid.

Step 2: 1-(2-((tert-butoxycarbonyl)amino)-7-azaspiro[3.5]nonane-7-carbonyl)-3-methyl-1H-imidazol-3-ium iodide. To a solution of tert-butyl (7-(1H-imidazole-1-carbonyl)-7-azaspiro[3.5]nonan-2-yl)carbamate (0.32 g, 0.96 mmol) in $CH_3CN$, MeI (0.18 mL, 2.9 mmol) was added. The reaction was stirred for 16 h at rt was concentrated under reduced pressure to afford the title compound (0.45 g, 99%). as a yellow solid.

Step 3: tert-butyl (7-((1-(4-((exo-6-((tert-butoxycarbonyl)amino)-3-azabicyclo[3.1.0]hexan-3-yl)methyl)phenyl)-2-oxo-1,2-dihydropyrimidin-4-yl)carbamoyl)-7-azaspiro[3.5]nonan-2-yl)carbamate. A suspension of tert-butyl (exo-3-(4-(4-amino-2-oxopyrimidin-1 (2H)-yl)benzyl)-3-azabicyclo[3.1.0]hexan-6-yl)carbamate (0.20 g, 0.5 mmol) and 1-(2-((tert-butoxycarbonyl)amino)-7-azaspiro[3.5]nonane-7-carbonyl)-3-methyl-1H-imidazol-3-ium iodide (0.24 g, 0.5 mmol) in $CH_3CN$ was refluxed for 16 h. The reaction was concentrated under reduces pressure and the residue was purified by flash column chromatography (gradient Hexanes to EtOAc:MeOH 80:20) to give the title compound (0.3 g, 90%) as a white solid.

Step 4: 2-amino-N-(1-(4-((exo-6-amino-3-azabicyclo[3.1.0]hexan-3-yl)methyl)phenyl)-2-oxo-1,2-dihydropyrimidin-4-yl)-7-azaspiro[3.5]nonane-7-carboxamide hydrochloride salt. Tert-butyl (7-((1-(4-((exo-6-((tert-butoxycarbonyl)amino)-3-azabicyclo[3.1.0]hexan-3-yl)methyl)phenyl)-2-oxo-1,2-dihydropyrimidin-4-yl)carbamoyl)-7-azaspiro[3.5]nonan-2-yl)carbamate (0.3 g, 0.45 mmol) was dissolved in MeOH·HCl solution and stirred for 4 h at rt The solvent was evaporated and the residue was dissolved in $CH_2Cl_2$:MeOH:$NH_4OH$ (8:1.8:0.2) purified by column chromatography using the (gradient, $CH_2Cl_2$ to $CH_2Cl_2$:MeOH:$NH_4OH$, 8:1.8:0.2) yield the title compound (0.16 g, 75%) as a white solid. $^1$H NMR (500 MHz, $D_2O$) δ 8.02 (d, 1H), 7.67 (d, 2H), 7.55 (d, 2H), 6.80 (d, 1H), 4.47 (s, 2H), 3.87 (p, 1H), 3.81-3.65 (m, 2H), 3.56 (t, 2H), 3.50 (t, 2H), 2.93-2.83 (m, 1H), 2.42 (br s, 2H), 2.40-2.34 (m, 2H), 2.02-1.97 (m, 2H), 1.74 (t, 2H), 1.70 (t, 2H). LCMS [M+H] 464.3.

Compound 61

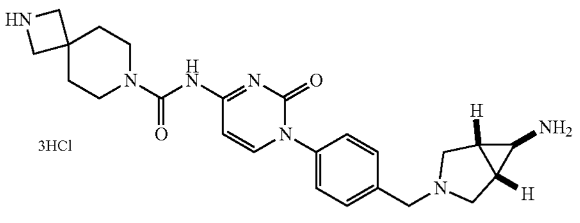

N-(1-(4-((exo-6-Amino-3-azabicyclo[3.1.0]hexan-3-yl)methyl)phenyl)-2-oxo-1,2-dihydropyrimidin-4-yl)-2,7-diazaspiro[3.5]nonane-7-carboxamide Hydrochloride Salt Prepared in a similar fashion to Scheme C-28 from 1-(2-(tert-butoxycarbonyl)-2,7-diazaspiro[3.5]nonane-7-carbonyl)-3-methyl-1H-imidazol-3-ium iodide and t-butyl ((exo-3-(4-(4-amino-2-oxopyrimidin-1 (2H)-yl)phenethyl)-3-azabicyclo[3.1.0]hexan-6-yl)methyl)carbamate. $^1$H NMR (500 MHz, $D_2O$) δ 8.02 (d, 1H), 7.62 (d, 2H), 7.50 (d, 2H), 6.77 (d, 1H), 4.42 (s, 2H), 3.92 (s, 2H), 3.87 (s, 2H), 3.76-3.58 (m, 4H), 3.52 (s, 4H), 2.83-2.78 (m, 1H), 2.36 (br s, 2H), 1.91 (br s, 4H). LCMS [M+H] 450.3.

Compound 62

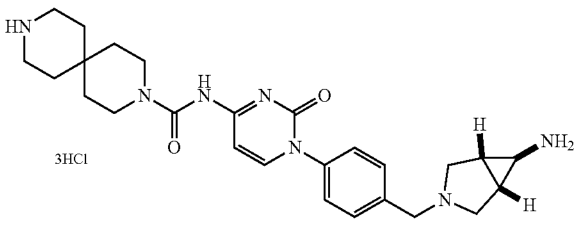

N-(1-(4-(2-(exo-6-(Aminomethyl)-3-azabicyclo[3.1.0]hexan-3-yl)ethyl)phenyl)-2-oxo-1,2-dihydropyrimidin-4-yl)-2,7-diazaspiro[3.5]nonane-7-carboxamide Hydrochloride Salt Prepared in a similar fashion to Scheme C-28 from 1-(2-(tert-butoxycarbonyl)-2,7-diazaspiro[3.5]nonane-7-carbonyl)-3-methyl-1H-imidazol-3-ium and t-butyl ((exo-3-(4-(4-amino-2-oxopyrimidin-1 (2H)-yl)phenethyl)-3-azabicyclo [3.1.0]hexan-6-yl)methyl)carbamate. $^1$H NMR (400 MHz, $D_2O$) δ 7.78 (d, 1H), 7.33 (d, 2H), 7.28 (d, 2H), 6.67 (d, 1H), 3.84 (s, 4H), 3.70 (d, 2H), 3.48-3.3.34 (m, 8H), 2.99 (t, 2H), 2.83 (d, 2H), 1.87-1.80 (m, 6H), 1.21-1.19 (m, 1H). LCMS [M+H] 478.2.

Compound 145

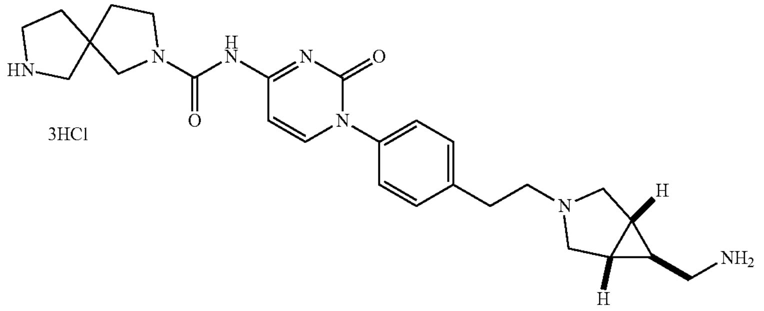

N-(1-(4-((exo-6-Amino-3-azabicyclo[3.1.0]hexan-3-yl)methyl)phenyl)-2-oxo-1,2-dihydropyrimidin-4-yl)-3,9-diazaspiro[5.5]undecane-3-carboxamide Hydrochloride Salt Prepared in a similar fashion to Scheme C-28 from 1-(9-(tert-butoxycarbonyl)-3,9-diazaspiro[5.5]undecane-3-carbonyl)-3-methyl-1H-imidazol-3-ium iodide and t-butyl ((exo-3-(4-(4-amino-2-oxopyrimidin-1 (2H)-yl)phenethyl)-3-azabicyclo[3.1.0]hexan-6-yl)methyl)carbamate. $^1$H NMR (500 MHz, $D_2O$) δ 8.05 (d, 1H), 7.61 (d, 2H), 7.50 (d, 2H), 6.78 (d, 1H), 4.41 (s, 2H), 3.76-3.58 (m, 4H), 3.55 (br s, 4H), 3.16 (br s, 4H), 2.83-2.78 (m, 1H), 2.35 (br s, 2H), 1.73 (br s, 4H), 1.61 (br s, 4H). LCMS [M+H] 478.3.

Compound 147

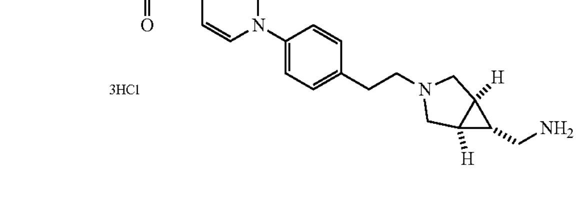

N-(1-(4-(2-(exo-6-(Aminomethyl)-3-azabicyclo[3.1.0]hexan-3-yl)ethyl)phenyl)-2-oxo-1,2-dihydropyrimidin-4-yl)-2,7-diazaspiro[4.4]nonane-2-carboxamide Hydrochloride Salt Scheme C-29

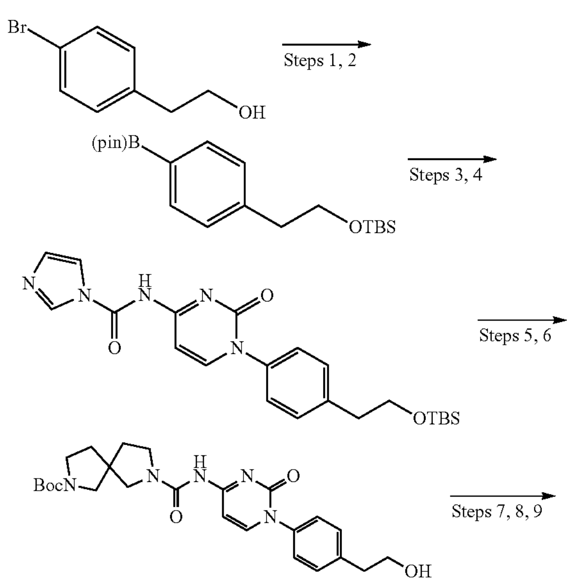

-continued

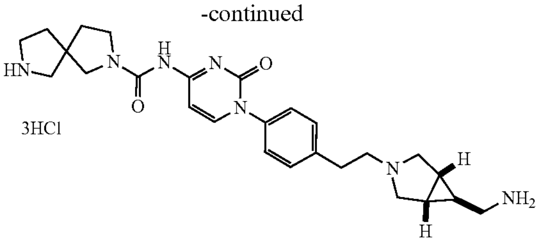

3HCl

Reagents: Step 1) TBDMSCl, Imidazole, DMF, rt, 12 h 2) n-BuLi, Isopropoxyboronic acid pinacol ester, THF, −78° C. to rt, 3 h 3) Cytosine, TMEDA, $Cu(OAc)_2{\cdot}H_2O$, $CH_3OH$:$H_2O$ (4:1), $O_2$, rt, 16 h 4) CDI, $CH_2Cl_2$, rt, 12 h 5) tert-butyl 2,7-diazaspiro[4.4]nonane-2-carboxylate, $CH_3CN$, 90° C., 16 h 6) TBAF, THF, rt, 16 h 7) DMP, $CH_2Cl_2$, rt, 3 h 8) $NaBH(OAc)_3$ DIPEA, DCE, rt, 16 h 9) 4.0 M HCl in dioxane, dioxane, rt, 4 h.

Step 1: (4-bromophenethoxy)(t-butyl)dimethylsilane. To a stirred solution of 2-(4-bromophenyl)ethan-1-ol (5.0 g, 2.5 mmol) in DMF (40 mL) was added imidazole (2.5 g, 3.7 mmol) and TBSCl (4.5 g, 3.0 mmol). The mixture was stirred at rt for 16 h, poured into $H_2O$ (150 mL) and extracted with EtOAc (3×100 mL). The extracts were dried ($Na_2SO_4$), filtered, and concentrated under reduced pressure to afford the title compound. $^1H$ NMR (400 MHz, $D_2O$) δ 7.46-7.43 (m, 2H), 7.17 (d, 2H), 3.74 (t, 2H), 2.70 (t, 2H), 0.81 (s, 9H), −0.06 (s, 6H).

Step 2: t-butyldimethyl(4-(4,4,5,5-tetramethyl-1,3,2-dioxaborolan-2-yl)phenethoxy)silane. To a stirred solution of (4-bromophenethoxy)(t-butyl)dimethylsilane (5.0 g, 15.9 mmol) in THF (50 mL) at −78° C. was added n-BuLi (2.5 M in hexane, 15.9 mL, 39.8 mmol) dropwise. The reaction mixture was stirred at −78° C. for 30 min, and isopropoxyboronic acid pinacol ester (4.44 g, 21.8 mmol) was added. The reaction mixture was warmed to rt and stirred for 3 h. The reaction mixture was poured into saturated $NH_4C_1$ solution (50 mL) and extracted with EtOAc (3×50 mL). The extracts were dried ($Na_2SO_4$), filtered, and concentrated under reduced pressure to afford the title compound.

Step 3: 4-amino-1-(4-(2-((t-butyldimethylsilyl)oxy)ethyl)phenyl)pyrimidin-2 (1H)-one. A mixture of t-butyldimethyl (4-(4,4,5,5-tetramethyl-1,3,2-dioxaborolan-2-yl)phenethoxy)silane (8.5 g, 2.52 mmol) and cytosine (2.81 g, 2.52 mmol) in $CH_3OH$:$H_2O$ (4:1, 150 mL) was stirred at rt open to air for 30 min. TMEDA (3.23 g, 4.2 mL, 2.78 mmol) and $Cu(OAc)_2{\cdot}H_2O$ (4.6 g, 2.53 mmol) were added and the mixture was stirred at rt open to air for 48 h. The reaction mixture was concentrated under reduced pressure, and cold $H_2O$ (100 mL) was added. The precipitate was collected by vacuum filtration, washed with $H_2O$ (2×100 mL), hexane (2×70 mL), and dried to afford the title compound. $^1H$ NMR (400 Mz, DMSO-$d_6$) δ 7.56 (d, 1H), 7.29-7.21 (m, 6H), 5.76 (d, 1H), 3.77 (t, 2H), 2.77 (t, 2H), 0.84 (s, 9H), 0.00 (s, 6H). LCMS [M+H] 346.1.

Step 4: N-(1-(4-(2-((t-butyldimethylsilyl)oxy)ethyl)phenyl)-2-oxo-1,2-dihydropyrimidin-4-yl)-1H-imidazole-1-carboxamide. To a stirred solution of 4-amino-1-(4-(2-((t-butyldimethylsilyl)oxy)ethyl)phenyl) pyrimidin-2 (1H)-one (0.2 g, 0.57 mmol) in $CH_2Cl_2$ (10 mL) was added CDI (0.75 g, 4.63 mmol). The mixture was stirred at rt for 12 h and concentrated under reduced pressure to afford the title compound, which was immediately used in the next step.

Step 5: t-Butyl 7-((1-(4-(2-((t-butyldimethylsilyl)oxy)ethyl)phenyl)-2-oxo-1,2-dihydropyrimidin-4-yl)carbamoyl)-2,7-diazaspiro[4.4]nonane-2-carboxylate. A mixture of N-(1-(4-(2-((t-butyldimethylsilyl)oxy)ethyl)phenyl)-2-oxo-1,2-dihydropyrimidin-4-yl)-1H-imidazole-1-carboxamide (0.19 g, 0.43 mmol) and t-butyl 2,7-diazaspiro[4.4]nonane-2-carboxylate (0.98 g, 0.43 mmol) in $CH_3CN$ (10 mL) was stirred at 90° C. for 16 h. The mixture was concentrated under reduced pressure and the residue was purified by column chromatography ($CH_2Cl_2$:MeOH) to afford the title compound. LCMS[M+H] 598.2.

Step 6: t-butyl 7-((1-(4-(2-hydroxyethyl)phenyl)-2-oxo-1,2-dihydropyrimidin-4-yl)carbamoyl)-2,7-diazaspiro[4.4]nonane-2-carboxylate. To a stirred solution of t-butyl 7-((1-(4-(2-((t-butyldimethylsilyl)oxy)ethyl)phenyl)-2-oxo-1,2-dihydropyrimidin-4-yl)carbamoyl)-2,7-diazaspiro[4.4]nonane-2-carboxylate (0.15 g, 0.25 mmol) in THF (10 mL) at 0° C. was added TBAF (1.0 M in THF, 1.00 mL, 1.00 mmol). The mixture was warmed to rt and stirred for 2 h. The reaction mixture was poured into sat. aq. $NaHCO_3$ (10 mL) and extracted with $CH_2Cl_2$ (3×10 mL). The extracts were dried ($Na_2SO_4$), filtered, concentrated under reduced pressure, and the residue was purified by column chromatography on silica gel ($CH_3OH$/$CH_2Cl_2$) to afford the title compound. LCMS[M+H] 484.1.

Step 7: t-butyl 7-((2-oxo-1-(4-(2-oxoethyl)phenyl)-1,2-dihydropyrimidin-4-yl)carbamoyl)-2,7-diazaspiro[4.4]nonane-2-carboxylate. To a stirred solution of t-butyl 7-((1-(4-(2-hydroxyethyl)phenyl)-2-oxo-1,2-dihydropyrimidin-4-yl)carbamoyl)-2,7-diazaspiro[4.4]nonane-2-carboxylate (0.13 g, 0.26 mmol) in DCE (5 mL) at 0° C. was added DMP (0.34 g, 0.80 mmol). The mixture was stirred at rt for 3 h, poured into saturated aqueous $NaHCO_3$ (20 mL), and extracted with DCE (3×10 mL). The extracts were dried ($Na_2SO_4$) and filtered, and the filtrate was used immediately in the next step.

Step 8: t-Butyl 7-((1-(4-(2-(exo-6-(((t-butoxycarbonyl)amino)methyl)-3-azabicyclo[3.1.0]hexan-3-yl)ethyl)phenyl)-2-oxo-1,2-dihydropyrimidin-4-yl)carbamoyl)-2,7-diazaspiro[4.4]nonane-2-carboxylate. To a mixture of the filtrate from the previous step, t-butyl ((exo-3-azabicyclo[3.1.0]hexan-6-yl)methyl)carbamate (0.069 g, 0.32 mmol), and DIPEA (0.07 ml, 0.40 mmol) at 0° C. under $N_2$ was added $NaBH(OAc)_3$ (0.057 g, 0.54 mmol). The mixture was stirred at rt for 16 h then concentrated under reduced pressure, and the residue was purified by column chromatography ($CH_2Cl_2$:MeOH) to afford the title compound. LCMS [M−Boc+H] 578.9.

Step 9: N-(1-(4-(2-(exo-6-(Aminomethyl)-3-azabicyclo[3.1.0]hexan-3-yl)ethyl)phenyl)-2-oxo-1,2-dihydropyrimidin-4-yl)-2,7-diazaspiro[4.4]nonane-2-carboxamide hydrochloride salt. To a solution of t-butyl 7-((1-(4-(2-(exo-6-(((t-butoxycarbonyl)amino)methyl)-3-azabicyclo[3.1.0]hexan-3-yl)ethyl)phenyl)-2-oxo-1,2-dihydropyrimidin-4-yl)carbamoyl)-2,7-diazaspiro[4.4]nonane-2-carboxylate (0.145 g, 0.26 mmol) in $CH_3OH$ (3 mL) was added 4.0 M HCl in dioxane (10 mL, 40.0 mmol). The mixture was stirred at rt for 3 h, concentrated under reduced pressure, and triturated with diethyl ether (10 mL). The residue was purified by HPLC to afford the title compound. $^1H$ NMR (400 MHz, $D_2O$) mixture of rotamers, δ 7.78 (d, 1H), 7.32 (d, 2H), 7.26 (d, 2H), 7.00 (m, 1H), 3.68 (d, 2H), 3.60-3.10 (m, 13H), 2.97 (t, 2H), 2.81 (d, 2H), 2.05-1.80 (m, 7H), 1.20-1.15 (m, 1H). LCMS [M+H] 478.3.

Compound 178
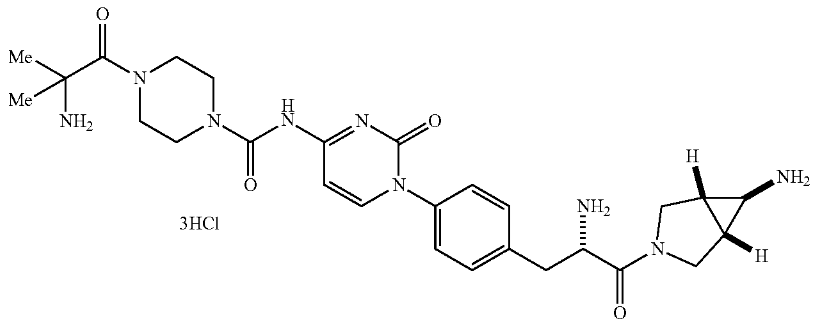
4-(2-Amino-2-methylpropanoyl)-N-(1-(4-((S)-2-amino-3-(exo-6-amino-3-azabicyclo[3.1.0]hexan-3-yl)-3-oxopropyl)phenyl)-2-oxo-1,2-dihydropyrimidin-4-yl)piperazine-1-carboxamide Hydrochloride Salt
Scheme C-30
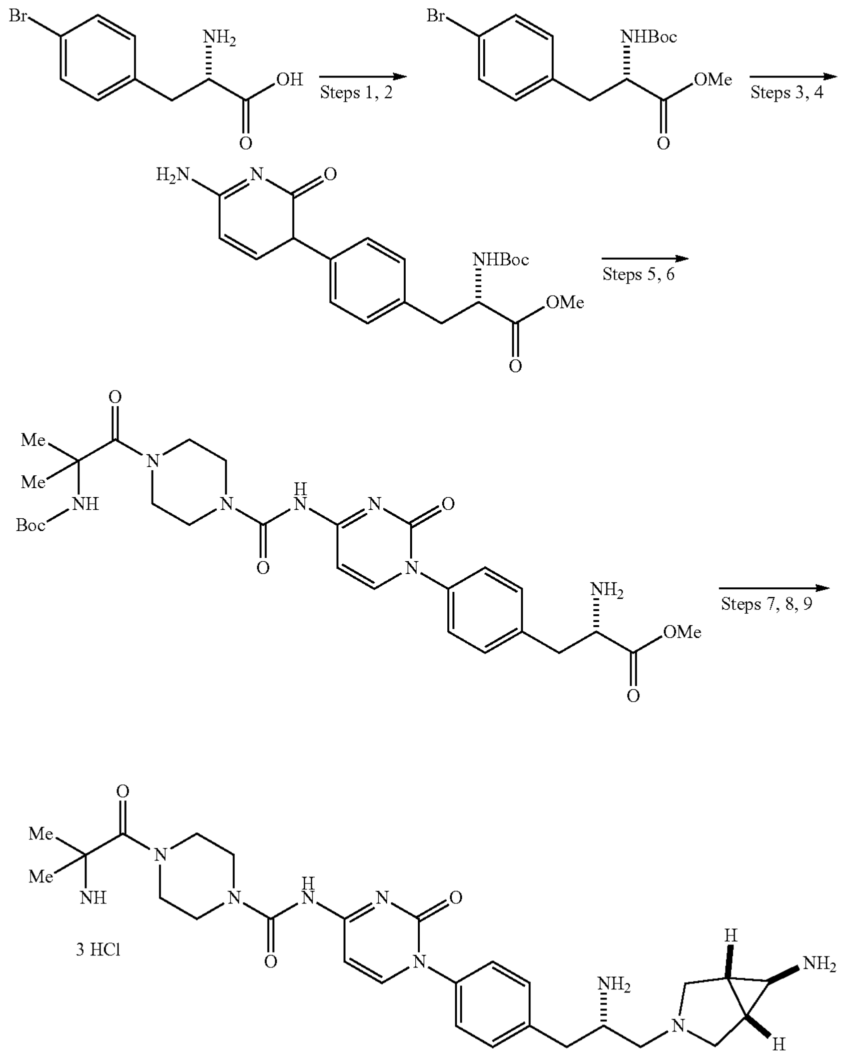

Reagents: 1) HCl, MeOH 2) $Boc_2O$, $NEt_3CH_2Cl_2$ 3) $Pd(dppf)_2$, KOAc, $B_2pin_2$ Dioxane, 100° C. 4) cytosine, $Cu(OAc)_2 \cdot H_2O$, TMEDA, MeOH, $H_2O$ 5) CDI, $CH_2Cl_2$ 6) t-butyl (2-methyl-1-oxo-1-(piperazin-1-yl)propan-2-yl)carbamate, $CH_3CN$, 80° C. 7) LiOH, THF, $H_2O$ 8) tert-butyl (exo-3-azabicyclo[3.1.0]hexan-6-yl)carbamate HATU, DIPEA, DMF 9) HCl, MeOH.

Step 1: methyl (S)-2-amino-3-(4-bromophenyl)propanoate. (S)-2-amino-3-(4-bromophenyl)propanoic acid (2.5 g, 10.20 mmol) was added to a solution of HCl in MeOH (100 mL) and the reaction was stirred for 16 h. The reaction mixture was concentrated under reduced pressure to afford the title compound.

Step 2: methyl (S)-3-(4-bromophenyl)-2-((t-butoxycarbonyl)amino)propanoate. To a solution of (S)-2-amino-3-(4-bromophenyl)propanoate (1.10 g, 3.74 mmol) in $CH_2Cl_2$ (100 mL) was added $NEt_3$ (2.0 mL, 14.96 mmol) followed by $Boc_2O$ (1.05 g, 4.86 mmol). The reaction mixture was stirred for 16 h and concentrated under reduced pressure and purified by column chromatography (Hexanes:EtOAc) to afford the title compound.

Step 3: methyl (S)-2-((t-butoxycarbonyl)amino)-3-(4-(4,4,5,5-tetramethyl-1,3,2-dioxaborolan-2-yl)phenyl)propanoate. A mixture of (S)-3-(4-bromophenyl)-2-((t-butoxycarbonyl)amino)propanoate (0.68 g, 1.90 mmol), $B_2Pin_2$ (0.96 g, 3.80 mmol), $Pd(dppf)_2$ (0.07 g, 5 mol %), and KOAc (0.46 g, 4.76 mmol) was evacuated and backfilled with $N_2$ 3 times. To this was added Dioxane (30 mL) and the crude mixture was subjected to 3 freeze pump thaw cycles. The mixture was placed under $N_2$ and heated to 100° C. for 16 h. The reaction mixture was stirred for 16 h and then concentrated under reduced pressure and purified by column chromatography (hexanes:EtOAc) to afford the desired compound.

Step 4: methyl (S)-3-(4-(4-amino-2-oxopyrimidin-1 (2H)-yl)phenyl)-2-((t-butoxycarbonyl)amino)propanoate. A suspension of cytosine (0.14 g, 1.3 mmol) and methyl (S)-2-((t-butoxycarbonyl)amino)-3-(4-(4,4,5,5-tetramethyl-1,3,2-dioxaborolan-2-yl)phenyl)propanoate (0.50 g, 1.3 mmol), in MeOH:$H_2O$ (4:1, 60 ml) was stirred at rt in open air for 30 min. TMEDA (0.2 ml, 1.6 mmol) and $Cu(OAc)_2 \cdot H_2O$ (0.3 g, 1.3 mmol) were added and the reaction was stirred in open air for 48 h at rt. The reaction mixture was concentrated under reduced pressure, and cold $H_2O$ (50 mL) was added. The precipitate was filtered and washed with $H_2O$ (5×50 mL), $Et_2O$ (3×30 mL), and $H_2O$ (2×30 mL) to afford the title compound.

Step 5: methyl (S)-3-(4-(4-(1H-imidazole-1-carboxamido)-2-oxopyrimidin-1 (2H)-yl)phenyl)-2-((t-butoxycarbonyl)amino)propanoate. A suspension of methyl (S)-3-(4-(4-amino-2-oxopyrimidin-1 (2H)-yl)phenyl)-2-((t-butoxycarbonyl)amino)propanoate (100 mg, 0.25 mmol) and CDI (70 mg, 0.42 mmol) in $CH_2Cl_2$ (20 mL) was stirred at rt for 16 h. The solvent was removed under reduced pressure to afford the title compound.

Step 6: methyl (S)-2-((t-butoxycarbonyl)amino)-3-(4-(4-(4-(2-((t-butoxycarbonyl)amino)-2-methylpropanoyl)piperazine-1-carboxamido)-2-oxopyrimidin-1 (2H)-yl)phenyl)propanoate. Methyl (S)-3-(4-(4-(1H-imidazole-1-carboxamido)-2-oxopyrimidin-1 (2H)-yl)phenyl)-2-((t-butoxycarbonyl)amino)propanoate (0.25 mmol assuming 100% yield) and t-butyl (2-methyl-1-oxo-1-(piperazin-1-yl)propan-2-yl)carbamate (115 mg, 0.42 mmol) were dissolved in $CH_3CN$ (20 mL) and heated to reflux for 2 h. The reaction mixture was concentrated under reduced pressure and the crude solid was dissolved in EtOAc (25 mL) and washed with $H_2O$ (3×20 mL). The reaction mixture was purified by column chromatography (Hexanes:EtOAc) to afford the title compound.

Step 7: (S)-2-((t-butoxycarbonyl)amino)-3-(4-(4-(4-(2-((t-butoxycarbonyl)amino)-2-methylpropanoyl)piperazine-1-carboxamido)-2-oxopyrimidin-1 (2H)-yl)phenyl)propanoic acid. To a solution of methyl (S)-2-((t-butoxycarbonyl)amino)-3-(4-(4-(4-(2-((t-butoxycarbonyl)amino)-2-methylpropanoyl)piperazine-1-carboxamido)-2-oxopyrimidin-1 (2H)-yl)phenyl)propanoate (50 mg, 0.07 mmol) in THF:$H_2O$ (1:1, 10 mL) was added LiOH (10 mg, 0.44 mmol) and the reaction was stirred for 2 h. The reaction mixture was acidified to pH 2 and extracted with EtOAc (3×20 mL) to afford the title compound.

Step 8: tert-butyl (exo-3-((S)-2-((tert-butoxycarbonyl)amino)-3-(4-(4-(4-(2-((tert-butoxycarbonyl)amino)-2-methylpropanoyl)piperazine-1-carboxamido)-2-oxopyrimidin-1 (2H)-yl)phenyl)propanoyl)-3-azabicyclo[3.1.0]hexan-6-yl)carbamate. To a suspension of (S)-2-((t-butoxycarbonyl)amino)-3-(4-(4-(4-(2-((t-butoxycarbonyl)amino)-2-methylpropanoyl)piperazine-1-carboxamido)-2-oxopyrimidin-1 (2H)-yl)phenyl)propanoic acid (10 mg, 0.02 mmol) in DMF (0.5 mL) was added HATU (6 mg, 0.02 mmol), DIPEA (0.003 mL, 0.02 mmol). To the suspension was added solid tert-butyl (exo-3-azabicyclo[3.1.0]hexan-6-yl)carbamate (4 mg, 0.02 mmol) and the mixture stirred at rt for 16 h. The solution was diluted with EtOAc (5 mL) and washed once sat. aq. LiCl (3×5 mL). The organic layer was concentrated under reduced pressure to afford the crude title compound.

4-(2-amino-2-methylpropanoyl)-N-(1-(4-((S)-2-amino-3-(exo-6-amino-3-azabicyclo[3.1.0]hexan-3-yl)-3-oxopropyl)phenyl)-2-oxo-1,2-dihydropyrimidin-4-yl)piperazine-1-carboxamide hydrochloride salt. tert-butyl (exo-3-((S)-2-((tert-butoxycarbonyl)amino)-3-(4-(4-(4-(2-((tert-butoxycarbonyl)amino)-2-methylpropanoyl)piperazine-1-carboxamido)-2-oxopyrimidin-1 (2H)-yl)phenyl)propanoyl)-3-azabicyclo[3.1.0]hexan-6-yl)carbamate was dissolved in a solution of HCl in MeOH (2N, 5 mL) and stirred for 4 h. The volatiles were removed under reduced pressure and the crude solid was purified by reverse phase HPLC ($H_2O$:$CH_3CN$:TFA) and concentrated under reduced pressure. Addition and evaporation under reduced pressure with HCl in MeOH (2N, 3×15 mL) afforded the title compound. $^1H$ NMR (400 MHz, $D_2O$) δ 8.08 (d, 1H), 7.60-7.42 (m, 4H), 6.85-6.79 (m, 1H), 4.56-4.48 (m, 1H), 3.96-3.54 (m, 11H), 3.51-3.36 (m, 1H), 3.31-3.23 (m, 1H), 3.16 (d, 1H), 2.11 (s, 1H), 2.04 (d, 1H), 1.75 (s, 6H), 1.52 (s, 1H). LCMS[M+H] 552.4.

Compound 105

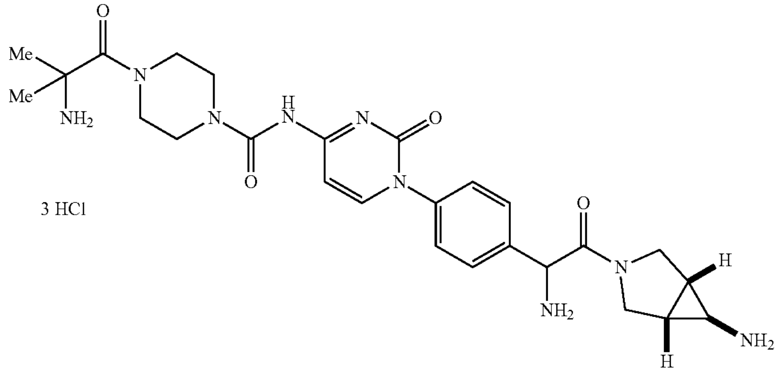

3 HCl

N-(1-(4-(1-Amino-2-(exo-6-amino-3-azabicyclo[3.1.0]hexan-3-yl)-2-oxoethyl)phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-30 from 2-amino-2-(4-(4-(4-(2-((t-butoxycarbonyl)amino)-2-methylpropanoyl)piperazine-1-carboxamido)-2-oxopyrimidin-1(2H)-yl)phenyl)acetic acid and tert-butyl (exo-3-azabicyclo[3.1.0]hexan-6-yl)carbamate. $^1$H NMR (400 MHz, $D_2O$) δ 8.04 (d, 1H), 7.74-7.59 (m, 4H), 6.86 (d, 1H), 5.40 (d, 1H), 3.95-3.65 (m, 9H), 3.58 (d, 1H), 3.26-3.16 (m, 1H), 3.14-3.06 (m, 1H), 2.55 (s, 1H), 2.18-2.06 (m, 2H), 1.75 (s, 6H). LCMS[M+H] 538.34

Compound 137

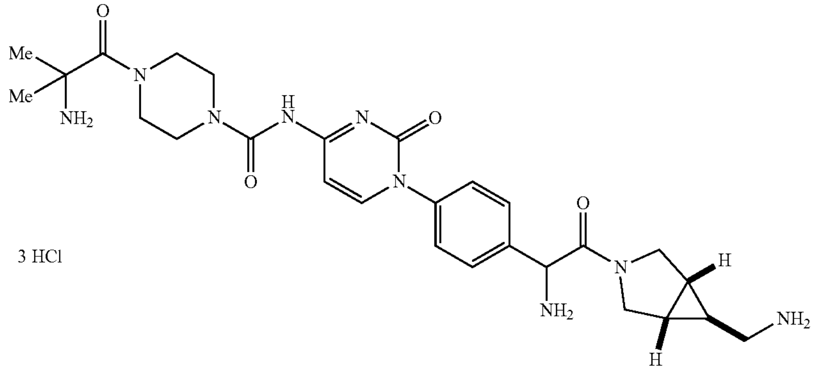

3 HCl

N-(1-(4-(1-Amino-2-(exo-6-(aminomethyl)-3-azabicyclo[3.1.0]hexan-3-yl)-2-oxoethyl)phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-30 from 2-amino-2-(4-(4-(4-(2-((t-butoxycarbonyl)amino)-2-methylpropanoyl)piperazine-1-carboxamido)-2-oxopyrimidin-1(2H)-yl)phenyl)acetic acid and t-butyl ((exo-3-azabicyclo[3.1.0]hexan-6-yl)methyl)carbamate. $^1$H NMR (400 MHz, $D_2O$) δ 8.08 (d, 1H), 7.73-7.58 (m, 4H), 6.88-6.79 (m, 1H), 5.38 (d, 1H), 3.92-3.67 (m, 12H), 3.66-3.45 (m, 1H), 3.10-2.75 (m, 3H), 1.73 (s, 6H), 0.72 (d, 1H). LCMS[M+H] 552.3.

Compound 182

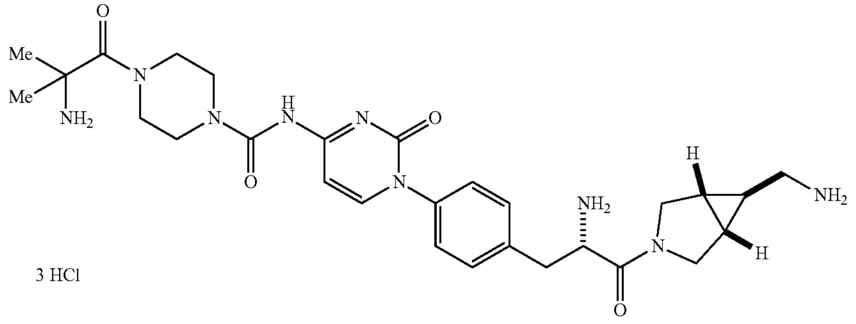

4-(2-Amino-2-methylpropanoyl)-N-(1-(4-((S)-2-amino-3-(exo-6-(aminomethyl)-3-azabicyclo[3.1.0]hexan-3-yl)-3-oxopropyl)phenyl)-2-oxo-1,2-dihydropyrimidin-4-yl)piperazine-1-carboxamide Hydrochloride Salt Prepared in a similar fashion to Scheme C-30 from (S)-2-amino-3-(4-(4-(4-(2-((t-butoxycarbonyl)amino)-2-methylpropanoyl)piperazine-1-carboxamido)-2-oxopyrimidin-1 (2H)-yl)phenyl)propanoic acid and t-butyl ((exo-3-azabicyclo[3.1.0]hexan-6-yl)methyl)carbamate. $^1$H NMR (400 MHz, $D_2O$) δ 8.11-8.03 (m, 1H), 7.55-7.44 (m, 4H), 6.85-6.78 (m, 1H), 4.51 (t, 1H), 3.90-3.66 (m, 10H), 3.57 (s, 1H), 3.45-3.10 (m, 2H), 3.04-2.87 (m, 2H), 2.79-2.69 (m, 1H), 1.75 (s, 8H), 0.62 (d, 1H). LCMS[M+H] 566.3.

Compound 183

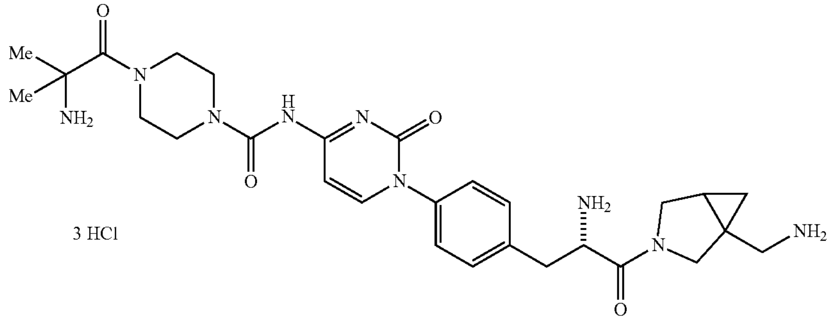

4-(2-Amino-2-methylpropanoyl)-N-(1-(4-((2S)-2-amino-3-(1-(aminomethyl)-3-azabicyclo[3.1.0]hexan-3-yl)-3-oxopropyl)phenyl)-2-oxo-1,2-dihydropyrimidin-4-yl)piperazine-1-carboxamide Hydrochloride Salt Prepared in a similar fashion to Scheme C-30 from (S)-2-amino-3-(4-(4-(4-(2-((t-butoxycarbonyl)amino)-2-methylpropanoyl)piperazine-1-carboxamido)-2-oxopyrimidin-1 (2H)-yl)phenyl)propanoic acid and t-butyl ((3-azabicyclo[3.1.0]hexan-1-yl)methyl)carbamate. $^1$H NMR (400 MHz, $D_2O$) δ 8.09-7.99 (m, 1H), 7.55-7.40 (m, 4H), 6.83 (d, 1H), 4.53 (s, 1H), 4.03-3.48 (m, 12H), 3.46-3.13 (m, 4H), 3.09-2.98 (m, 2H), 1.75 (s, 6H), 1.04-0.83 (m, 1H). LCMS [M+H] 566.2.

Compound 186
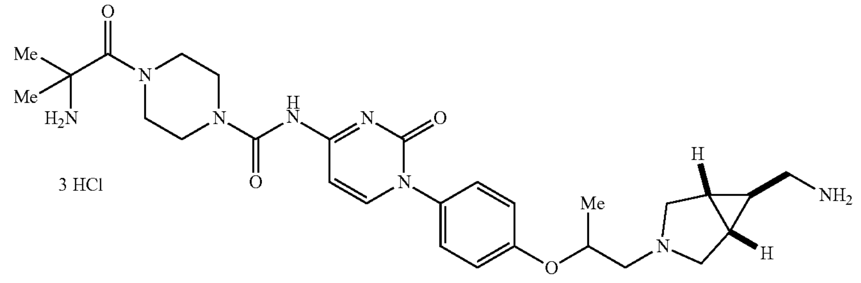
4-(2-Amino-2-methylpropanoyl)-N-(1-(4-((1-(exo-6-(aminomethyl)-3-azabicyclo[3.1.0]hexan-3-yl)propan-2-yl)oxy)phenyl)-2-oxo-1,2-dihydropyrimidin-4-yl)piperazine-1-carboxamide Hydrochloride Salt
Scheme C-31
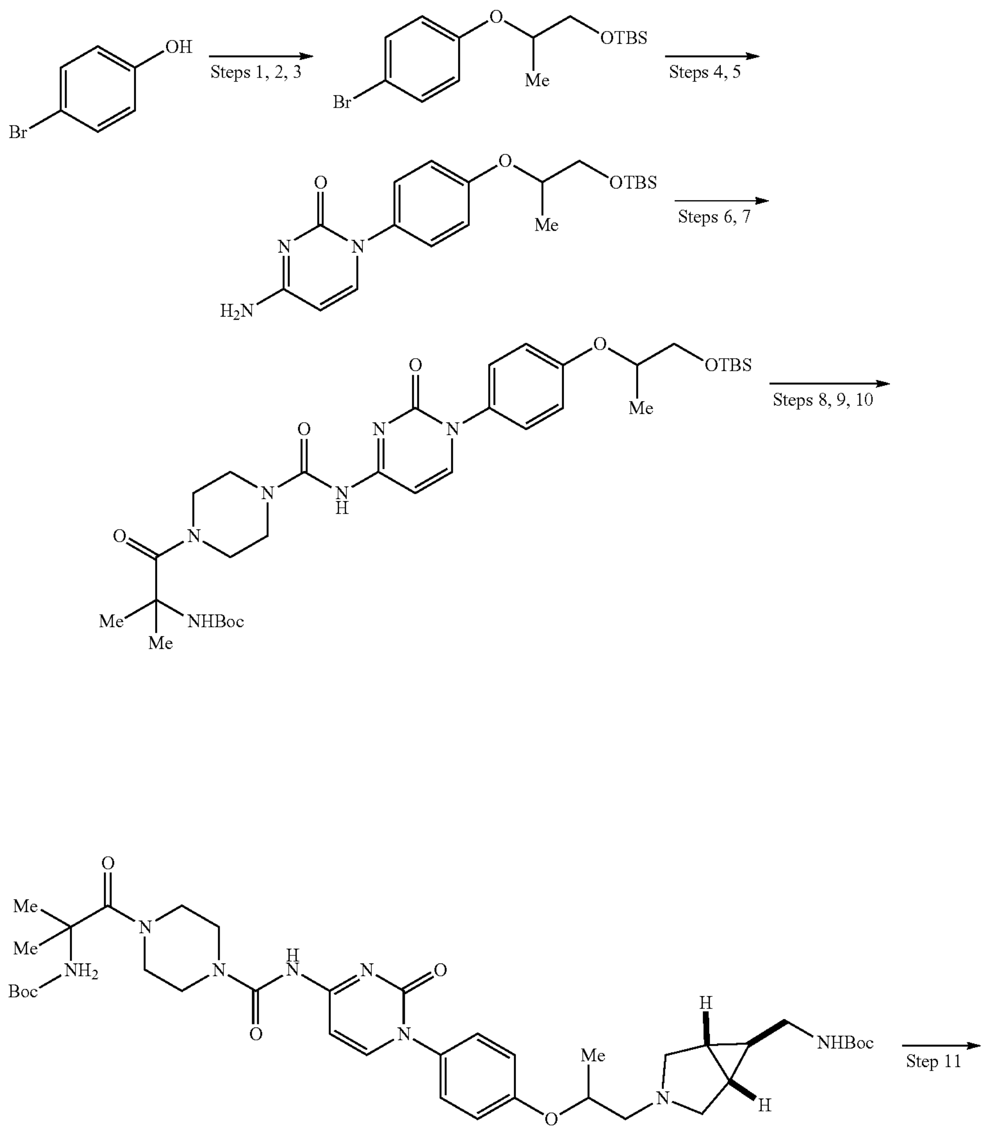

-continued

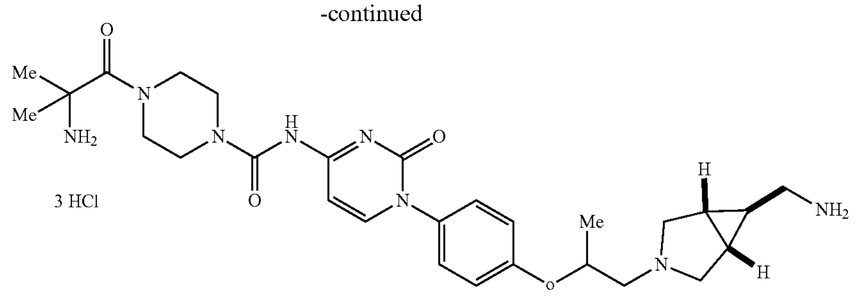

3 HCl

Reagents: 1) Methyl 2-hydroxypropanoate, DIAD, $PPh_3$ 0° C. to rt, 16 h 2) $NaBH_4$ EtOH, 0° C. to rt, 16 h 3) TBSCl, imidazole, $CH_2Cl_2$16 h 4) n-BuLi, THF, −78° C. $B(iPrO)_3$, 2N HCl 5) cytosine, TMEDA, $Cu(OAc)_2 \cdot H_2O$, 4:1 MeOH: $H_2O$ rt. 48 h 6) CDI, $CH_2Cl_2$, rt. 4 h 7) t-butyl (2-methyl-1-oxo-1-(piperazin-1-yl)propan-2-yl)carbamate $CH_3CN$, 85° C., 3 h 8) TBAF, THF 0° C. to rt, 16 h 9) DMP, $CH_2Cl_2$, rt, 15 min 10) t-butyl ((exo-3-azabicyclo[3.1.0]hexan-6-yl) methyl)carbamate, $NaBH_3CN$, MeOH, 16 h 11) HCl in MeOH, rt, 4 h.

Step 1: methyl 2-(4-bromophenoxy)propanoate. To a stirred solution of 4-bromophenol (2.50 g, 14.4 mmol), methyl 2-hydroxypropanoate (1.50 g, 14.4 mmol) and $PPh_3$ (3.77 g 14.4 mmol) at 0° C. was added DIAD (2.91 mL, 1.4 mmol) dropwise over 15 minutes. The reaction was warmed to rt and stirred for 16 h. The volatiles were removed under reduced pressure and the crude reaction mixture was purified by column chromatography to afford the title compound.

Step 2: 2-(4-bromophenoxy)propan-1-ol. To a solution of methyl 2-(4-bromophenoxy)propanoate (1.20 g, 4.59 mmol) in EtOH (40 mL) stirred at 0° C., was added $NaBH_4$ (521 mg, 13.8 mmol). The solution was warmed to rt and stirred for 36 h. The reaction mixture was concentrated under reduced pressure, dissolved in $CHCl_3$ (100 mL) and washed with 10% aq. NaOH solution (1×100 mL). The organic layer was dried over $Na_2SO_4$ and concentrated under reduced pressure to afford the title compound.

Step 3: (2-(4-bromophenoxy)propoxy)(tert-butyl)dimethylsilane. To a solution of 2-(4-bromophenoxy)propan-1-ol (1.07 g, 4.59 mmol) in $CH_2Cl_2$ (50 mL) was added imidazole (468 mg, 6.89 mmol) and TBSCl (1.03 g, 6.89 mmol). The solution was stirred at rt for 16 h. The reaction mixture concentrated under reduced pressure and the solid was dissolved in EtOAc (100 mL) and washed with $H_2O$ (1×100 mL). The organic layer was dried over $Na_2SO_4$ and concentrated under reduced pressure and purified by column chromatography (Hexanes:EtOAc) to afford the title compound.

Step 4: diisopropyl (4-((1-(hydroxy-t)propan-2-yl)oxy) phenyl)boronate. A solution of (2-(4-bromophenoxy) propoxy)(tert-butyl)dimethylsilane (350 mg, 3.21 mmol) in THF (50 mL) was cooled to −78° C. 2.5 M n-BuLi in Hexanes (3.80 mL, 9.63 mmol) was added dropwise over 30 min, maintaining the temperature below −60° C. The reaction was stirred for an additional 25 min, after which $B(iPrO)_3$ (1.12 mL, 4.82 mmol) was added dropwise over 30 min. The reaction mixture was warmed to rt and stirred for 15 min. 2N HCl (50 mL) was added and the reaction was stirred for 30 min. The biphasic mixture was separated and the aq. layer extracted with $CH_2Cl_2$ (2×50 mL). The combined organics were dried over $Na_2SO_4$ and concentrated under reduced pressure to afford the title compound.

Step 5: 4-amino-1-(4-((1-((t-butyldimethylsilyl)oxy)propan-2-yl)oxy)phenyl)pyrimidin-2 (1H)-one. A suspension of cytosine (355 mg, 3.20 mmol) and diisopropyl (4-((1-(hydroxy-t)propan-2-yl)oxy)phenyl)boronate (992 mg, 3.20 mmol), in MeOH:$H_2O$ (4:1, 100 mL) was stirred at rt in open air for 30 min. TMEDA (0.87 mL, 3.8 mmol) and $Cu(OAc)_2 \cdot H_2O$ (640 mg, 3.2 mmol) were added and the reaction was stirred in open air for 48 h at rt. The reaction mixture was concentrated under reduced pressure and cold $H_2O$ (100 mL) was added. The percipitate was filtered and washed with $H_2O$ (2×20 mL) and $Et_2O$ (3×20 mL) to afford the title compound.

Step 6: N-(1-(4-((1-((t-butyldimethylsilyl)oxy)propan-2-yl)oxy)phenyl)-2-oxo-1,2-dihydropyrimidin-4-yl)-1H-imidazole-1-carboxamide. A suspension of 4-amino-1-(4-((1-((t-butyldimethylsilyl)oxy)propan-2-yl)oxy)phenyl) pyrimidin-2 (1H)-one (100 mg, 0.267 mmol) and CDI (68 mg, 0.37 mmol) in $CH_2Cl_2$ (12 mL) was stirred for 16 h at rt. The solvent was removed reduced pressure, and the residue was triturated with EtOAc. The solids were collected to afford the title compound.

Step 7: t-butyl (1-(4-((1-(4-((1-((t-butyldimethylsilyl) oxy)propan-2-yl)oxy)phenyl)-2-oxo-1,2-dihydropyrimidin-4-yl)carbamoyl)piperazin-1-yl)-2-methyl-1-oxopropan-2-yl)carbamate. N-(1-(4-((1-((t-butyldimethylsilyl)oxy) propan-2-yl)oxy)phenyl)-2-oxo-1,2-dihydropyrimidin-4-yl)-1H-imidazole-1-carboxamide (122 mg, 0.260 mmol) and t-butyl (2-methyl-1-oxo-1-(piperazin-1-yl)propan-2-yl)carbamate (72 mg, 0.26 mmol) were dissolved in $CH_3CN$ (10 mL) and heated to reflux for 2 h. The reaction mixture was concentrated under reduced pressure and the crude reaction mixture was dissolved in EtOAc (25 mL) and washed with $H_2O$ (3×20 mL). The reaction mixture was purified by column chromatography (Hexanes:EtOAc) to afford the title compound.

Step 8: t-butyl (1-(4-((1-(4-((1-hydroxypropan-2-yl)oxy) phenyl)-2-oxo-1,2-dihydropyrimidin-4-yl)carbamoyl)piperazin-1-yl)-2-methyl-1-oxopropan-2-yl)carbamate. To a solution of t-butyl (1-(4-((1-(4-((1-((t-butyldimethylsilyl) oxy)propan-2-yl)oxy)phenyl)-2-oxo-1,2-dihydropyrimidin-4-yl)carbamoyl)piperazin-1-yl)-2-methyl-1-oxopropan-2-yl)carbamate (150 mg, 0.22 mmol) in THF (50 mL) at 0° C. was added 1.0 M TBAF in THF (0.45 mL, 0.45 mmol) dropwise over the span of 5 min. The solution was warmed to rt and stirred for 16 h. The crude reaction mixture was concentrated under reduced pressure and was purified by column chromatography to afford the title compound.

Step 9: t-butyl (2-methyl-1-oxo-1-(4-((2-oxo-1-(4-((1-oxopropan-2-yl)oxy)phenyl)-1,2-dihydropyrimidin-4-yl) carbamoyl)piperazin-1-yl)propan-2-yl)carbamate. To a stirred solution of t-butyl (1-(4-((1-(4-((1-hydroxypropan-2-yl)oxy)phenyl)-2-oxo-1,2-dihydropyrimidin-4-yl)carbamoyl)piperazin-1-yl)-2-methyl-1-oxopropan-2-yl)carbamate (40 mg, 0.072 mmol) in $CH_2Cl_2$:$H_2O$ (1000:1, 10 mL) was added DMP (44 mg, 0.010 mmol). The solution was stirred for 1 h. The crude reaction mixture was dissolved in additional $CH_2Cl_2$ (15 mL) and washed with aq. $NaHCO_3$/$Na_2S_2O_3$ (1×15 mL). The aq. layer was extracted with $CH_2Cl_2$ (1×15 mL). The combined organic layers were dried over $Na_2SO_4$ and concentrated under reduced pressure to give the title compound.

Step 10: t-butyl (1-(4-((1-(4-((1-(exo-6-(((t-butoxycarbonyl)amino)methyl)-3-azabicyclo[3.1.0]hexan-3-yl)propan-2-yl)oxy)phenyl)-2-oxo-1,2-dihydropyrimidin-4-yl)carbamoyl)piperazin-1-yl)-2-methyl-1-oxopropan-2-yl) carbamate. To a stirred solution of t-butyl (2-methyl-1-oxo-1-(4-((2-oxo-1-(4-((1-oxopropan-2-yl)oxy)phenyl)-1,2-dihydropyrimidin-4-yl)carbamoyl)piperazin-1-yl)propan-2-yl)carbamate (20 mg, 0.035 mmol) in MeOH, was added t-butyl ((exo-3-azabicyclo[3.1.0]hexan-6-yl)methyl)carbamate (11 mg, 0.053 mmol) and $NaBH_3CN$ (4.0 mg, 0.053 mmol). The reaction mixture was stirred for 16 h at rt. The reaction mixture was concentrated under reduced pressure, dissolved in $CHCl_3$ (15 mL) and washed with 10% aq. NaOH solution (1×15 mL). The organic layer was concentrates under reduced pressure to afford the title compound.

Step 11: 4-(2-amino-2-methylpropanoyl)-N-(1-(4-((1-(exo-6-(aminomethyl)-3-azabicyclo[3.1.0]hexan-3-yl)propan-2-yl)oxy)phenyl)-2-oxo-1,2-dihydropyrimidin-4-yl) piperazine-1-carboxamide hydrochloride salt. T-butyl (1-(4-((1-(4-((1-(exo-6-(((t-butoxycarbonyl)amino)methyl)-3-azabicyclo[3.1.0]hexan-3-yl)propan-2-yl)oxy)phenyl)-2-oxo-1,2-dihydropyrimidin-4-yl)carbamoyl)piperazin-1-yl)-2-methyl-1-oxopropan-2-yl)carbamate was dissolved in a solution of HCl in MeOH (2N, 5 mL) and stirred for 4 h. The reaction mixture was concentrated and the crude solid was purified by reverse phase HPLC ($H_2O$:$CH_3CN$:TFA) and concentrated under reduced pressure. Addition of HCl/MeOH and evaporation under reduced pressure afforded the title compound. $^1$HNMR (400 MHz, $D_2O$) δ 8.01 (d, 1H), 7.44 (d, 2H), 7.20 (d, 2H), 6.82 (d, 1H), 4.93 (s, 1H), 3.91-3.47 (m, 14H), 2.96 (d, 2H), 2.03 (s, 2H), 1.75 (s, 6H), 1.36 (d, 4H). LCMS[M+H] 553.3.

Compound 222

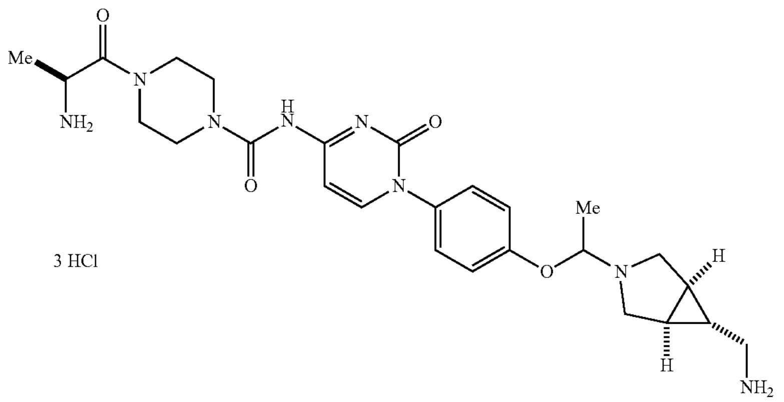

3 HCl 4-(L-alanyl)-N-(1-(4-(2-((exo)-6-(aminomethyl)-3-azabicyclo[3.1.0]hexan-3-yl)propyl)phenyl)-2-oxo-1,2-dihydropyrimidin-4-yl)piperazine-1-carboxamide Hydrochloride Salt Scheme C-32

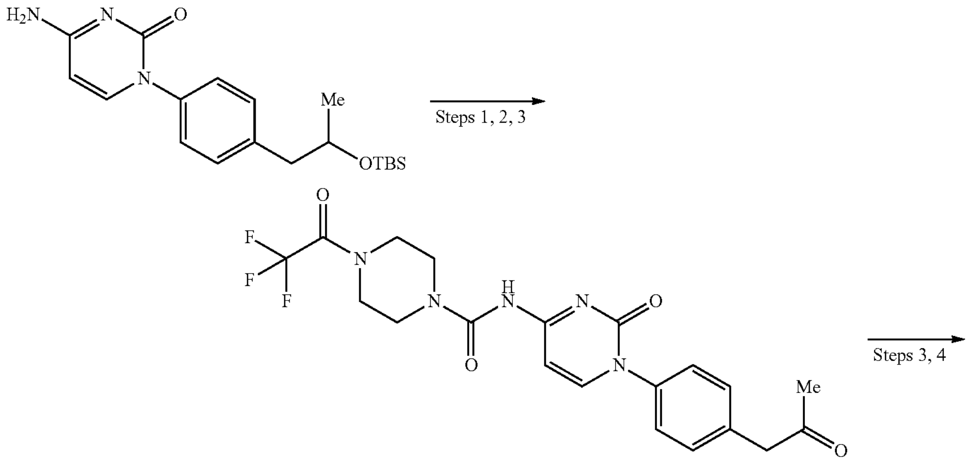

-continued

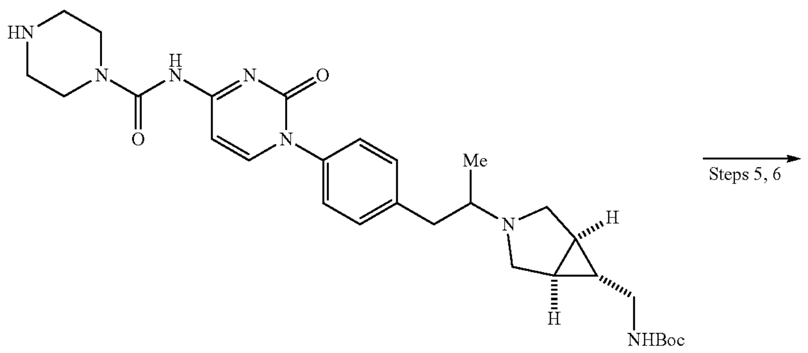

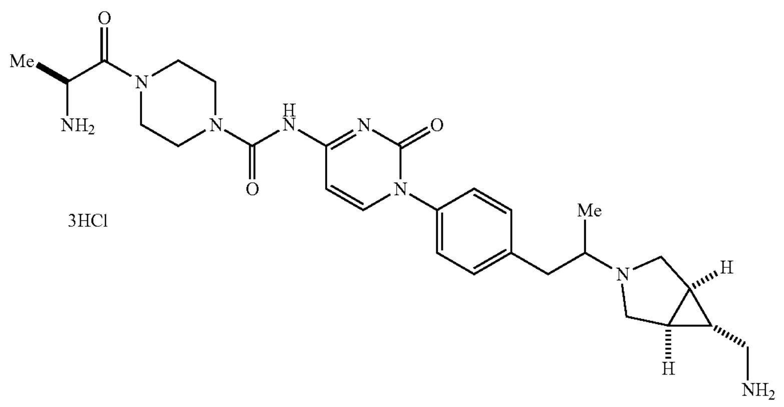

Reagents: 1) 3-methyl-1-(4-(2,2,2-trifluoroacetyl)piperazine-1-carbonyl)-1H-imidazol-3-ium iodide, $CH_3CN$, 85° C., 16 h 2) MeOH, TsOH, 30 min, rt. 3) DMP, $CH_2Cl_2$, rt, 1 h 4) t-butyl ((exo-3-azabicyclo[3.1.0]hexan-6-yl)methyl) carbamate, $NaBH_3CN$, MeOH, rt, 16 h 5) $K_2CO_3$, MeOH, rt, 3 h 5) Boc-amino isobutyric acid, HATU, DIPEA, DMF 16 h 6) HCl in MeOH, rt, 4 h.

Step 1: N-(1-(4-(2-((tert-butyldimethylsilyl)oxy)propyl)phenyl)-2-oxo-1,2-dihydropyrimidin-4-yl)-4-(2,2,2-trifluoroacetyl)piperazine-1-carboxamide. To a stirred solution of (2.5 g, 7.0 mmol) in $CH_3CN$ (250 mL) was added 3-methyl-1-(4-(2,2,2-trifluoroacetyl)piperazine-1-carbonyl)-1H-imidazol-3-ium iodide (7.1 g, 13.2 mmol) and the reaction was heated to 85° C. and refluxed for 16 h. The reaction mixture was concentrated under reduced pressure, which was purified by silica gel column chromatography ($CH_2Cl_2$:MeOH) to afford the desired compound as a yellow solid (85%).

Step 2: N-(1-(4-(2-hydroxypropyl)phenyl)-2-oxo-1,2-dihydropyrimidin-4-yl)-4-(2,2,2-trifluoroacetyl)piperazine-1-carboxamide. To a solution of N-(1-(4-(2-((tert-butyldimethylsilyl)oxy)propyl)phenyl)-2-oxo-1,2-dihydropyrimidin-4-yl)-4-(2,2,2-trifluoroacetyl)piperazine-1-carboxamide (280 mg, 0.50 mmol) in MeOH (20 mL) was added TsOH (180 mg, 1.0 mmol). The reaction was stirred at rt for 1 h. The reaction mixture was concentrated under reduced pressure, dissolved in $CH_2Cl_2$ (50 mL) and washed with sat. aq. aq. $NaHCO_3$ (1×50 mL). The organic layer was concentrated under reduced pressure and purified be column chromatography to afford the desired compound as a white solid (80%).

Step 3: N-(2-oxo-1-(4-(2-oxopropyl)phenyl)-1,2-dihydropyrimidin-4-yl)-4-(2,2,2-trifluoroacetyl)piperazine-1-carboxamide. To a stirred solution of N-(1-(4-(2-hydroxypropyl)phenyl)-2-oxo-1,2-dihydropyrimidin-4-yl)-4-(2,2,2-trifluoroacetyl)piperazine-1-carboxamide (200 mg, 0.44 mmol) in $CH_2Cl_2$ (10 mL) was added DMP (254.0 mg, 0.61 mmol). The solution was stirred for 1 h. The crude reaction mixture was dissolved in additional $CH_2Cl_2$ (50 mL) and washed with aq. $NaHCO_3/Na_2S_2O_3$ (1×50 mL). The aq. layer was extracted with $CH_2Cl_2$ (1×10 mL). The combined organic layers were dried over $Na_2SO_4$ and concentrated under reduced pressure to give the title compound which was used immediately in the next step.

Step 4: tert-butyl ((exo-3-(1-(4-(2-oxo-4-(4-(2,2,2-trifluoroacetyl)piperazine-1-carboxamido)pyrimidin-1 (2H)-yl)

phenyl)propan-2-yl)-3-azabicyclo[3.1.0]hexan-6-yl)methyl) carbamate. To a stirred solution of N-(2-oxo-1-(4-(2-oxopropyl)phenyl)-1,2-dihydropyrimidin-4-yl)-4-(2,2,2-trifluoroacetyl)piperazine-1-carboxamide (190 mg, 0.42 mmol) in MeOH, was added t-butyl ((exo-3-azabicyclo [3.1.0]hexan-6-yl)methyl)carbamate (107 mg, 0.50 mmol) and $NaBH_3CN$ (52 mg, 0.84 mmol). The reaction mixture was stirred for 16 h at rt. The reaction mixture was concentrated under reduced pressure, dissolved in $CHCl_3$ (100 mL) and washed with 10% aq. NaOH solution (1×100 mL). The crude reaction mixture was the purified by column chromatography ($MeOH:CHCl_3$) to afford the title compound.

Step 5: tert-butyl ((exo-3-(1-(4-(2-oxo-4-(piperazine-1-carboxamido)pyrimidin-1 (2H)-yl)phenyl)propan-2-yl)-3-azabicyclo[3.1.0]hexan-6-yl)methyl)carbamate. tert-butyl ((exo-3-(1-(4-(2-oxo-4-(4-(2,2,2-trifluoroacetyl)piperazine-1-carboxamido)pyrimidin-1 (2H)-yl)phenyl)propan-2-yl)-3-azabicyclo[3.1.0]hexan-6-yl)methyl)carbamate (245 mg, 0.38 mmol) and $K_2CO_3$ (138 mg, 1.0 mmol) were dissolved in MeOH (20 mL), and stirred at rt for 3 h. The reaction mixture was concentrated under reduced pressure and the crude solid was purified by column chromatography ($CH_2Cl_2:MeOH:NH_4OH$) to afford the title compound.

Step 6: tert-butyl ((2S)-1-(4-((1-(4-(2-(exo-6-(((tert-butoxycarbonyl)amino)methyl)-3-azabicyclo[3.1.0]hexan-3-yl)propyl)phenyl)-2-oxo-1,2-dihydropyrimidin-4-yl)carbamoyl)piperazin-1-yl)-1-oxopropan-2-yl)carbamate. To a stirring solution of tert-butyl ((exo-3-(1-(4-(2-oxo-4-(piperazine-1-carboxamido)pyrimidin-1 (2H)-yl)phenyl)propan-2-yl)-3-azabicyclo[3.1.0]hexan-6-yl)methyl)carbamate (21 mg, 0.04 mmol) in DMF (0.5 mL) was added (tert-butoxycarbonyl)-L-alanine (7 mg, 0.04 mmol) followed by DIPEA (80 μL, 0.05 mmol). The solution stirred for 5 min and HATU (15 mg, 0.05 mmol) was added and the solution was stirred for 8 h. The crude reaction mixture was dissolved in EtOAc (5 mL) and washed with aqueous LiCl (2×5 mL). The organic layer was dried over $Na_2SO_4$, concentrated under reduced pressure to afford the crude product.

Step 7: 4-(L-alanyl)-N-(1-(4-(2-((exo)-6-(aminomethyl)-3-azabicyclo[3.1.0]hexan-3-yl)propyl)phenyl)-2-oxo-1,2-dihydropyrimidin-4-yl)piperazine-1-carboxamide hydrochloride salt. tert-Butyl ((2S)-1-(4-((1-(4-(2-(exo-6-(((tert-butoxycarbonyl)amino)methyl)-3-azabicyclo[3.1.0]hexan-3-yl)propyl)phenyl)-2-oxo-1,2-dihydropyrimidin-4-yl) carbamoyl)piperazin-1-yl)-1-oxopropan-2-yl)carbamate was dissolved in a solution of HCl in MeOH (2N, 5 mL) and stirred for 4 h. The volatiles were removed under reduced pressure and the crude solid was purified by reverse phase HPLC ($H_2O:CH_3CN:TFA$) and concentrated under reduced pressure. Addition and evaporation under reduced pressure with HCl in MeOH (2N, 3×15 mL) afforded the title compound. $^1H$ NMR (400 MHz, $D_2O$) δ 7.89 (d, 1H), 7.45 (d, 4H), 6.85 (d, 1H), 4.56 (q, 1H), 3.90 (d, 1H), 3.83 (d, 1H), 3.77-3.64 (m, 10H), 3.63-3.56 (m, 1H), 3.42-3.35 (m, 1H), 3.00 (d, 2H), 2.90-2.80 (m, 1H), 2.14-2.03 (m, 2H), 1.53 (d, 3H), 1.42-1.32 (m, 1H), 1.27 (d, 3H). LCMS[M+H] 523.3.

Compound 87

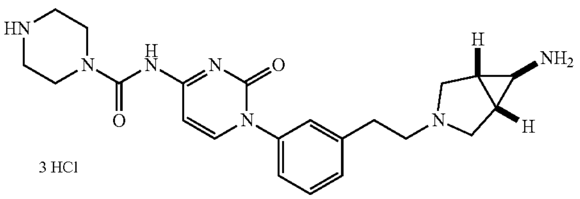

3 HCl

N-(1-(3-(2-(exo-6-Amino-3-azabicyclo[3.1.0]hexan-3-yl)ethyl)phenyl)-2-oxo-1,2-dihydropyrimidin-4-yl) piperazine-1-carboxamide Hydrochloride Salt Prepared in a similar fashion to Scheme C-32 from tert-butyl (exo-3-(3-(2-oxo-4-(4-(2,2,2-trifluoroacetyl)piperazine-1-carboxamido)pyrimidin-1 (2H)-yl)phenethyl)-3-azabicyclo[3.1.0]hexan-6-yl)carbamate $^1H$ NMR (500 MHz, $D_2O$) δ 7.91 (d, 1H), 7.62 (t, 1H), 7.51 (d, 1H), 7.44-7.41 (m, 2H), 6.84 (d, 1H), 3.94 (t, 4H), 3.66-3.55 (m, 4H), 3.41 (t, 4H), 3.19-3.13 (m, 4H), 2.71 (s, 1H), 2.46 (s, 2H). LCMS [M+H] 424.2.

Compound 88

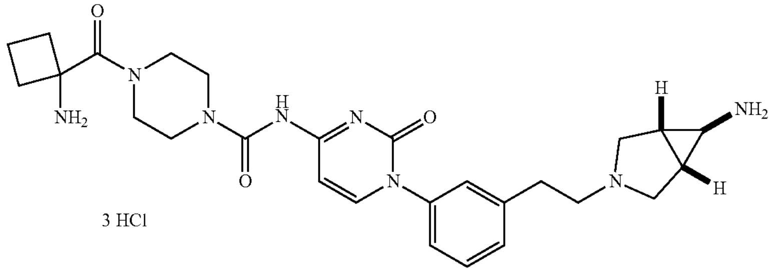

3 HCl

N-(1-(3-(2-(exo-6-Amino-3-azabicyclo[3.1.0]hexan-3-yl)ethyl)phenyl)-2-oxo-1,2-dihydropyrimidin-4-yl)-4-(1-aminocyclobutane-1-carbonyl)piperazine-1-carboxamide hydrochloride Salt Prepared in a similar fashion to Scheme C-32 from tert-butyl (exo-3-(3-(2-oxo-4-(piperazine-1-carboxamido) pyrimidin-1 (2H)-yl)phenethyl)-3-azabicyclo[3.1.0]hexan-6-yl)carbamate and 1-((tert-butoxycarbonyl)amino)cyclobutane-1-carboxylic acid. $^1$H NMR (500 MHz, $D_2O$) δ 8.00 (d, 1H), 7.64 (t, 1H), 7.53 (d, 1H), 7.47-7.42 (m, 2H), 6.90 (d, 1H), 4.00-3.93 (m, 2H), 3.84-3.78 (m, 8H), 3.68-3.59 (m, 4H), 3.18 (s, 2H), 2.98-2.87 (m, 3H), 2.54-2.46 (m, 4H), 2.41-2.34 (m, 1H), 2.22-2.12 (m, 1H). LCMS [M+H] 521.4.

Compound 223

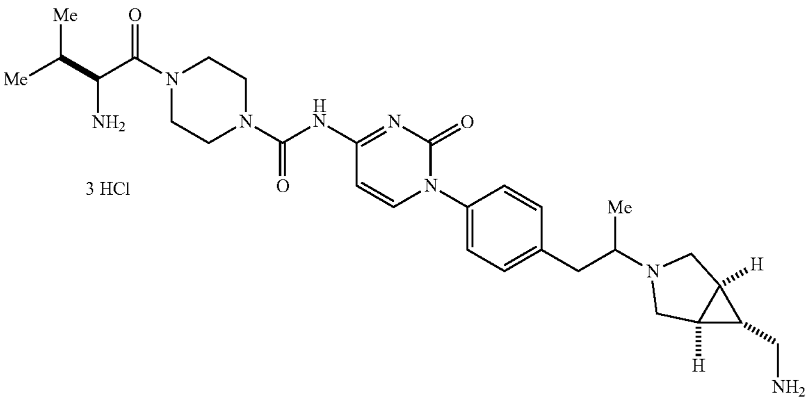

4-(L-Valyl)-N-(1-(4-(2-((exo)-6-(aminomethyl)-3-azabicyclo[3.1.0]hexan-3-yl)propyl)phenyl)-2-oxo-1,2-dihydropyrimidin-4-yl)piperazine-1-carboxamide Prepared in a similar fashion to Scheme C-32 from tert-butyl (((exo)-3-(1-(4-(2-oxo-4-(piperazine-1-carboxamido)pyrimidin-1 (2H)-yl)phenyl)propan-2-yl)-3-azabicyclo[3.1.0]hexan-6-yl)methyl)carbamate and (tert-butoxycarbonyl)-L-valine. $^1$H NMR (400 MHz, $D_2O$) δ 7.99 (d, 1H), 7.52-7.41 (m, 4H), 6.83 (d, 1H), 4.45 (d, 1H), 3.90 (d, 1H), 3.84 (d, 1H), 3.81-3.63 (m, 10H), 3.63-3.55 (m, 1H), 3.43-3.36 (m, 1H), 3.01 (d, 2H), 2.89-2.81 (m, 1H), 2.35-2.25 (m, 1H), 2.16-2.00 (m, 2H), 1.41-1.34 (m, 1H), 1.27 (d, 3H), 1.11 (d, 3H), 1.02 (d, 3H). LCMS[M+H] 551.3.

Compound 226

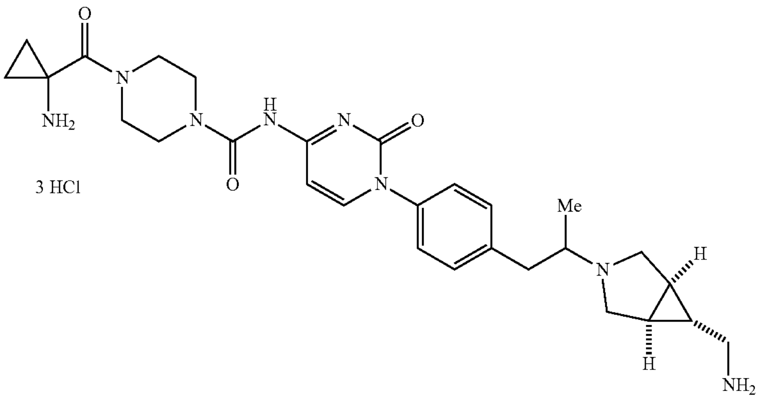

4-(1-Aminocyclopropane-1-carbonyl)-N-(1-(4-(2-((exo)-6-(aminomethyl)-3-azabicyclo[3.1.0]hexan-3-yl)propyl)phenyl)-2-oxo-1,2-dihydropyrimidin-4-yl) piperazine-1-carboxamide Prepared in a similar fashion to Scheme C-32 from tert-butyl (((exo)-3-(1-(4-(2-oxo-4-(piperazine-1-carboxamido)pyrimidin-1 (2H)-yl)phenyl)propan-2-yl)-3-azabicyclo[3.1.0]hexan-6-yl)methyl)carbamate and 1-((tert-butoxycarbonyl)amino)cyclopropane-1-carboxylic acid. $^1$H NMR (400 MHz, $D_2O$) δ 7.99 (d, 1H), 7.50-7.41 (m, 4H), 6.83 (d, 1H), 3.90 (d, 1H), 3.86-3.79 (m, 5H), 3.78-3.71 (m, 4H), 3.70-3.63 (m, 1H), 3.62-3.57 (m, 1H), 3.42-3.35 (m, 1H), 3.00 (d, 2H), 2.89-2.82 (m, 1H), 2.14-2.03 (m, 2H), 1.45 (s, 4H), 1.42-1.34 (m, 1H), 1.26 (d, 3H). LCMS[M+H] 535.2

Compound 227

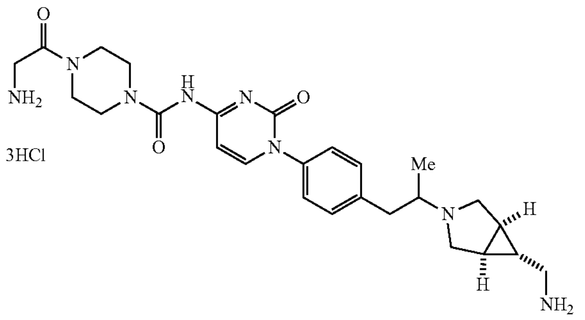

N-(1-(4-(2-((exo)-6-(Aminomethyl)-3-azabicyclo[3.1.0]hexan-3-yl)propyl)phenyl)-2-oxo-1,2-dihydropyrimidin-4-yl)-4-glycylpiperazine-1-carboxamide Prepared in a similar fashion to Scheme C-32 from tert-butyl (((exo)-3-(1-(4-(2-oxo-4-(piperazine-1-carboxamido)pyrimidin-1 (2H)-yl)phenyl)propan-2-yl)-3-azabicyclo[3.1.0]hexan-6-yl)methyl)carbamate and (tert-butoxycarbonyl)-glycine. $^1$H NMR (400 MHz, $D_2O$) δ 7.93 (d, 1H), 7.49-7.35 (m, 4H), 6.83 (d, 1H), 4.09 (s, 2H), 3.89 (d, 1H), 3.82 (d, 1H), 3.75-3.53 (m, 10H), 3.41-3.30 (m, 1H), 2.99 (d, 2H), 2.90-2.79 (m, 1H), 2.14-1.98 (m, 2H), 1.41-1.30 (m, 1H), 1.25 (d, 3H). LCMS[M+H] 509.4.

Compound 228

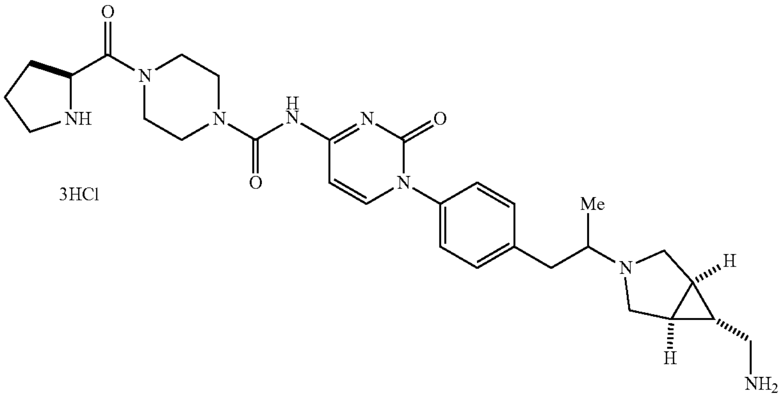

4-(L-Prolyl)-N-(1-(4-(2-((exo)-6-(aminomethyl)-3-azabicyclo[3.1.0]hexan-3-yl)propyl)phenyl)-2-oxo-1,2-dihydropyrimidin-4-yl)piperazine-1-carboxamide Prepared in a similar fashion to Scheme C-32 from tert-butyl (((exo)-3-(1-(4-(2-oxo-4-(piperazine-1-carboxamido)pyrimidin-1 (2H)-yl)phenyl)propan-2-yl)-3-azabicyclo[3.1.0]hexan-6-yl)methyl)carbamate and (tert-butoxycarbonyl)-L-proline. $^{1}$H NMR (400 MHz, $D_2O$) δ 8.03 (d, 1H), 7.53-7.41 (m, 4H), 6.84 (d, 1H), 3.91 (d, 1H), 3.84 (d, 1H), 3.80-3.63 (m, 10H), 3.63-3.57 (m, 1H), 3.54-3.36 (m, 3H), 3.01 (d, 2H), 2.90-2.81 (m, 1H), 2.64-2.52 (m, 1H), 2.20-1.99 (m, 5H), 1-(4-1.32 (m, 1H), 1.27 (d, 3H). LCMS[M+H] 549.3.

Compound 229

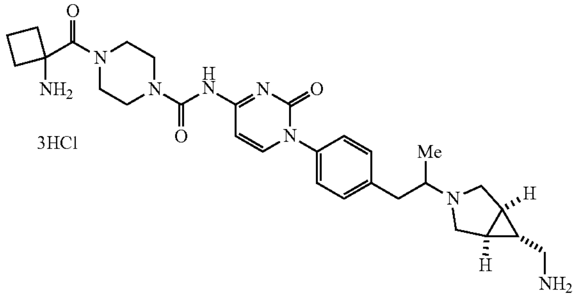

4-(1-Aminocyclobutane-1-carbonyl)-N-(1-(4-(2-((exo)-6-(aminomethyl)-3-azabicyclo[3.1.0]hexan-3-yl)propyl)phenyl)-2-oxo-1,2-dihydropyrimidin-4-yl)piperazine-1-carboxamide Prepared in a similar fashion to Scheme C-32 from tert-butyl (((exo)-3-(1-(4-(2-oxo-4-(piperazine-1-carboxamido)pyrimidin-1 (2H)-yl)phenyl)propan-2-yl)-3-azabicyclo[3.1.0]hexan-6-yl)methyl)carbamate and 1-((tert-butoxycarbonyl)amino)cyclobutane-1-carboxylic acid. $^{1}$H NMR (400 MHz, $D_2O$) δ 7.94 (d, 1H), 7.51-7.42 (m, 4H), 6.85 (d, 1H), 3.90 (d, 1H), 3.84 (d, 1H), 3.77 (s, 8H), 3.71-3.64 (m, 2H), 3.63-3.56 (m, 1H), 3.46-3.36 (m, 1H), 3.01 (d, 2H), 2.96-2.81 (m, 3H), 2.53-2.42 (m, 2H), 2.41-2.28 (m, 1H), 2.19-2.02 (m, 3H), 1.41-1.33 (m, 1H), 1.27 (d, 3H). LCMS [M+H] 549.3.

Compound 230

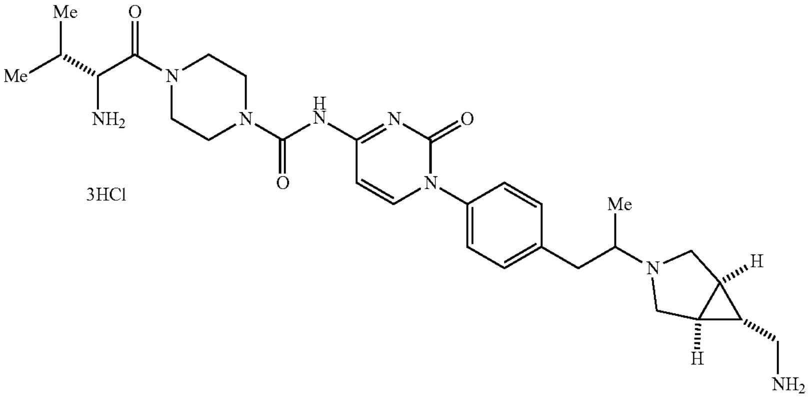

4-(D-valyl)-N-(1-(4-(2-((exo)-6-(Aminomethyl)-3-azabicyclo[3.1.0]hexan-3-yl)propyl)phenyl)-2-oxo-1,2-dihydropyrimidin-4-yl)piperazine-1-carboxamide Prepared in a similar fashion to Scheme C-32 from tert-butyl (((exo)-3-(1-(4-(2-oxo-4-(piperazine-1-carboxamido)pyrimidin-1 (2H)-yl)phenyl)propan-2-yl)-3-azabicyclo[3.1.0]hexan-6-yl)methyl)carbamate and (tert-butoxycarbonyl)-D-valine. $^{1}$H NMR (400 MHz, $D_2O$) δ 8.08 (d, 1H), 7.50-7.43 (m, 4H), 6.82 (d, 1H), 4.44 (d, 1H), 3.90 (d, 1H), 3.84 (d, 1H), 3.82-3.63 (m, 9H), 3.62-3.55 (m, 1H), 3.43-3.36 (m, 1H), 2.99 (d, 2H), 2.90-2.84 (m, 1H), 2.35-2.22 (m, 1H), 2.15-2.01 (m, 2H), 1.41-1.34 (m, 1H), 1.24 (d, 6.5 Hz, 3H), 1.11 (d, 3H), 1.02 (d, 3H). LCMS[M+H] 551.4.

Compound 231

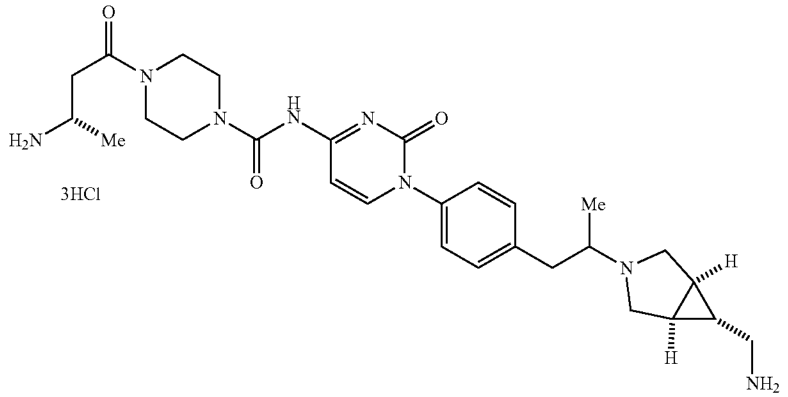

4-((S)-3-Aminobutanoyl)-N-(1-(4-(2-((exo)-6-(aminomethyl)-3-azabicyclo[3.1.0]hexan-3-yl)propyl)phenyl)-2-oxo-1,2-dihydropyrimidin-4-yl)piperazine-1-carboxamide Prepared in a similar fashion to Scheme C-32 from tert-butyl (((exo)-3-(1-(4-(2-oxo-4-(piperazine-1-carboxamido)pyrimidin-1 (2H)-yl)phenyl)propan-2-yl)-3-azabicyclo[3.1.0]hexan-6-yl)methyl)carbamate and (S)-3-((tert-butoxycarbonyl)amino)butanoic acid. $^{1}$H NMR (400 MHz, $D_2O$) δ 8.09 (d, 2H), 7.56-7.38 (m, 4H), 6.82 (d, 1H), 3.97-3.79 (m, 3H), 3.76-3.54 (m, 10H), 3.46-3.32 (m, 2H), 3.00 (d, 2H), 2.92-2.82 (m, 1H), 2.74-2.59 (m, 2H), 2.45-2.33 (m, 2H), 2.16-2.01 (m, 2H), 1.42-1.33 (m, 1H), 1.26 (d, 3H). LCMS[M+H] 537.4

Compound 232

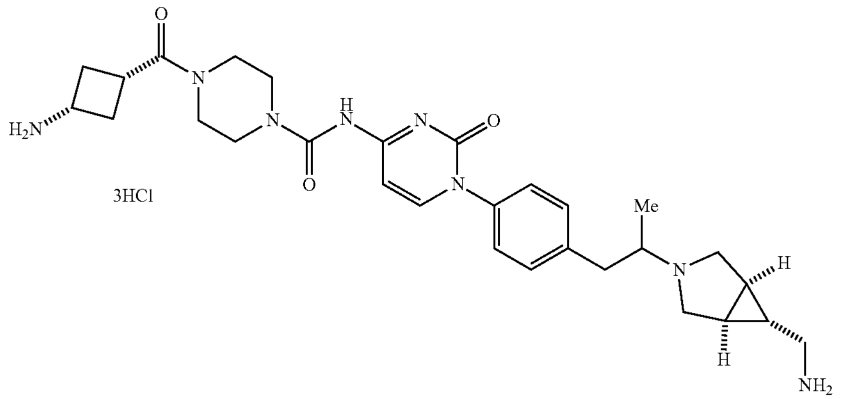

4-((cis)-3-Aminocyclobutane-1-carbonyl)-N-(1-(4-(2-((exo)-6-(aminomethyl)-3-azabicyclo[3.1.0]hexan-3-yl)propyl)phenyl)-2-oxo-1,2-dihydropyrimidin-4-yl)piperazine-1-carboxamide Prepared in a similar fashion to Scheme C-32 from tert-butyl (((exo)-3-(1-(4-(2-oxo-4-(piperazine-1-carboxamido)pyrimidin-1 (2H)-yl)phenyl)propan-2-yl)-3-azabicyclo[3.1.0]hexan-6-yl)methyl)carbamate and (cis)-3-((tert-butoxycarbonyl)amino)cyclobutane-1-carboxylic acid. $^{1}H$ NMR (400 MHz, $D_2O$) δ 8.06 (d, 1H), 7.53-7.42 (m, 4H), 6.83 (d, 1H), 3.90 (d, 1H), 3.87-3.56 (m, 11H), 3.43-3.37 (m, 1H), 3.02 (d, 2H), 2.98-2.91 (m, 1H), 2.90-2.74 (m, 2H), 2.15-2.01 (m, 2H), 1-(4-1.34 (m, 4H), 1.26 (d, 3H). LCMS [M+H] 549.2.

Compound 233

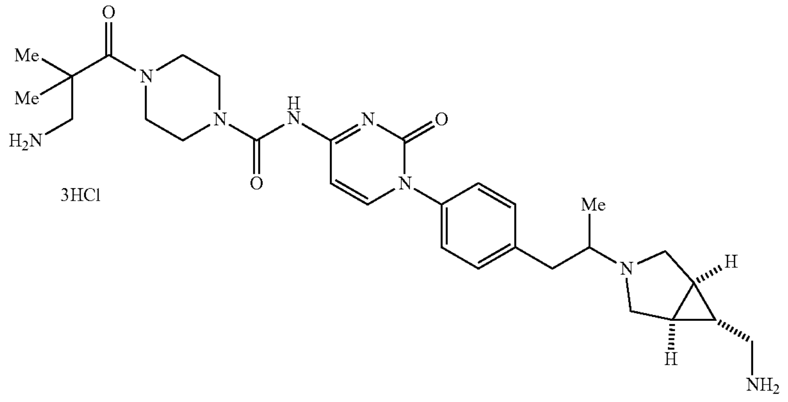

4-(3-Amino-2,2-dimethylpropanoyl)-N-(1-(4-(2-((exo)-6-(aminomethyl)-3-azabicyclo[3.1.0]hexan-3-yl)propyl)phenyl)-2-oxo-1,2-dihydropyrimidin-4-yl)piperazine-1-carboxamide Prepared in a similar fashion to Scheme C-32 from tert-butyl (((exo)-3-(1-(4-(2-oxo-4-(piperazine-1-carboxamido)pyrimidin-1 (2H)-yl)phenyl)propan-2-yl)-3-azabicyclo[3.1.0]hexan-6-yl)methyl)carbamate and 3-((tert-butoxycarbonyl)amino)-2,2-dimethylpropanoic acid. $^{1}H$ NMR (400 MHz, $D_2O$) δ 8.05 (d, 1H), 7.53-7.41 (m, 4H), 6.82 (d, 1H), 3.91 (d, 1H), 3.86-3.63 (m, 10H), 3.63-3.56 (m, 1H), 3.44-3.37 (m, 1H), 3.14 (s, 2H), 3.04-2.96 (m, 2H), 2.92-2.81 (m, 1H), 2.15-2.02 (m, 2H), 1.46 (s, 6H), 1.42-1.35 (m, 1H), 1.26 (t, 3H). LCMS[M+H] 551.4.

Compound 234

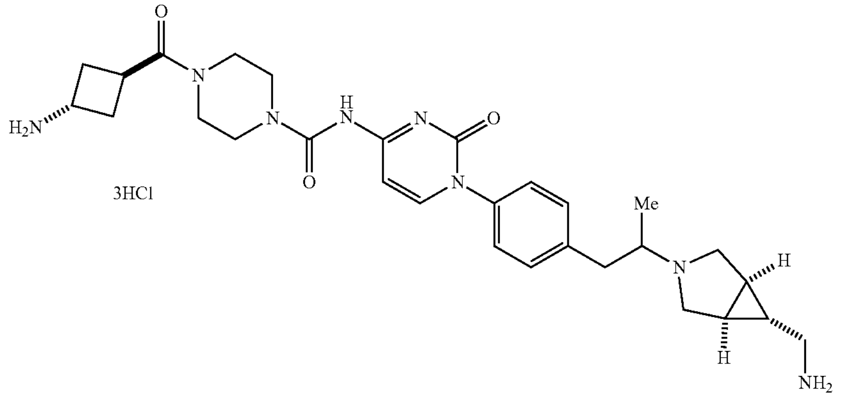

4-((trans)-3-Aminocyclobutane-1-carbonyl)-N-(1-(4-(2-((exo)-6-(aminomethyl)-3-azabicyclo[3.1.0]hexan-3-yl)propyl)phenyl)-2-oxo-1,2-dihydropyrimidin-4-yl)piperazine-1-carboxamide Prepared in a similar fashion to Scheme C-32 from tert-butyl (((exo)-3-(1-(4-(2-oxo-4-(piperazine-1-carboxamido)pyrimidin-1 (2H)-yl)phenyl)propan-2-yl)-3-azabicyclo[3.1.0]hexan-6-yl)methyl)carbamate and (trans)-3-((tert-butoxycarbonyl)amino)cyclobutane-1-carboxylic acid. $^1H$ NMR (400 MHz, $D_2O$) δ 7.99 (d, 1H), 7.52-7.41 (m, 4H), 6.84 (d, 1H), 3.99-3.78 (m, 3H), 3.73-3.55 (m, 11H), 3.44-3.37 (m, 1H), 3.01 (d, 2H), 2.92-2.80 (m, 1H), 2.73-2.63 (m, 2H), 2.58-2.48 (m, 2H), 2.15-2.00 (m, 2H), 1.37 (d, 1H), 1.27 (d, 3H). LCMS[M+H] 549.2.

Compound 235

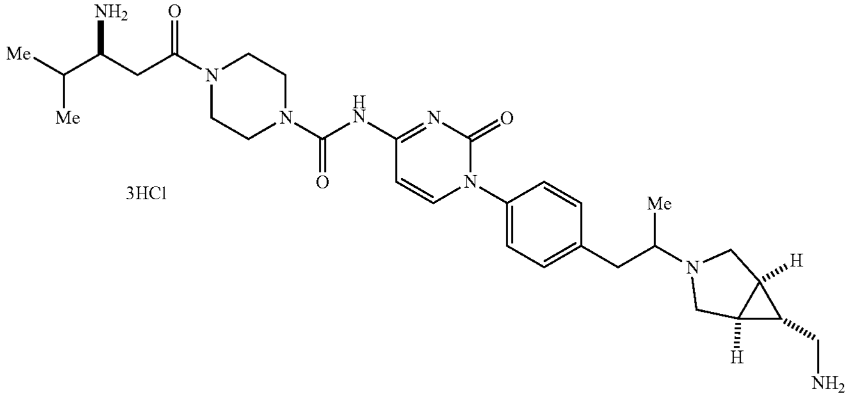

3HCl 4-((S)-3-Amino-4-methylpentanoyl)-N-(1-(4-(2-((exo)-6-(aminomethyl)-3-azabicyclo[3.1.0]hexan-3-yl)propyl)phenyl)-2-oxo-1,2-dihydropyrimidin-4-yl)piperazine-1-carboxamide Prepared in a similar fashion to Scheme C-32 from tert-butyl (((exo)-3-(1-(4-(2-oxo-4-(piperazine-1-carboxamido)pyrimidin-1 (2H)-yl)phenyl)propan-2-yl)-3-azabicyclo[3.1.0]hexan-6-yl)methyl)carbamate and (S)-3-((tert-butoxycarbonyl)amino)-4-methylpentanoic acid. $^1H$ NMR (400 MHz, $D_2O$) δ 8.06 (d, 1H), 7.51-7.42 (m, 4H), 6.82 (d, 1H), 3.90 (d, 1H), 3.83 (d, 1H), 3.78-3.50 (m, 12H), 3.44-3.36 (m, 1H), 3.04-2.94 (m, 3H), 2.89-2.66 (m, 2H), 2.18-1.98 (m, 2H), 1.39-1.32 (m, 1H), 1.26 (d, 3H), 1.11-0.97 (m, 6H). LCMS[M+H] 565.3.

Compound 236

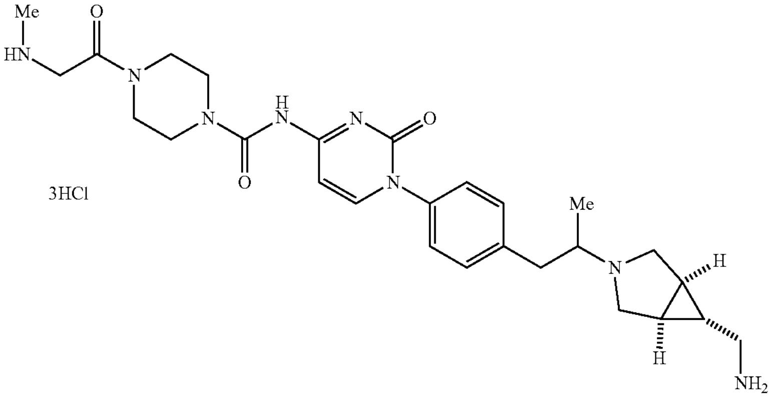

3HCl

N-(1-(4-(2-((exo)-6-(Aminomethyl)-3-azabicyclo[3.1.0]hexan-3-yl)propyl)phenyl)-2-oxo-1,2-dihydropyrimidin-4-yl)-4-(methylglycyl)piperazine-1-carboxamide Prepared in a similar fashion to Scheme C-32 from tert-butyl (((exo)-3-(1-(4-(2-oxo-4-(piperazine-1-carboxamido)pyrimidin-1 (2H)-yl)phenyl)propan-2-yl)-3-azabicyclo[3.1.0]hexan-6-yl)methyl)carbamate and N-(tert-butoxycarbonyl)-N-methylglycine. $^1$H NMR (400 MHz, $D_2O$) δ 8.02 (d, 1H), 7.50-7.42 (m, 4H), 6.83 (d, 1H), 4.19 (s, 2H), 3.90 (d, 1H), 3.84 (d, 1H), 3.79-3.63 (m, 7H), 3.63-3.56 (m, 3H), 3.42-3.37 (m, 1H), 3.00 (d, 2H), 2.88-2.82 (m, 1H), 2.81 (s, 3H), 2.16-2.01 (m, 2H), 1.41-1.33 (m, 1H), 1.26 (d, 3H). LCMS[M+H] 523.3.

Compound 239

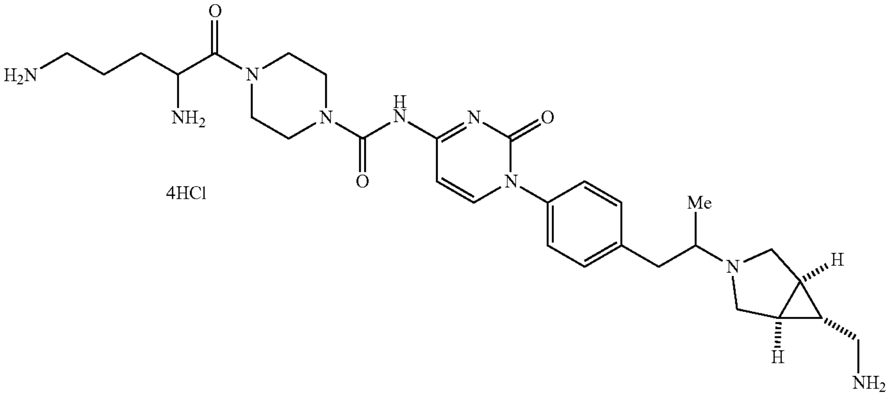

N-(1-(4-(2-((exo)-6-(Aminomethyl)-3-azabicyclo[3.1.0]hexan-3-yl)propyl)phenyl)-2-oxo-1,2-dihydropyrimidin-4-yl)-4-(2,5-diaminopentanoyl)piperazine-1-carboxamide Prepared in a similar fashion to Scheme C-32 from tert-butyl (((exo)-3-(1-(4-(2-oxo-4-(piperazine-1-carboxamido)pyrimidin-1 (2H)-yl)phenyl)propan-2-yl)-3-azabicyclo[3.1.0]hexan-6-yl)methyl)carbamate and 2,5-bis((tert-butoxycarbonyl)amino)pentanoic acid. LCMS[M+H] 566.4.

Compound 240

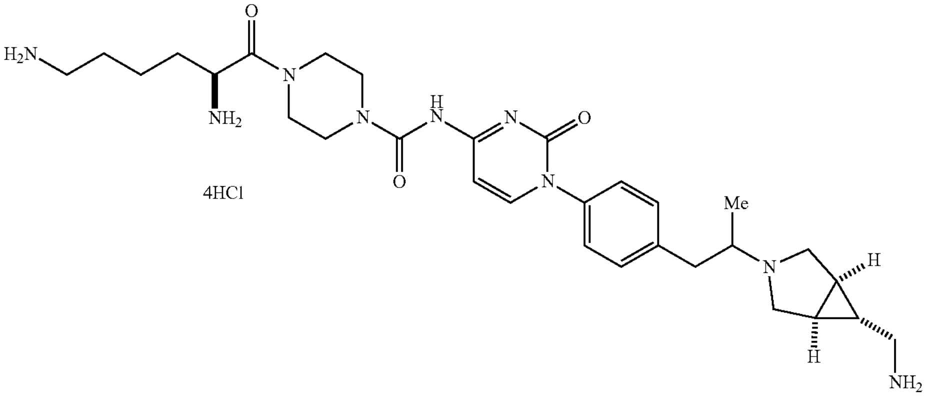

4-(L-lysyl)-N-(1-(4-(2-((exo)-6-(aminomethyl)-3-azabicyclo[3.1.0]hexan-3-yl)propyl)phenyl)-2-oxo-1,2-dihydropyrimidin-4-yl)piperazine-1-carboxamide Prepared in a similar fashion to Scheme C-32 from tert-butyl (((exo)-3-(1-(4-(2-oxo-4-(piperazine-1-carboxamido)pyrimidin-1 (2H)-yl)phenyl)propan-2-yl)-3-azabicyclo[3.1.0]hexan-6-yl)methyl)carbamate and $N^2$,$N^6$-bis(tert-butoxycarbonyl)-L-lysine. $^1$H NMR (400 MHz, $D_2O$) δ 7.94 (d, 1H), 7.55-7.41 (m, 4H), 6.85 (d, 1H), 4.59 (t, 1H), 3.90 (d, 1H), 3.87-3.63 (m, 10H), 3.63-3.57 (m, 1H), 3.43-3.33 (m, 2H), 3.08-2.94 (m, 3H), 2.92-2.78 (m, 1H), 2.17-2.03 (m, 2H), 2.01-1.89 (m, 2H), 1.80-1.65 (m, 2H), 1.59-1.44 (m, 2H), 1.41-1.32 (m, 1H), 1.26 (d, 3H). LCMS[M+H] 580.2.

Compound 224

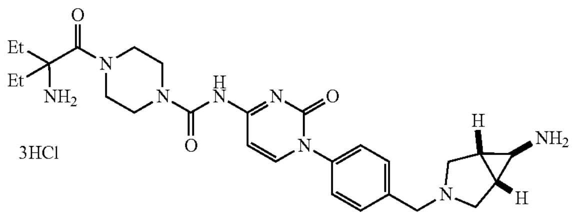

4-(2-Amino-2-ethylbutanoyl)-N-(1-(4-((exo-6-amino-3-azabicyclo[3.1.0]hexan-3-yl)methyl)phenyl)-2-oxo-1,2-dihydropyrimidin-4-yl)piperazine-1-carboxamide hydrochloride salt Prepared in a similar fashion to Scheme C-32 using tert-butyl ((exo-3-(4-(2-oxo-4-(piperazine-1-carboxamido)pyrimidin-1 (2H)-yl)benzyl)-3-azabicyclo[3.1.0]hexan-6-yl)carbamate (0.10 g, 0.20 mmol), and 2-((tert-butoxycarbonyl)amino)-2-ethylbutanoic acid (0.05 g, 0.20 mmol). $^1$H NMR (500 MHz, $D_2O$): δ 7.96 (d, 1H), 7.66 (d, 2H), 7.54 (d, 2H), 6.83 (d, 1H), 4.46 (s, 2H), 3.89-3.63 (m, 12H), 2.90-2.84 (m, 1H), 2.41 (s, 2H), 2.22-2.14 (m, 2H), 2.05-1.97 (m, 2H), 0.99 (t, 6H). LCMS [M+H] 523.4.

Compound 25

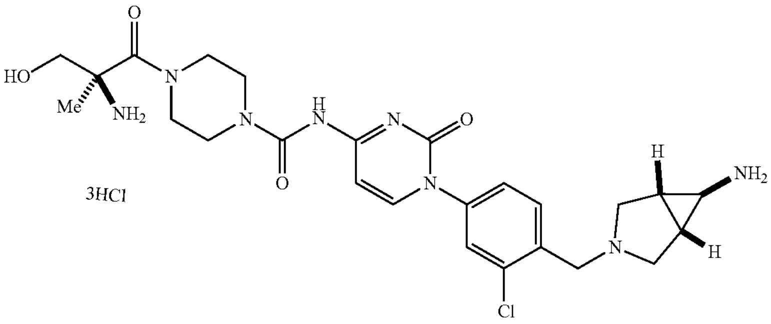

N-(1-(4-((exo-6-Amino-3-azabicyclo[3.1.0]hexan-3-yl)methyl)-3-chlorophenyl)-2-oxo-1,2-dihydropyrimidin-4-yl)-4-((S)-2-amino-3-hydroxy-2-methylpropanoyl)piperazine-1-carboxamide Hydrochloride Salt Prepared in a similar fashion to Scheme C-32 from tert-butyl (exo-3-(2-chloro-4-(2-oxo-4-(piperazine-1-carboxamido)pyrimidin-1 (2H)-yl)benzyl)-3-azabicyclo[3.1.0]hexan-6-yl)carbamate and (2R,4S)-3-(tert-butoxycarbonyl)-2-(tert-butyl)-4-methyloxazolidine-4-carboxylic acid. $^1$H NMR (400 MHz, $CD_3OD$) δ 7.68 (s, 1H), 7.52 (d, 2H), 7.34 (d, 1H), 6.54 (s 1H), 4.05 (d, 1H), 3.70-3.79 (m, 11H), 3.10 (d, 2H), 2.84 (s, 1H), 2.54 (d, 2H), 1.80 (s, 2H), 1.60 (s, 3H). LCMS [M+H] 545.1.

Compound 36

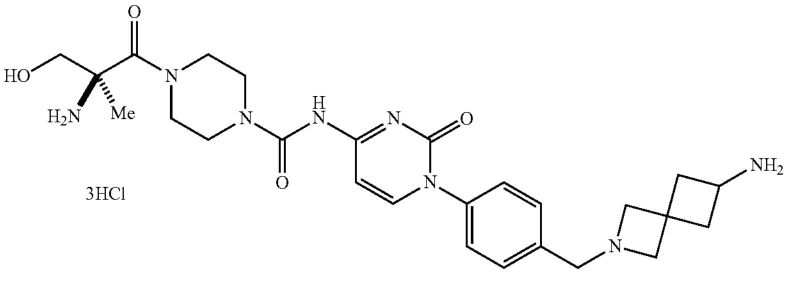

(S)—N-(1-(4-((6-Amino-2-azaspiro[3.3]heptan-2-yl)methyl)phenyl)-2-oxo-1,2-dihydropyrimidin-4-yl)-4-(2-amino-3-hydroxy-2-methylpropanoyl)piperazine-1-carboxamide Hydrochloride Salt Prepared in a similar fashion to Scheme C-32 from tert-butyl (2-(4-(2-oxo-4-(piperazine-1-carboxamido)pyrimidin-1 (2H)-yl)benzyl)-2-azaspiro[3.3]heptan-6-yl)carbamate and (2R,4S)-3-(tert-butoxycarbonyl)-2-(tert-butyl)-4-methyloxazolidine-4-carboxylic acid. $^1$H NMR (500 MHz, $D_2O$) δ 8.19 (d, 1H), 7.63 (d, 2H), 7.57 (d, 2H), 6.80 (d, 1H), 4.44 (s, 2H), 4.34-4.27 (m, 3H), 4.20-4.13 (m, 2H), 3.88 (d, 1H), 3.82-3.72 (m, 8H), 3.38 (t, 1H), 2.82-2.76 (m, 1H), 2.73-2.66 (m, 1H), 2.54-2.45 (m, 2H), 1.67 (s, 3H). LCMS [M+H] 525.1.

Compound 37

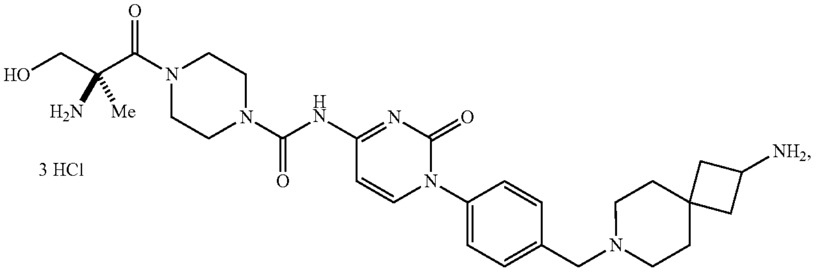

(S)—N-(1-(4-((6-Amino-7-azaspiro[3.5]nonan-7-yl)methyl)phenyl)-2-oxo-1,2-dihydropyrimidin-4-yl)-4-(2-amino-3-hydroxy-2-methylpropanoyl)piperazine-1-carboxamide Hydrochloride Salt Prepared in a similar fashion to Scheme C-32 from tert-butyl (7-(4-(2-oxo-4-(piperazine-1-carboxamido)pyrimidin-1 (2H)-yl)benzyl)-7-azaspiro[3.5]nonan-2-yl)carbamate and (2R,4S)-3-(tert-butoxycarbonyl)-2-(tert-butyl)-4-methyloxazolidine-4-carboxylic acid. $^{1}H$ NMR (500 MHz, $D_2O$) δ 8.12 (d, 1H), 7.68 (d, 2H), 7.58 (d, 2H), 6.83 (d, 1H), 4.38 (s, 2H), 4.16 (d, 1H), 3.90 (d, 1H), 3.88-3.74 (m, 8H), 3.50-3.39 (m, 3H), 3.13-3.00 (m, 2H), 2.50 (t, 1H), 2.29 (t, 1H), 2.11-2.00 (m, 3H), 1.99-1.80 (m, 3H), 1.68 (s, 3H). LCMS [M+H] 553.2.

Compound 40

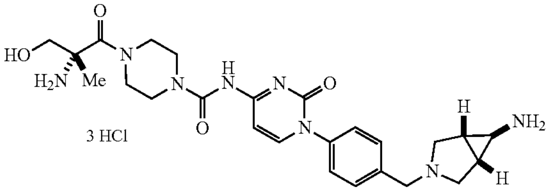

N-(1-(4-((exo-6-Amino-3-azabicyclo[3.1.0]hexan-3-yl)methyl)phenyl)-2-oxo-1,2-dihydropyrimidin-4-yl)-4-((R)-2-amino-3-hydroxy-2-methylpropanoyl)piperazine-1-carboxamide Hydrochloride Salt Prepared in a similar fashion to Scheme C-32 from tert-butyl (exo-3-(4-(2-oxo-4-(piperazine-1-carboxamido)pyrimidin-1 (2H)-yl)benzyl)-3-azabicyclo[3.1.0]hexan-6-yl)carbamate and (2S,4R)-3-(tert-butoxycarbonyl)-2-(tert-butyl)-4-methyloxazolidine-4-carboxylic acid. $^{1}H$ NMR (500 MHz, $D_2O$) δ 8.02 (d, 1H), 7.67 (d, 2H), 7.56 (d, 2H), 6.14 (d, 1H), 4.48 (s, 2H), 4.16 (d, 1H), 3.90 (d, 1H), 3.85-3.63 (m, 12H), 2.92-2.80 (m, 1H), 2.43 (s, 2H), 1.68 (s, 3H). LCMS [M+H] 511.3.

7.65 (d, 2H), 7.54 (d, 2H), 6.84 (d, 1H), 4.46 (s, 2H), 3.90-3.52 (m, 12H), 3.22-3.08 (m, 3H), 2.92-2.80 (m, 1H), 2.41 (s, 2H), 2.30-2.26 (m, 2H). LCMS [M+H] 510.2.

Compound 43

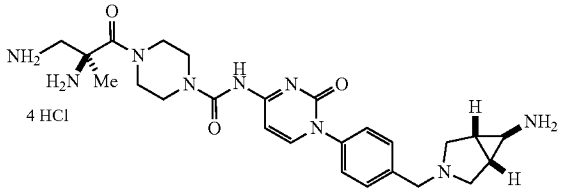

N-(1-(4-((exo-6-Amino-3-azabicyclo[3.1.0]hexan-3-yl)methyl)phenyl)-2-oxo-1,2-dihydropyrimidin-4-yl)-4-((S)-2,3-diaminopropanoyl)piperazine-1-carboxamide Hydrochloride Salt Prepared in a similar fashion to Scheme C-32 from tert-butyl (exo-3-(4-(2-oxo-4-(piperazine-1-carboxamido)pyrimidin-1 (2H)-yl)benzyl)-3-azabicyclo[3.1.0]hexan-6-yl)carbamate and (S)-2,3-bis((tert-butoxycarbonyl)amino)propanoic acid. $^{1}H$ NMR (500 MHz, $D_2O$) δ 7.88 (d, 1H), 7.76 (d, 2H), 7.55 (d, 2H), 6.86 (d, 1H), 4.94 (t, 1H), 4.47 (s, 2H), 3.92-3.51 (m, 14H), 2.92-2.80 (m, 1H), 2.43 (s, 2H). LCMS [M+H] 496.2.

Compound 44

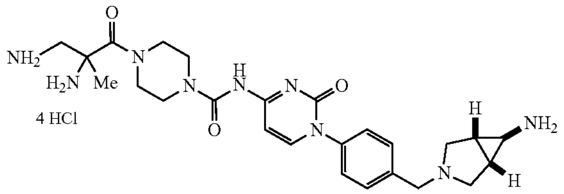

Compound 41

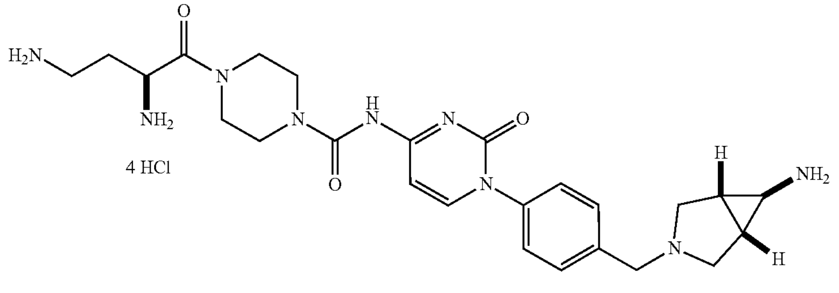

N-(1-(4-((exo-6-Amino-3-azabicyclo[3.1.0]hexan-3-yl)methyl)phenyl)-2-oxo-1,2-dihydropyrimidin-4-yl)-4-((S)-2,4-diaminobutanoyl)piperazine-1-carboxamide Hydrochloride salt Prepared in a similar fashion to Scheme C-32 from tert-butyl (exo-3-(4-(2-oxo-4-(piperazine-1-carboxamido)pyrimidin-1 (2H)-yl)benzyl)-3-azabicyclo[3.1.0]hexan-6-yl)carbamate and (S)-2,4-bis((tert-butoxycarbonyl)amino)butanoic acid. $^{1}H$ NMR (500 MHz, $D_2O$) δ 7.90 (d, 1H),

N-(1-(4-((exo-6-Amino-3-azabicyclo[3.1.0]hexan-3-yl)methyl)phenyl)-2-oxo-1,2-dihydropyrimidin-4-yl)-4-(2,3-diamino-2-methylpropanoyl)piperazine-1-carboxamide Hydrochloride Salt Prepared in a similar fashion to Scheme C-32 from tert-butyl (exo-3-(4-(2-oxo-4-(piperazine-1-carboxamido)pyrimidin-1 (2H)-yl)benzyl)-3-azabicyclo[3.1.0]hexan-6-yl)carbamate and 2,3-bis((tert-butoxycarbonyl)amino)-2-methylpropanoic acid. $^{1}H$ NMR (500 MHz, $D_2O$) δ 7.91 (d, 1H), 7.67 (d, 2H), 7.55 (d, 2H), 6.86 (d, 1H), 4.47 (s, 2H), 3.95-3.50 (m, 14H), 2.92-2.80 (m, 1H), 2.43 (s, 2H), 1.86 (s, 3H). LCMS [M+H] 510.2.
Compound 241
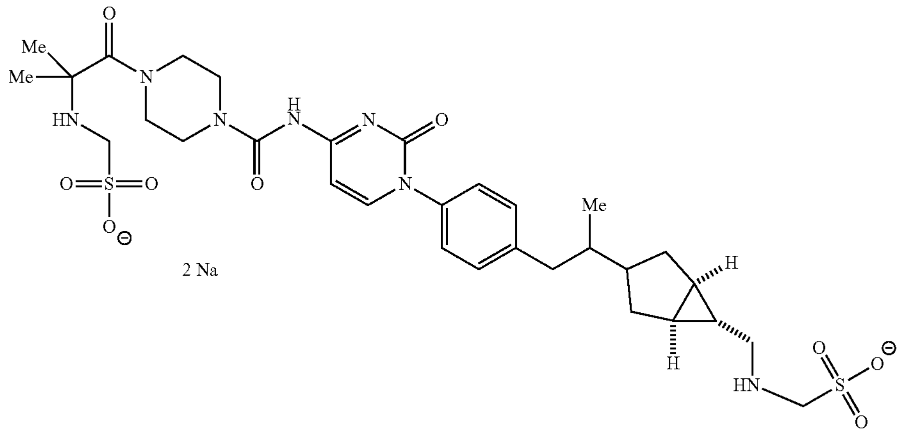
((2-methyl-1-oxo-1-(4-((2-oxo-1-(4-(2-((exo)-6-(((sulfonatomethyl)amino)methyl)-3-azabicyclo[3.1.0]hexan-3-yl)propyl)phenyl)-1,2-dihydropyrimidin-4-yl)carbamoyl)piperazin-1-yl)propan-2-yl)amino)methanesulfonate sodium salt
Scheme C-33
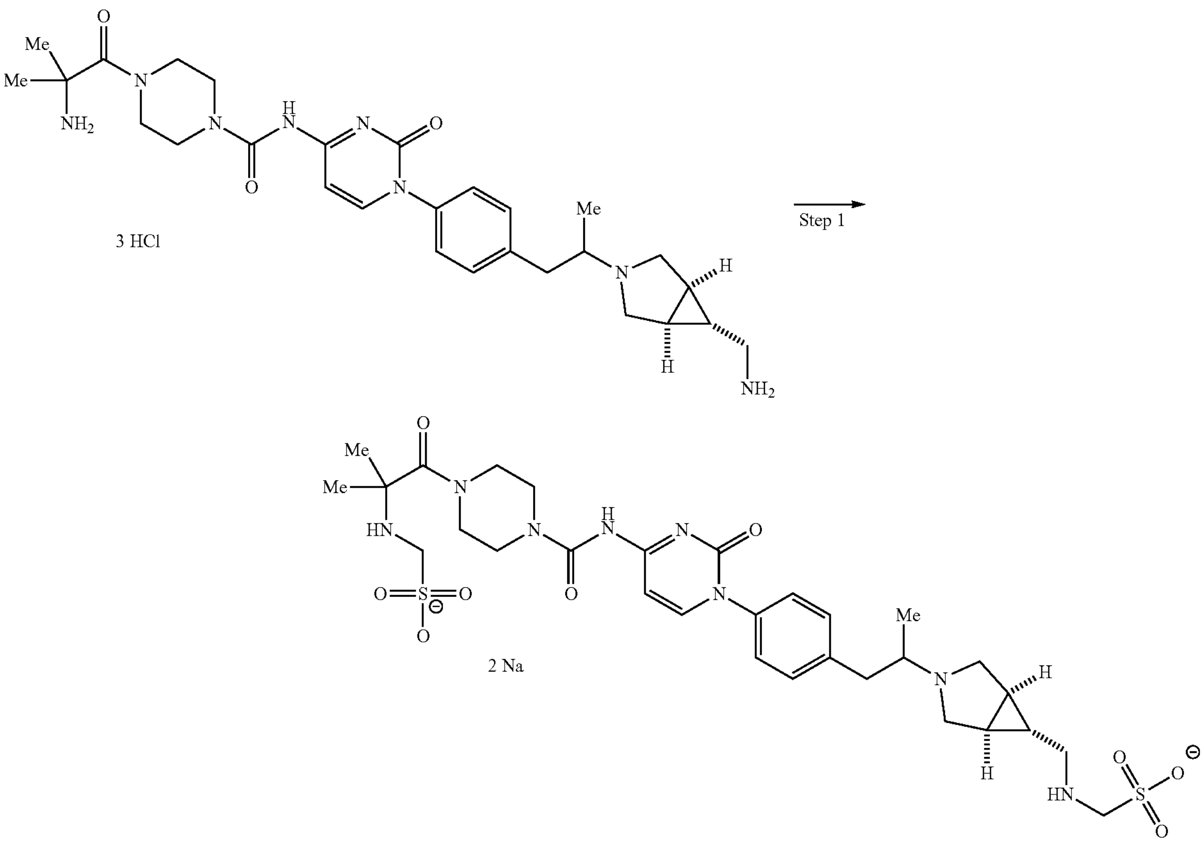

Reagents: Step 1 MeOH, tetra-alkylamonium carbonate, formalin, $NaHSO_3H_2O$, 3 h. rt. Step 1: ((2-methyl-1-oxo-1-(4-((2-oxo-1-(4-(2-((exo)-6-(((sulfonatomethyl)amino)methyl)-3-azabicyclo[3.1.0]hexan-3-yl)propyl)phenyl)-1,2-dihydropyrimidin-4-yl)carbamoyl)piperazin-1-yl)propan-2-yl)amino)methanesulfonate sodium salt. To a solution of 4-(2-amino-2-methylpropanoyl)-N-(1-(4-(2-((exo)-6-(aminomethyl)-3-azabicyclo[3.1.0]hexan-3-yl)propyl)phenyl)-2-oxo-1,2-dihydropyrimidin-4-yl)piperazine-1-carboxamide hydrochloride salt (50 mg, 0.07 mmol) was added polymer bound tetra-alkylamonium carbonate (mg 5, 0.40 mmol). The suspension was shaken for 30 min, and the solids were removed by filtration, concentrated under reduced pressure and dissolved in $H_2O$ (3 mL). Solid $NaHSO_3$ (0.08 mmol) and formalin (0.10 mmol) were added and the reaction mixture stirred for 30 min. and filtered. The filtrate was concentrated under reduced pressure to afford the title compound. $^1H$ NMR (400 MHz, $D_2O$) δ 8.07 (d, 1H), 7.23 (s, 4H), 6.53 (d, 1H), 4.57 (s, 2H), 4.45 (s, 2H), 3.66-3.47 (m, 9H), 3.44-3.29 (m, 3H), 3.16-3.09 (m, 1H), 2.82 (d, 2H), 2.67-2.53 (m, 1H), 1.81 (s, 2H), 1.50 (s, 6H), 1.26-1.08 (m, 1H), 0.98 (d, 3H).

Compound 220

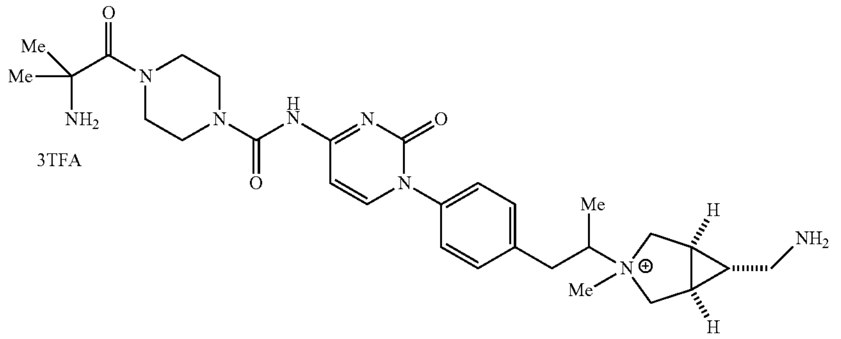

(exo)-3-(1-(4-(4-(4-(2-Amino-2-methylpropanoyl)piperazine-1-carboxamido)-2-oxopyrimidin-1 (2H)-yl)phenyl)propan-2-yl)-6-(aminomethyl)-3-methyl-3-azabicyclo[3.1.0]hexan-3-ium trifluoroacetate Salt Scheme C-34

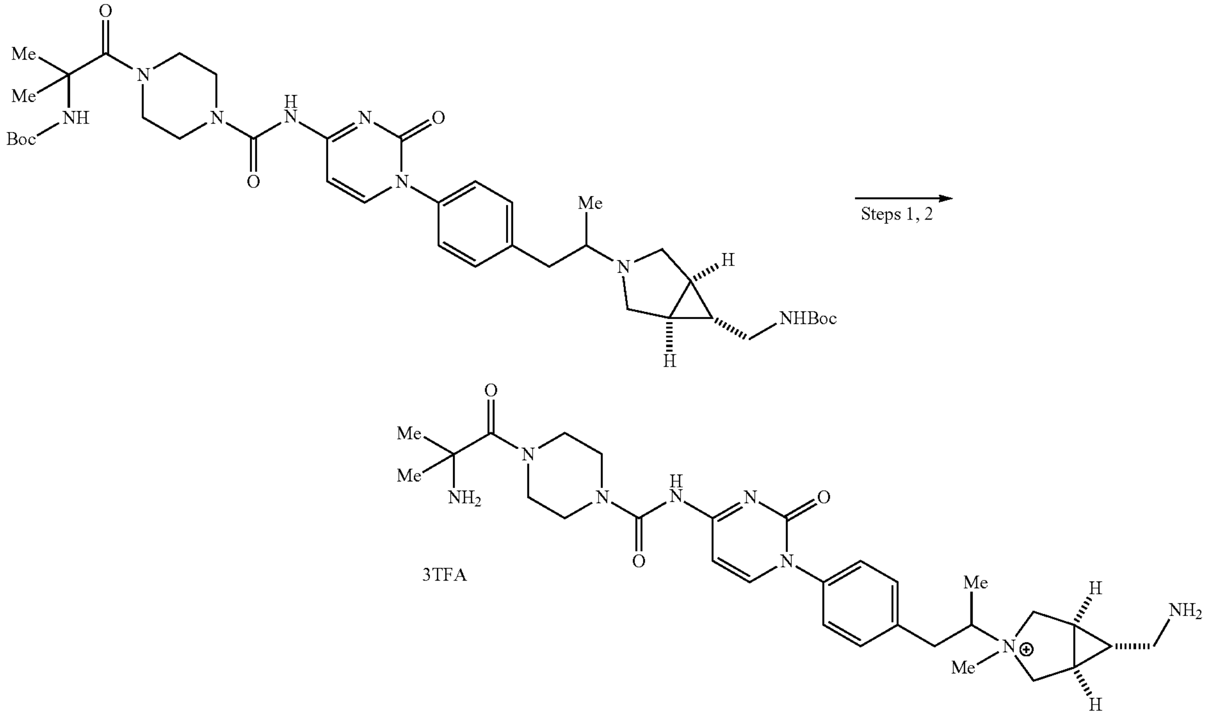

Reagents: 1) Met, $CH_3CN$, rt, 30 min 2) TFA, $CH_2Cl_2$, rt. 1 h.

Step 1: exo-3-(1-(4-(4-(4-(2-((tert-butoxycarbonyl)amino)-2-methylpropanoyl)piperazine-1-carboxamido)-2-oxopyrimidin-1 (2H)-yl)phenyl)propan-2-yl)-6-(((tert-butoxycarbonyl)amino)methyl)-3-methyl-3-azabicyclo[3.1.0]hexan-3-ium iodide. To a solution of tert-butyl ((exo-3-(1-(4-(4-(4-(2-((tert-butoxycarbonyl)amino)-2-methylpropanoyl)piperazine-1-carboxamido)-2-oxopyrimidin-1 (2H)-yl)phenyl)propan-2-yl)-3-azabicyclo[3.1.0]hexan-6-yl)methyl)carbamate (30 mg 0.04 mmol) in $CH_3CN$ (0.25 mL), was added Met (0.03 mL 0.4 mmol). The reaction was filtered and the title compound was collected as a white solid.

Step 2: (exo-3-(1-(4-(4-(4-(2-amino-2-methylpropanoyl)piperazine-1-carboxamido)-2-oxopyrimidin-1 (2H)-yl)phenyl)propan-2-yl)-6-(aminomethyl)-3-methyl-3-azabicyclo[3.1.0]hexan-3-ium trifluoroacetate salt. exo-3-(1-(4-(4-(4-(2-((tert-butoxycarbonyl)amino)-2-methylpropanoyl)piperazine-1-carboxamido)-2-oxopyrimidin-1 (2H)-yl)phenyl)propan-2-yl)-6-(((tert-butoxycarbonyl)amino)methyl)-3-methyl-3-azabicyclo[3.1.0]hexan-3-ium iodide was dissolved in $CH_2Cl_2$:TFA (1:1, 0.25 mL) and stirred for 1 h. The reaction mixture was concentrated under reduced pressure and the solid was triturated with $Et_2O$ to afford the desired compound as a yellow solid. LCMS[M+H] 551.3.

Compound 207

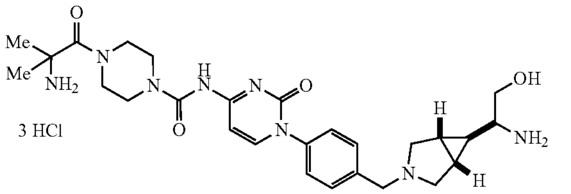

N-(1-(4-((exo-6-((S)-1-Amino-2-hydroxyethyl)-3-azabicyclo[3.1.0]hexan-3-yl)methyl)phenyl)-2-oxo-1,2-dihydropyrimidin-4-yl)-4-(2-amino-2-methylpropanoyl)piperazine-1-carboxamide Hydrochloride Salt Scheme C-35

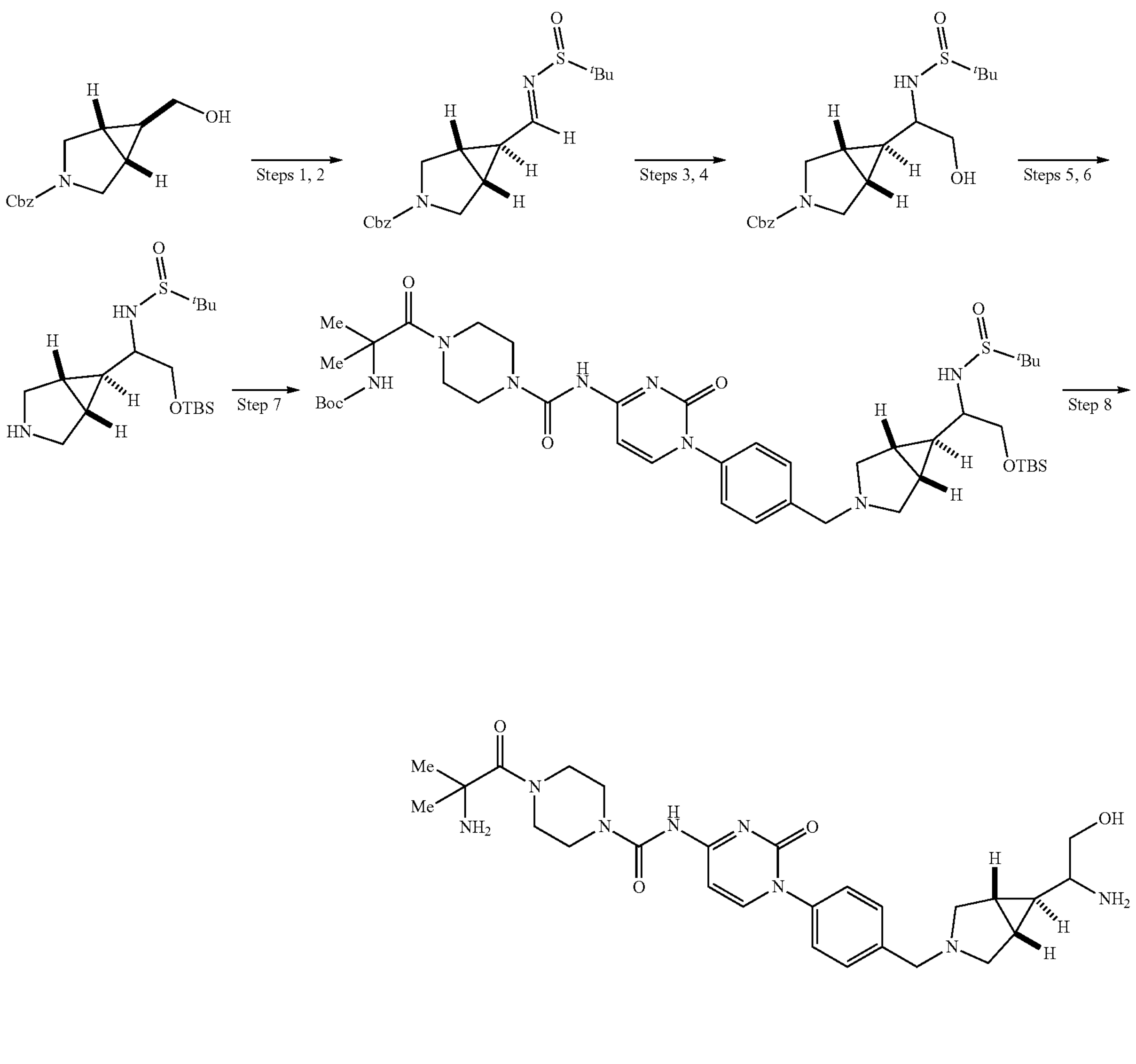

Reagents: Step 1) Oxalyl Chloride, DMSO, $Et_3N$, $CH_2Cl_2$, −78° C. rt, 2 h 2) (S)-(−)-2-methylpropane-2-sulfinamide, $Ti(OPr)_4$ THF, reflux, 16 h 3) (isopropoxydimethylsilyl)magnesium chloride, THF, −20° C. to rt, 16 h 4) $KHCO_3KF$, $H_2O_2$ THF:MeOH, rt to 50° C., 2 h 5) Imidazole, TBS-$C_1CH_2Cl_2$, rt, 16 h 6) $Pd(OH)_2$ MeOH, $H_2$ (g) atm, rt, 16 h 7) tert-Butyl (1-(44 (1-(4-formylphenyl)-2-oxo-1,2-dihydropyrimidin-4-yl)carbamoyl)piperazin-1-yl)-2-methyl-1-oxopropan-2-yl)carbamate, $NaBH(OAc)_3$ DIPEA, DCE:ACN, rt, 16 h 8) 2M HCl in MeOH, rt, 4 h.

Step 1: benzyl exo-6-formyl-3-azabicyclo[3.1.0]hexane-3-carboxylate. To a solution of Oxalyl chloride (4.6 g, 36 mmol) in $CH_2Cl_2$ (50 mL) at −78° C. under was added dropwise a solution of DMSO (5.9 g, 75 mmol) in $CH_2Cl_2$ (10 mL). After 15 min a solution of exo-6-(hydroxymethyl)-3-azabicyclo[3.1.0]hexane-3-carboxylate (7.41 g, 30 mmol) in $CH_2Cl_2$ (30 mL) was slowly added dropwise. The reaction mixture was stirred at −78° C. for 30 min, followed by the addition of $Et_3N$ (15.2 g, 150 mmol) dropwise. The reaction was stirred at −78° C. for 30 min and slowly warmed to rt. The reaction mixture was diluted with $CH_2Cl_2$ (200 mL), washed with sat. aq. $NaHCO_3$ and sat. aq. NaCl. The organic layer was separated, dried over $Na_2SO_4$, filtered and concentrated under reduced pressure. The residue was purified by column chromatography to yield the title compound (5.12 g, 69%) as a colorless solid.

Step 2: benzyl exo-6-((E)-((tert-butylsulfinyl)imino)methyl)-3-azabicyclo[3.1.0]hexane-3-carboxylate. To a solution of benzyl exo-6-formyl-3-azabicyclo[3.1.0]hexane-3-carboxylate (1 g, 4.08 mmol) in THF at rt, were added (S)-(−)-2-methylpropane-2-sulfinamide (0.45 g, 3.71 mmol) and $Ti(OPr)_4$ (1.16 g, 4.08 mmol). The reaction mixture was refluxed for 16 h. The solvent THF was evapourated and the residue was dissolved in $CH_2Cl_2$ (30 mL) and was poured into sat. $NaHCO_3$ and Celite® (3 g) and stirred for 0.5 h. The mixture was filtered, and the organic layer was separated. The organic layer was washed with sat. aq. NaCl, dried over $Na_2SO_4$, filtered and concentrated under reduced pressure to give the title compound (1.2 g, 86%) as a white solid.

Step 3: benzyl exo-6-(1-((tert-butylsulfinyl)amino)-2-(isopropoxydimethylsilyl)ethyl)-3-azabicyclo[3.1.0]hexane-3-carboxylate. To a solution of benzyl exo-6-((E)-((tert-butylsulfinyl)imino)methyl)-3-azabicyclo[3.1.0]hexane-3-carboxylate (3.1 g, 8.90 mmol) in dry THF (80 mL) at −20° C. was added (isopropoxydimethylsilyl)magnesium chloride (0.5 M solution, 18 mL, 8.90 mmol) dropwise. The mixture was stirred at rt for 1 h, poured into $H_2O$ (200 mL), and extracted with EtOAc (3×100 mL). The combined organics were washed with brine, dried over $Na_2SO_4$, filtered and concentrated under reduced pressure to afford the title compound (2.56 g, 61%) as a colorless oil.

Step 4: benzyl exo-6-(1-((tert-butylsulfinyl)amino)-2-hydroxyethyl)-3-azabicyclo[3.1.0]hexane-3-carboxylate. To a solution of benzyl exo-6-(1-((tert-butylsulfinyl)amino)-2-(isopropoxydimethylsilyl)ethyl)-3-azabicyclo[3.1.0]hexane-3-carboxylate (1.35 g, 2.81 mmol) dissolved in mixed solution of MeOH:THF (1:1) were added $KHCO_3$ (0.3 g, 2.81 mmol), KF (0.16 g, 5.62 mmol), and $H_2O_2$ (1 mL) at 0° C. The reaction mixture was stirred at 50° C. for 2 h, poured into $H_2O$ (200 mL), and extracted with EtOAc (3×100 mL). The combined organics were washed with brine, dried over $Na_2SO_4$, filtered and concentrated under reduced pressure. The residue was purified by column chromatography to afford the desired compound (0.7 g, 66%) as a yellow sticky solid.

Step 5: benzyl exo-6-(−2-((tert-butyldimethylsilyl)oxy)-1-((tert-butylsulfinyl)amino)ethyl)-3-azabicyclo[3.1.0]hexane-3-carboxylate. To a solution of Benzyl exo-6-(1-((tert-butylsulfinyl)amino)-2-hydroxyethyl)-3-azabicyclo[3.1.0]hexane-3-carboxylate (0.5 g, 1.32 mmol) in $CH_2Cl_2$ (20 mL) at rt, were added TBS-$C_1$ (0.3 g, 2.0 mmol), and imidazole (0.14 g, 2.0 mmol) under $N_2$. The reaction mixture was stirred for 16 h at rt, diluted with $CH_2Cl_2$ (15 mL), washed with $H_2O$, brine, dried over $Na_2SO_4$, filtered and concentrated under reduced pressure. The residue was purified by flash column chromatography to afford the title compound (0.58 g, 90%) as a colorless sticky solid.

Step 6: N-(1-(exo-3-Azabicyclo[3.1.0]hexan-6-yl)-2-((tert-butyldimethylsilyl)oxy)ethyl)-2-methylpropane-2-sulfinamide. Benzyl exo-6-(2-((tert-butyldimethylsilyl)oxy)-1-((tert-butylsulfinyl)amino)ethyl)-3-azabicyclo[3.1.0]hexane-3-carboxylate (0.58 g, 1.17 mmol) dissolved in MeOH (15 mL). The solution was degassed, and $Pd(OH)_2/C$ (20% by wt, 0.12 g) was added. The reaction mixture was stirred for 16 h at rt under a $H_2$ atmosphere. The mixture was filtered through Celite® and concentrated under reduced pressure to afford the title compound (0.4 g, 95%) as colorless semi-solid.

Step 7: tert-butyl (1-(4-((1-(4-((exo-6-(2-((tert-butyldimethylsilyl)oxy)-1-((tert-butylsulfinyl)amino)ethyl)-3-azabicyclo[3.1.0]hexan-3-yl)methyl)phenyl)-2-oxo-1,2-dihydropyrimidin-4-yl)carbamoyl)piperazin-1-yl)-2-methyl-1-oxopropan-2-yl)carbamate. To a solution of N-(1-(exo-3-azabicyclo[3.1.0]hexan-6-yl)-2-((tert-butyldimethylsilyl)oxy)ethyl)-2-methylpropane-2-sulfinamide (0.05 g, 0.14 mmol), and tert-Butyl (1-(4-((1-(4-formylphenyl)-2-oxo-1,2-dihydropyrimidin-4-yl)carbamoyl)piperazin-1-yl)-2-methyl-1-oxopropan-2-yl)carbamate (0.07 g, 0.14 mmol) in solution of DCE:$CH_3CN$ (4:1) at rt, were added $NaBH(OAc)_3$ (0.06 g, 0.28 mmol), and DIPEA (0.06 g, 0.42 mmol) and the reaction was stirred for 16 h. The reaction mixture was concentrated under reduced pressure. The residue was dissolved in EtOAc (15 mL), washed with saturated $NaHCO_3$, brine, dried over $Na_2SO_4$, filtered and concentrated under reduced pressure. The residue was purified by column chromatography to give (0.06 g, 50%) as a yellow solid.

Step 8: N-(1-(4-((exo-6-(1-amino-2-hydroxyethyl)-3-azabicyclo[3.1.0]hexan-3-yl)methyl)phenyl)-2-oxo-1,2-dihydropyrimidin-4-yl)-4-(2-amino-2-methylpropanoyl)piperazine-1-carboxamide hydrochloride salt. tert-Butyl (1-(4-((1-(4-((exo-6-(2-((tert-butyldimethylsilyl)oxy)-1-((tert-butylsulfinyl)amino)ethyl)-3-azabicyclo[3.1.0]hexan-3-yl)methyl)phenyl)-2-oxo-1,2-dihydropyrimidin-4-yl)carbamoyl)piperazin-1-yl)-2-methyl-1-oxopropan-2-yl)carbamate (0.06 g, 0.07 mmol) was dissolved in HCl in MeOH (10 mL) and stirred at rt for 4 h. The solvent was evaporated and the residue was purified by prep HPLC to afford the title compound (20 mg, 52%) as a yellow colored solid. $^1H$ NMR (500 MHz, $D_2O$): δ 8.03 (d, 1H), 7.74 (d, 2H), 7.62 (d, 2H), 6.91 (d, 1H), 4.53 (s, 2H), 3.92-3.89 (m, 2H), 3.84-3.73 (m, 10H), 3.69-3.66 (m, 2H), 2.90-2.84 (m, 1H), 2.20-2.13 (m, 2H), 1.79 (s, 6H), 1.42 (d, 1H). LCMS [M+H] 539.2.

Compound 210

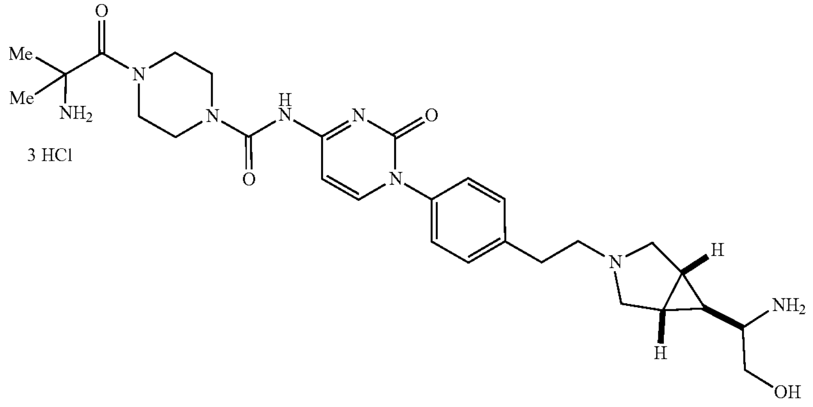

N-(1-(4-(2-(exo-6-((R)-1-Amino-2-hydroxyethyl)-3-azabicyclo[3.1.0]hexan-3-yl)ethyl)phenyl)-2-oxo-1,2-dihydropyrimidin-4-yl)-4-(2-amino-2-methylpropanoyl)piperazine-1-carboxamide Hydrochloride Salt Prepared in a similar fashion to Scheme C-35 using tert-butyl (2-methyl-1-oxo-1-(4-((2-oxo-1-(4-(2-oxoethyl)phenyl)-1,2-dihydropyrimidin-4-yl)carbamoyl)piperazin-1-yl)propan-2-yl)carbamate (0.10 g, 0.19 mmol), and N—((R)-1-(exo-3-azabicyclo[3.1.0]hexan-6-yl)-2-((tert-butyldimethylsilyl)oxy)ethyl)-2-methylpropane-2-sulfinamide (0.07 g, 0.19 mmol). $^1$H NMR (500 MHz, $D_2O$): δ 7.96 (d, 1H), 7.46 (d, 2H), 7.42 (d, 2H), 6.81 (d, 1H), 3.87-3.81 (m, 4H), 3.77-3.80 (m, 8H), 3.41-3.55 (m, 4H), 3.12 (t, 2H), 2.83-2.79 (m, 1H), 2.13-2.06 (m, 2H), 1.72 (s, 6H), 1.42 (dt, 1H). LCMS [M+H] 553.3.

Compound 246

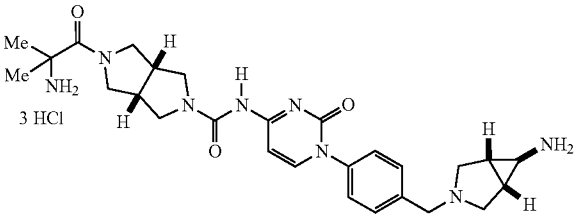

(cis)-5-(2-Amino-2-methylpropanoyl)-N-(1-(4-((exo-6-amino-3-azabicyclo[3.1.0]hexan-3-yl)methyl)phenyl)-2-oxo-1,2-dihydropyrimidin-4-yl)hexahydropyrrolo[3,4-c]pyrrole-2 (1H)-carboxamide Hydrochloride Salt Scheme C-36

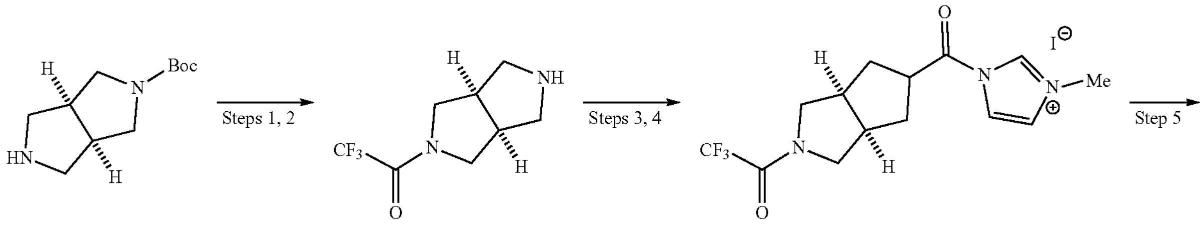

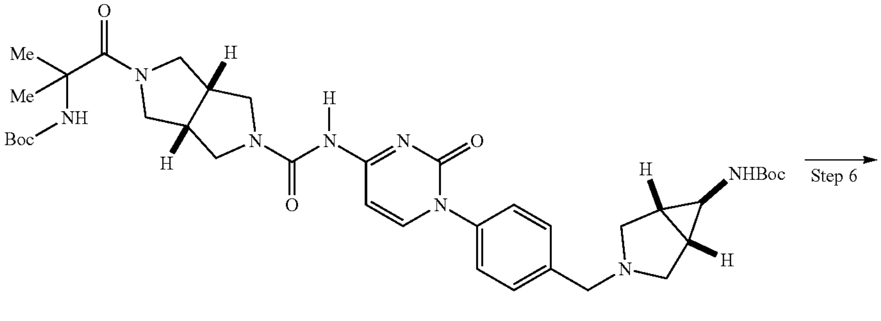

-continued

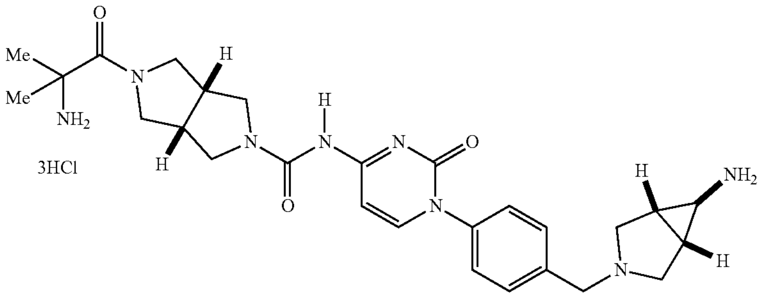

Reagents: Step 1) Trifluoroacetic anhydride, TEA, $CH_2Cl_2$, 0° C. to rt, 16 h 2) 2M HCl in MeOH, rt, 4 h 3) CDI, $CH_2Cl_2$, rt, 4 h 4) MeI, $CH_3CN$, rt, 16 h 5) tert-Butyl (exo-3-(4-(4-amino-2-oxopyrimidin-1 (2H)-yl)benzyl)-3-azabicyclo[3.1.0]hexan-6-yl)carbamate, $CH_3CN$, reflux, 16 h 6) HCl in MeOH, rt, 4 h.

Step 1: tert-Butyl (exo)-5-(2,2,2-trifluoroacetyl)hexahydropyrrolo[3,4-c]pyrrole-2 (1H)-carboxylate. To a stirring solution of tert-butyl (cis)-hexahydropyrrolo[3,4-c]pyrrole-2 (1H)-carboxylate (1.0 g, 4.72 mmol) in $CH_2Cl_2$ (30 mL) were added trifluoroacetic anhydride (1.49 g, 7.08 mmol), and $Et_3N$ (1.43 g, 14.2 mmol) at 0° C. The reaction mixture was warmed to rt and stirred for 16 h. The reaction mixture was diluted with $CH_2Cl_2$ (30 mL) and washed with saturated $NaHCO_3$ and brine. The organic phase was dried over $Na_2SO_4$, filtered and concentrated under reduced pressure to afford the title compound (1.45 g, Quant.) as a yellow solid.

Step 2: 2,2,2-trifluoro-1-((cis)-hexahydropyrrolo[3,4-c]pyrrol-2 (1H)-yl)ethan-1-one hydrochloride salt. tert-Butyl (cis)-5-(2,2,2-trifluoroacetyl)hexahydropyrrolo[3,4-c]pyrrole-2 (1H)-carboxylate (1.45 g, 4.72 mmol) was dissolved in 2N HCl in MeOH (50 mL) and stirred at rt for 4 h. The solvent was evaporated and concentrated under reduced pressure to afford the title compound (1.15 g, Quant.) as a yellow solid.

Step 3: 1-((cis)-5-(1H-imidazole-1-carbonyl)hexahydropyrrolo[3,4-c]pyrrol-2 (1H)-yl)-2,2,2-trifluoroethan-1-one. To a stirring suspension of 2,2,2-trifluoro-1-((cis)-hexahydropyrrolo[3,4-c]pyrrol-2 (1H)-yl)ethan-1-one hydrochloride salt (1.15 g, 4.72 mmol) in $CH_2Cl_2$ (20 mL) was added CDI (1.14 g, 7.07 mmol) at rt. The reaction mixture was stirred at rt for 16 h. The reaction mixture was concentrated under reduced pressure and purified by column chromatography to afford the title compound (1.07 g, 75%) as an off-white solid.

Step 4: 3-methyl-1-((cis)-5-(2,2,2-trifluoroacetyl)octahydropyrrolo[3,4-c]pyrrole-2-carbonyl)-1H-imidazol-3-ium iodide. To a solution of 1-((cis)-5-(1H-imidazole-1-carbonyl)hexahydropyrrolo[3,4-c]pyrrol-2 (1H)-yl)-2,2,2-trifluoroethan-1-one (1.07 g, 3.54 mmol) in $CH_3CN$ (25 mL) was added MeI (5.39 g, 35.4 mmol). The reaction mixture was stirred at rt for 16 h. The reaction mixture was concentrated under reduced pressure to afford the title compound (1.61 g, Quant.) as a pale yellow solid.

Step 5: tert-butyl (exo-3-(4-(4-((cis)-5-(2-((tert-butoxycarbonyl)amino)-2-methylpropanoyl)octahydropyrrolo[3,4-c]pyrrole-2-carboxamido)-2-oxopyrimidin-1 (2H)-yl)benzyl)-3-azabicyclo[3.1.0]hexan-6-yl)carbamate. To a stirring suspension of 3-methyl-1-((cis)-5-(2,2,2-trifluoroacetyl)octahydropyrrolo[3,4-c]pyrrole-2-carbonyl)-1H-imidazol-3-ium iodide (0.16 g, 0.34 mmol) in $CH_3CN$ (25 mL), was added tert-butyl (exo-3-(4-(4-amino-2-oxopyrimidin-1 (2H)-yl)benzyl)-3-azabicyclo[3.1.0]hexan-6-yl)carbamate (0.14 g, 0.34 mmol) at rt. The reaction mixture was refluxed for 16 h, the solvent was evaporated and purified using flash column chromatography to afford the title compound (0.15 g, 60%) as a brown colored solid.

Step 6: (cis)-5-(2-amino-2-methylpropanoyl)-N-(1-(4-((exo-6-amino-3-azabicyclo[3.1.0]hexan-3-yl)methyl)phenyl)-2-oxo-1,2-dihydropyrimidin-4-yl)hexahydropyrrolo[3,4-c]pyrrole-2 (1H)-carboxamide hydrochloride salt. The compound tert-butyl (exo-3-(4-(4-((cis)-5-(2-((tert-butoxycarbonyl)amino)-2-methylpropanoyl)octahydropyrrolo[3,4-c]pyrrole-2-carboxamido)-2-oxopyrimidin-1 (2H)-yl)benzyl)-3-azabicyclo[3.1.0]hexan-6-yl)carbamate (0.15 g, 0.21 mmol) was dissolved in 2N HCl in MeOH (15 mL) and stirred at rt for 4 h. The reaction mixture was concentrated under reduced pressure and the residue was purified by HPLC to result the title compound (35 mg, 45%) as a yellow colored solid. $^1H$ NMR (500 MHz, $CD_3OD$: δ 7.94 (d, 1H), 7.67 (d, 2H), 7.56 (d, 2H), 7.08 (d, 1H), 4.45 (s, 2H), 3.97-3.56 (m, 10H), 3.54-3.43 (m, 4H), 3.19-3.15 (m, 1H), 3.04-2.98 (m, 2H), 2.35 (s, 2H), 1.66 (s, 6H). LCMS [M+H] 521.3.

Compound 206

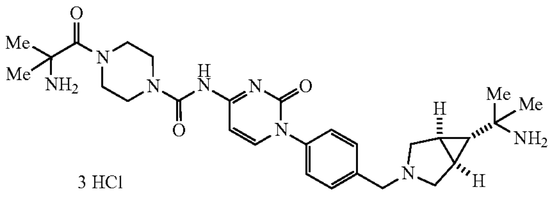

4-(2-Amino-2-methyl propanoyl)-N-(1-(4-((exo-6-(2-aminopropan-2-yl)-3-azabicyclo[3.1.0]hexan-3-yl)methyl)phenyl)-2-oxo-1,2-dihydropyrimidin-4-yl) piperazine-1-carboxamide Hydrochloride Salt Scheme C-37

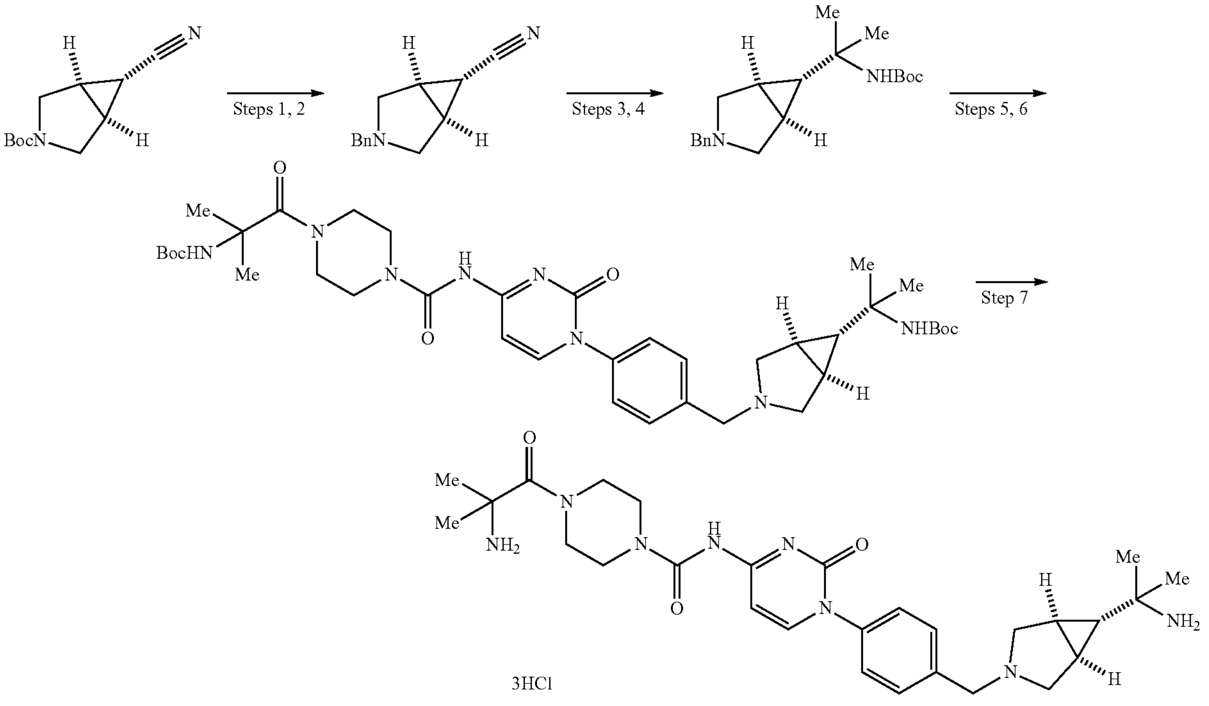

3HCl

Reagents: 1) TFA, $CH_2Cl_2$, rt, 1 h. 2) benzyl bromide, DIPEA, $CH_2Cl_2$, rt, 16 h. 3) MeLi, $CeCl_3$-78° C. to 0° C., 3.5 h. 4) $Boc_2O$, $Et_3N$, $CH_2Cl_2$, rt, 72 h. 5) $Pd(OH)_2/C$, Hz, MeOH, rt. 16 h. 6) ALDEHYDE, $NaBH_3CN$, MeOH, rt, 16 h. 7) HCl/MeOH, rt, 4 h.

Step 1: exo-3-azabicyclo[3.1.0]hexane-6-carbonitrile trifluoroacetate. To a solution of tert-butyl exo-6-cyano-3-azabicyclo[3.1.0]hexane-3-carboxylate (500 mg, 2.4 mmol) in $CH_2Cl_2$ (5 mL) at rt was added TFA (5 mL) and the reaction was stirred at rt for 1 h. The reaction mixture was concentrated under reduced pressure and the crude solid was triturated with $Et_2O$ to afford the desired product.

Step 2: exo-3-benzyl-3-azabicyclo[3.1.0]hexane-6-carbonitrile. To a stirred suspension of exo-3-azabicyclo[3.1.0]hexane-6-carbonitrile trifluoroacetate (400 mg, 1.8 mmol) in $CH_2Cl_2$ (5 mL) at rt was added DIPEA (0.62 mL, 3.6 mmol) and benzyl bromide (0.26 mL, 2.2 mmol). The reaction was stirred at rt for 16 h. The reaction mixture was concentrated under reduced pressure and the crude solid was dissolved in EtOAc (50 mL) and washed with $H_2O$ (1×50 mL). The organic layer was concentrated under reduced pressure and purified by flash chromatography (Hexanes:EtOAc) to afford the desired product.

Step 3: 2-(exo-3-benzyl-3-azabicyclo[3.1.0]hexan-6-yl)propan-2-amine. To a stirred suspension of exo-3-benzyl-3-azabicyclo[3.1.0]hexane-6-carbonitrile (200 mg, 1.0 mmol) and anhydrous $CeCl_3$ (250 mg, 1.0 mmol) in THF (12 mL) at −78° C. was added 1.4 M MeLi solution in $Et_2O$ (2.5 mL, 3.5 mmol) dropwise. The reaction was maintained at −78° C. for 1 h. The reaction was slowly warmed to 0° C. over 1 h and maintained at 0° C. for an addition 1.5 h. The reaction was quenched upon addition of $H_2O$ (1 mL). The reaction mixture was concentrated under reduced pressure and partitioned between $H_2O$ (25 mL) and $CHCl_3$ (25 mL). The layers were separated and the aqueous layer was extracted with $CHCl_3$ (2×25 mL). The combined organics were concentrated and purified by column chromatography ($NH_4OH$:MeOH:$CHCl_3$) to afford the desired product.

Step 4: tert-butyl (2-(exo-3-benzyl-3-azabicyclo[3.1.0]hexan-6-yl)propan-2-yl)carbamate. To a solution of 2-(exo-3-benzyl-3-azabicyclo[3.1.0]hexan-6-yl)propan-2-amine (68 mg, 0.29 mmol) in $CH_2Cl_2$ (5 mL) at rt was added $Et_3N$ (80 μL, 0.60 mmol) and ditert-butyl dicarbonate (77 mg, 0.35 mmol) and the reaction was stirred at rt for 72 h. The reaction mixture was concentrated under reduced pressure and the crude solid was dissolved in EtOAc (30 mL) and washed with $H_2O$ (1×30 mL). The organic layer was concentrated under reduced pressure and purified by flash chromatography (Hexanes:EtOAc) to afford the desired product.

Step 5: tert-butyl (2-(exo-3-azabicyclo[3.1.0]hexan-6-yl)propan-2-yl)carbamate. To a degassed solution of tert-butyl (2-(exo-3-benzyl-3-azabicyclo[3.1.0]hexan-6-yl)propan-2-yl)carbamate (40 mg, 0.13 mmol) in MeOH (5 mL), was added $Pd(OH)_2/C$ (4 mg, 0.03 mmol). The suspension was stirred under a $H_2$ atmosphere for 16 h. The reaction mixture was filtered through Celite® and the filtrate concentrated under reduced pressure to afford the title compound.

Step 6: tert-butyl (1-(4-((1-(4-((exo-6-(2-((tert-butoxycarbonyl)amino)propan-2-yl)-3-azabicyclo[3.1.0]hexan-3-yl)methyl)phenyl)-2-oxo-1,2-dihydropyrimidin-4-yl)carbamoyl)piperazin-1-yl)-2-methyl-1-oxopropan-2-yl)carbamate. To a solution of tert-butyl (1-(4-((1-(4-formylphenyl)-2-oxo-1,2-dihydropyrimidin-4-yl)carbamoyl)piperazin-1-yl)-2-methyl-1-oxopropan-2-yl)carbamate (25 mg, 0.05 mmol)

in MeOH (10 mL) was added tert-butyl (2-(exo-3-azabicyclo[3.1.0]hexan-6-yl)propan-2-yl)carbamate (15 mg, 0.06 mmol), $NaBH_3CN$ (6 mg, 0.1 mmol). The solution was stirred at rt for 16 h. The reaction mixture was concentrated under reduced pressure and dissolved in $CH_2Cl_2$. The solution was washed with sat. aq. aqueous $NaHCO_3$ (10 mL) and the aqueous layer extracted with $CH_2Cl_2$ (2×10 mL). The combined organic layers were dried over $Na_2SO_4$ and concentrated under reduced pressure to afford the crude title compound.

Step 7: 4-(2-amino-2-methylpropanoyl)-N-(1-(4-((exo-6-(2-aminopropan-2-yl)-3-azabicyclo[3.1.0]hexan-3-yl)methyl)phenyl)-2-oxo-1,2-dihydropyrimidin-4-yl)piperazine-1-carboxamide hydrochloride salt. tert-butyl (1-(4-((1-(4-((exo-6-(2-((tert-butoxycarbonyl)amino)propan-2-yl)-3-azabicyclo[3.1.0]hexan-3-yl)methyl)phenyl)-2-oxo-1,2-dihydropyrimidin-4-yl)carbamoyl)piperazin-1-yl)-2-methyl-1-oxopropan-2-yl)carbamate was dissolved in a 2N solution of HCl in MeOH (2N, 5 mL) and stirred for 4 h. The volatiles were removed under reduced pressure and the crude solid was purified by reverse phase HPLC ($H_2O$:$CH_3CN$:TFA) and concentrated under reduced pressure. Addition of with 2N HCl in MeOH (3×15 mL) and evaporation under reduced pressure afforded the title compound. $^1H$ NMR (400 MHz, $D_2O$) δ 8.10 (d, 1H), 7.72 (d, 2H), 7.59 (d, 2H), 6.85 (d, 2H), 4.50 (s, 2H), 3.80 (s, 4H), 3.76 (s, 4H), 3.74-3.61 (m, 4H), 2.16 (s, 2H), 1.75 (s, 6H), 1.38 (s, 1H), 1.28 (s, 6H). LCMS [M+H] 537.3.

Compound 205

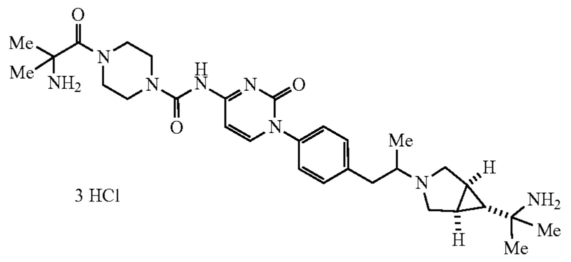

3 HCl 4-(2-Amino-2-methylpropanoyl)-N-(1-(4-(2-(6-(2-aminopropan-2-yl)-3-azabicyclo[3.1.0]hexan-3-yl)propyl)phenyl)-2-oxo-1,2-dihydropyrimidin-4-yl)piperazine-1-carboxamide Hydrochloride Salt Prepared as in scheme C-37 from tert-butyl tert-butyl (2-methyl-1-oxo-1-(4-(2-oxo-1-(4-(2-oxopropyl)phenyl)-1,2-dihydropyrimidin-4-yl)carbamoyl)piperazin-1-yl)propan-2-yl)carbamate and tert-butyl (2-(exo-3-azabicyclo[3.1.0]hexan-6-yl)propan-2-yl)carbamate. $^1H$ NMR (400 MHz, $D_2O$) δ 8.03 (d, 1H), 7.51-7.42 (m, 4H), 6.83 (d, 1H), 3.89 (d, 1H), 3.83 (d, 1H), 3.81 (s, 3H), 3.75 (s, 5H), 3.69 (d, 2H), 3.62 (d, 1H), 3.44-3.36 (m, 1H), 2.90-2.81 (m, 1H), 2.27-2.13 (m, 2H), 1.75 (s, 6H), 1.31 (s, 6H), 1.30-1.22 (m, 4H). LCMS [M+H]565.3.

Biological Examples

Standard Microbiological Activity:

A certified BSL-2 laboratory was used for testing. Compounds were evaluated using the broth microdilution minimum inhibitory concentration (MIC) and minimum bactericidal concentration (MBC) assays defined by Clinical and Laboratory Standards Institute (CLSI) in the M26-A guideline against *S. aureus* (Sa), *E. coli* (Ec), *K. pneumoniae* (Kp), *A. baumannn* (Ab), *E. faecalis* (Ef) and *P. aeruginosa* (Pa).

*E. coli* $S_{30}$ extract: Inhibition of bacterial protein synthesis was determined using the *E. coli* $S_{30}$ Extract System for Circular DNA (Promega catalog #L-2010) and Luciferase Assay Reagent (Promega catalog #E1500) with slight modifications to a published protocol. Fyfe, C., Sutcliffe, J. A. and Grossman, T. H. (2012) "Development and characterization of a *Pseudomonas aeruginosa* in vitro coupled transcription-translation assay system for evaluation of translation inhibitors" J. Microbiol. Methods 90(3), 256-261.

Compounds were serial diluted in 0.5 mL microcentrifuge tubes by mixing and transferring 50 μL from the highest concentration to 50 μL of water, mixing and transferring 50 μL of this 2-fold dilution to 50 μL of water. This mixing and transferring was repeated so that there are a total of 8 tubes with serial dilutions of compound at 10× the desired screening concentration that are ultimately diluted to 1× by the addition of S30 luciferase synthesis mixture. Serial dilutions of compounds were added (2 μL) to wells in a black round bottom 96-well plate. Water (2 μL) was used as a "no inhibitor" control in 4 wells/plate. No DNA control reaction mixture (20 μL; see below) was used as a control in 4 wells/plate for background luminescence. S30 luciferase synthesis mixture (18 μL; see below) was added to wells with compounds or water mixture and incubated at 37° C. for 1 hour. Reactions were stopped by transferring to 4° C. refrigerator for 5 minutes then 25 μL of luciferase activity mix was added. Luminescence was measured using a BioTek Synergy HTX plate reader. % Inhibition was determined relative to no inhibitor controls.

S30 luciferase synthesis mixture:
445 μL S30 extract, circular
712 μL S30 Premix without amino acids
4.45 μL pBESTluc™ DNA (1 μg/μL)
78 μL complete amino acid mixture
267 μL water No DNA control:
20 μL S30 extract, circular
32 μL S30 Premix without amino acids
7 μL complete amino acid mixture
21 μL water Rabbit Reticulocyte lysate Inhibition of eukaryotic protein synthesis was determined using the Rabbit Reticulocyte Lysate System, Nuclease-Treated from Promega (catalog #L-4960) with slight modifications to the manufacturer's protocol. Compounds were serial diluted in 0.5 mL microcentrifuge tubes by mixing and transferring 50 μL from the highest concentration to 50 μL of water, mixing and transferring 50 μL of this 2-fold dilution to 50 μL of water. This mixing and transferring was repeated so that there are a total of 8 tubes with serial dilutions of compound at 10× the desired screening concentration that are ultimately diluted to 1× by the addition of rabbit reticulocyte luciferase synthesis mixture. Serial dilutions of compounds were added (2.5 μL) to wells in a black round bottom 96-well plate. Water (2.5 μL) was used as a "no inhibitor" control in 4 wells/plate. No RNA control reaction mixture (2 μL; see below) was used as a control in 4 wells/plate for background luminescence. Rabbit reticulocyte luciferase synthesis mixture (22.5 μL; see below) was added to wells with compounds or water mixture and incubated at 30° C. for 90 minutes. Luciferase assay reagent (25 μL) was added with luminescence measured using a BioTek Synergy HTX plate reader. % Inhibition was determined relative to no inhibitor controls.

Rabbit Reticulocyte Luciferase Synthesis Mixture:
1,000 µL rabbit reticulocyte lysate
5.7 µL Luciferase Control RNA (1 µg/µL)
26 µL complete amino acid mixture
395 µL water
No RNA Control
70 µL rabbit reticulocyte lysate
2 µL complete amino acid mixture
28 µL water
Minimum Inhibitory Concentration (MIC)

MICs were determined using the Clinical Laboratory and Standards Institute (CLSI) Broth Microdilution Method with slight modification. Clinical and Laboratory Standards Institute (2012). "Methods for dilution antimicrobial susceptibility tests for bacteria that grow aerobically; approved standard, 9th ed. M07-A9 Clinical and Laboratory Standards Institute, Wayne, PA" Serial two-fold dilutions of compounds are prepared in sterile clear round-bottom 96-well plates.

To prepare microdilution trays, two-fold dilutions of antimicrobial agent are prepared in growth medium: Cation-Adjusted Mueller-Hinton Broth (CAMHB), or CAMHB supplemented with sodium bicarbonate (6.25 or 25 mM final concentration prepared from a 1.0M stock solution) or CAMHB supplemented with heat inactivated human serum (Fisher Cat. #BP2657100) 0-50% by adding 2004 of the highest concentration to be tested (64 µg/mL, for example) in row A, mixing and transferring 100 µL from row A to 100 µL growth medium in row B, then repeating the mixing and transferring through row H of the 96-well plate, discarding the excess 1004 remaining. This slight modification to the CLSI protocol enables evaluation of MICs for 3 compounds per plate in triplicate, albeit with only 8 compound dilutions (CLSI protocol enables 2 compounds in triplicate with 10 dilutions). Bacterial suspensions are added to a final concentration of $5\times10^4$ CFU/well by adding 5 µL of a 1:10 dilution of a 0.5 McFarland suspension ($1\times10^8$ CFU/mL) for each bacterium evaluated. Bacterial suspensions were prepared using the growth method described by CLSI. Well-isolated colonies (3-5 from an agar plate) were selected using a sterile loop and used to inoculate a tube containing 4 mL of CAMHB. The cultures are incubated at 35±2° C. until it achieves or exceeds the turbidity of the 0.5 McFarland standard, determined by measuring A600 (usually two to six hours). When growth exceeds a 0.5 McFarland standard, the turbidity is adjusted with broth to be equivalent to a 0.5 McFarland standard.

Data for compounds is provided in Table 15. An $IC_{50}$ value (µM) that is 1 µM or greater (% inhibition is ≤50% @ 1 µM) is designated by a "+". An $IC_{50}$ value that is 0.5 µM or greater and less than 1 µM (% inhibition is >50% and <90% @ 1 µM) is designated by a "++". An $IC_{50}$ value that is less than 0.5 µM (% inhibition is >90% @ 1 µM) is designated by "+++". An MIC (µg/mL) value that is 32 µg/mL or greater is designated by a "+". An MIC value (µg/mL) that is 8 µg/mL or greater and less than 32 µg/mL is designated by a "++". An MIC value (µg/mL) that is less than 8 µg/mL is designated by "+++". "NA" means not available.

TABLE 15

Biological Activity of Compounds of Formula I or a Pharmaceutically Acceptable Salt thereof

| No. | Sa + bicarb MIC | *E. coli* + bicarb MIC | Kp (1705) + bicearb MIC | Kp (060) + bicarb MIC | Pa MIC + bicarb | Ab + bicarb MIC | Ef + bicarb MIC | S30 $IC_{50}$ (µM/% inhib.) | Rabbit reticulocyte $IC_{50}$ (µM/% inhib.) |
|---|---|---|---|---|---|---|---|---|---|
| 1 | NA | NA | NA | NA | NA | NA | NA | +++ | + |
| 2 | NA | +++ | + | NA | NA | NA | NA | +++ | + |
| 3 | +++ | +++ | +++ | +++ | ++ | +++ | +++ | +++ | + |
| 4 | NA | +++ | ++ | +++ | + | + | +++ | +++ | + |
| 5 | NA | NA | NA | NA | NA | NA | NA | + | + |
| 6 | NA | NA | NA | NA | NA | NA | NA | + | + |
| 7 | NA | +++ | NA | ++ | + | NA | NA | +++ | + |
| 8 | NA | + | NA | NA | NA | NA | NA | + | NA |
| 9 | NA | + | NA | NA | NA | NA | NA | + | NA |
| 10 | NA | NA | NA | NA | NA | NA | NA | + | + |
| 11 | NA | NA | NA | NA | NA | NA | NA | + | + |
| 12 | NA | NA | NA | NA | NA | NA | NA | + | + |
| 13 | +++ | +++ | + | + | + | + | +++ | ++ | + |
| 14 | +++ | +++ | ++ | +++ | + | + | +++ | +++ | + |
| 15 | NA | + | + | NA | NA | NA | NA | + | NA |
| 16 | NA | ++ | + | NA | NA | NA | NA | + | + |
| 17 | NA | +++ | NA | ++ | + | NA | NA | +++ | + |
| 18 | NA | +++ | + | NA | NA | NA | NA | +++ | + |
| 19 | NA | +++ | + | NA | NA | NA | NA | ++ | + |
| 20 | +++ | +++ | + | + | + | + | ++ | + | + |
| 21 | NA | +++ | + | NA | NA | NA | NA | +++ | + |
| 22 | NA | +++ | + | NA | NA | NA | NA | +++ | + |
| 23 | +++ | +++ | ++ | ++ | + | + | +++ | +++ | + |
| 24 | NA | +++ | + | NA | NA | NA | NA | ++ | + |
| 25 | +++ | +++ | + | + | + | + | + | +++ | + |
| 26 | NA | +++ | + | NA | NA | NA | NA | + | NA |
| 27 | ++ | +++ | + | NA | + | NA | NA | +++ | + |
| 28 | +++ | +++ | + | +++ | + | + | +++ | +++ | + |
| 29 | +++ | +++ | + | + | + | + | ++ | ++ | + |
| 30 | +++ | +++ | ++ | ++ | ++ | ++ | +++ | +++ | + |
| 31 | NA | +++ | NA | ++ | + | NA | NA | +++ | + |
| 33 | +++ | +++ | +++ | +++ | ++ | ++ | +++ | +++ | + |
| 34 | +++ | +++ | ++ | ++ | + | + | ++ | +++ | + |
| 35 | NA | NA | NA | + | NA | + | ++ | +++ | + |

TABLE 15-continued

| Biological Activity of Compounds of Formula I or a Pharmaceutically Acceptable Salt thereof | | | | | | | | | |
|---|---|---|---|---|---|---|---|---|---|
| No. | Sa + bicarb MIC | *E. coli* + bicarb MIC | Kp (1705) + bicearb MIC | Kp (060) + bicarb MIC | Pa MIC + bicarb | Ab + bicarb MIC | Ef + bicarb MIC | S30 $IC_{50}$ (μM/% inhib.) | Rabbit reticulocyte $IC_{50}$ (μM/% inhib.) |
| 36 | NA | +++ | NA | +++ | + | + | + | +++ | + |
| 37 | NA | +++ | NA | ++ | ++ | NA | NA | +++ | + |
| 38 | NA | NA | NA | ++ | NA | + | ++ | +++ | + |
| 39 | NA | +++ | NA | NA | NA | NA | NA | +++ | + |
| 40 | +++ | +++ | + | ++ | + | + | +++ | +++ | + |
| 41 | + | + | + | ++ | + | + | + | + | + |
| 42 | ++ | +++ | + | + | + | + | ++ | +++ | + |
| 43 | NA | NA | NA | NA | NA | NA | NA | + | + |
| 44 | NA | NA | NA | NA | NA | NA | NA | + | + |
| 45 | +++ | +++ | +++ | ++ | ++ | + | +++ | +++ | + |
| 46 | ++ | +++ | + | + | + | NA | + | +++ | + |
| 47 | NA | ++ | + | NA | NA | NA | NA | ++ | + |
| 48 | +++ | +++ | + | ++ | + | + | ++ | ++ | + |
| 49 | +++ | +++ | ++ | ++ | + | + | ++ | +++ | + |
| 50 | NA | +++ | + | NA | NA | NA | NA | + | + |
| 51 | NA | + | + | NA | NA | NA | NA | + | + |
| 52 | NA | +++ | + | NA | NA | NA | NA | + | + |
| 53 | +++ | +++ | + | + | + | + | +++ | ++ | + |
| 54 | +++ | +++ | +++ | +++ | + | ++ | +++ | +++ | + |
| 55 | NA | NA | NA | NA | NA | NA | NA | +++ | + |
| 56 | + | ++ | + | + | + | + | + | + | + |
| 57 | NA | NA | NA | NA | NA | NA | NA | + | + |
| 58 | +++ | +++ | ++ | ++ | + | + | ++ | +++ | + |
| 59 | +++ | +++ | ++ | ++ | + | + | +++ | +++ | + |
| 60 | +++ | +++ | + | + | + | + | + | +++ | + |
| 61 | + | ++ | + | + | + | + | + | + | + |
| 62 | +++ | +++ | + | ++ | + | + | ++ | + | + |
| 63 | + | + | + | + | + | + | + | + | + |
| 64 | ++ | ++ | + | ++ | + | + | ++ | + | + |
| 65 | +++ | +++ | ++ | ++ | + | ++ | +++ | +++ | + |
| 66 | ++ | +++ | + | + | + | + | + | ++ | + |
| 67 | +++ | +++ | + | ++ | + | + | +++ | +++ | + |
| 68 | +++ | +++ | ++ | ++ | + | + | + | +++ | + |
| 69 | NA | +++ | + | NA | NA | NA | NA | +++ | + |
| 70 | NA | +++ | + | NA | NA | NA | NA | + | NA |
| 71 | NA | +++ | + | NA | NA | NA | NA | +++ | + |
| 72 | NA | +++ | +++ | NA | NA | NA | NA | +++ | + |
| 73 | +++ | +++ | ++ | ++ | + | + | ++ | +++ | + |
| 74 | ++ | ++ | + | + | + | + | + | + | + |
| 75 | +++ | +++ | ++ | ++ | + | + | ++ | +++ | + |
| 76 | NA | +++ | + | NA | NA | NA | NA | +++ | + |
| 77 | NA | +++ | + | NA | NA | NA | NA | +++ | + |
| 78 | NA | NA | NA | NA | NA | NA | NA | + | + |
| 79 | NA | NA | NA | NA | NA | NA | NA | + | + |
| 80 | +++ | +++ | + | + | + | + | + | +++ | + |
| 81 | ++ | +++ | ++ | + | + | + | NA | +++ | + |
| 82 | NA | +++ | + | NA | NA | NA | NA | +++ | + |
| 83 | +++ | +++ | + | + | + | + | + | ++ | + |
| 84 | NA | + | NA | NA | NA | NA | NA | + | NA |
| 85 | NA | + | NA | NA | NA | NA | NA | + | NA |
| 86 | NA | NA | NA | NA | NA | NA | NA | + | + |
| 87 | NA | NA | NA | NA | NA | NA | NA | + | + |
| 88 | NA | NA | NA | NA | NA | NA | NA | + | + |
| 89 | + | ++ | + | NA | + | NA | NA | + | NA |
| 90 | NA | NA | NA | NA | NA | NA | NA | + | + |
| 91 | NA | +++ | NA | +++ | +++ | NA | NA | +++ | + |
| 92 | NA | NA | NA | NA | NA | NA | NA | +++ | + |
| 93 | NA | +++ | ++ | ++ | +++ | + | +++ | +++ | + |
| 94 | +++ | +++ | ++ | ++ | ++ | + | ++ | +++ | + |
| 95 | +++ | +++ | ++ | + | + | + | + | +++ | + |
| 96 | +++ | +++ | ++ | + | ++ | + | +++ | +++ | + |
| 97 | NA | NA | NA | NA | NA | NA | NA | + | + |
| 98 | NA | NA | NA | NA | NA | NA | NA | + | + |
| 99 | +++ | +++ | ++ | ++ | + | + | ++ | ++ | + |
| 100 | +++ | +++ | ++ | + | + | ++ | +++ | +++ | + |
| 101 | +++ | +++ | + | + | + | ++ | +++ | +++ | + |
| 102 | +++ | +++ | + | + | ++ | + | ++ | +++ | + |
| 103 | ++ | ++ | + | + | + | + | ++ | ++ | + |
| 104 | NA | NA | NA | NA | NA | NA | NA | + | + |
| 105 | + | + | + | + | + | + | + | + | + |
| 106 | +++ | +++ | ++ | +++ | + | + | ++ | + | + |
| 107 | +++ | +++ | ++ | ++ | + | + | ++ | + | + |

TABLE 15-continued

Biological Activity of Compounds of Formula I or a Pharmaceutically Acceptable Salt thereof

| No. | Sa + bicarb MIC | *E. coli* + bicarb MIC | Kp (1705) + bicearb MIC | Kp (060) + bicarb MIC | Pa MIC + bicarb | Ab + bicarb MIC | Ef + bicarb MIC | S30 $IC_{50}$ (μM/% inhib.) | Rabbit reticulocyte $IC_{50}$ (μM/% inhib.) |
|---|---|---|---|---|---|---|---|---|---|
| 108 | +++ | +++ | ++ | +++ | + | + | + | + | + |
| 109 | +++ | +++ | + | + | + | + | + | +++ | + |
| 110 | +++ | +++ | ++ | ++ | + | + | ++ | ++ | + |
| 111 | +++ | +++ | + | + | + | + | ++ | + | + |
| 112 | +++ | +++ | ++ | +++ | + | + | ++ | ++ | + |
| 113 | + | +++ | ++ | + | + | + | + | + | + |
| 114 | +++ | +++ | +++ | +++ | ++ | ++ | +++ | +++ | + |
| 115 | +++ | +++ | +++ | +++ | + | + | +++ | +++ | + |
| 116 | +++ | +++ | +++ | +++ | ++ | +++ | ++ | +++ | + |
| 117 | +++ | +++ | +++ | +++ | ++ | ++ | +++ | +++ | + |
| 118 | NA | NA | NA | NA | NA | NA | NA | + | + |
| 119 | NA | NA | NA | NA | NA | NA | NA | + | + |
| 120 | +++ | +++ | +++ | +++ | ++ | + | ++ | +++ | + |
| 121 | +++ | +++ | +++ | ++ | ++ | + | ++ | ++ | + |
| 122 | +++ | +++ | +++ | +++ | +++ | ++ | +++ | +++ | + |
| 123 | +++ | +++ | ++ | ++ | + | + | +++ | +++ | + |
| 124 | +++ | +++ | ++ | + | ++ | + | +++ | +++ | + |
| 125 | +++ | +++ | ++ | ++ | ++ | + | +++ | +++ | + |
| 126 | +++ | +++ | ++ | ++ | ++ | ++ | ++ | +++ | + |
| 127 | ++ | +++ | ++ | + | ++ | + | ++ | +++ | + |
| 128 | +++ | +++ | ++ | ++ | + | + | ++ | +++ | + |
| 129 | +++ | +++ | ++ | + | ++ | + | ++ | +++ | + |
| 130 | +++ | +++ | +++ | ++ | ++ | ++ | +++ | +++ | + |
| 131 | +++ | +++ | + | + | + | ++ | +++ | +++ | + |
| 132 | ++ | +++ | ++ | ++ | ++ | + | ++ | +++ | + |
| 133 | ++ | +++ | ++ | ++ | + | + | ++ | +++ | + |
| 134 | +++ | +++ | +++ | +++ | ++ | ++ | +++ | +++ | + |
| 135 | +++ | +++ | +++ | +++ | +++ | +++ | +++ | +++ | + |
| 136 | + | + | + | + | + | + | + | + | + |
| 137 | + | + | + | + | + | + | + | ++ | + |
| 138 | +++ | +++ | + | ++ | + | + | ++ | ++ | + |
| 139 | +++ | +++ | +++ | +++ | ++ | ++ | +++ | +++ | + |
| 140 | +++ | +++ | +++ | +++ | ++ | ++ | +++ | +++ | + |
| 141 | +++ | +++ | +++ | +++ | +++ | ++ | +++ | +++ | + |
| 142 | ++ | +++ | + | + | + | + | ++ | ++ | + |
| 143 | ++ | +++ | + | + | + | + | ++ | ++ | + |
| 144 | + | ++ | ++ | + | + | + | + | + | + |
| 145 | ++ | +++ | ++ | ++ | + | + | + | + | + |
| 146 | +++ | +++ | +++ | +++ | ++ | ++ | +++ | + | + |
| 147 | +++ | +++ | + | ++ | + | + | + | + | + |
| 148 | + | + | + | + | + | + | + | + | + |
| 149 | ++ | ++ | + | + | + | + | + | + | + |
| 150 | +++ | +++ | +++ | +++ | +++ | +++ | +++ | +++ | + |
| 151 | +++ | +++ | +++ | +++ | ++ | ++ | +++ | +++ | + |
| 152 | + | ++ | + | + | + | + | + | + | + |
| 153 | +++ | +++ | +++ | +++ | ++ | +++ | +++ | +++ | + |
| 154 | +++ | +++ | +++ | +++ | +++ | +++ | +++ | +++ | + |
| 155 | +++ | +++ | +++ | +++ | +++ | +++ | +++ | +++ | + |
| 156 | +++ | +++ | +++ | +++ | +++ | +++ | +++ | +++ | + |
| 157 | +++ | +++ | + | + | + | + | ++ | +++ | + |
| 158 | NA | NA | NA | NA | NA | NA | NA | + | NA |
| 159 | NA | NA | NA | +++ | NA | NA | NA | + | + |
| 160 | + | +++ | + | + | + | + | + | + | + |
| 161 | +++ | +++ | +++ | ++ | + | + | ++ | +++ | + |
| 162 | ++ | ++ | + | + | + | + | + | + | + |
| 163 | +++ | +++ | + | + | + | + | + | + | + |
| 164 | +++ | +++ | ++ | ++ | + | ++ | +++ | +++ | + |
| 165 | +++ | +++ | +++ | +++ | + | ++ | +++ | ++ | + |
| 166 | +++ | +++ | +++ | +++ | + | ++ | +++ | +++ | + |
| 167 | +++ | +++ | +++ | +++ | ++ | ++ | +++ | +++ | + |
| 168 | +++ | +++ | +++ | +++ | + | + | +++ | +++ | + |
| 169 | + | ++ | + | + | + | + | + | + | + |
| 170 | + | +++ | + | + | + | + | + | +++ | + |
| 171 | + | ++ | + | + | + | + | + | + | + |
| 172 | +++ | +++ | ++ | +++ | + | ++ | +++ | +++ | + |
| 173 | + | +++ | + | + | + | + | + | + | + |
| 174 | +++ | +++ | + | + | + | + | ++ | + | + |
| 175 | +++ | +++ | + | + | + | + | +++ | + | + |
| 176 | +++ | +++ | ++ | +++ | + | + | ++ | + | + |
| 177 | +++ | +++ | ++ | +++ | + | + | ++ | + | + |
| 178 | + | + | + | + | + | + | + | + | + |
| 179 | +++ | ++ | + | + | + | + | + | + | + |

TABLE 15-continued

Biological Activity of Compounds of Formula I or a Pharmaceutically Acceptable Salt thereof

| No. | Sa + bicarb MIC | *E. coli* + bicarb MIC | Kp (1705) + bicearb MIC | Kp (060) + bicarb MIC | Pa MIC + bicarb | Ab + bicarb MIC | Ef + bicarb MIC | S30 $IC_{50}$ (μM/% inhib.) | Rabbit reticulocyte $IC_{50}$ (μM/% inhib.) |
|---|---|---|---|---|---|---|---|---|---|
| 180 | ++ | +++ | ++ | +++ | + | + | + | + | + |
| 181 | +++ | +++ | + | ++ | + | + | +++ | ++ | + |
| 182 | + | + | + | + | + | + | + | + | + |
| 183 | + | + | + | + | + | + | + | + | + |
| 184 | +++ | +++ | ++ | ++ | + | + | ++ | + | + |
| 185 | +++ | +++ | +++ | +++ | + | + | ++ | + | + |
| 186 | +++ | +++ | ++ | +++ | + | ++ | +++ | +++ | + |
| 187 | +++ | +++ | +++ | +++ | ++ | ++ | +++ | +++ | + |
| 188 | +++ | +++ | ++ | ++ | ++ | ++ | +++ | +++ | + |
| 189 | +++ | +++ | ++ | ++ | + | + | +++ | +++ | + |
| 190 | +++ | +++ | ++ | ++ | + | + | ++ | +++ | + |
| 191 | +++ | +++ | +++ | +++ | ++ | ++ | +++ | + | + |
| 192 | +++ | +++ | +++ | +++ | + | + | +++ | + | + |
| 193 | +++ | +++ | ++ | ++ | + | + | ++ | + | + |
| 194 | +++ | +++ | +++ | +++ | + | ++ | +++ | ++ | + |
| 195 | ++ | + | + | + | + | + | + | + | + |
| 196 | + | + | + | + | + | + | + | + | + |
| 197 | +++ | +++ | + | ++ | + | + | ++ | + | + |
| 198 | ++ | ++ | + | + | + | + | + | + | + |
| 199 | ++ | ++ | + | + | + | + | + | + | + |
| 200 | +++ | +++ | + | + | + | + | + | + | + |
| 201 | +++ | +++ | ++ | ++ | + | + | +++ | +++ | + |
| 202 | + | + | + | + | + | ++ | + | + | + |
| 203 | ++ | ++ | + | + | + | + | + | + | + |
| 204 | +++ | +++ | + | ++ | + | + | + | + | + |
| 205 | ++ | ++ | + | ++ | + | + | + | + | + |
| 206 | +++ | +++ | + | ++ | + | + | ++ | +++ | + |
| 207 | +++ | +++ | + | ++ | + | + | ++ | +++ | + |
| 208 | +++ | +++ | + | ++ | + | ++ | +++ | +++ | + |
| 209 | + | + | + | + | + | + | + | + | + |
| 210 | +++ | +++ | ++ | ++ | + | + | ++ | ++ | + |
| 211 | +++ | +++ | + | + | + | ++ | +++ | ++ | + |
| 212 | + | + | + | + | + | + | + | + | + |
| 213 | + | +++ | + | + | + | + | + | + | + |
| 214 | +++ | +++ | + | ++ | + | + | +++ | +++ | + |
| 215 | +++ | +++ | ++ | +++ | + | + | ++ | +++ | + |
| 216 | +++ | +++ | + | ++ | + | + | +++ | +++ | + |
| 217 | +++ | +++ | + | ++ | + | + | +++ | +++ | + |
| 218 | +++ | +++ | +++ | +++ | + | + | +++ | +++ | + |
| 219 | +++ | +++ | ++ | ++ | + | + | +++ | +++ | + |
| 220 | +++ | +++ | ++ | ++ | + | + | ++ | +++ | + |
| 221 | +++ | +++ | ++ | +++ | + | +++ | +++ | + | + |
| 222 | +++ | +++ | + | ++ | + | + | ++ | ++ | + |
| 223 | +++ | +++ | + | ++ | + | + | +++ | +++ | + |
| 224 | +++ | +++ | + | + | + | + | +++ | +++ | + |
| 225 | +++ | +++ | +++ | +++ | + | + | +++ | ++ | + |
| 226 | + | + | + | + | + | + | + | + | + |
| 227 | +++ | +++ | ++ | ++ | + | + | +++ | ++ | + |
| 228 | +++ | +++ | ++ | ++ | + | + | ++ | + | + |
| 229 | + | ++ | + | + | + | + | + | + | + |
| 230 | ++ | +++ | + | + | + | + | + | + | + |
| 231 | +++ | +++ | + | + | + | + | + | + | + |
| 232 | +++ | +++ | + | ++ | + | + | + | + | + |
| 233 | +++ | +++ | ++ | +++ | + | + | ++ | + | + |
| 234 | +++ | +++ | ++ | +++ | + | + | + | + | + |
| 235 | +++ | +++ | + | + | + | + | + | + | + |
| 236 | ++ | +++ | + | + | + | + | + | + | + |
| 237 | + | +++ | + | + | + | + | + | + | + |
| 238 | ++ | +++ | + | + | + | + | + | ++ | + |
| 239 | ++ | +++ | + | + | + | + | + | +++ | + |
| 240 | ++ | +++ | + | + | + | + | + | +++ | + |
| 241 | +++ | +++ | + | ++ | + | + | ++ | +++ | + |
| 242 | ++ | +++ | + | + | + | + | + | ++ | + |
| 243 | ++ | +++ | + | + | + | + | + | ++ | + |
| 244 | +++ | +++ | + | + | + | + | ++ | ++ | + |
| 245 | ++ | +++ | + | + | + | + | + | ++ | + |
| 246 | + | + | + | + | + | + | + | + | + |
| 247 | + | + | + | + | + | + | + | + | + |
| 248 | + | + | + | + | + | + | + | + | + |
| 249 | + | ++ | + | + | + | + | + | + | + |
| 250 | + | + | + | + | + | + | + | + | + |
| 251 | + | + | + | + | + | + | + | + | + |

TABLE 15-continued

Biological Activity of Compounds of Formula I or a Pharmaceutically Acceptable Salt thereof

| No. | Sa + bicarb MIC | *E. coli* + bicarb MIC | Kp (1705) + bicearb MIC | Kp (060) + bicarb MIC | Pa MIC + bicarb | Ab + bicarb MIC | Ef + bicarb MIC | S30 $IC_{50}$ (μM/% inhib.) | Rabbit reticulocyte $IC_{50}$ (μM/% inhib.) |
|---|---|---|---|---|---|---|---|---|---|
| 252 | +++ | +++ | + | + | + | + | + | ++ | + |
| 253 | + | + | + | + | + | + | + | + | + |
| 254 | + | ++ | + | + | + | + | + | ++ | + |
| 255 | + | ++ | + | + | + | + | + | ++ | + |

The invention claimed is:

1. A compound of formula I:

I

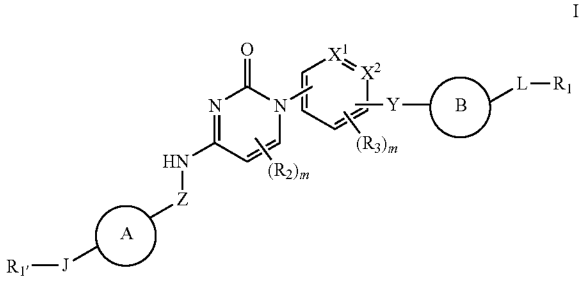

or a pharmaceutically acceptable salt thereof, wherein:

Z is (C═O);

ring A is selected from the group consisting of

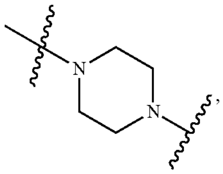
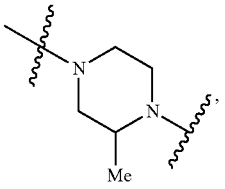
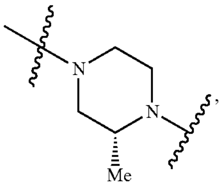
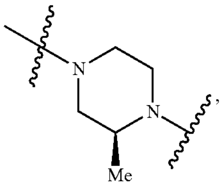
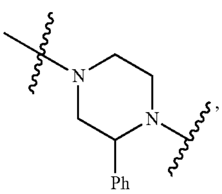
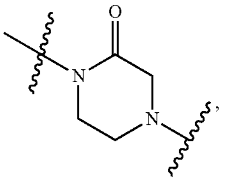
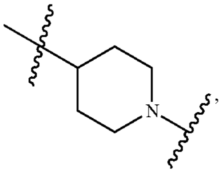
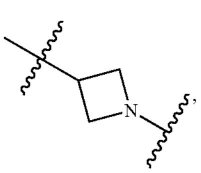

-continued

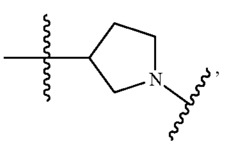
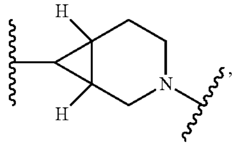
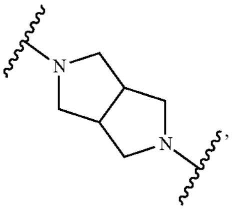
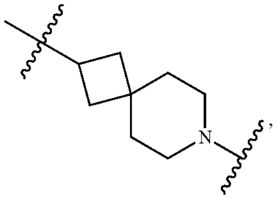
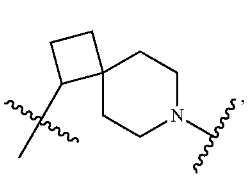
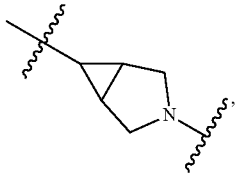
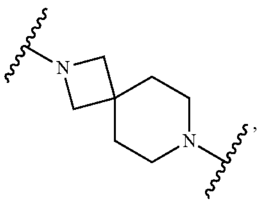
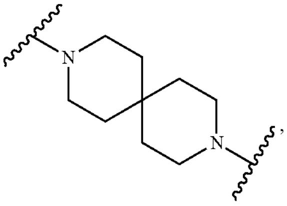
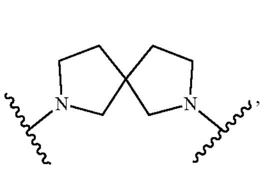
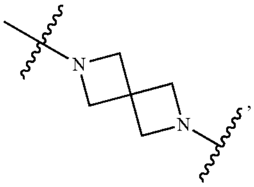
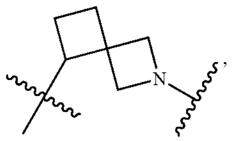
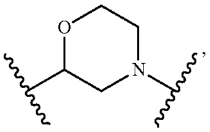
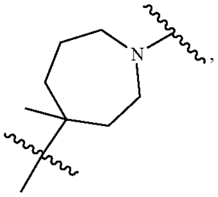

and

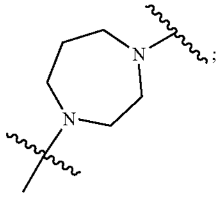

;

J is absent or is selected from the group consisting of —$CH_2$—, —$CH_2CH_2$—,

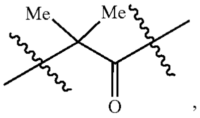,
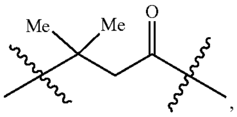,
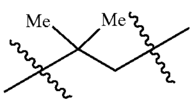,
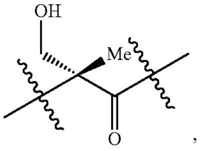,
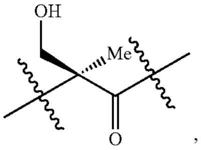,
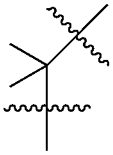,
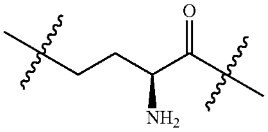
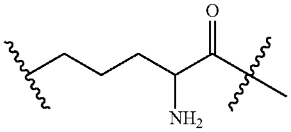,
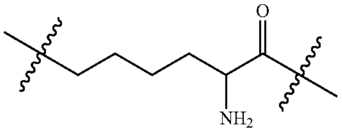,
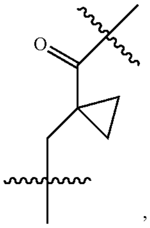,
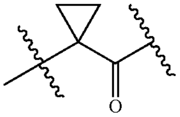,
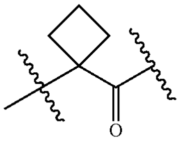,
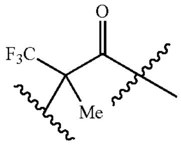,
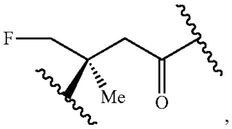,
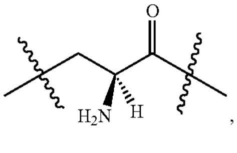,
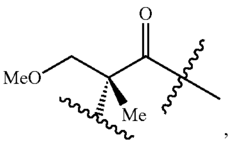,
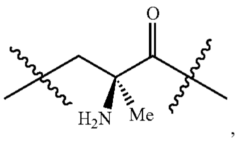,
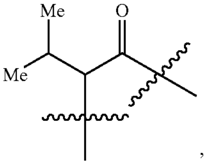, -continued

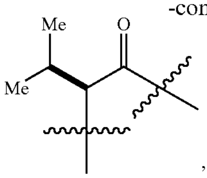,
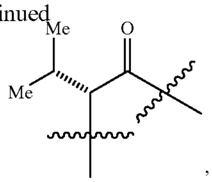,
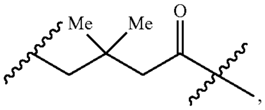,
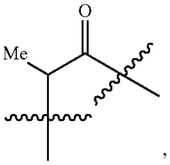,
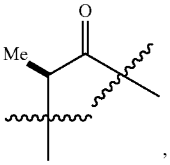,
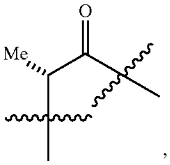,
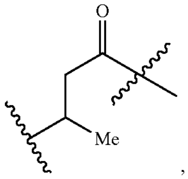,
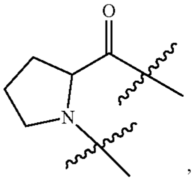,
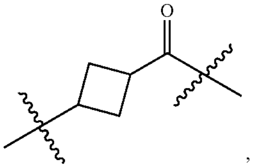,
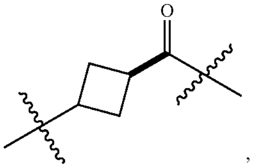,
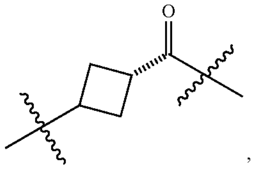, and
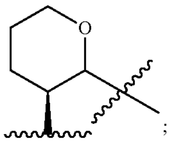;

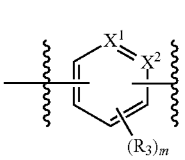 is 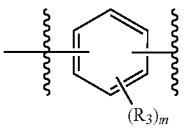 or 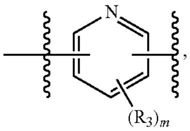, wherein each $R_3$ is independently selected from the group consisting of $C_1$-$C_6$ alkyl, $C_1$-$C_6$ alkoxy, halo, and $C_1$-$C_6$ haloalkyl, wherein m is 0, 1 or 2;

Y is a linear $C_1$-$C_8$ alkylene optionally substituted with OH, $NH_2$, CN, halo, $C_1$-$C_6$ alkyl, $C_1$-$C_6$ haloalkyl, COO($C_1$-$C_6$ alkyl), COOH, $CONH_2$, or $C_1$-$C_6$ alkoxy, and wherein up to two methylene units of the $C_1$-$C_8$alkylene are optionally and independently replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-$C_{3-8}$ cycloalkyl), NH(C═O), N—($C_{1-6}$ alkyl)(C═O), or (C═O);

ring B is a 5 to 12 membered fused, spiro, or bridged bicyclic heterocycloalkylene containing up to 3 nitrogen atoms, wherein the fused, spiro, or bridged bicyclic heterocycloalkylene is optionally substituted with up to three substituents independently selected from the group consisting of $C_1$-$C_6$ alkyl, $C_1$-$C_6$ alkoxy, halo, $C_1$-$C_6$ haloalkyl, OH, and $C_1$-$C_6$ hydroxyalkyl; or ring B is a 5 to 12 membered fused, spiro, or bridged bicyclic cycloalkylene optionally substituted with up to two substituents selected from the group consisting of $C_1$-$C_6$ alkyl, $C_1$-$C_6$ alkoxy, halo, $C_1$-$C_6$ haloalkyl, OH, and $C_1$-$C_6$ hydroxyalkyl;

L is absent, or is a linear or branched $C_1$-$C_6$ alkylene optionally substituted with $C_1$-$C_6$ alkoxy, halo, CN, OH, $NH_2$, COO($C_1$-$C_6$ alkyl), or $CONH_2$, wherein one methylene unit of the $C_1$-$C_6$ alkylene may be replaced with O, NH, (C═O), or N—($C_{1-6}$ alkyl);

$R_1$ is H, $NH_2$, NH($C_1$-$C_6$ alkyl), NHCO($C_1$-$C_6$ alkyl), or NH($C_1$-$C_6$ alkyl-$SO_3^-$);

$R_1$' is H, $NH_2$, NH($C_1$-$C_6$ alkyl), NHCO($C_1$-$C_6$ alkyl), or NH($C_1$-$C_6$ alkyl-$SO_3^-$); and $R_2$ is independently selected from the group consisting of $C_1$-$C_6$ alkyl, halo, $C_1$-$C_6$ haloalkyl, O($C_1$-$C_6$ haloalkyl), and $C_1$-$C_6$ alkoxy, and n is 0, 1, or 2.

2. The compound of claim 1 or a pharmaceutically acceptable salt thereof, wherein

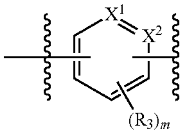

is selected from the group consisting of

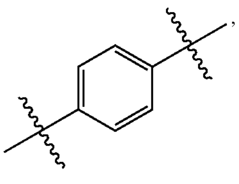,

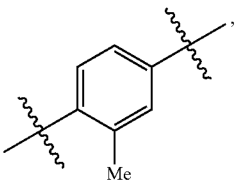,

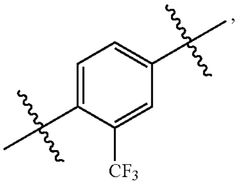,

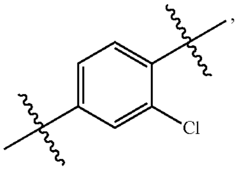,

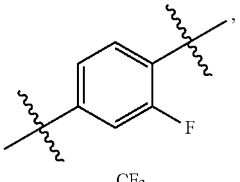,

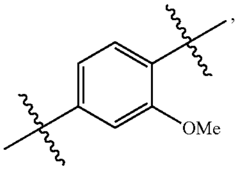,

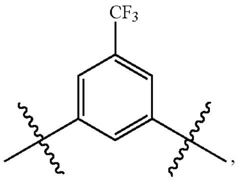,

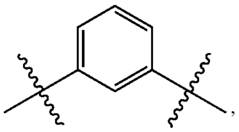,

-continued

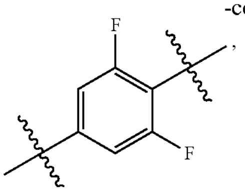, and

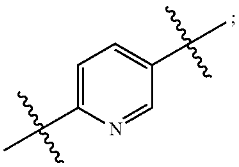;

and/or

Y is selected from the group consisting of $CH_2$, $CH(CH_3)$, CH(COOEt) CH(COOH),

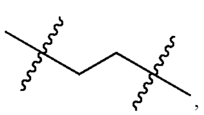,

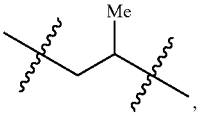,

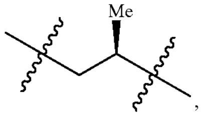,

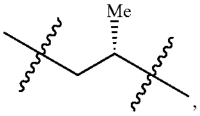,

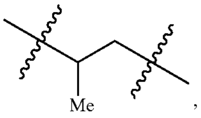,

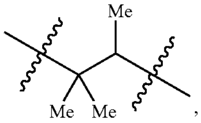,

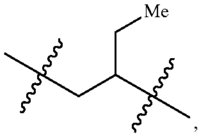,

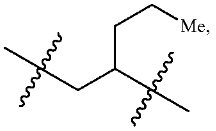

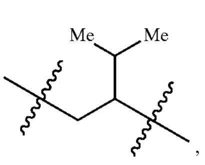,

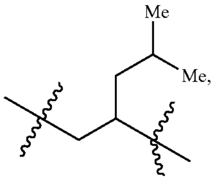

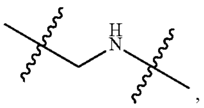,

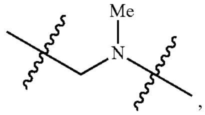,

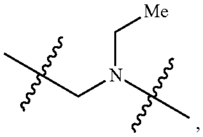,

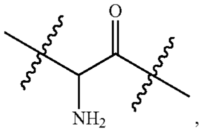,

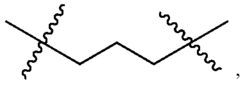,

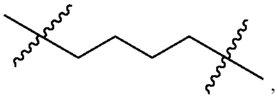,

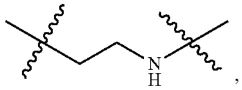,

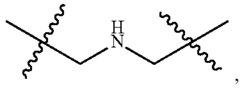,

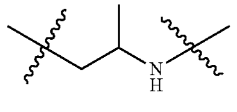,

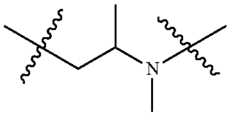,

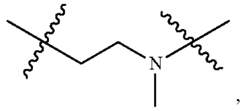,

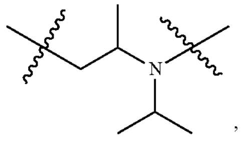,

-continued
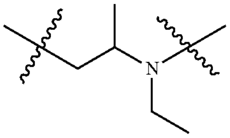,
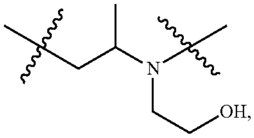,
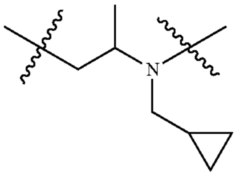,
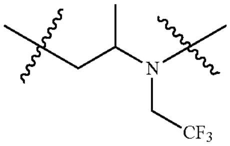,
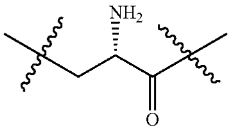,
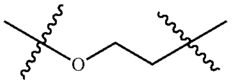,
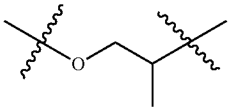,
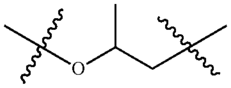, and
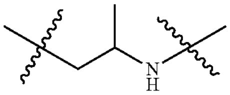;
and/or
ring B is selected from the group consisting of
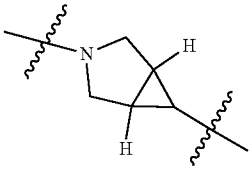,
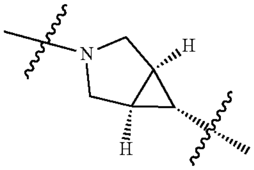,
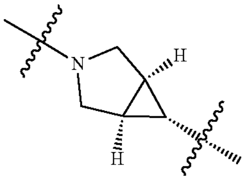,
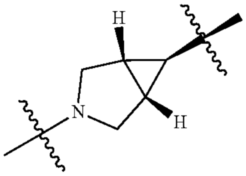,
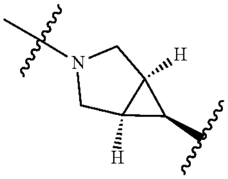,
-continued
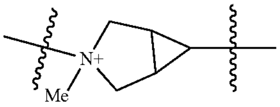,
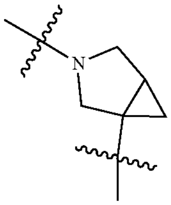,
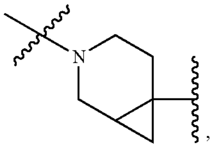,
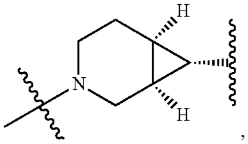,
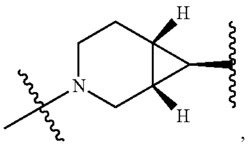,
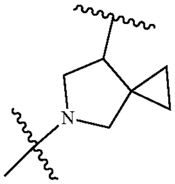,
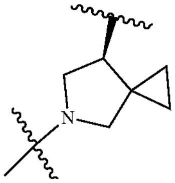,
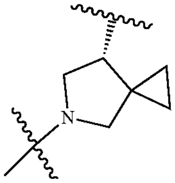,
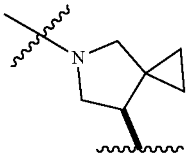,
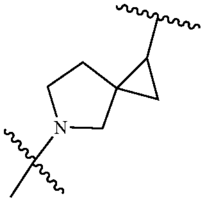, -continued
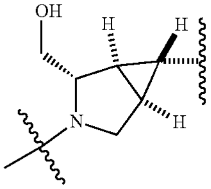
,
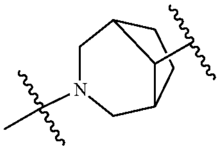
,
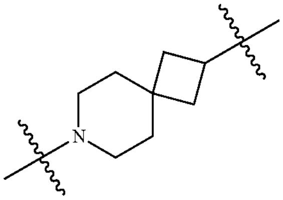
,
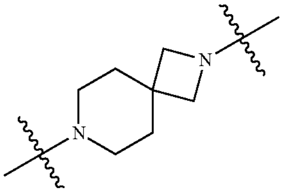
,
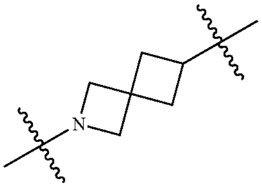
,
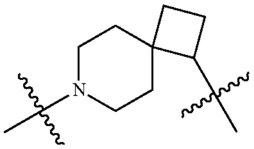
,
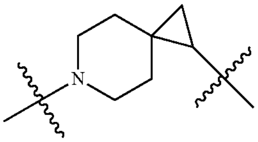
,
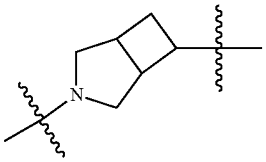
,
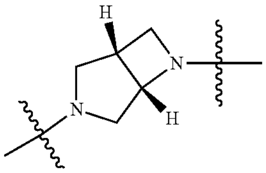
,
-continued
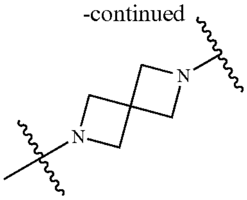
,
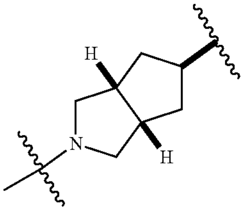
,
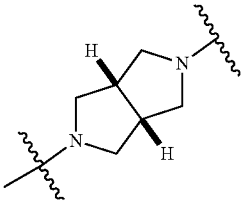
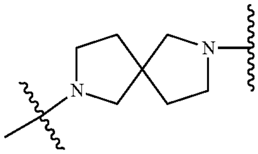
,
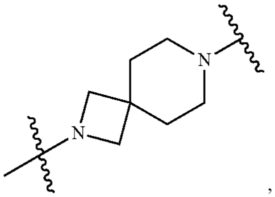
,
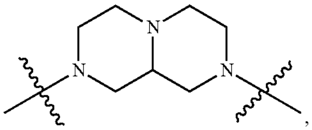
,
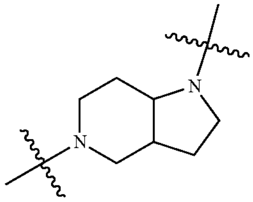
,
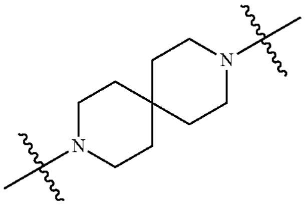
,
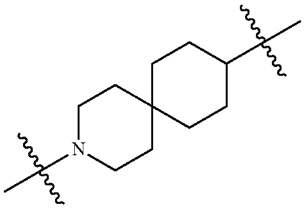
, -continued
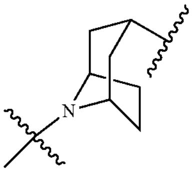
,
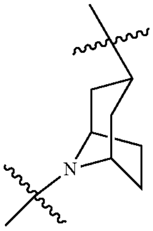
,
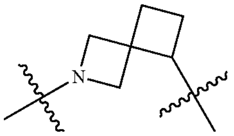
,
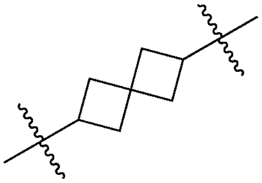
,
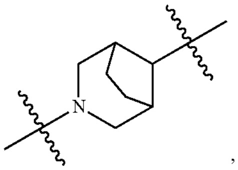
,
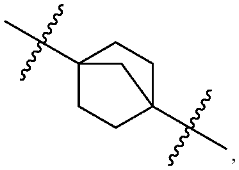
,
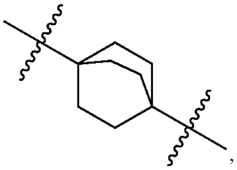
,
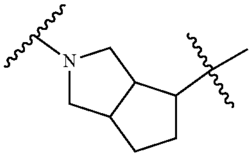
,
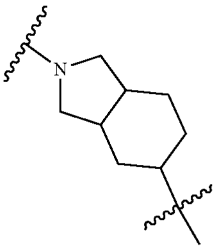
,
-continued
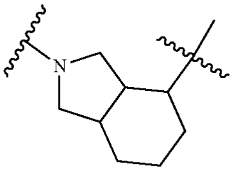
,
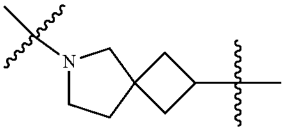
, and
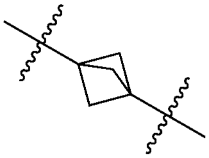
.
3. The compound of claim 1 or a pharmaceutically acceptable salt thereof, wherein:
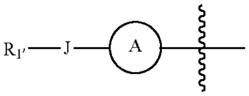
is selected from the group consisting of
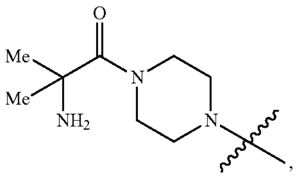
,
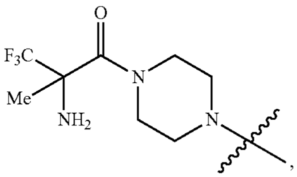
,
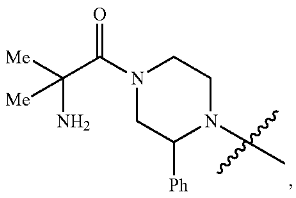
,
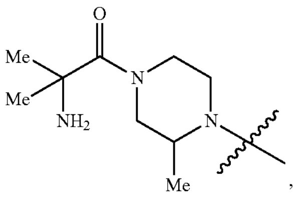
, -continued
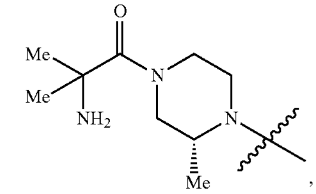
,
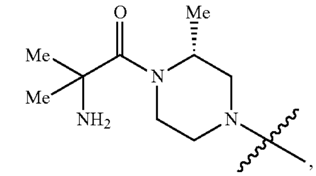
,
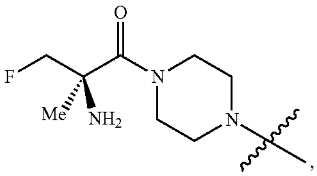
,
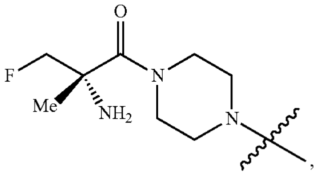
,
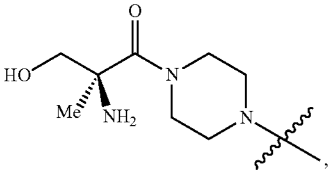
,
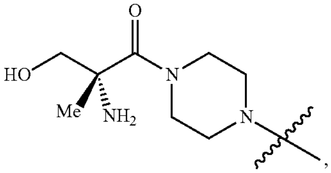
,
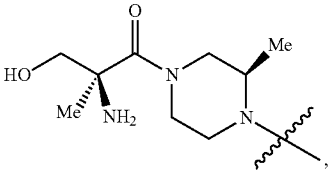
,
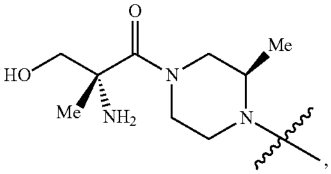
,
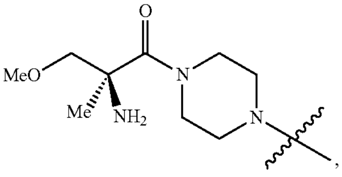
,
-continued
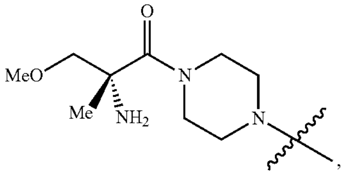
,
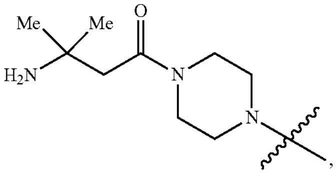
,
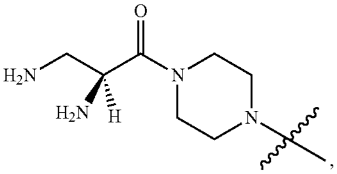
,
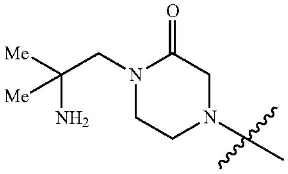
,
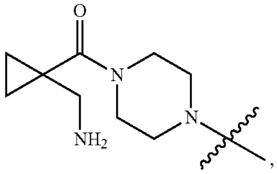
,
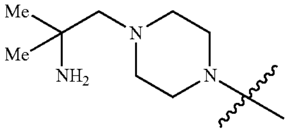
,
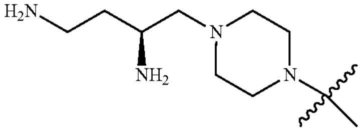
,
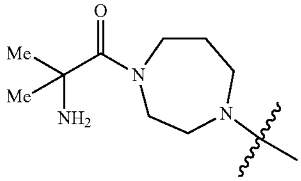
,
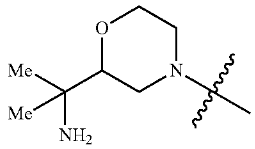
,
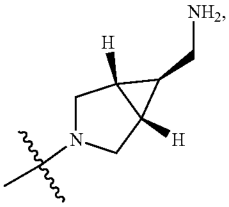

-continued
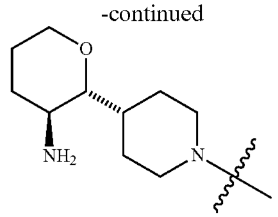
,
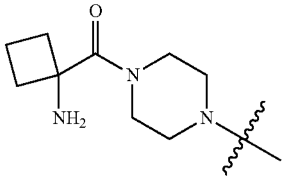
,
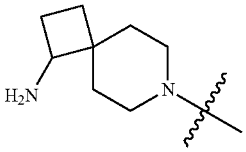
,
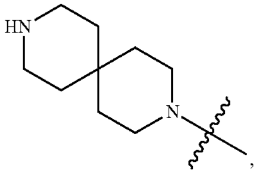
,
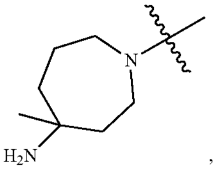
,
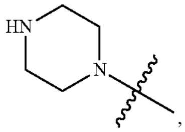
,
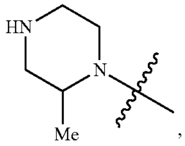
,
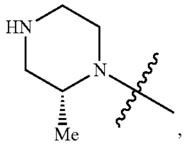
,
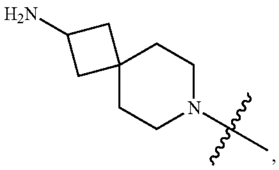
,
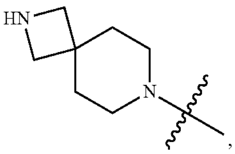
,
-continued
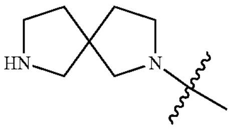
,
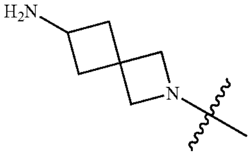
,
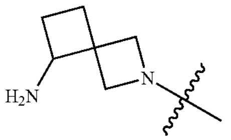
,
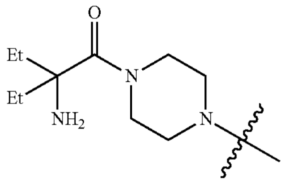
,
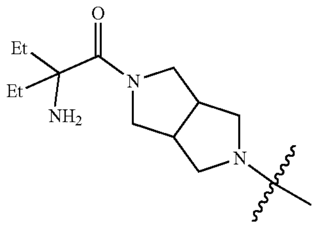
,
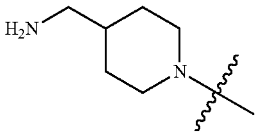
,
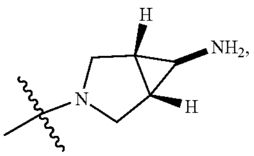
,
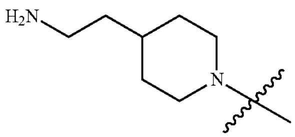
,
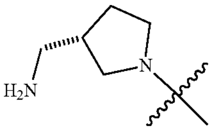
,
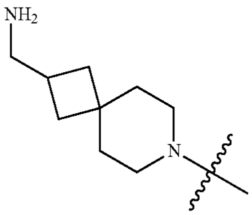
,
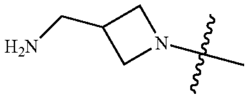
, -continued
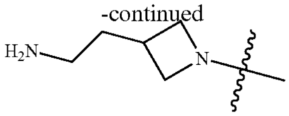
,
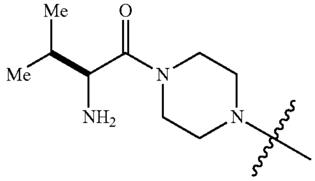
,
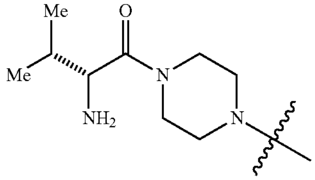
,
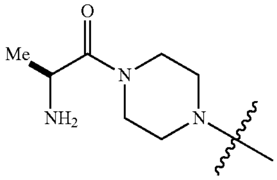
,
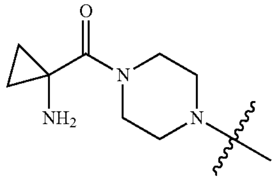
,
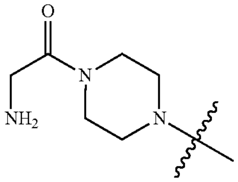
,
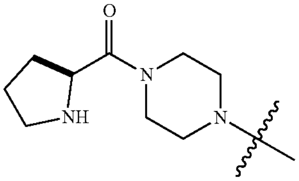
,
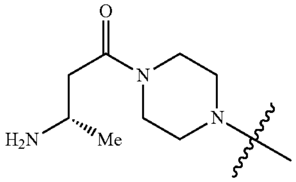
,
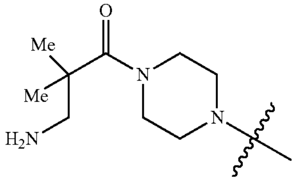
,
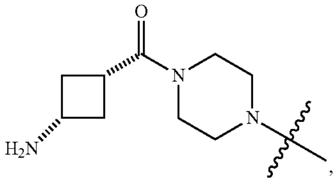
,
-continued
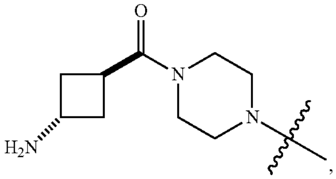
,
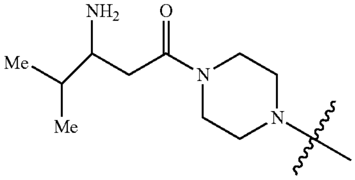
,
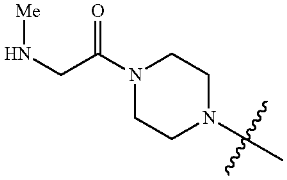
,
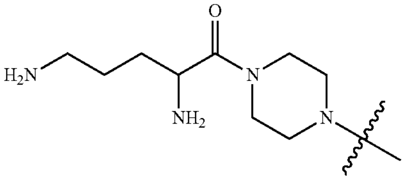
,
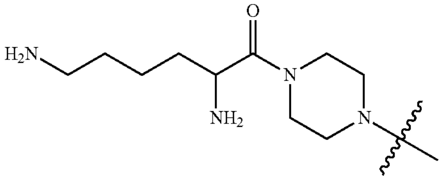
, and
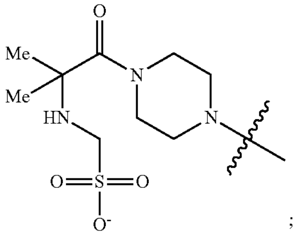
;
and/or
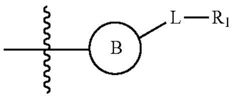
is selected from the group consisting of
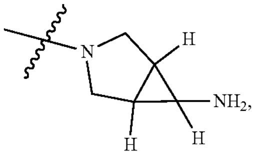

-continued
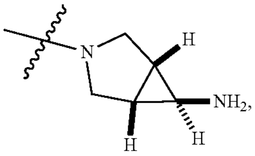
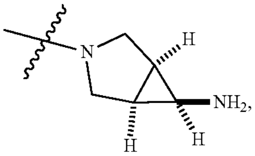
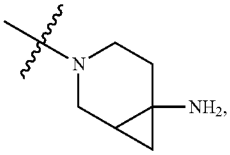
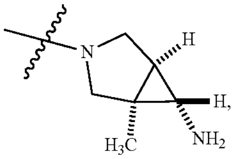
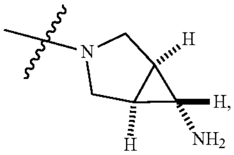
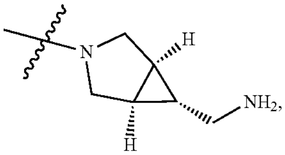
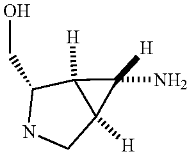
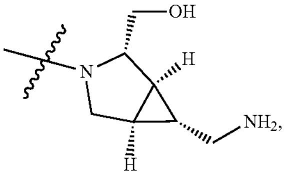
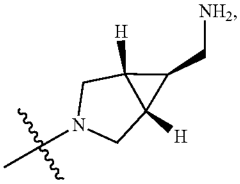
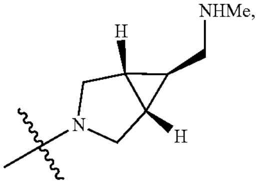
-continued
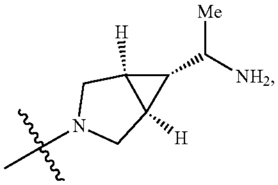
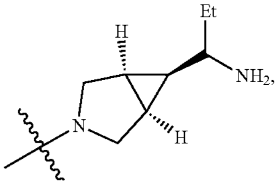
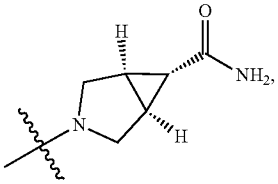
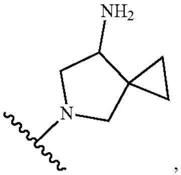
,
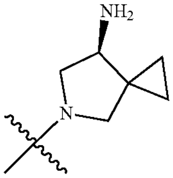
,
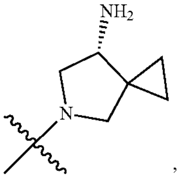
,
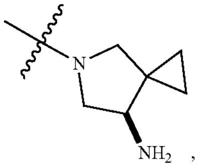
,
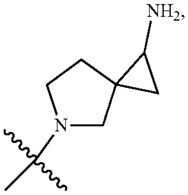
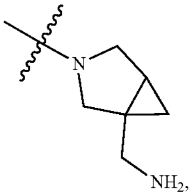
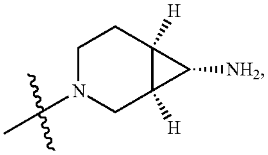
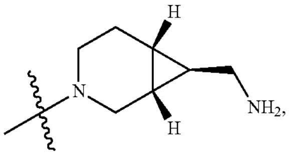

-continued
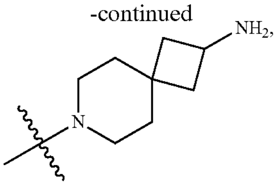
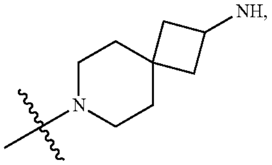
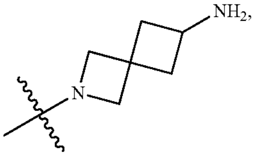
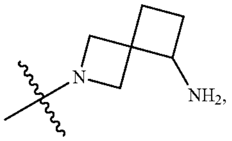
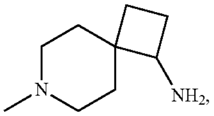
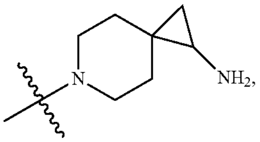
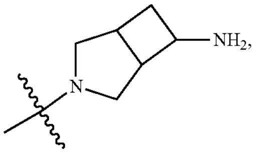
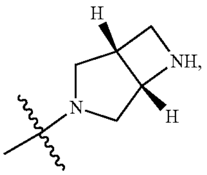
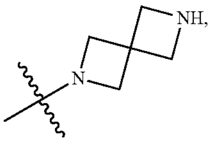
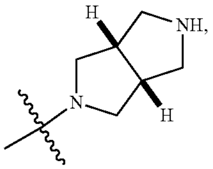
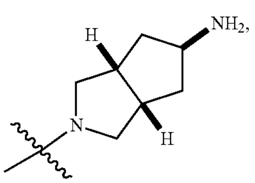
-continued
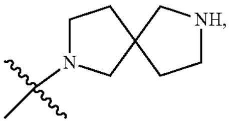
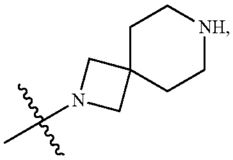
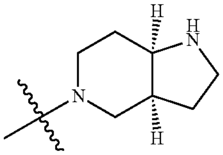
,
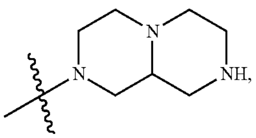
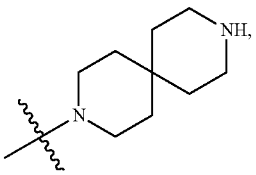
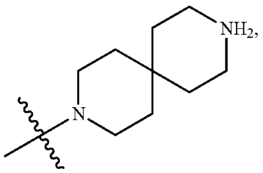
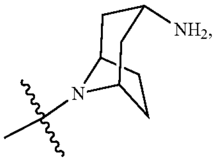
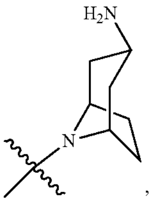
,
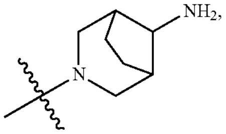
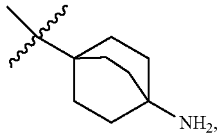
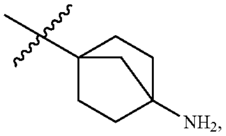

-continued
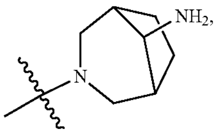
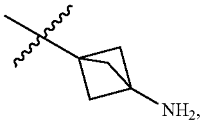
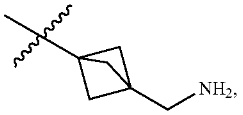
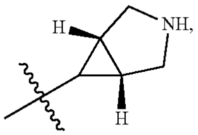
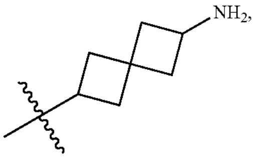
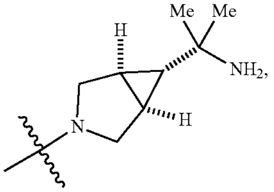
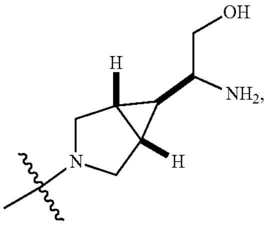
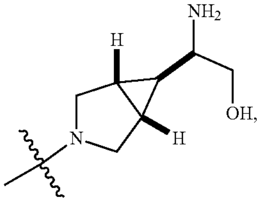
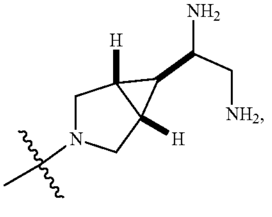
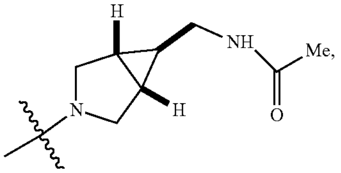
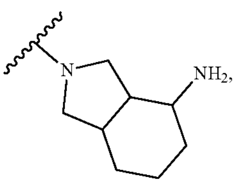
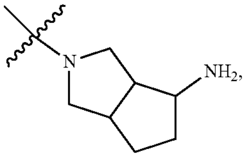
-continued
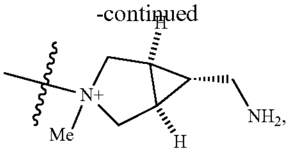
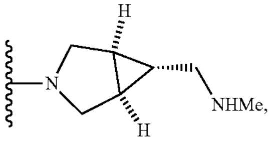
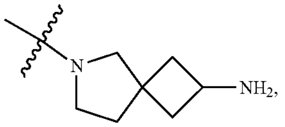
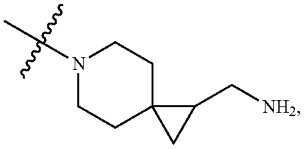
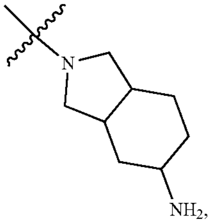
and
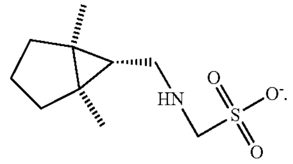
4. The compound of claim 1 or a pharmaceutically acceptable salt thereof which is a compound of formula IIA or IIB:
IIA
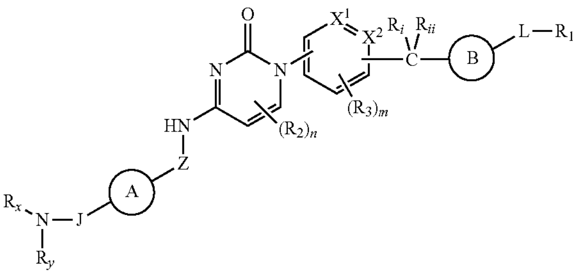
IIB
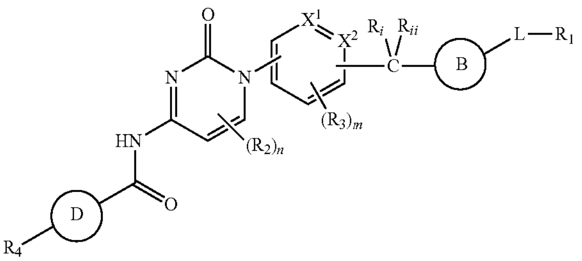
wherein:
L is absent, or is a linear or branched $C_1$-$C_6$ alkylene, wherein one methylene unit of the $C_1$-$C_6$ alkylene may be independently replaced with O, NH, (C═O), or N—($C_{1-6}$ alkyl);

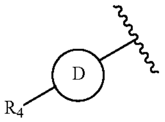

is selected from the group consisting of

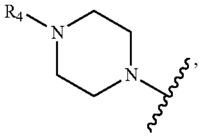
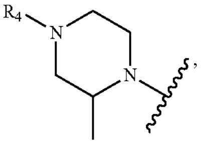
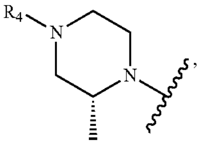
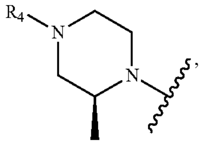
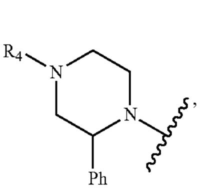
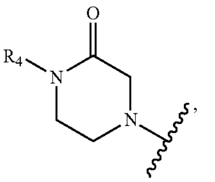
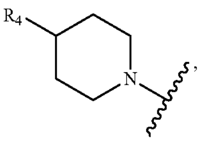
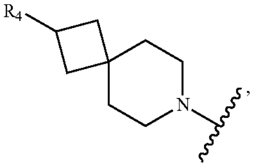
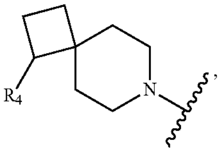
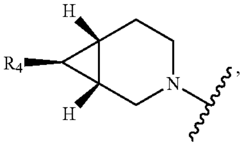
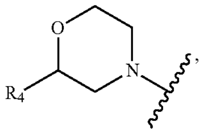
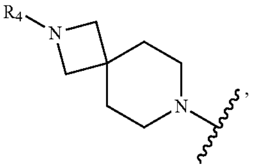
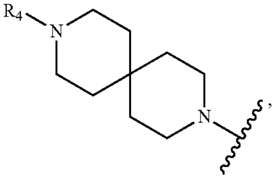
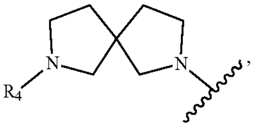
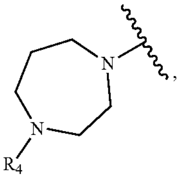
and
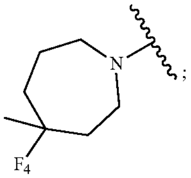

$R_i$ and $R_{ii}$ are each independently H, OH, $NH_2$, CN, halo, $C_1$-$C_6$ alkyl, $C_1$-$C_6$ haloalkyl, COO($C_1$-$C_6$ alkyl), COOH, $CONH_2$, or $C_1$-$C_6$ alkoxy;

$R_1$ and $R_4$ are each independently H, $NH_2$ or NH($C_1$-$C_6$ alkyl); and $NR_xR_y$ is $NH_2$ or NH($C_1$-$C_6$ alkyl).

5. The compound of claim 4 or a pharmaceutically acceptable salt thereof, wherein ring A is selected from the group consisting of

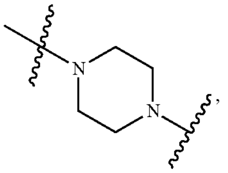
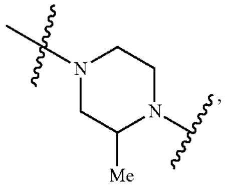
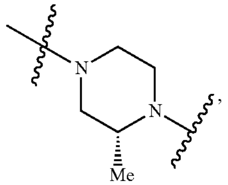
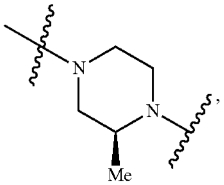
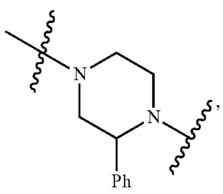
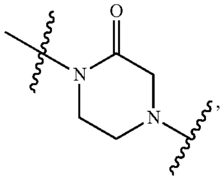
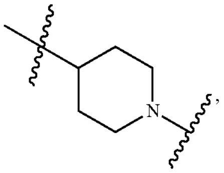
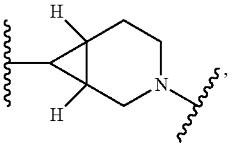
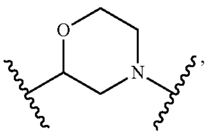
and
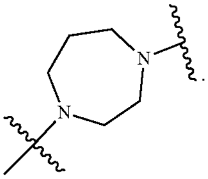

and/or $CR_iR_{ii}$ is selected from the group consisting of $CH_2$, CH($C_1$-$C_6$ alkyl), C($C_1$-$C_6$ alkyl)$_2$, CH—COO($C_1$-$C_6$ alkyl) and CHCOOH; and/or ring B is selected from the group consisting of

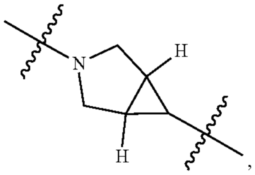
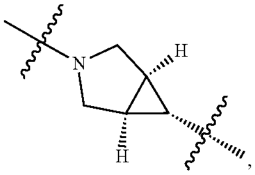

-continued
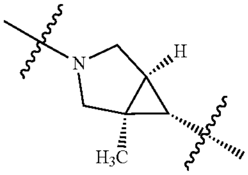,
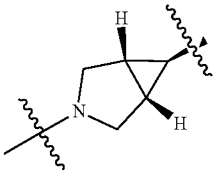,
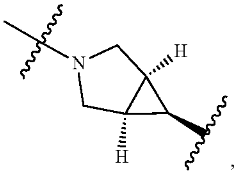,
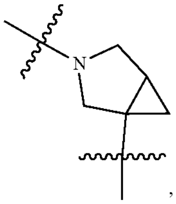,
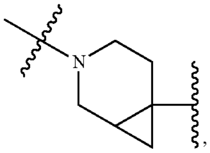,
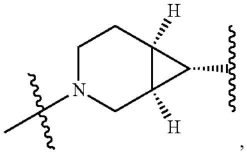,
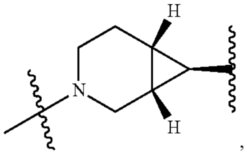,
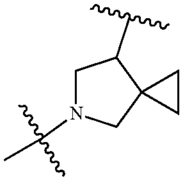, 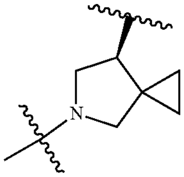,
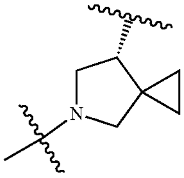, 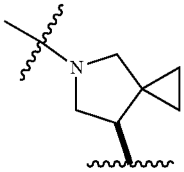,
-continued
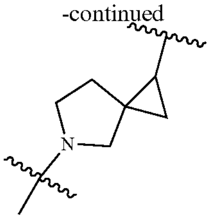,
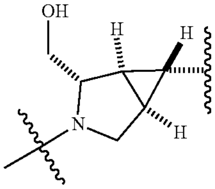,
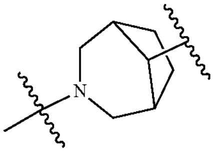,
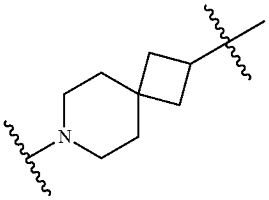,
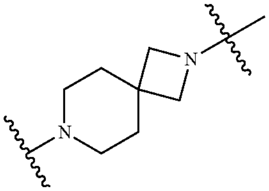,
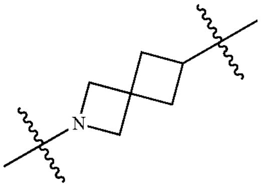,
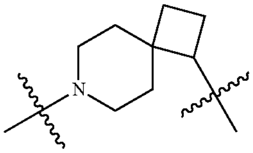,
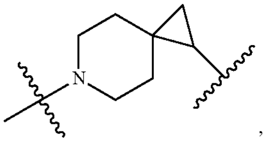,
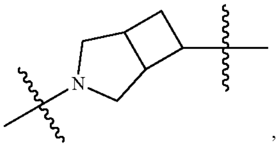,
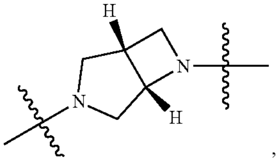, -continued

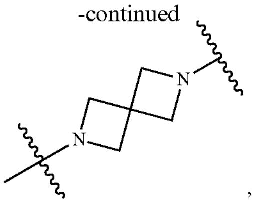

,

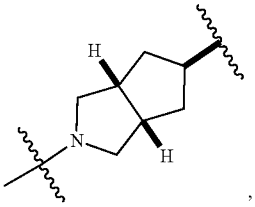

,

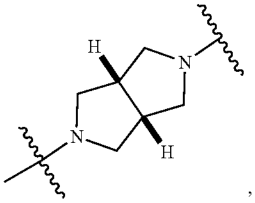

,

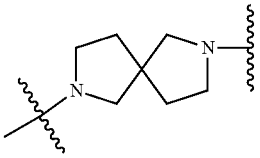

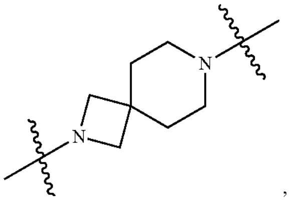

,

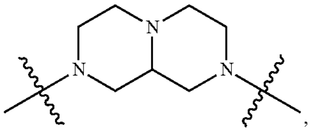

,

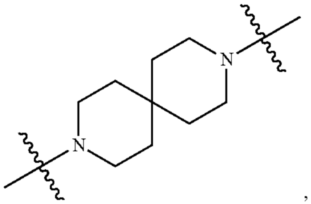

,

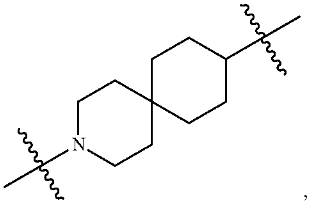

,

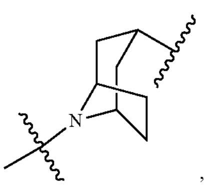

,

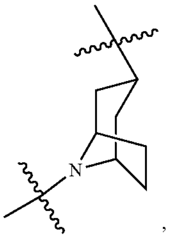

, and

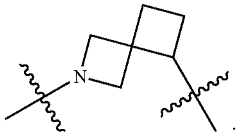

.

6. The compound of claim 1 or a pharmaceutically acceptable salt thereof which is a compound of formula IIIA or IIIB:

IIIA

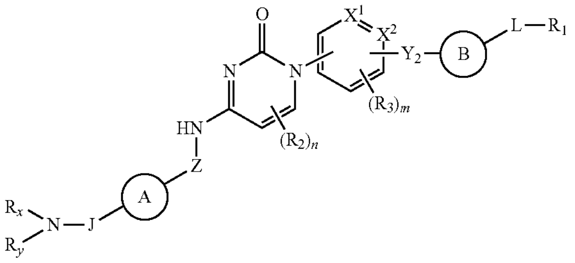

IIIB

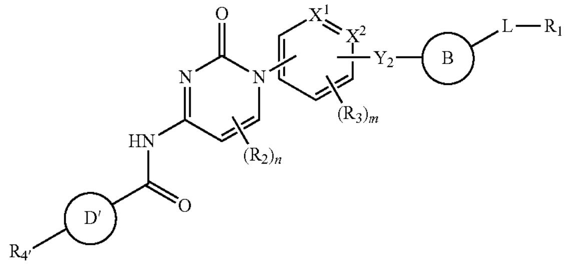

wherein:

L is absent, or is a linear or branched $C_1$-$C_6$ alkylene, wherein one methylene unit of the $C_1$-$C_6$ alkylene may be independently replaced with O, NH, (C═O), or N—($C_{1-6}$ alkyl);

$Y_2$ is ethylene optionally substituted with OH, $NH_2$, halo, $C_1$-$C_6$ alkyl, or $C_1$-$C_6$ alkoxy, and wherein one methylene unit of the ethylene may be replaced by O, NH, N—($C_1$-$C_6$ alkyl), N—($C_1$-$C_6$ hydroxyalkyl), N—($C_1$-$C_6$ haloalkyl), N—($C_{1-6}$ alkylene-cycloalkyl), NH(C═O), N—($C_{1-6}$ alkyl) (C═O), or (C═O);

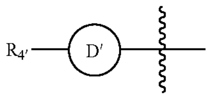

is selected from the group consisting of

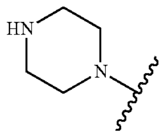

,

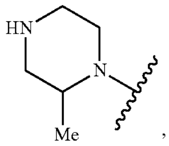

,

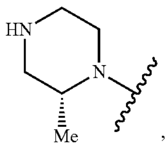

,

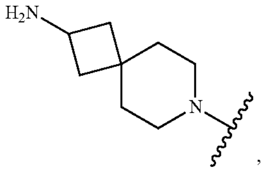

,

-continued

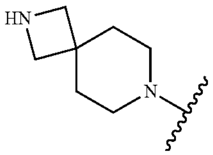,
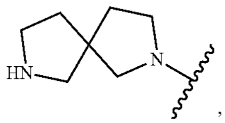,
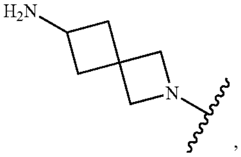, and
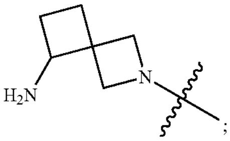;

$R_1$ and $R_4$' are each independently H, $NH_2$ or NH($C_1$-$C_6$ alkyl); and $NR_xR_y$ is $NH_2$ or NH($C_1$-$C_6$ alkyl).

7. The compound of claim 6 or a pharmaceutically acceptable salt thereof, wherein ring A is selected from the group consisting of

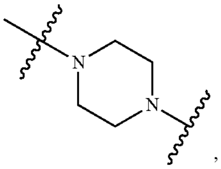,
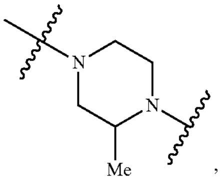, and
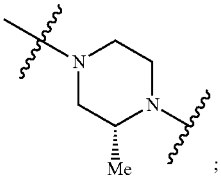;

and/or $Y_2$ is selected from the group consisting of

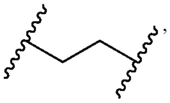,
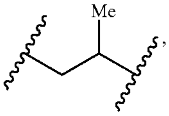,
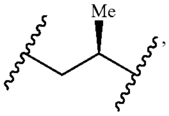,
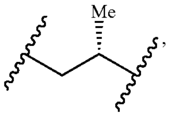,
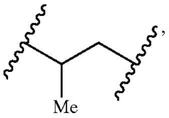,
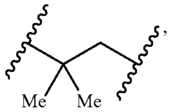,
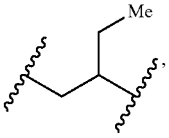,
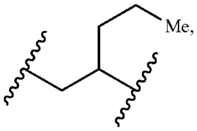,
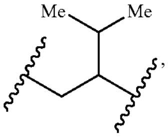,
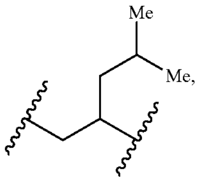,
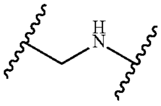,
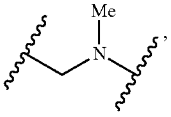, -continued

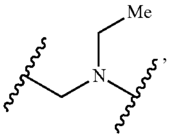, and
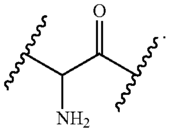.

and/or ring B is selected from the group consisting of

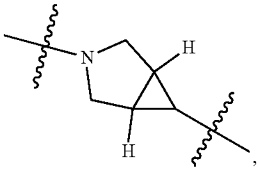,
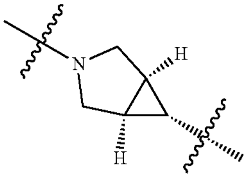,
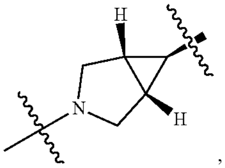,
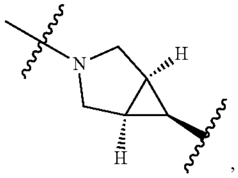,
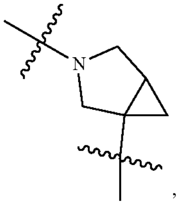,
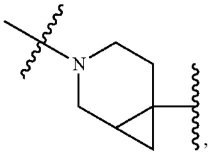,
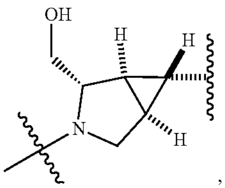, -continued
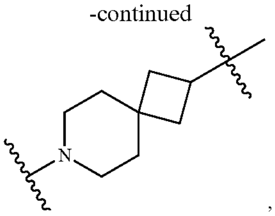
,
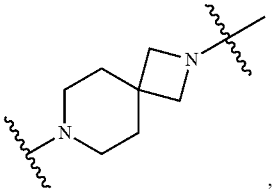
,
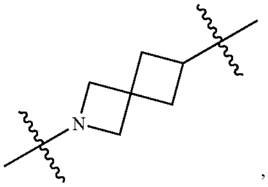
,
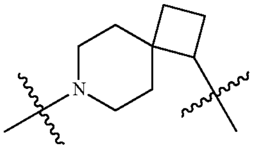
,
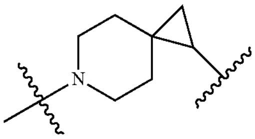
,
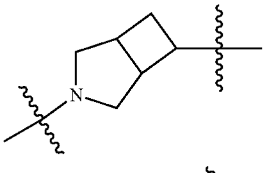
,
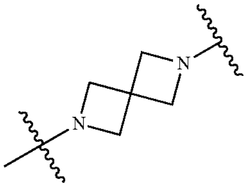
,
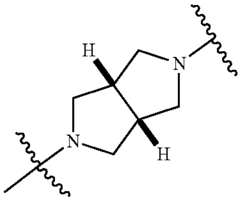
,
-continued
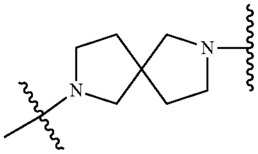
,
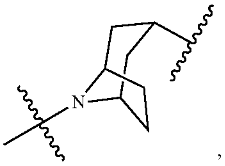
,
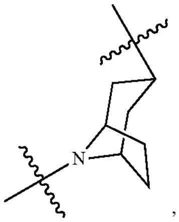
,
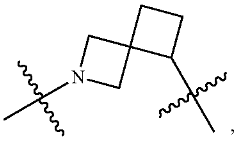
,
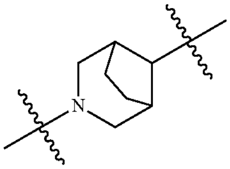
,
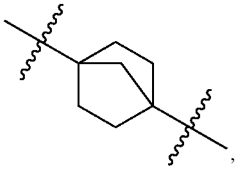
,
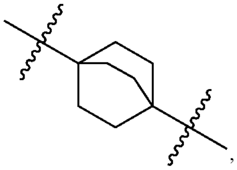
, and
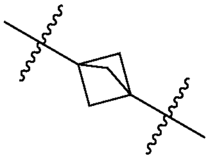
.
8. The compound of claim 1, selected from the compounds listed in Table 7, Table 8, Table 9, Table 10, or Table 11 or pharmaceutically acceptable salts thereof:

TABLE 7
| No. | Salt Structure | Free Base Structure |
|---|---|---|
| 1 | 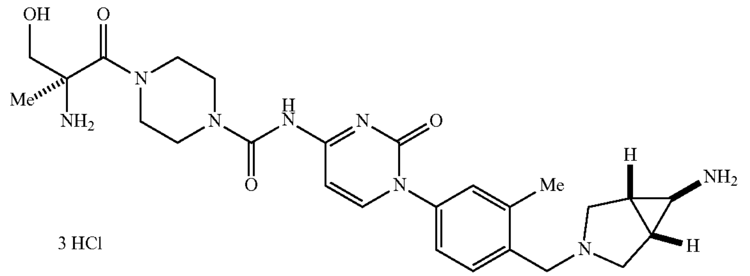 [SMILES: Cc1cc(-n2ccc(NC(=O)N3CCN(C(=O)[C@@](C)(N)CO)CC3)nc2=O)ccc1CN1C[C@@H]2[C@@H](N)[C@@H]2C1] 3 HCl | 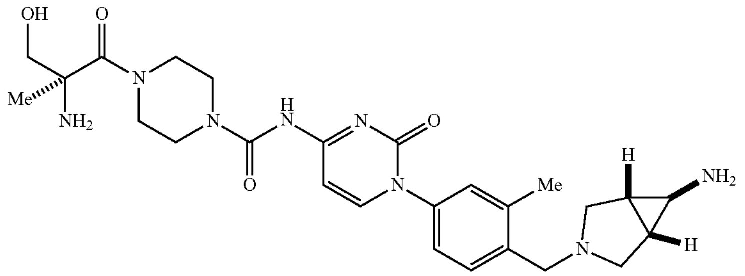 [SMILES: Cc1cc(-n2ccc(NC(=O)N3CCN(C(=O)[C@@](C)(N)CO)CC3)nc2=O)ccc1CN1C[C@@H]2[C@@H](N)[C@@H]2C1] |
| 2 | 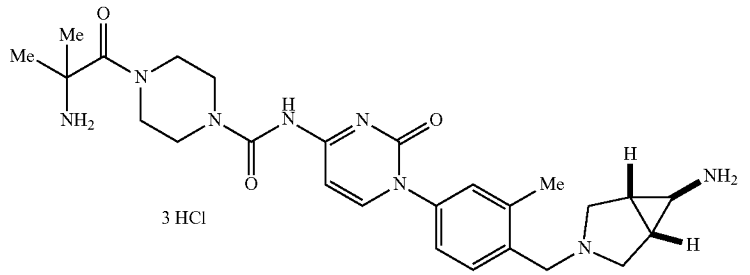 [SMILES: Cc1cc(-n2ccc(NC(=O)N3CCN(C(=O)C(C)(C)N)CC3)nc2=O)ccc1CN1C[C@@H]2[C@@H](N)[C@@H]2C1] 3 HCl | 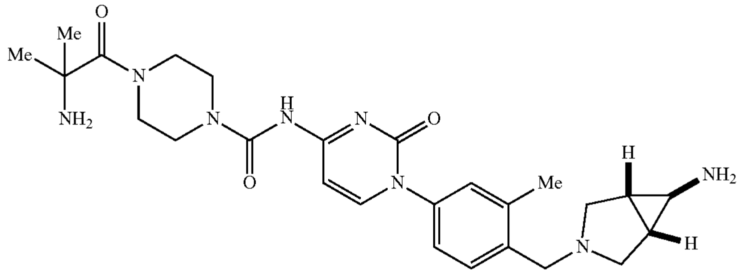 [SMILES: Cc1cc(-n2ccc(NC(=O)N3CCN(C(=O)C(C)(C)N)CC3)nc2=O)ccc1CN1C[C@@H]2[C@@H](N)[C@@H]2C1] |
| 3 | 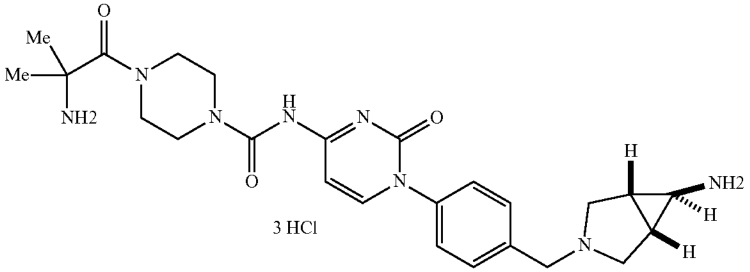 [SMILES: CC(C)(N)C(=O)N1CCN(C(=O)Nc2ccn(-c3ccc(CN4C[C@@H]5[C@@H](N)[C@@H]5C4)cc3)c(=O)n2)CC1] 3 HCl | 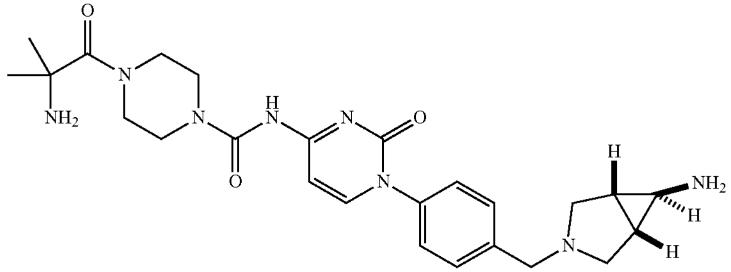 [SMILES: CC(C)(N)C(=O)N1CCN(C(=O)Nc2ccn(-c3ccc(CN4C[C@@H]5[C@@H](N)[C@@H]5C4)cc3)c(=O)n2)CC1] |
| 4 | 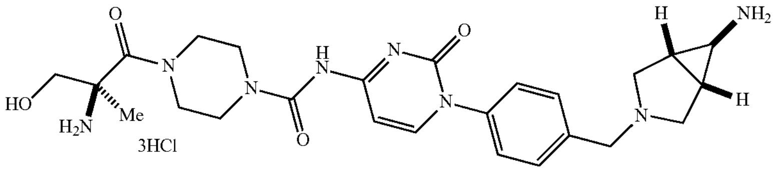 [SMILES: C[C@](N)(CO)C(=O)N1CCN(C(=O)Nc2ccn(-c3ccc(CN4C[C@@H]5[C@@H](N)[C@@H]5C4)cc3)c(=O)n2)CC1] 3HCl | 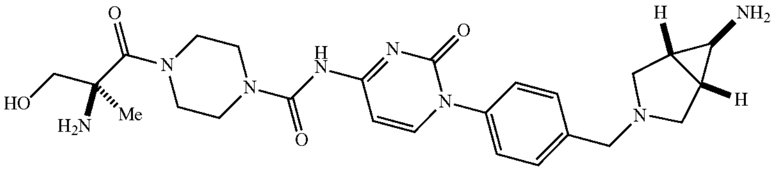 [SMILES: C[C@](N)(CO)C(=O)N1CCN(C(=O)Nc2ccn(-c3ccc(CN4C[C@@H]5[C@@H](N)[C@@H]5C4)cc3)c(=O)n2)CC1] |

TABLE 7-continued
| No. | Salt Structure | Free Base Structure |
|---|---|---|
| 5 | 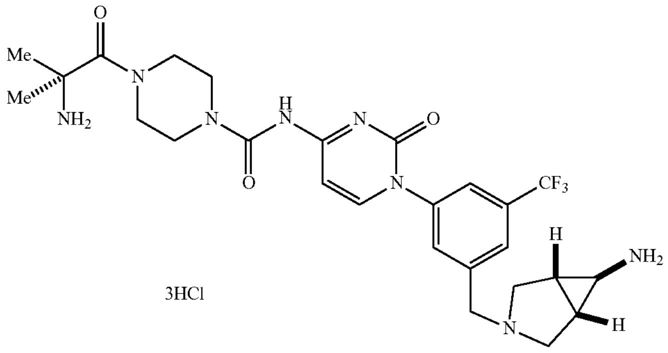 3HCl | 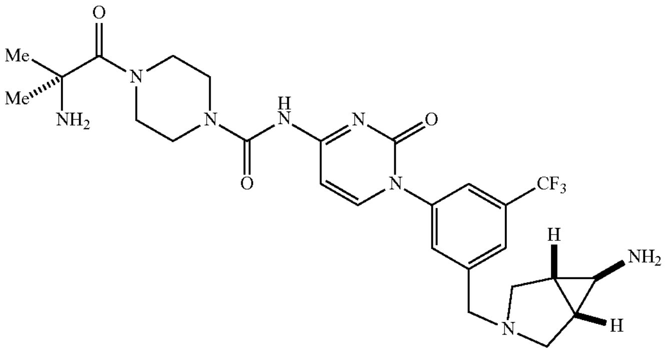 |
| 6 | 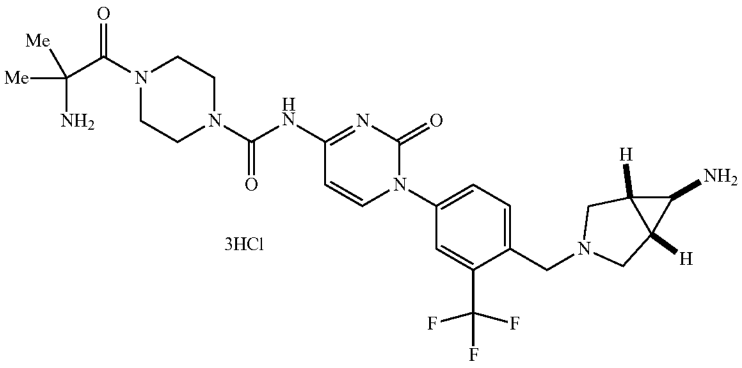 [SMILES: CC(C)(N)C(=O)N1CCN(C(=O)Nc2ccn(-c3ccc(CN4C[C@@H]5[C@@H](N)[C@@H]5C4)c(C(F)(F)F)c3)c(=O)n2)CC1] 3HCl | 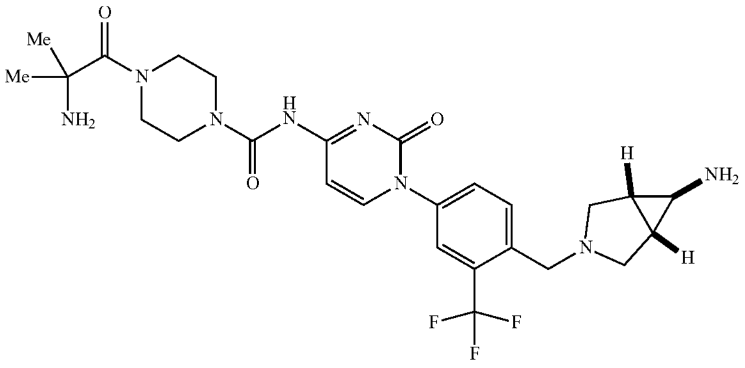 [SMILES: CC(C)(N)C(=O)N1CCN(C(=O)Nc2ccn(-c3ccc(CN4C[C@@H]5[C@@H](N)[C@@H]5C4)c(C(F)(F)F)c3)c(=O)n2)CC1] |
| 7 | 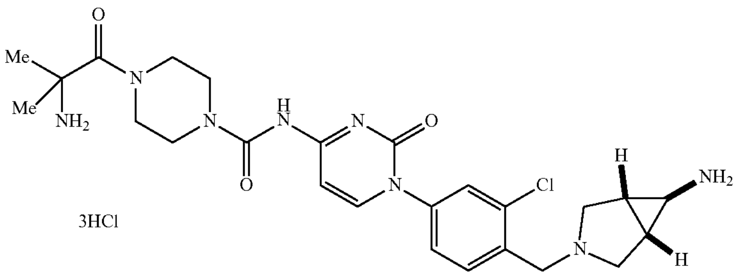 [SMILES: CC(C)(N)C(=O)N1CCN(C(=O)Nc2ccn(-c3ccc(CN4C[C@@H]5[C@@H](N)[C@@H]5C4)c(Cl)c3)c(=O)n2)CC1] 3HCl | 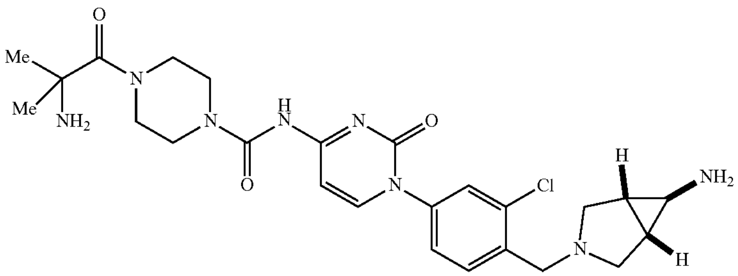 [SMILES: CC(C)(N)C(=O)N1CCN(C(=O)Nc2ccn(-c3ccc(CN4C[C@@H]5[C@@H](N)[C@@H]5C4)c(Cl)c3)c(=O)n2)CC1] |

TABLE 7-continued
| No. | Salt Structure | Free Base Structure |
|---|---|---|
| 8 | 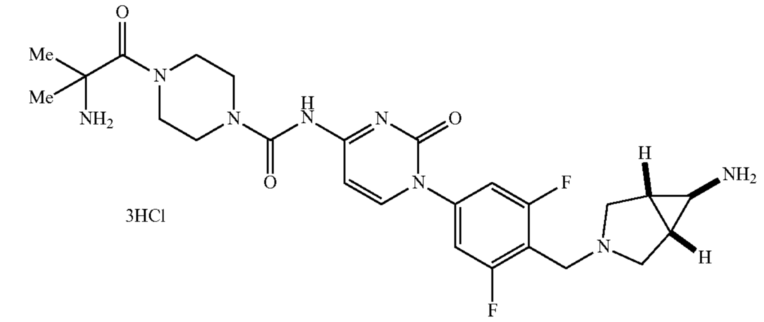 [SMILES: CC(C)(N)C(=O)N1CCN(C(=O)Nc2ccn(-c3cc(F)c(CN4C[C@@H]5[C@@H](N)[C@@H]5C4)c(F)c3)c(=O)n2)CC1] 3HCl | 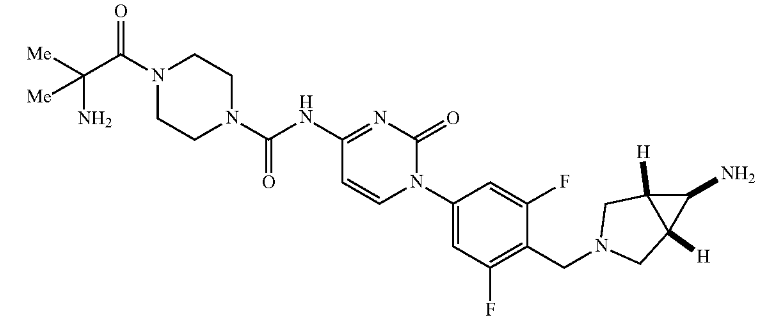 [SMILES: CC(C)(N)C(=O)N1CCN(C(=O)Nc2ccn(-c3cc(F)c(CN4C[C@@H]5[C@@H](N)[C@@H]5C4)c(F)c3)c(=O)n2)CC1] |
| 9 | 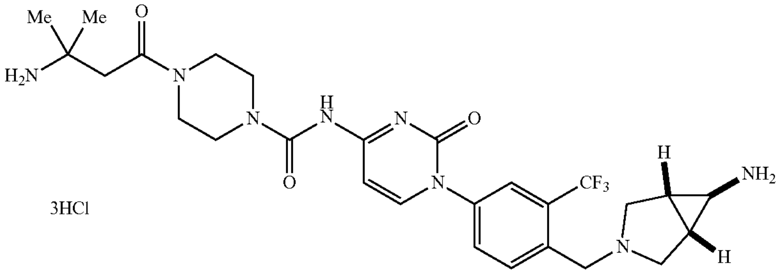 [SMILES: CC(C)(N)CC(=O)N1CCN(C(=O)Nc2ccn(-c3ccc(CN4C[C@@H]5[C@@H](N)[C@@H]5C4)c(C(F)(F)F)c3)c(=O)n2)CC1] 3HCl | 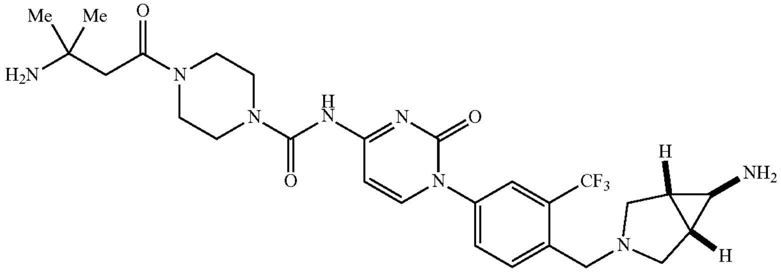 [SMILES: CC(C)(N)CC(=O)N1CCN(C(=O)Nc2ccn(-c3ccc(CN4C[C@@H]5[C@@H](N)[C@@H]5C4)c(C(F)(F)F)c3)c(=O)n2)CC1] |
| 10 | 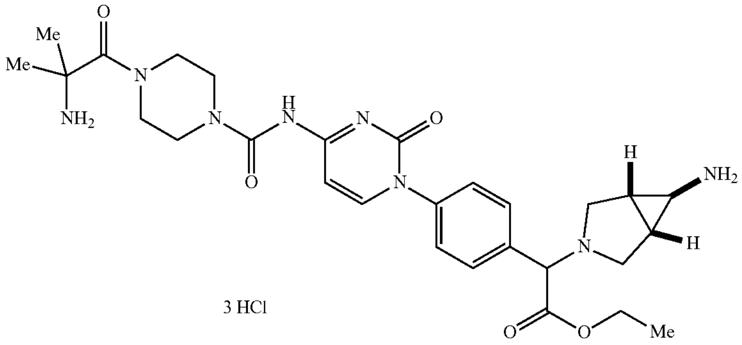 [SMILES: CCOC(=O)C(c1ccc(-n2ccc(NC(=O)N3CCN(C(=O)C(C)(C)N)CC3)nc2=O)cc1)N1C[C@@H]2[C@@H](N)[C@@H]2C1] 3 HCl | 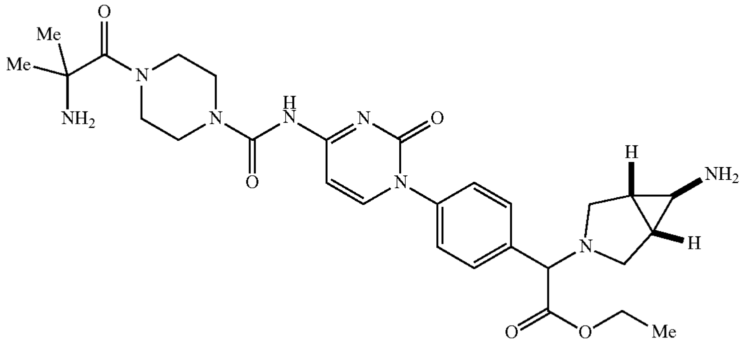 [SMILES: CCOC(=O)C(c1ccc(-n2ccc(NC(=O)N3CCN(C(=O)C(C)(C)N)CC3)nc2=O)cc1)N1C[C@@H]2[C@@H](N)[C@@H]2C1] |

TABLE 7-continued
| No. | Salt Structure | Free Base Structure |
|---|---|---|
| 11 | 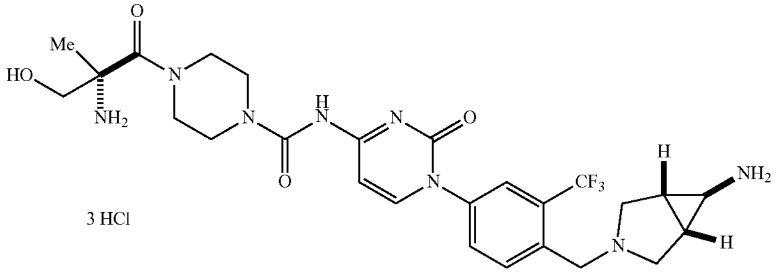 [SMILES: C[C@](N)(CO)C(=O)N1CCN(C(=O)Nc2ccn(-c3ccc(CN4C[C@@H]5[C@@H](N)[C@@H]5C4)c(C(F)(F)F)c3)c(=O)n2)CC1] 3 HCl | 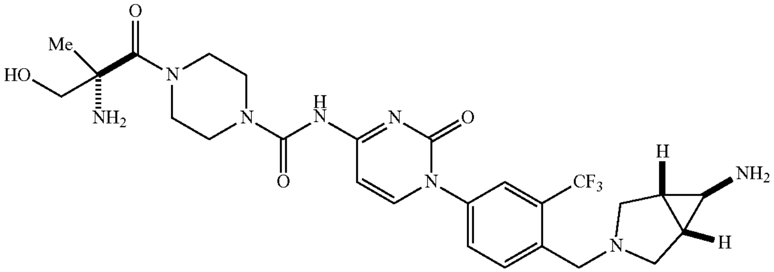 [SMILES: C[C@](N)(CO)C(=O)N1CCN(C(=O)Nc2ccn(-c3ccc(CN4C[C@@H]5[C@@H](N)[C@@H]5C4)c(C(F)(F)F)c3)c(=O)n2)CC1] |
| 12 | 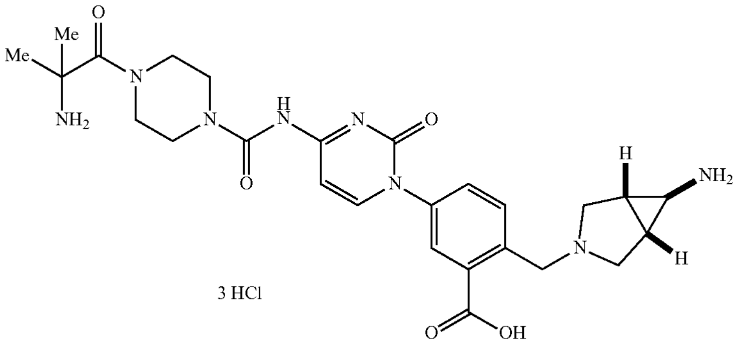 [SMILES: CC(C)(N)C(=O)N1CCN(C(=O)Nc2ccn(-c3ccc(CN4C[C@@H]5[C@@H](N)[C@@H]5C4)c(C(=O)O)c3)c(=O)n2)CC1] 3 HCl | 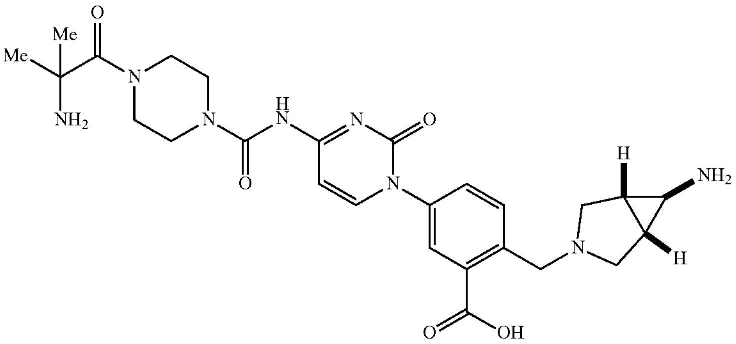 [SMILES: CC(C)(N)C(=O)N1CCN(C(=O)Nc2ccn(-c3ccc(CN4C[C@@H]5[C@@H](N)[C@@H]5C4)c(C(=O)O)c3)c(=O)n2)CC1] |
| 13 | 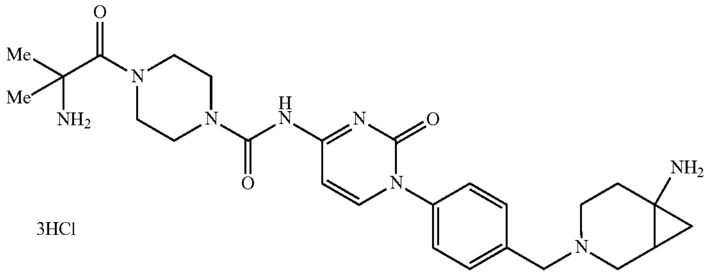 [SMILES: CC(C)(N)C(=O)N1CCN(C(=O)Nc2ccn(-c3ccc(CN4CCC5(N)CC5C4)cc3)c(=O)n2)CC1] 3HCl | 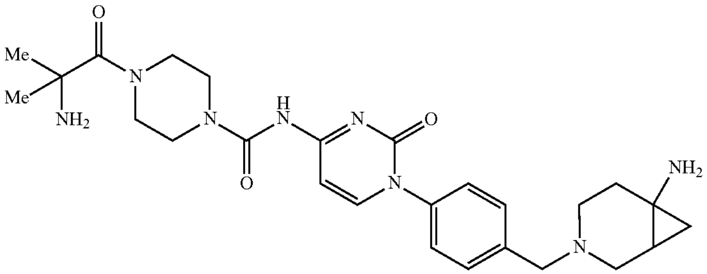 [SMILES: CC(C)(N)C(=O)N1CCN(C(=O)Nc2ccn(-c3ccc(CN4CCC5(N)CC5C4)cc3)c(=O)n2)CC1] |

TABLE 7-continued
| No. | Salt Structure | Free Base Structure |
|---|---|---|
| 14 | 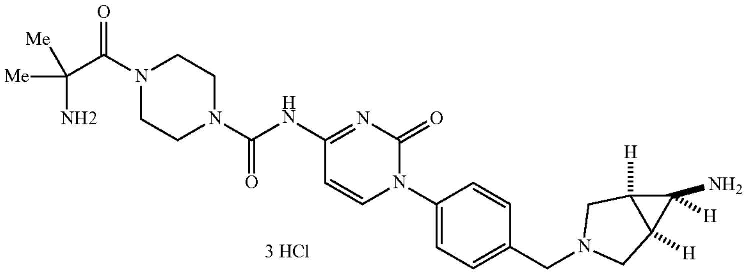 [SMILES: CC(C)(N)C(=O)N1CCN(C(=O)Nc2ccn(-c3ccc(CN4C[C@@H]5[C@H](N)[C@@H]5C4)cc3)c(=O)n2)CC1] 3 HCl | 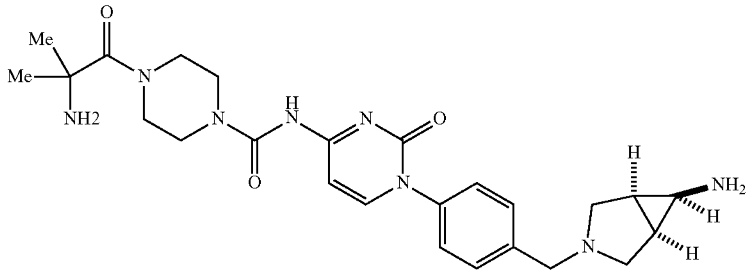 [SMILES: CC(C)(N)C(=O)N1CCN(C(=O)Nc2ccn(-c3ccc(CN4C[C@@H]5[C@H](N)[C@@H]5C4)cc3)c(=O)n2)CC1] |
| 15 | 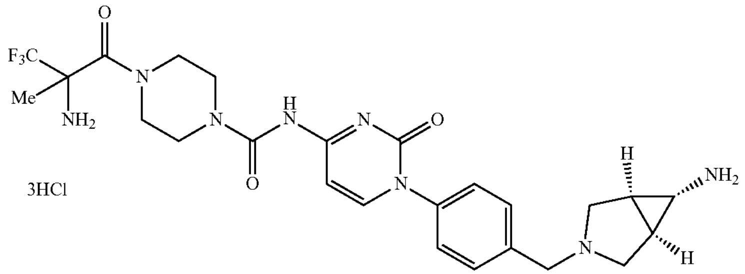 [SMILES: CC(N)(C(=O)N1CCN(C(=O)Nc2ccn(-c3ccc(CN4C[C@@H]5[C@@H](N)[C@@H]5C4)cc3)c(=O)n2)CC1)C(F)(F)F] 3HCl | 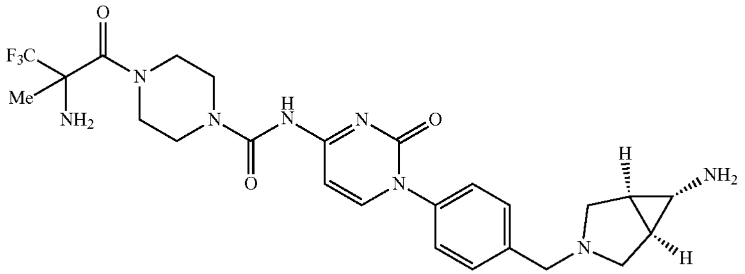 [SMILES: CC(N)(C(=O)N1CCN(C(=O)Nc2ccn(-c3ccc(CN4C[C@@H]5[C@@H](N)[C@@H]5C4)cc3)c(=O)n2)CC1)C(F)(F)F] |
| 16 | 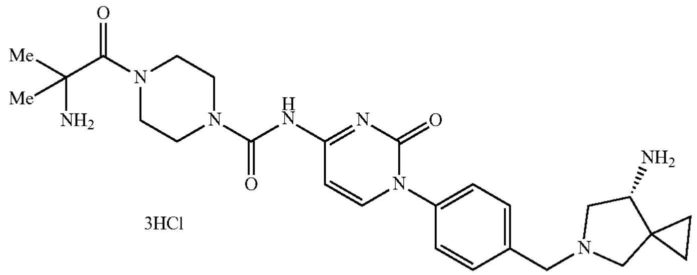 [SMILES: CC(C)(N)C(=O)N1CCN(C(=O)Nc2ccn(-c3ccc(CN4C[C@H](N)C5(CC5)C4)cc3)c(=O)n2)CC1] 3HCl | 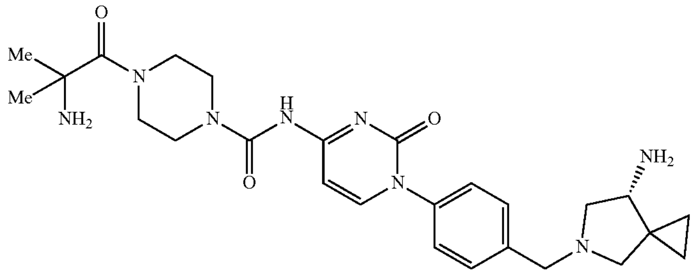 [SMILES: CC(C)(N)C(=O)N1CCN(C(=O)Nc2ccn(-c3ccc(CN4C[C@H](N)C5(CC5)C4)cc3)c(=O)n2)CC1] |

TABLE 7-continued
| No. | Salt Structure | Free Base Structure |
|---|---|---|
| 17 | 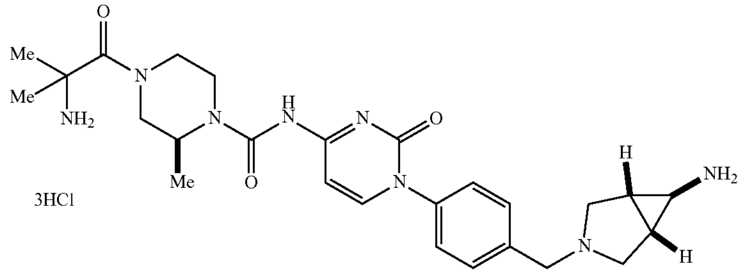 [SMILES: C[C@H]1CN(C(=O)C(C)(C)N)CCN1C(=O)Nc1ccn(-c2ccc(CN3C[C@@H]4[C@@H](N)[C@@H]4C3)cc2)c(=O)n1] 3HCl | 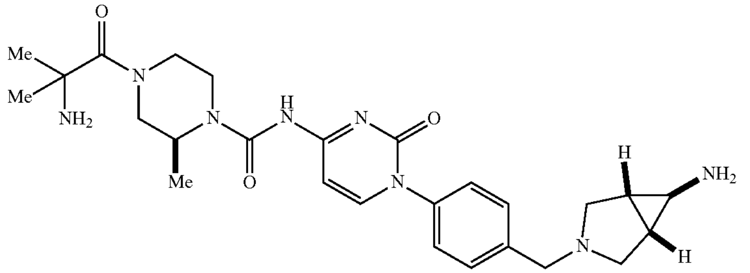 [SMILES: C[C@H]1CN(C(=O)C(C)(C)N)CCN1C(=O)Nc1ccn(-c2ccc(CN3C[C@@H]4[C@@H](N)[C@@H]4C3)cc2)c(=O)n1] |
| 18 | 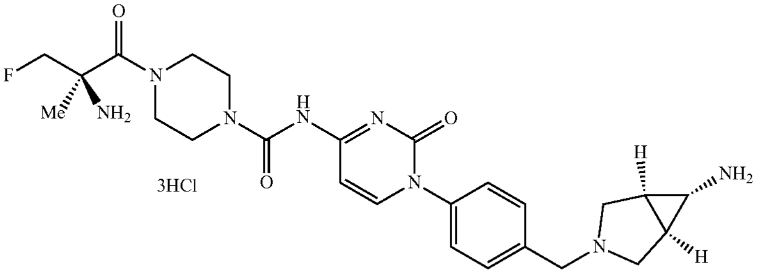 [SMILES: C[C@](N)(CF)C(=O)N1CCN(C(=O)Nc2ccn(-c3ccc(CN4C[C@@H]5[C@@H](N)[C@@H]5C4)cc3)c(=O)n2)CC1] 3HCl | 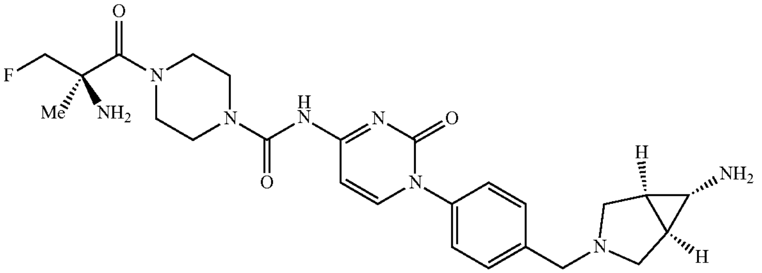 [SMILES: C[C@](N)(CF)C(=O)N1CCN(C(=O)Nc2ccn(-c3ccc(CN4C[C@@H]5[C@@H](N)[C@@H]5C4)cc3)c(=O)n2)CC1] |
| 19 | 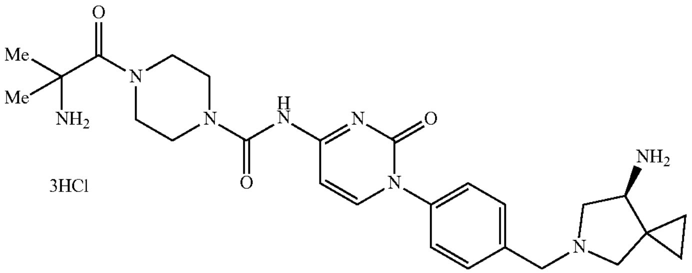 [SMILES: CC(C)(N)C(=O)N1CCN(C(=O)Nc2ccn(-c3ccc(CN4C[C@@H](N)C5(CC5)C4)cc3)c(=O)n2)CC1] 3HCl | 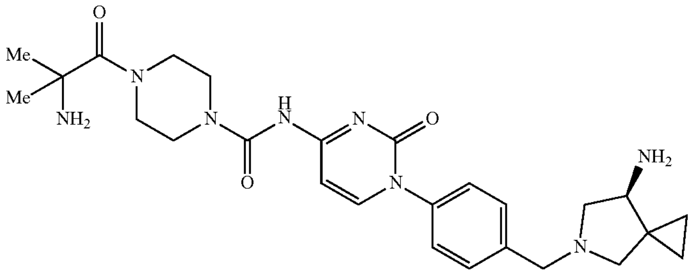 [SMILES: CC(C)(N)C(=O)N1CCN(C(=O)Nc2ccn(-c3ccc(CN4C[C@@H](N)C5(CC5)C4)cc3)c(=O)n2)CC1] |

TABLE 7-continued
| No. | Salt Structure | Free Base Structure |
|---|---|---|
| 20 | 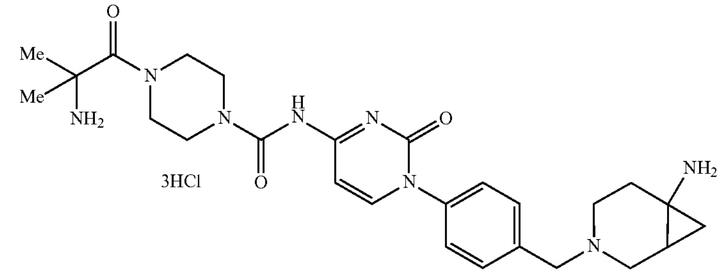 [SMILES: CC(C)(N)C(=O)N1CCN(C(=O)Nc2ccn(-c3ccc(CN4CCC5(N)CC5C4)cc3)c(=O)n2)CC1] 3HCl | 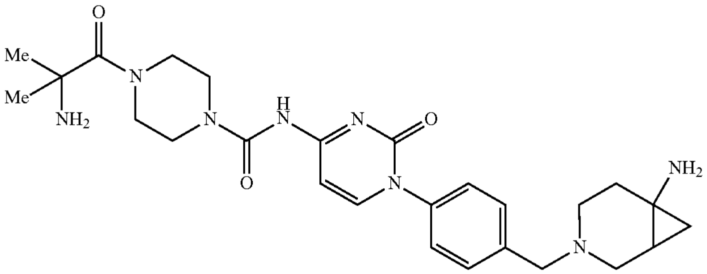 [SMILES: CC(C)(N)C(=O)N1CCN(C(=O)Nc2ccn(-c3ccc(CN4CCC5(N)CC5C4)cc3)c(=O)n2)CC1] |
| 21 | 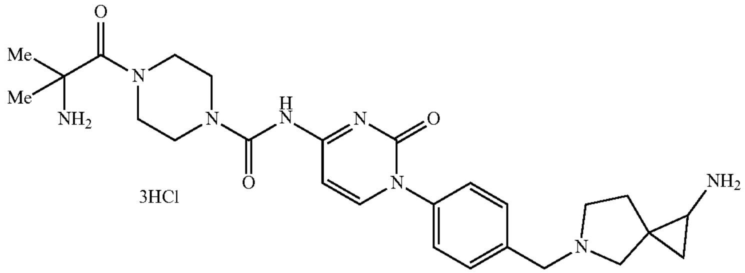 [SMILES: CC(C)(N)C(=O)N1CCN(C(=O)Nc2ccn(-c3ccc(CN4CCC5(CC5N)C4)cc3)c(=O)n2)CC1] 3HCl | 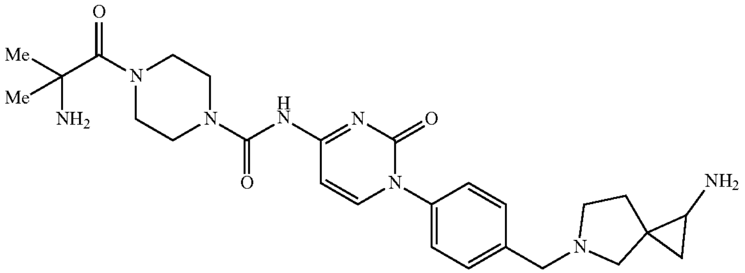 [SMILES: CC(C)(N)C(=O)N1CCN(C(=O)Nc2ccn(-c3ccc(CN4CCC5(CC5N)C4)cc3)c(=O)n2)CC1] |
| 22 | 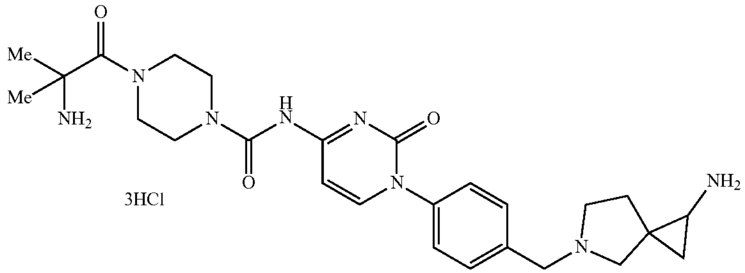 [SMILES: CC(C)(N)C(=O)N1CCN(C(=O)Nc2ccn(-c3ccc(CN4CCC5(CC5N)C4)cc3)c(=O)n2)CC1] 3HCl | 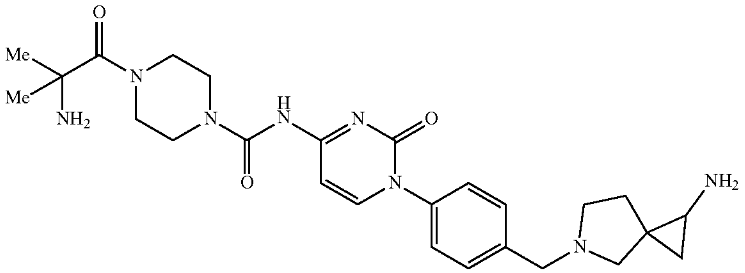 [SMILES: CC(C)(N)C(=O)N1CCN(C(=O)Nc2ccn(-c3ccc(CN4CCC5(CC5N)C4)cc3)c(=O)n2)CC1] |

TABLE 7-continued
| No. | Salt Structure | Free Base Structure |
|---|---|---|
| 23 | 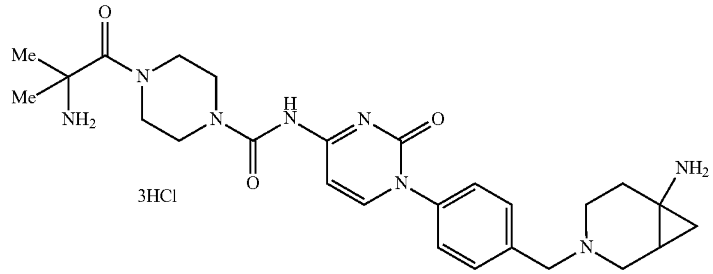 [SMILES: CC(C)(N)C(=O)N1CCN(C(=O)Nc2ccn(-c3ccc(CN4CCC5(N)CC5C4)cc3)c(=O)n2)CC1] 3HCl | 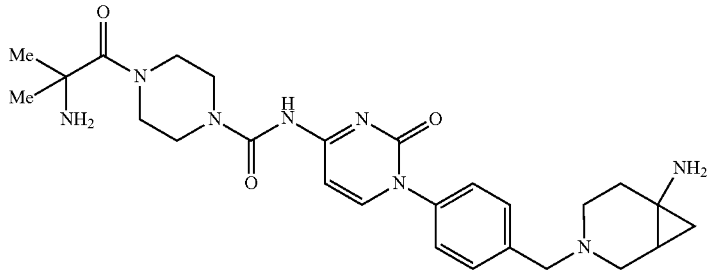 [SMILES: CC(C)(N)C(=O)N1CCN(C(=O)Nc2ccn(-c3ccc(CN4CCC5(N)CC5C4)cc3)c(=O)n2)CC1] |
| 24 | 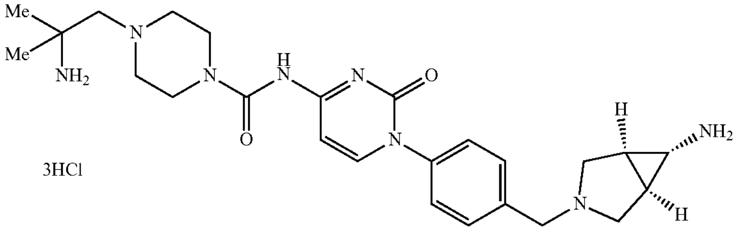 [SMILES: CC(C)(N)CN1CCN(C(=O)Nc2ccn(-c3ccc(CN4C[C@@H]5[C@@H](N)[C@@H]5C4)cc3)c(=O)n2)CC1] 3HCl | 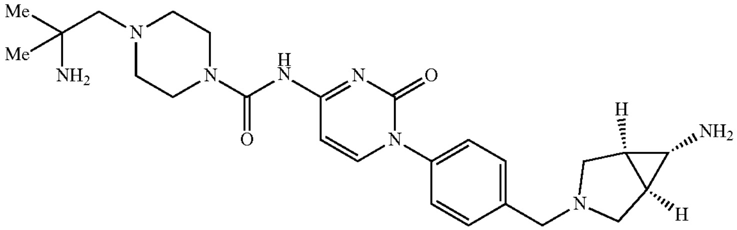 [SMILES: CC(C)(N)CN1CCN(C(=O)Nc2ccn(-c3ccc(CN4C[C@@H]5[C@@H](N)[C@@H]5C4)cc3)c(=O)n2)CC1] |
| 25 | 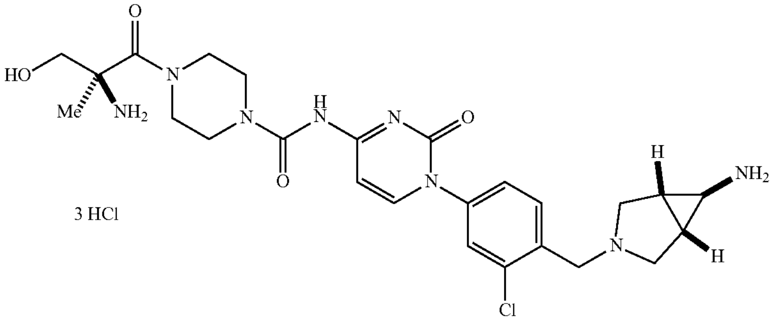 [SMILES: C[C@](N)(CO)C(=O)N1CCN(C(=O)Nc2ccn(-c3ccc(CN4C[C@@H]5[C@@H](N)[C@@H]5C4)c(Cl)c3)c(=O)n2)CC1] 3 HCl | 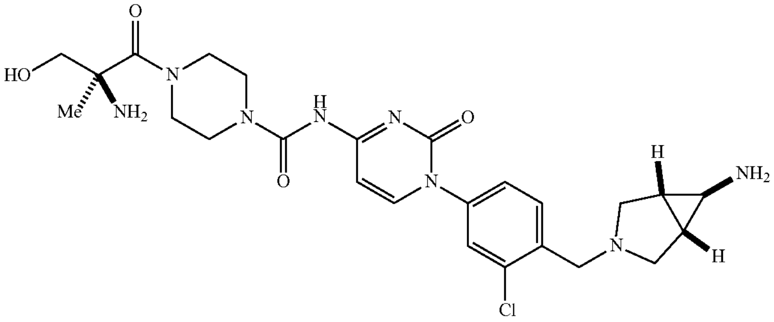 [SMILES: C[C@](N)(CO)C(=O)N1CCN(C(=O)Nc2ccn(-c3ccc(CN4C[C@@H]5[C@@H](N)[C@@H]5C4)c(Cl)c3)c(=O)n2)CC1] |

TABLE 7-continued
| No. | Salt Structure | Free Base Structure |
|---|---|---|
| 26 | 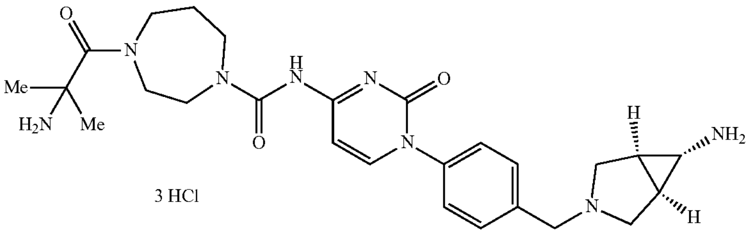 [SMILES: CC(C)(N)C(=O)N1CCCN(C(=O)Nc2ccn(-c3ccc(CN4C[C@@H]5[C@@H](N)[C@@H]5C4)cc3)c(=O)n2)CC1] 3 HCl | 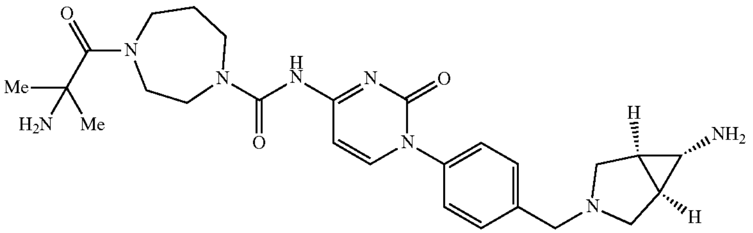 [SMILES: CC(C)(N)C(=O)N1CCCN(C(=O)Nc2ccn(-c3ccc(CN4C[C@@H]5[C@@H](N)[C@@H]5C4)cc3)c(=O)n2)CC1] |
| 27 | 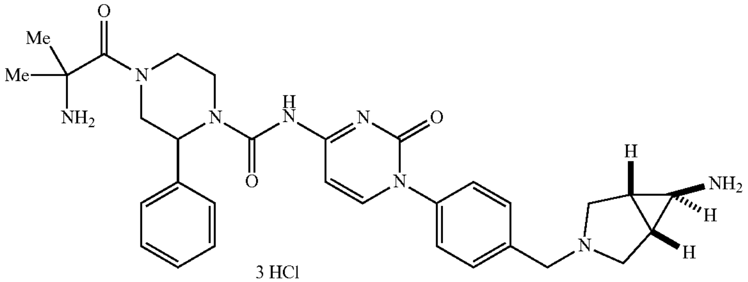 [SMILES: CC(C)(N)C(=O)N1CCN(C(=O)Nc2ccn(-c3ccc(CN4C[C@@H]5[C@@H](N)[C@@H]5C4)cc3)c(=O)n2)C(c2ccccc2)C1] 3 HCl | 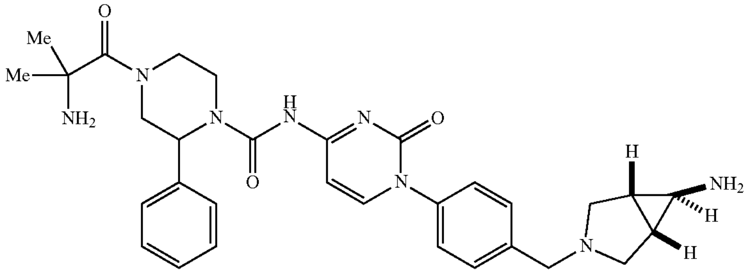 [SMILES: CC(C)(N)C(=O)N1CCN(C(=O)Nc2ccn(-c3ccc(CN4C[C@@H]5[C@@H](N)[C@@H]5C4)cc3)c(=O)n2)C(c2ccccc2)C1] |
| 28 | 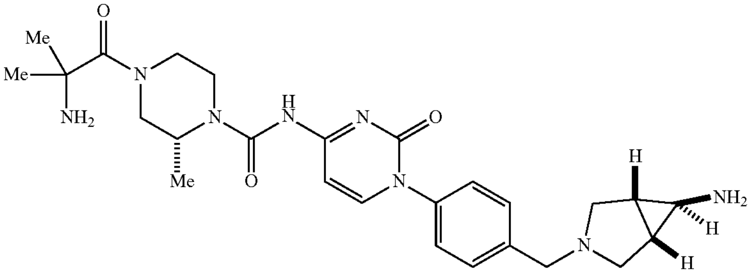 [SMILES: C[C@@H]1CN(C(=O)C(C)(C)N)CCN1C(=O)Nc1ccn(-c2ccc(CN3C[C@@H]4[C@@H](N)[C@@H]4C3)cc2)c(=O)n1] 3 HCl | 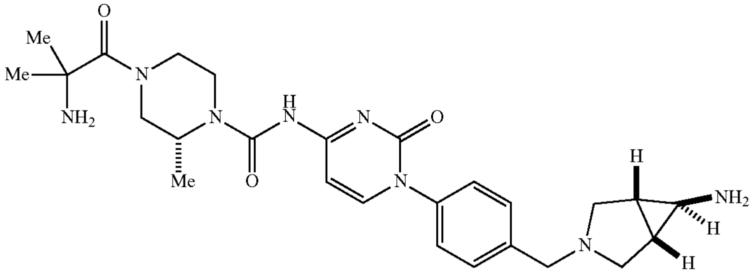 |

TABLE 7-continued
| No. | Salt Structure | Free Base Structure |
|---|---|---|
| 29 | 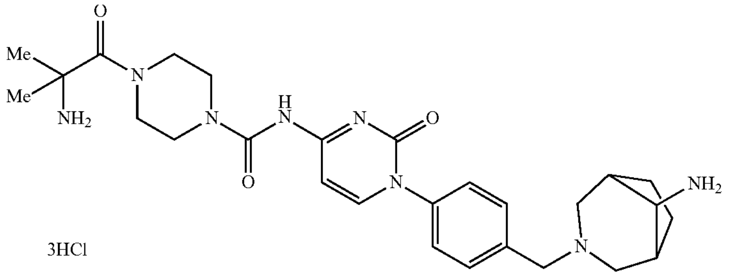 [SMILES: CC(C)(N)C(=O)N1CCN(C(=O)Nc2ccn(-c3ccc(CN4CC5CCC(C4)C5N)cc3)c(=O)n2)CC1] 3HCl | 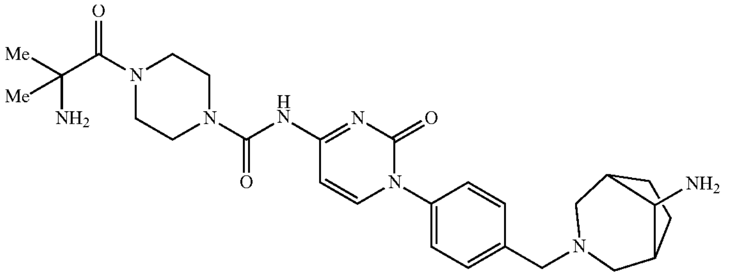 [SMILES: CC(C)(N)C(=O)N1CCN(C(=O)Nc2ccn(-c3ccc(CN4CC5CCC(C4)C5N)cc3)c(=O)n2)CC1] |
| 30 | 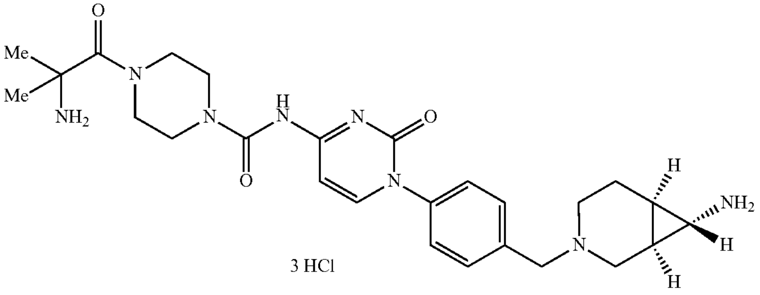 [SMILES: CC(C)(N)C(=O)N1CCN(C(=O)Nc2ccn(-c3ccc(CN4CC[C@H]5[C@H](N)[C@H]5C4)cc3)c(=O)n2)CC1] 3 HCl | 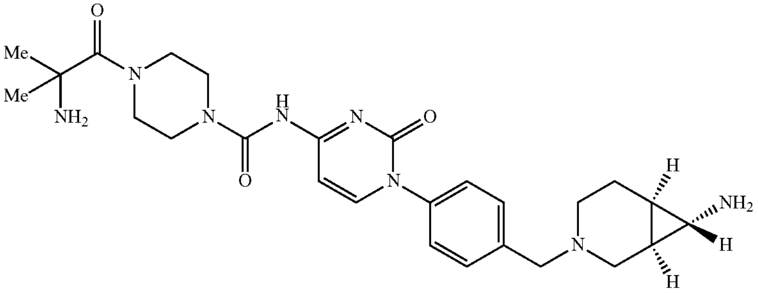 [SMILES: CC(C)(N)C(=O)N1CCN(C(=O)Nc2ccn(-c3ccc(CN4CC[C@H]5[C@H](N)[C@H]5C4)cc3)c(=O)n2)CC1] |
| 31 | 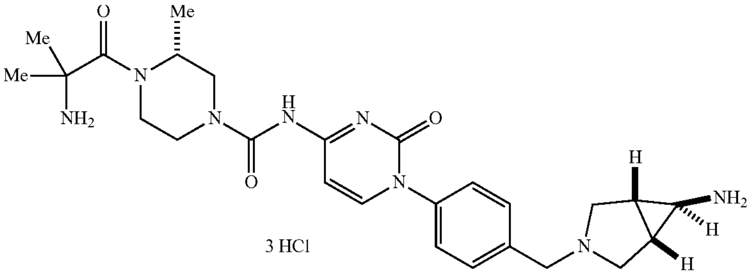 [SMILES: C[C@@H]1CN(C(=O)Nc2ccn(-c3ccc(CN4C[C@@H]5[C@@H](N)[C@@H]5C4)cc3)c(=O)n2)CCN1C(=O)C(C)(C)N] 3 HCl | 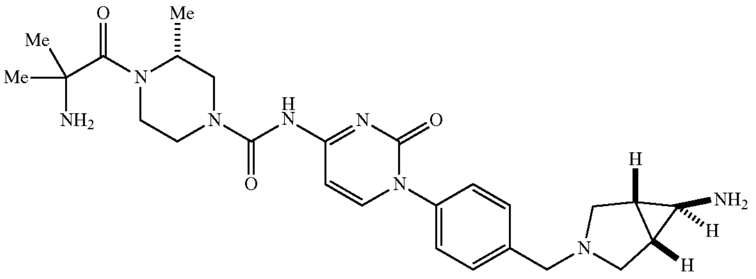 [SMILES: C[C@@H]1CN(C(=O)Nc2ccn(-c3ccc(CN4C[C@@H]5[C@@H](N)[C@@H]5C4)cc3)c(=O)n2)CCN1C(=O)C(C)(C)N] |

TABLE 7-continued
| No. | Salt Structure | Free Base Structure |
| --- | --- | --- |
| 32 | 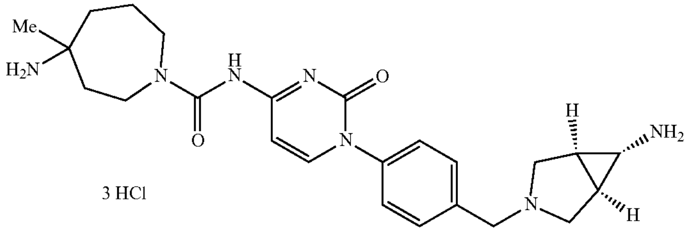 [SMILES: CC1(N)CCCN(C(=O)Nc2ccn(-c3ccc(CN4C[C@@H]5[C@@H](N)[C@@H]5C4)cc3)c(=O)n2)CC1] 3 HCl | 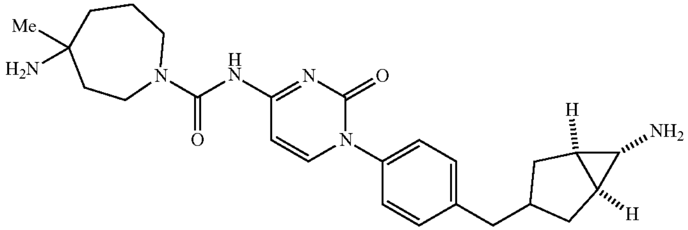 [SMILES: CC1(N)CCCN(C(=O)Nc2ccn(-c3ccc(CC4C[C@@H]5[C@@H](N)[C@@H]5C4)cc3)c(=O)n2)CC1] |
| 33 | 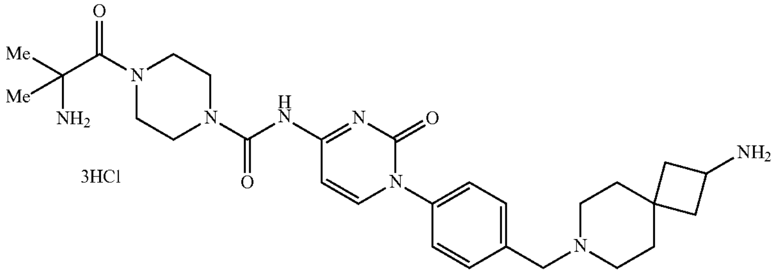 [SMILES: CC(C)(N)C(=O)N1CCN(C(=O)Nc2ccn(-c3ccc(CN4CCC5(CC4)CC(N)C5)cc3)c(=O)n2)CC1] 3HCl | 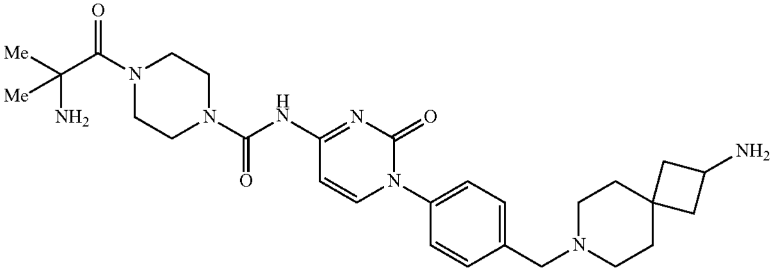 [SMILES: CC(C)(N)C(=O)N1CCN(C(=O)Nc2ccn(-c3ccc(CN4CCC5(CC4)CC(N)C5)cc3)c(=O)n2)CC1] |
| 34 | 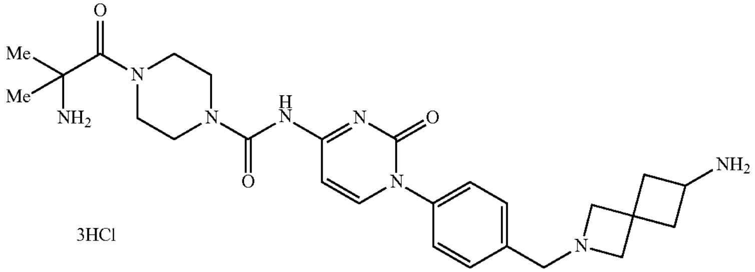 [SMILES: CC(C)(N)C(=O)N1CCN(C(=O)Nc2ccn(-c3ccc(CN4CC5(CC(N)C5)C4)cc3)c(=O)n2)CC1] 3HCl | 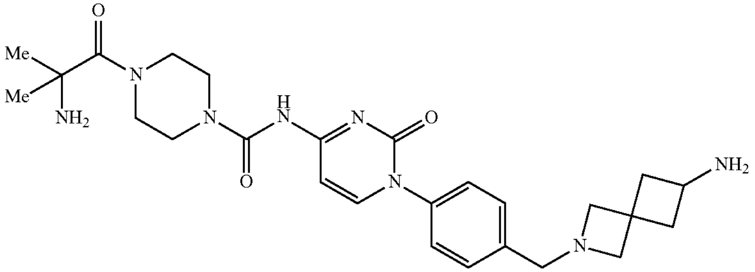 [SMILES: CC(C)(N)C(=O)N1CCN(C(=O)Nc2ccn(-c3ccc(CN4CC5(CC(N)C5)C4)cc3)c(=O)n2)CC1] |

TABLE 7-continued
| No. | Salt Structure | Free Base Structure |
| --- | --- | --- |
| 35 | 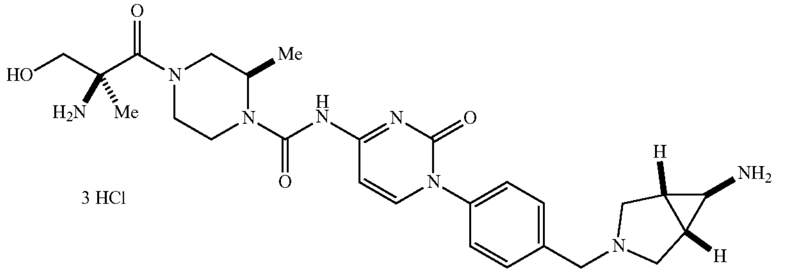 [SMILES: C[C@@H]1CN(C(=O)[C@@](C)(N)CO)CCN1C(=O)Nc1ccn(-c2ccc(CN3C[C@@H]4[C@@H](N)[C@@H]4C3)cc2)c(=O)n1] 3 HCl | 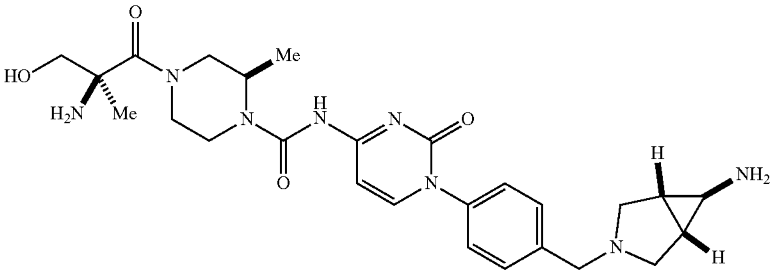 [SMILES: C[C@@H]1CN(C(=O)[C@@](C)(N)CO)CCN1C(=O)Nc1ccn(-c2ccc(CN3C[C@@H]4[C@@H](N)[C@@H]4C3)cc2)c(=O)n1] |
| 36 | 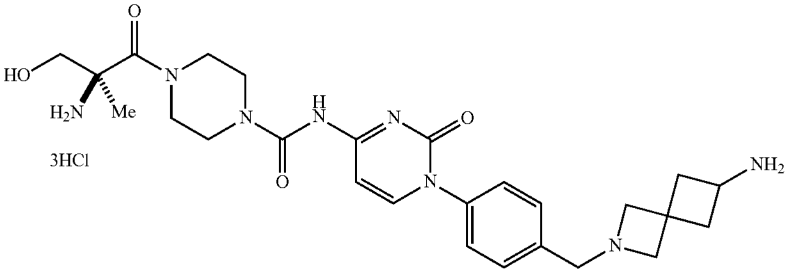 [SMILES: C[C@](N)(CO)C(=O)N1CCN(C(=O)Nc2ccn(-c3ccc(CN4CC5(CC(N)C5)C4)cc3)c(=O)n2)CC1] 3HCl | 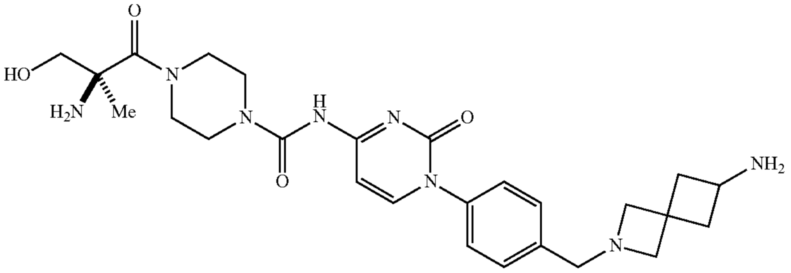 [SMILES: C[C@](N)(CO)C(=O)N1CCN(C(=O)Nc2ccn(-c3ccc(CN4CC5(CC(N)C5)C4)cc3)c(=O)n2)CC1] |
| 37 | 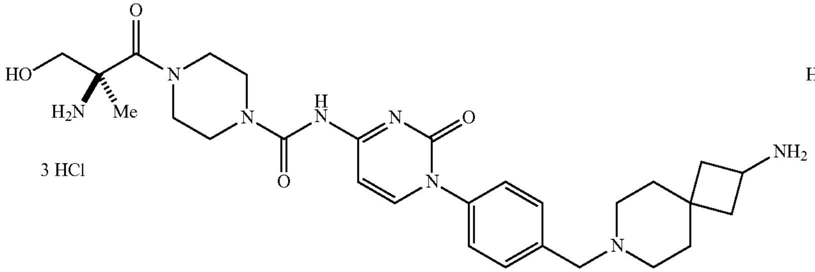 3 HCl | 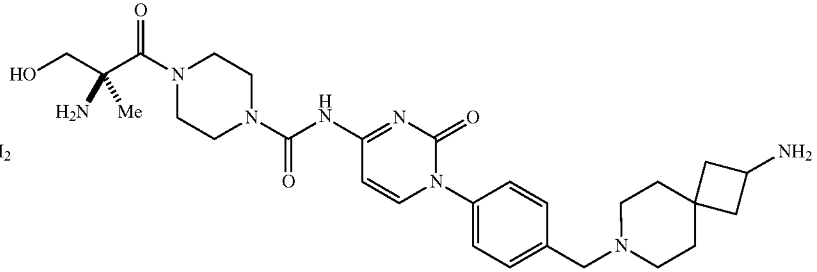 |

TABLE 7-continued
| No. | Salt Structure | Free Base Structure |
|---|---|---|
| 38 | 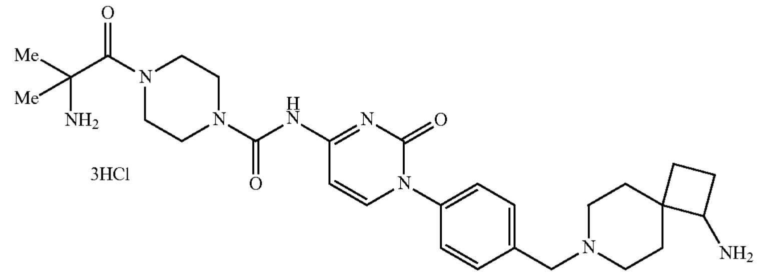 [SMILES: CC(C)(N)C(=O)N1CCN(C(=O)Nc2ccn(-c3ccc(CN4CCC5(CCC5N)CC4)cc3)c(=O)n2)CC1] 3HCl | 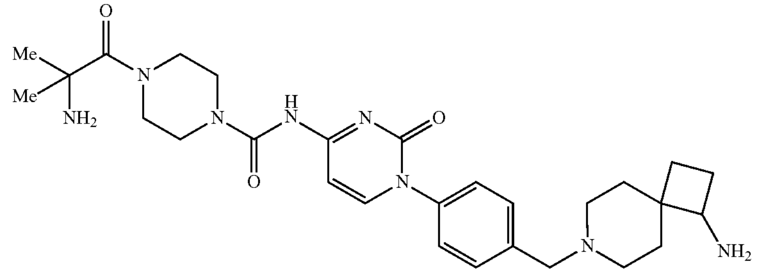 [SMILES: CC(C)(N)C(=O)N1CCN(C(=O)Nc2ccn(-c3ccc(CN4CCC5(CCC5N)CC4)cc3)c(=O)n2)CC1] |
| 39 | 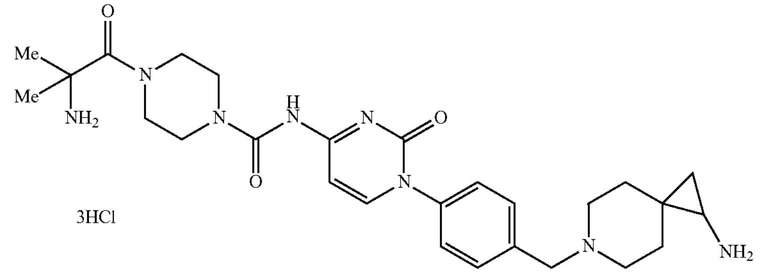 [SMILES: CC(C)(N)C(=O)N1CCN(C(=O)Nc2ccn(-c3ccc(CN4CCC5(CC4)CC5N)cc3)c(=O)n2)CC1] 3HCl | 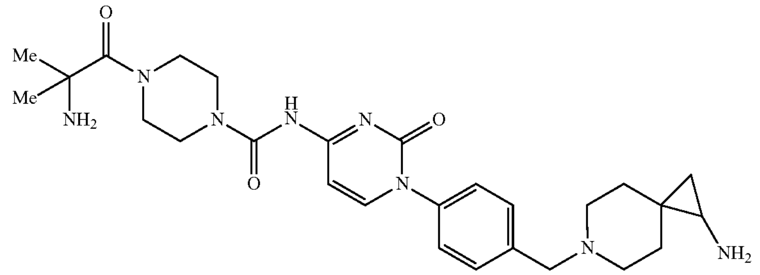 [SMILES: CC(C)(N)C(=O)N1CCN(C(=O)Nc2ccn(-c3ccc(CN4CCC5(CC4)CC5N)cc3)c(=O)n2)CC1] |
| 40 | 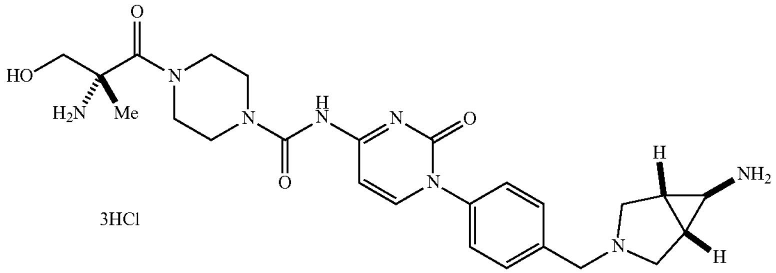 [SMILES: C[C@@](N)(CO)C(=O)N1CCN(C(=O)Nc2ccn(-c3ccc(CN4C[C@@H]5[C@@H](N)[C@@H]5C4)cc3)c(=O)n2)CC1] 3HCl | 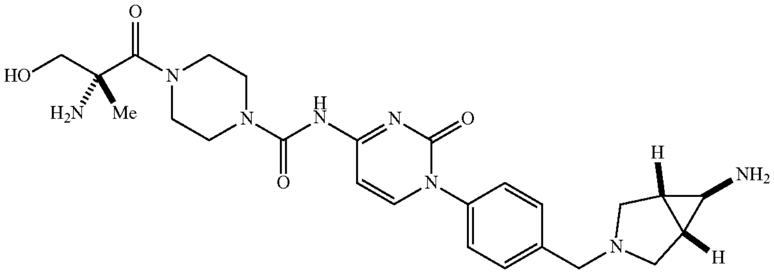 [SMILES: C[C@@](N)(CO)C(=O)N1CCN(C(=O)Nc2ccn(-c3ccc(CN4C[C@@H]5[C@@H](N)[C@@H]5C4)cc3)c(=O)n2)CC1] |

TABLE 7-continued
| No. | Salt Structure | Free Base Structure |
|---|---|---|
| 41 | 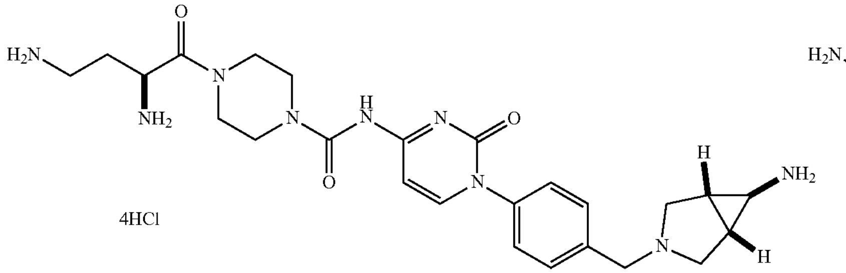 4HCl | 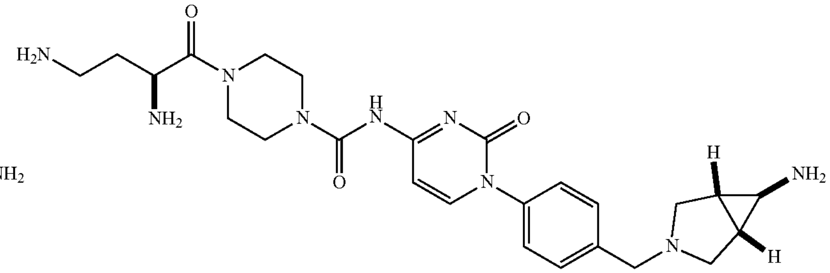 |
| 42 | 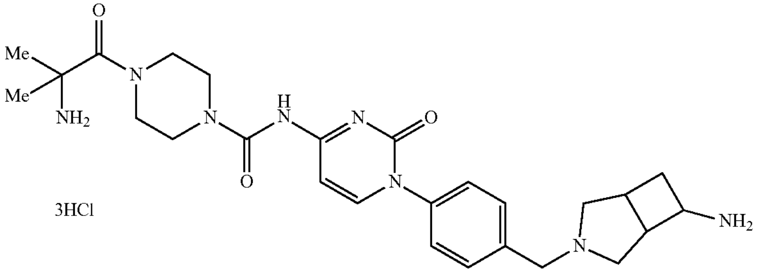 [SMILES: CC(C)(N)C(=O)N1CCN(C(=O)Nc2ccn(-c3ccc(CN4CC5CC(N)C5C4)cc3)c(=O)n2)CC1] 3HCl | 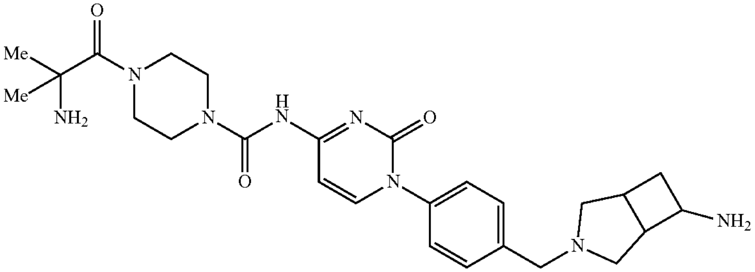 [SMILES: CC(C)(N)C(=O)N1CCN(C(=O)Nc2ccn(-c3ccc(CN4CC5CC(N)C5C4)cc3)c(=O)n2)CC1] |
| 43 | 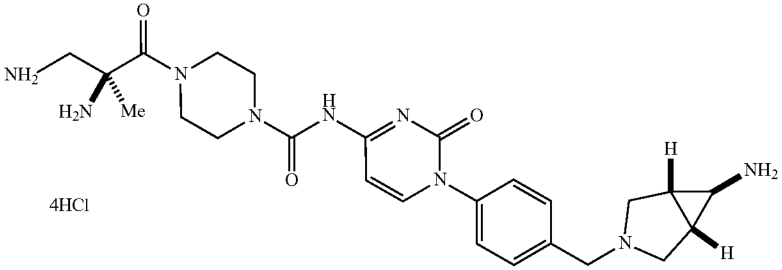 [SMILES: C[C@](N)(CN)C(=O)N1CCN(C(=O)Nc2ccn(-c3ccc(CN4C[C@@H]5[C@@H](N)[C@@H]5C4)cc3)c(=O)n2)CC1] 4HCl | 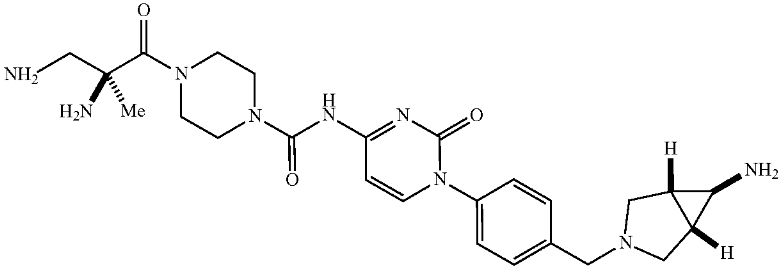 [SMILES: C[C@](N)(CN)C(=O)N1CCN(C(=O)Nc2ccn(-c3ccc(CN4C[C@@H]5[C@@H](N)[C@@H]5C4)cc3)c(=O)n2)CC1] |

TABLE 7-continued
| No. | Salt Structure | Free Base Structure |
|---|---|---|
| 44 | 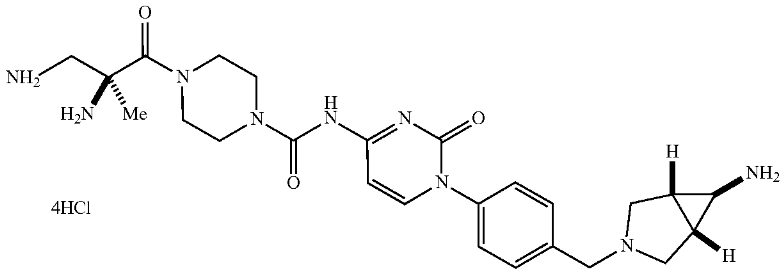 [SMILES: C[C@](N)(CN)C(=O)N1CCN(C(=O)Nc2ccn(-c3ccc(CN4C[C@@H]5[C@@H](N)[C@@H]5C4)cc3)c(=O)n2)CC1] 4HCl | 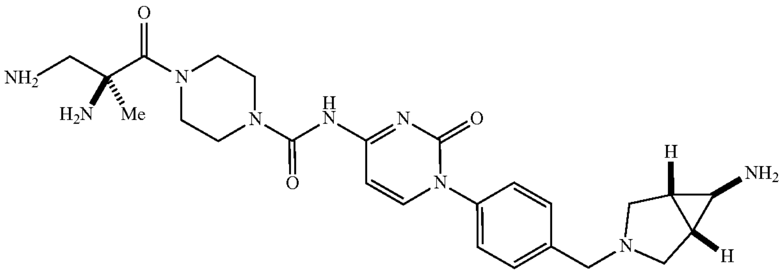 [SMILES: C[C@](N)(CN)C(=O)N1CCN(C(=O)Nc2ccn(-c3ccc(CN4C[C@@H]5[C@@H](N)[C@@H]5C4)cc3)c(=O)n2)CC1] |
| 45 | 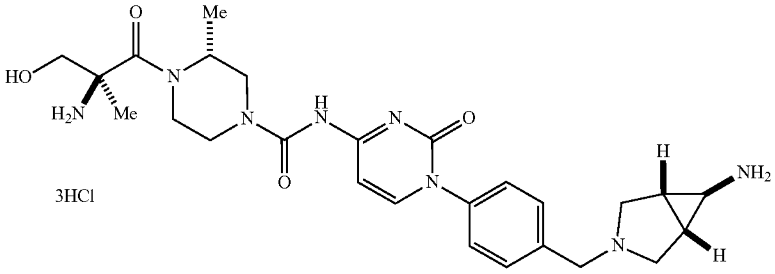 [SMILES: C[C@@H]1CN(C(=O)Nc2ccn(-c3ccc(CN4C[C@@H]5[C@@H](N)[C@@H]5C4)cc3)c(=O)n2)CCN1C(=O)[C@@](C)(N)CO] 3HCl | 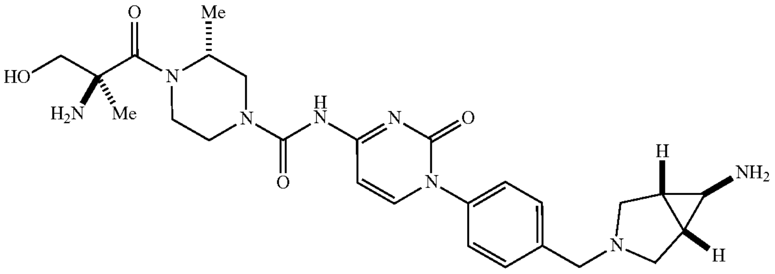 [SMILES: C[C@@H]1CN(C(=O)Nc2ccn(-c3ccc(CN4C[C@@H]5[C@@H](N)[C@@H]5C4)cc3)c(=O)n2)CCN1C(=O)[C@@](C)(N)CO] |
| 46 | 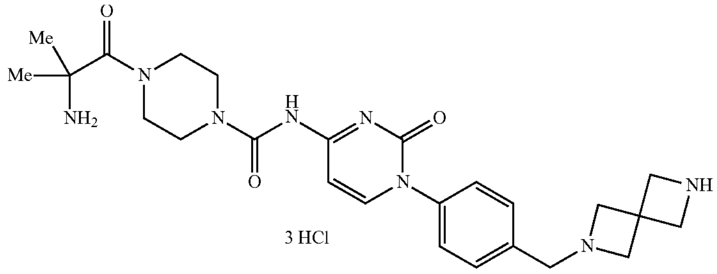 [SMILES: CC(C)(N)C(=O)N1CCN(C(=O)Nc2ccn(-c3ccc(CN4CC5(CNC5)C4)cc3)c(=O)n2)CC1] 3 HCl | 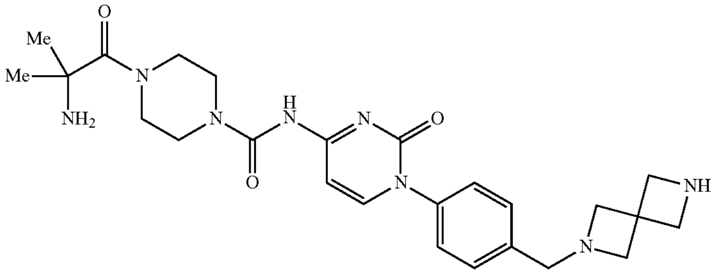 [SMILES: CC(C)(N)C(=O)N1CCN(C(=O)Nc2ccn(-c3ccc(CN4CC5(CNC5)C4)cc3)c(=O)n2)CC1] |

TABLE 7-continued
| No. | Salt Structure | Free Base Structure |
|---|---|---|
| 47 | 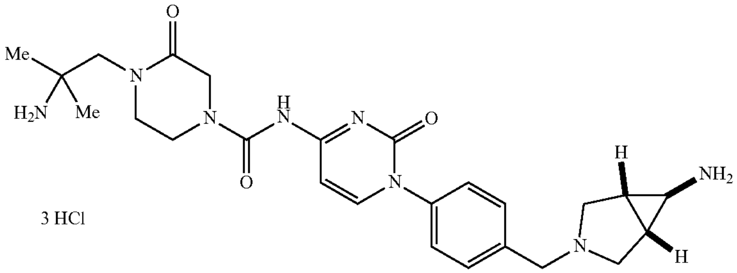 [SMILES: CC(C)(N)CN1CCN(C(=O)Nc2ccn(-c3ccc(CN4C[C@@H]5[C@@H](N)[C@@H]5C4)cc3)c(=O)n2)CC1=O] 3 HCl | 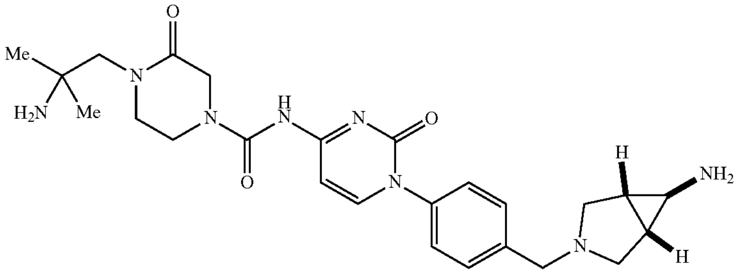 [SMILES: CC(C)(N)CN1CCN(C(=O)Nc2ccn(-c3ccc(CN4C[C@@H]5[C@@H](N)[C@@H]5C4)cc3)c(=O)n2)CC1=O] |
| 48 | 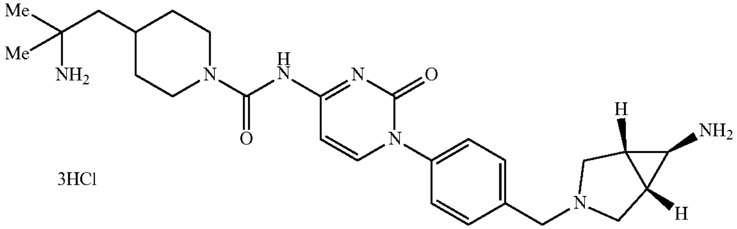 [SMILES: CC(C)(N)CC1CCN(C(=O)Nc2ccn(-c3ccc(CN4C[C@@H]5[C@@H](N)[C@@H]5C4)cc3)c(=O)n2)CC1] 3HCl | 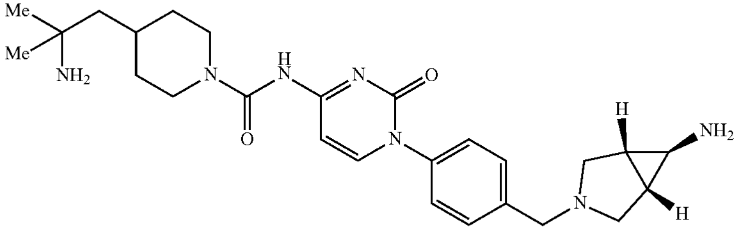 [SMILES: CC(C)(N)CC1CCN(C(=O)Nc2ccn(-c3ccc(CN4C[C@@H]5[C@@H](N)[C@@H]5C4)cc3)c(=O)n2)CC1] |
| 49 | 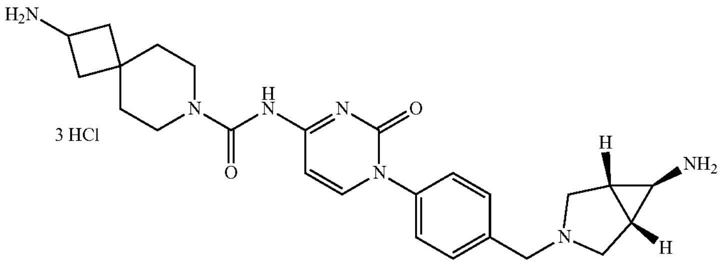 [SMILES: NC1CC2(CCN(C(=O)Nc3ccn(-c4ccc(CN5C[C@@H]6[C@@H](N)[C@@H]6C5)cc4)c(=O)n3)CC2)C1] 3 HCl | 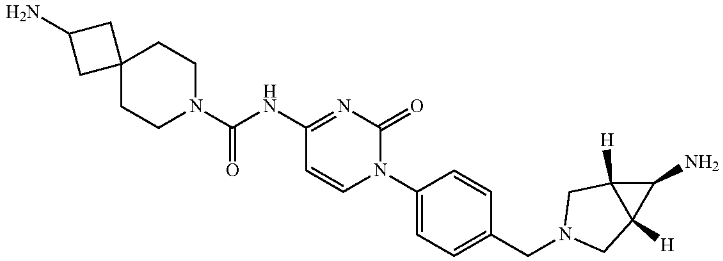 [SMILES: NC1CC2(CCN(C(=O)Nc3ccn(-c4ccc(CN5C[C@@H]6[C@@H](N)[C@@H]6C5)cc4)c(=O)n3)CC2)C1] |
| 50 | 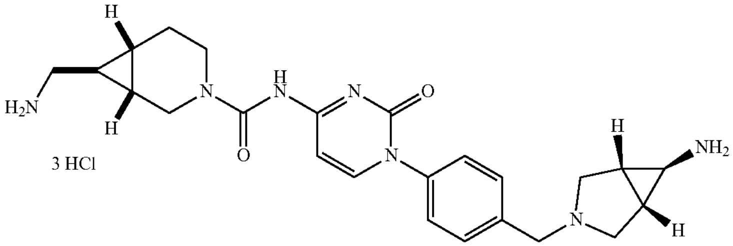 [SMILES: NC[C@H]1[C@@H]2CCN(C(=O)Nc3ccn(-c4ccc(CN5C[C@@H]6[C@@H](N)[C@@H]6C5)cc4)c(=O)n3)C[C@H]12] 3 HCl | 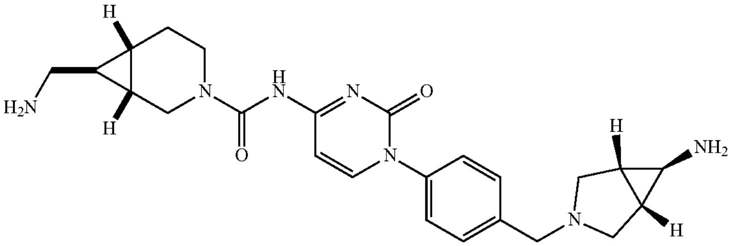 [SMILES: NC[C@H]1[C@@H]2CCN(C(=O)Nc3ccn(-c4ccc(CN5C[C@@H]6[C@@H](N)[C@@H]6C5)cc4)c(=O)n3)C[C@H]12] |

TABLE 7-continued
| No. | Salt Structure | Free Base Structure |
|---|---|---|
| 51 | 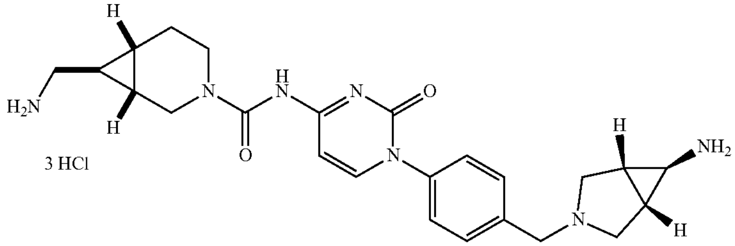 [SMILES: NC[C@H]1[C@@H]2CCN(C(=O)Nc3ccn(-c4ccc(CN5C[C@@H]6[C@@H](N)[C@@H]6C5)cc4)c(=O)n3)C[C@H]12] 3 HCl | 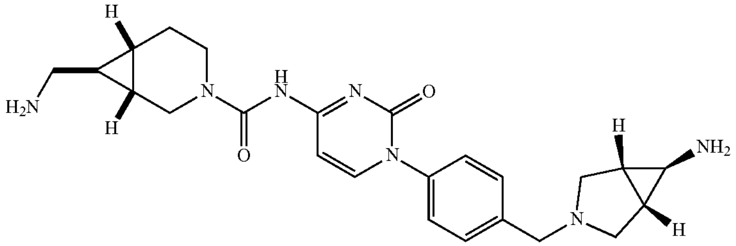 [SMILES: NC[C@H]1[C@@H]2CCN(C(=O)Nc3ccn(-c4ccc(CN5C[C@@H]6[C@@H](N)[C@@H]6C5)cc4)c(=O)n3)C[C@H]12] |
| 52 | 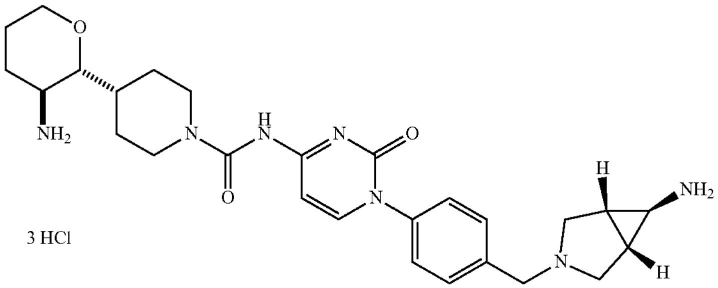 3 HCl | 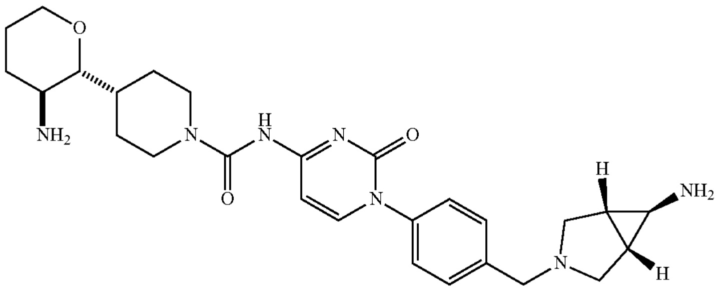 |
| 53 | 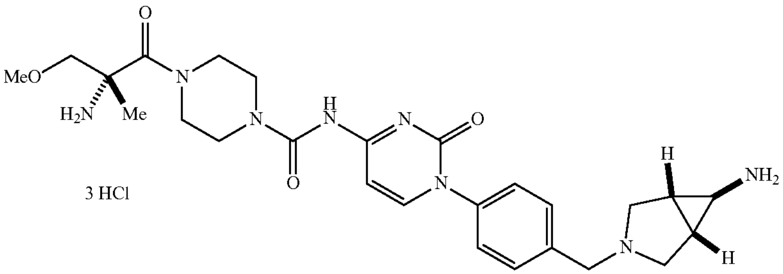 [SMILES: COC[C@@](C)(N)C(=O)N1CCN(C(=O)Nc2ccn(-c3ccc(CN4C[C@@H]5[C@@H](N)[C@@H]5C4)cc3)c(=O)n2)CC1] 3 HCl | 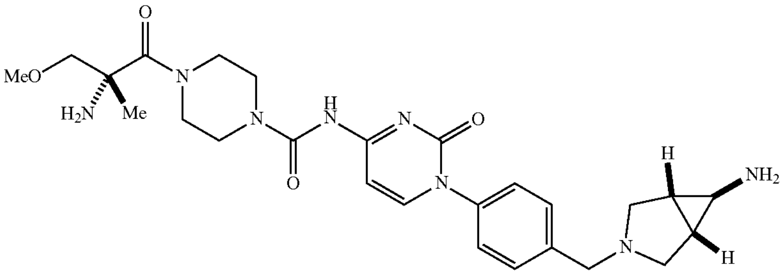 [SMILES: COC[C@@](C)(N)C(=O)N1CCN(C(=O)Nc2ccn(-c3ccc(CN4C[C@@H]5[C@@H](N)[C@@H]5C4)cc3)c(=O)n2)CC1] |

TABLE 7-continued
| No. | Salt Structure | Free Base Structure |
| --- | --- | --- |
| 54 | 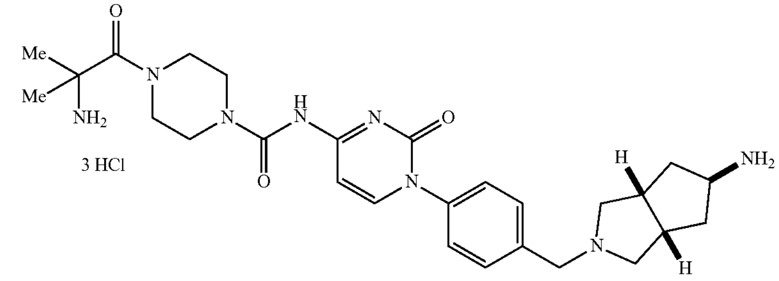 [SMILES: CC(C)(N)C(=O)N1CCN(C(=O)Nc2ccn(-c3ccc(CN4C[C@H]5C[C@H](N)C[C@H]5C4)cc3)c(=O)n2)CC1] 3 HCl | 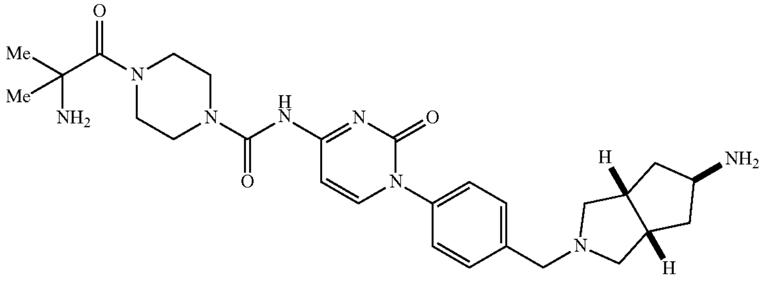 [SMILES: CC(C)(N)C(=O)N1CCN(C(=O)Nc2ccn(-c3ccc(CN4C[C@H]5C[C@H](N)C[C@H]5C4)cc3)c(=O)n2)CC1] |
| 55 | 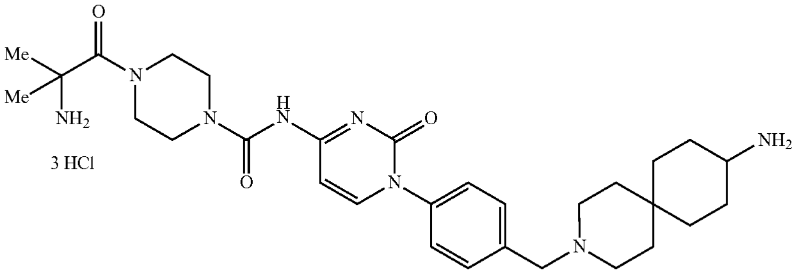 [SMILES: CC(C)(N)C(=O)N1CCN(C(=O)Nc2ccn(-c3ccc(CN4CCC5(CCC(N)CC5)CC4)cc3)c(=O)n2)CC1] 3 HCl | 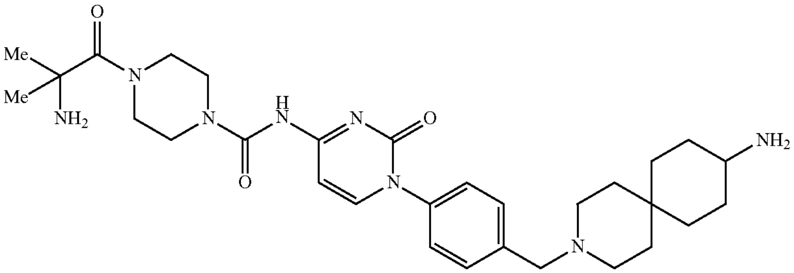 [SMILES: CC(C)(N)C(=O)N1CCN(C(=O)Nc2ccn(-c3ccc(CN4CCC5(CCC(N)CC5)CC4)cc3)c(=O)n2)CC1] |
| 56 | 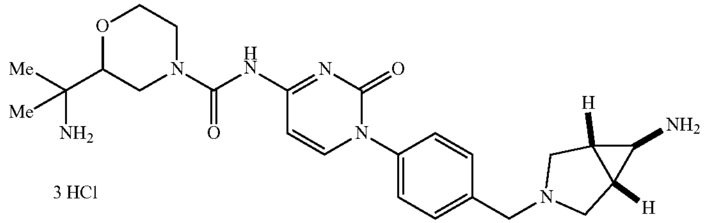 [SMILES: CC(C)(N)C1CN(C(=O)Nc2ccn(-c3ccc(CN4C[C@@H]5[C@@H](N)[C@@H]5C4)cc3)c(=O)n2)CCO1] 3 HCl | 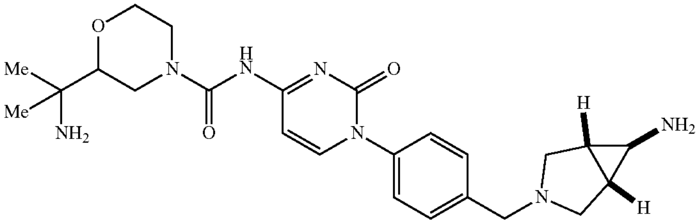 [SMILES: CC(C)(N)C1CN(C(=O)Nc2ccn(-c3ccc(CN4C[C@@H]5[C@@H](N)[C@@H]5C4)cc3)c(=O)n2)CCO1] |

TABLE 7-continued
| No. | Salt Structure | Free Base Structure |
|---|---|---|
| 57 | 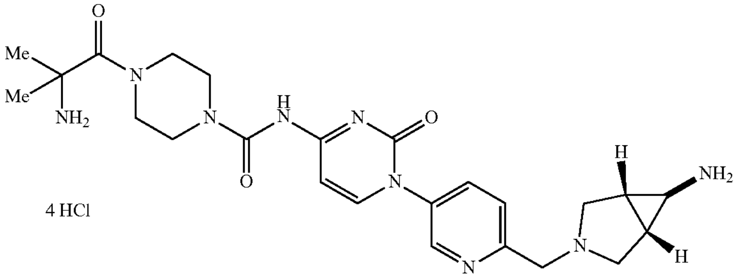 [SMILES: CC(C)(N)C(=O)N1CCN(C(=O)Nc2ccn(-c3ccc(CN4C[C@@H]5[C@@H](N)[C@@H]5C4)nc3)c(=O)n2)CC1] 4 HCl | 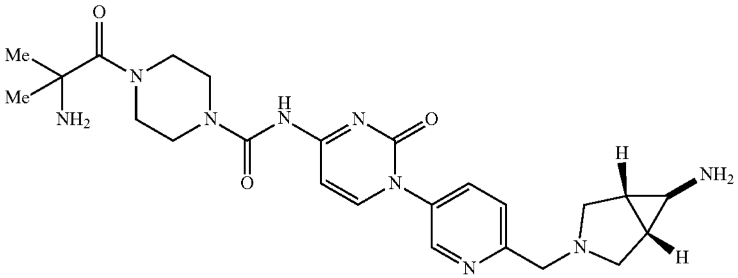 [SMILES: CC(C)(N)C(=O)N1CCN(C(=O)Nc2ccn(-c3ccc(CN4C[C@@H]5[C@@H](N)[C@@H]5C4)nc3)c(=O)n2)CC1] |
| 58 | 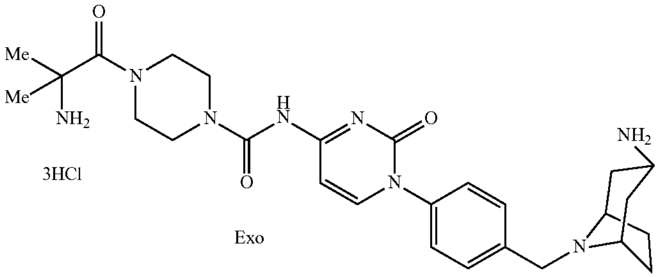 [SMILES: CC(C)(N)C(=O)N1CCN(C(=O)Nc2ccn(-c3ccc(CN4C5CCC4CC(N)C5)cc3)c(=O)n2)CC1] 3HCl Exo | 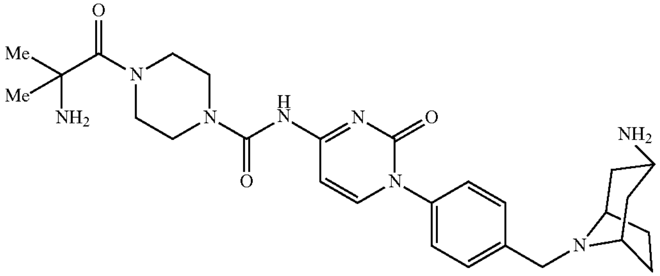 [SMILES: CC(C)(N)C(=O)N1CCN(C(=O)Nc2ccn(-c3ccc(CN4C5CCC4CC(N)C5)cc3)c(=O)n2)CC1] |
| 59 | 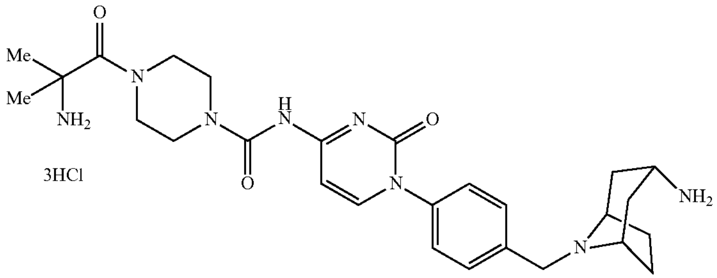 [SMILES: CC(C)(N)C(=O)N1CCN(C(=O)Nc2ccn(-c3ccc(CN4C5CCC4CC(N)C5)cc3)c(=O)n2)CC1] 3HCl | 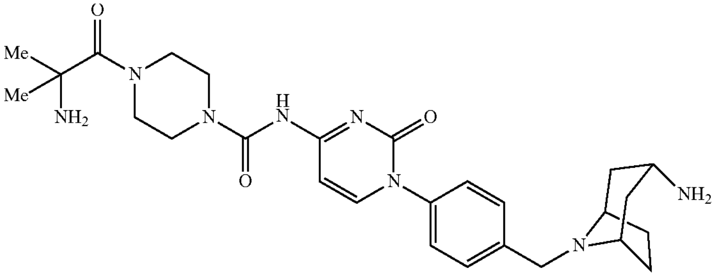 [SMILES: CC(C)(N)C(=O)N1CCN(C(=O)Nc2ccn(-c3ccc(CN4C5CCC4CC(N)C5)cc3)c(=O)n2)CC1] |

TABLE 7-continued
| No. | Salt Structure | Free Base Structure |
| --- | --- | --- |
| 60 | 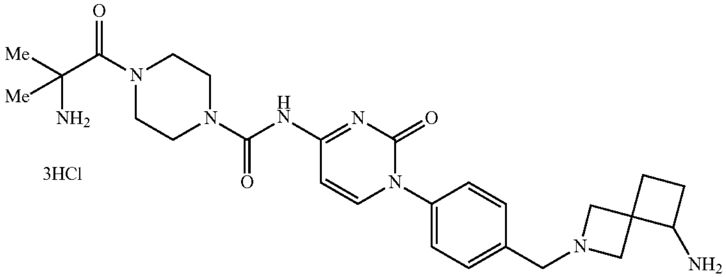 [SMILES: CC(C)(N)C(=O)N1CCN(C(=O)Nc2ccn(-c3ccc(CN4CC5(CCC5N)C4)cc3)c(=O)n2)CC1] 3HCl | 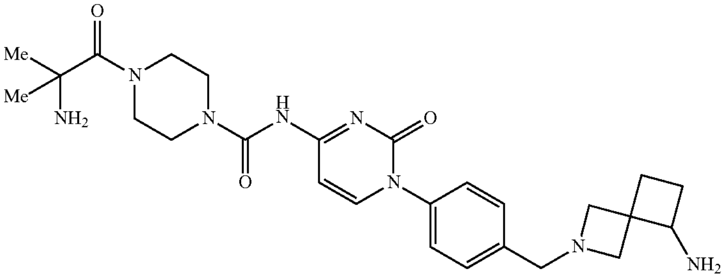 |
| 61 | 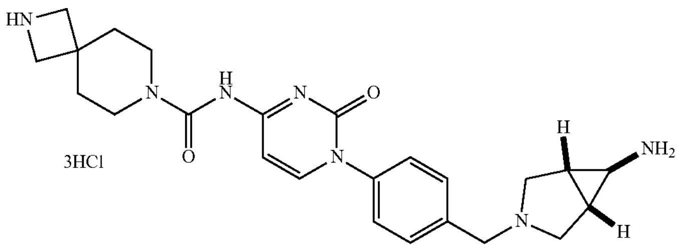 [SMILES: N[C@@H]1[C@H]2CN(Cc3ccc(-n4ccc(NC(=O)N5CCC6(CC5)CNC6)nc4=O)cc3)C[C@@H]12] 3HCl | 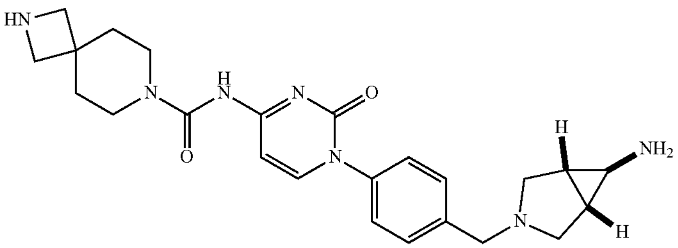 [SMILES: N[C@@H]1[C@H]2CN(Cc3ccc(-n4ccc(NC(=O)N5CCC6(CC5)CNC6)nc4=O)cc3)C[C@@H]12] |
| 62 | 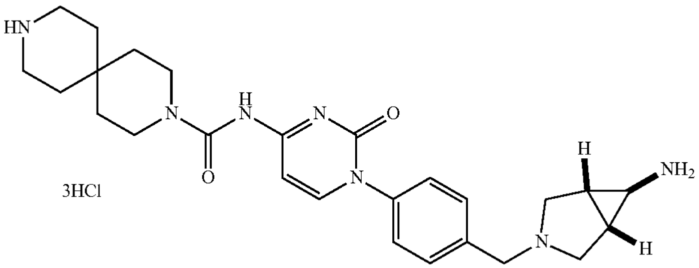 [SMILES: N[C@@H]1[C@H]2CN(Cc3ccc(-n4ccc(NC(=O)N5CCC6(CCNCC6)CC5)nc4=O)cc3)C[C@@H]12] 3HCl | 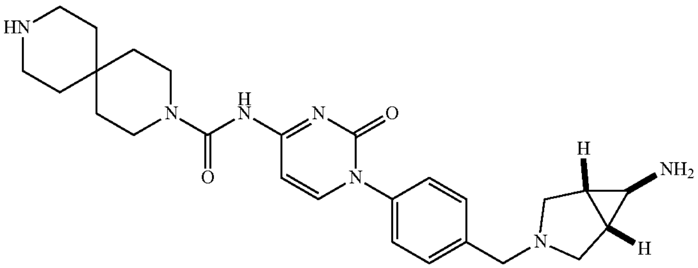 [SMILES: N[C@@H]1[C@H]2CN(Cc3ccc(-n4ccc(NC(=O)N5CCC6(CCNCC6)CC5)nc4=O)cc3)C[C@@H]12] |
| 63 | 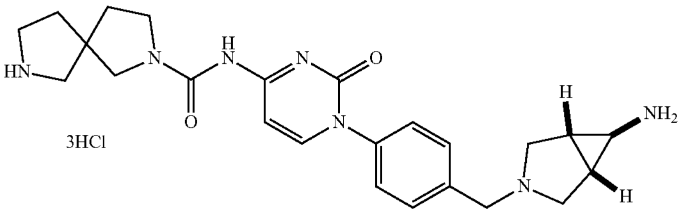 [SMILES: N[C@@H]1[C@H]2CN(Cc3ccc(-n4ccc(NC(=O)N5CCC6(CCNC6)C5)nc4=O)cc3)C[C@@H]12] 3HCl | 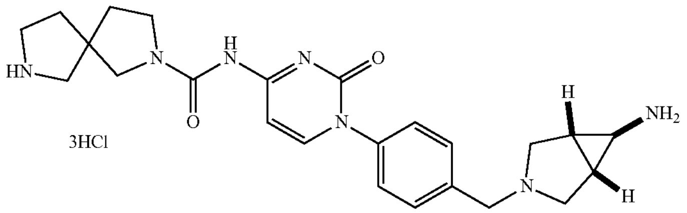 [SMILES: N[C@@H]1[C@H]2CN(Cc3ccc(-n4ccc(NC(=O)N5CCC6(CCNC6)C5)nc4=O)cc3)C[C@@H]12] 3HCl |

TABLE 7-continued
| No. | Salt Structure | Free Base Structure |
|---|---|---|
| 64 | 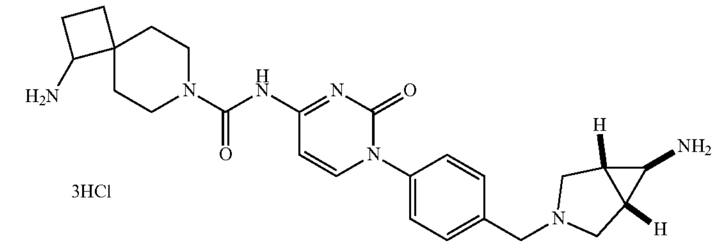 [SMILES: NC1CCC12CCN(C(=O)Nc1ccn(-c3ccc(CN4C[C@@H]5[C@@H](N)[C@@H]5C4)cc3)c(=O)n1)CC2] 3HCl | 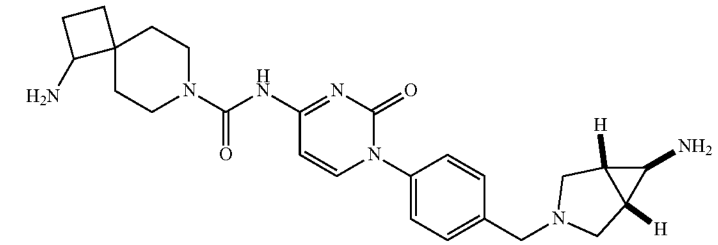 [SMILES: NC1CCC12CCN(C(=O)Nc1ccn(-c3ccc(CN4C[C@@H]5[C@@H](N)[C@@H]5C4)cc3)c(=O)n1)CC2] |
| 65 | 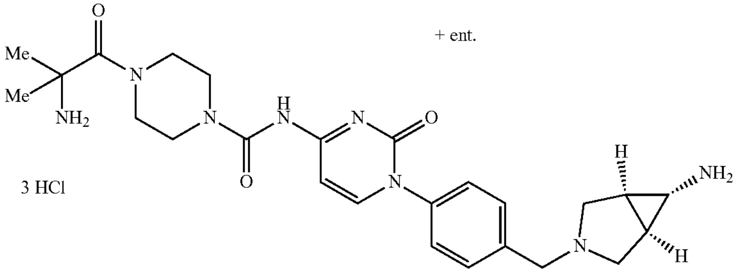 [SMILES: CC(C)(N)C(=O)N1CCN(C(=O)Nc2ccn(-c3ccc(CN4C[C@@H]5[C@@H](N)[C@@H]5C4)cc3)c(=O)n2)CC1] + ent. 3 HCl | 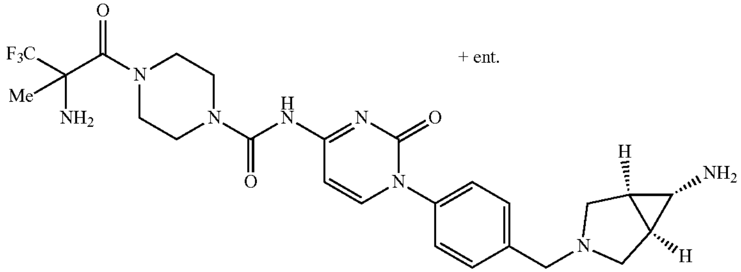 [SMILES: CC(N)(C(=O)N1CCN(C(=O)Nc2ccn(-c3ccc(CN4C[C@@H]5[C@@H](N)[C@@H]5C4)cc3)c(=O)n2)CC1)C(F)(F)F] + ent. |
| 66 | 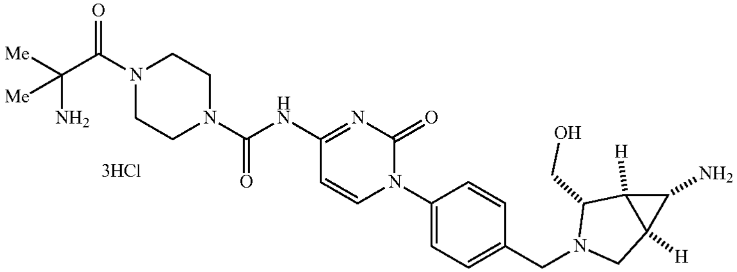 [SMILES: CC(C)(N)C(=O)N1CCN(C(=O)Nc2ccn(-c3ccc(CN4C[C@@H]5[C@@H](N)[C@@H]5[C@H]4CO)cc3)c(=O)n2)CC1] 3HCl | 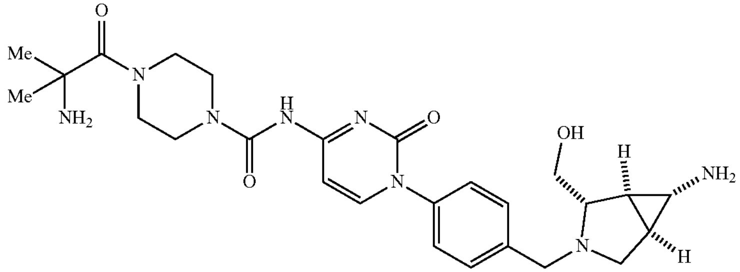 [SMILES: CC(C)(N)C(=O)N1CCN(C(=O)Nc2ccn(-c3ccc(CN4C[C@@H]5[C@@H](N)[C@@H]5[C@H]4CO)cc3)c(=O)n2)CC1] |

TABLE 7-continued
| No. | Salt Structure | Free Base Structure |
|---|---|---|
| 67 | 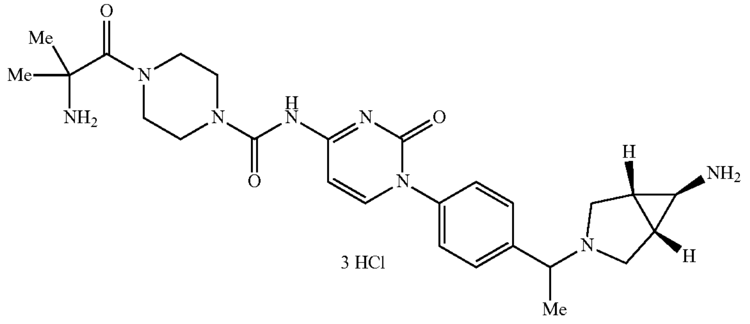 [SMILES: CC(c1ccc(-n2ccc(NC(=O)N3CCN(C(=O)C(C)(C)N)CC3)nc2=O)cc1)N1C[C@@H]2[C@@H](N)[C@@H]2C1] 3 HCl | 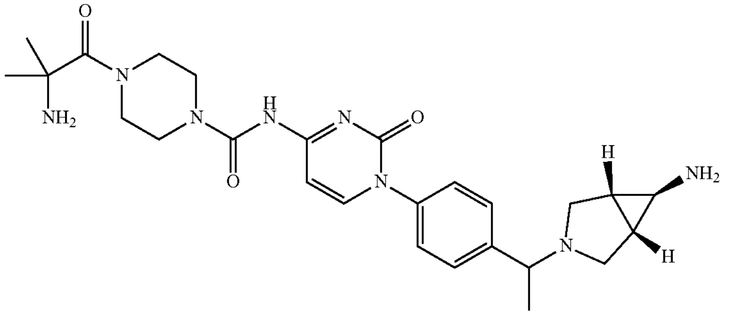 [SMILES: CC(c1ccc(-n2ccc(NC(=O)N3CCN(C(=O)C(C)(C)N)CC3)nc2=O)cc1)N1C[C@@H]2[C@@H](N)[C@@H]2C1] |
| 68 | 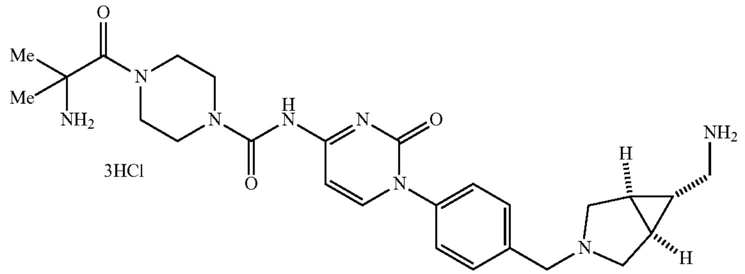 [SMILES: CC(C)(N)C(=O)N1CCN(C(=O)Nc2ccn(-c3ccc(CN4C[C@@H]5[C@@H](CN)[C@@H]5C4)cc3)c(=O)n2)CC1] 3HCl | 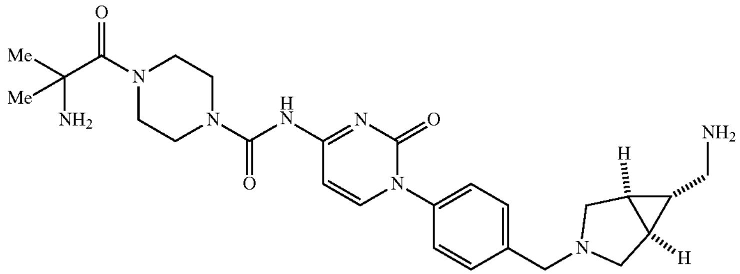 [SMILES: CC(C)(N)C(=O)N1CCN(C(=O)Nc2ccn(-c3ccc(CN4C[C@@H]5[C@@H](CN)[C@@H]5C4)cc3)c(=O)n2)CC1] |
| 69 | 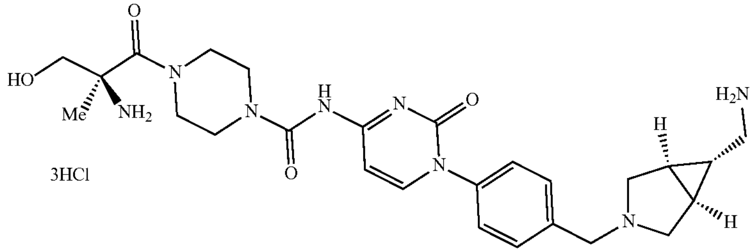 [SMILES: C[C@](N)(CO)C(=O)N1CCN(C(=O)Nc2ccn(-c3ccc(CN4C[C@@H]5[C@@H](CN)[C@@H]5C4)cc3)c(=O)n2)CC1] 3HCl | 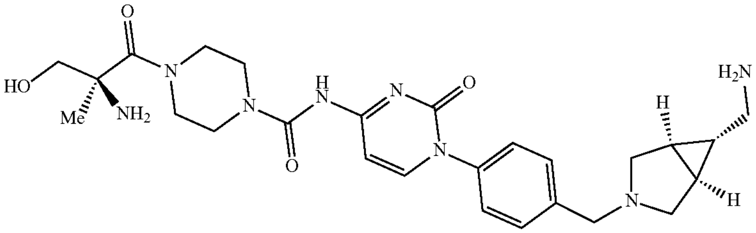 [SMILES: C[C@](N)(CO)C(=O)N1CCN(C(=O)Nc2ccn(-c3ccc(CN4C[C@@H]5[C@@H](CN)[C@@H]5C4)cc3)c(=O)n2)CC1] |

TABLE 7-continued
| No. | Salt Structure | Free Base Structure |
|---|---|---|
| 70 | 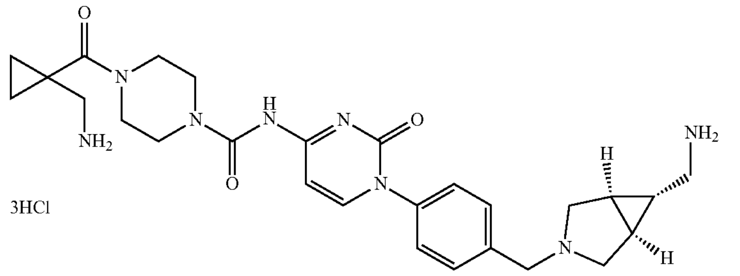 [SMILES: NC[C@@H]1[C@H]2CN(Cc3ccc(-n4ccc(NC(=O)N5CCN(C(=O)C6(CN)CC6)CC5)nc4=O)cc3)C[C@@H]12] 3HCl | 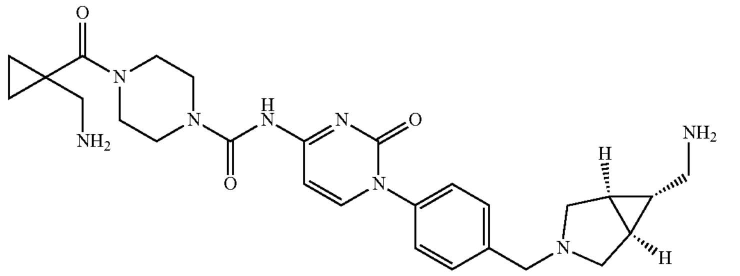 [SMILES: NC[C@@H]1[C@H]2CN(Cc3ccc(-n4ccc(NC(=O)N5CCN(C(=O)C6(CN)CC6)CC5)nc4=O)cc3)C[C@@H]12] |
| 71 | 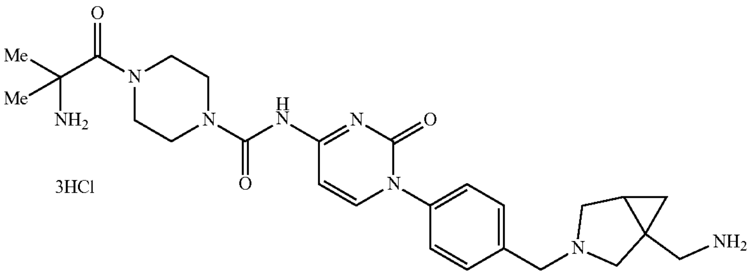 [SMILES: CC(C)(N)C(=O)N1CCN(C(=O)Nc2ccn(-c3ccc(CN4CC5CC5(CN)C4)cc3)c(=O)n2)CC1] 3HCl | 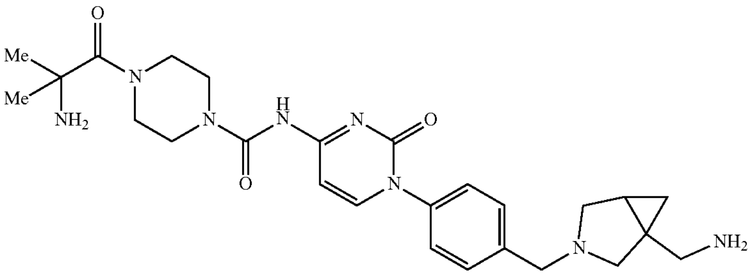 [SMILES: CC(C)(N)C(=O)N1CCN(C(=O)Nc2ccn(-c3ccc(CN4CC5CC5(CN)C4)cc3)c(=O)n2)CC1] |
| 72 | 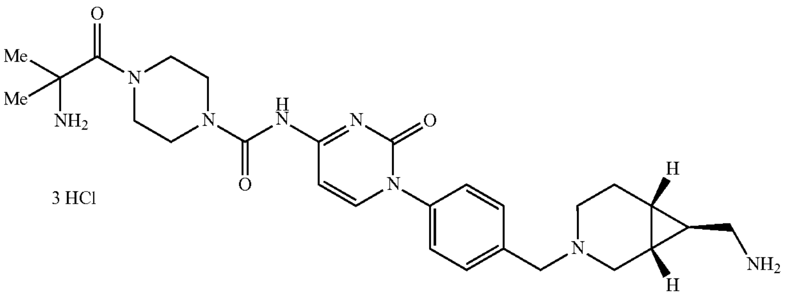 [SMILES: CC(C)(N)C(=O)N1CCN(C(=O)Nc2ccn(-c3ccc(CN4CC[C@@H]5[C@@H](CN)[C@@H]5C4)cc3)c(=O)n2)CC1] 3 HCl | 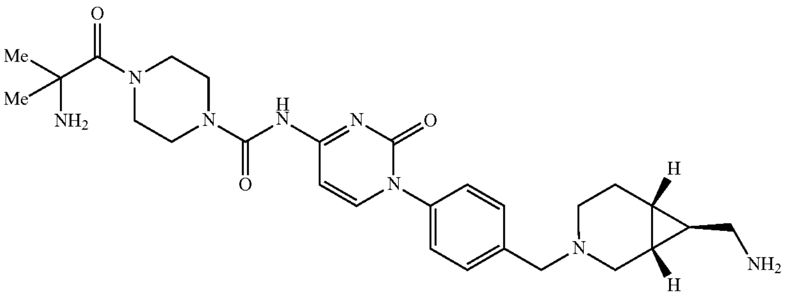 [SMILES: CC(C)(N)C(=O)N1CCN(C(=O)Nc2ccn(-c3ccc(CN4CC[C@@H]5[C@@H](CN)[C@@H]5C4)cc3)c(=O)n2)CC1] |

TABLE 7-continued
| No. | Salt Structure | Free Base Structure |
|---|---|---|
| 73 | 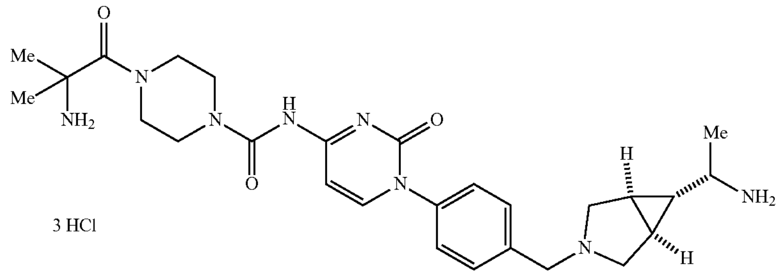 [SMILES: CC(N)[C@H]1[C@@H]2CN(Cc3ccc(-n4ccc(NC(=O)N5CCN(C(=O)C(C)(C)N)CC5)nc4=O)cc3)C[C@@H]21] 3 HCl | 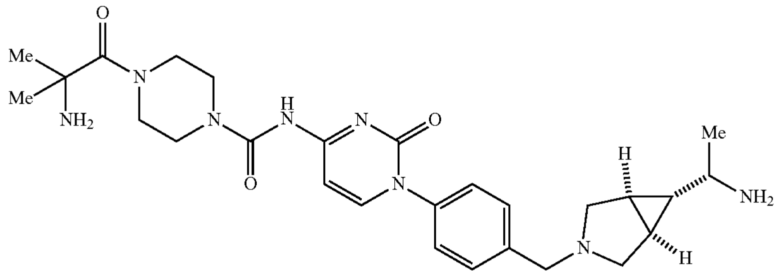 [SMILES: CC(N)[C@H]1[C@@H]2CN(Cc3ccc(-n4ccc(NC(=O)N5CCN(C(=O)C(C)(C)N)CC5)nc4=O)cc3)C[C@@H]21] |
| 74 | 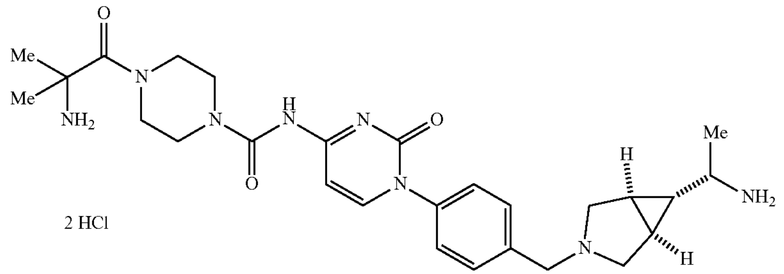 [SMILES: CC(N)[C@H]1[C@@H]2CN(Cc3ccc(-n4ccc(NC(=O)N5CCN(C(=O)C(C)(C)N)CC5)nc4=O)cc3)C[C@@H]21] 2 HCl | 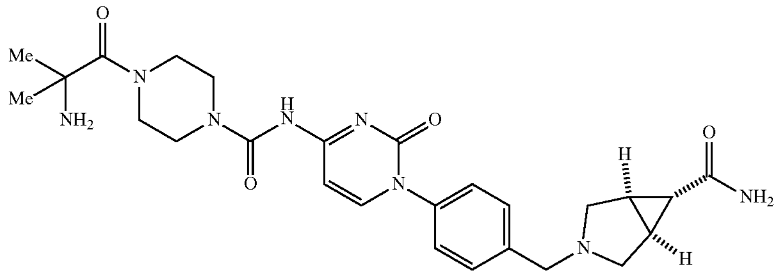 [SMILES: CC(C)(N)C(=O)N1CCN(C(=O)Nc2ccn(-c3ccc(CN4C[C@@H]5[C@H](C4)[C@H]5C(N)=O)cc3)c(=O)n2)CC1] |
| 75 | 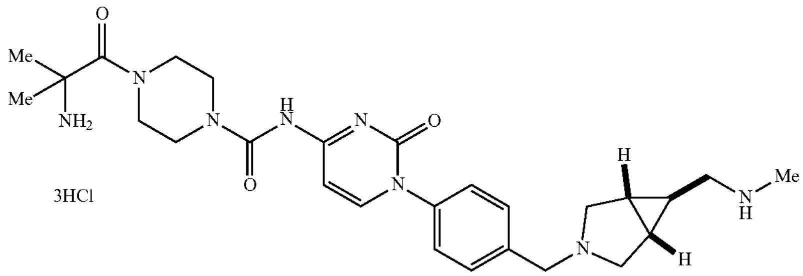 [SMILES: CNC[C@@H]1[C@H]2CN(Cc3ccc(-n4ccc(NC(=O)N5CCN(C(=O)C(C)(C)N)CC5)nc4=O)cc3)C[C@@H]12] 3HCl | 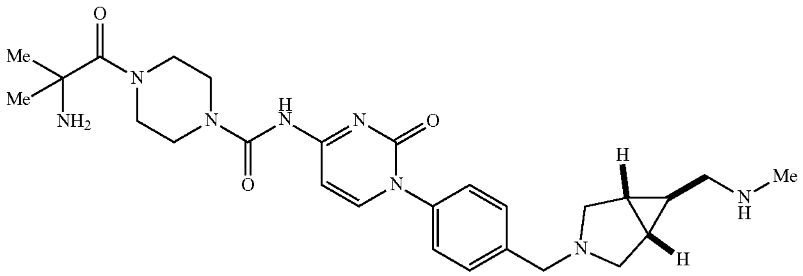 [SMILES: CNC[C@@H]1[C@H]2CN(Cc3ccc(-n4ccc(NC(=O)N5CCN(C(=O)C(C)(C)N)CC5)nc4=O)cc3)C[C@@H]12] |

TABLE 7-continued
| No. | Salt Structure | Free Base Structure |
|---|---|---|
| 76 | 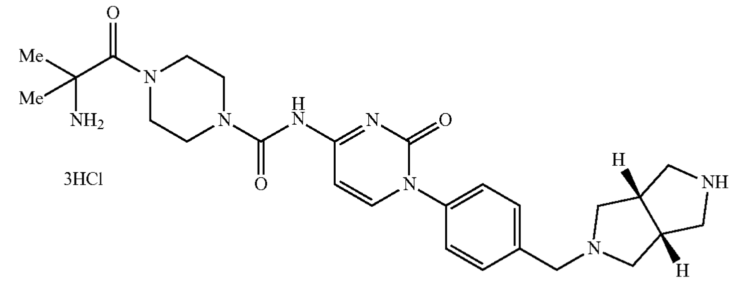 [SMILES: CC(C)(N)C(=O)N1CCN(C(=O)Nc2ccn(-c3ccc(CN4C[C@H]5CNC[C@H]5C4)cc3)c(=O)n2)CC1] 3HCl | 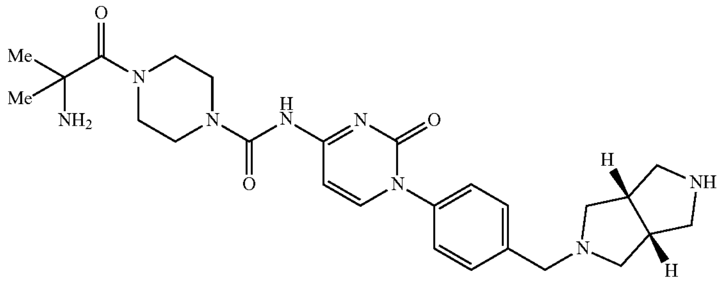 [SMILES: CC(C)(N)C(=O)N1CCN(C(=O)Nc2ccn(-c3ccc(CN4C[C@H]5CNC[C@H]5C4)cc3)c(=O)n2)CC1] |
| 77 | 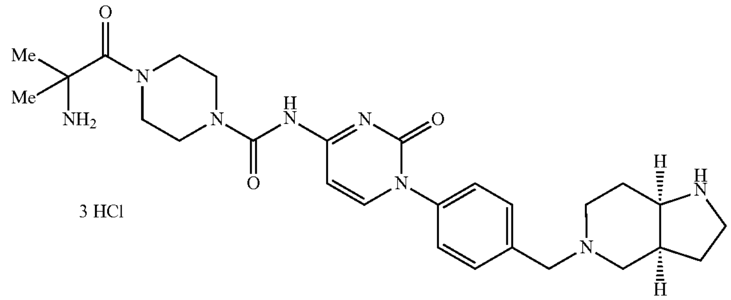 [SMILES: CC(C)(N)C(=O)N1CCN(C(=O)Nc2ccn(-c3ccc(CN4CC[C@H]5NCC[C@H]5C4)cc3)c(=O)n2)CC1] 3 HCl | 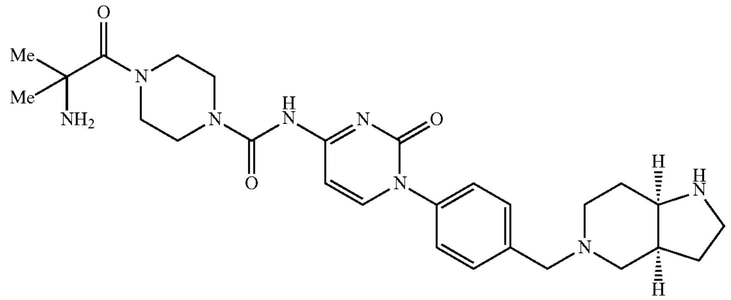 [SMILES: CC(C)(N)C(=O)N1CCN(C(=O)Nc2ccn(-c3ccc(CN4CC[C@H]5NCC[C@H]5C4)cc3)c(=O)n2)CC1] |
| 78 | 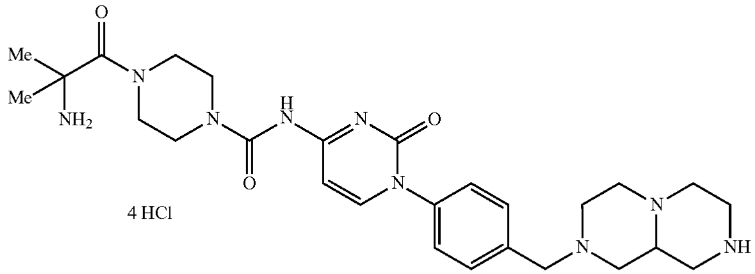 [SMILES: CC(C)(N)C(=O)N1CCN(C(=O)Nc2ccn(-c3ccc(CN4CCN5CCNCC5C4)cc3)c(=O)n2)CC1] 4 HCl | 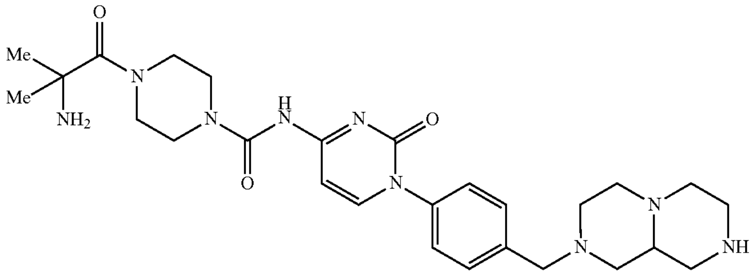 [SMILES: CC(C)(N)C(=O)N1CCN(C(=O)Nc2ccn(-c3ccc(CN4CCN5CCNCC5C4)cc3)c(=O)n2)CC1] |

TABLE 7-continued
| No. | Salt Structure | Free Base Structure |
|---|---|---|
| 79 | 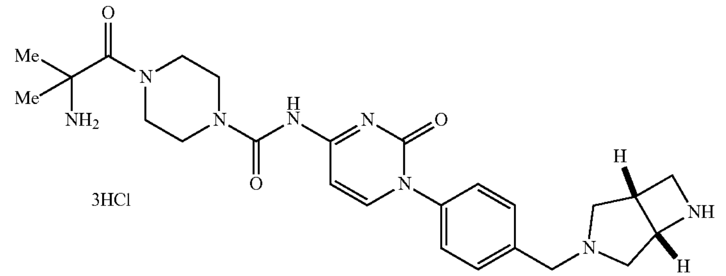 [SMILES: CC(C)(N)C(=O)N1CCN(C(=O)Nc2ccn(-c3ccc(CN4C[C@@H]5CN[C@@H]5C4)cc3)c(=O)n2)CC1] 3HCl | 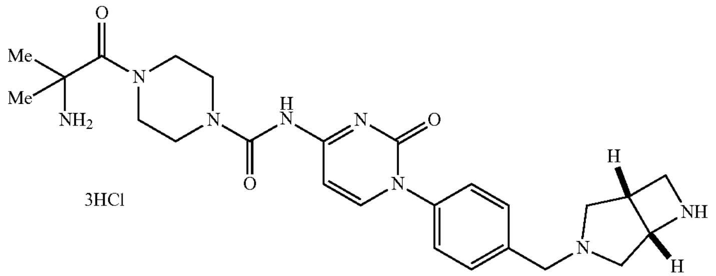 [SMILES: CC(C)(N)C(=O)N1CCN(C(=O)Nc2ccn(-c3ccc(CN4C[C@@H]5CN[C@@H]5C4)cc3)c(=O)n2)CC1] 3HCl |
| 80 | 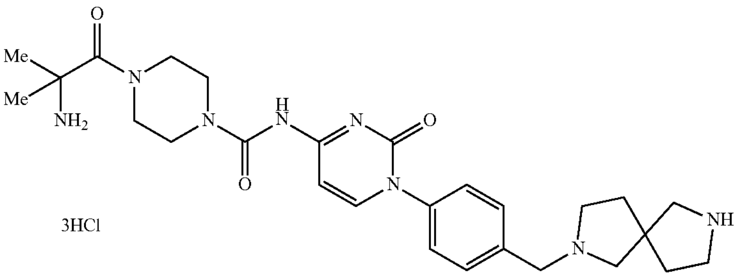 [SMILES: CC(C)(N)C(=O)N1CCN(C(=O)Nc2ccn(-c3ccc(CN4CCC5(CCNC5)C4)cc3)c(=O)n2)CC1] 3HCl | 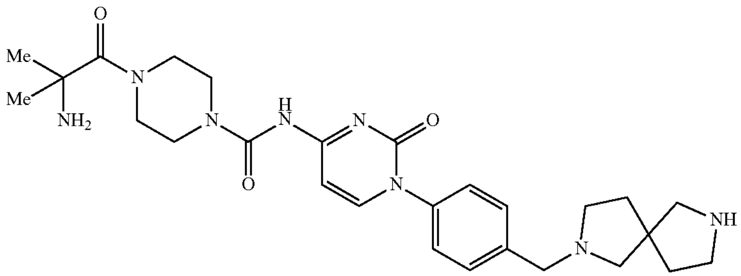 [SMILES: CC(C)(N)C(=O)N1CCN(C(=O)Nc2ccn(-c3ccc(CN4CCC5(CCNC5)C4)cc3)c(=O)n2)CC1] |
| 81 | 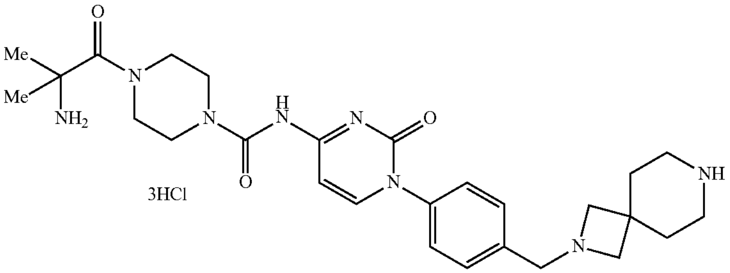 [SMILES: CC(C)(N)C(=O)N1CCN(C(=O)Nc2ccn(-c3ccc(CN4CC5(CCNCC5)C4)cc3)c(=O)n2)CC1] 3HCl | 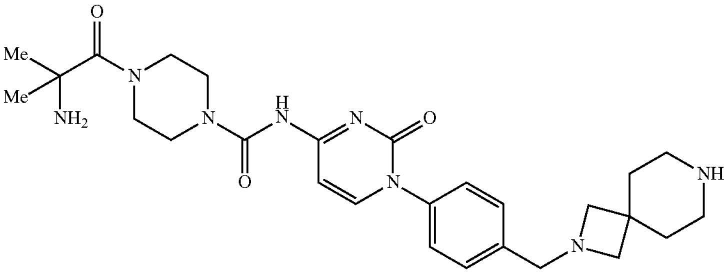 [SMILES: CC(C)(N)C(=O)N1CCN(C(=O)Nc2ccn(-c3ccc(CN4CC5(CCNCC5)C4)cc3)c(=O)n2)CC1] |

TABLE 7-continued
| No. | Salt Structure | Free Base Structure |
|---|---|---|
| 82 | 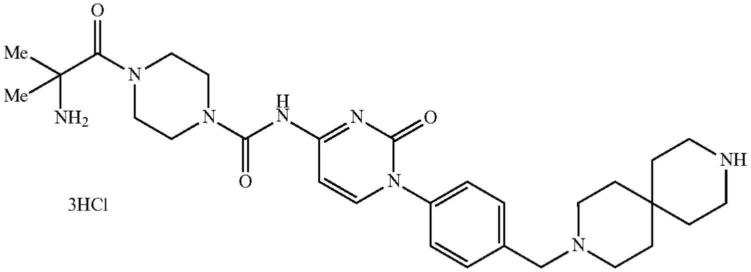 [SMILES: CC(C)(N)C(=O)N1CCN(C(=O)Nc2ccn(-c3ccc(CN4CCC5(CCNCC5)CC4)cc3)c(=O)n2)CC1] 3HCl | 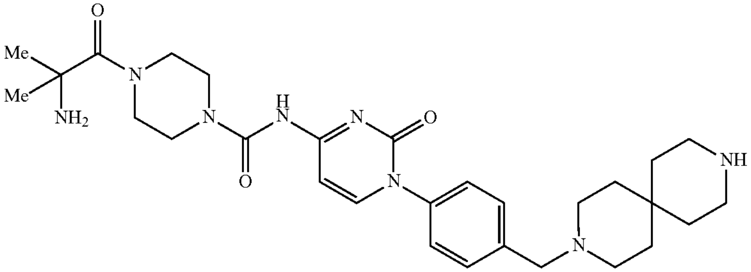 [SMILES: CC(C)(N)C(=O)N1CCN(C(=O)Nc2ccn(-c3ccc(CN4CCC5(CCNCC5)CC4)cc3)c(=O)n2)CC1] |
| 83 | 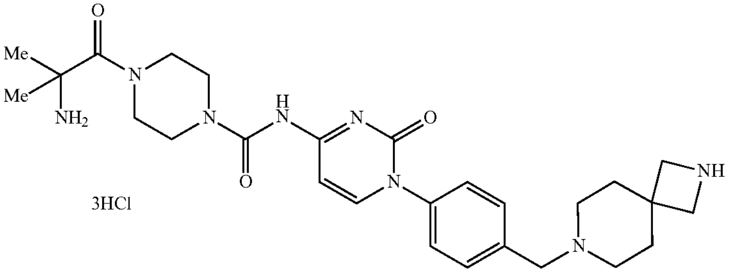 [SMILES: CC(C)(N)C(=O)N1CCN(C(=O)Nc2ccn(-c3ccc(CN4CCC5(CC4)CNC5)cc3)c(=O)n2)CC1] 3HCl | 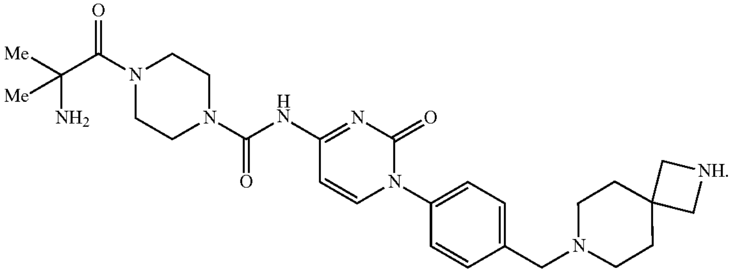 [SMILES: CC(C)(N)C(=O)N1CCN(C(=O)Nc2ccn(-c3ccc(CN4CCC5(CC4)CNC5)cc3)c(=O)n2)CC1] |

TABLE 8
| No. | Salt Structure | Free Base Structure |
|---|---|---|
| 84 | 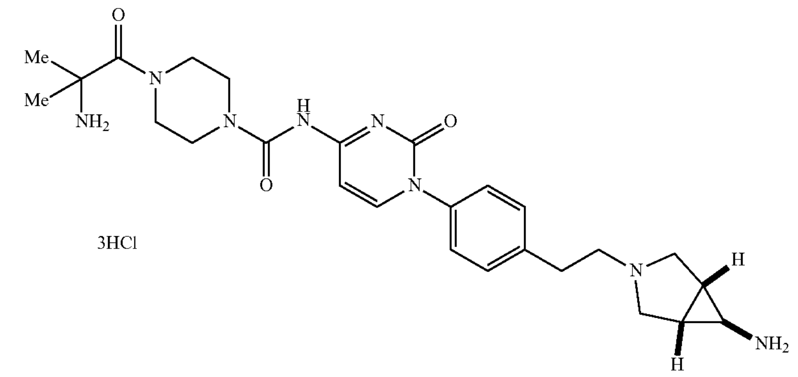 [SMILES: CC(C)(N)C(=O)N1CCN(C(=O)Nc2ccn(-c3ccc(CCN4C[C@@H]5[C@@H](N)[C@@H]5C4)cc3)c(=O)n2)CC1] 3HCl | 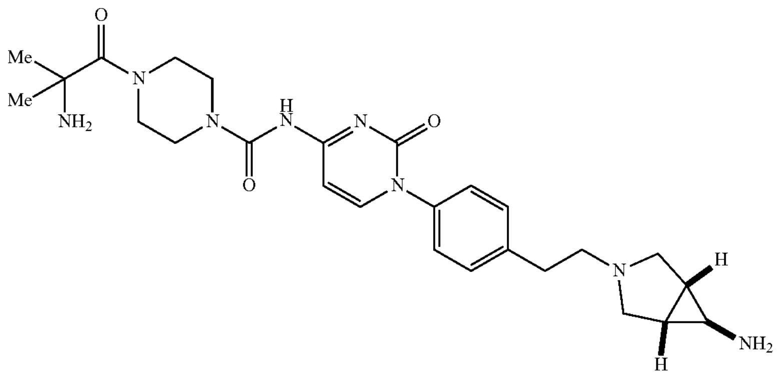 [SMILES: CC(C)(N)C(=O)N1CCN(C(=O)Nc2ccn(-c3ccc(CCN4C[C@@H]5[C@@H](N)[C@@H]5C4)cc3)c(=O)n2)CC1] |
| 85 | 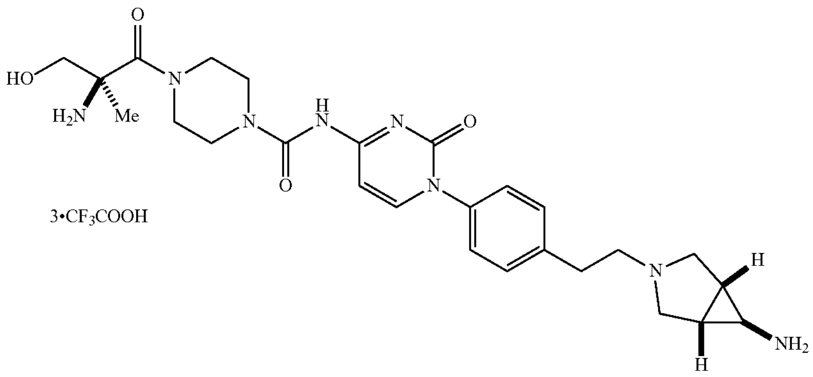 [SMILES: C[C@](N)(CO)C(=O)N1CCN(C(=O)Nc2ccn(-c3ccc(CCN4C[C@@H]5[C@@H](N)[C@@H]5C4)cc3)c(=O)n2)CC1] 3•$CF_3COOH$ | 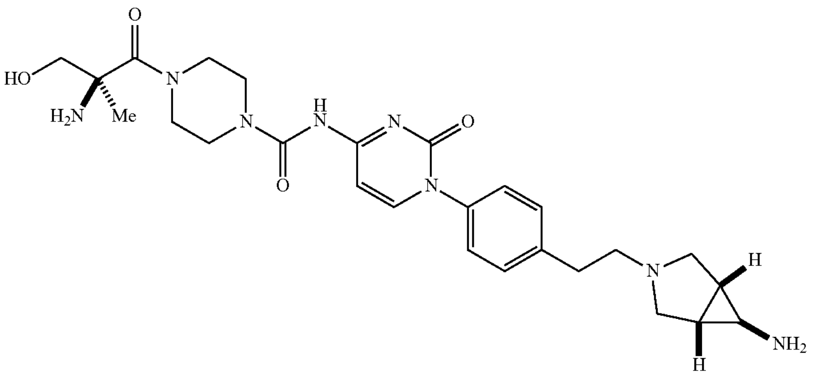 [SMILES: C[C@](N)(CO)C(=O)N1CCN(C(=O)Nc2ccn(-c3ccc(CCN4C[C@@H]5[C@@H](N)[C@@H]5C4)cc3)c(=O)n2)CC1] |

TABLE 8-continued
| No. | Salt Structure | Free Base Structure |
|---|---|---|
| 86 | 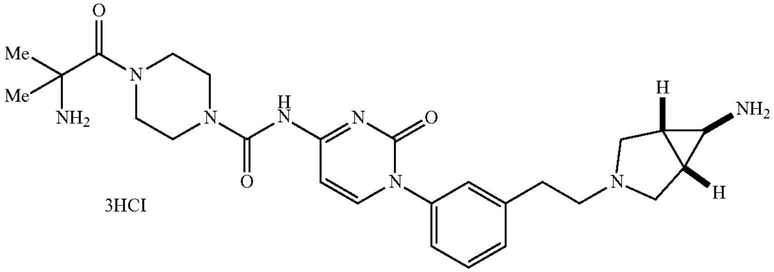 [SMILES: CC(C)(N)C(=O)N1CCN(C(=O)Nc2ccn(-c3cccc(CCN4C[C@@H]5[C@@H](N)[C@@H]5C4)c3)c(=O)n2)CC1] 3HCI | 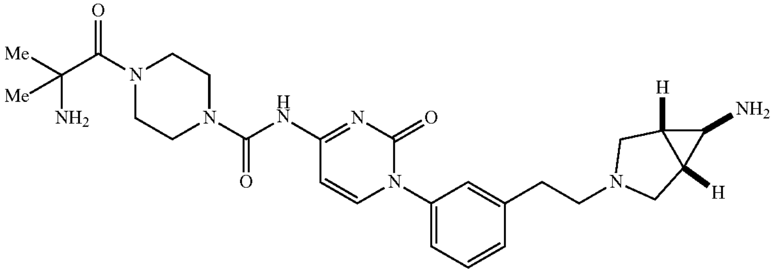 [SMILES: CC(C)(N)C(=O)N1CCN(C(=O)Nc2ccn(-c3cccc(CCN4C[C@@H]5[C@@H](N)[C@@H]5C4)c3)c(=O)n2)CC1] |
| 87 | 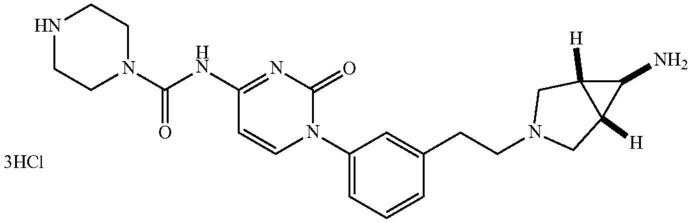 [SMILES: N[C@@H]1[C@H]2CN(CCc3cccc(-n4ccc(NC(=O)N5CCNCC5)nc4=O)c3)C[C@@H]12] 3HCl | 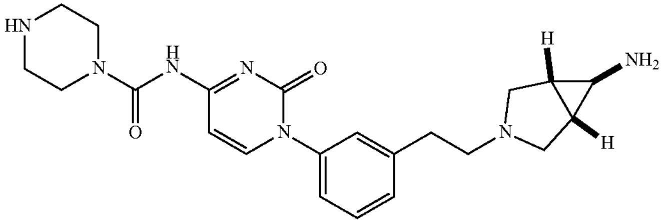 [SMILES: N[C@@H]1[C@H]2CN(CCc3cccc(-n4ccc(NC(=O)N5CCNCC5)nc4=O)c3)C[C@@H]12] |
| 88 | 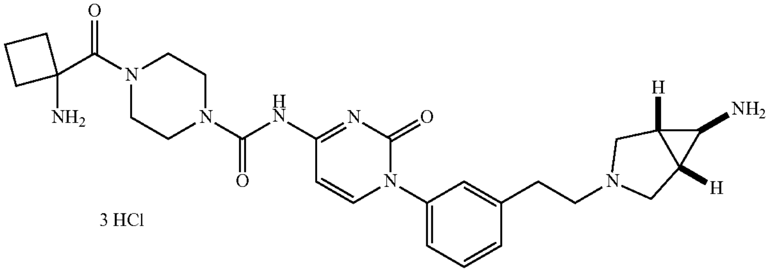 [SMILES: N[C@@H]1[C@H]2CN(CCc3cccc(-n4ccc(NC(=O)N5CCN(C(=O)C6(N)CCC6)CC5)nc4=O)c3)C[C@@H]12] 3 HCl | 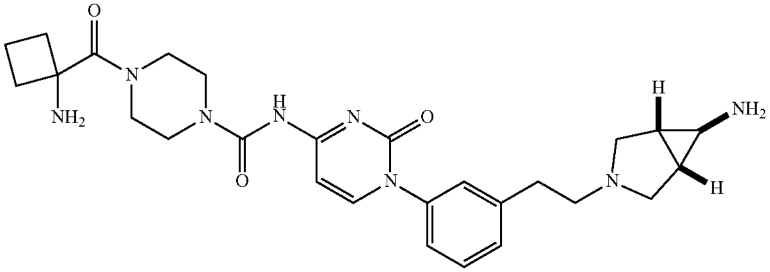 [SMILES: N[C@@H]1[C@H]2CN(CCc3cccc(-n4ccc(NC(=O)N5CCN(C(=O)C6(N)CCC6)CC5)nc4=O)c3)C[C@@H]12] |
| 89 | 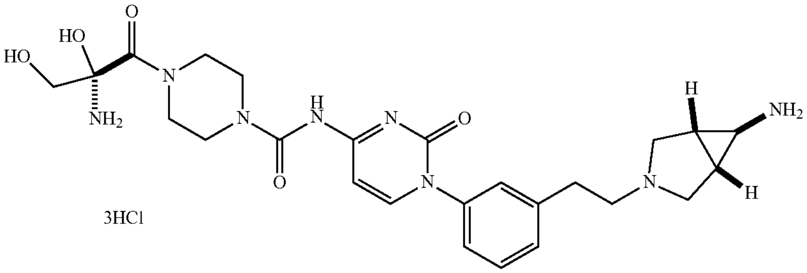 [SMILES: N[C@@H]1[C@H]2CN(CCc3cccc(-n4ccc(NC(=O)N5CCN(C(=O)[C@](N)(O)CO)CC5)nc4=O)c3)C[C@@H]12] 3HCl | 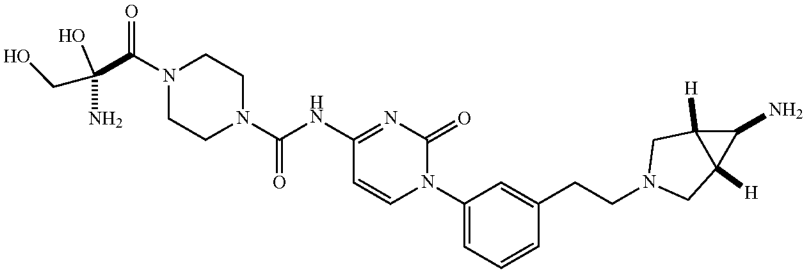 |

TABLE 8-continued
| No. | Salt Structure | Free Base Structure |
|---|---|---|
| 90 | 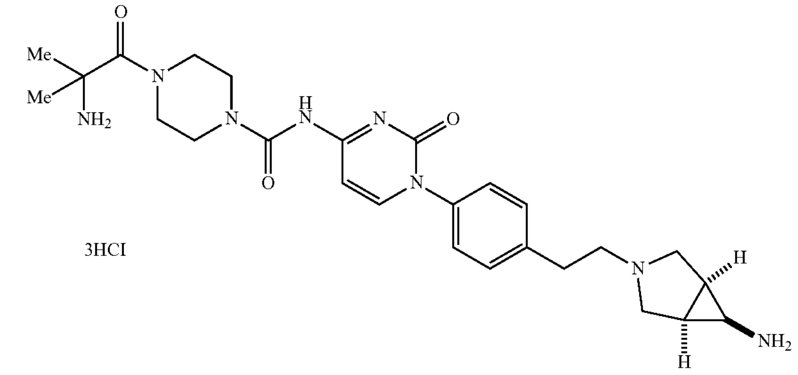 [SMILES: CC(C)(N)C(=O)N1CCN(C(=O)Nc2ccn(-c3ccc(CCN4C[C@@H]5[C@H](N)[C@@H]5C4)cc3)c(=O)n2)CC1] 3HCI | 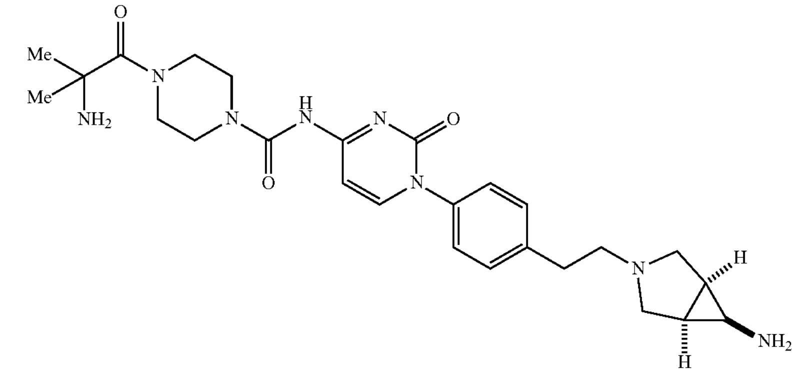 [SMILES: CC(C)(N)C(=O)N1CCN(C(=O)Nc2ccn(-c3ccc(CCN4C[C@@H]5[C@H](N)[C@@H]5C4)cc3)c(=O)n2)CC1] |
| 91 | 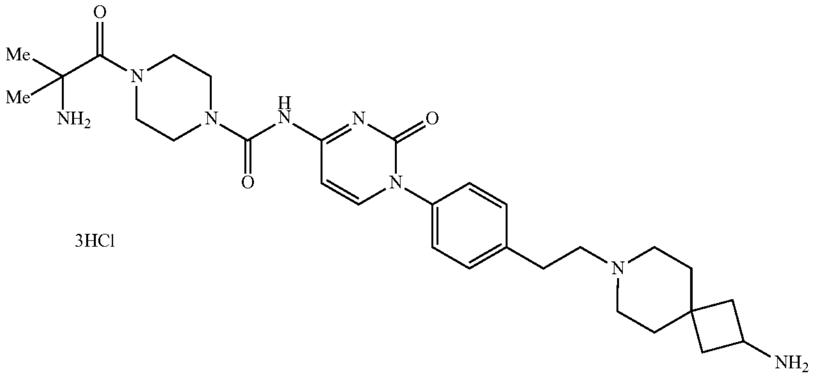 [SMILES: CC(C)(N)C(=O)N1CCN(C(=O)Nc2ccn(-c3ccc(CCN4CCC5(CC4)CC(N)C5)cc3)c(=O)n2)CC1] 3HCl | 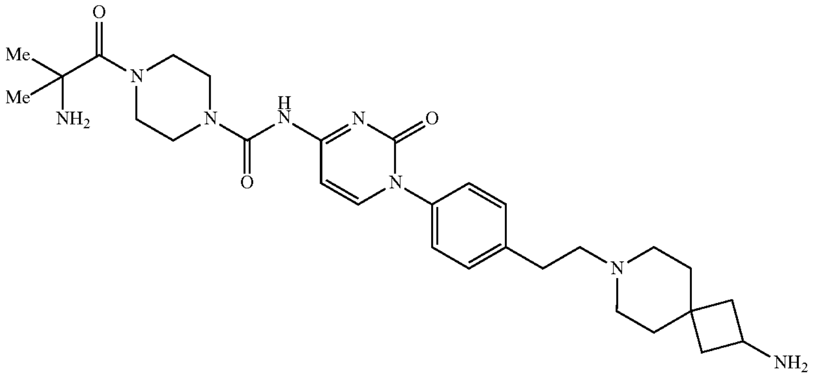 [SMILES: CC(C)(N)C(=O)N1CCN(C(=O)Nc2ccn(-c3ccc(CCN4CCC5(CC4)CC(N)C5)cc3)c(=O)n2)CC1] |

TABLE 8-continued
| No. | Salt Structure | Free Base Structure |
|---|---|---|
| 92 | 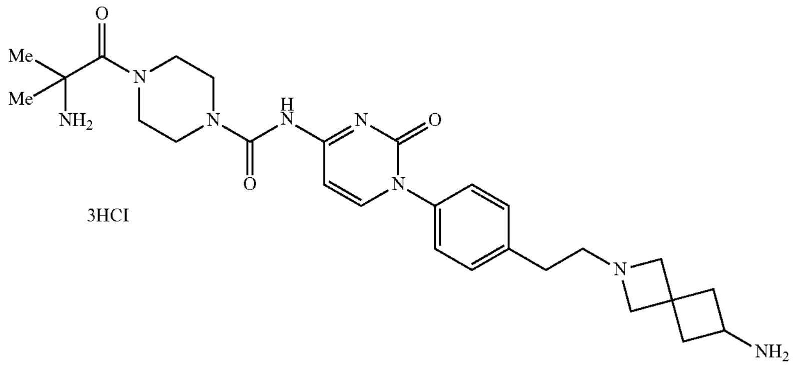 [SMILES: CC(C)(N)C(=O)N1CCN(C(=O)Nc2ccn(-c3ccc(CCN4CC5(CC(N)C5)C4)cc3)c(=O)n2)CC1] 3HCl | 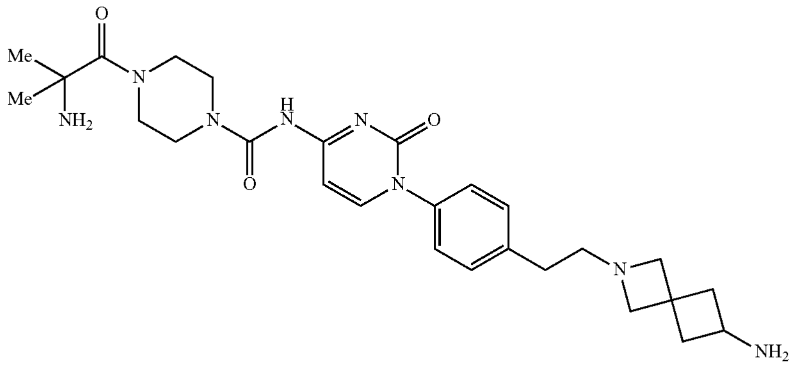 [SMILES: CC(C)(N)C(=O)N1CCN(C(=O)Nc2ccn(-c3ccc(CCN4CC5(CC(N)C5)C4)cc3)c(=O)n2)CC1] |
| 93 | 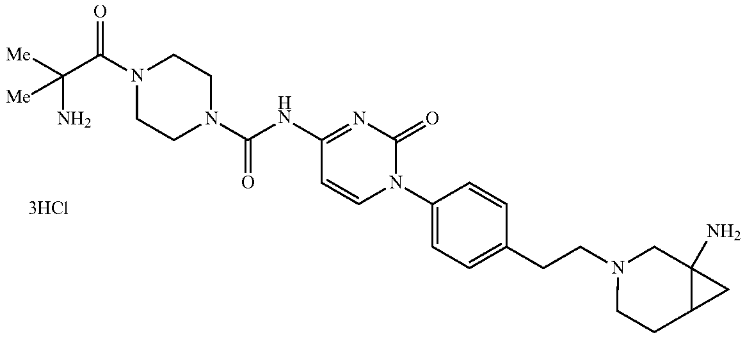 [SMILES: CC(C)(N)C(=O)N1CCN(C(=O)Nc2ccn(-c3ccc(CCN4CCC5CC5(N)C4)cc3)c(=O)n2)CC1] 3HCl | 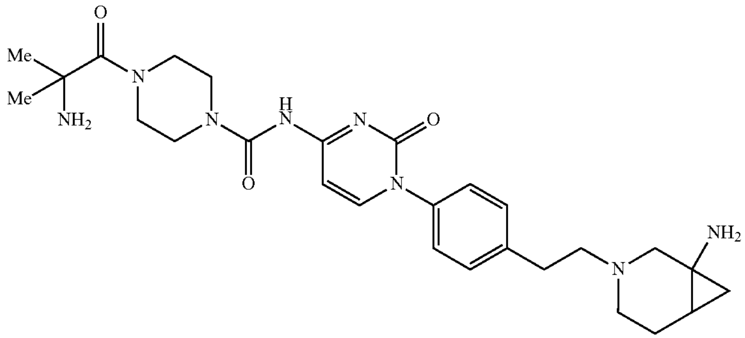 [SMILES: CC(C)(N)C(=O)N1CCN(C(=O)Nc2ccn(-c3ccc(CCN4CCC5CC5(N)C4)cc3)c(=O)n2)CC1] |
| 94 | 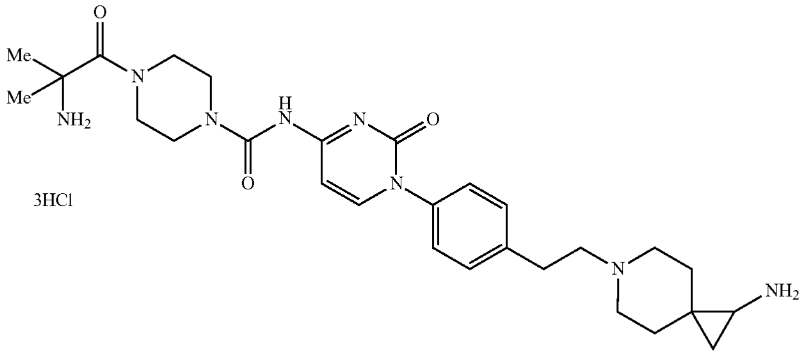 [SMILES: CC(C)(N)C(=O)N1CCN(C(=O)Nc2ccn(-c3ccc(CCN4CCC5(CC4)CC5N)cc3)c(=O)n2)CC1] 3HCl | 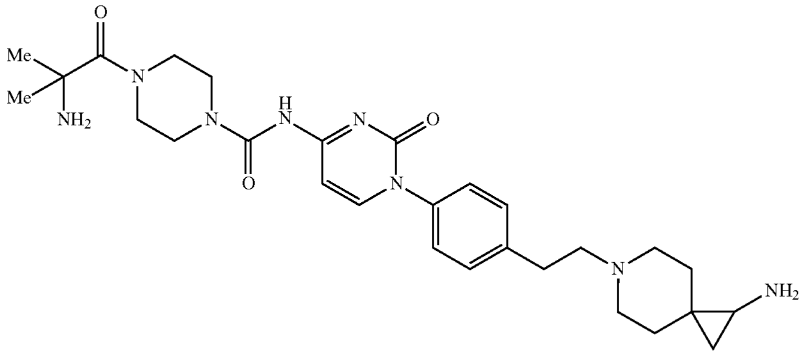 [SMILES: CC(C)(N)C(=O)N1CCN(C(=O)Nc2ccn(-c3ccc(CCN4CCC5(CC4)CC5N)cc3)c(=O)n2)CC1] |

TABLE 8-continued
| No. | Salt Structure | Free Base Structure |
|---|---|---|
| 95 | 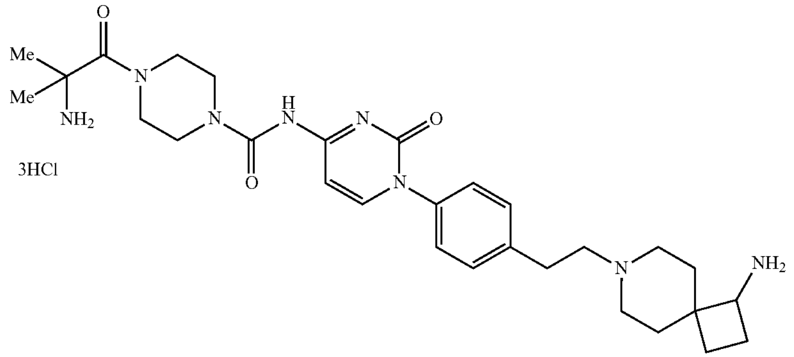 [SMILES: CC(C)(N)C(=O)N1CCN(C(=O)Nc2ccn(-c3ccc(CCN4CCC5(CCC5N)CC4)cc3)c(=O)n2)CC1] 3HCl | 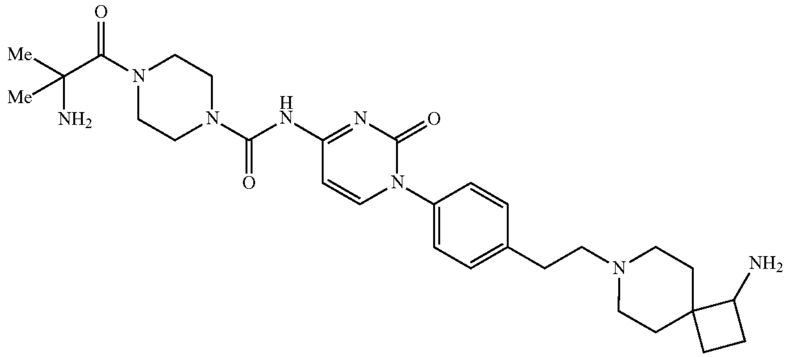 [SMILES: CC(C)(N)C(=O)N1CCN(C(=O)Nc2ccn(-c3ccc(CCN4CCC5(CCC5N)CC4)cc3)c(=O)n2)CC1] |
| 96 | 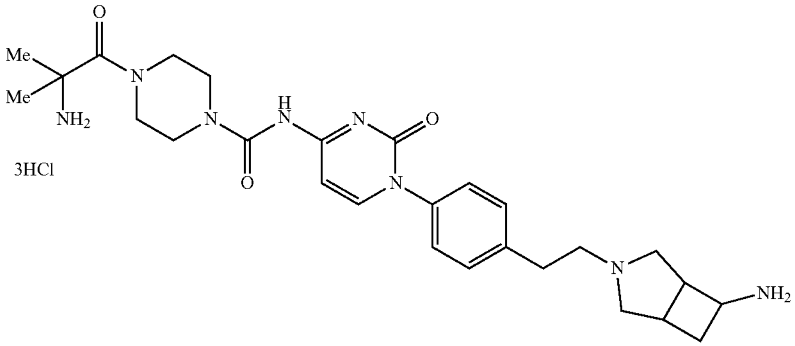 [SMILES: CC(C)(N)C(=O)N1CCN(C(=O)Nc2ccn(-c3ccc(CCN4CC5CC(N)C5C4)cc3)c(=O)n2)CC1] 3HCl | 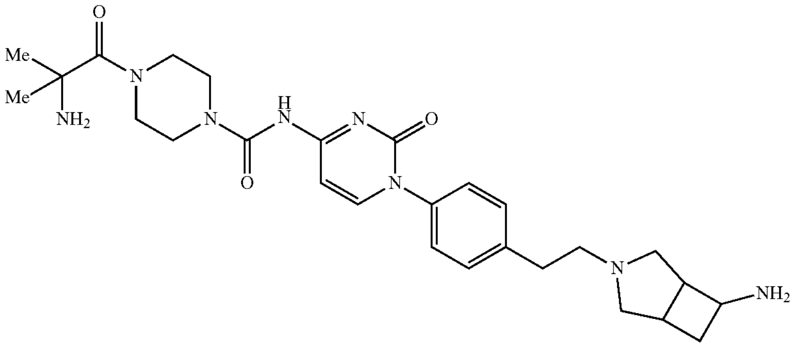 [SMILES: CC(C)(N)C(=O)N1CCN(C(=O)Nc2ccn(-c3ccc(CCN4CC5CC(N)C5C4)cc3)c(=O)n2)CC1] |

TABLE 8-continued
| No. | Salt Structure | Free Base Structure |
| --- | --- | --- |
| 97 | 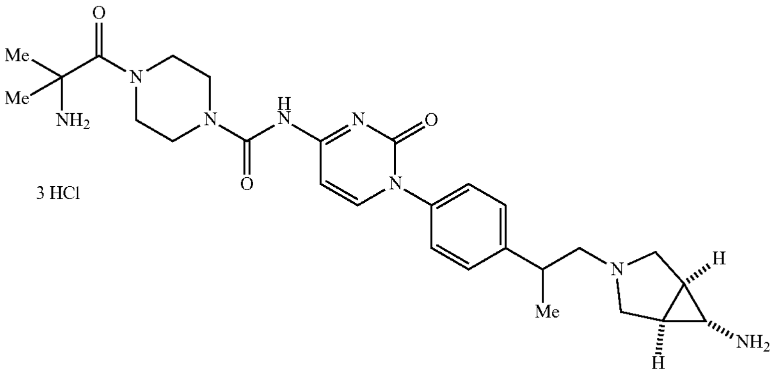 [SMILES: CC(CN1C[C@@H]2[C@@H](N)[C@@H]2C1)c1ccc(-n2ccc(NC(=O)N3CCN(C(=O)C(C)(C)N)CC3)nc2=O)cc1] 3 HCl | 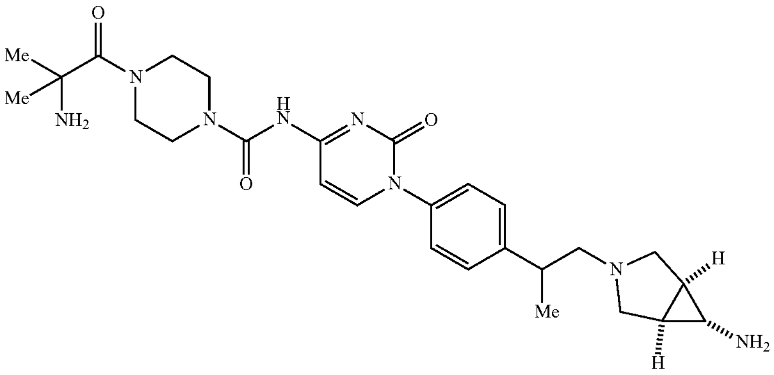 [SMILES: CC(CN1C[C@@H]2[C@@H](N)[C@@H]2C1)c1ccc(-n2ccc(NC(=O)N3CCN(C(=O)C(C)(C)N)CC3)nc2=O)cc1] |
| 98 | 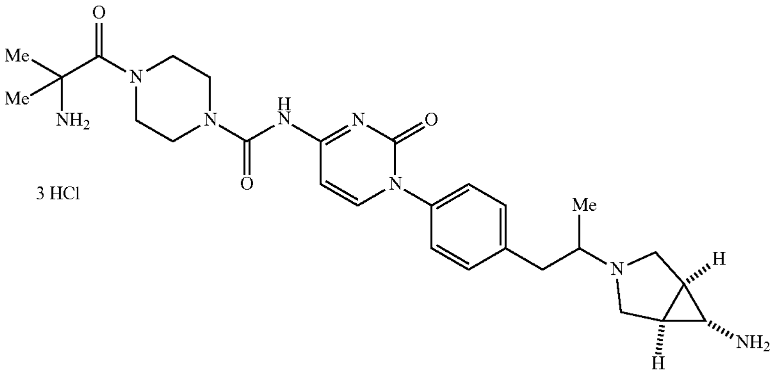 [SMILES: CC(Cc1ccc(-n2ccc(NC(=O)N3CCN(C(=O)C(C)(C)N)CC3)nc2=O)cc1)N1C[C@@H]2[C@@H](N)[C@@H]2C1] 3 HCl | 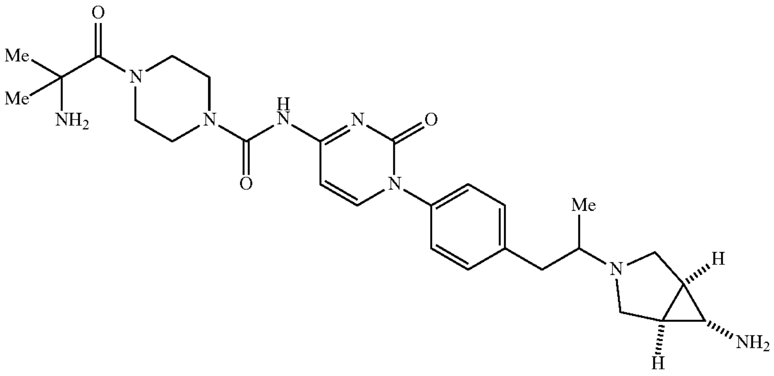 [SMILES: CC(Cc1ccc(-n2ccc(NC(=O)N3CCN(C(=O)C(C)(C)N)CC3)nc2=O)cc1)N1C[C@@H]2[C@@H](N)[C@@H]2C1] |

TABLE 8-continued
| No. | Salt Structure | Free Base Structure |
|---|---|---|
| 99 | 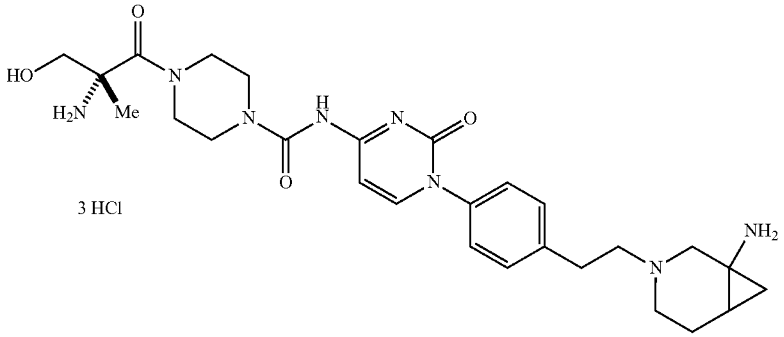 [SMILES: C[C@@](N)(CO)C(=O)N1CCN(C(=O)Nc2ccn(-c3ccc(CCN4CCC5CC5(N)C4)cc3)c(=O)n2)CC1] 3 HCl | 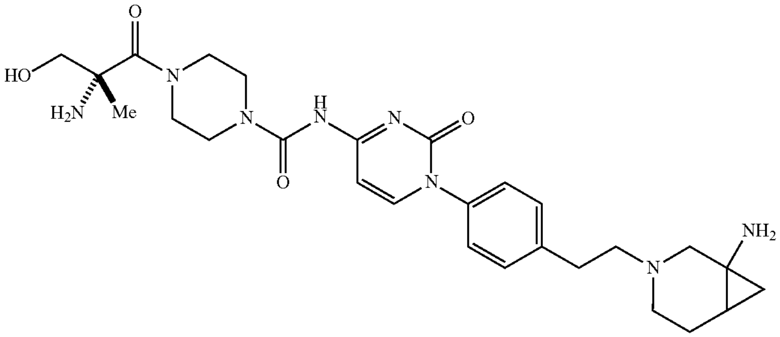 [SMILES: C[C@@](N)(CO)C(=O)N1CCN(C(=O)Nc2ccn(-c3ccc(CCN4CCC5CC5(N)C4)cc3)c(=O)n2)CC1] |
| 100 | 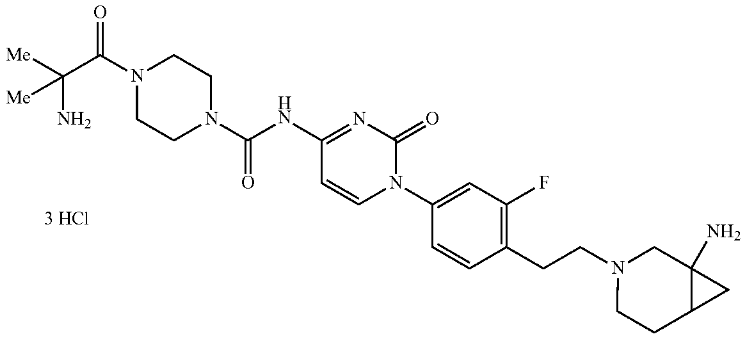 [SMILES: CC(C)(N)C(=O)N1CCN(C(=O)Nc2ccn(-c3ccc(CCN4CCC5CC5(N)C4)c(F)c3)c(=O)n2)CC1] 3 HCl | 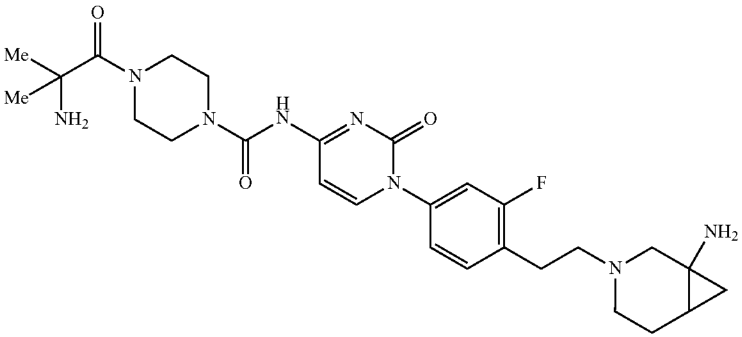 [SMILES: CC(C)(N)C(=O)N1CCN(C(=O)Nc2ccn(-c3ccc(CCN4CCC5CC5(N)C4)c(F)c3)c(=O)n2)CC1] |
| 101 | 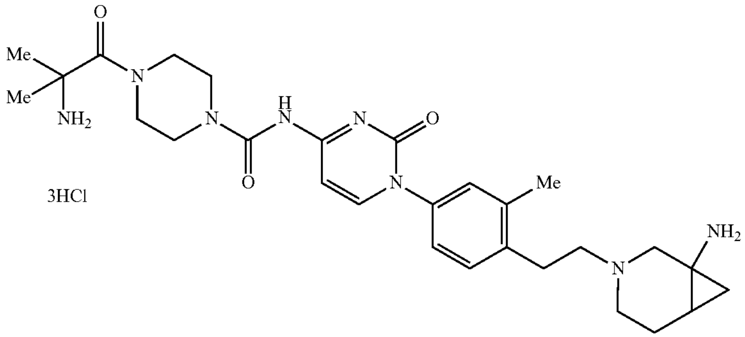 [SMILES: Cc1cc(-n2ccc(NC(=O)N3CCN(C(=O)C(C)(C)N)CC3)nc2=O)ccc1CCN1CCC2CC2(N)C1] 3HCl | 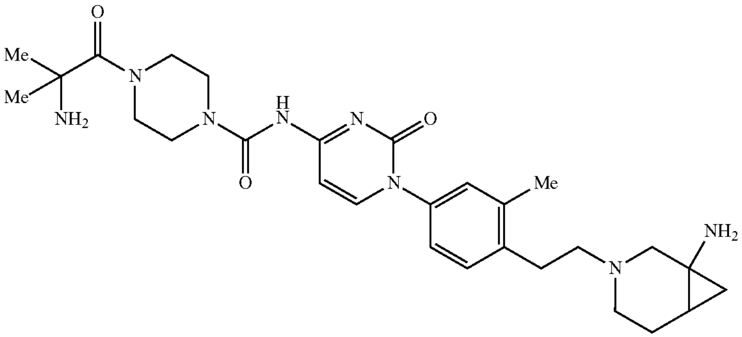 |

TABLE 8-continued
| No. | Salt Structure | Free Base Structure |
|---|---|---|
| 102 | 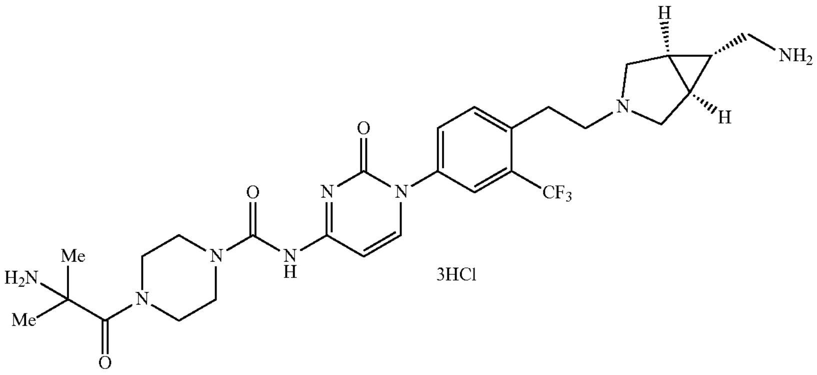 [SMILES: CC(C)(N)C(=O)N1CCN(C(=O)Nc2ccn(-c3ccc(CCN4C[C@@H]5[C@@H](CN)[C@@H]5C4)c(C(F)(F)F)c3)c(=O)n2)CC1] 3HCl | 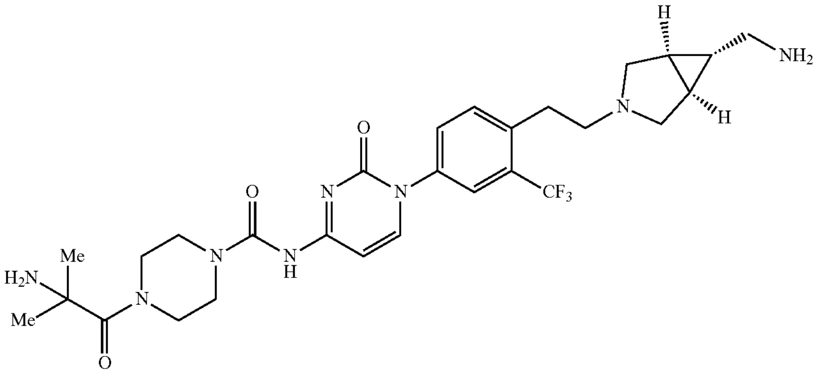 [SMILES: CC(C)(N)C(=O)N1CCN(C(=O)Nc2ccn(-c3ccc(CCN4C[C@@H]5[C@@H](CN)[C@@H]5C4)c(C(F)(F)F)c3)c(=O)n2)CC1] |
| 103 | 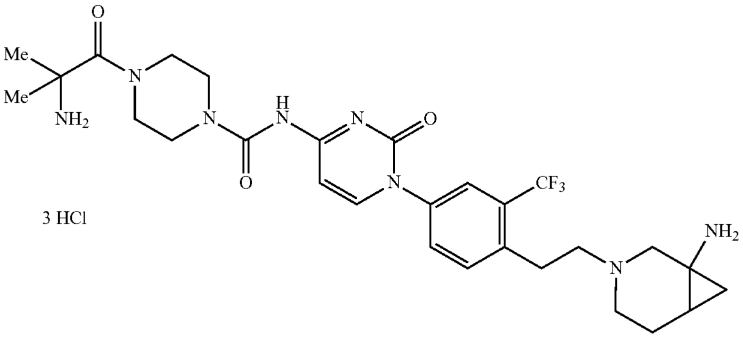 3 HCl | 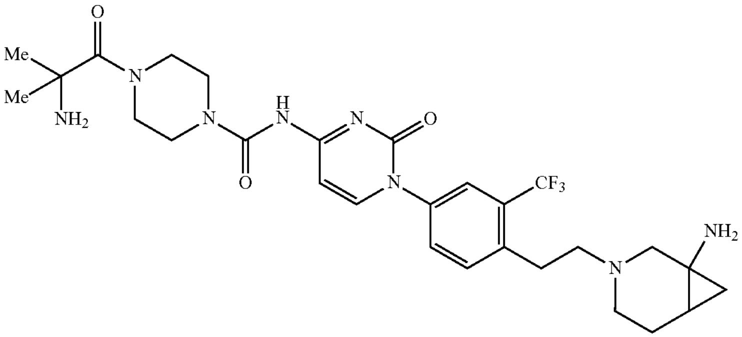 |

TABLE 8-continued
| No. | Salt Structure | Free Base Structure |
|---|---|---|
| 104 | 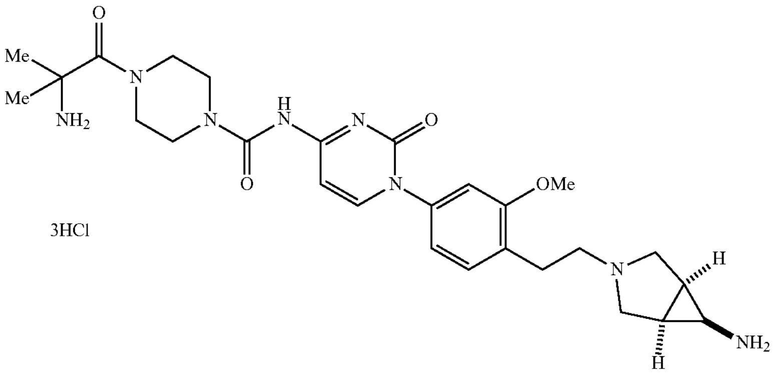 [SMILES: COc1cc(-n2ccc(NC(=O)N3CCN(C(=O)C(C)(C)N)CC3)nc2=O)ccc1CCN1C[C@@H]2[C@H](N)[C@@H]2C1] 3HCl | 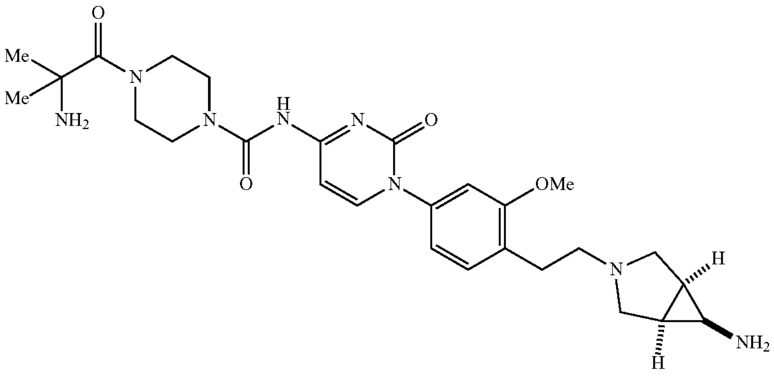 [SMILES: COc1cc(-n2ccc(NC(=O)N3CCN(C(=O)C(C)(C)N)CC3)nc2=O)ccc1CCN1C[C@@H]2[C@H](N)[C@@H]2C1] |
| 105 | 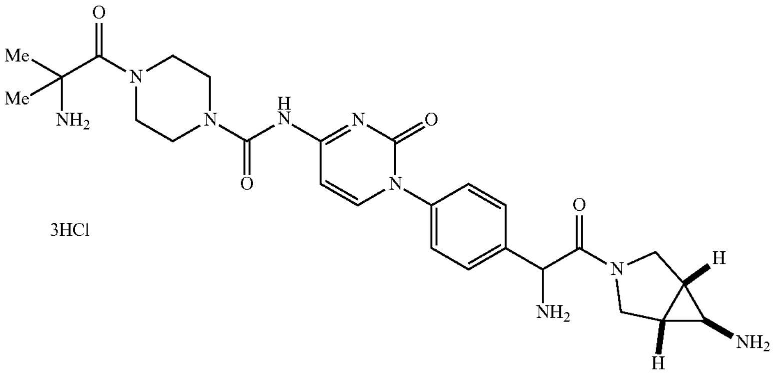 [SMILES: CC(C)(N)C(=O)N1CCN(C(=O)Nc2ccn(-c3ccc(C(N)C(=O)N4C[C@@H]5[C@@H](N)[C@@H]5C4)cc3)c(=O)n2)CC1] 3HCl | 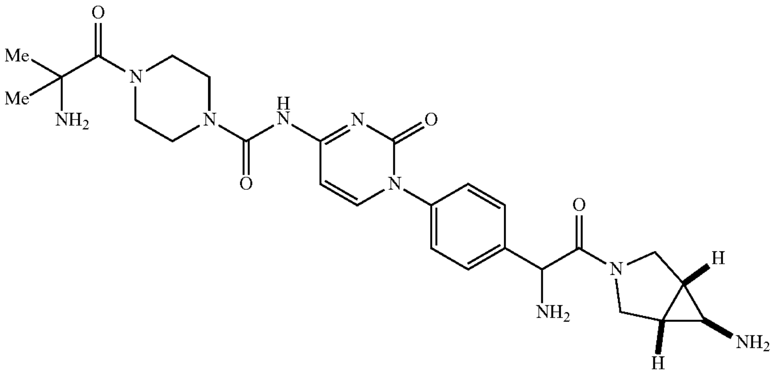 [SMILES: CC(C)(N)C(=O)N1CCN(C(=O)Nc2ccn(-c3ccc(C(N)C(=O)N4C[C@@H]5[C@@H](N)[C@@H]5C4)cc3)c(=O)n2)CC1] |
| 106 | 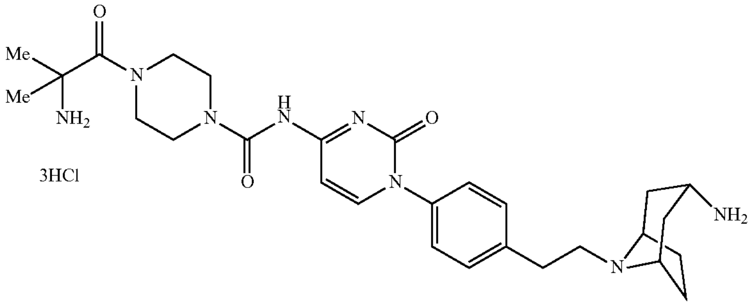 [SMILES: CC(C)(N)C(=O)N1CCN(C(=O)Nc2ccn(-c3ccc(CCN4C5CCC4CC(N)C5)cc3)c(=O)n2)CC1] 3HCl | 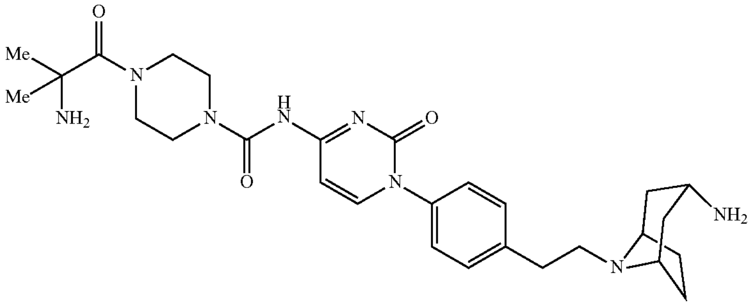 [SMILES: CC(C)(N)C(=O)N1CCN(C(=O)Nc2ccn(-c3ccc(CCN4C5CCC4CC(N)C5)cc3)c(=O)n2)CC1] |

TABLE 8-continued
| No. | Salt Structure | Free Base Structure |
| --- | --- | --- |
| 107 | 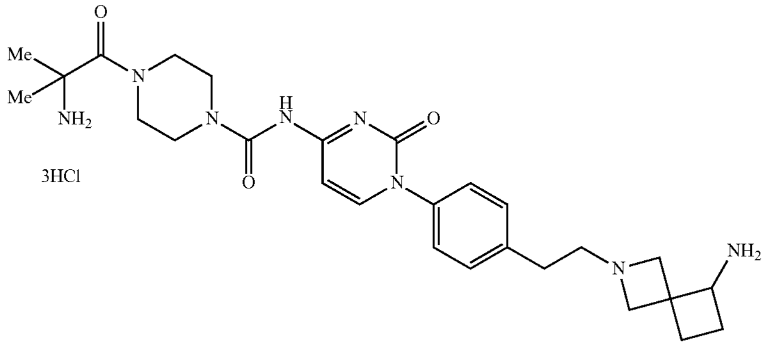 [SMILES: CC(C)(N)C(=O)N1CCN(C(=O)Nc2ccn(-c3ccc(CCN4CC5(CCC5N)C4)cc3)c(=O)n2)CC1] 3HCl | 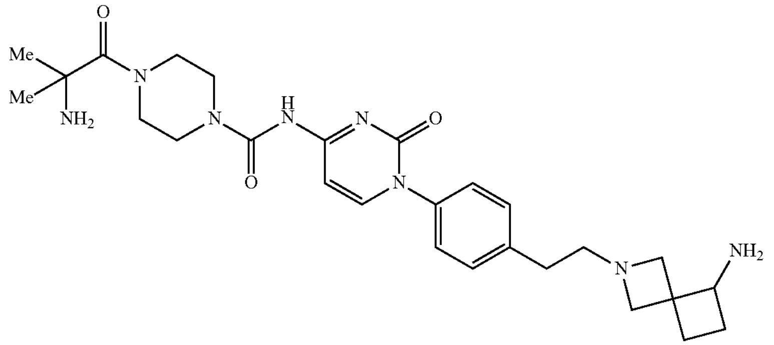 [SMILES: CC(C)(N)C(=O)N1CCN(C(=O)Nc2ccn(-c3ccc(CCN4CC5(CCC5N)C4)cc3)c(=O)n2)CC1] |
| 108 | 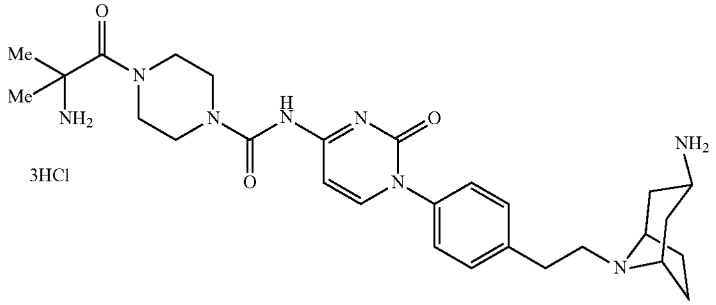 [SMILES: CC(C)(N)C(=O)N1CCN(C(=O)Nc2ccn(-c3ccc(CCN4C5CCC4CC(N)C5)cc3)c(=O)n2)CC1] 3HCl | 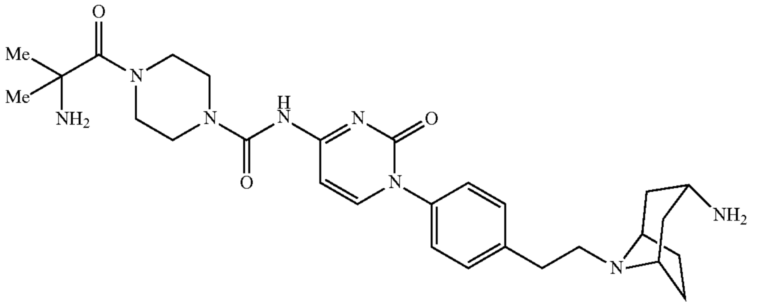 [SMILES: CC(C)(N)C(=O)N1CCN(C(=O)Nc2ccn(-c3ccc(CCN4C5CCC4CC(N)C5)cc3)c(=O)n2)CC1] |
| 109 | 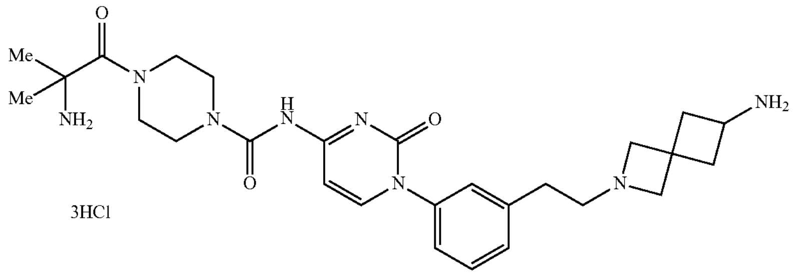 [SMILES: CC(C)(N)C(=O)N1CCN(C(=O)Nc2ccn(-c3cccc(CCN4CC5(CC(N)C5)C4)c3)c(=O)n2)CC1] 3HCl | 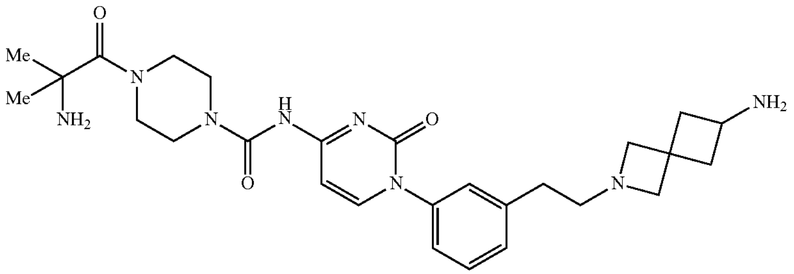 [SMILES: CC(C)(N)C(=O)N1CCN(C(=O)Nc2ccn(-c3cccc(CCN4CC5(CC(N)C5)C4)c3)c(=O)n2)CC1] |

TABLE 8-continued
| No. | Salt Structure | Free Base Structure |
| --- | --- | --- |
| 110 | 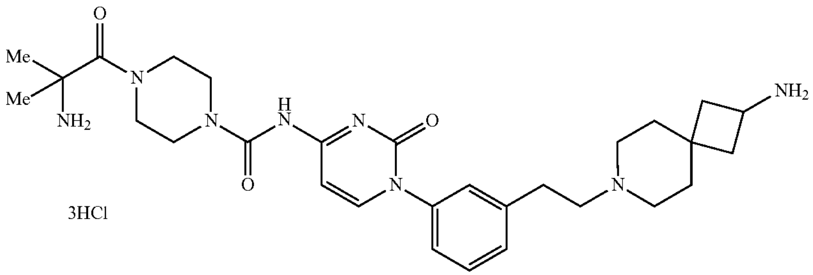 [SMILES: CC(C)(N)C(=O)N1CCN(C(=O)Nc2ccn(-c3cccc(CCN4CCC5(CC4)CC(N)C5)c3)c(=O)n2)CC1] 3HCl | 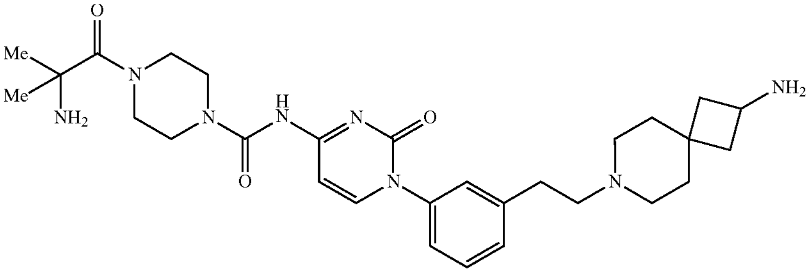 [SMILES: CC(C)(N)C(=O)N1CCN(C(=O)Nc2ccn(-c3cccc(CCN4CCC5(CC4)CC(N)C5)c3)c(=O)n2)CC1] |
| 111 | 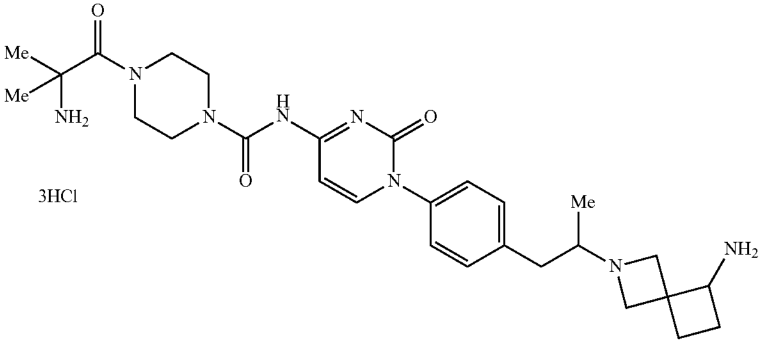 [SMILES: CC(Cc1ccc(-n2ccc(NC(=O)N3CCN(C(=O)C(C)(C)N)CC3)nc2=O)cc1)N1CC2(CCC2N)C1] 3HCl | 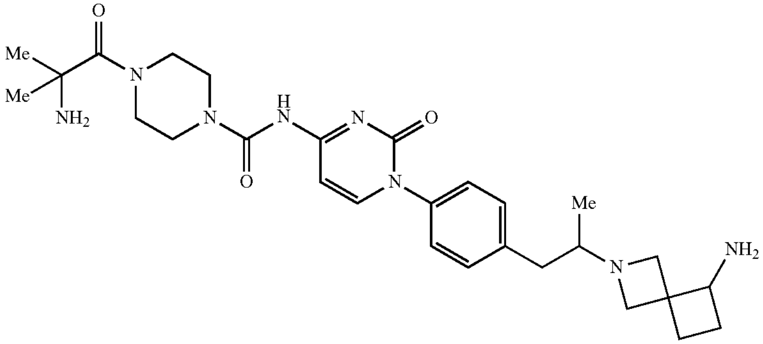 [SMILES: CC(Cc1ccc(-n2ccc(NC(=O)N3CCN(C(=O)C(C)(C)N)CC3)nc2=O)cc1)N1CC2(CCC2N)C1] |
| 112 | 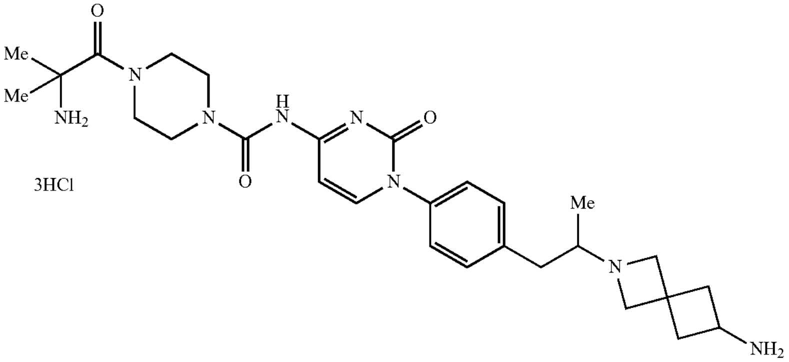 3HCl | 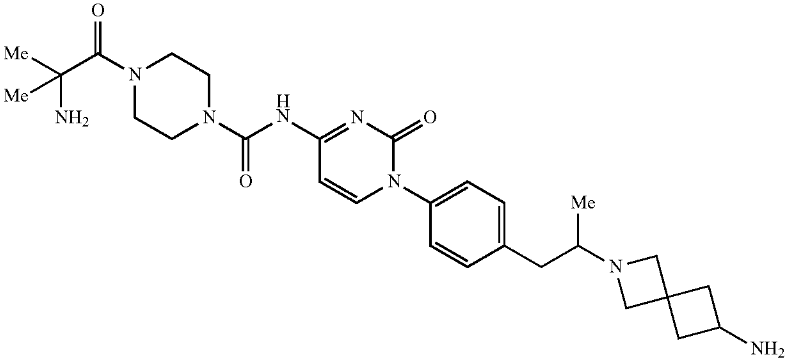 [SMILES: CC(Cc1ccc(-n2ccc(NC(=O)N3CCN(C(=O)C(C)(C)N)CC3)nc2=O)cc1)N1CC2(CC(N)C2)C1] |

TABLE 8-continued
| No. | Salt Structure | Free Base Structure |
|---|---|---|
| 113 | 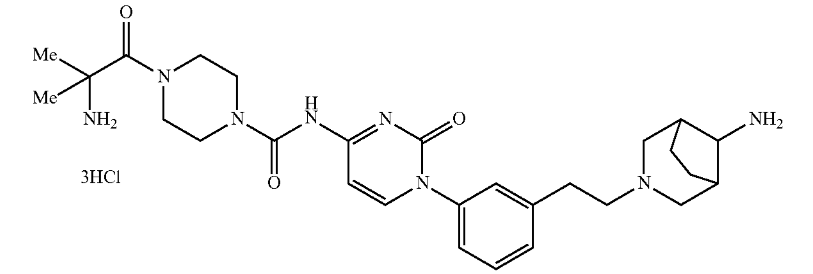 [SMILES: CC(C)(N)C(=O)N1CCN(C(=O)Nc2ccn(-c3cccc(CCN4CC5CCC(C4)C5N)c3)c(=O)n2)CC1] 3HCl | 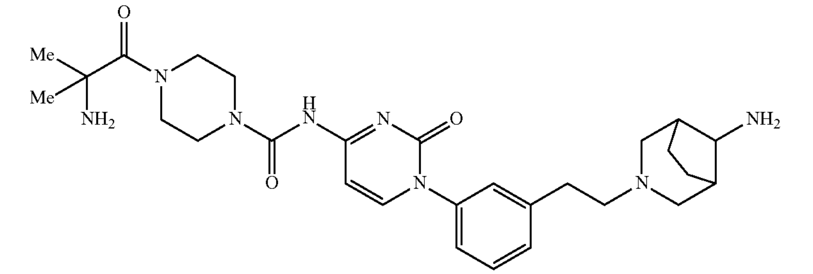 [SMILES: CC(C)(N)C(=O)N1CCN(C(=O)Nc2ccn(-c3cccc(CCN4CC5CCC(C4)C5N)c3)c(=O)n2)CC1] |
| 114 | 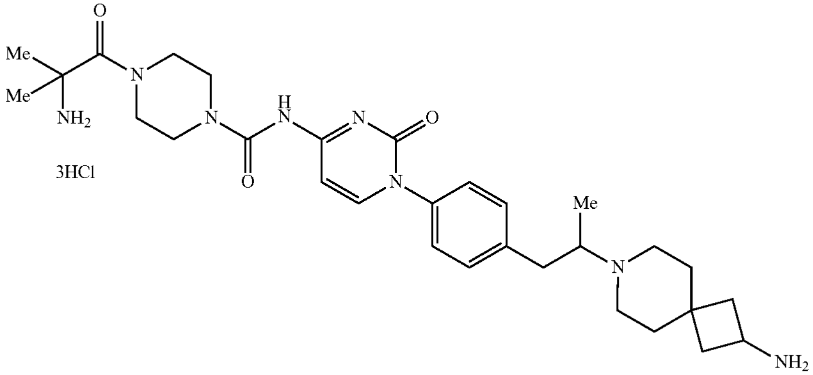 [SMILES: CC(Cc1ccc(-n2ccc(NC(=O)N3CCN(C(=O)C(C)(C)N)CC3)nc2=O)cc1)N1CCC2(CC1)CC(N)C2] 3HCl | 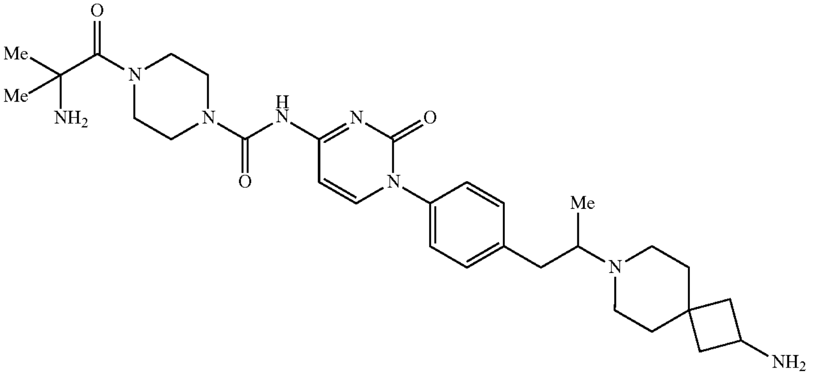 [SMILES: CC(Cc1ccc(-n2ccc(NC(=O)N3CCN(C(=O)C(C)(C)N)CC3)nc2=O)cc1)N1CCC2(CC1)CC(N)C2] |
| 115 | 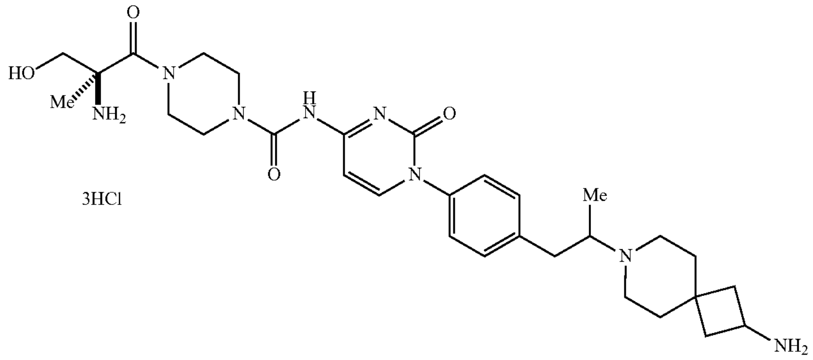 3HCl | 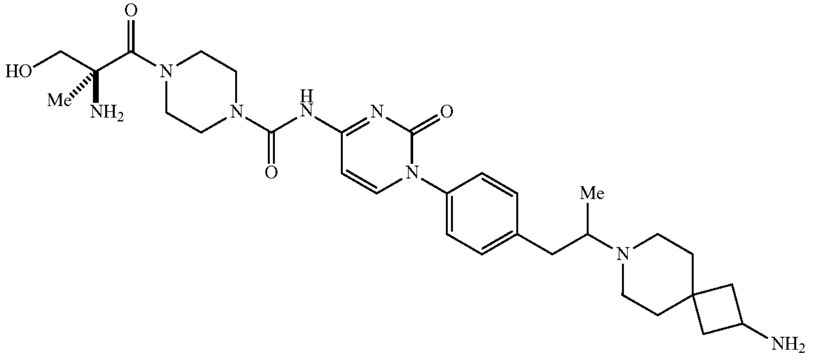 |

TABLE 8-continued
| No. | Salt Structure | Free Base Structure |
|---|---|---|
| 116 | 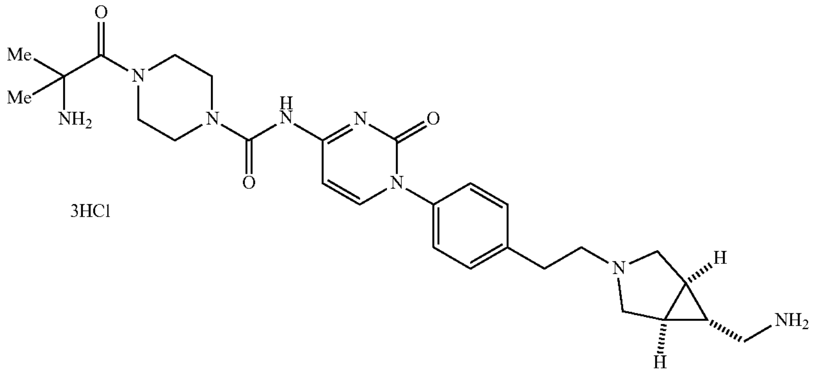 [SMILES: CC(C)(N)C(=O)N1CCN(C(=O)Nc2ccn(-c3ccc(CCN4C[C@@H]5[C@@H](CN)[C@@H]5C4)cc3)c(=O)n2)CC1] 3HCl | 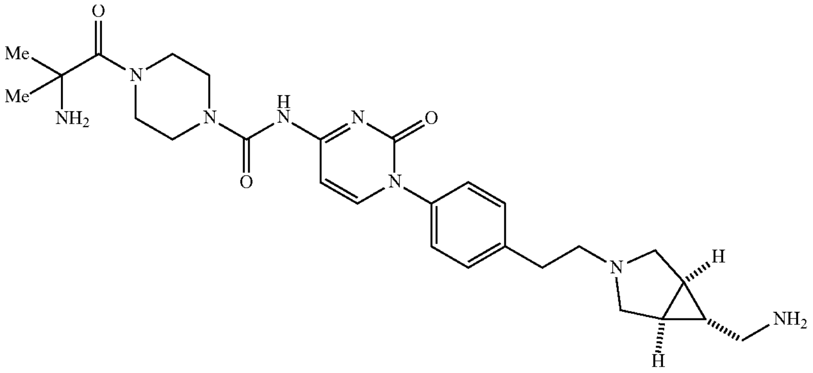 [SMILES: CC(C)(N)C(=O)N1CCN(C(=O)Nc2ccn(-c3ccc(CCN4C[C@@H]5[C@@H](CN)[C@@H]5C4)cc3)c(=O)n2)CC1] |
| 117 | 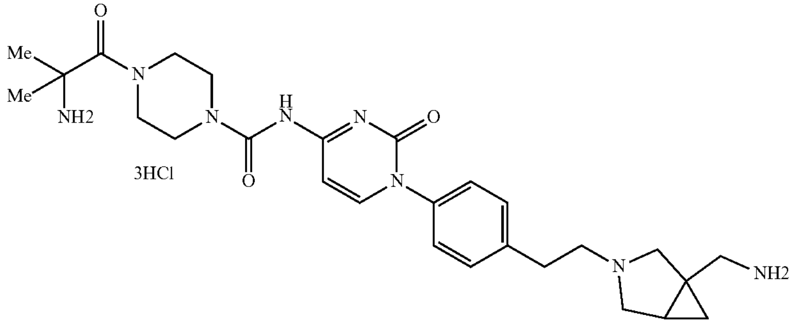 [SMILES: CC(C)(N)C(=O)N1CCN(C(=O)Nc2ccn(-c3ccc(CCN4CC5CC5(CN)C4)cc3)c(=O)n2)CC1] 3HCl | 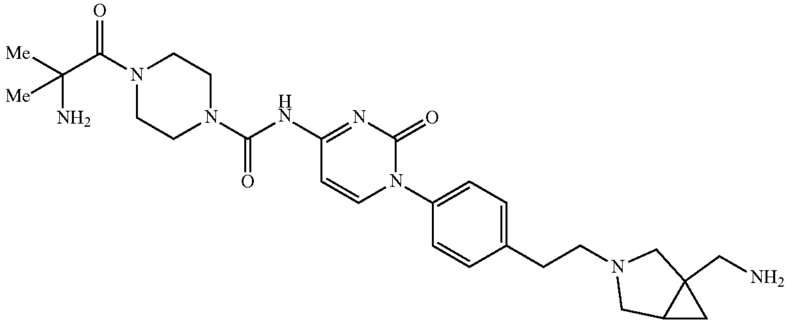 [SMILES: CC(C)(N)C(=O)N1CCN(C(=O)Nc2ccn(-c3ccc(CCN4CC5CC5(CN)C4)cc3)c(=O)n2)CC1] |

TABLE 8-continued
| No. | Salt Structure | Free Base Structure |
|---|---|---|
| 118 | 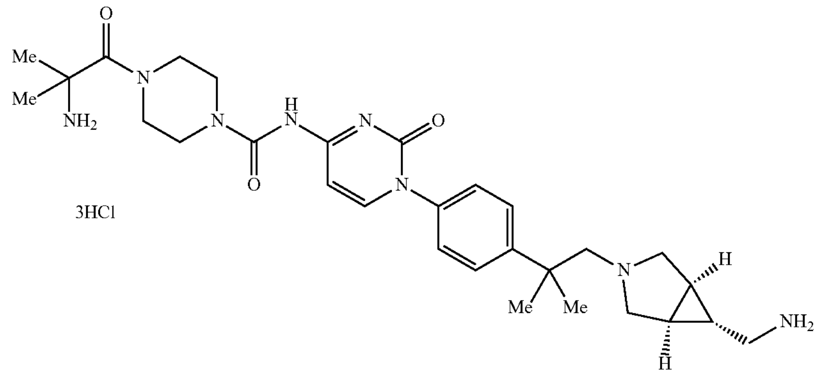 [SMILES: CC(C)(N)C(=O)N1CCN(C(=O)Nc2ccn(-c3ccc(C(C)(C)CN4C[C@@H]5[C@@H](CN)[C@@H]5C4)cc3)c(=O)n2)CC1] 3HCl | 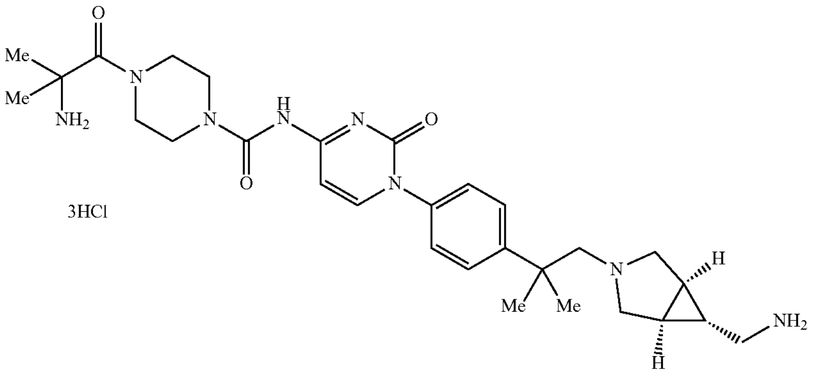 [SMILES: CC(C)(N)C(=O)N1CCN(C(=O)Nc2ccn(-c3ccc(C(C)(C)CN4C[C@@H]5[C@@H](CN)[C@@H]5C4)cc3)c(=O)n2)CC1] 3HCl |
| 119 | 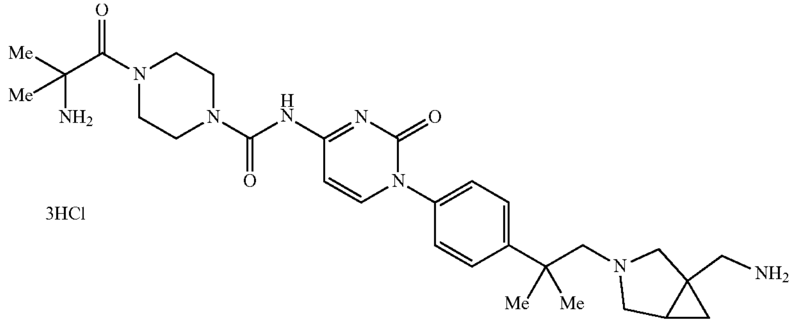 [SMILES: CC(C)(N)C(=O)N1CCN(C(=O)Nc2ccn(-c3ccc(C(C)(C)CN4CC5CC5(CN)C4)cc3)c(=O)n2)CC1] 3HCl | 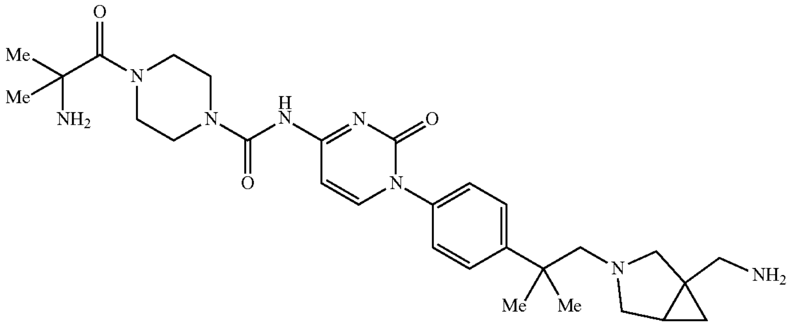 [SMILES: CC(C)(N)C(=O)N1CCN(C(=O)Nc2ccn(-c3ccc(C(C)(C)CN4CC5CC5(CN)C4)cc3)c(=O)n2)CC1] |
| 120 | 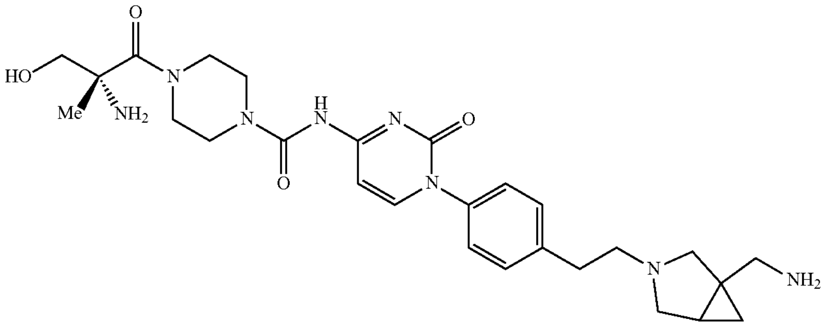 [SMILES: C[C@@](N)(CO)C(=O)N1CCN(C(=O)Nc2ccn(-c3ccc(CCN4CC5CC5(CN)C4)cc3)c(=O)n2)CC1] | 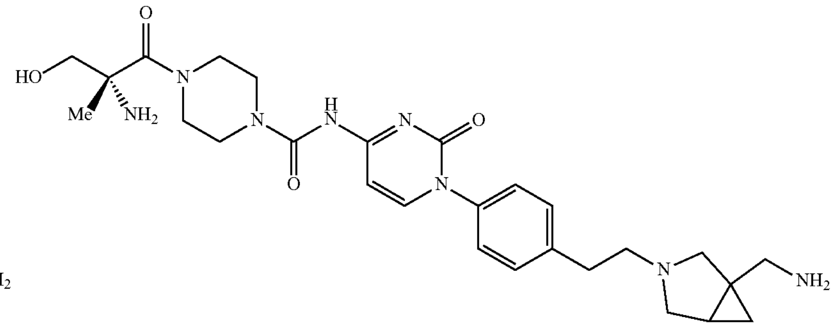 |

TABLE 8-continued
| No. | Salt Structure | Free Base Structure |
|---|---|---|
| 121 | 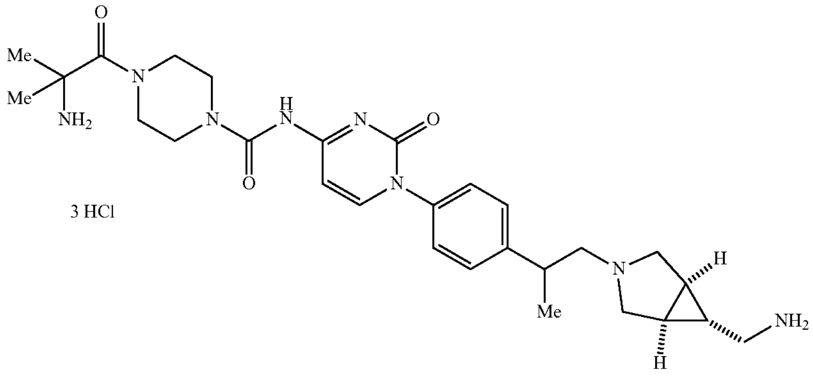 [SMILES: CC(CN1C[C@@H]2[C@@H](CN)[C@@H]2C1)c1ccc(-n2ccc(NC(=O)N3CCN(C(=O)C(C)(C)N)CC3)nc2=O)cc1] 3 HCl | 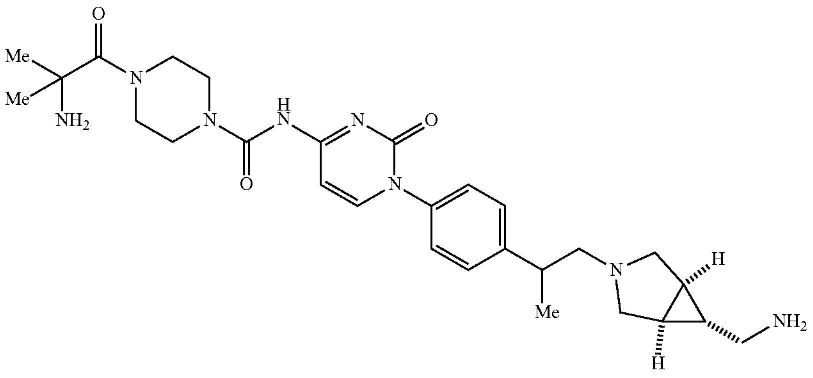 [SMILES: CC(CN1C[C@@H]2[C@@H](CN)[C@@H]2C1)c1ccc(-n2ccc(NC(=O)N3CCN(C(=O)C(C)(C)N)CC3)nc2=O)cc1] |
| 122 | 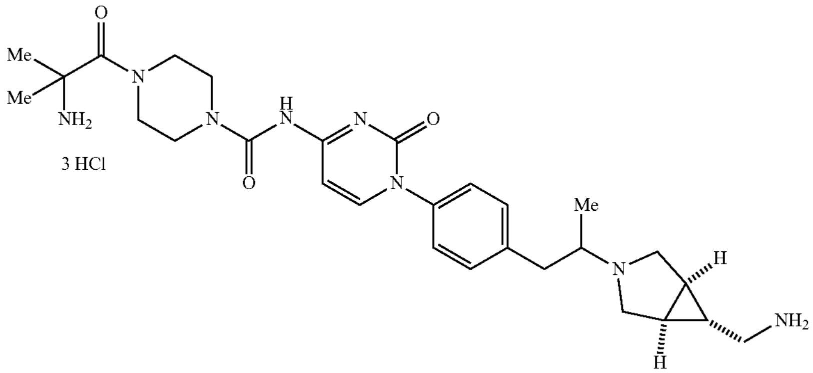 [SMILES: CC(Cc1ccc(-n2ccc(NC(=O)N3CCN(C(=O)C(C)(C)N)CC3)nc2=O)cc1)N1C[C@@H]2[C@@H](CN)[C@@H]2C1] 3 HCl | 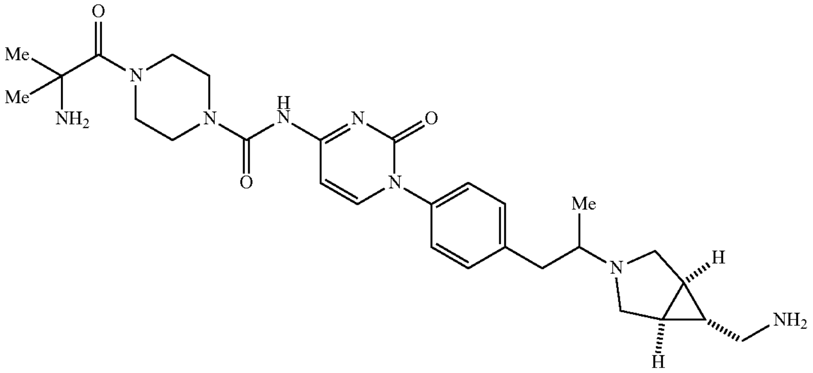 [SMILES: CC(Cc1ccc(-n2ccc(NC(=O)N3CCN(C(=O)C(C)(C)N)CC3)nc2=O)cc1)N1C[C@@H]2[C@@H](CN)[C@@H]2C1] |

TABLE 8-continued
| No. | Salt Structure | Free Base Structure |
|---|---|---|
| 123 | 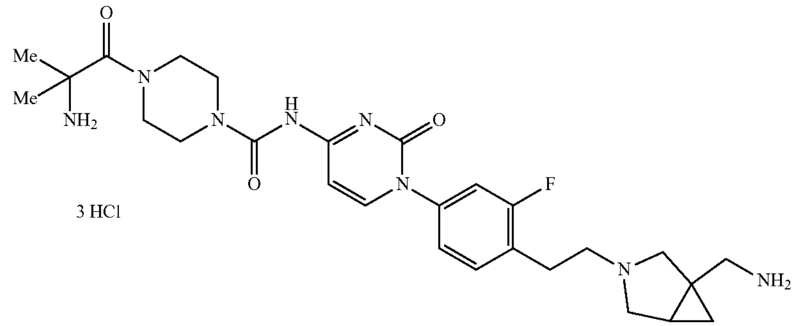 [SMILES: CC(C)(N)C(=O)N1CCN(C(=O)Nc2ccn(-c3ccc(CCN4CC5CC5(CN)C4)c(F)c3)c(=O)n2)CC1] 3 HCl | 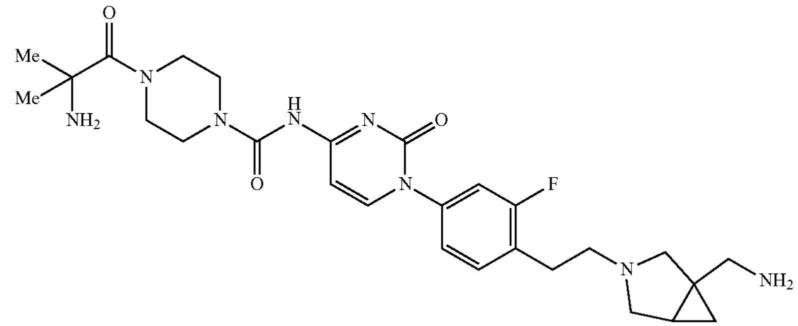 [SMILES: CC(C)(N)C(=O)N1CCN(C(=O)Nc2ccn(-c3ccc(CCN4CC5CC5(CN)C4)c(F)c3)c(=O)n2)CC1] |
| 124 | 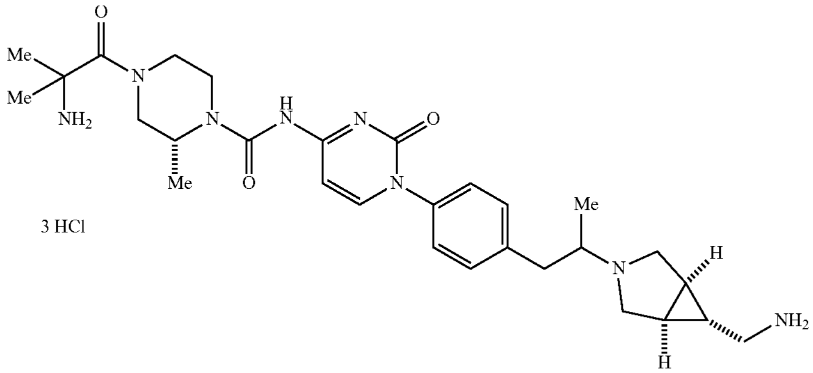 [SMILES: CC(Cc1ccc(-n2ccc(NC(=O)N3CCN(C(=O)C(C)(C)N)C[C@H]3C)nc2=O)cc1)N1C[C@@H]2[C@@H](CN)[C@@H]2C1] 3 HCl | 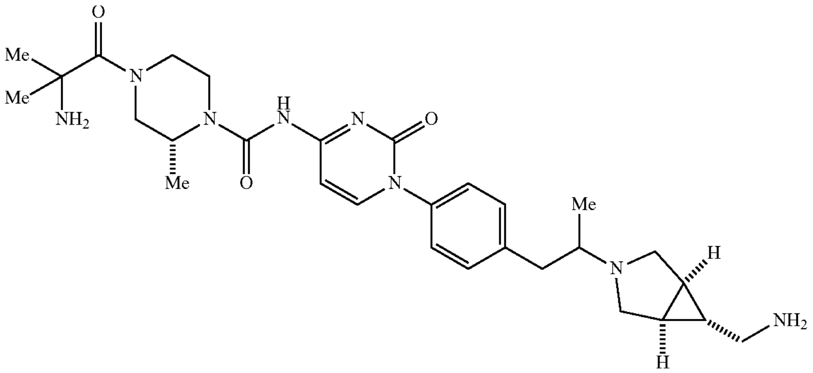 [SMILES: CC(Cc1ccc(-n2ccc(NC(=O)N3CCN(C(=O)C(C)(C)N)C[C@H]3C)nc2=O)cc1)N1C[C@@H]2[C@@H](CN)[C@@H]2C1] |
| 125 | 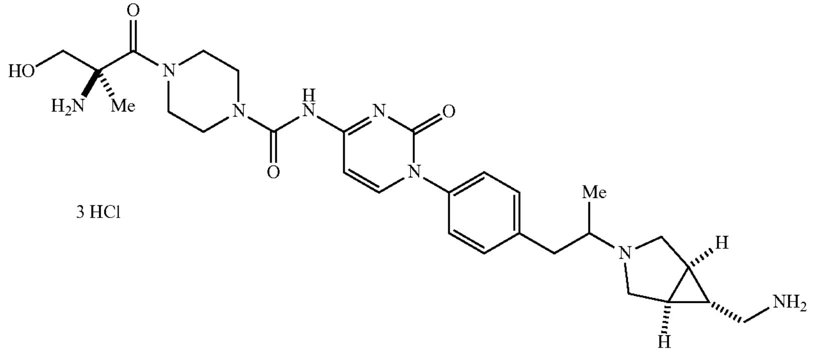 [SMILES: CC(Cc1ccc(-n2ccc(NC(=O)N3CCN(C(=O)[C@@](C)(N)CO)CC3)nc2=O)cc1)N1C[C@@H]2[C@@H](CN)[C@@H]2C1] 3 HCl | 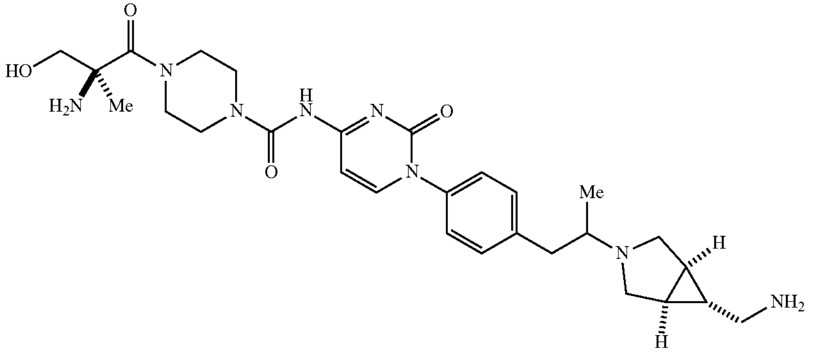 [SMILES: CC(Cc1ccc(-n2ccc(NC(=O)N3CCN(C(=O)[C@@](C)(N)CO)CC3)nc2=O)cc1)N1C[C@@H]2[C@@H](CN)[C@@H]2C1] |

TABLE 8-continued
| No. | Salt Structure | Free Base Structure |
| --- | --- | --- |
| 126 | 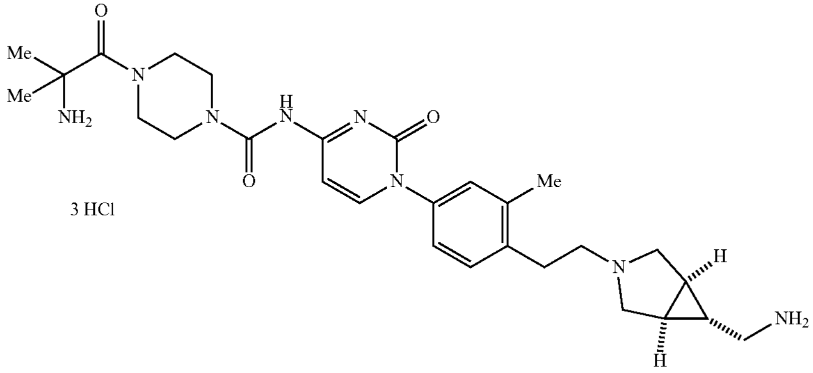 [SMILES: Cc1cc(-n2ccc(NC(=O)N3CCN(C(=O)C(C)(C)N)CC3)nc2=O)ccc1CCN1C[C@@H]2[C@@H](CN)[C@@H]2C1] 3 HCl | 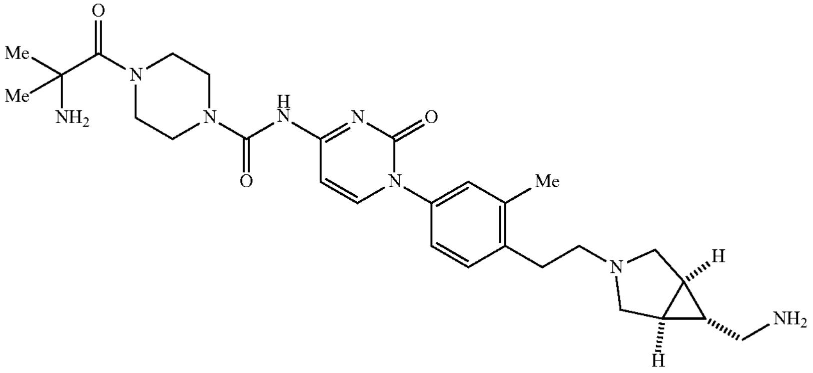 [SMILES: Cc1cc(-n2ccc(NC(=O)N3CCN(C(=O)C(C)(C)N)CC3)nc2=O)ccc1CCN1C[C@@H]2[C@@H](CN)[C@@H]2C1] |
| 127 | 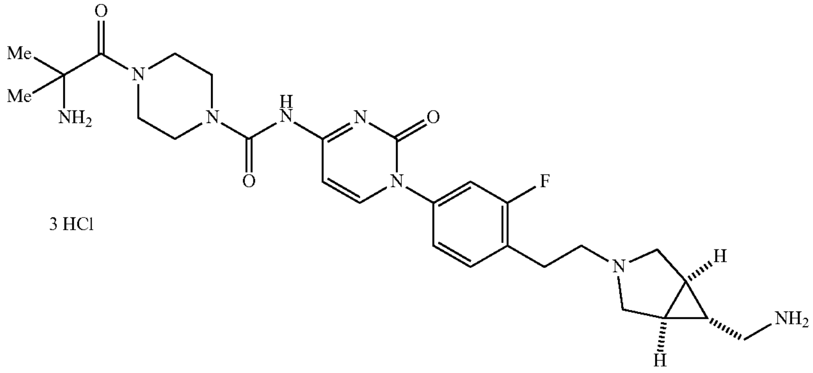 [SMILES: CC(C)(N)C(=O)N1CCN(C(=O)Nc2ccn(-c3ccc(CCN4C[C@@H]5[C@@H](CN)[C@@H]5C4)c(F)c3)c(=O)n2)CC1] 3 HCl | 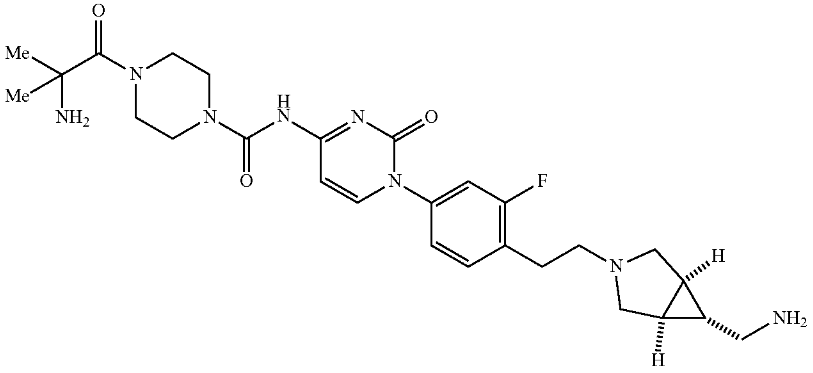 [SMILES: CC(C)(N)C(=O)N1CCN(C(=O)Nc2ccn(-c3ccc(CCN4C[C@@H]5[C@@H](CN)[C@@H]5C4)c(F)c3)c(=O)n2)CC1] |

TABLE 8-continued
| No. | Salt Structure | Free Base Structure |
|---|---|---|
| 128 | 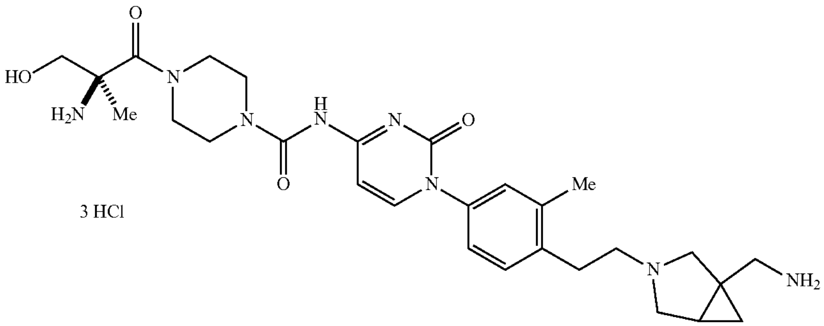 [SMILES: Cc1cc(-n2ccc(NC(=O)N3CCN(C(=O)[C@@](C)(N)CO)CC3)nc2=O)ccc1CCN1CC2CC2(CN)C1] 3 HCl | 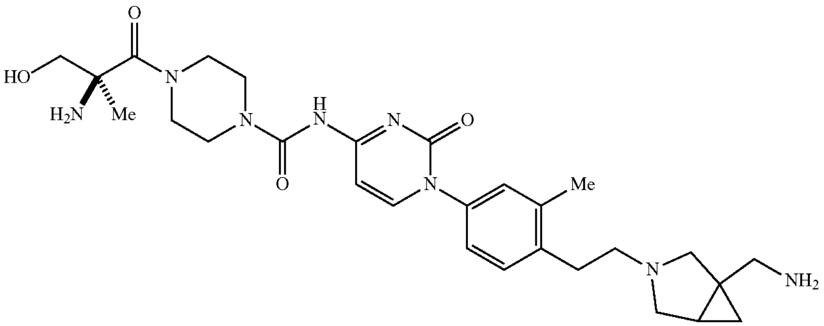 [SMILES: Cc1cc(-n2ccc(NC(=O)N3CCN(C(=O)[C@@](C)(N)CO)CC3)nc2=O)ccc1CCN1CC2CC2(CN)C1] |
| 129 | 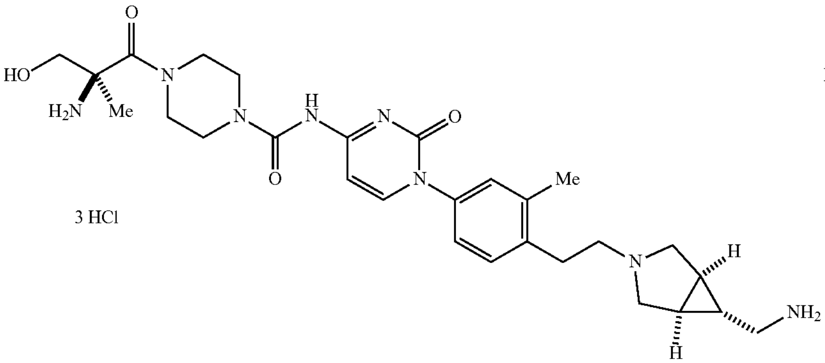 [SMILES: Cc1cc(-n2ccc(NC(=O)N3CCN(C(=O)[C@@](C)(N)CO)CC3)nc2=O)ccc1CCN1C[C@@H]2[C@@H](CN)[C@@H]2C1] 3 HCl | 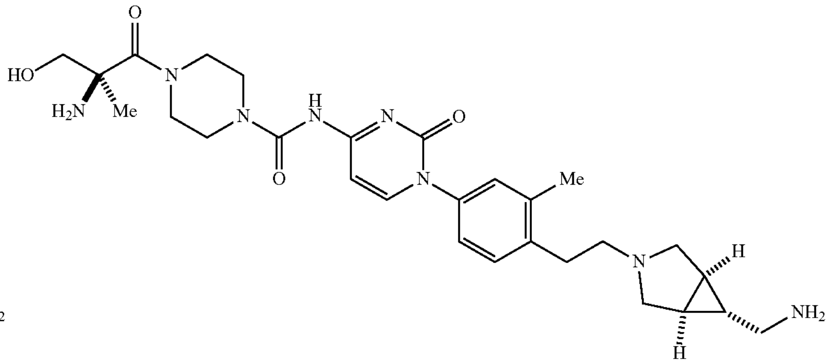 |
| 130 | 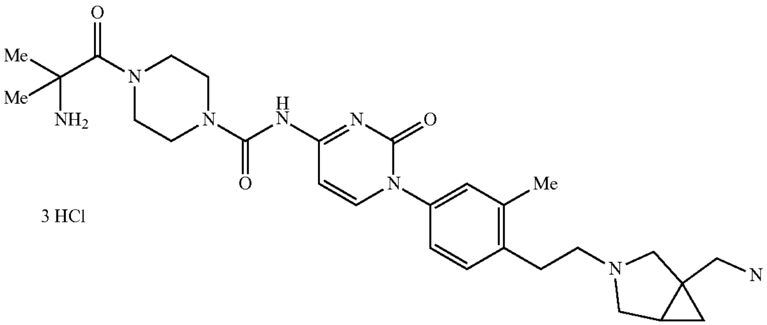 [SMILES: Cc1cc(-n2ccc(NC(=O)N3CCN(C(=O)C(C)(C)N)CC3)nc2=O)ccc1CCN1CC2CC2(CN)C1] 3 HCl | 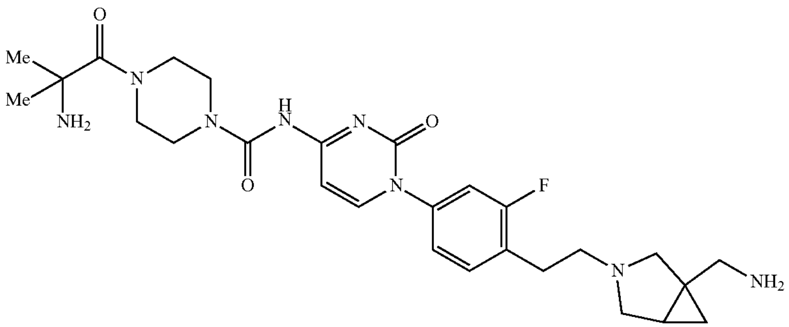 [SMILES: CC(C)(N)C(=O)N1CCN(C(=O)Nc2ccn(-c3ccc(CCN4CC5CC5(CN)C4)c(F)c3)c(=O)n2)CC1] |

TABLE 8-continued
| No. | Salt Structure | Free Base Structure |
|---|---|---|
| 131 | 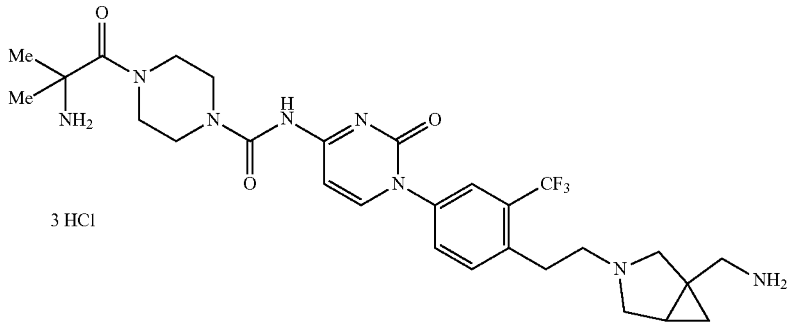 [SMILES: CC(C)(N)C(=O)N1CCN(C(=O)Nc2ccn(-c3ccc(CCN4CC5CC5(CN)C4)c(C(F)(F)F)c3)c(=O)n2)CC1] 3 HCl | 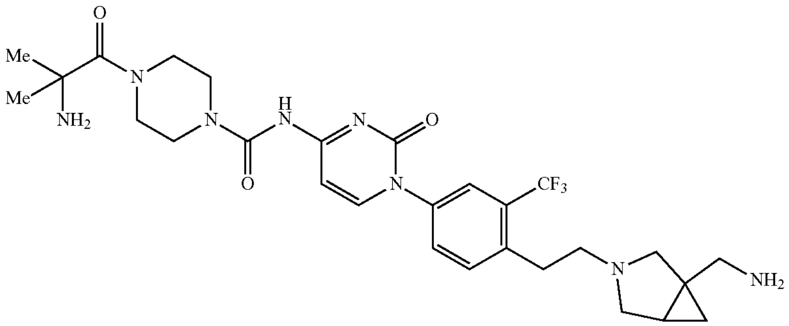 [SMILES: CC(C)(N)C(=O)N1CCN(C(=O)Nc2ccn(-c3ccc(CCN4CC5CC5(CN)C4)c(C(F)(F)F)c3)c(=O)n2)CC1] |
| 132 | 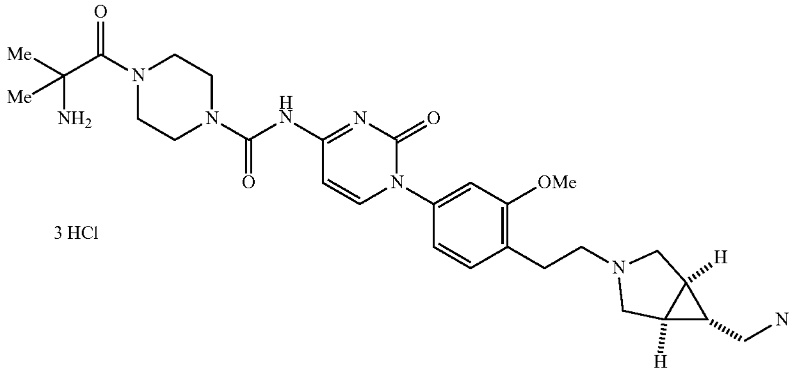 [SMILES: COc1cc(-n2ccc(NC(=O)N3CCN(C(=O)C(C)(C)N)CC3)nc2=O)ccc1CCN1C[C@@H]2[C@@H](CN)[C@@H]2C1] 3 HCl | 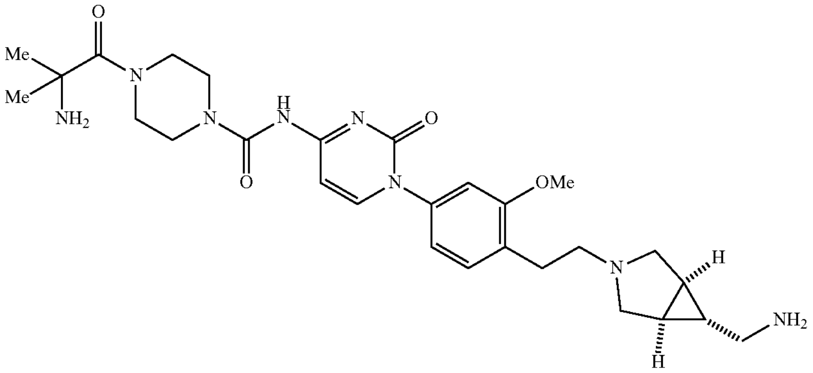 [SMILES: COc1cc(-n2ccc(NC(=O)N3CCN(C(=O)C(C)(C)N)CC3)nc2=O)ccc1CCN1C[C@@H]2[C@@H](CN)[C@@H]2C1] |
| 133 | 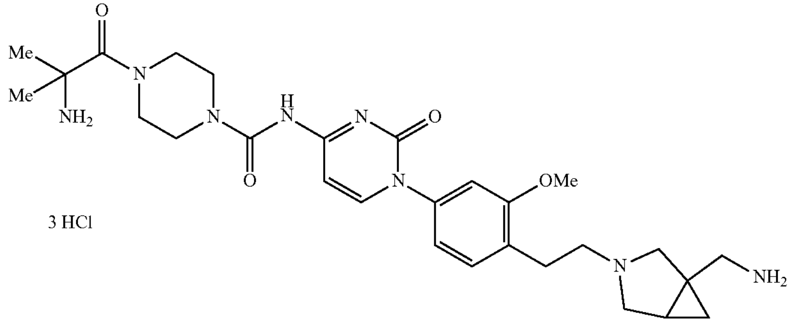 [SMILES: COc1cc(-n2ccc(NC(=O)N3CCN(C(=O)C(C)(C)N)CC3)nc2=O)ccc1CCN1CC2CC2(CN)C1] 3 HCl | 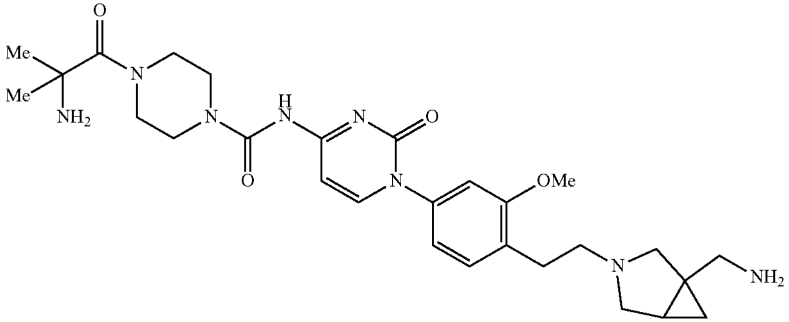 [SMILES: COc1cc(-n2ccc(NC(=O)N3CCN(C(=O)C(C)(C)N)CC3)nc2=O)ccc1CCN1CC2CC2(CN)C1] |

TABLE 8-continued
| No. | Salt Structure | Free Base Structure |
| --- | --- | --- |
| 134 | 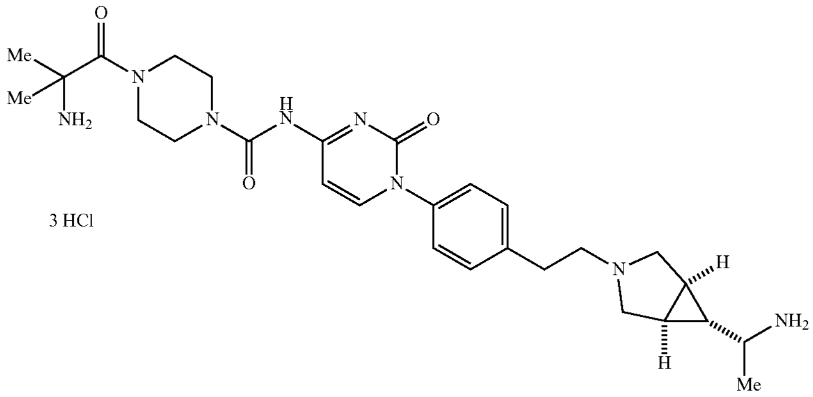 [SMILES: CC(N)[C@H]1[C@@H]2CN(CCc3ccc(-n4ccc(NC(=O)N5CCN(C(=O)C(C)(C)N)CC5)nc4=O)cc3)C[C@@H]21] 3 HCl | 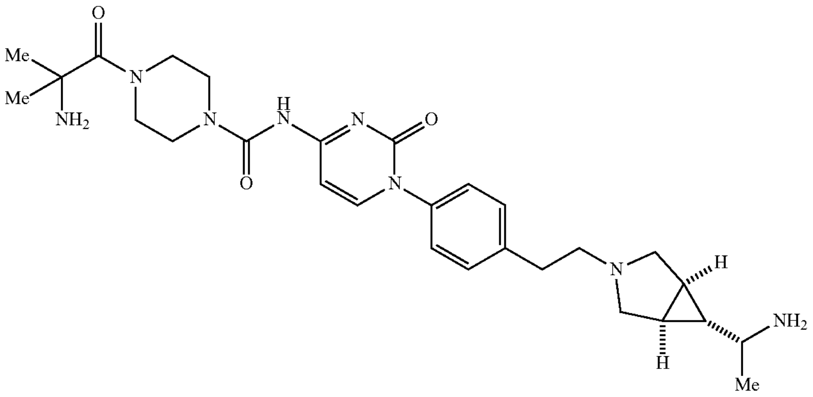 [SMILES: CC(N)[C@H]1[C@@H]2CN(CCc3ccc(-n4ccc(NC(=O)N5CCN(C(=O)C(C)(C)N)CC5)nc4=O)cc3)C[C@@H]21] |
| 135 | 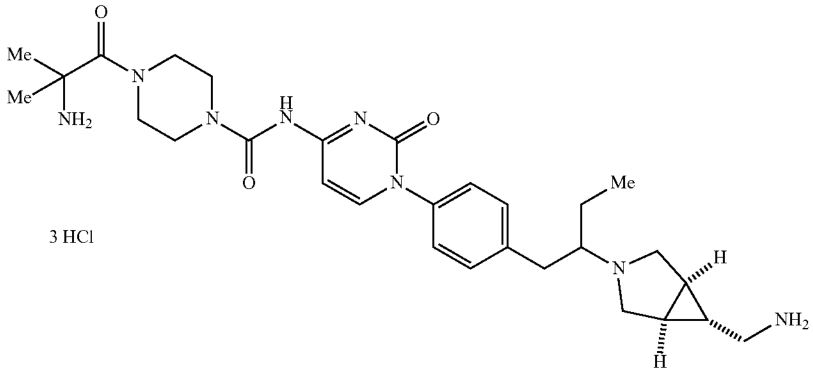 [SMILES: CCC(Cc1ccc(-n2ccc(NC(=O)N3CCN(C(=O)C(C)(C)N)CC3)nc2=O)cc1)N1C[C@@H]2[C@@H](CN)[C@@H]2C1] 3 HCl | 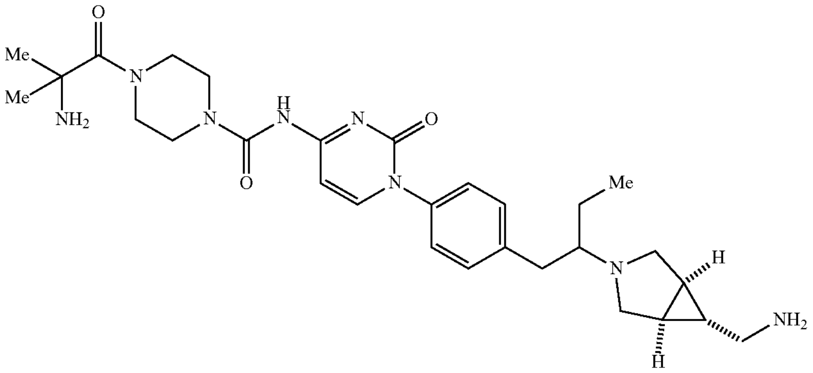 [SMILES: CCC(Cc1ccc(-n2ccc(NC(=O)N3CCN(C(=O)C(C)(C)N)CC3)nc2=O)cc1)N1C[C@@H]2[C@@H](CN)[C@@H]2C1] |

TABLE 8-continued
| No. | Salt Structure | Free Base Structure |
|---|---|---|
| 136 | 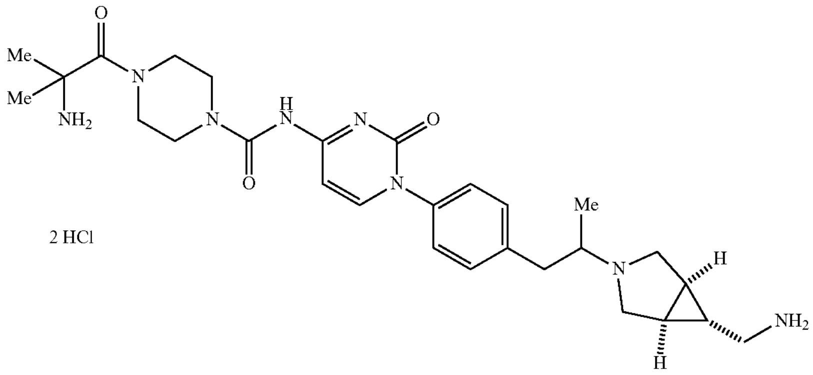 [SMILES: CC(Cc1ccc(-n2ccc(NC(=O)N3CCN(C(=O)C(C)(C)N)CC3)nc2=O)cc1)N1C[C@@H]2[C@@H](CN)[C@@H]2C1] 2 HCl | 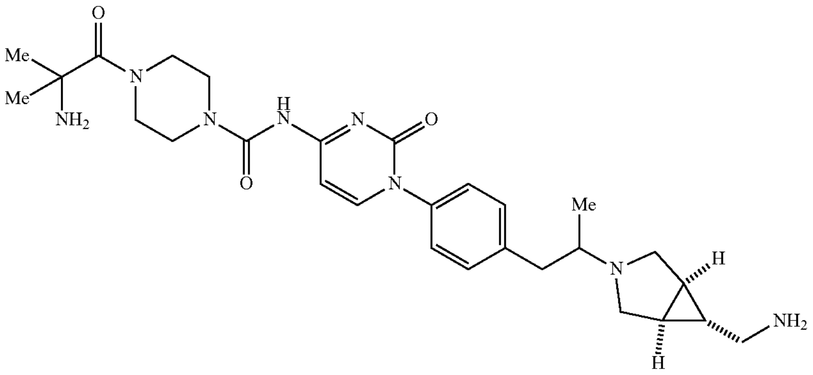 [SMILES: CC(Cc1ccc(-n2ccc(NC(=O)N3CCN(C(=O)C(C)(C)N)CC3)nc2=O)cc1)N1C[C@@H]2[C@@H](CN)[C@@H]2C1] |
| 137 | 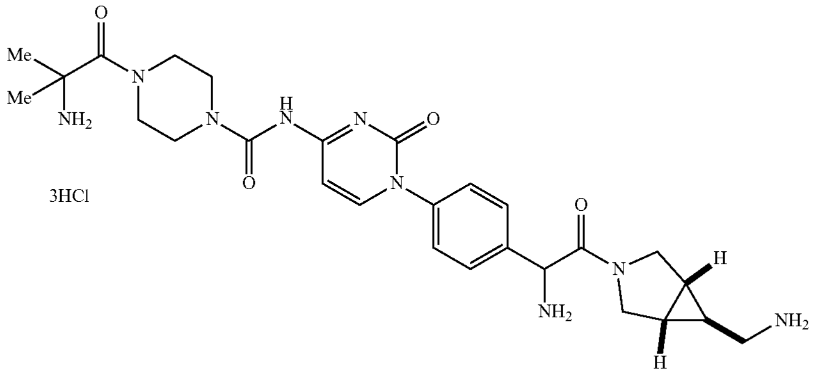 [SMILES: CC(C)(N)C(=O)N1CCN(C(=O)Nc2ccn(-c3ccc(C(N)C(=O)N4C[C@@H]5[C@@H](CN)[C@@H]5C4)cc3)c(=O)n2)CC1] 3HCl | 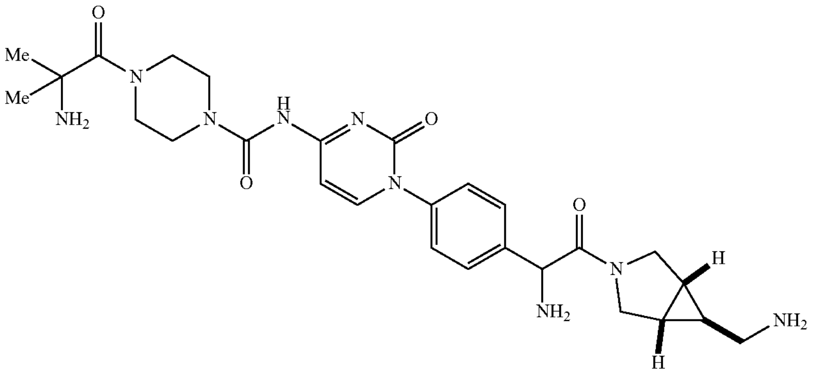 [SMILES: CC(C)(N)C(=O)N1CCN(C(=O)Nc2ccn(-c3ccc(C(N)C(=O)N4C[C@@H]5[C@@H](CN)[C@@H]5C4)cc3)c(=O)n2)CC1] |

TABLE 8-continued
| No. | Salt Structure | Free Base Structure |
|---|---|---|
| 138 | 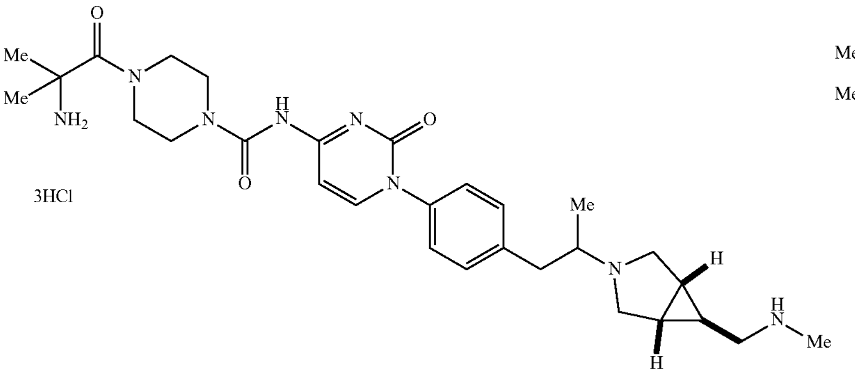 3HCl | 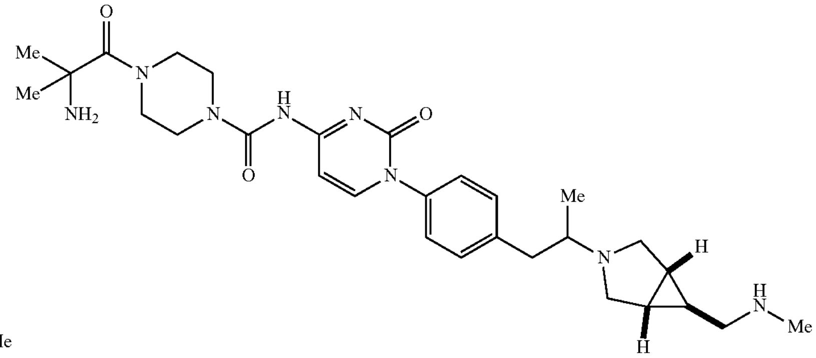 |
| 139 | 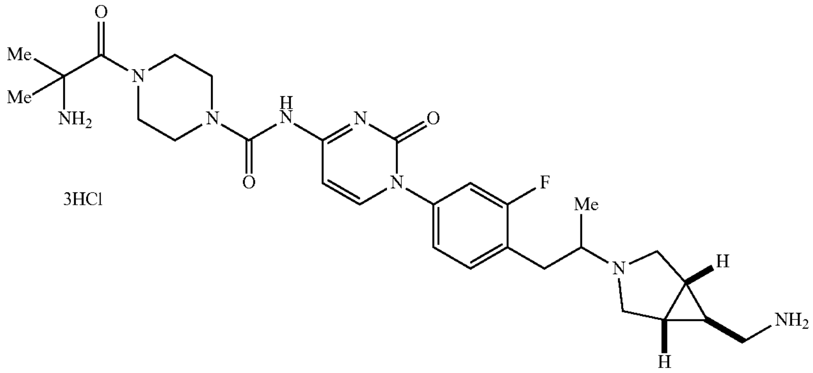 [SMILES: CC(Cc1ccc(-n2ccc(NC(=O)N3CCN(C(=O)C(C)(C)N)CC3)nc2=O)cc1F)N1C[C@@H]2[C@@H](CN)[C@@H]2C1] 3HCl | 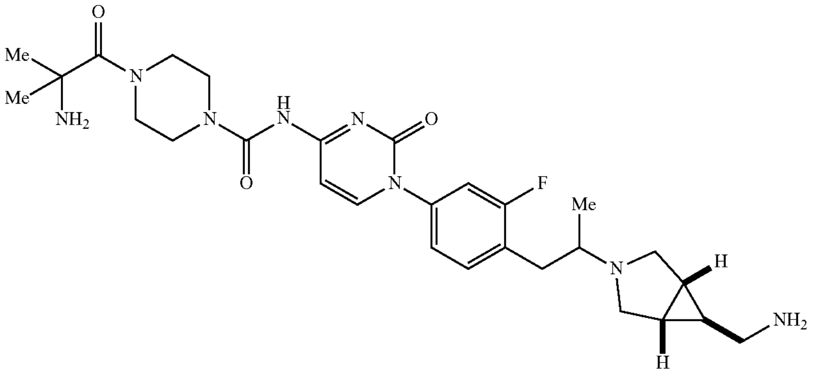 [SMILES: CC(Cc1ccc(-n2ccc(NC(=O)N3CCN(C(=O)C(C)(C)N)CC3)nc2=O)cc1F)N1C[C@@H]2[C@@H](CN)[C@@H]2C1] |

TABLE 8-continued
| No. | Salt Structure | Free Base Structure |
|---|---|---|
| 140 | 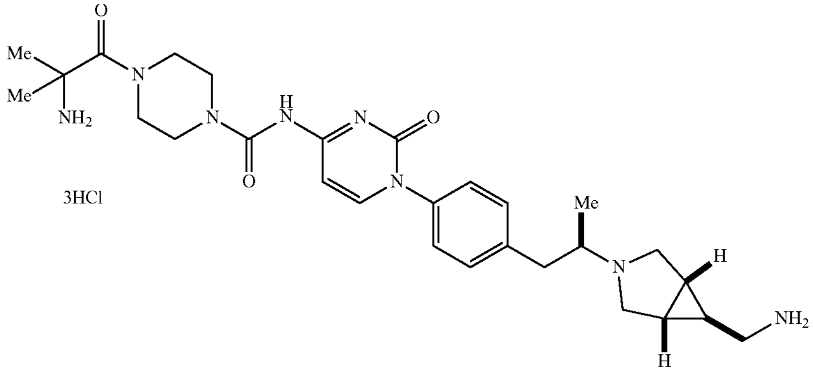 [SMILES: C[C@H](Cc1ccc(-n2ccc(NC(=O)N3CCN(C(=O)C(C)(C)N)CC3)nc2=O)cc1)N1C[C@@H]2[C@@H](CN)[C@@H]2C1] 3HCl | 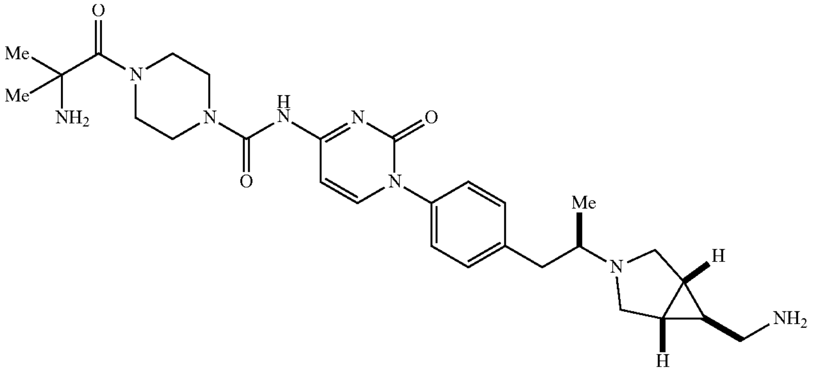 [SMILES: C[C@H](Cc1ccc(-n2ccc(NC(=O)N3CCN(C(=O)C(C)(C)N)CC3)nc2=O)cc1)N1C[C@@H]2[C@@H](CN)[C@@H]2C1] |
| 141 | 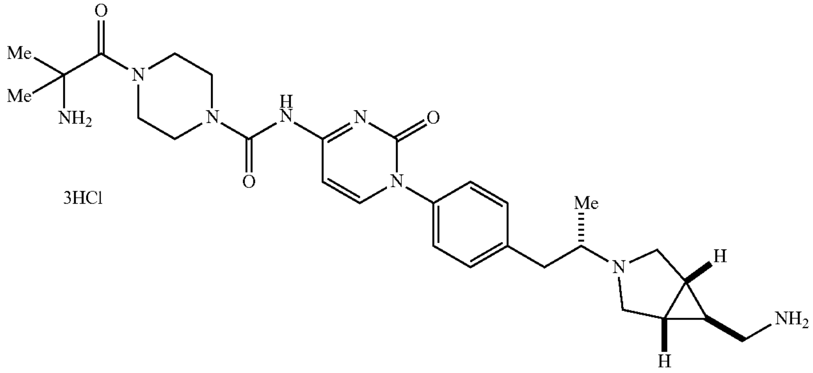 [SMILES: C[C@@H](Cc1ccc(-n2ccc(NC(=O)N3CCN(C(=O)C(C)(C)N)CC3)nc2=O)cc1)N1C[C@@H]2[C@@H](CN)[C@@H]2C1] 3HCl | 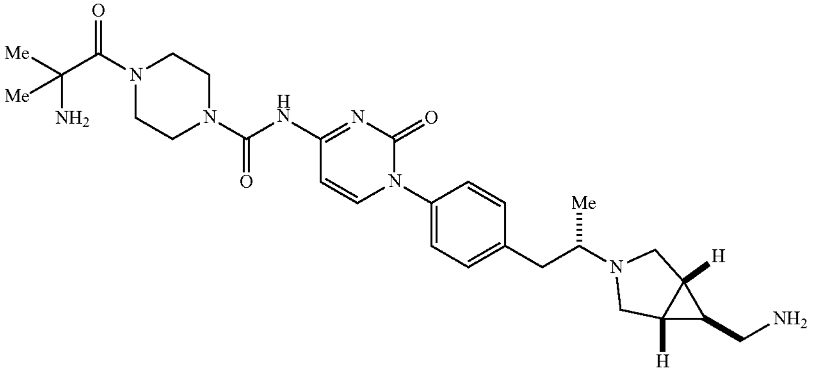 [SMILES: C[C@@H](Cc1ccc(-n2ccc(NC(=O)N3CCN(C(=O)C(C)(C)N)CC3)nc2=O)cc1)N1C[C@@H]2[C@@H](CN)[C@@H]2C1] |
| 142 | 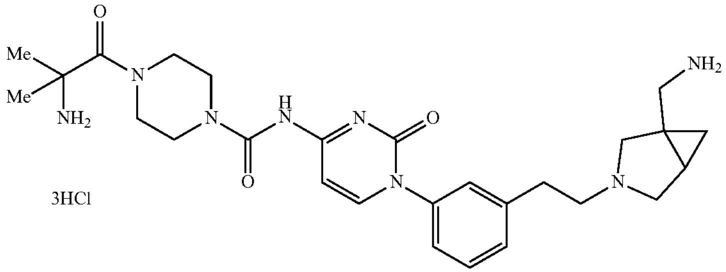 [SMILES: CC(C)(N)C(=O)N1CCN(C(=O)Nc2ccn(-c3cccc(CCN4CC5CC5(CN)C4)c3)c(=O)n2)CC1] 3HCl | 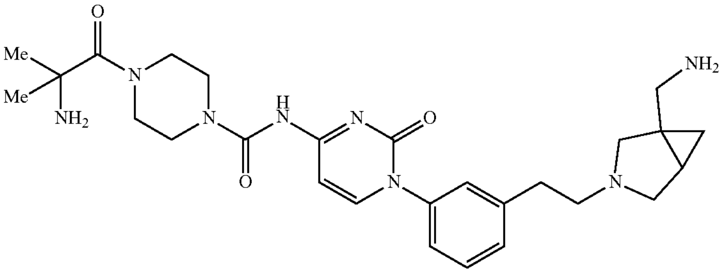 [SMILES: CC(C)(N)C(=O)N1CCN(C(=O)Nc2ccn(-c3cccc(CCN4CC5CC5(CN)C4)c3)c(=O)n2)CC1] |

TABLE 8-continued
| No. | Salt Structure | Free Base Structure |
|---|---|---|
| 143 | 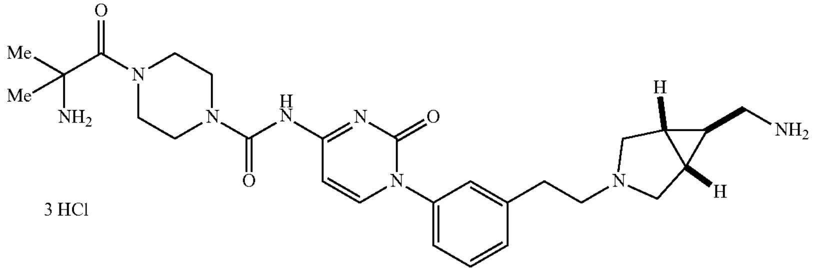 [SMILES: CC(C)(N)C(=O)N1CCN(C(=O)Nc2ccn(-c3cccc(CCN4C[C@@H]5[C@@H](CN)[C@@H]5C4)c3)c(=O)n2)CC1] 3 HCl | 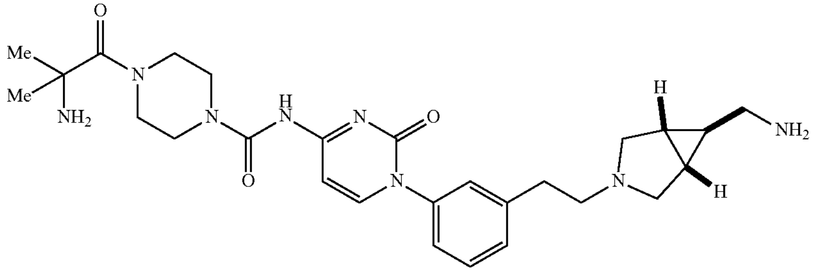 [SMILES: CC(C)(N)C(=O)N1CCN(C(=O)Nc2ccn(-c3cccc(CCN4C[C@@H]5[C@@H](CN)[C@@H]5C4)c3)c(=O)n2)CC1] |
| 144 | 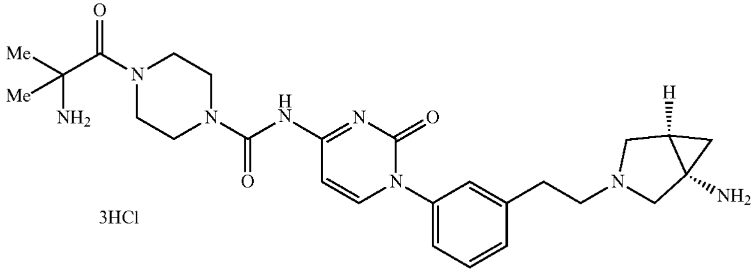 [SMILES: CC(C)(N)C(=O)N1CCN(C(=O)Nc2ccn(-c3cccc(CCN4C[C@H]5C[C@@]5(N)C4)c3)c(=O)n2)CC1] 3HCl | 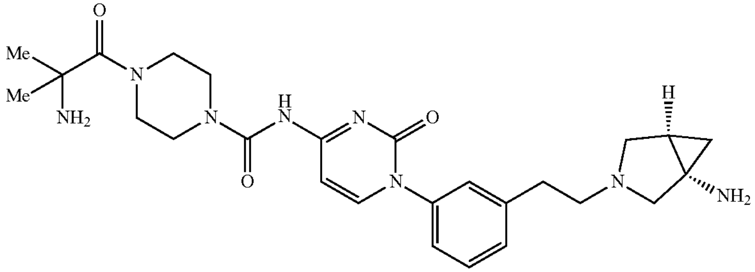 [SMILES: CC(C)(N)C(=O)N1CCN(C(=O)Nc2ccn(-c3cccc(CCN4C[C@H]5C[C@@]5(N)C4)c3)c(=O)n2)CC1] |
| 145 | 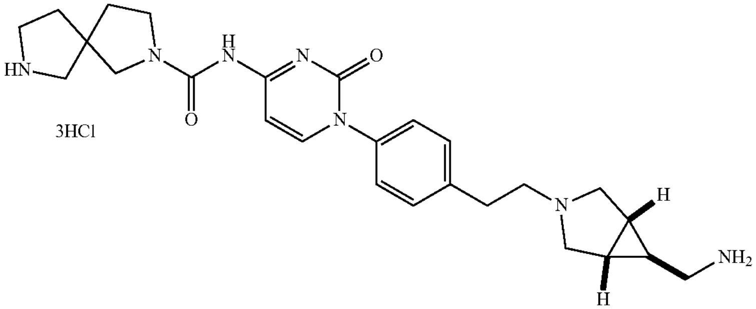 [SMILES: NC[C@@H]1[C@H]2CN(CCc3ccc(-n4ccc(NC(=O)N5CCC6(CCNC6)C5)nc4=O)cc3)C[C@@H]12] 3HCl | 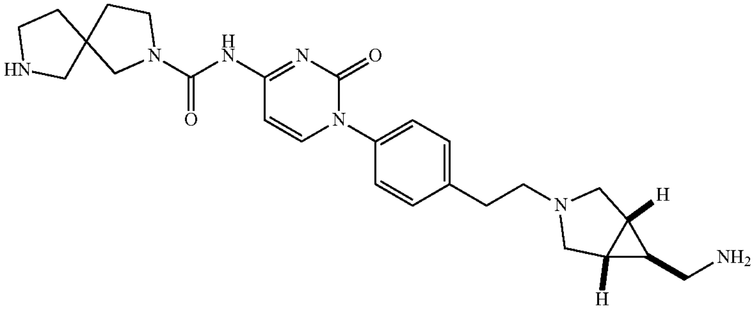 [SMILES: NC[C@@H]1[C@H]2CN(CCc3ccc(-n4ccc(NC(=O)N5CCC6(CCNC6)C5)nc4=O)cc3)C[C@@H]12] |

TABLE 8-continued
| No. | Salt Structure | Free Base Structure |
|---|---|---|
| 146 | 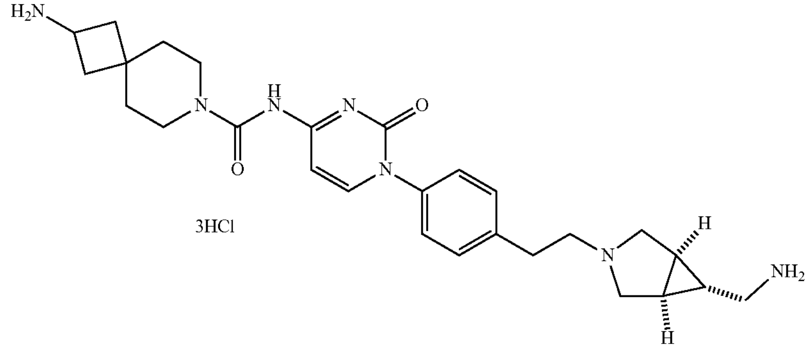 [SMILES: NC[C@@H]1[C@H]2CN(CCc3ccc(-n4ccc(NC(=O)N5CCC6(CC5)CC(N)C6)nc4=O)cc3)C[C@@H]12] 3HCl | 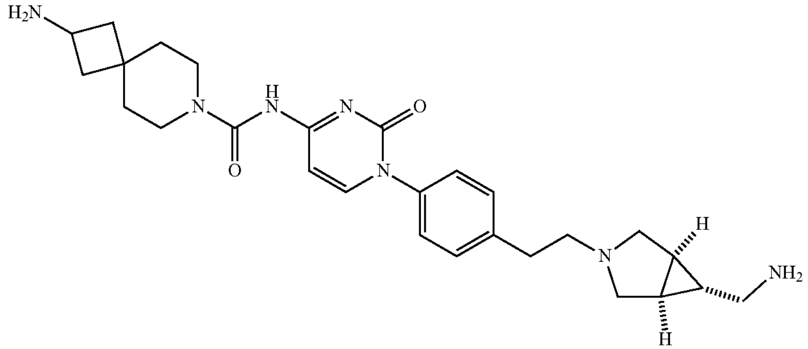 [SMILES: NC[C@@H]1[C@H]2CN(CCc3ccc(-n4ccc(NC(=O)N5CCC6(CC5)CC(N)C6)nc4=O)cc3)C[C@@H]12] |
| 147 | 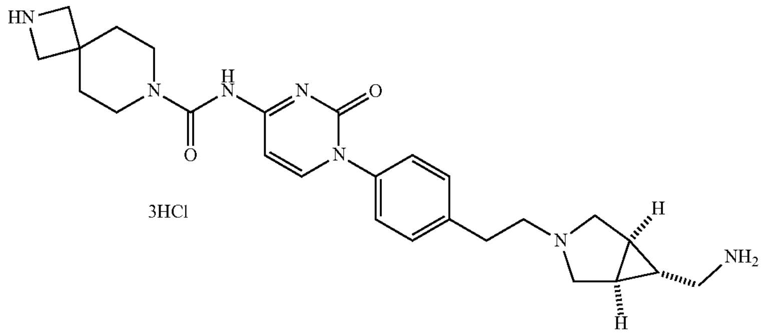 [SMILES: NC[C@@H]1[C@H]2CN(CCc3ccc(-n4ccc(NC(=O)N5CCC6(CC5)CNC6)nc4=O)cc3)C[C@@H]12] 3HCl | 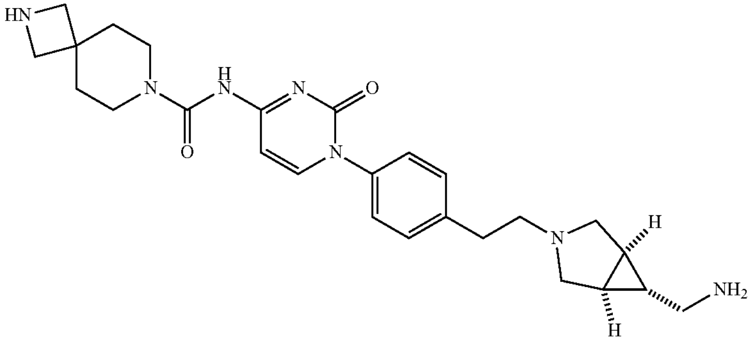 [SMILES: NC[C@@H]1[C@H]2CN(CCc3ccc(-n4ccc(NC(=O)N5CCC6(CC5)CNC6)nc4=O)cc3)C[C@@H]12] |
| 148 | 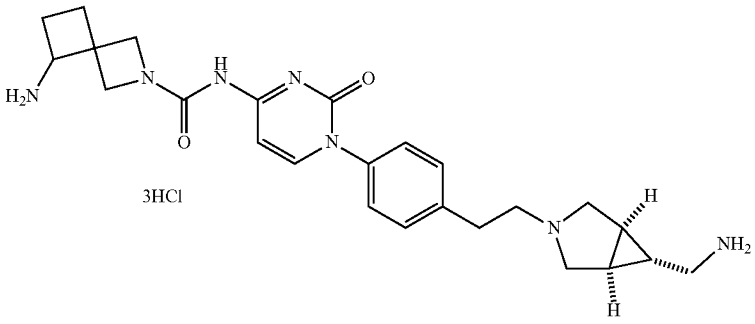 [SMILES: NC[C@@H]1[C@H]2CN(CCc3ccc(-n4ccc(NC(=O)N5CC6(CCC6N)C5)nc4=O)cc3)C[C@@H]12] 3HCl | 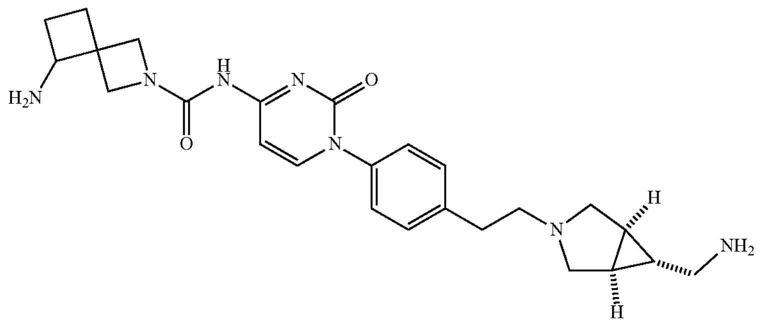 [SMILES: NC[C@@H]1[C@H]2CN(CCc3ccc(-n4ccc(NC(=O)N5CC6(CCC6N)C5)nc4=O)cc3)C[C@@H]12] |

TABLE 8-continued
| No. | Salt Structure | Free Base Structure |
|---|---|---|
| 149 | 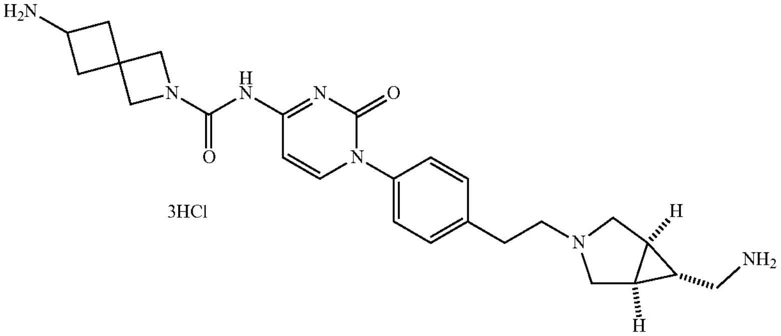 [SMILES: NC[C@@H]1[C@H]2CN(CCc3ccc(-n4ccc(NC(=O)N5CC6(CC(N)C6)C5)nc4=O)cc3)C[C@@H]12] 3HCl | 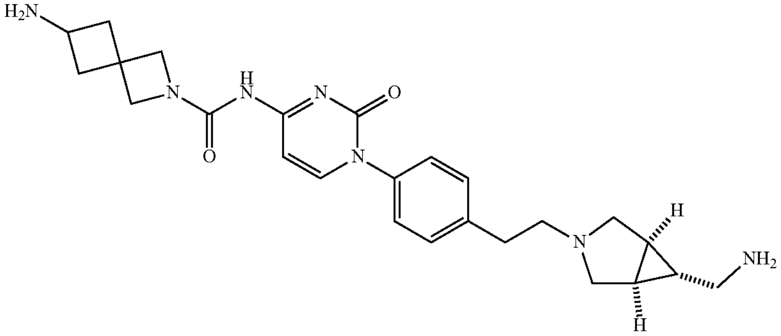 [SMILES: NC[C@@H]1[C@H]2CN(CCc3ccc(-n4ccc(NC(=O)N5CC6(CC(N)C6)C5)nc4=O)cc3)C[C@@H]12] |
| 150 | 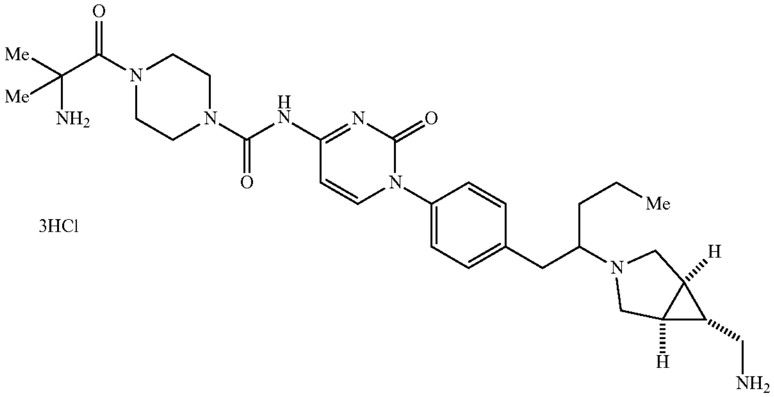 [SMILES: CCCC(Cc1ccc(-n2ccc(NC(=O)N3CCN(C(=O)C(C)(C)N)CC3)nc2=O)cc1)N1C[C@@H]2[C@@H](CN)[C@@H]2C1] 3HCl | 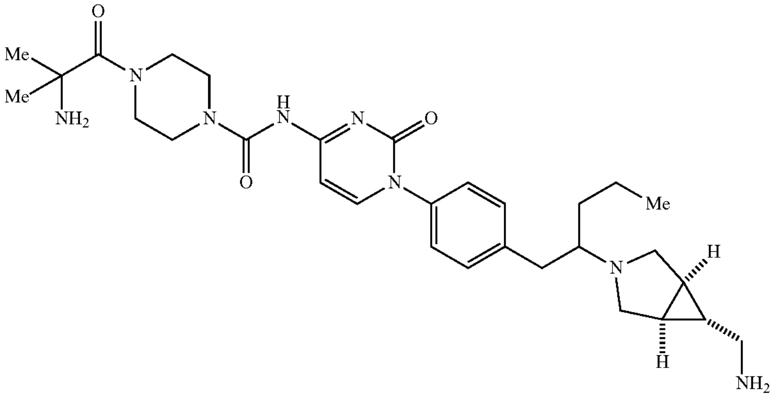 [SMILES: CCCC(Cc1ccc(-n2ccc(NC(=O)N3CCN(C(=O)C(C)(C)N)CC3)nc2=O)cc1)N1C[C@@H]2[C@@H](CN)[C@@H]2C1] |

TABLE 8-continued
| No. | Salt Structure | Free Base Structure |
|---|---|---|
| 151 | 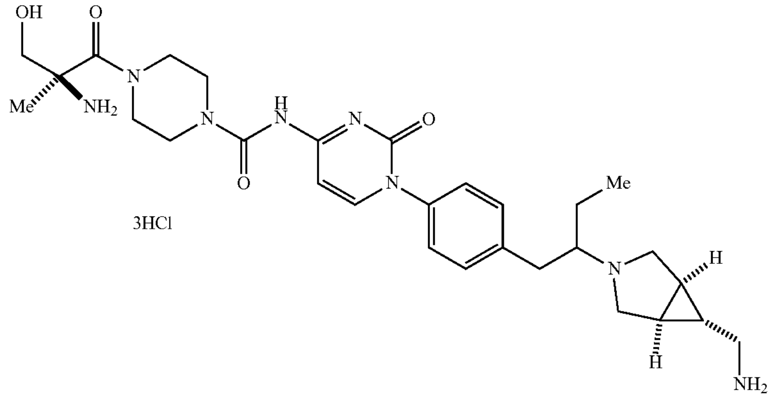 [SMILES: CCC(Cc1ccc(-n2ccc(NC(=O)N3CCN(C(=O)[C@@](C)(N)CO)CC3)nc2=O)cc1)N1C[C@@H]2[C@@H](CN)[C@@H]2C1] 3HCl | 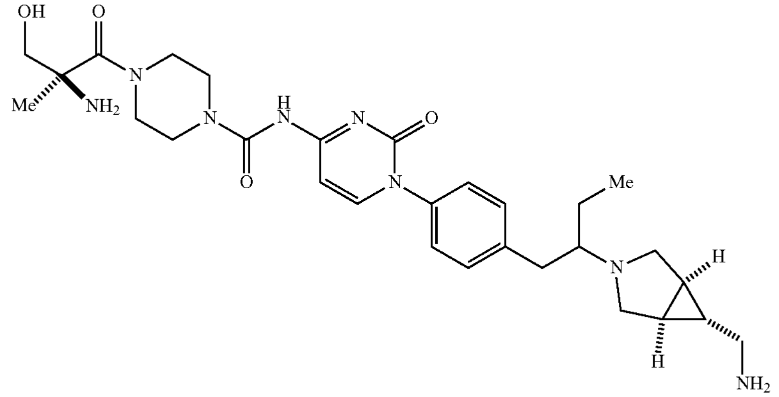 [SMILES: CCC(Cc1ccc(-n2ccc(NC(=O)N3CCN(C(=O)[C@@](C)(N)CO)CC3)nc2=O)cc1)N1C[C@@H]2[C@@H](CN)[C@@H]2C1] |
| 152 | 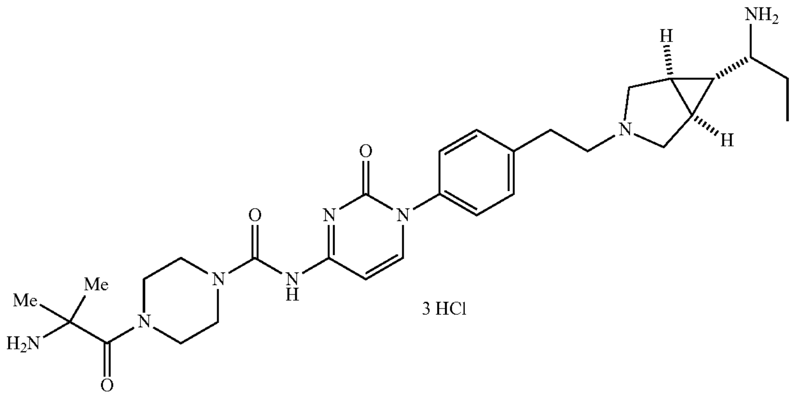 [SMILES: CC[C@@H](N)C1[C@H]2CN(CCc3ccc(-n4ccc(NC(=O)N5CCN(C(=O)C(C)(C)N)CC5)nc4=O)cc3)C[C@@H]12] 3 HCl | 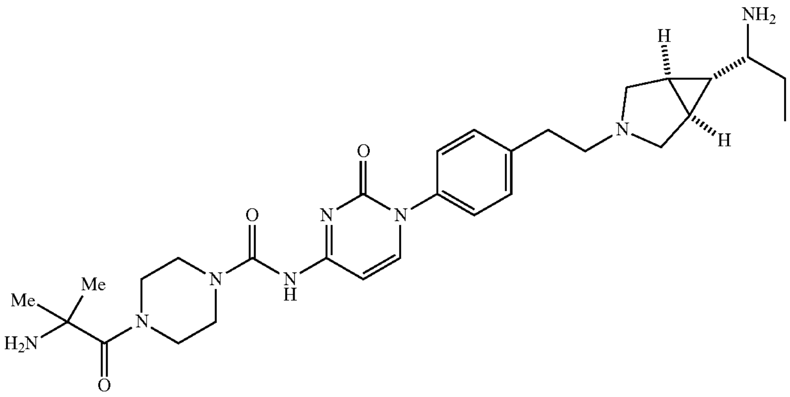 [SMILES: CC[C@@H](N)C1[C@H]2CN(CCc3ccc(-n4ccc(NC(=O)N5CCN(C(=O)C(C)(C)N)CC5)nc4=O)cc3)C[C@@H]12] |

TABLE 8-continued
| No. | Salt Structure | Free Base Structure |
|---|---|---|
| 153 | 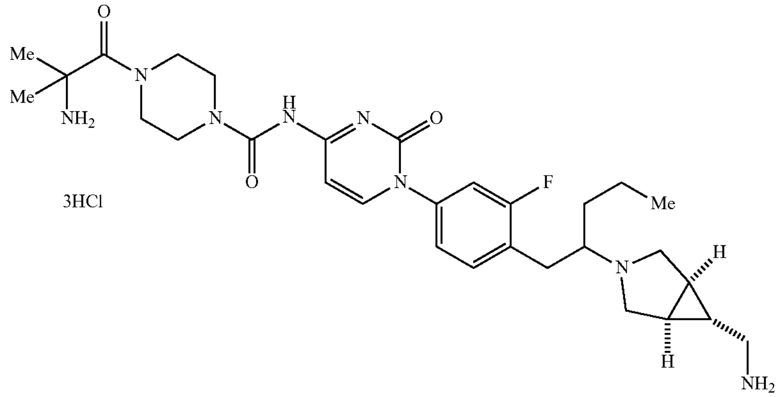 [SMILES: CCCC(Cc1ccc(-n2ccc(NC(=O)N3CCN(C(=O)C(C)(C)N)CC3)nc2=O)cc1F)N1C[C@@H]2[C@@H](CN)[C@@H]2C1] 3HCl | 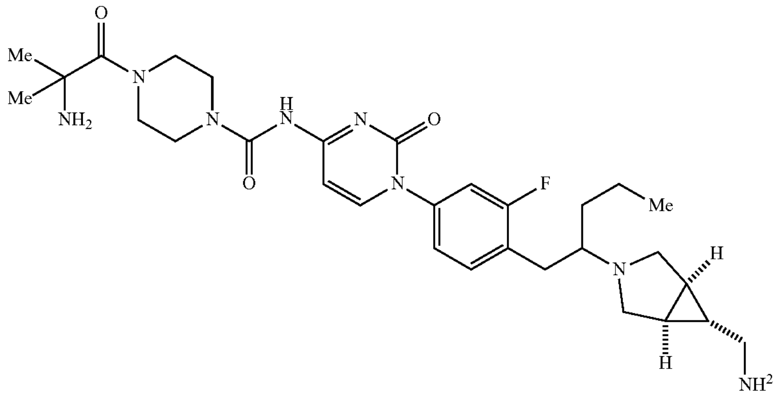 [SMILES: CCCC(Cc1ccc(-n2ccc(NC(=O)N3CCN(C(=O)C(C)(C)N)CC3)nc2=O)cc1F)N1C[C@@H]2[C@@H](CN)[C@@H]2C1] |
| 154 | 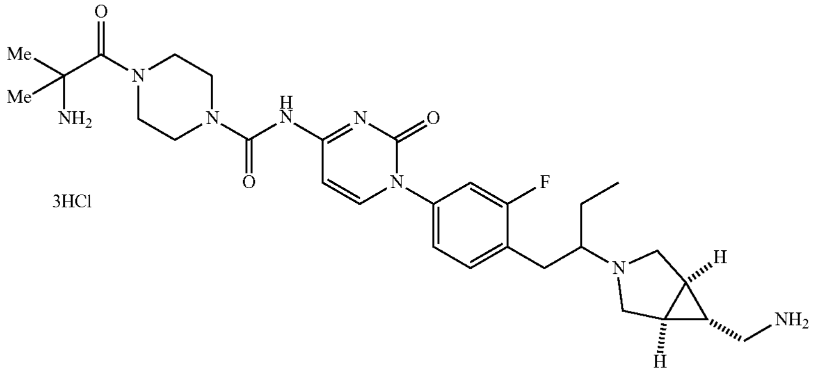 [SMILES: CCC(Cc1ccc(-n2ccc(NC(=O)N3CCN(C(=O)C(C)(C)N)CC3)nc2=O)cc1F)N1C[C@@H]2[C@@H](CN)[C@@H]2C1] 3HCl | 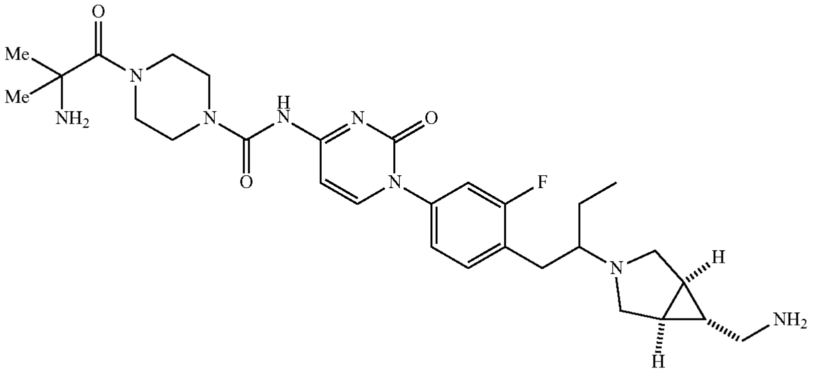 [SMILES: CCC(Cc1ccc(-n2ccc(NC(=O)N3CCN(C(=O)C(C)(C)N)CC3)nc2=O)cc1F)N1C[C@@H]2[C@@H](CN)[C@@H]2C1] |

TABLE 8-continued
| No. | Salt Structure | Free Base Structure |
|---|---|---|
| 155 | 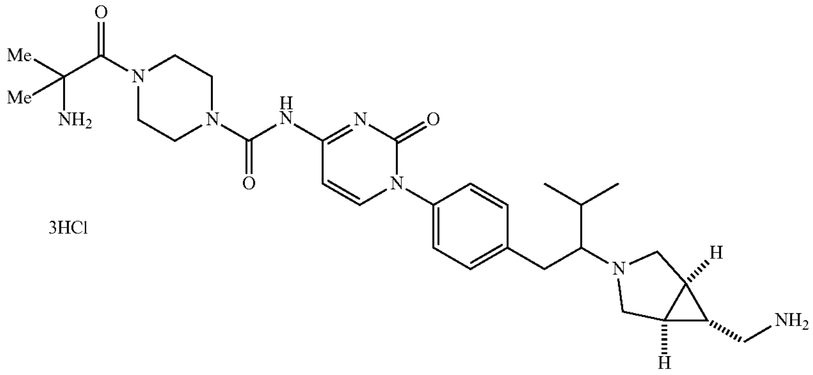 [SMILES: CC(C)C(Cc1ccc(-n2ccc(NC(=O)N3CCN(C(=O)C(C)(C)N)CC3)nc2=O)cc1)N1C[C@@H]2[C@@H](CN)[C@@H]2C1] 3HCl | 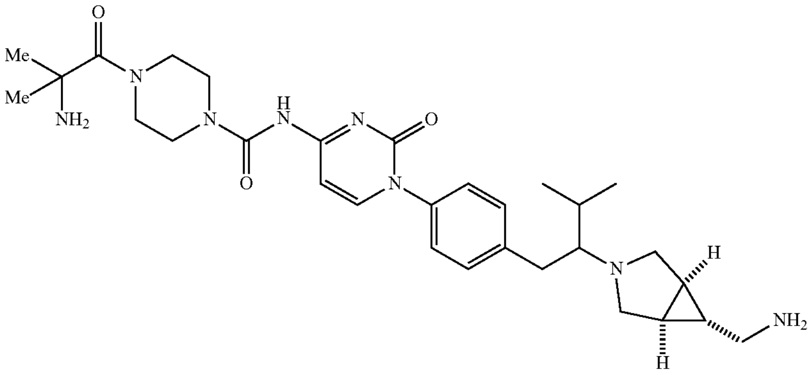 [SMILES: CC(C)C(Cc1ccc(-n2ccc(NC(=O)N3CCN(C(=O)C(C)(C)N)CC3)nc2=O)cc1)N1C[C@@H]2[C@@H](CN)[C@@H]2C1] |
| 156 | 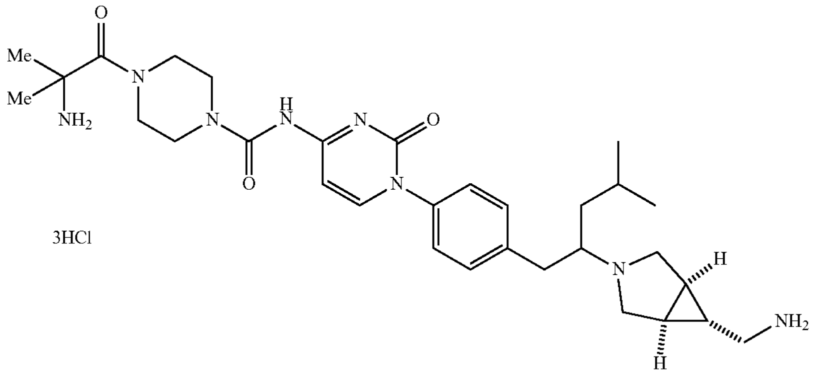 [SMILES: CC(C)CC(Cc1ccc(-n2ccc(NC(=O)N3CCN(C(=O)C(C)(C)N)CC3)nc2=O)cc1)N1C[C@@H]2[C@@H](CN)[C@@H]2C1] 3HCl | 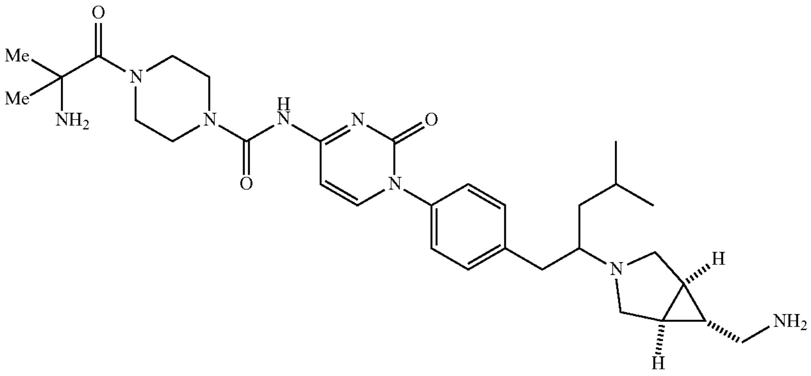 [SMILES: CC(C)CC(Cc1ccc(-n2ccc(NC(=O)N3CCN(C(=O)C(C)(C)N)CC3)nc2=O)cc1)N1C[C@@H]2[C@@H](CN)[C@@H]2C1] |

TABLE 8-continued
| No. | Salt Structure | Free Base Structure |
|---|---|---|
| 157 | 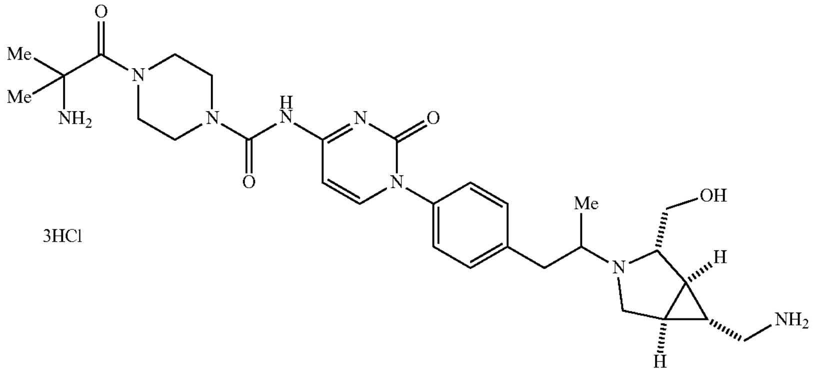 [SMILES: CC(Cc1ccc(-n2ccc(NC(=O)N3CCN(C(=O)C(C)(C)N)CC3)nc2=O)cc1)N1C[C@@H]2[C@@H](CN)[C@@H]2[C@H]1CO] 3HCl | 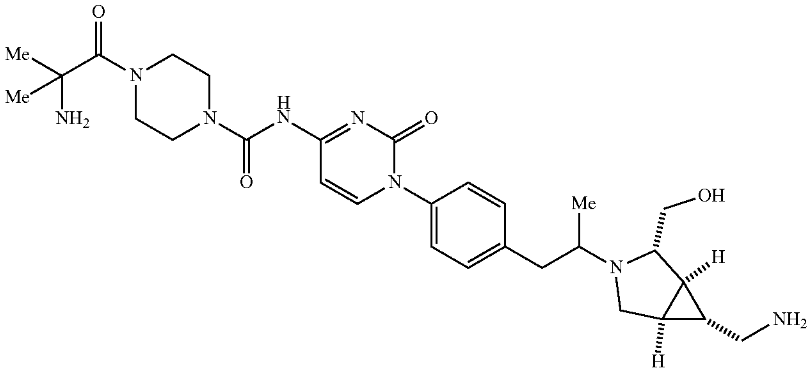 [SMILES: CC(Cc1ccc(-n2ccc(NC(=O)N3CCN(C(=O)C(C)(C)N)CC3)nc2=O)cc1)N1C[C@@H]2[C@@H](CN)[C@@H]2[C@H]1CO] |
| 158 | 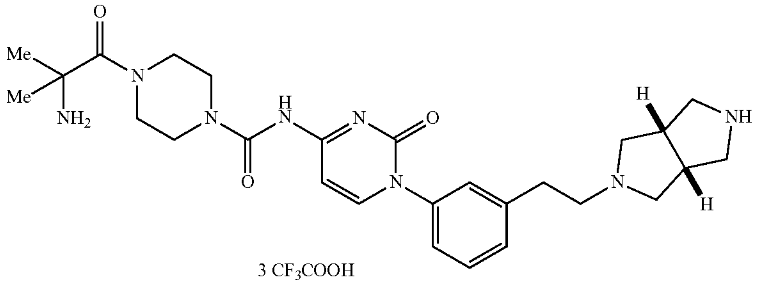 [SMILES: CC(C)(N)C(=O)N1CCN(C(=O)Nc2ccn(-c3cccc(CCN4C[C@H]5CNC[C@H]5C4)c3)c(=O)n2)CC1] 3 $CF_3COOH$ | 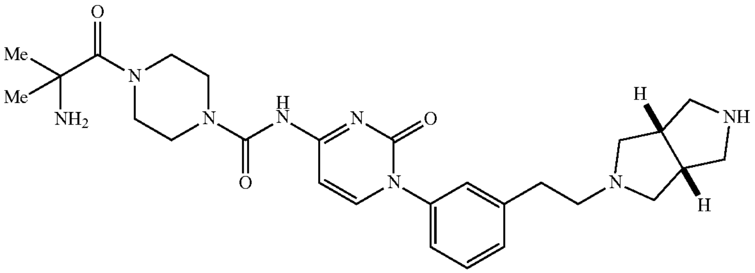 [SMILES: CC(C)(N)C(=O)N1CCN(C(=O)Nc2ccn(-c3cccc(CCN4C[C@H]5CNC[C@H]5C4)c3)c(=O)n2)CC1] |
| 159 | 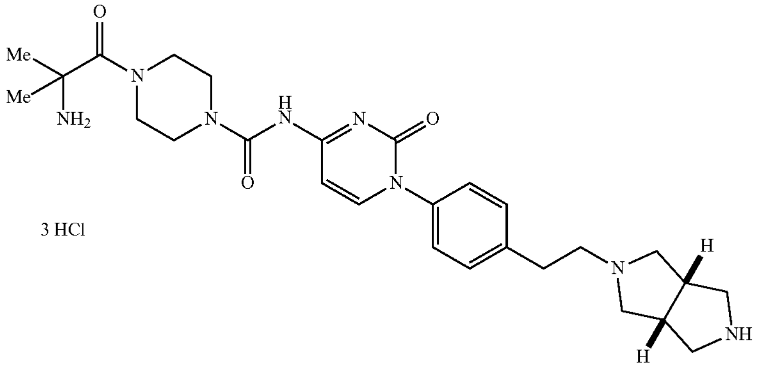 [SMILES: CC(C)(N)C(=O)N1CCN(C(=O)Nc2ccn(-c3ccc(CCN4C[C@H]5CNC[C@H]5C4)cc3)c(=O)n2)CC1] 3 HCl | 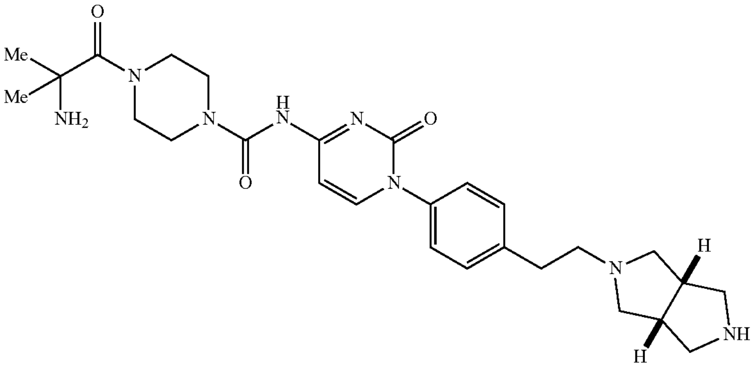 [SMILES: CC(C)(N)C(=O)N1CCN(C(=O)Nc2ccn(-c3ccc(CCN4C[C@H]5CNC[C@H]5C4)cc3)c(=O)n2)CC1] |

TABLE 8-continued
| No. | Salt Structure | Free Base Structure |
|---|---|---|
| 160 | 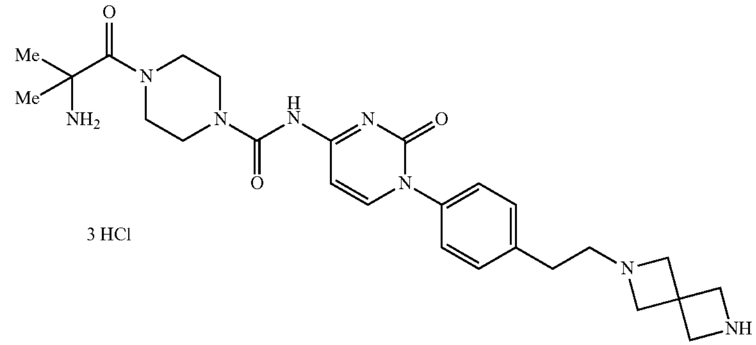 [SMILES: CC(C)(N)C(=O)N1CCN(C(=O)Nc2ccn(-c3ccc(CCN4CC5(CNC5)C4)cc3)c(=O)n2)CC1] 3 HCl | 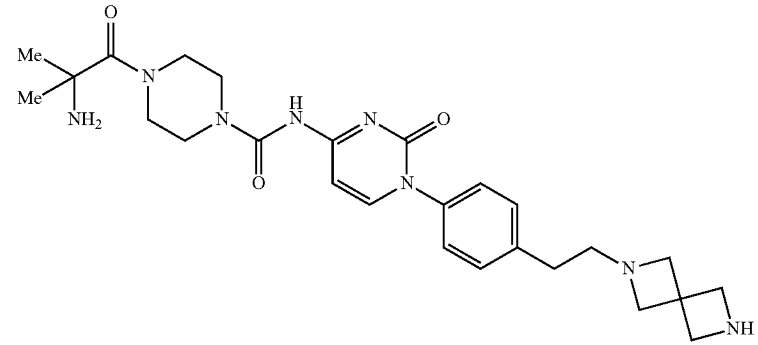 [SMILES: CC(C)(N)C(=O)N1CCN(C(=O)Nc2ccn(-c3ccc(CCN4CC5(CNC5)C4)cc3)c(=O)n2)CC1] |
| 161 | 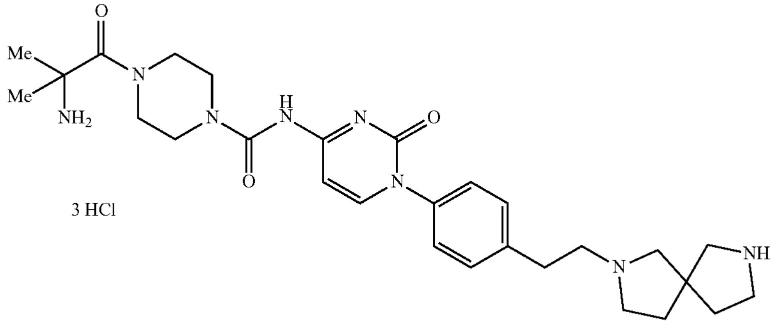 [SMILES: CC(C)(N)C(=O)N1CCN(C(=O)Nc2ccn(-c3ccc(CCN4CCC5(CCNC5)C4)cc3)c(=O)n2)CC1] 3 HCl | 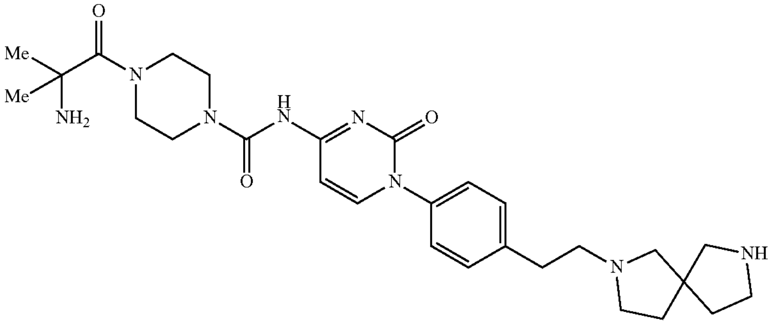 [SMILES: CC(C)(N)C(=O)N1CCN(C(=O)Nc2ccn(-c3ccc(CCN4CCC5(CCNC5)C4)cc3)c(=O)n2)CC1] |
| 162 | 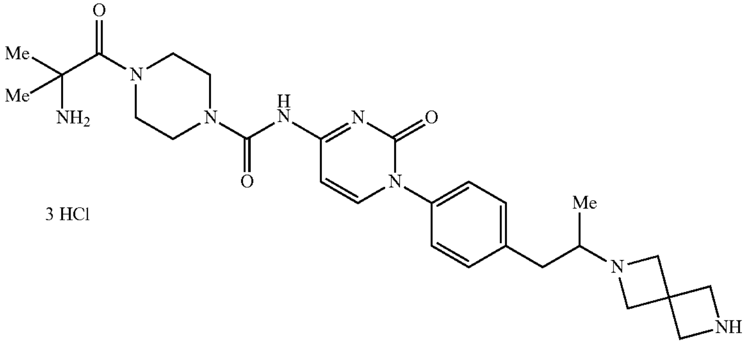 [SMILES: CC(Cc1ccc(-n2ccc(NC(=O)N3CCN(C(=O)C(C)(C)N)CC3)nc2=O)cc1)N1CC2(CNC2)C1] 3 HCl | 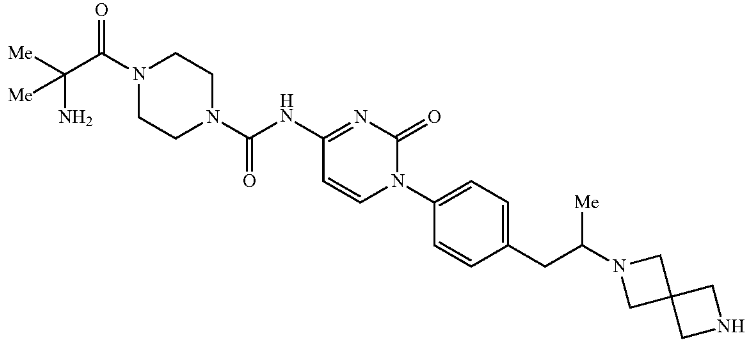 [SMILES: CC(Cc1ccc(-n2ccc(NC(=O)N3CCN(C(=O)C(C)(C)N)CC3)nc2=O)cc1)N1CC2(CNC2)C1] |

TABLE 8-continued
| No. | Salt Structure | Free Base Structure |
|---|---|---|
| 163 | 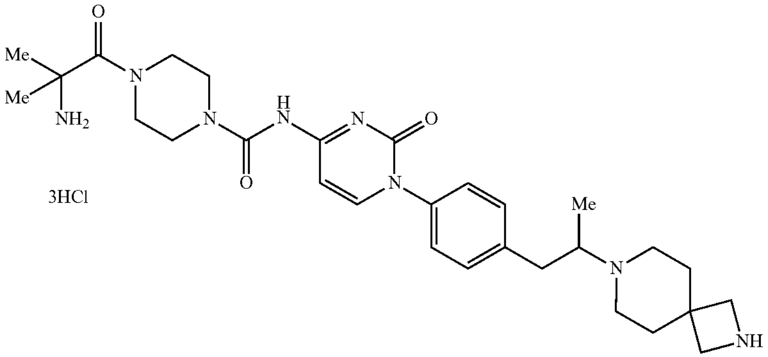 [SMILES: CC(Cc1ccc(-n2ccc(NC(=O)N3CCN(C(=O)C(C)(C)N)CC3)nc2=O)cc1)N1CCC2(CC1)CNC2] 3HCl | 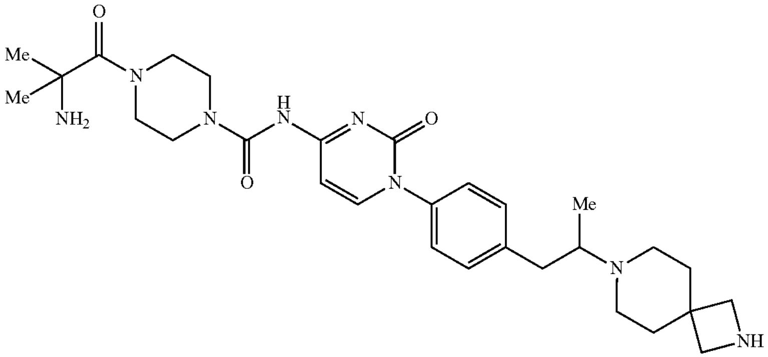 [SMILES: CC(Cc1ccc(-n2ccc(NC(=O)N3CCN(C(=O)C(C)(C)N)CC3)nc2=O)cc1)N1CCC2(CC1)CNC2] |
| 164 | 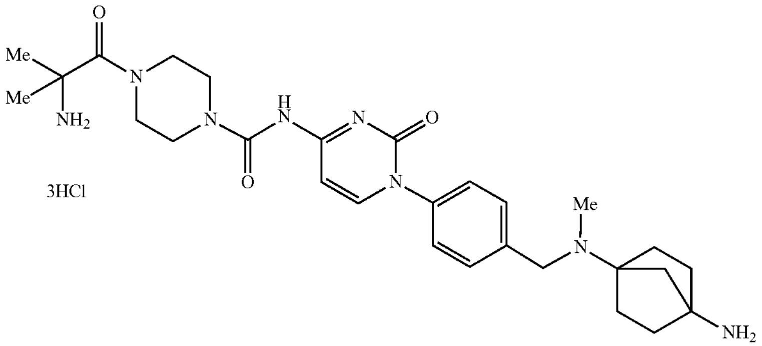 3HCl | 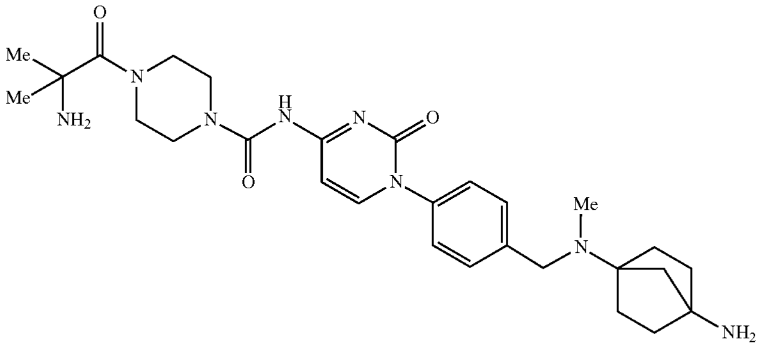 |
| 165 | 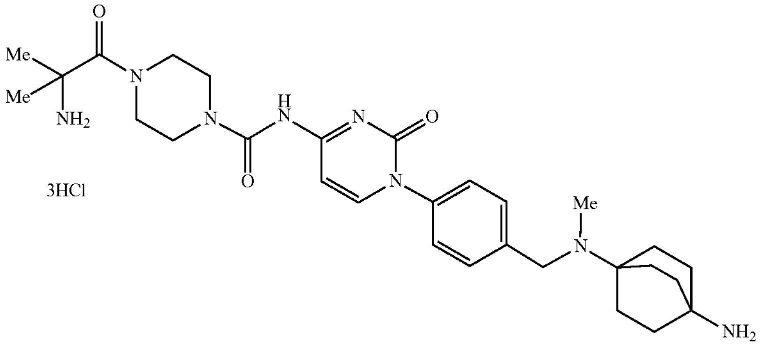 [SMILES: CN(Cc1ccc(-n2ccc(NC(=O)N3CCN(C(=O)C(C)(C)N)CC3)nc2=O)cc1)C12CCC(N)(CC1)CC2] 3HCl | 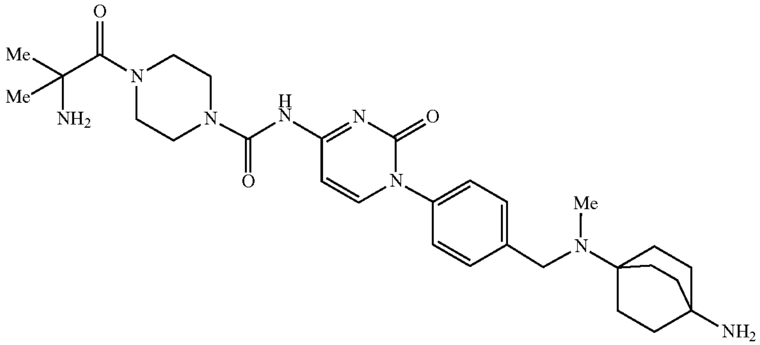 |

TABLE 8-continued
| No. | Salt Structure | Free Base Structure |
|---|---|---|
| 166 | 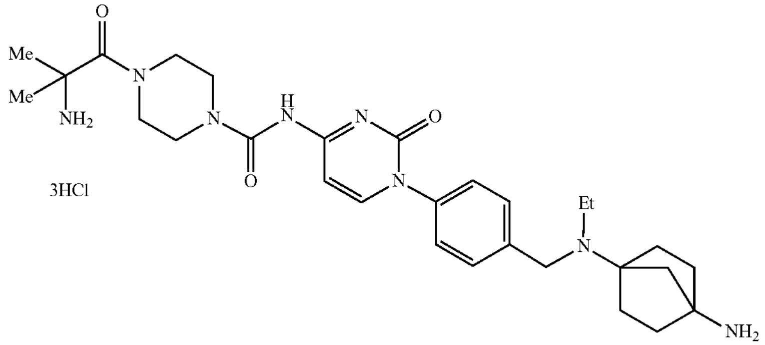 3HCl | 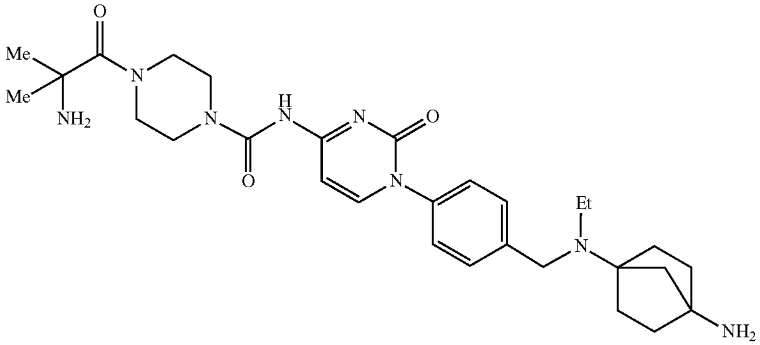 |
| 167 | 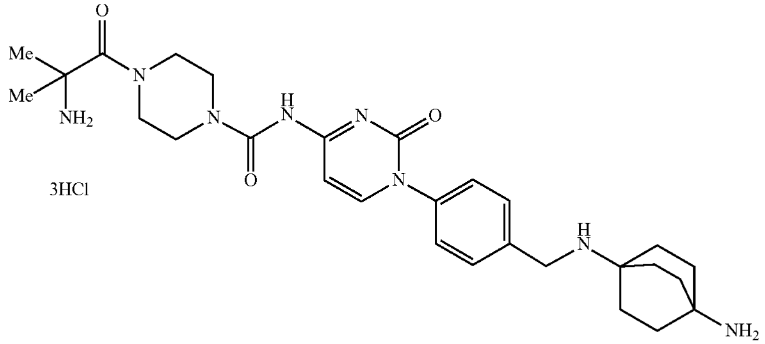 3HCl | 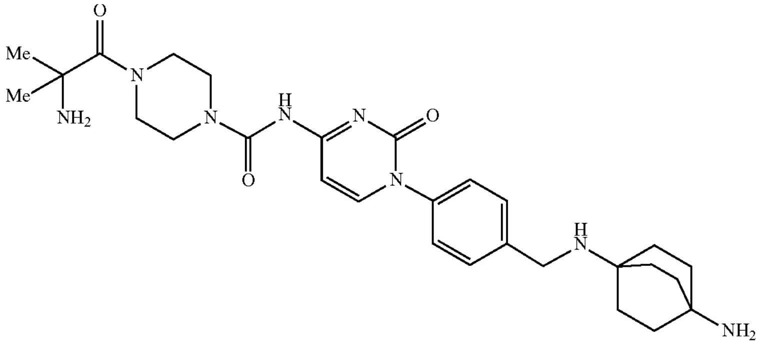 |
| 168 | 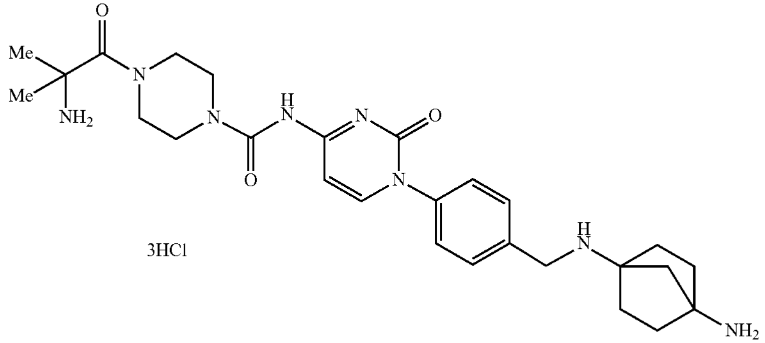 3HCl | 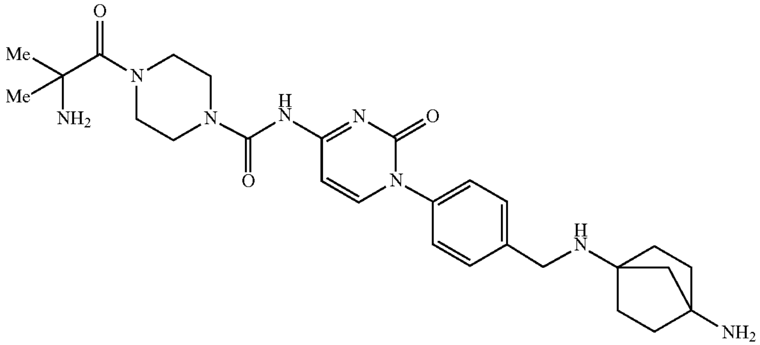 |

TABLE 8-continued
| No. | Salt Structure | Free Base Structure |
| --- | --- | --- |
| 169 | 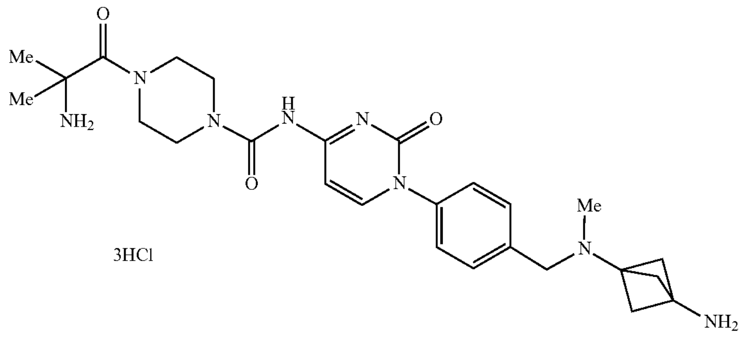 [SMILES: CN(Cc1ccc(-n2ccc(NC(=O)N3CCN(C(=O)C(C)(C)N)CC3)nc2=O)cc1)C12CC(N)(C1)C2] 3HCl | 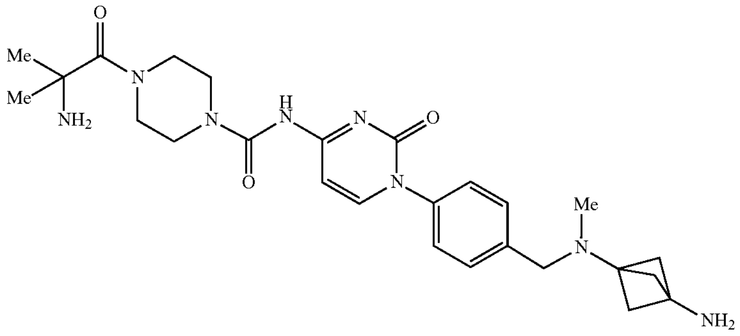 [SMILES: CN(Cc1ccc(-n2ccc(NC(=O)N3CCN(C(=O)C(C)(C)N)CC3)nc2=O)cc1)C12CC(N)(C1)C2] |
| 170 | 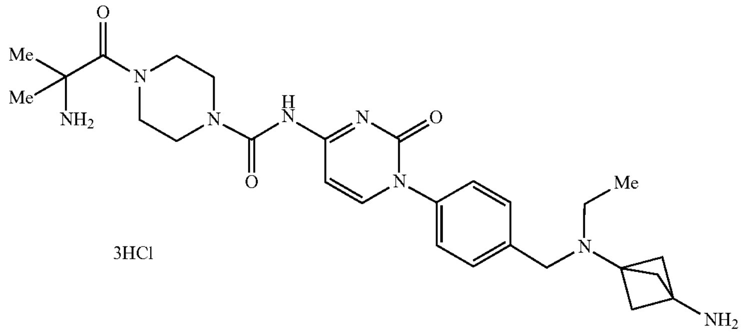 [SMILES: CCN(Cc1ccc(-n2ccc(NC(=O)N3CCN(C(=O)C(C)(C)N)CC3)nc2=O)cc1)C12CC(N)(C1)C2] 3HCl | 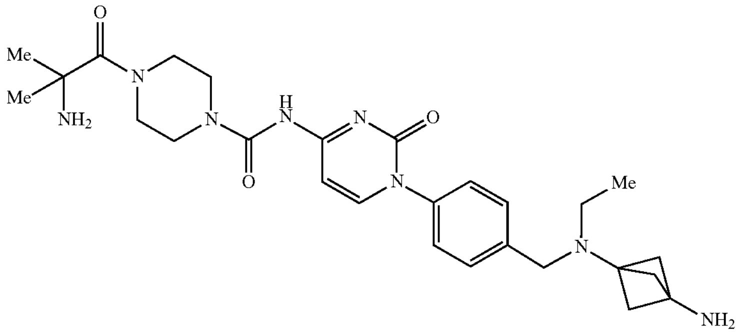 [SMILES: CCN(Cc1ccc(-n2ccc(NC(=O)N3CCN(C(=O)C(C)(C)N)CC3)nc2=O)cc1)C12CC(N)(C1)C2] |
| 171 | 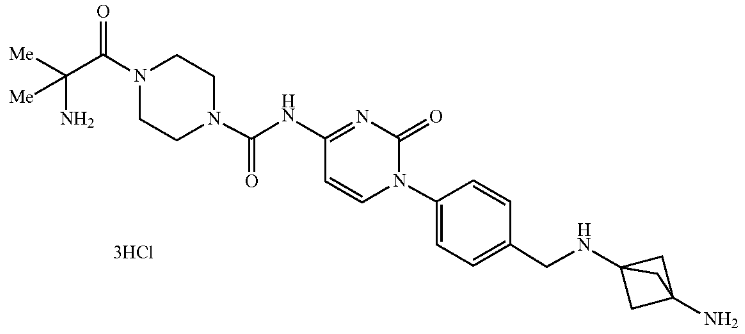 [SMILES: CC(C)(N)C(=O)N1CCN(C(=O)Nc2ccn(-c3ccc(CNC45CC(N)(C4)C5)cc3)c(=O)n2)CC1] 3HCl | 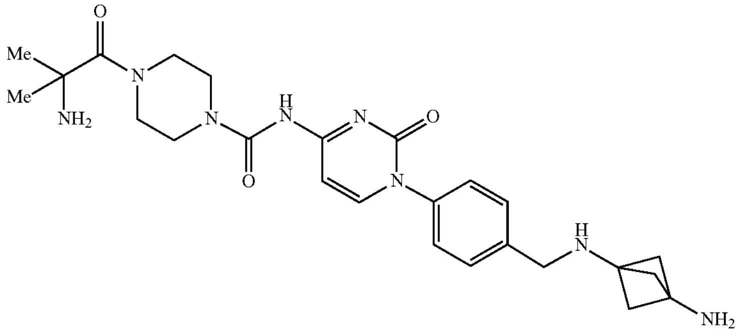 [SMILES: CC(C)(N)C(=O)N1CCN(C(=O)Nc2ccn(-c3ccc(CNC45CC(N)(C4)C5)cc3)c(=O)n2)CC1] |

TABLE 8-continued
| No. | Salt Structure | Free Base Structure |
|---|---|---|
| 172 | 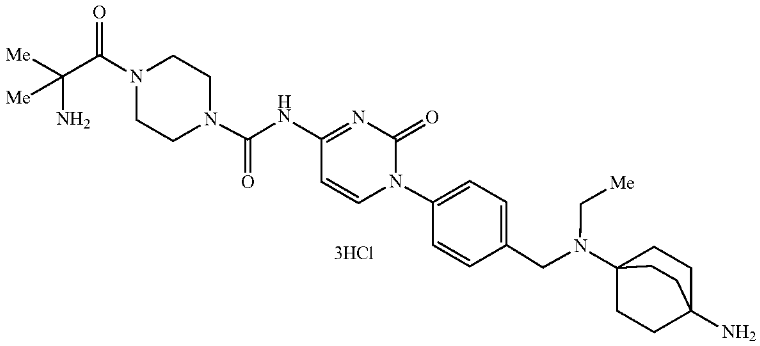 [SMILES: CCN(Cc1ccc(-n2ccc(NC(=O)N3CCN(C(=O)C(C)(C)N)CC3)nc2=O)cc1)C12CCC(N)(CC1)CC2] 3HCl | 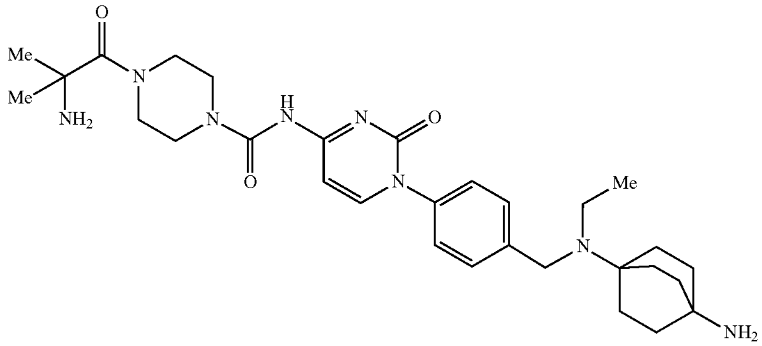 |
| 173 | 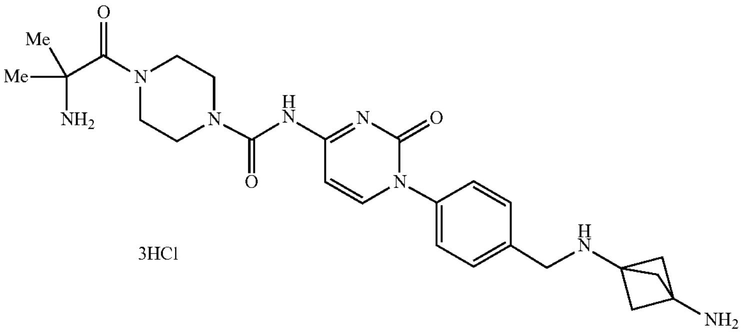 [SMILES: CC(C)(N)C(=O)N1CCN(C(=O)Nc2ccn(-c3ccc(CNC45CC(N)(C4)C5)cc3)c(=O)n2)CC1] 3HCl | 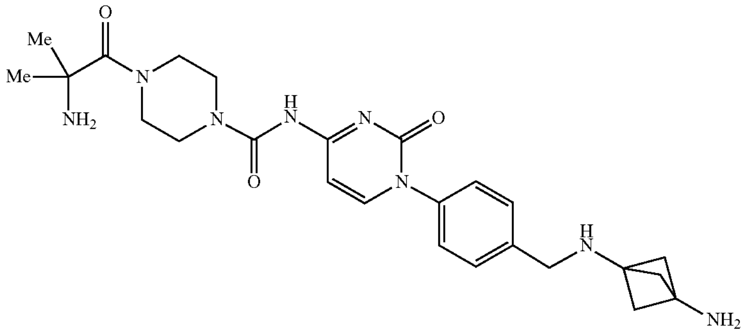 [SMILES: CC(C)(N)C(=O)N1CCN(C(=O)Nc2ccn(-c3ccc(CNC45CC(N)(C4)C5)cc3)c(=O)n2)CC1] |
| 174 | 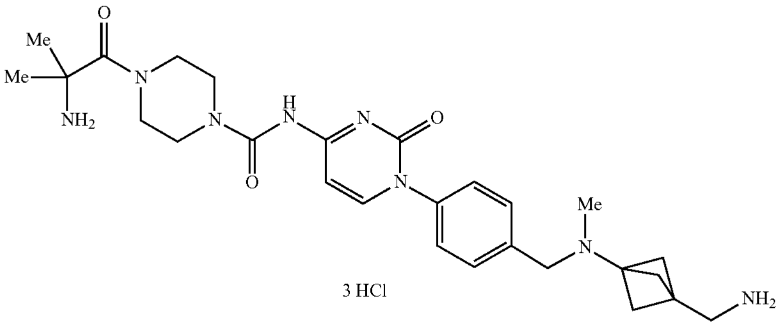 [SMILES: CN(Cc1ccc(-n2ccc(NC(=O)N3CCN(C(=O)C(C)(C)N)CC3)nc2=O)cc1)C12CC(CN)(C1)C2] 3 HCl | 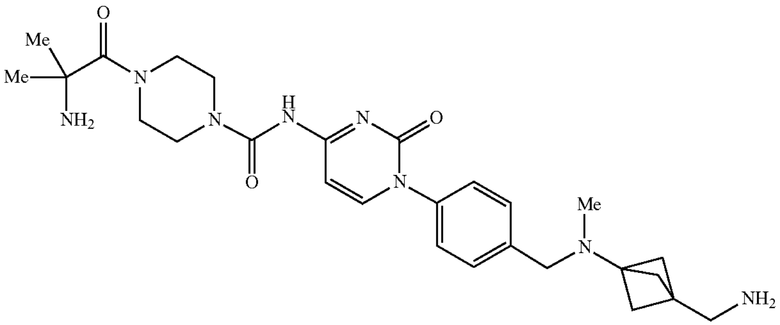 [SMILES: CN(Cc1ccc(-n2ccc(NC(=O)N3CCN(C(=O)C(C)(C)N)CC3)nc2=O)cc1)C12CC(CN)(C1)C2] |

TABLE 8-continued
| No. | Salt Structure | Free Base Structure |
|---|---|---|
| 175 | 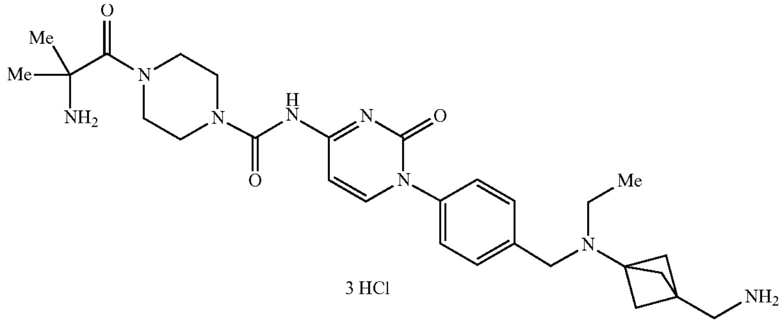 [SMILES: CCN(Cc1ccc(-n2ccc(NC(=O)N3CCN(C(=O)C(C)(C)N)CC3)nc2=O)cc1)C12CC(CN)(C1)C2] 3 HCl | 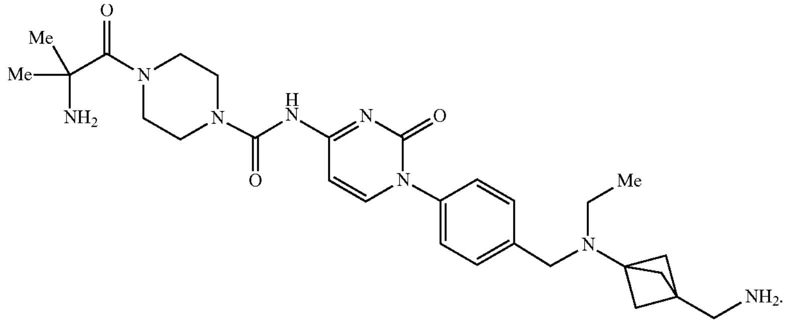 [SMILES: CCN(Cc1ccc(-n2ccc(NC(=O)N3CCN(C(=O)C(C)(C)N)CC3)nc2=O)cc1)C12CC(CN)(C1)C2] |

TABLE 9
| No. | Salt Structure | Free Base Structure |
|---|---|---|
| 176 | 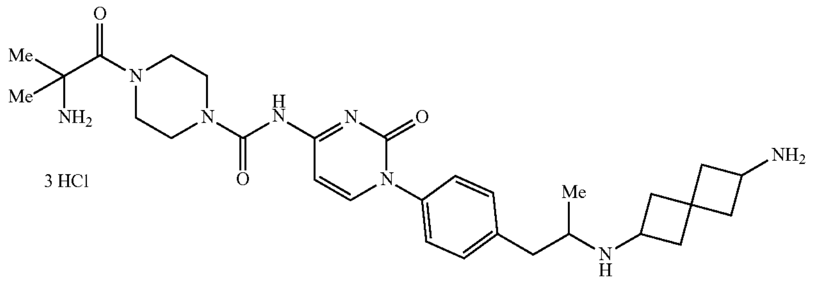 [SMILES: CC(Cc1ccc(-n2ccc(NC(=O)N3CCN(C(=O)C(C)(C)N)CC3)nc2=O)cc1)NC1CC2(CC(N)C2)C1] 3 HCl | 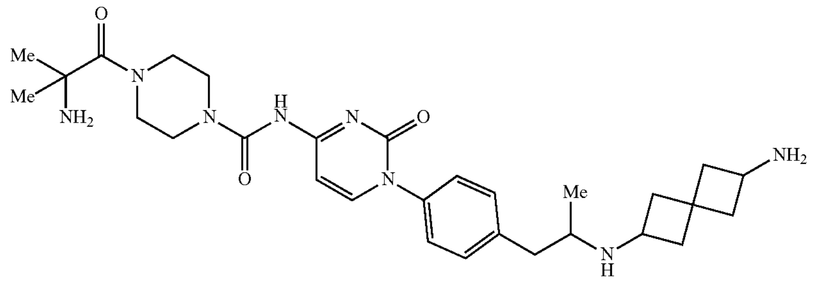 [SMILES: CC(Cc1ccc(-n2ccc(NC(=O)N3CCN(C(=O)C(C)(C)N)CC3)nc2=O)cc1)NC1CC2(CC(N)C2)C1] |
| 177 | 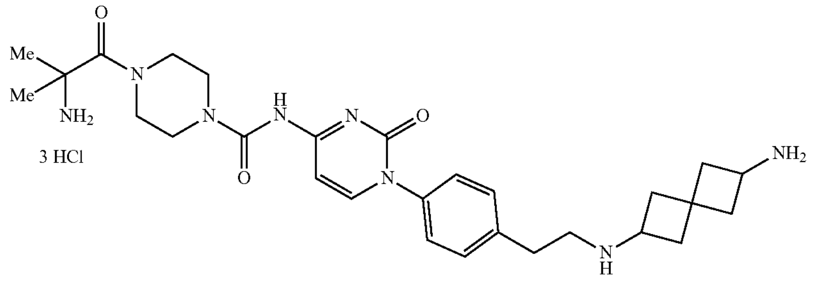 [SMILES: CC(C)(N)C(=O)N1CCN(C(=O)Nc2ccn(-c3ccc(CCNC4CC5(CC(N)C5)C4)cc3)c(=O)n2)CC1] 3 HCl | 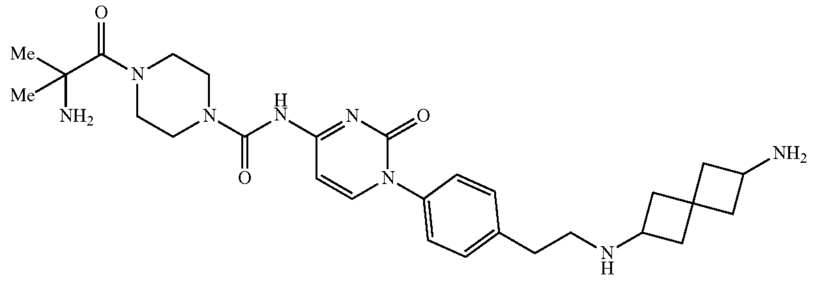 [SMILES: CC(C)(N)C(=O)N1CCN(C(=O)Nc2ccn(-c3ccc(CCNC4CC5(CC(N)C5)C4)cc3)c(=O)n2)CC1] |
| 178 | 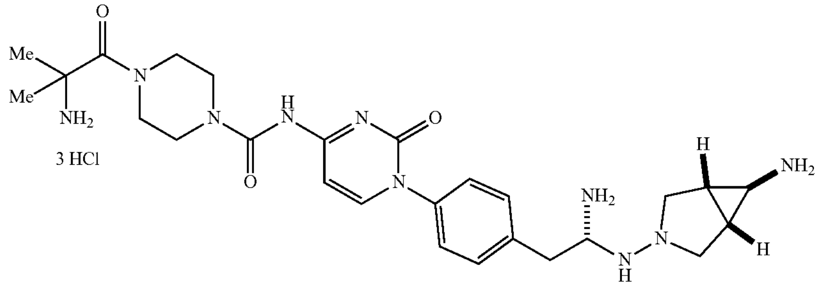 [SMILES: CC(C)(N)C(=O)N1CCN(C(=O)Nc2ccn(-c3ccc(C[C@H](N)NN4C[C@@H]5[C@@H](N)[C@@H]5C4)cc3)c(=O)n2)CC1] 3 HCl | 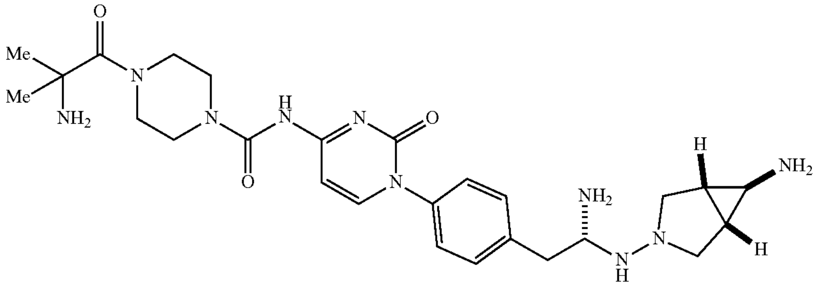 [SMILES: CC(C)(N)C(=O)N1CCN(C(=O)Nc2ccn(-c3ccc(C[C@H](N)NN4C[C@@H]5[C@@H](N)[C@@H]5C4)cc3)c(=O)n2)CC1] |

TABLE 9-continued
| No. | Salt Structure | Free Base Structure |
|---|---|---|
| 179 | 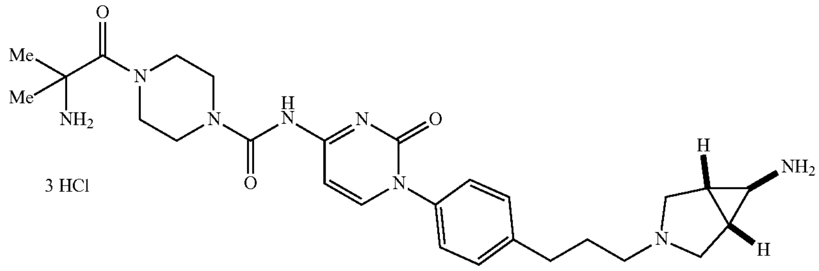 [SMILES: CC(C)(N)C(=O)N1CCN(C(=O)Nc2ccn(-c3ccc(CCCN4C[C@@H]5[C@@H](N)[C@@H]5C4)cc3)c(=O)n2)CC1] 3 HCl | 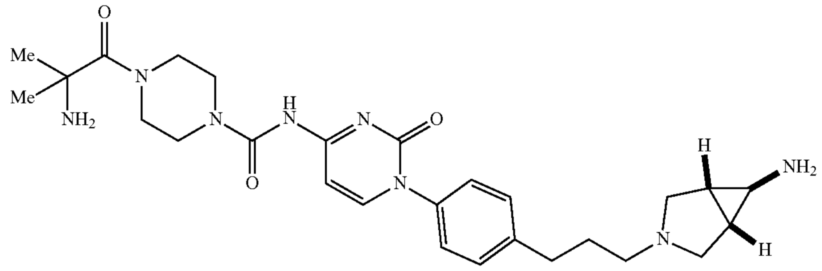 [SMILES: CC(C)(N)C(=O)N1CCN(C(=O)Nc2ccn(-c3ccc(CCCN4C[C@@H]5[C@@H](N)[C@@H]5C4)cc3)c(=O)n2)CC1] |
| 180 | 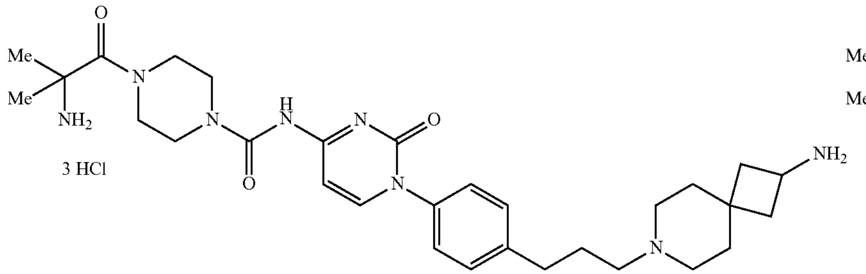 3 HCl | 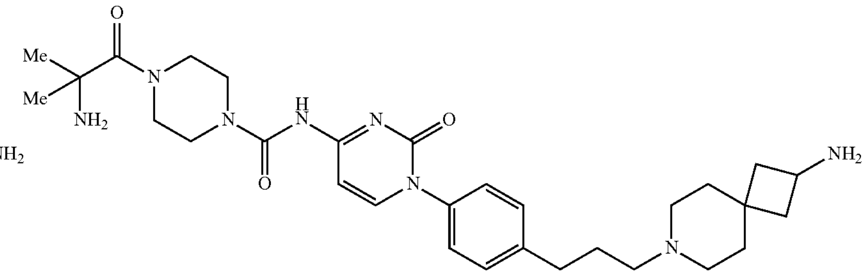 |
| 181 | 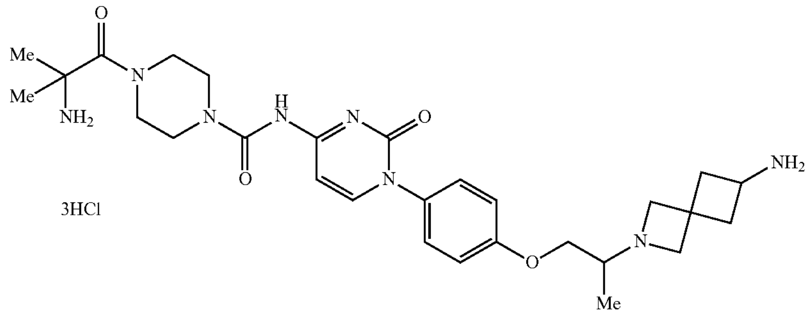 [SMILES: CC(COc1ccc(-n2ccc(NC(=O)N3CCN(C(=O)C(C)(C)N)CC3)nc2=O)cc1)N1CC2(CC(N)C2)C1] 3HCl | 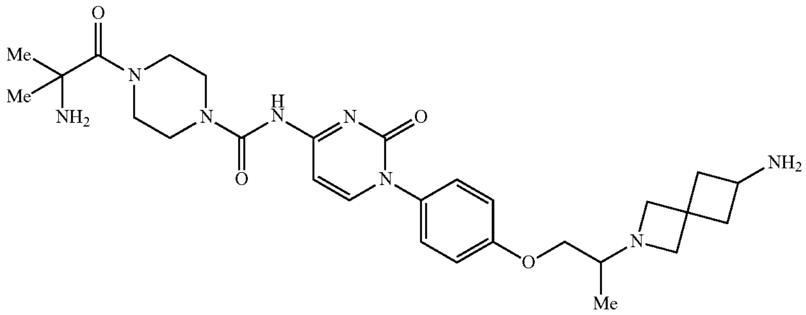 [SMILES: CC(COc1ccc(-n2ccc(NC(=O)N3CCN(C(=O)C(C)(C)N)CC3)nc2=O)cc1)N1CC2(CC(N)C2)C1] |

TABLE 9-continued
| No. | Salt Structure | Free Base Structure |
|---|---|---|
| 182 | 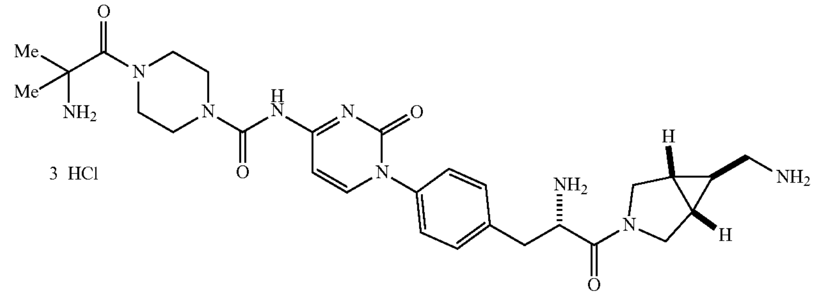 [SMILES: CC(C)(N)C(=O)N1CCN(C(=O)Nc2ccn(-c3ccc(C[C@H](N)C(=O)N4C[C@@H]5[C@@H](CN)[C@@H]5C4)cc3)c(=O)n2)CC1] 3 HCl | 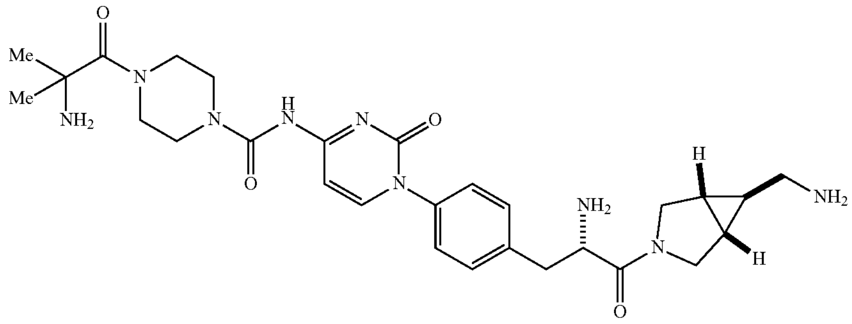 [SMILES: CC(C)(N)C(=O)N1CCN(C(=O)Nc2ccn(-c3ccc(C[C@H](N)C(=O)N4C[C@@H]5[C@@H](CN)[C@@H]5C4)cc3)c(=O)n2)CC1] |
| 183 | 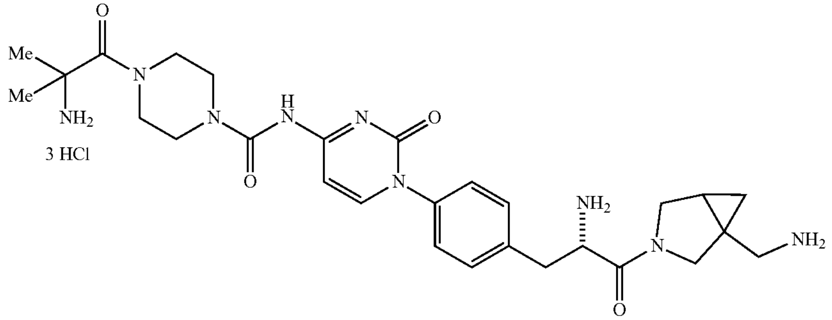 [SMILES: CC(C)(N)C(=O)N1CCN(C(=O)Nc2ccn(-c3ccc(C[C@H](N)C(=O)N4CC5CC5(CN)C4)cc3)c(=O)n2)CC1] 3 HCl | 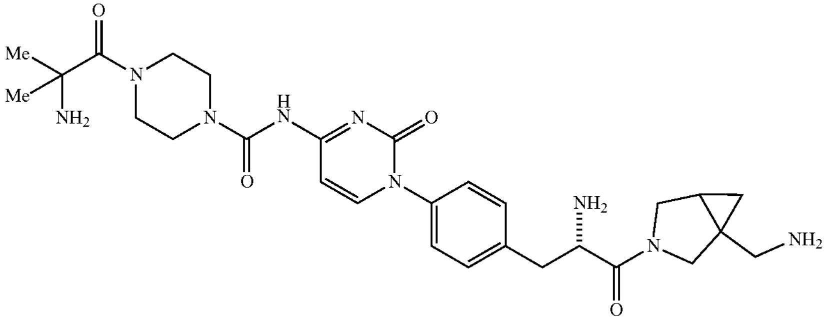 [SMILES: CC(C)(N)C(=O)N1CCN(C(=O)Nc2ccn(-c3ccc(C[C@H](N)C(=O)N4CC5CC5(CN)C4)cc3)c(=O)n2)CC1] |
| 184 | 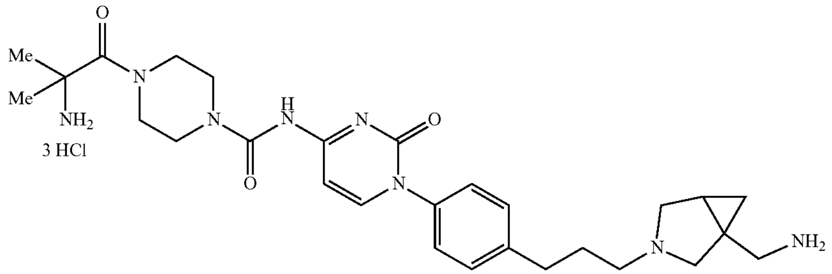 [SMILES: CC(C)(N)C(=O)N1CCN(C(=O)Nc2ccn(-c3ccc(CCCN4CC5CC5(CN)C4)cc3)c(=O)n2)CC1] 3 HCl | 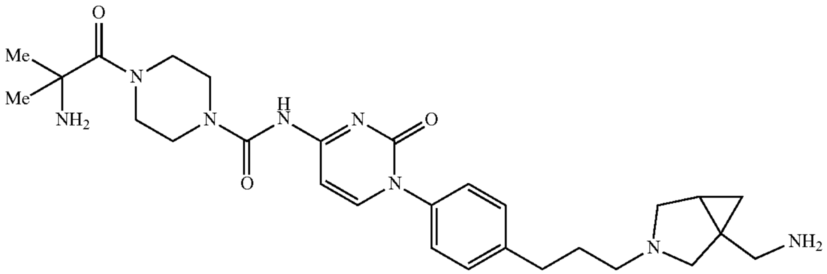 [SMILES: CC(C)(N)C(=O)N1CCN(C(=O)Nc2ccn(-c3ccc(CCCN4CC5CC5(CN)C4)cc3)c(=O)n2)CC1] |

TABLE 9-continued
| No. | Salt Structure | Free Base Structure |
|---|---|---|
| 185 | 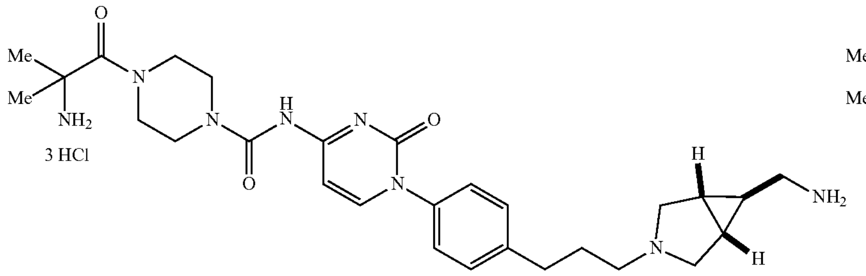 3 HCl | 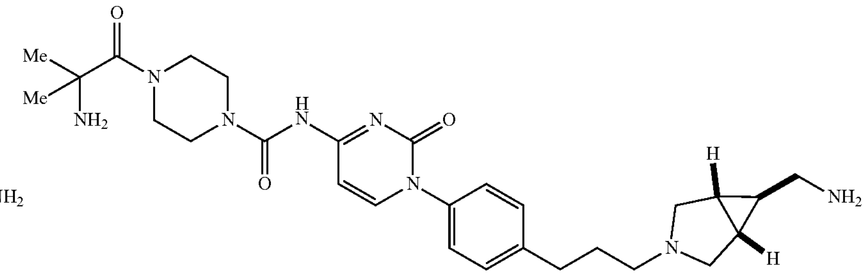 |
| 186 | 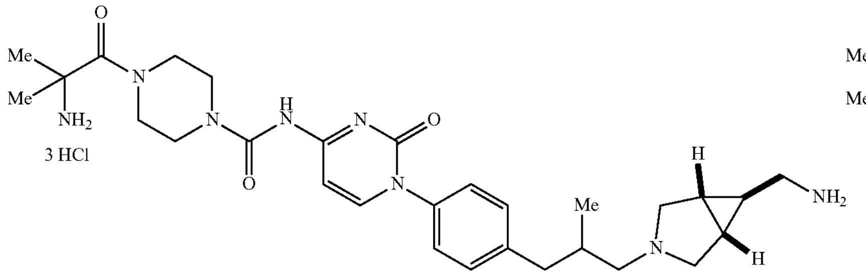 3 HCl | 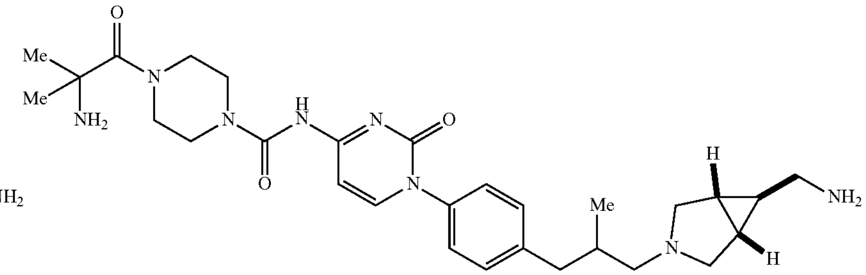 |
| 187 | 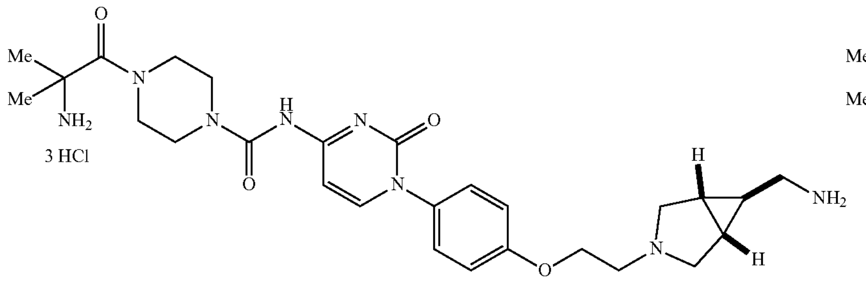 3 HCl | 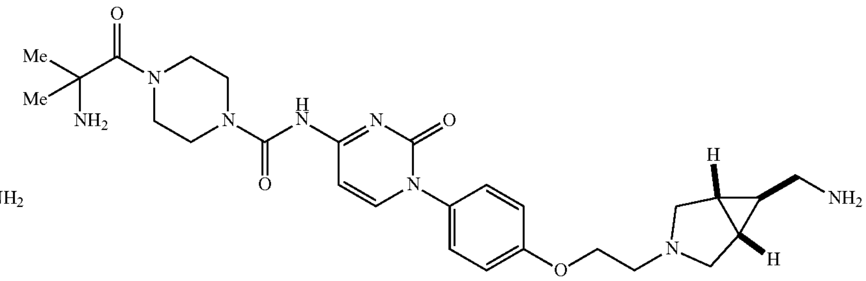 |

TABLE 9-continued
| No. | Salt Structure | Free Base Structure |
|---|---|---|
| 188 | 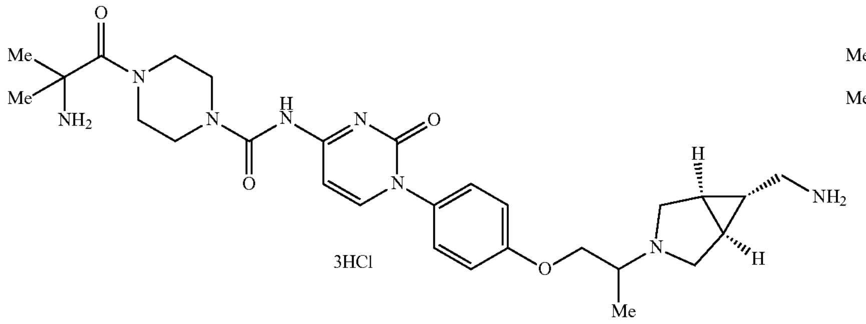 3HCl | 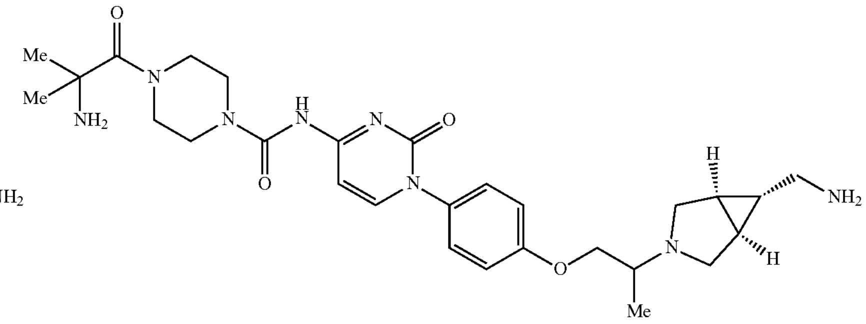 |
| 189 | 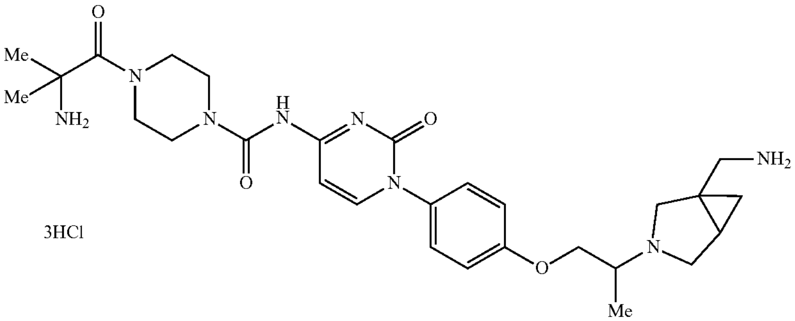 [SMILES: CC(COc1ccc(-n2ccc(NC(=O)N3CCN(C(=O)C(C)(C)N)CC3)nc2=O)cc1)N1CC2CC2(CN)C1] 3HCl | 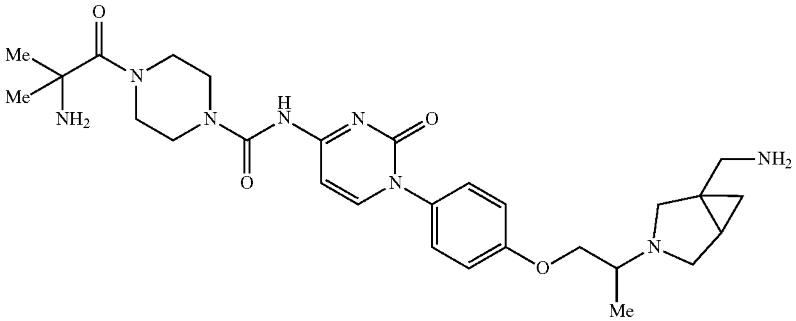 [SMILES: CC(COc1ccc(-n2ccc(NC(=O)N3CCN(C(=O)C(C)(C)N)CC3)nc2=O)cc1)N1CC2CC2(CN)C1] |
| 190 | 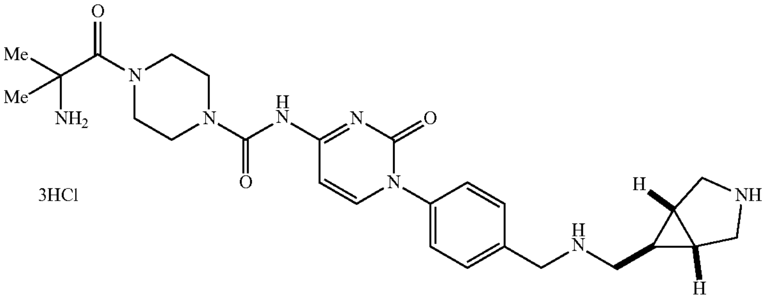 [SMILES: CC(C)(N)C(=O)N1CCN(C(=O)Nc2ccn(-c3ccc(CNC[C@@H]4[C@H]5CNC[C@@H]45)cc3)c(=O)n2)CC1] 3HCl | 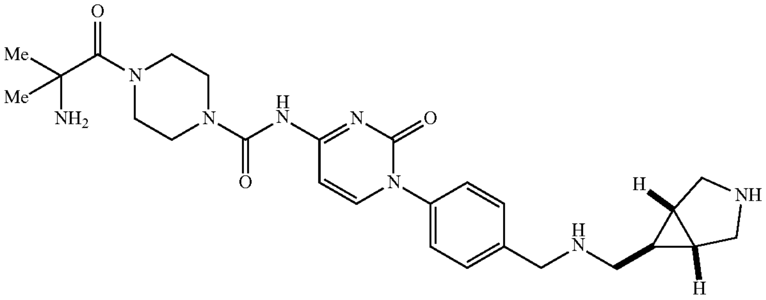 [SMILES: CC(C)(N)C(=O)N1CCN(C(=O)Nc2ccn(-c3ccc(CNC[C@@H]4[C@H]5CNC[C@@H]45)cc3)c(=O)n2)CC1] |

TABLE 9-continued
| No. | Salt Structure | Free Base Structure |
|---|---|---|
| 191 | 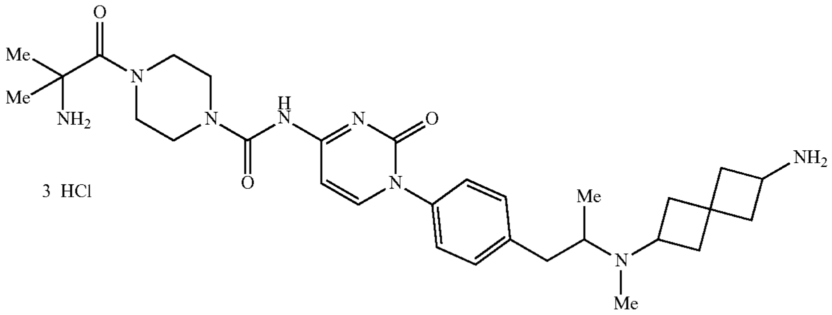 [SMILES: CC(Cc1ccc(-n2ccc(NC(=O)N3CCN(C(=O)C(C)(C)N)CC3)nc2=O)cc1)N(C)C1CC2(CC(N)C2)C1] 3 HCl | 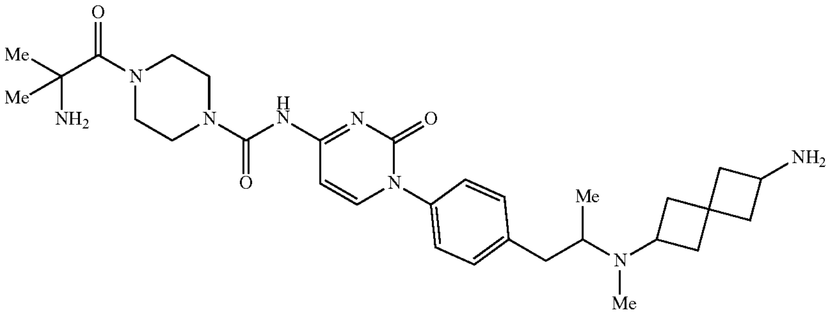 [SMILES: CC(Cc1ccc(-n2ccc(NC(=O)N3CCN(C(=O)C(C)(C)N)CC3)nc2=O)cc1)N(C)C1CC2(CC(N)C2)C1] |
| 192 | 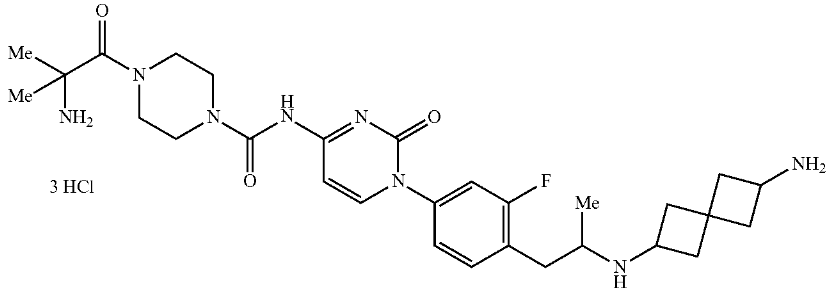 [SMILES: CC(Cc1ccc(-n2ccc(NC(=O)N3CCN(C(=O)C(C)(C)N)CC3)nc2=O)cc1F)NC1CC2(CC(N)C2)C1] 3 HCl | 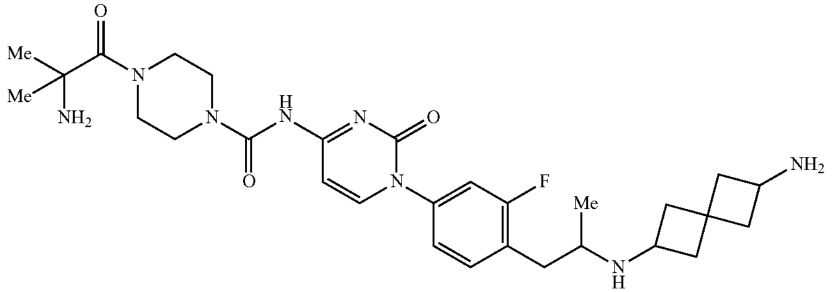 [SMILES: CC(Cc1ccc(-n2ccc(NC(=O)N3CCN(C(=O)C(C)(C)N)CC3)nc2=O)cc1F)NC1CC2(CC(N)C2)C1] |
| 193 | 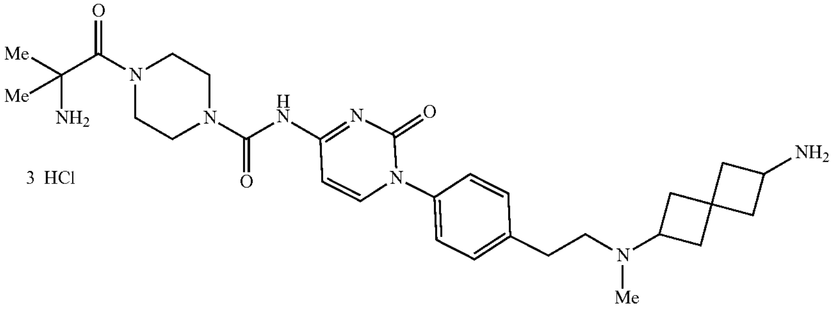 [SMILES: CN(CCc1ccc(-n2ccc(NC(=O)N3CCN(C(=O)C(C)(C)N)CC3)nc2=O)cc1)C1CC2(CC(N)C2)C1] 3 HCl | 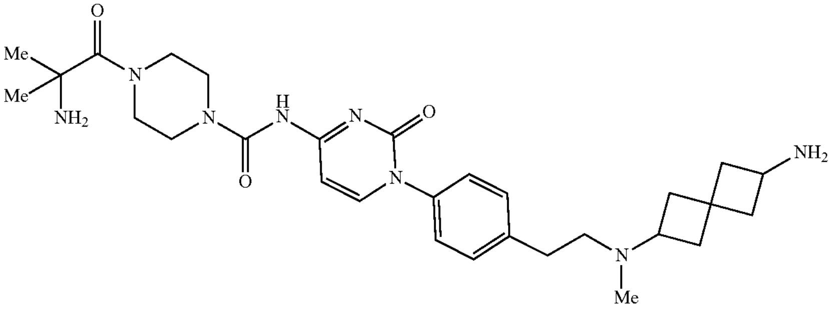 [SMILES: CN(CCc1ccc(-n2ccc(NC(=O)N3CCN(C(=O)C(C)(C)N)CC3)nc2=O)cc1)C1CC2(CC(N)C2)C1] |

TABLE 9-continued
| No. | Salt Structure | Free Base Structure |
|---|---|---|
| 194 | 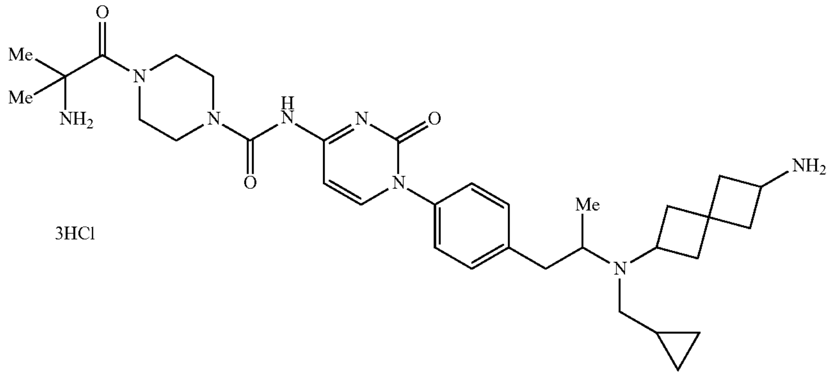 [SMILES: CC(Cc1ccc(-n2ccc(NC(=O)N3CCN(C(=O)C(C)(C)N)CC3)nc2=O)cc1)N(CC1CC1)C1CC2(CC(N)C2)C1] 3HCl | 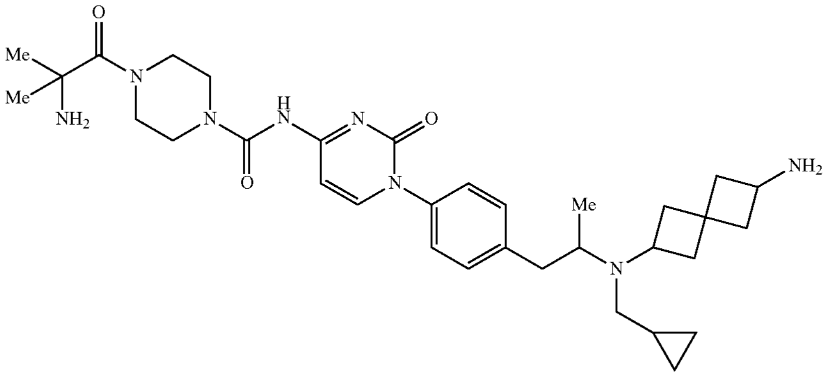 [SMILES: CC(Cc1ccc(-n2ccc(NC(=O)N3CCN(C(=O)C(C)(C)N)CC3)nc2=O)cc1)N(CC1CC1)C1CC2(CC(N)C2)C1] |
| 195 | 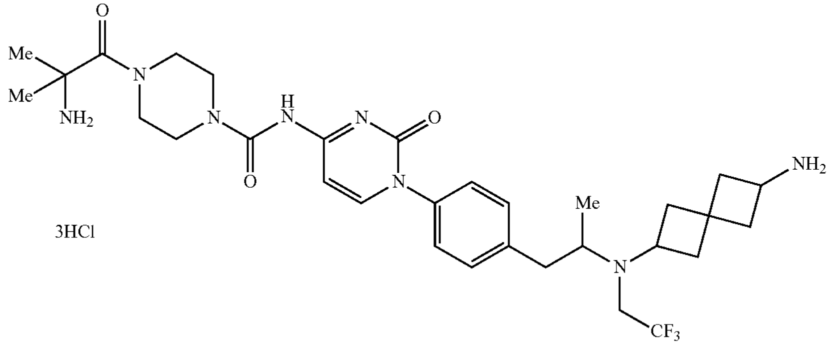 [SMILES: CC(Cc1ccc(-n2ccc(NC(=O)N3CCN(C(=O)C(C)(C)N)CC3)nc2=O)cc1)N(CC(F)(F)F)C1CC2(CC(N)C2)C1] 3HCl | 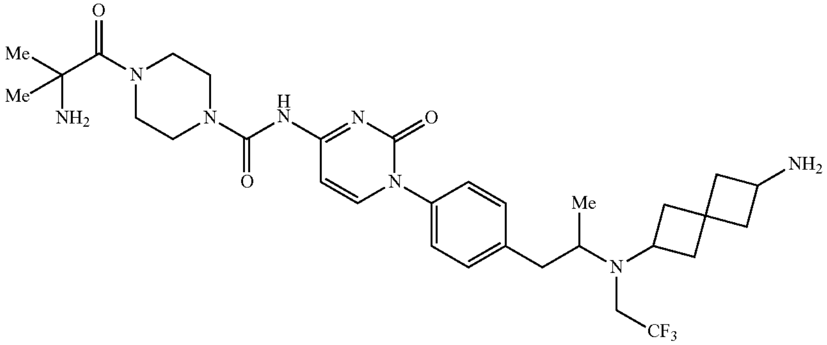 [SMILES: CC(Cc1ccc(-n2ccc(NC(=O)N3CCN(C(=O)C(C)(C)N)CC3)nc2=O)cc1)N(CC(F)(F)F)C1CC2(CC(N)C2)C1] |
| 196 | 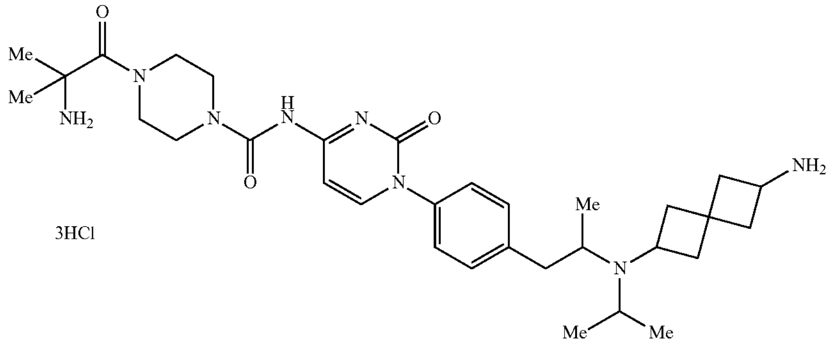 [SMILES: CC(C)N(C(C)Cc1ccc(-n2ccc(NC(=O)N3CCN(C(=O)C(C)(C)N)CC3)nc2=O)cc1)C1CC2(CC(N)C2)C1] 3HCl | 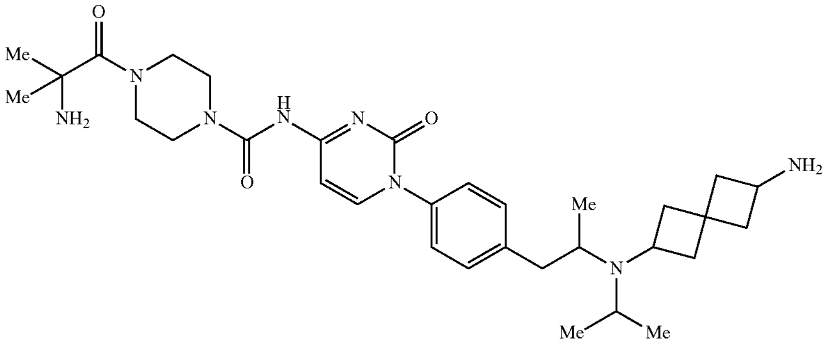 [SMILES: CC(C)N(C(C)Cc1ccc(-n2ccc(NC(=O)N3CCN(C(=O)C(C)(C)N)CC3)nc2=O)cc1)C1CC2(CC(N)C2)C1] |

TABLE 9-continued
| No. | Salt Structure | Free Base Structure |
| --- | --- | --- |
| 197 | 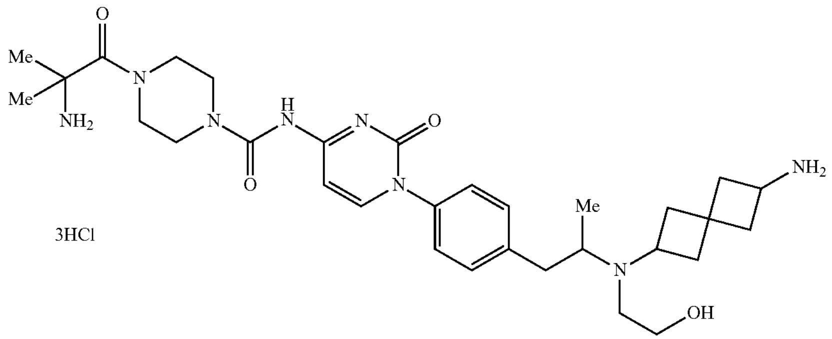 [SMILES: CC(Cc1ccc(-n2ccc(NC(=O)N3CCN(C(=O)C(C)(C)N)CC3)nc2=O)cc1)N(CCO)C1CC2(CC(N)C2)C1] 3HCl | 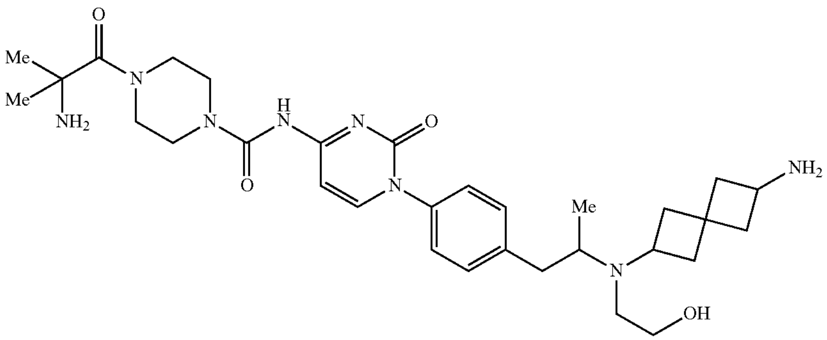 [SMILES: CC(Cc1ccc(-n2ccc(NC(=O)N3CCN(C(=O)C(C)(C)N)CC3)nc2=O)cc1)N(CCO)C1CC2(CC(N)C2)C1] |
| 198 | 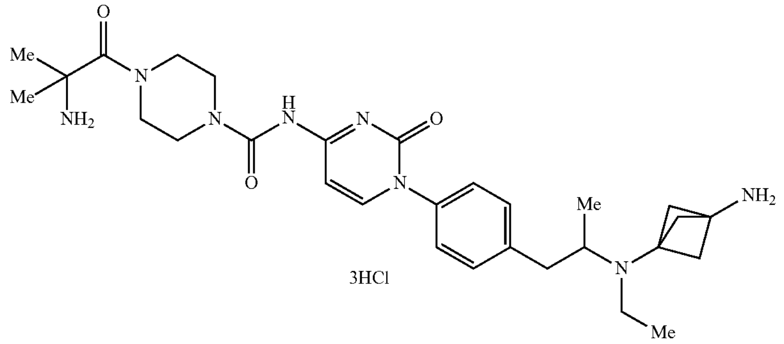 [SMILES: CCN(C(C)Cc1ccc(-n2ccc(NC(=O)N3CCN(C(=O)C(C)(C)N)CC3)nc2=O)cc1)C12CC(N)(C1)C2] 3HCl | 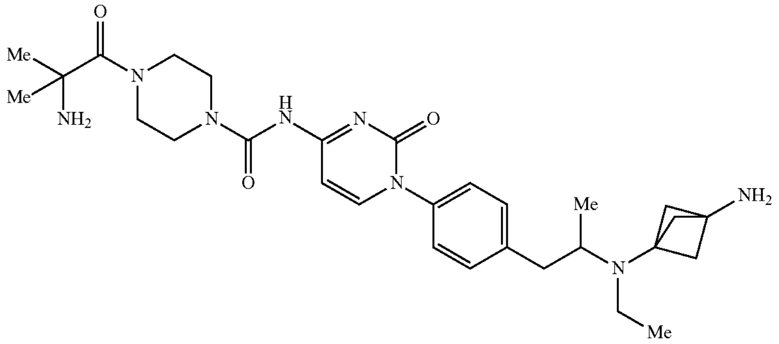 [SMILES: CCN(C(C)Cc1ccc(-n2ccc(NC(=O)N3CCN(C(=O)C(C)(C)N)CC3)nc2=O)cc1)C12CC(N)(C1)C2] |
| 199 | 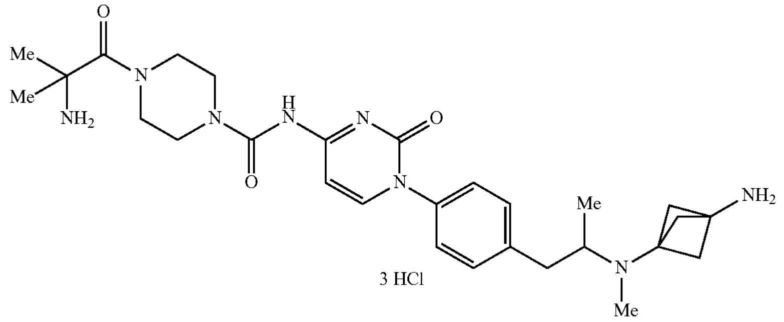 [SMILES: CC(Cc1ccc(-n2ccc(NC(=O)N3CCN(C(=O)C(C)(C)N)CC3)nc2=O)cc1)N(C)C12CC(N)(C1)C2] 3 HCl | 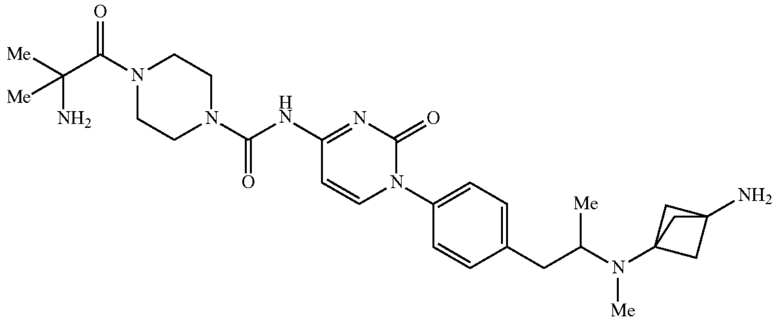 [SMILES: CC(Cc1ccc(-n2ccc(NC(=O)N3CCN(C(=O)C(C)(C)N)CC3)nc2=O)cc1)N(C)C12CC(N)(C1)C2] |

TABLE 9-continued
| No. | Salt Structure | Free Base Structure |
|---|---|---|
| 200 | 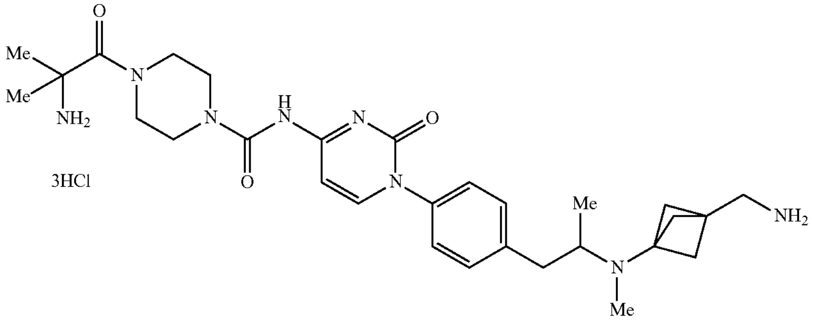 [SMILES: CC(Cc1ccc(-n2ccc(NC(=O)N3CCN(C(=O)C(C)(C)N)CC3)nc2=O)cc1)N(C)C12CC(CN)(C1)C2] 3HCl | 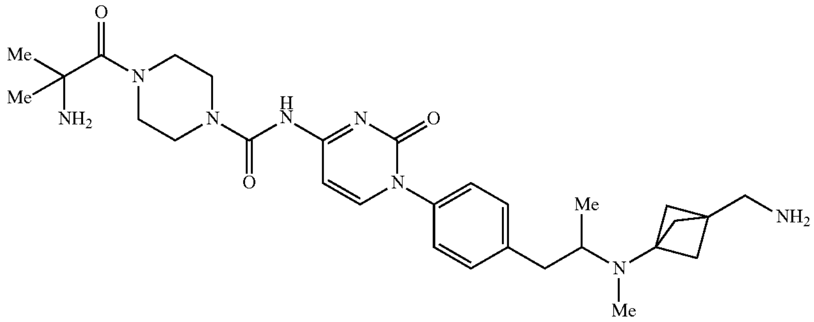 [SMILES: CC(Cc1ccc(-n2ccc(NC(=O)N3CCN(C(=O)C(C)(C)N)CC3)nc2=O)cc1)N(C)C12CC(CN)(C1)C2] |
| 201 | 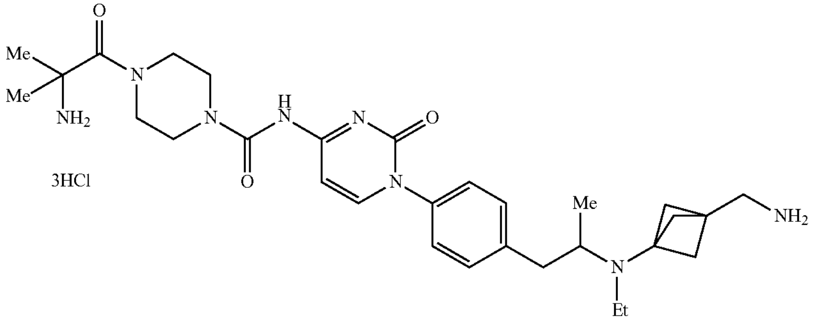 [SMILES: CCN(C(C)Cc1ccc(-n2ccc(NC(=O)N3CCN(C(=O)C(C)(C)N)CC3)nc2=O)cc1)C12CC(CN)(C1)C2] 3HCl | 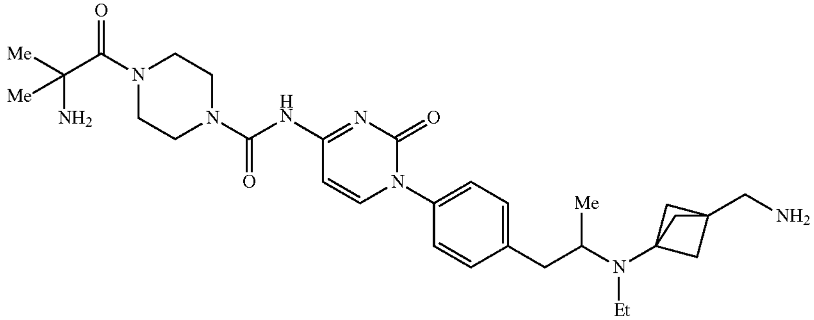 [SMILES: CCN(C(C)Cc1ccc(-n2ccc(NC(=O)N3CCN(C(=O)C(C)(C)N)CC3)nc2=O)cc1)C12CC(CN)(C1)C2] |
| 202 | 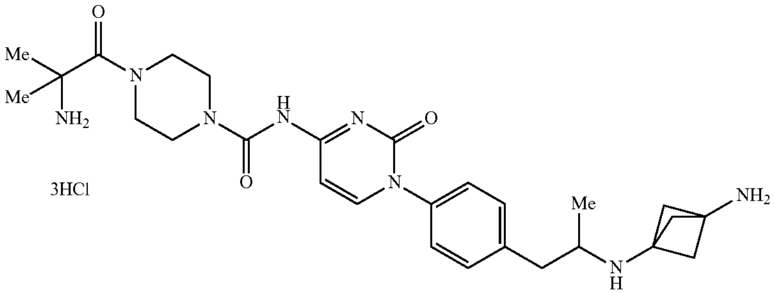 [SMILES: CC(Cc1ccc(-n2ccc(NC(=O)N3CCN(C(=O)C(C)(C)N)CC3)nc2=O)cc1)NC12CC(N)(C1)C2] 3HCl | 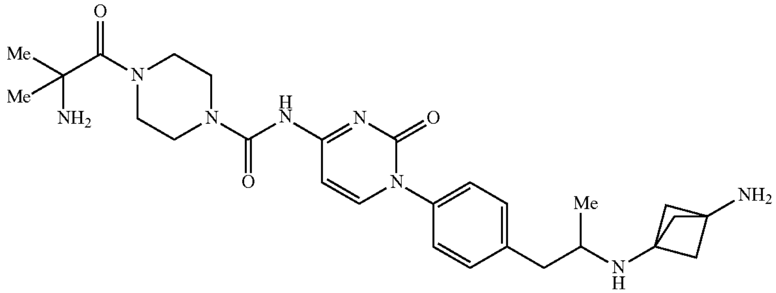 [SMILES: CC(Cc1ccc(-n2ccc(NC(=O)N3CCN(C(=O)C(C)(C)N)CC3)nc2=O)cc1)NC12CC(N)(C1)C2] |

TABLE 9-continued
| No. | Salt Structure | Free Base Structure |
|---|---|---|
| 203 | 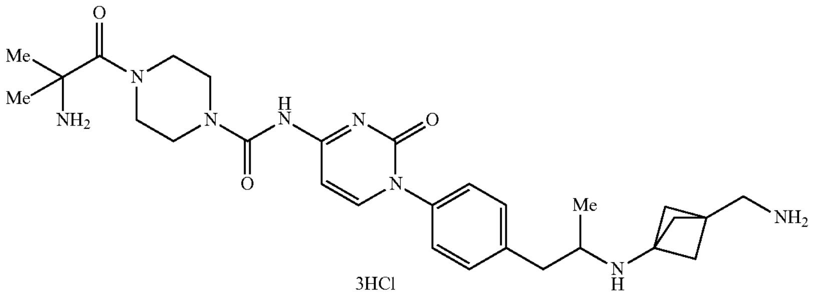 [SMILES: CC(Cc1ccc(-n2ccc(NC(=O)N3CCN(C(=O)C(C)(C)N)CC3)nc2=O)cc1)NC12CC(CN)(C1)C2] 3HCl | 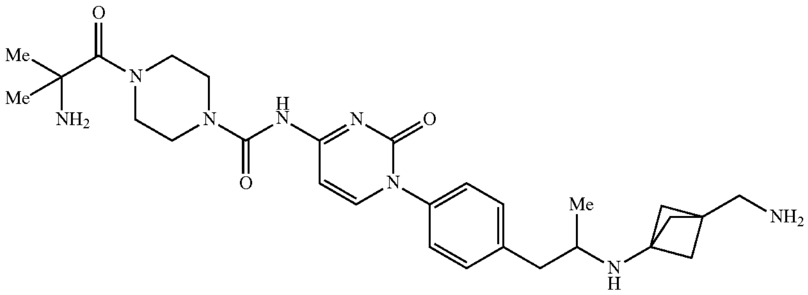 [SMILES: CC(Cc1ccc(-n2ccc(NC(=O)N3CCN(C(=O)C(C)(C)N)CC3)nc2=O)cc1)NC12CC(CN)(C1)C2] |
| 204 | 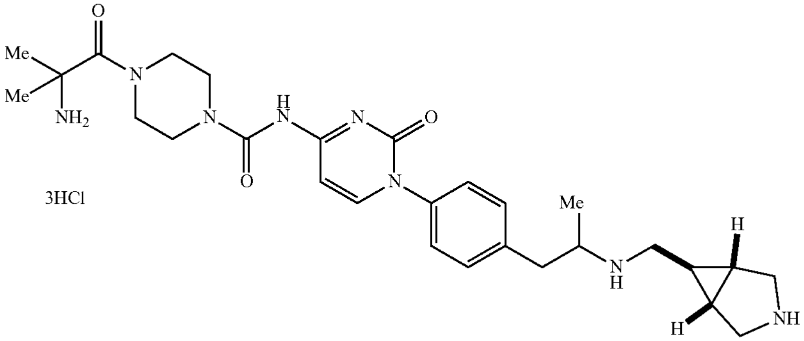 3HCl | 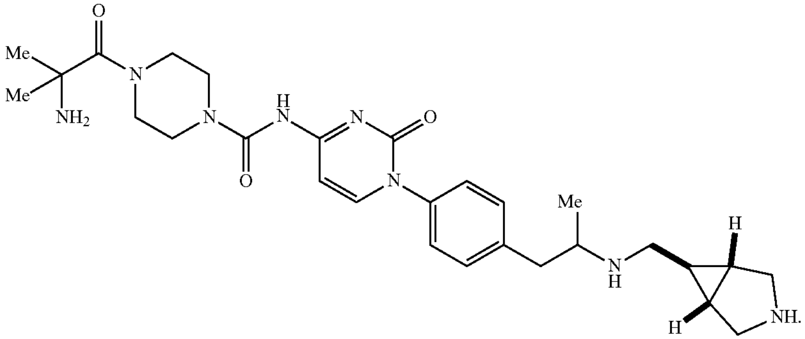 |

TABLE 10
| No. | Structure |
|---|---|
| 205 | 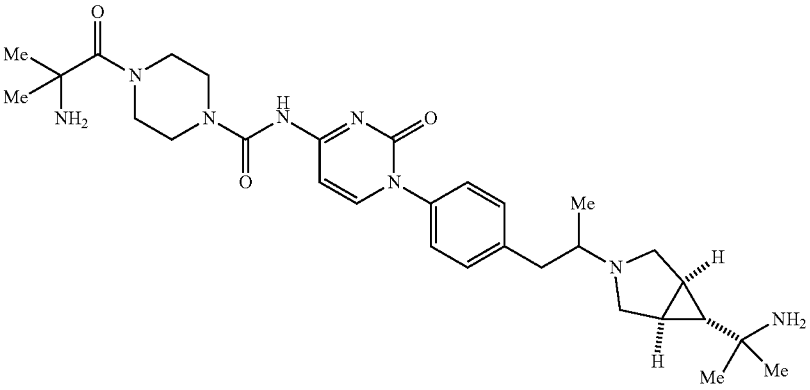 [SMILES: CC(Cc1ccc(-n2ccc(NC(=O)N3CCN(C(=O)C(C)(C)N)CC3)nc2=O)cc1)N1C[C@@H]2[C@H](C1)[C@H]2C(C)(C)N] |
| 206 | 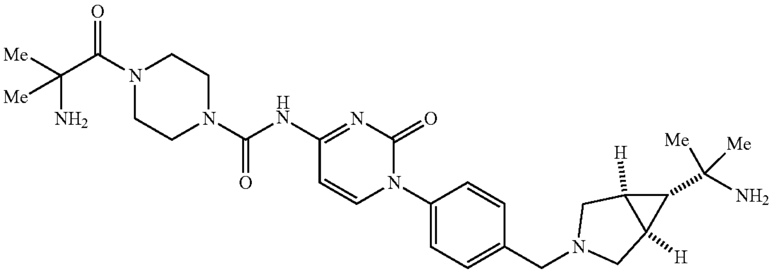 [SMILES: CC(C)(N)C(=O)N1CCN(C(=O)Nc2ccn(-c3ccc(CN4C[C@@H]5[C@H](C4)[C@H]5C(C)(C)N)cc3)c(=O)n2)CC1] |
| 207 | 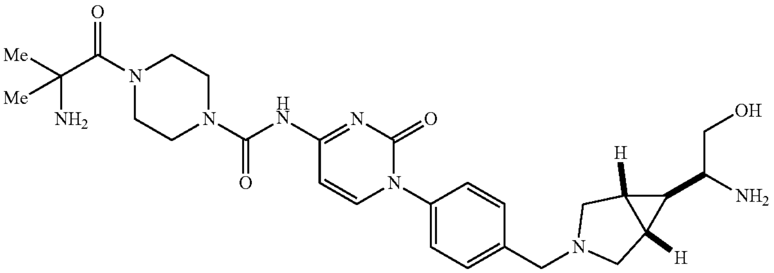 [SMILES: CC(C)(N)C(=O)N1CCN(C(=O)Nc2ccn(-c3ccc(CN4C[C@@H]5C([C@H](N)CO)[C@@H]5C4)cc3)c(=O)n2)CC1] |
| 208 | 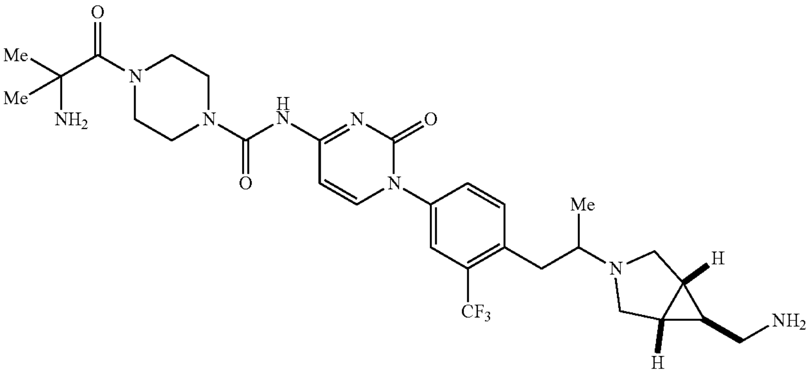 [SMILES: CC(Cc1ccc(-n2ccc(NC(=O)N3CCN(C(=O)C(C)(C)N)CC3)nc2=O)cc1C(F)(F)F)N1C[C@@H]2[C@@H](CN)[C@@H]2C1] |

TABLE 10-continued
| No. | Structure |
| --- | --- |
| 209 | 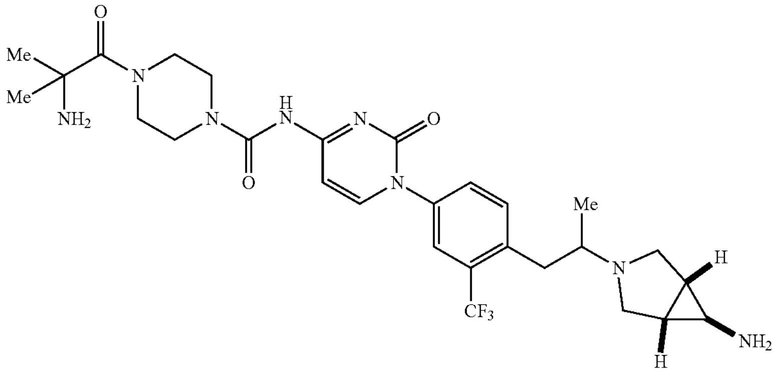 [SMILES: CC(Cc1ccc(-n2ccc(NC(=O)N3CCN(C(=O)C(C)(C)N)CC3)nc2=O)cc1C(F)(F)F)N1C[C@@H]2[C@@H](N)[C@@H]2C1] |
| 210 | 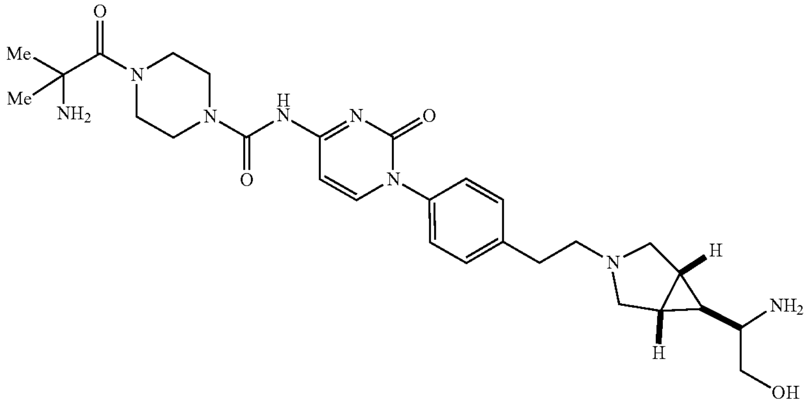 [SMILES: CC(C)(N)C(=O)N1CCN(C(=O)Nc2ccn(-c3ccc(CCN4C[C@@H]5[C@H](C4)[C@H]5C(N)CO)cc3)c(=O)n2)CC1] |
| 211 | 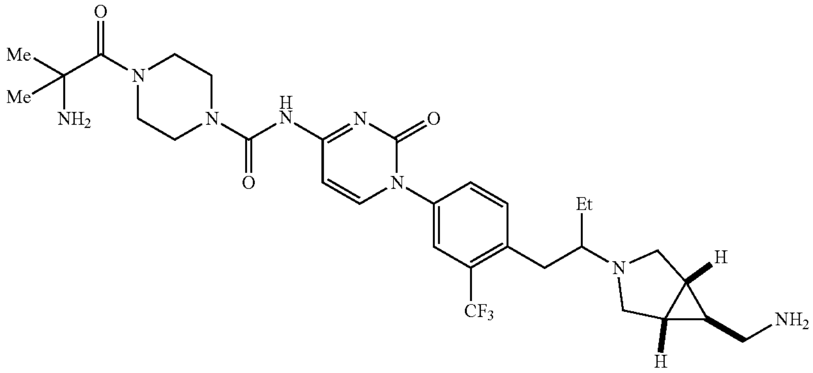 [SMILES: CCC(Cc1ccc(-n2ccc(NC(=O)N3CCN(C(=O)C(C)(C)N)CC3)nc2=O)cc1C(F)(F)F)N1C[C@@H]2[C@@H](CN)[C@@H]2C1] |
| 212 | 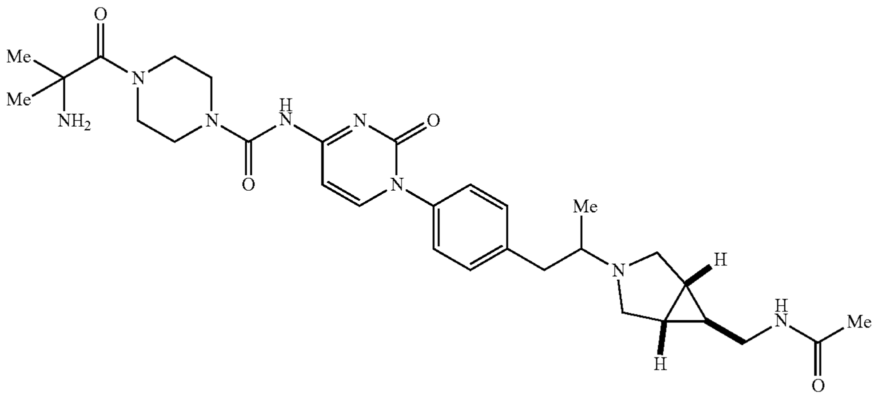 [SMILES: CC(=O)NC[C@@H]1[C@H]2CN(C(C)Cc3ccc(-n4ccc(NC(=O)N5CCN(C(=O)C(C)(C)N)CC5)nc4=O)cc3)C[C@@H]12] |

TABLE 10-continued
| No. | Structure |
| --- | --- |
| 213 | 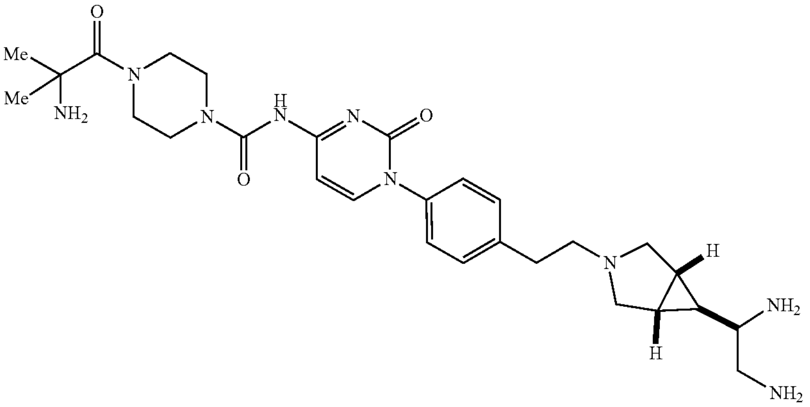 [SMILES: CC(C)(N)C(=O)N1CCN(C(=O)Nc2ccn(-c3ccc(CCN4C[C@@H]5[C@H](C4)[C@H]5C(N)CN)cc3)c(=O)n2)CC1] |
| 214 | 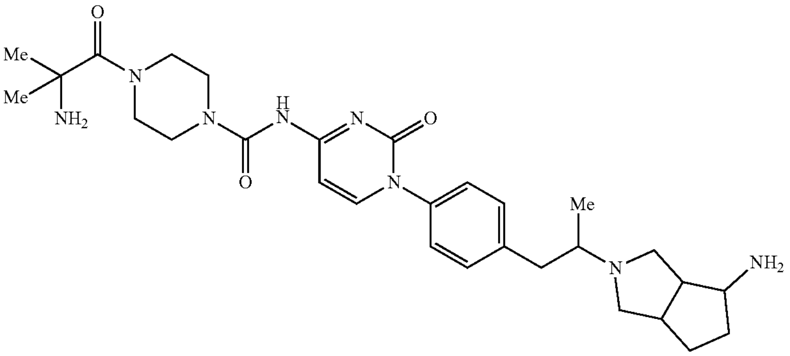 |
| 215 | 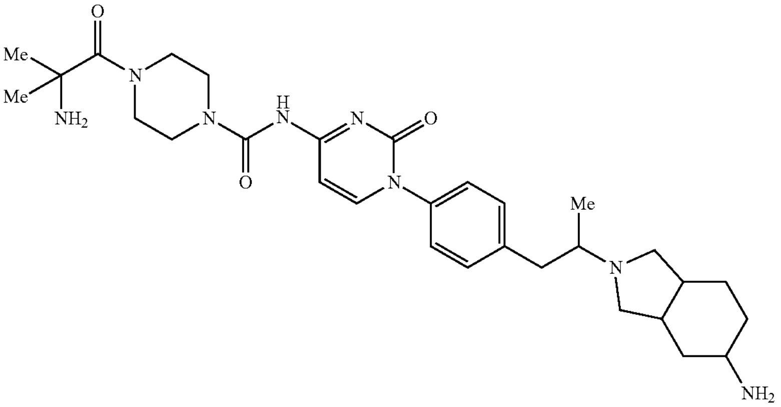 [SMILES: CC(Cc1ccc(-n2ccc(NC(=O)N3CCN(C(=O)C(C)(C)N)CC3)nc2=O)cc1)N1CC2CCC(N)CC2C1] |
| 216 | 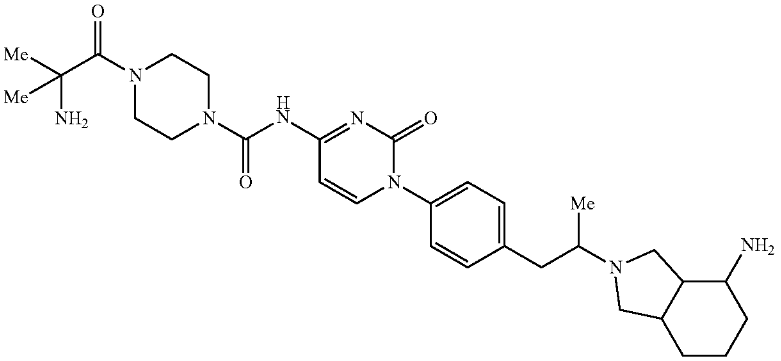 |

TABLE 10-continued
| No. | Structure |
|---|---|
| 217 | 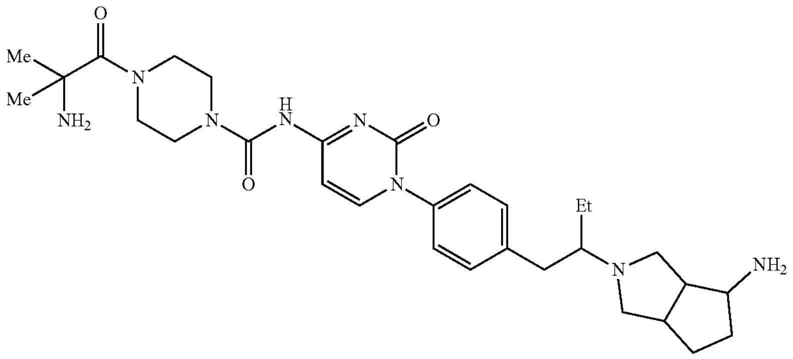 [SMILES: CCC(Cc1ccc(-n2ccc(NC(=O)N3CCN(C(=O)C(C)(C)N)CC3)nc2=O)cc1)N1CC2CCC(N)C2C1] |
| 218 | 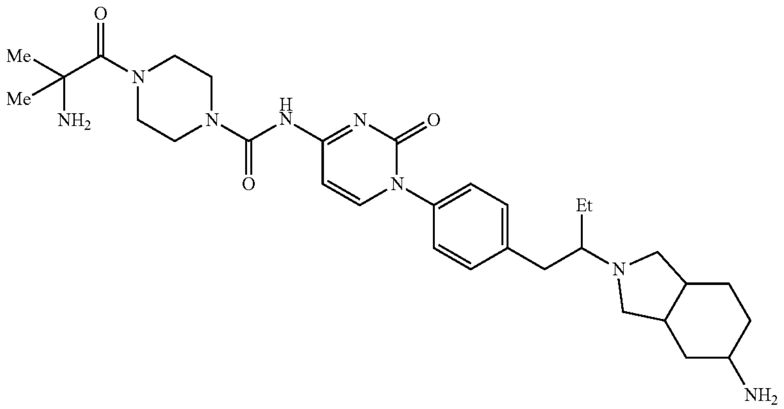 [SMILES: CCC(Cc1ccc(-n2ccc(NC(=O)N3CCN(C(=O)C(C)(C)N)CC3)nc2=O)cc1)N1CC2CCC(N)CC2C1] |
| 219 | 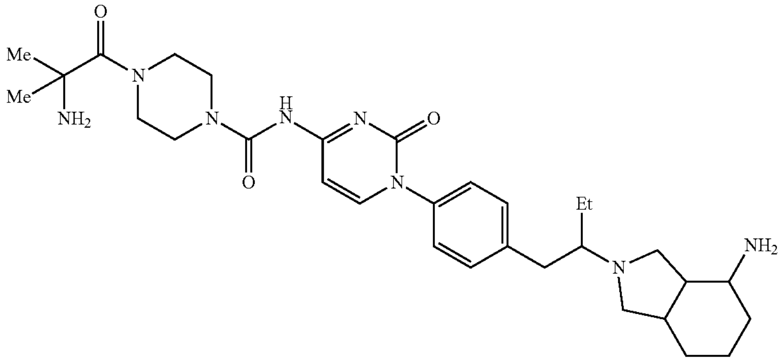 [SMILES: CCC(Cc1ccc(-n2ccc(NC(=O)N3CCN(C(=O)C(C)(C)N)CC3)nc2=O)cc1)N1CC2CCCC(N)C2C1] |
| 220 | 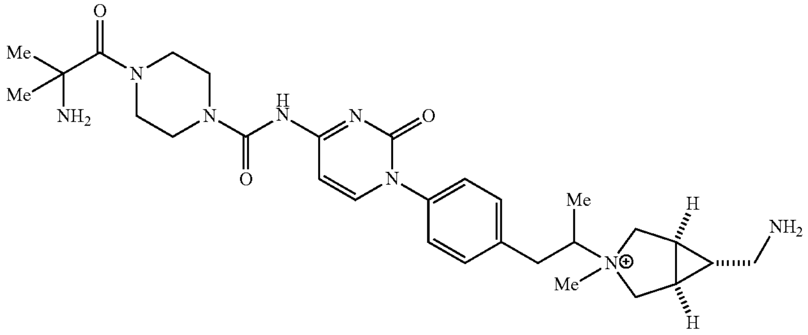 [SMILES: CC(Cc1ccc(-n2ccc(NC(=O)N3CCN(C(=O)C(C)(C)N)CC3)nc2=O)cc1)[N+]1(C)C[C@@H]2[C@@H](CN)[C@@H]2C1] |

TABLE 10-continued
| No. | Structure |
|---|---|
| 221 | 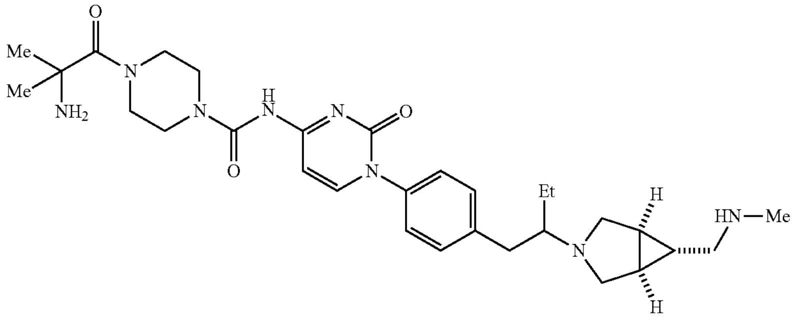 [SMILES: CCC(Cc1ccc(-n2ccc(NC(=O)N3CCN(C(=O)C(C)(C)N)CC3)nc2=O)cc1)N1C[C@@H]2[C@@H](CNC)[C@@H]2C1] |
| 222 | 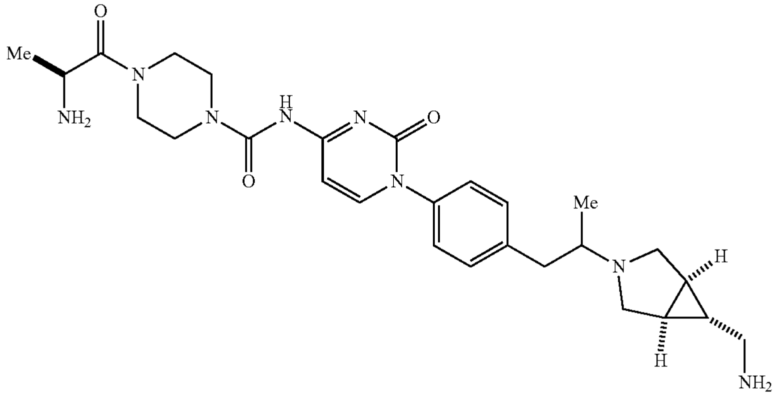 [SMILES: CC(Cc1ccc(-n2ccc(NC(=O)N3CCN(C(=O)[C@H](C)N)CC3)nc2=O)cc1)N1C[C@@H]2[C@@H](CN)[C@@H]2C1] |
| 223 | 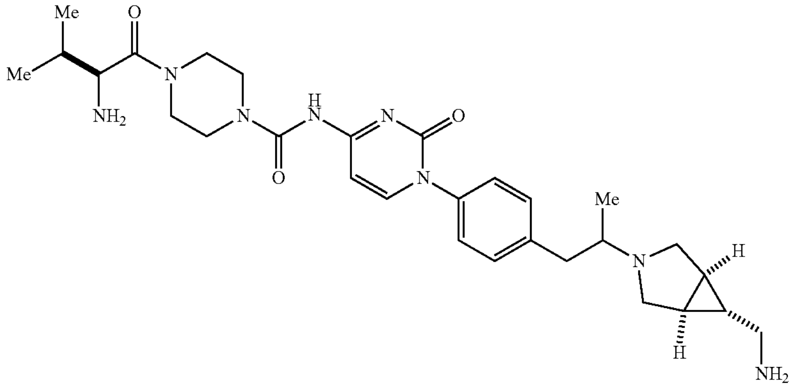 [SMILES: CC(C)[C@H](N)C(=O)N1CCN(C(=O)Nc2ccn(-c3ccc(CC(C)N4C[C@@H]5[C@@H](CN)[C@@H]5C4)cc3)c(=O)n2)CC1] |
| 224 | 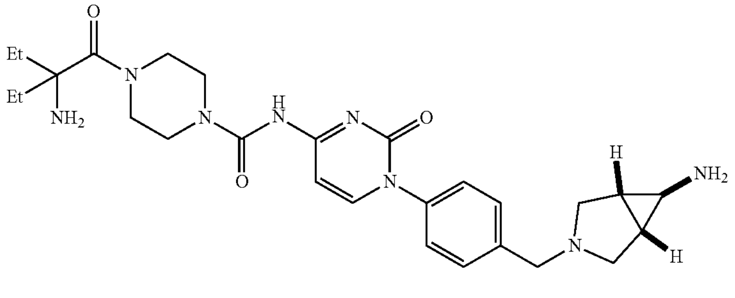 [SMILES: CCC(N)(CC)C(=O)N1CCN(C(=O)Nc2ccn(-c3ccc(CN4C[C@@H]5[C@@H](N)[C@@H]5C4)cc3)c(=O)n2)CC1] |

TABLE 10-continued
| No. | Structure |
|---|---|
| 225 | 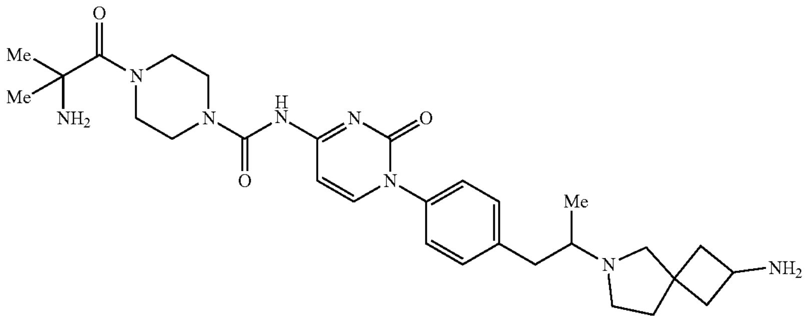 [SMILES: CC(Cc1ccc(-n2ccc(NC(=O)N3CCN(C(=O)C(C)(C)N)CC3)nc2=O)cc1)N1CCC2(CC(N)C2)C1] |
| 226 | 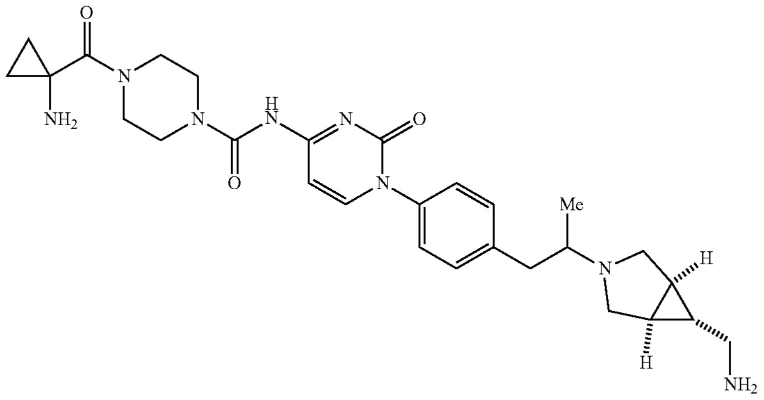 [SMILES: CC(Cc1ccc(-n2ccc(NC(=O)N3CCN(C(=O)C4(N)CC4)CC3)nc2=O)cc1)N1C[C@@H]2[C@@H](CN)[C@@H]2C1] |
| 227 | 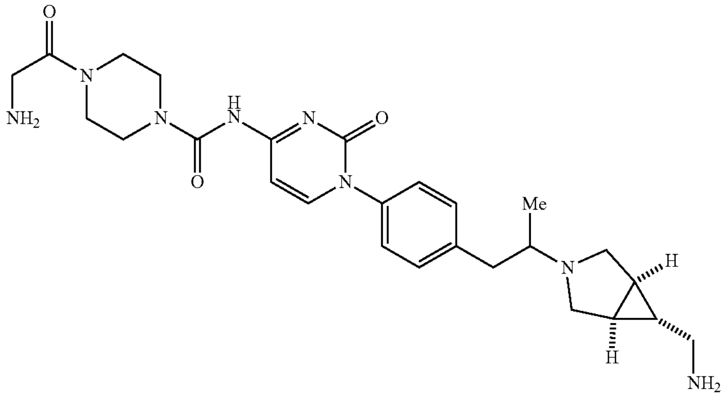 [SMILES: CC(Cc1ccc(-n2ccc(NC(=O)N3CCN(C(=O)CN)CC3)nc2=O)cc1)N1C[C@@H]2[C@@H](CN)[C@@H]2C1] |
| 228 | 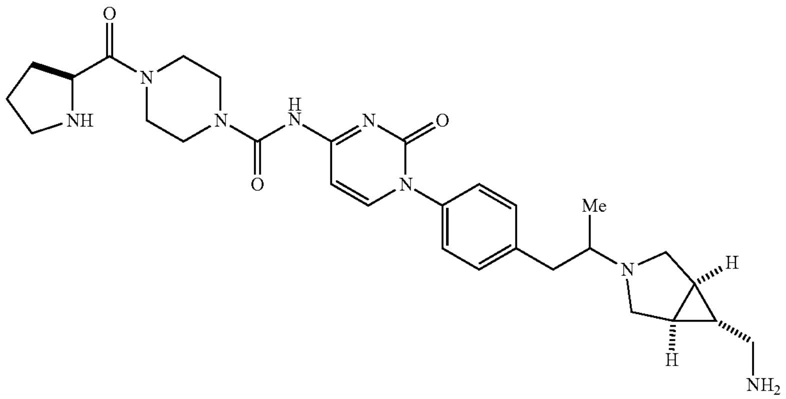 [SMILES: CC(Cc1ccc(-n2ccc(NC(=O)N3CCN(C(=O)[C@@H]4CCCN4)CC3)nc2=O)cc1)N1C[C@@H]2[C@@H](CN)[C@@H]2C1] |

TABLE 10-continued
| No. | Structure |
| --- | --- |
| 229 | 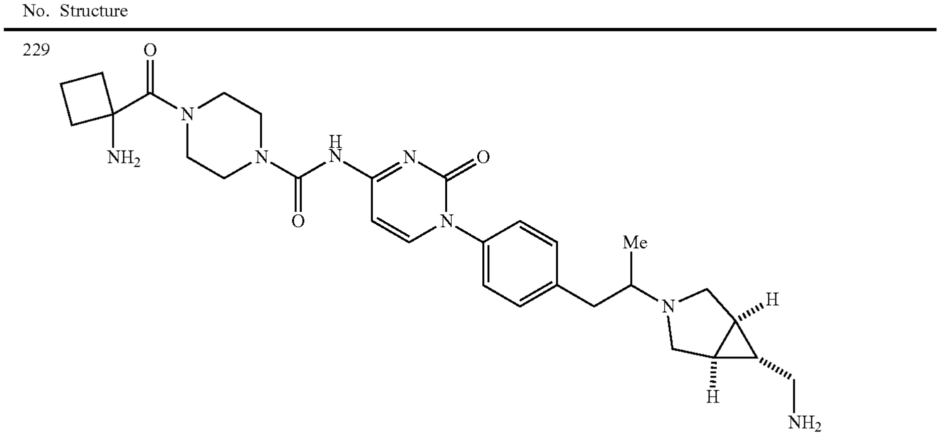 |
| 230 | 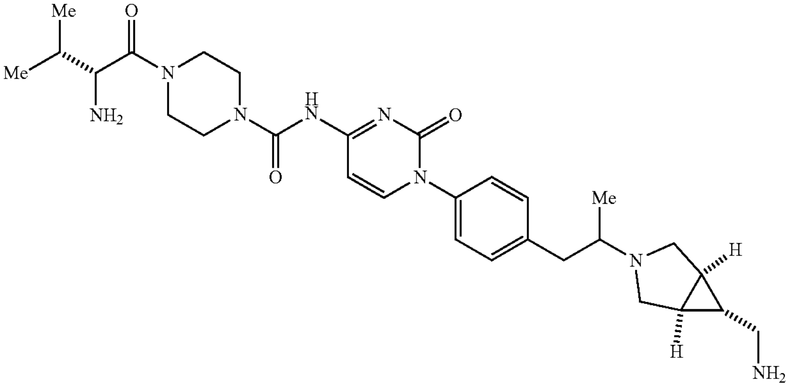 [SMILES: CC(C)[C@@H](N)C(=O)N1CCN(C(=O)Nc2ccn(-c3ccc(CC(C)N4C[C@@H]5[C@@H](CN)[C@@H]5C4)cc3)c(=O)n2)CC1] |
| 231 | 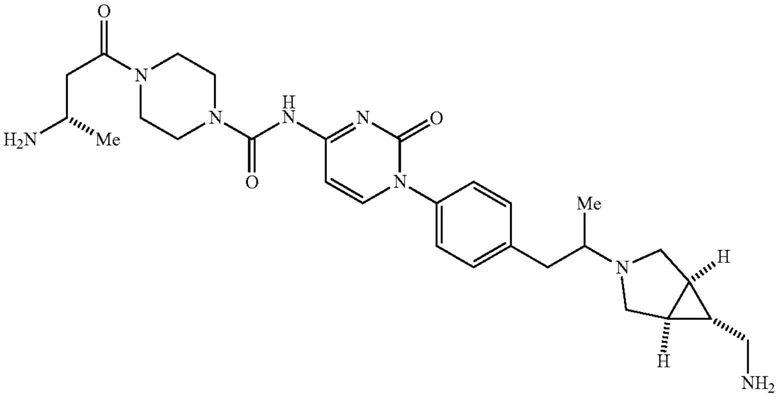 [SMILES: CC(Cc1ccc(-n2ccc(NC(=O)N3CCN(C(=O)C[C@H](C)N)CC3)nc2=O)cc1)N1C[C@@H]2[C@@H](CN)[C@@H]2C1] |
| 232 | 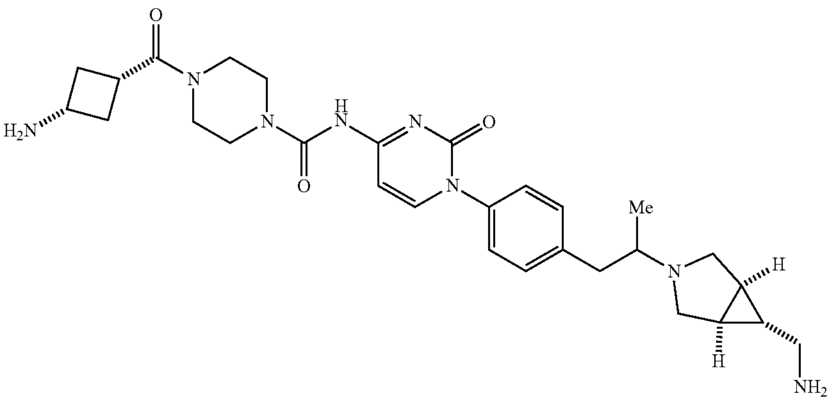 |

TABLE 10-continued
| No. | Structure |
|---|---|
| 233 | 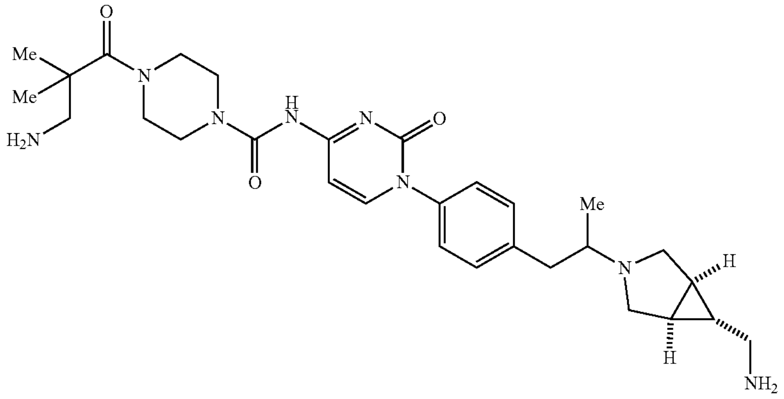 [SMILES: CC(Cc1ccc(-n2ccc(NC(=O)N3CCN(C(=O)C(C)(C)CN)CC3)nc2=O)cc1)N1C[C@@H]2[C@@H](CN)[C@@H]2C1] |
| 234 | 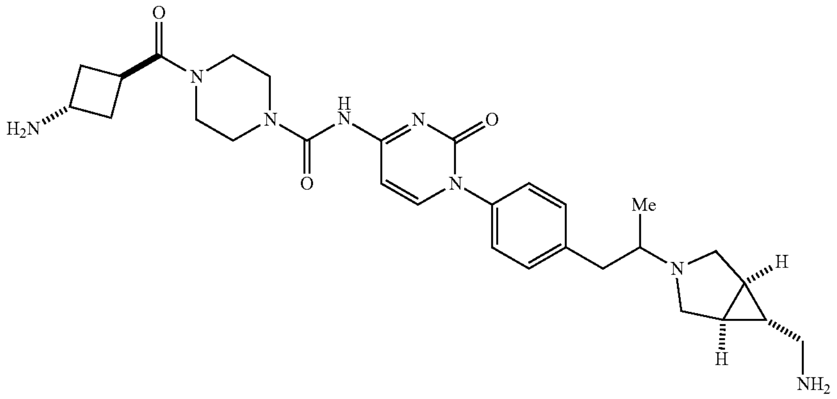 |
| 235 | 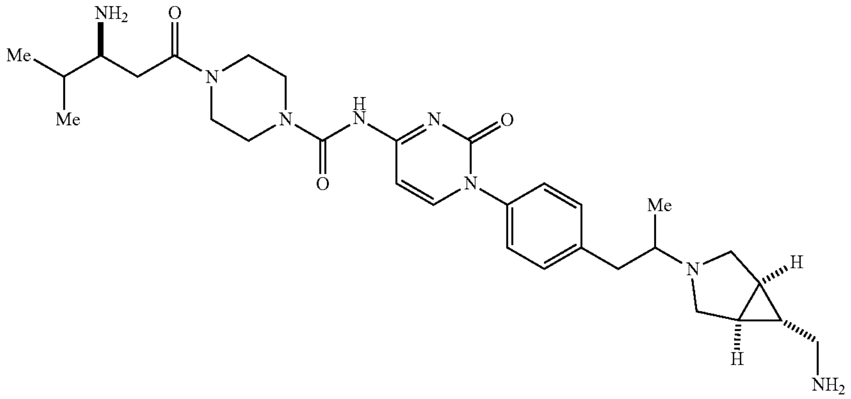 [SMILES: CC(C)[C@@H](N)CC(=O)N1CCN(C(=O)Nc2ccn(-c3ccc(CC(C)N4C[C@@H]5[C@@H](CN)[C@@H]5C4)cc3)c(=O)n2)CC1] |
| 236 | 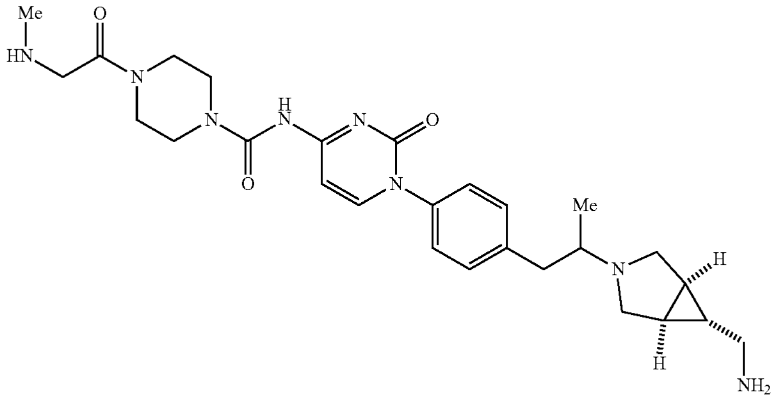 [SMILES: CNCC(=O)N1CCN(C(=O)Nc2ccn(-c3ccc(CC(C)N4C[C@@H]5[C@@H](CN)[C@@H]5C4)cc3)c(=O)n2)CC1] |

TABLE 10-continued
| No. | Structure |
|---|---|
| 237 | 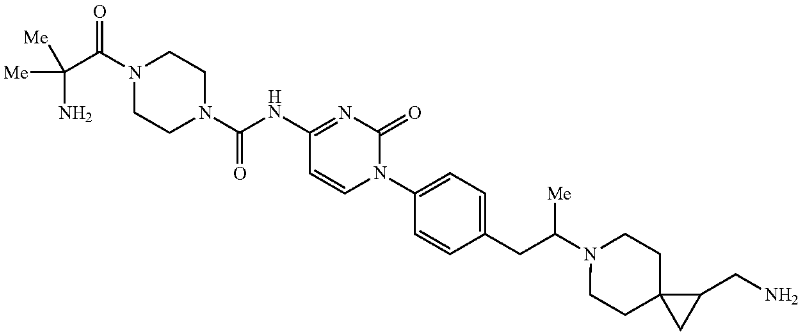 [SMILES: CC(Cc1ccc(-n2ccc(NC(=O)N3CCN(C(=O)C(C)(C)N)CC3)nc2=O)cc1)N1CCC2(CC1)CC2CN] |
| 238 | 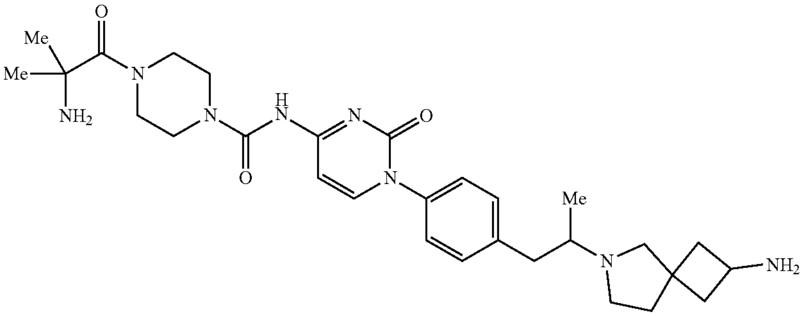 [SMILES: CC(Cc1ccc(-n2ccc(NC(=O)N3CCN(C(=O)C(C)(C)N)CC3)nc2=O)cc1)N1CCC2(CC(N)C2)C1] |
| 239 | 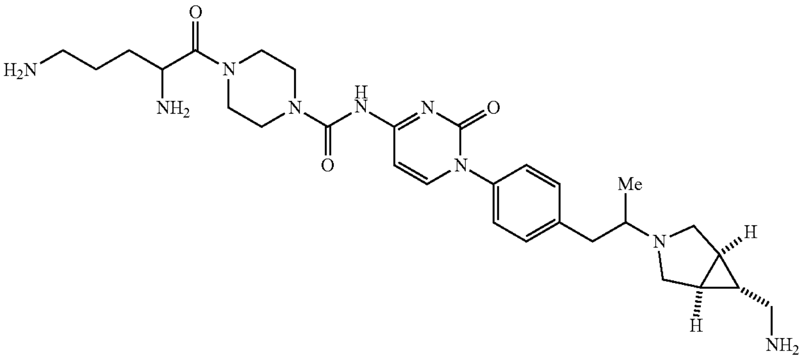 [SMILES: CC(Cc1ccc(-n2ccc(NC(=O)N3CCN(C(=O)C(N)CCCN)CC3)nc2=O)cc1)N1C[C@@H]2[C@@H](CN)[C@@H]2C1] |
| 240 | 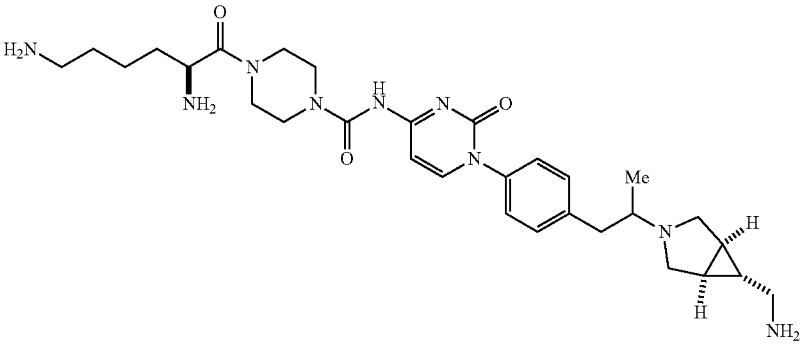 [SMILES: CC(Cc1ccc(-n2ccc(NC(=O)N3CCN(C(=O)[C@@H](N)CCCCN)CC3)nc2=O)cc1)N1C[C@@H]2[C@@H](CN)[C@@H]2C1] |

TABLE 10-continued
| No. | Structure |
|---|---|
| 241 | 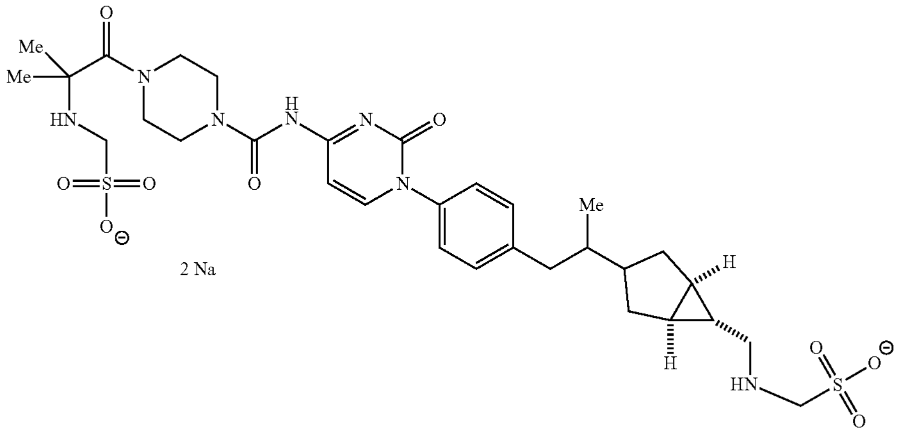 [SMILES: CC(Cc1ccc(-n2ccc(NC(=O)N3CCN(C(=O)C(C)(C)NCS(=O)(=O)[O-])CC3)nc2=O)cc1)C1C[C@@H]2[C@@H](CNCS(=O)(=O)[O-])[C@@H]2C1] |
| 242 | 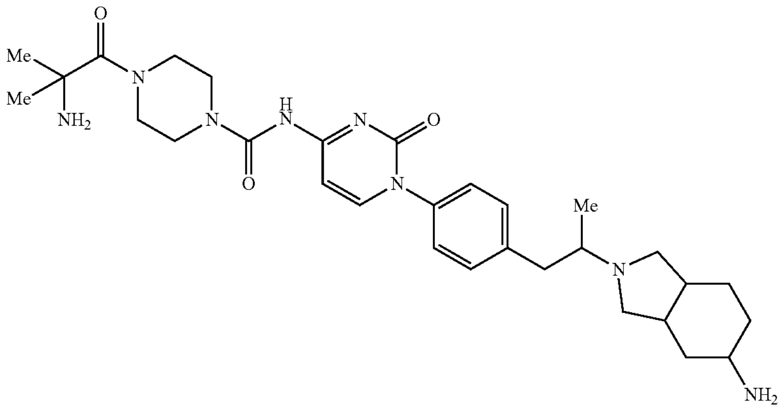<br>Diastereomer-1 |
| 243 | 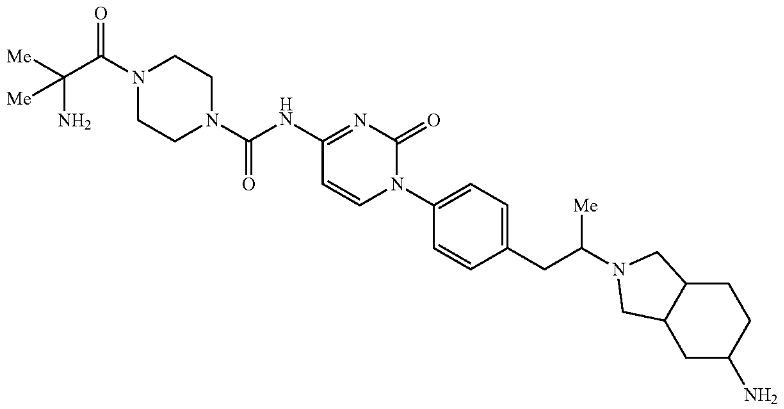<br>Diastereomer-2 |

TABLE 10-continued
| No. | Structure |
|---|---|
| 244 | 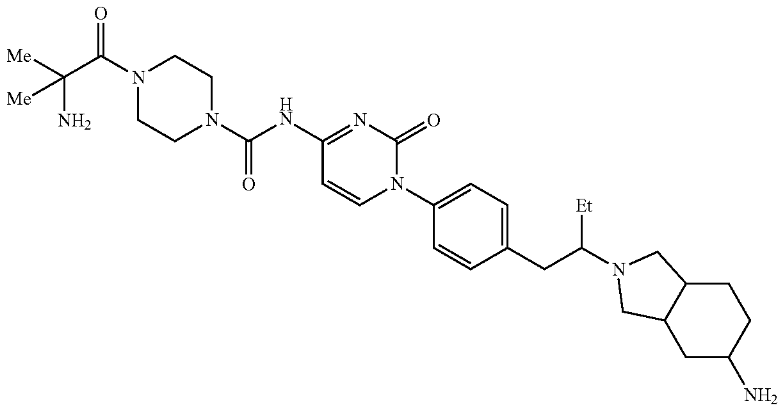<br>Diastereomer-1 |
| 245 | 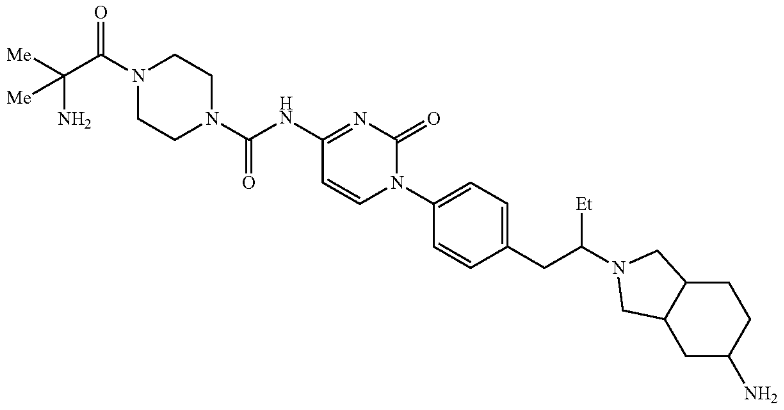<br>Diastereomer-2 |
| 246 | 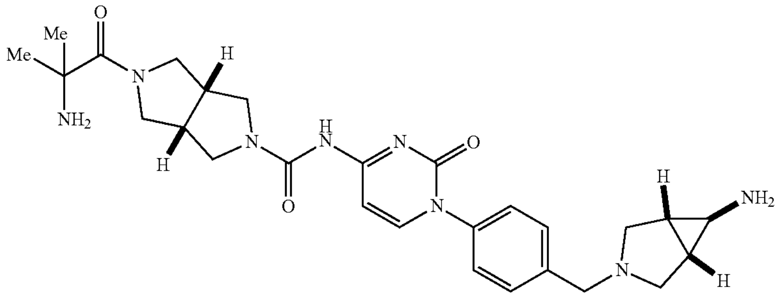 [SMILES: CC(C)(N)C(=O)N1C[C@H]2CN(C(=O)Nc3ccn(-c4ccc(CN5C[C@@H]6[C@@H](N)[C@@H]6C5)cc4)c(=O)n3)C[C@H]2C1] |
| 247 | 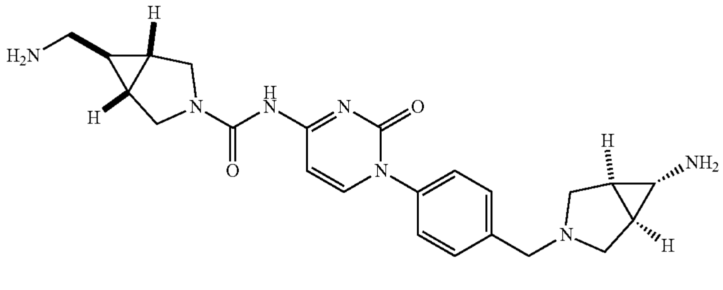 [SMILES: NC[C@@H]1[C@H]2CN(C(=O)Nc3ccn(-c4ccc(CN5C[C@@H]6[C@@H](N)[C@@H]6C5)cc4)c(=O)n3)C[C@@H]12] |

TABLE 10-continued
| No. | Structure |
|---|---|
| 248 | 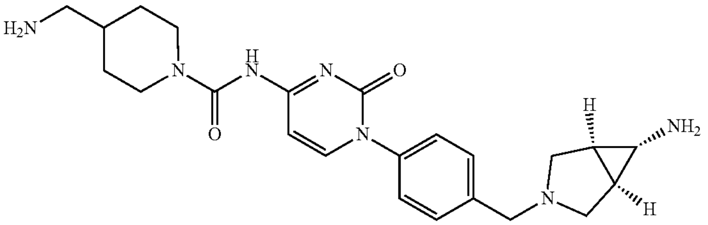 [SMILES: NCC1CCN(C(=O)Nc2ccn(-c3ccc(CN4C[C@@H]5[C@@H](N)[C@@H]5C4)cc3)c(=O)n2)CC1] |
| 249 | 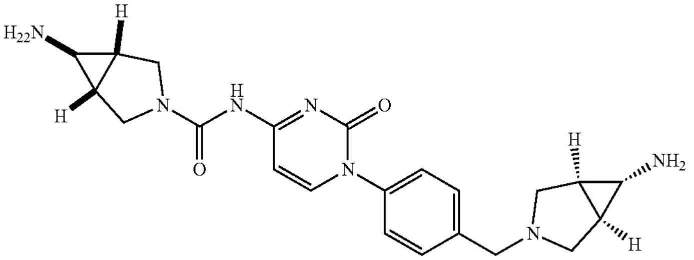 |
| 250 | 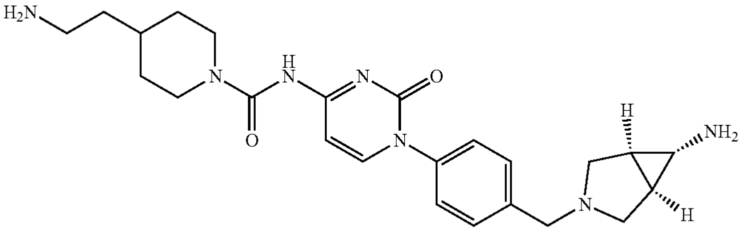 [SMILES: NCCC1CCN(C(=O)Nc2ccn(-c3ccc(CN4C[C@@H]5[C@@H](N)[C@@H]5C4)cc3)c(=O)n2)CC1] |
| 251 | 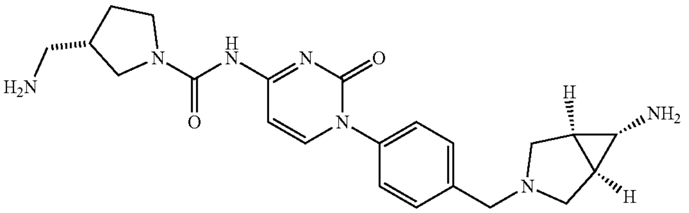 [SMILES: NC[C@@H]1CCN(C(=O)Nc2ccn(-c3ccc(CN4C[C@@H]5[C@@H](N)[C@@H]5C4)cc3)c(=O)n2)C1] |
| 252 | 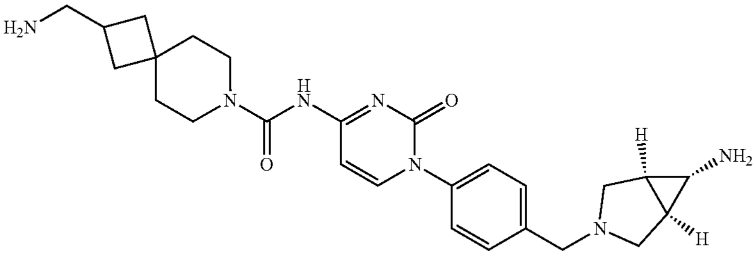 [SMILES: NCC1CC2(CCN(C(=O)Nc3ccn(-c4ccc(CN5C[C@@H]6[C@@H](N)[C@@H]6C5)cc4)c(=O)n3)CC2)C1] |
| 253 | 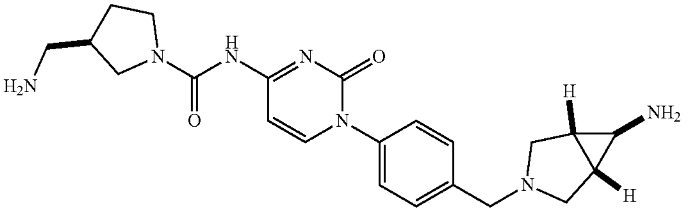 [SMILES: NC[C@H]1CCN(C(=O)Nc2ccn(-c3ccc(CN4C[C@@H]5[C@@H](N)[C@@H]5C4)cc3)c(=O)n2)C1] |

TABLE 10-continued
| No. | Structure |
| --- | --- |
| 254 | 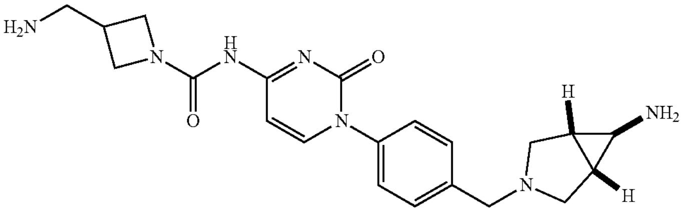 [SMILES: NCC1CN(C(=O)Nc2ccn(-c3ccc(CN4C[C@@H]5[C@@H](N)[C@@H]5C4)cc3)c(=O)n2)C1] |
| 255 | 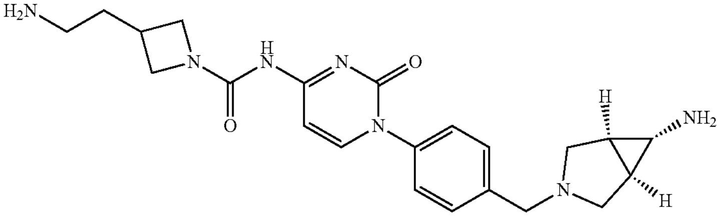 [SMILES: NCCC1CN(C(=O)Nc2ccn(-c3ccc(CN4C[C@@H]5[C@@H](N)[C@@H]5C4)cc3)c(=O)n2)C1] |
TABLE 11
| Structure |
| --- |
| 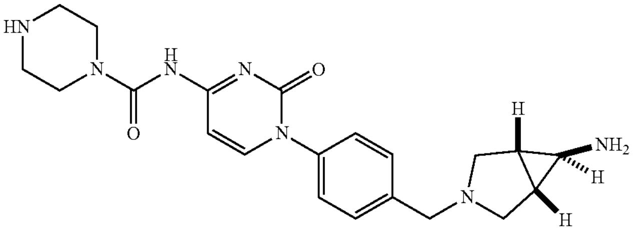 [SMILES: N[C@@H]1[C@H]2CN(Cc3ccc(-n4ccc(NC(=O)N5CCNCC5)nc4=O)cc3)C[C@@H]12] |
| 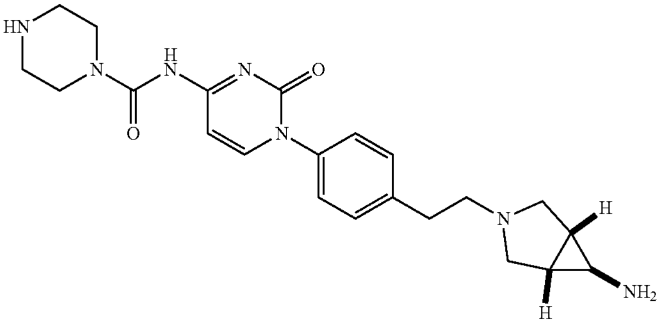 [SMILES: N[C@@H]1[C@H]2CN(CCc3ccc(-n4ccc(NC(=O)N5CCNCC5)nc4=O)cc3)C[C@@H]12] |
| 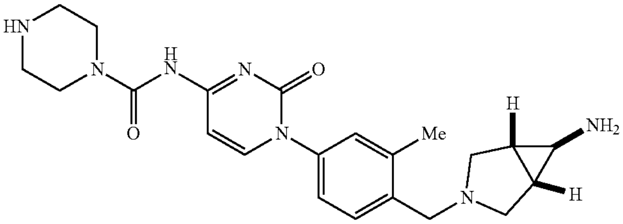 [SMILES: Cc1cc(-n2ccc(NC(=O)N3CCNCC3)nc2=O)ccc1CN1C[C@@H]2[C@@H](N)[C@@H]2C1] |
| 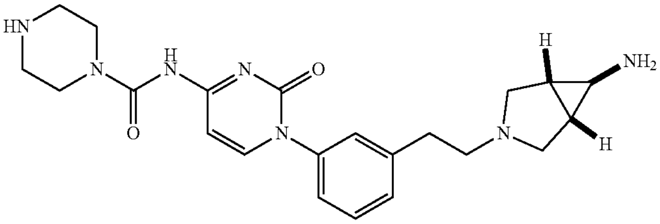 [SMILES: N[C@@H]1[C@H]2CN(CCc3cccc(-n4ccc(NC(=O)N5CCNCC5)nc4=O)c3)C[C@@H]12] |

TABLE 11-continued
| Structure |
| --- |
| 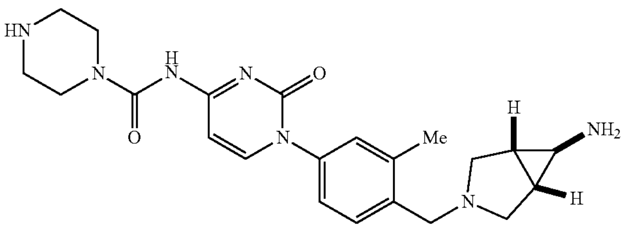 |
| 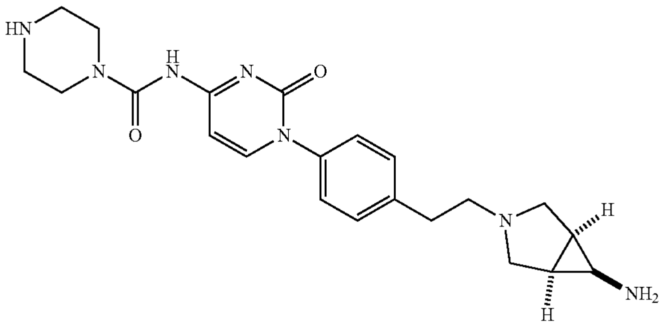 [SMILES: N[C@H]1[C@H]2CN(CCc3ccc(-n4ccc(NC(=O)N5CCNCC5)nc4=O)cc3)C[C@@H]12] |
| 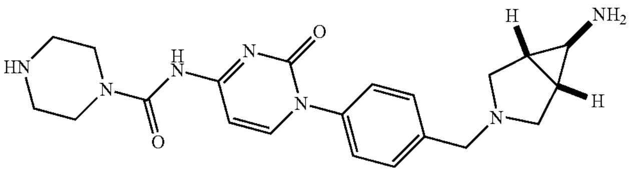 [SMILES: N[C@@H]1[C@H]2CN(Cc3ccc(-n4ccc(NC(=O)N5CCNCC5)nc4=O)cc3)C[C@@H]12] |
| 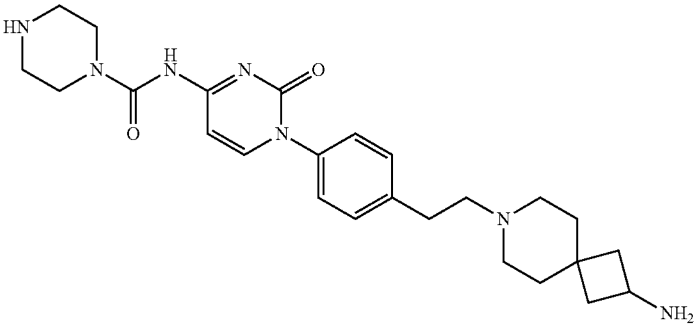 [SMILES: NC1CC2(CCN(CCc3ccc(-n4ccc(NC(=O)N5CCNCC5)nc4=O)cc3)CC2)C1] |
| 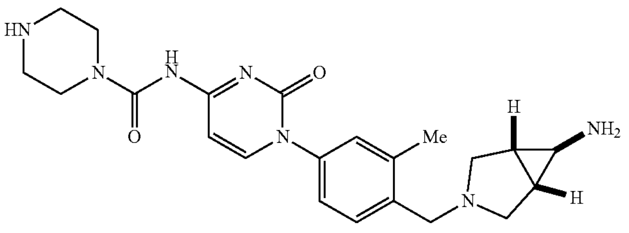 [SMILES: Cc1cc(-n2ccc(NC(=O)N3CCNCC3)nc2=O)ccc1CN1C[C@@H]2[C@@H](N)[C@@H]2C1] |

TABLE 11-continued
| Structure |
|---|
| 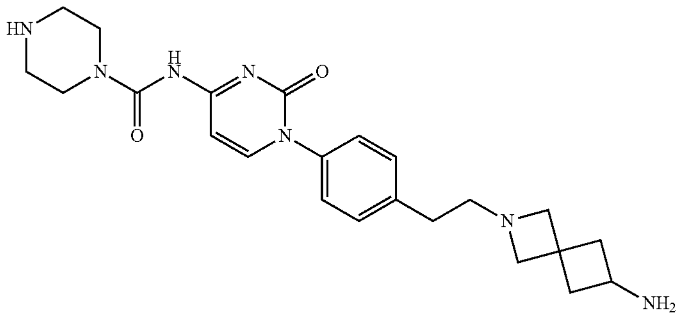 [SMILES: NC1CC2(C1)CN(CCc1ccc(-n3ccc(NC(=O)N4CCNCC4)nc3=O)cc1)C2] |
| 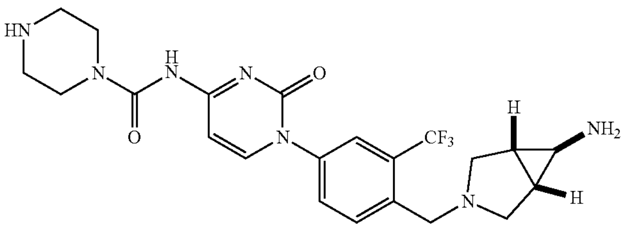 [SMILES: N[C@@H]1[C@H]2CN(Cc3ccc(-n4ccc(NC(=O)N5CCNCC5)nc4=O)cc3C(F)(F)F)C[C@@H]12] |
| 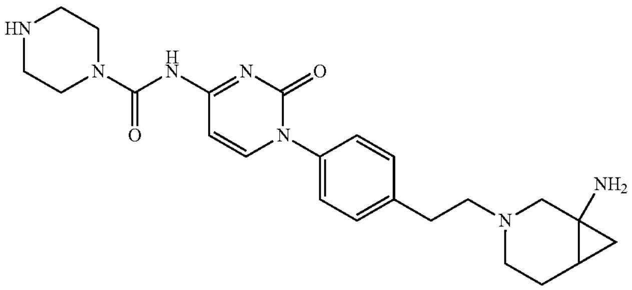 [SMILES: NC12CC1CCN(CCc1ccc(-n3ccc(NC(=O)N4CCNCC4)nc3=O)cc1)C2] |
| 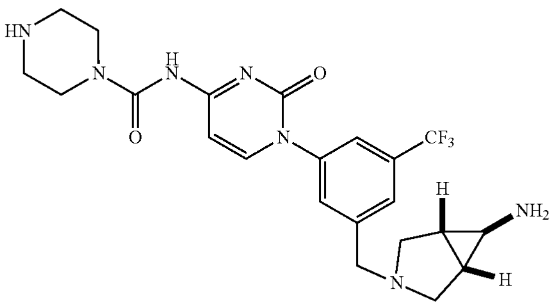 [SMILES: N[C@@H]1[C@H]2CN(Cc3cc(-n4ccc(NC(=O)N5CCNCC5)nc4=O)cc(C(F)(F)F)c3)C[C@@H]12] |
| 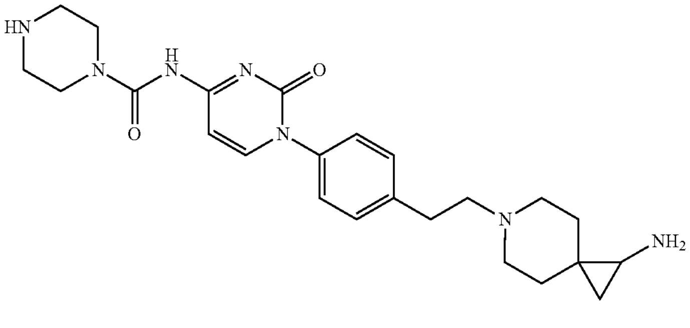 [SMILES: NC1CC12CCN(CCc1ccc(-n3ccc(NC(=O)N4CCNCC4)nc3=O)cc1)CC2] |

TABLE 11-continued
| Structure |
| --- |
| 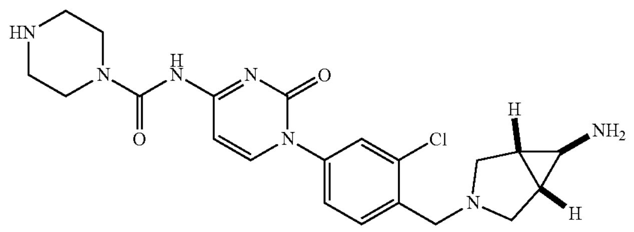 [SMILES: N[C@@H]1[C@H]2CN(Cc3ccc(-n4ccc(NC(=O)N5CCNCC5)nc4=O)cc3Cl)C[C@@H]12] |
| 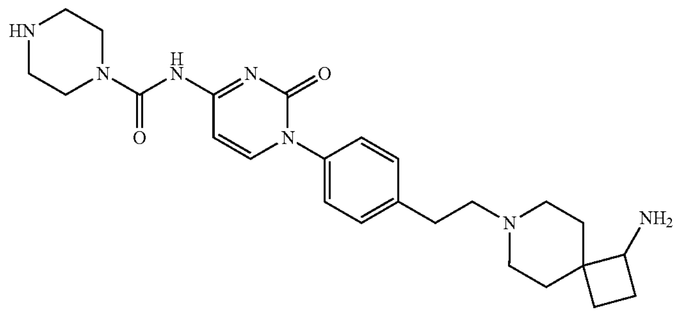 [SMILES: NC1CCC12CCN(CCc1ccc(-n3ccc(NC(=O)N4CCNCC4)nc3=O)cc1)CC2] |
| 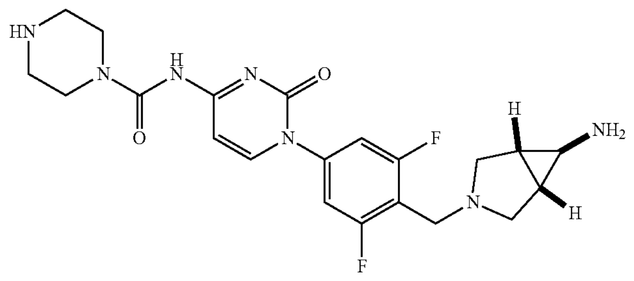 [SMILES: N[C@@H]1[C@H]2CN(Cc3c(F)cc(-n4ccc(NC(=O)N5CCNCC5)nc4=O)cc3F)C[C@@H]12] |
| 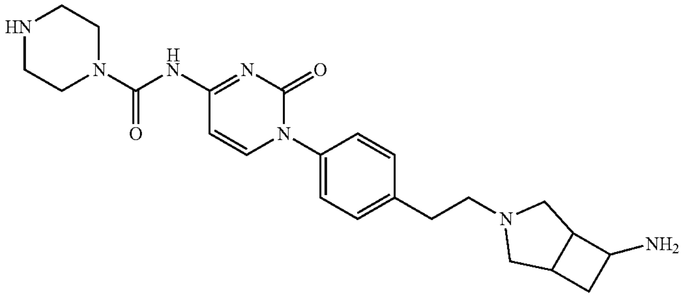 [SMILES: NC1CC2CN(CCc3ccc(-n4ccc(NC(=O)N5CCNCC5)nc4=O)cc3)CC12] |
| 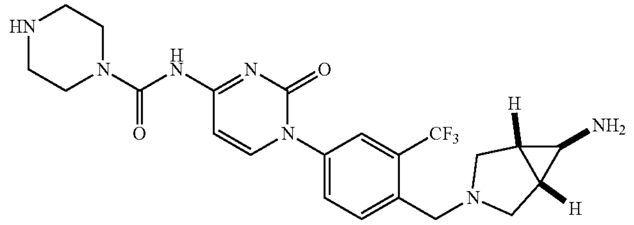 [SMILES: N[C@@H]1[C@H]2CN(Cc3ccc(-n4ccc(NC(=O)N5CCNCC5)nc4=O)cc3C(F)(F)F)C[C@@H]12] |

TABLE 11-continued
| Structure |
|---|
| 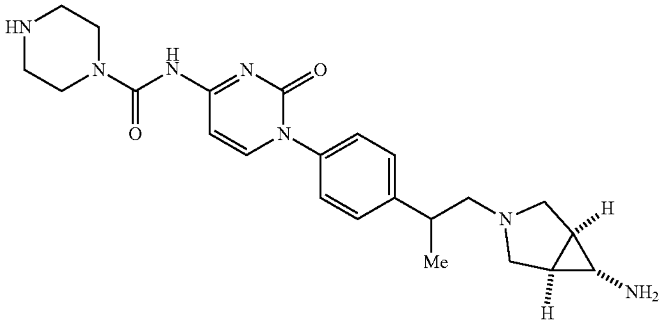 [SMILES: CC(CN1C[C@@H]2[C@@H](N)[C@@H]2C1)c1ccc(-n2ccc(NC(=O)N3CCNCC3)nc2=O)cc1] |
| 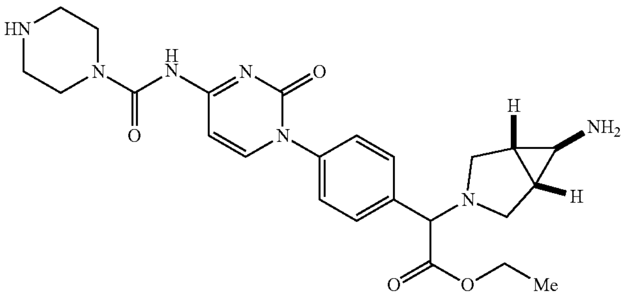 [SMILES: CCOC(=O)C(c1ccc(-n2ccc(NC(=O)N3CCNCC3)nc2=O)cc1)N1C[C@@H]2[C@@H](N)[C@@H]2C1] |
| 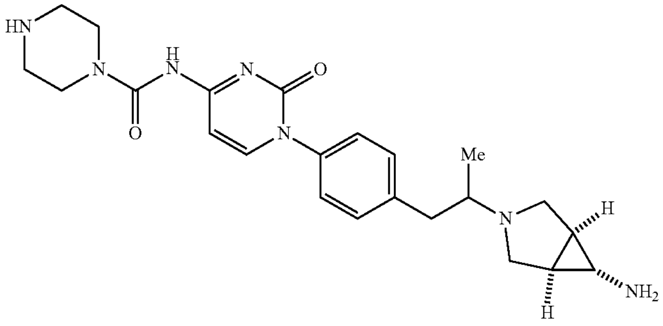 [SMILES: CC(Cc1ccc(-n2ccc(NC(=O)N3CCNCC3)nc2=O)cc1)N1C[C@@H]2[C@@H](N)[C@@H]2C1] |
| 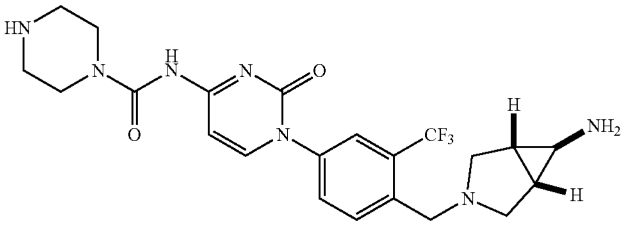 [SMILES: N[C@@H]1[C@H]2CN(Cc3ccc(-n4ccc(NC(=O)N5CCNCC5)nc4=O)cc3C(F)(F)F)C[C@@H]12] |
| 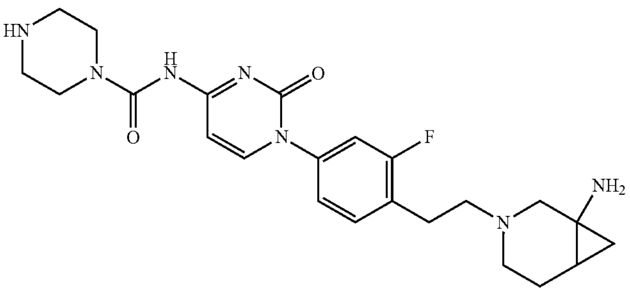 [SMILES: NC12CC1CCN(CCc1ccc(-n3ccc(NC(=O)N4CCNCC4)nc3=O)cc1F)C2] |

TABLE 11-continued
| Structure |
| --- |
| 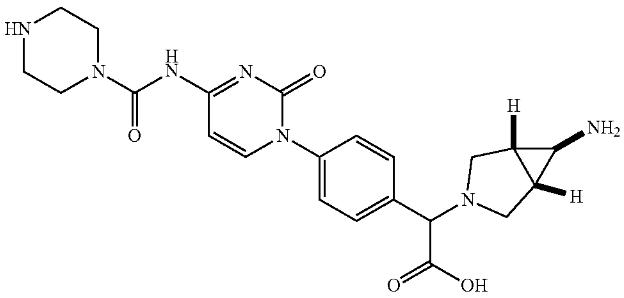 [SMILES: N[C@@H]1[C@H]2CN(C(C(=O)O)c3ccc(-n4ccc(NC(=O)N5CCNCC5)nc4=O)cc3)C[C@@H]12] |
| 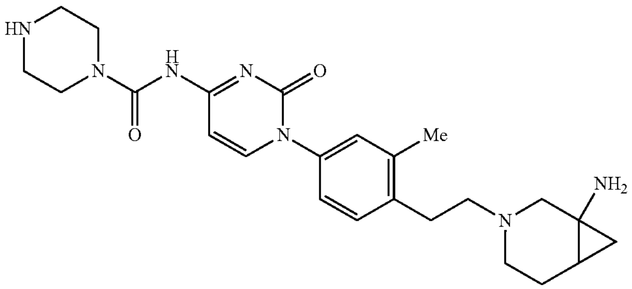 [SMILES: Cc1cc(-n2ccc(NC(=O)N3CCNCC3)nc2=O)ccc1CCN1CCC2CC2(N)C1] |
| 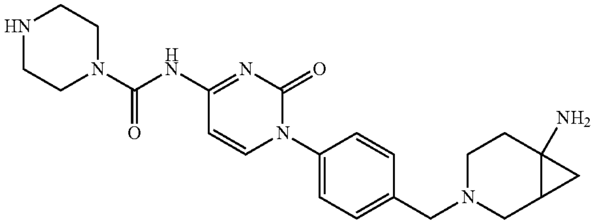 [SMILES: NC12CCN(Cc3ccc(-n4ccc(NC(=O)N5CCNCC5)nc4=O)cc3)CC1C2] |
| 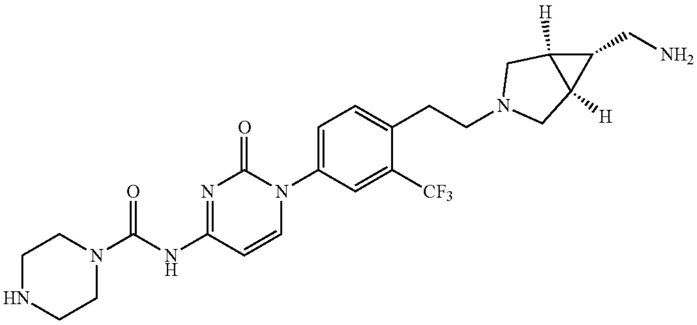 [SMILES: NC[C@@H]1[C@H]2CN(CCc3ccc(-n4ccc(NC(=O)N5CCNCC5)nc4=O)cc3C(F)(F)F)C[C@@H]12] |
| 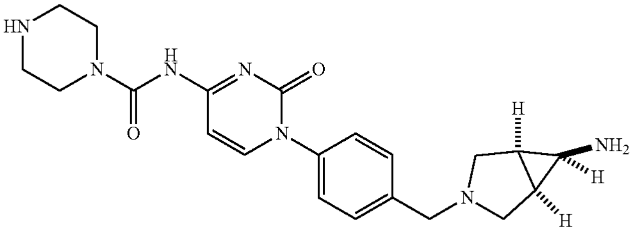 [SMILES: N[C@H]1[C@H]2CN(Cc3ccc(-n4ccc(NC(=O)N5CCNCC5)nc4=O)cc3)C[C@@H]12] |

TABLE 11-continued
| Structure |
| --- |
| 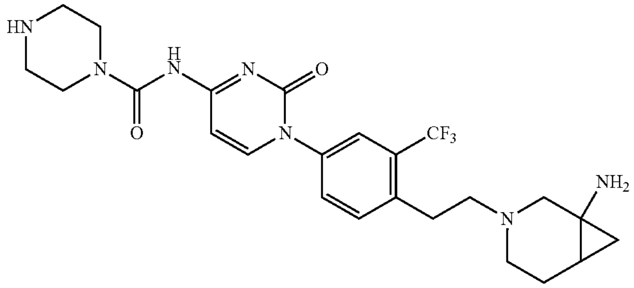 |
| 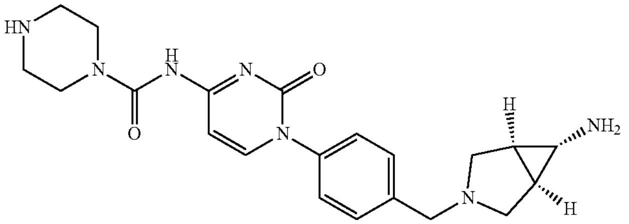 [SMILES: N[C@@H]1[C@H]2CN(Cc3ccc(-n4ccc(NC(=O)N5CCNCC5)nc4=O)cc3)C[C@@H]12] |
| 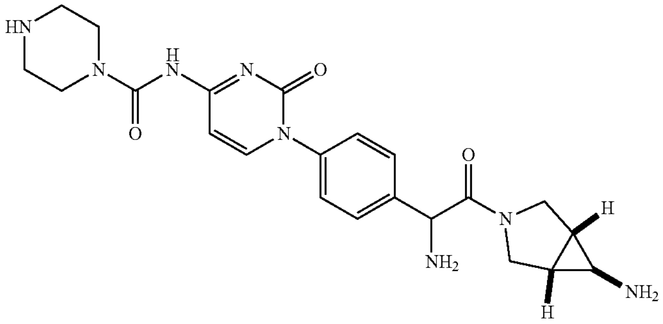 [SMILES: NC(C(=O)N1C[C@@H]2[C@@H](N)[C@@H]2C1)c1ccc(-n2ccc(NC(=O)N3CCNCC3)nc2=O)cc1] |
| 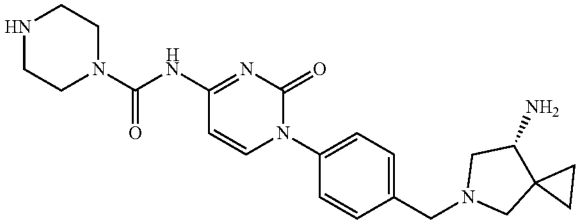 [SMILES: N[C@H]1CN(Cc2ccc(-n3ccc(NC(=O)N4CCNCC4)nc3=O)cc2)CC12CC2] |
| 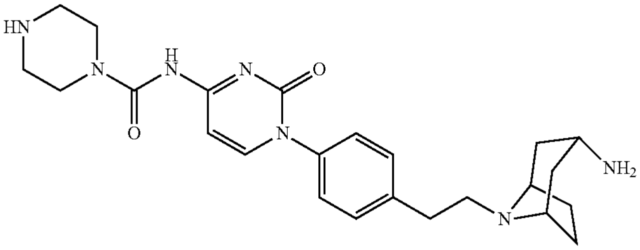 [SMILES: NC1CC2CCC(C1)N2CCc1ccc(-n2ccc(NC(=O)N3CCNCC3)nc2=O)cc1] |
| 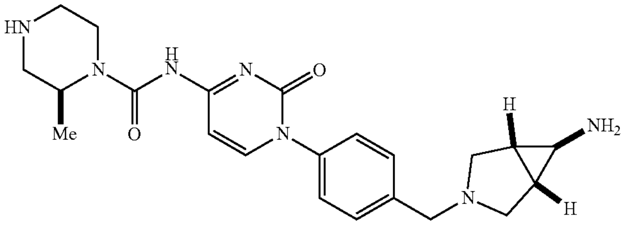 [SMILES: C[C@H]1CNCCN1C(=O)Nc1ccn(-c2ccc(CN3C[C@@H]4[C@@H](N)[C@@H]4C3)cc2)c(=O)n1] |

TABLE 11-continued
| Structure |
| --- |
| 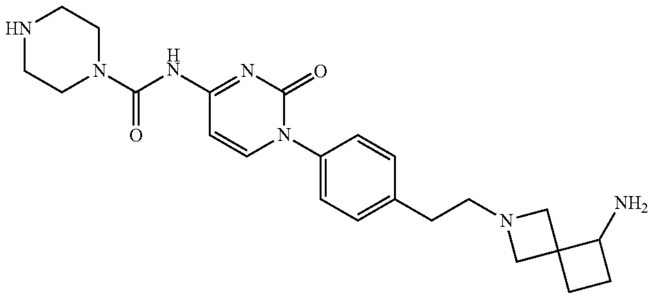 [SMILES: NC1CCC12CN(CCc1ccc(-n3ccc(NC(=O)N4CCNCC4)nc3=O)cc1)C2] |
| 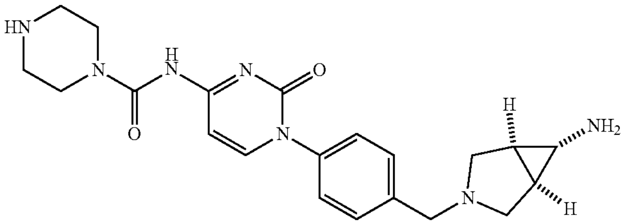 [SMILES: N[C@@H]1[C@H]2CN(Cc3ccc(-n4ccc(NC(=O)N5CCNCC5)nc4=O)cc3)C[C@@H]12] |
| 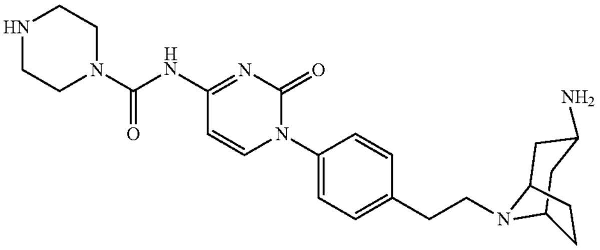 [SMILES: NC1CC2CCC(C1)N2CCc1ccc(-n2ccc(NC(=O)N3CCNCC3)nc2=O)cc1] |
| 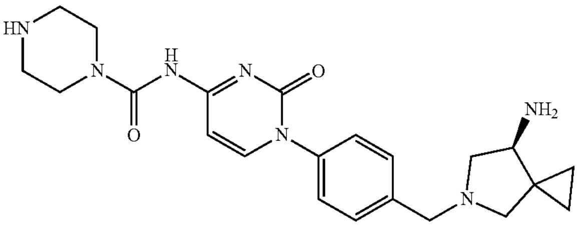 [SMILES: N[C@@H]1CN(Cc2ccc(-n3ccc(NC(=O)N4CCNCC4)nc3=O)cc2)CC12CC2] |
| 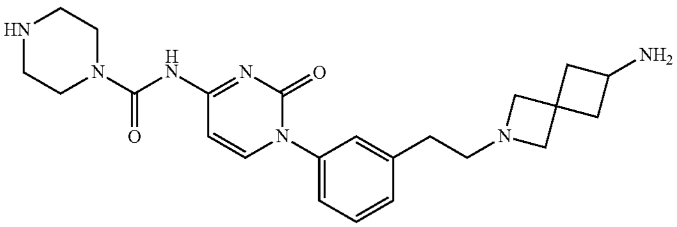 [SMILES: NC1CC2(C1)CN(CCc1cccc(-n3ccc(NC(=O)N4CCNCC4)nc3=O)c1)C2] |
| 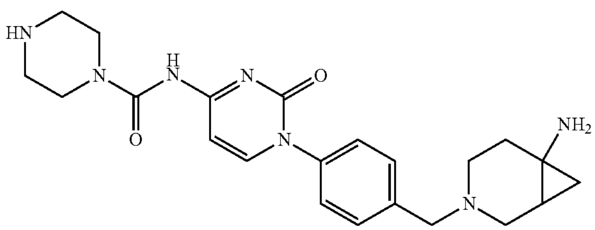 [SMILES: NC12CCN(Cc3ccc(-n4ccc(NC(=O)N5CCNCC5)nc4=O)cc3)CC1C2] |

TABLE 11-continued
| Structure |
| --- |
| 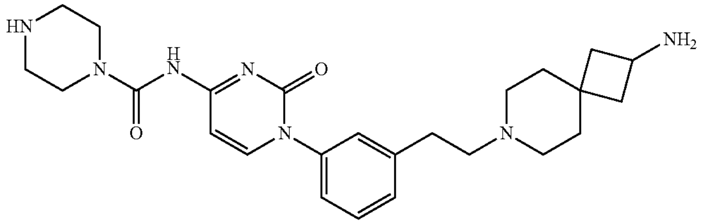 [SMILES: NC1CC2(CCN(CCc3cccc(-n4ccc(NC(=O)N5CCNCC5)nc4=O)c3)CC2)C1] |
| 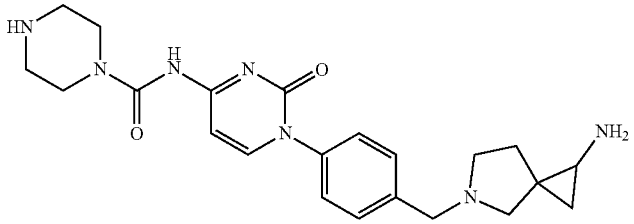 [SMILES: NC1CC12CCN(Cc1ccc(-n3ccc(NC(=O)N4CCNCC4)nc3=O)cc1)C2] |
| 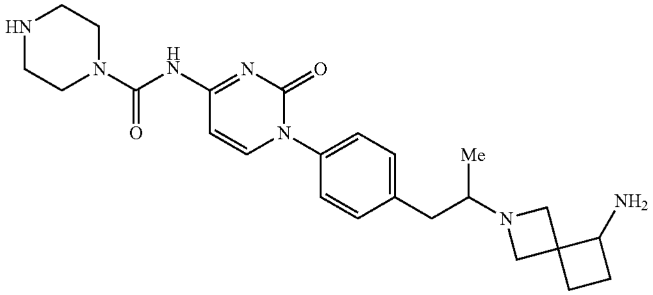 [SMILES: CC(Cc1ccc(-n2ccc(NC(=O)N3CCNCC3)nc2=O)cc1)N1CC2(CCC2N)C1] |
| 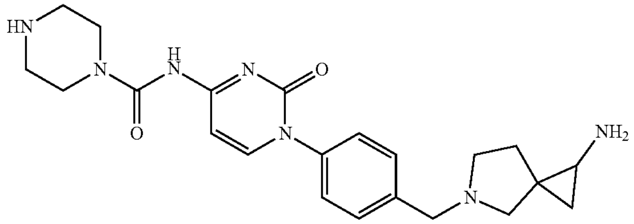 [SMILES: NC1CC12CCN(Cc1ccc(-n3ccc(NC(=O)N4CCNCC4)nc3=O)cc1)C2] |
| 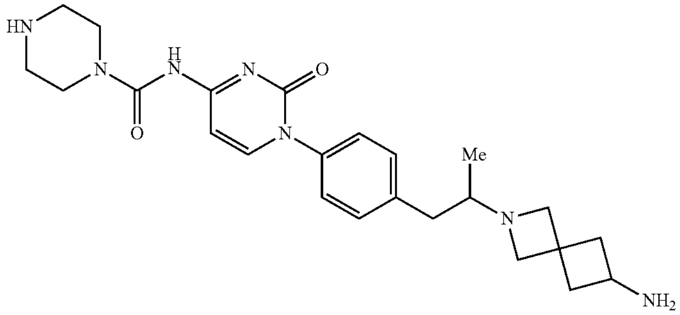 [SMILES: CC(Cc1ccc(-n2ccc(NC(=O)N3CCNCC3)nc2=O)cc1)N1CC2(CC(N)C2)C1] |
| 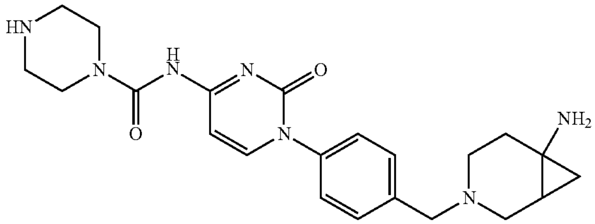 [SMILES: NC12CCN(Cc3ccc(-n4ccc(NC(=O)N5CCNCC5)nc4=O)cc3)CC1C2] |

TABLE 11-continued
| Structure |
|---|
| 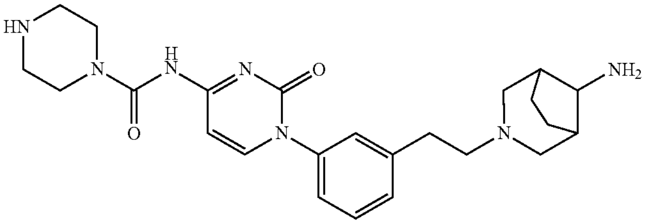 [SMILES: NC1C2CCC1CN(CCc1cccc(-n3ccc(NC(=O)N4CCNCC4)nc3=O)c1)C2] |
| 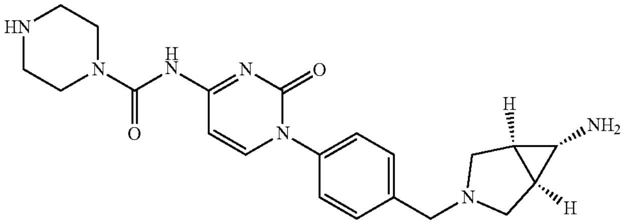 [SMILES: N[C@@H]1[C@H]2CN(Cc3ccc(-n4ccc(NC(=O)N5CCNCC5)nc4=O)cc3)C[C@@H]12] |
| 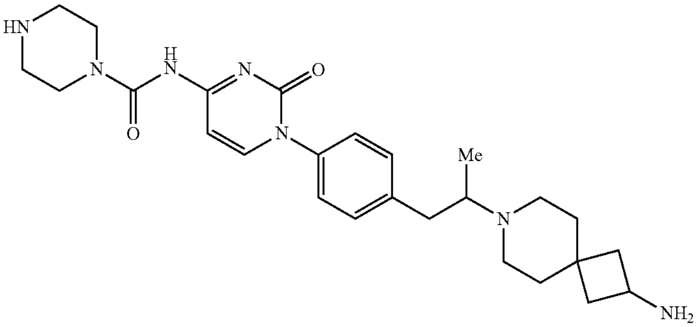 [SMILES: CC(Cc1ccc(-n2ccc(NC(=O)N3CCNCC3)nc2=O)cc1)N1CCC2(CC1)CC(N)C2] |
| 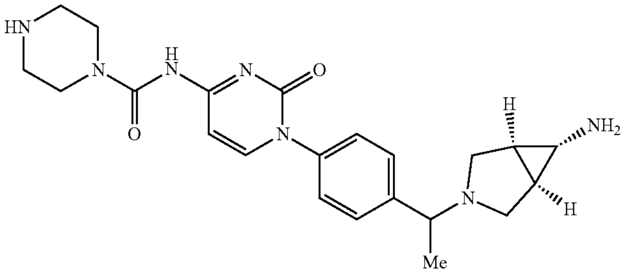 [SMILES: CC(c1ccc(-n2ccc(NC(=O)N3CCNCC3)nc2=O)cc1)N1C[C@@H]2[C@@H](N)[C@@H]2C1] |
| 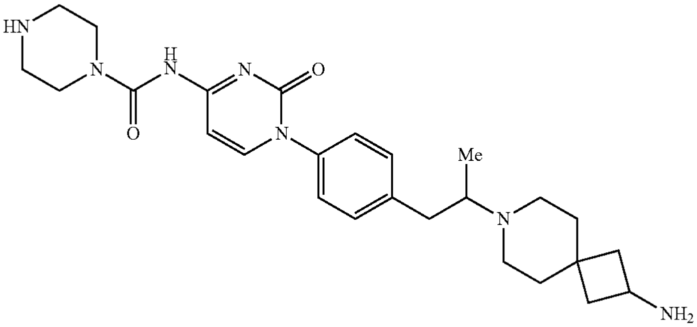 [SMILES: CC(Cc1ccc(-n2ccc(NC(=O)N3CCNCC3)nc2=O)cc1)N1CCC2(CC1)CC(N)C2] |

TABLE 11-continued
| Structure |
| --- |
| 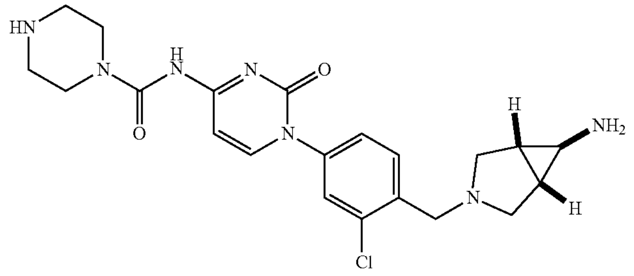 [SMILES: N[C@@H]1[C@H]2CN(Cc3ccc(-n4ccc(NC(=O)N5CCNCC5)nc4=O)cc3Cl)C[C@@H]12] |
| 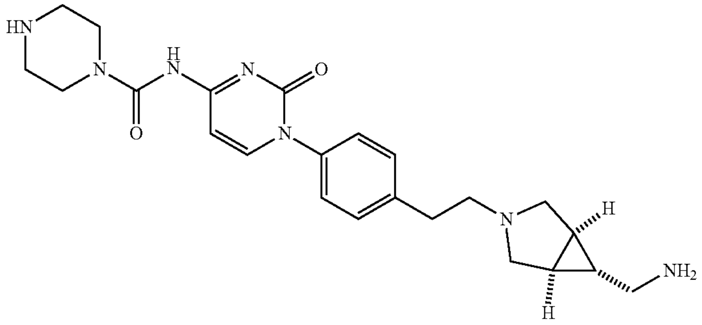 [SMILES: NC[C@@H]1[C@H]2CN(CCc3ccc(-n4ccc(NC(=O)N5CCNCC5)nc4=O)cc3)C[C@@H]12] |
| 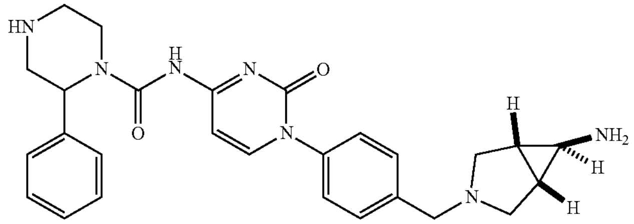 [SMILES: N[C@@H]1[C@H]2CN(Cc3ccc(-n4ccc(NC(=O)N5CCNCC5c5ccccc5)nc4=O)cc3)C[C@@H]12] |
| 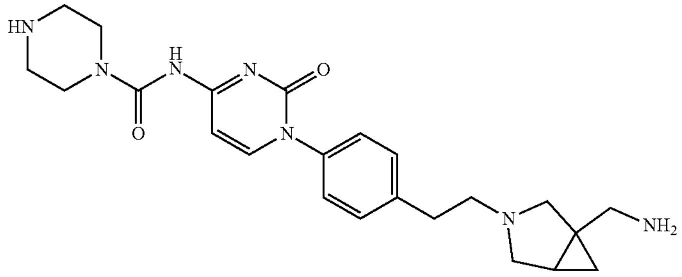 [SMILES: NCC12CC1CN(CCc1ccc(-n3ccc(NC(=O)N4CCNCC4)nc3=O)cc1)C2] |
| 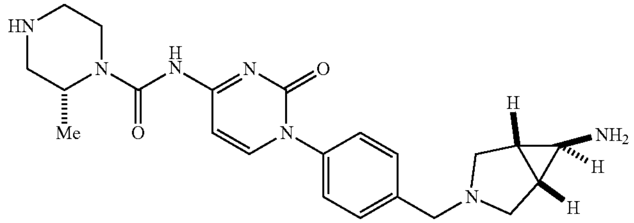 [SMILES: C[C@@H]1CNCCN1C(=O)Nc1ccn(-c2ccc(CN3C[C@@H]4[C@@H](N)[C@@H]4C3)cc2)c(=O)n1] |

TABLE 11-continued
| Structure |
| --- |
| 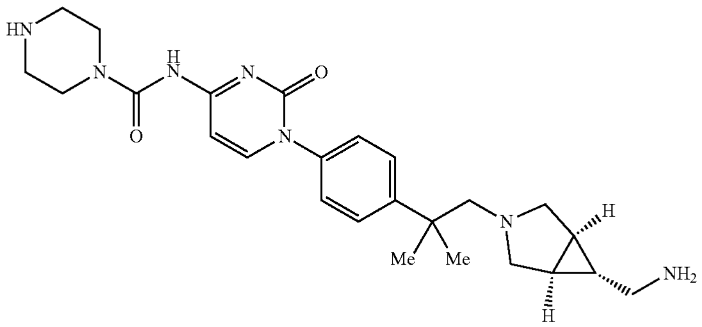 [SMILES: CC(C)(CN1C[C@@H]2[C@@H](CN)[C@@H]2C1)c1ccc(-n2ccc(NC(=O)N3CCNCC3)nc2=O)cc1] |
| 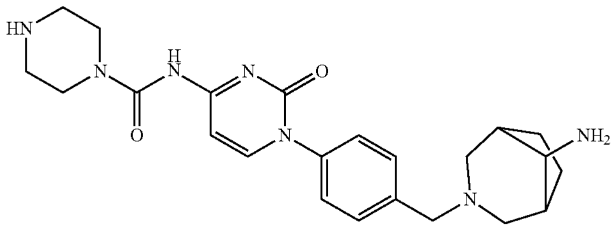 [SMILES: NC1C2CCC1CN(Cc1ccc(-n3ccc(NC(=O)N4CCNCC4)nc3=O)cc1)C2] |
| 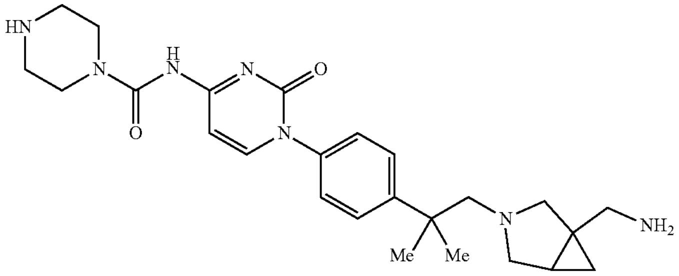 [SMILES: CC(C)(CN1CC2CC2(CN)C1)c1ccc(-n2ccc(NC(=O)N3CCNCC3)nc2=O)cc1] |
| 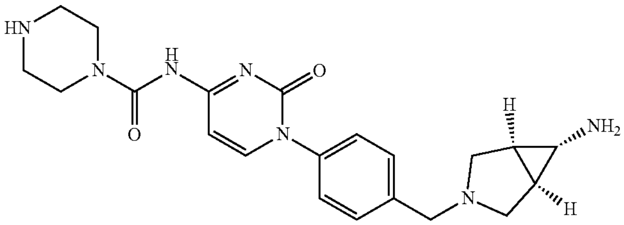 [SMILES: N[C@@H]1[C@H]2CN(Cc3ccc(-n4ccc(NC(=O)N5CCNCC5)nc4=O)cc3)C[C@@H]12] |
| 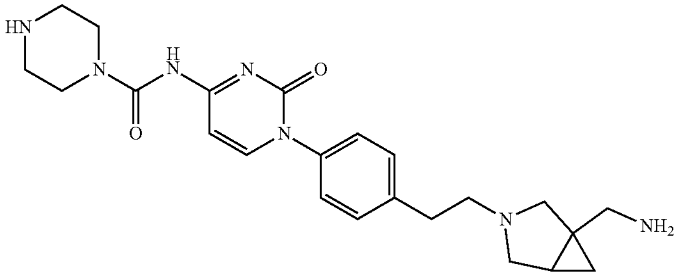 [SMILES: NCC12CC1CN(CCc1ccc(-n3ccc(NC(=O)N4CCNCC4)nc3=O)cc1)C2] |

TABLE 11-continued
| Structure |
| --- |
| 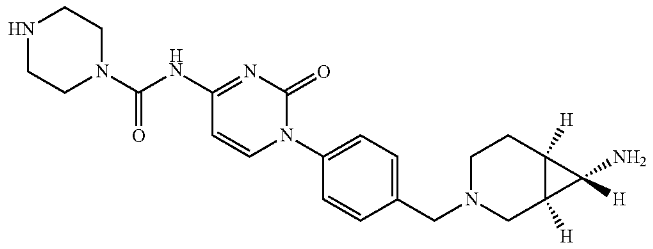 [SMILES: N[C@@H]1[C@H]2CN(Cc3ccc(-n4ccc(NC(=O)N5CCNCC5)nc4=O)cc3)CC[C@@H]12] |
| 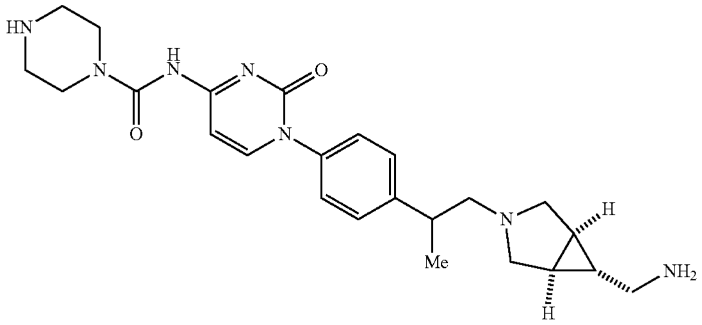 [SMILES: CC(CN1C[C@@H]2[C@@H](CN)[C@@H]2C1)c1ccc(-n2ccc(NC(=O)N3CCNCC3)nc2=O)cc1] |
| 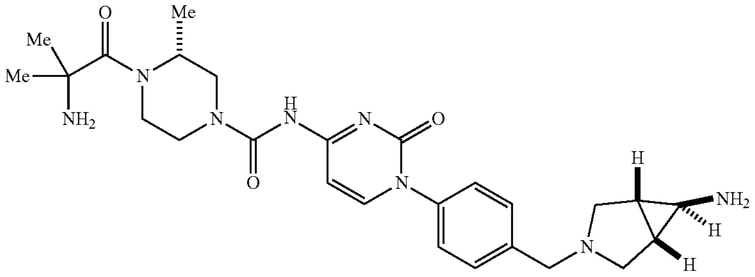 [SMILES: C[C@@H]1CN(C(=O)Nc2ccn(-c3ccc(CN4C[C@@H]5[C@@H](N)[C@@H]5C4)cc3)c(=O)n2)CCN1C(=O)C(C)(C)N] |
| 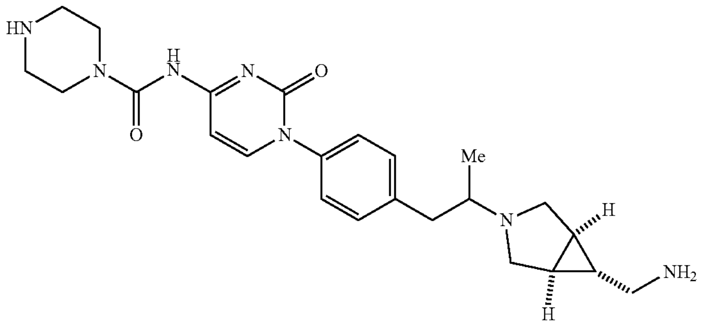 [SMILES: CC(Cc1ccc(-n2ccc(NC(=O)N3CCNCC3)nc2=O)cc1)N1C[C@@H]2[C@@H](CN)[C@@H]2C1] |
| 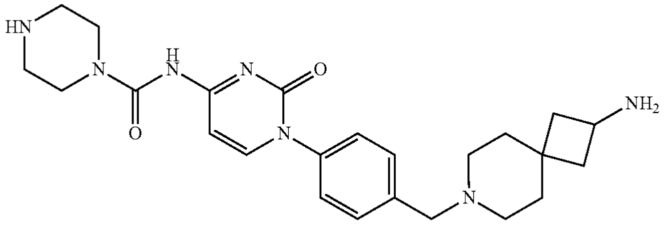 [SMILES: NC1CC2(CCN(Cc3ccc(-n4ccc(NC(=O)N5CCNCC5)nc4=O)cc3)CC2)C1] |

TABLE 11-continued
| Structure |
| --- |
| 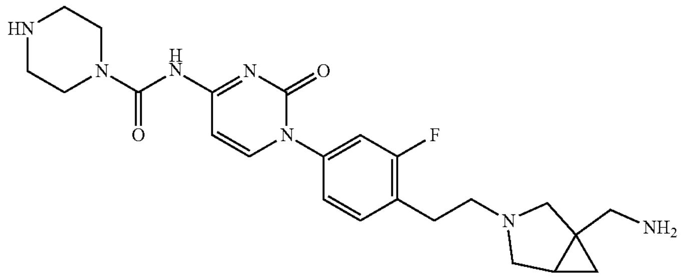 [SMILES: NCC12CC1CN(CCc1ccc(-n3ccc(NC(=O)N4CCNCC4)nc3=O)cc1F)C2] |
| 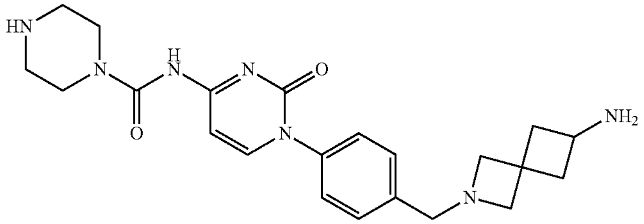 [SMILES: NC1CC2(C1)CN(Cc1ccc(-n3ccc(NC(=O)N4CCNCC4)nc3=O)cc1)C2] |
| 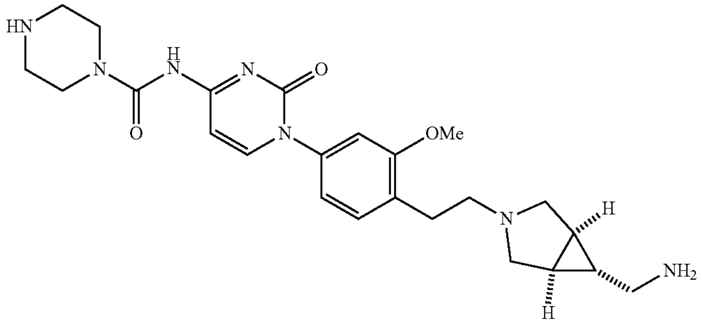 [SMILES: COc1cc(-n2ccc(NC(=O)N3CCNCC3)nc2=O)ccc1CCN1C[C@@H]2[C@@H](CN)[C@@H]2C1] |
| 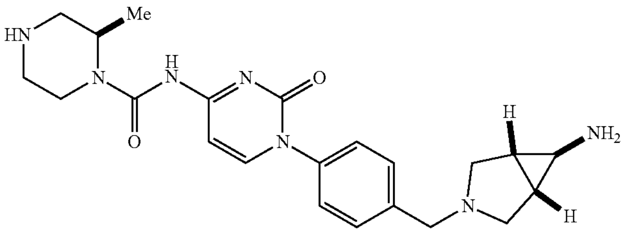 [SMILES: C[C@@H]1CNCCN1C(=O)Nc1ccn(-c2ccc(CN3C[C@@H]4[C@@H](N)[C@@H]4C3)cc2)c(=O)n1] |
| 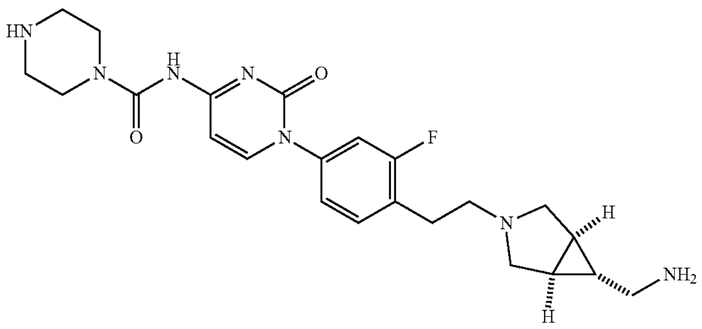 [SMILES: NC[C@@H]1[C@H]2CN(CCc3ccc(-n4ccc(NC(=O)N5CCNCC5)nc4=O)cc3F)C[C@@H]12] |

TABLE 11-continued
| Structure |
| --- |
| 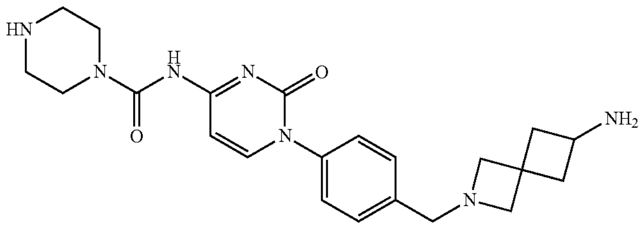 [SMILES: NC1CC2(C1)CN(Cc1ccc(-n3ccc(NC(=O)N4CCNCC4)nc3=O)cc1)C2] |
| 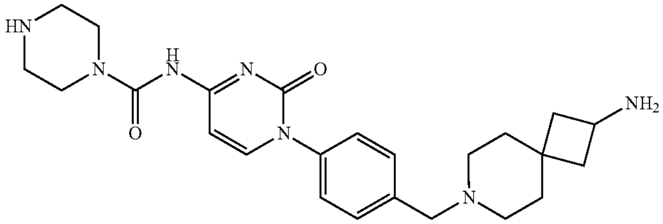 [SMILES: NC1CC2(CCN(Cc3ccc(-n4ccc(NC(=O)N5CCNCC5)nc4=O)cc3)CC2)C1] |
| 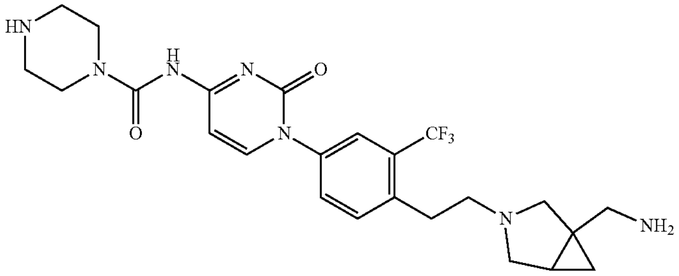 [SMILES: NCC12CC1CN(CCc1ccc(-n3ccc(NC(=O)N4CCNCC4)nc3=O)cc1C(F)(F)F)C2] |
| 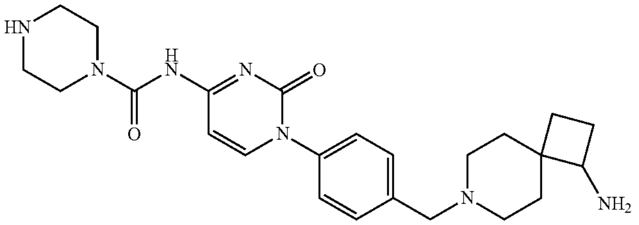 [SMILES: NC1CCC12CCN(Cc1ccc(-n3ccc(NC(=O)N4CCNCC4)nc3=O)cc1)CC2] |
| 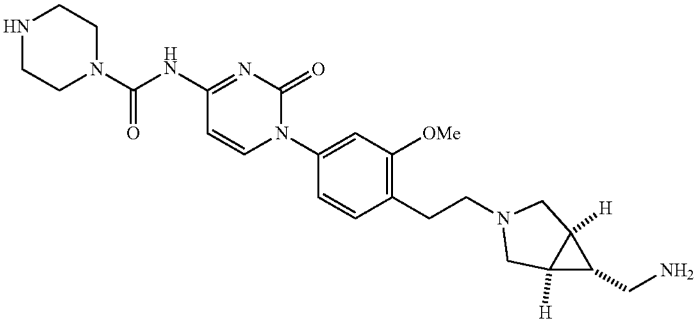 [SMILES: COc1cc(-n2ccc(NC(=O)N3CCNCC3)nc2=O)ccc1CCN1C[C@@H]2[C@@H](CN)[C@@H]2C1] |
| 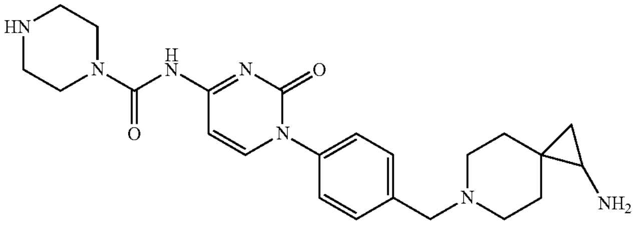 [SMILES: NC1CC12CCN(Cc1ccc(-n3ccc(NC(=O)N4CCNCC4)nc3=O)cc1)CC2] |

TABLE 11-continued
| Structure |
|---|
| 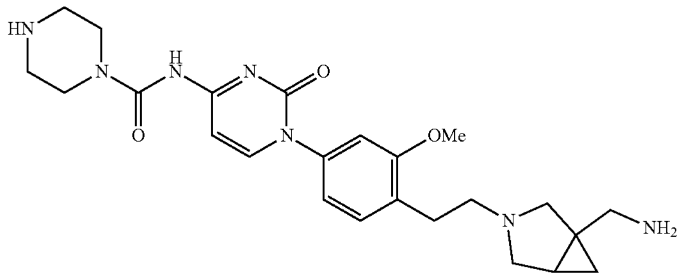 [SMILES: COc1cc(-n2ccc(NC(=O)N3CCNCC3)nc2=O)ccc1CCN1CC2CC2(CN)C1] |
| 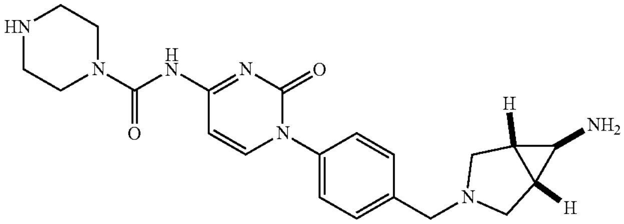 [SMILES: N[C@@H]1[C@H]2CN(Cc3ccc(-n4ccc(NC(=O)N5CCNCC5)nc4=O)cc3)C[C@@H]12] |
| 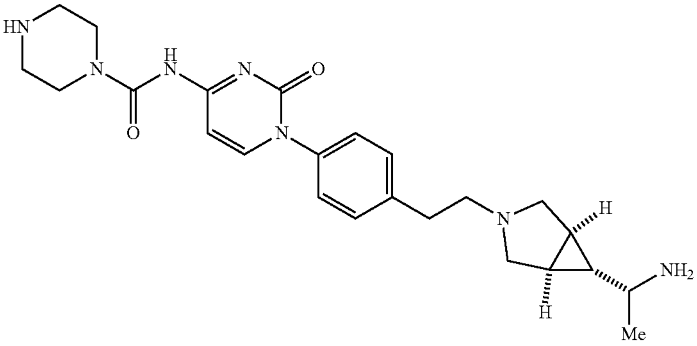 [SMILES: CC(N)[C@H]1[C@@H]2CN(CCc3ccc(-n4ccc(NC(=O)N5CCNCC5)nc4=O)cc3)C[C@@H]21] |
| 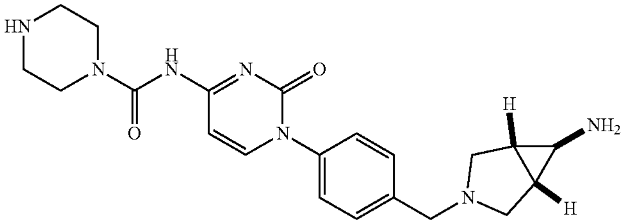 [SMILES: N[C@@H]1[C@H]2CN(Cc3ccc(-n4ccc(NC(=O)N5CCNCC5)nc4=O)cc3)C[C@@H]12] |
| 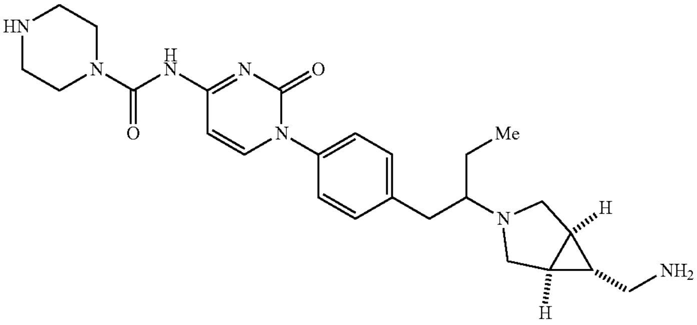 [SMILES: CCC(Cc1ccc(-n2ccc(NC(=O)N3CCNCC3)nc2=O)cc1)N1C[C@@H]2[C@@H](CN)[C@@H]2C1] |

TABLE 11-continued
| Structure |
|---|
| 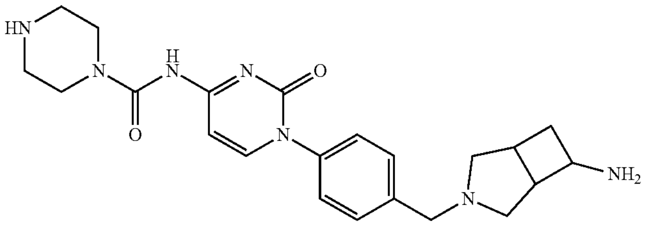 [SMILES: NC1CC2CN(Cc3ccc(-n4ccc(NC(=O)N5CCNCC5)nc4=O)cc3)CC12] |
| 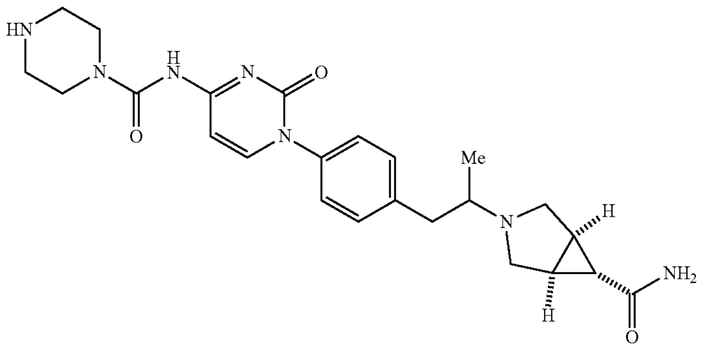 [SMILES: CC(Cc1ccc(-n2ccc(NC(=O)N3CCNCC3)nc2=O)cc1)N1C[C@@H]2[C@H](C1)[C@H]2C(N)=O] |
| 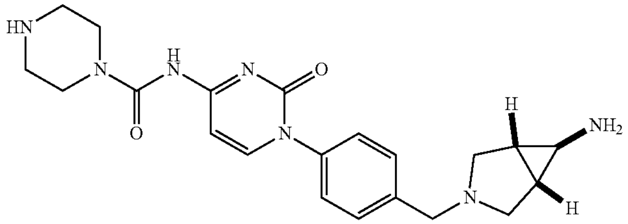 [SMILES: N[C@@H]1[C@H]2CN(Cc3ccc(-n4ccc(NC(=O)N5CCNCC5)nc4=O)cc3)C[C@@H]12] |
| 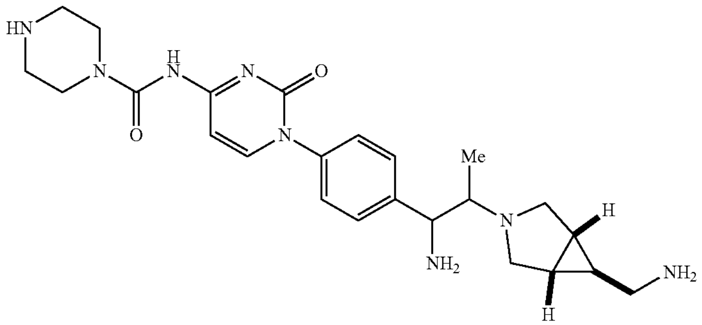 [SMILES: CC(C(N)c1ccc(-n2ccc(NC(=O)N3CCNCC3)nc2=O)cc1)N1C[C@@H]2[C@@H](CN)[C@@H]2C1] |
| 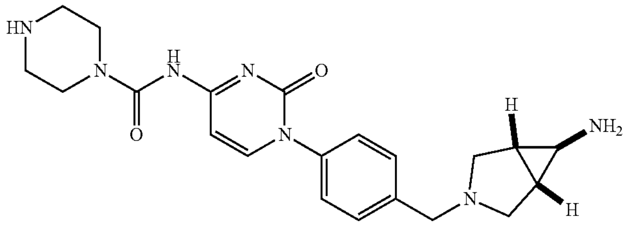 [SMILES: N[C@@H]1[C@H]2CN(Cc3ccc(-n4ccc(NC(=O)N5CCNCC5)nc4=O)cc3)C[C@@H]12] |

TABLE 11-continued
| Structure |
| --- |
| 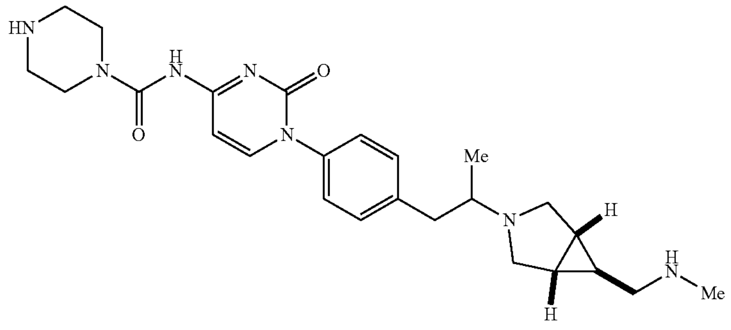 [SMILES: CNC[C@@H]1[C@H]2CN(C(C)Cc3ccc(-n4ccc(NC(=O)N5CCNCC5)nc4=O)cc3)C[C@@H]12] |
| 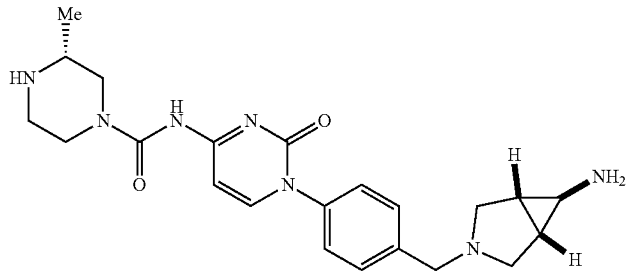 [SMILES: C[C@@H]1CN(C(=O)Nc2ccn(-c3ccc(CN4C[C@@H]5[C@@H](N)[C@@H]5C4)cc3)c(=O)n2)CCN1] |
| 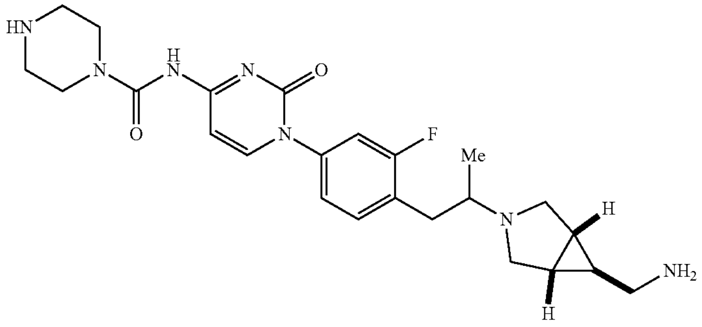 [SMILES: CC(Cc1ccc(-n2ccc(NC(=O)N3CCNCC3)nc2=O)cc1F)N1C[C@@H]2[C@@H](CN)[C@@H]2C1] |
| 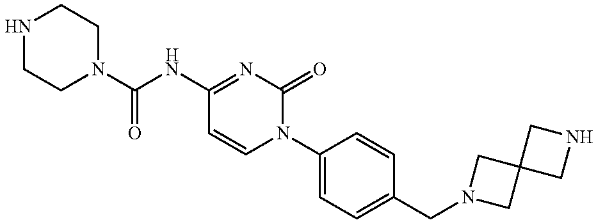 [SMILES: O=C(Nc1ccn(-c2ccc(CN3CC4(CNC4)C3)cc2)c(=O)n1)N1CCNCC1] |
| 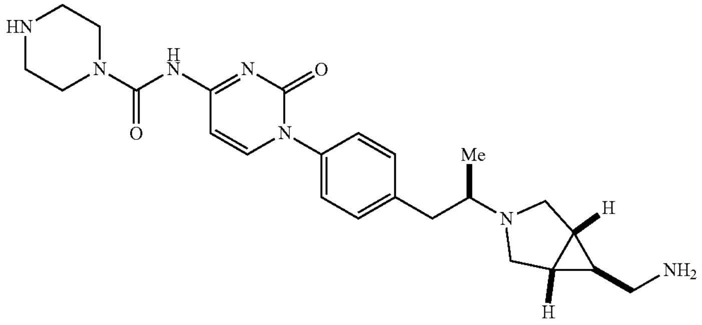 [SMILES: C[C@H](Cc1ccc(-n2ccc(NC(=O)N3CCNCC3)nc2=O)cc1)N1C[C@@H]2[C@@H](CN)[C@@H]2C1] |

TABLE 11-continued
| Structure |
|---|
| 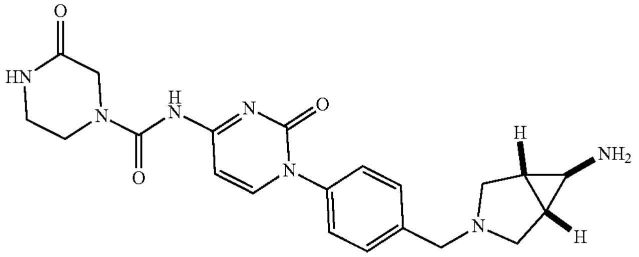 [SMILES: N[C@@H]1[C@H]2CN(Cc3ccc(-n4ccc(NC(=O)N5CCNC(=O)C5)nc4=O)cc3)C[C@@H]12] |
| 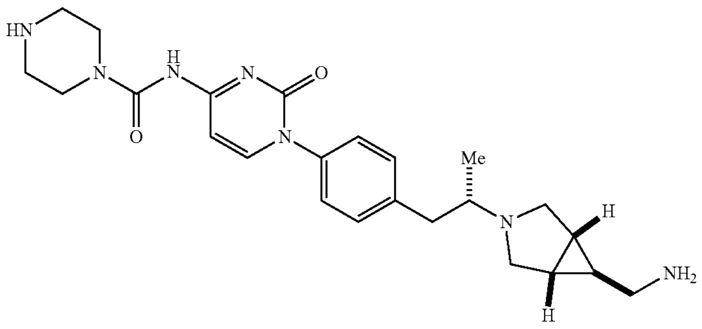 [SMILES: C[C@@H](Cc1ccc(-n2ccc(NC(=O)N3CCNCC3)nc2=O)cc1)N1C[C@@H]2[C@@H](CN)[C@@H]2C1] |
| 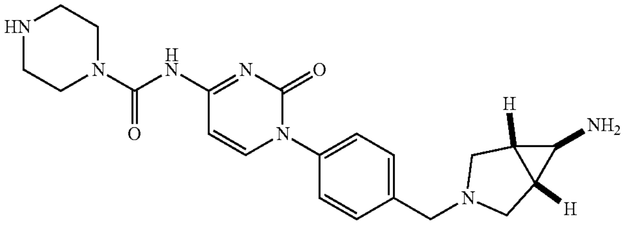 [SMILES: N[C@@H]1[C@H]2CN(Cc3ccc(-n4ccc(NC(=O)N5CCNCC5)nc4=O)cc3)C[C@@H]12] |
| 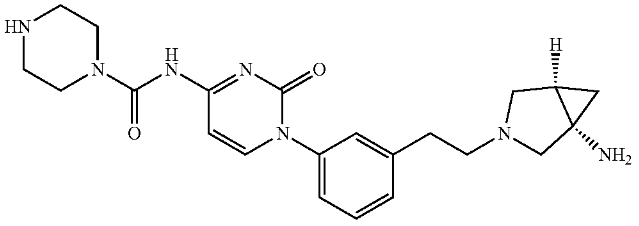 [SMILES: N[C@@]12C[C@@H]1CN(CCc1cccc(-n3ccc(NC(=O)N4CCNCC4)nc3=O)c1)C2] |
| 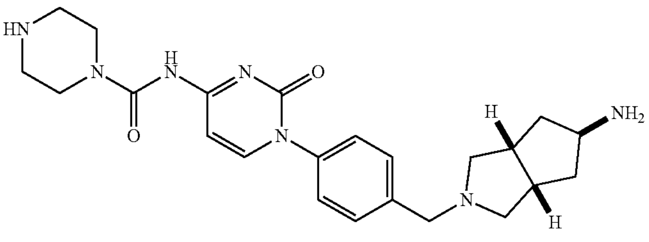 [SMILES: N[C@H]1C[C@@H]2CN(Cc3ccc(-n4ccc(NC(=O)N5CCNCC5)nc4=O)cc3)C[C@@H]2C1] |
| 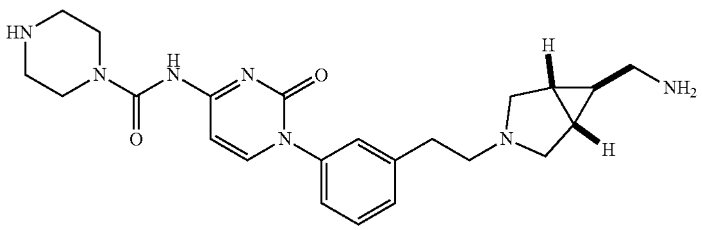 [SMILES: NC[C@@H]1[C@H]2CN(CCc3cccc(-n4ccc(NC(=O)N5CCNCC5)nc4=O)c3)C[C@@H]12] |

TABLE 11-continued
| Structure |
| --- |
| 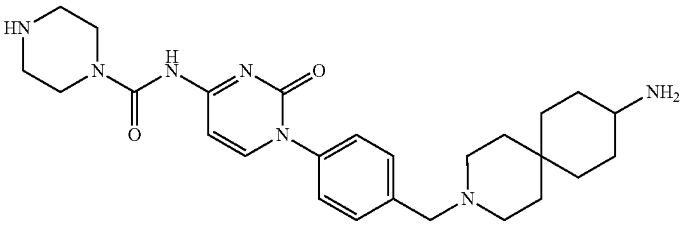 [SMILES: NC1CCC2(CC1)CCN(Cc1ccc(-n3ccc(NC(=O)N4CCNCC4)nc3=O)cc1)CC2] |
| 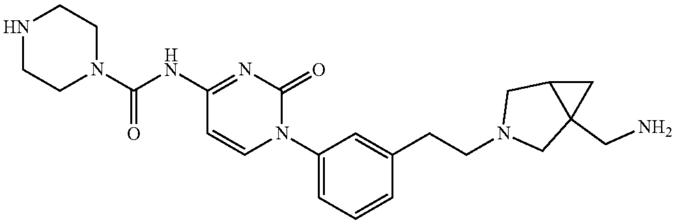 [SMILES: NCC12CC1CN(CCc1cccc(-n3ccc(NC(=O)N4CCNCC4)nc3=O)c1)C2] |
| 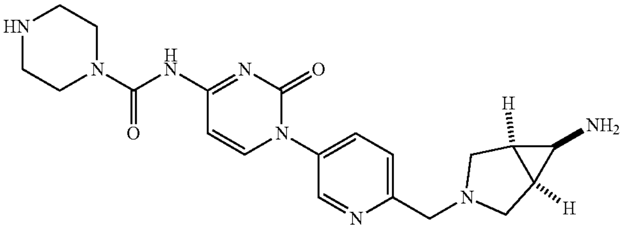 [SMILES: N[C@H]1[C@H]2CN(Cc3ccc(-n4ccc(NC(=O)N5CCNCC5)nc4=O)cn3)C[C@@H]12] |
| 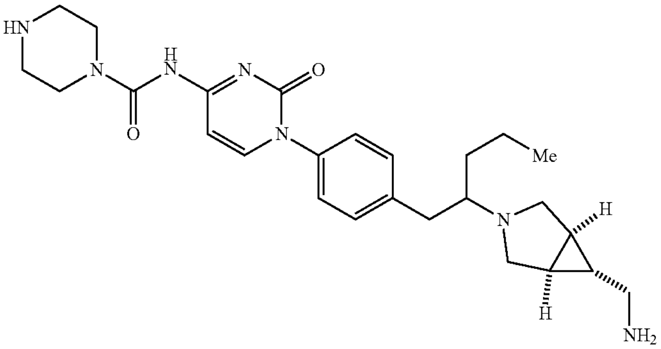 [SMILES: CCCC(Cc1ccc(-n2ccc(NC(=O)N3CCNCC3)nc2=O)cc1)N1C[C@@H]2[C@@H](CN)[C@@H]2C1] |
| 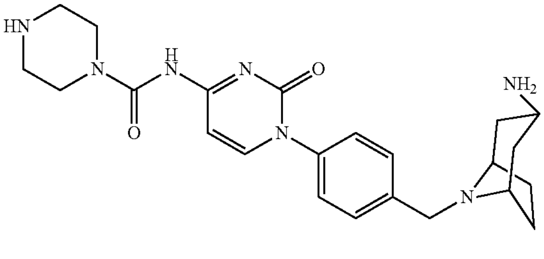 [SMILES: NC1CC2CCC(C1)N2Cc1ccc(-n2ccc(NC(=O)N3CCNCC3)nc2=O)cc1] |

TABLE 11-continued
| Structure |
|---|
| 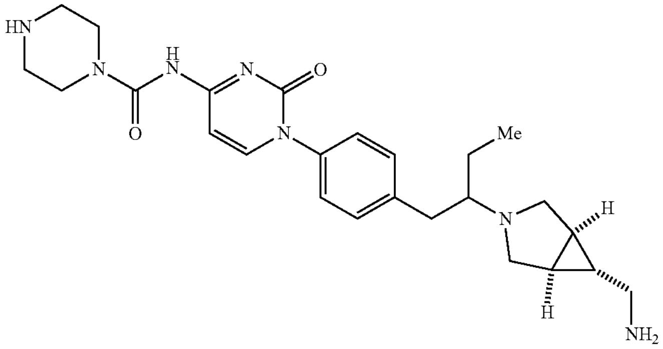 [SMILES: CCC(Cc1ccc(-n2ccc(NC(=O)N3CCNCC3)nc2=O)cc1)N1C[C@@H]2[C@@H](CN)[C@@H]2C1] |
| 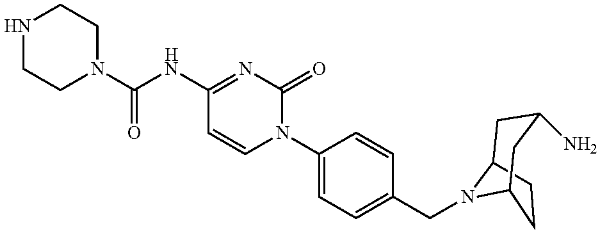 [SMILES: NC1CC2CCC(C1)N2Cc1ccc(-n2ccc(NC(=O)N3CCNCC3)nc2=O)cc1] |
| 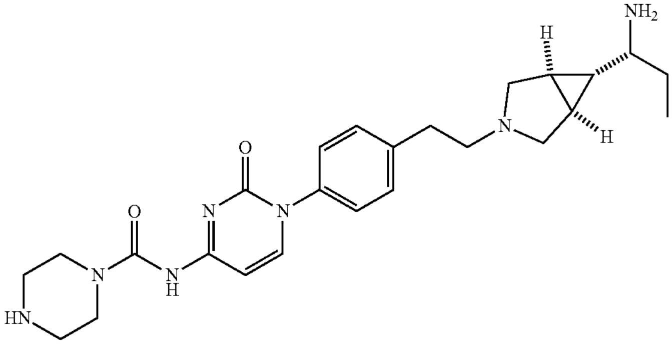 [SMILES: CC[C@@H](N)C1[C@H]2CN(CCc3ccc(-n4ccc(NC(=O)N5CCNCC5)nc4=O)cc3)C[C@@H]12] |
| 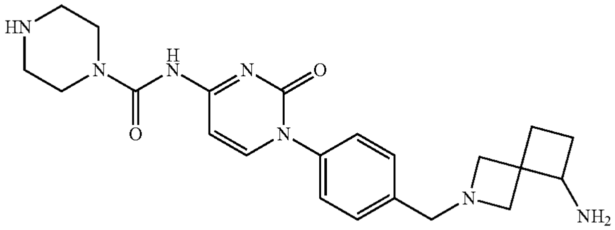 [SMILES: NC1CCC12CN(Cc1ccc(-n3ccc(NC(=O)N4CCNCC4)nc3=O)cc1)C2] |
| 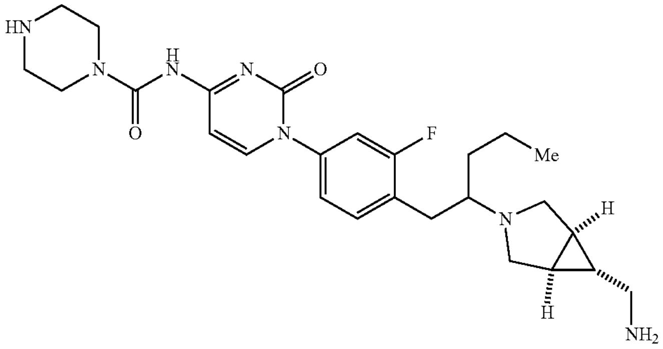 |

TABLE 11-continued
| Structure |
| --- |
| 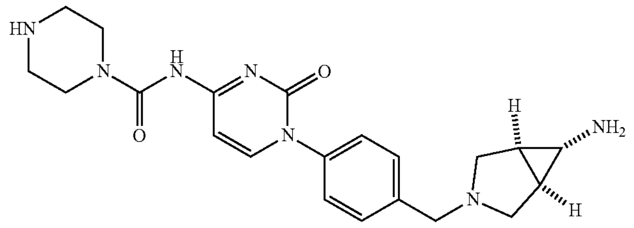 [SMILES: N[C@@H]1[C@H]2CN(Cc3ccc(-n4ccc(NC(=O)N5CCNCC5)nc4=O)cc3)C[C@@H]12] |
| 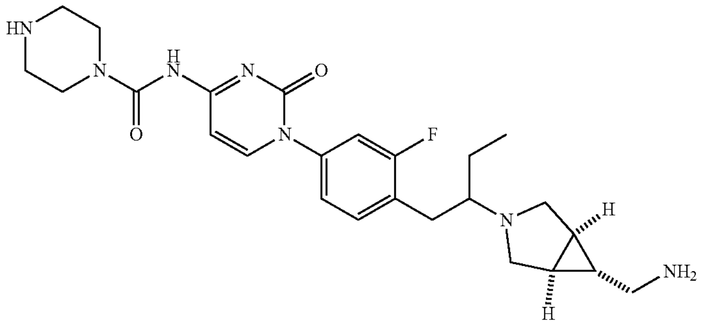 [SMILES: CCC(Cc1ccc(-n2ccc(NC(=O)N3CCNCC3)nc2=O)cc1F)N1C[C@@H]2[C@@H](CN)[C@@H]2C1] |
| 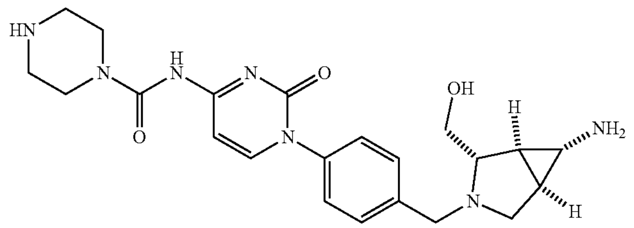 [SMILES: N[C@@H]1[C@H]2CN(Cc3ccc(-n4ccc(NC(=O)N5CCNCC5)nc4=O)cc3)[C@H](CO)[C@@H]12] |
| 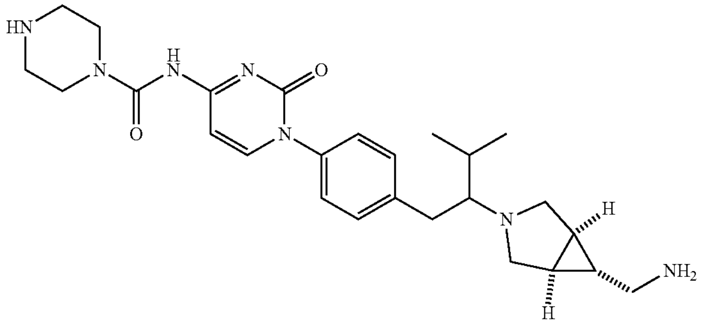 [SMILES: CC(C)C(Cc1ccc(-n2ccc(NC(=O)N3CCNCC3)nc2=O)cc1)N1C[C@@H]2[C@@H](CN)[C@@H]2C1] |
| 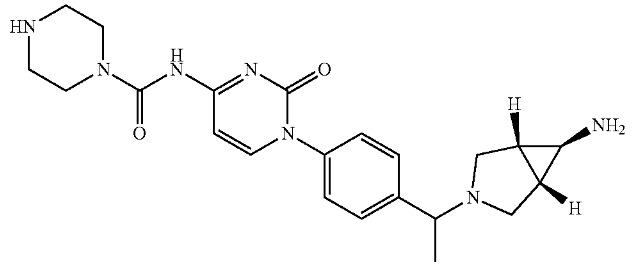 [SMILES: CC(c1ccc(-n2ccc(NC(=O)N3CCNCC3)nc2=O)cc1)N1C[C@@H]2[C@@H](N)[C@@H]2C1] |

TABLE 11-continued
| Structure |
|---|
| 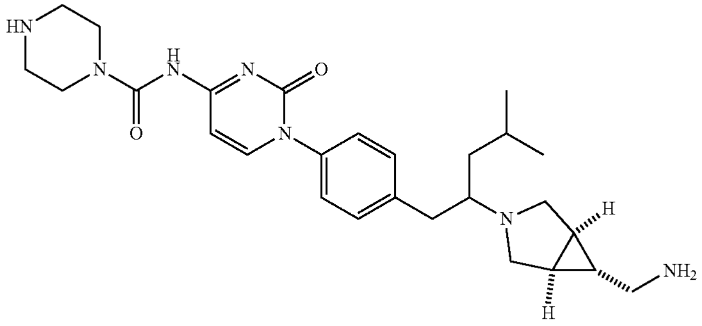 [SMILES: CC(C)CC(Cc1ccc(-n2ccc(NC(=O)N3CCNCC3)nc2=O)cc1)N1C[C@@H]2[C@@H](CN)[C@@H]2C1] |
| 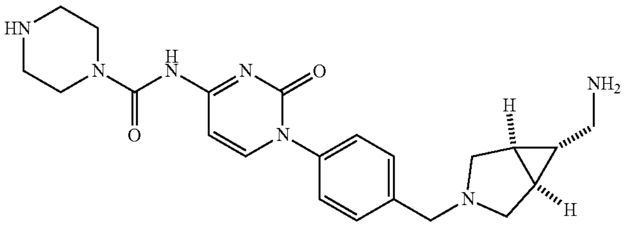 [SMILES: NC[C@@H]1[C@H]2CN(Cc3ccc(-n4ccc(NC(=O)N5CCNCC5)nc4=O)cc3)C[C@@H]12] |
| 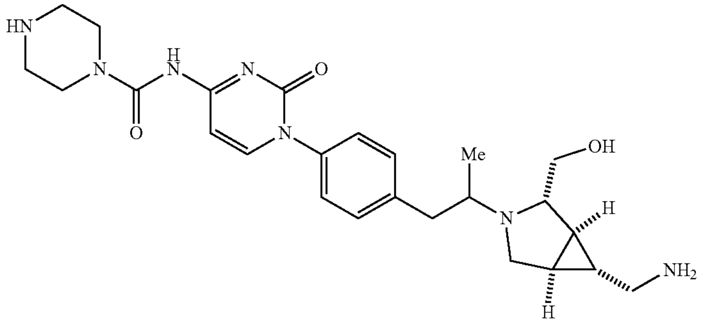 [SMILES: CC(Cc1ccc(-n2ccc(NC(=O)N3CCNCC3)nc2=O)cc1)N1C[C@@H]2[C@@H](CN)[C@@H]2[C@H]1CO] |
| 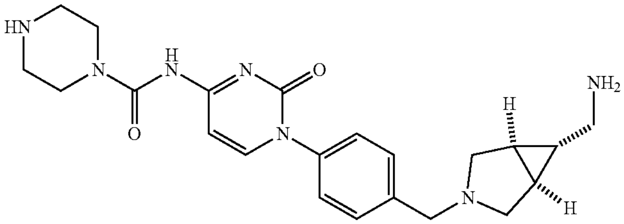 [SMILES: NC[C@@H]1[C@H]2CN(Cc3ccc(-n4ccc(NC(=O)N5CCNCC5)nc4=O)cc3)C[C@@H]12] |
| 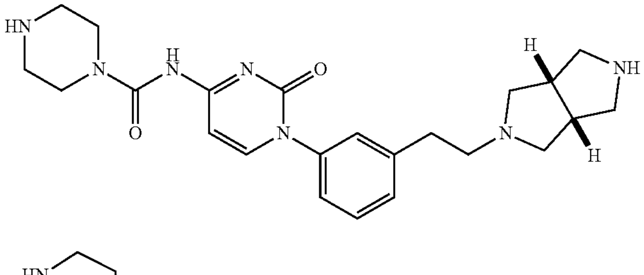 |
| 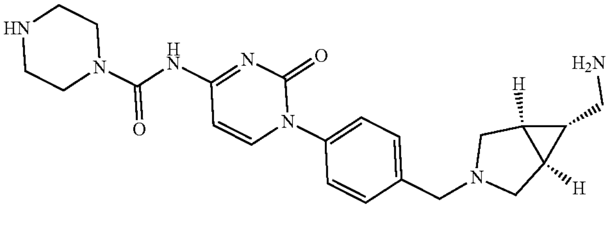 [SMILES: NC[C@@H]1[C@H]2CN(Cc3ccc(-n4ccc(NC(=O)N5CCNCC5)nc4=O)cc3)C[C@@H]12] |

TABLE 11-continued
| Structure |
| --- |
| 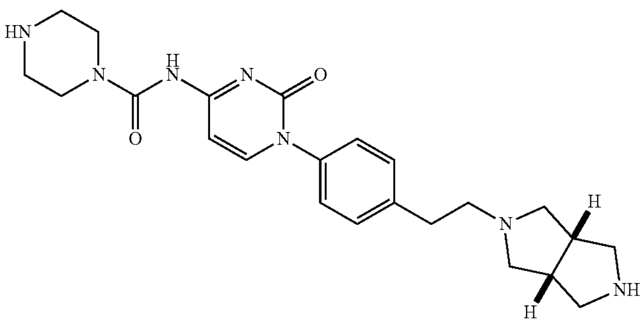 [SMILES: O=C(Nc1ccn(-c2ccc(CCN3C[C@H]4CNC[C@H]4C3)cc2)c(=O)n1)N1CCNCC1] |
| 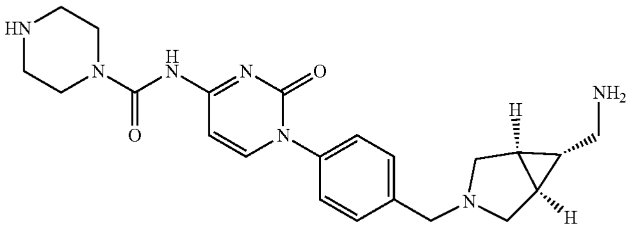 [SMILES: NC[C@@H]1[C@H]2CN(Cc3ccc(-n4ccc(NC(=O)N5CCNCC5)nc4=O)cc3)C[C@@H]12] |
| 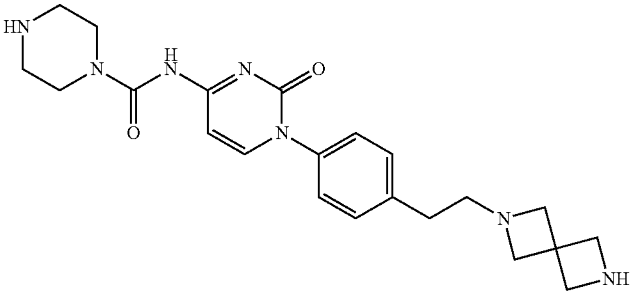 [SMILES: O=C(Nc1ccn(-c2ccc(CCN3CC4(CNC4)C3)cc2)c(=O)n1)N1CCNCC1] |
| 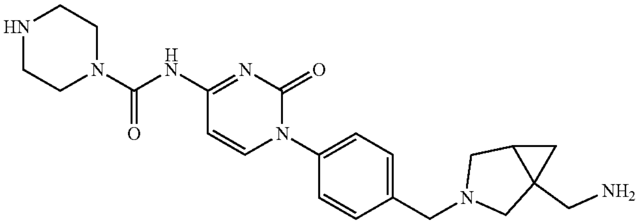 [SMILES: NCC12CC1CN(Cc1ccc(-n3ccc(NC(=O)N4CCNCC4)nc3=O)cc1)C2] |
| 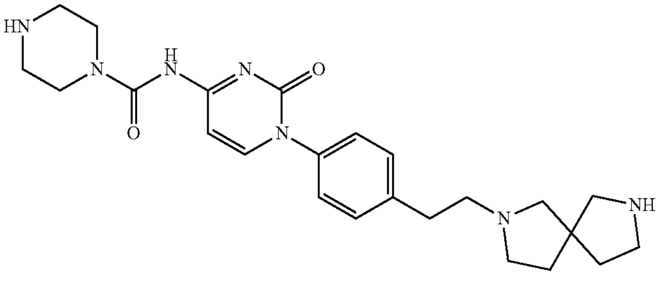 [SMILES: O=C(Nc1ccn(-c2ccc(CCN3CCC4(CCNC4)C3)cc2)c(=O)n1)N1CCNCC1] |

TABLE 11-continued
| Structure |
|---|
| 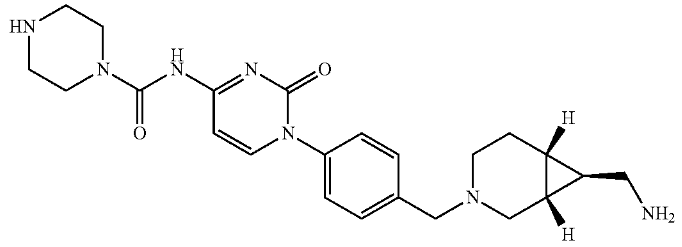 [SMILES: NC[C@@H]1[C@H]2CCN(Cc3ccc(-n4ccc(NC(=O)N5CCNCC5)nc4=O)cc3)C[C@@H]12] |
| 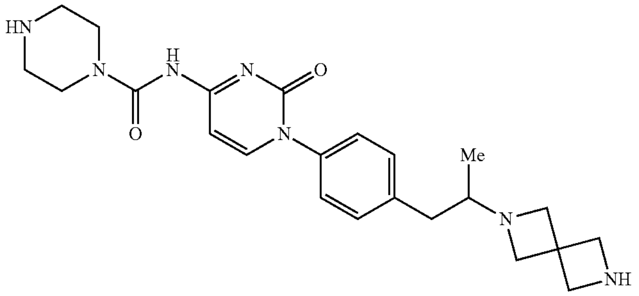 [SMILES: CC(Cc1ccc(-n2ccc(NC(=O)N3CCNCC3)nc2=O)cc1)N1CC2(CNC2)C1] |
| 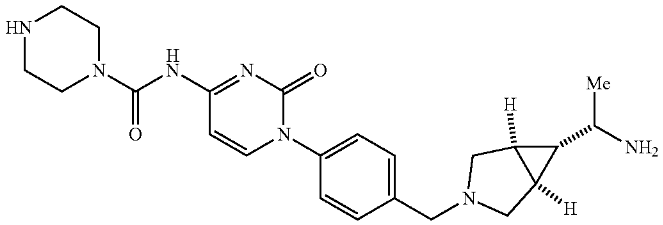 [SMILES: C[C@H](N)C1[C@H]2CN(Cc3ccc(-n4ccc(NC(=O)N5CCNCC5)nc4=O)cc3)C[C@@H]12] |
| 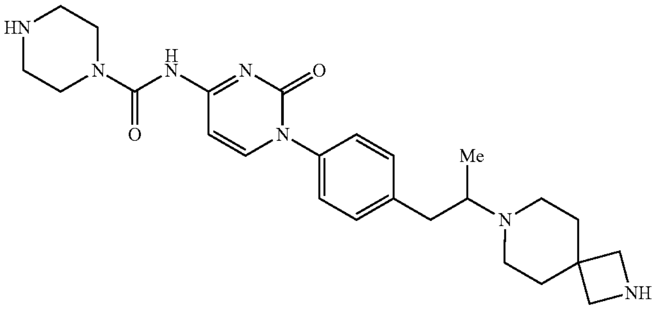 [SMILES: CC(Cc1ccc(-n2ccc(NC(=O)N3CCNCC3)nc2=O)cc1)N1CCC2(CC1)CNC2] |
| 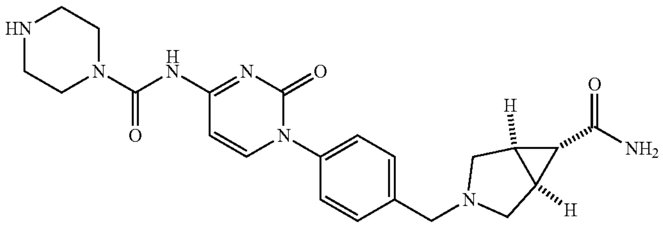 |

TABLE 11-continued
| Structure |
|---|
| 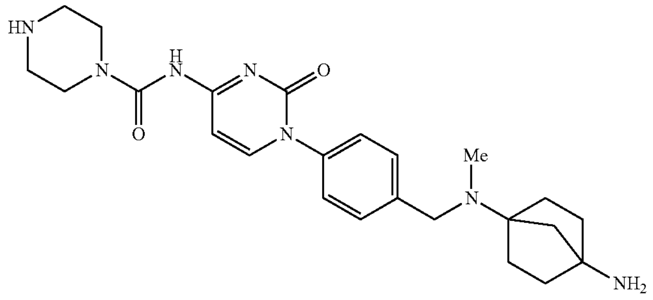 [SMILES: CN(Cc1ccc(-n2ccc(NC(=O)N3CCNCC3)nc2=O)cc1)C12CCC(N)(CC1)C2] |
| 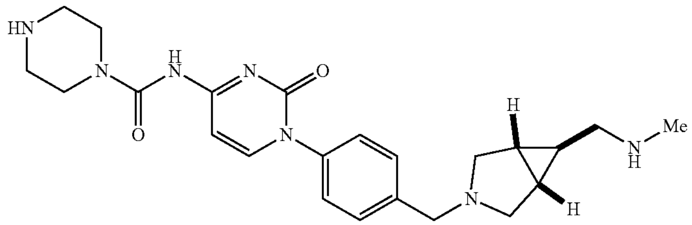 [SMILES: CNC[C@@H]1[C@H]2CN(Cc3ccc(-n4ccc(NC(=O)N5CCNCC5)nc4=O)cc3)C[C@@H]12] |
| 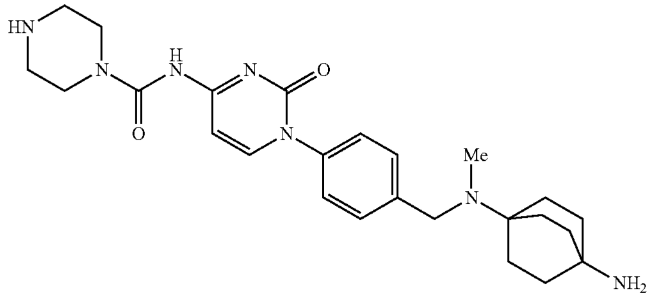 [SMILES: CN(Cc1ccc(-n2ccc(NC(=O)N3CCNCC3)nc2=O)cc1)C12CCC(N)(CC1)CC2] |
| 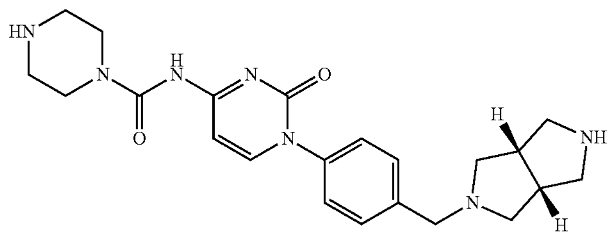 [SMILES: O=C(Nc1ccn(-c2ccc(CN3C[C@H]4CNC[C@H]4C3)cc2)c(=O)n1)N1CCNCC1] |
| 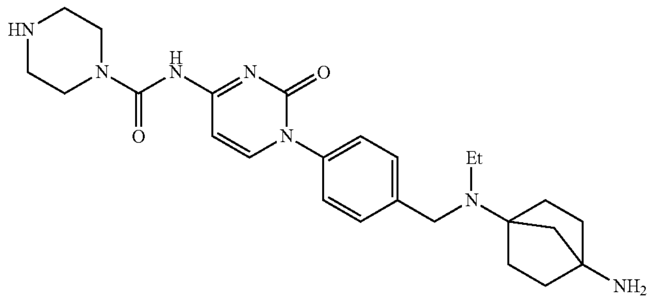 [SMILES: CCN(Cc1ccc(-n2ccc(NC(=O)N3CCNCC3)nc2=O)cc1)C12CCC(N)(CC1)C2] |

TABLE 11-continued
| Structure |
| --- |
| 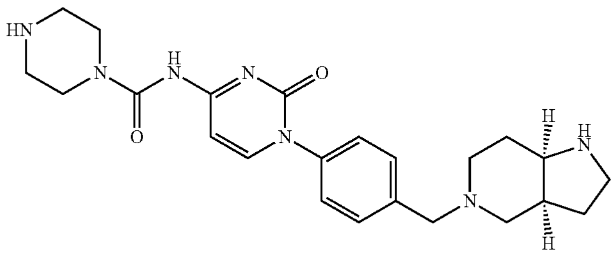 [SMILES: O=C(Nc1ccn(-c2ccc(CN3CC[C@H]4NCC[C@H]4C3)cc2)c(=O)n1)N1CCNCC1] |
| 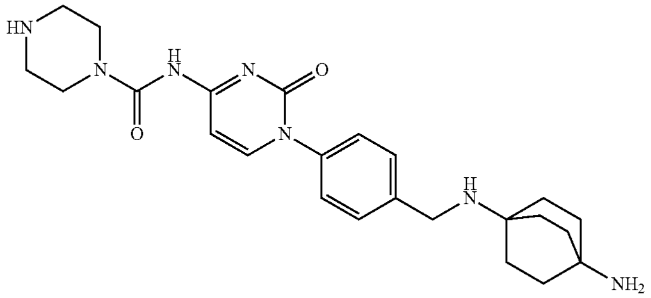 [SMILES: NC12CCC(NCc3ccc(-n4ccc(NC(=O)N5CCNCC5)nc4=O)cc3)(CC1)CC2] |
| 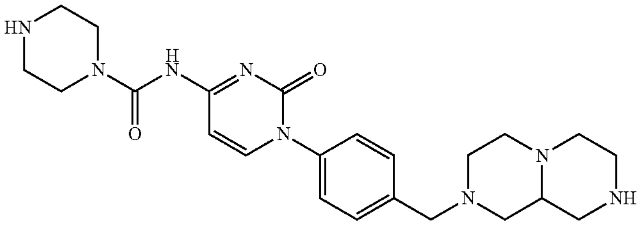 [SMILES: O=C(Nc1ccn(-c2ccc(CN3CCN4CCNCC4C3)cc2)c(=O)n1)N1CCNCC1] |
| 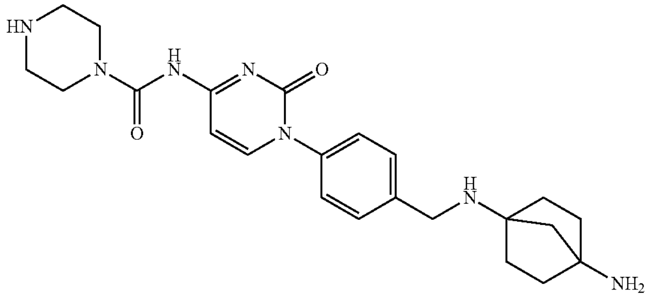 [SMILES: NC12CCC(NCc3ccc(-n4ccc(NC(=O)N5CCNCC5)nc4=O)cc3)(CC1)C2] |
| 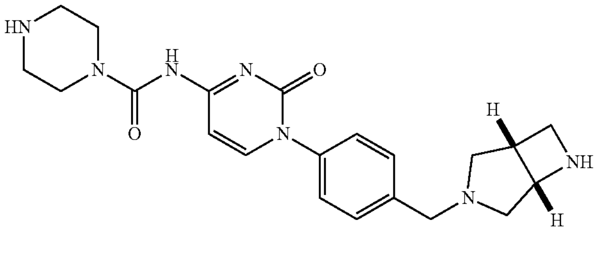 [SMILES: O=C(Nc1ccn(-c2ccc(CN3C[C@@H]4CN[C@@H]4C3)cc2)c(=O)n1)N1CCNCC1] |

TABLE 11-continued
| Structure |
|---|
| 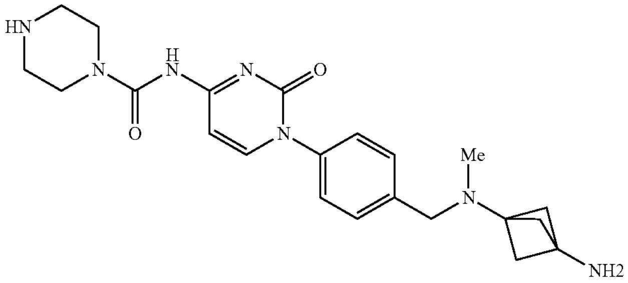 [SMILES: CN(Cc1ccc(-n2ccc(NC(=O)N3CCNCC3)nc2=O)cc1)C12CC(N)(C1)C2] |
| 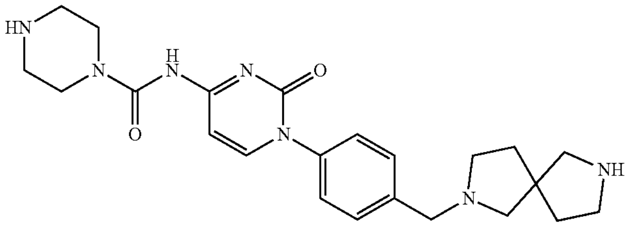 [SMILES: O=C(Nc1ccn(-c2ccc(CN3CCC4(CCNC4)C3)cc2)c(=O)n1)N1CCNCC1] |
| 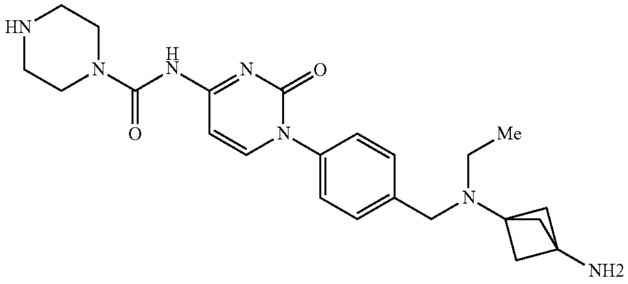 [SMILES: CCN(Cc1ccc(-n2ccc(NC(=O)N3CCNCC3)nc2=O)cc1)C12CC(N)(C1)C2] |
| 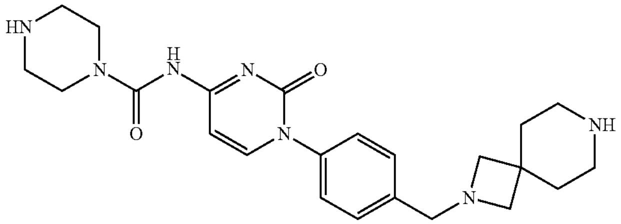 [SMILES: O=C(Nc1ccn(-c2ccc(CN3CC4(CCNCC4)C3)cc2)c(=O)n1)N1CCNCC1] |
| 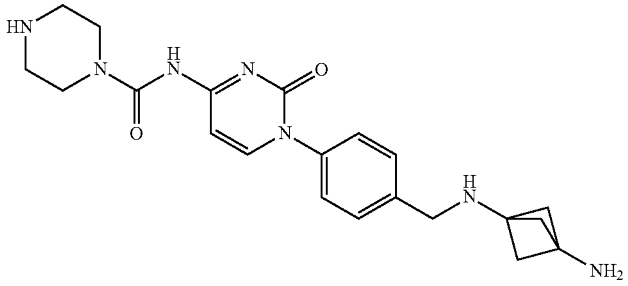 [SMILES: NC12CC(NCc3ccc(-n4ccc(NC(=O)N5CCNCC5)nc4=O)cc3)(C1)C2] |
| 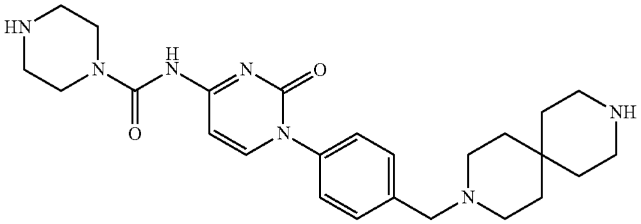 [SMILES: O=C(Nc1ccn(-c2ccc(CN3CCC4(CCNCC4)CC3)cc2)c(=O)n1)N1CCNCC1] |

TABLE 11-continued
| Structure |
| --- |
| 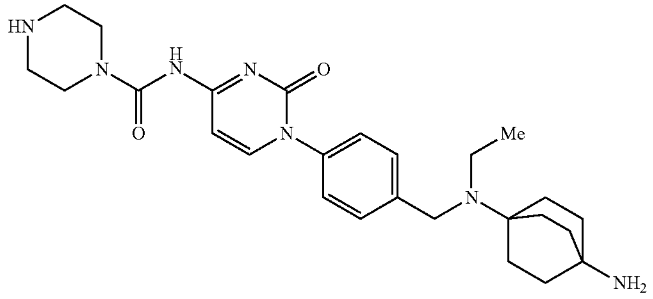 [SMILES: CCN(Cc1ccc(-n2ccc(NC(=O)N3CCNCC3)nc2=O)cc1)C12CCC(N)(CC1)CC2] |
| 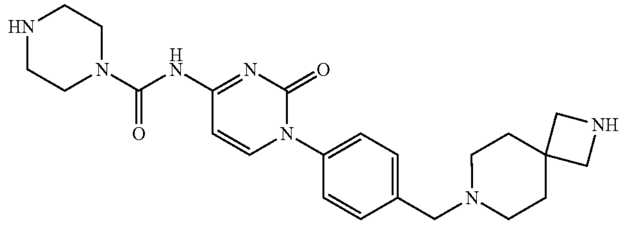 [SMILES: O=C(Nc1ccn(-c2ccc(CN3CCC4(CC3)CNC4)cc2)c(=O)n1)N1CCNCC1] |
| 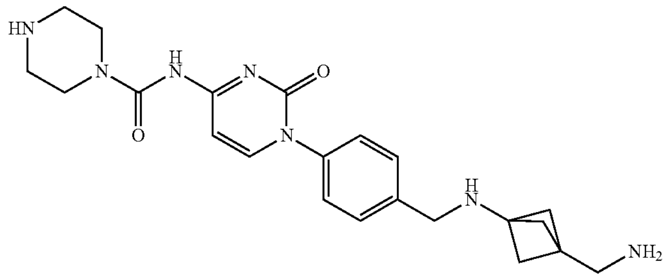 [SMILES: NCC12CC(NCc3ccc(-n4ccc(NC(=O)N5CCNCC5)nc4=O)cc3)(C1)C2] |
| 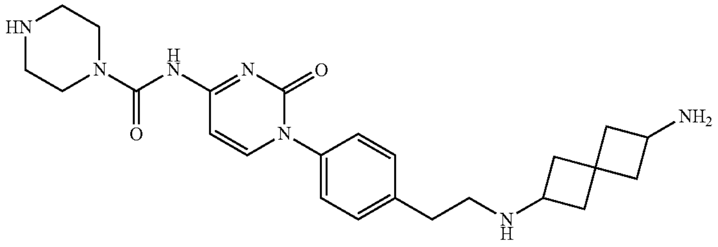 [SMILES: NC1CC2(C1)CC(NCCc1ccc(-n3ccc(NC(=O)N4CCNCC4)nc3=O)cc1)C2] |
| 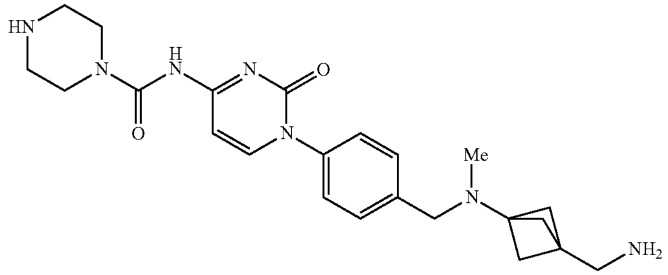 [SMILES: CN(Cc1ccc(-n2ccc(NC(=O)N3CCNCC3)nc2=O)cc1)C12CC(CN)(C1)C2] |
| 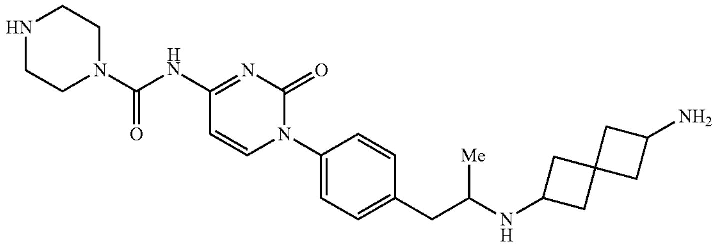 [SMILES: CC(Cc1ccc(-n2ccc(NC(=O)N3CCNCC3)nc2=O)cc1)NC1CC2(CC(N)C2)C1] |

TABLE 11-continued
| Structure |
|---|
| 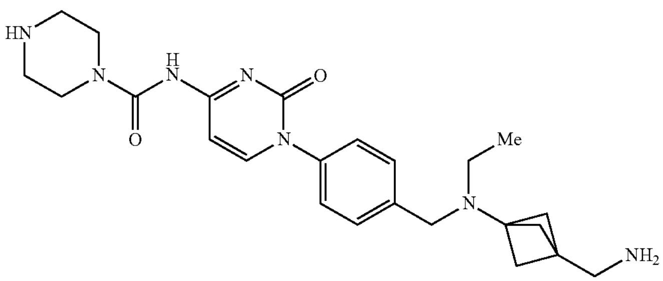 [SMILES: CCN(Cc1ccc(-n2ccc(NC(=O)N3CCNCC3)nc2=O)cc1)C12CC(CN)(C1)C2] |
| 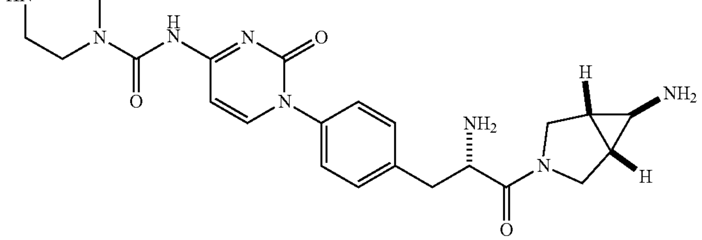 |
| 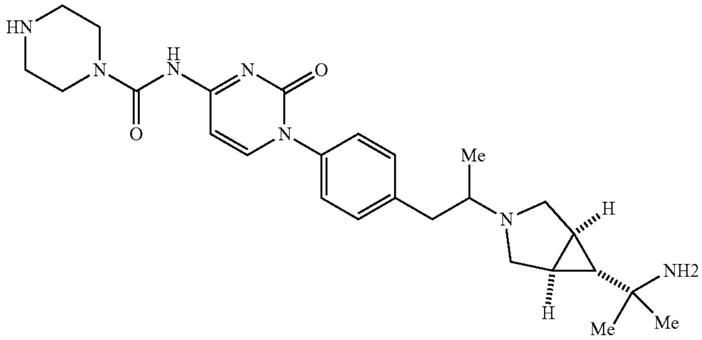 |
| 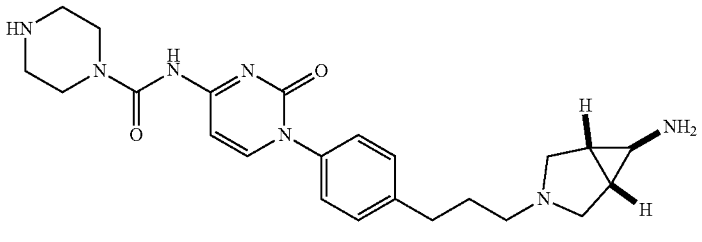 [SMILES: N[C@@H]1[C@H]2CN(CCCc3ccc(-n4ccc(NC(=O)N5CCNCC5)nc4=O)cc3)C[C@@H]12] |
| 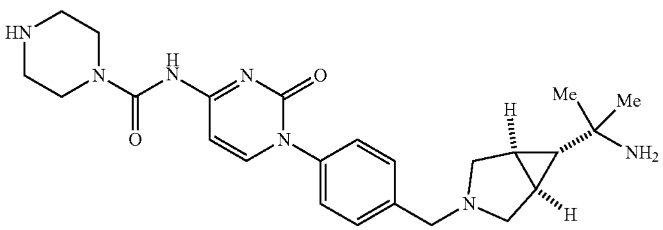 |

TABLE 11-continued
| Structure |
| --- |
| 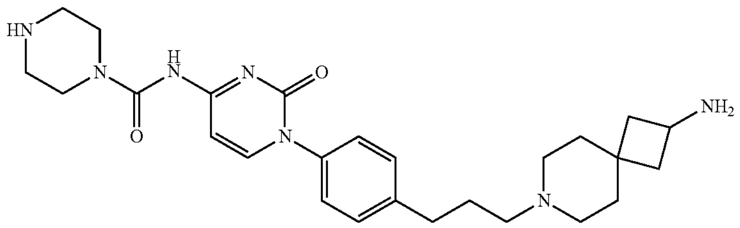 [SMILES: NC1CC2(CCN(CCCc3ccc(-n4ccc(NC(=O)N5CCNCC5)nc4=O)cc3)CC2)C1] |
| 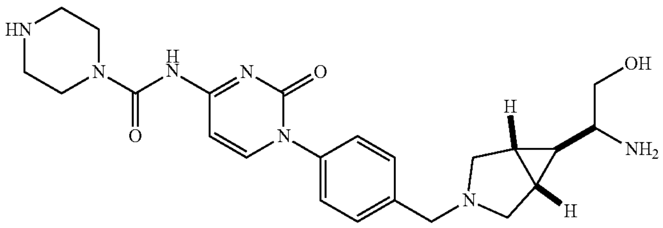 [SMILES: N[C@H](CO)C1[C@H]2CN(Cc3ccc(-n4ccc(NC(=O)N5CCNCC5)nc4=O)cc3)C[C@@H]12] |
| 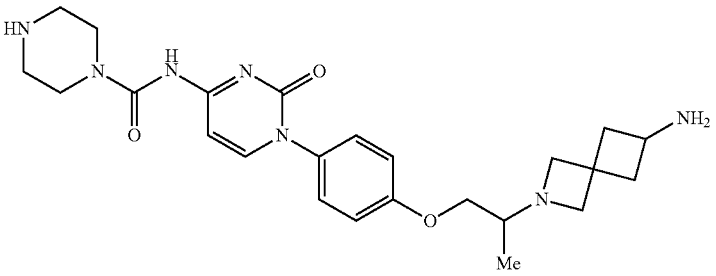 [SMILES: CC(COc1ccc(-n2ccc(NC(=O)N3CCNCC3)nc2=O)cc1)N1CC2(CC(N)C2)C1] |
| 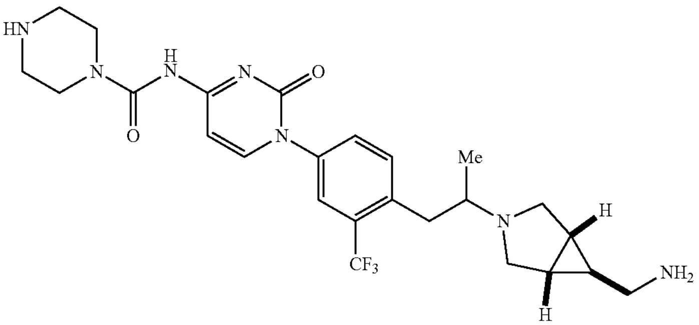 |
| 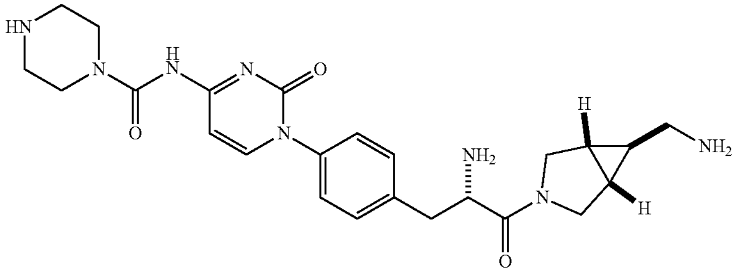 [SMILES: NC[C@@H]1[C@H]2CN(C(=O)[C@@H](N)Cc3ccc(-n4ccc(NC(=O)N5CCNCC5)nc4=O)cc3)C[C@@H]12] |

TABLE 11-continued
| Structure |
| --- |
| 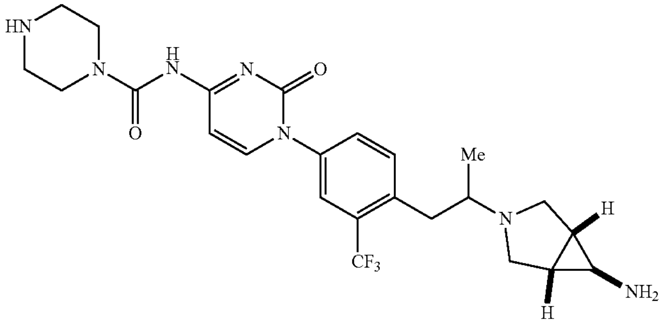 [SMILES: CC(Cc1ccc(-n2ccc(NC(=O)N3CCNCC3)nc2=O)cc1C(F)(F)F)N1C[C@@H]2[C@@H](N)[C@@H]2C1] |
| 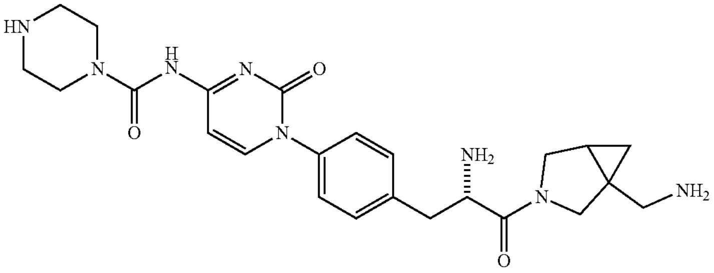 [SMILES: NCC12CC1CN(C(=O)[C@@H](N)Cc1ccc(-n3ccc(NC(=O)N4CCNCC4)nc3=O)cc1)C2] |
| 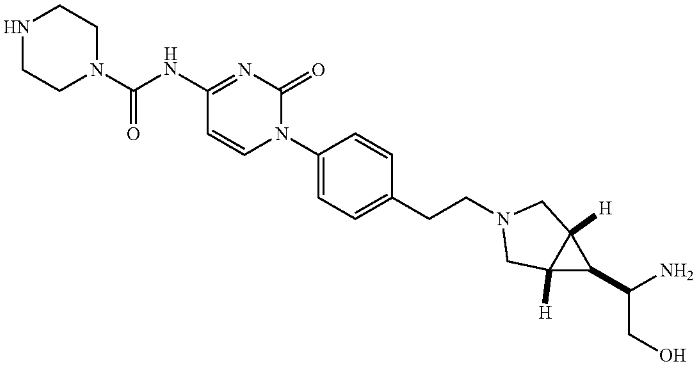 [SMILES: NC(CO)[C@H]1[C@@H]2CN(CCc3ccc(-n4ccc(NC(=O)N5CCNCC5)nc4=O)cc3)C[C@@H]21] |
| 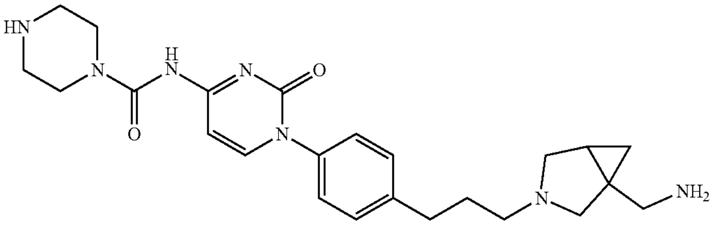 [SMILES: NCC12CC1CN(CCCc1ccc(-n3ccc(NC(=O)N4CCNCC4)nc3=O)cc1)C2] |
| 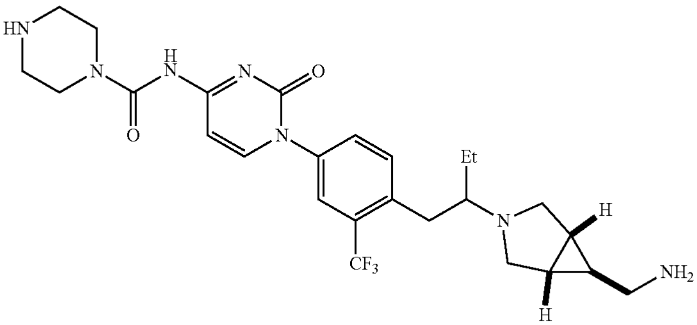 [SMILES: CCC(Cc1ccc(-n2ccc(NC(=O)N3CCNCC3)nc2=O)cc1C(F)(F)F)N1C[C@@H]2[C@@H](CN)[C@@H]2C1] |

TABLE 11-continued
| Structure |
| --- |
| 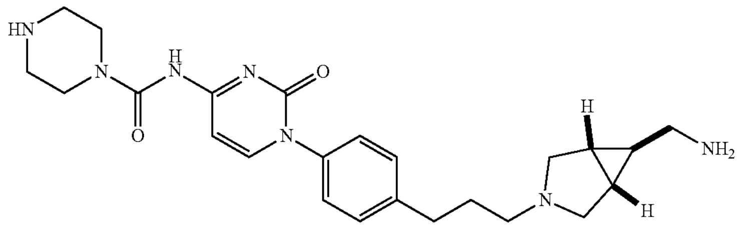 [SMILES: NC[C@@H]1[C@H]2CN(CCCc3ccc(-n4ccc(NC(=O)N5CCNCC5)nc4=O)cc3)C[C@@H]12] |
| 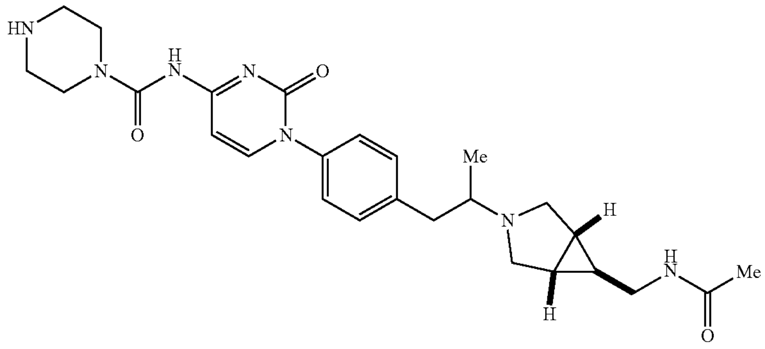 [SMILES: CC(=O)NC[C@@H]1[C@H]2CN(C(C)Cc3ccc(-n4ccc(NC(=O)N5CCNCC5)nc4=O)cc3)C[C@@H]12] |
| 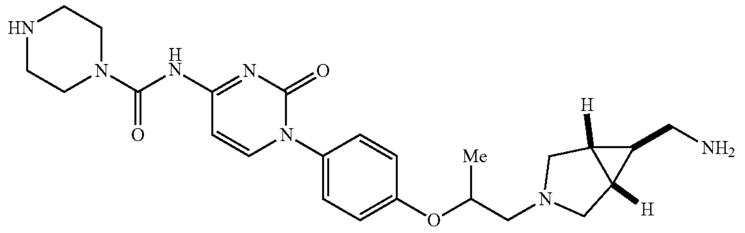 [SMILES: CC(CN1C[C@@H]2[C@@H](CN)[C@@H]2C1)Oc1ccc(-n2ccc(NC(=O)N3CCNCC3)nc2=O)cc1] |
| 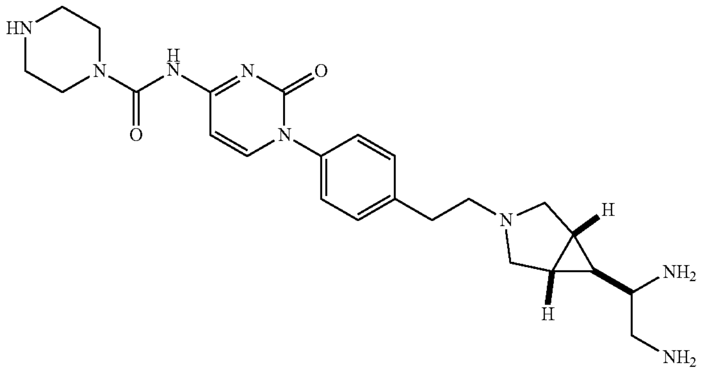 [SMILES: NCC(N)[C@H]1[C@@H]2CN(CCc3ccc(-n4ccc(NC(=O)N5CCNCC5)nc4=O)cc3)C[C@@H]21] |
| 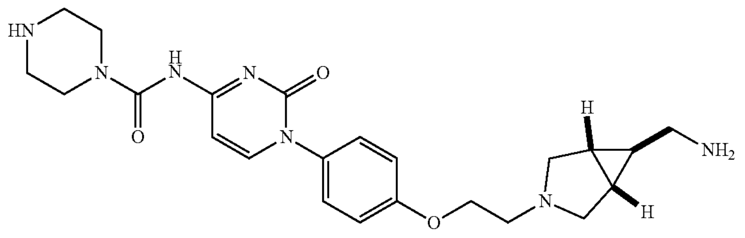 [SMILES: NC[C@@H]1[C@H]2CN(CCOc3ccc(-n4ccc(NC(=O)N5CCNCC5)nc4=O)cc3)C[C@@H]12] |

TABLE 11-continued
| Structure |
|---|
| 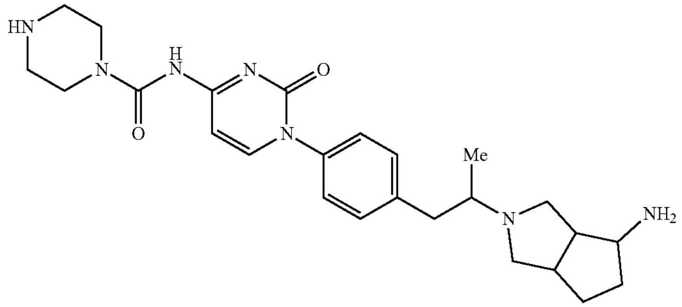 [SMILES: CC(Cc1ccc(-n2ccc(NC(=O)N3CCNCC3)nc2=O)cc1)N1CC2CCC(N)C2C1] |
| 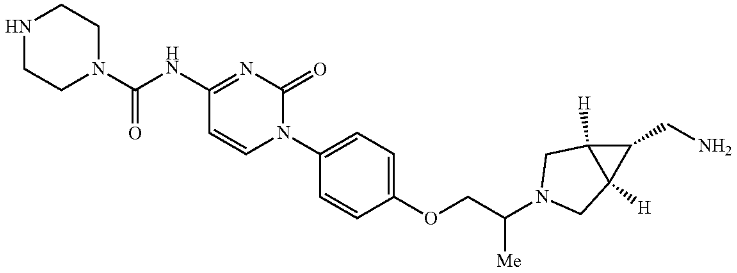 [SMILES: CC(COc1ccc(-n2ccc(NC(=O)N3CCNCC3)nc2=O)cc1)N1C[C@@H]2[C@@H](CN)[C@@H]2C1] |
| 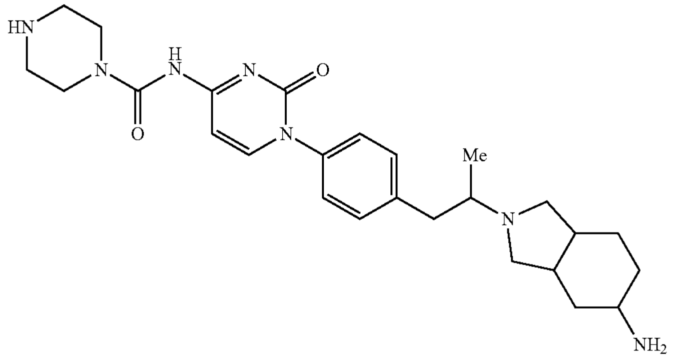 [SMILES: CC(Cc1ccc(-n2ccc(NC(=O)N3CCNCC3)nc2=O)cc1)N1CC2CCC(N)CC2C1] |
| 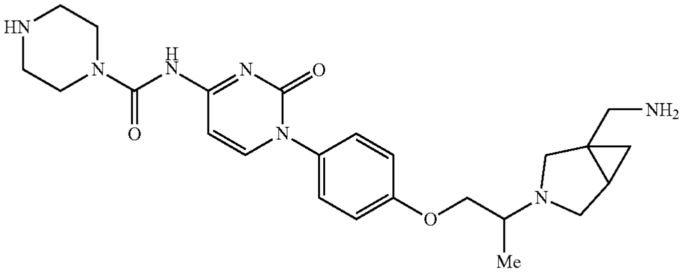 [SMILES: CC(COc1ccc(-n2ccc(NC(=O)N3CCNCC3)nc2=O)cc1)N1CC2CC2(CN)C1] |
| 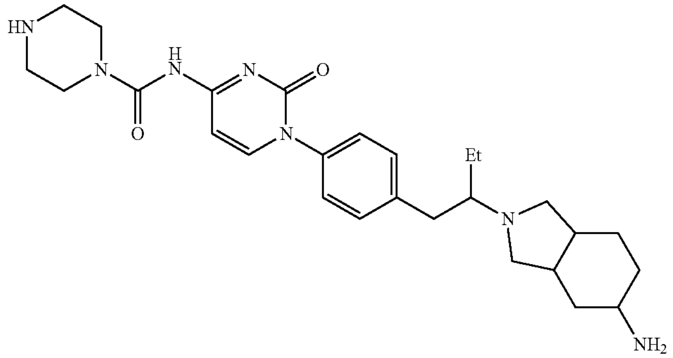 [SMILES: CCC(Cc1ccc(-n2ccc(NC(=O)N3CCNCC3)nc2=O)cc1)N1CC2CCC(N)CC2C1] |

TABLE 11-continued
| Structure |
| --- |
| 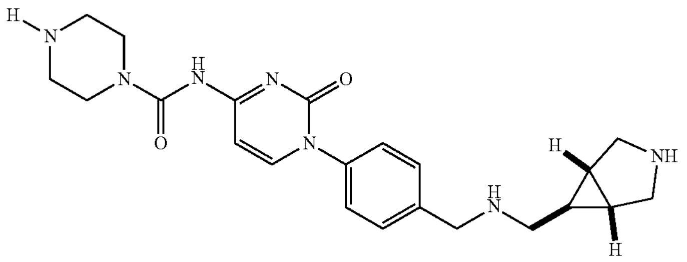 [SMILES: O=C(Nc1ccn(-c2ccc(CNC[C@@H]3[C@H]4CNC[C@@H]34)cc2)c(=O)n1)N1CCNCC1] |
| 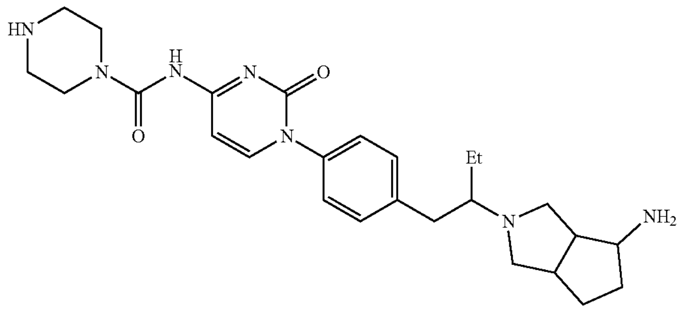 [SMILES: CCC(Cc1ccc(-n2ccc(NC(=O)N3CCNCC3)nc2=O)cc1)N1CC2CCC(N)C2C1] |
| 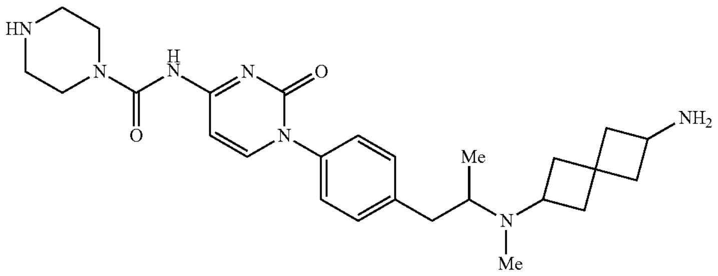 [SMILES: CC(Cc1ccc(-n2ccc(NC(=O)N3CCNCC3)nc2=O)cc1)N(C)C1CC2(CC(N)C2)C1] |
| 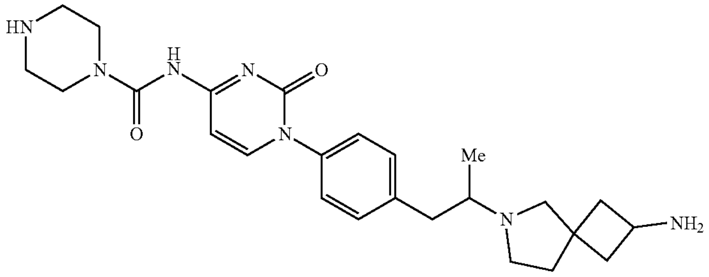 [SMILES: CC(Cc1ccc(-n2ccc(NC(=O)N3CCNCC3)nc2=O)cc1)N1CCC2(CC(N)C2)C1] |
| 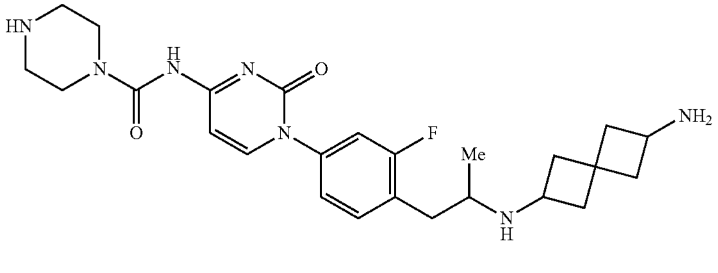 [SMILES: CC(Cc1ccc(-n2ccc(NC(=O)N3CCNCC3)nc2=O)cc1F)NC1CC2(CC(N)C2)C1] |

TABLE 11-continued
| Structure |
|---|
| 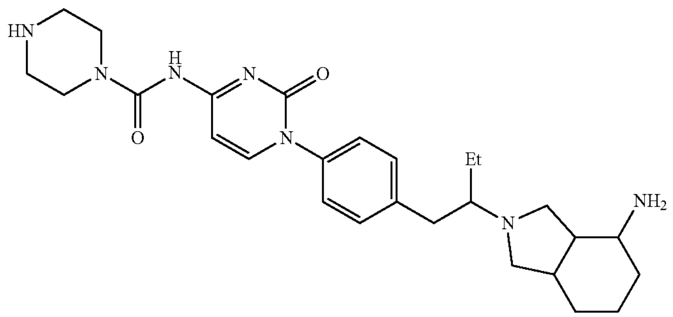 [SMILES: CCC(Cc1ccc(-n2ccc(NC(=O)N3CCNCC3)nc2=O)cc1)N1CC2CCCC(N)C2C1] |
| 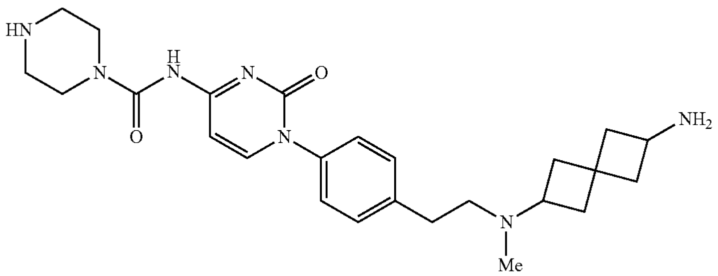 [SMILES: CN(CCc1ccc(-n2ccc(NC(=O)N3CCNCC3)nc2=O)cc1)C1CC2(CC(N)C2)C1] |
| 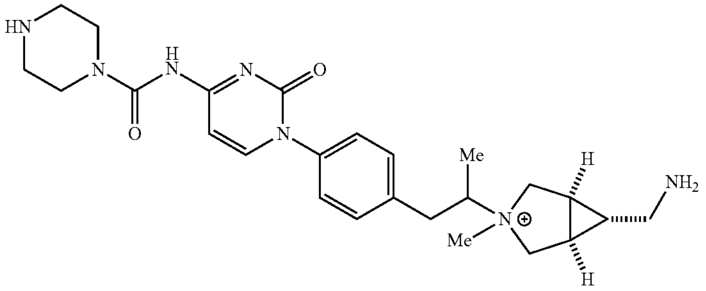 [SMILES: CC(Cc1ccc(-n2ccc(NC(=O)N3CCNCC3)nc2=O)cc1)[N+]1(C)C[C@@H]2[C@@H](CN)[C@@H]2C1] |
| 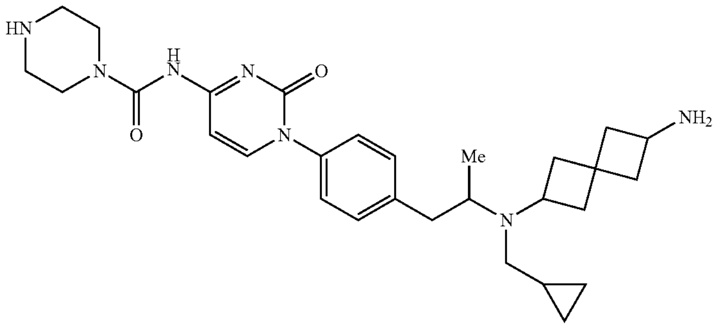 [SMILES: CC(Cc1ccc(-n2ccc(NC(=O)N3CCNCC3)nc2=O)cc1)N(CC1CC1)C1CC2(CC(N)C2)C1] |
| 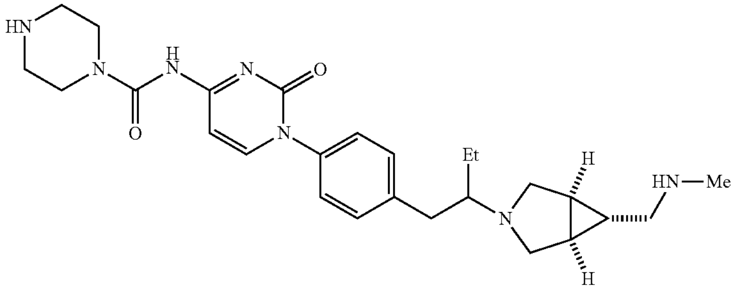 [SMILES: CCC(Cc1ccc(-n2ccc(NC(=O)N3CCNCC3)nc2=O)cc1)N1C[C@@H]2[C@@H](CNC)[C@@H]2C1] |

TABLE 11-continued
| Structure |
| --- |
| 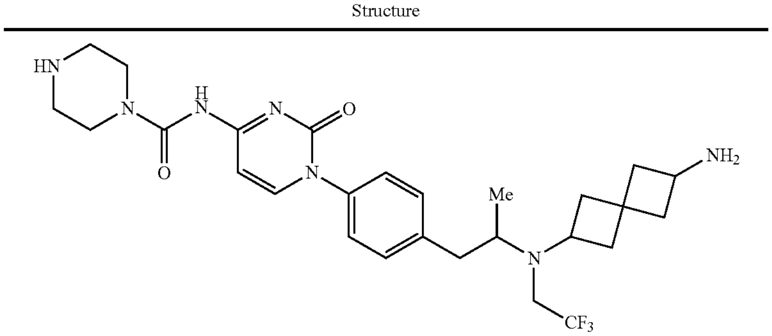 |
| 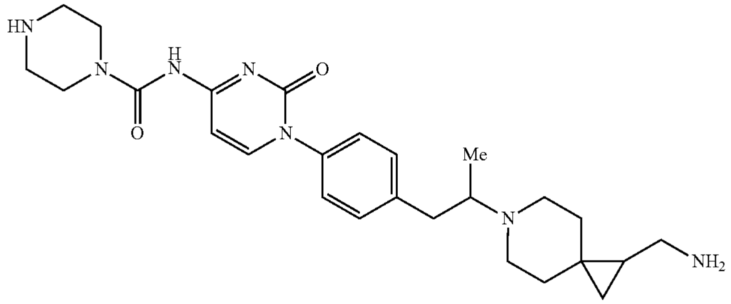 [SMILES: CC(Cc1ccc(-n2ccc(NC(=O)N3CCNCC3)nc2=O)cc1)N1CCC2(CC1)CC2CN] |
| 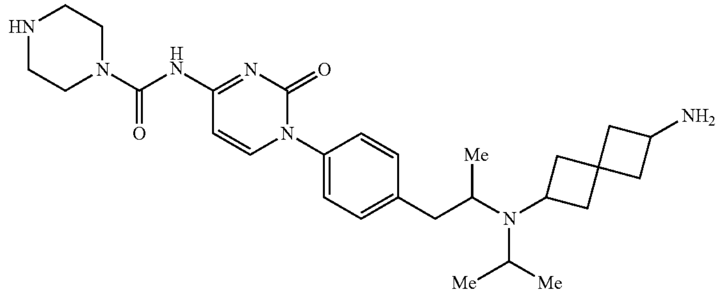 [SMILES: CC(C)N(C(C)Cc1ccc(-n2ccc(NC(=O)N3CCNCC3)nc2=O)cc1)C1CC2(CC(N)C2)C1] |
| 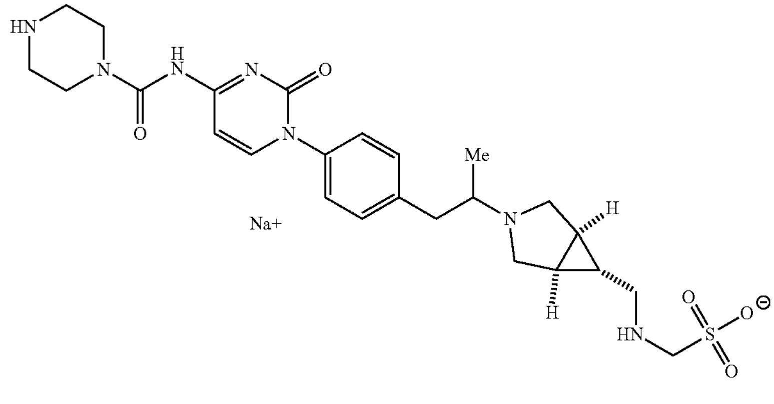 [SMILES: CC(Cc1ccc(-n2ccc(NC(=O)N3CCNCC3)nc2=O)cc1)N1C[C@@H]2[C@@H](CNCS(=O)(=O)[O-])[C@@H]2C1 ; [Na+]] |
| 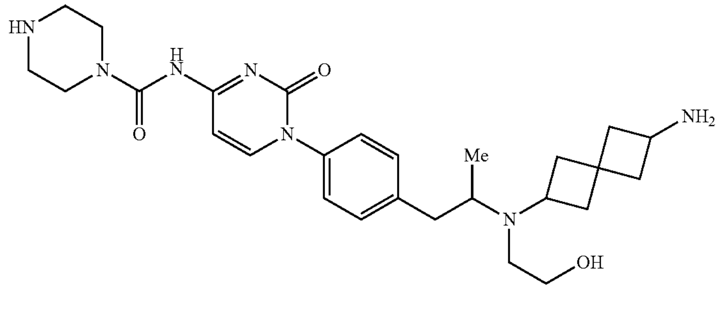 [SMILES: CC(Cc1ccc(-n2ccc(NC(=O)N3CCNCC3)nc2=O)cc1)N(CCO)C1CC2(CC(N)C2)C1] |

TABLE 11-continued
| Structure |
| --- |
| 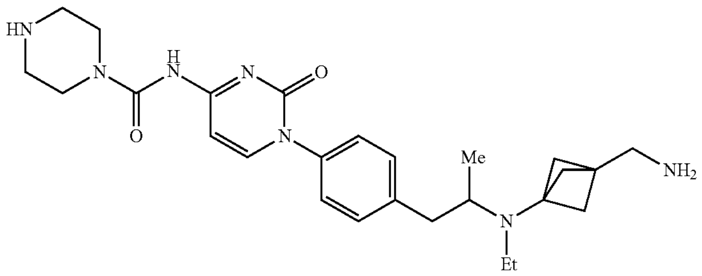 [SMILES: CCN(C(C)Cc1ccc(-n2ccc(NC(=O)N3CCNCC3)nc2=O)cc1)C12CC(CN)(C1)C2] |
| 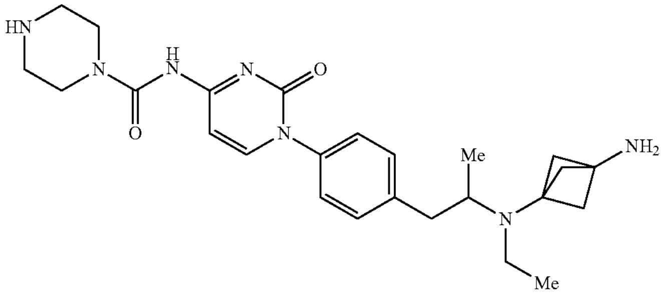 [SMILES: CCN(C(C)Cc1ccc(-n2ccc(NC(=O)N3CCNCC3)nc2=O)cc1)C12CC(N)(C1)C2] |
| 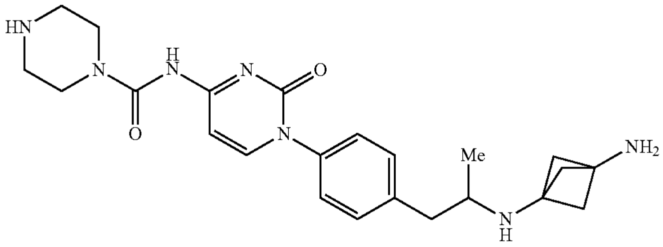 [SMILES: CC(Cc1ccc(-n2ccc(NC(=O)N3CCNCC3)nc2=O)cc1)NC12CC(N)(C1)C2] |
| 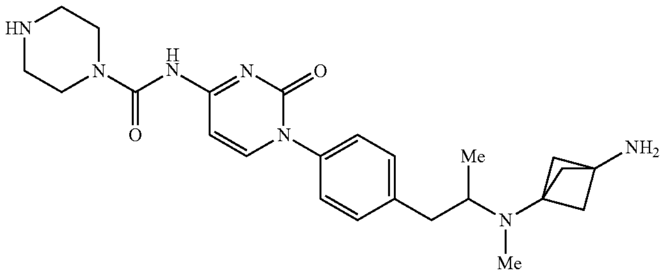 [SMILES: CC(Cc1ccc(-n2ccc(NC(=O)N3CCNCC3)nc2=O)cc1)N(C)C12CC(N)(C1)C2] |
| 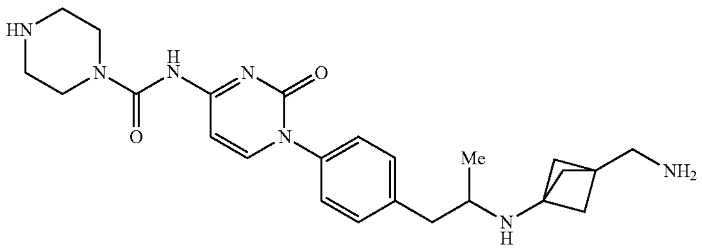 [SMILES: CC(Cc1ccc(-n2ccc(NC(=O)N3CCNCC3)nc2=O)cc1)NC12CC(CN)(C1)C2] |

TABLE 11-continued
| Structure |
| --- |
| 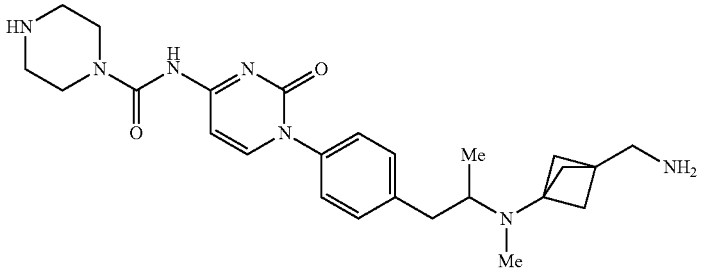 [SMILES: CC(Cc1ccc(-n2ccc(NC(=O)N3CCNCC3)nc2=O)cc1)N(C)C12CC(CN)(C1)C2] |
| 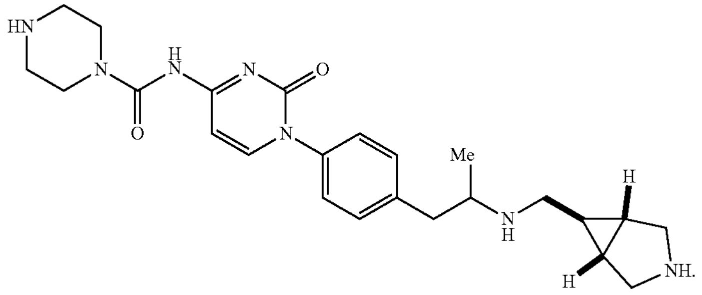 |
9. The compound of claim 1, wherein:
ring A is selected from the group consisting of
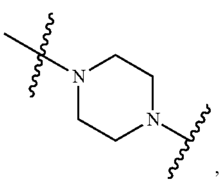
,
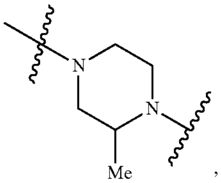
,
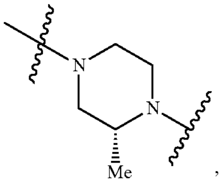
,
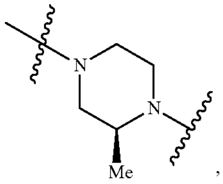
,
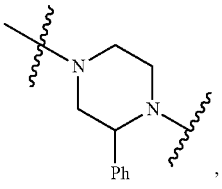
,
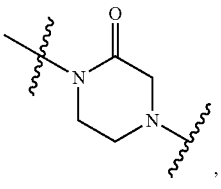
, and
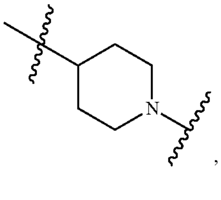
,
J is
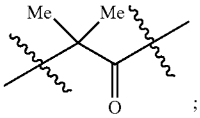 [SMILES: *C(=O)C(*)(C)C]
;
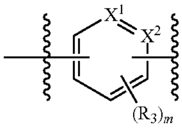
is
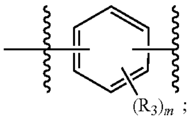
;
Y is $CH_2$;
ring B is selected from the group consisting of
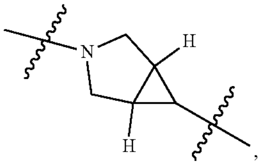
,
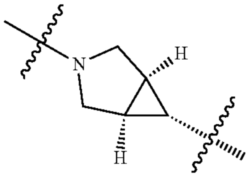
,
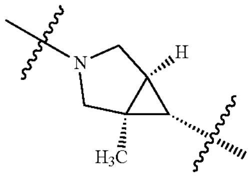
,
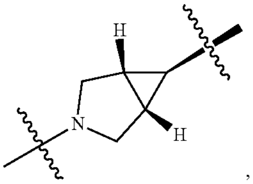
, -continued
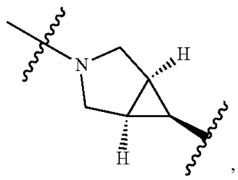
,
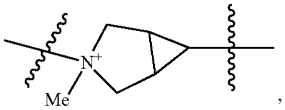
, and
-continued
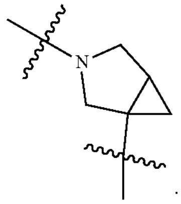
.
10. The compound of claim 9 which is:
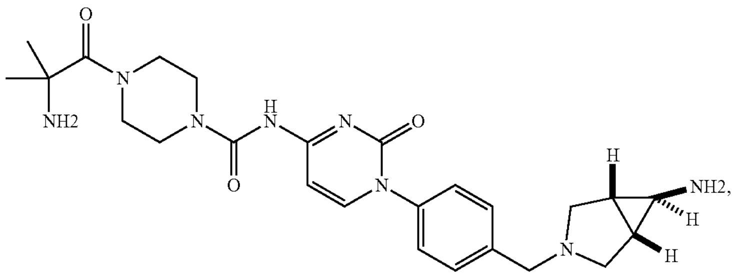
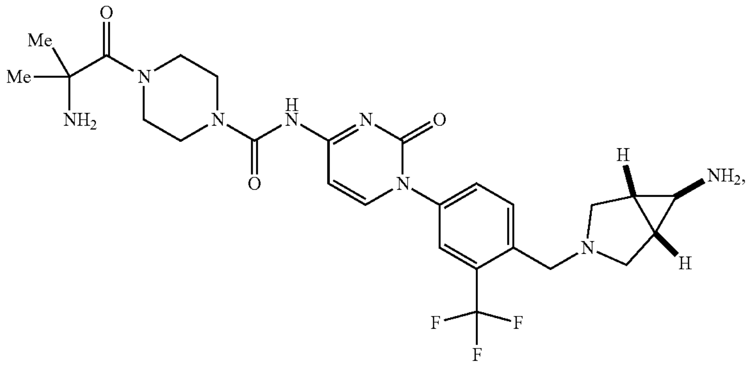
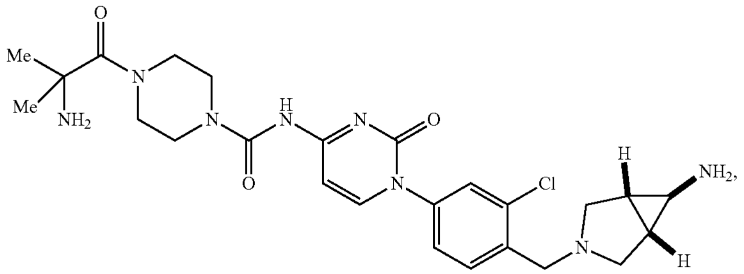
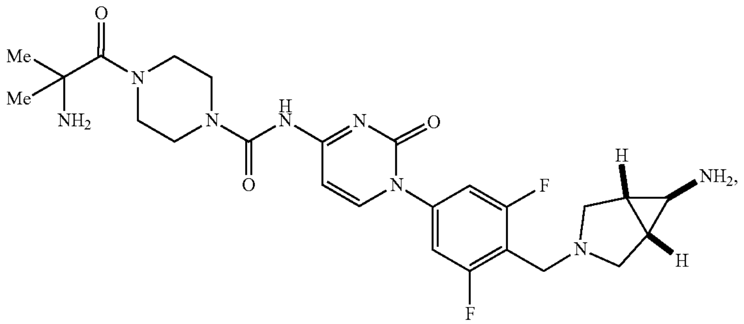

-continued
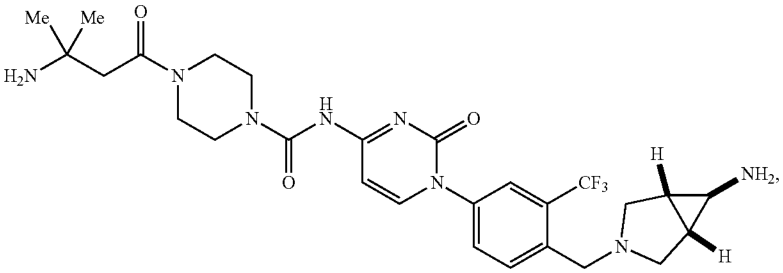
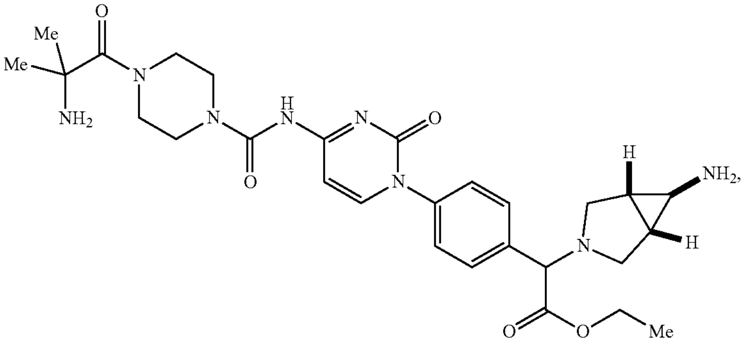
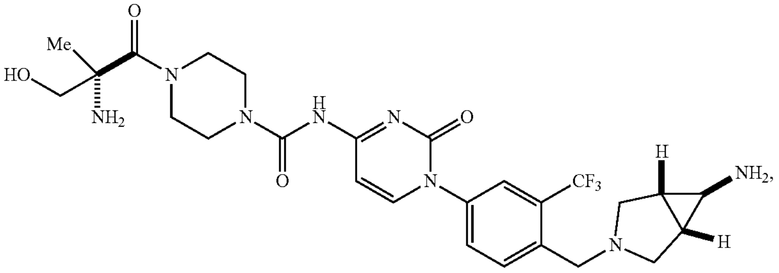
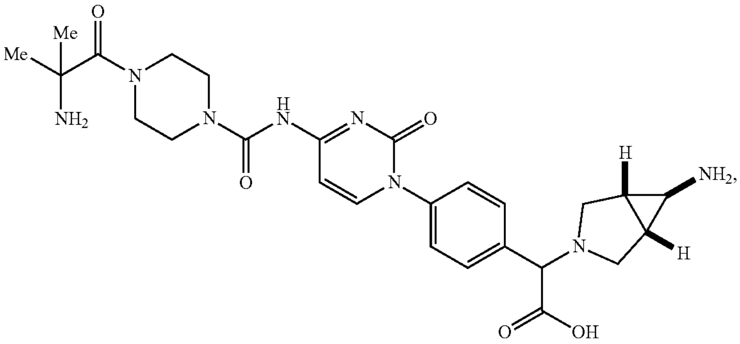
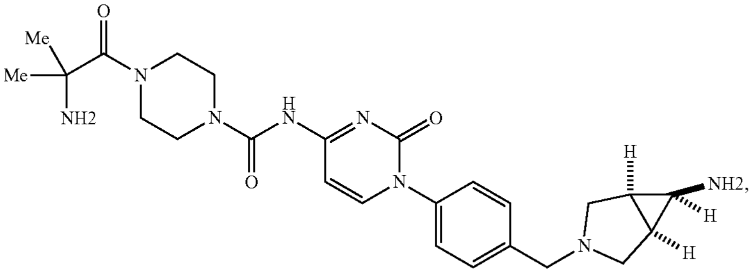

-continued
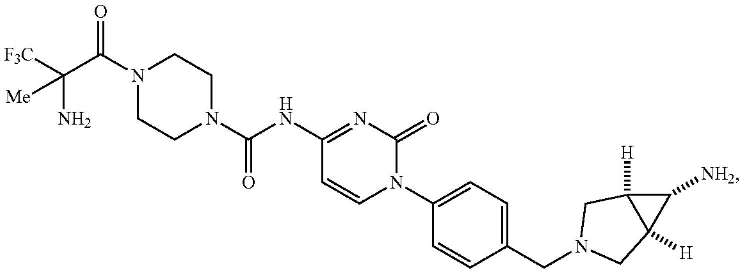
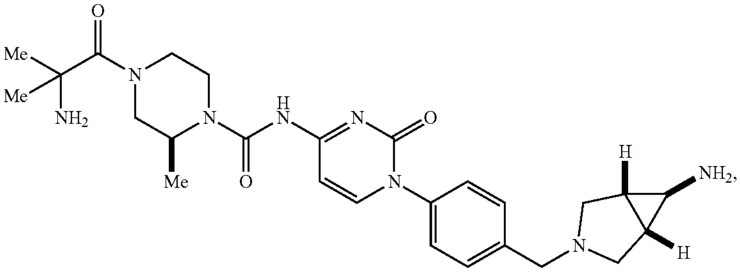
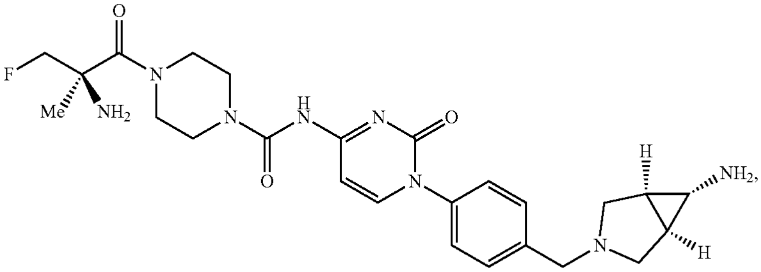
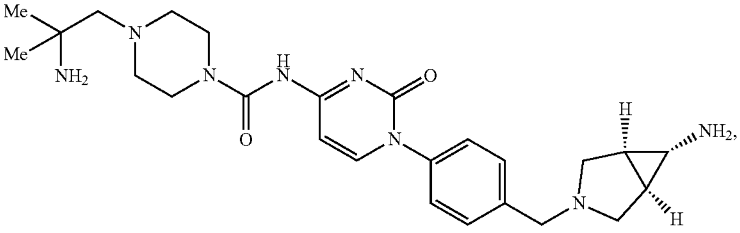
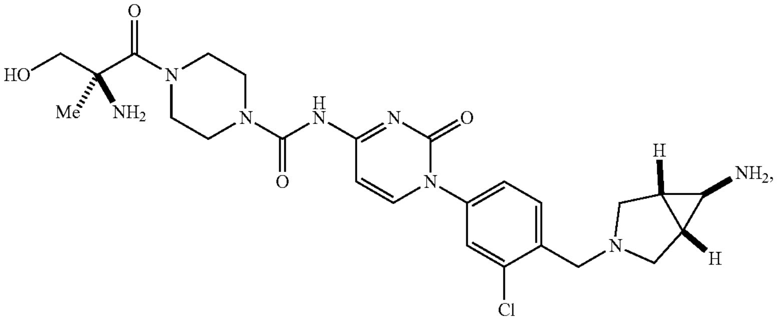
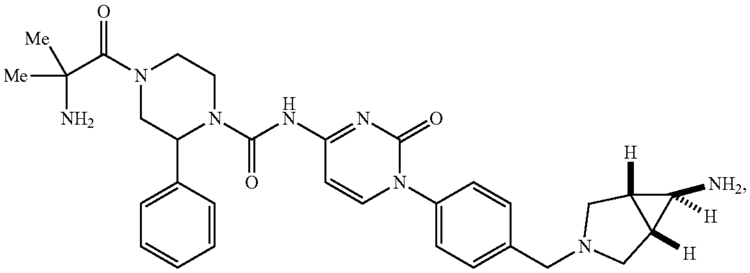

-continued
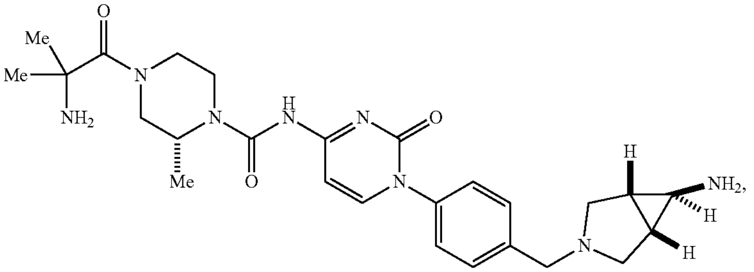
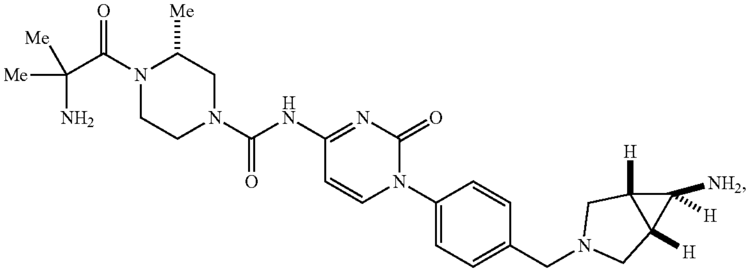
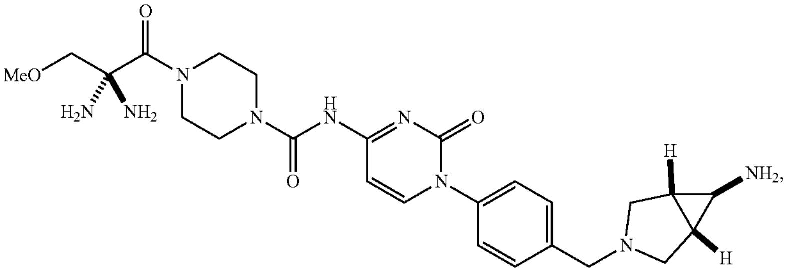
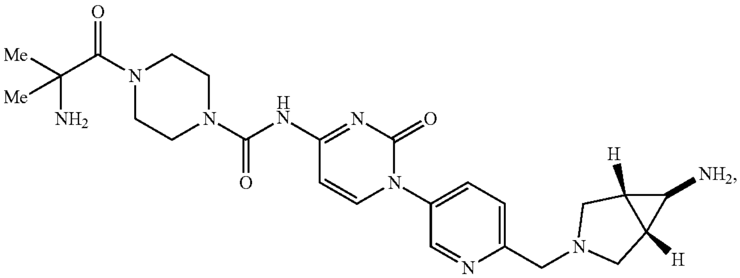
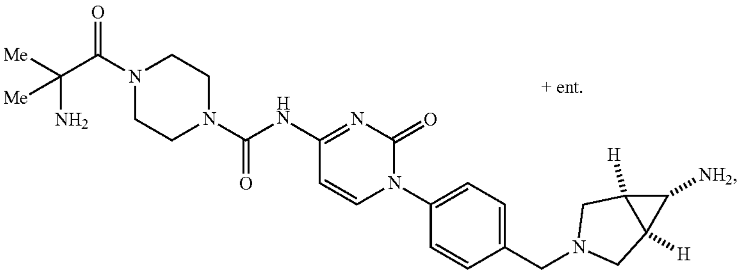
+ ent.
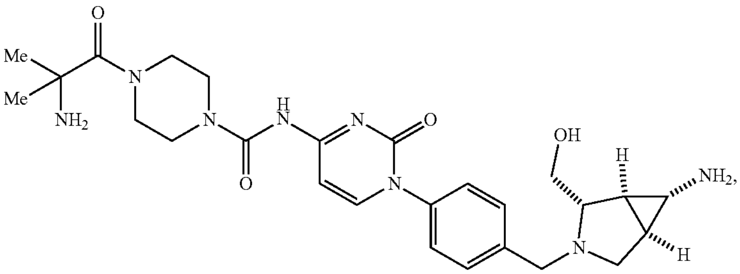

-continued

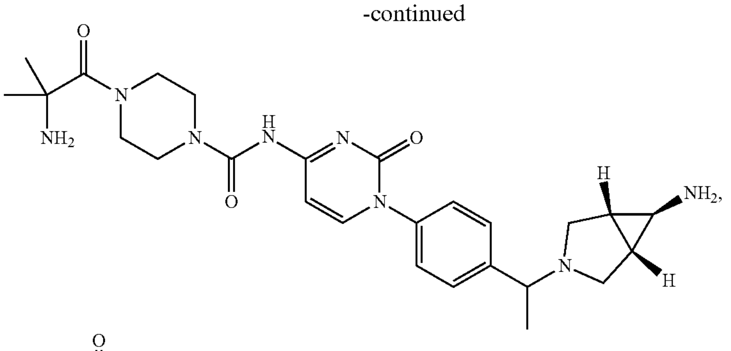

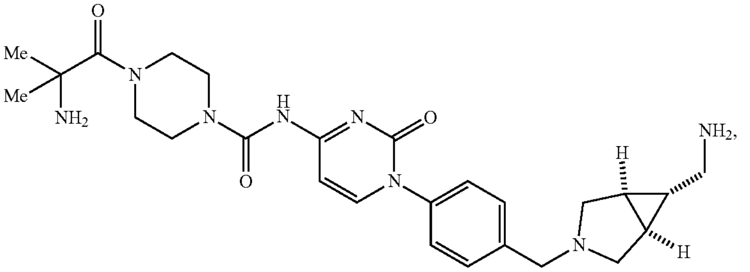

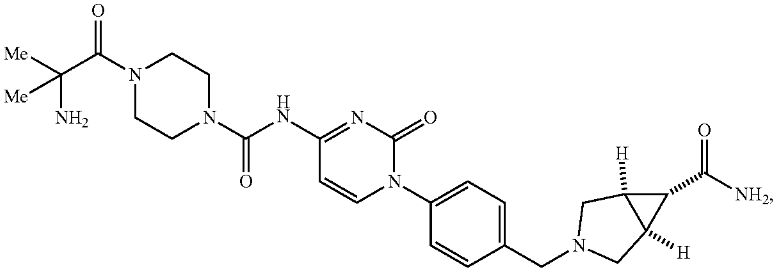

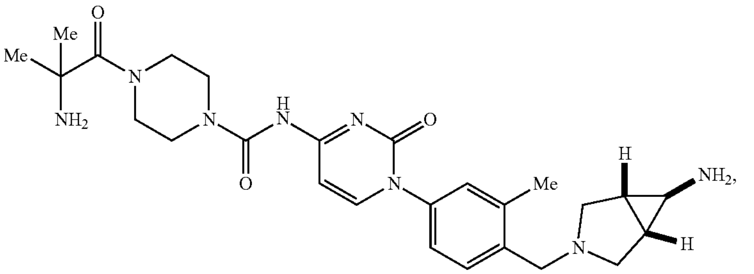

or

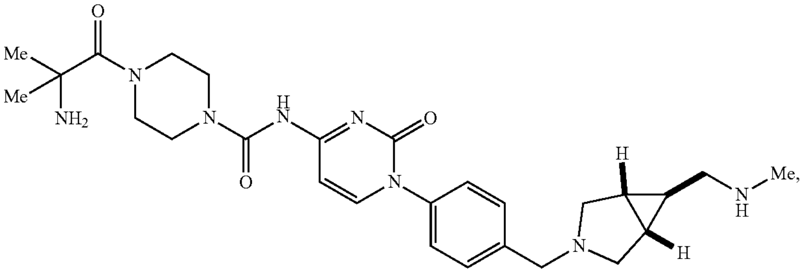

or a pharmaceutically acceptable salt thereof.

11. A pharmaceutical composition comprising a compound of claim 1, or a pharmaceutically acceptable salt thereof, and a pharmaceutically acceptable excipient.

12. A method of treating a bacterial infection in a patient in need of such treatment, comprising administering to the patient a compound as recited in claim 1.

13. The method of claim 12, wherein the bacterial infection is caused by a bacterium including gram positive and gram negative bacteria, selected from *Francisella tularensis, Burkholderia mallei, Burkholderia pseudomallei, Bacillus anthracis, Yersinia pestis, Salmonella, Clostridium difficile, Citrobacter, Enterobacter, Burkholderia* genus, *cepacia, Mycobacterium, Proteus, Streptococcus, Serratia, Enterobacteriaceae, Escherichia, Klebsiella, Pseudomonas*, and Acinitobacter.

* * * * *